US007858843B2

(12) United States Patent
Culbertson et al.

(10) Patent No.: US 7,858,843 B2
(45) Date of Patent: Dec. 28, 2010

(54) GENE DISRUPTIONS, COMPOSITIONS AND METHODS RELATING THERETO

(75) Inventors: Ling Ling Culbertson, Spring, TX (US); Frederic J. de Sauvage, Foster City, CA (US); Charles Montgomery, Jay, OK (US); Zheng-Zheng Shi, The Woodlands, TX (US); Mary Jean Sparks, Magnolia, TX (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/814,361

(22) PCT Filed: May 18, 2006

(86) PCT No.: PCT/US2006/019651

§ 371 (c)(1),
(2), (4) Date: Jul. 19, 2007

(87) PCT Pub. No.: WO2006/132788

PCT Pub. Date: Dec. 14, 2006

(65) Prior Publication Data

US 2009/0313707 A1 Dec. 17, 2009

Related U.S. Application Data

(60) Provisional application No. 60/780,262, filed on Mar. 7, 2006, provisional application No. 60/687,900, filed on Jun. 6, 2005.

(51) Int. Cl.
*G01N 33/00* (2006.01)
*C12N 5/06* (2006.01)
*C12Q 1/02* (2006.01)

(52) U.S. Cl. ........................... 800/3; 435/325; 435/354; 435/29

(58) Field of Classification Search ....................... None
See application file for complete search history.

(56) References Cited

U.S. PATENT DOCUMENTS

| | | | |
|---|---|---|---|
| 2003/0027281 | A1 | 2/2003 | Baker et al. |
| 2003/0040053 | A1 | 2/2003 | Baker et al. |
| 2003/0215908 | A1 | 11/2003 | Ashkenazi et al. |

FOREIGN PATENT DOCUMENTS

| | | | |
|---|---|---|---|
| EP | 1 386 931 | A1 | 2/2004 |

OTHER PUBLICATIONS

Yu et al. J. Biol. Chem. 278:17350-17359; 2003.*

Nakae et al (Immunity. 2002; 17:375-387).*

Abe et al., "Lysosomal phospholipase A2 is selectively expressed in alveolar macrophages" *J Biol Chem.* 279 (41) :42605-11 (Oct. 8, 2004).

Abu-Elheiga et al., "Continuous Fatty Acid Oxidation and Reduced Fat Storage in Mice Lacking Acetyl-CoA Carboxylase 2" *Science* 291 (5513) :2613-16 (Mar. 30, 2001).

Adam et al., "Comprehensive proteomic analysis of breast cancer cell membranes reveals unique proteins with potential roles in clinical cancer" *J Biol Chem.* 278 (8) :6482-9 (Feb. 21, 2003).

Afar et al., "Preclinical validation of anti-TMEFF2-auristatin E-conjugated antibodies in the treatment of prostate cancer" *Mol Cancer Ther.* 3 (8) :921-32 (Aug. 2004).

Alpy et al., "Mentho, a MLN64 homologue devoid of the START domain" *J Biol Chem.* 277 (52) :50780-7 (Dec. 27, 2002).

Ang et al., "Spatial and temporal expression of Wnt and Dickkopf genes during murine lens development" *Gene Expr Patterns.* May 2004;4(3):289-95 4 (3) :289-95.

Baeza et al., "Rapid down regulation of pyroglutamyl peptidase II activity by arachidonic acid in primary cultures of adenohypophyseal cells" *Life Sci.* 68 (17) :2051-60 (Mar. 16, 2001).

Ben-Porath and Benvenisty, "Characterization of a tumor-associated gene, a member of a novel family of genes encoding membrane glycoproteins" *Gene* 183 (1-2) :69-75 (Dec. 12, 1996).

Berditchevski, "Complexes of tetraspanins with integrins: more than meets the eye" *J Cell Sci.* 114 (Pt 23) :4143-51. (Dec. 2001).

Biunno et al., "Isolation of a pancreas-specific gene located on human chromosome 14q31: expression analysis in human pancreatic ductal carcinomas" *Genomics* 46 (2) :284-6 (Dec. 1, 1997).

(Continued)

*Primary Examiner*—Scott Long
(74) *Attorney, Agent, or Firm*—Bonny Yeung; Christopher De Vry; Ginger R. Dreger

(57) ABSTRACT

The present invention relates to transgenic animals, as well as compositions and methods relating to the characterization of gene function. Specifically, the present invention provides transgenic mice comprising disruptions in PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

3 Claims, 156 Drawing Sheets

OTHER PUBLICATIONS

Bono et al., "Layilin, a novel integral membrane protein, is a hyaluronan receptor" *Mol. Biol. Cell*12 (4) :891-900 (2001).

Borowsky and Hynes, "Layilin, a novel talin-binding transmembrane protein homologous with C-type lectins, is localized in membrane ruffles" *Cell Biol.* 143 (2) :429-42 (Oct. 19, 1998).

Bottcher et al., "The transmembrane protein XFLRT3 forms a complex with FGF receptors and promotes FGF signalling" *Nature Cell Biology* 6: 38-44 (2004).

Bouchon et al., "Cutting Edge: Activation of NK cell-mediated cytotoxicity by a SAP-independent receptor of the CD2 family" *J Immunol.* 167 (10) :5517-21 (Nov. 15, 2001).

Bouis et al., "Effects of the CDT6/ANGX gene on tumour growth in immune competent mice" *In Vivo.* 17 (2) :157-61 (Mar.-Apr. 2003).

Brott and Sokol, "Regulation of Wnt/LRP Signaling by Distinct Domains of Dickkopf Proteins" *Molecular & Cellular Biology* 22 (17) :6100-6110 (Sep. 2002).

Cattaneo et al., "Identification of a region within SEL1L protein required for tumour growth inhibition" *Gene* 326:149-56 (Feb. 4, 2004).

Chalhoub et al., "Grey-lethal mutation induces severe malignant autosomal recessive osteopetrosis in mouse and human" *Nat Med.* 9 (4) :399-406 (Apr. 2003).

Charpantier et al., "Effects of estrogen on global gene expression: identification of novel targets of estrogen action" *Cancer Research* 60 (21) :5977-83 (Nov. 1, 2000).

Chen et al., "cDNA cloning, genomic structure, and chromosome mapping of the human epithelial membrane protein CL-20 gene (EMP1), a member of the PMP22 family" *Genomics* 41 (1) :40-8 (Apr. 1, 1997).

Cheng and Russell, "Mammalian wax biosynthesis. II. Expression cloning of wax synthase cDNAs encoding a member of the acyltransferase enzyme family" *J Biol Chem.* 279 (36) :37798-807 (Sep. 3, 2004).

Chiaramonte et al., "Notch signal transduction is not regulated by SEL1L in leukaemia and lymphoma cells in culture" *Anticancer Res.* 22 (6C) :4211-4 (Nov.-Dec. 2002).

Clark et al., "The secreted protein discovery initiative (SPDI), a large-scale effort to identify novel human secreted and transmembrane proteins: a bioinformatics assessment" *Genome Research* 13 (10) :2265-2270 (Oct. 2003).

Colonna et al., "Molecular characterization of two novel C-type lectin-like receptors, one of which is selectively expressed in human dendritic cells" *Eur J Immunol.* 30 (2) :697-704 (Feb. 2000).

Coyne et al., "Role of claudin interactions in airway tight junctional permeability" *Am J Physiol Lung Cell Mol Physiol.* 285 (5) :L1166-78 (Nov. 2003).

Cui et al., "Cloning of human myeloid-associated differentiation marker (MYADM) gene whose expression was up-regulated in NB4 cells induced by all-trans retinoic acid" *Mol Biol Rep.* 28 (3) :123-38 (2001).

Dail et al., "SHEP1 function in cell migration is impaired by a single amino acid mutation that disrupts association with the scaffolding protein cas but not with Ras GTPases" *J Biol Chem.* 279 (40) :41892-902 (Oct. 1, 2004).

DeLorey et al., "Mice lacking the β3 subunit of the GABAA receptor have the epilepsy phenotype and many of the behavorial characteristics of Angelman syndrome" *J Neurosci.* 18 (20) :8505-14 (Oct. 15, 1998).

Dgany et al., "Congenital dyserythropoietic anemia type I is caused by mutations in codanin-1" *Am J Hum Genet.* 71 (6) :1467-74 (Dec. 2002).

Dodelet et al., "A novel signaling intermediate, SHEP1, directly couples Eph receptors to R-Ras and Rap1A" *J Biol Chem.* 274 (45) : 31941-6 (Nov. 5, 1999).

Doerks et al., "GRAM, a novel domain in glucosyltransferases, myotubularins and other putative membrane-associated proteins" *Trends Biochem Sci.* 25 (10) :483-5 (Oct. 2000).

Donoviel et al., "Cloning and characterization of Sel-11, a murine homolog of the C. elegans sel-1 gene" *Mech Dev.* 78 (1-2) :203-7 (Nov. 1998).

Duan et al., "Identification of Human Intestinal Alkaline Sphingomyelinase as a Novel Ecto-enzyme Related to the Nucleotide Phosphodiesterase Family" *Journal of Biological Chemistry* 278 (40) : 38528-38536 (2003).

Erne et al., "Rafts in adult peripheral nerve myelin contain major structural myelin proteins and myelin and lymphocyte protein (MAL) and CD59 as specific markers" *Neurochem* 82 (3) :550-62 (Aug. 2002).

Esther et al., "Mice Lacking angiotensin-converting enzyme have low blood pressure, renal pathology, and reduced male fertility" *Laboratory Investigation* 74 (5) :953-65 (May 1996).

Ferrante et al., "Molecular and biochemical characterisation of a novel sulphatase gene: Arylsulfatase G (ARSG" *Eur J Hum Genet.* 10 (12) :813-8 (Dec. 2002).

Fessler et al., "Papilin, a novel component of basement membranes, in relation to ADAMTS metalloproteases and ECM development" *Int J Biochem Cell Biol.* 36 (6) :1079-84 (Jun. 2004).

Fischer et al., "Promotion of G alpha i3 subunit down-regulation by GIPN, a putative E3 ubiquitin ligase that interacts with RGS-GAIP" *Proc Natl Acad Sci U S A.* 100 (14) :8270-5 (Jul. 2003).

Fletcher et al., "hAG-2 and hAG-3, human homologues of genes involved in differentiation, are associated with oestrogen receptor-positive breast tumours and interact with metastasis gene C4.4a and dystroglycan" *Br J Cancer* 88 (4) :579-85 (Feb. 24, 2003).

Frank et al., "Developmental expression pattern of the myelin proteolipid MAL indicates different functions of MAL for immature Schwann cells and in a late step of CNS myelinogenesis" *J Neurochem.* 73 (2) :587-97 (Aug. 1999).

Frank et al., "MAL, a proteolipid in glycosphingolipid enriched domains: functional implications in myelin and beyond" *Prog Neurobiol.* 60 (6) :531-44 (Apr. 2000).

Fu and Kamp, "E2a-Pbx1 induces aberrant expression of tissue-specific and developmentally regulated genes when expressed in NIH 3T3 fibroblasts" *Mol Cell Biol.* 17 (3) :1503-12 (Mar. 1997).

Furthauer et al., "Sef is a feedback-induced antagonist of Ras/MAPK-mediated FGF signalling" *Nat Cell Biol.* 4 (2) :170-4 (Feb. 2002).

Furuse et al., "Claudin-1 and -2: novel integral membrane proteins localizing at tight junctions with no sequence similarity to occludin" *J Cell Biol.* 141 (7) :1539-50 (Jun. 29, 1998).

Furuse et al., "Claudin-based tight junctions are crucial for the mammalian epidermal barrier: a lesson from claudin-1-deficient mice" *J Cell Biol.* 156 (6) :1099-111 (Mar. 18, 2002).

Garlanda et al., "Intestinal inflammation in mice deficient in Tir8, an inhibitory member of the IL-1 receptor family" *Proc Natl Acad Sci U S A.* 101 (10) :3522-6 (Mar. 9, 2004).

Georgas et al., "Characterisation of Criml expression in the developing mouse urogenital tract reveals a sexually dimorphic gonadal expression pattern" *Dev Dyn.* 219 (4) :582-7 (Dec. 2000).

Gery and Koeffler, "Repression of the TMEFF2 promoter by c-Myc" *J Mol Biol.* 328 (5) :977-83 (May 16, 2003).

Gery et al., "TMEFF2 is an androgen-regulated gene exhibiting antiproliferative effects in prostate cancer cells" *Oncogene* 21 (31) : 4739-46 (Jul. 18, 2002).

Glienke et al., "CRIM1 is involved in endothelial cell capillary formation in vitro and is expressed in blood vessels in vivo" *Mech Dev.* 119 (2) :165-75 (Dec. 2002).

Grant and Greenwald, "Structure, function, and expression of SeL-1, a negative regulator of LIN-12 and GLP-1 in C. elegans" *Development* 124 (3) :637-44 (Feb. 1997).

Heiskala et al., "The roles of claudin superfamily proteins in paracellular transport" *Traffic* 2 (2) :93-8 (Feb. 2001).

Higuchi et al., "Molecular cloning, genomic structure, and expression analysis of MUC20, a novel mucin protein, up-regulated in injured kidney" *J Biol Chem.* 279 (3) :1968-79 (Jan. 16, 2004).

Higuchi et al., "MUC20 suppresses the hepatocyte growth factor-induced Grb2-Ras pathway by binding to a multifunctional docking site of met" *Mol Cell Biol.* 24 (17) :7456-68 (Sep. 2004).

Hiraoka et al., "Cloning and characterization of a lysosomal phospholipase A2, 1-O-acylceramide synthase" *J Biol Chem.* 277 (12) :10090-9 (Mar. 22, 2002).

Hooper et al., "Mouse matriptase-2: identification, characterization and comparative mRNA expression analysis with mouse hepsin in adult and embryonic tissues" *Biochemical Journal* 373 (Pt 3) :689-702 (Aug. 1, 2003).
Horie et al., "Identification and characterization of TMEFF2, a novel survival factor for hippocampal and mesencephalic neurons" *Genomics* 67 (2) :146-52 (Jul. 15, 2000).
Hurst et al., "New IL-17 family members promote Th1 or Th2 responses in the lung: in vivo function of the novel cytokine IL-25" *J Immunol.* 169 (1) :443-53 (Jul. 1, 2002).
Ihalmo et al., "Filtrin is a novel member of nephrin-like proteins" *Biochem Biophys Res Commun.* 300 (2) :364-70 (Jan. 10, 2003).
Ioka et al., "Expression cloning and characterization of a novel glycosylphosphatidylinositol-anchored high density lipoprotein-binding protein, GPI-HBP1" *J Biol Chem.* 278 (9) :7344-9 (Feb. 28, 2003).
Izumoto et al., "Hepatoma-derived growth factor belongs to a gene family in mice showing significant homology in the amino terminus" *Biochem Biophys Res Commun.* 238 (1) :26-32 (Sep. 8, 1997).
Kang et al., "BOC, an Ig superfamily member, associates with CDO to positively regulate myogenic differentiation" *EMBO Journal* 21 (1-2) :114-124 (Jan. 15, 2002).
Kang et al., "Promyogenic members of the Ig and cadherin families associate to positively regulate differentiation" *Proc Natl Acad Sci U S A* 100 (7) :3989-3994 (Apr. 1, 2003).
Katoh and Katoh, "Identification and characterization of human FCHSD1 and FCHSD2 genes in silico" *Int J Mol Med.* 13 (5) :749-54 (May 2004).
Kawaguchi et al., "Activation of extracellular signal-regulated kinase (ERK)1/2, but not p38 and c-Jun N-terminal kinase, is involved in signaling of a novel cytokine, ML-1" *J Biol Chem.* 277 (18) :15229-32 (May 3, 2002).
Kawaguchi et al., "Induction of granulocyte-macrophage colony-stimulating factor by a new cytokine, ML-1 (IL-17F), via Raf I-MEK-ERK pathway" *J Allergy Clin Immunol.* 114 (2) :444-50 (Aug. 2004).
Kawamura et al., "cDNA of a novel mRNA expressed predominantly in mouse kidney" *Biochem Genet.* 39 (1-2) :33-42 (Feb. 2001).
Kelly et al., "Kinetic investigation of the specificity of porcine brain thyrotropin-releasing hormone-degrading ectoenzyme for thyrotropin-releasing hormone-like peptides" *J Biol Chem.* 275 (22) :16746-51 (Jun. 2, 2000).
King et al., "Organisation of the mouse and human 5T4 oncofoetal leucine-rich glycoprotein genes and expression in foetal and adult murine tissues" *Biochim Biophys Acta.* 1445 (3) :257-70 (Jun. 9, 1999).
Kingsbury et al., "Cloning, expression, and function of BLAME, a novel member of the CD2 family" *J. Immunol.* 166 (9) :5675-80 (May 1, 2001).
Kishima et al., "Hepatoma-derived growth factor stimulates cell growth after translocation to the nucleus by nuclear localization signals" *J Biol Chem.* 277 (12) :10315-22 (Mar. 22, 2002).
Kolle et al., "CRIM1, a novel gene encoding a cysteine-rich repeat protein, is developmentally regulated and implicated in vertebrate CNS development and organogenesis" *Mech Dev.* 90 (2) :181-93 (Feb. 2000).
Korkmaz et al., "Molecular cloning and characterization of STAMP1, a highly prostate-specific six transmembrane protein that is overexpressed in prostate cancer" *J Biol Chem.* 277 (39) :36689-96 (Sep. 27, 2002).
Kovalenko et al., "Sef inhibits fibroblast growth factor signaling by inhibiting FGFR1 tyrosine phosphorylation and subsequent ERK activation" *J Biol Chem.* 278 (16) :14087-91 (Apr. 18, 2003).
Kramerova et al., "Papilin in development; a pericellular protein with a homology to the ADAMTS metalloproteinases" *Development* 127 (24) :5475-85 (Dec. 2000).
Krupnik et al., "Functional and Structural Diversity of the Human Dickkopf Gene Family." *Gene* 238 (2) :301-313 (1999).
Kumaresan et al., "CS1, a novel member of the CD2 family, is homophilic and regulates NK cell function" *Mol Immunol.* 39 (1-2) : 1-8 (Sep. 2002).
Lacy et al., "Identification of FLRT1, FLRT2, and FLRT3: A Novel Family of Transmembrane Leucine-Rich Repeat Proteins" *Genomics* 62:417-426 (1999).
Langenbach et al., "Prostaglandin Synthase 1 Gene Disruption in Mice Reduces Arachidonic Acid-Induced Inflammation and Indomethancin-Induced Gastric Ulceration" *Cell* 83 (3) :483-92 (Nov. 3, 1995).
Lauren et al., "A novel gene family encoding leucine-rich repeat transmembrane proteins differentially expressed in the nervous system" *Genomics* 81:411-421 (2003).
Laurent et al., "The human c-Fes tyrosine kinase binds tubulin and microtubules through separate domains and promotes microtubule assembly" *Mol Cell Biol.* 24 (21) :9351-8 (Nov. 2004).
Le Naour et al., "Tetraspanins connect several types of Ig proteins: IgM is a novel component of the tetraspanin web on B-lymphoid cells" *Cancer Immunol Immunother.* 53 (3) :148-52 (Mar. 2004).
Lee, et al., "IL-17E, a Novel Proinflammatory Ligand for the IL-17 Receptor Homolog IL-17Rh1" *The Journal of Biological Chemistry* 276 (2) :1660-1664 (2001).
Li et al., "Cloning and characterization of the IL-17B and IL-17C two new members of the IL-17 cytokine family" *Proc. Natl. Acad. Sci. USA* 97 (2) :773-778 (2000).
Li et al., "Expression of claudin-7 and -8 along the mouse nephron" *Am J Physiol Renal Physiol.* 286 (6) :F1063-71 (Jun. 2004).
Li et al., "Second cysteine-rich domain of Dickkopf-2 activates canonical Wnt signaling pathway via LRP-6 independently of dishevelled" *J Biol Chem.* 277 (8) :5977-81 (Feb. 22, 2002)..
Liang et al., "The gene for a novel transmembrane protein containing epidermal growth factor and follistatin domains is frequently hypermethylated in human tumor cells" *Cancer Research* 60(17):4907-12 (Sep. 1, 2000).
Lin et al., "Tomoregulin ectodomain shedding by proinflammatory cytokines" *Life Sci.* 73(13):1617-27 (Aug. 15, 2003).
Lobsiger et al., "Identification and characterization of a cDNA and the structural gene encoding the mouse epithelial membrane protein-1" *Genomics* 36 (3) :379-87 (Sep. 15, 1996).
Lovicu et al., "Expression of Criml during murine ocular development" *Mech Dev.* 94 (1-2) :261-5 (Jun. 2000).
Magyar et al., "Myelin and lymphocyte protein (MAL/MVP17/VIP17) and plasmolipin are members of an extended gene family" *Gene* 189 (2) :269-75 (Apr. 21, 1997).
Mantovani et al., "Extracellular and intracellular decoys in the tuning of inflammatory cytokines and Toll-like receptors: the new entry TIR8/SIGIRR" *J Leukoc Biol.* 75 (5) :738-42 (May 2004).
Manya et al., "Loss-of-function of an N-acetylglucosaminyltransferase, POMGnT1, in muscle-eye-brain disease" *Biochem Biophys Res Commun.* 306 (1) :93-7 (Jun. 20, 2003).
Mao'and Niehrs, "Kremen2 modulates Dickkopf2 activity during Wnt/LRP6 signaling" *Gene* 302(1-2):179-83 (Jan. 2, 2003).
Marazuela and Alonso, "Expression of MAL and MAL2, two elements of the protein machinery for raft-mediated transport, in normal and neoplastic human tissue" *Histol Histopathol.* 19 (3) :925-33 (Jul. 2004).
Marvin et al., "Identification and characterization of a novel squamous cell-associated gene related to PMP22" *J Biol Chem.* 270 (48 ):28910-6 (Dec. 1, 1995).
Monaghan et al., "Dickkopf Genes are Co-ordinately Expressed in Mesodermal Lineages" *Mech. Dev.* 87 (1-2) :45-56 (1999).
Morita et al., "Claudin multigene family encoding four-transmembrane domain protein components of tight junction strands" *Proc Natl Acad Sci U S A* 96 (2) :511-6 (Jan. 19, 1999).
Moseley et al., "Interleukin-17 family and IL-17 receptors" *Cytokine And Growth Factor Reviews* 14 (2) :155-174 (Apr 2003).
Mulieri et al., "Expression of the boc gene during murine embryogenesis" *Dev Dyn.* 223 (3) :379-88 (Mar. 2002).
Murphy et al., "A novel immunoglobulin superfamily receptor (19A) related to CD2 is expressed on activated lymphocytes and promotes homotypic B-cell adhesion" *Biochemical Journal* 361 (Pt 3) :431-6 (Feb. 1, 2002).
Myers, "Isolation of a cDNA Encoding 5T4 Oncofetal Trophoblast Glycoprotein" *The Journal of Biological Chemistry* 269 (12) :9319-9324 (Mar. 25, 1994).

Neira et al., "A new gene (rmSTG) specific for taste buds is found by laser capture microdissection" *Mamm Genome* 12 (1) :60-6 (Jan. 2001).
Numasaki et al., "IL-17 and IL-17F modulate GM-CSF production by lung microvascular endothelial cells stimulated with IL-lbeta and/or TNF-alpha" *Immunol Lett*. 95 (2) :175-84 (Sep. 2004).
O'Brien et al., "Characterization of five novel human genes in the 11q13-q22 region" *Biochem Biophys Res Commun*. 273 (1) :90-4 (Jun. 24, 2000).
O'Neill, "SIGIRR puts the brakes on Toll-like receptors" *Nat Immunol*. 4 (9) :823-4 (Sep. 2003).
Oda et al., "Interleukin-17F induces pulmonary neutrophilia and amplifies antigen-induced allergic response" *Am J Respir Crit Care Med*. 171 (1) :12-8 (Jan 1, 2005).
Ohta et al., "Tsukushi functions as an organizer inducer by inhibition of BMP activity in cooperation with chordin" *Dev Cell* 7(3):347-58 (Sep. 2004).
Oku et al., "Peroxisome degradation requires catalytically active sterol glucosyltransferase with a GRAM domain" *EMBO Journal* 22 (13) :3231-41 (Jul. 1, 2003).
Orlandi et al., "SEL1L expression decreases breast tumor cell aggressiveness in vivo and in vitro"*Cancer Research* 62 (2) :567-74 (Jan. 15, 2002).
Overall et al., "Protease degradomics: mass spectrometry discovery of protease substrates and the CLIP-CHIP, a dedicated DNA microarray of all human proteases and inhibitors" *Biol Chem*. 385(6):493-504 (Jun. 2004).
Pallesen et al., "Isolation and characterization of MUC15, a novel cell membrane-associated mucin" *Eur J. Biochem*. 269 (11) :2755-63 (Jun. 2002).
Peek et al., "Molecular cloning of a new angiopoietinlike factor from the human cornea" *Invest Ophthalmol Vis Sci*. 39 (10) :1782-8 (Sep. 1998).
Peek et al., "The angiopoietin-like factor cornea-derived transcript 6 is a putative morphogen for human cornea" *J Biol Chem*. 277 (1) :686-93 (Jan. 4, 2002).
Pettersson et al., "Isolation of MYADM, a novel hematopoietic-associated marker gene expressed in multipotent progenitor cells and up-regulated during myeloid differentiation" *J Leukoc Biol*. 67 (3) : 423-31 (Mar. 2000).
Pielage et al., "The *Drosophila* cell survival gene discs lost encodes a cytoplasmic Codanin-l-like protein, not a homolog of tight junction PDZ protein Patj" *Dev Cell* 5 (6) :841-51 (Dec. 2003).
Polentarutti et al., "Unique pattern of expression and inhibition of IL-1 signaling by the IL-1 receptor family member TIR8/SIGIRR" *Eur Cytokine Netw*. 14 (4) :211-8 (Oct. 2003).
Porkka et al., "Cloning and characterization of a novel six-transmembrane protein STEAP2, expressed in normal and malignant prostate" *Laboratory Investigations* 82(11):1573-82 (Nov. 2002).
Preger et al., "Alternative splicing generates an isoform of the human Sef gene with altered subcellular localization and specificity" *Proc Nati Acad Sci U S A* 101 (5) :1229-34 (Feb. 3, 2004).
Puertollano et al., "Recombinant expression of the MAL proteolipid, a component of glycolipid-enriched membrane microdomains, induces the formation of vesicular structures in insect cells" *J Biol Chem* . 272 (29) :18311-5 (Jul. 18, 1997).
Robinson et al., "Missense mutations in CRELD1 are associated with cardiac atrioventricular septal defects" *Am J Hum Genet*. 72(4): 1047-52 (Apr. 2003).
Ross et al., "Podocan, a novel small leucine-rich repeat protein expressed in the sclerotic glomerular lesion of experimental HIV-associated nephropathy" *J Biol Chem*. 278 (35) :33248-55 (Aug. 29, 2003).
Ruegg et al., "B4B, a novel growth-arrest gene, is expressed by a subset of progenitor/pre-B lymphocytes negative for cytoplasmic mu-chain" *J Immunol*. 157(1):72-80 (Jul. 1, 1996).
Rupp et al., "Identification, genomic organization and mRNA expression of CRELD1, the founding member of a unique family of matricellular proteins" *Gene* 293 (1-2) :47-57 (Jun. 26, 2002).
Saito et al., "A secreted type of beta 1,6-N-acetylglucosaminyltransferase V (GnT-V) induces tumor angiogenesis without mediation of glycosylation: a novel function of GnT-V distinct from the original glycosyltransferase activity" *J Biol Chem*. 277 (19) :17002-8 (May 10, 2002).
Sakakibara and Hattori, "Chat, a Cas/HEF1-associated adaptor protein that integrates multiple signaling pathways" *J Biol Chem*. 275(9):6404-10 (Mar 3, 2000).
Sakakibara et al., "A novel hematopoietic adaptor protein, Chat-H, positively regulates T cell receptor-mediated interleukin-2 production by Jurkat cells" *J Biol Chem*. 278 (8) :6012-7 (Feb. 21, 2003).
Sakakibara et al., "Novel function of Chat in controlling cell adhesion via Cas-Crk-C3G-pathway-mediated Rapl activation" *J Cell Sci*. 115 (Pt 24) :4915-24 (Dec. 15, 2002).
Sanchez-Pulido et al., "ACRATA: a novel electron transfer domain associated to apoptosis and cancer" *BMC Cancer* 4 :98 (Dec. 29, 2004).
Saravanan et al., "Specific downregulation and mistargeting of the lipid raft-associated protein MAL in a glycolipid storage disorder" *Neurobiol Dis*. 16 (2) :396-406(Jul. 2004).
Sasaki et al., "Dynamic behavior of paired claudin strands within apposing plasma membranes" *Proc Natl Acad Sci U S A*. 100 (7) : 3971-6 (Apr. 1, 2003).
Schachter, "The role of the GlcNAc(beta)1,2Man(alpha)—moiety in mammalian development. Null mutations of the genes encoding UDP-N-acetylglucosamine: . . . " *Biochim Biophys Acta*. 1573 (3) : 292-300 (Dec. 19, 2002).
Schaeren-Wiemers et al., "The raft-associated protein MAL is required for maintenance of proper axon--glia interactions in the central nervous system" *J Cell Biol*. 166 (5) :731-42 (Aug. 30, 2004).
Schmitmeier et al., "Purification and characterization of the thyrotropin-releasing hormone (TRH)—degrading serum enzyme and its identification as a product of liver origin" *Eur J Biochem*. 269 (4) :1278-86 (Feb. 2002).
Schomburg et al., "Human TRH—degrading ectoenzyme cDNA cloning, functional expression, genomic structure and chromosomal assignment" *Eur J Biochem*. 265 (1) :415-22 (Oct. 1, 1999).
Scorilas et al., "Molecular characterization of a new gene, CEAL1, encoding for a carcinoembryonic antigen-like protein with a highly conserved domain of eukaryotic translation initiation factors" *Gene*. 310:79-89 (May 22, 2003).
Sellin et al., "NEPH1 defines a novel family of podocin interacting proteins" *FASEB J*. 17 (1) :115-117 (Jan. 2003).
Serru et al., "Sequence and expression of seven new tetraspans" *Biochim Biophys Acta* 1478 (1) :159-63 (Mar. 16, 2000).
Shaw et al., "Glycosylation and epitope mapping of the 5T4 glycoprotein oncofoetal antigen" *Biochemical Journal* 363(Pt 1):137-45 (Apr. 1, 2002).
Shi et al., "A Novel Cytokine Receptor-Ligand Pair: Identification, Molecular Characterization and In Vivo Immunomodulatory Activity" *Journal of Biological Chemistry* 275 (25) :19167-19176 (Jun. 23, 2000).
Shimizu-Hirota et al., "Functional characterization of podocan, a member of a new class in the small leucine-rich repeat protein family" *FEBS Letters* 563(1-3):69-74 (Apr. 9, 2004).
Sobanov et al., "A novel cluster of lectin-like receptor genes expressed in monocytic, dendritic and endothelial cells maps close to the NK receptor genes in the human NK gene complex" *Eur J Immunol*. 31 (12) :3493-503 (Dec. 2001).
Starnes et al., "Cutting Edge: IL-17F, a Novel Cytokine Selectively Expressed in Activated T Cells and Monocytes, Regulates Angiogenesis and Endothelial Cell Cytokine Production" *Journal of Immunology*. 167:4137-4140 (2001).
Sun et al., "Kirrel2, a novel immunoglobulin superfamily gene expressed primarily in beta cells of the pancreatic islets" *Genomics* 82 (2) :130-42 (Aug. 2003).
Swisshelm et al., "SEMP1, a senescence-associated cDNA isolated from human mammary epithelial cells, is a member of an epithelial membrane protein superfamily" *Gene* 226 (2) :285-95 (Jan. 21, 1999).
Takahashi et al., "Role for Fes/Fps tyrosine kinase in microtubule nucleation through is Fes/CIP4 homology domain" *J Biol Chem*. 278 (49) :49129-33 (Dec. 5, 2003).
Taniguchi et al., "Worldwide distribution and broader clinical spectrum of muscle-eye-brain disease" Hum Mol Genet. 12 (5) :527-34 (Mar. 1, 2003).

Taniyama et al., "Cloning and expression of a novel lysophospholipase which structurally resembles lecithin cholesterol acyltransferase" *Biochem Biophys Res Commun.* 257 (1) :50-6 (Apr. 2, 1999).
Tarrant et al., "Tetraspanins: molecular organisers of the leukocyte surface" *Trends Immunol.* 24(11):61077 (Nov 2003).
Thomassen et al., "Identification and characterization of SIGIRR, a molecule representing a novel subtype of the IL-1R superfamily" *Cytokine* 11 (6) :389-99 (Jun. 1999).
Tian, "EVI27 encodes a novel membrane protein with homology to the IL-17 receptor" *Oncogene* 19:2098-2109 (2000).
Tominaga et al., "The novel gene fad104, containing a fibronectin type III domain, has a significant role in adipogenesis" *BS Lett.* 577 (1-2) :49-54 (Nov. 5, 2004).
Torii et al., "Sef is a spatial regulator for Ras/MAP kinase signaling" *Dev Cell* 7(1) :33-44 (Jul. 2004).
Tovar et al., "Mouse novel Ly9: a new member of the expanding CD150 (SLAM) family of leukocyte cell-surface receptors" *Immunogenetics* 54 (6) :394-402 (Sep. 2002).
Tsang et al., "Identification of Sef, a novel modulator of FGF signalling" *Nat Cell Biol.* 4 (2) :165-9 (Feb 2002).
Tucker et al., "The thrombospondin type 1 repeat superfamily" *Int J Biochem Cell Biol.* 36 (6) :969-74 (2004).
Uchida et al., "A novel epidermal growth factor-like molecule containing two follistatin modules stimulates tyrosine phosphorylation of erbB-4 in MKN28 gastric cancer cells" *chem Biophys Res Commun.* 266 (2) :593-602 (Dec. 20, 1999).
Velasco et al., "Matriptase-2, a membrane-bound mosaic serine proteinase predominantly expressed in human liver and showing degrading activity against extracellular matrix proteins" *J Biol Chem.* 277 (40) :37637-46 (Oct. 4, 2002).
Vervoort et al., "POMGnTl gene alterations in a family with neurological abnormalities" *Ann Neurol.* 56(1):143-8 (Jul. 2004).
Wald et al., "SIGIRR, a negative regulator of Toll-like receptor-interleukin 1 receptor signaling" *Nat. Immunol.* 4 (9) :920-7 (Sep. 2003).
Wang et al., "Analysis of gene expression profile induced by EMP-1 in esophageal cancer cells using cDNA Microarray" *World J Gastroenterol.* 9 (3) :392-8 (Mar. 2003).
Ward et al., "The 5T4 oncofoetal antigen is an early differentiation marker of mouse ES cells and its absence is a useful means to assess pluripotency" *J Cell Sci.* 116 (Pt 22) :4533-42 (Nov. 15, 2003).
Wegorzewska et al., "Overexpression of the immunoglobulin superfamily members CDO and BOC enhances differentiation of the human rhabdomyosarcoma cell line RD" *Mol Carcinog.* 37 (1) :1-4 (May 2003).
Wilkinson et al., "CRIM1 regulates the rate of processing and delivery of bone morphogenetic proteins to the cell surface" *J Biol Chem.* 278 (36) :34181-8 (Sep. 5, 2003).
Wright et al., "The L6 membrane proteins—a new four-transmembrane superfamily" *Protein Sci.* 9 (8) :1594-600 (Aug. 2000).
Wu et al., "Generation of Committed Erythroid BFU-E and CFU-E Progenitors Does Not Require Erythropoietin or the Erythropoietin Receptor" *Cell* 83 (1) :59-67 (Oct. 6, 1995).
Wu et al., "Identification of one exon deletion of intestinal alkaline sphingomyelinase in colon cancer HT-29 cells and a differentiation-related expression of the wild-type enzyme in Caco-2 cells" *Carcinogenesis* 25 (8) :1327-33 (Aug. 2004).
Wulf and Suter, "Embryonic expression of epithelial membrane protein 1 in early neurons" *Brain Res Dev Brain Res.* 116 (2) :169-80 (Sep. 6, 1999).
Xiong et al., "hSef inhibits PC-12 cell differentiation by interfering with Ras-mitogen-activated protein kinase MAPK signaling" *J Biol Chem.* 278 (50) : 50273-82 (Dec. 12, 2003).
Xu et al., "A novel liver-specific zona pellucida domain containing protein that is expressed rarely in hepatocellular carcinoma" *Hepatology* 38 (3) :735-44 (Sep. 2003).
Xu et al., "Identification of LZP gene from Mus musculus and Rattus norvegicus coding for a novel liver-specific ZP domain-containing secretory protein" *DNA Seq.* 15 (2) :81-7 (Apr. 2004).
Yang et al., "A novel interleukin-17 receptor-like protein identified in human umbilical vein endothelial cells antagonizes basic fibroblast growth factor-induced signaling" *J Biol Chem.* 278 (35) :33232-8 (Aug. 29, 2003).
Yang et al., "Sef interacts with TAKl and mediates JNK activation and apoptosis" *J Biol Chem* . 279 (37) :38099-102 (Sep. 10, 2004).
Yoshida et al., "Muscular dystrophy and neuronal migration disorder caused by mutations in a glycosyltransferase, POMGnT1" *Dev Cell* 1 (5) :717-24 (Nov. 2001).
Yu et al., "Claudin-8 expression in Madin-Darby canine kidney cells augments the paracellular barrier to cation permeation" *J Biol Chem.* 278 (19) :17350-9 (May 9, 2003).
Zhang et al., "Cloning and expression of a novel UDP-GlcNAc:alpha-D-mannoside beta1,2-N-acetylglucosaminyltransferase homologous to UDP-G1cNAc:alpha-3-D-mannoside beta1,2-N-acetylglucosaminyltransferase I" *Biochemical Journal* 361(Pt 1 ):153-62 (Jan. 1, 2002).
Gerhard, D.S., et al., *Genome Res.*—14:2121-2127 (2004).
Serru, V., et al., *Biochimica et Biophysica Acta*—1478(1):159-163 (2000).
Thomas, K.R., et al., *Cell*—51:503-512 (1987).
Kawaii, et al., "Functional annotation of a full-length mouse cDNA collection" Nature, vol. 409, No. 6821, pp. 685-690, (2001).

* cited by examiner

FIGURE 1

AAGAGCAGCGGCGAGGCGGCGGTGGTGGCTGAGTCCGTGGTGGCAGAGGCGAAGGCGACA
GCTCTAGGGGTTGGCACCGGCCCCGAGAGGAGGATGCGGGTCCGGATAGGGCTGACGCTG
CTGCTGTGTGCGGTGCTGCTGAGCTTGGCCTCGGCGTCCTCGGATGAAGAAGGCAGCCAG
GATGAATCCTTAGATTCCAAGACTACTTTGACATCAGATGAGTCAGTAAAGGACCACACT
ACTGCAGGCAGAGTAGTTGCTGGTCAAATATTTCTTGATTCAGAAGAATCTGAATTAGAA
TCCTCTATTCAAGAAGAGGAAGACAGCCTCAAGAGCCAAGAGGGGGAGAGTGTCACAGAA
GATATCAGCTTTCTAGAGTCTCCAAATCCAGAAAACAAGGACTATGAAGAGCCAAAGAAA
GTACGGAAACCAGCTTTGACCGCCATTGAAGGCACAGCACATGGGGAGCCCTGCCACTTC
CCTTTTCTTTTCCTAGATAAGGAGTATGATGAATGTACATCAGATGGGAGGGAAGATGGC
AGACTGTGGTGTGCTACAACCTATGACTACAAAGCAGATGAAAAGTGGGGCTTTTGTGAA
ACTGAAGAAGAGGCTGCTAAGAGACGGCAGATGCAGGAAGCAGAAATGGTGTATCAAACT
GGAATGAAAATCCTTAATGGAAGCAATAAGAAAAGCCAAAAAAGAGAAGCATATCGGTAT
CTCCAAAAGGCAGCAAGCATGAACCATACCAAAGCCCTGGAGAGAGTGTCATATGCTCTT
TTATTTGGTGATTACTTGCCACAGAATATCCAGGCAGCGAGAGAGATGTTTGAGAAGCTG
ACTGAGGAAGGCTCTCCCAAGGGACAGACTGCTCTTGGCTTTCTGTATGCCTCTGGACTT
GGTGTTAATTCAAGTCAGGCAAAGGCTCTTGTATATTATACATTTGGAGCTCTTGGGGGC
AATCTAATAGCCCACATGGTTTTGGGTTACAGATACTGGGCTGGCATCGGCGTCCTCCAG
AGTTGTGAATCTGCCCTGACTCACTATCGTCTTGTTGCCAATCATGTTGCTAGTGATATC
TCGCTAACAGGAGGCTCAGTAGTACAGAGAATACGGCTGCCTGATGAAGTGGAAAATCCA
GGAATGAACAGTGGAATGCTAGAAGAAGATTTGATTCAATATTACCAGTTCCTAGCTGAA
AAAGGTGATGTACAAGCACAGGTTGGTCTTGGACAACTGCACCTGCACGGAGGGCGTGGA
GTAGAACAGAATCATCAGAGAGCATTTGACTACTTCAATTTAGCAGCAAATGCTGGCAAT
TCACATGCCATGGCCTTTTTGGGAAAGATGTATTCGGAAGGAAGTGACATTGTACCTCAG
AGTAATGAGACAGCTCTCCACTACTTTAAGAAAGCTGCTGACATGGGCAACCCAGTTGGA
CAGAGTGGGCTTGGAATGGCCTACCTCTATGGGAGAGGAGTTCAAGTTAATTATGATCTA
GCCCTTAAGTATTTCCAGAAAGCTGCTGAACAAGGCTGGGTGGATGGGCAGCTACAGCTT
GGTTCCATGTACTATAATGGCATTGGAGTCAAGAGAGATTATAAACAGGCCTTGAAGTAT
TTTAATTTAGCTTCTCAGGGAGGCCATATCTTGGCTTTCTATAACCTAGCTCAGATGCAT
GCCAGTGGCACCGGCGTGATGCGATCATGTCACACTGCAGTGGAGTTGTTTAAGAATGTA
TGTGAACGAGGCCGTTGGTCTGAAAGGCTTATGACTGCCTATAACAGCTATAAAGATGGC
GATTACAATGCTGCAGTGATCCAGTACCTCCTCCTGGCTGAACAGGGCTATGAAGTGGCA
CAAAGCAATGCAGCCTTTATTCTTGATCAGAGAGAAGCAAGCATTGTAGGTGAGAATGAA
ACTTATCCCAGAGCTTTGCTACATTGGAACAGGGCCGCCTCTCAAGGCTATACTGTGGCT
AGAATTAAGCTCGGAGACTACCATTTCTATGGGTTTGGCACCGATGTAGATTATGAAACT
GCATTTATTCATTACCGTCTGGCTTCTGAGCAGCAACACAGTGCACAAGCTATGTTTAAT
CTGGGATATATGCATGAGAAAGGACTGGGCATTAAACAGGATATTCACCTTGCGAAACGT
TTTTATGACATGGCAGCTGAAGCCAGCCCAGATGCACAAGTTCCAGTCTTCCTAGCCCTC
TGCAAATTGGGCGTCGTCTATTTCTTGCAGTACATACGGGAAACAAACATTCGAGATATG
TTCACCCAACTTGATATGGACCAGCTTTTGGGACCTGAGTGGGACCTTTACCTCATGACC
ATCATTGCGCTGCTGTTGGGAACAGTCATAGCTTACAGGCAAAGGCAGCACCAAGACATG

CCTGCACCCAGGCCTCCAGGGCCACGGCCAGCTCCACCCCAGCAGGAGGGGCCACCAGAG

FIGURE 1 Continued

CAGCAGCCACCACAGTAATAGGCACTGGGTCCAGCCTTGATCAGTGACAGCGAAGGAAGT
TATCTGCTGGGAACACTTGCATTTGATTTAGGACCTTGGATCAGTGGTCACCTCCCAGAA
GAGGCACGGCACAAGGAAGCATTGAATTCCTAAAGCTGCTTAGAATCTGATGCCTTTATT
TTCAGGGATAAGTAACTCTTACCTAAACTGAGCTGAATGTTTGTTTCAGTGCCATATGGA
ATAACAACTTTCAGTGGCTTTTTTTTTTCTTTTCTGGAAACATATGTGAGACACTCAGAG
TAATGTCTACTGTATCCAGCTATCTTTCTTGGATCCTTTTGGTCATTATTTCAGTGTGCA
TAAGTTCTTAATGTCAACCATCTTTAAGGTATTGTGCATCGACACTAAAAACTGATCAGT
GTAAAAAGGAAAACCCAGTTGCAAGTTTAAACGTGTTCGAAAGTCTGAAAATAGAACTTG
CCTTTTAAGTTAAAAAAAAAAAAAAGCTATCTTGAAAATGTTTTGGAACTGCGATAACTGA
GAAACTCTTACCAGTCCACATGCAATTAGACATATTCAGCATATTTGTTATTTTAAAAGG
GAGGGTTGGGAGGTTTCTTATTGGTGATTGTCACACGGTATACCATACTCCTCTCCTTCA
AAGAATGAAAGGCCTTGTTAAGGAGTTTTTTGTGAGCTTTACTTCTTTGGAATGGAATAT
ACTTATGCAAAACCTTGTGAACTGACTCCTTGCACTAACGCGAGTTTGCCCCACCTACTC
TGTAATTTGCTTGTTTGTTTTGAATATACAGAGCCTTGATCCAGAAGCCAGAGGATGGAC
TAAGTGGGAGAAATTAGAAAACAAAACGAACTCTGGTTGGGGTACTACGATCACAGACAC
AGACATACTTTTCCTAAAGTTGAAGCATTTGTTCCCAGGATTTATTTTACTTTGCATTTC
CTTTTGCACAAAGAACACATCACCATTTCCTTTTGCACAAAGAACACATCACC

FIGURE 2

><Tue Dec 4 13:44:42 PST 2001 DNA284870 [min]
></usr/seqdb2/sst/DNA/Dnaseqs.min/ss.DNA284870
><subunit 1 of 1, 794 aa, 1 stop
><MW: 88723, pI: 5.33, NX(S/T): 5

MRVRIGLTLLLCAVLLSLASASSDEEGSQDESLDSKTTLTSDESVKDHTTAGRVVAGQIF
LDSEESELESSIQEEEDSLKSQEGESVTEDISFLESPNPENKDYEEPKKVRKPALTAIEG
TAHGEPCHFPFLFLDKEYDECTSDGREDGRLWCATTYDYKADEKWGFCETEEEAAKRRQM
QEAEMVYQTGMKILNGSNKKSQKREAYRYLQKAASMNHTKALERVSYALLFGDYLPQNIQ
AAREMFEKLTEEGSPKGQTALGFLYASGLGVNSSQAKALVYYTFGALGGNLIAHMVLGYR
YWAGIGVLQSCESALTHYRLVANHVASDISLTGGSVVQRIRLPDEVENPGMNSGMLEEDL
IQYYQFLAEKGDVQAQVGLGQLHLHGGRGVEQNHQRAFDYFNLAANAGNSHAMAFLGKMY
SEGSDIVPQSNETALHYFKKAADMGNPVGQSGLGMAYLYGRGVQVNYDLALKYFQKAAEQ
GWVDGQLQLGSMYYNGIGVKRDYKQALKYFNLASQGGHILAFYNLAQMHASGTGVMRSCH
TAVELFKNVCERGRWSERLMTAYNSYKDGDYNAAVIQYLLLAEQGYEVAQSNAAFILDQR
EASIVGENETYPRALLHWNRAASQGYTVARIKLGDYHFYGFGTDVDYETAFIHYRLASEQ
QHSAQAMFNLGYMHEKGLGIKQDIHLAKRFYDMAAEASPDAQVPVFLALCKLGVVYFLQY
IRETNIRDMFTQLDMDQLLGPEWDLYLMTIIALLLGTVIAYRQRQHQDMPAPRPPGPRPA
PPQQEGPPEQQPPQ

FIGURE 3

TGCCGGGCTGCGGGGCGCCTTGACTCTCCCTCCACCCTGCCTCCTCGGGCTCCACTCGTCTGCCCCTGGACTCC
CGTCTCCTCCTGTCCTCCGGCTTCCCAGAGCTCCCTCCTTATGGCAGCAGCTTCCCGCGTCTCCGGCGCAGCTT
CTCAGCGGACGACCCTCTCGCTCCGGGGCTGAGCCCAGTCCCTGGATGTTGCTGAAACTCTCGAGATCATGCGC
GGGTTTGGCTGCTGCTTCCCCGCCGGGTGCCACTGCCACCGCCGCCGCCTCTGCTGCCGCCGTCCGCGGGATGC
TCAGTAGCCCGCTGCCCGGCCCCCGCGATCCTGTGTTCCTCGGAAGCCGTTTGCTGCTGCAGAGTTGCACGAAC
TAGTCATGGTGCTGTGGGAGTCCCCGCGGCAGTGCAGCAGCTGGACACTTTGCGAGGGCTTTTGCTGGCTGCTG
CTGCTGCCCGTCATGCTACTCATCGTAGCCCGCCCGGTGAAGCTCGCTGCTTTCCCTACCTCCTTAAGTGACTG
CCAAACGCCCACCGGCTGGAATTGCTCTGGTTATGATGACAGAGAAAATGATCTCTTCCTCTGTGACACCAACA
CCTGTAAATTTGATGGGGAATGTTTAAGAATTGGAGACACTGTGACTTGCGTCTGTCAGTTCAAGTGCAACAAT
GACTATGTGCCTGTGTGTGGCTCCAATGGGGAGAGCTACCAGAATGAGTGTTACCTGCGACAGGCTGCATGCAA
ACAGCAGAGTGAGATACTTGTGGTGTCAGAAGGATCATGTGCCACAGATGCAGGATCAGGATCTGGAGATGGAG
TCCATGAAGGCTCTGGAGAAACTAGTCAAAAGGAGACATCCACCTGTGATATTTGCCAGTTTGGTGCAGAATGT
GACGAAGATGCCGAGGATGTCTGGTGTGTGTGTAATATTGACTGTTCTCAAACCAACTTCAATCCCCTCTGCGC
TTCTGATGGGAAATCTTATGATAATGCATGCCAAATCAAAGAAGCATCGTGTCAGAAACAGGAGAAAATTGAAG
TCATGTCTTTGGGTCGATGTCAAGATAACACAACTACAACTACTAAGTCTGAAGATGGGCATTATGCAAGAACA
GATTATGCAGAGAATGCTAACAAATTAGAAGAAAGTGCCAGAGAACACCACATACCTTGTCCGGAACATTACAA
TGGCTTCTGCATGCATGGGAAGTGTGAGCATTCTATCAATATGCAGGAGCCATCTTGCAGGTGTGATGCTGGTT
ATACTGGACAACACTGTGAAAAAAAGGACTACAGTGTTCTATACGTTGTTCCCGGTCCTGTACGATTTCAGTAT
GTCTTAATCGCAGCTGTGATTGGAACAATTCAGATTGCTGTCATCTGTGTGGTGGTCCTCTGCATCACAAGGAA
ATGCCCCAGAAGCAACAGAATTCACAGACAGAAGCAAAATACAGGGCACTACAGTTCAGACAATACAACAAGAG
CGTCCACGAGGTTAATCTAAAGGGAGCATGTTTCACAGTGGCTGGACTACCGAGAGCTTGGACTACACAATACA
GTATTATAGACAAAAGAATAAGACAAGAGATCTACACATGTTGCCTTGCATTTGTGGTAATCTACACCAATGAA
AACATGTACTACAGCTATATTTGATTATGTATGGATATATTTGAAATAGTATACATTGTCTTGATGTTTTTTCT
GTAATGTAAATAAACTATTTATATCACACAATATAGTTTTTTCTTTCCCATGTATTTGTTATATATAATAAATA
CTCAGTGATGAG

FIGURE 4

MVLWESPRQCSSWTLCEGFCWLLLLPVMLLIVARPVKLAAFPTSLSDCQTPTGWNCSGY
DDRENDLFLCDTNTCKFDGECLRIGDTVTCVCQFKCNNDYVPVCGSNGESYQNECYLRQ
AACKQQSEILVVSEGSCATDAGSGSGDGVHEGSGETSQKETSTCDICQFGAECDEDAED
VWCVCNIDCSQTNFNPLCASDGKSYDNACQIKEASCQKQEKIEVMSLGRCQDNTTTTTK
SEDGHYARTDYAENANKLEESAREHHIPCPEHYNGFCMHGKCEHSINMQEPSCRCDAGY
TGQHCEKKDYSVLYVVPGPVRFQYVLIAAVIGTIQIAVICVVVLCITRKCPRSNRIHRQ
KQNTGHYSSDNTTRASTRLI

FIGURE 5

CGGACGCGTGGGCGGACGCGTGGGCGGCCCACGGCGCCCGCGGGCTGGGGCGGTCGCTTCT
TCCTTCTCCGTGGCCTACGAGGGTCCCCAGCCTGGGTAAAGATGGCCCCATGGCCCCCGAA
GGGCCTAGTCCCAGCTGTGCTCTGGGGCCTCAGCCTCTTCCTCAACCTCCCAGGACCTATC
TGGCTCCAGCCCTCTCCACCTCCCCAGTCTTCTCCCCCGCCTCAGCCCCATCCGTGTCATA
CCTGCCGGGGACTGGTTGACAGCTTTAACAAGGGCCTGGAGAGAACCATCCGGGACAACTT
TGGAGGTGGAAACACTGCCTGGGAGGAAGAGAATTTGTCCAAATACAAAGACAGTGAGACC
CGCCTGGTAGAGGTGCTGGAGGGTGTGTGCAGCAAGTCAGACTTCGAGTGCCACCGCCTGC
TGGAGCTGAGTGAGGAGCTGGTGGAGAGCTGGTGGTTTCACAAGCAGCAGGAGGCCCCGGA
CCTCTTCCAGTGGCTGTGCTCAGATTCCCTGAAGCTCTGCTGCCCCGCAGGCACCTTCGGG
CCCTCCTGCCTTCCCTGTCCTGGGGGAACAGAGAGGCCCTGCGGTGGCTACGGGCAGTGTG
AAGGAGAAGGGACACGAGGGGGCAGCGGGCACTGTGACTGCCAAGCCGGCTACGGGGGTGA
GGCCTGTGGCCAGTGTGGCCTTGGCTACTTTGAGGCAGAACGCAACGCCAGCCATCTGGTA
TGTTCGGCTTGTTTTGGCCCCTGTGCCCGATGCTCAGGACCTGAGGAATCAAACTGTTTGC
AATGCAAGAAGGGCTGGGCCCTGCATCACCTCAAGTGTGTAGACATTGATGAGTGTGGCAC
AGAGGGAGCCAACTGTGGAGCTGACCAATTCTGCGTGAACACTGAGGGCTCCTATGAGTGC
CGAGACTGTGCCAAGGCCTGCCTAGGCTGCATGGGGGCAGGGCCAGGTCGCTGTAAGAAGT
GTAGCCCTGGCTATCAGCAGGTGGGCTCCAAGTGTCTCGATGTGGATGAGTGTGAGACAGA
GGTGTGTCCGGGAGAGAACAAGCAGTGTGAAAACACCGAGGGCGGTTATCGCTGCATCTGT
GCCGAGGGCTACAAGCAGATGGAAGGCATCTGTGTGAAGGAGCAGATCCCAGAGTCAGCAG
GCTTCTTCTCAGAGATGACAGAAGACGAGTTGGTGGTGCTGCAGCAGATGTTCTTTGGCAT
CATCATCTGTGCACTGGCCACGCTGGCTGCTAAGGGCGACTTGGTGTTCACCGCCATCTTC
ATTGGGGCTGTGGCGGCCATGACTGGCTACTGGTTGTCAGAGCGCAGTGACCGTGTGCTGG
AGGGCTTCATCAAGGGCAGATAATCGCGGCCACCACCTGTAGGACCTCCTCCCACCCACGC
TGCCCCCAGAGCTTGGGCTGCCCTCCTGCTGGACACTCAGGACAGCTTGGTTTATTTTTGA
GAGTGGGGTAAGCACCCCTACCTGCCTTACAGAGCAGCCCAGGTACCCAGGCCCGGGCAGA
CAAGGCCCCTGGGGTAAAAAGTAGCCCTGAAGGTGGATACCATGAGCTCTTCACCTGGCGG
GGACTGGCAGGCTTCACAATGTGTGAATTTCAAAAGTTTTTCCTTAATGGTGGCTGCTAGA
GCTTTGGCCCCTGCTTAGGATTAGGTGGTCCTCACAGGGGTGGGGCCATCACAGCTCCCTC
CTGCCAGCTGCATGCTGCCAGTTCCTGTTCTGTGTTCACCACATCCCCACACCCCATTGCC
ACTTATTTATTCATCTCAGGAAATAAAGAAAGGTCTTGGAAAGTTAAAAAAAAAAAAAAAA
AAAAAAAA

FIGURE 6

MAPWPPKGLVPAVLWGLSLFLNLPGPIWLQPSPPPQSSPPPQPHPCHTCRGLVDSFNKGLE
RTIRDNFGGGNTAWEEENLSKYKDSETRLVEVLEGVCSKSDFECHRLLELSEELVESWWFH
KQQEAPDLFQWLCSDSLKLCCPAGTFGPSCLPCPGGTERPCGGYGQCEGEGTRGGSGHCDC
QAGYGGEACGQCGLGYFEAERNASHLVCSACFGPCARCSGPEESNCLQCKKGWALHHLKCV
DIDECGTEGANCGADQFCVNTEGSYECRDCAKACLGCMGAGPGRCKKCSPGYQQVGSKCLD
VDECETEVCPGENKQCENTEGGYRCICAEGYKQMEGICVKEQIPESAGFFSEMTEDELVVL
QQMFFGIIICALATLAAKGDLVFTAIFIGAVAAMTGYWLSERSDRVLEGFIKGR

Signal sequence:

amino acids 1-29

Transmembrane domain:

amino acids 372-395

N-glycosylation site.

amino acids 79-83, 205-209 cAMP- and cGMP-dependent protein kinase phosphorylation site.

amino acids 290-294

Casein kinase II phosphorylation site.

amino acids 63-67, 73-77, 99-103, 101-105, 222-226, 359-263

N-myristoylation site.

amino acids 8-14, 51-57, 59-65, 69-75, 70-76, 167-173, 173-179, 177-183, 188-194, 250-256, 253-259, 267-273, 280-286, 283-289, 326-332, 372-378, 395-401

Aspartic acid and asparagine hydroxylation site.

amino acids 321-333

EGF-like domain cysteine pattern signature.

amino acids 181-193

FIGURE 7

CCCACGCGTCCGGTCTCGCTCGCTCGCGCAGCGGCGGCAGCAGAGGTCGCGCACAGATGCG
GGTTAGACTGGCGGGGGGAGGAGGCGGAGGAGGGAAGGAAGCTGCATGCATGAGACCCACA
GACTCTTGCAAGCTGGATGCCCTCTGTGGATGAAAGATGTATCATGGAATGAACCCGAGCA
ATGGAGATGGATTTCTAGAGCAGCAGCAGCAGCAGCAGCAACCTCAGTCCCCCCAGAGACT
CTTGGCCGTGATCCTGTGGTTTCAGCTGGCGCTGTGCTTCGGCCCTGCACAGCTCACGGGC
GGGTTCGATGACCTTCAAGTGTGTGCTGACCCCGGCATTCCCGAGAATGGCTTCAGGACCC
CCAGCGGAGGGGTTTTCTTTGAAGGCTCTGTAGCCCGATTTCACTGCCAAGACGGATTCAA
GCTGAAGGGCGCTACAAAGAGACTGTGTTTGAAGCATTTTAATGGAACCCTAGGCTGGATC
CCAAGTGATAATTCCATCTGTGTGCAAGAAGATTGCCGTATCCCTCAAATCGAAGATGCTG
AGATTCATAACAAGACATATAGACATGGAGAGAAGCTAATCATCACTTGTCATGAAGGATT
CAAGATCCGGTACCCCGACCTACACAATATGGTTTCATTATGTCGCGATGATGGAACGTGG
AATAATCTGCCCATCTGTCAAGGCTGCCTGAGACCTCTAGCCTCTTCTAATGGCTATGTAA
ACATCTCTGAGCTCCAGACCTCCTTCCCGGTGGGGACTGTGATCTCCTATCGCTGCTTTCC
CGGATTTAAACTTGATGGGTCTGCGTATCTTGAGTGCTTACAAAACCTTATCTGGTCGTCC
AGCCCACCCCGGTGCCTTGCTCTGGAAGCCCAAGTCTGTCCACTACCTCCAATGGTGAGTC
ACGGAGATTTCGTCTGCCACCCGCGGCCTTGTGAGCGCTACAACCACGGAACTGTGGTGGA
GTTTTACTGCGATCCTGGCTACAGCCTCACCAGCGACTACAAGTACATCACCTGCCAGTAT
GGAGAGTGGTTTCCTTCTTATCAAGTCTACTGCATCAAATCAGAGCAAACGTGGCCCAGCA
CCCATGAGACCCTCCTGACCACGTGGAAGATTGTGGCGTTCACGGCAACCAGTGTGCTGCT
GGTGCTGCTGCTCGTCATCCTGGCCAGGATGTTCCAGACCAAGTTCAAGGCCCACTTTCCC
CCCAGGGGGCCTCCCCGGAGTTCCAGCAGTGACCCTGACTTTGTGGTGGTAGACGGCGTGC
CCGTCATGCTCCCGTCCTATGACGAAGCTGTGAGTGGCGGCTTGAGTGCCTTAGGCCCCGG
GTACATGGCCTCTGTGGGCCAGGGCTGCCCCTTACCCGTGGACGACCAGAGCCCCCCAGCA
TACCCCGGCTCAGGGGACACGGACACAGGCCCAGGGGAGTCAGAAACCTGTGACAGCGTCT
CAGGCTCTTCTGAGCTGCTCCAAAGTCTGTATTCACCTCCCAGGTGCCAAGAGAGCACCCA
CCCTGCTTCGGACAACCCTGACATAATTGCCAGCACGGCAGAGGAGGTGGCATCCACCAGC
CCAGGCATCCATCATGCCCACTGGGTGTTGTTCCTAAGAAACTGATTGATTAAAAAATTTC
CCAAAGTGTCCTGAAGTGTCTCTTCAAATACATGTTGATCTGTGGAGTTGATTCCTTTCCT
TCTCTTGGTTTTAGACAAATGTAAACAAAGCTCTGATCCTTAAAATTGCTATGCTGATAGA
GTGGTGAGGGCTGGAAGCTTGATCAAGTCCTGTTTCTTCTTGACACAGACTGATTAAAAAT
TAAAAGNAAAAAA

FIGURE 8

MYHGMNPSNGDGFLEQQQQQQQPQSPQRLLAVILWFQLALCFGPAQLTGGFDDLQVCADPG
IPENGFRTPSGGVFFEGSVARFHCQDGFKLKGATKRLCLKHFNGTLGWIPSDNSICVQEDC
RIPQIEDAEIHNKTYRHGEKLIITCHEGFKIRYPDLHNMVSLCRDDGTWNNLPICQGCLRP
LASSNGYVNISELQTSFPVGTVISYRCFPGFKLDGSAYLECLQNLIWSSSPPRCLALEAQV
CPLPPMVSHGDFVCHPRPCERYNHGTVVEFYCDPGYSLTSDYKYITCQYGEWFPSYQVYCI
KSEQTWPSTHETLLTTWKIVAFTATSVLLVLLLVILARMFQTKFKAHFPPRGPPRSSSSDP
DFVVVDGVPVMLPSYDEAVSGGLSALGPGYMASVGQGCPLPVDDQSPPAYPGSGDTDTGPG
ESETCDSVSGSSELLQSLYSPPRCQESTHPASDNPDIIASTAEEVASTSPGIHHAHWVLFLRN

Signal sequence:

amino acids 1-41

Transmembrane domain:

amino acids 325-344

N-glycosylation site.

amino acids 104-108, 134-138, 192-196

Casein kinase II phosphorylation site.

amino acids 8-12, 146-150, 252-256, 270-274, 313-317, 362-366, 364-368, 380-384, 467-471, 468-472

N-myristoylation site.

amino acids 4-10, 61-67, 169-175, 203-209, 387-393, 418-424, 478-484

Prokaryotic membrane lipoprotein lipid attachment site.

amino acids 394-405

FIGURE 9

CCCACGCGTCCGCTCCGCGCCCTCCCCCCCGCCTCCCGTGCGGTCCGTCGGTGGCCTAGAG
ATGCTGCTGCCGCGGTTGCAGTTGTCGCGCACGCCTCTGCCCGCCAGCCCGCTCCACCGCC
GTAGCGCCCGAGTGTCGGGGGGCGCACCCGAGTCGGGCCATGAGGCCGGGAACCGCGCTAC
AGGCCGTGCTGCTGGCCGTGCTGCTGGTGGGGCTGCGGGCCGCGACGGGTCGCCTGCTGAG
TGCCTCGGATTTGGACCTCAGAGGAGGGCAGCCAGTCTGCCGGGGAGGGACACAGAGGCCT
TGTTATAAAGTCATTTACTTCCATGATACTTCTCGAAGACTGAACTTTGAGGAAGCCAAAG
AAGCCTGCAGGAGGGATGGAGGCCAGCTAGTCAGCATCGAGTCTGAAGATGAACAGAAACT
GATAGAAAAGTTCATTGAAAACCTCTTGCCATCTGATGGTGACTTCTGGATTGGGCTCAGG
AGGCGTGAGGAGAAACAAAGCAATAGCACAGCCTGCCAGGACCTTTATGCTTGGACTGATG
GCAGCATATCACAATTTAGGAACTGGTATGTGGATGAGCCGTCCTGCGGCAGCGAGGTCTG
CGTGGTCATGTACCATCAGCCATCGGCACCCGCTGGCATCGGAGGCCCCTACATGTTCCAG
TGGAATGATGACCGGTGCAACATGAAGAACAATTTCATTTGCAAATATTCTGATGAGAAAC
CAGCAGTTCCTTCTAGAGAAGCTGAAGGTGAGGAAACAGAGCTGACAACACCTGTACTTCC
AGAAGAAACACAGGAAGAAGATGCCAAAAAAACATTTAAAGAAAGTAGAGAAGCTGCCTTG
AATCTGGCCTACATCCTAATCCCCAGCATTCCCCTTCTCCTCCTCCTTGTGGTCACCACAG
TTGTATGTTGGGTTTGGATCTGTAGAAAAAGAAAACGGGAGCAGCCAGACCCTAGCACAAA
GAAGCAACACACCATCTGGCCCTCTCCTCACCAGGGAAACAGCCCGGACCTAGAGGTCTAC
AATGTCATAAGAAAACAAAGCGAAGCTGACTTAGCTGAGACCCGGCCAGACCTGAAGAATA
TTTCATTCCGAGTGTGTTCGGGAGAAGCCACTCCCGATGACATGTCTTGTGACTATGACAA
CATGGCTGTGAACCCATCAGAAAGTGGGTTTGTGACTCTGGTGAGCGTGGAGAGTGGATTT
GTGACCAATGACATTTATGAGTTCTCCCCAGACCAAATGGGGAGGAGTAAGGAGTCTGGAT
GGGTGGAAAATGAAATATATGGTTATTAGGACATATAAAAAACTGAAACTGACAACAATGG
AAAAGAAATGATAAGCAAAATCCTCTTATTTTCTATAAGGAAAATACACAGAAGGTCTATG
AACAAGCTTAGATCAGGTCCTGTGGATGAGCATGTGGTCCCCACGACCTCCTGTTGGACCC
CCACGTTTTGGCTGTATCCTTTATCCCAGCCAGTCATCCAGCTCGACCTTATGAGAAGGTA
CCTTGCCCAGGTCTGGCACATAGTAGAGTCTCAATAAATGTCACTTGGTTGGTTGTATCTA
ACTTTTAAGGGACAGAGCTTTACCTGGCAGTGATAAAGATGGGCTGTGGAGCTTGGAAAAC
CACCTCTGTTTTCCTTGCTCTATACAGCAGCACATATTATCATACAGACAGAAAATCCAGA
ATCTTTTCAAAGCCCACATATGGTAGCACAGGTTGGCCTGTGCATCGGCAATTCTCATATC
TGTTTTTTTCAAAGAATAAAATCAAATAAAGAGCAGGAAAAAAAAA

FIGURE 10

MRPGTALQAVLLAVLLVGLRAATGRLLSASDLDLRGGQPVCRGGTQRPCYKVIYFHDTSRR
LNFEEAKEACRRDGGQLVSIESEDEQKLIEKFIENLLPSDGDFWIGLRRREEKQSNSTACQ
DLYAWTDGSISQFRNWYVDEPSCGSEVCVVMYHQPSAPAGIGGPYMFQWNDDRCNMKNNFI
CKYSDEKPAVPSREAEGEETELTTPVLPEETQEEDAKKTFKESREAALNLAYILIPSIPLL
LLLVVTTVVCWVWICRKRKREQPDPSTKKQHTIWPSPHQGNSPDLEVYNVIRKQSEADLAE
TRPDLKNISFRVCSGEATPDDMSCDYDNMAVNPSESGFVTLVSVESGFVTNDIYEFSPDQM
GRSKESGWVENEIYGY

Signal sequence:

amino acids 1-21

Transmembrane domain:

amino acids 235-254

N-glycosylation site.

amino acids 117-121, 312-316 cAMP- and cGMP-dependent protein kinase phosphorylation site.

amino acids 296-300

Casein kinase II phosphorylation site.

amino acids 28-32, 30-34, 83-87, 100-104, 214-218, 222-226, 299-303, 306-310, 323-327

N-myristoylation site.

amino acids 18-24, 37-43, 76-82, 146-152

FIGURE 11

ACTTGCCATCACCTGTTGCCAGTGTGGAAAAATTCTCCCTGTTGAATTTTTTGCACATGGA
GGACAGCAGCAAAGAGGGCAACACAGGCTGATAAGACCAGAGACAGCAGGGAGATTATTTT
ACCATACGCCCTCAGGACGTTCCCTCTAGCTGGAGTTCTGGACTTCAACAGAACCCCATCC
AGTCATTTTGATTTTGCTGTTTATTTTTTTTTTCTTTTTCTTTTTCCCACCACATTGTATT
TTATTTCCGTACTTCAGAAATGGGCCTACAGACCACAAAGTGGCCCAGCCATGGGGCTTTT
TTCCTGAAGTCTTGGCTTATCATTTCCCTGGGGCTCTACTCACAGGTGTCCAAACTCCTGG
CCTGCCCTAGTGTGTGCCGCTGCGACAGGAACTTTGTCTACTGTAATGAGCGAAGCTTGAC
CTCAGTGCCTCTTGGGATCCCGGAGGGCGTAACCGTACTCTACCTCCACAACAACCAAATT
AATAATGCTGGATTTCCTGCAGAACTGCACAATGTACAGTCGGTGCACACGGTCTACCTGT
ATGGCAACCAACTGGACGAATTCCCCATGAACCTTCCCAAGAATGTCAGAGTTCTCCATTT
GCAGGAAAACAATATTCAGACCATTTCACGGGCTGCTCTTGCCCAGCTCTTGAAGCTTGAA
GAGCTGCACCTGGATGACAACTCCATATCCACAGTGGGGGTGGAAGACGGGGCCTTCCGGG
AGGCTATTAGCCTCAAATTGTTGTTTTTGTCTAAGAATCACCTGAGCAGTGTGCCTGTTGG
GCTTCCTGTGGACTTGCAAGAGCTGAGAGTGGATGAAAATCGAATTGCTGTCATATCCGAC
ATGGCCTTCCAGAATCTCACGAGCTTGGAGCGTCTTATTGTGGACGGGAACCTCCTGACCA
ACAAGGGTATCGCCGAGGGCACCTTCAGCCATCTCACCAAGCTCAAGGAATTTTCAATTGT
ACGTAATTCGCTGTCCCACCCTCCTCCCGATCTCCCAGGTACGCATCTGATCAGGCTCTAT
TTGCAGGACAACCAGATAAACCACATTCCTTTGACAGCCTTCTCAAATCTGCGTAAGCTGG
AACGGCTGGATATATCCAACAACCAACTGCGGATGCTGACTCAAGGGGTTTTTGATAATCT
CTCCAACCTGAAGCAGCTCACTGCTCGGAATAACCCTTGGTTTTGTGACTGCAGTATTAAA
TGGGTCACAGAATGGCTCAAATATATCCCTTCATCTCTCAACGTGCGGGGTTTCATGTGCC
AAGGTCCTGAACAAGTCCGGGGGATGGCCGTCAGGGAATTAAATATGAATCTTTTGTCCTG
TCCCACCACGACCCCCGGCCTGCCTCTCTTCACCCCAGCCCCAAGTACAGCTTCTCCGACC
ACTCAGCCTCCCACCCTCTCTATTCCAAACCCTAGCAGAAGCTACACGCCTCCAACTCCTA
CCACATCGAAACTTCCCACGATTCCTGACTGGGATGGCAGAGAAAGAGTGACCCCACCTAT
TTCTGAACGGATCCAGCTCTCTATCCATTTTGTGAATGATACTTCCATTCAAGTCAGCTGG
CTCTCTCTCTTCACCGTGATGGCATACAAACTCACATGGGTGAAAATGGGCCACAGTTTAG
TAGGGGGCATCGTTCAGGAGCGCATAGTCAGCGGTGAGAAGCAACACCTGAGCCTGGTTAA
CTTAGAGCCCCGATCCACCTATCGGATTTGTTTAGTGCCACTGGATGCTTTTAACTACCGC
GCGGTAGAAGACACCATTTGTTCAGAGGCCACCACCCATGCCTCCTATCTGAACAACGGCA
GCAACACAGCGTCCAGCCATGAGCAGACGACGTCCCACAGCATGGGCTCCCCCTTTCTGCT
GGCGGGCTTGATCGGGGGCGCGGTGATATTTGTGCTGGTGGTCTTGCTCAGCGTCTTTTGC
TGGCATATGCACAAAAAGGGGCGCTACACCTCCCAGAAGTGGAAATACAACCGGGGCCGGC
GGAAAGATGATTATTGCGAGGCAGGCACCAAGAAGGACAACTCCATCCTGGAGATGACAGA
AACCAGTTTTCAGATCGTCTCCTTAAATAACGATCAACTCCTTAAAGGAGATTTCAGACTG

FIGURE 11 Continued

CAGCCCATTTACACCCCAAATGGGGGCATTAATTACACAGACTGCCATATCCCCAACAACA
TGCGATACTGCAACAGCAGCGTGCCAGACCTGGAGCACTGCCATACGTGACAGCCAGAGGC
CCAGCGTTATCAAGGCGGACAATTAGACTCTTGAGAACACACTCGTGTGTGCACATAAAGA
CACGCAGATTACATTTGATAAATGTTACACAGATGCATTTGTGCATTTGAATACTCTGTAA
TTTATACGGTGTACTATATAATGGGATTTAAAAAAAGTGCTATCTTTTCTATTTCAAGTTA
ATTACAAACAGTTTTGTAACTCTTTGCTTTTTAAATCTT

FIGURE 12

MGLQTTKWPSHGAFFLKSWLIISLGLYSQVSKLLACPSVCRCDRNFVYCNERSLTSVPLGI
PEGVTVLYLHNNQINNAGFPAELHNVQSVHTVYLYGNQLDEFPMNLPKNVRVLHLQENNIQ
TISRAALAQLLKLEELHLDDNSISTVGVEDGAFREAISLKLLFLSKNHLSSVPVGLPVDLQ
ELRVDENRIAVISDMAFQNLTSLERLIVDGNLLTNKGIAEGTFSHLTKLKEFSIVRNSLSH
PPPDLPGTHLIRLYLQDNQINHIPLTAFSNLRKLERLDISNNQLRMLTQGVFDNLSNLKQL
TARNNPWFCDCSIKWVTEWLKYIPSSLNVRGFMCQGPEQVRGMAVRELNMNLLSCPTTTPG
LPLFTPAPSTASPTTQPPTLSIPNPSRSYTPPTPTTSKLPTIPDWDGRERVTPPISERIQL
SIHFVNDTSIQVSWLSLFTVMAYKLTWVKMGHSLVGGIVQERIVSGEKQHLSLVNLEPRST
YRICLVPLDAFNYRAVEDTICSEATTHASYLNNGSNTASSHEQTTSHSMGSPFLLAGLIGG
AVIFVLVVLLSVFCWHMHKKGRYTSQKWKYNRGRRKDDYCEAGTKKDNSILEMTETSFQIV
SLNNDQLLKGDFRLQPIYTPNGGINYTDCHIPNNMRYCNSSVPDLEHCHT

Signal peptide:

amino acids 1-42

Transmembrane domain:

amino acids 542-561

N-glycosylation site.

amino acids 202-206, 298-302, 433-437, 521-525, 635-639, 649-653

Casein kinase II phosphorylation site.

amino acids 204-208, 407-411, 527-531, 593-597, 598-602, 651-655

Tyrosine kinase phosphorylation site.

amino acids 319-328

N-myristoylation site.

amino acids 2-8, 60-66, 149-155, 213-219, 220-226, 294-300, 522-528, 545-551, 633-639

Amidation site.

amino acids 581-585

Leucine zipper pattern.

amino acids 164-186

Phospholipase A2 aspartic acid active site.

amino acids 39-50

FIGURE 13

TAGGAGGTCCCCGGGTTGCCGGCGGCGACAGCGGGGGAAGCATGACTGCTGTGGGCCGAA
GGTGCCCCGCGCTGGGGTCCCGAGGGGCTGCTGGAGAGCCAGAGGCTGGCAGCGACTATG
TGAAGTTCTCCAAGGAGAAGTACATCCTGGACTCATCGCCAGAGAAACTCCACAAGGAAT
TGGAGGAGGAGCTCAAACTCAGCAGCACGGATCTCCGCAGCCATGCCTGGTACCATGGCC
GCATCCCCCGAGAGGTCTCGGAGACCTTGGTACAACGCAACGGCGACTTCCTCATCCGGG
ACTCGCTCACCAGCCTGGGCGACTATGTGCTCACGTGCCGCTGGCGCAACCAGGCCTTGC
ACTTCAAGATCAACAAGGTGGTGGTGAAGGCAGGCGAGAGCTACACACACATCCAGTACC
TGTTTGAGCAGGAGAGCTTTGACCACGTGCCCGCCCTCGTGCGCTATCATGTGGGCAGCC
GCAAGGCTGTGTCAGAGCAGAGTGGTGCCATCATCTACTGCCCGGTGAACCGCACCTTCC
CACTGCGCTACCTCGAGGCCAGCTATGGCCTGGGACAGGGGAGTAGCAAGCCTGCTAGCC
CCGTCAGCCCCTCAGGCCCCAAGGGCAGCCACATGAAGCGGCGCAGCGTCACCATGACCG
ATGGGCTCACTGCTGACAAGGTCACCCGCAGCGATGGCTGCCCCACCAGTACGTCGCTGC
CCCGCCCTCGGGACTCCATCCGCAGCTGTGCCCTCAGCATGGACCAGATCCCAGACCTGC
ACTCACCCATGTCGCCCATCTCCGAGAGCCCTAGCTCCCCTGCCTACAGCACTGTAACCC
GTGTCCATGCCGCCCCTGCAGCCCCTTCTGCCACAGCATTGCCTGCCTCCCCTGTCGCCC
GCTGTTCCAGTGAGCCCCAGCTGTGTCCCGGAAGTGCCCCAAAGACCCATGGGGAGTCAG
ACAAGGGCCCCCACACCAGCCCCTCCCACACCCTTGGCAAGGCCTCCCCGTCACCATCAC
TCAGCAGCTACAGTGACCCGGACTCTGGCCACTACTGCCAGCTCCAGCCTCCCGTGCGTG
GCAGCCGAGAGTGGGCAGCGACTGAGACCTCCAGCCAGCAGGCCAGGAGCTATGGGGAGA
GGCTAAAGGAACTGTCAGAAAATGGGGCCCCTGAAGGGGACTGGGGCAAGACCTTCACAG
TCCCCATCGTGGAAGTCACTTCTTCCTTCAACCCGGCCACCTTCCAGTCACTACTGATCC
CCAGGGATAACCGGCCACTGGAGGTGGGCCTTCTGCGCAAGGTCAAGGAGCTGCTGGCAG
AAGTGGATGCCCGGACGCTGGCCCGGCATGTCACCAAGGTGGACTGCCTGGTTGCTAGGA
TACTGGGCGTTACCAAGGAGATGCAGACCCTAATGGGAGTCCGCTGGGGCATGGAACTGC
TCACCCTCCCCCATGGCCGGCAGCTACGCCTAGACCTGCTGGAAAGGTTCCACACCATGT
CCATCATGCTGGCCGTGGACATCCTGGGCTGCACCGGCTCTGCGGAGGAGCGGGCAGCGC
TGCTGCACAAGACCATTCAGCTGGCGGCCGAGCTACGGGGGACTATGGGCAACATGTTCA
GCTTCGCGGCGGTCATGGGTGCCCTGGACATGGCTCAGATTTCTCGGCTGGAGCAGACAT
GGGTGACCCTGCGGCAGCGACACACAGAGGGTGCCATCCTGTACGAGAAGAAGCTCAAGC
CTTTTCTCAAGAGCCTCAACGAGGGCAAAGAAGGCCCGCCGCTGAGCAACACCACGTTTC
CTCATGTGCTGCCCCTCATCACCCTGCTGGAGTGTGACTCGGCCCCACCAGAGGGCCCTG
AGCCCTGGGGCAGCACGGAGCACGGCGTGGAGGTGGTGCTGGCTCACCTGGAGGCCGCCC
GCACAGTGGCACACCACGGAGGCCTGTACCACACCAATGCTGAAGTCAAGCTGCAGGGGT
TCCAGGCCCGGCCGGAGCTCCTGGAGGTGTTCAGCACGGAGTTCCAGATGCGCCTTCTCT
GGGGCAGTCAGGGTGCCAGCAGCAGCCAGGCCCGGCGCTATGAGAAGTTCGACAAGGTCC
TCACTGCCCTGTCCCACAAGCTGGAACCTGCTGTCCGCTCCAGCGAGCTGTGA

FIGURE 14

><Tue May 2 15:06:10 PDT 2000 DNA61601 [min]
></usr/seqdb2/sst/DNA/Dnaseqs.min/ss.DNA61601
><subunit 1 of 1, 703 aa, 1 stop
><MW: 77088, pI: 8.35, NX(S/T): 2
MTAVGRRCPALGSRGAAGEPEAGSDYVKFSKEKYILDSSPEKLHKELEEELKLSSTDLRS
HAWYHGRIPREVSETLVQRNGDFLIRDSLTSLGDYVLTCRWRNQALHFKINKVVVKAGES
YTHIQYLFEQESFDHVPALVRYHVGSRKAVSEQSGAIIYCPVNRTFPLRYLEASYGLGQG
SSKPASPVSPSGPKGSHMKRRSVTMTDGLTADKVTRSDGCPTSTSLPRPRDSIRSCALSM
DQIPDLHSPMSPISESPSSPAYSTVTRVHAAPAAPSATALPASPVARCSSEPQLCPGSAP
KTHGESDKGPHTSPSHTLGKASPSPSLSSYSDPDSGHYCQLQPPVRGSREWAATETSSQQ
ARSYGERLKELSENGAPEGDWGKTFTVPIVEVTSSFNPATFQSLLIPRDNRPLEVGLLRK
VKELLAEVDARTLARHVTKVDCLVARILGVTKEMQTLMGVRWGMELLTLPHGRQLRLDLL
ERFHTMSIMLAVDILGCTGSAEERAALLHKTIQLAAELRGTMGNMFSFAAVMGALDMAQI
SRLEQTWVTLRQRHTEGAILYEKKLKPFLKSLNEGKEGPPLSNTTFPHVLPLITLLECDS
APPEGPEPWGSTEHGVEVVLAHLEAARTVAHHGGLYHTNAEVKLQGFQARPELLEVFSTE
FQMRLLWGSQGASSSQARRYEKFDKVLTALSHKLEPAVRSSEL

FIGURE 15

CAAAACTTGCGTCGCGGAGAGCGCCCAGCTTGACTTGAATGGAAGGAGCCCGAGCCCGCGGAGCGCAGCTGAGA
CTGGGGGAGCGCGTTCGGCCTGTGGGGCGCCGCTCGGCGCCGGGGCGCAGCAGGGAAGGGGAAGCTGTGGTCTG
CCCTGCTCCACGAGGCGCCACTGGTGTGAACCGGGAGAGCCCCTGGGTGGTCCCGTCCCCTATCCCTCCTTTAT
ATAGAAACCTTCCACACTGGGAAGGCAGCGGCGAGGCAGGAGGGCTCATGGTGAGCAAGGAGGCCGGCTGATCT
GCAGGCGCACAGCATTCCGAGTTTACAGATTTTTACAGATACCAAATGGAAGGCGAGGAGGCAGAACAGCCTGC
CTGGTTCCATCAGCCCTGGCGCCCAGGCGCATCTGACTCGGCACCCCCTGCAGGCACCATGGCCCAGAGCCGGG
TGCTGCTGCTCCTGCTGCTGCTGCCGCCACAGCTGCACCTGGGACCTGTGCTTGCCGTGAGGGCCCCAGGATTT
GGCCGAAGTGGCGGCCACAGCCTGAGCCCCGAAGAGAACGAATTTGCGGAGGAGGAGCCGGTGCTGGTACTGAG
CCCTGAGGAGCCCGGGCCTGGCCCAGCCGCGGTCAGCTGCCCCCGAGACTGTGCCTGTTCCCAGGAGGGCGTCG
TGGACTGTGGCGGTATTGACCTGCGTGAGTTCCCGGGGGACCTGCCTGAGCACACCAACCACCTATCTCTGCAG
AACAACCAGCTGGAAAAGATCTACCCTGAGGAGCTCTCCCGGCTGCACCGGCTGGAGACACTGAACCTGCAAAA
CAACCGCCTGACTTCCCGAGGGCTCCCAGAGAAGGCGTTTGAGCATCTGACCAACCTCAATTACCTGTACTTGG
CCAATAACAAGCTGACCTTGGCACCCCGCTTCCTGCCAAACGCCCTGATCAGTGTGGACTTTGCTGCCAACTAT
CTCACCAAGATCTATGGGCTCACCTTTGGCCAGAAGCCAAACTTGAGGTCTGTGTACCTGCACAACAACAAGCT
GGCAGACGCCGGGCTGCCGGACAACATGTTCAACGGCTCCAGCAACGTCGAGGTCCTCATCCTGTCCAGCAACT
TCCTGCGCCACGTGCCCAAGCACCTGCCGCCTGCCCTGTACAAGCTGCACCTCAAGAACAACAAGCTGGAGAAG
ATCCCCCCGGGGGCCTTCAGCGAGCTGAGCAGCCTGCGCGAGCTATACCTGCAGAACAACTACCTGACTGACGA
GGGCCTGGACAACGAGACCTTCTGGAAGCTCTCCAGCCTGGAGTACCTGGATCTGTCCAGCAACAACCTGTCTC
GGGTCCCAGCTGGGCTGCCGCGCAGCCTGGTGCTGCTGCACTTGGAGAAGAACGCCATCCGGAGCGTGGACGCG
AATGTGCTGACCCCCATCCGCAGCCTGGAGTACCTGCTGCTGCACAGCAACCAGCTGCGGGAGCAGGGCATCCA
CCCACTGGCCTTCCAGGGCCTCAAGCGGTTGCACACGGTGCACCTGTACAACAACGCGCTGGAGCGCGTGCCCA
GTGGCCTGCCTCGCCGCGTGCGCACCCTCATGATCCTGCACAACCAGATCACAGGCATTGGCCGCGAAGACTTT
GCCACCACCTACTTCCTGGAGGAGCTCAACCTCAGCTACAACCGCATCACCAGCCCACAGGTGCACCGCGACGC
CTTCCGCAAGCTGCGCCTGCTGCGCTCGCTGGACCTGTCGGGCAACCGGCTGCACACGCTGCCACCTGGGCTGC
CTCGAAATGTCCATGTGCTGAAGGTCAAGCGCAATGAGCTGGCTGCCTTGGCACGAGGGGCGCTGGCGGGCATG
GCTCAGCTGCGTGAGCTGTACCTCACCAGCAACCGACTGCGCAGCCGAGCCCTGGGCCCCCGTGCCTGGGTGGA
CCTCGCCCATCTGCAGCTGCTGGACATCGCCGGGAATCAGCTCACAGAGATCCCCGAGGGGCTCCCCGAGTCAC
TTGAGTACCTGTACCTGCAGAACAACAAGATTAGTGCGGTGCCCGCCAATGCCTTCGACTCCACGCCCAACCTC
AAGGGGATCTTTCTCAGGTTTAACAAGCTGGCTGTGGGCTCCGTGGTGGACAGTGCCTTCCGGAGGCTGAAGCA
CCTGCAGGTCTTGGACATTGAAGGCAACTTAGAGTTTGGTGACATTTCCAAGGACCGTGGCCGCTTGGGGAAGG
AAAAGGAGGAGGAGGAAGAGGAGGAGGAGGAGGAAGAGGAAACAAGATAGTGACAAGGTGATGCAGATGTGACC
TAGGATGATGGACCGCCGGACTCTTTTCTGCAGCACACGCCTGTGTGCTGTGAGCCCCCCACTCTGCCGTGCTC
ACACAGACACACCCAGCTGCACACATGAGGCATCCCACATGACACGGGCTGACACAGTCTCATATCCCCACCCC
TTCCCACGGCGTGTCCCACGGCCAGACACATGCACACACATCACACCCTCAAACACCCAGCTCAGCCACACACA
ACTACCCTCCAAACCACCACAGTCTCTGTCACACCCCCACTACCGCTGCCACGCCCTCTGAATCATGCAGGGAA
GGGTCTGCCCCTGCCCTGGCACACACAGGCACCCATTCCCTCCCCCTGCTGACATGTGTATGCGTATGCATACA
CACCACACACACACACATGCACAAGTCATGTGCGAACAGCCCTCCAAAGCCTATGCCACAGACAGCTCTTGCCC
CAGCCAGAATCAGCCATAGCAGCTCGCCGTCTGCCCTGTCCATCTGTCCGTCCGTTCCCTGGAGAAGACACAAG
GGTATCCATGCTCTGTGGCCAGGTGCCTGCCACCCTCTGGAACTCACAAAAGCTGGCTTTTATTCCTTTCCCAT
CCTATGGGGACAGGAGCCTTCAGGACTGCTGGCCTGGCCTGGCCCACCCTGCTCCTCCAGGTGCTGGGCAGTCA
CTCTGCTAAGAGTCCCTCCCTGCCACGCCCTGGCAGGACACAGGCACTTTTCCAATGGGCAAGCCCAGTGGAGG

FIGURE 15 Continued

CAGGATGGGAGAGCCCCCTGGGTGCTGCTGGGGCCTTGGGGCAGGAGTGAAGCAGAGGTGATGGGGCTGGGCTG
AGCCAGGGAGGAAGGACCCAGCTGCACCTAGGAGACACCTTTGTTCTTCAGGCCTGTGGGGGAAGTTCCGGGTG
CCTTTATTTTTTATTCTTTTCTAAGGAAAAAAATGATAAAAATCTCAAAGCTGATTTTTCTTGTTATAGAAAAA
CTAATATAAAAGCATTATCCCTATCCCTGCAAAAAAAAAA

FIGURE 16

MEGEEAEQPAWFHQPWRPGASDSAPPAGTMAQSRVLLLLLLLPPQLHLGPVLAVRAPGFGR
SGGHSLSPEENEFAEEEPVLVLSPEEPGPGPAAVSCPRDCACSQEGVVDCGGIDLREFPGD
LPEHTNHLSLQNNQLEKIYPEELSRLHRLETLNLQNNRLTSRGLPEKAFEHLTNLNYLYLA
NNKLTLAPRFLPNALISVDFAANYLTKIYGLTFGQKPNLRSVYLHNNKLADAGLPDNMFNG
SSNVEVLILSSNFLRHVPKHLPPALYKLHLKNNKLEKIPPGAFSELSSLRELYLQNNYLTD
EGLDNETFWKLSSLEYLDLSSNNLSRVPAGLPRSLVLLHLEKNAIRSVDANVLTPIRSLEY
LLLHSNQLREQGIHPLAFQGLKRLHTVHLYNNALERVPSGLPRRVRTLMILHNQITGIGRE
DFATTYFLEELNLSYNRITSPQVHRDAFRKLRLLRSLDLSGNRLHTLPPGLPRNVHVLKVK
RNELAALARGALAGMAQLRELYLTSNRLRSRALGPRAWVDLAHLQLLDIAGNQLTEIPEGL
PESLEYLYLQNNKISAVPANAFDSTPNLKGIFLRFNKLAVGSVVDSAFRRLKHLQVLDIEG
NLEFGDISKDRGRLGKEKEEEEEEEEEEEETR

Signal sequence:

amino acids 1-48

N-glycosylation site.

amino acids 243-247, 310-314, 328-332, 439-443

Casein kinase II phosphorylation site.

amino acids 68-72, 84-88, 246-250, 292-296, 317-321, 591-595

N-myristoylation site.

amino acids 19-25, 107-113, 213-219, 217-223, 236-242, 335-341, 477-483, 498-502, 539-545, 548-554

Leucine zipper pattern.

amino acids 116-138, 251-273, 258-280, 322-344, 464-486, 471-493, 535-557

FIGURE 17

AGTCCTGCCCAGCTCTTGGATCAGTCTGCTGGCCGAGGAGCCCGGTGGAGCCAGGGGTGACCCTGGAGCCCAGC
CTGCCCCGAGGAGGCCCCGGCTCAGAGCCATGCCAGGTGTCTGTGATAGGGCCCCTGACTTCCTCTCCCCGTCT
GAAGACCAGGTGCTGAGGCCTGCCTTGGGCAGCTCAGTGGCTCTGAACTGCACGGCTTGGGTAGTCTCTGGGCC
CCACTGCTCCCTGCCTTCAGTCCAGTGGCTGAAAGACGGGCTTCCATTGGGAATTGGGGGCCACTACAGCCTCC
ACGAGTACTCCTGGGTCAAGGCCAACCTGTCAGAGGTGCTTGTGTCCAGTGTCCTGGGGGTCAACGTGACCAGC
ACTGAAGTCTATGGGGCCTTCACCTGCTCCATCCAGAACATCAGCTTCTCCTCCTTCACTCTTCAGAGAGCTGG
CCCTACAAGCCACGTGGCTGCGGTGCTGGCCTCCCTCCTGGTCCTGCTGGCCCTGCTGCTGGCCGCCCTGCTCT
ATGTCAAGTGCCGTCTCAACGTGCTGCTCTGGTACCAGGACGCGTATGGGGAGGTGGAGATAAACGACGGGAAG
CTCTACGACGCCTACGTCTCCTACAGCGACTGCCCCGAGGACCGCAAGTTCGTGAACTTCATCCTAAAGCCGCA
GCTGGAGCGGCGTCGGGGCTACAAGCTCTTCCTGGACGACCGCGACCTCCTGCCGCGCGCTGAGCCCTCCGCCG
ACCTCTTGGTGAACCTGAGCCGCTGCCGACGCCTCATCGTGGTGCTTTCGGACGCCTTCCTGAGCCGGGCCTGG
TGCAGCCACAGCTTCCGGGAGGGCCTGTGCCGGCTGCTGGAGCTCACCCGCAGACCCATCTTCATCACCTTCGA
GGGCCAGAGGCGCGACCCCGCGCACCCGGCGCTCCGCCTGCTGCGCCAGCACCGCCACCTGGTGACCTTGCTGC
TCTGGAGGCCCGGCTCCGTGACTCCTTCCTCCGATTTTTGGAAAGAAGTGCAGCTGGCGCTGCCGCGGAAGGTG
CGGTACAGGCCGGTGGAAGGAGACCCCCAGACGCAGCTGCAGGACGACAAGGACCCCATGCTGATTCTTCGAGG
CCGAGTCCCTGAGGGCCGGGCCCTGGACTCAGAGGTGGACCCGGACCCTGAGGGCGACCTGGGTATGCCCGCCC
AGCCCCACTCCCCAACTGGAGAAGCTCAGCACAGGGCGGAGTGGGGGCAGGCACAGGGCACAGGGCCTGGAGGG
GCTCTAGGTGTTGAGGACTCTTCCCGGCACCGGGAGCCCCTGCACGGCCTCTGCCCTGGAGGTGCTCGGCCCTC
GGTCTGCCTGGGAACTTCCTGGGCCTCACAGGCCATCACAGCAGGGGGTGAGCAGGGGCAGCCCCTGGCAGTGG
GTCTGGGCCAAGGCTGTGGGTGGCCACCTCAGGCGTCTCGGTCTCCCCACCCCAGGTGTCCGGGGGCCTGTTTT
TGGAGAGCCATCAGCTCCACCGCACACCAGTGGGGTCTCGCTGGGAGAGAGCCGGAGCAGCGAAGTGGACGTCT
CGGATCTCGGCTCGCGAAACTACAGTGCCCGCACAGACTTCTACTGCCTGGTGTCCAAGGATGATATGTAGCTC
CCACCCCAGAGTGCAGGATCA

FIGURE 18

MPGVCDRAPDFLSPSEDQVLRPALGSSVALNCTAWVVSGPHCSLPSVQWLKDGLPLGIGGHYSLHEYSWVKANL
SEVLVSSVLGVNVTSTEVYGAFTCSIQNISFSSFTLQRAGPTSHVAAVLASLLVLLALLLAALLYVKCRLNVLL
WYQDAYGEVEINDGKLYDAYVSYSDCPEDRKFVNFILKPQLERRRGYKLFLDDRDLLPRAEPSADLLVNLSRCR
RLIVVLSDAFLSRAWCSHSFREGLCRLLELTRRPIFITFEGQRRDPAHPALRLLRQHRHLVTLLLWRPGSVTPS
SDFWKEVQLALPRKVRYRPVEGDPQTQLQDDKDPMLILRGRVPEGRALDSEVDPDPEGDLGMPAQPHSPTGEAQ
HRAEWGQAQGTGPGGALGVEDSSRHREPLHGLCPGGARPSVCLGTSWASQAITAGGEQGQPLAVGLGQGCGWPP
QASRSPHPRCPGACFWRAISSTAHQWGLAGREPEQRSGRLGSRLAKLQCPHRLLLPGVQG

Transmembrane domain: Amino acids 120-140

N-glycosylation sites: Amino acids 31-35;73-77;86-90;102-106;
217-221

N-myristoylation sites: Amino acids 25-31;53-59;59-65;84-90;
94-100;376-382;380-386;384-390;388-394;
401-407;406-412;414-420;425-431;429-43
5;
435-441;437-443;485-491

Prokaryotic membrane lipoprotein lipid attachment site:
Amino acids 430-441

Leucine zipper pattern: Amino acids 123-145

FIGURE 19

GAAAGCTATAGGCTACCCATTCAGCTCCCCTGTCAGAGACTCAAGCTTTGAGAAAGGCTAGCAAAGAGCAAGGA
AAGAGAGAAAACAACAAAGTGGCGAGGCCCTCAGAGTGAAAGCGTAAGGTTCAGTCAGCCTGCTGCAGCTTTGC
AGACCTCAGCTGGGCATCTCCAGACTCCCCTGAAGGAAGAGCCTTCCTCACCCAAACCCACAAAAGATGCTGAA
AAAGCCTCTCTCAGCTGTGACCTGGCTCTGCATTTTCATCGTGGCCTTTGTCAGCCACCCAGCGTGGCTGCAGA
AGCTCTCTAAGCACAAGACACCAGCACAGCCACAGCTCAAAGCGGCCAACTGCTGTGAGGAGGTGAAGGAGCTC
AAGGCCCAAGTTGCCAACCTTAGCAGCCTGCTGAGTGAACTGAACAAGAAGCAGGAGAGGGACTGGGTCAGCGT
GGTCATGCAGGTGATGGAGCTGGAGAGCAACAGCAAGCGCATGGAGTCGCGGCTCACAGATGCTGAGAGCAAGT
ACTCCGAGATGAACAACCAAATTGACATCATGCAGCTGCAGGCAGCACAGACGGTCACTCAGACCTCCGCAGAT
GCCATCTACGACTGCTCTTCCCTCTACCAGAAGAACTACCGCATCTCTGGAGTGTATAAGCTTCCTCCTGATGA
CTTCCTGGGCAGCCCTGAACTGGAGGTGTTCTGTGACATGGAGACTTCAGGCGGAGGCTGGACCATCATCCAGA
GACGAAAAAGTGGCCTTGTCTCCTTCTACCGGGACTGGAAGCAGTACAAGCAGGGCTTTGGCAGCATCCGTGGG
GACTTCTGGCTGGGGAACGAACACATCCACCGGCTCTCCAGACAGCCAACCCGGCTGCGTGTAGAGATGGAGGA
CTGGGAGGGCAACCTGCGCTACGCTGAGTATAGCCACTTTGTTTTGGGCAATGAACTCAACAGCTATCGCCTCT
TCCTGGGGAACTACACTGGCAATGTGGGGAACACGCCCTCCAGTATCATAACAACACAGCCTTCAGCACCAAGG
ACAAGGACAATGACAACTGCTTGGACAAGTGTGCACAGCTCCGCAAAGGTGGCTACTGGTACAACTGCTGCACA
GACTCCAACCTCAATGGAGTGTACTACCGCCTGGGTGAGCACAATAAGCACCTGGATGGCATCACCTGGTATGG
CTGGCATGGATCTACCTACTCCCTCAAACGGGTGGAGATGAAAATCCGCCCAGAAGACTTCAAGCCTTAAAAGG
AGGCTGCCGTGGAGCACGGATACAGAAACTGAGACACGTGGAGACTGGATGAGGGCAGATGAGGACAGGAAGAG
AGTGTTAGAAAGGGTAGGACTGAGAAACAGCCTATAATCTCCAAAGAAAGAATAAGTCTCCAAGGAGCACAAAA
AAATCATATGTACCAAGGATGTTACAGTAAACAGGATGAACTATTTAAACCCACTGGGTCCTGCCACATCCTTC
TCAAGGTGGTAGACTGAGTGGGGTCTCTCTGCCCAAGATCCCTGACATAGCAGTAGCTTGTCTTTTCCACATGA
TTTGTCTGTGAAAGAAAATAATTTTGAGATCGTTTTATCTATTTTCTCTACGGCTTAGGCTATGTGAGGGCAAA
ACACAAATCCCTTTGCTAAAAAGAACCATATTATTTTGATTCTCAAAGGATAGGCCTTTGAGTGTTAGAGAAAG
GAGTGAAGGAGGCAGGTGGGAAATGGTATTTCTATTTTTAAATCCAGTGAAATTATCTTGAGTCTACACATTAT
TTTTAAAACACAAAAATTGTTCGGCTGGAACTGACCCAGGCTGGACTTGCGGGGAGGAAACTCCAGGGCACTGC
ATCTGGCGATCAGACTCTGAGCACTGCCCCTGCTCGCCTTGGTCATGTACAGCACTGAAAGGAATGAAGCACCA
GCAGGAGGTGGACAGAGTCTCTCATGGATGCCGGCACAAAACTGCCTTAAAATATTCATAGTTAATACAGGTAT
ATCTATTTTTATTTACTTTGTAAGAAACAAGCTCAAGGAGCTTCCTTTTAAATTTTGTCTGTAGGAAATGGTTG
AAAACTGAAGGTAGATGGTGTTATAGTTAATAATAAATGCTGTAAATAAGCATCTCACTTTGTAAAAATAAAAT
ATTGTGGTTTTGTTTTAAACATTCAACGTTTCTTTTCCTTCTACAATAAACACTTTCAAAATGTG

FIGURE 20

MLKKPLSAVTWLCIFIVAFVSHPAWLQKLSKHKTPAQPQLKAANCCEEVKELKAQVANLSSLLSELNKKQERDW
VSVVMQVMELESNSKRMESRLTDAESKYSEMNNQIDIMQLQAAQTVTQTSADAIYDCSSLYQKNYRISGVYKLP
PDDFLGSPELEVFCDMETSGGGWTIIQRRKSGLVSFYRDWKQYKQGFGSIRGDFWLGNEHIHRLSRQPTRLRVE
MEDWEGNLRYAEYSHFVLGNELNSYRLFLGNYTGNVGNDALQYHNNTAFSTKDKDNDNCLDKCAQLRKGGYWYN
CCTDSNLNGVYYRLGEHNKHLDGITWYGWHGSTYSLKRVEMKIRPEDFKP

FIGURE 21

TGCGGCGACCGTCGTACACCATGGGCCTCCACCTCCGCCCCTACCGTGTGGGGCTGCTCCCGGATGGCCTCCTG
TTCCTCTTGCTGCTGCTAATGCTGCTCGCGGACCCAGCGCTCCCGGCCGGACGTCACCCCCCAGTGGTGCTGGT
CCCTGGTGATTTGGGTAACCAACTGGAAGCCAAGCTGGACAAGCCGACAGTGGTGCACTACCTCTGCTCCAAGA
AGACCGAAAGCTACTTCACAATCTGGCTGAACCTGGAACTGCTGCTGCCTGTCATCATTGACTGCTGGATTGAC
AATATCAGGCTGGTTTACAACAAAACATCCAGGGCCACCCAGTTTCCTGATGGTGTGGATGTACGTGTCCCTGG
CTTTGGGAAGACCTTCTCACTGGAGTTCCTGGACCCCAGCAAAAGCAGCGTGGGTTCCTATTTCCACACCATGG
TGGAGAGCCTTGTGGGCTGGGGCTACACACGGGGTGAGGATGTCCGAGGGGCTCCCTATGACTGGCGCCGAGCC
CCAAATGAAAACGGGCCCTACTTCCTGGCCCTCCGCGAGATGATCGAGGAGATGTACCAGCTGTATGGGGGCCC
CGTGGTGCTGGTTGCCCACAGTATGGGCAACATGTACACGCTCTACTTTCTGCAGCGGCAGCCGCAGGCCTGGA
AGGACAAGTATATCCGGGCCTTCGTGTCACTGGGTGCGCCCTGGGGGGGCGTGGCCAAGACCCTGCGCGTCCTG
GCTTCAGGAGACAACAACCGGATCCCAGTCATCGGGCCCCTGAAGATCCGGGAGCAGCAGCGGTCAGCTGTCTC
CACCAGCTGGCTGCTGCCCTACAACTACACATGGTCACCTGAGAAGGTGTTCGTGCAGACACCCACAATCAACT
ACACACTGCGGGACTACCGCAAGTTCTTCCAGGACATCGGCTTTGAAGATGGCTGGCTCATGCGGCAGGACACA
GAAGGGCTGGTGGAAGCCACGATGCCACCTGGCGTGCAGCTGCACTGCCTCTATGGTACTGGCGTCCCCACACC
AGACTCCTTCTACTATGAGAGCTTCCCTGACCGTGACCCTAAAATCTGCTTTGGTGACGGCGATGGTACTGTGA
ACTTGAAGAGTGCCCTGCAGTGCCAGGCCTGGCAGAGCCGCCAGGAGCACCAAGTGTTGCTGCAGGAGCTGCCA
GGCAGCGAGCACATCGAGATGCTGGCCAACGCCACCACCCTGGCCTATCTGAAACGTGTGCTCCTTGGGCCCTG
ACTCCTGTGCCACAGGACTCCTGTGGCTCGGCCGTGGACCTGCTGTTGGCCTCTGGGGCTGTCATGGCCCACGC
GTTTTGCAAAGTTTGTGACTCACCATTCAAGGCCCCGAGTCTTGGACTGTGAAGCATCTGCCATGGGGAAGTGC
TGTTTGTTATCCTTTCTCTGTGGCAGTGAAGAAGGAAGAAATGAGAGTCTAGACTCAAGGGACACTGGATGGCA
AGAATGCTGCTGATGGTGGAACTGCTGTGACCTTAGGACTGGCTCCACAGGGTGGACTGGCTGGGCCCTGGTCC
CAGTCCCTGCCTGGGGCCATGTGTCCCCCTATTCCTGTGGGCTTTTCATACTTGCCTACTGGGCCCTGGCCCCG
CAGCCTTCCTATGAGGGATGTTACTGGGCTGTGGTCCTGTACCCAGAGGTCCCAGGGATCGGCTCCTGGCCCCT
CGGGTGACCCTTCCCACACACCAGCCACAGATAGGCCTGCCACTGGTCATGGGTAGCTAGAGCTGCTGGCTTCC
CTGTGGCTTAGCTGGTGGCCAGCCTGACTGGCTTCCTGGGCGAGCCTAGTAGCTCCTGCAGGCAGGGGCAGTTT
GTTGCGTTCTTCGTGGTTCCCAGGCCCTGGGACATCTCACTCCACTCCTACCTCCCTTACCACCAGGAGCATTC
AAGCTCTGGATTGGGCAGCAGATGTGCCCCCAGTCCCGCAGGCTGTGTTCCAGGGGCCCTGATTTCCTCGGATG
TGCTATTGGCCCCAGGACTGAAGCTGCCTCCCTTCACCCTGGGACTGTGGTTCCAAGGATGAGAGCAGGGGTTG
GAGCCATGGCCTTCTGGGAACCTATGGAGAAAGGGAATCCAAGGAAGCAGCCAAGGCTGCTCGCAGCTTCCCTG
AGCTGCACCTCTTGCTAACCCCACCATCACACTGCCACCCTGCCCTAGGGTCTCACTAGTACCAAGTGGGTCAG
CACAGGGCTGAGGATGGGGCTCCTATCCACCCTGGCCAGCACCCAGCTTAGTGCTGGGACTAGCCCAGAAACTT
GAATGGGACCCTGAGAGAGCCAGGGGTCCCCTGAGGCCCCCCTAGGGGCTTTCTGTCTGCCCCAGGGTGCTCCA
TGGATCTCCCTGTGGCAGCAGGCATGGAGAGTCAGGGCTGCCTTCATGGCAGTAGGCTCTAAGTGGGTGACTGG
CCACAGGCCGAGAAAAGGGTACAGCCTCTAGGTGGGGTTCCCAAAGACGCCTTCAGGCTGGACTGAGCTGCTCT
CCCACAGGGTTTCTGTGCAGCTGGATTTTCTCTGTTGCATACATGCCTGGCATCTGTCTCCCCTTGTTCCTGAG
TGGCCCCACATGGGGCTCTGAGCAGGCTGTATCTGGATTCTGGCAATAAAAGTACTCTGGATGCTGTAAAAAAA
AAAAAAAAAAAAAAA

FIGURE 22

></usr/seqdb2/sst/DNA/Dnaseqs.min/ss.DNA44189
><subunit 1 of 1, 412 aa, 1 stop
><MW: 46658, pI: 6.65, NX(S/T): 4
MGLHLRPYRVGLLPDGLLFLLLLLMLLADPALPAGRHPPVVLVPGDLGNQLEAKLDKPTVVHYLCSKKTESYFT
IWLNLELLLPVIIDCWIDNIRLVYNKTSRATQFPDGVDVRVPGFGKTFSLEFLDPSKSSVGSYFHTMVESLVGW
GYTRGEDVRGAPYDWRRAPNENGPYFLALREMIEEMYQLYGGPVVLVAHSMGNMYTLYFLQRQPQAWKDKYIRA
FVSLGAPWGGVAKTLRVLASGDNNRIPVIGPLKIREQQRSAVSTSWLLPYNYTWSPEKVFVQTPTINYTLRDYR
KFFQDIGFEDGWLMRQDTEGLVEATMPPGVQLHCLYGTGVPTPDSFYYESFPDRDPKICFGDGDGTVNLKSALQ
CQAWQSRQEHQVLLQELPGSEHIEMLANATTLAYLKRVLLGP

Important features:
Signal peptide:
amino acids 1-28

Potential lipid substrate binding site:
amino acids 147-164

N-glycosylation sites.
amino acids 99-102, 273-276, 289-292 and 398-401

Lipases, serine proteins
amino acids 189-201

Beta-transducin family Trp-Asp repeat
amino acids 353-365

FIGURE 23

GAGCCACCTACCCTGCTCCGAGGCCAGGCCTGCAGGGCCTCATCGGCCAGAGGGTGATCAGTGAGCAGAAGGAT
GCCCGTGGCCGAGGCCCCCCAGGTGGCTGGCGGGCAGGGGGACGGAGGTGATGGCGAGGAAGCGGAGCCAGAGG
GGATGTTCAAGGCCTGTGAGGACTCCAAGAGAAAAGCCCGGGGCTACCTCCGCCTGGTGCCCCTGTTTGTGCTG
CTGGCCCTGCTCGTGCTGGCTTCGGCGGGGGTGCTACTCTGGTATTTCCTAGGGTACAAGGCGGAGGTGATGGT
CAGCCAGGTGTACTCAGGCAGTCTGCGTGTACTCAATCGCCACTTCTCCCAGGATCTTACCCGCCGGGAATCTA
GTGCCTTCCGCAGTGAAACCGCCAAAGCCCAGAAGATGCTCAAGGAGCTCATCACCAGCACCCGCCTGGGAACT
TACTACAACTCCAGCTCCGTCTATTCCTTTGGGGAGGGACCCCTCACCTGCTTCTTCTGGTTCATTCTCCAAAT
CCCCGAGCACCGCCGGCTGATGCTGAGCCCCGAGGTGGTGCAGGCACTGCTGGTGGAGGAGCTGCTGTCCACAG
TCAACAGCTCGGCTGCCGTCCCCTACAGGGCCGAGTACGAAGTGGACCCCGAGGGCCTAGTGATCCTGGAAGCC
AGTGTGAAAGACATAGCTGCATTGAATTCCACGCTGGGTTGTTACCGCTACAGCTACGTGGGCCAGGGCCAGGT
CCTCCGGCTGAAGGGGCCTGACCACCTGGCCTCCAGCTGCCTGTGGCACCTGCAGGGCCCCAAGGACCTCATGC
TCAAACTCCGGCTGGAGTGGACGCTGGCAGAGTGCCGGGACCGACTGGCCATGTATGACGTGGCCGGGCCCCTG
GAGAAGAGGCTCATCACCTCGGTGTACGGCTGCAGCCGCCAGGAGCCCGTGGTGGAGGTTCTGGCGTCGGGGGC
CATCATGGCGGTCGTCTGGAAGAAGGGCCTGCACAGCTACTACGACCCCTTCGTGCTCTCCGTGCAGCCGGTGG
TCTTCCAGGCCTGTGAAGTGAACCTGACGCTGGACAACAGGCTCGACTCCCAGGGCGTCCTCAGCACCCCGTAC
TTCCCCAGCTACTACTCGCCCCAAACCCACTGCTCCTGGCACCTCACGGTGCCCTCTCTGGACTACGGCTTGGC
CCTCTGGTTTGATGCCTATGCACTGAGGAGGCAGAAGTATGATTTGCCGTGCACCCAGGGCCAGTGGACGATCC
AGAACAGGAGGCTGTGTGGCTTGCGCATCCTGCAGCCCTACGCCGAGAGGATCCCCGTGGTGGCCACGGCCGGG
ATCACCATCAACTTCACCTCCCAGATCTCCCTCACCGGGCCCGGTGTGCGGGTGCACTATGGCTTGTACAACCA
GTCGGACCCCTGCCCTGGAGAGTTCCTCTGTTCTGTGAATGGACTCTGTGTCCCTGCCTGTGATGGGGTCAAGG
ACTGCCCCAACGGCCTGGATGAGAGAAACTGCGTTTGCAGAGCCACATTCCAGTGCAAAGAGGACAGCACATGC
ATCTCACTGCCCAAGGTCTGTGATGGGCAGCCTGATTGTCTCAACGGCAGCGATGAAGAGCAGTGCCAGGAAGG
GGTGCCATGTGGGACATTCACCTTCCAGTGTGAGGACCGGAGCTGCGTGAAGAAGCCCAACCCGCAGTGTGATG
GGCGGCCCGACTGCAGGGACGGCTCGGATGAGGAGCACTGTGACTGTGGCCTCCAGGGCCCCTCCAGCCGCATT
GTTGGTGGAGCTGTGTCCTCCGAGGGTGAGTGGCCATGGCAGGCCAGCCTCCAGGTTCGGGGTCGACACATCTG
TGGGGGGGCCCTCATCGCTGACCGCTGGGTGATAACAGCTGCCCACTGCTTCCAGGAGGACAGCATGGCCTCCA
CGGTGCTGTGGACCGTGTTCCTGGGCAAGGTGTGGCAGAACTCGCGCTGGCCTGGAGAGGTGTCCTTCAAGGTG
AGCCGCCTGCTCCTGCACCCGTACCACGAAGAGGACAGCCATGACTACGACGTGGCGCTGCTGCAGCTCGACCA
CCCGGTGGTGCGCTCGGCCGCCGTGCGCCCCGTCTGCCTGCCCGCGCGCTCCCACTTCTTCGAGCCCGGCCTGC
ACTGCTGGATTACGGGCTGGGGCGCCTTGCGCGAGGGCGGCCCCATCAGCAACGCTCTGCAGAAAGTGGATGTG
CAGTTGATCCCACAGGACCTGTGCAGCGAGGCCTATCGCTACCAGGTGACGCCACGCATGCTGTGTGCCGGCTA
CCGCAAGGGCAAGAAGGATGCCTGTCAGGGTGACTCAGGTGGTCCGCTGGTGTGCAAGGCACTCAGTGGCCGCT
GGTTCCTGGCGGGGCTGGTCAGCTGGGGCCTGGGCTGTGGCCGGCCTAACTACTTCGGCGTCTACACCCGCATC
ACAGGTGTGATCAGCTGGATCCAGCAAGTGGTGACCTGAGGAACTGCCCCCCTGCAAAGCAGGGCCCACCTCCT
GGACTCAGAGAGCCCAGGGCAACTGCCAAGCAGGGGGACAAGTATTCTGGCGGGGGGTGGGGGAGAGAGCAGGC
CCTGTGGTGGCAGGAGGTGGCATCTTGTCTCGTCCCTGATGTCTGCTCCAGTGATGGCAGGAGGATGGAGAAGT
GCCAGCAGCTGGGGGTCAAGACGTCCCCTGAGGACCCAGGCCCACACCCAGCCCTTCTGCCTCCCAATTCTCTC
TCCTCCGTCCCCTTCCTCCACTGCTGCCTAATGCAAGGCAGTGGCTCAGCAGCAAGAATGCTGGTTCTACATCC
CGAGGAGTGTCTGAGGTGCGCCCCACTCTGTACAGAGGCTGTTTGGGCAGCCTTGCCTCCAGAGAGCAGATTCC
AGCTTCGGAAGCCCCTGGTCTAACTTGGGATCTGGGAATGGAAGGTGCTCCCATCGGAGGGGACCCTCAGAGCC
CTGGAGACTGCCAGGTGGGCCTGCTGCCACTGTAAGCCAAAAGGTGGGGAAGTCCTGACTCCAGGGTCCTTGCC
CCACCCCTGCCTGCCACCTGGGCCCTCACAGCCCAGACCCTCACTGGGAGGTGAGCTCAGCTGCCCTTTGGAAT

FIGURE 23 Continued

AAAGCTGCCTGATCAAAAAAAAAAAAAAAAAAAAA

FIGURE 24

></usr/seqdb2/sst/DNA/Dnaseqs.min/ss.DNA49152
><subunit 1 of 1, 802 aa, 1 stop
><MW: 88846, pI: 6.41, NX(S/T): 7

MPVAEAPQVAGGQGDGGDGEEAEPEGMFKACEDSKRKARGYLRLVPLFVLLALLVLASAGVLLWYFLGYKAEVM
VSQVYSGSLRVLNRHFSQDLTRRESSAFRSETAKAQKMLKELITSTRLGTYYNSSSVYSFGEGPLTCFFWFILQ
IPEHRRLMLSPEVVQALLVEELLSTVNSSAAVPYRAEYEVDPEGLVILEASVKDIAALNSTLGCYRYSYVGQGQ
VLRLKGPDHLASSCLWHLQGPKDLMLKLRLEWTLAECRDRLAMYDVAGPLEKRLITSVYGCSRQEPVVEVLASG
AIMAVVWKKGLHSYYDPFVLSVQPVVFQACEVNLTLDNRLDSQGVLSTPYFPSYYSPQTHCSWHLTVPSLDYGL
ALWFDAYALRRQKYDLPCTQGQWTIQNRRLCGLRILQPYAERIPVVATAGITINFTSQISLTGPGVRVHYGLYN
QSDPCPGEFLCSVNGLCVPACDGVKDCPNGLDERNCVCRATFQCKEDSTCISLPKVCDGQPDCLNGSDEEQCQE
GVPCGTFTFQCEDRSCVKKPNPQCDGRPDCRDGSDEEHCDCGLQGPSSRIVGGAVSSEGEWPWQASLQVRGRHI
CGGALIADRWVITAAHCFQEDSMASTVLWTVFLGKVWQNSRWPGEVSFKVSRLLLHPYHEEDSHDYDVALLQLD
HPVVRSAAVRPVCLPARSHFFEPGLHCWITGWGALREGGPISNALQKVDVQLIPQDLCSEAYRYQVTPRMLCAG
YRKGKKDACQGDSGGPLVCKALSGRWFLAGLVSWGLGCGRPNYFGVYTRITGVISWIQQVVT

Important features:

Type II transmembrane domain:

amino acids 46-67

Serine proteases, trypsin family, histidine active site.

amino acids 604-609

N-glycosylation sites.

amino acids 127-130, 175-178, 207-210, 329-332, 424-427, 444-447 and 509-512

Kringle domains.

amino acids 746-758 and 592-609

Homologous region to Kallikrein Light Chain:

amino acids 568-779

Homologous region to Low-density lipoprotein receptor:

amino acids 451-567

FIGURE 25

GCAACCTCAGCTTCTAGTATCCAGACTCCAGCGCCGCCCCGGGCGCGGACCCCAACCCCGACCCAGAGCTTCTC
CAGCGGCGGCGCAGCGAGCAGGGCTCCCCGCCTTAACTTCCTCCGCGGGGCCCAGCCACCTTCGGGAGTCCGGG
TTGCCCACCTGCAAACTCTCCGCCTTCTGCACCTGCCACCCCTGAGCCAGCGCGGGCCCCCGAGCGAGTCATGG
CCAACGCGGGGCTGCAGCTGTTGGGCTTCATTCTCGCCTTCCTGGGATGGATCGGCGCCATCGTCAGCACTGCC
CTGCCCCAGTGGAGGATTTACTCCTATGCCGGCGACAACATCGTGACCGCCCAGGCCATGTACGAGGGGCTGTG
GATGTCCTGCGTGTCGCAGAGCACCGGGCAGATCCAGTGCAAAGTCTTTGACTCCTTGCTGAATCTGAGCAGCA
CATTGCAAGCAACCCGTGCCTTGATGGTGGTTGGCATCCTCCTGGGAGTGATAGCAATCTTTGTGGCCACCGTT
GGCATGAAGTGTATGAAGTGCTTGGAAGACGATGAGGTGCAGAAGATGAGGATGGCTGTCATTGGGGGTGCGAT
ATTTCTTCTTGCAGGTCTGGCTATTTTAGTTGCCACAGCATGGTATGGCAATAGAATCGTTCAAGAATTCTATG
ACCCTATGACCCCAGTCAATGCCAGGTACGAATTTGGTCAGGCTCTCTTCACTGGCTGGGCTGCTGCTTCTCTC
TGCCTTCTGGGAGGTGCCCTACTTTGCTGTTCCTGTCCCCGAAAAACAACCTCTTACCCAACACCAAGGCCCTA
TCCAAAACCTGCACCTTCCAGCGGGAAAGACTACGTGTGACACAGAGGCAAAAGGAGAAAATCATGTTGAAACA
AACCGAAAATGGACATTGAGATACTATCATTAACATTAGGACCTTAGAATTTTGGGTATTGTAATCTGAAGTAT
GGTATTACAAAACAAACAAACAAACAAAAAACCCATGTGTTAAAATACTCAGTGCTAAACATGGCTTAATCTTA
TTTTATCTTCTTTCCTCAATATAGGAGGGAAGATTTTTCCATTTGTATTACTGCTTCCCATTGAGTAATCATAC
TCAAATGGGGGAAGGGGTGCTCCTTAAATATATATAGATATGTATATATACATGTTTTTCTATTAAAAATAGAC
AGTAAAATACTATTCTCATTATGTTGATACTAGCATACTTAAAATATCTCTAAAATAGGTAAATGTATTTAATT
CCATATTGATGAAGATGTTTATTGGTATATTTTCTTTTTCGTCCTTATATACATATGTAACAGTCAAATATCAT
TTACTCTTCTTCATTAGCTTTGGGTGCCTTTGCCACAAGACCTAGCCTAATTTACCAAGGATGAATTCTTTCAA
TTCTTCATGCGTGCCCTTTTCATATACTTATTTTATTTTTTACCATAATCTTATAGCACTTGCATCGTTATTAA
GCCCTTATTTGTTTTGTGTTTCATTGGTCTCTATCTCCTGAATCTAACACATTTCATAGCCTACATTTTAGTTT
CTAAAGCCAAGAAGAATTTATTACAAATCAGAACTTTGGAGGCAAATCTTTCTGCATGACCAAAGTGATAAATT
CCTGTTGACCTTCCCACACAATCCCTGTACTCTGACCCATAGCACTCTTGTTTGCTTTGAAAATATTTGTCCAA
TTGAGTAGCTGCATGCTGTTCCCCCAGGTGTTGTAACACAACTTTATTGATTGAATTTTTAAGCTACTTATTCA
TAGTTTTATATCCCCCTAAACTACCTTTTTGTTCCCCATTCCTTAATTGTATTGTTTTCCCAAGTGTAATTATC
ATGCGTTTTATATCTTCCTAATAAGGTGTGGTCTGTTTGTCTGAACAAAGTGCTAGACTTTCTGGAGTGATAAT
CTGGTGACAAATATTCTCTCTGTAGCTGTAAGCAAGTCACTTAATCTTTCTACCTCTTTTTTCTATCTGCCAAA
TTGAGATAATGATACTTAACCAGTTAGAAGAGGTAGTGTGAATATTAATTAGTTTATATTACTCTTATTCTTTG
AACATGAACTATGCCTATGTAGTGTCTTTATTTGCTCAGCTGGCTGAGACACTGAAGAAGTCACTGAACAAAAC
CTACACACGTACCTTCATGTGATTCACTGCCTTCCTCTCTCTACCAGTCTATTTCCACTGAACAAAACCTACAC
ACATACCTTCATGTGGTTCAGTGCCTTCCTCTCTCTACCAGTCTATTTCCACTGAACAAAACCTACGCACATAC
CTTCATGTGGCTCAGTGCCTTCCTCTCTCTACCAGTCTATTTCCATTCTTTCAGCTGTGTCTGACATGTTTGTG
CTCTGTTCCATTTTAACAACTGCTCTTACTTTTCCAGTCTGTACAGAATGCTATTTCACTTGAGCAAGATGATG
TAATGGAAAGGGTGTTGGCACTGGTGTCTGGAGACCTGGATTTGAGTCTTGGTGCTATCAATCACCGTCTGTGT
TTGAGCAAGGCATTTGGCTGCTGTAAGCTTATTGCTTCATCTGTAAGCGGTGGTTTGTAATTCCTGATCTTCCC
ACCTCACAGTGATGTTGTGGGGATCCAGTGAGATAGAATACATGTAAGTGTGGTTTTGTAATTTAAAAAGTGCT
ATACTAAGGGAAAGAATTGAGGAATTAACTGCATACGTTTTGGTGTTGCTTTTCAAATGTTTGAAAATAAAAAA
AATGTTAAG

FIGURE 26

></usr/seqdb2/sst/DNA/Dnaseqs.min/ss.DNA52185
><subunit 1 of 1, 211 aa, 1 stop
><MW: 22744, pI: 8.51, NX(S/T): 1
MANAGLQLLGFILAFLGWIGAIVSTALPQWRIYSYAGDNIVTAQAMYEGLWMSCVSQSTGQ
IQCKVFDSLLNLSSTLQATRALMVVGILLGVIAIFVATVGMKCMKCLEDDEVQKMRMAVIG
GAIFLLAGLAILVATAWYGNRIVQEFYDPMTPVNARYEFGQALFTGWAAASLCLLGGALLC
CSCPRKTTSYPTPRPYPKPAPSSGKDYV

Important features:

Signal peptide:

amino acids 1-21

Transmembrane domains:

amino acids 82-102, 118-142 and 161-187

N-glycosylation site.

amino acids 72-75

PMP-22 / EMP / MP20 family proteins amino acids 70-111

ABC-2 type transport system integral membrane protein amino acids 119-133

FIGURE 27

GGCTCGAGCGTTTCTGAGCCAGGGGTGACCATGACCTGCTGCGAAGGATGGACATCCTGCA
ATGGATTCAGCCTGCTGGTTCTACTGCTGTTAGGAGTAGTTCTCAATGCGATACCTCTAAT
TGTCAGCTTAGTTGAGGAAGACCAATTTTCTCAAAACCCCATCTCTTGCTTTGAGTGGTGG
TTCCCAGGAATTATAGGAGCAGGTCTGATGGCCATTCCAGCAACAACAATGTCCTTGACAG
CAAGAAAAAGAGCGTGCTGCAACAACAGAACTGGAATGTTTCTTTCATCATTTTTCAGTGT
GATCACAGTCATTGGTGCTCTGTATTGCATGCTGATATCCATCCAGGCTCTCTTAAAAGGT
CCTCTCATGTGTAATTCTCCAAGCAACAGTAATGCCAATTGTGAATTTTCATTGAAAAACA
TCAGTGACATTCATCCAGAATCCTTCAACTTGCAGTGGTTTTTCAATGACTCTTGTGCACC
TCCTACTGGTTTCAATAAACCCACCAGTAACGACACCATGGCGAGTGGCTGGAGAGCATCT
AGTTTCCACTTCGATTCTGAAGAAAACAAACATAGGCTTATCCACTTCTCAGTATTTTTAG
GTCTATTGCTTGTTGGAATTCTGGAGGTCCTGTTTGGGCTCAGTCAGATAGTCATCGGTTT
CCTTGGCTGTCTGTGTGGAGTCTCTAAGCGAAGAAGTCAAATTGTGTAGTTTAATGGGAAT
AAAATGTAAGTATCAGTAGTTTGAAAAAAAAAAA

FIGURE 28

MTCCEGWTSCNGFSLLVLLLLGVVLNAIPLIVSLVEEDQFSQNPISCFEWWFPGIIGAGLM
AIPATTMSLTARKRACCNNRTGMFLSSFFSVITVIGALYCMLISIQALLKGPLMCNSPSNS
NANCEFSLKNISDIHPESFNLQWFFNDSCAPPTGFNKPTSNDTMASGWRASSFHFDSEENK
HRLIHFSVFLGLLLVGILEVLFGLSQIVIGFLGCLCGVSKRRSQIV

FIGURE 29

GGCACGAGGCGGCGGGGCAGTCGCGGGATGCGCCCGGGAGCCACAGCCTGAGGCCCTCAGG
TCTCTGCAGGTGTCGTGGAGGAACCTAGCACCTGCCATCCTCTTCCCCAATTTGCCACTTC
CAGCAGCTTTAGCCCATGAGGAGGATGTGACCGGGACTGAGTCAGGAGCCCTCTGGAAGCA
TGGAGACTGTGGTGATTGTTGCCATAGGTGTGCTGGCCACCATCTTTCTGGCTTCGTTTGC
AGCCTTGGTGCTGGTTTGCAGGCAGCGCTACTGCCGGCCGCGAGACCTGCTGCAGCGCTAT
GATTCTAAGCCCATTGTGGACCTCATTGGTGCCATGGAGACCCAGTCTGAGCCCTCTGAGT
TAGAACTGGACGATGTCGTTATCACCAACCCCCACATTGAGGCCATTCTGGAGAATGAAGA
CTGGATCGAAGATGCCTCGGGTCTCATGTCCCACTGCATTGCCATCTTGAAGATTTGTCAC
ACTCTGACAGAGAAGCTTGTTGCCATGACAATGGGCTCTGGGGCCAAGATGAAGACTTCAG
CCAGTGTCAGCGACATCATTGTGGTGGCCAAGCGGATCAGCCCCAGGGTGGATGATGTTGT
GAAGTCGATGTACCCTCCGTTGGACCCCAAACTCCTGGACGCACGGACGACTGCCCTGCTC
CTGTCTGTCAGTCACCTGGTGCTGGTGACAAGGAATGCCTGCCATCTGACGGGAGGCCTGG
ACTGGATTGACCAGTCTCTGTCGGCTGCTGAGGAGCATTTGGAAGTCCTTCGAGAAGCAGC
CCTAGCTTCTGAGCCAGATAAAGGCCTCCCAGGCCCTGAAGGCTTCCTGCAGGAGCAGTCT
GCAATTTAGTGCCTACAGGCCAGCAGCTAGCCATGAAGGCCCCTGCCGCCATCCCTGGATG
GCTCAGCTTAGCCTTCTACTTTTTCCTATAGAGTTAGTTGTTCTCCACGGCTGGAGAGTTC
AGCTGTGTGTGCATAGTAAAGCAGGAGATCCCCGTCAGTTTATGCCTCTTTTGCAGTTGCA
AACTGTGGCTGGTGAGTGGCAGTCTAATACTACAGTTAGGGGAGATGCCATTCACTCTCTG
CAAGAGGAGTATTGAAAACTGGTGGACTGTCAGCTTTATTTAGCTCACCTAGTGTTTTCAA
GAAAATTGAGCCACCGTCTAAGAAATCAAGAGGTTTCACATTAAAATTAGAATTTCTGGCC
TCTCTCGATCGGTCAGAATGTGTGGCAATTCTGATCTGCATTTTCAGAAGAGGACAATCAA
TTGAAACTAAGTAGGGGTTTCTTCTTTTGGCAAGACTTGTACTCTCTCACCTGGCCTGTTT
CATTTATTTGTATTATCTGCCTGGTCCCTGAGGCGTCTGGGTCTCTCCTCTCCCTTGCAGG
TTTGGGTTTGAAGCTGAGGAACTACAAAGTTGATGATTTCTTTTTTATCTTTATGCCTGCA
ATTTTACCTAGCTACCACTAGGTGGATAGTAAATTTATACTTATGTTTCCCTCAAAAAAAA
AAAAAAA

FIGURE 30

METVVIVAIGVLATIFLASFAALVLVCRQRYCRPRDLLQRYDSKPIVDLIGAMETQSEPSE
LELDDVVITNPHIEAILENEDWIEDASGLMSHCIAILKICHTLTEKLVAMTMGSGAKMKTS
ASVSDIIVVAKRISPRVDDVVKSMYPPLDPKLLDARTTALLLSVSHLVLVTRNACHLTGGL
DWIDQSLSAAEEHLEVLREAALASEPDKGLPGPEGFLQEQSAI

FIGURE 31

CTGTCGTCTTTGCTTCAGCCGCAGTCGCCACTGGCTGCCTGAGGTGCTCTTACAGCCTGTT
CCAAGTGTGGCTTAATCCGTCTCCACCACCAGATCTTTCTCCGTGGATTCCTCTGCTAAGA
CCGCTGCCATGCCAGTGACGGTAACCCGCACCACCATCACAACCACCACGACGTCATCTTC
GGGCCTGGGGTCCCCCATGATCGTGGGGTCCCCTCGGGCCCTGACACAGCCCCTGGGTCTC
CTTCGCCTGCTGCAGCTGGTGTCTACCTGCGTGGCCTTCTCGCTGGTGGCTAGCGTGGGCG
CCTGGACGGGGTCCATGGGCAACTGGTCCATGTTCACCTGGTGCTTCTGCTTCTCCGTGAC
CCTGATCATCCTCATCGTGGAGCTGTGCGGGCTCCAGGCCCGCTTCCCCCTGTCTTGGCGC
AACTTCCCCATCACCTTCGCCTGCTATGCGGCCCTCTTCTGCCTCTCGGCCTCCATCATCT
ACCCCACCACCTATGTCCAGTTCCTGTCCCACGGCCGTTCGCGGGACCACGCCATCGCCGC
CACCTTCTTCTCCTGCATCGCGTGTGTGGCTTACGCCACCGAAGTGGCCTGGACCCGGGCC
CGGCCCGGCGAGATCACTGGCTATATGGCCACCGTACCCGGGCTGCTGAAGGTGCTGGAGA
CCTTCGTTGCCTGCATCATCTTCGCGTTCATCAGCGACCCCAACCTGTACCAGCACCAGCC
GGCCCTGGAGTGGTGCGTGGCGGTGTACGCCATCTGCTTCATCCTAGCGGCCATCGCCATC
CTGCTGAACCTGGGGGAGTGCACCAACGTGCTACCCATCCCCTTCCCCAGCTTCCTGTCGG
GGCTGGCCTTGCTGTCTGTCCTCCTCTATGCCACCGCCCTTGTTCTCTGGCCCCTCTACCA
GTTCGATGAGAAGTATGGCGGCCAGCCTCGGCGCTCGAGAGATGTAAGCTGCAGCCGCAGC
CATGCCTACTACGTGTGTGCCTGGGACCGCCGACTGGCTGTGGCCATCCTGACGGCCATCA
ACCTACTGGCGTATGTGGCTGACCTGGTGCACTCTGCCCACCTGGTTTTTGTCAAGGTCTA
AGACTCTCCCAAGAGGCTCCCGTTCCCTCTCCAACCTCTTTGTTCTTCTTGCCCGAGTTTT
CTTTATGGAGTACTTCTTTCCTCCGCCTTTCCTCTGTTTTCCTCTTCCTGTCTCCCCTCCC
TCCCACCTTTTTCTTTCCTTCCCAATTCCTTGCACTCTAACCAGTTCTTGGATGCATCTTC
TTCCTTCCCTTTCCTCTTGCTGTTTCCTTCCTGTGTTGTTTTGTTGCCCACATCCTGTTTT
CACCCCTGAGCTGTTTCTCTTTTTCTTTTCTTTCTTTTTTTTTTTTTTTTTTAAGACGGAT
TCTCACTCTGTGGCCCAGGCTGGAGTGCAGTGGTGCGATCTCAGCTCACTGCAACCCCCGC
CTCCTGGGTTCAAGCGATTCTCCTCCCCCAGCCTCCCAAGTAGCTGGGAGGACAGGTGTGA
GCTGCCGCACCCAGCCTGTTTCTCTTTTTCCACTCTTCTTTTTTTCTCATCTCTTTTCTGGG
TTGCCTGTCGGCTTTCTTATCTGCCTGTTTTGCAAGCACCTTCTCCTGTGTCCTTGGGAGC
CCTGAGACTTCTTTCTCTCCTTGCCTCCACCCACCTCCAAAGGTGCTGAGCTCACATCCAC
ACCCCTTGCAGCCGTCCATGCCACAGCCCCCCAAGGGGCCCCATTGCCAAAGCATGCCTGC
CCACCCTCGCTGTGCCTTAGTCAGTGTGTACGTGTGTGTGTGTGTGTGTTTGGGGGGTGGG
GGGTGGGTAGCTGGGGATTGGGCCCTCTTTCTCCCAGTGGAGGAAGGTGTGCAGTGTACTT
CCCCTTTAAATTAAAAAACATATATATATATATATATTTGGAGGTCAGTAATTTCCAATGGGC
GGGAGGCATTAAGCACCGACCCTGGGTCCCTAGGCCCCGCCTGGCACTCAGCCTTGCCAGA
GATTGGCTCCAGAATTTTTGCCAGGCTTACAGAACACCCACTGCCTAGAGGCCATCTTAAA
GGAAGCAGGGGCTGGATGCCTTTCATCCCAACTATTCTCTGTGGTATGAAAAAG

FIGURE 32

</usr/seqdb2/sst/DNA/Dnaseqs.min/ss.DNA58727
<subunit 1 of 1, 322 aa, 1 stop
<MW: 35274, pI: 8.57, NX(S/T): 1
MPVTVTRTTITTTTTSSSGLGSPMIVGSPRALTQPLGLLRLLQLVSTCVAFSLVASVGAWT
GSMGNWSMFTWCFCFSVTLIILIVELCGLQARFPLSWRNFPITFACYAALFCLSASIIYPT
TYVQFLSHGRSRDHAIAATFFSCIACVAYATEVAWTRARPGEITGYMATVPGLLKVLETFV
ACIIFAFISDPNLYQHQPALEWCVAVYAICFILAAIAILLNLGECTNVLPIPFPSFLSGLA
LLSVLLYATALVLWPLYQFDEKYGGQPRRSRDVSCSRSHAYYVCAWDRRLAVAILTAINLL
AYVADLVHSAHLVFVKV

Important features:

Transmembrane domains:

amino acids 41-60 (type II), 66-85, 101-120, 137-153, 171-192, 205-226, 235-255 and 294-312

N-glycosylation site.

amino acids 66-69

Glycosaminoglycan attachment site.

amino acids 18-21

FIGURE 33

GCCAGGTGTGCAGGCCGCTCCAAGCCCAGCCTGCCCCGCTGCCGCCACCATGACGCTCCTCCCCGGCCTCCTGT
TTCTGACCTGGCTGCACACATGCCTGGCCCACCATGACCCCTCCCTCAGGGGGCACCCCCACAGTCACGGTACC
CCACACTGCTACTCGGCTGAGGAACTGCCCCTCGGCCAGGCCCCCCCACACCTGCTGGCTCGAGGTGCCAAGTG
GGGGCAGGCTTTGCCTGTAGCCCTGGTGTCCAGCCTGGAGGCAGCAAGCCACAGGGGGAGGCACGAGAGGCCCT
CAGCTACGACCCAGTGCCCGGTGCTGCGGCCGGAGGAGGTGTTGGAGGCAGACACCCACCAGCGCTCCATCTCA
CCCTGGAGATACCGTGTGGACACGGATGAGGACCGCTATCCACAGAAGCTGGCCTTCGCCGAGTGCCTGTGCAG
AGGCTGTATCGATGCACGGACGGGCCGCGAGACAGCTGCGCTCAACTCCGTGCGGCTGCTCCAGAGCCTGCTGG
TGCTGCGCCGCCGGCCCTGCTCCCGCGACGGCTCGGGGCTCCCCACACCTGGGGCCTTTGCCTTCCACACCGAG
TTCATCCACGTCCCCGTCGGCTGCACCTGCGTGCTGCCCCGTTCAGTGTGACCGCCGAGGCCGTGGGGCCCCTA
GACTGGACACGTGTGCTCCCCAGAGGGCACCCCCTATTTATGTGTATTTATTGTTATTTATATGCCTCCCCCAA
CACTACCCTTGGGGTCTGGGCATTCCCCGTGTCTGGAGGACAGCCCCCCACTGTTCTCCTCATCTCCAGCCTCA
GTAGTTGGGGGTAGAAGGAGCTCAGCACCTCTTCCAGCCCTTAAAGCTGCAGAAAAGGTGTCACACGGCTGCCT
GTACCTTGGCTCCCTGTCCTGCTCCCGGCTTCCCTTACCCTATCACTGGCCTCAGGCCCCGCAGGCTGCCTCTT
CCCAACCTCCTTGGAAGTACCCCTGTTTCTTAAACAATTATTTAAGTGTACGTGTATTATTAAACTGATGAACA
CATCCCCAAAA

FIGURE 34

MTLLPGLLFLTWLHTCLAHHDPSLRGHPHSHGTPHCYSAEELPLGQAPPHLLARGAKWGQALPVALVSSLEAAS
HRGRHERPSATTQCPVLRPEEVLEADTHQRSISPWRYRVDTDEDRYPQKLAFAECLCRGCIDARTGRETAALNS
VRLLQSLLVLRRRPCSRDGSGLPTPGAFAFHTEFIHVPVGCTCVLPRSV

| | |
|---|---|
| Signal peptide: | Amino acids 1-18 |
| Tyrosine kinase phosphorylation site: | Amino acids 112-121 |
| N-myristoylation sites: | Amino acids 32-38;55-61;133-139 |
| Leucine zipper pattern: | Amino acids 3-25 |
| Homologous region to IL-17: | Amino acids 99-195 |

FIGURE 35

GTGGCTTCATTTCAGTGGCTGACTTCCAGAGAGCAATATGGCTGGTTCCCCAACATGCCTC
ACCCTCATCTATATCCTTTGGCAGCTCACAGGGTCAGCAGCCTCTGGACCCGTGAAAGAGC
TGGTCGGTTCCGTTGGTGGGGCCGTGACTTTCCCCCTGAAGTCCAAAGTAAAGCAAGTTGA
CTCTATTGTCTGGACCTTCAACACAACCCCTCTTGTCACCATACAGCCAGAAGGGGGCACT
ATCATAGTGACCCAAAATCGTAATAGGGAGAGAGTAGACTTCCCAGATGGAGGCTACTCCC
TGAAGCTCAGCAAACTGAAGAAGAATGACTCAGGGATCTACTATGTGGGGATATACAGCTC
ATCACTCCAGCAGCCCTCCACCCAGGAGTACGTGCTGCATGTCTACGAGCACCTGTCAAAG
CCTAAAGTCACCATGGGTCTGCAGAGCAATAAGAATGGCACCTGTGTGACCAATCTGACAT
GCTGCATGGAACATGGGGAAGAGGATGTGATTTATACCTGGAAGGCCCTGGGGCAAGCAGC
CAATGAGTCCCATAATGGGTCCATCCTCCCCATCTCCTGGAGATGGGGAGAAAGTGATATG
ACCTTCATCTGCGTTGCCAGGAACCCTGTCAGCAGAAACTTCTCAAGCCCCATCCTTGCCA
GGAAGCTCTGTGAAGGTGCTGCTGATGACCCAGATTCCTCCATGGTCCTCCTGTGTCTCCT
GTTGGTGCCCCTCCTGCTCAGTCTCTTTGTACTGGGGCTATTTCTTTGGTTTCTGAAGAGA
GAGAGACAAGAAGAGTACATTGAAGAGAAGAAGAGAGTGGACATTTGTCGGGAAACTCCTA
ACATATGCCCCCATTCTGGAGAGAACACAGAGTACGACACAATCCCTCACACTAATAGAAC
AATCCTAAAGGAAGATCCAGCAAATACGGTTTACTCCACTGTGGAAATACCGAAAAAGATG
GAAAATCCCCACTCACTGCTCACGATGCCAGACACACCAAGGCTATTTGCCTATGAGAATG
TTATCTAGACAGCAGTGCACTCCCCTAAGTCTCTGCTCA

FIGURE 36

MAGSPTCLTLIYILWQLTGSAASGPVKELVGSVGGAVTFPLKSKVKQVDSIVWTFNTTPLV
TIQPEGGTIIVTQNRNRERVDFPDGGYSLKLSKLKKNDSGIYYVGIYSSSLQQPSTQEYVL
HVYEHLSKPKVTMGLQSNKNGTCVTNLTCCMEHGEEDVIYTWKALGQAANESHNGSILPIS
WRWGESDMTFICVARNPVSRNFSSPILARKLCEGAADDPDSSMVLLCLLLVPLLLSLFVLG
LFLWFLKRERQEEYIEEKKRVDICRETPNICPHSGENTEYDTIPHTNRTILKEDPANTVYS
TVEIPKKMENPHSLLTMPDTPRLFAYENVI

FIGURE 37

GTTTCTCATAGTTGGCGTCTTCTAAAGGAAAAACACTAAAATGAGGAACTCAGCGGACCGGGAGCGACGCAGCT
TGAGGGAAGCATCCCTAGCTGTTGGCGCAGAGGGGCGAGGCTGAAGCCGAGTGGCCCGAGGTGTCTGAGGGGCT
GGGGCAAAGGTGAAAGAGTTTCAGAACAAGCTTCCTGGAACCCATGACCCATGAAGTCTTGTCGACATTTATAC
CGTCTGAGGGTAGCAGCTCGAAACTAGAAGAAGTGGAGTGTTGCCAGGGACGGCAGTATCTCTTTGTGTGACCC
TGGCGGCCTATGGGACGTTGGCTTCAGACCTTTGTGATACACCATGCTGCGTGGGACGATGACGGCGTGGAGAG
GAATGAGGCCTGAGGTCACACTGGCTTGCCTCCTCCTAGCCACAGCAGGCTGCTTTGCTGACTTGAACGAGGTC
CCTCAGGTCACCGTCCAGCCTGCGTCCACCGTCCAGAAGCCCGGAGGCACTGTGATCTTGGGCTGCGTGGTGGA
ACCTCCAAGGATGAATGTAACCTGGCGCCTGAATGGAAAGGAGCTGAATGGCTCGGATGATGCTCTGGGTGTCC
TCATCACCCACGGGACCCTCGTCATCACTGCCCTTAACAACCACACTGTGGGACGGTACCAGTGTGTGGCCCGG
ATGCCTGCGGGGGCTGTGGCCAGCGTGCCAGCCACTGTGACACTAGCCAATCTCCAGGACTTCAAGTTAGATGT
GCAGCACGTGATTGAAGTGGATGAGGGAAACACAGCAGTCATTGCCTGCCACCTGCCTGAGAGCCACCCCAAAG
CCCAGGTCCGGTACAGCGTCAAACAAGAGTGGCTGGAGGCCTCCAGAGGTAACTACCTGATCATGCCCTCAGGG
AACCTCCAGATTGTGAATGCCAGCCAGGAGGACGAGGGCATGTACAAGTGTGCAGCCTACAACCCAGTGACCCA
GGAAGTGAAAACCTCCGGCTCCAGCGACAGGCTACGTGTGCGCCGCTCCACCGCTGAGGCTGCCCGCATCATCT
ACCCCCCAGAGGCCCAAACCATCATCGTCACCAAAGGCCAGAGTCTCATTCTGGAGTGTGTGGCCAGTGGAATC
CCACCCCCACGGGTCACCTGGGCCAAGGATGGGTCCAGTGTCACCGGCTACAACAAGACGCGCTTCCTGCTGAG
CAACCTCCTCATCGACACCACCAGCGAGGAGGACTCAGGCACCTACCGCTGCATGGCCGACAATGGGGTTGGGC
AGCCCGGGGCAGCGGTCATCCTCTACAATGTCCAGGTGTTTGAACCCCCTGAGGTCACCATGGAGCTATCCCAG
CTGGTCATCCCCTGGGGCCAGAGTGCCAAGCTTACCTGTGAGGTGCGTGGGAACCCCCCGCCCTCCGTGCTGTG
GCTGAGGAATGCTGTGCCCCTCATCTCCAGCCAGCGCCTCCGGCTCTCCCGCAGGGCCCTGCGCGTGCTCAGCA
TGGGGCCTGAGGACGAAGGCGTCTACCAGTGCATGGCCGAGAACGAGGTTGGGAGCGCCCATGCCGTAGTCCAG
CTGCGGACCTCCAGGCCAAGCATAACCCCAAGGCTATGGCAGGATGCTGAGCTGGCTACTGGCACACCTCCTGT
ATCACCCTCCAAACTCGGCAACCCTGAGCAGATGCTGAGGGGGCAACCGGCGCTCCCCAGACCCCCAACGTCAG
TGGGGCCTGCTTCCCCGAAGTGTCCAGGAGAGAAGGGGCAGGGGGCTCCCGCCGAGGCTCCCATCATCCTCAGC
TCGCCCCGCACCTCCAAGACAGACTCATATGAACTGGTGTGGCGGCCTCGGCATGAGGGCAGTGGCCGGGCGCC
AATCCTCTACTATGTGGTGAAACACCGCAAGCAGGTCACAAATTCCTCTGACGATTGGACCATCTCTGGCATTC
CAGCCAACCAGCACCGCCTGACCCTCACCAGACTTGACCCCGGGAGCTTGTATGAAGTGGAGATGGCAGCTTAC
AACTGTGCGGGAGAGGGCCAGACAGCCATGGTCACCTTCCGAACTGGACGGCGGCCCAAACCCGAGATCATGGC
CAGCAAAGAGCAGCAGATCCAGAGAGACGACCCTGGAGCCAGTCCCCAGAGCAGCAGCCAGCCAGACCACGGCC
GCCTCTCCCCCCCAGAAGCTCCCGACAGGCCCACCATCTCCACGGCCTCCGAGACCTCAGTGTACGTGACCTGG
ATTCCCCGTGGGAATGGTGGGTTCCCAATCCAGTCCTTCCGTGTGGAGTACAAGAAGCTAAAGAAAGTGGGAGA
CTGGATTCTGGCCACCAGCGCCATCCCCCCATCGCGGCTGTCCGTGGAGATCACGGGCCTAGAGAAAGGCACCT
CCTACAAGTTTCGAGTCCGGGCTCTGAACATGCTGGGGGAGAGCGAGCCCAGCGCCCCCTCTCGGCCCTACGTG
GTGTCGGGCTACAGCGGTCGCGTGTACGAGAGGCCCGTGGCAGGTCCTTATATCACCTTCACGGATGCGGTCAA
TGAGACCACCATCATGCTCAAGTGGATGTACATCCCAGCAAGTAACAACAACACCCCAATCCATGGCTTTTATA
TCTATTATCGACCCACAGACAGTGACAATGATAGTGACTACAAGAAGGATATGGTGGAAGGGGACAAGTACTGG
CACTCCATCAGCCACCTGCAGCCAGAGACCTCCTACGACATTAAGATGCAGTGCTTCAATGAAGGAGGGGAGAG
CGAGTTCAGCAACGTGATGATCTGTGAGACCAAAGCTCGGAAGTCTTCTGGCCAGCCTGGTCGACTGCCACCCC
CAACTCTGGCCCCACCACAGCCGCCCCTTCCTGAAACCATAGAGCGGCCGGTGGGCACTGGGGCCATGGTGGCT
CGCTCCAGCGACCTGCCCTATCTGATTGTCGGGGTCGTCCTGGGCTCCATCGTTCTCATCATCGTCACCTTCAT
CCCCTTCTGCTTGTGGAGGGCCTGGTCTAAGCAAAAACATACAACAGACCTGGGTTTTCCTCGAAGTGCCCTTC
CACCCTCCTGCCCGTATACTATGGTGCCATTGGAGGACTCCCAGGCCACCAGGCCAGTGGACAGCCCTACCTC

AGTGGCATCAGTGGACGGGCCTGTGCTAATGGGATCCACATGAATAGGGGCTGCCCCTCGGCTGCAGTGGGCTA

FIGURE 37 Continued

CCCGGGCATGAAGCCCCAGCAGCACTGCCCAGGCGAGCTTCAGCAGCAGAGTGACACCAGCAGCCTGCTGAGGC
AGACCCATCTTGGCAATGGATATGACCCCCAAAGTCACCAGATCACGAGGGGTCCCAAGTCTAGCCCGGACGAG
GGCTCTTTCTTATACACACTGCCCGACGACTCCACTCACCAGCTGCTGCAGCCCCATCACGACTGCTGCCAACG
CCAGGAGCAGCCTGCTGCTGTGGGCCAGTCAGGGGTGAGGAGAGCCCCCGACAGTCCTGTCCTGGAAGCAGTGT
GGGACCCTCCATTTCACTCAGGGCCCCCATGCTGCTTGGGCCTTGTGCCAGTTGAAGAGGTGGACAGTCCTGAC
TCCTGCCAAGTGAGTGGAGGAGACTGGTGTCCCCAGCACCCCGTAGGGGCCTACGTAGGACAGGAACCTGGAAT
GCAGCTCTCCCCGGGGCCACTGGTGCGTGTGTCTTTTGAAACACCACCTCTCACAATTTAGGCAGAAGCTGATA
TCCCAGAAAGACTATATATTGTTTTTTTTTTAAAAAAAAAAGAAGAAAAAAGAGACAGAGAAAATTGGTATTTA
TTTTTCTATTATAGCCATATTTATATATTTATGCACTTGTAAATAAATGTATATGTTTTATAATTCTGGAGAGA
CATAAGGAGTCCTACCCGTTGAGGTTGGAGAGGGAAAATAAAGAAGCTGCCACCTAACAGGAGTCACCCAGGAA
AGCACCGCACAGGCTGGCGCGGGACAGACTCCTAACCTGGGGCCTCTGCAGTGGCAGGCGAGGCTGCAGGAGGC
CCACAGATAAGCTGGCAAGAGGAAGGATCCCAGGCACATGGTTCATCACGAGCATGAGGGAACAGCAAGGGGCA
CGGTATCACAGCCTGGAGACACCCACACAGATGGCTGGATCCGGTGCTACGGGAAACATTTTCCTAAGATGCCC
ATGAGAACAGACCAAGATGTGTACAGCACTATGAGCATTAAAAAACCTTCCAGAATCAATAATCCGTGGCAACA
TATCTCTGTAAAAACAAACACTGTAACTTCTAAATAAATGTTTAGTCTTCCCTGTAAAA

FIGURE 38

MLRGTMTAWRGMRPEVTLACLLLATAGCFADLNEVPQVTVQPASTVQKPGGTVILGCVVEPPRMNVTWRLNGKE
LNGSDDALGVLITHGTLVITALNNHTVGRYQCVARMPAGAVASVPATVTLANLQDFKLDVQHVIEVDEGNTAVI
ACHLPESHPKAQVRYSVKQEWLEASRGNYLIMPSGNLQIVNASQEDEGMYKCAAYNPVTQEVKTSGSSDRLRVR
RSTAEAARIIYPPEAQTIIVTKGQSLILECVASGIPPPRVTWAKDGSSVTGYNKTRFLLSNLLIDTTSEEDSGT
YRCMADNGVGQPGAAVILYNVQVFEPPEVTMELSQLVIPWGQSAKLTCEVRGNPPPSVLWLRNAVPLISSQRLR
LSRRALRVLSMGPEDEGVYQCMAENEVGSAHAVVQLRTSRPSITPRLWQDAELATGTPPVSPSKLGNPEQMLRG
QPALPRPPTSVGPASPKCPGEKGQGAPAEAPIILSSPRTSKTDSYELVWRPRHEGSGRAPILYYVVKHRKQVTN
SSDDWTISGIPANQHRLTLTRLDPGSLYEVEMAAYNCAGEGQTAMVTFRTGRRPKPEIMASKEQQIQRDDPGAS
PQSSSQPDHGRLSPPEAPDRPTISTASETSVYVTWIPRGNGGFPIQSFRVEYKKLKKVGDWILATSAIPPSRLS
VEITGLEKGTSYKFRVRALNMLGESEPSAPSRPYVVSGYSGRVYERPVAGPYITFTDAVNETTIMLKWMYIPAS
NNNTPIHGFYIYYRPTDSDNDSDYKKDMVEGDKYWHSISHLQPETSYDIKMQCFNEGGESEFSNVMICETKARK
SSGQPGRLPPPTLAPPQPPLPETIERPVGTGAMVARSSDLPYLIVGVVLGSIVLIIVTFIPFCLWRAWSKQKHT
TDLGFPRSALPPSCPYTMVPLGGLPGHQASGQPYLSGISGRACANGIHMNRGCPSAAVGYPGMKPQQHCPGELQ
QQSDTSSLLRQTHLGNGYDPQSHQITRGPKSSPDEGSFLYTLPDDSTHQLLQPHHDCCQRQEQPAAVGQSGVRR
APDSPVLEAVWDPPFHSGPPCCLGLVPVEEVDSPDSCQVSGGDWCPQHPVGAYVGQEPGMQLSPGPLVRVSFET
PPLTI

Signal peptide:

amino acids 1-30

Transmembrane domain:

amino acids 16-30 (type II), 854-879

FIGURE 39

CATTTCCAACAAGAGCACTGGCCAAGTCAGCTTCTTCTGAGAGAGTCTCTAGAAGACATGA
TGCTACACTCAGCTTTGGGTCTCTGCCTCTTACTCGTCACAGTTTCTTCCAACCTTGCCAT
TGCAATAAAAAAGGAAAAGAGGCCTCCTCAGACACTCTCAAGAGGATGGGGAGATGACATC
ACTTGGGTACAAACTTATGAAGAAGGTCTCTTTTATGCTCAAAAAAGTAAGAAGCCATTAA
TGGTTATTCATCACCTGGAGGATTGTCAATACTCTCAAGCACTAAAGAAAGTATTTGCCCA
AAATGAAGAAATACAAGAAATGGCTCAGAATAAGTTCATCATGCTAAACCTTATGCATGAA
ACCACTGATAAGAATTTATCACCTGATGGGCAATATGTGCCTAGAATCATGTTTGTAGACC
CTTCTTTAACAGTTAGAGCTGACATAGCTGGAAGATACTCTAACAGATTGTACACATATGA
GCCTCGGGATTTACCCCTATTGATAGAAAACATGAAGAAAGCATTAAGACTTATTCAGTCA
GAGCTATAAGAGATGATGGAAAAAAGCCTTCACTTCAAAGAAGTCAAATTTCATGAAGAAA
ACCTCTGGCACATTGACAAATACTAAATGTGCAAGTATATAGATTTTGTAATATTACTATT
TAGTTTTTTTAATGTGTTTGCAATAGTCTTATTAAAATAAATGTTTTTTAAATCTGA

FIGURE 40

</usr/seqdb2/sst/DNA/Dnaseqs.min/ss.DNA64896
<subunit 1 of 1, 166 aa, 1 stop
<MW: 19171, pI: 8.26, NX(S/T): 1
MMLHSALGLCLLLVTVSSNLAIAIKKEKRPPQTLSRGWGDDITWVQTYEEGLFYAQKSKKP
LMVIHHLEDCQYSQALKKVFAQNEEIQEMAQNKFIMLNLMHETTDKNLSPDGQYVPRIMFV
DPSLTVRADIAGRYSNRLYTYEPRDLPLLIENMKKALRLIQSEL

Important features:

Signal peptide:

amino acids 1-23

N-myristoylation site.

amino acids 51-57

FIGURE 41

CTAGCCTGCGCCAAGGGGTAGTGAGACCGCGCGGCAACAGCTTGCGGCTGCGGGGAGCTCC
CGTGGGCGCTCCGCTGGCTGTGCAGGCGGCCATGGATTCCTTGCGGAAAATGCTGATCTCA
GTCGCAATGCTGGGCGCAGGGGCTGGCGTGGGCTACGCGCTCCTCGTTATCGTGACCCCGG
GAGAGCGGCGGAAGCAGGAAATGCTAAAGGAGATGCCACTGCAGGACCCAAGGAGCAGGGA
GGAGGCGGCCAGGACCCAGCAGCTATTGCTGGCCACTCTGCAGGAGGCAGCGACCACGCAG
GAGAACGTGGCCTGGAGGAAGAACTGGATGGTTGGCGGCGAAGGCGGCGCCAGCGGGAGGT
CACCGTGAGACCGGACTTGCCTCCGTGGGCGCCGGACCTTGGCTTGGGCGCAGGAATCCGA
GGCAGCCTTTCTCCTTCGTGGGCCCAGCGGAGAGTCCGGACCGAGATACCATGCCAGGACT
CTCCGGGGTCCTGTGAGCTGCCGTCGGGTGAGCACGTTTCCCCCAAACCCTGGACTGACTG
CTTTAAGGTCCGCAAGGCGGGCCAGGGCCGAGACGCGAGTCGGATGTGGTGAACTGAAAGA
ACCAATAAAATCATGTTCCTCCAAAAAAAAAAAAAAAAAAAAAAAAAAAAAAAAAAAAAAA
AAAAAAAAAAAAAAAAAAAAAA

FIGURE 42

MDSLRKMLISVAMLGAGAGVGYALLVIVTPGERRKQEMLKEMPLQDPRSREEAARTQQLLL
ATLQEAATTQENVAWRKNWMVGGEGGASGRSP

Signal peptide:

amino acids 1-18

FIGURE 43

GACCGGTCCCTCCGGTCCTGGATGTGCGGACTCTGCTGCAGCGAGGGCTGCAGGCCCGCCGGGCGGTGCTCACC
GTGCCCTGGCTGGTGGAGTTTCTCTCCTTTGCTGACCATGTTGTTCCCTTGCTGGAATATTACCGGGACATCTT
CACTCTCCTGCTGCGCCTGCACCGGAGCTTGGTGTTGTCGCAGGAGAGTGAGGGGAAGATGTGTTTCCTGAACA
AGCTGCTGCTACTTGCTGTCCTGGGCTGGCTTTTCCAGATTCCCACAGTCCCTGAGGACTTGTTCTTTCTGGAA
GAGGGTCCCTCATATGCCTTTGAGGTGGACACAGTAGCCCCAGAGCATGGCTTGGACAATGCGCCTGTGGTGGA
CCAGCAGCTGCTCTACACCTGCTGCCCCTACATCGGAGAGCTCCGGAAACTGCTCGCTTCGTGGGTGTCAGGCA
GTAGTGGACGGAGTGGGGGCTTCATGAGGAAAATCACCCCCACCACTACCACCAGCCTGGGAGCCCAGCCTTCC
CAGACCAGCCAGGGGCTGCAGGCACAGCTCGCCCAGGCCTTTTTCCACAACCAGCCGCCCTCCTTGCGCCGGAC
CGTAGAGTTCGTGGCAGAAAGAATTGGATCAAACTGTGTCAAACATATCAAGGCTACACTGGTGGCAGATCTGG
TGCGCCAGGCAGAGTCACTTCTCCAAGAGCAGCTGGTGACACAGGGAGAGGAAGGGGGAGACCCAGCCCAGCTG
TTGGAGATCTTGTGTTCCCAGCTGTGCCCTCACGGGGCCCAGGCATTGGCCCTGGGGCGGGAGTTCTGTCAAAG
GAAGAGCCCTGGGGCTGTGCGGGCGCTGCTTCCAGAGGAGACCCCGGCAGCCGTTCTGAGCAGTGCAGAGAACA
TTGCTGTGGGGCTTGCAACAGAGAAAGCCTGTGCTTGGCTGTCAGCCAACATCACAGCACTGATCAGGAGGGAG
GTGAAAGCAGCAGTGAGTCGCACACTTCGAGCCCAGGGTCCTGAACCTGCTGCCCGGGGGGAGCGGAGGGGCTG
CTCCCGCGCCTGACGTGCTCTCCTTGGCCGTGGGGCCACGGGACCCTGACGAGGGAGTCTCCCCAGAGCATCTG
GAACAGCTCCTAGGCCAGCTGGGCCAGACGCTGCGGTGCCGCCAGTTCCTGTGCCCACCTGCTGAGCAGCATCT
GGCAAAGTGCTCTGTGGAGTTAGCTTCCCTCCTCGTTGCAGATCAAATTCCTATCCTAGGGCCCCCGGCACAGT
ACAGGCTGGAGAGAGGGCAGGCTCGAAGGCTTCTGCACATGCTGCTTTCCTTGTGGAAGGAAGACTTTCAGGGG
CCGGTTCCGCTGCAGCTGCTGCTGAGCCCAAGAAATGTGGGGCTTCTGGCAGACACAAGGCCAAGGGAGTGGGA
CTTGCTGCTATTCTTGCTACGGGAGCTGGTGGAGAAGGGTCTGATGGGACGGATGGAGATAGAGGCCTGCCTGG
GCAGCCTCCACCAGGCCCAGTGGCCAGGGGACTTTGCTGAAGAATTAGCAACACTGTCTAATCTGTTTCTAGCC
GAGCCCCACCTGCCAGAACCCCAGCTAAGAGCCTGTGAGTTGGTGCAGCCAAACCGGGGCACTGTGCTGGCCCA
GAGCTAGGGCTGAGAAGTGGCCCTGCCTTGGGCATTGCACCAGAACCCTGGACCCCCGCCTCACGAGGAGGCCC
AAGTGCCCAATGCAGACCCTCACTGGTTGGGGTGTAGCTGGGTCTACAGTCAGACTTCCTGCTCTAAGGGTGTC
ACTGCCTGGCATCCCACCACGCGAATCCTAGAGGAAGGAGAGTTGGCCTGATTTGGGATTATGGCAGAAAAGTC
CAGAGATGCCAGTCCTGGAGTAGAAGAGGTGGTGTTTGTTTATCTCTTGGATACTAAATGAAATGAGGTGTGTG
GGCTTGTCAACACAGAATTCAAGCCTCATTTGCTATCCCAGCATCTCTTAAAACTTTGTAGTCTTGGAATTCAT
GACAGAGGCAAATGACTCCTGCTTAACTTATGAAGAAAGTTAAAACATGAATCTTGGGAGTCTACATTTTCTTA
TCACCAGGAGCTGGACTGCCATCTCCTTATAAATGCCTAACACAGGCCGGGTCTGGTGGCTCATGCCTGTAATC
CCAGCACTTTGAGAGGCCTGAGGTCGGCGGACTGCCTGAGGTCAGGAATTCAAGACCAGCCTGGCCAACATGGC
AAAACCCCATCTCTACTAAAAATAAAAAAATTATTAGCTGGGCATGGTGGTGTGTGCCTGTAATCCCAGCTACT
CAGGAGGATGAGGCAGGAGACCTGCTTGAACCTGGAGGTGGAGGTTGCAGTGAGCCGAGGTCGCACCACTGCAC
TCCAGTCTGGGTAACAGAGCGAGACTTTCTAGAAAAAGCCTAACAAACAGATAAGGTAGGACTCAACCAACTGA
AACCTGACTTTCCCCCTGTACCTTCAGCCCCTGTGCAGGTAGTAACCTCTTGAGACCTCTCCCTGACCAGGGAC
CAAGCACAGGGCATTTAGAGCTTTTTAGAATAAACTGGTTTTCTTTAAAAAAAAAAAAAAAAAAAAGGGCGGCCG
CCCTTTTTTTTTTTTTTTTTTTTTTTTTTTTTTTTTTTTTTTTTTTTTTTAAAAAGGGCTTTTATTAAAATTC
TCCCCACACGATGGCTCCTGCAATCTGCCACAGCTCTGGGGCGTGTCCTGTAGGGAAAGGCCCTGTTTTCCCTG
AGGCGGGGCTGGGCTTGTCCATGGGTCCGCGGAGCTGGCCGTGCTTGGCGCCCTGGCGTGTGTCTAGCTGCTTC
TTGCCGGGCACAGAGCTGCGGGGTCTGGGGGCACCGGGAGCTAAGAGCAGGCTCTGGTGCAGGGGTGGAGGCCT
GTCTCTTAACCGACACCCTGAGGTGCTCCTGAGATGCTGGGTCCACCCTGAGTGGCACGGGGAGCAGCTGTGGC
CGGTGCTCCTTCYTAGGCCAGTCCTGGGGAAACTAAGCTCGGGCCCTTCTTTGCAAAGACCGAGGATGGGGTGG
GTGTGGGGGACTCATGGGGAATGGCCTGAGGAGCTACGTGTGAAGAGGGCGCCGGTTTGTTGGCTGCAGCGGCC

FIGURE 43 Continued

TGGAGCGCCTCTCTCCTGAGCCTCAGTTTCCCTTTCCGTCTAATGAAGAACATGCCGTCTCGGTGTCTCAGGGC
TATTAGGACTTGCCCTCAGGAAGTGGCCTTGGACGAGCGTCATGTTATTTTCACAACTGTCCTGCGACGTTGGC
CTGGGCACGTCATGGAATGGCCCATGTCCCTCTGCTGCGTGGACGTCGCGGTCGGGAGTGCGCAGCCAGAGGCG
GGGCCAGACGTGCGCCTGGGGGTGAGGGGAGGCGCCCCGGGAGGGCCTCACAGGAAGTTGGGCTCCCGCACCAC
CAGGCAGGGCGGGCTCCCGCCGCCGCCGCCGCCACCACCGTCCAGGGGCCGGTAGACAAAGTGGAAGTCGCGCT
TGGGCTCGCTGCGCAGCAGGTAGCCCTTGATGCAGTGCGGCAGCGCGTCGTCCGCCAGCTGGAAGCAGCGCCCG
TCCACCAGCACGAACAGCCGGTGCGCCT

FIGURE 44

MCFLNKLLLLAVLGWLFQIPTVPEDLFFLEEGPSYAFEVDTVAPEHGLDNAPVVDQQLLYTCCPYIGELRKLLA
SWVSGSSGRSGGFMRKITPTTTTSLGAQPSQTSQGLQAQLAQAFFHNQPPSLRRTVEFVAERIGSNCVKHIKAT
LVADLVRQAESLLQEQLVTQGEEGGDPAQLLEILCSQLCPHGAQALALGREFCQRKSPGAVRALLPEETPAAVL
SSAENIAVGLATEKACAWLSANITALIRREVKAAVSRTLRAQGPEPAARGERRGCSRA

Signal peptide:
amino acids 1-18

N-glycosylation site.
amino acids 244-248 cAMP- and cGMP-dependent protein kinase phosphorylation site.
amino acids 89-93

Casein kinase II phosphorylation site.
amino acids 21-25, 167-171, 223-227

N-myristoylation site.
amino acids 100-106, 172-178, 207-213

Microbodies C-terminal targeting signal.
amino acids 278-282

FIGURE 45

CCCACGCGTCCGCCCACGCGTCCGCCCACGCGTCCGCCCACGCGTCCGCCCACGCGTCCGCCCACGCGTCCGCC
CACGCGTCCGGTGCAAGCTCGCGCCGCACACTGCCTGGTGGAGGGAAGGAGCCCGGGCGCCTCTCGCCGCTCCC
CGCGCCGCCGTCCGCACCTCCCCACCGCCCGCCGCCCGCCGCCCGCCGCCCGCAAAGCATGAGTGAGCCCGCTC
TCTGCAGCTGCCCGGGGCGCGAATGGCAGGCTGTTTCCGCGGAGTAAAAGGTGGCGCCGGTCAGTGGTCGTTTC
CAATGACGGACATTAACCAGACTGTCAGATCCTGGGGAGTCGCGAGCCCCGAGTTTGGAGTTTTTTCCCCCCAC
AACGTCACAGTCCGAACTGCAGAGGGAAAGGAAGGCGGCAGGAAGGCGAAGCTCGGGCTCCGGCACGTAGTTGG
GAAACTTGCGGGTCCTAGAAGTCGCCTCCCCGCCTTGCCGGCCGCCCTTGCAGCCCCGAGCCGAGCAGCAAAGT
GAGACATTGTGCGCCTGCCAGATCCGCCGGCCGCGGACCGGGGCTGCCTCGGAAACACAGAGGGGTCTTCTCTC
GCCCTGCATATAATTAGCCTGCACACAAAGGGAGCAGCTGAATGGAGGTTGTCACTCTCTGGAAAAGGATTTCT
GACCGAGCGCTTCCAATGGACATTCTCCAGTCTCTCTGGAAAGATTCTCGCTAATGGATTTCCTGCTGCTCGGT
CTCTGTCTATACTGGCTGCTGAGGAGGCCCTCGGGGGTGGTCTTGTGTCTGCTGGGGGCCTGCTTTCAGATGCT
GCCCGCCGCCCCCAGCGGGTGCCCGCAGCTGTGCCGGTGCGAGGGGCGGCTGCTGTACTGCGAGGCGCTCAACC
TCACCGAGGCGCCCCACAACCTGTCCGGCCTGCTGGGCTTGTCCCTGCGCTACAACAGCCTCTCGGAGCTGCGC
GCCGGCCAGTTCACGGGGTTAATGCAGCTCACGTGGCTCTATCTGGATCACAATCACATCTGCTCCGTGCAGGG
GGACGCCTTTCAGAAACTGCGCCGAGTTAAGGAACTCACGCTGAGTTCCAACCAGATCACCCAACTGCCCAACA
CCACCTTCCGGCCCATGCCCAACCTGCGCAGCGTGGACCTCTCGTACAACAAGCTGCAGGCGCTCGCGCCCGAC
CTCTTCCACGGGCTGCGGAAGCTCACCACGCTGCATATGCGGGCCAACGCCATCCAGTTTGTGCCCGTGCGCAT
CTTCCAGGACTGCCGCAGCCTCAAGTTTCTCGACATCGGATACAATCAGCTCAAGAGTCTGGCGCGCAACTCTT
TCGCCGGCTTGTTTAAGCTCACCGAGCTGCACCTCGAGCACAACGACTTGGTCAAGGTGAACTTCGCCCACTTC
CCGCGCCTCATCTCCCTGCACTCGCTCTGCCTGCGGAGGAACAAGGTGGCCATTGTGGTCAGCTCGCTGGACTG
GGTTTGGAACCTGGAGAAAATGGACTTGTCGGGCAACGAGATCGAGTACATGGAGCCCCATGTGTTCGAGACCG
TGCCGCACCTGCAGTCCCTGCAGCTGGACTCCAACCGCCTCACCTACATCGAGCCCCGGATCCTCAACTCTTGG
AAGTCCCTGACAAGCATCACCCTGGCCGGGAACCTGTGGGATTGCGGGCGCAACGTGTGTGCCCTAGCCTCGTG
GCTCAGCAACTTCCAGGGGCGCTACGATGGCAACTTGCAGTGCGCCAGCCCGGAGTACGCACAGGGCGAGGACG
TCCTGGACGCCGTGTACGCCTTCCACCTGTGCGAGGATGGGGCCGAGCCCACCAGCGGCCACCTGCTCTCGGCC
GTCACCAACCGCAGTGATCTGGGGCCCCCTGCCAGCTCGGCCACCACGCTCGCGGACGGCGGGGAGGGGCAGCA
CGACGGCACATTCGAGCCTGCCACCGTGGCTCTTCCAGGCGGCGAGCACGCCGAGAACGCCGTGCAGATCCACA
AGGTGGTCACGGGCACCATGGCCCTCATCTTCTCCTTCCTCATCGTGGTCCTGGTGCTCTACGTGTCCTGGAAG
TGTTTCCCAGCCAGCCTCAGGCAGCTCAGACAGTGCTTTGTCACGCAGCGCAGGAAGCAAAAGCAGAAACAGAC
CATGCATCAGATGGCTGCCATGTCTGCCCAGGAATACTACGTTGATTACAAACCGAACCACATTGAGGGAGCCC
TGGTGATCATCAACGAGTATGGCTCGTGTACCTGCCACCAGCAGCCCGCGAGGGAATGCGAGGTGTGATTGTCC
CAGTGGCTCTCAACCCATGCGCTACCAAATACGCCTGGGCAGCCGGGACGGGCCGGCGGGCACCAGGCTGGGGT
CTCCTTGTCTGTGCTCTGATATGCTCCTTGACTGAAACTTTAAGGGGATCTCTCCCAGAGACTTGACATTTTAG
CTTTATTGTGTCTTAAAAACAAAAGCGAATTAAAACACAACAAAAAACCCCACCCCACAACCTTCAGGACAGTC
TATCTTAAATTTCATATGAGAACTCCTTCCTCCCTTTGAAGATCTGTCCATATTCAGGAATCTGAGAGTGTAAA
AAAGGTGGCCATAAGACAGAGAGAGAATAATCGTGCTTTGTTTTATGCTACTCCTCCCACCCTGCCCATGATTA
AACATCATGTATGTAGAAGATCTTAAGTCCATACGCATTTCATGAAGAACCATTGGAAAGAGGAATCTGCAATC
TGGGAGCTTAAGAGCAAATGATGACCATAGAAAGCTATGTTCTTACTTTGTGTGTGTGTCTGTATGTTTCTGCG
TTGTGTGTCTTTGTAGGCAAGCAAACGTTGTCTACACAAACGGGAATTTAGCTCACATCATTTCATGCCCCTGT
GCCTCTAGCTCTGGAGATTGGTGGGGGAGGTGGGGGAAACGGCAGGAATAAGGGAAAGTGGTAGTTTTAACT
AAGGTTTTGTAACACTTGAAATCTTTTCTTTCTCAAATTAATTATCTTTAAGCTTCAAGAAACTTGCTCTGACC
CCTCTAAGCAAACTACTAAGCATTTAAAAGAGAATCTAATTTTTAAAGGTGTAGCACCTTTTTTTTTATTCTTC
CCACAGAGGGTGCTAATCTCATTATGCTGTGCTATCTGAAAAGAACTTAAGGCCACAATTCACGTCTCGTCCTG
GGCATTGTGATGGATTGACCCTCCATTTGCAGTACCTTCCCAGCTGATTAAAGTTCAGCAGTGGTATTGAGGTT
TTTCGAATATTTATATAGAAAAAAAGTCTTTTCACATGACAAATGACACTCTCACACCAGTCTTAGCCCTAGTA
GTTTTTTAGGTTGGACCAGAGGAAGCAGGTTAAATGAGACCTGTCCTCTGCTGCACTCAGAAAAAATAGGCAGT
CCCTGATGCTCAGATCTTAGCCTTGATATTAATAGTTGAGACCACCTACCCACAATGCAGCCTATACTCCCAAG
ACTACAAAGTTACCATCGCAAAGGAAAGGTTATTCCAGTAAAAGGAAATAGTTTTCTCAACCATTTAAAAATAT
TCTTCTGAACTCATCAAAGTAGAAGAGCCCCCAACCTTTTCTCTCTGCCTTCAAGAAGGCAGACATTTGGTATG
ATTTAGCATCAACAACACATTTATGAGTATATGTAAGTAATCAGAGGGGCAAATGCCACTTGTTATTCCTCCCA
AGTTTTCCAAGCAAGTACACACAGATCTCTGGTAGGATTAGGGGCCACTTGTGTTTCCGGCTTATTTTAGTCGA
CTTGTCAGCAAGTTTGATGCCTAGTCTATCTGACATGGCCCAGTAGAACAGGGCATTGATGGATCACATGAGAT
GGTAGAAGGAACATCATCACATACCCCTCTCACAGAGAAAATTATCAAAGAACCAGAAATTATATCTGTTTTGG
AGCAAGAGTGTCATAATGTTTCAGGGTAGTCAAAATAAACATAAATTATCTCCTCTAGATGAGTGGCGATGTTG
GCTGATTTGGGTCTGCCATTGACAGAATGTCAAATAAAAAGGAATTAGCTAGAATATGACCATTAAATGTGCTT
CTGAAATATATTTTGAGATAGGTTTAGAATGTCA

FIGURE 46

MDFLLLGLCLYWLLRRPSGVVLCLLGACFQMLPAAPSGCPQLCRCEGRLLYCEALNLTEAPHNLSGLLGLSLRY
NSLSELRAGQFTGLMQLTWLYLDHNHICSVQGDAFQKLRRVKELTLSSNQITQLPNTTFRPMPNLRSVDLSYNK
LQALAPDLFHGLRKLTTLHMRANAIQFVPVRIFQDCRSLKFLDIGYNQLKSLARNSFAGLFKLTELHLEHNDLV
KVNFAHFPRLISLHSLCLRRNKVAIVVSSLDWVWNLEKMDLSGNEIEYMEPHVFETVPHLQSLQLDSNRLTYIE
PRILNSWKSLTSITLAGNLWDCGRNVCALASWLSNFQGRYDGNLQCASPEYAQGEDVLDAVYAFHLCEDGAEPT
SGHLLSAVTNRSDLGPPASSATTLADGGEGQHDGTFEPATVALPGGEHAENAVQIHKVVTGTMALIFSFLIVVL
VLYVSWKCFPASLRQLRQCFVTQRRKQKQKQTMHQMAAMSAQEYYVDYKPNHIEGALVIINEYGSCTCHQQPAR
ECEV

FIGURE 47

AGCGGGTCTCGCTTGGGTTCCGCTAATTTCTGTCCTGAGGCGTGAGACTGAGTTCATAGGGTCCTGGGTCCCCG
AACCAGGAAGGGTTGAGGGAACACAATCTGCAAGCCCCCGCGACCCAAGTGAGGGGCCCCGTGTTGGGGTCCTC
CCTCCCTTTGCATTCCCACCCCTCCGGGCTTTGCGTCTTCCTGGGGACCCCCTCGCCGGGAGATGGCCGCGTTG
ATGCGGAGCAAGGATTCGTCCTGCTGCCTGCTCCTACTGGCCGCGGTGCTGATGGTGGAGAGCTCACAGATCGG
CAGTTCGCGGGCCAAACTCAACTCCATCAAGTCCTCTCTGGGCGGGGAGACGCCTGGTCAGGCCGCCAATCGAT
CTGCGGGCATGTACCAAGGACTGGCATTCGGCGGCAGTAAGAAGGGCAAAAACCTGGGGCAGGCCTACCCTTGT
AGCAGTGATAAGGAGTGTGAAGTTGGGAGGTATTGCCACAGTCCCCACCAAGGATCATCGGCCTGCATGGTGTG
TCGGAGAAAAAAGAAGCGCTGCCACCGAGATGGCATGTGCTGCCCCAGTACCCGCTGCAATAATGGCATCTGTA
TCCCAGTTACTGAAAGCATCTTAACCCCTCACATCCCGGCTCTGGATGGTACTCGGCACAGAGATCGAAACCAC
GGTCATTACTCAAACCATGACTTGGGATGGCAGAATCTAGGAAGACCACACACTAAGATGTCACATATAAAAGG
GCATGAAGGAGACCCCTGCCTACGATCATCAGACTGCATTGAAGGGTTTTGCTGTGCTCGTCATTTCTGGACCA
AAATCTGCAAACCAGTGCTCCATCAGGGGGAAGTCTGTACCAAACAACGCAAGAAGGGTTCTCATGGGCTGGAA
ATTTTCCAGCGTTGCGACTGTGCGAAGGGCCTGTCTTGCAAAGTATGGAAAGATGCCACCTACTCCTCCAAAGC
CAGACTCCATGTGTGTCAGAAAATTTGATCACCATTGAGGAACATCATCAATTGCAGACTGTGAAGTTGTGTAT
TTAATGCATTATAGCATGGTGGAAAATAAGGTTCAGATGCAGAAGAATGGCTAAAATAAGAAACGTGATAAGAA
TATAGATGATCACAAAAAGGGAGAAAGAAAACATGAACTGAATAGATTAGAATGGGTGACAAATGCAGTGCAGC
CAGTGTTTCCATTATGCAACTTGTCTATGTAAATAATGTACACATTTGTGGAAAATGCTATTATTAAGAGAACA
AGCACACAGTGGAAATTACTGATGAGTAGCATGTGACTTTCCAAGAGTTTAGGTTGTGCTGGAGGAGAGGTTTC
CTTCAGATTGCTGATTGCTTATACAAATAACCTACATGCCAGATTTCTATTCAACGTTAGAGTTTAACAAAATA
CTCCTAGAATAACTTGTTATACAATAGGTTCTAAAAATAAAATTGCTAAACAAGAAATGAAAACATGGAGCATT
GTTAATTTACAACAGAAAATTACCTTTTGATTTGTAACACTACTTCTGCTGTTCAATCAAGAGTCTTGGTAGAT
AAGAAAAAAATCAGTCAATATTTCCAAATAATTGCAAAATAATGGCCAGTTGTTTAGGAAGGCCTTTAGGAAGA
CAAATAAATAACAAACAAACAGCCACAAATACTTTTTTTTCAAAATTTTAGTTTTACCTGTAATTAATAAGAAC
TGATACAAGACAAAAACAGTTCCTTCAGATTCTACGGAATGACAGTATATCTCTCTTTATCCTATGTGATTCCT
GCTCTGAATGCATTATATTTTCCAAACTATACCCATAAATTGTGACTAGTAAAATACTTACACAGAGCAGAATT
TTCACAGATGGCAAAAAAATTTAAAGATGTCCAATATATGTGGAAAAGAGCTAACAGAGAGATCATTATTTCT
TAAAGATTGGCCATAACCTATATTTTGATAGAATTAGATTGGTAAATACATGTATTCATACATACTCTGTGGTA
ATAGAGACTTAAGCTGGATCTGTACTGCACTGGAGTAAGCAAGAAAATTGGGAAAACTTTTTCGTTTGTTCAGG
TTTTGGCAACACATAGATCATATGTCTGAGGCACAAGTTGGCTGTTCATCTTTGAAACCAGGGGATGCACAGTC
TAAATGAATATCTGCATGGGATTTGCTATCATAATATTTACTATGCAGATGAATTCAGTGTGAGGTCCTGTGTC
CGTACTATCCTCAAATTATTTATTTTATAGTGCTGAGATCCTCAAATAATCTCAATTTCAGGAGGTTTCACAAA
ATGTACTCCTGAAGTAGACAGAGTAGTGAGGTTTCATTGCCCTCTATAAGCTTCTGACTAGCCAATGGCATCAT
CCAATTTTCTTCCCAAACCTCTGCAGCATCTGCTTTATTGCCAAAGGGCTAGTTTCGGTTTTCTGCAGCCATTG
CGGTTAAAAAATATAAGTAGGATAACTTGTAAAACCTGCATATTGCTAATCTATAGACACCACAGTTTCTAAAT
TCTTTGAAACCACTTTACTACTTTTTTTAAACTTAACTCAGTTCTAAATACTTTGTCTGGAGCACAAAACAATA
AAAGGTTATCTTATAGTCGTGACTTTAAACTTTTGTAGACCACAATTCACTTTTTAGTTTTCTTTTACTTAAAT
CCCATCTGCAGTCTCAAATTTAAGTTCTCCCAGTAGAGATTGAGTTTGAGCCTGTATATCTATTAAAAATTTCA
ACTTCCCACATATATTTACTAAGATGATTAAGACTTACATTTTCTGCACAGGTCTGCAAAAACAAAAATTATAA
ACTAGTCCATCCAAGAACCAAAGTTTGTATAAACAGGTTGCTATAAGCTTGTGAAATGAAAATGGAACATTTCA
ATCAAACATTTCCTATATAACAATTATTATATTTACAATTTGGTTTCTGCAATATTTTTCTTATGTCCACCCTT
TTAAAAATTATTATTTGAAGTAATTTATTTACAGGAAATGTTAATGAGATGTATTTTCTTATAGAGATATTTCT
TACAGAAAGCTTTGTAGCAGAATATATTTGCAGCTATTGACTTTGTAATTTAGGAAAAATGTATAATAAGATAA
AATCTATTAAATTTTTCTCCTCTAAAACTGAAAAAAAAAAAAAAAAAAAAAAAAAAAAA

FIGURE 48

MAALMRSKDSSCCLLLLAAVLMVESSQIGSSRAKLNSIKSSLGGETPGQAANRSAGMYQGLAFGGSKKGKNLGQ
AYPCSSDKECEVGRYCHSPHQGSSACMVCRRKKKRCHRDGMCCPSTRCNNGICIPVTESILTPHIPALDGTRHR
DRNHGHYSNHDLGWQNLGRPHTKMSHIKGHEGDPCLRSSDCIEGFCCARHFWTKICKPVLHQGEVCTKQRKKGS
HGLEIFQRCDCAKGLSCKVWKDATYSSKARLHVCQKI

Signal peptide:
amino acids 1-25

FIGURE 49

CGTGGGCCGGGGTCGCGCAGCGGGCTGTGGGCGCGCCCGGAGGAGCGACCGCCGCAGTTCT
CGAGCTCCAGCTGCATTCCCTCCGCGTCCGCCCCACGCTTCTCCCGCTCCGGGCCCCGCAA
TGGCCCAGGCAGTGTGGTCGCGCCTCGGCCGCATCCTCTGGCTTGCCTGCCTCCTGCCCTG
GGCCCCGGCAGGGGTGGCCGCAGGCCTGTATGAACTCAATCTCACCACCGATAGCCCTGCC
ACCACGGGAGCGGTGGTGACCATCTCGGCCAGCCTGGTGGCCAAGGACAACGGCAGCCTGG
CCCTGCCCGCTGACGCCCACCTCTACCGCTTCCACTGGATCCACACCCCGCTGGTGCTTAC
TGGCAAGATGGAGAAGGGTCTCAGCTCCACCATCCGTGTGGTCGGCCACGTGCCCGGGGAA
TTCCCGGTCTCTGTCTGGGTCACTGCCGCTGACTGCTGGATGTGCCAGCCTGTGGCCAGGG
GCTTTGTGGTCCTCCCCATCACAGAGTTCCTCGTGGGGGACCTTGTTGTCACCCAGAACAC
TTCCCTACCCTGGCCCAGCTCCTATCTCACTAAGACCGTCCTGAAAGTCTCCTTCCTCCTC
CACGACCCGAGCAACTTCCTCAAGACCGCCTTGTTTCTCTACAGCTGGGACTTCGGGGACG
GGACCCAGATGGTGACTGAAGACTCCGTGGTCTATTATAACTATTCCATCATCGGGACCTT
CACCGTGAAGCTCAAAGTGGTGGCGGAGTGGGAAGAGGTGGAGCCGGATGCCACGAGGGCT
GTGAAGCAGAAGACCGGGGACTTCTCCGCCTCGCTGAAGCTGCAGGAAACCCTTCGAGGCA
TCCAAGTGTTGGGGCCCACCCTAATTCAGACCTTCCAAAAGATGACCGTGACCTTGAACTT
CCTGGGGAGCCCTCCTCTGACTGTGTGCTGGCGTCTCAAGCCTGAGTGCCTCCCGCTGGAG
GAAGGGGAGTGCCACCCTGTGTCCGTGGCCAGCACAGCGTACAACCTGACCCACACCTTCA
GGGACCCTGGGGACTACTGCTTCAGCATCCGGGCCGAGAATATCATCAGCAAGACACATCA
GTACCACAAGATCCAGGTGTGGCCCTCCAGAATCCAGCCGGCTGTCTTTGCTTTCCCATGT
GCTACACTTATCACTGTGATGTTGGCCTTCATCATGTACATGACCCTGCGGAATGCCACTC
AGCAAAAGGACATGGTGGAGAACCCGGAGCCACCCTCTGGGGTCAGGTGCTGCTGCCAGAT
GTGCTGTGGGCCTTTCTTGCTGGAGACTCCATCTGAGTACCTGGAAATTGTTCGTGAGAAC
CACGGGCTGCTCCCGCCCCTCTATAAGTCTGTCAAAACTTACACCGTGTGAGCACTCCCCC
TCCCCACCCCATCTCAGTGTTAACTGACTGCTGACTTGGAGTTTCCAGCAGGGTGGTGTGC
ACCACTGACCAGGAGGGGTTCATTTGCGTGGGGCTGTTGGCCTGGATCATCCATCCATCTG
TACAGTTCAGCCACTGCCACAAGCCCCTCCCTCTCTGTCACCCCTGACCCCAGCCATTCAC
CCATCTGTACAGTCCAGCCACTGACATAAGCCCCACTCGGTTACCACCCCCTTGACCCCCT
ACCTTTGAAGAGGCTTCGTGCAGGACTTTGATGCTTGGGGTGTTCCGTGTTGACTCCTAGG
TGGGCCTGGCTGCCCACTGCCCATTCCTCTCATATTGGCACATCTGCTGTCCATTGGGGGT
TCTCAGTTTCCTCCCCCAGACAGCCCTACCTGTGCCAGAGAGCTAGAAAGAAGGTCATAAA
GGGTTAAAAATCCATAACTAAAGGTTGTACACATAGATGGGCACACTCACAGAGAGAAGTG
TGCATGTACACACACCACACACACACACACACACACACACACAGAAATATAAACACATGCG
TCACATGGGCATTTCAGATGATCAGCTCTGTATCTGGTTAAGTCGGTTGCTGGGATGCACC
CTGCACTAGAGCTGAAAGGAAATTTGACCTCCAAGCAGCCCTGACAGGTTCTGGGCCCGGG
CCCTCCCTTTGTGCTTTGTCTCTGCAGTTCTTGCGCCCTTTATAAGGCCATCCTAGTCCCT
GCTGGCTGGCAGGGGCCTGGATGGGGGGCAGGACTAATACTGAGTGATTGCAGAGTGCTTT
ATAAATATCACCTTATTTTATCGAAACCCATCTGTGAAACTTTCACTGAGGAAAAGGCCTT
GCAGCGGTAGAAGAGGTTGAGTCAAGGCCGGGCGCGGTGGCTCACGCCTGTAATCCCAGCA
CTTTGGGAGGCCGAGGCGGGTGGATCACGAGATCAGGAGATCGAGACCACCCTGGCTAACA
CGGTGAAACCCCGTCTCTACTAAAAAAATACAAAAAGTTAGCCGGGCGTGGTGGTGGGTGC
CTGTAGTCCCAGCTACTCGGGAGGCTGAGGCAGGAGAATGGTGCGAACCCGGGAGGCGGAG
CTTGCAGTGAGCCCAGATGGCGCCACTGCACTCCAGCCTGAGTGACAGAGCGAGACTCTGT
CTCCA

FIGURE 50

MAQAVWSRLGRILWLACLLPWAPAGVAAGLYELNLTTDSPATTGAVVTISASLVAKDNGSL
ALPADAHLYRFHWIHTPLVLTGKMEKGLSSTIRVVGHVPGEFPVSVWVTAADCWMCQPVAR
GFVVLPITEFLVGDLVVTQNTSLPWPSSYLTKTVLKVSFLLHDPSNFLKTALFLYSWDFGD
GTQMVTEDSVVYYNYSIIGTFTVKLKVVAEWEEVEPDATRAVKQKTGDFSASLKLQETLRG
IQVLGPTLIQTFQKMTVTLNFLGSPPLTVCWRLKPECLPLEEGECHPVSVASTAYNLTHTF
RDPGDYCFSIRAENIISKTHQYHKIQVWPSRIQPAVFAFPCATLITVMLAFIMYMTLRNAT
QQKDMVENPEPPSGVRCCCQMCCGPFLLETPSEYLEIVRENHGLLPPLYKSVKTYTV

Important features of the protein:
Signal peptide:
amino acids 1-24

Transmembrane domain:
amino acids 339-362

N-glycosylation sites.
amino acids 34-37, 58-61, 142-145, 197-200, 300-303 and 364-367

FIGURE 51

CTATGAAGAAGCTTCCTGGAAAACAATAAGCAAAGGAAAACAAATGTGTCCCATCTCACAT
GGTTCTACCCTACTAAAGACAGGAAGATCATAAACTGACAGATACTGAAATTGTAAGAGTT
GGAAACTACATTTTGCAAAGTCATTGAACTCTGAGCTCAGTTGCAGTACTCGGGAAGCCAT
GCAGGATGAAGATGGATACATCACCTTAAATATTAAAACTCGGAAACCAGCTCTCGTCTCC
GTTGGCCCTGCATCCTCCTCCTGGTGGCGTGTGATGGCTTTGATTCTGCTGATCCTGTGCG
TGGGGATGGTTGTCGGGCTGGTGGCTCTGGGGATTTGGTCTGTCATGCAGCGCAATTACCT
ACAAGATGAGAATGAAAATCGCACAGGAACTCTGCAACAATTAGCAAAGCGCTTCTGTCAA
TATGTGGTAAAACAATCAGAACTAAAGGGCACTTTCAAAGGTCATAAATGCAGCCCCTGTG
ACACAAACTGGAGATATTATGGAGATAGCTGCTATGGGTTCTTCAGGCACAACTTAACATG
GGAAGAGAGTAAGCAGTACTGCACTGACATGAATGCTACTCTCCTGAAGATTGACAACCGG
AACATTGTGGAGTACATCAAAGCCAGGACTCATTTAATTCGTTGGGTCGGATTATCTCGCC
AGAAGTCGAATGAGGTCTGGAAGTGGGAGGATGGCTCGGTTATCTCAGAAAATATGTTTGA
GTTTTTGGAAGATGGAAAAGGAAATATGAATTGTGCTTATTTTCATAATGGGAAAATGCAC
CCTACCTTCTGTGAGAACAAACATTATTTAATGTGTGAGAGGAAGGCTGGCATGACCAAGG
TGGACCAACTACCTTAATGCAAAGAGGTGGACAGGATAACACAGATAAGGGCTTTATTGTA
CAATAAAAGATATGTATGAATGCATCAGTAGCTGAAAAAAAAAAAAAA

FIGURE 52

MQDEDGYITLNIKTRKPALVSVGPASSSWWRVMALILLILCVGMVVGLVALGIWSVMQRNY
LQDENENRTGTLQQLAKRFCQYVVKQSELKGTFKGHKCSPCDTNWRYYGDSCYGFFRHNLT
WEESKQYCTDMNATLLKIDNRNIVEYIKARTHLIRWVGLSRQKSNEVWKWEDGSVISENMF
EFLEDGKGNMNCAYFHNGKMHPTFCENKHYLMCERKAGMTKVDQLP

FIGURE 53

CCCTGACCTCCCTGAGCCACACTGAGCTGGAAGCCGCAGAGGTCATCCTGGAGCATGCCCACCGCGGGGAGCAG
ACAACCTCCCAGGTAAGCTGGGAGCAAGACCTGAAGCTGTTTCTTCAGGAGCCTGGTGTATTTTCCCCCACCCC
ACCTCAGCAGTTTCAGCCAGCAGGGACTGATCAGGTGTGTGTCCTGGAGTGGGGAGCAGAAGGCGTGGCTGGCA
AGAGTGGCCTGGAGAAAGAGGTTCAGCGCTTGACCAGCCGAGCTGCCCGTGACTACAAGATCCAGAACCATGGG
CATCGGGTGAGGTGGGGGGGCACAGGTGTCATGTGCACCTTCTTGTCTCAGCAAGAAGAGCTGAGAGAGGGGAT
CTTGGAGCCATTGAGGGTGTCATGGAGCTACAGAGGGGAGGGAAAGGTATTTTAAGGTAACAGTGTGGCACAAT
AGTTAAGAGCACAGTTTTTGGAGCTAGACCGACATAGGTTCAAATTCTCTTCTGTTGCTTCCTAGTTCTGTAGC
CCCAGGTAAGGGAGTGACTTAACCTCTCTGGACTTCAATTTCCTCATCACTAAAGTAGGGCCAATAATAGCACC
CACCTCATAGGGAAGATTAAATGACATAATGTATGTGATGCAACTAGCAAAGTACCAGTCCCATAGTAAGTCAT
GCCCCACAGTATTTCCACCCACCCCTGTTCTCTGCCTTCCCAACCAGGTACTGCAACGACTGGAGCAGAGGCGG
CAGCAGGCTTCAGAGCGGGAGGCTCCAAGCATAGAACAGAGGTTACAGGAAGTGCGAGAGAGCATCCGCCGGGC
ACAGGTGAGCCAGGTGAAGGGGGCTGCCCGGCTGGCCCTGCTGCAGGGGGCTGGCTTAGATGTGGAGCGCTGGC
TGAAGCCAGCCATGACCCAGGCCCAGGATGAGGTGGAGCAGGAGCGGCGGCTCAGTGAGGCTCGGCTGTCCCAG
AGGGACCTCTCTCCAACCGCTGAGGATGCTGAGCTTTCTGACTTTGAGGAATGTGAGGAGACGGGAGAGCTCTT
TGAGGAGCCTGCCCCCCAAGCCCTGGCCACGAGGGCCCTCCCCTGCCCTGCACACGTGGTATTTCGCTATCAGG
CAGGGCGTGAGGATGAGCTGACAATCACGGAGGGTGAGTGGCTGGAGGTCATAGAGGAGGGAGATGCTGACGAA
TGGGTCAAGGCTCGGAACCAGCACGGCGAGGTAGGCTTTGTCCCTGAGCGATATCTCAACTTCCCGGACCTCTC
CCTCCCAGAGAGCAGCCAAGACAGTGACAATCCCTGCGGGGCAGAGCCCACAGCATTCCTGGCACAGGCCCTGT
ACAGCTACACCGGACAGAGTGCAGAGGAGCTGAGCTTCCCTGAGGGGGCACTCATCCGTCTGCTGCCCCGGGCC
CAAGATGGAGTAGATGACGGCTTCTGGAGGGGAGAATTTGGGGGCCGTGTTGGGGTCTTCCCCTCCCTGCTGGT
GGAAGAGCTGCTTGGCCCCCCAGGGCCACCTGAACTCTCTGACCCTGAACAGATGCTGCCGTCCCCTTCTCCTC
CCAGCTTCTCCCCACCTGCACCTACCTCTGTGTTGGATGGCCCCCTGCACCTGTCCTGCCTGGGGACAAAGCC
CTGGACTTCCCTGGGTTCCTGGACATGATGGCACCTCGACTCAGGCCGATGCGTCCACCACCTCCCCCGCCGGC
TAAAGCCCCGGATCCTGGCCACCCAGATCCCCTCACCTGAAGGCCAGGGAAGCCTTGACCCCCAGTGATGCTGC
TGTCCCTATCTTCAAGCTGTCAGACCACACCATCAATGATCCAGAGCAACACAGCCAAAAGCTGGAATCGCCCT
TATTTCCACCCTCACCTCCAAGGGTGGAAACTTGCCCCTTCCCATTTCTAGAGCTGGAACCCACTCCTTTTTTT
CCCATTGTTCTATCATCTCTAGGACCGGAACTACTACCTTCTCTTCTGTCATGACCCTATCTAGGGTGGTGAAA
TGCCTGAAATCTCTGGGGCTGGAAACCATCCATCAAGGTCTCTAGTAGTTCTGGCCCACCTCTTTCCCCACCCT
GGCTCCATGACCCACCCCACTCTGGATGCCAGGGTCACTGGGGTTGGGCTGGGGAGAGGAACAGGCCTTGGGAA
TCAGGAGCTGGAGCCAGGATGCGAAGCAGCTGTAATGGTCTGAGCGGATTTATTGACAATGAATAAAGGGCACG
AAGGCCAGGCCAGGGCCTGGGCCTCTTGTGCTAAGAGGGCAGGGGGCCTACGGTGCTATTGCTTTAGGGGCCCA
CCACGGGCAGGGGCCTGCTCCCAGCTGCCACGCTCTATCATATGGAGCGAGGTGTTGGGGAAGGCGGGGCAGGC
AGCCTGTTGCAGGCAGGGGAAGGAGAAGAGACTGAGGGGCTGTGACCTCTCCTGAGGCCCCCAGCCTGAGACTG
TGCAACTCCAGGTGGAAGTAGAGCTGGTCCCTCAGCTGGGGGGCAGTGCTGTCCAGTGGAGGGGAGGGCTTTCA
CGCCCACCCACCCCCTGGCCCTGCCAGCTGGTAGTCCATCAGCACAATGAAGGAGACTTGGAGAAGAGGAAGAA
TAACACTGTTGCTTCCTGTTCAAGCTGTGTCCAGCTTTTCCCCTGGGGCTCCAGGACCTTCCCTACCTCCACCA
CCAAACCAAGGGATTTATAGCAAAGGCTAAGCCTGCAGTTTACTCTGGGGGTTCAGGGAGCCGAAAGGCTTAAA
TAGTTTAAGTAGGTGATGGGAAGATGAGATTACCTCATTTAGGGCTCAGGCAGACTCACCTCACATACTCCCTG
CTCCCTGTGGTAGAGACACCTGAGAGAAAGGGGAGGGGTCAACAATGAGAGACCAGGAGTAGGTCCTATCAGTG
CCCCCCAGAGTAGAGAGCAATAAGAGCCCAGCCCAGTGCAGTCCCGGCTGTGTTTTCCTACCTGGTGATCAGAA
GTGTCTGGTTTGCTTGGCTGCCCATTTGCCTCTTGAGTGGGCAGCCCTGGGCTTGGGCCCCTCCCTCCGGCCCT
CAGTGTTGGCTCTGCAGAAGCTCTGGGGTTCCCTTCAAGTGCACGAGGGGTTAGGCTGCTGTCCCTGAGTCCTC
CATTCTGTACTGGGGGGCTGGCTAGGACCTGGGGCTGTGGCCTCTCAGGGGGCAGCCTCTCCATGGCAGGCATC
CCTGCCTTGGGCTGCCCTCCCCCAGACCCCTGACCACCCCCTGGGTCCTGTCCCCCACCAGAGCCCCAGCTCCT
GTCTGTGGGGGAGCCATCACGGTGTTCGTGCAGTCCATAGCGCTTCTCAATGTGTGTCACCCGGAACCTGGGAG
GGGAGGGAACACTGGGGTTTAGGACCACAACTCAGAGGCTGCTTGGCCCTCCCCTCTGACCAGGGACATCCTGA
GTTTGGTGGCTACTTCCCTCTGGCCTAAGGTAGGGGAGGCCTTCTCAGATTGTGGGGCACATTGTGTAGCCTGA
CTTCTGCTGGAGCTCCCAGTCCAGGAGGAAAGAGCCAAGGCCCACTTTTGGGATCAGGTGCCTGATCACTGGGC
CCCCTACCTCAGCCCCCCTTTCCCTGGAGCACCTGCCCCACCTGCCCACAGAGAACACAGTGGTCTCCCCTGTC
CGGGGGCGGCTTTTTCCTTCCTTGGAGCGTCCCTGACGGACAAGTGGAGGCCTCTTGCTGCGGCTGCAATGGAT
GCAAGGGGCTGCAGAGCCCAGGTGCACTGTGTGATGATGGGAGGGGGCTCCGTCCTGCAGGCTGGAGGTGGCAT
CCACACTGGACAGCAGGAGGAGGGGAGTGAGGGTAACATTTCCATTTCCCTTCATGTTTTGTTTCTTACGTTCT
TTCAGCATGCTCCTTAAAACCCCAGAAGCCCCAATTTCCCCAAGCCCCATTTTTTCTTGTCTTTATCTAATAAA
CTCAATATTAAG

FIGURE 54

></usr/seqdb2/sst/DNA/Dnaseqs.min/ss.DNA73401

><subunit 1 of 1, 370 aa, 1 stop

><MW: 40685, pI: 4.53, NX(S/T): 0

MQLAKYQSHSKSCPTVFPPTPVLCLPNQVLQRLEQRRQQASEREAPSIEQRLQEVRESIRRAQVSQVKGAARLA

LLQGAGLDVERWLKPAMTQAQDEVEQERRLSEARLSQRDLSPTAEDAELSDFEECEETGELFEEPAPQALATRA

LPCPAHVVFRYQAGREDELTITEGEWLEVIEEGDADEWVKARNQHGEVGFVPERYLNFPDLSLPESSQDSDNPC

GAEPTAFLAQALYSYTGQSAEELSFPEGALIRLLPRAQDGVDDGFWRGEFGGRVGVFPSLLVEELLGPPGPPEL

SDPEQMLPSPSPPSFSPPAPTSVLDGPPAPVLPGDKALDFPGFLDMMAPRLRPMRPPPPPPAKAPDPGHPDPLT

FIGURE 55

CCCACGCGTCCGCCCACGCGTCCGGGTGCCACTCGCGCGCCGGCCGCGCTCCGGGCTTCTCTTTTCCCTCCGAC
GCGCCACGGCTGCCCAGACATTCCGGCTGCCGGGTCTGGAGAGCTCCCCGAACCCCTCCGCGGAGAGGAGCGAG
GCGGCGCCAGGGTGGCCCCCGGGGCGCGCTTGGTCTCGGAGAAGCGGGGACGAGGCCGGAGGATGAGCGACTGA
GGGCGACGCGGGCACTGACGCGAGTTGGGGCCGCGACTACCGGCAGCTGACAGCGCGATGAGCGACTCCCCAGA
GACGCCCTAGCCCGGTGTGCGCGCCAGGCGGAGCGCGCAGGTGGGGCTGGGCTGTTAGTGGTCCGCCCCACGCG
GGTCGCCGGCCGGCCCAGGATGGGCGCTGGCAACCCGGGCCCGCGCCCGCCGCTGCTACCCCTGCGCCCGCTGC
GAGCCCGGCGTCCGGCCCGCGCCCTGCGCTCATGGACGGCGGCTCCCGGCTGGCGGCGGCGCGCCCCCGGGCTG
TGAATGCGACTCGCCCCTCGGCCGCGCTCCCCGCCCGCCCGCCCGCCGGGACGTGGTAGGGGATGCCCAGCTCC
ACTGCGATGGCAGTTGGCGCGCTCTCCAGTTCCCTCCTGGTCACCTGCTGCCTGATGGTGGCTCTGTGCAGTCC
GAGCATCCCGCTGGAGAAGCTGGCCCAGGCACCAGAGCAGCCGGGCCAGGAGAAGCGTGAGCACGCCACTCGGG
ACGGCCCGGGGCGGGTGAACGAGCTCGGGCGCCCGGCGAGGGACGAGGGCGGCAGCGGCCGGGACTGGAAGAGC
AAGAGCGGCCGTGGGCTCGCCGGCCGTGAGCCGTGGAGCAAGCTGAAGCAGGCCTGGGTCTCCCAGGGCGGGGG
CGCCAAGGCCGGGGATCTGCAGGTCCGGCCCCGCGGGGACACCCCGCAGGCGGAAGCCCTGGCCGCAGCCGCCC
AGGACGCGATTGGCCCGGAACTCGCGCCCACGCCCGAGCCACCCGAGGAGTACGTGTACCCGGACTACCGTGGC
AAGGGCTGCGTGGACGAGAGCGGCTTCGTGTACGCGATCGGGGAGAAGTTCGCGCCGGGCCCCTCGGCCTGCCC
GTGCCTGTGCACCGAGGAGGGGCCGCTGTGCGCGCAGCCCGAGTGCCCGAGGCTGCACCCGCGCTGCATCCACG
TCGACACGAGCCAGTGCTGCCCGCAGTGCAAGGAGAGGAAGAACTACTGCGAGTTCCGGGGCAAGACCTATCAG
ACTTTGGAGGAGTTCGTGGTGTCTCCATGCGAGAGGTGTCGCTGTGAAGCCAACGGTGAGGTGCTATGCACAGT
GTCAGCGTGTCCCCAGACGGAGTGTGTGGACCCTGTGTACGAGCCTGATCAGTGCTGTCCCATCTGCAAAAATG
GTCCAAACTGCTTTGCAGAAACCGCGGTGATCCCTGCTGGCAGAGAAGTGAAGACTGACGAGTGCACCATATGC
CACTGTACTTATGAGGAAGGCACATGGAGAATCGAGCGGCAGGCCATGTGCACGAGACATGAATGCAGGCAAAT
GTAGACGCTTCCCAGAACACAAACTCTGACTTTTTCTAGAACATTTTACTGATGTGAACATTCTAGATGACTCT
GGGAACTATCAGTCAAAGAAGACTTTTGATGAGGAATAATGGAAAATTGTTGGTACTTTTCCTTTTCTTGATAA
CAGTTACTACAACAGAAGGAAATGGATATATTTCAAAACATCAACAAGAACTTTGGGCATAAAATCCTTCTCTA
AATAAATGTGCTATTTTCACAGTAAGTACACAAAAGTACACTATTATATATCAAATGTATTTCTATAATCCCTC
CATTAGAGAGCTTATATAAGTGTTTTCTATAGATGCAGATTAAAAATGCTGTGTTGTCAACCGTCAAAAAAAAA
AAAAAAAAAAAAAAAAAA

FIGURE 56

MPSSTAMAVGALSSSLLVTCCLMVALCSPSIPLEKLAQAPEQPGQEKREHATRDGPGRVNELGRPARDEGGSGR
DWKSKSGRGLAGREPWSKLKQAWVSQGGGAKAGDLQVRPRGDTPQAEALAAAAQDAIGPELAPTPEPPEEYVYP
DYRGKGCVDESGFVYAIGEKFAPGPSACPCLCTEEGPLCAQPECPRLHPRCIHVDTSQCCPQCKERKNYCEFRG
KTYQTLEEFVVSPCERCRCEANGEVLCTVSACPQTECVDPVYEPDQCCPICKNGPNCFAETAVIPAGREVKTDE
CTICHCTYEEGTWRIERQAMCTRHECRQM

Important features:

Signal peptide:

amino acids 1-27

Transmembrane domain:

amino acids 11-30

Glycosaminoglycan attachment site.

amino acids 80-83

N-myristoylation sites.

amino acids 10-15, 102-107, 103-108

Cell attachment sequence.

amino acids 114-117

EGF-like domain cysteine pattern signature.

amino acids 176-187

FIGURE 57

GGAGGCGGAGGCCGCGGCGAGCCGGGCCGAGCAGTGAGGGCCCTAGCGGGGCCCGAGCGGGGCCCGGGGCCCCT
AAGCCATTCCTGAAGTCATGGGCTGGCCAGGACATTGGTGACCCGCCAATCCGGTATGGACGACTGGAAGCCCA
GCCCCCTCATCAAGCCCTTTGGGGCTCGGAAGAAGCGGAGCTGGTACCTTACCTGGAAGTATAAACTGACAAAC
CAGCGGGCCCTGCGGAGATTCTGTCAGACAGGGGCCGTGCTTTTCCTGCTGGTGACTGTCATTGTCAATATCAA
GTTGATCCTGGACACTCGGCGAGCCATCAGTGAAGCCAATGAAGACCCAGAGCCAGAGCAAGACTATGATGAGG
CCCTAGGCCGCCTGGAGCCCCCACGGCGCAGAGGCAGTGGTCCCCGGCGGGTCCTGGACGTAGAGGTGTATTCA
AGTCGCAGCAAAGTATATGTGGCAGTGGATGGCACCACGGTGCTGGAGGATGAGGCCCGGGAGCAGGGCCGGGG
CATCCATGTCATTGTCCTCAACCAGGCCACGGGCCACGTGATGGCAAAACGTGTGTTTGACACGTACTCACCTC
ATGAGGATGAGGCCATGGTGCTATTCCTCAACATGGTAGCGCCCGGCCGAGTGCTCATCTGCACTGTCAAGGAT
GAGGGCTCCTTCCACCTCAAGGACACAGCCAAGGCTCTGCTGAGGAGCCTGGGCAGCCAGGCTGGCCCTGCCCT
GGGCTGGAGGGACACATGGGCCTTCGTGGGACGAAAAGGAGGTCCTGTCTTCGGGGAGAAACATTCTAAGTCAC
CTGCCCTCTCTTCCTGGGGGGACCCAGTCCTGCTGAAGACAGATGTGCCATTGAGCTCAGCAGAAGAGGCAGAG
TGCCACTGGGCAGACACAGAGCTGAACCGTCGCCGCCGGCGCTTCTGCAGCAAAGTTGAGGGCTATGGAAGTGT
ATGCAGCTGCAAGGACCCCACACCCATCGAGTTCAGCCCTGACCCACTCCCAGACAACAAGGTCCTCAATGTGC
CTGTGGCTGTCATTGCAGGGAACCGACCCAATTACCTGTACAGGATGCTGCGCTCTCTGCTTTCAGCCCAGGGG
GTGTCTCCTCAGATGATAACAGTTTTCATTGACGGCTACTATGAGGAACCCATGGATGTGGTGGCACTGTTTGG
TCTGAGGGGCATCCAGCATACTCCCATCAGCATCAAGAATGCCCGCGTGTCTCAGCACTACAAGGCCAGCCTCA
CTGCCACTTTCAACCTGTTTCCGGAGGCCAAGTTTGCTGTGGTTCTGGAAGAGGACCTGGACATTGCTGTGGAT
TTTTTCAGTTTCCTGAGCCAATCCATCCACCTACTGGAGGAGGATGACAGCCTGTACTGCATCTCTGCCTGGAA
TGACCAGGGGTATGAACACACGGCTGAGGACCCAGCACTACTGTACCGTGTGGAGACCATGCCTGGGCTGGGCT
GGGTGCTCAGGAGGTCCTTGTACAAGGAGGAGCTTGAGCCCAAGTGGCCTACACCGGAAAAGCTCTGGGATTGG
GACATGTGGATGCGGATGCCTGAACAACGCCGGGGCCGAGAGTGCATCATCCCTGACGTTTCCCGATCCTACCA
CTTTGGCATCGTCGGCCTCAACATGAATGGCTACTTTCACGAGGCCTACTTCAAGAAGCACAAGTTCAACACGG
TTCCAGGTGTCCAGCTCAGGAATGTGGACAGTCTGAAGAAAGAAGCTTATGAAGTGGAAGTTCACAGGCTGCTC
AGTGAGGCTGAGGTTCTGGACCACAGCAAGAACCCTTGTGAAGACTCTTTCCTGCCAGACACAGAGGGCCACAC
CTACGTGGCCTTTATTCGAATGGAGAAAGATGATGACTTCACCACCTGGACCCAGCTTGCCAAGTGCCTCCATA
TCTGGGACCTGGATGTGCGTGGCAACCATCGGGGCCTGTGGAGATTGTTTCGGAAGAAGAACCACTTCCTGGTG
GTGGGGGTCCCGGCTTCCCCCTACTCAGTGAAGAAGCCACCCTCAGTCACCCCAATTTTCCTGGAGCCACCCCC
AAAGGAGGAGGGAGCCCCAGGAGCCCCAGAACAGACATGAGACCTCCTCCAGGACCCTGCGGGGCTGGGTACTG
TGTACCCCCAGGCTGGCTAGCCCTTCCCTCCATCCTGTAGGATTTTGTAGATGCTGGTAGGGGCTGGGGCTACC
TTGTTTTTAACATGAGACTTAATTACTAACTCCAAGGGGAGGGTTCCCCTGCTCCAACACCCCGTTCCTGAGTT
AAAAGTCTATTTATTTACTTCCTTGTTGGAGAAGGGCAGGAGAGTACCTGGGAATCATTACGATCCCTAGCAGC
TCATCCTGCCCTTTGAATACCCTCACTTTCCAGGCCTGGCTCAGAATCTAACCTATTTATTGACTGTCCTGAGG
GCCTTGAAAACAGGCCGAACCTGGAGGGCCTGGATTTCTTTTTGGGCTGGAATGCTGCCCTGAGGGTGGGGCTG
GCTCTTACTCAGGAAACTGCTGTGCCCAACCCATGGACAGGCCCAGCTGGGCCCACATGCTGACACAGACTCA
CTCAGAGACCCTTAGACACTGGACCAGGCCTCCTCTCAGCCTTCTCTTTGTCCAGATTTCCAAAGCTGGATAAG
TTGGTCATTGATTAAAAAAGGAGAAGCCCTCTGGGAAAAAAAAAAAAAAAAAAAAAAAAA

FIGURE 58

></usr/seqdb2/sst/DNA/Dnaseqs.min/ss.DNA61185
><subunit 1 of 1, 660 aa, 1 stop
><MW: 75220, pI: 6.76, NX(S/T): 0
MDDWKPSPLIKPFGARKKRSWYLTWKYKLTNQRALRRFCQTGAVLFLLVTVIVNIKLILDTRRAISEANEDPEP
EQDYDEALGRLEPPRRRGSGPRRVLDVEVYSSRSKVYVAVDGTTVLEDEAREQGRGIHVIVLNQATGHVMAKRV
FDTYSPHEDEAMVLFLNMVAPGRVLICTVKDEGSFHLKDTAKALLRSLGSQAGPALGWRDTWAFVGRKGGPVFG
EKHSKSPALSSWGDPVLLKTDVPLSSAEEAECHWADTELNRRRRRFCSKVEGYGSVCSCKDPTPIEFSPDPLPD
NKVLNVPVAVIAGNRPNYLYRMLRSLLSAQGVSPQMITVFIDGYYEEPMDVVALFGLRGIQHTPISIKNARVSQ
HYKASLTATFNLFPEAKFAVVLEEDLDIAVDFFSFLSQSIHLLEEDDSLYCISAWNDQGYEHTAEDPALLYRVE
TMPGLGWVLRRSLYKEELEPKWPTPEKLWDWDMWMRMPEQRRGRECIIPDVSRSYHFGIVGLNMNGYFHEAYFK
KHKFNTVPGVQLRNVDSLKKEAYEVEVHRLLSEAEVLDHSKNPCEDSFLPDTEGHTYVAFIRMEKDDDFTTWTQ
LAKCLHIWDLDVRGNHRGLWRLFRKKNHFLVVGVPASPYSVKKPPSVTPIFLEPPPKEEGAPGAPEQT

Important features of the protein:

Transmembrane domain:

amino acids 38-55

Homologous region to Mouse GNT1 amino acids 229-660

FIGURE 59

GGTTCCTGGGCGCTCTGTTACACAAGCAAGATACAGCCAGCCCCACCTAATTTTGTTTCCC
TGGCACCCTCCTGCTCAGTGCGACATTGTCACACTTAACCCATCTGTTTTCTCTAATGCAC
GACAGATTCCTTTCAGACAGGACAACTGTGATATTTCAGTTCCTGATTGTAAATACCTCCT
AAGCCTGAAGCTTCTGTTACTAGCCATTGTGAGCTTCAGTTTCTTCATCTGCAAAATGGGC
ATAATACAATCTATTCTTGCCACATCAAGGGATTGTTATTCCTTTAAAAAAAAACCAATAC
CAAAGAAGCCTACAATGTTGGCCTTAGCCAAAATTCTGTTGATTTCAACGTTGTTTTATTC
ACTTCTATCGGGGAGCCATGGAAAAGAAAATCAAGACATAAACACAACACAGAACATTGCA
GAAGTTTTTAAAACAATGGAAAATAAACCTATTTCTTTGGAAAGTGAAGCAAACTTAAACT
CAGATAAAGAAAATATAACCACCTCAAATCTCAAGGCGAGTCATTCCCCTCCTTTGAATCT
ACCCAACAACAGCCACGGAATAACAGATTTCTCCAGTAACTCATCAGCAGAGCATTCTTTG
GGCAGTCTAAAACCCACATCTACCATTTCCACAAGCCCTCCCTTGATCCATAGCTTTGTTT
CTAAAGTGCCTTGGAATGCACCTATAGCAGATGAAGATCTTTTGCCCATCTCAGCACATCC
CAATGCTACACCTGCTCTGTCTTCAGAAAACTTCACTTGGTCTTTGGTCAATGACACCGTG
AAAACTCCTGATAACAGTTCCATTACAGTTAGCATCCTCTCTTCAGAACCAACTTCTCCAT
CTGTGACCCCCTTGATAGTGGAACCAAGTGGATGGCTTACCACAAACAGTGATAGCTTCAC
TGGGTTTACCCCTTATCAAGAAAAAACAACTCTACAGCCTACCTTAAAATTCACCAATAAT
TCAAAACTCTTTCCAAATACGTCAGATCCCCAAAAAGAAAATAGAAATACAGGAATAGTAT
TCGGGGCCATTTTAGGTGCTATTCTGGGTGTCTCATTGCTTACTCTTGTGGGCTACTTGTT
GTGTGGAAAAAGGAAAACGGATTCATTTTCCCATCGGCGACTTTATGACGACAGAAATGAA
CCAGTTCTGCGATTAGACAATGCACCGGAACCTTATGATGTGAGTTTTGGGAATTCTAGCT
ACTACAATCCAACTTTGAATGATTCAGCCATGCCAGAAAGTGAAGAAAATGCACGTGATGG
CATTCCTATGGATGACATACCTCCACTTCGTACTTCTGTATAGAACTAACAGCAAAAAGGC
GTTAAACAGCAAGTGTCATCTACATCCTAGCCTTTTGACAAATTCATCTTTCAAAAGGTTA
CACAAAATTACTGTCACGTGGATTTTGTCAAGGAGAATCATAAAAGCAGGAGACCAGTAGC
AGAAATGTAGACAGGATGTATCATCCAAAGGTTTTCTTTCTTACAATTTTTGGCCATCCTG
AGGCATTTACTAAGTAGCCTTAATTTGTATTTTAGTAGTATTTTCTTAGTAGAAAATATTT
GTGGAATCAGATAAAACTAAAAGATTTCACCATTACAGCCCTGCCTCATAACTAAATAATA
AAAATTATTCCACCAAAAAAATTCTAAAACAATGAAGATGACTCTTTACTGCTCTGCCTGAA
GCCCTAGTACCATAATTCAAGATTGCATTTTCTTAAATGAAAATTGAAAGGGTGCTTTTTA
AAGAAAATTTGACTTAAAGCTAAAAAGAGGACATAGCCCAGAGTTTCTGTTATTGGGAAAT
TGAGGCAATAGAAATGACAGACCTGTATTCTAGTACGTTATAATTTTCTAGATCAGCACAC
ACATGATCAGCCCACTGAGTTATGAAGCTGACAATGACTGCATTCAACGGGGCCATGGCAG
GAAAGCTGACCCTACCCAGGAAAGTAATAGCTTCTTTAAAAGTCTTCAAAGGTTTTGGGAA
TTTTAACTTGTCTTAATATATCTTAGGCTTCAATTATTTGGGTGCCTTAAAAACTCAATGA
GAATCATGGT

FIGURE 60

></usr/seqdb2/sst/DNA/Dnaseqs.min/ss.DNA58732
><subunit 1 of 1, 334 aa, 1 stop
><MW: 36294, pI: 4.98, NX(S/T): 13

MLALAKILLISTLFYSLLSGSHGKENQDINTTQNIAEVFKTMENKPISLESEANLNSDKEN
ITTSNLKASHSPPLNLPNNSHGITDFSSNSSAEHSLGSLKPTSTISTSPPLIHSFVSKVPW
NAPIADEDLLPISAHPNATPALSSENFTWSLVNDTVKTPDNSSITVSILSSEPTSPSVTPL
IVEPSGWLTTNSDSFTGFTPYQEKTTLQPTLKFTNNSKLFPNTSDPQKENRNTGIVFGAIL
GAILGVSLLTLVGYLLCGKRKTDSFSHRRLYDDRNEPVLRLDNAPEPYDVSFGNSSYYNPT
LNDSAMPESEENARDGIPMDDIPPLRTSV

Signal peptide:
amino acids 1-23

Transmembrane domain:
amino acids 235-262

N-glycosylation site.
amino acids 30-34, 61-65, 79-83, 90-94, 148-152, 155-159, 163-167, 218-222, 225-229, 298-302, 307-311

FIGURE 61

AGAGAAAGAAGCGTCTCCAGCTGAAGCCAATGCAGCCCTCCGGCTCTCCGCGAAGAAGTTCCCTGCCCCGATGA
GCCCCCGCCGTGCGTCCCCGACTATCCCCAGGCGGGCGTGGGGCACCGGGCCCAGCGCCGACGATCGCTGCCGT
TTTGCCCTTGGGAGTAGGATGTGGTGAAAGGATGGGGCTTCTCCCTTACGGGGCTCACAATGGCCAGAGAAGAT
TCCGTGAAGTGTCTGCGCTGCCTGCTCTACGCCCTCAATCTGCTCTTTTGGTTAATGTCCATCAGTGTGTTGGC
AGTTTCTGCTTGGATGAGGGACTACCTAAATAATGTTCTCACTTTAACTGCAGAAACGAGGGTAGAGGAAGCAG
TCATTTTGACTTACTTTCCTGTGGTTCATCCGGTCATGATTGCTGTTTGCTGTTTCCTTATCATTGTGGGGATG
TTAGGATATTGTGGAACGGTGAAAAGAAATCTGTTGCTTCTTGCATGGTACTTTGGAAGTTTGCTTGTCATTTT
CTGTGTAGAACTGGCTTGTGGCGTTTGGACATATGAACAGGAACTTATGGTTCCAGTACAATGGTCAGATATGG
TCACTTTGAAAGCCAGGATGACAAATTATGGATTACCTAGATATCGGTGGCTTACTCATGCTTGGAATTTTTTT
CAGAGAGAGTTTAAGTGCTGTGGAGTAGTATATTTCACTGACTGGTTGGAAATGACAGAGATGGACTGGCCCCC
AGATTCCTGCTGTGTTAGAGAATTCCCAGGATGTTCCAAACAGGCCCACCAGGAAGATCTCAGTGACCTTTATC
AAGAGGGTTGTGGGAAGAAAATGTATTCCTTTTTGAGAGGAACCAAACAACTGCAGGTGCTGAGGTTTCTGGGA
ATCTCCATTGGGGTGACACAAATCCTGGCCATGATTCTCACCATTACTCTGCTCTGGGCTCTGTATTATGATAG
AAGGGAGCCTGGGACAGACCAAATGATGTCCTTGAAGAATGACAACTCTCAGCACCTGTCATGTCCCTCAGTAG
AACTGTTGAAACCAAGCCTGTCAAGAATCTTTGAACACACATCCATGGCAAACAGCTTTAATACACACTTTGAG
ATGGAGGAGTTATAAAAAGAAATGTCACAGAAGAAAACCACAAACTTGTTTTATTGGACTTGTGAATTTTTGAG
TACATACTATGTGTTTCAGAAATATGTAGAAATAAAAATGTTGCCATAAAATAACACCTAAGCATATACTATTC
TATGCTTTAAAATGAGGATGGAAAAGTTTCATGTCATAAGTCACCACCTGGACAATAATTGATGCCCTTAAAAT
GCTGAAGACAGATGTCATACCCACTGTGTAGCCTGTGTATGACTTTTACTGAACACAGTTATGTTTTGAGGCAG
CATGGTTTGATTAGCATTTCCGCATCCATGCAAACGAGTCACATATGGTGGGACTGGAGCCATAGTAAAGGTTG
ATTTACTTCTACCAACTAGTATATAAAGTACTAATTAAATGCTAACATAGGAAGTTAGAAAATACTAATAACTT
TTATTACTCAGCGATCTATTCTTCTGATGCTAAATAAATTATATATCAGAAAACTTTCAATATTGGTGACTACC
TAAATGTGATTTTTGCTGGTTACTAAAATATTCTTACCACTTAAAAGAGCAAGCTAACACATTGTCTTAAGCTG
ATCAGGGATTTTTTGTATATAAGTCTGTGTTAAATCTGTATAATTCAGTCGATTTCAGTTCTGATAATGTTAAG
AATAACCATTATGAAAAGGAAAATTTGTCCTGTATAGCATCATTATTTTTAGCCTTTCCTGTTAATAAAGCTTT
ACTATTCTGTCCTGGGCTTATATTACACATATAACTGTTATTTAAATACTTAACCACTAATTTTGAAAATTACC
AGTGTGATACATAGGAATCATTATTCAGAATGTAGTCTGGTCTTTAGGAAGTATTAATAAGAAAATTTGCACAT
AACTTAGTTGATTCAGAAAGGACTTGTATGCTGTTTTTCTCCCAAATGAAGACTCTTTTTGACACTAAACACTT
TTTAAAAAGCTTATCTTTGCCTTCTCCAAACAAGAAGCAATAGTCTCCAAGTCAATATAAATTCTACAGAAAAT
AGTGTTCTTTTTCTCCAGAAAAATGCTTGTGAGAATCATTAAAACATGTGACAATTTAGAGATTCTTTGTTTTA
TTTCACTGATTAATATACTGTGGCAAATTACACAGATTATTAAATTTTTTTACAAGAGTATAGTATATTTATTT
GAAATGGGAAAAGTGCATTTTACTGTATTTTGTGTATTTTGTTTATTTCTCAGAATATGGAAAGAAAATTAAAA
TGTGTCAATAAATATTTTCTAGAGAGTAA

FIGURE 62

></usr/seqdb2/sst/DNA/Dnaseqs.min/ss.DNA68880
><subunit 1 of 1, 305 aa, 1 stop
><MW: 35383, pI: 5.99, NX(S/T): 0
MAREDSVKCLRCLLYALNLLFWLMSISVLAVSAWMRDYLNNVLTLTAETRVEEAVILTYFP
VVHPVMIAVCCFLIIVGMLGYCGTVKRNLLLLAWYFGSLLVIFCVELACGVWTYEQELMVP
VQWSDMVTLKARMTNYGLPRYRWLTHAWNFFQREFKCCGVVYFTDWLEMTEMDWPPDSCCV
REFPGCSKQAHQEDLSDLYQEGCGKKMYSFLRGTKQLQVLRFLGISIGVTQILAMILTITL
LWALYYDRREPGTDQMMSLKNDNSQHLSCPSVELLKPSLSRIFEHTSMANSFNTHFEMEEL

Signal peptide:
amino acids 1-33

Transmembrane domains:
amino acids 12-35, 57-86, 94-114, 226-248

FIGURE 63

GGAAAAACTGTTCTCTTCTGTGGCACAGAGAACCCTGCTTCAAAGCAGAAGTAGCAGTTCC
GGAGTCCAGCTGGCTAAAACTCATCCCAGAGGATAATGGCAACCCATGCCTTAGAAATCGC
TGGGCTGTTTCTTGGTGGTGTTGGAATGGTGGGCACAGTGGCTGTCACTGTCATGCCTCAG
TGGAGAGTGTCGGCCTTCATTGAAAACAACATCGTGGTTTTTGAAAACTTCTGGGAAGGAC
TGTGGATGAATTGCGTGAGGCAGGCTAACATCAGGATGCAGTGCAAAATCTATGATTCCCT
GCTGGCTCTTTCTCCGGACCTACAGGCAGCCAGAGGACTGATGTGTGCTGCTTCCGTGATG
TCCTTCTTGGCTTTCATGATGGCCATCCTTGGCATGAAATGCACCAGGTGCACGGGGGACA
ATGAGAAGGTGAAGGCTCACATTCTGCTGACGGCTGGAATCATCTTCATCATCACGGGCAT
GGTGGTGCTCATCCCTGTGAGCTGGGTTGCCAATGCCATCATCAGAGATTTCTATAACTCA
ATAGTGAATGTTGCCCAAAAACGTGAGCTTGGAGAAGCTCTCTACTTAGGATGGACCACGG
CACTGGTGCTGATTGTTGGAGGAGCTCTGTTCTGCTGCGTTTTTTGTTGCAACGAAAAGAG
CAGTAGCTACAGATACTCGATACCTTCCCATCGCACAACCCAAAAAAGTTATCACACCGGA
AAGAAGTCACCGAGCGTCTACTCCAGAAGTCAGTATGTGTAGTTGTGTATGTTTTTTTAAC
TTTACTATAAAGCCATGCAAATGACAAAAATCTATATTACTTTCTCAAAATGGACCCCAAA
GAAACTTTGATTTACTGTTCTTAACTGCCTAATCTTAATTACAGGAACTGTGCATCAGCTA
TTTATGATTCTATAAGCTATTTCAGCAGAATGAGATATTAAACCCAATGCTTTGATTGTTC
TAGAAAGTATAGTAATTTGTTTTCTAAGGTGGTTCAAGCATCTACTCTTTTTATCATTTAC
TTCAAAATGACATTGCTAAAGACTGCATTATTTTACTACTGTAATTTCTCCACGACATAGC
ATTATGTACATAGATGAGTGTAACATTTATATCTCACATAGAGACATGCTTATATGGTTTT
ATTTAAAATGAAATGCCAGTCCATTACACTGAATAAATAGAACTCAACTATTGCTTTTCAG
GGAAATCATGGATAGGGTTGAAGAAGGTTACTATTAATTGTTTAAAAACAGCTTAGGGATT
AATGTCCTCCATTTATAATGAAGATTAAAATGAAGGCTTTAATCAGCATTGTAAAGGAAAT
TGAATGGCTTTCTGATATGCTGTTTTTAGCCTAGGAGTTAGAAATCCTAACTTCTTTATC
CTCTTCTCCCAGAGGCTTTTTTTTTCTTGTGTATTAAATTAACATTTTTAAAACGCAGATA
TTTTGTCAAGGGGCTTTGCATTCAAACTGCTTTTCCAGGGCTATACTCAGAAGAAAGATAA
AAGTGTGATCTAAGAAAAAGTGATGGTTTTAGGAAAGTGAAAATATTTTTGTTTTTGTATT
TGAAGAAGAATGATGCATTTTGACAAGAAATCATATATGTATGGATATATTTTAATAAGTA
TTTGAGTACAGACTTTGAGGTTTCATCAATATAAATAAAAGAGCAGAAAAATATGTCTTGG
TTTTCATTTGCTTACCAAAAAAACAACAACAAAAAAAGTTGTCCTTTGAGAACTTCACCTG
CTCCTATGTGGGTACCTGAGTCAAAATTGTCATTTTTGTTCTGTGAAAAATAAATTTCCTT
CTTGTACCATTTCTGTTTAGTTTTACTAAAATCTGTAAATACTGTATTTTTCTGTTTATTC
CAAATTTGATGAAACTGACAATCCAATTTGAAAGTTTGTGTCGACGTCTGTCTAGCTTAAA
TGAATGTGTTCTATTTGCTTTATACATTTATATTAATAAATTGTACATTTTTCTAATT

FIGURE 64

></usr/seqdb2/sst/DNA/Dnaseqs.min/ss.DNA73735

><subunit 1 of 1, 225 aa, 1 stop

><MW: 24845, pI: 9.07, NX(S/T): 0

MATHALEIAGLFLGGVGMVGTVAVTVMPQWRVSAFIENNIVVFENFWEGLWMNCVRQANIR
MQCKIYDSLLALSPDLQAARGLMCAASVMSFLAFMMAILGMKCTRCTGDNEKVKAHILLTA
GIIFIITGMVVLIPVSWVANAIIRDFYNSIVNVAQKRELGEALYLGWTTALVLIVGGALFC
CVFCCNEKSSSYRYSIPSHRTTQKSYHTGKKSPSVYSRSQYV

Signal peptide:

amino acids 1-17

Transmembrane domains:

amino acids 82-101, 118-145, 164-188

FIGURE 65

CGGACGCGTGGGCGGACGCGTGGGCGGACGCGTGGGTCTCTGCGGGGAGACGCCAGCCTGC
GTCTGCCATGGGGCTCGGGTTGAGGGGCTGGGGACGTCCTCTGCTGACTGTGGCCACCGCC
CTGATGCTGCCCGTGAAGCCCCCCGCAGGCTCCTGGGGGGCCCAGATCATCGGGGGCCACG
AGGTGACCCCCCACTCCAGGCCCTACATGGCATCCGTGCGCTTCGGGGGCCAACATCACTG
CGGAGGCTTCCTGCTGCGAGCCCGCTGGGTGGTCTCGGCCGCCCACTGCTTCAGCCACAGA
GACCTCCGCACTGGCCTGGTGGTGCTGGGCGCCCACGTCCTGAGTACTGCGGAGCCCACCC
AGCAGGTGTTTGGCATCGATGCTCTCACCACGCACCCCGACTACCACCCCATGACCCACGC
CAACGACATCTGCCTGCTGCGGCTGAACGGCTCTGCTGTCCTGGGCCCTGCAGTGGGGCTG
CTGAGGCTGCCAGGGAGAAGGGCCAGGCCCCCCACAGCGGGGACACGGTGCCGGGTGGCTG
GCTGGGGCTTCGTGTCTGACTTTGAGGAGCTGCCGCCTGGACTGATGGAGGCCAAGGTCCG
AGTGCTGGACCCGGACGTCTGCAACAGCTCCTGGAAGGGCCACCTGACACTTACCATGCTC
TGCACCCGCAGTGGGGACAGCCACAGACGGGGCTTCTGCTCGGCCGACTCCGGAGGGCCCC
TGGTGTGCAGGAACCGGGCTCACGGCCTCGTTTCCTTCTCGGGCCTCTGGTGCGGCGACCC
CAAGACCCCCGACGTGTACACGCAGGTGTCCGCCTTTGTGGCCTGGATCTGGGACGTGGTT
CGGCGGAGCAGTCCCCAGCCCGGCCCCCTGCCTGGGACCACCAGGCCCCCAGGAGAAGCCG
CCTGAGCCACAACCTTGCGGCATGCAAATGAGATGGCCGCTCCAGGCCTGGAATGTTCCGT
GGCTGGGCCCCACGGGAAGCCTGATGTTCAGGGTTGGGGTGGGACGGGCAGCGGTGGGGCA
CACCCATTCCACATGCAAAGGGCAGAAGCAAACCCAGTAAAATGTTAACTGACAAAAAAAA
AAAAAAAAAAAAGAAA

FIGURE 66

></usr/seqdb2/sst/DNA/Dnaseqs.min/ss.DNA62845

><subunit 1 of 1, 283 aa, 1 stop

><MW: 30350, pI: 9.66, NX(S/T): 2

MGLGLRGWGRPLLTVATALMLPVKPPAGSWGAQIIGGHEVTPHSRPYMASVRFGGQHHCGG
FLLRARWVVSAAHCFSHRDLRTGLVVLGAHVLSTAEPTQQVFGIDALTTHPDYHPMTHAND
ICLLRLNGSAVLGPAVGLLRLPGRRARPPTAGTRCRVAGWGFVSDFEELPPGLMEAKVRVL
DPDVCNSSWKGHLTLTMLCTRSGDSHRRGFCSADSGGPLVCRNRAHGLVSFSGLWCGDPKT
PDVYTQVSAFVAWIWDVVRRSSPQPGPLPGTTRPPGEAA

Signal peptide:

amino acids 1-30

FIGURE 67

CCGCCGCCGCAGCCGCTACCGCCGCTGCAGCCGCTTTCCGCGGCCTGGGCCTCTCGCCGTCAGCATGCCACACG

CCTTCAAGCCCGGGGACTTGGTGTTCGCTAAGATGAAGGGCTACCCTCACTGGCCTGCCAGGATCGACGACATC

GCGGATGGCGCCGTGAAGCCCCCACCCAACAAGTACCCCATCTTTTTCTTTGGCACACACGAAACAGCCTTCCT

GGGACCCAAGGACCTGTTCCCCTACGACAAATGTAAAGACAAGTACGGGAAGCCCAACAAGAGGAAAGGCTTCA

ATGAAGGGCTGTGGGAGATCCAGAACAACCCCCACGCCAGCTACAGCGCCCCTCCGCCAGTGAGCTCCTCCGAC

AGCGAGGCCCCCGAGGCCAACCCCGCCGACGGCAGTGACGCTGACGAGGACGATGAGGACCGGGGGGTCATGGC

CGTCACAGCGGTAACCGCCACAGCTGCCAGCGACAGGATGGAGAGCGACTCAGACTCAGACAAGAGTAGCGACA

ACAGTGGCCTGAAGAGGAAGACGCCTGCGCTAAAGATGTCGGTCTCGAAACGAGCCCGAAAGGCCTCCAGCGAC

CTGGATCAGGCCAGCGTGTCCCCATCCGAAGAGGAGAACTCGGAAAGCTCATCTGAGTCGGAGAAGACCAGCGA

CCAGGACTTCACACCTGAGAAGAAAGCAGCGGTCCGGGCGCCACGGAGGGGCCCTCTGGGGGGACGGAAAAAAA

AGAAGGCGCCGTCAGCCTCCGACTCCGACTCCAAGGCCGATTCGGACGGGGCCAAGCCTGAGCCGGTGGCCATG

GCGCGGTCGGCGTCCTCCTCCTCCTCTTCCTCCTCCTCCTCCGACTCCGATGTGTCTGTGAAGAAGCCTCCGAG

GGGCAGGAAGCCAGCGGAGAAGCCTCTCCCGAAGCCGCGAGGGCGGAAACCGAAGCCTGAACGGCCTCCGTCCA

GCTCCAGCAGTGACAGTGACAGCGACGAGGTGGACCGCATCAGTGAGTGGAAGCGGCGGGACGAGGCGCGGAGG

CGCGAGCTGGAGGCCCGGCGGCGGCGAGAGCAGGAGGAGGAGCTGCGGCGCCTGCGGGAGCAGGAGAAGGAGGA

GAAGGAGCGGAGGCGCGAGCGGGCCGACCGCGGGGAGGCTGAGCGGGGCAGCGGCGGCAGCAGCGGGGACGAGC

TCAGGGAGGACGATGAGCCCGTCAAGAAGCGGGGACGCAAGGGCCGGGGCCGGGGTCCCCCGTCCTCCTCTGAC

TCCGAGCCCGAGGCCGAGCTGGAGAGAGAGGCCAAGAAATCAGCGAAGAAGCCGCAGTCCTCAAGCACAGAGCC

CGCCAGGAAACCTGGCCAGAAGGAGAAGAGAGTGCGGCCCGAGGAGAAGCAACAAGCCAAGCCCGTGAAGGTGG

AGCGGACCCGGAAGCGGTCCGAGGGCTTCTCGATGGACAGGAAGGTAGAGAAGAAGAAAGAGCCCTCCGTGGAG

GAGAAGCTGCAGAAGCTGCACAGTGAGATCAAGTTTGCCCTAAAGGTCGACAGCCCGGACGTGAAGAGGTGCCT

GAATGCCCTAGAGGAGCTGGGAACCCTGCAGGTGACCTCTCAGATCCTCCAGAAGAACACAGACGTGGTGGCCA

CCTTGAAGAAGATTCGCCGTTACAAAGCGAACAAGGACGTAATGGAGAAGGCAGCAGAAGTCTATACCCGGCTC

AAGTCGCGGGTCCTCGGCCCAAAGATCGAGGCGGTGCAGAAAGTGAACAAGGCTGGGATGGAGAAGGAGAAGGC

CGAGGAGAAGCTGGCCGGGGAGGAGCTGGCCGGGGAGGAGGCCCCCCAGGAGAAGGCGGAGGACAAGCCCAGCA

CCGATCTCTCAGCCCCAGTGAATGGCGAGGCCACATCACAGAAGGGGGAGAGCGCAGAGGACAAGGAGCACGAG

GAGGGTCGGGACTCGGAGGAGGGGCCAAGGTGTGGCTCCTCTGAAGACCTGCACGACAGCGTACGGGAGGGTCC

CGACCTGGACAGGCCTGGGAGCGACCGGCAGGAGCGCGAGAGGGCACGGGGGGACTCGGAGGCCCTGGACGAGG

AGAGCTGAGCCGCGGGCAGCCAGGCCCAGCCCCCGCCCGAGCTCAGGCTGCCCCTCTCCTTCCCCGGCTCGCAG

GAGAGCAGAGCAGAGAACTGTGGGGAACGCTGTGCTGTTTGTATTTGTTCCCTTGGGTTTTTTTTTCCTGCCTA

ATTTCTGTGATTTCCAACCAACATGAAATGACTATAAACGGTTTTTTAATGA

FIGURE 68

></usr/seqdb2/sst/DNA/Dnaseqs.min/ss.DNA71286

><subunit 1 of 1, 671 aa, 1 stop

><MW: 74317, pI: 7.61, NX(S/T): 0

MPHAFKPGDLVFAKMKGYPHWPARIDDIADGAVKPPPNKYPIFFFGTHETAFLGPKDLFPY
DKCKDKYGKPNKRKGFNEGLWEIQNNPHASYSAPPPVSSSDSEAPEANPADGSDADEDDED
RGVMAVTAVTATAASDRMESDSDSDKSSDNSGLKRKTPALKMSVSKRARKASSDLDQASVS
PSEEENSESSSESEKTSDQDFTPEKKAAVRAPRRGPLGGRKKKKAPSASDSDSKADSDGAK
PEPVAMARSASSSSSSSSSSDSDVSVKKPPRGRKPAEKPLPKPRGRKPKPERPPSSSSSDS
DSDEVDRISEWKRRDEARRRELEARRRREQEEELRRLREQEKEEKERRRERADRGEAERGS
GGSSGDELREDDEPVKKRGRKGRGRGPPSSSDSEPEAELEREAKKSAKKPQSSSTEPARKP
GQKEKRVRPEEKQQAKPVKVERTRKRSEGFSMDRKVEKKKEPSVEEKLQKLHSEIKFALKV
DSPDVKRCLNALEELGTLQVTSQILQKNTDVVATLKKIRRYKANKDVMEKAAEVYTRLKSR
VLGPKIEAVQKVNKAGMEKEKAEEKLAGEELAGEEAPQEKAEDKPSTDLSAPVNGEATSQK
GESAEDKEHEEGRDSEEGPRCGSSEDLHDSVREGPDLDRPGSDRQERERARGDSEALDEES

Signal peptide:

amino acids 1-13

FIGURE 69

GAGCGGAGTAAAATCTCCACAAGCTGGGAACAAACCTCGTCCCAACTCCCACCCACCGGCGTTTCTCCAGCTCG
ATCTGGAGGCTGCTTCGCCAGTGTGGGACGCAGCTGACGCCCGCTTATTAGCTCTCGCTGCGTCGCCCCGGCTC
AGAAGCTCCGTGGCGGCGGCGACCGTGACGAGAAGCCCACGGCCAGCTCAGTTCTCTTCTACTTTGGGAGAGAG
AGAAAGTCAGATGCCCCTTTTAAACTCCCTCTTCAAAACTCATCTCCTGGGTGACTGAGTTAATAGAGTGGATA
CAACCTTGCTGAAGATGAAGAATATACAATATTGAGGATATTTTTTTCTTTTTTTTTTCAAGTCTTGATTTGTG
GCTTACCTCAAGTTACCATTTTTCAGTCAAGTCTGTTTGTTTGCTTCTTCAGAAATGTTTTTTACAATCTCAAG
AAAAAATATGTCCCAGAAATTGAGTTTACTGTTGCTTGTATTTGGACTCATTTGGGGATTGATGTTACTGCACT
ATACTTTTCAACAACCAAGACATCAAAGCAGTGTCAAGTTACGTGAGCAAATACTAGACTTAAGCAAAAGATAT
GTTAAAGCTCTAGCAGAGGAAAATAAGAACACAGTGGATGTCGAGAACGGTGCTTCTATGGCAGGATATGCGGA
TCTGAAAAGAACAATTGCTGTCCTTCTGGATGACATTTTGCAACGATTGGTGAAGCTGGAGAACAAAGTTGACT
ATATTGTTGTGAATGGCTCAGCAGCCAACACCACCAATGGTACTAGTGGGAATTTGGTGCCAGTAACCACAAAT
AAAAGAACGAATGTCTCGGGCAGTATCAGATAGCAGTTGAAAATCACCTTGTGCTGCTCCATCCACTGTGGATT
ATATCCTATGGCAGAAAAGCTTTATAATTGCTGGCTTAGGACAGAGCAATACTTTACAATAAAAGCTCTACACA
TTTTCAAGGAGTATGCTGGATTCATGGAACTCTAATTCTGTACATAAAAATTTTAAAGTTATTTGTTTGCTTTC
AGGCAAGTCTGTTCAATGCTGTACTATGTCCTTAAAGAGAATTTGGTAACTTGGTTGATGTGGTAAGCAGATAG
GTGAGTTTTGTATAAATCTTTTGTGTTTGAGATCAAGCTGAAATGAAAACACTGAAAAACATGGATTCATTTCT
ATAACACATTTATTTAAGTATATAACACGTTTTTTGGACAAGTGAAGAATGTTTAATCATTCTGTCATTTGTTC
TCAATAGATGTAACTGTTAGACTACGGCTATTTGAAAAAATGTGCTTATTGTACTATATTTTGTTATTCCAATT
ATGAGCAGAGAAAGGAAATATAATGTTGAAAATAATGTTTTGAAATCATGACCCAAAGAATGTATTGATTTGCA
CTATCCTTCAGAATAACTGAAGGTTAATTATTGTATATTTTTAAAAATTACACTTATAAGAGTATAATCTTGAA
ATGGGTAGCAGCCACTGTCCATTACCTATCGTAAACATTGGGGCAATTTAATAACAGCATTAAAATAGTTGTAA
ACTCTAATCTTATACTTATTGAAGAATAAAAGATATTTTTATGATGAGAGTAACAATAAAGTATTCATGATTTT
TCACATACATGAATGTTCATTTAAAAGTTTAATCCTTTGAGTGTCTATGCTATCAGGAAAGCACATTATTTCCA
TATTTGGGTTAATTTTGCTTTTATTATATTGGTCTAGGAGGAAGGGACTTTGGAGAATGGAACTCTTGAGGACT
TTAGCCAGGTGTATATAATAAAGGTACTTTTGTGCTGCATTAAATTGCTTGGAAAGTGTTAACATTATATTATA
TAAGAGTATCCTTTATGAAATTTTGAATTTGTATAACAGATGCATTAGATATTCATTTTATATAATGGCCACTT
AAAATAAGAACATTTAAAATATAAACTATGAAGATTGACTATCTTTTCAGGAAAAAAGCTGTATATAGCACAGG
GAACCCTAATCTTGGGTAATTCTAGTATAAAACAAATTATACTTTTATTTAAATTTCCCTTGTAGCAAATCTAA
TTGCCACATGGTGCCCTATATTTCATAGTATTTATTCTCTATAGTAACTGCTTAAGTGCAGCTAGCTTCTAGAT
TTAGACTATATAGAATTTAGATATTGTATTGTTCGTCATTATAATATGCTACCACATGTAGCAATAATTACAAT
ATTTTATTAAAATAAATATGTGAAATATTGTTTCATGAAAGACAGATTTCCAAATCTCTCTTCTCTTCTCTGTA
CTGTCTACCTTTATGTGAAGAAATTAATTATATGCCATTGCCAGGT

FIGURE 70

></usr/seqdb2/sst/DNA/Dnaseqs.min/ss.DNA77648
><subunit 1 of 1, 140 aa, 1 stop
><MW: 15668, pI: 10.14, NX(S/T): 5
MFFTISRKNMSQKLSLLLLVFGLIWGLMLLHYTFQQPRHQSSVKLREQILDLSKRYVKALA
EENKNTVDVENGASMAGYADLKRTIAVLLDDILQRLVKLENKVDYIVVNGSAANTTNGTSG
NLVPVTTNKRTNVSGSIR

Important features of the protein:

Signal peptide:

amino acids 1-26

FIGURE 71

GCTGAGCGTGTGCGCGGTACGGGGCTCTCCTGCCTTCTGGGCTCCAACGCAGCTCTGTGGCTGAACTGGGTGCT
CATCACGGGAACTGCTGGGCTATGGAATACAGATGTGGCAGCTCAGGTAGCCCCAAATTGCCTGGAAGAATACA
TCATGTTTTTCGATAAGAAGAAATTGTAGGATCCAGTTTTTTTTTAACCGCCCCCTCCCCACCCCCCAAAAAA
ACTGTAAAGATGCAAAAACGTAATATCCATGAAGATCCTATTACCTAGGAAGATTTTGATGTTTTGCTGCGAAT
GCGGTGTTGGGATTTATTTGTTCTTGGAGTGTTCTGCGTGGCTGGCAAAGAATAATGTTCCAAAATCGGTCCAT
CTCCCAAGGGGTCCAATTTTTCTTCCTGGGTGTCAGCGAGCCCTGACTCACTACAGTGCAGCTGACAGGGGCTG
TCATGCAACTGGCCCCTAAGCCAAAGCAAAAGACCTAAGGACGACCTTTGAACAATACAAAGGATGGGTTTCAA
TGTAATTAGGCTACTGAGCGGATCAGCTGTAGCACTGGTTATAGCCCCCACTGTCTTACTGACAATGCTTTCTT
CTGCCGAACGAGGATGCCCTAAGGGCTGTAGGTGTGAAGGCAAAATGGTATATTGTGAATCTCAGAAATTACAG
GAGATACCCTCAAGTATATCTGCTGGTTGCTTAGGTTTGTCCCTTCGCTATAACAGCCTTCAAAAACTTAAGTA
TAATCAATTTAAAGGGCTCAACCAGCTCACCTGGCTATACCTTGACCATAACCATATCAGCAATATTGACGAAA
ATGCTTTTAATGGAATACGCAGACTCAAAGAGCTGATTCTTAGTTCCAATAGAATCTCCTATTTTCTTAACAAT
ACCTTCAGACCTGTGACAAATTTACGGAACTTGGATCTGTCCTATAATCAGCTGCATTCTCTGGGATCTGAACA
GTTTCGGGGCTTGCGGAAGCTGCTGAGTTTACATTTACGGTCTAACTCCCTGAGAACCATCCCTGTGCGAATAT
TCCAAGACTGCCGCAACCTGGAACTTTTGGACCTGGGATATAACCGGATCCGAAGTTTAGCCAGGAATGTCTTT
GCTGGCATGATCAGACTCAAAGAACTTCACCTGGAGCACAATCAATTTTCCAAGCTCAACCTGGCCCTTTTTCC
AAGGTTGGTCAGCCTTCAGAACCTTTACTTGCAGTGGAATAAAATCAGTGTCATAGGACAGACCATGTCCTGGA
CCTGGAGCTCCTTACAAAGGCTTGATTTATCAGGCAATGAGATCGAAGCTTTCAGTGGACCCAGTGTTTTCCAG
TGTGTCCCGAATCTGCAGCGCCTCAACCTGGATTCCAACAAGCTCACATTTATTGGTCAAGAGATTTTGGATTC
TTGGATATCCCTCAATGACATCAGTCTTGCTGGGAATATATGGGAATGCAGCAGAAATATTTGCTCCCTTGTAA
ACTGGCTGAAAAGTTTTAAAGGTCTAAGGGAGAATACAATTATCTGTGCCAGTCCCAAAGAGCTGCAAGGAGTA
AATGTGATCGATGCAGTGAAGAACTACAGCATCTGTGGCAAAAGTACTACAGAGAGGTTTGATCTGGCCAGGGC
TCTCCCAAAGCCGACGTTTAAGCCCAAGCTCCCCAGGCCGAAGCATGAGAGCAAACCCCCTTTGCCCCCGACGG
TGGGAGCCACAGAGCCCGGCCCAGAGACCGATGCTGACGCCGAGCACATCTCTTTCCATAAAATCATCGCGGGC
AGCGTGGCGCTTTTCCTGTCCGTGCTCGTCATCCTGCTGGTTATCTACGTGTCATGGAAGCGGTACCCTGCGAG
CATGAAGCAGCTGCAGCAGCGCTCCCTCATGCGAAGGCACAGGAAAAAGAAAAGACAGTCCCTAAAGCAAATGA
CTCCCAGCACCCAGGAATTTTATGTAGATTATAAACCCACCAACACGGAGACCAGCGAGATGCTGCTGAATGGG
ACGGGACCCTGCACCTATAACAAATCGGGCTCCAGGGAGTGTGAGGTATGAACCATTGTGATAAAAAGAGCTCT
TAAAAGCTGGGAAATAAGTGGTGCTTTATTGAACTCTGGTGACTATCAAGGGAACGCGATGCCCCCCCTCCCCT
TCCCTCTCCCTCTCACTTTGGTGGCAAGATCCTTCCTTGTCCGTTTTAGTGCATTCATAATACTGGTCATTTTC
CTCTCATACATAATCAACCCATTGAAATTTAAATACCACAATCAATGTGAAGCTTGAACTCCGGTTTAATATAA
TACCTATTGTATAAGACCCTTTACTGATTCCATTAATGTCGCATTTGTTTTAAGATAAAACTTCTTTCATAGGT
AAAAAAAAAAA

FIGURE 72

></usr/seqdb2/sst/DNA/Dnaseqs.min/ss.DNA77301

><subunit 1 of 1, 513 aa, 1 stop

><MW: 58266, pI: 9.84, NX(S/T): 4

MGFNVIRLLSGSAVALVIAPTVLLTMLSSAERGCPKGCRCEGKMVYCESQKLQEIPSSISA
GCLGLSLRYNSLQKLKYNQFKGLNQLTWLYLDHNHISNIDENAFNGIRRLKELILSSNRIS
YFLNNTFRPVTNLRNLDLSYNQLHSLGSEQFRGLRKLLSLHLRSNSLRTIPVRIFQDCRNL
ELLDLGYNRIRSLARNVFAGMIRLKELHLEHNQFSKLNLALFPRLVSLQNLYLQWNKISVI
GQTMSWTWSSLQRLDLSGNEIEAFSGPSVFQCVPNLQRLNLDSNKLTFIGQEILDSWISLN
DISLAGNIWECSRNICSLVNWLKSFKGLRENTIICASPKELQGVNVIDAVKNYSICGKSTT
ERFDLARALPKPTFKPKLPRPKHESKPPLPPTVGATEPGPETDADAEHISFHKIIAGSVAL
FLSVLVILLVIYVSWKRYPASMKQLQQRSLMRRHRKKKRQSLKQMTPSTQEFYVDYKPTNT
ETSEMLLNGTGPCTYNKSGSRECEV

Important features of the protein:

Signal peptide:

amino acids 1-33

Transmembrane domain:

amino acids 420-442

N-glycosylation sites.

amino acids 126-129, 357-360, 496-499, 504-507 cAMP- and cGMP-dependent protein kinase phosphorylation site.

amino acids 465-468

Tyrosine kinase phosphorylation site.

amino acids 136-142

N-myristoylation sites.

amino acids 11-16, 33-38, 245-250, 332-337, 497-502, 507-512

FIGURE 73

CCAAGGCCAGAGCTGTGGACACCTTATCCCACTCATCCTCATCCTCTTCCTCTGATAAAGCCCCTACCAGTGCT
GATAAAGTCTTTCTCGTGAGAGCCTAGAGGCCTTAAAAAAAAAAGTGCTTGAAAGAGAAGGGGACAAAGGAACA
CCAGTATTAAGAGGATTTTCCAGTGTTTCTGGCAGTTGGTCCAGAAGGATGCCTCCATTCCTGCTTCTCACCTG
CCTCTTCATCACAGGCACCTCCGTGTCACCCGTGGCCCTAGATCCTTGTTCTGCTTACATCAGCCTGAATGAGC
CCTGGAGGAACACTGACCACCAGTTGGATGAGTCTCAAGGTCCTCCTCTATGTGACAACCATGTGAATGGGGAG
TGGTACCACTTCACGGGCATGGCGGGAGATGCCATGCCTACCTTCTGCATACCAGAAAACCACTGTGGAACCCA
CGCACCTGTCTGGCTCAATGGCAGCCACCCCCTAGAAGGCGACGGCATTGTGCAACGCCAGGCTTGTGCCAGCT
TCAATGGGAACTGCTGTCTCTGGAACACCACGGTGGAAGTCAAGGCTTGCCCTGGAGGCTACTATGTGTATCGT
CTGACCAAGCCCAGCGTCTGCTTCCACGTCTACTGTGGTCATTTTTATGACATCTGCGACGAGGACTGCCATGG
CAGCTGCTCAGATACCAGCGAGTGCACATGCGCTCCAGGAACTGTGCTAGGCCCTGACAGGCAGACATGCTTTG
ATGAAAATGAATGTGAGCAAAACAACGGTGGCTGCAGTGAGATCTGTGTGAACCTCAAAAACTCCTACCGCTGT
GAGTGTGGGGTTGGCCGTGTGCTAAGAAGTGATGGCAAGACTTGTGAAGACGTTGAAGGATGCCACAATAACAA
TGGTGGCTGCAGCCACTCTTGCCTTGGATCTGAGAAAGGCTACCAGTGTGAATGTCCCCGGGGCCTGGTGCTGT
CTGAGGATAACCACACTTGCCAAGTCCCTGTGTTGTGCAAATCAAATGCCATTGAAGTGAACATCCCCAGGGAG
CTGGTTGGTGGCCTGGAGCTCTTCCTGACCAACACCTCCTGCCGAGGAGTGTCCAACGGCACCCATGTCAACAT
CCTCTTCTCTCTCAAGACATGTGGTACAGTGGTCGATGTGGTGAATGACAAGATTGTGGCCAGCAACCTCGTGA
CAGGTCTACCCAAGCAGACCCCGGGGAGCAGCGGGGACTTCATCATCCGAACCAGCAAGCTGCTGATCCCGGTG
ACCTGCGAGTTTCCACGCCTGTACACCATTTCTGAAGGATACGTTCCCAACCTTCGAAACTCCCCACTGGAAAT
CATGAGCCGAAATCATGGGATCTTCCCATTCACTCTGGAGATCTTCAAGGACAATGAGTTTGAAGAGCCTTACC
GGGAAGCTCTGCCCACCCTCAAGCTTCGTGACTCCCTCTACTTTGGCATTGAGCCCGTGGTGCACGTGAGCGGC
TTGGAAAGCTTGGTGGAGAGCTGCTTTGCCACCCCCACCTCCAAGATCGACGAGGTCCTGAAATACTACCTCAT
CCGGGATGGCTGTGTTTCAGATGACTCGGTAAAGCAGTACACATCCCGGGATCACCTAGCAAAGCACTTCCAGG
TCCCTGTCTTCAAGTTTGTGGGCAAAGACCACAAGGAAGTGTTTCTGCACTGCCGGGTTCTTGTCTGTGGAGTG
TTGGACGAGCGTTCCCGCTGTGCCCAGGGTTGCCACCGGCGAATGCGTCGTGGGGCAGGAGGAGAGGACTCAGC
CGGTCTACAGGGCCAGACGCTAACAGGCGGCCCGATCCGCATCGACTGGGAGGACTAGTTCGTAGCCATACCTC
GAGTCCCTGCATTGGACGGCTCTGCTCTTTGGAGCTTCTCCCCCCACCGCCCTCTAAGAACATCTGCCAACAGC
TGGGTTCAGACTTCACACTGTGAGTTCAGACTCCCAGCACCAACTCACTCTGATTCTGGTCCATTCAGTGGGCA
CAGGTCACAGCACTGCTGAACAATGTGGCCTGGGTGGGGTTTCATCTTTCTAGGGTTGAAAACTAAACTGTCCA
CCCAGAAAGACACTCACCCCATTTCCCTCATTTCTTTCCTACACTTAAATACCTCGTGTATGGTGCAATCAGAC
CACAAAATCAGAAGCTGGGTATAATATTTCAAGTTACAAACCCTAGAAAAATTAAACAGTTACTGAAATTATGA
CTTAAATACCCAATGACTCCTTAAATATGTAAATTATAGTTATACCTTGAAATTTCAATTCAAATGCAGACTAA
TTATAGGGAATTTGGAAGTGTATCAATAAAACAGTATATAATTTT

FIGURE 74

MPPFLLLTCLFITGTSVSPVALDPCSAYISLNEPWRNTDHQLDESQGPPLCDNHVNGEWYH
FTGMAGDAMPTFCIPENHCGTHAPVWLNGSHPLEGDGIVQRQACASFNGNCCLWNTTVEVK
ACPGGYYVYRLTKPSVCFHVYCGHFYDICDEDCHGSCSDTSECTCAPGTVLGPDRQTCFDE
NECEQNNGGCSEICVNLKNSYRCECGVGRVLRSDGKTCEDVEGCHNNNGGCSHSCLGSEKG
YQCECPRGLVLSEDNHTCQVPVLCKSNAIEVNIPRELVGGLELFLTNTSCRGVSNGTHVNI
LFSLKTCGTVVDVVNDKIVASNLVTGLPKQTPGSSGDFIIRTSKLLIPVTCEFPRLYTISE
GYVPNLRNSPLEIMSRNHGIFPFTLEIFKDNEFEEPYREALPTLKLRDSLYFGIEPVVHVS
GLESLVESCFATPTSKIDEVLKYYLIRDGCVSDDSVKQYTSRDHLAKHFQVPVFKFVGKDH
KEVFLHCRVLVCGVLDERSRCAQGCHRRMRRGAGGEDSAGLQGQTLTGGPIRIDWED

Important features of the protein:

Signal peptide:

amino acids 1-16

N-glycosylation sites.

amino acids 89-93, 116-120, 259-263, 291-295, 299-303

Tyrosine kinase phosphorylation sites.

amino acids 411-418, 443-451

N-myristoylation sites.

amino acids 226-232, 233-239, 240-246, 252-258, 296-302, 300-306, 522-528, 531-537

Aspartic acid and asparagine hydroxylation site.

amino acids 197-209

ZP domain proteins.

amino acids 431-457

Calcium-binding EGF-like proteins.

amino acids 191-212, 232-253

FIGURE 75

CGCCAAGCATGCAGTAAAGGCTGAAAATCTGGGTCACAGCTGAGGAAGACCTCAGACATGGAGTCCAGGATGTG
GCCTGCGCTGCTGCTGTCCCACCTCCTCCCTCTCTGGCCACTGCTGTTGCTGCCCCTCCCACCGCCTGCTCAGG
GCTCTTCATCCTCCCCTCGAACCCCACCAGCCCCAGCCCGCCCCCCGTGTGCCAGGGGAGGCCCCTCGGCCCCA
CGTCATGTGTGCGTGTGGGAGCGAGCACCTCCACCAAGCCGATCTCCTCGGGTCCCAAGATCACGTCGGCAAGT
CCTGCCTGGCACTGCACCCCCAGCCACCCCATCAGGCTTTGAGGAGGGGCCGCCCTCATCCCAATACCCCTGGG
CTATCGTGTGGGGTCCCACCGTGTCTCGAGAGGATGGAGGGGACCCCAACTCTGCCAATCCCGGATTTCTGGAC
TATGGTTTTGCAGCCCCTCATGGGCTCGCAACCCCACACCCCAACTCAGACTCCATGCGAGGTGATGGAGATGG
GCTTATCCTTGGAGAGGCACCTGCCACCCTGCGGCCATTCCTGTTCGGGGGCCGTGGGGAAGGTGTGGACCCCC
AGCTCTATGTCACAATTACCATCTCCATCATCATTGTTCTCGTGGCCACTGGCATCATCTTCAAGTTCTGCTGG
GACCGCAGCCAGAAGCGACGCAGACCCTCAGGGCAGCAAGGTGCCCTGAGGCAGGAGGAGAGCCAGCAGCCACT
GACAGACCTGTCCCCGGCTGGAGTCACTGTGCTGGGGGCCTTCGGGGACTCACCTACCCCCACCCCTGACCATG
AGGAGCCCCGAGGGGGACCCCGGCCTGGGATGCCCCACCCCAAGGGGGCTCCAGCCTTCCAGTTGAACCGGTGA
GGGCAGGGGCAATGGGATGGGAGGGCAAAGAGGGAAGGCAACTTAGGTCTTCAGAGCTGGGGTGGGGGTGCCCT
CTGGATGGGTAGTGAGGAGGCAGGCGTGGCCTCCCACAGCCCCTGGCCCTCCCAAGGGGGCTGGACCAGCTCCT
CTCTGGGAGGCACCCTTCCTTCTCCCAGTCTCTCAGGATCTGTGTCCTATTCTCTGCTGCCCATAACTCCAACT
CTGCCCTCTTTGGTTTTTTCTCATGCCACCTTGTCTAAGACAACTCTGCCCTCTTAACCTTGATTCCCCCTCTT
TGTCTTGAACTTCCCCTTCTATTCTGGCCTACCCCTTGGTTCCTGACTGTGCCCTTTCCCTCTTCCTCTCAGGA
TTCCCCTGGTGAATCTGTGATGCCCCCAATGTTGGGGTGCAGCCAAGCAGGAGGCCAAGGGGCCGGCACAGCCC
CCATCCCACTGAGGGTGGGGCAGCTGTGGGGAGCTGGGGCCACAGGGGCTCCTGGCTCCTGCCCCTTGCACACC
ACCCGGAACACTCCCCAGCCCCACGGGCAATCCTATCTGCTCGCCCTCCTGCAGGTGGGGGCCTCACATATCTG
TGACTTCGGGTCCCTGTCCCCACCCTTGTGCACTCACATGAAAGCCTTGCACACTCACCTCCACCTTCACAGGC
CATTTGCACACGCTCCTGCACCCTCTCCCCGTCCATACCGCTCCGCTCAGCTGACTCTCATGTTCTCTCGTCTC
ACATTTGCACTCTCTCCTTCCCACATTCTGTGCTCAGCTCACTCAGTGGTCAGCGTTTCCTGCACACTTTACCT
CTCATGTGCGTTTCCCGGCCTGATGTTGTGGTGGTGTGCGGCGTGCTCACTCTCTCCCTCATGAACACCCACCC
ACCTCGTTTCCGCAGCCCCTGCGTGCTGCTCCAGAGGTGGGTGGGAGGTGAGCTGGGGGCTCCTTGGGCCCTCA
TCGGTCATGGTCTCGTCCCATTCCACACCATTTGTTTCTCTGTCTCCCCATCCTACTCCAAGGATGCCGGCATC
ACCCTGAGGGCTCCCCCTTGGGAATGGGGTAGTGAGGCCCCAGACTTCACCCCCAGCCCACTGCTAAAATCTGT
TTTCTGACAGATGGGTTTTGGGGAGTCGCCTGCTGCACTACATGAGAAAGGGACTCCCATTTGCCCTTCCCTTT
CTCCTACAGTCCCTTTTGTCTTGTCTGTCCTGGCTGTCTGTGTGTGTGCCATTCTCTGGACTTCAGAGCCCCCT
GAGCCAGTCCTCCCTTCCCAGCCTCCCTTTGGGCCTCCCTAACTCCACCTAGGCTGCCAGGGACCGGAGTCAGC
TGGTTCAAGGCCATCGGGAGCTCTGCCTCCAAGTCTACCCTTCCCTTCCCGGACTCCCTCCTGTCCCCTCCTTT
CCTCCCTCCTTCCTTCCACTCTCCTTCCTTTTGCTTCCCTGCCCTTTCCCCCTCCTCAGGTTCTTCCCTCCTTC
TCACTGGTTTTTCCACCTTCCTCCTTCCCTTCTTCCCTGGCTCCTAGGCTGTGATATATATTTTTGTATTATCT
CTTTCTTCTTCTTGTGGTGATCATCTTGAATTACTGTGGGATGTAAGTTTCAAAATTTTCAAATAAAGCCTTTG
CAAGATAA

FIGURE 76

Signal peptide: Amino acids 1-33

Transmembrane domain: Amino acids 178-198 cAMP- and cGMP-dependent protein kinase phosphorylation site:
Amino acids 210-214

N-myristoylation sites: Amino acids 117-123; 154-160; 214-220

Cell attachment sequence: Amino acids 149-152

MESRMWPALLLSHLLPLWPLLLLPLPPPAQGSSSSPRTPPAPARPPCARGGPSAPRHVCVWERAPPPSRSPRVP
RSRRQVLPGTAPPATPSGFEEGPPSSQYPWAIVWGPTVSREDGGDPNSANPGFLDYGFAAPHGLATPHPNSDSM
RGDGDGLILGEAPATLRPFLFGGRGEGVDPQLYVTITISIIIVLVATGIIFKFCWDRSQKRRRPSGQQGALRQE
ESQQPLTDLSPAGVTVLGAFGDSPTPTPDHEEPRGGPRPGMPHPKGAPAFQLNR

FIGURE 77

GGCTGCGCCCAGGCCGGCGGGCCCAGCAGCTGCGAACCGCCGGCGCACCACCTGTTTCCGCGCCCGGGGACTTC
CCCGGCGGGGCTCAGAAGTGTGGGGTCGGTCGCTTGGCTTCCCCTGGCGTCAGCGACCCAGGGTAACCTCCTCC
ACTGCTGCGTGCCGTGCAGGCCTGCCTGTGTGAGAGCCACGTGTGCCGCGCTCTGGGCACAGCCTTGGAAAGTC
AGGACCGCGACGGCAGCAGAGCAGAAACCTTACAGAAACATGAAGCCCTCAACCATCTGCTACTCAGTTATTCG
GGGCTGACGGCGGCTTCTAGAACATCCAGGTGTTCTGCAGATGCGAGAACTCATCCTGTAGTCACCAGATGGAG
TCCCAAACAGCCAAGCAGATGTAAGGCCTGTGCTGTGGCTCTGAGGCCCTGAATACAGAAGGGTCACTTTCTTA
GTGGCCAAAGAGCAGTTGTTGACATTGATGTCTAATTATTGAACACGACCAGTCATTTTACTGAGCTGCAGTGA
GGAAACACTGACCATAGAAGATCAAGCCAAATGAGGGATTGCAAATTTCCTGATTCTTTTGAATTAGGATTCCA
GATGGGGGCCTCATTTCTACAGCCCCCAACATTCCTATAGCCGTTATCACTGCCATCACCACTGCCACCAGCAT
CTTCTTGCAGATTCCACCCCTGCTCCCCAGAGACTTCCTGCTTTGAAAGTGAGCAGAAAGGAAGCTCTCAGAAA
AATCTCTAGTGGTGGCTGCCGTCGCTCCAGACAATCGGAATCCTGCCTTCACCACCATGGGCTGGCTTTTTCTA
AAGGTTTTGTTGGCGGGAGTGAGTTTCTCAGGATTTCTTTATCCTCTTGTGGATTTTTGCATCAGTGGGAAAAC
AAGAGGACAGAAGCCAAACTTTGTGATTATTTTGGCCGATGACATGGGGTGGGGTGACCTGGGAGCAAACTGGG
CAGAAACAAAGGACACTGCCAACCTTGATAAGATGGCTTCGGAGGGAATGAGGTTTGTGGATTTCCATGCAGCT
GCCTCCACCTGCTCACCCTCCCGGGCTTCCTTGCTCACCGGCCGGCTTGGCCTTCGCAATGGAGTCACACGCAA
CTTTGCAGTCACTTCTGTGGGAGGCCTTCCGCTCAACGAGACCACCTTGGCAGAGGTGCTGCAGCAGGCGGGTT
ACGTCACTGGGATAATAGGCAAATGGCATCTTGGACACCACGGCTCTTATCACCCCAACTTCCGTGGTTTTGAT
TACTACTTTGGAATCCCATATAGCCATGATATGGGCTGTACTGATACTCCAGGCTACAACCACCCTCCTTGTCC
AGCGTGTCCACAGGGTGATGGACCATCAAGGAACCTTCAAAGAGACTGTTACACTGACGTGGCCCTCCCTCTTT
ATGAAAACCTCAACATTGTGGAGCAGCCGGTGAACTTGAGCAGCCTTGCCCAGAAGTATGCTGAGAAAGCAACC
CAGTTCATCCAGCGTGCAAGCACCAGCGGGAGGCCCTTCCTGCTCTATGTGGCTCTGGCCCACATGCACGTGCC
CTTACCTGTGACTCAGCTACCAGCAGCGCCACGGGGCAGAAGCCTGTATGGTGCAGGGCTCTGGGAGATGGACA
GTCTGGTGGGCCAGATCAAGGACAAAGTTGACCACACAGTGAAGGAAAACACATTCCTCTGGTTTACAGGAGAC
AATGGCCCGTGGGCTCAGAAGTGTGAGCTAGCGGGCAGTGTGGGTCCCTTCACTGGATTTTGGCAAACTCGTCA
AGGGGGAAGTCCAGCCAAGCAGACGACCTGGGAAGGAGGGCACCGGGTCCCAGCACTGGCTTACTGGCCTGGCA
GAGTTCCAGTTAATGTCACCAGCACTGCCTTGTTAAGCGTGCTGGACATTTTTCCAACTGTGGTAGCCCTGGCC
CAGGCCAGCTTACCTCAAGGACGGCGCTTTGATGGTGTGGACGTCTCCGAGGTGCTCTTTGGCCGGTCACAGCC
TGGGCACAGGGTGCTGTTCCACCCCAACAGCGGGGCAGCTGGAGAGTTTGGAGCCCTGCAGACTGTCCGCCTGG
AGCGTTACAAGGCCTTCTACATTACCGGTGGAGCCAGGGCGTGTGATGGGAGCATGGTGCCTGAGCTGCAGCAT
AAGTTTCCTCTGATTTTCAACCTGGAAGACGATACCGCAGAAGCTGTGCCCCTAGAAAGAGGTGGTGCGGAGTA
CCAGGCTGTGCTGCCCGAGGTCAGAAAGGTTCTTGCAGACGTCCTCCAAGACATTGCCAACGACAACATCTCCA
GCGCAGATTACACTCAGGACCCTTCAGTAACTCCCTGCTGTAATCCCTACCAAATTGCCTGCCGCTGTCAAGCC
GCATAACAGACCAATTTTTATTCCACGAGGAGGAGTACCTGGAAATTAGGCAAGTTTGCTTCCAAATTTCATTT
TTACCCTCTTTACAAACACACGCTTTAGTTTAGTCTTGGAGTTTAGTTTTGGAGTTAGCCTTGCATATCCCTTC
TGTATCCTGTCCCCCCTCCACGCCGACCCGAGAGCAGCTGAGCTGCGCTGGCTCTGGGCAGGGAGTGTGCCTTA
ATGGGAAGCACACGGGCTTTGGAGTCAGGCACAGGTGCCAGCTCCAGCTTTTGAACTTGGGCAATTGTTTAACC
TAACCTGCAAGTTGATTTTGAGGGTTAAATAAAGGCATACATGAAAATGCCTGGCAACTTTAAAAAAAAAAAA

FIGURE 78

MGWLFLKVLLAGVSFSGFLYPLVDFCISGKTRGQKPNFVIILADDMGWGDLGANWAETKDT
ANLDKMASEGMRFVDFHAAASTCSPSRASLLTGRLGLRNGVTRNFAVTSVGGLPLNETTLA
EVLQQAGYVTGIIGKWHLGHHGSYHPNFRGFDYYFGIPYSHDMGCTDTPGYNHPPCPACPQ
GDGPSRNLQRDCYTDVALPLYENLNIVEQPVNLSSLAQKYAEKATQFIQRASTSGRPFLLY
VALAHMHVPLPVTQLPAAPRGRSLYGAGLWEMDSLVGQIKDKVDHTVKENTFLWFTGDNGP
WAQKCELAGSVGPFTGFWQTRQGGSPAKQTTWEGGHRVPALAYWPGRVPVNVTSTALLSVL
DIFPTVVALAQASLPQGRRFDGVDVSEVLFGRSQPGHRVLFHPNSGAAGEFGALQTVRLER
YKAFYITGGARACDGSMVPELQHKFPLIFNLEDDTAEAVPLERGGAEYQAVLPEVRKVLAD
VLQDIANDNISSADYTQDPSVTPCCNPYQIACRCQAA

Important features of the protein:

Signal peptide:

amino acids 1-16

Transmembrane domain:

amino acids 353-373

N-glycosylation sites.

amino acids 117-120, 215-218, 356-359, 397-500

N-myristoylation sites.

amino acids 12-17, 33-38, 52-57, 97-102, 101-106, 113-118, 158-163, 328-333, 388-393, 418-423, 435-440, 436-441

Amidation site.

amino acids 382-385

Sulfatases signature 2.

amino acids 129-138

FIGURE 79

CGCGGCCGGGCCGCCGGGGTGAGCGTGCCGAGGCGGCTGTGGCGCAGGCTTCCAGCCCCCACCATGCCGTGGCC
CCTGCTGCTGCTGCTGGCCGTGAGTGGGGCCCAGACAACCCGGCCATGCTTCCCCGGGTGCCAATGCGAGGTGG
AGACCTTCGGCCTTTTCGACAGCTTCAGCCTGACTCGGGTGGATTGTAGCGGCCTGGGCCCCCACATCATGCCG
GTGCCCATCCCTCTGGACACAGCCCACTTGGACCTGTCCTCCAACCGGCTGGAGATGGTGAATGAGTCGGTGTT
GGCGGGGCCGGGCTACACGACGTTGGCTGGCCTGGATCTCAGCCACAACCTGCTCACCAGCATCTCACCCACTG
CCTTCTCCCGCCTTCGCTACCTGGAGTCGCTTGACCTCAGCCACAATGGCCTGACAGCCCTGCCAGCCGAGAGC
TTCACCAGCTCACCCCTGAGCGACGTGAACCTTAGCCACAACCAGCTCCGGGAGGTCTCAGTGTCTGCCTTCAC
GACGCACAGTCAGGGCCGGGCACTACACGTGGACCTCTCCCACAACCTCATTCACCGCCTCGTGCCCCACCCCA
CGAGGGCCGGCCTGCCTGCGCCCACCATTCAGAGCCTGAACCTGGCCTGGAACCGGCTCCATGCCGTGCCCAAC
CTCCGAGACTTGCCCCTGCGCTACCTGAGCCTGGATGGGAACCCTCTAGCTGTCATTGGTCCGGGTGCCTTCGC
GGGGCTGGGAGGCCTTACACACCTGTCTCTGGCCAGCCTGCAGAGGCTCCCTGAGCTGGCGCCCAGTGGCTTCC
GTGAGCTACCGGGCCTGCAGGTCCTGGACCTGTCGGGCAACCCCAAGCTTAACTGGGCAGGAGCTGAGGTGTTT
TCAGGCCTGAGCTCCCTGCAGGAGCTGGACCTTTCGGGCACCAACCTGGTGCCCCTGCCTGAGGCGCTGCTCCT
CCACCTCCCGGCACTGCAGAGCGTCAGCGTGGGCCAGGATGTGCGGTGCCGGCGCCTGGTGCGGGAGGGCACCT
ACCCCCGGAGGCCTGGCTCCAGCCCCAAGGTGCCCCTGCACTGCGTAGACACCCGGGAATCTGCTGCCAGGGGC
CCCACCATCTTGTGACAAATGGTGTGGCCCAGGGCCACATAACAGACTGCTGTCCTGGGCTGCCTCAGGTCCCG
AGTAACTTATGTTCAATGTGCCAACACCAGTGGGGAGCCCGCAGGCCTATGTGGCAGCGTCACCACAGGAGTTG
TGGGCCTAGGAGAGGCTTTGGACCTGGGAGCCACACCTAGGAGCAAAGTCTCACCCCTTTGTCTACGTTGCTTC
CCCAAACCATGAGCAGAGGGACTTCGATGCCAAACCAGACTCGGGTCCCCTCCTGCTTCCCTTCCCCACTTATC
CCCCAAGTGCCTTCCCTCATGCCTGGGCCGGCCTGACCCGCAATGGGCAGAGGGTGGGTGGGACCCCCTGCTGC
AGGGCAGAGTTCAGGTCCACTGGGCTGAGTGTCCCCTTGGGCCCATGGCCCAGTCACTCAGGGGCGAGTTTCTT
TTCTAACATAGCCCTTTCTTTGCCATGAGGCCATGAGGCCCGCTTCATCCTTTTCTATTTCCCTAGAACCTTAA
TGGTAGAAGGAATTGCAAAGAATCAAGTCCACCCTTCTCATGTGACAGATGGGGAAACTGAGGCCTTGAGAAGG
AAAAAGGCTAATCTAAGTTCCTGCGGGCAGTGGCATGACTGGAGCACAGCCTCCTGCCTCCCAGCCCGGACCCA
ATGCACTTTCTTGTCTCCTCTAATAAGCCCCACCCTCCCCGCCTGGGCTCCCCTTGCTGCCCTTGCCTGTTCCC
CATTAGCACAGGAGTAGCAGCAGCAGGACAGGCAAGAGCCTCACAAGTGGGACTCTGGGCCTCTGACCAGCTGT
GCGGCATGGGCTAAGTCACTCTGCCCTTCGGAGCCTCTGGAAGCTTAGGGCACATTGGTTCCAGCCTAGCCAGT
TTCTCACCCTGGGTTGGGGTCCCCCAGCATCCAGACTGGAAACCTACCCATTTTCCCCTGAGCATCCTCTAGAT
GCTGCCCCAAGGAGTTGCTGCAGTTCTGGAGCCTCATCTGGCTGGGATCTCCAAGGGGCCTCCTGGATTCAGTC
CCCACTGGCCCTGAGCACGACAGCCCTTCTTACCCTCCCAGGAATGCCGTGAAAGGAGACAAGGTCTGCCCGAC
CCATGTCTATGCTCTACCCCCAGGGCAGCATCTCAGCTTCCGAACCCTGGGCTGTTTCCTTAGTCTTCATTTTA
TAAAAGTTGTTGCCTTTTTAACGGAGTGTCACTTTCAACCGGCCTCCCCTACCCCTGCTGGCCGGGGATGGAGA
CATGTCATTTGTAAAAGCAGAAAAAGGTTGCATTTGTTCACTTTTGTAATATTGTCCTGGGCCTGTGTTGGGGT
GTTGGGGGAAGCTGGGCATCAGTGGCCACATGGGCATCAGGGGCTGGCCCCACAGAGACCCCACAGGGCAGTGA
GCTCTGTCTTCCCCCACCTGCCTAGCCCATCATCTATCTAACCGGTCCTTGATTTAATAAACACTATAAAAGGT
TTAAAAAAAAAAAAAAAAAAAAAAAAAAAAAAAAAAAAAAAAAAAAA

FIGURE 80

></usr/seqdb2/sst/DNA/Dnaseqs.min/ss.DNA77652
><subunit 1 of 1, 353 aa, 1 stop
><MW: 37847, pI: 6.80, NX(S/T): 2
MPWPLLLLLAVSGAQTTRPCFPGCQCEVETFGLFDSFSLTRVDCSGLGPHIMPVPIPLDTA
HLDLSSNRLEMVNESVLAGPGYTTLAGLDLSHNLLTSISPTAFSRLRYLESLDLSHNGLTA
LPAESFTSSPLSDVNLSHNQLREVSVSAFTTHSQGRALHVDLSHNLIHRLVPHPTRAGLPA
PTIQSLNLAWNRLHAVPNLRDLPLRYLSLDGNPLAVIGPGAFAGLGGLTHLSLASLQRLPE
LAPSGFRELPGLQVLDLSGNPKLNWAGAEVFSGLSSLQELDLSGTNLVPLPEALLLHLPAL
QSVSVGQDVRCRRLVREGTYPRRPGSSPKVPLHCVDTRESAARGPTIL

Signal peptide:
amino acids 1-16

Transmembrane domains:
amino acids 215-232, 287-304

FIGURE 81

CGGGCCAGCCTGGGGCGGCCGGCCAGGAACCACCCGTTAAGGTGTCTTCTCTTTAGGGATG
GTGAGGTTGGAAAAAGACTCCTGTAACCCTCCTCCAGG<u>ATG</u>AACCACCTGCCAGAAGACAT
GGAGAACGCTCTCACCGGGAGCCAGAGCTCCCATGCTTCTCTGCGCAATATCCATTCCATC
AACCCCACACAACTCATGGCCAGGATTGAGTCCTATGAAGGAAGGGAAAAGAAAGGCATAT
CTGATGTCAGGAGGACTTTCTGTTTGTTTGTCACCTTTGACCTCTTATTCGTAACATTACT
GTGGATAATAGAGTTAAATGTGAATGGAGGCATTGAGAACACATTAGAGAAGGAGGTGATG
CAGTATGACTACTATTCTTCATATTTTGATATATTTCTTCTGGCAGTTTTTCGATTTAAAG
TGTTAATACTTGCATATGCTGTGTGCAGACTGCGCCATTGGTGGGCAATAGCGTTGACAAC
GGCAGTGACCAGTGCCTTTTTACTAGCAAAAGTGATCCTTTCGAAGCTTTTCTCTCAAGGG
GCTTTTGGCTATGTGCTGCCCATCATTTCATTCATCCTTGCCTGGATTGAGACGTGGTTCC
TGGATTTCAAAGTGTTACCTCAAGAAGCAGAAGAAGAAAACAGACTCCTGATAGTTCAGGA
TGCTTCAGAGAGGGCAGCACTTATACCTGGTGGTCTTTCTGATGGTCAGTTTTATTCCCCT
CCTGAATCCGAAGCAGGATCTGAAGAAGCTGAAGAAAAACAGGACAGTGAGAAACCACTTT
TAGAACTA<u>TGA</u>GTACTACTTTTGTTAAATGTGAAAAACCCTCACAGAAAGTCATCGAGGCA
AAAAGAGGCAGGCAGTGGAGTCTCCCTGTCGACAGTAAAGTTGAAATGGTGACGTCCACTG
CTGGCTTTATTGAACAGCTAATAAAGATTTATTTATTGTAATACCTCACAAACGTTGTACC
ATATCCATGCACATTTAGTTGCCTGCCTGTGGCTGGTAAGGTAATGTCATGATTCATCCTC
TCTTCAGTGAGACTGAGCCTGATGTGTTAACAAATAGGTGAAGAAAGTCTTGTGCTGTATT
CCTAATCAAAAGACTTAATATATTGAAGTAACACTTTTTTAGTAAGCAAGATACCTTTTTA
TTTCAATTCACAGAATGGAATTTTTTTGTTTCATGTCTCAGATTTATTTTGTATTTCTTTT
TTAACACTCTACATTTCCCTTGTTTTTTAACTCATGCACATGTGCTCTTTGTACAGTTTTA
AAAAGTGTAATAAAATCTGACATGTCAATGTGGCTAGTTTTATTTTTCTTGTTTTGCATTA
TGTGTATGGCCTGAAGTGTTGGACTTGCAAAAGGGGAAGAAAGGAATTGCGAATACATGTA
AAATGTCACCAGACATTTGTATTATTTTTATCATGAAATCATGTTTTTCTCTGATTGTTCT
GAAATGTTCTAAATACTCTTATTTTGAATGCACAAAATGACTTAAACCATTCATATCATGT
TTCCTTTGCGTTCAGCCAATTTCAATTAAAATGAACTAAATTAAAAA

FIGURE 82

MNHLPEDMENALTGSQSSHASLRNIHSINPTQLMARIESYEGREKKGISDVRRTFCLFVTF
DLLFVTLLWIIELNVNGGIENTLEKEVMQYDYYSSYFDIFLLAVFRFKVLILAYAVCRLRH
WWAIALTTAVTSAFLLAKVILSKLFSQGAFGYVLPIISFILAWIETWFLDFKVLPQEAEEE
NRLLIVQDASERAALIPGGLSDGQFYSPPESEAGSEEAEEKQDSEKPLLEL

Important features of the protein:

Signal peptide:

amino acids 1-20

Transmembrane domains:

amino acids 54-72, 100-118, 130-144, 146-166

N-myristoylation sites.

amino acids 14-20, 78-84, 79-85, 202-208, 217-223

FIGURE 83

CCGTCATCCCCCTGCAGCCACCCTTCCCAGAGTCCTTTGCCCAGGCCACCCCAGGCTTCTT
GGCAGCCCTGCCGGGCCACTTGTCTTCATGTCTGCCAGGGGGAGGTGGGAAGGAGGTGGGA
GGAGGGCGTGCAGAGGCAGTCTGGGCTTGGCCAGAGCTCAGGGTGCTGAGCGTGTGACCAG
CAGTGAGCAGAGGCCGGCCATGGCCAGCCTGGGGCTGCTGCTCCTGCTCTTACTGACAGCA
CTGCCACCGCTGTGGTCCTCCTCACTGCCTGGGCTGGACACTGCTGAAAGTAAAGCCACCA
TTGCAGACCTGATCCTGTCTGCGCTGGAGAGAGCCACCGTCTTCCTAGAACAGAGGCTGCC
TGAAATCAACCTGGATGGCATGGTGGGGGTCCGAGTGCTGGAAGAGCAGCTAAAAAGTGTC
CGGGAGAAGTGGGCCCAGGAGCCCCTGCTGCAGCCGCTGAGCCTGCGCGTGGGGATGCTGG
GGGAGAAGCTGGAGGCTGCCATCCAGAGATCCCTCCACTACCTCAAGCTGAGTGATCCCAA
GTACCTAAGAGAGTTCCAGCTGACCCTCCAGCCCGGGTTTTGGAAGCTCCCACATGCCTGG
ATCCACACTGATGCCTCCTTGGTGTACCCCACGTTCGGGCCCCAGGACTCATTCTCAGAGG
AGAGAAGTGACGTGTGCCTGGTGCAGCTGCTGGGAACCGGGACGGACAGCAGCGAGCCCTG
CGGCCTCTCAGACCTCTGCAGGAGCCTCATGACCAAGCCCGGCTGCTCAGGCTACTGCCTG
TCCCACCAACTGCTCTTCTTCCTCTGGGCCAGAATGAGGGGATGCACACAGGGACCACTCC
AACAGAGCCAGGACTATATCAACCTCTTCTGCGCCAACATGATGGACTTGAACCGCAGAGC
TGAGGCCATCGGATACGCCTACCCTACCCGGGACATCTTCATGGAAAACATCATGTTCTGT
GGAATGGGCGGCTTCTCCGACTTCTACAAGCTCCGGTGGCTGGAGGCCATTCTCAGCTGGC
AGAAACAGCAGGAAGGATGCTTCGGGGAGCCTGATGCTGAAGATGAAGAATTATCTAAAGC
TATTCAATATCAGCAGCATTTTTCGAGGAGAGTGAAGAGGCGAGAAAAACAATTTCCAGAT
TCTCGCTCTGTTGCTCAGGCTGGAGTACAGTGGCGCAATCTCGGCTCACTGCAACCTTTGC
CTCCTGGGTTCAAGCAATTCTCTTGCCTCATCCTCCCGAGTAGCTGGGACTACAGGAGCGT
GCCACCATACCTGGCTAATTTTTATATTTTTTTAGTAGAGACAGGGTTTCATCATGTTGCT
CATGCTGGTCTCGAACTCCTGATCTCAAGAGATCCGCCCACCTCAGGCTCCCAAAGTGTGG
GATTATAGGTGTGAGCCACCGTGTCTGGCTGAAAAGCACTTTCAAAGAGACTGTGTTGAAT
AAAGGGCCAAGGTTCTTGCCACCCAGCACTCATGGGGGCTCTCTCCCCTAGATGGCTGCTC
CTCCCACAACACAGCCACAGCAGTGGCAGCCCTGGGTGGCTTCCTATACATCCTGGCAGAA
TACCCCCCAGCAAACAGAGAGCCACACCCATCCACACCGCCACCACCAAGCAGCCGCTGAG
ACGGACGGTTCCATGCCAGCTGCCTGGAGGAGGAACAGACCCCTTTAGTCCTCATCCCTTA
GATCCTGGAGGGCACGGATCACATCCTGGGAAGAAGGCATCTGGAGGATAAGCAAAGCCAC
CCCGACACCCAATCTTGGAAGCCCTGAGTAGGCAGGGCCAGGGTAGGTGGGGGCCGGGAGG
GACCCAGGTGTGAACGGATGAATAAAGTTCAACTGCAACTGAAAAAAAAAAA

FIGURE 84

MSARGRWEGGGRRACRGSLGLARAQGAERVTSSEQRPAMASLGLLLLLLLTALPPLWSSSL
PGLDTAESKATIADLILSALERATVFLEQRLPEINLDGMVGVRVLEEQLKSVREKWAQEPL
LQPLSLRVGMLGEKLEAAIQRSLHYLKLSDPKYLREFQLTLQPGFWKLPHAWIHTDASLVY
PTFGPQDSFSEERSDVCLVQLLGTGTDSSEPCGLSDLCRSLMTKPGCSGYCLSHQLLFFLW
ARMRGCTQGPLQQSQDYINLFCANMMDLNRRAEAIGYAYPTRDIFMENIMFCGMGGFSDFY
KLRWLEAILSWQKQQEGCFGEPDAEDEELSKAIQYQQHFSRRVKRREKQFPDSRSVAQAGV
QWRNLGSLQPLPPGFKQFSCLILPSSWDYRSVPPYLANFYIFLVETGFHHVAHAGLELLIS
RDPPTSGSQSVGL

Important features of the protein:

Signal peptide:

amino acids 1-26

Transmembrane domain:

amino acids 39-56

Tyrosine kinase phosphorylation sites.

amino acids 149-156, 274-282

N-myristoylation sites.

amino acids 10-16, 20-26, 63-69, 208-214

Amidation site.

amino acids 10-14

Glycoprotein hormones beta chain signature 1.

amino acids 230-237

FIGURE 85

GGTCTGAGTGCAGAGCTGCTGTCATGGCGGCCGCTCTGTGGGGCTTCTTTCCCGTCCTGCT
GCTGCTGCTGCTATCGGGGGATGTCCAGAGCTCGGAGGTGCCCGGGGCTGCTGCTGAGGGA
TCGGGAGGGAGTGGGGTCGGCATAGGAGATCGCTTCAAGATTGAGGGGCGTGCAGTTGTTC
CAGGGGTGAAGCCTCAGGACTGGATCTCGGCGGCCCGAGTGCTGGTAGACGGAGAAGAGCA
CGTCGGTTTCCTTAAGACAGATGGGAGTTTTGTGGTTCATGATATACCTTCTGGATCTTAT
GTAGTGGAAGTTGTATCTCCAGCTTACAGATTTGATCCCGTTCGAGTGGATATCACTTCGA
AAGGAAAAATGAGAGCAAGATATGTGAATTACATCAAAACATCAGAGGTTGTCAGACTGCC
CTATCCTCTCCAAATGAAATCTTCAGGTCCACCTTCTTACTTTATTAAAAGGGAATCGTGG
GGCTGGACAGACTTTCTAATGAACCCAATGGTTATGATGATGGTTCTTCCTTTATTGATAT
TTGTGCTTCTGCCTAAAGTGGTCAACACAAGTGATCCTGACATGAGACGGGAAATGGAGCA
GTCAATGAATATGCTGAATTCCAACCATGAGTTGCCTGATGTTTCTGAGTTCATGACAAGA
CTCTTCTCTTCAAAATCATCTGGCAAATCTAGCAGCGGCAGCAGTAAAACAGGCAAAAGTG
GGGCTGGCAAAAGGAGGTAGTCAGGCCGTCCAGAGCTGGCATTTGCACAAACACGGCAACA
CTGGGTGGCATCCAAGTCTTGGAAAACCGTGTGAAGCAACTACTATAAACTTGAGTCATCC
CGACGTTGATCTCTTACAACTGTGTATGTTAACTTTTTAGCACATGTTTTGTACTTGGTAC
ACGAGAAAACCCAGCTTTCATCTTTTGTCTGTATGAGGTCAATATTGATGTCACTGAATTA
ATTACAGTGTCCTATAGAAAATGCCATTAATAAATTATATGAACTACTATACATTATGTAT
ATTAATTAAAACATCTTAATCCAGAAATCAAAAAAAAAAAAAAAAAAAAAAAAAAAAA

FIGURE 86

MAAALWGFFPVLLLLLLSGDVQSSEVPGAAAEGSGGSGVGIGDRFKIEGRAVVPGVKPQDW
ISAARVLVDGEEHVGFLKTDGSFVVHDIPSGSYVVEVVSPAYRFDPVRVDITSKGKMRARY
VNYIKTSEVVRLPYPLQMKSSGPPSYFIKRESWGWTDFLMNPMVMMMVLPLLIFVLLPKVV
NTSDPDMRREMEQSMNMLNSNHELPDVSEFMTRLFSSKSSGKSSSGSSKTGKSGAGKRR

Important features of the protein:

Signal sequence:

amino acids 1-23

Transmembrane domain:

amino acids 161-182

N-glycosylation site.

amino acids 184-187

Glycosaminoglycan attachment sites.

amino acids 37-40, 236-239 cAMP- and cGMP-dependent protein kinase phosphorylation site.

amino acids 151-154

N-myristoylation sites.

amino acids 33-38, 36-41, 38-44, 229-234

Amidation site.

amino acids 238-241

ATP/GTP-binding site motif A (P-loop).

amino acids 229-236

FIGURE 87

CAGGATGCAGGGCCGCGTGGCAGGGAGCTGCGCTCCTCTGGGCCTGCTCCTGGTCTGTCTT
CATCTCCCAGGCCTCTTTGCCCGGAGCATCGGTGTTGTGGAGGAGAAAGTTTCCCAAAACT
TCGGGACCAACTTGCCTCAGCTCGGACAACCTTCCTCCACTGGCCCCTCTAACTCTGAACA
TCCGCAGCCCGCTCTGGACCCTAGGTCTAATGACTTGGCAAGGGTTCCTCTGAAGCTCAGC
GTGCCTCCATCAGATGGCTTCCCACCTGCAGGAGGTTCTGCAGTGCAGAGGTGGCCTCCAT
CGTGGGGGCTGCCTGCCATGGATTCCTGGCCCCCTGAGGATCCTTGGCAGATGATGGCTGC
TGCGGCTGAGGACCGCCTGGGGGAAGCGCTGCCTGAAGAACTCTCTTACCTCTCCAGTGCT
GCGGCCCTCGCTCCGGGCAGTGGCCCTTTGCCTGGGGAGTCTTCTCCCGATGCCACAGGCC
TCTCACCTGAGGCTTCACTCCTCCACCAGGACTCGGAGTCCAGACGACTGCCCCGTTCTAA
TTCACTGGGAGCCGGGGGAAAAATCCTTTCCCAACGCCCTCCCTGGTCTCTCATCCACAGG
GTTCTGCCTGATCACCCCTGGGGTACCCTGAATCCCAGTGTGTCCTGGGGAGGTGGAGGCC
CTGGGACTGGTTGGGGAACGAGGCCCATGCCACACCCTGAGGGAATCTGGGGTATCAATAA
TCAACCCCCAGGTACCAGCTGGGGAAATATTAATCGGTATCCAGGAGGCAGCTGGGGAAAT
ATTAATCGGTATCCAGGAGGCAGCTGGGGGAATATTAATCGGTATCCAGGAGGCAGCTGGG
GGAATATTCATCTATACCCAGGTATCAATAACCCATTTCCTCCTGGAGTTCTCCGCCCTCC
TGGCTCTTCTTGGAACATCCCAGCTGGCTTCCCTAATCCTCCAAGCCCTAGGTTGCAGTGG
GGCTAGAGCACGATAGAGGGAAACCCAACATTGGGAGTTAGAGTCCTGCTCCCGCCCCTTG
CTGTGTGGGCTCAATCCAGGCCCTGTTAACATGTTTCCAGCACTATCCCCACTTTTCAGTG
CCTCCCCTGCTCATCTCCAATAAAATAAAAGCACTTATGAAAAAAAAAAAAAAAAAAAAAA
AAAAAAAAAAAAAAAAAAAAAAAAAAAAAAAAAAAAAAAAAAAAAAAAAAAAAAAAAAAAA
AAAAAAAAAAAAAA

FIGURE 88

MQGRVAGSCAPLGLLLVCLHLPGLFARSIGVVEEKVSQNFGTNLPQLGQPSSTGPSNSEHP
QPALDPRSNDLARVPLKLSVPPSDGFPPAGGSAVQRWPPSWGLPAMDSWPPEDPWQMMAAA
AEDRLGEALPEELSYLSSAAALAPGSGPLPGESSPDATGLSPEASLLHQDSESRRLPRSNS
LGAGGKILSQRPPWSLIHRVLPDHPWGTLNPSVSWGGGGPGTGWGTRPMPHPEGIWGINNQ
PPGTSWGNINRYPGGSWGNINRYPGGSWGNINRYPGGSWGNIHLYPGINNPFPPGVLRPPG
SSWNIPAGFPNPPSPRLQWG

Important features of the protein:

Signal peptide:

amino acids 1-26

Casein kinase II phosphorylation sites.

amino acids 56-59, 155-158

N-myristoylation sites.

amino acids 48-53, 220-225, 221-226, 224-229, 247-252, 258-263, 259-264, 269-274, 270-275, 280-285, 281-286, 305-310

FIGURE 89

GCCGCCGGCCCGGGCTGGAGCCGAGCGCAGCAGCCACCGCCGCCGCCGCGCCAGAAGTTTGGGTTGAACCGGAG
CTGCCGGGAGGAAACTTTTTTCTTTTTTCCCCCTCCCTCCCGGGAGGAGGAGGAGGAGGAGGGGAAGCTGC
CGCCGGCGCCAAGGCTCGTGGGCTCGGGGTCGGCGCGGCCCGCAGAAGGGGCGGGGCCTCGCCCCGCGAGGGG
AGGCGCGCCCCGGGGGCCCCGAGAGGGGCGGTGAGGACCGCGGGCTGCTGGTGCGGCGGCGGCGCGTGTGC
CCCGCGCAGGGGAGGGCGCCCGCCCCGCTCCCGGCCCGGCTGCGAGGAGGAGGCGGCGGCGGCGCAGGAGG<u>ATG</u>
TACTTGGTGGCGGGGGACAGGGGGTTGGCCGGCTGCGGGCACCTCCTGGTCTCGCTGCTGGGGCTGCTGCTGCT
GCTGGCGCGCTCCGGCACCCGGGCGCTGGTCTGCCTGCCCTGTGACGAGTCCAAGTGCGAGGAGCCCAGGAACT
GCCCGGGGAGCATCGTGCAGGGCGTCTGCGGCTGCTGCTACACGTGCGCCAGCCAGAGGAACGAGAGCTGCGGC
GGCACCTTCGGGATTTACGGAACCTGCGACCGGGGGCTGCGTTGTGTCATCCGCCCCCCGCTCAATGGCGACTC
CCTCACCGAGTACGAAGCGGGCGTTTGCGAAGATGAGAACTGGACTGATGACCAACTGCTTGGTTTTAAACCAT
GCAATGAAAACCTTATTGCTGGCTGCAATATAATCAATGGGAAATGTGAATGTAACACCATTCGAACCTGCAGC
AATCCCTTTGAGTTTCCAAGTCAGGATATGTGCCTTTCAGCTTTAAAGAGAATTGAAGAAGAGAAGCCAGATTG
CTCCAAGGCCCGCTGTGAAGTCCAGTTCTCTCCACGTTGTCCTGAAGATTCTGTTCTGATCGAGGGTTATGCTC
CTCCTGGGGAGTGCTGTCCCTTACCCAGCCGCTGCGTGTGCAACCCCGCAGGCTGTCTGCGCAAAGTCTGCCAG
CCGGGAAACCTGAACATACTAGTGTCAAAAGCCTCAGGGAAGCCGGGAGAGTGCTGTGACCTCTATGAGTGCAA
ACCAGTTTTCGGCGTGGACTGCAGGACTGTGGAATGCCCTCCTGTTCAGCAGACCGCGTGTCCCCCGGACAGCT
ATGAAACTCAAGTCAGACTAACTGCAGATGGTTGCTGTACTTTGCCAACAAGATGCGAGTGTCTCTCTGGCTTA
TGTGGTTTCCCCGTGTGTGAGGTGGGATCCACTCCCCGCATAGTCTCTCGTGGCGATGGGACACCTGGAAAGTG
CTGTGATGTCTTTGAATGTGTTAATGATACAAAGCCAGCCTGCGTATTTAACAATGTGGAATATTATGATGGAG
ACATGTTTCGAATGGACAACTGTCGGTTCTGTCGATGCCAAGGGGGCGTTGCCATCTGCTTCACTGCCCAGTGT
GGTGAGATAAACTGCGAGAGGTACTACGTGCCCGAAGGAGAGTGCTGCCCAGTGTGTGAAGATCCAGTGTATCC
TTTTAATAATCCCGCTGGCTGCTATGCCAATGGCCTGATCCTTGCCCACGGAGACCGGTGGCGGGAAGACGACT
GCACATTCTGCCAGTGCGTCAACGGTGAACGCCACTGCGTTGCGACCGTCTGCGGACAGACCTGCACAAACCCT
GTGAAAGTGCCTGGGGAGTGTTGCCCTGTGTGCGAAGAACCAACCATCATCACAGTTGATCCACCTGCATGTGG
GGAGTTATCAAACTGCACTCTGACAGGGAAGGACTGCATTAATGGTTTCAAACGCGATCACAATGGTTGTCGGA
CCTGTCAGTGCATAAACACCGAGGAACTATGTTCAGAACGTAAACAAGGCTGCACCTTGAACTGTCCCTTCGGT
TTCCTTACTGATGCCCAAAACTGTGAGATCTGTGAGTGCCGCCCAAGGCCCAAGAAGTGCAGACCCATAATCTG
TGACAAGTATTGTCCACTTGGATTGCTGAAGAATAAGCACGGCTGTGACATCTGTCGCTGTAAGAAATGTCCAG
AGCTCTCATGCAGTAAGATCTGCCCCTTGGGTTTCCAGCAGGACAGTCACGGCTGTCTTATCTGCAAGTGCAGA
GAGGCCTCTGCTTCAGCTGGGCCACCCATCCTGTCGGGCACTTGTCTCACCGTGGATGGTCATCATCATAAAAA
TGAGGAGAGCTGGCACGATGGGTGCCGGGAATGCTACTGTCTCAATGGACGGGAAATGTGTGCCCTGATCACCT
GCCCGGTGCCTGCCTGTGGCAACCCCACCATTCACCCTGGACAGTGCTGCCCATCATGTGCAGATGACTTTGTG
GTGCAGAAGCCAGAGCTCAGTACTCCCTCCATTTGCCACGCCCCTGGAGGAGAATACTTTGTGGAAGGAGAAAC
GTGGAACATTGACTCCTGTACTCAGTGCACCTGCCACAGCGGACGGGTGCTGTGTGAGACAGAGGTGTGCCCAC
CGCTGCTCTGCCAGAACCCCTCACGCACCCAGGATTCCTGCTGCCCACAGTGTACAGATCAACCTTTTCGGCCT
TCCTTGTCCCGCAATAACAGCGTACCTAATTACTGCAAAAATGATGAAGGGGATATATTCCTGGCAGCTGAGTC
CTGGAAGCCTGACGTTTGTACCAGCTGCATCTGCATTGATAGCGTAATTAGCTGTTTCTCTGAGTCCTGCCCTT
CTGTATCCTGTGAAAGACCTGTCTTGAGAAAAGGCCAGTGTTGTCCCTACTGCATAGAAGACACAATTCCAAAG
AAGGTGGTGTGCCACTTCAGTGGGAAGGCCTATGCCGACGAGGAGCGGTGGGACCTTGACAGCTGCACCCACTG
CTACTGCCTGCAGGGCCAGACCCTCTGCTCGACCGTCAGCTGCCCCCCTCTGCCCTGTGTTGAGCCCATCAACG
TGGAAGGAAGTTGCTGCCCAATGTGTCCAGAAATGTATGTCCCAGAACCAACCAATATACCCATTGAGAAGACA
AACCATCGAGGAGAGGTTGACCTGGAGGTTCCCCTGTGGCCCACGCCTAGTGAAAATGATATCGTCCATCTCCC

TAGAGATATGGGTCACCTCCAGGTAGATTACAGAGATAACAGGCTGCACCCAAGTGAAGATTCTTCACTGGACT

FIGURE 89 Continued

CCATTGCCTCAGTTGTGGTTCCCATAATTATATGCCTCTCTATTATAATAGCATTCCTATTCATCAATCAGAAG
AAACAGTGGATACCACTGCTTTGCTGGTATCGAACACCAACTAAGCCTTCTTCCTTAAATAATCAGCTAGTATC
TGTGGACTGCAAGAAAGGAACCAGAGTCCAGGTGGACAGTTCCCAGAGAATGCTAAGAATTGCAGAACCAGATG
CAAGATTCAGTGGCTTCTACAGCATGCAAAAACAGAACCATCTACAGGCAGACAATTTCTACCAAACAGTGTGA
AGAAAGGCAACTAGGATGAGGTTTCAAAAGACGGAAGACGACTAAATCTGCTCTAAAAAGTAAACTAGAATTTG
TGCACTTGCTTAGTGGATTGTATTGGATTGTGACTTGATGTACAGCGCTAAGACCTTACTGGGATGGGCTCTGT
CTACAGCAATGTGCAGAACAAGCATTCCCACTTTTCCTCAAAAAA

FIGURE 90

MYLVAGDRGLAGCGHLLVSLLGLLLLLARSGTRALVCLPCDESKCEEPRNCPGSIVQGVCGCCYTCASQRNESC
GGTFGIYGTCDRGLRCVIRPPLNGDSLTEYEAGVCEDENWTDDQLLGFKPCNENLIAGCNIINGKCECNTIRTC
SNPFEFPSQDMCLSALKRIEEEKPDCSKARCEVQFSPRCPEDSVLIEGYAPPGECCPLPSRCVCNPAGCLRKVC
QPGNLNILVSKASGKPGECCDLYECKPVFGVDCRTVECPPVQQTACPPDSYETQVRLTADGCCTLPTRCECLSG
LCGFPVCEVGSTPRIVSRGDGTPGKCCDVFECVNDTKPACVFNNVEYYDGDMFRMDNCRFCRCQGGVAICFTAQ
CGEINCERYYVPEGECCPVCEDPVYPFNNPAGCYANGLILAHGDRWREDDCTFCQCVNGERHCVATVCGQTCTN
PVKVPGECCPVCEEPTIITVDPPACGELSNCTLTGKDCINGFKRDHNGCRTCQCINTEELCSERKQGCTLNCPF
GFLTDAQNCEICECRPRPKKCRPIICDKYCPLGLLKNKHGCDICRCKKCPELSCSKICPLGFQQDSHGCLICKC
REASASAGPPILSGTCLTVDGHHHKNEESWHDGCRECYCLNGREMCALITCPVPACGNPTIHPGQCCPSCADDF
VVQKPELSTPSICHAPGGEYFVEGETWNIDSCTQCTCHSGRVLCETEVCPPLLCQNPSRTQDSCCPQCTDQPFR
PSLSRNNSVPNYCKNDEGDIFLAAESWKPDVCTSCICIDSVISCFSESCPSVSCERPVLRKGQCCPYCIEDTIP
KKVVCHFSGKAYADEERWDLDSCTHCYCLQGQTLCSTVSCPPLPCVEPINVEGSCCPMCPEMYVPEPTNIPIEK
TNHRGEVDLEVPLWPTPSENDIVHLPRDMGHLQVDYRDNRLHPSEDSSLDSIASVVVPIIICLSIIIAFLFINQ
KKQWIPLLCWYRTPTKPSSLNNQLVSVDCKKGTRVQVDSSQRMLRIAEPDARFSGFYSMQKQNHLQADNFYQTV

Important features of the protein:

Signal peptide:

amino acids 1-34

Transmembrane domain:

amino acids 940-962

N-glycosylation sites.

amino acids 71-75, 113-117, 330-334, 474-478, 746-750 cAMP- and cGMP-dependent protein kinase phosphorylation site.

amino acids 992-996

N-myristoylation site.

amino acids 9-15, 58-64, 61-67, 75-81, 79-85, 362-368, 402-408, 407-413, 439-445, 492-498, 511-517, 551-557, 558-564, 586-592, 606-612, 625-631, 845-851

Prokaryotic membrane lipoprotein lipid attachment site.

amino acids 52-63, 844-855

Cell attachment sequence.

amino acids 314-317

Leucine zipper pattern.

amino acids 3-25

Eukaryotic thiol (cysteine) proteases cysteine active site.

amino acids 57-69

VWFC domain proteins.

amino acids 448-456, 382-390

C-terminal cystine knot proteins amino acids 60-86

FIGURE 91

GCAAAAGGAAGGGAGGGAAGCACTCCATCATCTCACTGGGAAGAACGGCACGGGCATACCT
GCAGCTACTGGGGTTCCACTGGGCTTGAGGGTCGATTTTTCACCTTTTGAAGGACAAGATG
CATTGGAAGATGTTGCTGCTTCTGCTGTTGTATTACAATGCTGAGGCTTCTATGTGCCACA
GGTGGAGCAGGGCTGTGCTCTTCCCTGCCGCCCACCGGCCAAAGAGGTCCTCATCACTGCC
ATTGAACCCAGTCCTGCAGACCTCCCTGGAGGAGGTGGAGCTGCTCTACGAGTTCCTGCTG
GCCGAACTTGAGATCAGCCCTGACCTGCAGATCTCCATCAAGGACGAGGAGCTGGCCTCCT
TGCGGAAGGCCTCAGACTTCCGCACCGTCTGCAACAACGTCATCCCCAAGAGCATCCCAGA
CATCCGCCGGCTCAGCGCCAGCCTCTCCAGCCACCCTGGCATCCTCAAGAAAGAAGACTTT
GAAAGGACAGTGCTGACCCTGGCCTACACAGCCTACCGCACAGCCCTGTCCCACGGCCATC
AGAAGGACATCTGGGCGCAGTCCCTCGTTAGCCTCTTCCAGGCCCTGAGGCACGACTTGAT
GCGCTCCTCACAGCCGGGAGTACCTCCCTGAGAGACTGGCCCACACCAGGACCTCAGAGCA
GGGACCAGCACAGTAATCCAGAAAGTCTTCATTCTCTACTCCATTTACAGAGACCAGCAAC
AAAACACTTACCGCTGACACAGAGCAGCAGAGATCAAACAGTAACCCCGATGCTCTTTTCT
CCTTGTAGTTTCCTGGAAGACACATCTGATTCATGCCATCATGTGACCTGGGCTGGAAGAA
AGGGCTGGAATGGTCATTCAAGACGCCTCCATGGGCAGAATGGTTTGCCTATGGCAGGCAG
AATTCTGATATGCTTCAACCCAGAGCAGTGGCCACACACTCAAGAGTGAGAACAGGCGTGA
GCCACCGTGCCTGGCCCAGGATCTAAAAACTTTCTAAGTTTCCTCCATCGTTGGCATCCTC
ACAGCTATCTCCAATGTCACTCAAGAGACATCAACAGACATTTAACTGCTGCAGACTTCAT
TGCTCTGTCACCTCACCTTGAATCTAACAAATCAAAGTATTTCTGCAGGTCCAATGGTCTA
AAATCAAATGCTTGTTAAATGACTTTTTACAACACCCCTTACTTTCCTAATCCATTTCAAT
CTTATTTTTTTTATTGTGGTAAAAAACACATCACGTAAAATGTACCATCTTAACCATTTTT
AAGCATATGGTACAGCAGTGTTAACTCCATGCATGTTGTGAAACAGACCCCCGGAACTTTC
TCATCTTGTAATTCTGAAGTTCTATACCCACCGAACAACTCCTCTTTTCCCCTTCCCCCTG
CCTGCCCCAGCTCTTGGCACCATTATTCTGCTTTCTGTTTTTGAGAGTCTGACTACTTAAG
ATACCTCATACAAGCGGGATCTGGCTTACATTTCTTGAGCATTGTATTCTGGAAAAGTGTT
TCCTTCCTCTGAAAAATGGGTAGAGTTCTGAAGGAGAACTACTGGTCTTATTGTACACTTG
CTGTACCTATTTTTATTTAACAAATATTCATCTATGGTATAATAAAGATGTCATGGTTGGA
AAAAAAAAAAAAAAAAAAAAAAA

FIGURE 92

></usr/seqdb2/sst/DNA/Dnaseqs.min/ss.DNA96893

><subunit 1 of 1, 173 aa, 1 stop

><MW: 19733, pI: 8.78, NX(S/T): 0

MHWKMLLLLLLYYNAEASMCHRWSRAVLFPAAHRPKRSSSLPLNPVLQTSLEEVELLYEF
LLAELEISPDLQISIKDEELASLRKASDFRTVCNNVIPKSIPDIRRLSASLSSHPGILKK
EDFERTVLTLAYTAYRTALSHGHQKDIWAQSLVSLFQALRHDLMRSSQPGVPP

Important features of the protein:

Signal peptide:

Amino acids 1-17 cAMP- and cGMP-dependent protein kinase phosphorylation sites:

Amino acids 36-40;84-88;105-109

FIGURE 93

CACCATGCCTGGGGGGTGCTCCCGGGGCCCCGCCGCCGGGGACGGGCGTCTGCGGCTGGC
GCGACTAGCGCTGGTACTCCTGGGCTGGGTCTCCTCGTCTTCTCCCACCTCCTCGGCATC
CTCCTTCTCCTCCTCGGCGCCGTTCCTGGCTTCCGCCGTGTCCGCCCAGCCCCCGCTGCC
GGACCAGTGCCCCGCGCTGTGCGAGTGCTCCGAGGCAGCGCGCACAGTCAAGTGCGTTAA
CCGCAATCTGACCGAGGTGCCCACGGACCTGCCCGCCTACGTGCGCAACCTCTTCCTTAC
CGGCAACCAGCTGGCCGTGCTCCCTGCCGGCGCCTTCGCCCGCCGGCCGCCGCTGGCGGA
GCTGGCCGCGCTCAACCTCAGCGGCAGCCGCCTGGACGAGGTGCGCGCGGGCGCCTTCGA
GCATCTGCCCAGCCTGCGCCAGCTCGACCTCAGCCACAACCCACTGGCCGACCTCAGTCC
CTTCGCTTTCTCGGGCAGCAATGCCAGCGTCTCGGCCCCCAGTCCCCTTGTGGAACTGAT
CCTGAACCACATCGTGCCCCCTGAAGATGAGCGGCAGAACCGGAGCTTCGAGGGCATGGT
GGTGGCGGCCCTGCTGGCGGGCCGTGCACTGCAGGGGCTCCGCCGCTTGGAGCTGGCCAG
CAACCACTTCCTTTACCTGCCGCGGGATGTGCTGGCCCAACTGCCCAGCCTCAGGCACCT
GGACTTAAGTAATAATTCGCTGGTGAGCCTGACCTACGTGTCCTTCCGCAACCTGACACA
TCTAGAAAGCCTCCACCTGGAGGACAATGCCCTCAAGGTCCTTCACAATGGCACCCTGGC
TGAGTTGCAAGGTCTACCCCACATTAGGGTTTTCCTGGACAACAATCCCTGGGTCTGCGA
CTGCCACATGGCAGACATGGTGACCTGGCTCAAGGAAACAGAGGTAGTGCAGGGCAAAGA
CCGGCTCACCTGTGCATATCCGGAAAAAATGAGGAATCGGGTCCTCTTGGAACTCAACAG
TGCTGACCTGGACTGTGACCCGATTCTTCCCCCATCCCTGCAAACCTCTTATGTCTTCCT
GGGTATTGTTTTAGCCCTGATAGGCGCTATTTTCCTCCTGGTTTTGTATTTGAACCGCAA
GGGGATAAAAAAGTGGATGCATAACATCAGAGATGCCTGCAGGGATCACATGGAAGGGTA
TCATTACAGATATGAAATCAATGCGGACCCCAGATTAACAAACCTCAGTTCTAACTCGGA
TGTCTGAGAAATATTAGAGGACAGACCAAGGACAACTCTGCATGAGATGTAG

FIGURE 94

><Sequence Version 1, Tue Jan 7 15:33:00 2003 DNA336539 [min]
></usr/seqdb2/sst/DNA/Dnaseqs.min/ss.DNA336539
><subunit 1 of 1, 420 aa, 1 stop
><MW: 46032, pI: 6.76, NX(S/T): 8
MPGGCSRGPAAGDGRLRLARLALVLLGWVSSSSPTSSASSFSSSAPFLASAVSAQPPLPD
QCPALCECSEAARTVKCVNRNLTEVPTDLPAYVRNLFLTGNQLAVLPAGAFARRPPLAEL
AALNLSGSRLDEVRAGAFEHLPSLRQLDLSHNPLADLSPFAFSGSNASVSAPSPLVELIL
NHIVPPEDERQNRSFEGMVVAALLAGRALQGLRRLELASNHFLYLPRDVLAQLPSLRHLD
LSNNSLVSLTYVSFRNLTHLESLHLEDNALKVLHNGTLAELQGLPHIRVFLDNNPWVCDC
HMADMVTWLKETEVVQGKDRLTCAYPEKMRNRVLLELNSADLDCDPILPPSLQTSYVFLG
IVLALIGAIFLLVLYLNRKGIKKWMHNIRDACRDHMEGYHYRYEINADPRLTNLSSNSDV

FIGURE 95

GGCTTCTACAGTCCACAACACCCACCAGCCCCAGGCCCAGCAGAATGAGCCCAGTGAGTG
CCGGGGCTCCCAGTTTGGCTGTTGCTATGACAACGTGGCCACTGCAGCCGGTCCTCTTGG
GGAAGGCTGTGTGGGCCAGCCCAGCCATGCCTACCCCGTGCGGTGCCTGCTGCCCAGTGC
CCATGGCTCTTGTGCAGACTGGGCTGCCCGCTGGTACTTCGTTGCCTCTGTGGGCCAATG
TAACCGCTTCTGGTATGGCGGCTGCCATGGCAATGCCAATAACTTTGCCTCGGAGCAAGA
GTGCATGAGCAGCTGCCAGGGATCTCTCCATGGGCCCCGTCGTCCCCAGCCTGGGGCTTC
TGGAAGGAGCACCCACACGGATGGTGGCGGCAGCAGTCCTGCAGGCGAGCAGGAACCCAG
CCAGCACAGGACAGGGGCCGCGGTGCAGAGAAAGCCCTGGCCTTCTGGTGGTCTCTGGCG
GCAAGACCAACAGCCTGGGCCAGGGGAGGCCCCCCACACCCAGGCCTTTGGAGAATGGCC
ATGGGGGCAGGAGCTTGGGTCCAGGGCCCCTGGACTGGGTGGAGATGCCGGATCACCAGC
GCCACCCTTCCACAGCTCCTCCTACAGATCTCACTTCCCACCTCTCCAGGATTAGCTTGG
CAGGTGTGGAGCCCTCGTTGGTGCAGGCAGCCCTGGGGCAGTTGGTGCGGCTCTCCTGCT
CAGACGACACTGCCCCGGAATCCCAGGCTGCCTGGCAGAAAGATGGCCAGCCCATCTCCT
CTGACAGGCACAGGCTGCAGTTCGACGGATCCCTGATCATCCACCCCCTGCAGGCAGAGG
ACGCGGGCACCTACAGCTGTGGCAGCACCCGGCCAGGCCGCGACTCCCAGAAGATCCAAC
TCCGCATTATAGGGGGTGACATGGCCGTGCTGTCTGAGGCTGAGCTGAGCCGCTTCCCTC
AGCCCAGGGACCCAGCTCAGGACTTTGGCCAAGCGGGGGCTGCTGGGCCCCTGGGGGCCA
TCCCCTCTTCACACCCACAGCCTGCAAACAGGCTGCGTTTGGACCAGAACCAGCCCCGGG
TGGTGGATGCCAGTCCAGGCCAGCGGATCCGGATGACCTGCCGTGCCGAAGGCTTCCCGC
CCCCAGCCATCGAGTGGCAGAGAGATGGGCAGCCTGTCTCTTCTCCCAGACACCAGCTGC
AGCCTGATGGCTCCCTGGTCATTAGCCGAGTGGCTGTAGAAGATGGCGGCTTCTACACCT
GTGTCGCTTTCAATGGGCAGGACCGAGACCAGCGATGGGTCCAGCTCAGAGTTCTGGGGG
AGCTGACAATCTCAGGACTGCCCCCTACTGTGACAGTGCCAGAGGGTGATACGGCCAGGC
TATTGTGTGTGGTAGCAGGAGAAAGTGTGAACATCAGGTGGTCCAGGAACGGGCTACCTG
TGCAGGCTGATGGCCACCGTGTCCACCAGTCCCCAGATGGCACGCTGCTCATTTACAACT
TGCGGGCCAGGGATGAGGGCTCCTACATGTGCAGTGCCTACCAGGGGAGCCAGGCAGTCA
GCCGCAGCACCGAGGTGAAGGTGGTCTCACCAGCACCCACCGCCCAGCCCAGGGACCCTG
GCAGGGACTGCGTCGACCAGCCAGAGCTGGCCAACTGTGATTTGATCCTGCAGGCCCAGC
TTTGTGGCAATGAGTATTACTCCAGCTTCTGCTGTGCCAGCTGTTCACGTTTCCAGCCTC
ACGCTCAGCCCATCTGGCAGTAGGGATGAAGGCTAGTTCCAGCCCCAGTCCAAAATAGTT
CATAGGGCTAGGGAGAAAGGAAGATGGACTCTTGGCTTCCTCTCTCTGGCTGGCAAAGGG
AGTTATCTTCTGGAATACATTAGCTCTTTCAAAAACCCACCCAGTGTTTAGCCTCAACGG
CAGCCAGTTACCAGCTTCTCTCTGTAGCCTTCAGCAGTGTTTGCATCTCTGACATAACCA
CAGGCTGCTGTTTTCAAGAAGAGCAATCTGTTTGGATAAGAAAAACCTTTACTTTACAGC
TTCCCTTTATAATTTGTTACACAGGAATAGTTAAATGCATTTGTTTGTTTGTTTTTTGAG
ACGGAGTTTCACTCTTGTTGCCCAGGCTGGAGGGCAATGGCGCGATCTCAGCTCACTGCA
ACCTCCGTCTCCTGGGTTCTTGATTCTCCTGTGTCAGCCTTCTGAGTAGCTGGGATTACA
GATGCCTATCACCATGCCTGGGTAATTTTTGTATTTTTAGTTGAGATGGGGTTTCGCCAT
GTTGGCCAGGCTGGTCTCGAACTTCTGACCTCAGATGATCTGCCCGCCTCAGCCTCCCAA
AGTGCTGGGATTACAGGCATGAGCCACCACGCCCAGCCATCAATGCATTTTTTTTATTTT
TTTTTTGAGACAGAGTTTCGCACTTCTTGCCCAGGCTGGAGTACAATGGTGCGATCTTGG
CTCACTGCAACCTCCACCTCCTGGGTTCAAGCGCTTCTCCAGCCTCAGCCTCCTGAGTAG

FIGURE 95 Continued

CTGGGATTACAGGTATGTGCCACCATGCCTGGCTAATTTTGTATTTTTGGTGGAGACGGG
GTTTCTCCATGTTGGTCAGACTGGTCTTGAACTCCCGACCTCAGGTAATCCGCCCGCCTC
CGCCTCCCAAAATGCTGGGATTAGAGGTGTGAGCCACTGTGCCCAGCCCATCAATGTGTT
TTAAAGCTAGCTGTCAGGGTTCCACTTAATTTAAAGCTGGGCAGGGAGATGTGTAATGAT
TTCAAAGTTAACACCTGTTTGTTTTCTAAAGGGCATGCCAAGTCCTGCTGTATCAGGGAA
GTATTCTGTGCTAAAATCAGCGATGGTTCATTGCTCTAGTCTCTCTCACCCTTCTAGGCA
GTGCATCAGTCAGCTCTAAATCTGGTGCAGAGGGTTAACAGCATAACCCTTGTTGGCAAA
ATGGAATAGATGTTAAGACCTCAAATAGGGATTTGGGATGAAACAGCTGCAGTTAGCACT
GTTATCTGAGCATGAAAGAACTGGAAACGCTCCTTACGTCGAGATGTTGGACCTTGAAGC
CCTCCTGAGGCCAACATGCAAATCTGGCTGTGACGGTTCATCTGACACCTGTGTAAAGCT
GACCAGCCTGCTCTGTACAGTGACAATGAGGAGCCCCTCTCTTCCTTAAGTAGGAATCTG
TGAAGCAAAATGTTTGCTGCCAAAGACAAATCAGACTGTCAGTCATTAAAAACAGCATTA
GCAGGATGAGGATAGCAATGGGGAAGGGTTGTGGGCAATGCAGTAACAGGGAAATGGCTT
CAGAAATGGTTTGAGTTGGAAGACAACATTCTTCATCTCTCAGGACTTCTAATTCCTTGA
TGCTAAAAGAAGAGGCATGGATTCTATGAGCTTCCAAGTCCCTTTCCACTTTAACCTTCT
ACAAATCTTTCAGAGGACTGCCTAGTAGCAAAGGTTATTCCTGGACACAGGAAAGACGGG
CATTACAGGGACCAAAGCTCTGAAAGGTGACTTTTATTACCAACACACTGGCTGGAAAAG
GGACAAACCACATCACGGGTGAGTGATACTTCTCAGTCTTCTCTACTCATTCAACAAAGG
AAATGTGGGCTGGGGCAGAGGTCTTTTTTCATTTAATACTGGAAAAATATTGAAGAGCAT
CCATGTTCACTTATGGCTGGTTTTGCTATAGAAATTGGAAAATAAAGGCCACTTTTTTG

FIGURE 96

><Thu Jun 24 12:35:18 PDT 1999 DNA62849 [min]
></usr/seqdb2/sst/DNA/Dnaseqs.min/ss.DNA62849
><subunit 1 of 1, 477 aa, 1 stop
><MW: 51112, pI: 6.66, NX(S/T): 0

MGPVVPSLGLLEGAPTRMVAAAVLQASRNPASTGQGPRCRESPGLLVVSGGKTNSLGQGR
PPTPRPLENGHGGRSLGPGPLDWVEMPDHQRHPSTAPPTDLTSHLSRISLAGVEPSLVQA
ALGQLVRLSCSDDTAPESQAAWQKDGQPISSDRHRLQFDGSLIIHPLQAEDAGTYSCGST
RPGRDSQKIQLRIIGGDMAVLSEAELSRFPQPRDPAQDFGQAGAAGPLGAIPSSHPQPAN
RLRLDQNQPRVVDASPGQRIRMTCRAEGFPPPAIEWQRDGQPVSSPRHQLQPDGSLVISR
VAVEDGGFYTCVAFNGQDRDQRWVQLRVLGELTISGLPPTVTVPEGDTARLLCVVAGESV
NIRWSRNGLPVQADGHRVHQSPDGTLLIYNLRARDEGSYMCSAYQGSQAVSRSTEVKVVS
PAPTAQPRDPGRDCVDQPELANCDLILQAQLCGNEYYSSFCCASCSRFQPHAQPIWQ

FIGURE 97

GGCGGCGGGAGCAGCGAAGGGGGCGGCAGGGATCCTCCAGGCTGCCGGCTGGGAAGGCGT
GGGCGACCCGGTGTGTGGCGCGCCCAGAGCCCCGCGTTTCAGCCCTAGGGAAGGAAGCCA
GTTGAGGGAAGTTCTCCATGAATGTACGTCACAATGATGATGACCGACCAAATCCCTCTG
GAACTGCCACCATTGCTGAACGGAGAGGTAGCCATGATGCCCCACTTGGTGAATGGAGAT
GCAGCTCAGCATGTTATTCTCGTTCAAGTTAATCCAGGTGAGACTTTCACAATAAGAGCA
GAGGATGGAACACTTCAGTGCATTCAAGGACCTGCTGAAGTTCCCATGATGTCACCCAAT
GGATCCATTCCTCCCATTCATGTGCCTCCAGGTTATATCTCACAGGTGATTGAAGATAGT
ACTGGAGTCCGCCGGGTGGTGGTCACACCCCAGTCTCCTGAGTGTTATCCCCCAAGCTAC
CCCTCAGCCATGTCTCCAACCCATCATCTCCCTCCCTATCTGACTCACCATCCACATTTT
ATTCATAACTCACACACGGCTTACTACCCACCTGTTACCGGACCTGGAGATATGCCGCCT
CAGTTTTTTCCCCAGCATCATCTTCCCCACACAATATATGGTGAGCAAGAAATTATACCA
TTTTATGGAATGTCAAGCTACATCACCCGAGAAGACCAGTACAGCAAGCCTCCGCACAAA
AAACTGAAAGACCGCCAGATCGATCGCCAGAACCGCCTCAACAGCCCTCCTTCTTCTATC
TACAAAAGCAGCTGCACAACAGTATACAATGGCTATGGGAAGGGCCATAGTGGTGGAAGT
GGCGGAGGCGGCAGCGGTAGTGGTCCCGGAATTAAGAAAACAGAGCGACGAGCAAGAAGC
AGCCCAAAGTCGAATGATTCAGACTTGCAAGAATATGAGTTGGAAGTAAAGAGGGTGCAA
GACATTCTTTCGGGAATAGAGAAACCACAGGTTTCTAATATTCAGGCAAGAGCAGTTGTG
TTGTCCTGGGCTCCCCCTGTTGGACTTTCCTGTGGACCCCACAGTGGTCTTTCCTTCCCC
TACAGTTACGAGGTGGCCTTATCAGACAAAGGACGAGATGGAAAATACAAGATAATTTAC
AGTGGAGAAGAATTAGAATGTAACCTGAAAGATCTTAGACCAGCAACAGATTATCATGTG
AGGGTGTATGCCATGTACAATTCCGTAAAGGGATCCTGCTCCGAGCCTGTTAGCTTCACC
ACCCACAGCTGTGCACCCGAGTGTCCTTTCCCCCCTAAGCTGGCACATAGGAGCAAAAGT
TCACTAACCCTGCAGTGGAAGGCACCAATTGACAACGGTTCAAAAATCACCAACTACCTT
TTAGAGTGGGATGAGGGAAAAAGAAATAGTGGTTTCAGACAGTGCTTCTTCGGGAGCCAG
AAGCACTGCAAGTTGACAAAGCTTTGTCCGGCAATGGGGTACACATTCAGGCTGGCCGCT
CGAAACGACATTGGCACCAGTGGTTATAGCCAAGAGGTGGTGTGCTACACATTAGGAAAT
ATCCCTCAGATGCCTTCTGCACTAAGGCTGGTTCGAGCTGGCATCACATGGGTCACGTTG
CAGTGGAGTAAGCCAGAAGGCTGTTCACCCGAGGAAGTGATCACCTACACCTTGGAAATT
CAGGAGGATGAAAATGATAACCTTTTCCACCCAAAATACACTGGAGAGGATTTAACCTGT
ACTGTGAAAAATCTCAAAAGAAGCACACAGTATAAATTCAGGCTGACTGCTTCTAATACG
GAAGGAAAAAGCTGTCCAAGCGAAGTTCTTGTTTGTACGACGAGTCCTGACAGGCCTGGA
CCTCCTACCAGACCGCTTGTCAAAGGCCCAGTTACATCTCATGGCTTTAGTGTCAAATGG
GATCCCCCTAAGGACAATGGTGGTTCAGAAATCCTCAAGTACTTGCTAGAGATTACTGAT
GGAAATTCTGAAGCGAATCAGTGGGAAGTGGCCTACAGTGGGTCGGCTACCGAATACACC
TTCACCCACTTGAAACCAGGCACTTTGTACAAACTCCGAGCATGCTGCATCAGTACCGGC
GGACACAGCCAGTGTTCTGAAAGTCTCCCTGTTCGCACACTAAGCATTGCACCAGGTCAA
TGTCGACCACCGAGGGTTTTGGGTAGACCAAAGCACAAAGAAGTCCACTTAGAGTGGGAT
GTTCCTGCATCGGAAAGTGGCTGTGAGGTCTCAGAGTACAGCGTGGAGATGACGGAGCCC
GAAGACGTAGCCTCGGAAGTGTACCATGGCCCAGAGCTGGAGTGCACCGTCGGCAACCTG
CTTCCTGGAACCGTGTATCGCTTCCGGGTGAGGGCTCTGAATGATGGAGGGTATGGTCCC
TATTCTGATGTCTCAGAAATTACCACTGCTGCAGGGCCTCCTGGACAATGCAAAGCACCT
TGTATTTCTTGTACACCTGATGGATGTGTCTTAGTGGGTTGGGAGAGTCCTGATAGTTCT

GGTGCTGACATCTCAGAGTACAGGTTGGAATGGGGAGAAGATGAAGAATCCTTAGAACTC

FIGURE 97 Continued

ATTTATCATGGGACAGACACCCGTTTTGAAATAAGAGACCTGTTGCCTGCTGCACAGTAT
TGCTGTAGACTACAGGCCTTCAATCAAGCAGGGGCAGGGCCGTACAGTGAACTTGTCCTT
TGCCAGACGCCAGCGTCTGCCCCTGACCCCGTCTCCACTCTCTGTGTCCTGGAGGAGGAG
CCCCTTGATGCCTACCCTGATTCACCTTCTGCGTGCCTTGTACTGAACTGGGAAGAGCCG
TGCAATAACGGATCTGAAATCCTTGCTTACACCATTGATCTAGGAGACACTAGCATTACC
GTGGGCAACACCACCATGCATGTTATGAAAGATCTCCTTCCAGAAACCACCTACCGGATC
AGAATTCAGGCTATAAATGAAATTGGAGCTGGACCATTTAGTCAGTTCATTAAAGCAAAA
ACTCGGCCATTACCACCCTTGCCTCCTAGGCTAGAATGTGCTGCTGCTGGTCCTCAGAGC
CTGAAGCTAAAATGGGGAGACAGTAACTCCAAGACACATGCTGCTGAGGACATTGTGTAC
ACACTACAGCTGGAGGACAGAAACAAGAGGTTTATTTCAATCTACAGAGGACCCAGCCAC
ACCTACAAGGTCCAGAGACTGACGGAATTCACATGCTACTCCTTCAGAATCCAGGCAGCA
AGCGAGGCTGGAGAAGGGCCCTTCTCAGAAACCTATACCTTCAGCACAACCAAAAGTGTC
CCCCCCACCATCAAAGCACCTCGAGTAACACAGTTAGAAGTAAATTCATGTGAAATTTTA
TGGGAGACGGTACCATCAATGAAAGGTGACCCTGTTAACTACATTCTGCAGGTATTGGTT
GGAAGAGAATCTGAGTACAAACAGGTGTACAAGGGAGAAGAAGCCACATTCCAAATCTCA
GGCCTCCAGACCAACACAGACTACAGGTTCCGCGTATGTGCGTGTCGTCGCTGTTTAGAC
ACCTCTCAGGAGCTAAGCGGAGCCTTCAGCCCCTCTGCGGCTTTTGTATTACAACGAAGT
GAGGTCATGCTTACAGGGGACATGGGGAGCTTAGATGATCCCAAAATGAAGAGCATGATG
CCTACTGATGAACAGTTTGCAGCCATCATTGTGCTTGGCTTTGCAACTTTGTCCATTTTA
TTTGCCTTTATATTACAGTACTTCTTAATGAAGTAAACCCAACAAAACTAGAGGTATGAA
TTAATGCTACACATTTTAATACACACATTTATTCAGATACTCCCCTTTTTAAAGCCCTTT
TGTTTTTTGATTTATATACTCTGTTTTACAGATTTAGCTAGAAAAAAAATGTCAGTGTTT
TGGTGCACCTTTTTGAAATGCAAAACTAGGAAAAGGTTAAACTGGATTTTTTTTAAAAA
AAAAAAAAAAAAAAAAAA

FIGURE 98

><Fri Apr 20 10:24:40 PDT 2001 DNA222844 [min]
></usr/seqdb2/sst/DNA/Dnaseqs.min/ss.DNA222844
><subunit 1 of 1, 1204 aa, 1 stop
><MW: 132941, pI: 5.92, NX(S/T): 5

MYVTMMMTDQIPLELPPLLNGEVAMMPHLVNGDAAQHVILVQVNPGETFTIRAEDGTLQC
IQGPAEVPMMSPNGSIPPIHVPPGYISQVIEDSTGVRRVVVTPQSPECYPPSYPSAMSPT
HHLPPYLTHHPHFIHNSHTAYYPPVTGPGDMPPQFFPQHHLPHTIYGEQEIIPFYGMSSY
ITREDQYSKPPHKKLKDRQIDRQNRLNSPPSSIYKSSCTTVYNGYGKGHSGGSGGGGSGS
GPGIKKTERRARSSPKSNDSDLQEYELEVKRVQDILSGIEKPQVSNIQARAVVLSWAPPV
GLSCGPHSGLSFPYSYEVALSDKGRDGKYKIIYSGEELECNLKDLRPATDYHVRVYAMYN
SVKGSCSEPVSFTTHSCAPECPFPPKLAHRSKSSLTLQWKAPIDNGSKITNYLLEWDEGK
RNSGFRQCFFGSQKHCKLTKLCPAMGYTFRLAARNDIGTSGYSQEVVCYTLGNIPQMPSA
LRLVRAGITWVTLQWSKPEGCSPEEVITYTLEIQEDENDNLFHPKYTGEDLTCTVKNLKR
STQYKFRLTASNTEGKSCPSEVLVCTTSPDRPGPPTRPLVKGPVTSHGFSVKWDPPKDNG
GSEILKYLLEITDGNSEANQWEVAYSGSATEYTFTHLKPGTLYKLRACCISTGGHSQCSE
SLPVRTLSIAPGQCRPPRVLGRPKHKEVHLEWDVPASESGCEVSEYSVEMTEPEDVASEV
YHGPELECTVGNLLPGTVYRFRVRALNDGGYGPYSDVSEITTAAGPPGQCKAPCISCTPD
GCVLVGWESPDSSGADISEYRLEWGEDEESLELIYHGTDTRFEIRDLLPAAQYCCRLQAF
NQAGAGPYSELVLCQTPASAPDPVSTLCVLEEEPLDAYPDSPSACLVLNWEEPCNNGSEI
LAYTIDLGDTSITVGNTTMHVMKDLLPETTYRIRIQAINEIGAGPFSQFIKAKTRPLPPL
PPRLECAAAGPQSLKLKWGDSNSKTHAAEDIVYTLQLEDRNKRFISIYRGPSHTYKVQRL
TEFTCYSFRIQAASEAGEGPFSETYTFSTTKSVPPTIKAPRVTQLEVNSCEILWETVPSM
KGDPVNYILQVLVGRESEYKQVYKGEEATFQISGLQTNTDYRFRVCACRRCLDTSQELSG
AFSPSAAFVLQRSEVMLTGDMGSLDDPKMKSMMPTDEQFAAIIVLGFATLSILFAFILQY
FLMK

FIGURE 99

CCCAAAGAGGTGAGGAGCCGGCAGCGGGGGCGGCTGTAACTGTGAGGAAGGCTGCAGAGTGGCGACGTCTACGC
CGTAGGTTGGAGGCTGTGGGGGGTGGCCGGGCGCCAGCTCCCAGGCCGCAGAAGTGACCTGCGGTGGAGTTCCC
TCCTCGCTGCTGGAGAACGGAGGGAGAAGGTTGCTGGCCGGGTGAAAGTGCCTCCCTCTGCTTGACGGGGCTGA
GGGGCCCGAAGTCTAGGGCGTCCGTAGTCGCCCCGGCCTCCGTGAAGCCCCAGGTCTAGAGATATGACCCGAGA
GTGCCCATCTCCGGCCCCGGGGCCTGGGGCTCCGCTGAGTGGATCGGTGCTGGCAGAGGCGGCAGTAGTGTTTG
CAGTGGTGCTGAGCATCCACGCAACCGTATGGGACCGATACTCGTGGTGCGCCGTGGCCCTCGCAGTGCAGGCC
TTCTACGTCCAATACAAGTGGGACCGGCTGCTACAGCAGGGAAGCGCCGTCTTCCAGTTCCGAATGTCCGCAAA
CAGTGGCCTATTGCCCGCCTCCATGGTCATGCCTTTGCTTGGACTAGTCATGAAGGAGCGGTGCCAGACTGCTG
GGAACCCGTTCTTTGAGCGTTTTGGCATTGTGGTGGCAGCCACTGGCATGGCAGTGGCCCTCTTCTCATCAGTG
TTGGCGCTCGGCATCACTCGCCCAGTGCCAACCAACACTTGTGTCATCTTGGGCTTGGCTGGAGGTGTTATCAT
TTATATCATGAAGCACTCGTTGAGCGTGGGGGAGGTGATCGAAGTCCTGGAAGTCCTTCTGATCTTCGTTTATC
TCAACATGATCCTGCTGTACCTGCTGCCCCGCTGCTTCACCCCTGGTGAGGCACTGCTGGTATTGGGTGGCATT
AGCTTTGTCCTCAACCAGCTCATCAAGCGCTCTCTGACACTGGTGGAAAGTCAGGGGGACCCAGTGGACTTCTT
CCTGCTGGTGGTGGTAGTAGGGATGGTACTCATGGGCATTTTCTTCAGCACTCTGTTTGTCTTCATGGACTCAG
GCACCTGGGCCTCCTCCATCTTCTTCCACCTCATGACCTGTGTGCTGAGCCTTGGTGTGGTCCTACCCTGGCTG
CACCGGCTCATCCGCAGGAATCCCCTGCTCTGGCTTCTTCAGTTTCTCTTCCAGACAGACACCCGCATCTACCT
CCTAGCCTATTGGTCTCTGCTGGCCACCTTGGCCTGCCTGGTGGTGCTGTACCAGAATGCCAAGCGGTCATCTT
CCGAGTCCAAGAAGCACCAGGCCCCCACCATCGCCCGAAAGTATTTCCACCTCATTGTGGTAGCCACCTACATC
CCAGGTATCATCTTTGACCGGCCACTGCTCTATGTAGCCGCCACTGTATGCCTGGCGGTCTTCATCTTCCTGGA
GTATGTGCGCTACTTCCGCATCAAGCCTTTGGGTCACACTCTACGGAGCTTCCTGTCCCTTTTTCTGGATGAAC
GAGACAGTGGACCACTCATTCTGACACACATCTACCTGCTCCTGGGCATGTCTCTTCCCATCTGGCTGATCCCC
AGACCCTGCACACAGAAGGGTAGCCTGGGAGGAGCCAGGGCCCTCGTCCCCTATGCCGGTGTCCTGGCTGTGGG
TGTGGGTGATACTGTGGCCTCCATCTTCGGTAGCACCATGGGGGAGATCCGCTGGCCTGGAACCAAAAAGACTT
TTGAGGGGACCATGACATCTATATTTGCGCAGATCATTTCTGTAGCTCTGATCTTAATCTTTGACAGTGGAGTG
GACCTAAACTACAGTTATGCTTGGATTTTGGGGTCCATCAGCACTGTGTCCCTCCTGGAAGCATACACTACACA
GATAGACAATCTCCTTCTGCCTCTCTACCTCCTGATATTGCTGATGGCCTAGCTGTTACAGTGCAGCAGCAGTG
ACGGAGGAAACAGACATGGGGAGGGTGAACAGTCCCCACAGCAGACAGCTACTTGGGCATGAAGAGCCAAGGTG
TGAAAAGCAGATTTGATTTTTCAGTTGATTCAGATTTAAAATAAAAAGCAAAGCTCTCCTAGTTCTA

FIGURE 100

></usr/seqdb2/sst/DNA/Dnaseqs.min/ss.DNA97003
><subunit 1 of 1, 538 aa, 1 stop
><MW: 59268, pI: 8.94, NX(S/T): 1

MTRECPSPAPGPGAPLSGSVLAEAAVVFAVVLSIHATVWDRYSWCAVALAVQAFYVQYKW
DRLLQQGSAVFQFRMSANSGLLPASMVMPLLGLVMKERCQTAGNPFFERFGIVVAATGMA
VALFSSVLALGITRPVPTNTCVILGLAGGVIIYIMKHSLSVGEVIEVLEVLLIFVYLNMI
LLYLLPRCFTPGEALLVLGGISFVLNQLIKRSLTLVESQGDPVDFFLLVVVVGMVLMGIF
FSTLFVFMDSGTWASSIFFHLMTCVLSLGVVLPWLHRLIRRNPLLWLLQFLFQTDTRIYL
LAYWSLLATLACLVVLYQNAKRSSSESKKHQAPTIARKYFHLIVVATYIPGIIFDRPLLY
VAATVCLAVFIFLEYVRYFRIKPLGHTLRSFLSLFLDERDSGPLILTHIYLLLGMSLPIW
LIPRPCTQKGSLGGARALVPYAGVLAVGVGDTVASIFGSTMGEIRWPGTKKTFEGTMTSI
FAQIISVALILIFDSGVDLNYSYAWILGSISTVSLLEAYTTQIDNLLLPLYLLILLMA

Important features of the protein:

Signal peptide:

Amino acids 1-36

Transmembrane domains:

Amino acids 77-95;111-133;161-184;225-248;
255-273;299-314;348-373;406-421;
435-456;480-497

N-glycosylation sites:

Amino acids 500-504 cAMP- and cGMP-dependent protein kinase phosphorylation site:

Amino acids 321-325

N-myristoylation sites:

Amino acids 13-19;18-24;80-86;111-117;
118-124;145-151;238-244;251-257;
430-436;433-439;448-454;458-464;
468-474;475-481;496-502;508-514

Prokaryotic membrane lipoprotein lipid attachment site:

Amino acids 302-313

FIGURE 101

CACTGCCCGTCCGCTCTTCAGCAGCCGGTCGCGGGCGGTGGAAAAGCGAGTGAAGAGAGCGCGACGGCGGCGGC
GGCGGCGGCGCAGCTATTGCTGGACGGCCAGTGGGAGAGCGAGGCCTGAGCCTCTGCGTCTAGGATCAAAATGG
TTTCAATCCCAGAATACTATGAAGGCAAGAACGTCCTCCTCACAGGAGCTACCGGTTTTCTAGGGAAGGTGCTT
CTGGAAAAGTTGCTGAGGTCTTGTCCTAAGGTGAATTCAGTATATGTTTTGGTGAGGCAGAAAGCTGGACAGAC
ACCACAAGAGCGAGTGGAAGAAGTCCTTAGTGGCAAGCTTTTTGACAGATTGAGAGATGAAAATCCAGATTTTA
GAGAGAAAATTATAGCAATCAACAGCGAACTCACCCAACCTAAACTGGCTCTCAGTGAAGAAGATAAAGAGGTG
ATCATAGATTCTACCAATATTATATTCCACTGTGCAGCTACAGTAAGGTTTAATGAAAATTTAAGAGATGCTGT
TCAGTTAAATGTGATTGCAACGCGACAGCTTATTCTCCTTGCACAACAAATGAAGAATCTGGAAGTGTTCATGC
ATGTATCAACAGCATATGCCTACTGTAATCGCAAGCATATTGATGAAGTAGTCTATCCACCACCTGTGGATCCC
AAGAAGCTGATTGATTCTTTAGAGTGGATGGATGATGGCCTAGTAAATGATATCACGCCAAAATTGATAGGAGA
CAGACCTAATACATACATATACACAAAAGCATTGGCAGAATATGTTGTACAACAAGAAGGAGCAAAACTAAATG
TGGCAATTGTAAGGCCATCGATTGTTGGTGCCAGTTGGAAAGAACCTTTTCCAGGATGGATTGATAACTTTAAT
GGACCAAGTGGTCTCTTTATTGCGGCAGGGAAAGGAATTCTTCGAACAATACGTGCCTCCAACAATGCCCTTGC
AGATCTTGTTCCTGTAGATGTAGTTGTCAACATGAGTCTTGCGGCAGCCTGGTATTCCGGAGTTAATAGACCAA
GAAACATCATGGTGTATAATTGTACAACAGGCAGCACTAATCCTTTCCACTGGGGTGAAGTTGAGTACCATGTA
ATTTCCACTTTCAAGAGGAATCCTCTCGAACAGGCCTTCAGACGGCCCAATGTAAATCTAACCTCCAATCATCT
TTTATATCATTACTGGATTGCTGTAAGCCATAAGGCCCCAGCATTCCTGTATGATATCTACCTCAGGATGACTG
GAAGAAGCCCAAGGATGATGAAAACAATAACTCGTCTTCACAAAGCTATGGTGTTTCTTGAATATTTCACAAGT
AATTCTTGGGTTTGGAATACTGAGAATGTCAATATGTTAATGAATCAACTAAACCCTGAAGATAAAAAGACCTT
CAATATTGATGTACGGCAGTTACATTGGGCAGAATATATAGAGAACTACTGCTTGGGAACTAAGAAGTACGTAT
TGAATGAAGAAATGTCTGGCCTCCCTGCAGCCAGAAAACATCTGAACAAGTTGCGGAATATACGTTATGGTTTT
AATACTATCCTTGTGATCCTCATCTGGCGCATTTTTATTGCAAGATCACAAATGGCAAGAAATATCTGGTACTT
TGTGGTTAGTCTGTGTTACAAGTTTTTGTCATACTTCCGAGCATCCAGCACTATGAGATACTGAAGACCAAGGA
TTCAGCATTAGAACATCTATACATATGGTGATCTAAATGTACAAAATGTAAAATGTATAAGTCATCTCACTTTT
TGTCAAGACATTAAACCATCTTAGATCGGAGTGTGAAGTAAATTATGGTATATTTTATGTAACATTTTAATGTT
TATGCTCATAAAACTTAGTGAACACACTGTGTTATGCCAGCTCAAATCTACAGTAGCCACCAAAACCATGACTT
AATATTTTGAGCCCTAGAAGAAAGGGGTGTGCTGAGGACAAGAGTGGGGAAATAGGAACACTGACCAGTATAAC
TGTGCAATTCTGGAACATATTAATTAAAATAATATGCCTTAACATATAGTGAATTTCTAATTCTAATGTTCAGT
GCAATGGAAGACATTTATTTGGACAGTATACTAGCAAAGTTGGTAGATATTTGATTCTTCATTTTTTGTTTTTT
TCATTAGTTGAAGTGGGTTTTAGTTTTGTTTAAAATTATAACCAGCGTATTTTCACATCATTCTGTAAGTTAAA
TGATATCAAACATGAAAGAGATGTTCTCATTTTTCTTTTTCTGATTAAACGTCTGATGCATATCATTTTTCTAT
AAGTAATCAGTTGCTTTTAAAATCAGAAGGCTATATTATTCTAATGACCCTATTCGATCTAAATGGGTTTGAGA
ATCCATATCAGCAACATACGTGTTTTTTGACAGAAAGTGAAAACAAATTCCGTAAAACTGTTAGTATCAAAAAG
AATAGGAATACAGTTTTCTTTTCCACATTATGATCAAATAAAAATCTTGTGAGATTGTTAAAAA

FIGURE 102

></usr/seqdb2/sst/DNA/Dnaseqs.min/ss.DNA94849

><subunit 1 of 1, 515 aa, 1 stop

><MW: 59357, pI: 9.40, NX(S/T): 3

MVSIPEYYEGKNVLLTGATGFLGKVLLEKLLRSCPKVNSVYVLVRQKAGQTPQERVEEVLS
GKLFDRLRDENPDFREKIIAINSELTQPKLALSEEDKEVIIDSTNIIFHCAATVRFNENLR
DAVQLNVIATRQLILLAQQMKNLEVFMHVSTAYAYCNRKHIDEVVYPPPVDPKKLIDSLEW
MDDGLVNDITPKLIGDRPNTYIYTKALAEYVVQQEGAKLNVAIVRPSIVGASWKEPFPGWI
DNFNGPSGLFIAAGKGILRTIRASNNALADLVPVDVVVNMSLAAAWYSGVNRPRNIMVYNC
TTGSTNPFHWGEVEYHVISTFKRNPLEQAFRRPNVNLTSNHLLYHYWIAVSHKAPAFLYDI
YLRMTGRSPRMMKTITRLHKAMVFLEYFTSNSWVWNTENVNMLMNQLNPEDKKTFNIDVRQ
LHWAEYIENYCLGTKKYVLNEEMSGLPAARKHLNKLRNIRYGFNTILVILIWRIFIARSQM
ARNIWYFVVSLCYKFLSYFRASSTMRY

Important features of the protein:

Transmembrane domain:

Amino acids 469-488

N-glycosylation sites:

Amino acids 283-287;304-308;341-345

Tyrosine kinase phosphorylation site:

Amino acids 160-169

N-myristoylation sites:

Amino acids 219-225;252-258;260-266;452-458

Leucine zipper pattern:

Amino acids 439-461

FIGURE 103

CCGGCGATGTCGCTCGTGCTGCTAAGCCTGGCCGCGCTGTGCAGGAGCGCCGTACCCCGAGAGCCGACCGTTCA
ATGTGGCTCTGAAACTGGGCCATCTCCAGAGTGGATGCTACAACATGATCTAATCCCCGGAGACTTGAGGGACC
TCCGAGTAGAACCTGTTACAACTAGTGTTGCAACAGGGGACTATTCAATTTTGATGAATGTAAGCTGGGTACTC
CGGGCAGATGCCAGCATCCGCTTGTTGAAGGCCACCAAGATTTGTGTGACGGGCAAAAGCAACTTCCAGTCCTA
CAGCTGTGTGAGGTGCAATTACACAGAGGCCTTCCAGACTCAGACCAGACCCTCTGGTGGTAAATGGACATTTT
CCTACATCGGCTTCCCTGTAGAGCTGAACACAGTCTATTTCATTGGGGCCCATAATATTCCTAATGCAAATATG
AATGAAGATGGCCCTTCCATGTCTGTGAATTTCACCTCACCAGGCTGCCTAGACCACATAATGAAATATAAAAA
AAAGTGTGTCAAGGCCGGAAGCCTGTGGGATCCGAACATCACTGCTTGTAAGAAGAATGAGGAGACAGTAGAAG
TGAACTTCACAACCACTCCCCTGGGAAACAGATACATGGCTCTTATCCAACACAGCACTATCATCGGGTTTTCT
CAGGTGTTTGAGCCACACCAGAAGAAACAAACGCGAGCTTCAGTGGTGATTCCAGTGACTGGGGATAGTGAAGG
TGCTACGGTGCAGCTGACTCCATATTTTCCTACTTGTGGCAGCGACTGCATCCGACATAAAGGAACAGTTGTGC
TCTGCCCACAAACAGGCGTCCCTTTCCCTCTGGATAACAACAAAAGCAAGCCGGGAGGCTGGCTGCCTCTCCTC
CTGCTGTCTCTGCTGGTGGCCACATGGGTGCTGGTGGCAGGGATCTATCTAATGTGGAGGCACGAAAGGATCAA
GAAGACTTCCTTTTCTACCACCACACTACTGCCCCCCATTAAGGTTCTTGTGGTTTACCCATCTGAAATATGTT
TCCATCACACAATTTGTTACTTCACTGAATTTCTTCAAAACCATTGCAGAAGTGAGGTCATCCTTGAAAAGTGG
CAGAAAAAGAAAATAGCAGAGATGGGTCCAGTGCAGTGGCTTGCCACTCAAAAGAAGGCAGCAGACAAAGTCGT
CTTCCTTCTTTCCAATGACGTCAACAGTGTGTGCGATGGTACCTGTGGCAAGAGCGAGGGCAGTCCCAGTGAGA
ACTCTCAAGACCTCTTCCCCCTTGCCTTTAACCTTTTCTGCAGTGATCTAAGAAGCCAGATTCATCTGCACAAA
TACGTGGTGGTCTACTTTAGAGAGATTGATACAAAAGACGATTACAATGCTCTCAGTGTCTGCCCCAAGTACCA
CCTCATGAAGGATGCCACTGCTTTCTGTGCAGAACTTCTCCATGTCAAGCAGCAGGTGTCAGCAGGAAAAAGAT
CACAAGCCTGCCACGATGGCTGCTGCTCCTTGTAG

FIGURE 104

MSLVLLSLAALCRSAVPREPTVQCGSETGPSPEWMLQHDLIPGDLRDLRVEPVTTSVATGDYSILMNVSWVLRA
DASIRLLKATKICVTGKSNFQSYSCVRCNYTEAFQTQTRPSGGKWTFSYIGFPVELNTVYFIGAHNIPNANMNE
DGPSMSVNFTSPGCLDHIMKYKKKCVKAGSLWDPNITACKKNEETVEVNFTTTPLGNRYMALIQHSTIIGFSQV
FEPHQKKQTRASVVIPVTGDSEGATVQLTPYFPTCGSDCIRHKGTVVLCPQTGVPFPLDNNKSKPGGWLPLLLL
SLLVATWVLVAGIYLMWRHERIKKTSFSTTTLLPPIKVLVVYPSEICFHHTICYFTEFLQNHCRSEVILEKWQK
KKIAEMGPVQWLATQKKAADKVVFLLSNDVNSVCDGTCGKSEGSPSENSQDLFPLAFNLFCSDLRSQIHLHKYV
VVYFREIDTKDDYNALSVCPKYHLMKDATAFCAELLHVKQQVSAGKRSQACHDGCCSL

| | |
|---|---|
| Signal sequence: | Amino acids 1-14 |
| Transmembrane domain: | Amino acids 290-309 |
| N-glycosylation sites: | Amino acids 67-70;103-106;156-159;<br>183-186;197-200;283-286 |
| cAMP- and cGMP-dependent protein kinase phosphorylation sites: | Amino acids 228-231;319-322 |
| N-myristoylation site: | Amino acids 116-121 |
| Amidation site: | Amino acids 488-491 |

FIGURE 105

GCAGCTCACCCTTCGCAGCCGCGATGGGGGAAGACGACGCCGCGCTTCGGGCTGGCAGCA
GGGGGCTCTCCGACCCGTGGGCAGACTCAGTGGGAGTGCGACCCCGCACCACGGAGCGCC
ACATCGCCGTACACAAGCGGCTTGTGCTGGCCTTCGCTGTGTCCCTCGTGGCATTGCTCG
CGGTCACAATGCTCGCTGTGCTGCTCAGCCTGCGCTTCGACGAGTGCGGGGCGAGTGCCA
CGCCAGGCGCCGACGGTGGCCCCTCAGGCTTTCCGGAGCGCGGCGGCAACGGGAGCCTCC
CTGGATCGGCCCGGCGCAACCACCACGCAGGCGGGGACTCCTGGCAGCCCGAGGCGGGTG
GGGTGGCCAGTCCGGGGACCACGTCGGCCCAGCCGCCGTCGGAGGAGGAGCGGGAGCCGT
GGGAGCCGTGGACGCAGCTGCGCCTGTCGGGCCACCTGAAGCCGCTGCACTACAATCTGA
TGCTCACCGCCTTCATGGAGAACTTCACCTTCTCCGGGGAGGTCAACGTGGAGATCGCGT
GCCGGAACGCCACCCGCTACGTAGTGCTGCACGCTTCCCGAGTGGCGGTGGAGAAAGTGC
AGCTGGCCGAGGACCGGGCGTTCGGGGCTGTCCCTGTAGCCGGTTTTTCCTCTACCCGC
AAACCCAGGTCTTAGTGGTGGTGCTGAATAGGACACTGGACGCGCAGAGGAATTACAATC
TGAAGATTATCTACAACGCGCTCATCGAGAATGAGCTCCTGGGCTTCTTCCGCAGCTCCT
ATGTGCTCCACGGGGAGAGAAGATTCCTTGGTGTTACTCAGTTTTCGCCTACACATGCCA
GAAAGGCATTTCCTTGTTTTGATGAGCCAATCTACAAGGCTACTTTCAAAATCAGCATCA
AGCATCAAGCAACCTATTTATCTTTATCTAATATGCCAGTGGAAACTTCCGTGTTTGAGG
AAGATGGATGGGTTACGGATCACTTTTCACAGACCCCTCTCATGTCCACATATTATTTAG
CCTGGGCAATTTGCAACTTCACATACAGAGAAACTACCACCAAGAGTGGGGTTGTAGTAC
GATTATATGCAAGACCTGATGCTATCAGAAGAGGATCCGGGGACTATGCTCTCCATATAA
CAAAGAGATTAATAGAATTTTATGAAGACTACTTTAAAGTGCCCTATTCCTTGCCAAAAC
TAGATCTTTTAGCTGTGCCTAAGCATCCGTATGCTGCTATGGAGAACTGGGGACTAAGTA
TTTTTGTGGAACAAAGAATACTGCTGGATCCCAGTGTTTCATCTATTTCTTATTTGCTGG
ATGTCACCATGGTCATTGTTCATGAGATATGTCACCAGTGGTTTGGTGACCTTGTGACGC
CTGTGTGGTGGGAAGACGTGTGGCTGAAGGAAGGGTTTGCTCACTACTTTGAATTTGTTG
GTACAGACTACCTCTATCCTGGCTGGAACATGGAAAAGCAGAGGTTTCTGACCGATGTTC
TGCATGAAGTGATGCTGCTGGACGGTTTGGCCAGTTCCCATCCAGTATCACAGGAAGTGC
TGCAGGCAACAGATATTGACAGGGTGTTTGACTGGATCGCATATAAAAAGGGTGCTGCTT
TAATAAGAATGCTGGCTAATTTTATGGGCCATTCAGTTTTCCAGAGGGGTTTGCAAGATT
ATTTAACCATTCATAAGTATGGTAATGCAGCCAGAAATGATCTCTGGAATACATTATCGG
AGGCTTTAAAAAGAAATGGGAAATATGTAAATATACAAGAAGTAATGGATCAGTGGACAC
TCCAGATGGGTTATCCTGTTATCACCATCTTGGGAAACACAACAGCAGAAAATAGAATAA
TAATTACCCAACAGCATTTTATCTATGATATCAGTGCTAAAACTAAAGCACTTAAACTTC
AGAATAACAGTTACCTGTGGCAGATTCCATTAACTATTGTGGTAGGAAATAGAAGCCATG
TGTCTTCAGAAGCAATTATTTGGGTGTCTAACAAATCAGAGCACCACAGAATAACTTATT
TGGACAAAGGAAGCTGGCTGCTGGGGAACATCAATCAAACTGGCTATTTTAGAGTCAACT
ATGACCTAAGGAACTGGAGATTATTAATTGATCAATTAATCCGGAATCATGAGGTTCTTT
CTGTCAGTAACCGAGCGGGCTTGATCGATGATGCCTTCAGCCTAGCCAGGGCTGGCTATT
TGCCTCAGAATATTCCTCTGGAGATTATCAGATACCTGTCTGAGGAGAAGGATTTTCTTC
CTTGGCATGCTGCCAGCCGAGCTCTTTATCCTCTAGATAAATTACTGGACCGCATGGAAA
ACTACAACATTTTCAATGAATATATTTTAAAGCAAGTTGCAACAACATATATCAAGCTTG
GGTGGCCGAAAAATAATTTTAATGGATCTCTTGTTCAAGCATCCTACCAACATGAAGAAC
TACGTAGAGAAGTTATAATGCTGGCCTGCAGTTTTGGCAACAAGCACTGTCACCAACAGG

CATCAACACTTATTTCAGATTGGATTTCCAGCAACAGGAACAGAATACCACTAAATGTTA

FIGURE 105 Continued

GAGACATCGTATACTGTACAGGAGTGTCACTACTGGATGAGGATGTCTGGGAATTCATAT
GGATGAAATTCCATTCCACCACAGCAGTTTCTGAGAAGAAAATATTATTGGAAGCCTTAA
CTTGCAGTGATGACAGGAATTTATTAAACAGGCTTCTAAATCTGTCACTGAATTCTGAGG
TGGTGCTGGATCAAGATGCAATTGATGTCATAATCCATGTAGCTCGAAATCCACATGGTC
GAGACCTTGCCTGGAAGTTTTTCAGGGATAAATGGAAGATATTAAATACCAGGTATGGAG
AAGCATTGTTTATGTATTCCAAACTCATCAGTGGTGTCACAGAATTTCTTAATACTGAAG
GTGAACTCAAAGAGCTCAAGAACTTCATGAAAAACTATGATGGGGTAGCTGCTGCTTCTT
TCTCACGAGCTGTGGAAACTGTCGAAGCCAATGTGCGCTGGAAAATGCTTTACCAAGACG
AGCTTTTCCAATGGTTAGGAAAAGCTCTAAGACACTAATATATGTATCTTATAAACAAAC
AATTCAACTCAGAAGTTTATGAGAAGACACGCTTTTTGTGGAATGAGGAAAATGTACTAC
CTAGAAAATGGCCAGATTTTCAGTGTTAACGTGTGGGAGGAATTTTTTTTTTTAGTTTTT
ATTTTTTGGTTTTGGGGGATATTTTTTATTTGTTTCATTCATTCTGTTCTGTTTCTCTAC
TGGGTGTTCCTCTCTAAAGAAACTCTTGCAAGTGAAACTAGCCATGATTGCTTCAGCTGT
ACATTCCTTGCTGTACAGGACCAAATATGATAGTGATGCATGTTGATGTTACAGTCAATT
TGGAAAAACATATTCAGAATATCTGTGCATGGATATATTGTCCTGCCTGTGTTCCAGCAT
GCTTATTTCAAACGTCCAGTGTTGTGTGTGAATATGTGTTACACCTAGGATGGGCATTAT
GCAAAAGCACAAAGATTATATATGACAATCAGTATTGCAATGAAAGAAAAACTAAAAACA
GAAATGATATTCTCAATTTTGGGCAATGTGAGAGGTAAAATAGCCCTTGACATGATGAAC
ATCACTTATTTCAGCACTTGGATTGTCTGGCAATGATTACTGTGTTGCTAACTCATTTTC
TTTGAGTTAAAGCTGTGTATACATTTTAAAAGGCATATAGATAGTGTATGCATATGTATA
TGTACATAGGGAAGCCCCATATGTATATAGTATGTTGTACACTGCACATGTACAAAGAAT
GTCTTCAGATCAAAGAAAATTTATCTCTTTTTATAAACTTAAGGACAGTTGCAAAAGGCT
TCAAGGAATTTATCTCAACATTATTCTTTCTATGTCCTAACTAAATTTCTCAACTGTTAT
GAATTTTTCATCTACTTCTTGAACAGTGGTCTATTCTGCTACATGAAGATGAATACAAAC
AAAATTTTTGTATAAACTCCCAAAAAAAAAAAAAAAAAAA

FIGURE 106

MGEDDAALRAGSRGLSDPWADSVGVRPRTTERHIAVHKRLVLAFAVSLVALLAVTMLAVL
LSLRFDECGASATPGADGGPSGFPERGGNGSLPGSARRNHHAGGDSWQPEAGGVASPGTT
SAQPPSEEEREPWEPWTQLRLSGHLKPLHYNLMLTAFMENFTFSGEVNVEIACRNATRYV
VLHASRVAVEKVQLAEDRAFGAVPVAGFFLYPQTQVLVVVLNRTLDAQRNYNLKIIYNAL
IENELLGFFRSSYVLHGERRFLGVTQFSPTHARKAFPCFDEPIYKATFKISIKHQATYLS
LSNMPVETSVFEEDGWVTDHFSQTPLMSTYYLAWAICNFTYRETTTKSGVVVRLYARPDA
IRRGSGDYALHITKRLIEFYEDYFKVPYSLPKLDLLAVPKHPYAAMENWGLSIFVEQRIL
LDPSVSSISYLLDVTMVIVHEICHQWFGDLVTPVWWEDVWLKEGFAHYFEFVGTDYLYPG
WNMEKQRFLTDVLHEVMLLDGLASSHPVSQEVLQATDIDRVFDWIAYKKGAALIRMLANF
MGHSVFQRGLQDYLTIHKYGNAARNDLWNTLSEALKRNGKYVNIQEVMDQWTLQMGYPVI
TILGNTTAENRIIITQQHFIYDISAKTKALKLQNNSYLWQIPLTIVVGNRSHVSSEAIIW
VSNKSEHHRITYLDKGSWLLGNINQTGYFRVNYDLRNWRLLIDQLIRNHEVLSVSNRAGL
IDDAFSLARAGYLPQNIPLEIIRYLSEEKDFLPWHAASRALYPLDKLLDRMENYNIFNEY
ILKQVATTYIKLGWPKNNFNGSLVQASYQHEELRREVIMLACSFGNKHCHQQASTLISDW
ISSNRNRIPLNVRDIVYCTGVSLLDEDVWEFIWMKFHSTTAVSEKKILLEALTCSDDRNL
LNRLLNLSLNSEVVLDQDAIDVIIHVARNPHGRDLAWKFFRDKWKILNTRYGEALFMYSK
LISGVTEFLNTEGELKELKNFMKNYDGVAAASFSRAVETVEANVRWKMLYQDELFQWLGK
ALRH 89-92 N-glycosylation site
160-163 N-glycosylation site
175-178 N-glycosylation site
222-225 N-glycosylation site
338-341 N-glycosylation site
605-608 N-glycosylation site
634-637 N-glycosylation site
649-652 N-glycosylation site
663-666 N-glycosylation site
684-687 N-glycosylation site
800-803 N-glycosylation site
906-909 N-glycosylation site
362-365 cAMP- and cGMP-dependent protein kinase phosphorylation site
126-129 Casein kinase II phosphorylation site
309-319 Casein kinase II phosphorylation site
340-343 Casein kinase II phosphorylation site
516-519 Casein kinase II phosphorylation site
570-573 Casein kinase II phosphorylation site
606-609 Casein kinase II phosphorylation site
671-674 Casein kinase II phosphorylation site
862-865 Casein kinase II phosphorylation site
893-896 Casein kinase II phosphorylation site
971-974 Casein kinase II phosphorylation site

FIGURE 106 Continued

| | |
|---|---|
| 520-527 | Tyrosine kinase phosphorylation site |
| 78-83 | N-myristoylation site |
| 87-92 | N-myristoylation site |
| 90-95 | N-myristoylation site |
| 118-123 | N-myristoylation site |
| 501-506 | N-myristoylation site |
| 604-609 | N-myristoylation site |
| 825-830 | N-myristoylation site |
| 987-992 | N-myristoylation site |
| 437-446 | Neutral zinc metallopeptidases, zinc-binding region signature |

FIGURE 107

CTTTCCTTATCTGTGTGTACTCTTATCTCACTGTTCTATTTTTTCTCCTCATTTATATTA
ACTCTTTCTTACCTTTTTTTCTGAACTTCTAGGCCTTCTCTTTCCAGAACTGGTGGAAGA
CAAATGAAACGGCCAAGATGGTAAGAAACAAGCCGCATTTCTCCTTGGGGAGACTGATAA
TTTAAAAGGTTTGTTGTGTCAGAAACATTCCCAGCTTCATCACCAACCCTTTCCTTCCAC
CTCTGCCCACTGGAGACCACTTACATCCCGAAGCGGACGCGGCAGCTGAAGTCAGGAAAC
CATGCATCACATTAGCAGGAGCCAACTGCAGACTTTAAACTCCGTTCAACATGTGGATGC
GGCAGAGAAATGACCTGTCCAGACAAGCCGGGGCAGCTCATAAACTGGTTCATCTGCTCC
CTGTGCGTCCCGCGGGTGCGTAAGCTCTGGAGCAGCCGGCGTCCAAGGACCCGGAGAAAC
CTTCTGCTGGGCACTGCGTGTGCCATCTACTTGGGCTTCCTGGTGAGCCAGGTGGGGAGG
GCCTCTCTCCAGCATGGACAGGCGGCTGAGAAGGGGCCACATCGCAGCCGCGACACCGCC
GAGCCATCCTTCCCTGAGATACCCCTGGATGGTACCCTGGCCCCTCCAGAGTCCCAGGGC
AATGGGTCCACTCTGCAGCCCAATGTGGTGTACATTACCCTACGCTCCAAGCGCAGCAAG
CCGGCCAATATCCGTGGCACCGTGAAGCCCAAGCGCAGGAAAAAGCATGCAGTGGCATCG
GCTGCCCCAGGGCAGGAGGCTTTGGTCGGACCATCCCTTCAGCCGCAGGAAGCGGCAAGG
GAAGCTGATGCTGTAGCACCTGGGTACGCTCAGGGAGCAAACCTGGTTAAGATTGGAGAG
CGACCCTGGAGGTTGGTGCGGGGTCCGGGAGTGCGAGCCGGGGGCCCAGACTTCCTGCAG
CCCAGCTCCAGGGAGAGCAACATTAGGATCTACAGCGAGAGCGCCCCCTCCTGGCTGAGC
AAAGATGACATCCGAAGAATGCGACTCTTGGCGGACAGCGCAGTGGCAGGGCTCCGGCCT
GTGTCCTCTAGGAGCGGAGCCCGTTTGCTGGTGCTGGAGGGGGGCGCACCTGGCGCTGTG
CTCCGCTGTGGCCCTAGCCCCTGTGGGCTTCTCAAGCAGCCCTTGGACATGAGTGAGGTG
TTTGCCTTCCACCTAGACAGGATCCTGGGGCTCAACAGGACCCTGCCGTCTGTGAGCAGG
AAAGCAGAGTTCATCCAAGATGGCCGCCCATGCCCCATCATTCTTTGGGATGCATCTTTA
TCTTCAGCAAGTAATGACACCCATTCTTCTGTTAAGCTCACCTGGGGAACTTATCAGCAG
TTGCTGAAACAGAAATGCTGGCAGAATGGCCGAGTACCCAAGCCTGAATCAGGTTGTACT
GAAATACATCATCATGAGTGGTCCAAGATGGCACTCTTTGATTTTTTGTTACAGATTTAT
AATCGCTTAGATACAAATTGCTGTGGATTCAGACCTCGCAAGGAAGATGCCTGTGTACAG
AATGGATTGAGGCCAAAATGTGATGACCAAGGTTCTGCGGCTCTAGCACACATTATCCAG
CGAAAGCATGACCCAAGGCATTTGGTTTTTATAGACAACAAGGGTTTCTTTGACAGGAGT
GAAGATAACTTAAACTTCAAATTGTTAGAAGGCATCAAAGAGTTTCCAGCTTCTGCAGTT
TCTGTTTTGAAGAGCCAGCACTTACGGCAGAAACTTCTTCAGTCTCTGTTTCTTGATAAA
GTGTATTGGGAAAGTCAAGGAGGTAGACAAGGAATTGAAAAGCTTATCGATGTAATAGAA
CACAGAGCCAAAATTCTTATCACCTATATCAATGCACACGGGGTCAAAGTATTACCTATG
AATGAATGACAAAAGAATCTTCTGGCTAGGGTGTTAGATATATTTATGCATTTTTGGTTT
TGTTTTTAAATCAAGCACATCAACCTCAAGCCCGTTTAGCAATGAGGCAGTGTAGATGAA
TACGTAAAATAAATGACTTTAACCAAGTAGCTATAAAGGGACTTAGCACTGTATGCATAC
TTAAAAAGGTTTTGAAAAACAAACTACTTGAGAAATATTTGTTTATATTTTTCTCTAACA
TCATGCTATGTGTCAGTCTGAACATCTGACAACAGAAATTTCAGTTATTATTCTAGCTAA
GTTTTGAAAACATTTGTCATGCTGTTTAATAGAAAACTGCAAACCAGAGATACTGACTCC
ATTAATAAACCATATTTTGTGCCGTTTTGACTGTTCTGACCAAATACTAATGGGAACAAT
TCTTGACGTTTTTCTGTTGCTGATTGTTAACATAGAGCAGTCTCTACACTACCCTGAGGC
AACTCTACATTGGAACACTGAGGCTTACAGCCTGCAAGAGCATCAGAGCTGACCATACAT
TTAAACAGAAATGCTGGTTTATTTGCAAAATCACCAGTATATTTTCTATTGTGTCTATAA

FIGURE 107 Continued

AAAATCAGTCATTTAAGTACAAGAATCATATTTTCCATTCCTTTTTAGAAATTTATTTTG
TTGTCCCTATGGAAATCATTCACATCTGACAATTTATATGTTAAAGAGTTTTACTCTCTC
TATTTTGGTCCAATTTGTATCTAGTGGCTGAGAAATTAAATAATTCTAAAGTATGAAGTT
ACCTATCTGAAAATGTACTTACAGAGTATCATTTTAAAATGGATGTCTCTTTAAAAATTT
TGTTACTTTTACCAACAATGTAATATAATTTATGTATATTTTATTAATAATAGTGAATTC
CTTAAAATTTGTTCTATGTACTTATATTTAATTTGATTTAATGGTTACTGCCCAGATATT
GAGAAATGGTTCAAATATTGAGTGTGTTTCAATAA

FIGURE 108

><Fri Jun 25 15:00:51 PDT 1999 DNA98380 [min]
></usr/seqdb2/sst/DNA/Dnaseqs.min/ss.DNA98380
><subunit 1 of 1, 519 aa, 1 stop
><MW: 57552, pI: 10.01, NX(S/T): 3

MTCPDKPGQLINWFICSLCVPRVRKLWSSRRPRTRRNLLLGTACAIYLGFLVSQVGRASL
QHGQAAEKGPHRSRDTAEPSFPEIPLDGTLAPPESQGNGSTLQPNVVYITLRSKRSKPAN
IRGTVKPKRRKKHAVASAAPGQEALVGPSLQPQEAAREADAVAPGYAQGANLVKIGERPW
RLVRGPGVRAGGPDFLQPSSRESNIRIYSESAPSWLSKDDIRRMRLLADSAVAGLRPVSS
RSGARLLVLEGGAPGAVLRCGPSPCGLLKQPLDMSEVFAFHLDRILGLNRTLPSVSRKAE
FIQDGRPCPIILWDASLSSASNDTHSSVKLTWGTYQQLLKQKCWQNGRVPKPESGCTEIH
HHEWSKMALFDFLLQIYNRLDTNCCGFRPRKEDACVQNGLRPKCDDQGSAALAHIIQRKH
DPRHLVFIDNKGFFDRSEDNLNFKLLEGIKEFPASAVSVLKSQHLRQKLLQSLFLDKVYW
ESQGGRQGIEKLIDVIEHRAKILITYINAHGVKVLPMNE

FIGURE 109

GGAAAGAGTGCTGGTACTACAACCAGGAAGTGACAGATAATGTGCTTTAAACTACATTAG
AAAAGCTTCTCATAGCAAAACTGAGAGATTGAAGCAGTGATTATTTTTACATAGTTGTCA
TTAAATATTTGGAGCTCTGCTGTGCATAGAGATGGCAACATACTTAGAATACACAGCTTT
CTGGGCCAGAAATTGATCTTCTGACTTTTGAGCCTTATCTGATTACTGCTTGGTTCATCT
TTATTTTGTTAAACTACTCTGTAGGCTGAAAGGGAGAGACTCTCCTTGGTTTGCAGAGCC
TGACTAGACAGGAATTCTGGCAACTGCTCCAGCAGAACTATGGCACTGAGCTAGGTTTAA
ATGCTGAGGAGATGGAAAACTTGTCACTGTCGATTGAGGATGTGCAGCCAAGAAGTCCAG
GAAGAAGCAGCTTGGATGACTCTGGGGAGAGAGATGAAAAATTATCCAAGTCAATCAGTT
TTACCAGTGAATCAATTAGTCGGGTTTCAGAAACAGAGTCATTCGATGGAAATTCATCAA
AAGGAGGATTAGGCAAAGAGGAGTCCCAAAATGAGAAACAGACCAAAAAGAGTCTCTTAC
CAACTTTGGAAAAGAAGTTAACTAGAGTGCCATCAAAGTCACTGGACTTGAATAAAAATG
AATATCTTTCTCTGGACAAAAGCAGCACTTCAGATTCTGTTGATGAAGAAAATGTTCCTG
AGAAAGATCTTCATGGAAGACTTTTTATCAACCGTATTTTTCATATCAGTGCTGACAGAA
TGTTTGAATTGCTCTTTACCAGTTCACGCTTTATGCAGAAATTTGCCAGTTCTAGAAATA
TAATAGATGTAGTATCTACCCCTTGGACTGCAGAACTTGGAGGTGATCAGCTGAGAACGA
TGACCTACACTATAGTCCTTAATAGTCCACTTACTGGAAAATGCACTGCTGCCACTGAAA
AGCAGACACTGTATAAAGAAAGTCGGGAAGCACGATTTTATTTGGTAGATTCAGAAGTAC
TGACACATGATGTCCCCTACCATGATTACTTCTATACCGTGAACAGATACTGTATCATCC
GATCTTCAAAACAGAAATGCAGGCTAAGAGTTTCCACAGATTTGAAATACAGAAAACAGC
CATGGGGCCTTGTCAAATCTTTAATTGAAAAGAATTCCTGGAGTTCTTTGGAGGACTATT
TCAAACAGCTTGAATCAGATTTGTTAATTGAAGAATCTGTATTAAATCAGGCCATTGAAG
ACCCTGGAAAACTTACTGGCCTACGAAGGAGAAGGCGAACCTTCAACCGAACAGCAGAAA
CAGTTCCTAAACTTTCCTCTCAGCATTCCTCTGGAGATGTGGGCTTAGGTGCCAAAGGGG
ATATTACAGGAAAGAAAAAGGAAATGGAAAACTATAACGTCACTCTTATTGTGGTAATGA
GTATTTTTGTGTTGTTATTAGTTTTGTTGAATGTGACACTGTTTCTGAAGCTGTCAAAGA
TAGAACATGCTGCTCAGTCCTTTTACCGTCTCCGCCTCCAAGAAGAGAAATCTTTAAATT
TAGCCTCTGATATGGTGTCAAGAGCAGAAACTATTCAGAAGAATAAAGATCAGGCCCATC
GTTTAAAGGGAGTGCTCCGAGACTCCATAGTGATGCTTGAACAGCTGAAGAGCTCACTCA
TTATGCTTCAGAAAACGTTTGATCTACTAAATAAGAATAAGACTGGCATGGCTGTTGAAA
GCTAGTGATCTGAAGGACTAAAACCGCAGAGATACTTGGAACTTAAAGAAAATACCTGGA
AGAAAACCAGACGAATGAAGGATTTTGGCATAGAACATTTCTATGTTTTTTCATTATTGA
GATTTCTAATATGAACATTTCTTTCAGTAACATTTATTTGATAATTAGTTTCTGCTGGCC
TTAATAATCCATCCTTTCACTTCTTATAGATATTTTTAAGCTGTGAATTTCTTCAGTGAA
CCATGAAATATATTATAGAACTGAATTTCTCTGATACAAAAAGAAAATGACACACCCTGA
ATTGAGTGGTATGGTCTCATTTCTACAGTGAAGTCTGATGCTTTGTTAGCACAGAATCCG
TACATGTCCAATAGGTCGCTTTTGTAACTGAGATAAGACCAAGAGGATAAACAGGACAAT
ATAAGAAGAAACCTCTATGTCATTACTGATTTTAAAGGTTCTGTTTTCAGGCATATAACA
TTTCCAGGTTTGTGTACTGTAAAGATTATAATGTCTTCATTTATTTAGCATGCAAATTTA
ATAGTCAAACTTTTTGAATCTGCATGTTGATGATGATTATCAGAAAGGGTCTTCTGCCAT
GCTGTATCTTTATGAAAGAAATAGTTGTTTTTTCTTAAGGTAACTATCAGAGGTGGGATT
ATCTTGCCTCCTCACTTAGAATACCAACAGTCAAAAGGAAGAACCATCCTCTGAGTTTTA
AAAACCAGAAGGTTATGTTAAAATCTGGGCATTTAGTGACAGATCAAATGCATACTTGAA

FIGURE 109 Continued

CTAAGATTGGCTTCAGCTTAGCAGTCTTTCATGGTGGAAGTGACACATCTGGTTGAAAAT
AATTTGTGTATTTTCAGTAACCATGTATGGCTTCCTTCTTTATGTATGTGTGTGACTTGT
TTTAATTGGTAAGTTATAAGCCAGACATAGATTTTAGCTCTTTAATAAAAACTTCAGGGG
CACGTATGTCCCAGTACAAGTGTACTGACTATCAAGTTTTAACTCAGATGCAAGCTTTGG
CTCTTTCATAAAAAGTTTTTATGCATATGTGTCTCCATACAAGTGGCTCATTAAAATAAG
AACTTTGTAAACTGACTTAAAATCAGATATTTTTTCAAGAGTTAGGGAAAGTTGAAGTGT
TTTACTGTTTTGTCTCTTGAGCCCTTTCTCTGGGGAAAAAATACATATCCATCTATCTAT
CTATATATAAACTGTGTATACATTCTTACTGTTTGAACAACTATTGCCTTTAATTAAATG
TTTCATTTTTCTCCAGAGTCCCCAAAGCCACATGGCATTATTATAGTCATTTTTGAGATG
CCTGTAGAGAATGAAAGTATTGACTCCGTTAGAGGGAAAATGGGTTTCTCTGGGTGAATT
CCAACGAAGCATACCTAGGGGTAACAGTGAACCTACCTGGGTTTGTTTTGTTTTGGTAAG
GATTTATGTAGTGTCTGGCTGTAAGCAAGAATGAGTGGATTATAAACTTGAAGATTTCTC
TGTTAAAGTCACAAAAATGATCGACAAACAATATTTTTGTGATGTTTATTTAAACGTTGT
ATTTTATAACATACTTCAAGGAAGAGTATCGAAGTAAGTTGCTTTATAAATTAAGACTAA
ATTCGTATGGATGCAGAATTCAATTAATAAAATTTGAGCCTGTTACGTAAATTGAATATT
AATAAAATTGAAAATTTCAAAA

FIGURE 110

MENLSLSIEDVQPRSPGRSSLDDSGERDEKLSKSISFTSESISRVSETESFDGNSSKGGL
GKEESQNEKQTKKSLLPTLEKKLTRVPSKSLDLNKNEYLSLDKSSTSDSVDEENVPEKDL
HGRLFINRIFHISADRMFELLFTSSRFMQKFASSRNIIDVVSTPWTAELGGDQLRTMTYT
IVLNSPLTGKCTAATEKQTLYKESREARFYLVDSEVLTHDVPYHDYFYTVNRYCIIRSSK
QKCRLRVSTDLKYRKQPWGLVKSLIEKNSWSSLEDYFKQLESDLLIEESVLNQAIEDPGK
LTGLRRRRRTFNRTAETVPKLSSQHSSGDVGLGAKGDITGKKKEMENYNVTLIVVMSIFV
LLLVLLNVTLFLKLSKIEHAAQSFYRLRLQEEKSLNLASDMVSRAETIQKNKDQAHRLKG
VLRDSIVMLEQLKSSLIMLQKTFDLLNKNKTGMAVES

| | |
|---|---|
| 3-7 | N-glycosylation site |
| 54-58 | N-glycosylation site |
| 312-316 | N-glycosylation site |
| 349-353 | N-glycosylation site |
| 367-371 | N-glycosylation site |
| 449-453 | N-glycosylation site |
| | |
| 81-85 | cAMP- and cGMP-dependent protein kinase phosphorylation site |
| 307-311 | cAMP- and cGMP-dependent protein kinase phosphorylation site |
| | |
| 7-11 | Casein kinase II phosphorylation site |
| 19-23 | Casein kinase II phosphorylation site |
| 20-24 | Casein kinase II phosphorylation site |
| 46-50 | Casein kinase II phosphorylation site |
| 65-69 | Casein kinase II phosphorylation site |
| 105-109 | Casein kinase II phosphorylation site |
| 109-113 | Casein kinase II phosphorylation site |
| 263-267 | Casein kinase II phosphorylation site |
| 271-275 | Casein kinase II phosphorylation site |
| 272-276 | Casein kinase II phosphorylation site |
| 326-330 | Casein kinase II phosphorylation site |
| 375-379 | Casein kinase II phosphorylation site |
| 403-407 | Casein kinase II phosphorylation site |
| | |
| 202-211 | Tyrosine kinase phosphorylation site |
| 246-255 | Tyrosine kinase phosphorylation site |
| 341-350 | Tyrosine kinase phosphorylation site |
| | |
| 259-265 | N-myristoylation site |
| | |
| 339-343 | Amidation site |

FIGURE 111

CGGACGCGTGGGGCCGTATGCGCGGCTCTGTGGAGTGCACCTGGGGTTGGGGGCACTGTG
CCCCCAGCCCCCTGCTCCTTTGGACTCTACTTCTGTTTGCAGCCCCATTTGGCCTGCTGG
GGGAGAAGACCCGCCAGGTGTCTCTGGAGGTCATCCCTAACTGGCTGGGCCCCCTGCAGA
ACCTGCTTCATATACGGGCAGTGGGCACCAATTCCACACTGCACTATGTGTGGAGCAGCC
TGGGGCCTCTGGCAGTGGTAATGGTGGCCACCAACACCCCCCACAGCACCCTGAGCATCA
ACTGGAGCCTCCTGCTATCCCCTGAGCCCGATGGGGGCCTGATGGTGCTCCCTAAGGACA
GCATTCAGTTTTCTTCTGCCCTTGTTTTTACCAGGCTGCTTGAGTTTGACAGCACCAACG
TGTCCGATACGGCAGCAAAGCCTTTGGGAAGACCATATCCTCCATACTCCTTGGCCGATT
TCTCTTGGAACAACATCACTGATTCATTGGATCCTGCCACCCTGAGTGCCACATTTCAAG
GCCACCCCATGAACGACCCTACCAGGACTTTTGCCAATGGCAGCCTGGCCTTCAGGGTCC
AGGCCTTTTCCAGGTCCAGCCGACCAGCCCAACCCCCTCGCCTCCTGCACACAGCAGACA
CCTGTCAGCTAGAGGTGGCCCTGATTGGAGCCTCTCCCCGGGGAAACCGTTCCCTGTTTG
GGCTGGAGGTAGCCACATTGGGCCAGGGCCCTGACTGCCCCTCAATGCAGGAGCAGCACT
CCATCGACGATGAATATGCACCGGCCGTCTTCCAGTTGGACCAGCTACTGTGGGGCTCCC
TCCCATCAGGCTTTGCACAGTGGCGACCAGTGGCTTACTCCCAGAAGCCGGGGGGCCGAG
AATCAGCCCTGCCCTGCCAAGCTTCCCCTCTTCATCCTGCCTTAGCATACTCTCTTCCCC
AGTCACCCATTGTCCGAGCCTTCTTTGGGTCCCAGAATAACTTCTGTGCCTTCAATCTGA
CGTTCGGGGCTTCCACAGGCCCTGGCTATTGGGACCAACACTACCTCAGCTGGTCGATGC
TCCTGGGTGTGGGCTTCCCTCCAGTGGACGGCTTGTCCCCACTAGTCCTGGGCATCATGG
CAGTGGCCCTGGGTGCCCCAGGGCTCATGCTGCTAGGGGGCGGCTTGGTTCTGCTGCTGC
ACCACAAGAAGTACTCAGAGTACCAGTCCATAAATTAAGGCCCGCTCTCTGGAGGGAAGG
ACATTACTGAACCTGTCTTGCTGTGCCTCGAAACTCTGGAGGTTGGAGCATCAAGTTCCA
GCCGGCCCCTTCACTCCCCCATCTTGCTTTTCTGTGGAACCTCAGAGGCCAGCCTCGACT
TCCTGGAGACCCCCAGGTGGGGCTTCCTTCATACTTTGTTGGGGGACTTTGGAGGCGGGC
AGGGGACAGGGCTATTGATAAGGTCCCCTTGGTGTTGCCTTCTTGCATCTCCACACATTT
CCCTTGGATGGGACTTGCAGGCCTAAATGAGAGGCATTCTGACTGGTTGGCTGCCCTGGA
AGGCAAGAAAATAGATTTATTTTTTTCACAGGGAAAAAAAAAAAA

FIGURE 112

MRGSVECTWGWGHCAPSPLLLWTLLLFAAPFGLLGEKTRQVSLEVIPNWLGPLQNLLHIR
AVGTNSTLHYVWSSLGPLAVVMVATNTPHSTLSINWSLLLSPEPDGGLMVLPKDSIQFSS
ALVFTRLLEFDSTNVSDTAAKPLGRPYPPYSLADFSWNNITDSLDPATLSATFQGHPMND
PTRTFANGSLAFRVQAFSRSSRPAQPPRLLHTADTCQLEVALIGASPRGNRSLFGLEVAT
LGQGPDCPSMQEQHSIDDEYAPAVFQLDQLLWGSLPSGFAQWRPVAYSQKPGGRESALPC
QASPLHPALAYSLPQSPIVRAFFGSQNNFCAFNLTFGASTGPGYWDQHYLSWSMLLGVGF
PPVDGLSPLVLGIMAVALGAPGLMLLGGGLVLLLHHKKYSEYQSIN 65-69 N-glycosylation site
95-99 N-glycosylation site
134-138 N-glycosylation site
159-163 N-glycosylation site
187-191 N-glycosylation site
230-234 N-glycosylation site
333-337 N-glycosylation site 397-401 cAMP- and cGMP-dependent protein kinase phosphorylation site 151-155 Casein kinase II phosphorylation site
249-253 Casein kinase II phosphorylation site
255-259 Casein kinase II phosphorylation site 3-9 N-myristoylation site
63-69 N-myristoylation site
235-241 N-myristoylation site
273-279 N-myristoylation site
292-298 N-myristoylation site
324-330 N-myristoylation site 371-393 Leucine zipper pattern

FIGURE 113

GGAAAAGGTACCCGCGAGAGACAGCCAGCAGTTCTGTGGAGCAGCGGTGGCCGGCTAGGA
TGGGCTGTCTCTGGGGTCTGGCTCTGCCCCTTTTCTTCTTCTGCTGGGAGGTTGGGGTCT
CTGGGAGCTCTGCAGGCCCCAGCACCCGCAGAGCAGACACTGCGATGACAACGGACGACA
CAGAAGTGCCCGCTATGACTCTAGCACCGGGCCACGCCGCTCTGGAAACTCAAACGCTGA
GCGCTGAGACCTCTTCTAGGGCCTCAACCCCAGCCGGCCCCATTCCAGAAGCAGAGACCA
GGGGAGCCAAGAGAATTTCCCCTGCAAGAGAGACCAGGAGTTTCACAAAAACATCTCCCA
ACTTCATGGTGCTGATCGCCACCTCCGTGGAGACATCAGCCGCCAGTGGCAGCCCCGAGG
GAGCTGGAATGACCACAGTTCAGACCATCACAGGCAGTGATCCCGAGGAAGCCATCTTTG
ACACCCTTTGCACCGATGACAGCTCTGAAGAGGCAAAGACACTCACAATGGACATATTGA
CATTGGCTCACACCTCCACAGAAGCTAAGGGCCTGTCCTCAGAGAGCAGTGCCTCTTCCG
ACGGCCCCCATCCAGTCATCACCCCGTCACGGGCCTCAGAGAGCAGCGCCTCTTCCGACG
GCCCCCATCCAGTCATCACCCCGTCACGGGCCTCAGAGAGCAGCGCCTCTTCCGACGGCC
CCCATCCAGTCATCACCCCGTCATGGTCCCCGGGATCTGATGTCACTCTCCTCGCTGAAG
CCCTGGTGACTGTCACAAACATCGAGGTTATTAATTGCAGCATCACAGAAATAGAAACAA
CAACTTCCAGCATCCCTGGGGCCTCAGACATAGATCTCATCCCCACGGAAGGGGTGAAGG
CCTCGTCCACCTCCGATCCACCAGCTCTGCCTGACTCCACTGAAGCAAAACCACACATCA
CTGAGGTCACAGCCTCTGCCGAGACCCTGTCCACAGCCGGCACCACAGAGTCAGCTGCAC
CTCATGCCACGGTTGGGACCCCACTCCCCACTAACAGCGCCACAGAAAGAGAAGTGACAG
CACCCGGGGCCACGACCCTCAGTGGAGCTCTGGTCACAGTTAGCAGGAATCCCCTGGAAG
AAACCTCAGCCCTCTCTGTTGAGACACCAAGTTACGTCAAAGTCTCAGGAGCAGCTCCGG
TCTCCATAGAGGCTGGGTCAGCAGTGGGCAAAACAACTTCCTTTGCTGGGAGCTCTGCTT
CCTCCTACAGCCCCTCGGAAGCCGCCCTCAAGAACTTCACCCCTTCAGAGACACCGACCA
TGGACATCGCAACCAAGGGGCCCTTCCCCACCAGCAGGGACCCTCTTCCTTCTGTCCCTC
CGACTACAACCAACAGCAGCCGAGGGACGAACAGCACCTTAGCCAAGATCACAACCTCAG
CGAAGACCACGATGAAGCCCCAACAGCCACGCCCACGACTGCCCGGACGAGGCCGACCAC
AGACGTGAGTGCAGGTGAAAATGGAGGTTTCCTCCTCCTGCGGCTGAGTGTGGCTTCCCC
GGAAGACCTCACTGACCCCAGAGTGGCAGAAAGGCTGATGCAGCAGCTCCACCGGGAACT
CCACGCCCACGCGCCTCACTTCCAGGTCTCCTTACTGCGTGTCAGGAGAGGCTAACGGAC
ATCAGCTGCAGCCAGGCATGTCCCGTATGCCAAAAGAGGGTGCTGCCCCTAGCCTGGGCC
CCCACCGACAGACTGCAGCTGCGTTACTGTGCTGAGAGGTACCCAGAAGGTTCCCATGAA
GGGCAGCATGTCCAAGCCCCTAACCCCAGATGTGGCAACAGGACCCTCGCTCACATCCAC
CGGAGTGTATGTATGGGGAGGGGCTTCACCTGTTCCCAGAGGTGTCCTTGGACTCACCTT
GGCACATGTTCTGTGTTTCAGTAAAGAGAGACCTGATCACCCATCTGTGTGCTTCCATCC
TGCATTAAAATTCACTCAGTGTGGCCCAAAAAAAA

FIGURE 114

MGCLWGLALPLFFFCWEVGVSGSSAGPSTRRADTAMTTDDTEVPAMTLAPGHAALETQTL
SAETSSRASTPAGPIPEAETRGAKRISPARETRSFTKTSPNFMVLIATSVETSAASGSPE
GAGMTTVQTITGSDPEEAIFDTLCTDDSSEEAKTLTMDILTLAHTSTEAKGLSSESSASS
DGPHPVITPSRASESSASSDGPHPVITPSRASESSASSDGPHPVITPSWSPGSDVTLLAE
ALVTVTNIEVINCSITEIETTTSSIPGASDIDLIPTEGVKASSTSDPPALPDSTEAKPHI
TEVTASAETLSTAGTTESAAPHATVGTPLPTNSATEREVTAPGATTLSGALVTVSRNPLE
ETSALSVETPSYVKVSGAAPVSIEAGSAVGKTTSFAGSSASSYSPSEAALKNFTPSETPT
MDIATKGPFPTSRDPLPSVPPTTTNSSRGTNSTLAKITTSAKTTMKPQQPRPRLPGRGRP
QT

| | |
|---|---|
| 252-256 | N-glycosylation site |
| 445-449 | N-glycosylation site |
| 451-455 | N-glycosylation site |
| 84-90 | cAMP-and cGMP-dependent protein kinase phosphorylation site |
| 37 -41 | Casein kinase II phosphorylation site |
| 108-112 | Casein kinase II phosphorylation site |
| 131-135 | Casein kinase II phosphorylation site |
| 133-137 | Casein kinase II phosphorylation site |
| 148-152 | Casein kinase II phosphorylation site |
| 165-169 | Casein kinase II phosphorylation site |
| 246-250 | Casein kinase II phosphorylation site |
| 254-258 | Casein kinase II phosphorylation site |
| 256-260 | Casein kinase II phosphorylation site |
| 269-273 | Casein kinase II phosphorylation site |
| 283-287 | Casein kinase II phosphorylation site |
| 333-337 | Casein kinase II phosphorylation site |
| 335-339 | Casein kinase II phosphorylation site |
| 404-408 | Casein kinase II phosphorylation site |
| 414-418 | Casein kinase II phosphorylation site |
| 431-435 | Casein kinase II phosphorylation site |
| 2-8 | N-myristoylation site |
| 19-25 | N-myristoylation site |
| 117-123 | N-myristoylation site |
| 121-127 | N-myristoylation site |
| 232-238 | N-myristoylation site |
| 278-284 | N-myristoylation site |
| 314-320 | N-myristoylation site |
| 349-355 | N-myristoylation site |
| 386-392 | N-myristoylation site |
| 397-403 | N-myristoylation site |
| 449-455 | N-myristoylation site |
| 385-393 | ATP/GTP-binding site motif A (P-loop) |

FIGURE 115

GCGAGGCGGCCGCTGTCTTCTGCTGCGGCTTCCGCGACCACAAGTACTGCTGCGACGACC
CGCACAGCTTCTTCCCCTACGAGCACAGCTACATGTGGTGGCTCAGCATTGGCGCTCTCA
TAGGCCTGTCCGTAGCAGCAGTGGTTCTTCTCGCCTTCATTGTTACCGCCTGTGTGCTCT
GCTACCTGTTCATCAGCTCTAAGCCCCACACAAAGTTGGACCTGGGCTTGAGCTTACAGA
CAGCAGGCCCTGAGGAGGTTTCTCCTGACTGCCAAGGTGTGAACACAGGCATGGCGGCAG
AAGTGCCAAAAGTGAGCCCTCTCCAGCAGAGTTACTCCTGCTTGAACCCGCAGCTGGAGA
GCAATGAGGGGCAGGCTGTGAACTCCAAACGCCTCCTCCATCATTGCTTCATGGCCACAG
TGACCACCAGTGACATTCCAGGCAGCCCTGAGGAAGCCTCTGTACCCAACCCTGACCTAT
GTGGACCAGTCCCATAAACATTCAATAAATGTCTCCATACCATCAA

FIGURE 116

MWWLSIGALIGLSVAAVVLLAFIVTACVLCYLFISSKPHTKLDLGLSLQTAGPEEVSPDC
QGVNTGMAAEVPKVSPLQQSYSCLNPQLESNEGQAVNSKRLLHHCFMATVTTSDIPGSPE
EASVPNPDLCGPVP

| | |
|---|---|
| 40-44 | Casein kinase II phosphorylation site |
| 111-115 | Casein kinase II phosphorylation site |
| 118-122 | Casein kinase II phosphorylation site |
| 7-13 | N-myristoylation site |
| 11-17 | N-myristoylation site |
| 62-68 | N-myristoylation site |
| 93-99 | N-myristoylation site |
| 17-28 | Prokaryotic membrane lipoprotein lipid attachment site |

FIGURE 117

CCTCTGTCTGTGCTCCCATCCCAGGGAGTATAGGTGGAGCCTCCAGAGCCCATGGACAGG
GCATGCTGGGGCTGGGCCAGCCCCAGCGGTGTCTCTAAGGCACCCCTGGGATCCCCACTG
AGCTGGCCTACTTCAGACAGCCAGGGCCCACCCCTCTGGCCCCCTTAGTGTCCAGCTCGT
GGCCCCTTGGCATTTCCACAAGACGCCAAGATGGAGATTCCCATGGGGACCCAGGGCTGC
TTCTCAAAGAGCCTCCTGCTCTCAGCCTCAATCCTGGTCCTCTGGATGCTCCAAGGCTCC
CAGGCAGCTCTCTACATCCAGAAGATTCCAGAGCAGCCTCAAAAGAACCAGGACCTTCTC
CTGTCAGTCCAGGGTGTCCCAGACACCTTCCAGGACTTCAACTGGTACCTGGGGGAGGAG
ACGTACGGAGGCACGAGGCTATTTACCTACATCCCTGGGATACAACGGCCTCAGAGGGAT
GGCAGTGCCATGGGACAGCGAGACATCGTGGGCTTCCCCAATGGTTCCATGCTGCTGCGC
CGCGCCCAGCCTACAGACAGTGGCACCTACCAAGTAGCCATTACCATCAACTCTGAATGG
ACTATGAAGGCCAAGACTGAGGTCCAGGTAGCTGAAAAGAATAAGGAGCTGCCCAGTACA
CACCTGCCCACCAACGCTGGGATCCTGGCGGCCACCATCATTGGATCTCTTGCTGCCGGG
GCCCTTCTCATCAGCTGCATTGCCTATCTCCTGGTGACAAGGAACTGGAGGGGCCAGAGC
CACAGACTGCCTGCTCCGAGGGGCCAGGGATCTCTGTCCATCTTGTGCTCGGCTGTATCC
CCAGTGCCTTCAGTGACGCCCAGCACATGGATGGCGACCACAGAGAAGCCAGAATTGGGC
CCTGCTCATGATGCTGGTGACAACAACATCTATGAAGTGATGCCCTCTCCAGTCCTCCTG
GTGTCCCCCATCAGTGACACAAGGTCCATAAACCCAGCCCGGCCCCTGCCCACACCCCCA
CACCTGCAGGCGGAGCCAGAGAACCACCAGTACCAGCAGGACCTGCTAAACCCCGACCCT
GCCCCCTACTGCCAGCTGGTGCCAACTTCCTGATGGGTCCTGGGCCAGGCCAGCCAGGGA
GAAGACAAGGCCCCAGCCCTCCTCTGGGAGCCTCACACCTGAGACCAGCAGGACAAGGCC
ATTGGGGGCTGTGGGGCCGATGAGGTGGACTCAGCCAAAGACTCAGCAGCACATGGGGCA
GGTGTCCTGGCAGGGGGACAGGAGACTGTAACAGGCCCAGGTCCTTGTGCAGCCCCTGAA
TGCACGCCCGCCTTCGGTCTGTTCCTTCAAGCAAGCTGGCCTGGGCCATGTGCCTGTGAA
AGGCAGGCTCTGGCCCCTTTCCATGCCAAAGTCCCCCAAGATCTGGATATCTGGGGACAA
GATGGTGGCCTCAGGCCTGCCTCCCAGGCAGTTGGCTGGGCTCCCAACTGTCTGTCCTCA
ATGCCCTACCCCAACTCCACTAGTGACCCTCAGAGTCTTCTCCCCTTAGGACAAGGCAGA
CACCCCACCATGCGGGCCTCAGGTGGCAGAGAGGCCCAGCCTCACAGGCCTGTGGCCCCA
CACACCAGTCCCAGCAAGGTGACCACGGCTGCTGGACCCCTTCCCTGTTCAGGCAGGCCC
AGCCCCTCTCAGAACCTGCTGCCAGCTGCTGGTCTTGGCCCCCACCCTGAATCTTACTGA
GTCCCTCTGGGCAGCAGCTCCCTTCTCCACCCCACCCCAGCACCCGTCCCAAATGTGGCC
TCAGCTTGTCCTCCCCTTCCCCAAACTATGCATTCATTCAGCAATAAATGAGCCTTTGCT
GCA

FIGURE 118

><Wed Aug 18 11:18:02 PDT 1999 DNA119535 [min]
></usr/seqdb2/sst/DNA/Dnaseqs.min/ss.DNA119535
><subunit 1 of 1, 300 aa, 1 stop
><MW: 32638, pI: 6.02, NX(S/T): 1
MEIPMGTQGCFSKSLLLSASILVLWMLQGSQAALYIQKIPEQPQKNQDLLLSVQGVPDTF
QDFNWYLGEETYGGTRLFTYIPGIQRPQRDGSAMGQRDIVGFPNGSMLLRRAQPTDSGTY
QVAITINSEWTMKAKTEVQVAEKNKELPSTHLPTNAGILAATIIGSLAAGALLISCIAYL
LVTRNWRGQSHRLPAPRGQGSLSILCSAVSPVPSVTPSTWMATTEKPELGPAHDAGDNNI
YEVMPSPVLLVSPISDTRSINPARPLPTPPHLQAEPENHQYQQDLLNPDPAPYCQLVPTS

FIGURE 119

AGCATGAGAGGCCTGGCCGTCCTCCTCACTGTGGCTCTGGCCACGCTCCTGGCTCCCGGG
GCCGGAGCACCGGTACAAAGTCAGGGCTCCCAGAACAAGCTGCTCCTGGTGTCCTTCGAC
GGCTTCCGCTGGAACTACGACCAGGATGTGGACACCCCCAACCTGGACGCCATGGCCCGA
GACGGGGTGAAGGCACGCTACATGACCCCCGCCTTTGTCACCATGACCAGCCCCTGCCAC
TTCACCCTGGTCACCGGCAAATATATCGAGAACCACGGGGTGGTTCACAACATGTACTAC
AACATCACCAGCAAGGTGAAGCTGCCCTACCACGCCACGCTGGGCATCCAGAGGTGGTGG
GACAACGGCAGCGTGCCCATCTGGATCACAGCCCAGAGGCAGGGCCTGAGGGCTGGCTCC
TTCTTCTACCCGGGCGGGAACGTCACCTACCAAGGGGTGGCTGTGACGCGGAGCCGGAAA
GAAGGCATCGCACACAACTACAAAAATGAGACGGAGTGGAGAGCGAACATCGACACAGTG
ATGGCGTGGTTCACAGAGGAGGACCTGGATCTGGTCACACTCTACTTCGGGGAGCCGGAC
TCCACGGGCCACAGGTACGGCCCCGAGTCCCCGGAGAGGAGGGAGATGGTGCGGCAGGTG
GACCGGACCGTGGGCTACCTCCGGGAGAGCATCGCGCGCAACCACCTCACAGACCGCCTC
AACCTGATCATCACATCCGACCACGGCATGACGACCGTGGACAAACGGGCTGGCGACCTG
GTTGAATTCCACAAGTTCCCCAACTTCACCTTCCGGGACATCGAGTTTGAGCTCCTGGAC
TACGGACCAAACGGGATGCTGCTCCCTAAAGAAGGGAGGCTGGAGAAGGTGTACGATGCC
CTCAAGGACGCCCACCCCAAGCTCCACGTCTACAAGAAGGAGGCGTTCCCCGAGGCCTTC
CACTACGCCAACAACCCCAGGGTCACACCCCTGCTGATGTACAGCGACCTTGGCTACGTC
ATCCATGGGAGAATTAACGTCCAGTTCAACAATGGGGAGCACGGCTTTGACAACAAGGAC
ATGGACATGAAGACCATCTTCCGCGCTGTGGGCCCTAGCTTCAGGGCGGGCCTGGAGGTG
GAGCCCTTTGAGAGCGTCCACGTGTACGAGCTCATGTGCCGGCTGCTGGGCATCGTGCCC
GAGGCCAACGATGGGCACCTAGCTACTCTGCTGCCCATGCTGCACACAGAATCTGCTCTT
CCGCCTGATGGAAGGCCTACTCTCCTGCCCAAGGGAAGATCTGCTCTCCCGCCCAGCAGC
AGGCCCCTCCTCGTGATGGGACTGCTGGGGACCGTGATTCTTCTGTCTGAGGTCGCATAA
CGCCCCATGGCTCAAGGAAGCCGCCGGGAGCTGCCCGCAGGCCCTGGGCCGGCTGTCTCG
CTGCGATGCTCTGCTGGTCGCGGACGGACCCTGCCTCCCCAGCTTATCCCAGGCCAGAGG
CTGCATGCCACTGTCCCCGGCAGCGCCAACCCCTGCTTGGCTGTTATGGTGCTGGTAATA
AGCCTCGCAGCCCAGGTCCAGAGCCCCCGGCGAGCCGGTCCCATAACCGGCCCCCTGCCC
CTGCCCCTGCTCCTGCTCCTCCCCTTCGGGCCCCCTCCTCCTGCAAAACCCGCTCCCGAA
GCGGCGCTGCCGTCTGCAGCCACGCGGGGGCGCGCGGGAGCTCTGCGGGCGCTGGAACCT
GCAGACCCGGCCTCGGTCAGCTGGGAGGGGCCCGCCCCGGCACAAAGCACCCATGGGAAT
AAAGGCCAAGCCGCGACAGTCAAAAAAAAA

FIGURE 120

MRGLAVLLTVALATLLAPGAGAPVQSQGSQNKLLLVSFDGFRWNYDQDVDTPNLDAMARD
GVKARYMTPAFVTMTSPCHFTLVTGKYIENHGVVHNMYYNITSKVKLPYHATLGIQRWWD
NGSVPIWITAQRQGLRAGSFFYPGGNVTYQGVAVTRSRKEGIAHNYKNETEWRANIDTVM
AWFTEEDLDLVTLYFGEPDSTGHRYGPESPERREMVRQVDRTVGYLRESIARNHLTDRLN
LIITSDHGMTTVDKRAGDLVEFHKFPNFTFRDIEFELLDYGPNGMLLPKEGRLEKVYDAL
KDAHPKLHVYKKEAFPEAFHYANNPRVTPLLMYSDLGYVIHGRINVQFNNGEHGFDNKDM
DMKTIFRAVGPSFRAGLEVEPFESVHVYELMCRLLGIVPEANDGHLATLLPMLHTESALP
PDGRPTLLPKGRSALPPSSRPLLVMGLLGTVILLSEVA

Important features of the protein:
Signal peptide:

1-22

Transmembrane domain:

None

Motif name: N-glycosylation site.

100-104
121-125
146-150
168-172
267-271

Motif name: N-myristoylation site.

92-98
134-140
144-150
151-157
161-167
446-452

Motif name: Leucine zipper pattern.

GCGGCAGCAGCGCGGGCCCCAGCAGCCTCGGCAGCCACAGCCGCTGCAGCCGGGGCAGCC
TCCGCTGCTGTCGCCTCCTCTGATGCGCTTGCCCTCTCCCGGCCCCGGGACTCCGGGAGA
ATGTGGGTCCTAGGCATCGCGGCAACTTTTTGCGGATTGTTCTTGCTTCCAGGCTTTGCG
CTGCAAATCCAGTGCTACCAGTGTGAAGAATTCCAGCTGAACAACGACTGCTCCTCCCCC
GAGTTCATTGTGAATTGCACGGTGAACGTTCAAGACATGTGTCAGAAAGAAGTGATGGAG
CAAAGTGCCGGGATCATGTACCGCAAGTCCTGTGCATCATCAGCGGCCTGTCTCATCGCC
TCTGCCGGGTACCAGTCCTTCTGCTCCCCAGGGAAACTGAACTCAGTTTGCATCAGCTGC
TGCAACACCCCTCTTTGTAACGGGCCAAGGCCCAAGAAAAGGGGAAGTTCTGCCTCGGCC
CTCAGGCCAGGGCTCCGCACCACCATCCTGTTCCTCAAATTAGCCCTCTTCTCGGCACAC
TGCTGAAGCTGAAGGAGATGCCACCCCCTCCTGCATTGTTCTTCCAGCCCTCGCCCCCAA
CCCCCCACCTCCCTGAGTGAGTTTCTTCTGGGTGTCCTTTTATTCTGGGTAGGGAGCGGG
AGTCCGTGTTCTCTTTTGTTCCTGTGCAAATAATGAAAGAGCTCGGTAAAGCATTCTGAA
TAAATTCAGCCTGACTGAATTTTCAGTATGTACTTGAAGGAAGGAGGTGGAGTGAAAGTT
CACCCCCATGTCTGTGTAACCGGAGTCAAGGCCAGGCTGGCAGAGTCAGTCCTTAGAAGT
CACTGAGGTGGGCATCTGCCTTTTGTAAAGCCTCCAGTGTCCATTCCATCCCTGATGGGG
GCATAGTTTGAGACTGCAGAGTGAGAGTGACGTTTTCTTAGGGCTGGAGGGCCAGTTCCC
ACTCAAGGCTCCCTCGCTTGACATTCAAACTTCATGCTCCTGAAAACCATTCTCTGCAGC
AGAATTGGCTGGTTTCGCGCCTGAGTTGGGCTCTAGTGACTCGAGACTCAATGACTGGGA
CTTAGACTGGGGCTCGGCCTCGCTCTGAAAAGTGCTTAAGAAAATCTTCTCAGTTCTCCT
TGCAGAGGACTGGCGCCGGGACGCGAAGAGCAACGGGCGCTGCACAAAGCGGGCGCTGTC
GGTGGTGGAGTGCGCATGTACGCGCAGGCGCTTCTCGTGGTTGGCGTGCTGCAGCGACAG
GCGGCAGCACAGCACCTGCACGAACACCCGCCGAAACTGCTGCGAGGACACCGTGTACAG
GAGCGGGTTGATGACCGAGCTGAGGTAGAAAAACGTCTCCGAGAAGGGGAGGAGGATCAT
GTACGCCCGGAAGTAGGACCTCGTCCAGTCGTGCTTGGGTTTGGCCGCAGCCATGATCCT
CCGAATCTGGTTGGGCATCCAGCATACGGCCAATGTCACAACAATCAGCCCTGGGCAGAC
ACGAGCAGGAGGGAGAGACAGAGA

FIGURE 122

MWVLGIAATFCGLFLLPGFALQIQCYQCEEFQLNNDCSSPEFIVNCTVNVQDMCQKEVME
QSAGIMYRKSCASSAACLIASAGYQSFCSPGKLNSVCISCCNTPLCNGPRPKKRGSSASA
LRPGLRTTILFLKLALFSAHC

Important features of the protein:
Signal peptide:

1-22

Transmembrane domain:

None

Motif name: N-glycosylation site.

45-49

Motif name: cAMP- and cGMP-dependent protein kinase phosphorylation site.

113-117

Motif name: N-myristoylation site.

5-11
115-121
124-130

Motif name: Ly-6 / u-PAR domain proteins 94-107

FIGURE 123

AGCACTCTCCAGCCTCTCACCGCAAAATTACACACCCCAGTACACCAGCAGAGGAAACTT
ATAACCTCGGGAGGCGGGTCCTTCCCCTCAGTGCGGTCACATACTTCCAGAAGAGCGGAC
CAGGGCTGCTGCCAGCACCTGCCACTCAGAGCGCCTCTGTCGCTGGGACCCTTCAGAACT
CTCTTTGCTCACAAGTTACCAAAAAAAAAAGAGCCAACATGTTGGTATTGCTGGCTGGTA
TCTTTGTGGTCCACATCGCTACTGTTATTATGCTATTTGTTAGCACCATTGCCAATGTCT
GGTTGGTTTCCAATACGGTAGATGCATCAGTAGGTCTTTGGAAAAACTGTACCAACATTA
GCTGCAGTGACAGCCTGTCATATGCCAGTGAAGATGCCCTCAAGACAGTGCAGGCCTTCA
TGATTCTCTCTATCATCTTCTGTGTCATTGCCCTCCTGGTCTTCGTGTTCCAGCTCTTCA
CCATGGAGAAGGGAAACCGGTTCTTCCTCTCAGGGGCCACCACACTGGTGTGCTGGCTGT
GCATTCTTGTGGGGGTGTCCATCTACACTAGTCATTATGCGAATCGTGATGGAACGCAGT
ATCACCACGGCTATTCCTACATCCTGGGCTGGATCTGCTTCTGCTTCAGCTTCATCATCG
GCGTTCTCTATCTGGTCCTGAGAAAGAAATAAGGCCGGACGAGTTCATGGGGATCTGGGG
GGTGGGGAGGAGGAAGCCGTTGAATCTGGGAGGGAAGTGGAGGTTGCTGTACAGGAAAAA
CCGAGATAGGGGAGGGGGGAGGGGGAAGCAAAGGGGGGAGGTCAAATCCCAAACCATTAC
TGAGGGGATTCTCTACTGCCAAGCCCCTGCCCTGGGGAGAAAGTAGTTGGCTAGTACTTT
GATGCTCCCTTGATGGGGTCCAGAGAGCCTCCCTGCAGCCACCAGACTTGGCCTCCAGCT
GTTCTTAGTGACACACACTGTCTGGGGCCCCATCAGCTGCCACAACACCAGCCCCACTTC
TGGGTCATGCACTGAGGTCCACAGACCTACTGCACTGAGTTAAAATAGCGGTACAAGTTC
TGGCAAGAGCAGATACTGTCTTTGTGCTGAATACGCTAAGCCTGGAAGCCATCCTGCCCT
TCTGACCCAAAGCAAAACATCACATTCCAGTCTGAAGTGCCTACTGGGGGGCTTTGGCCT
GTGAGCCATTGTCCCTCTTTGGAACAGATATTTAGCTCTGTGGAATTCAGTGACAAAATG
GGAGGAGGAAAGAGAGTTTGTAAGGTCATGCTGGTGGGTTAGCTAAACCAAGAAGGAGAC
CTTTTCACAATGGAAAACCTGGGGGATGGTCAGAGCCCAGTCGAGACCTCACACACGGCT
GTCCCTCATGGAGACCTCATGCCATGGTCTTTGCTAGGCCTCTTGCTGAAAGCCAAGGCA
GCTCTTCTGGAGTTTCTCTAAAGTCACTAGTGAACAATTCGGTGGTAAAAGTACCACACA
AACTATGGGATCCAAGGGGCAGTCTTGCAACAGTGCCATGTTAGGGTTATGTTTTTAGGA
TTCCCCTCAATGCAGTCAGTGTTTCTTTTAAGTATACAACAGGAGAGAGATGGACATGGC
TCATTGTAGCACAATCCTATTACTCTTCCTCTAACATTTTTGAGGAAGTTTTGTCTAATT
ATCAATATTGAGGATCAGGGCTCCTAGGCTCAGTGGTAGCTCTGGCTTAGACACCACCTG
GAGTGATCACCTCTTGGGGACCCTGCCTATCCCACTTCACAGGTGAGGCATGGCAATTCT
GGAAGCTGATTAAAACACACATAAACCAAAACCAAACAACAGGCCCTTGGGTGAAAGGTG
CTATATAATTGTGAAGTATTAAGCCTACCGTATTTCAGCCATGATAAGAACAGAGTGCCT
GCATTCCCAGGAAAATACGAAAATCCCATGAGATAAATAAAAATATAGGTGATGGGCAGA
TCTTTTCTTTAAAATAAAAAAGCAAAAACTCTTGTGGTACCTAGTCAGATGGTAGACGAG
CTGTCTGCTGCCGCAGGAGCACCTCTATACAGGACTTAGAAGTAGTATGTTATTCCTGGT
TAAGCAGGCATTGCTTTGCCCTGGAGCAGCTATTTTAAGCCATCTCAGATTCTGTCTAAA
GGGGTTTTTTGGGAAGACGTTTTCTTTATCGCCCTGAGAAGATCTACCCCAGGGAGAATC
TGAGACATCTTGCCTACTTTTCTTTATTAGCTTTCTCCTCATCCATTTCTTTTATACCTT
TCCTTTTTGGGGAGTTGTTATGCCATGATTTTTGGTATTTATGTAAAAGGATTATTACTA
ATTCTATTTCTCTATGTTTATTCTAGTTAAGGAAATGTTGAGGGCAAGCCACCAAATTAC
CTAGGCTGAGGTTAGAGAGATTGGCCAGCAAAAACTGTGGGAAGATGAACTTTGTCATTA
TGATTTCATTATCACATGATTATAGAAGGCTGTCTTAGTGCAAAAAACATACTTACATTT

FIGURE 123 Continued

CAGACATATCCAAAGGGAATACTCACATTTTGTTAAGAAGTTGAACTATGACTGGAGTAA
ACCATGTATTCCCTTATCTTTTACTTTTTTTCTGTGACATTTATGTCTCATGTAATTTGC
ATTACTCTGGTGGATTGTTCTAGTACTGTATTGGGCTTCTTCGTTAATAGATTATTTCAT
ATACTATAATTGTAAATATTTTGATACAAATGTTTATAACTCTAGGGATATAAAAACAGA
TTCTGATTCCCTTCAAAAAAAAAAAA

FIGURE 124

></usr/seqdb2/sst/DNA/Dnaseqs.min/ss.DNA226874
><subunit 1 of 1, 157 aa, 1 stop
><MW: 17563, pI: 8.34, NX(S/T): 2
MLVLLAGIFVVHIATVIMLFVSTIANVWLVSNTVDASVGLWKNCTNISCSDSLSYASEDA
LKTVQAFMILSIIFCVIALLVFVFQLFTMEKGNRFFLSGATTLVCWLCILVGVSIYTSHY
ANRDGTQYHHGYSYILGWICFCFSFIIGVLYLVLRKK

FIGURE 125

GTCTGCGCGGAGTCTGAGCGGCGCTCGTCCCGTCCCAAGGCCGACGCCAGCACGCCGTCA
TGGCCCCCGCAGCGGCGACGGGGGGCAGCACCCTGCCCAGTGGCTTCTCGGTCTTCACCA
CCTTGCCCGACTTGCTCTTCATCTTTGAGTTTATCTTCGGGGGCCTGGTGTGGATCCTGG
TGGCCTCCTCCCTGGTGCCCTGGCCCCTGGTCCAGGGCTGGGTGATGTTCGTGTCTGTGT
TCTGCTTCGTGGCCACCACCACCTTGATCATCCTGTACATAATTGGAGCCCACGGTGGAG
AGACTTCCTGGGTCACCTTGGACGCAGCCTACCACTGCACCGCTGCCCTCTTTTACCTCA
GCGCCTCAGTCCTGGAGGCCCTGGCCACCATCACGATGCAAGACGGCTTCACCTACAGGC
ACTACCATGAAAACATTGCTGCCGTGGTGTTCTCCTACATAGCCACTCTGCTCTACGTGG
TCCATGCGGTGTTCTCTTTAATCAGATGGAAGTCTTCATAAAGCCGCAGTAGAACTTGAG
CTGAAAACCCAGATGGTGTTAACTGGCCGCCCCACTTTCCGGCATAACTTTTTAGAAAAC
AGAAATGCCCTTGATGGTGGAAAAAAGAAAACAACCACCCCCCCACTGCCCAAAAAAAAA
AGCCCTGCCCTGTTGCTCGTGGGTGCTGTGTTTACTCTCCCGTGTGCCTTCGCGTCCGGG
TTGGGAGCTTGCTGTGTCTAACCTCCAACTGCTGTGCTGTCTGCTAGGGTCACCTCCTGT
TTGTGAAAGGGGACCTTCTTGTTCGGGGGTGGGAAGTGGCGACCGTGACCTGAGAAGGAA
AGAAAGATCCTCTGCTGACCCCTGGAGCAGCTCTCGAGAACTACCTGTTGGTATTGTCCA
CAAGCTCTCCCGAGCGCCCCATCTTGTGCCATGTTTTAAGTCTTCATGGATGTTCTGCAT
GTCATGGGGACTAAAACTCACCCAACAGATCTTTCCAGAGGTCCATGGTGGAAGACGATA
ACCCTGTGAAATACTTTATAAAATGTCTTAATGTTC

FIGURE 126

></usr/seqdb2/sst/DNA/Dnaseqs.min/ss.DNA227033
><subunit 1 of 1, 153 aa, 1 stop
><MW: 16714, pI: 5.89, NX(S/T): 0
MAPAAATGGSTLPSGFSVFTTLPDLLFIFEFIFGGLVWILVASSLVPWPLVQGWVMFVSV
FCFVATTTLIILYIIGAHGGETSWVTLDAAYHCTAALFYLSASVLEALATITMQDGFTYR
HYHENIAAVVFSYIATLLYVVHAVFSLIRWKSS

FIGURE 127

CCGCGGAACTGGCAGGCGTTTCAGAGCGTCAGAGGCTGCGGATGAGCAGACTTGGAGGACTCCAGGCCAGAGAC
TAGGCTGGGCGAAGAGTCGAGCGTGAAGGGGGCTCCGGGCCAGGGTGACAGGAGGCGTGCTTGAGAGGAAGAAG
TTGACGGGAAGGCCAGTGCGACGGCAAATCTCGTGAACCTTGGGGGACGAATGCTCAGGATGCGGGTCCCCGCC
CTCCTCGTCCTCCTCTTCTGCTTCAGAGGGAGAGCAGGCCCGTCGCCCCATTTCCTGCAACAGCCAGAGGACCT
GGTGGTGCTGCTGGGGGAGGAAGCCCGGCTGCCGTGTGCTCTGGGCGCCTACTGGGGGCTAGTTCAGTGGACTA
AGAGTGGG
CTGGCCCTAGGGGGCCAAAGGGACCTACCAGGGTGGTCCCGGTACTGGATATCAGGGAATGCAGCCAATGGCCA
GCATGACCTCCACATTAGGCCCGTGGAGCTAGAGGATGAAGCATCATATGAATGTCAGGCTACACAAGCAGGCC
TCCGCTCCAGACCAGCCCAACTGCACGTGCTGGTCCCCCCAGAAGCCCCCCAGGTGCTGGGCGGCCCCTCTGTG
TCTCTGGTTGCTGGAGTTCCTGCGAACCTGACATGTCGGAGCCGTGGGGATGCCCGCCCTACCCCTGAATTGCT
GTGGTTCCGAGATGGGGTCCTGTTGGATGGAGCCACCTTTCATCAGACCCTGCTGAAGGAAGGGACCCCTGGGT
CAGTGGAGAGCACCTTAACCCTGACCCCTTTCAGCCATGATGATGGAGCCACCTTTGTCTGCCGGGCCCGGAGC
CAGGCCCTGCCCACAGGAAGAGACACAGCTATCACACTGAGCCTGCAGTACCCCCCAGAGGTGACTCTGTCTGC
TTCGCCACACACTGTGCAGGAGGGAGAGAAGGTCATTTTCCTGTGCCAGGCCACAGCCCAGCCTCCTGTCACAG
GCTACAGGTGGGCAAAAGGGGGCTCTCCGGTGCTCGGGGCCCGCGGGCCAAGGTTAGAGGTCGTGGCAGACGCC
TCGTTCCTGACTGAGCCCGTGTCCTGCGAGGTCAGCAACGCCGTGGGTAGCGCCAACCGCAGTACTGCGCTGGA
TGTGCTGTTTGGGCCGATTCTGCAGGCAAAGCCGGAGCCCGTGTCCGTGGACGTGGGGGAAGACGCTTCCTTCA
GCTGCGCCTGGCGCGGGAACCCGCTTCCACGGGTAACCTGGACCCGCCGCGGTGGCGCGCAGGTGCTGGGCTCT
GGAGCCACACTGCGTCTTCCGTCGGTGGGGCCCGAGGACGCAGGCGACTATGTGTGCAGAGCTGAGGCTGGGCT
ATCGGGCCTGCGGGGCGGCGCCGCGGAGGCTCGGCTGACTGTGAACGCTCCCCCAGTAGTGACCGCCCTGCACT
CTGCGCCTGCCTTCCTGAGGGGCCCTGCTCGCCTCCAGTGTCTGGTTTTCGCCTCTCCCGCCCCAGATGCCGTG
GTCTGGTCTTGGGATGAGGGCTTCCTGGAGGCGGGGTCGCAGGGCCGGTTCCTGGTGGAGACATTCCCTGCCCC
AGAGAGCCGCGGGGGACTGGGTCCGGGCCTGATCTCTGTGCTACACATTTCGGGGACCCAGGAGTCTGACTTTA
GCAGGAGCTTTAACTGCAGTGCCCGGAACCGGCTGGGCGAGGGAGGTGCCCAGGCCAGCCTGGGCCGTAGAGAC
TTGCTGCCCACTGTGCGGATAGTGGCCGGAGTGGCCGCTGCCACCACAACTCTCCTTATGGTCATCACTGGGGT
GGCCCTCTGCTGCTGGCGCCACAGCAAGGCCTCAGCCTCTTTCTCCGAGCAAAAGAACCTGATGCGAATCCCTG
GCAGCAGCGACGGCTCCAGTTCACGAGGTCCTGAAGAAGAGGAGACAGGCAGCCGCGAGGACCGGGGCCCCATT
GTGCACACTGACCACAGTGATCTGGTTCTGGAGGAGGAAGGGACTCTGGAGACCAAGGACCCAACCAACGGTTA
CTACAAGGTCCGAGGAGTCAGTGTGAGCCTGAGCCTTGGCGAAGCCCCTGGAGGAGGTCTCTTCCTGCCACCAC
CCTCCCCCCTTGGGCCCCCAGGGACCCCTACCTTCTATGACTTCAACCCACACCTGGGCATGGTCCCCCCCTGC
AGACTTTACAGAGCCAGGGCAGGCTATCTCACCACACCCCACCCTCGAGCTTTCACCAGCTACATCAAACCCAC
ATCCTTTGGGCCCCCAGATCTGGCCCCCGGGACTCCCCCCTTCCCATATGCTGCCTTCCCCACACCTAGCCACC
CGCGTCTCCAGACTCACGTGTGACATCTTTCCAATGGAAGAGTCCTGGGATCTCCAACTTGCCATAATGGATTG
TTCTGATTTCTGAGGAGCCAGGACAAGTTGGCGACCTTACTCCTCCAAAACTGAACACAAGGGGAGGGAAAGAT
CATTACATTTGTCAGGAGCATTTGTATACAGTCAGCTCAGCCAAAGGAGATGCCCCAAGTGGGAGCAACATGGC
CACCCAATATGCCCACCTATTCCCCGGTGTAAAAGAGATTCAAGATGGCAGGTAGGCCCTTTGAGGAGAGATGG
GGACAGGGCAGTGGGTGTTGGGAGTTTGGGGCCGGGATGGAAGTTGTTTCTAGCCACTGAAAGAAGATATTTCA
AGATGACCATCTGCATTGAGAGGAAAGGTAGCATAGGATAGATGAAGATGAAGAGCATACCAGGCCCCACCCTG
GCTCTCCCTGAGGGGAACTTTGCTCGGCCAATGGAAATGCAGCCAAGATGGCCATATACTCCCTAGGAACCCAA
AATGGCCACCATCTTGATTTTACTTTCCTTAAAGACTCAGAAAGACTTGGACCCAAGGAGTGGGGATACAGTGA
GAATTACCACTGTTGGGGCAAAATATTGGGATAAAAATATTTATGTTTAATAATAAAAAAAAGTCAAAGAGAAA
AAAAA

FIGURE 128

></usr/seqdb2/sst/DNA/Dnaseqs.min/ss.DNA145841

><subunit 1 of 1, 708 aa, 1 stop

><MW: 75093, pI: 6.65, NX(S/T): 3

MLRMRVPALLVLLFCFRGRAGPSPHFLQQPEDLVVLLGEEARLPCALGAYWGLVQWTKSG
LALGGQRDLPGWSRYWISGNAANGQHDLHIRPVELEDEASYECQATQAGLRSRPAQLHVL
VPPEAPQVLGGPSVSLVAGVPANLTCRSRGDARPTPELLWFRDGVLLDGATFHQTLLKEG
TPGSVESTLTLTPFSHDDGATFVCRARSQALPTGRDTAITLSLQYPPEVTLSASPHTVQE
GEKVIFLCQATAQPPVTGYRWAKGGSPVLGARGPRLEVVADASFLTEPVSCEVSNAVGSA
NRSTALDVLFGPILQAKPEPVSVDVGEDASFSCAWRGNPLPRVTWTRRGGAQVLGSGATL
RLPSVGPEDAGDYVCRAEAGLSGLRGGAAEARLTVNAPPVVTALHSAPAFLRGPARLQCL
VFASPAPDAVVWSWDEGFLEAGSQGRFLVETFPAPESRGGLGPGLISVLHISGTQESDFS
RSFNCSARNRLGEGGAQASLGRRDLLPTVRIVAGVAAATTTLLMVITGVALCCWRHSKAS
ASFSEQKNLMRIPGSSDGSSSRGPEEEETGSREDRGPIVHTDHSDLVLEEEGTLETKDPT
NGYYKVRGVSVSLSLGEAPGGGLFLPPPSPLGPPGTPTFYDFNPHLGMVPPCRLYRARAG
YLTTPHPRAFTSYIKPTSFGPPDLAPGTPPFPYAAFPTPSHPRLQTHV

Important features of the protein:

Signal peptide:

Amino acids 1-20

Transmembrane domain:

Amino acids 511-531

N-glycosylation sites:

Amino acids 143-147;301-305;484-488

N-myristoylation sites:

Amino acids 48-54;60-66;79-85;139-145;180-186;183-189;355-361;383-389;
387-393;460-466;473-479;494-500;495-501;514-520;528-534;
554-560;592-598;608-614

Amidation site:

Amino acids 500-504

Cell attachment sequence:

Amino acids 149-152

Multicopper oxidases signature 1:

Amino acids 445-466

Immunoglobulin domain:

Amino acids 326-377

FIGURE 129

GGACCACAGCTCCTCCCGTGCATCCACTCGGCCTGGGAGGTTCTGGATTTTGGCTGTCGA
GGGAGTTTGCCTGCCTCTCCAGAGAAAGATGGTCATGAGGCCCCTGTGGAGTCTGCTTCT
CTGGGAAGCCCTACTTCCCATTACAGTTACTGGTGCCCAAGTGCTGAGCAAAGTCGGGGG
CTCGGTGCTGCTGGTGGCAGCGCGTCCCCCTGGCTTCCAAGTCCGTGAGGCTATCTGGCG
ATCTCTCTGGCCTTCAGAAGAGCTCCTGGCCACGTTTTTCCGAGGCTCCCTGGAGACTCT
GTACCATTCCCGCTTCCTGGGCCGAGCCCAGCTACACAGCAACCTCAGCCTGGAGCTCGG
GCCGCTGGAGTCTGGAGACAGCGGCAACTTCTCCGTGTTGATGGTGGACACAAGGGGCCA
GCCCTGGACCCAGACCCTCCAGCTCAAGGTGTACGATGCAGTGCCCAGGCCCGTGGTACA
AGTGTTCATTGCTGTAGAAAGGGATGCTCAGCCCTCCAAGACCTGCCAGGTTTTCTTGTC
CTGTTGGGCCCCCAACATCAGCGAAATAACCTATAGCTGGCGACGGGAGACAACCATGGA
CTTTGGTATGGAACCACACAGCCTCTTCACAGACGGACAGGTGCTGAGCATTTCCCTGGG
ACCAGGAGACAGAGATGTGGCCTATTCCTGCATTGTCTCCAACCCTGTCAGCTGGGACTT
GGCCACAGTCACGCCCTGGGATAGCTGTCATCATGAGGCAGCACCAGGGAAGGCCTCCTA
CAAAGATGTGCTGCTGGTGGTGGTGCCTGTCTCGCTGCTCCTGATGCTGGTTACTCTCTT
CTCTGCCTGGCACTGGTGCCCCTGCTCAGGGAAAAAGAAAAAGGATGTCCATGCTGACAG
AGTGGGTCCAGAGACAGAGAACCCCCTTGTGCAGGATCTGCCATAAAGGACAATATGAAC
TGATGCCTGGACTATCAGTAACCCCACTGCACAGGCACACGATGCTCTGGGACATAACTG
GTGCCTGGAAATCACCATGGTCCTCATATCTCCCATGGGAATCCTGTCCTGCCTCGAAGG
AGCAGCCTGGGCAGCCATCACACCACGAGGACAGGAAGCACCAGCACGTTTCACACCTCC
CCCTTCCCTCTCCCATCTTCTCATATCCTGGCTCTTCTCTGGGCAAGATGAGCCAAGCAG
AACATTCCATCCAGGACACTGGAAGTTCTCCAGGATCCAGATCCATGGGGACATTAATAG
TCCAAGGCATTCCCTCCCCCACCACTATTCATAAAGTATTAACCAACTGGCACCAAGGAA
TTGCCTCCAGCCTGAGTCCTAGGCTCTAAAAGATATTACATATTTGAACTAATAGAGGAA
CTCTGAGTCACCCATGCCAGCATCAGCTTCAGCCCCAGACCCTGCAGTTTGAGATCTGAT
GCTTCCTGAGGGCCAAGGCATTGCTGTAAGAAAAGGTCTAGAAATAGGTGAAAGTGAGAG
GTGGGGGACAGGGGTTTCTCTTTCTGGCCTAAGGACTTTCAGGTAATCAGAGTTCATGGG
CCCTCAAAGGTAAATTGCAGTTGTAGACACCGAGGATGGTTGACAACCCATGGTTGAGAT
GGGCACCGTTTTGCAGGAAACACCATATTAATAGACATCCTCACCATCTCCATCCGCTCT
CACGCCTCCTGCAGGATCTGGGAGTGAGGGTGGAGAGTCTTTCCTCACGCTCCAGCACAG
TGGCCAGGAAAAGAAATACTGAATTTGCCCCAGCCAACAGGACGTTCTTGCACAACTTCA
AGAAAAGCAGCTCAGCTCAGGATGAGTCTTCCTGCCTGAAACTGAGAGAGTGAAGAACCA
TAAAACGCTATGCAGAAGGAACATTATGGAGAGAAAGGGTACTGAGGCACTCTAGAATCT
GCCACATTCATTTTCAAATGCAAATGCAGAAGACTTACCTTAGTTCAAGGGGAGGGGACA
AAGACCCCACAGCCCAACAGCAGGACTGTAGAGGTCACTCTGACTCCATCAAACTTTTTA
TTGTGGCCATCTTAGGAAAATACATTCTGCCCCTGAATGATTCTGTCTAGAAAAGCTCTG
GAGTATTGATCACTACTGGAAAAACACTTAAGGAGCTAAACTTACCTTCGGGGATTATTA
GCTGATAAGGTTCACAGTTTCTCTCACCCAGGTGTAACTGGATTTTTTCTGGGGCCTCAA
TCCAGTCTTGATAACAGCGAGGAAAGAGGTATTGAAGAAACAGGGGTGGGTTTGAAGTAC
TATTTTCCCCAGGGTGGCTTCAATCTCCCCACCTAGGATGTCAGCCCTGTCCAAGGACCT
TCCCTCTTCTCCCCCAGTTCCCTGGGCAATCACTTCACCTTGGACAAAGGATCAGCACAG
CTGGCCTCCAGATCCACATCACCACTCTTCCACTCGATTGTTCCCAGATCCTCCCTGCCT
GGCCTGCTCAGAGGTTCCCTGTTGGTAACCTGGCTTTATCAAATTCTCATCCCTTTCCCA
CACCCACTTCTCTCCTATCACCTTCCCCCAAGATTACCTGAACAGGGTCCATGGCCACTC
AACCTGTCAGCTTGCACCATCCCCACCTGCCACCTACAGTCAGGCCACATGCCTGGTCAC
TGAATCATGCAAAACTGGCCTCAGTCCCTAAAAATGATGTGGAAAGGAAAGCCCAGGATC
TGACAATGAGCCCTGGTGGATTTGTGGGGAAAAAATACACAGCACTCCCCACCTTTCTTT
CGTTCATCTCCAGGGCCCCACCTCAGATCAAAGCAGCTCTGGATGAGATGGGACCTGCAG
CTCTCCCTCCACAAGGTGACTCTTAGCAACCTCATTTCGACAGTGGTTTGTAGCGTGGTG
CACCAGGGCCTTGTTGAACAGATCCACACTGCTCTAATAAAGTTCCCATCCTTAATGACT
CACTTGTCAACTAGTGGACTAATTAACCCTCCACCAAAAAAACACAAAGTGCTTCTGTGA
GACCAATTTTGTGCTAATGAGCATTGAGACTGATGCTTTGTAAGTCACACCACAACAAAT
ATTGATTGAGGGCGCTGCATGTGCTGGGTACATTTCTTGGCACTTGGGAATCAGTAGTCA
AGCGAAACCCTTGCCTTTGAGAGTTTATGGTCTGGATAATATAAATAAACAAGTAAGCAT
AAAAAAAAAAAAAAAAA

FIGURE 130

><Wed Dec 6 14:16:26 2000 DNA188342 [min]
></usr/seqdb2/sst/DNA/Dnaseqs.min/ss.DNA188342
><subunit 1 of 1, 285 aa, 1 stop
><MW: 31670, pI: 6.12, NX(S/T): 3
MVMRPLWSLLLWEALLPITVTGAQVLSKVGGSVLLVAARPPGFQVREAIWRSLWPSEELL
ATFFRGSLETLYHSRFLGRAQLHSNLSLELGPLESGDSGNFSVLMVDTRGQPWTQTLQLK
VYDAVPRPVVQVFIAVERDAQPSKTCQVFLSCWAPNISEITYSWRRETTMDFGMEPHSLF
TDGQVLSISLGPGDRDVAYSCIVSNPVSWDLATVTPWDSCHHEAAPGKASYKDVLLVVVP
VSLLLMLVTLFSAWHWCPCSGKKKKDVHADRVGPETENPLVQDLP

FIGURE 131

GGGAAGCCATGGAGCCGCGGGCGCTCGTCACGGCGCTCAGCCTCGGCCTCAGCCTGTGCTCCCTGGGGCTGCTC
GTCACGGCCATCTTCACCGACCACTGGTACGAGACCGACCCCCGGCGCCACAAGGAGAGCTGCGAGCGCAGCCG
CGCGGGCGCCGACCCCCCGGACCAGAAGAACCGCCTGATGCCGCTGTCGCACCTACTCGGGCCTCTGGAGGAAG
TGCTACTTCCTGGGCATCGACCGGGACATCGACACCCTCATCCTGAAAGGTATTGCGCAGCGATGCACGGCCAT
CAAGTACCACTTTTCTCAGCCCATCCGCTTGCGAAACATTCCTTTTAATTTAACCAAGACCATACAGCAAGATG
AGTGGCACCTGCTTCGGATATTTTGCACCATTTCCCTCTGTACTTATGCCGCCAGTATCTCGTATGATTTGAAC
CGGCTCCCAAAGCTAATTTATAGCCTGCCTGCTGATGTGGAACATGGTTACAGCTGGTCCATCTTTTGCGCCTG
GTGCAGTTTAGGCTTTATTGTGGCAGCTGGAGGTCTCTGCATCGCTTATCCGTTTATTAGCCGGACCAAGATTG
CACAGCTAAAGTCTGGCAGAGACTCCACGGTATGACTGTCCTCACTGGGCCTGTCCAAGCACAAAGCGGTCTTT
TACATTCCAACCTGTTGCCTGCCAGCCCTTTCTGGATTACTGATAGAAAATCATGCAAAACCTCCCAACCTTTC
TAAGGACAAGACTACTGTGGATTCAAGTGCTTTAATGACTATTTATGCGTTGACTGTGAGAATAGGGAGCAGTG
CCATGGGACATTTCTAGGTGTAGAGAAAGAAGAAACTGCAATGGAAAAATTTGTATGATTTCCATTTATTTCAG
AAAGTTTGTATGTAACAATTACCCGAGAGTCATTTCTACTTGCAAAAGGATTCGTAACAAAGCGAGTATAATTT
TCTTGTCATTGTATCATGCTTGTTAAATTTTAATGCAGCATCTTCAGAACTTGTCCTGATGGTGTCTTATTGTG
TCAGCACCAAATATTTGTGCATTATTTGTGGACGTTCCTTGTCACAGGAAGATTCTTCTTCTGTTGCCTTATTG
TTTTTTTTTTTTTTTTAAGTCTCTTCTCTGTCTTTGTACTGGAATCGAAATCATAAGATAAACAGATCAAACGT
GCTTAAGAGCTAACTCGTGACACTATGCAGTATTGTTTGAAGACCTGTTGTTCAACCTCTGTCTCTTTATGTTA
ATGGATTTCTGCATTAAATGACTGCCCCCC

FIGURE 132

MEPRALVTALSLGLSLCSLGLLVTAIFTDHWYETDPRRHKESCERSRAGADPPDQKNRLM
PLSHLLGPLEEVLLPGHRPGHRHPHPERYCAAMHGHQVPLFSAHPLAKHSF

Important features of the protein:

Signal peptide:

1-17

N-myristoylation site.

CAAAGCGGCGGCTGTCCGCGGTGCCGGCTGGGGGCGGAGAGGCGGCGGTGGGCTCCCTGGG
GTGTGTGAGCCCGGTGATGGAGCCGGGCCCGACAGCCGCGCAGCGGAGGTGTTCGTTGCCG
CCGTGGCTGCCGCTGGGGCTGCTGCTGTGGTCGGGGCTGGCCCTGGGCGCGCTCCCCTTCG
GCAGCAGTCCGCACAGGGTCTTCCACGACCTCCTGTCGGAGCAGCAGTTGCTGGAGGTGGA
GGACTTGTCCCTGTCCCTCCTGCAGGGTGGAGGGCTGGGGCCTCTGTCGCTGCCCCCGGAC
CTGCCGGATCTGGATCCTGAGTGCCGGGAGCTCCTGCTGGACTTCGCCAACAGCAGCGCAG
AGCTGACAGGGTGTCTGGTGCGCAGCGCCCGGCCCGTGCGCCTCTGTCAGACCTGCTACCC
CCTCTTCCAACAGGTCGTCAGCAAGATGGACAACATCAGCCGAGCCGCGGGGAATACTTCA
GAGAGTCAGAGTTGTGCCAGAAGTCTCTTAATGGCAGATAGAATGCAAATAGTTGTGATTC
TCTCAGAATTTTTTAATACCACATGGCAGGAGGCAAATTGTGCAAATTGTTTAACAAACAA
CAGTGAAGAATTATCAAACAGCACAGTATATTTCCTTAATCTATTTAATCACACCCTGACC
TGCTTTGAACATAACCTTCAGGGGAATGCACATAGTCTTTTACAGACAAAAAATTATTCAG
AAGTATGCAAAAACTGCCGTGAAGCATACAAAACTCTGAGTAGTCTGTACAGTGAAATGCA
AAAAATGAATGAACTTGAGAATAAGGCTGAACCTGGAACACATTTATGCATTGATGTGGAA
GATGCAATGAACATCACTCGAAAACTATGGAGTCGAACTTTCAACTGTTCAGTCCCTTGCA
GTGACACAGTGCCTGTAATTGCTGTTTCTGTGTTCATTCTCTTTCTACCTGTTGTCTTCTA
CCTTAGTAGCTTTCTTCACTCAGAGCAAAAGAAACGCAAACTCATTCTGCCCAAACGTCTC
AAGTCCAGTACCAGTTTTGCAAATATTCAGGAAAATTCAAACTGAGACCTACAAAATGGAG
AATTGACATATCACGTGAATGAATGGTGGAAGACACAACTTGGTTTCAGAAAGAAGATAAA
CTGTGATTTGACAAGTCAAGCTCTTAAGAAATACAAGGACTTCAGATCCATTTTTAAATAA
GAATTTTCGATTTTTCTTTCCTTTTCCACTTCTTTCTAACAGATTTGGATATTTTTAATTT
CCAG

FIGURE 134

></usr/seqdb2/sst/DNA/Dnaseqs.min/ss.DNA168028
><subunit 1 of 1, 334 aa, 1 stop
><MW: 37257, pI: 5.95, NX(S/T): 10
MEPGPTAAQRRCSLPPWLPLGLLLWSGLALGALPFGSSPHRVFHDLLSEQQLLEVEDLSL
SLLQGGGLGPLSLPPDLPDLDPECRELLLDFANSSAELTGCLVRSARPVRLCQTCYPLFQ
QVVSKMDNISRAAGNTSESQSCARSLLMADRMQIVVILSEFFNTTWQEANCANCLTNNSE
ELSNSTVYFLNLFNHTLTCFEHNLQGNAHSLLQTKNYSEVCKNCREAYKTLSSLYSEMQK
MNELENKAEPGTHLCIDVEDAMNITRKLWSRTFNCSVPCSDTVPVIAVSVFILFLPVVFY
LSSFLHSEQKKRKLILPKRLKSSTSFANIQENSN

Important features of the protein:

Signal peptide:

Amino acids 1-31

Transmembrane domain:

Amino acids 278-300

N-glycosylation sites:

Amino acids 93-97;128-132;135-139;163-167;177-181;
184-188;194-198;216-220;263-267;274-278 cAMP- and cGMP-dependent protein kinase phosphorylation site:

Amino acids 10-14

N-myristoylation sites:

Amino acids 27-33;206-212;251-257

Leucine zipper pattern:

Amino acids 190-212

FIGURE 135

GCCAGGCCCTATCTCCCTGCCAGGAGGCCGGAGTGGGGGAGGTCAGACGGGGCGGTTGGAGGGGGAGGGATGCC
ACGCGCTTCTGCCTCAGGTGTTCCTGCGTTGTTTGTCAGTGGAGAGCAGGGAGTGGGGCCAGCCAGCAGAAACA
GTGGGCTGTACAACATCACCTTCAAATATGACAATTGTACCACCTACTTGAATCCAGTGGGGAAGCATGTGATT
GCTGACGCCCAGAATATCACCATCAGCCAGTATGCTTGCCATGACCAAGTGGCAGTCACCATTCTTTGGTCCCC
AGGGGCCCTCGGCATCGAATTCCTGAAAGGATTTCGGGTAATACTGGAGGAGCTGAAGTCGGAGGGAAGACAGT
GCCAACAACTGATTCTAAAGGATCCGAAGCAGCTCAACAGTAGCTTCAAAAGAACTGGAATGGAATCTCAACCT
TTCCTGAATATGAAATTTGAAACGGATTATTTCGTAAAGGTTGTCCCTTTTCCTTCCATTAAAAACGAAAGCAA
TTACCACCCTTTCTTCTTTAGAACCCGAGCCTGTGACCTGTTGTTACAGCCGGACAATCTAGCTTGTAAACCCT
TCTGGAAGCCTCGGAACCTGAACATCAGCCAGCATGGCTCGGACATGCAGGTGTCCTTCGACCACGCACCGCAT
GGCTCGGACATGCAGGTGTCCTTCGACCACGCACCGCACAACTTCGGCTTCCGTTTCTTCTATCTTCACTACAA
GCTCAAGCACGAAGGACCTTTCAAGCGAAAGACCTGTAAGCAGGAGCAAACTACAGAGATGACCAGCTGCCTCC
TTCAAAATGTTTCTCCAGGGGATTATATAATTGAGCTGGTGGATGACACTAACACAACAAGAAAAGTGATGCAT
TATGCCTTAAAGCCAGTGCACTCCCCGTGGGCCGGGCCCATCAGAGCCGTGGCCATCACAGTGCCACTGGTAGT
CATATCGGCATTCGCGACGCTCTTCACTGTGATGTGCCGCAAGAAGCAACAAGAAAATATATATTCACATTTAG
ATGAAGAGAGCTCTGAGTCTTCCACATACACTGCAGCACTCCCAAGAGAGAGGCTCCGGCCGCGGCCGAAGGTC
TTTCTCTGCTATTCCAGTAAAGATGGCCAGAATCACATGAATGTCGTCCAGTGTTTCGCCTACTTCCTCCAGGA
CTTCTGTGGCTGTGAGGTGGCTCTGGACCTGTGGGAAGACTTCAGCCTCTGTAGAGAAGGGCAGAGAGAATGGG
TCATCCAGAAGATCCACGAGTCCCAGTTCATCATTGTGGTTTGTTCCAAAGGTATGAAGTACTTTGTGGACAAG
AAGAACTACAAACACAAAGGAGGTGGCCGAGGCTCGGGGAAAGGAGAGCTCTTCCTGGTGGCGGTGTCAGCCAT
TGCCGAAAAGCTCCGCCAGGCCAAGCAGAGTTCGTCCGCGGCGCTCAGCAAGTTTATCGCCGTCTACTTTGATT
ATTCCTGCGAGGGAGACGTCCCCGGTATCCTAGACCTGAGTACCAAGTACAGACTCATGGACAATCTTCCTCAG
CTCTGTTCCCACCTGCACTCCCGAGACCACGGCCTCCAGGAGCCGGGGCAGCACACGCGACAGGGCAGCAGAAG
GAACTACTTCCGGAGCAAGTCAGGCCGGTCCCTATACGTCGCCATTTGCAACATGCACCAGTTTATTGACGAGG
AGCCCGACTGGTTCGAAAAGCAGTTCGTTCCCTTCCATCCTCCTCCACTGCGCTACCGGGAGCCAGTCTTGGAG
AAATTTGATTCGGGCTTGGTTTTAAATGATGTCATGTGCAAACCAGGGCCTGAGAGTGACTTCTGCCTAAAGGT
AGAGGCGGCTGTTCTTGGGGCAACCGGACCAGCCGACTCCCAGCACGAGAGTCAGCATGGGGGCCTGGACCAAG
ACGGGGAGGCCCGGCCTGCCCTTGACGGTAGCGCCGCCCTGCAACCCCTGCTGCACACGGTGAAAGCCGGCAGC
CCCTCGGACATGCCGCGGGACTCAGGCATCTATGACTCGTCTGTGCCCTCATCCGAGCTGTCTCTGCCACTGAT
GGAAGGACTCTCGACGGACCAGACAGAAACGTCTTCCCTGACGGAGAGCGTGTCCTCCTCTTCAGGCCTGGGTG
AGGAGGAACCTCCTGCCCTTCCTTCCAAGCTCCTCTCTTCTGGGTCATGCAAAGCAGATCTTGGTTGCCGCAGC
TACACTGATGAACTCCACGCGGTCGCCCCTTTGTAACAAAACGAAAGAGTCTAAGCATTGCCACTTTAAAAAAA
AAAAAAAAAAAAAAAAAAAAAAAA

FIGURE 136

MPRASASGVPALFVSGEQGVGPASRNSGLYNITFKYDNCTTYLNPVGKHVIADAQNITISQYACHDQVAVTILW
SPGALGIEFLKGFRVILEELKSEGRQCQQLILKDPKQLNSSFKRTGMESQPFLNMKFETDYFVKVVPFPSIKNE
SNYHPFFFRTRACDLLLQPDNLACKPFWKPRNLNISQHGSDMQVSFDHAPHGSDMQVSFDHAPHNFGFRFFYLH
YKLKHEGPFKRKTCKQEQTTEMTSCLLQNVSPGDYIIELVDDTNTTRKVMHYALKPVHSPWAGPIRAVAITVPL
VVISAFATLFTVMCRKKQQENIYSHLDEESSESSTYTAALPRERLRPRPKVFLCYSSKDGQNHMNVVQCFAYFL
QDFCGCEVALDLWEDFSLCREGQREWVIQKIHESQFIIVVCSKGMKYFVDKKNYKHKGGGRGSGKGELFLVAVS
AIAEKLRQAKQSSSAALSKFIAVYFDYSCEGDVPGILDLSTKYRLMDNLPQLCSHLHSRDHGLQEPGQHTRQGS
RRNYFRSKSGRSLYVAICNMHQFIDEEPDWFEKQFVPFHPPPLRYREPVLEKFDSGLVLNDVMCKPGPESDFCL
KVEAAVLGATGPADSQHESQHGGLDQDGEARPALDGSAALQPLLHTVKAGSPSDMPRDSGIYDSSVPSSELSLP
LMEGLSTDQTETSSLTESVSSSSGLGEEEPPALPSKLLSSGSCKADLGCRSYTDELHAVAPL

| | |
|---|---|
| Transmembrane domain: | Amino acids 283-307 |
| N-glycosylation sites: | Amino acids 31-34;38-41;56-59;<br>113-116;147-150;182-185;266-269 |
| Glycosaminoglycan attachment sites: | Amino acids 433-436;689-692 |
| cAMP- and cGMP-dependent protein kinase phosphorylation: | Amino acids 232-235 |
| Tyrosine kinase phosphorylation sites: | Amino acids 312-319;416-424 |
| N-myristoylation site: | Amino acids 19-24;375-380;428-433;<br>429-434;432-437;517-522;574-579;<br>652-657;707-712 |

FIGURE 137

CAACTGCACCTCGGTTCTATCGATAGCCACCAGCGCAACATGACAGTGAAGACCCTGCATGGCCCAGCCATGGT
CAAGTACTTGCTGCTGTCGATATTGGGGCTTGCCTTTCTGAGTGAGGCGGCAGCTCGGAAAATCCCCAAAGTAG
GACATACTTTTTTCCAAAAGCCTGAGAGTTGCCCGCCTGTGCCAGGAGGTAGTATGAAGCTTGACATTGGCATC
ATCAATGAAAACCAGCGCGTTTCCATGTCACGTAACATCGAGAGCCGCTCCACCTCCCCCTGGAATTACACTGT
CACTTGGGACCCCAACCGGTACCCCTCGGAAGTTGTACAGGCCCAGTGTAGGAACTTGGGCTGCATCAATGCTC
AAGGAAAGGAAGACATCTCCATGAATTCCGTTCCCATCCAGCAAGAGACCCTGGTCGTCCGGAGGAAGCACCAA
GGCTGCTCTGTTTCTTTCCAGTTGGAGAAGGTGCTGGTGACTGTTGGCTGCACCTGCGTCACCCCTGTCATCCA
CCATGTGCAGTAAGAGGTGCATATCCACTCAGCTGAAGAAG

FIGURE 138

MTVKTLHGPAMVKYLLLSILGLAFLSEAAARKIPKVGHTFFQKPESCPPVPGGSMKLDIGIINENQRVSMSRNI
ESRSTSPWNYTVTWDPNRYPSEVVQAQCRNLGCINAQGKEDISMNSVPIQQETLVVRRKHQGCSVSFQLEKVLV
TVGCTCVTPVIHHVQ

| | |
|---|---|
| Signal sequence: | Amino acids 1-30 |
| N-glycosylation site: | Amino acids 83-86 |
| N-myristoylation sites: | Amino acids 106-111;136-141 |

FIGURE 139

TTCTGCTATAGAGATGGAACAGTATATGGAAAGCTCCCAAGAAAGTGAAGAGAGGAAATT
GGAAAATTGTGAGTGGACCTTCTGATACTGCTCCTCCTTGCGTGGAAAAGGGGAAAGAAC
TGCATGCATATTATTCAGCGTCCTATATTCAAAGGATATTCTTGGTGATCTTGGAAGTGT
CCGTATCATGGAATCAATCTCTATGATGGGAAGCCCTAAGAGCCTTAGTGAAACTTGTTT
ACCTAATGGCATAAATGGTATCAAAGATGCAAGGAAGGTCACTGTAGGTGTGATTGGAAG
TGGAGATTTTGCCAAATCCTTGACCATTCGACTTATTAGATGCGGCTATCATGTGGTCAT
AGGAAGTAGAAATCCTAAGTTTGCTTCTGAATTTTTTCCTCATGTGGTAGATGTCACTCA
TCATGAAGATGCTCTCACAAAAACAAATATAATATTTGTTGCTATACACAGAGAACATTA
TACCTCCCTGTGGGACCTGAGACATCTGCTTGTGGGTAAAATCCTGATTGATGTGAGCAA
TAACATGAGGATAAACCAGTACCCAGAATCCAATGCTGAATATTTGGCTTCATTATTCCC
AGATTCTTTGATTGTCAAAGGATTTAATGTTGTCTCAGCTTGGGCACTTCAGTTAGGACC
TAAGGATGCCAGCCGGCAGGTTTATATATGCAGCAACAATATTCAAGCGCGACAACAGGT
TATTGAACTTGCCCGCCAGTTGAATTTCATTCCCATTGACTTGGGATCCTTATCATCAGC
CAGAGAGATTGAAAATTTACCCCTACGACTCTTTACTCTCTGGAGAGGGCCAGTGGTGGT
AGCTATAAGCTTGGCCACATTTTTTTCCTTTATTCCTTTGTCAGAGATGTGATTCATCC
ATATGCTAGAAACCAACAGAGTGACTTTTACAAAATTCCTATAGAGATTGTGAATAAAAC
CTTACCTATAGTTGCCATTACTTTGCTCTCCCTAGTATACCTTGCAGGTCTTCTGGCAGC
TGCTTATCAACTTTATTACGGCACCAAGTATAGGAGATTTCCACCTTGGTTGGAAACCTG
GTTACAGTGTAGAAAACAGCTTGGATTACTAAGTTTTTTCTTCGCTATGGTCCATGTTGC
CTACAGCCTCTGCTTACCGATGAGAAGGTCAGAGAGATATTTGTTTCTCAACATGGCTTA
TCAGCAGGTTCATGCAAATATTGAAAACTCTTGGAATGAGGAAGAAGTTTGGAGAATTGA
AATGTATATCTCCTTTGGCATAATGAGCCTTGGCTTACTTTCCCTCCTGGCAGTCACTTC
TATCCCTTCAGTGAGCAATGCTTTAAACTGGAGAGAATTCAGTTTTATTCAGTCTACACT
TGGATATGTCGCTCTGCTCATAAGTACTTTCCATGTTTTAATTTATGGATGGAAACGAGC
TTTTGAGGAAGAGTACTACAGATTTTATACACCACCAAACTTTGTTCTTGCTCTTGTTTT
GCCCTCAATTGTAATTCTGGATCTTTTGCAGCTTTGCAGATACCCAGACTGAGCTGGAAC
TGGAATTTGTCTTCCTATTGACTCTACTTCTTTAAAAGCGGCTGCCCATTACATTCCTCA
GCTGTCCTTGCAGTTAGGTGTACATGTGACTGAGTGTTGGCCAGTGAGATGAAGTCTCCT
CAAAGGAAGGCAGCATGTGTCCTTTTTCATCCCTTCATCTTGCTGCTGGGATTGTGGATA
TAACAGGAGCCCTGGCAGCTGTCTCCAGAGGATCAAAGCCACACCCAAAGAGTAAGGCAG
ATTAGAGACCAGAAAGACCTTGACTACTTCCCTACTTCCACTGCTTTTTCCTGCATTTAA
GCCATTGTAAATCTGGGTGTGTTACATGAAGTGAAAATTAATTCTTTCTGCCCTTCAGTT
CTTTATCCTGATACCATTTAACACTGTCTGAATTAACTAGACTGCAATAATTCTTTCTTT
TGAAAGCTTTTAAAGGATAATGTGCAATTCACATTAAAATTGATTTTCCATTGTCAATTA
GTTATACTCATTTTCCTGCCTTGATCTTTCATTAGATATTTTGTATCTGCTTGGAATATA
TTATCTTCTTTTTAACTGTGTAATTGGTAATTACTAAAACTCTGTAATCTCCAAAATATT
GCTATCAAATTACACACCATGTTTTCTATCATTCTCATAGATCTGCCTTATAAACATTTA
AATAAAAAGTACTATTTAATGATTTAACTTCTGTTTTGAAAAAAAAAAAAAAAAAAAAAA
AAA

FIGURE 140

MESISMMGSPKSLSETCLPNGINGIKDARKVTVGVIGSGDFAKSLTIRLIRCGYHVVIGS
RNPKFASEFFPHVVDVTHHEDALTKTNIIFVAIHREHYTSLWDLRHLLVGKILIDVSNNM
RINQYPESNAEYLASLFPDSLIVKGFNVVSAWALQLGPKDASRQVYICSNNIQARQQVIE
LARQLNFIPIDLGSLSSAREIENLPLRLFTLWRGPVVVAISLATFFFLYSFVRDVIHPYA
RNQQSDFYKIPIEIVNKTLPIVAITLLSLVYLAGLLAAAYQLYYGTKYRRFPPWLETWLQ
CRKQLGLLSFFFAMVHVAYSLCLPMRRSERYLFLNMAYQQVHANIENSWNEEEVWRIEMY
ISFGIMSLGLLSLLAVTSIPSVSNALNWREFSFIQSTLGYVALLISTFHVLIYGWKRAFE
EEYYRFYTPPNFVLALVLPSIVILDLLQLCRYPD

Transmembrane domain:
210-230
256-278
360-382
391-412
430-450

N-glycosylation site.
256-259 cAMP- and cGMP-dependent protein kinase phosphorylation site.
29-32

Tyrosine kinase phosphorylation site.
416-424

N-myristoylation site.
8-13
24-29
34-39
193-198
274-279

FIGURE 141

CAGAGCCCTGCGGGAGGACTCAGAGTCAGGGACACAGCAGCGTCCGGCGAGATGAAGGCG
CTTGGGGCTGTCCTGCTTGCCCTCTTGCTGTGCGGGCGGCCAGGGAGAGGGCAGACACAG
CAGGAGGAAGAGGAAGAGGACGAGGACCACGGGCCAGATGACTACGACGAGGAAGATGAG
GATGAGGTGGAAGAGGAGGAGACCAACAGGCTCCCTGGTGGCAGGAGCAGAGTGCTGCTG
CGGTGCTACACCTGCAAGTCCCTGCCCAGGGACGAGCGCTGCAACCTGACGCAGAACTGC
TCACATGGCCAGACCTGCACAACCCTCATTGCCCACGGGAACACCGAGTCAGGCCTCCTG
ACCACCCACTCCACGTGGTGCACAGACAGCTGCCAGCCCATCACCAAGACGGTGGAGGGG
ACCCAGGTGACCATGACCTGCTGCCAGTCCAGCCTGTGCAATGTCCCACCCTGGCAAAGC
TCCCGAGTCCAGGACCCAACAGGCAAGGGGGCAGGCGGCCCCCGGGGCAGCTCCGAAACT
GTGGGCGCAGCCCTCCTGCTCAACCTCCTTGCCGGCCTTGGAGCAATGGGGGCCAGGAGA
CCCTGACCCACGGCCCCTCCCCACCCCCACCCGGCTCACCCCCGGCCCTGCCAGCACTCT
GTCTGGTACCTTCCCCTCCTGCCCCTGCACCAGCTTTGGAGAATGGATTTGGAGTGTCTT
GGGCGATCCAGCCAGCGCAGGCCCCCCGGCCCGGTTGCTTCCTCAGTTCCCGGCTGTGTC
CTTGGTGTCCTTTCTCCACCACCTGTGAGCAGCAAGACTGCCGCACGTGGGCGCTGGGTC
CAGACCTCGGCTGCCACGTCCCAGGACCTGCAGCCCTCACGGGGGCTGGGGATCCCCATC
AGCACAGCCAGGCAGAGATGATACCCACCACACACCTGGGGGCCCCCACACCCAGTCCTC
ACCCTTAACTTCTGCCATGGGAATTTCTCCATCTGCAGCAGTCACACGGGCCCACCCTGC
CCTTCCCCAGGTCGGCCTCTCCGCTGTCTGGAGGGAAGGGGATTTGGAGGGAGGCTGTCG
TCGCCCCCAGGAAAGACGGGCCTGGGGGAGGCGGGACAGTGGGAGAGGCGCGCTGAGGAT
GAGAGGGCACAGGGAGGTGGGTTGGGGTGAGGCCACATGCGGAGGGGCGGGGCGGGGCGG
GGCTGGGGGGACAGGCACCAAGTATGAAGAGGATGGGGCCAGCGGGGCCTGTCTGGCTGT
GGCGTGAGCACCGCTATGGGAGACCCTGCTTGGAAAGTGAACTTGCAGCCTTGGATGGGG
AAGGGCCAGATGCTGGGTGGGTGCCTGTCACCTTGAGGTGACCATCTAGGGTCAGTACCT
GCTGGGCTTAGGACAGCGCCTGAGGCTGGGAATACCTGTCTCTGCTCTAGCAGAGGCTAA
AGCAGGCTAGAGCAGTGGAGGGGTGGAGTTGATGAAAGGAGAGGAGTAGATGAGATGGAA
TTTTTCCAGCCTCATCCTGGCCTGCCCTCTAGACTCCAGTCCCCAAGCCCTCAGCCTAGT
GGGTGTCATGGATGGATCTGGGGGTGTCAGACAGGCTACCCTGTGCCAGGGAGGGGGCAG
AATGGGCCTGCAGCTTCCTGCAGAGGAAGCAGGACTGGGTAGCAGAGCCGGGAAGGTGGG
TGGCCCATTACAGGGGGGTCCCCAGGGTGTCCTCTGGCAGGGCTGTGACTGCTGCAAGCT
CTGCCTTCACCAGTAGCTGGTGCCAGGACAGAGCTCTGGGACAGCAGGCAGAGGCCGAGC
CTGGGCCACAGCTCAGCCACTGACTTGGGTATCAGTTTCCCCTTCTGAGAAGTACAGAGT
GAGACTTAAAGAACCCCTAGATCCCCACCAGTTCAACACTCCATTAACTGGGAAGCCCAG
AGTCCTGTCCGGCCTGCCAAGTTCATCCTGGTGGACAGCGGGAGGCCTCCGCTAACTGTT
CTCTTCTTTTCCTTATTAATAAAACACACAATGCCTAGCTGGGGGGTCGGAAGGCAAATG
CCCTAGATGGTGGGGTCACGTCTTTCTCCTTCTCCTTCCTCCTTCTGCTGGCTGAAGTGA
TGACTGGAGCTCAGCAACCACTTTGCACCATGAGGCAGCACTGAGCACGGTAGGGCAGCC
TGGTGAGAGGGGCCTAGCTCGCTGCCGACAGAAGTCACTGCCTACCTCAGGGTCCCCTTA
CCTGGGTGGGAAATAAATTTCTGCTGTGTTGAAGCTAAAAAAAAAAAAAAAAAAAAAAAA
AAAAAAAAAAAAAAAAAAAA

FIGURE 142

><Tue Apr 10 13:20:25 2001 DNA171732 [min]
></usr/seqdb2/sst/DNA/Dnaseqs.min/ss.DNA171732
><subunit 1 of 1, 184 aa, 1 stop
><MW: 19806, pI: 4.74, NX(S/T): 2
MKALGAVLLALLLCGRPGRGQTQQEEEEEDEDHGPDDYDEEDEDEVEEEETNRLPGGRSR
VLLRCYTCKSLPRDERCNLTQNCSHGQTCTTLIAHGNTESGLLTTHSTWCTDSCQPITKT
VEGTQVTMTCCQSSLCNVPPWQSSRVQDPTGKGAGGPRGSSETVGAALLLNLLAGLGAMG
ARRP Important features of the protein:

Signal peptide:
1-20
Transmembrane domain:
160-180

N-glycosylation site.
78-81
82-85

N-myristoylation site.
86-91
96-101
101-106
123-128
155-160
159-164
177-182

Ly-6 / u-PAR domain proteins
7-26
61-80
124-137

GENE DISRUPTIONS, COMPOSITIONS AND METHODS RELATING THERETO

RELATED APPLICATIONS

This application is a US national stage continuation application claiming priority under 35 USC §371 of international application PCT/US2006/019651, filed May 18, 2006, which claims priority under 35 USC §119 to U.S. Provisional Applications: 60/780,262 filed Mar. 7, 2006 and 60/687,900 filed Jun. 6, 2005.

FIELD OF THE INVENTION

The present invention relates to compositions, including transgenic and knockout animals and methods of using such compositions for the diagnosis and treatment of diseases or disorders.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., *Lab. Invest.,* 74:953-965 (1996)] and cyclooxygenase-1 (COX1) genes [Langenbach, R. et al., *Cell* 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., *Cell,* 83:59-67 (1996)], in which a consequence of the mutation is deficient red blood cell production, and the GABA(A)-R-ββ3 knockout [DeLorey, T. M., J. *Neurosci.,* 18:8505-8514 (1998)], in which the mutant mice show hyperactivity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-Elheiga, L. et al., *Science,* 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels; immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide cDNA as disclosed herein, the coding sequence of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide lacking the signal peptide as disclosed herein, the coding sequence of an extracellular domain of a transmembrane PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human 2 protein cDNAs deposited with the ATCC as disclosed herein, or (b) the complement of the DNA molecule of (a).

Another aspect of the invention provides an isolated nucleic acid molecule comprising a nucleotide sequence encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides are contemplated.

The invention also provides fragments of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide coding sequence, or the complement thereof, that may find use as, for example, hybridization probes, for encoding fragments of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide that may optionally encode a polypeptide comprising a binding site for an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term "about" means the referenced nucleotide sequence length plus or minus 10% of that referenced length. It is noted that novel fragments of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding nucleotide sequence may be determined in a routine manner by aligning the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding nucleotide sequence with other known nucleotide sequences using any of a number of well known sequence alignment programs and determining which PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding nucleotide sequence fragment(s) are novel. All of such PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding nucleotide sequences are contemplated herein. Also contemplated are the PRO69122, PRO204, PRO214, PRO222, PRO234, PRO265, PRO309, PRO332, PRO342, PRO356, PRO540, PRO618, PRO944, PRO994, PRO1079, PRO110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fragments encoded by these nucleotide molecule fragments, preferably those PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fragments that comprise a binding site for an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention provides isolated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides encoded by any of the isolated nucleic acid sequences hereinabove identified.

In a certain aspect, the invention concerns an isolated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polypeptides will have or have no more than one conservative amino acid substitution as compared to the native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence, alternatively will have or will have no more than 2, 3, 4, 5, 6, 7, 8, 9, or 10 conservative amino acid substitution as compared to the native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence.

In a specific aspect, the invention provides an isolated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and recovering the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide from the cell culture.

Another aspect the invention provides an isolated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and recovering the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide from the cell culture.

The invention provides agonists and antagonists of a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as defined herein. In particular, the agonist or antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody or a small molecule.

The invention provides a method of identifying agonists or antagonists to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which comprise contacting the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with a candidate molecule and monitoring a biological activity mediated by said PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Preferably, the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

The invention provides a composition of matter comprising a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, or an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as herein described, or an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, in combination with a carrier. Optionally, the carrier is a pharmaceutically acceptable carrier.

The invention provides the use of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, or an agonist or antagonist thereof as hereinbefore described, or anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, for the preparation of a medicament useful in the treatment of a condition which is responsive to the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In another aspect, the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopeniadue to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

The invention also provides an isolated cell derived from a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality. The invention also provides a method of identifying an agent that modulates a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for the PRO69122, PRO204, PRO214, PRO222, PRO234, PRO265, PRO309, PRO332, PRO342, PRO356, PRO540, PRO618, PRO944, PRO994, PRO1079, PRO111, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; anoncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

The invention also provides an agent which modulates the phenotype associated with gene disruption. In one aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of identifying an agent that modulates a physiological characteristic associated with a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

The invention also provides an agent that modulates a physiological characteristic which is associated with gene disruption. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of identifying an agent which modulates a behavior associated with a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti- PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43−− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti- PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) contacting a test agent with a host cell expressing a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide; and (b) determining whether the test agent modulates the expression of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by the host cell.

The invention also provides an agent that modulates the expression of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO2110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250, polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti- PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of evaluating a therapeutic agent capable of affecting a condition associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a therapeutic agent which is capable of affecting a condition associated with gene disruption. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Komzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal cell culture, each cell of said culture comprising a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; anoncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agent is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In yet another aspect, the agonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody. In still another aspect, the antagonist agent is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

The invention also provides a method of modulating a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a host cell expressing said PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a non-human transgenic animal cell culture, each cell of said culture comprising a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, an effective amount of an agent identified as treating or preventing or ameliorating said disorder, or agonists or antagonists thereof, thereby effectively treating or preventing or ameliorating said disorder.

B. Further Embodiments

In yet further embodiments, the invention is directed to the following set of potential claims for this application:

1. A method of identifying a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of Claim 1, wherein the non-human transgenic animal is heterozygous for the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

3. The method of Claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; anoncological disorder; a bone metabolic abnormality or disorder; a lipid metabolic disorder; or a developmental abnormality.

4. The method of Claim 3, wherein the neurological disorder is an increased anxiety-like response during open field activity testing.

5. The method of Claim 3, wherein the neurological disorder is a decreased anxiety-like response during open field activity testing.

6. The method of Claim 3, wherein the neurological disorder is an abnormal circadian rhythm during home-cage activity testing.

7. The method of Claim 3, wherein the neurological disorder is an enhanced motor coordination during inverted screen testing.

8. The method of Claim 3, wherein the neurological disorder is an impaired motor coordination during inverted screen testing.

9. The method of Claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of Claim 3, wherein the eye abnormality is a retinal abnormality.

11. The method of Claim 3, wherein the eye abnormality is consistent with vision problems or blindness.

12. The method of Claim 10, wherein the retinal abnormality is consistent with retinitis pigmentosa.

13. The method of Claim 10, wherein the retinal abnormality is characterized by retinal degeneration or retinal dysplasia.

14. The method of Claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of Claim 3, wherein the eye abnormality is a cataract.

16. The method of Claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

17. The method of Claim 3, wherein the developmental abnormality comprises embryonic lethality or reduced viability.

18. The method of Claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of Claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

20. The method of Claim 3, wherein the bone metabolic abnormality or disorder is arthritis, osteoporosis or osteopetrosis.

21. The method of Claim 1, wherein the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43−IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

22. An isolated cell derived from a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

23. The isolated cell of Claim 22 which is a murine cell.

24. The isolated cell of Claim 23, wherein the murine cell is an embryonic stem cell.

25. The isolated cell of Claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

27. The method of Claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of Claim 27, wherein the neurological disorder is an increased anxiety-like response during open field activity testing.

29. The method of Claim 27, wherein the neurological disorder is a decreased anxiety-like response during open field activity testing.

30. The method of Claim 27, wherein the neurological disorder is an abnormal circadian rhythm during home-cage activity testing.

31. The method of Claim 27, wherein the neurological disorder is an enhanced motor coordination during inverted screen testing.

32. The method of Claim 27, wherein the neurological disorder is an impaired motor coordination during inverted screen testing.

33. The method of Claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of Claim 27, wherein the eye abnormality is a retinal abnormality.

35. The method of Claim 27, wherein the eye abnormality is consistent with vision problems or blindness.

36. The method of Claim 34, wherein the retinal abnormality is consistent with retinitis pigmentosa.

37. The method of Claim 34, wherein the retinal abnormality is characterized by retinal degeneration or retinal dysplasia.

38. The method of Claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of Claim 27, wherein the eye abnormality is a cataract.

40. The method of Claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

41. The method of Claim 27, wherein the developmental abnormality comprises embryonic lethality or reduced viability.

42. The method of Claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of Claim 27, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of Claim 27, wherein said bone metabolic abnormality or disorder is arthritis, osteoporosis or osteopetrosis.

45. The method of Claim 26, wherein the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

46. An agent identified by the method of Claim 26.

47. The agent of Claim 46 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

48. The agent of Claim 47, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

49. The agent of Claim 47, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

50. A method of identifying an agent that modulates a physiological characteristic associated with a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of Claim 50, wherein the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

52. An agent identified by the method of Claim 50.

53. The agent of Claim 52 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

54. The agent of Claim 53, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

55. The agent of Claim 53, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

56. A method of identifying an agent which modulates a behavior associated with a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of Claim 56, wherein the behavior is an increased anxiety-like response during open field activity testing.

58. The method of Claim 56, wherein the behavior is a decreased anxiety-like response during open field activity testing.

59. The method of Claim 56, wherein the behavior is an abnormal circadian rhythm during home-cage activity testing.

60. The method of Claim 56, wherein the behavior is an enhanced motor coordination during inverted screen testing.

61. The method of Claim 56, wherein the behavior is an impaired motor coordination during inverted screen testing.

62. The method of Claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of Claim 56.

64. The agent of Claim 63 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

65. The agent of Claim 64, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

66. The agent of Claim 64, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of Claim 67, wherein the neurological disorder is an increased anxiety-like response during open field activity testing.

69. The method of Claim 67, wherein the neurological disorder is a decreased anxiety-like response during open field activity testing.

70. The method of Claim 67, wherein the neurological disorder is an abnormal circadian rhythm during home-cage activity testing.

71. The method of Claim 67, wherein the neurological disorder is an enhanced motor coordination during inverted screen testing.

72. The method of Claim 67, wherein the neurological disorder is an impaired motor coordination during inverted screen testing.

73. The method of Claim 73, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of Claim 67, wherein the eye abnormality is a retinal abnormality.

75. The method of Claim 67, wherein the eye abnormality is consistent with vision problems or blindness.

76. The method of Claim 74, wherein the retinal abnormality is consistent with retinitis pigmentosa.

77. The method of Claim 74, wherein the retinal abnormality is characterized by retinal degeneration or retinal dysplasia.

78. The method of Claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinaucho-roidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of Claim 67, wherein the eye abnormality is a cataract.

80. The method of Claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

81. The method of Claim 67, wherein the developmental abnormality comprises embryonic lethality or reduced viability.

82. The method of Claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of Claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; ortransplantation associated diseases including graft rejection and graft-versus-host disease.

84. The method of Claim 67, wherein said bone metabolic abnormality or disorder is arthritis, osteoporosis or osteopetrosis.

85. The method of Claim 67, wherein the non-human transgenic animal exhibits at least one of the following physiological characteristics compared with gender matched wild-type littermates: increased anxiety-like response during open field testing; decreased anxiety during open field testing; hypoactivity with no circadian rhythm; increased total distance traveled during open field testing (hyperactivity); decreased locomotor activity during open field testing; abnormal circadian rhythm during home-cage activity testing (low activity during the light phase); abnormal circadian rhythm during home-cage activity testing including decreased ambulatory counts; abnormal circadian rhythm during home-cage activity testing including increased ambulatory counts; whiskers absent due to anxiety phenotype; enhanced circadian rhythm; increased stress induced hyperthermia with increased stress response (increased anxiety); increased resistance to stress induced hyperthermia; decreased resistance to stress induced hyperthermia; enhanced motor coordination during inverted screen testing; impaired motor coordination during inverted screen testing; increased immobility in tail suspension (increased depressive-like response); increased depressive-like response during tail suspension testing; decreased depressive-like response during tail suspension testing; clutched hind limbs during tail suspension testing; decreased startle response during prepulse inhibition testing; no startle response indicating deafness; increased prepulse inhibition with enhanced sensorimotor gating/attention; increased latency on hotplate indicative of decreased sensitivity to heat-induced pain; opthamological abnormalities; corneal epidermidalization of the corneal stroma with scarring and blocked vision; metaplasia of the cornea and sclera; attenuated retinal arteries; retinal hemorrhage; optic nerve abnormalities; dilated optic disc; increased intraocular pressure; corneal epithelialization with underdeveloped eyelids; retinal degeneration; agenesis of the Harderian gland; retinal vessel disorganization, microaneurysms and retinal capillary leakage; impaired vision; decreased heart rate; decreased mean systolic blood pressure; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; enhanced glucose tolerance; impaired glucose tolerance; decreased mean serum insulin levels; ketonemia; decreased mean serum calcium; blood urobilinogen, nitrites, protein and ketones; decreased sodium and chloride; increased bilirubin; notable lipemia; increased uric acid and potassium levels; increased mean serum alkaline phosphatase levels; decreased mean serum alkaline phosphatase levels; blood in the urine; glucosuria; increased nitrituria; ketonuria; increased mean percentage of natural killer cells; decreased mean percentage of natural killer cells; abnormal leukocyte count; leukopenia due to lymphopenia and granulocytopenia; increased mean percentage of CD4 cells; decreased mean percentage of CD4 cells; decreased mean percentage of CD8 cells; reduced percentage of naive CD4 and CD8 T cells in lymph nodes; increased mean percentage of B cells in peripheral blood; decrease total white blood cells and lymphocyte counts; decreased absolute lymphocyte counts; increased mean absolute monocyte count; increased mean absolute neutrophil count; decreased in mean serum IgA levels; increase in mean serum IgA levels; increase in IgG1 levels; decreased mean serum IgG1 levels; decreased mean serum IgG1, IgG3, IgG2b and IgG2a levels; decreased mean serum IgG2a levels; decreased mean serum IgG2b levels; decreased mean serum IgG3 and IgM levels; increase in mean serum IgG2a levels; increase in mean serum IgG1, IgG2a and IgG3 levels; increase in mean serum IgG3 levels; anemia; decreased red blood cell count, decreased hemoglobin and decreased hematocrit with increased mean red blood cell count; increased mean corpuscular volume; decreased mean corpuscular volume; decreased mean corpuscular hemoglobin; increased red blood cell distribution width; defect in erythropoiesis; increased IgM+ IgD+ and B220hi/CD43− cells in bone marrow; decreased percentage of B220hi/CD43− IgM+ IgD+ cells in bone marrow; increased percentage of TCRB+ cells in Peyer's patches; reduction in naive T cells (especially CD4) in lymph nodes; increased percentage of CD11b+CD11c− cells (monocytes) in spleen; increased percentage of IgM+, CD117+ cells in bone marrow, higher percentage of dead B cells, decreased B cells, increased CD4 and CD8 T cells in lymph; B cells increased in bone marrow and significantly decreased in lymph node; notably decreased CD21hiCD23med B cells in spleen; decrease in Peyer's patch B220+ cells; decreased mean percentages of CD8 and natural killer cells with increased mean percentage of B cells; reduced number of TCRB+ CD38+ activated T cells in Peyer's patches; decreased mean percentage of CD4 cells with increased mean percentage of B cells; decreased B220+ CD38low and IgM in Payer's patches; increased mean platelet count; decreased mean platelet count; widespread apoptosis and loss of T lymphocytes in the thymic cortex and depletion of T cells in spleen; increased mean serum IgG2a response to an ovalbumin challenge; decreased to no serum IgG1 and IgG2a response to ovalbumin challenge; increased mean serum IgG1 response to an ovalbumin challenge; decreased mean serum TNF-alpha, MCP-1 and IL-6 responses to LPS challenge; increased mean serum MCP-1 response to a LPS challenge; increased mean serum TNF-alpha response to a LPS challenge; increased mean serum IL-6 response to a LPS challenge; increased skin fibroblast proliferation; decreased skin fibroblast proliferation; increased mean percent of total body fat and total fat mass; increased mean body weight; increased mean body length; increased total tissue mass (TTM); increased lean body mass (LBM); increased femoral bone mineral density (BMD); increased vertebral bone mineral density (BMD); increased bone mineral density (BMD); increased total body volumetric bone mineral density (vBMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD); decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; marked osteopetrosis with increased bone mineralization; chronic inflammation in various tissues; thymic atrophy; systemic histiocytic storage disease affecting macrophages in liver, spleen and mesenteric lymph nodes; reduced liver size; chronic active hepatitis with focal hepatocyte necrosis; fatty changes in the liver; increased intracytoplasmic vacuolization of glycogen in hepatocytes; pancreatic dyserythropoietic anemia (type 1); multifocal neuronal necrosis; diffuse abiotrophy of the cerebellum granule cell layer; multifocal developmental malformation of the brain; hydronephosis; diffuse alopecia; epidermal hyperkeratosis; hypochromasia and anisocytosis characterized by abnormal erythrocytes (abnormally low hemoglobin and decreased erythropoiesis); growth retardation; development abnormalities; granulocytic hypoplasia of bone marrow; decreased numbers of myeloid granulocytic cell precursors; decreased granulocytopoiesis; no teeth; stunted growth with general reduction in all organ size; myocardial defects with defective structure and arrangement of the cardiac myocytes; cardiomyopathy with condensed eosinophilic sarcoplasm; congestive heart failure; pancreatic islets of Langerhans smaller and distribution of alpha (glycogen) and beta (insulin) cells altered; notable histopathologic alteration in cytoplasm of all cells in the zona fasciculata of the adrenal gland consistent with altered lipid/cholesterol uptake or metabolism (elevated cholesterol and triglycerides); infertility; testicular degeneration; vacuolar degeneration of seminiferous tubules; hypospermia; atrophic testes; ovarian and uterine hypoplasia; mammary gland was represented with just a few ducts; growth retardation with reduced viability; and embryonic lethality.

86. An agent identified by the method of Claim 67.

87. The agent of Claim 86 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

88. The agent of Claim 87, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

89. The agent of Claim 87, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

90. A therapeutic agent identified by the method of Claim 67.

91. A method of identifying an agent that modulates the expression of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) contacting a test agent with a host cell expressing a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide; and (b) determining whether the test agent modulates the expression of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by the host cell.

92. An agent identified by the method of Claim 91.

93. The agent of Claim 92 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

94. The agent of Claim 93, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

95. The agent of Claim 93, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

96. A method of evaluating a therapeutic agent capable of affecting a condition associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal whose genome comprises a disruption of the gene which encodes for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of Claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of Claim 96.

99. The therapeutic agent of Claim 98 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

100. The therapeutic agent of Claim 99, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

101. The therapeutic agent of Claim 99, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody.

102. A pharmaceutical composition comprising the therapeutic agent of Claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject in need of such treatment whom may already have the disorder, or may be prone to have the disorder or may be in whom the disorder is to be prevented, a therapeutically effective amount of the therapeutic agent of Claim 94, or agonists or antagonists thereof, thereby effectively treating or preventing or ameliorating said disorder.

104. The method of Claim 103, wherein the neurological disorder is an increased anxiety-like response during open field activity testing.

105. The method of Claim 103, wherein the neurological disorder is a decreased anxiety-like response during open field activity testing.

106. The method of Claim 103, wherein the neurological disorder is an abnormal circadian rhythm during home-cage activity testing.

107. The method of Claim 103, wherein the neurological disorder is an enhanced motor coordination during inverted screen testing.

108. The method of Claim 103, wherein the neurological disorder is an impaired motor coordination during inverted screen testing.

109. The method of Claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of Claim 103, wherein the eye abnormality is a retinal abnormality.

111. The method of Claim 103, wherein the eye abnormality is consistent with vision problems or blindness.

112. The method of Claim 110, wherein the retinal abnormality is consistent with retinitis pigmentosa.

113. The method of Claim 110, wherein the retinal abnormality is characterized by retinal degeneration or retinal dysplasia.

114. The method of Claim 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of Claim 103, wherein the eye abnormality is a cataract.

116. The method of Claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

117. The method of Claim 103, wherein the developmental abnormality comprises embryonic lethality or reduced viability.

118. The method of Claim 103, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of Claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; ortransplantation associated diseases including graft rejection and graft-versus-host disease.

120. The method of Claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising:

(a) providing a non-human transgenic animal cell culture, each cell of said culture comprising a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of Claim 121, wherein the neurological disorder is an increased anxiety-like response during open field activity testing.

123. The method of Claim 121, wherein the neurological disorder is a decreased anxiety-like response during open field activity testing.

124. The method of Claim 121, wherein the neurological disorder is an abnormal circadian rhythm during home-cage activity testing.

125. The method of Claim 121, wherein the neurological disorder is an enhanced motor coordination during inverted screen testing.

126. The method of Claim 121, wherein the neurological disorder is an impaired motor coordination during inverted screen testing.

127. The method of Claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of Claim 121, wherein the eye abnormality is a retinal abnormality.

129. The method of Claim 121, wherein the eye abnormality is consistent with vision problems or blindness.

130. The method of Claim 128, wherein the retinal abnormality is consistent with retinitis pigmentosa.

131. The method of Claim 128, wherein the retinal abnormality is characterized by retinal degeneration or retinal dysplasia.

132. The method of Claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinauchoroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of Claim 121, wherein the eye abnormality is a cataract.

134. The method of Claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

135. The method of Claim 121, wherein the developmental abnormality comprises embryonic lethality or reduced viability.

136. The method of Claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of Claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; ortransplantation associated diseases including graft rejection and graft-versus-host disease.

138. The method of Claim 121, wherein said bone metabolic abnormality or disorder is arthritis, osteoporosis or osteopetrosis.

139. An agent identified by the method of Claim 121.

140. The agent of Claim 139 which is an agonist or antagonist of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

141. The agent of Claim 140, wherein the agonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

142. The agent of Claim 140, wherein the antagonist is an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO 19646, anti-PRO21718, anti-PRO 19820, anti-PRO21201, anti-PRO20026, anti-PRO20110, anti-PRO23203 or anti-PRO35250 antibody.

143. A therapeutic agent identified by the method of Claim 121.

144. A method of modulating a phenotype associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already have the phenotype, or may be prone to have the phenotype or may be in whom the phenotype is to be prevented, an effective amount of the agent of Claim 46, or agonists or antagonists thereof, thereby effectively modulating the phenotype.

145. A method of modulating a physiological characteristic associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already exhibit the physiological characteristic, or may be prone to exhibit the physiological characteristic or may be in whom the physiological characteristic is to be prevented, an effective amount of the agent of Claim 52, or agonists or antagonists thereof, thereby effectively modulating the physiological characteristic.

146. A method of modulating a behavior associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may already exhibit the behavior, or may be prone to exhibit the behavior or may be in whom the exhibited behavior is to be prevented, an effective amount of the agent of Claim 63, or agonists or antagonists thereof, thereby effectively modulating the behavior.

147. A method of modulating the expression of a PRO69122, PRO204, PRO214, PRO222, PRO234, PRO265, PRO285, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a host cell expressing said PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, an effective amount of the agent of Claim 92, or agonists or antagonists thereof, thereby effectively modulating the expression of said polypeptide.

148. A method of modulating a condition associated with a disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a subject whom may have the condition, or may be prone to have the condition or may be in whom the condition is to be prevented, a therapeutically effective amount of the therapeutic agent of Claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the method comprising administering to a non-human transgenic animal cell culture, each cell of said culture comprising a disruption of the gene which encodes for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, a therapeutically effective amount of the agent of Claim 139, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO69122 cDNA, wherein SEQ ID NO:1 is a clone designated herein as "DNA284870" (UNQ128).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO204 cDNA, wherein SEQ ID NO:3 is a clone designated herein as "DNA30871-1157" (UNQ178).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO214 cDNA, wherein SEQ ID NO:5 is a clone designated herein as "DNA32286-1191" (UNQ188).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO222 cDNA, wherein SEQ ID NO:7 is a clone designated herein as "DNA33107-1135" (UNQ196).

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO234 cDNA, wherein SEQ ID NO:9 is a clone designated herein as "DNA35557-1137" (UNQ208).

FIG. 10 shows the amino acid sequence (SEQ ID NO: 10) derived from the coding sequence of SEQ ID NO:9 shown in FIG. 9.

FIG. 11 shows a nucleotide sequence (SEQ ID NO:11) of a native sequence PRO265 cDNA, wherein SEQ ID NO:11 is a clone designated herein as "DNA36350-1158" (UNQ232).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO309 cDNA, wherein SEQ ID NO:13 is a clone designated herein as "DNA61601-1223" (UNQ272).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO332 cDNA, wherein SEQ ID NO:15 is a clone designated herein as "DNA40982-1235" (UNQ293).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO342 cDNA, wherein SEQ ID NO:17 is a clone designated herein as "DNA38649" (UNQ301).

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO356 cDNA, wherein SEQ ID NO:19 is a clone designated herein as "DNA47470-1130P1" (UNQ313).

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO540 cDNA, wherein SEQ ID NO:21 is a clone designated herein as "DNA44189-1322" (UNQ341).

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO618 cDNA, wherein SEQ ID NO:23 is a clone designated herein as "DNA49152-1324" (UNQ354).

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO944 cDNA, wherein SEQ ID NO:25 is a clone designated herein as "DNA52185-1370" (UNQ481).

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO994 cDNA, wherein SEQ ID NO:27 is a clone designated herein as "DNA58855-1422" (UNQ518).

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO1079 cDNA, wherein SEQ ID NO:29 is a clone designated herein as "DNA56050-1455" (UNQ536).

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1110 cDNA, wherein SEQ ID NO:31 is a clone designated herein as "DNA58727-1474" (UNQ553).

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1122 cDNA, wherein SEQ ID NO:33 is a clone designated herein as "DNA62377-1381-1" (UNQ561).

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1138 cDNA, wherein SEQ ID NO:35 is a clone designated herein as "DNA58850-1495" (UNQ576).

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO 1190 cDNA, wherein SEQ ID NO:37 is a clone designated herein as "DNA59586-1520" (UNQ604).

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1272 cDNA, wherein SEQ ID NO:39 is a clone designated herein as "DNA64896-1539" (UNQ642).

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1286 cDNA, wherein SEQ ID NO:41 is a clone designated herein as "DNA64903-1553" (UNQ655).

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1295 cDNA, wherein SEQ ID NO:43 is a clone designated herein as "DNA59218-1559" (UNQ664).

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1309 cDNA, wherein SEQ ID NO:45 is a clone designated herein as "DNA59588-1571" (UNQ675).

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO1316 cDNA, wherein SEQ ID NO:47 is a clone designated herein as "DNA60608-1577" (UNQ682).

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO1383 cDNA, wherein SEQ ID NO:49 is a clone designated herein as "DNA58743-1609" (UNQ719).

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO1384 cDNA, wherein SEQ ID NO:51 is a clone designated herein as "DNA71159-1617" (UNQ721).

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO1431 cDNA, wherein SEQ ID NO:53 is a clone designated herein as "DNA73401-1633" (UNQ737).

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO1434 cDNA, wherein SEQ ID NO:55 is a clone designated herein as "DNA68818-2536" (UNQ739).

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO1475 cDNA, wherein SEQ ID NO:57 is a clone designated herein as "DNA61185-1646" (UNQ746).

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO1481 cDNA, wherein SEQ ID NO:59 is a clone designated herein as "DNA58732-1650" (UNQ750).

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO1568 cDNA, wherein SEQ ID NO:61 is a clone designated herein as "DNA68880-1676" (UNQ774).

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO1573 cDNA, wherein SEQ ID NO:63 is a clone designated herein as "DNA73735-1681" (UNQ779).

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO1599 cDNA, wherein SEQ ID NO:65 is a clone designated herein as "DNA62845-1684" (UNQ782).

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO1604 cDNA, wherein SEQ ID NO:67 is a clone designated herein as "DNA71286-1687" (UNQ785).

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO1605 cDNA, wherein SEQ ID NO:69 is a clone designated herein as "DNA77648-1688" (UNQ786).

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO1693 cDNA, wherein SEQ ID NO:71 is a clone designated herein as "DNA77301-1708" (UNQ803).

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO1753 cDNA, wherein SEQ ID NO:73 is a clone designated herein as "DNA68883-1691" (UNQ826).

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO1755 cDNA, wherein SEQ ID NO:75 is a clone designated herein as "DNA76396-1698" (UNQ828).

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO1777 cDNA, wherein SEQ ID NO:77 is a clone designated herein as "DNA71235-1706" (UNQ839).

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO1788 cDNA, wherein SEQ ID NO:79 is a clone designated herein as "DNA77652-2505" (UNQ850).

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO1864 cDNA, wherein SEQ ID NO:81 is a clone designated herein as "DNA45409-2511" (UNQ855).

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO1925 cDNA, wherein SEQ ID NO:83 is a clone designated herein as "DNA82302-2529" (UNQ904).

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO1926 cDNA, wherein SEQ ID NO:85 is a clone designated herein as "DNA82340-2530" (UNQ905).

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO3566 cDNA, wherein SEQ ID NO:87 is a clone designated herein as "DNA59844-2542" (UNQ1840).

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO4330 cDNA, wherein SEQ ID NO:89 is a clone designated herein as "DNA90842-2574" (UNQ1886).

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO4423 cDNA, wherein SEQ ID NO:91 is a clone designated herein as "DNA96893-2621" (UNQ1940).

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO36935 cDNA, wherein SEQ ID NO:93 is a clone designated herein as "DNA336539" (UNQ2257).

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO4977 cDNA, wherein SEQ ID NO:95 is a clone designated herein as "DNA62849-2647" (UNQ2420).

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO4979 cDNA, wherein SEQ ID NO:97 is a clone designated herein as "DNA222844" (UNQ2421).

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO4980 cDNA, wherein SEQ ID NO:99 is a clone designated herein as "DNA97003-2649" (UNQ2422).

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO4981 cDNA, wherein SEQ ID NO:101 is a clone designated herein as "DNA94849-2960" (UNQ2423).

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO5801 cDNA, wherein SEQ ID NO:103 is a clone designated herein as "DNA115291-2681" (UNQ2501).

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO5995 cDNA, wherein SEQ ID NO:105 is a clone designated herein as "DNA96988-2685" (UNQ2507).

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO6001 cDNA, wherein SEQ ID NO:107 is a clone designated herein as "DNA98380" (UNQ2512).

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO6095 cDNA, wherein SEQ ID NO:109 is a clone designated herein as "DNA105680-2710" (UNQ2543).

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO6182 cDNA, wherein SEQ ID NO:111 is a clone designated herein as "DNA110700-2716" (UNQ2553).

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO7170 cDNA, wherein SEQ ID NO:113 is a clone designated herein as "DNA108722-2743" (UNQ2782).

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO7171 cDNA, wherein SEQ ID NO:115 is a clone designated herein as "DNA108670-2744" (UNQ2783).

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO7436 cDNA, wherein SEQ ID NO:117 is a clone designated herein as "DNA119535-2756" (UNQ2973).

FIG. 118 shows the amino acid sequence (SEQ ID NO:118) derived from the coding sequence of SEQ ID NO:117 shown in FIG. 117.

FIG. 119 shows a nucleotide sequence (SEQ ID NO:119) of a native sequence PRO9912 cDNA, wherein SEQ ID NO:119 is a clone designated herein as "DNA108700-2802" (UNQ3077).

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO9917 cDNA, wherein SEQ ID NO:121 is a clone designated herein as "DNA119474-2803" (UNQ3079).

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO37337 cDNA, wherein SEQ ID NO:123 is a clone designated herein as "DNA226874" (UNQ5291).

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO37496 cDNA, wherein SEQ ID NO:125 is a clone designated herein as "DNA227033" (UNQ5407).

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO19646 cDNA, wherein SEQ ID NO:127 is a clone designated herein as "DNA145841-2868" (UNQ5827).

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO21718 cDNA, wherein SEQ ID NO:129 is a clone designated herein as "DNA188342" (UNQ5893).

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO19820 cDNA, wherein SEQ ID NO:131 is a clone designated herein as "DNA149911-2885" (UNQ5926).

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO21201 cDNA, wherein SEQ ID NO:133 is a clone designated herein as "DNA168028-2956" (UNQ6098).

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO20026 cDNA, wherein SEQ ID NO:135 is a clone designated herein as "DNA154095-2998" (UNQ6115).

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO20110 cDNA, wherein SEQ ID NO:137 is a clone designated herein as "DNA166819-1381R1P1" (UNQ6129).

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO23203 cDNA, wherein SEQ ID NO:139 is a clone designated herein as "DNA185171-2994" (UNQ6507).

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO35250 cDNA, wherein SEQ ID NO:141 is a clone designated herein as "DNA171732-3100" (UNQ9574).

FIG. 142 shows the amino acid sequence (SEQ ID NO:142) derived from the coding sequence of SEQ ID NO:141 shown in FIG. 141.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide" comprises a polypeptide having the same amino acid sequence as the corresponding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide derived from nature. Such native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO 19646, PRO21718, PRO 19820, PRO21201, PRO20026, PRO20110, PRO23203 or PRO35250 polypeptides can be isolated from nature or can be produced by recombinant or synthetic means. The term "native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide" specifically encompasses naturally-occurring truncated or secreted forms of the specific PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide (e.g., an extracellular domain sequence), naturally-occurring variant forms (e.g., alternatively spliced forms) and naturally-occurring allelic variants of the polypeptide. The invention provides native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides disclosed herein which are mature or full-length native sequence polypeptides comprising the full-length amino acids sequences shown in the accompanying figures. Start and stop codons are shown in bold font and underlined in the figures. However, while the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides.

The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide "extracellular domain" or "ECD" refers to a form of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which is essentially free of the transmembrane and cytoplasmic domains. Ordinarily, a PRO69122, PRO204, PRO214, PRO222, PRO234, PRO265, PRO309, PRO332, PRO342, PRO356, PRO540, PR618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide ECD will have less than 1% of such transmembrane and/or cytoplasmic domains and preferably, will have less than 0.5% of such domains. It will be understood that any transmembrane domains identified for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide variant" means a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, preferably an active PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, as defined herein having at least about 80% amino acid sequence identity with a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence lacking the signal peptide as disclosed herein, an extracellular domain of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, with or without the signal peptide, as disclosed herein or any other fragment of a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein (such as those encoded by a nucleic acid that represents only a portion of the complete coding sequence for a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide). Such PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide variants include, for instance, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides wherein one or more amino acid residues are added, or deleted, at the N- or C-terminus of the full-length native amino acid sequence. Ordinarily, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence lacking the signal peptide as disclosed herein, an extracellular domain of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, with or without the signal peptide, as disclosed herein or any other specifically defined fragment of a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein. Ordinarily, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polypeptides will have no more than one conservative amino acid substitution as compared to the native PRO69122, PRO204, PRO214, PRO222, PRO234, PRO265, PRO309, PRO332, PRO342, PRO356, PRO540, PRO618, PRO944, PRO994, PRO1079, PRO1110, PRO122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence, alternatively will have or will have no more than 2, 3, 4, 5, 6, 7, 8, 9, or 10 conservative amino acid substitution as compared to the native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence.

"Percent (%) amino acid sequence identity" with respect to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequences identified herein is defined as the percentage of amino acid residues in a candidate sequence that are identical with the amino acid residues in the specific PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polynucleotide" or "PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant nucleic acid sequence" means a nucleic acid molecule which encodes a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, preferably an active PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, as defined herein and which has at least about 80% nucleic acid sequence identity with a nucleotide acid sequence encoding a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein, a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence lacking the signal peptide as disclosed herein, an extracellular domain of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, with or without the signal peptide, as disclosed herein or any other fragment of a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein (such as those encoded by a nucleic acid that represents only a portion of the complete coding sequence for a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide). Ordinarily, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein, a full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence lacking the signal peptide as disclosed herein, an extracellular domain of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, with or without the signal sequence, as disclosed herein or any other fragment of a full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide sequence as disclosed herein. Variants do not encompass the native nucleotide sequence.

Ordinarily, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding nucleic acid sequences identified herein is defined as the percentage of nucleotides in a candidate sequence that are identical with the nucleotides in the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polynucleotides which are nucleic acid molecules that encode a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and which are capable of hybridizing, preferably under stringent hybridization and wash conditions, to nucleotide sequences encoding a full-length PRO69122, PRO204, PRO214, PRO222, PRO234, PRO265, PRO309, PRO332, PRO342, PRO356, PRO540, PRO618, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as disclosed herein. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polypeptides may be those that are encoded by a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant polynucleotide.

The term "full-length coding region" when used in reference to a nucleic acid encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide refers to the sequence of nucleotides which encode the full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide of the invention (which is often shown between start and stop codons, inclusive thereof, in the accompanying figures). The term "full-length coding region" when used in reference to an ATCC deposited nucleic acid refers to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide natural environment will not be present. Ordinarily, however, isolated polypeptide will be prepared by at least one purification step.

An "isolated" PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which retain a biological and/or an immunological activity of native or naturally-occurring PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, wherein "biological" activity refers to a biological function (either inhibitory or stimulatory) caused by a native or naturally-occurring PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide other than the ability to induce the production of an antibody against an antigenic epitope possessed by a native or naturally-occurring PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and an "immunological" activity refers to the ability to induce the production of an antibody against an antigenic epitope possessed by a native or naturally-occurring PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

The term "antagonist" is used in the broadest sense [unless otherwise qualified], and includes any molecule that partially or fully blocks, inhibits, or neutralizes a biological activity of a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide disclosed herein. In a similar manner, the term "agonist" is used in the broadest sense [unless otherwise qualified] and includes any molecule that mimics a biological activity of a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide disclosed herein. Suitable agonist or antagonist molecules specifically include agonist or antagonist antibodies or antibody fragments, fragments or amino acid sequence variants of native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides, peptides, antisense oligonucleotides, small organic molecules, etc. Methods for identifying agonists or antagonists of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO501, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may comprise contacting a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with a candidate agonist or antagonist molecule and measuring a detectable change in one or more biological activities normally associated with the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By "solid phase" is meant anon-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, a PRO69122, PRO204, PRO214, PRO222, PRO234, PRO265, PRO309, PRO332, PRO342, PRO356, PRO540, PRO618, PRO944, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide, a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell in filtration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al, *J. Am. Coll. Cardiol.,* 4: 1500-1506 (1984); Smith et al., *J. Am. Coll. Cardiol.,* 5: 869-874 (1985). A prolonged left ventricular relaxation has been detected in early essential hypertension, in spite of normal or supranormal systolic function. Hartford et al., *Hypertension,* 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.,* 53: 1583-7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.,* 316: 780-789 (1987); Spirito et al., *N. Engl. J. Med.,* 320: 749-755 (1989); Louie and Edwards, *Prog. Cardiovasc. Dis.,* 36: 275-308 (1994); Wigle et al., *Circulation,* 92: 1680-1692 (1995)), the heterogenecity of which is accentuated by the fact that it afflicts patients of all ages. Spirito et al., *N. Eng. J. Med.,* 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.,* 326: 1108-1114 (1992); Schwartz et al, *Circulation,* 91: 532-540 (1995); Marian and Roberts, *Circulation,* 92: 1336-1347 (1995); Thierfelder et al., *Cell,* 77: 701-712 (1994); Watkins et al., *Nat. Gen.,* 11: 434-437 (1995). Besides β-myosin heavy chain, other locations of genetic mutations include cardiac troponin T, alpha topomyosin, cardiac myosin binding protein C, essential myosin light chain, and regulatory myosin light chain. See, Malik and Watkins, *Curr. Opin. Cardiol.,* 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Specific examples of other autoimmune diseases as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Behcet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic ceratoscleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubellavirus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodo sum lepro sum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various ophthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule is an amount capable of inhibiting the growth of a cell, especially tumor, e.g., cancer cell, either in vitro or in vivo. A "growth inhibitory amount" of an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule for purposes of inhibiting neoplastic cell growth may be determined empirically and in a routine manner.

A "cytotoxic amount" of an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule is an amount capable of causing the destruction of a cell, especially tumor, e.g., cancer cell, either in vitro or in vivo. A "cytotoxic amount" of an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecule for purposes of inhibiting neoplastic cell growth may be determined empirically and in a routine manner.

The term "antibody" is used in the broadest sense and specifically covers, for example, single anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody monoclonal antibodies (including agonist, antagonist, and neutralizing antibodies), anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody compositions with polyepitopic specificity, polyclonal antibodies, single chain anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti- PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies, and fragments of anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495(1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al.,

*Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptide" is an oligopeptide that binds, preferably specifically, to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as described herein. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptides may be chemically synthesized using known oligopeptide synthesis methodology or may be prepared and purified using recombinant technology. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as described herein. PRO69122, PRO204, PRO214, PRO222, PRO234, PRO265, PRO309, PRO332, PRO342, PRO356, PRO540, PRO618, PRO944, PRO994, PRO1079, PRO110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833, 092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. U.S.A.,* 82:178-182(1985); Geysen et al., in *Synthetic Peptides as Antigens,* 130-149 (1986); Geysen et al., *J. Immunol. Meth.,* 102:259-274 (1987); Schoofs et al., *J. Immunol.,* 140:611-616 (1988), Cwirla, S. E. et al. (1990) *Proc. Natl. Acad. Sci. USA,* 87:6378; Lowman, H. B. et al. (1991) *Biochemistry,* 30:10832; Clackson, T. et al. (1991) *Nature,* 352: 624; Marks, J. D. et al. (1991), *J. Mol.*

*Biol.,* 222:581; Kang, A. S. et al. (1991) *Proc. Natl. Acad. Sci. USA,* 88:8363, and Smith, G. P. (1991) *Current Opin. Biotechnol.,* 2:668).

A "PRO69122, PRO204, PRO214, PRO222, PRO234, PRO265, PRO309, PRO332, PRO342, PRO356, PRO540, PRO618, PRO944, PRO994, PRO1079, PRO110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO2110, PRO23203 or PRO35250 binding organic molecule" is an organic molecule other than an oligopeptide or antibody as defined herein that binds, preferably specifically, to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as described herein. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecules may be identified and chemically synthesized using known methodology (see, e.g., PCT Publication Nos. WO00/00823 and WO00/39585). PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding organic molecules are usually less than about 2000 daltons in size, alternatively less than about 1500, 750, 500, 250 or 200 daltons in size, wherein such organic molecules that are capable of binding, preferably specifically, to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a "PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250" or a "growth inhibitory" antibody, oligopeptide or other organic molecule is one which results in measurable growth inhibition of cancer cells expressing or overexpressing the appropriate PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be a transmembrane polypeptide expressed on the surface of a cancer cell or may be a polypeptide that is produced and secreted by a cancer cell. Preferred growth inhibitory anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies, oligopeptides or organic molecules inhibit growth of PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as cannustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, preferably a cell that overexpresses a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as compared to a normal cell of the same tissue type. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11(1995)) or 7AAD can be assessed relative to untreated cells. Preferred cell death-inducing antibodies, oligopeptides or other organic molecules are those which induce PI uptake in the PI uptake assay in BT474 cells.

As used herein, the term "immunoadhesion" designates antibody-like molecules which combine the binding specificity of a heterologous protein (an "adhesion") with the effector functions of immunoglobulin constant domains. Structurally, the immunoadhesions comprise a fusion of an amino acid sequence with the desired binding specificity which is other than the antigen recognition and binding site of an antibody (i.e., is "heterologous"), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

"Replication-preventing agent" is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:

1. Prostate cancer: androgens, docetaxel, paclitaxel, estramustine, doxorubicin, mitoxantrone, antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI's).

2. Stomach cancer: 5-fluorouracil (5FU), XELODA™ capecitabine, methotrexate, etoposide, cisplatin/carboplatin, pacliitaxel, docetaxel, gemcitabine, doxorubicin, and CPT-11 (camptothcin-11; irinotecan, USA Brand Name: CAMPTOSAR®).

3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI's.

4. Colorectal cancer: 5FU, XELODA™ capecitabine, CPT-11, oxaliplatin, AVASTIN™ anti-VEGF, TARCEVA™ erlotinib and other EGFR TKI's, and ERBITUX™ (formerly known as IMC-C225) human:murine-chimerized monoclonal antibody that binds to EGFR and blocks the ability of EGF to initiate receptor activation and signaling to the tumor.

5. Renal cancer: IL-2, interferon alpha, AVASTIN™ anti-VEGF, MEGACE™ (Megestrol acetate) progestin, vinblastine, TARCEVA™ erlotinib, and other EGFR TKI's.

A "growth inhibitory agent" when used herein refers to a compound or composition which inhibits growth of a cell, especially a PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-expressing cancer cell, either in vitro or in vivo. Thus, the growth inhibitory agent may be one which significantly reduces the percentage of PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yewtree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; ©) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene.

The term "native expression" refers to the expression of the full-length polypeptide encoded by the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene, at expression levels present in the wild-type mouse. Thus, a disruption in which there is "no native expression" of the endogenous PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene refers to a partial or complete reduction of the expression of at least a portion of a polypeptide encoded by an endogenous PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene of a single cell, selected cells, or all of the cells of a mammal.

The term "knockout" refers to the disruption of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding any of the specific human PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding genes or variants thereof (ie. the disruption results in a replacement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 targeting construct. A "PRO69122, PRO204, PRO214, PRO222, PRO234, PRO265, PRO309, PRO332, PRO342, PRO356, PRO540, PRO618, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 targeting construct" includes a DNA sequence homologous to at least one portion of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene and is capable of producing a disruption in a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene in a host cell.

The term "transgenic cell" refers to a cell containing within its genome a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or fetus in utero, whether by mating or otherwise, and whether or not the embryo goes to term.

As used herein, the terms "selective marker" and position selection marker" refer to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene function, expression, activity, or alternatively a phenotype associated with PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is implicated, including pathological conditions and behavioral observations.

TABLE 1

```
/*
 *
 * C-C increased from 12 to 15
 * Z is average of EQ
 * B is average of ND
 * match with stop is _M; stop-stop = 0; J (joker) match = 0
 */
#define   _M      -8      /* value of a match with a stop */
int       _day[26][26] = {
/*    A B C D E F G H I J K L M N O P Q R S T U V W X Y Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M, 0,_M,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
/*
 */
#include <stdio.h>
#include <ctype.h>
#define   MAXJMP      16      /* max jumps in a diag */
#define   MAXGAP      24      /* don't continue to penalize gaps larger than this */
#define   JMPS        1024    /* max jmps in an path */
#define   MX          4       /* save if there's at least MX-1 bases since last jmp */
#define   DMAT        3       /* value of matching bases */
#define   DMIS        0       /* penalty for mismatched bases */
#define   DINS0       8       /* penalty for a gap */
#define   DINS1       1       /* penalty per base */
#define   PINS0       8       /* penalty for a gap */
#define   PINS1       4       /* penalty per residue */
struct jmp {
          short             n[MAXJMP];      /* size of jmp (neg for dely) */
          unsigned short    x[MAXJMP];      /* base no. of jmp in seq x */
};                                          /* limits seq to 2^16 -1 */
struct diag {
          int               score;          /* score at last jmp */
          long              offset;         /* offset of prev block */
          short             ijmp;           /* current jmp index */
          struct jmp        jp;             /* list of jmps */
};
struct path {
          int       spc;                    /* number of leading spaces */
          short     n[JMPS];/* size of jmp (gap) */
          int       x[JMPS];/* loc of jmp (last elem before gap) */
};
char      *ofile;                           /* output file name */
char      *namex[2];                        /* seq names: getseqs( ) */
char      *prog;                            /* prog name for err msgs */
char      *seqx[2];                         /* seqs: getseqs( ) */
int       dmax;                             /* best diag: nw( ) */
int       dmax0;                            /* final diag */
int       dna;                              /* set if dna: main( ) */
int       endgaps;                          /* set if penalizing end gaps */
int       gapx, gapy;                       /* total gaps in seqs */
int       len0, len1;                       /* seq lens */
int       ngapx, ngapy;                     /* total size of gaps */
int       smax;                             /* max score: nw( ) */
int       *xbm;                             /* bitmap for matching */
```

TABLE 1-continued

```
long            offset;                 /* current offset in jmp file */
struct  diag    *dx;                    /* holds diagonals */
struct  path    pp[2];                  /* holds path for seqs */
char            *calloc( ), *malloc( ), *index( ), *strcpy( );
char            *getseq( ), *g_calloc( );
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"
static  _dbval[26] = {
        1,14,2,13,0,0,4,11,0,0,12,0,3,15,0,0,0,5,6,8,8,7,9,0,10,0
};
static  _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)                                                                    main
        int     ac;
        char    *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;                    /* 1 to penalize endgaps */
        ofile = "align.out";            /* output file */
        nw( );          /* fill in the matrix, get the possible jmps */
        readjmps( );    /* get the actual jmps */
        print( );       /* print stats, alignment */
        cleanup(0);     /* unlink any tmp files */}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                           nw
{
        char            *px, *py;               /* seqs and ptrs */
        int             *ndely, *dely;          /* keep track of dely */
        int             ndelx, delx;            /* keep track of delx */
        int             *tmp;                   /* for swapping row0, row1 */
        int             mis;                    /* score for each type */
        int             ins0, ins1;             /* insertion penalties */
        register        id;                     /* diagonal index */
        register        ij;                     /* jmp index */
        register        *col0, *col1;           /* score for curr, last row */
        register        xx, yy;                 /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
```

TABLE 1-continued

```
        smax = −10000;
        if (endgaps) {
                for (col0[0] = dely[0] = −ins0, yy = 1; yy <= len1; yy++) {
                        col0[yy] = dely[yy] = col0[yy−1] − ins1;
                        ndely[yy] = yy;
                }
                col0[0] = 0;            /* Waterman Bull Math Biol 84 */
        }
        else
                for (yy = 1; yy <= len1; yy++)
                        dely[yy] = −ins0;
        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = −(ins0+ins1);
                        else
                                col1[0] = delx = col0[0] − ins1;
                        ndelx = xx;
                }
                else {
                        col1[0] = 0;
                        delx = −ins0;
                        ndelx = 0;
                }
                                                                        ...nw
for (py = seqx[1], yy = 1; yy <= len1; py++, yy++) {
        mis = col0[yy−1];
        if (dna)
                mis += (xbm[*px−'A']&xbm[*py−'A'])? DMAT : DMIS;
        else
                mis += _day[*px−'A'][*py−'A'];
        /* update penalty for del in x seq;
         * favor new del over ongong del
         * ignore MAXGAP if weighting endgaps
         */
        if (endgaps || ndely[yy] < MAXGAP) {
                if (col0[yy] − ins0 >= dely[yy]) {
                        dely[yy] = col0[yy] − (ins0+ins1);
                        ndely[yy] = 1;
                } else {
                        dely[yy] −= ins1;
                        ndely[yy]++;
                }
        } else {
                if (col0[yy] − (ins0+ins1) >= dely[yy]) {
                        dely[yy] = col0[yy] − (ins0+ins1);
                        ndely[yy] = 1;
                } else
                        ndely[yy]++;
        }
        /* update penalty for del in y seq;
         * favor new del over ongong del
         */
        if (endgaps || ndelx < MAXGAP) {
                if (col1[yy−1] − ins0 >= delx) {
                        delx = col1[yy−1] − (ins0+ins1);
                        ndelx = 1;
                } else {
                        delx −= ins1;
                        ndelx++;
                }
        } else {
                if (col1[yy−1] − (ins0+ins1) >= delx) {
                        delx = col1[yy−1] − (ins0+ins1);
                        ndelx = 1;
                } else
                        ndelx++;
        }
        /* pick the maximum score; we're favoring
         * mis over any del and delx over dely
         */
                                                                        ...nw
        id = xx − yy + len1 − 1;
        if (mis >= delx && mis >= dely[yy])
                col1[yy] = mis;
```

TABLE 1-continued

```
                else if (delx >= dely[yy]) {
                        col1[yy] = delx;
                        ij = dx[id].ijmp;
                        if (dx[id].jp.n[0] && (!dna || (ndelx >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                         */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;                    }
(void) free((char *)ndely);
(void) free((char *)dely);
(void) free((char *)col0);
(void) free((char *)col1);                              }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC         3
#define P_LINE      256         /* maximum output line */
#define P_SPC       3           /* space between name or num and seq */
extern      _day[26][26];
int         olen;               /* set output line length */
FILE        *fx;                /* output file */
print( )                                                                        print
{
        int     lx, ly, firstgap, lastgap;          /* overlap */
```

TABLE 1-continued

```
        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr__align( );           }
/*
 * trace back the best path, count matches
 */
static
getmat(lx, ly, firstgap, lastgap)                                                       getmat
        int     lx, ly;                         /* "core" (minus endgaps) */
        int     firstgap, lastgap;              /* leading trailing overlap */
{
        int                     nm, i0, i1, siz0, siz1;
        char                    outx[32];
        double                  pct;
        register                n0, n1;
        register char           *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
```

TABLE 1-continued

```
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                    ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
 * print alignment of described in struct path pp[ ]
 */
static
pr_align( )                                                                  pr_align
{
        int             nn;     /* char count */
        int             more;
        register        I;
        for (I = 0, lmax = 0; I < 2; I++) {
                nn = stripname(namex[i]);
                if (nn > lmax)
                        lmax = nn;
                nc[i] = 1;
                ni[i] = 1;
                siz[i] = ij[i] = 0;
                ps[i] = seqx[i];
                po[i] = out[i];                 }
        for (nn = nm = 0, more = 1; more; ) {                                ...pr_align
                for (I = more = 0; I < 2; I++) {
                        /*
                         * do we have more of this sequence?
                         */
                        if (!*ps[i])
                                continue;
                        more++;
                        if (pp[i].spc) {        /* leading space */
                                *po[i]++ = ' ';
                                pp[i].spc--;
                        }
                        else if (siz[i]) {      /* in a gap */
                                *po[i]++ = '-';
                                siz[i]--;
                        }
                        else {                  /* we're putting a seq element
                                                 */
                                *po[i] = *ps[i];
                                if (islower(*ps[i]))
```

TABLE 1-continued

```
                                *ps[i] = toupper(*ps[i]);
                        po[i]++;
                        ps[i]++;
                        /*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock( );
                for (I = 0; I < 2; I++)
                        po[i] = out[i];
                nn = 0;
        }
    }
}
/*
 * dump a block of lines, including numbers, stars: pr_align( )
 */
static
dumpblock( )                                                    dumpblock
{
        register I;
        for (I = 0; I < 2; I++)
                *po[i]-- = '\0';
                                                                ...dumpblock
        (void) putc('\n', fx);
        for (I = 0; I < 2; I++) {
                if (*out[i] && (*out[i] != ' ' || *(po[i]) != ' ')) {
                        if (I == 0)
                                nums(I);
                        if (I == 0 && *out[1])
                                stars( );
                        putline(I);
                        if (I == 0 && *out[1])
                                fprintf(fx, star);
                        if (I == 1)
                                nums(I);
                }
        }
}
/*
 * put out a number line: dumpblock( )
 */
static
nums(ix)                                                        nums
        int     ix;     /* index in out[ ] holding seq line */
{
        char            nline[P_LINE];
        register        I, j;
        register char   *pn, *px, *py;
        for (pn = nline, I = 0; I < lmax+P_SPC; I++, pn++)
                *pn = ' ';
        for (I = nc[ix], py = out[ix]; *py; py++, pn++) {
                if (*py == ' ' || *py == '-')
                        *pn = ' ';
                else {
                        if (I%10 == 0 || (I == 1 && nc[ix] != 1)) {
                                j = (I < 0)? -I : I;
                                for (px = pn; j; j /= 10, px--)
                                        *px = j%10 + '0';
                                if (I < 0)
                                        *px = '-';
                        }
                        else
                                *pn = ' ';
                        I++;
                }
        }
```

TABLE 1-continued

```
		*pn = '\0';
		nc[ix] = I;
		for (pn = nline; *pn; pn++)
			(void) putc(*pn, fx);
		(void) putc('\n', fx);
}
/*
 * put out a line (name, [num], seq, [num]): dumpblock( )
 */
static
putline(ix)                                                          putline
		int	ix;	{
                                                                     ...putline
		int		I;
		register char	*px;
		for (px = namex[ix], I = 0; *px && *px != ':'; px++, I++)
			(void) putc(*px, fx);
		for (; I < lmax+P_SPC; I++)
			(void) putc(' ', fx);
		/* these count from 1:
		 * ni[ ] is current element (from 1)
		 * nc[ ] is number at start of current line
		 */
		for (px = out[ix]; *px; px++)
			(void) putc(*px&0x7F, fx);
		(void) putc('\n', fx);
}
/*
 * put a line of stars (seqs always in out[0], out[1]): dumpblock( )
 */
static
stars( )                                                             stars
{
		int		I;
		register char	*p0, *p1, cx, *px;
		if (!*out[0] || (*out[0] == ' ' && *(po[0]) == ' ') ||
		    !*out[1] || (*out[1] == ' ' && *(po[1]) == ' '))
			return;
		px = star;
		for (I = lmax+P_SPC; I; I−−)
			*px++ = ' ';
		for (p0 = out[0], p1 = out[1]; *p0 && *p1; p0++, p1++) {
			if (isalpha(*p0) && isalpha(*p1)) {
				if (xbm[*p0−'A']&xbm[*p1−'A']) {
					cx = '*';
					nm++;
				}
				else if (!dna && _day[*p0−'A'][*p1−'A'] > 0)
					cx = '.';
				else
					cx = ' ';
			}
			else
				cx = ' ';
			*px++ = cx;
		}
		*px++ = '\n';
		*px = '\0';
}
/*
 * strip path or prefix from pn, return len: pr_align( )
 */
static
stripname(pn)                                                        stripname
		char	*pn;	/* file name (may be path) */
{
		register char	*px, *py;
		py = 0;
		for (px = pn; *px; px++)
			if (*px == '/')
				py = px + 1;
		if (py)
			(void) strcpy(pn, py);
		return(strlen(pn));
}
/*
 * cleanup( ) -- cleanup any tmp file
 * getseq( ) -- read in seq, set dna, len, maxlen
 * g_calloc( ) -- calloc( ) with error checkin
```

TABLE 1-continued

```
 * readjmps( ) -- get the good jmps, from tmp file if necessary
 * writejmps( ) -- write a filled array of jmps to a tmp file: nw( )
 */
#include "nw.h"
#include <sys/file.h>
char    *jname = "/tmp/homgXXXXXX";          /* tmp file for jmps */
FILE    *fj;
int     cleanup( );                          /* cleanup tmp file */
long    lseek( );
/*
 * remove any tmp file if we blow
 */
cleanup(I)                                                              cleanup
        int     I;
{
        if (fj)
                (void) unlink(jname);
        exit(I);
}
/*
 * read, return ptr to seq, set dna, len, maxlen
 * skip lines starting with ';', '<', or '>'
 * seq in upper or lower case
 */
char    *
getseq(file, len)                                                       getseq
        char    *file;  /* file name */
        int     *len;   /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                        ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                   g_calloc
        char    *msg;           /* program, calling routine */
        int     nx, sz;         /* number and size of elements */
{
        char            *px, *calloc( );
        if ((px = calloc((unsigned)nx, (unsigned)sz)) == 0) {
```

TABLE 1-continued

```
		if (*msg) {
			fprintf(stderr, "%s: g_calloc( ) failed %s (n=%d, sz=%d)\n", prog, msg, nx, sz);
			exit(1);
		}
	}
	return(px);
}
/*
 * get final jmps from dx[ ] or tmp file, set pp[ ], reset dmax: main( )
 */
readjmps( )                                                                    readjmps
{
	int		fd = -1;
	int		siz, i0, i1;
	register	I, j, xx;
	if (fj) {
		(void) fclose(fj);
		if ((fd = open(jname, O_RDONLY, 0)) < 0) {
			fprintf(stderr, "%s: can't open( ) %s\n", prog, jname);
			cleanup(1);
		}
	}
	for (I = i0 = i1 = 0, dmax0 = dmax, xx = len0; ; I++) {
		while (1) {
			for (j = dx[dmax].ijmp; j >= 0 && dx[dmax].jp.x[j] >= xx; j--)
				;
                                                                               ...readjmps
			if (j < 0 && dx[dmax].offset && fj) {
				(void) lseek(fd, dx[dmax].offset, 0);
				(void) read(fd, (char *)&dx[dmax].jp, sizeof(struct jmp));
				(void) read(fd, (char *)&dx[dmax].offset, sizeof(dx[dmax].offset));
				dx[dmax].ijmp = MAXJMP-1; }
			else
				break;		}
		if (I >= JMPS) {
			fprintf(stderr, "%s: too many gaps in alignment\n", prog);
			cleanup(1);
		}
		if (j >= 0) {
			siz = dx[dmax].jp.n[j];
			xx = dx[dmax].jp.x[j];
			dmax += siz;
		if (siz < 0) {				/* gap in second seq */
				pp[1].n[i1] = -siz;
				xx += siz;
				/* id = xx - yy + len1 - 1			*/
				pp[1].x[i1] = xx - dmax + len1 - 1;
				gapy++;
				ngapy -= siz;
/* ignore MAXGAP when doing endgaps */
				siz = (-siz < MAXGAP || endgaps)? -siz : MAXGAP;
				i1++;
			}
			else if (siz > 0) {	/* gap in first seq */
				pp[0].n[i0] = siz;
				pp[0].x[i0] = xx;
				gapx++;
				ngapx += siz;
/* ignore MAXGAP when doing endgaps */
				siz = (siz < MAXGAP || endgaps)? siz : MAXGAP;
				i0++;
			}
		}
		else
			break;
	}
	/* reverse the order of jmps */
	for (j = 0, i0--; j < i0; j++, i0--) {
		I = pp[0].n[j]; pp[0].n[j] = pp[0].n[i0]; pp[0].n[i0] = I;
		I = pp[0].x[j]; pp[0].x[j] = pp[0].x[i0]; pp[0].x[i0] = I;
	}
	for (j = 0, i1--; j < i1; j++, i1--) {
		I = pp[1].n[j]; pp[1].n[j] = pp[1].n[i1]; pp[1].n[i1] = I;
		I = pp[1].x[j]; pp[1].x[j] = pp[1].x[i1]; pp[1].x[i1] = I;
	}
	if (fd >= 0)
		(void) close(fd);
	if (fj) {
		(void) unlink(jname);
```

TABLE 1-continued

```
                fj = 0;
                offset = 0;
        }                               }
/*
 * write a filled jmp struct offset of the prev one (if any): nw( )
 */
writejmps(ix)                                                    writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 Polypeptides The present invention provides newly identified and isolated nucleotide sequences encoding polypeptides referred to in the present application as PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides. In particular, cDNAs encoding various PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides and encoding nucleic acids described herein, Applicants have identified what is believed to be the reading frame best identifiable with the sequence information available at the time.

B. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO4979, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptide Variants In addition to the full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides described herein, it is contemplated that PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variants can be prepared. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variants can be prepared by introducing appropriate nucleotide changes into the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 DNA, and/or by synthesis of the desired PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Those skilled in the art will appreciate that amino acid changes may alter post-translational processes of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, such as changing the number or position of glycosylation sites or altering the membrane anchoring characteristics.

Variations in the native full-length sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or in various domains of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide that results in a change in the amino acid sequence of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as compared with the native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Optionally the variation is by substitution of at least one amino acid with any other amino acid in one or more of the domains of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Guidance in determining which amino acid residue may be inserted, substituted or deleted without adversely affecting the desired activity may be found by comparing the sequence of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693,

PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 fragments may be prepared by any of a number of conventional techniques. Desired peptide fragments may be chemically synthesized. An alternative approach involves generating PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fragments share at least one biological and/or immunological activity with the native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
|---|---|---|
| Ala (A) | Val; Leu; Ile | Val |
| Arg ®) | Lys; Gln; Asn | Lys |
| Asn (N) | Gln; His; Asp, Lys; Arg | Gln |
| Asp (D) | Glu; Asn | Glu |
| Cys ©) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells *Gene,* 34:315 (1985)], restriction selection mutagenesis [Wells et al., *Philos. Trans. R. Soc. London Ser*A, 317:415 (1986)] or other known techniques can be performed on the cloned DNA to produce the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptides Covalent modifications of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides are included within the scope of this invention. One type of covalent modification includes reacting targeted amino acid residues of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with an organic derivatizing agent that is capable of reacting with selected side chains or the N- or C-terminal residues of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Derivatization with bifunctional agents is useful, for instance, for crosslinking PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides to a water-insoluble support matrix or surface for use in the method for purifying anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide included within the scope of this invention comprises altering the native glycosylation pattern of the polypeptide. "Altering the native glycosylation pattern" is intended for purposes herein to mean deleting one or more carbohydrate moieties found in native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides (either by removing the underlying glycosylation site or by deleting the glycosylation by chemical and/or enzymatic means), and/or adding one or more glycosylation sites that are not present in the native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. In addition, the phrase includes qualitative changes in the glycosylation of the native proteins, involving a change in the nature and proportions of the various carbohydrate moieties present.

Addition of glycosylation sites to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be accomplished by altering the amino acid sequence. The alteration may be made, for example, by the addition of, or substitution by, one or more serine or threonine residues to the native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 (for O-linked glycosylation sites). The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 amino acid sequence may optionally be altered through changes at the DNA level, particularly by mutating the DNA encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide at preselected bases such that codons are generated that will translate into the desired amino acids.

Another means of increasing the number of carbohydrate moieties on the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides comprises linking the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO69122, PRO204, PRO214, PRO222, PRO234, PRO265, PRO309, PRO332, PRO342, PRO356, PRO540,

PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides of the present invention may also be modified in a way to form a chimeric molecule comprising the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide fused to another, heterologous polypeptide or amino acid sequence.

Such a chimeric molecule comprises a fusion of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with a tag polypeptide which provides an epitope to which an anti-tag antibody can selectively bind. The epitope tag is generally placed at the amino- or carboxyl-terminus of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. The presence of such epitope-tagged forms of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 polypeptide can be detected using an antibody against the tag polypeptide. Also, provision of the epitope tag enables the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

The chimeric molecule may comprise a fusion of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptides The description below relates primarily to production of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides by culturing cells transformed or transfected with a vector containing PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acid. It is, of course, contemplated that alternative methods, which are well known in the art, may be employed to prepare PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides. For instance, the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 sequence, or portions thereof may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.,* 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be chemically synthesized separately and combined using chemical or enzymatic methods to produce the full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

1. Isolation of DNA Encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptides DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides may be obtained from a cDNA library prepared from tissue believed to possess the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 mRNA and to express it at a detectable level. Accordingly, human PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-DNA can be conveniently obtained from a cDNA library prepared from human tissue, such as described in the Examples. The PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding gene may also be obtained from a genomic library or by known synthetic procedures (e.g., automated nucleic acid synthesis).

Libraries can be screened with probes (such as antibodies to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype to tonA ptr3; *E. coli* W3110 strain 27C7 (ATCC 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244, 234); *Neurospora crassa* (Case et al., *Proc. Natl. Acad. Sci.*

*USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

An example of suitable selectable markers for mammalian cells are those that enable the identification of cells competent to take up the PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PR019820-, PRO21201-, PRO20026-, PRO20110-, PRO23203- or PRO35250-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides Still other methods, vectors, and host cells suitable for adaptation to the synthesis of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or against a synthetic peptide based on the DNA sequences provided herein or against exogenous sequence fused to PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO 19646-, PRO21718-, PRO19820-, PRO21201-, PRO20026-, PRO20110-, PRO23203- or PRO35250-DNA and encoding a specific antibody epitope.

5. Purification of Polypeptide

Forms of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides may be recovered from culture medium or from host cell lysates. If membrane-bound, it can be released from the membrane using a suitable detergent solution (e.g. Triton-X 100) or by enzymatic cleavage. Cells employed in expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides can be disrupted by various physical or chemical means, such as freeze-thaw cycling, sonication, mechanical disruption, or cell lysing agents.

It may be desired to purify PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide produced.

E. Uses for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptides Nucleotide sequences (or their complement) encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO 19820, PRO21201, PRO20026, PRO20110, PRO23203 or PRO35250 polypeptides have various applications in the art of molecular biology, including uses as hybridization probes, in chromosome and gene mapping and in the generation of anti-sense RNA and DNA. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acid will also be useful for the preparation of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides by the recombinant techniques described herein.

The full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene, or portions thereof may be used as hybridization probes for a cDNA library to isolate the full-length PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 cDNA or to isolate still other cDNAs (for instance, those encoding naturally-occurring variants of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides from other species) which have a desired sequence identity to the native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250. By way of example, a screening method will comprise isolating the coding region of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acids include antisense or sense oligonucleotides comprising a singe-stranded nucleic acid sequence (either RNA or DNA) capable of binding to target PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO 19646, PRO21718, PRO 19820, PRO21201, PRO20026, PRO20110, PRO23203 or PRO35250 mRNA (sense) or PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 DNA (antisense) sequences. Antisenseorsense oligonucleotides, according to the present invention, comprise a fragment of the coding region of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of anoligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026 PRO20110, PRO23203 or PRO35250 coding sequences.

Nucleotide sequences encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can also be used to construct hybridization probes for mapping the gene which encodes that PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 encode a prote in which binds to another protein (for example, where the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is a receptor), the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can be used to isolate correlative ligand(s). Screening assays can be designed to find lead compounds that mimic the biological activity of a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or a receptor for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide which can be used to clone genomic DNA encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide in accordance with established techniques and the genomic sequences used to generate transgenic animals that contain cells which express DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO 19646, PRO21718, PRO 19820, PRO21201, PRO20026, PRO20110, PRO23203 or PRO35250 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci. USA,* 82:6148-6152 (1985)); gene targeting in embryonic stem cells (Thompson, et al., *Cell,* 56:313-321 (1989)); nonspecific insertional inactivation using a gene trap vector (U.S. Pat. No. 6,436,707); electroporation of embryos (Lo, *Mol. Cell. Biol,* 3:1803-1814 (1983)); and sperm-mediated gene transfer (Lavitrano, et al., *Cell,* 57:717-723 (1989)); etc. Typically, particular cells would be targeted for a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 transgene incorporation with tissue-specific enhancers. Transgenic animals that include a copy of a transgene encoding a PRO69122, PRO204, PRO214, PRO222, PRO234, PRO265, PRO309, PR0332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide introduced into the germ line of the animal at an embryonic stage can be used to examine the effect of increased expression of DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition. Alternatively, non-human homologues of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides can be used to construct a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 "knockout" animal which has a defective or altered gene encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 proteins as a result of homologous recombination between the endogenous gene encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides and altered genomic DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides introduced into an embryonic stem cell of the animal. Preferably the knock out animal is a mammal. More preferably, the mammal is a rodent such as a rat or mouse. For example, cDNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides can be used to clone genomic DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides in accordance with established techniques. A portion of the genomic DNA encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical/ Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO69122, PRO204, PRO214, PRO222, PRO234, PRO265, PRO309, PRO332, PRO342, PRO356, PRO540, PRO618, PRO944, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.,* 222:742-47 (1996)).

Nucleic acid encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides described herein may also be employed as molecular weight markers for protein electrophoresis purposes and the isolated nucleic acid sequences may be used for recombinantly expressing those markers.

The nucleic acid molecules encoding the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides or fragments thereof described herein are useful for chromosome identification. In this regard, there exists an ongoing need to identify new chromosome markers, since relatively few chromosome marking reagents, based upon actual sequence data are presently available. Each PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acid molecule of the present invention can be used as a chromosome marker.

The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides and nucleic acid molecules of the present invention may also be used diagnostically for tissue typing, wherein the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides of the present invention may be differentially expressed in one tissue as compared to another, preferably in a diseased tissue as compared to a normal tissue of the same tissue type. PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 nucleic acid molecules will find use for generating probes for PCR, Northern analysis, Southern analysis and Western analysis.

The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides described herein may also be employed as therapeutic agents. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides of the present invention can be formulated according to known methods to prepare pharmaceutically useful compositions, whereby the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is desired in a formulation with release characteristics suitable for the treatment of any disease or disorder requiring administration of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, microencapsulation of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide (agonists) or prevent the effect of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide (antagonists). Agonists that mimic a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide would be especially valuable therapeutically in those instances where a negative phenotype is observed based on findings with the non-human transgenic animal whose genome comprises a disruption of the gene which encodes for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Antagonists that prevent the effects of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide would be especially valuable therapeutically in those instances where a positive phenotype is observed based upon observations with the non-human transgenic knockout animal. Screening assays for antagonist drug candidates are designed to identify compounds that bind or complex with the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO 19646, PRO21718, PRO 19820, PRO21201, PRO20026, PRO20110, PRO23203 or PRO35250 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide encoded by a nucleic acid identified herein under conditions and for a time sufficient to allow these two components to interact.

In binding assays, the interaction is binding and the complex formed can be isolated or detected in the reaction mixture. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and drying. Alternatively, an immobilized antibody, e.g., a monoclonal antibody, specific for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be added to a cell along with the compound to be screened for a particular activity and the ability of the compound to inhibit the activity of interest in the presence of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide indicates that the compound is an antagonist to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Alternatively, antagonists may be detected by combining the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and a potential antagonist with membrane-bound PRO69122, PRO204, PRO214, PRO222, PRO234, PRO265, PRO309, PRO332, PRO342, PRO356, PRO540, PRO618, PRO944, PRO994, PRO1079, PRO1110, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide receptors or recombinant receptors under appropriate conditions for a competitive inhibition assay. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can be labeled, such as by radioactivity, such that the number of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and a cDNA library created from this RNA is divided into pools and used to transfect COS cells or other cells that are not responsive to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Transfected cells that are grown on glass slides are exposed to labeled PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, would be administering a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 antagonist to a wild-type mouse in order to mimic a known knockout phenotype. Thus, one would initially knockout the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene of interest and observe the resultant phenotype as a consequence of knocking out or disrupting the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene. Subsequently, one could then assess the effectiveness of an antagonist to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by administering an antagonist to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to a wild-type mouse. An effective antagonist would be expected to mimic the phenotypic effect that was initially observed in the knockout animal.

Likewise, one could assess the effect of an agonist to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, by administering a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 agonist to a non-human transgenic mouse in order to ameliorate a known negative knockout phenotype. Thus, one would initially knockout the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene of interest and observe the resultant phenotype as a consequence of knocking out or disrupting the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 gene. Subsequently, one could then assess the effectiveness of an agonist to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by administering an agonist to the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to a the non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled PRO69122, PRO204, PRO214, PRO222, PRO234, PRO265, PRO309, PRO332, PRO342, PRO356, PRO540, PRO618, PRO944, PRO994, PRO1079, PRO1110, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide in the presence of the candidate compound. The ability of the compound to enhance or block this interaction could then be measured.

More specific examples of potential antagonists include an oligonucleotide that binds to the fusions of immunoglobulin with the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO69122, PRO204, PRO214, PRO222, PRO234, PRO265, PRO309, PRO332, PRO342, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide that recognizes the receptor but imparts no effect, thereby competitively inhibiting the action of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

Another potential PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. The antisense RNA oligonucleotide hybridizes to the mRNA in vivo and blocks translation of the mRNA molecule into the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, thereby blocking the normal biological activity of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by anyone or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO69122, Anti-PRO204, Anti-PRO214, Anti-PRO222, Anti-PRO234, Anti-PRO265, Anti-PRO309, Anti-PRO332, Anti-PRO342, Anti-PRO356, Anti-PRO540, Anti-PRO618, Anti-PRO944, Anti-PRO994, Anti-PRO1079, Anti-PRO1110, Anti-PRO1122 Anti-PRO1138, Anti-PRO1190 Anti-PRO1272, Anti-PRO1286, Anti-PRO1295, Anti-PRO1309, Anti-PRO1316, Anti-PRO1383, Anti-PRO1384, Anti-PRO1431, Anti-PRO1434, Anti-PRO1475, Anti-PRO1481, Anti-PRO1568, Anti-PRO1573, Anti-PRO1599, Anti-PRO1604, Anti-PRO1605, Anti-PRO1693, Anti-PRO1753, Anti-PRO1755, Anti-PRO1777, Anti-PRO1788, Anti-PRO1864, Anti-PRO1925, Anti-PRO1926, Anti-PRO3566, Anti-PRO4330, Anti-PRO4423, Anti-PRO36935, Anti-PRO4977, Anti-PRO4979, Anti-PRO4980, Anti-PRO4981, Anti-PRO5801, Anti-PRO5995, Anti-PRO6001, Anti-PRO6095, Anti-PRO6182, Anti-PRO7170, Anti-PRO7171, Anti-PRO7436, Anti-PRO9912, Anti-PRO9917, Anti-PRO37337, Anti-PRO37496, Anti-PRO19646, Anti-PRO21718, Anti-PRO19820, Anti-PRO21201, Anti-PRO20026, Anti-PRO20110, Anti-PRO23203 or Anti-PRO35250 Antibodies The present invention provides anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va. USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.,* 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. On. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 protein as described herein. Other such antibodies may combine a PRO69122, PRO204, PRO214, PRO222, PRO234, PRO265, PRO309, PRO332, PRO342, PRO356, PRO540, PRO618, PRO944, PRO994, PRO1079, PRO1110, PRO-1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 binding site with a binding site for another protein. Alternatively, an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-expressing cell. Bispecific antibodies may also be used to localize cytotoxic agents to cells which express a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide. These antibodies possess a PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti- ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO69122, Anti-PRO204, Anti-PRO214, Anti-PRO222, Anti-PRO234, Anti-PRO265, Anti-PRO309, Anti-PRO332, Anti-PRO342, Anti-PRO356, Anti-PRO540, Anti-PRO618, Anti-PRO944, Anti-PRO994, Anti-PRO1079, Anti-PRO1110, Anti-PRO1122, Anti-PRO1138, Anti-PRO1190, Anti-PRO1272, Anti-PRO1286, Anti-PRO1295, Anti-PRO1309, Anti-PRO1316, Anti-PRO1383, Anti-PRO1384, Anti-PRO1431, Anti-PRO1434, Anti-PRO1475, Anti-PRO1481, Anti-PRO1568, Anti-PRO1573, Anti-PRO1599, Anti-PRO1604, Anti-PRO1605, Anti-PRO1693, Anti-PRO1753, Anti-PRO1755, Anti-PRO1777, Anti-PRO1788, Anti-PRO1864, Anti-PRO1925, Anti-PRO1926, Anti-PRO3566, Anti-PRO4330, Anti-PRO4423, Anti-PRO36935, Anti-PRO4977, Anti-PRO4979, Anti-PRO4980, Anti-PRO4981, Anti-PRO5801, Anti-PRO5995, Anti-PRO6001, Anti-PRO6095, Anti-PRO6182, Anti-PRO7170, Anti-PRO7171, Anti-PRO7436, Anti-PRO9912, Anti-PRO9917, Anti-PRO37337, Anti-PRO37496, Anti-PRO19646, Anti-PRO21718, Anti-PRO19820, Anti-PRO21201, Anti-PRO20026, Anti-PRO20110, Anti-PRO23203 or Anti-PRO35250 Antibody-Maytansinoid Conjugates (Immunoconjugates)

Anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody-maytansinoid conjugates are prepared by chemically linking an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131

(1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti- PRO21718, anti-PRO19820, anti-PRO21201, anti-PRO20026, anti-PRO20110, anti-PRO23203 or anti-PRO35250 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

11. Pharmaceutical Compositions of Antibodies

Antibodies specifically binding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide identified herein, as well as other molecules identified by the screening assays disclosed herein before, can be administered for the treatment of various disorders in the form of pharmaceutical compositions.

If the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO69122, Anti-PRO204, Anti-PRO214, Anti-PRO222, Anti-PRO234, Anti-PRO265, Anti-PRO309, Anti-PRO332, Anti-PRO342, Anti-PRO356, Anti-PRO540, Anti-PRO618, Anti-PRO944, Anti-PRO994, Anti-PRO1079, Anti-PRO1110, Anti-PRO1122, Anti-PRO1138, Anti-PRO1190, Anti-PRO1272, Anti-PRO1286, Anti-PRO1295, Anti-PRO1309, Anti-PRO1316, Anti-PRO1383, Anti-PRO1384, Anti-PRO1431, Anti-PRO1434, Anti-PRO1475, Anti-PRO1481, Anti-PRO1568, Anti-PRO1573, Anti-PRO1599, Anti-PRO1604, Anti-PRO1605, Anti-PRO1693, Anti-PRO1753, Anti-PRO1755, Anti-PRO1777, Anti-PRO1788, Anti-PRO1864, Anti-PRO1925, Anti-PRO1926, Anti-PRO3566, Anti-PRO4330, Anti-PRO4423, Anti-PRO36935, Anti-PRO4977, Anti-PRO4979, Anti-PRO4980, Anti-PRO4981, Anti-PRO5801, Anti-PRO5995, Anti-PRO6001, Anti-PRO6095, Anti-PRO6182, Anti-PRO7170, Anti-PRO7171, Anti-PRO7436, Anti-PRO9912, Anti-PRO9917, Anti-PRO37337, Anti-PRO37496, Anti-PRO19646, Anti-PRO21718, Anti-PRO19820, Anti-PRO21201, Anti-PRO20026, Anti-PRO20110, Anti-PRO23203 or Anti-PRO35250 Antibodies The anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies of the invention have various therapeutic and/or diagnostic utilities for a neurological disorder; a cardiovascular, endothelial or angiogenic disorder; an immunological disorder; an oncological disorder, an embryonic developmental disorder or lethality, or a metabolic abnormality. For example, anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies may be used in diagnostic assays for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies also are useful for the affinity purification of PRO69122, PRO204, PRO214, PRO222, PRO234, PRO265, PRO309, PRO332, PRO342, PRO356, PRO540, PRO618, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides from recombinant cell culture or natural sources. In this process, the antibodies against PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides are immobilized on a suitable support, such a Sephadex resin or filter paper, using methods well known in the art. The immobilized antibody then is contacted with a sample containing the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide to be purified, and thereafter the support is washed with a suitable solvent that will remove substantially all the material in the sample except the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, which is bound to the immobilized antibody. Finally, the support is washed with another suitable solvent that will release the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, $MAL^+$, $SUC^+$, $GAL^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.,* 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.,* 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

```
                                         (SEQ ID NO: 143)
5'-TGTAAAACGACGGCCAGTTAAATAGACCTGCAATTATTAATCT-3'
```

The sequence of reverse oligonucleotide 2 was:

```
                                         (SEQ ID NO: 144)
5'-CAGGAAACAGCTATGACCACCTGCACACCTGCAAATCCATT-3'
```

PCR was then performed as follows:

| | | | |
|---|---|---|---|
| a. | | Denature | 92° C., 5 minutes |
| b. | 3 cycles of: | Denature | 92° C., 30 seconds |
| | | Anneal | 59° C., 30 seconds |
| | | Extend | 72° C., 60 seconds |
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below. In addition, the sequence of DNA284870 encoding PRO69122 polypeptides was identified from GenBank accession no.: AF052059; the sequence of DNA38649 encoding PRO342 polypeptides was identified from GenBank accession no.: AY358342; the sequence of DNA336539 encoding PRO36935 polypeptides was identified from GenBank accession no.: Z29083 the sequence of DNA222844 encoding PRO4979 polypeptides (also known as PRO38844 polypeptides) was identified from GenBank accession no.: AB098597; the sequence of DNA98380 encoding PRO6001 polypeptides was identified from GenBank accession no.: AY358785; the sequence of DNA226874 encoding PRO37337 polypeptides was identified from GenBank accession no.: Y07909; the sequence of DNA227033 encoding PRO37496 polypeptides was identified from GenBank accession no.: BC003006; and the sequence of DNA188342 encoding PRO21718 polypeptides was identified from GenBank accession no.: AF146761.

TABLE 7

| Material | ATCC Dep. No. | Deposit Date |
|---|---|---|
| DNA30871-1157 | 209380 | Oct. 16, 1997 |
| DNA32286-1191 | 209385 | Oct. 16, 1997 |
| DNA33107-1135 | 209251 | Sep. 16, 1997 |
| DNA35557-1137 | 209255 | Sep. 16, 1998 |
| DNA36350-1158 | 209378 | Oct. 16, 1997 |
| DNA61601-1223 | 209713 | Mar. 31, 1998 |
| DNA40982-1235 | 209433 | Nov. 7, 1997 |
| DNA47470-1130P1 | 209422 | Oct. 28, 1997 |
| DNA44189-1322 | 209699 | Mar. 26, 1998 |
| DNA49152-1324 | 209813 | Apr. 28, 1998 |
| DNA52185-1370 | 209861 | May 14, 1998 |
| DNA58855-1422 | 203018 | Jun. 23, 1998 |
| DNA56050-1455 | 203011 | Jun. 23, 1998 |
| DNA58727-1474 | 203171 | Sep. 1, 1998 |
| DNA62377-1381-1 | 203552 | Dec. 22, 1998 |
| DNA58850-1495 | 209956 | Jun. 9, 1998 |
| DNA59586-1520 | 203288 | Sep. 29, 1998 |
| DNA64896-1539 | 203238 | Sep. 9, 1998 |
| DNA64903-1553 | 203223 | Sep. 15, 1998 |
| DNA59218-1559 | 203287 | Sep. 29, 1998 |
| DNA59588-1571 | 203106 | Aug. 11, 1998 |
| DNA60608-1577 | 203126 | Aug. 18, 1998 |
| DNA58743-1609 | 203154 | Aug. 25, 1998 |
| DNA71159-1617 | 203135 | Aug. 18, 1998 |
| DNA73401-1633 | 203273 | Sep. 22, 1998 |
| DNA68818-2536 | 203657 | Feb. 9, 1999 |
| DNA61185-1646 | 203464 | Nov. 17, 1998 |
| DNA58732-1650 | 203290 | Sep. 29, 1998 |
| DNA68880-1676 | 203319 | Oct. 6, 1998 |
| DNA73735-1681 | 203356 | Oct. 20, 1998 |
| DNA62845-1684 | 203361 | Oct. 20, 1998 |
| DNA71286-1687 | 203357 | Oct. 20, 1998 |
| DNA77648-1688 | 203408 | Oct. 27, 1998 |
| DNA77301-1708 | 203407 | Oct. 27, 1998 |
| DNA68883-1691 | 203535 | Dec. 15, 1998 |
| DNA76396-1698 | 203471 | Nov. 17, 1998 |
| DNA77652-2505 | 203480 | Nov. 17, 1998 |
| DNA71235-1706 | 203584 | Jan. 12, 1999 |
| DNA45409-2511 | 203579 | Jan. 12, 1999 |
| DNA82302-2529 | 203534 | Dec. 15, 1998 |
| DNA82340-2530 | 203547 | Dec. 22, 1998 |
| DNA59844-2542 | 203650 | Feb. 9, 1999 |
| DNA90842-2574 | 203845 | Mar. 16, 1999 |
| DNA96893-2621 | PTA-12 | May 4, 1999 |
| DNA62849-2647 | PTA-205 | Jun. 8, 1999 |
| DNA97003-2649 | PTA-43 | May 11, 1999 |
| DNA94849-2960 | PTA-2306 | Jul. 25, 2000 |
| DNA115291-2681 | PTA-202 | Jun. 8, 1999 |
| DNA96988-2685 | PTA-384 | Jul. 20, 1999 |
| DNA105680-2710 | PTA-483 | Aug. 3, 1999 |
| DNA110700-2716 | PTA-512 | Aug. 10, 1999 |
| DNA108722-2743 | PTA-552 | Aug. 17, 1999 |
| DNA108670-2744 | PTA-546 | Aug. 17, 1999 |
| DNA119535-2756 | PTA-613 | Aug. 31, 1999 |
| DNA108700-2802 | PTA-1093 | Dec. 22, 1999 |
| DNA119474-2803 | PTA-1097 | Dec. 22, 1999 |
| DNA145841-2868 | PTA-1678 | Apr. 11, 2000 |
| DNA149911-2885 | PTA-1776 | Apr. 25, 2000 |
| DNA168028-2956 | PTA-2304 | Jul. 25, 2000 |
| DNA154095-2998 | PTA-2591 | Oct. 10, 2000 |
| DNA185171-2994 | PTA-2513 | Sep. 26, 2000 |
| DNA171732-3100 | PTA-3329 | Apr. 24, 2001 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA Clones Encoding Human PRO204 Polypeptides [UNQ178]

An expressed sequence tag (EST) DNA database (LIFESEQ®, Incyte Pharmaceuticals, Palo Alto, Calif.) was searched and an EST was identified. Human fetal retina cDNA libraries were screened with PCR oligonucleotide primers and confirmed by hybridization with synthetic oligonucleotide probe which was based upon the EST sequence.

```
hybridization probe:
                                        (SEQ ID NO: 145)
5'-GGCATGCAGCAGCTGGACATTTGCGAGGGCTTTTGCTGGCTG-3'

forward PCR primer:
                                        (SEQ ID NO: 146)
5'-CTGCTGCAGAGTTGCACGAAC-3'

reverse PCR primer 1:
                                        (SEQ ID NO: 147)
5'-CAGTTGTTGTTGTCACAGAGAAG-3'

reverse PCR primer 2:
                                        (SEQ ID NO: 148)
5'-AGTTCGTGCAACTCTGCAGCAG-3'
```

A cDNA clone was identified and sequenced in entirety. The entire nucleotide sequence of the identified clone DNA3087-1157 is shown in FIG. 3 (SEQ ID NO:3). Clone DNA30871-1157 (SEQ ID NO:3) contains a single open reading frame with an apparent translation initiation site at nucleotide positions 376-378 and ending at the stop codon (TAA) found at nucleotide positions 1498-1500 (FIG. 3; SEQ ID NO:3), as indicated by bolded underline. The predicted PRO204 polypeptide precursor (i.e., UNQ178, SEQ ID NO:4) is 374 amino acids long, has a calculated molecular weight of 39,285 daltons, a pI of 6.06 and is shown in FIG. 4. A cDNA containing DNA encoding UNQ178 (SEQ ID NO:3) has been deposited with the ATTC on Oct. 16, 1997 and has been assigned deposit number 209380.

Example 5

Isolation of cDNA Clones Encoding Human PRO214 Polypeptides [UNQ188]

A consensus DNA sequence was assembled using phrap as described in Example 1 above. This consensus DNA sequence is designated herein as DNA28744. Based on this consensus sequence, oligonucleotides were synthesized: 1) to identify by PCR a cDNA library that contained the sequence of interest, and 2) for use as probes to isolate a clone of the full-length coding sequence.

In order to screen several libraries for a source of a full-length clone, DNA from the libraries was screened by PCR amplification with the PCR primer pair identified below. A positive library was then used to isolate clones encoding the PRO214 gene using the probe oligonucleotide and one of the PCR primers.

RNA for construction of the cDNA libraries was isolated from human fetal lung tissue.

A cDNA clone was sequenced in its entirety. The full length nucleotide sequence of DNA32286-1191 is shown in FIG. 5 (SEQ ID NO:5). DNA32286-1191 contains a single open reading frame with an apparent translational initiation site at nucleotide position 103 (FIG. 5; SEQ ID NO:5). The predicted polypeptide precursor is 420 amino acids long (FIG. 6; SEQ ID NO:6).

Based on a BLAST and FastA sequence alignment analysis of the full-length sequence, PRO214 polypeptide shows amino acid sequence identity to HT protein and/or Fibulin (49% and 38%, respectively).

The oligonucleotide sequences used in the above procedure were the following:

```
28744.p (OLI555)
5'-CCTGGCTATCAGCAGGTGGGCTCCAAGTGTC (SEQ ID NO: 149)
TCGATGTGGATGAGTGTGA-3'

28744.f (OLI556)
5'-ATTCTGCGTGAACACTGAGGGC-3'       (SEQ ID NO: 150)

28744.r (OLI557)
5'-ATCTGCTTGTAGCCCTCGGCAC-3'       (SEQ ID NO: 151)
```

Example 6

Isolation of cDNA Clones Encoding Human PRO222 Polypeptides [UNQ196]

A consensus DNA sequence was assembled relative to the other identified EST sequences as described in Example 1 above, wherein the consensus sequence is designated herein as DNA28771. Based on the DNA28771 consensus sequence, oligonucleotides were synthesized to identify by PCR a cDNA library that contained the sequence of interest and for use as probes to isolate a clone of the full-length coding sequence for PRO222.

A pair of PCR primers (forward and reverse) were synthesized:

```
forward PCR primer
5'-ATCTCCTATCGCTGCTTTCCCGG-3' (SEQ ID NO: 152)

reverse PCR primer
5'-AGCCAGGATCGCAGTAAAACTCC-3' (SEQ ID NO: 153)
```

Additionally, a synthetic oligonucleotide hybridization probe was constructed from the consensus DNA28771 sequence which had the following nucleotide sequence:

```
hybridization probe
5'-ATTTAAACTTGATGGGTCTGCGTATCTTGAG (SEQ ID NO: 154)
TGCTTACAAAACCTTATCT-3'
```

In order to screen several libraries for a source of a full-length clone, DNA from the libraries was screened by PCR amplification with the PCR primer pair identified above. A positive library was then used to isolate clones encoding the PRO222 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO222 [herein designated as DNA33107-1135] and the derived protein sequence for PRO222.

The entire nucleotide sequence of DNA33107-1135 is shown in FIG. 7 (SEQ ID NO:7). Clone DNA33107-1135 contains a single open reading frame with an apparent translational initiation site at nucleotide positions 159-161 and ending at the stop codon at nucleotide positions 1629-1631 (FIG. 7; SEQ ID NO:7). The predicted polypeptide precursor is 490 amino acids long (FIG. 8; SEQ ID NO:8). Clone DNA33107-1135 has been deposited with ATCC on Sep. 16, 1997 and is assigned ATCC deposit no. ATCC 209251.

Based on a BLAST and FastA sequence alignment analysis of the full-length sequence, PRO222 shows amino acid sequence identity to mouse complement factor h precursor (25-26%), complement receptor (27-29%), mouse complement C3b receptor type 2 long form precursor (25-47%) and human hypothetical protein kiaa0247 (40%).

Example 7

Isolation of cDNA Clones Encoding Human PRO234 Polypeptides [UNQ208]

A consensus DNA sequence was assembled (DNA30926) using phrap as described in Example 1 above. Based on this consensus sequence, oligonucleotides were synthesized: 1) to identify by PCR a cDNA library that contained the sequence of interest, and 2) for use as probes to isolate a clone of the full-length coding sequence.

RNA for the construction of the cDNA libraries was isolated using standard isolation protocols, e.g., Ausubel et al., Current Protocols in Molecular Biology, from tissue or cell line sources or it was purchased from commercial sources (e.g., Clontech). The cDNA libraries used to isolate the cDNA clones were constructed by standard methods (e.g., Ausubel et al.) using commercially available reagents (e.g., Invitrogen). This library was derived from 22 week old fetal brain tissue.

A cDNA clone was sequenced in its entirety and is herein designated DNA35557-1137 (SEQ ID NO:9). The entire nucleotide sequence of DNA355557-1137 is shown in FIG. 9 (SEQ ID NO:9). The predicted polypeptide precursor is 382 amino acids long (designated PRO234; SEQ ID NO:10; FIG. 10) and has a calculated molecular weight of approximately 43.1 kDa.

The oligonucleotide sequences used in the above procedure were the following:

```
30926.p (OLI826) (SEQ ID NO: 155):
5'-GTTCATTGAAAACCTCTTGCCATCT GATGGTGACTTCTGGAT
TGGGCTCA-3'

30926.f (OLI827) (SEQ ID NO: 156):
5'-AAGCCAAAGAAGCCTGCAGGAGGG-3'

30926.r (OLI828) (SEQ ID NO: 157):
5'-CAGTCCAAGCATAAAGGTCCTGGC-3'
```

Example 8

Isolation of cDNA Clones Encoding Human PRO265 Polypeptides [UNQ232]

A consensus DNA sequence was assembled relative to other EST sequences as described in Example 1 above using phrap. This consensus sequence is herein designated DNA33679. Based on the DNA33679 consensus sequence, oligonucleotides were synthesized: 1) to identify by PCR a cDNA library that contained the sequence of interest, and 2) for use as probes to isolate a clone of the full-length coding sequence for PRO265.

PCR primers (two forward and one reverse) were synthesized:

```
forward PCR primer A:
5'-CGGTCTACCTGTATGGCAACC-3';  (SEQ ID NO: 158)

forward PCR primer B:
5'-GCAGGACAACCAGATAAACCAC-3'; (SEQ ID NO: 159)

reverse PCR primer
5'-ACGCAGATTTGAGAAGGCTGTC-3'  (SEQ ID NO: 160)
```

Additionally, a synthetic oligonucleotide hybridization probe was constructed from the consensus DNA33679 sequence which had the following nucleotide sequence

```
hybridization probe
5'-TTCACGGGCTGCTCTTGCCCAGCTCTTGAAG (SEQ ID NO: 161)
CTTGAAGAGCTGCAC-3'
```

In order to screen several libraries for a source of a full-length clone, DNA from the libraries was screened by PCR amplification with PCR primer pairs identified above. A positive library was then used to isolate clones encoding the PRO265 gene using the probe oligonucleotide and one of the PCR primers.

RNA for construction of the cDNA libraries was isolated from human a fetal brain library.

DNA sequencing of the clones isolated as described above gave the full-length DNA sequence for PRO265 [herein designated as DNA36350-1158] (SEQ ID NO:11) and the derived protein sequence for PRO265.

The entire nucleotide sequence of DNA36350-1158 is shown in FIG. 11 (SEQ ID NO:11). Clone DNA36350-1158 contains a single open reading frame with an apparent translational initiation site at nucleotide positions 352-354 and ending at the stop codon at positions 2332-2334 (FIG. 11). The predicted polypeptide precursor is 660 amino acids long (FIG. 12; SEQ ID NO:12). Clone DNA36350-1158 has been deposited with ATCC on Oct. 16, 1997 and is assigned ATCC deposit no. ATCC 209378.

Analysis of the amino acid sequence of the full-length PRO265 polypeptide suggests that portions of it possess significant homology to the fibromodulin and the fibromodulin precursor, thereby indicating that PRO265 may be a novel member of the leucine rich repeat family, particularly related to fibromodulin.

Example 9

Isolation of cDNA Clones Encoding Human PRO309 Polypeptides [UNQ272]

An expressed sequence tag (EST) DNA database (LIFESEQ™, Incyte Pharmaceuticals, Palo Alto, Calif.) was searched and an EST was identified which was in a fetal pancreas library which shared significant identity which the adaptor protein Shc. A full length cDNA corresponding to the isolated EST was cloned from a human fetal kidney library using an in vivo cloning technique (Nsp1) in pRK5. There is a single long open reading frame which encodes a 576 amino acid protein. The C-terminus of Nsp1 has no significant identity to any known mammalian proteins. This C-terminal sequence was then used to re-screen the EST database, wherein was found an additional fragment. From this sequence was constructed cloning and enrichment primers, and the corresponding full length sequence was isolated for Nsp3 using an in vivo cloning technique from a human placenta library in pRK5. The probes used for the cloning of the full length sequences were the following:

```
Nsp1:
Cloning:
                                              (SEQ ID NO: 162)
ACTGAGGCCTGTTGAAAGTGCAGAGCTCAG

Enrichment Primer:
                                              (SEQ ID NO: 163)
GCTGAAGAAGAGCTTCAG

Nsp3:
Cloning:
                                              (SEQ ID NO: 164)
GGCCAGCATGATGGACATGGTGTGGAACCTTTCCAGCAGGTCTAGGCGTA

Enrichment Primer:
                                              (SEQ ID NO: 165)
GGTGCAGCCCAGGATGTC
```

Nsp3 has an SH2 domain and a potential SH3 interaction domain (PS region). The proteins lack apparent kinase or phosphatase domains. cDNA clones Nsp1 Nsp3 were sequenced in their entirety. The entire nucleotide sequence of DNA61601-1223 [FIG. 13; SEQ ID NO:13] encoding PRO309 polypeptides [FIG. 14; SEQ ID NO:14] has been deposited with ATCC Mar. 31, 1998 and is assigned ATCC deposit number 209713.

Example 10

Isolation of cDNA Clones Encoding Human PRO332 Polypeptides [UNQ293]

Based upon an ECD homology search performed as described in Example 1 above, a consensus DNA sequence designated herein as DNA36688 was assembled. Based on the DNA36688 consensus sequence, oligonucleotides were synthesized to identify by PCR a cDNA library that contained the sequence of interest and for use as probes to isolate a clone of the full-length coding sequence for PRO332.

A pair of PCR primers (forward and reverse) were synthesized:

```
5'-GCATTGGCCGCGAGACTTTGCC-3'  (SEQ ID NO: 166)

5'-GCGGCCACGGTCCTTGGAAATG-3'  (SEQ ID NO: 167)
```

A probe was also synthesized:

```
5'-TGGAGGAGCTCAACCTCAGCTACAACCGCAT (SEQ ID NO: 168)
CACCAGCCCACAGG-3'
```

In order to screen several libraries for a source of a full-length clone, DNA from the libraries was screened by PCR amplification with the PCR primer pair identified above. A positive library was then used to isolate clones encoding the PRO332 gene using the probe oligonucleotide and one of the PCR primers.

RNA for construction of the cDNA libraries was isolated from a human fetal liver library (LIB229).

DNA sequencing of the clones isolated as described above gave the full-length DNA sequence for DNA40982-1235 and the derived protein sequence for PRO332.

The entire nucleotide sequence of DNA40982-1235 is shown in FIG. 15 (SEQ ID NO:15). Clone DNA40982-1235 contains a single open reading frame (with an apparent translational initiation site at nucleotide positions 342-344, as indicated in FIG. 15). The predicted polypeptide precursor is 642 amino acids long (FIG. 16; SEQ ID NO:16), and has a calculated molecular weight of 72,067 (pI: 6.60). Clone DNA40982-1235 has been deposited with ATCC Nov. 7, 1997 and is assigned ATCC deposit no. ATCC 209433.

Based on a BLAST and FastA sequence alignment analysis of the full-length sequence, PRO332 shows about 30-40% amino acid sequence identity with a series of known proteoglycan sequences, including, for example, fibromodulin and fibromodulin precursor sequences of various species (FMOD BOVIN, FMOD CHICK, FMOD RAT, FMOD MOUSE, FMOD HUMAN, P R36773), osteomodulin sequences (AB0001141, AB007848 1), decorin sequences (CFU831411, OCU033941, P R42266, P R42267, P R42260, P R89439), keratan sulfate proteoglycans (BTU483601, AF0228901), corneal proteoglycan (AF0222561), and bone/cartilage proteoglycans and proteoglycane precursors (PGS1 BOVIN, PGS2 MOUSE, PGS2 HUMAN).

Example 11

Isolation of cDNA Clones Encoding Human PRO356 (NL4) Polypeptides [UNQ313]

An expressed sequence tag (EST) DNA database (LIFESEQ®, Incyte Pharmaceuticals, Palo Alto, Calif.) was searched and an EST (#2939340) was identified which showed homology to human TIE-2 L1 and TIE-2 L2.

Based on the EST, a pair of PCR primers (forward and reverse), and a probe were synthesized:

```
                                              (SEQ ID NO: 169)
NL4,5-1: 5'-TTCAGCACCAAGGACAAGGACAATGACAACT-3'

                                              (SEQ ID NO: 170)
NL4,3-1: 5'-TGTGCACACTTGTCCAAGCAGTTGTCATTGTC-3'

                                              (SEQ ID NO: 171)
NL4,3-3: 5'-GTAGTACACTCCATTGAGGTTGG-3'.
```

Oligo dT primed cDNA libraries were prepared from uterus mRNA purchased from Clontech, Inc. (Palo Alto, Calif., USA, catalog #6537-1) in the vector pRK5D using reagents and protocols from Life Technologies, Gaithersburg, Md. (Super Script Plasmid System). pRK5D is a cloning vector that has an sp6 transcription initiation site followed by an SfiI restriction enzyme site preceding the XhoI/NotI cDNA cloning sites. The cDNA was primed with oligo dT containing a NotI site, linked with blunt to SalI hemikinased adaptors, cleaved with NotI, sized to greater than 1000 bp appropriately by gel electrophoresis, and cloned in a defined orientation into XhoI/NotI-cleaved pRK5D.

In order to screen several libraries for a source of a full-length clone, DNA from the libraries was screened by PCR amplification with the PCR primer pair identified above. A positive library was then used to isolate clones encoding the PRO356 gene using the probe oligonucleotide and one of the PCR primers.

DNA sequencing of the clones isolated as described above gave a full-length DNA sequence DNA47470-1130P1 (SEQ ID NO:19; FIG. 19) and the derived PRO356 protein (SEQ ID NO:20; FIG. 20) shown in FIGS. 19 & 20 respectively.

The entire nucleotide sequence of DNA47470-1130P1 is shown in FIG. 19 (SEQ ID NO:19). Clone DNA47470-1130P1 (SEQ ID NO:19) contains a single open reading frame with an apparent translation initiation site at nucleotide positions 215-217, and a TAA stop codon at nucleotide positions 1038-1040, as indicated by bolded underline. The predicted PRO356 polypeptide shown in FIG. 20 is 346 amino acids long (SEQ ID NO:20), has a calculated molecular weight of 40,018 daltons and a pI of 8.19. A cDNA clone containing DNA47470-1130P1 (SEQ ID NO:19) has been deposited with ATCC on Oct. 28, 1997 and is assigned ATCC deposit no. 209422.

Further analysis of the PRO356 polypeptide of FIG. 20 (SEQ ID NO:20) reveals: a signal peptide at amino acid residues 1 to about 26, N-glycosylation sites at about residues 58-62, 253-257 and 267-271, glycosyaminoglycan attachment sites at residues 167-171, a cAMP- and cGMP-dependent protein kinase phosphorylation site at about residues 176-180, N-myristoylation sites at about residues 168-174, 196-202, 241-247, 252-258, 256-262, 327-333, a cell attachment sequence at about residues 199-202, and fibrinogen beta and gamma chains C-terminal domain proteins at about residues 160-198, 201-210, 219-256, 266-279, 283-313.

Example 12

Isolation of cDNA Clones Encoding Human PRO540 Polypeptides [UNQ341]

A consensus sequence was obtained relative to a variety of EST sequences as described in Example 1 above, wherein the consensus sequence obtained is herein designated DNA39631. Based on the DNA39631 consensus sequence, oligonucleotides were synthesized: 1) to identify by PCR a cDNA library that contained the sequence of interest, and 2) for use as probes to isolate a clone of the full-length coding sequence for PRO540.

Forward and reverse PCR primers were synthesized:

```
forward PCR primer
5'-CTGGGGCTACACACGGGGTGAGG-3'     (SEQ ID NO: 172)

reverse PCR primer
5'-GGTGCCGCTGCAGAAAGTAGAGCG-3'    (SEQ ID NO: 173)
```

Additionally, a synthetic oligonucleotide hybridization probe was constructed from the consensus DNA40654 sequence which had the following nucleotide sequence

```
hybridization probe
5'-GCCCCAAATGAAAACGGGCCCTACTTCCTGG (SEQ ID NO: 174)
CCCTCCGCGAGATG-3'
```

In order to screen several libraries for a source of a full-length clone, DNA from the libraries was screened by PCR amplification with one of the PCR primer pairs identified above. A positive library was then used to isolate clones encoding the PRO540 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO540 [herein designated as UNQ341 (DNA44189-1322)] (SEQ ID NO:21) and the derived protein sequence for PRO540.

The entire nucleotide sequence of UNQ341 (DNA44189-1322) is shown in FIG. 21 (SEQ ID NO:21). Clone UNQ341 (DNA44189-1322) contains a single open reading frame with an apparent translational initiation site at nucleotide positions 21-23 and ending at the stop codon at nucleotide positions 1257-1259 (FIG. 21). The predicted polypeptide precursor is 412 amino acids long (FIG. 22; SEQ ID NO:22). The full-length PRO540 protein shown in FIG. 22 has an estimated molecular weight of about 46,658 daltons and a pI of about 6.65. Important regions of the amino acid sequence of PRO540 include the signal peptide, potential N-glycosylation sites, a potential lipid substrate binding site, a sequence typical of lipases and serine proteins, and a beta-transducin family Trp-Asp repeat. Clone UNQ341 (DNA44189-1322) has been deposited with ATCC on Mar. 26, 1998 and is assigned ATCC deposit no. 209699.

Example 13

Isolation of cDNA Clones Encoding Human PRO618 Polypeptides [UNQ354]

A consensus sequence was obtained relative to a variety of EST sequences as described in Example 1 above, wherein the consensus sequence obtained is herein designated DNA30900. Based on the DNA30900 consensus sequence, oligonucleotides were synthesized: 1) to identify by PCR a cDNA library that contained the sequence of interest, and 2) for use as probes to isolate a clone of the full-length coding sequence for PRO618.

Forward and reverse PCR primers were synthesized:

```
forward PCR primer
5'-TAACAGCTGCCCACTGCTTCCAGG-3'    (SEQ ID NO: 175)

reverse PCR primer
5'-TAATCCAGCAGTGCAGGCCGGG-3'      (SEQ ID NO: 176)
```

Additionally, a synthetic oligonucleotide hybridization probe was constructed from the consensus DNA30900 sequence which had the following nucleotide sequence

```
hybridization probe
5'-ATGGCCTCCACGGTGCTGTGGACCGTGTTC  (SEQ ID NO: 177)
CTGGGCAAGGTGTGGCAGAA-3'
```

Screening of the above described library gave rise to the partial cDNA clone designated herein DNA3559. Extension of this sequence using repeated cycles of BLAST and phrap gave rise to a nucleotide sequence designated herein as DNA43335. Primers based upon the DNA43335 consensus sequence were then prepared as follows.

```
forward PCR primer
5'-TGCCTATGCACTGAGGAGGCAGAAG-3'   (SEQ ID NO: 178)

reverse PCR primer
5'-AGGCAGGGACACAGAGTCCATTCAC-3'   (SEQ ID NO: 179)
```

Additionally, a synthetic oligonucleotide hybridization probe was constructed from the consensus DNA43335 sequence which had the following nucleotide sequence

```
hybridization probe
5'-AGTATGATTTGCCGTGCACCCAGGGCCAGTG (SEQ ID NO: 180)
GACGATCCAGAACAGGAGG-3'
```

In order to screen several libraries for a source of a full-length clone, DNA from the libraries was screened by PCR amplification with one of the PCR primer pairs identified above. A positive library was then used to isolate full length clones encoding the PRO618 gene using the second probe oligonucleotide and one of the second set of PCR primers. RNA for construction of the cDNA libraries was isolated from human fetal liver tissue (LIB229).

DNA sequencing of the clones isolated as described above gave the full-length DNA sequence for PRO618 [herein designated as UNQ354 (DNA49152-1324)] (SEQ ID NO:23) and the derived protein sequence for PRO618.

Figure 23:
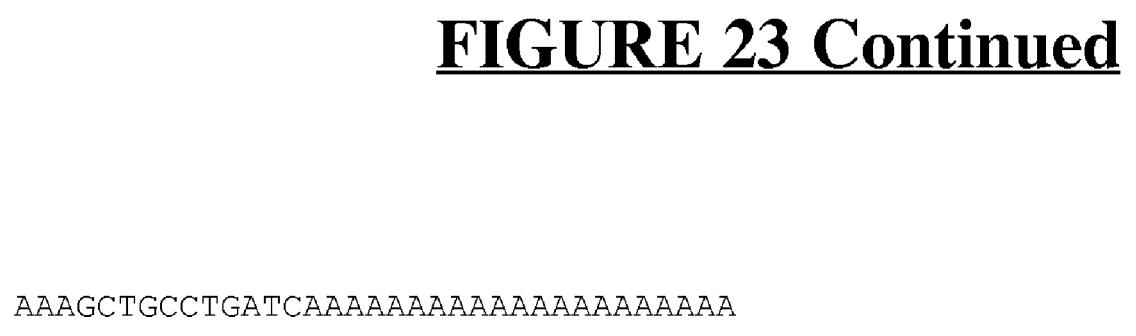

The entire nucleotide sequence of UNQ354 (DNA49152-1324) is shown in FIG. 23 (SEQ ID NO:23). Clone UNQ354 (DNA49152-1324) contains a single open reading frame with an apparent translational initiation site at nucleotide positions 73-75 and ending at the stop codon at nucleotide positions 2479-2481 (FIG. 23). The predicted polypeptide precursor is 802 amino acids long (FIG. 24; SEQ ID NO:24). The full-length PRO618 protein shown in FIG. 24 has an estimated molecular weight of about 88,846 daltons and a pI of about 6.41. Important regions of the amino acid sequence of PRO618 include type II transmembrane domain, a sequence typical of a protease, trypsin family, histidine active site, multiple N-glycosylation sites, two sequences typical of a Kringle domain, two regions having sequence similarity to Kallikrein light chain, and a region having sequence similarity to low-density lipoprotein receptor. Clone UNQ354 (DNA49152-1324) has been deposited with ATCC on Apr. 28, 1998 and is assigned ATCC deposit no. 209813.

Example 14

Isolation of cDNA Clones Encoding Human PRO944 Polypeptides [UNQ481]

A consensus sequence was obtained relative to a variety of EST sequences as described in Example 1 above, wherein the consensus sequence obtained is herein designated DNA47374. A variety of proprietary Genentech EST sequences were employed in the assembly. Based on the DNA47374 consensus sequence, oligonucleotides were synthesized: 1) to identify by PCR a cDNA library that contained the sequence of interest, and 2) for use as probes to isolate a clone of the full-length coding sequence for PRO944.

A pair of PCR primers (forward and reverse) were synthesized:

```
forward PCR primer
5'-CGAGCGAGTCATGGCCAACGC-3'       (SEQ ID NO: 181)

reverse PCR primer
5'-GTGTCACACGTAGTCTTTCCCGCTGG-3'  (SEQ ID NO: 182)
```

Additionally, a synthetic oligonucleotide hybridization probe was constructed from the consensus DNA47374 sequence which had the following nucleotide sequence

```
hybridization probe
                                          (SEQ ID NO: 183)
5'-CTGCAGCTGTTGGGCTTCATTCTCGCCTTCCTGGGATGGATCG-3'
```

In order to screen several libraries for a source of a full-length clone, DNA from the libraries was screened by PCR amplification with the PCR primer pair identified above. A positive library was then used to isolate clones encoding the PRO944 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO944 [herein designated as UNQ481 (DNA52185-1370)] (SEQ ID NO:25) and the derived protein sequence for PRO944.

The entire nucleotide sequence of UNQ481 (DNA52185-1370) is shown in FIG. 25 (SEQ ID NO:25). Clone UNQ481 (DNA52185-1370) contains a single open reading frame with an apparent translational initiation site at nucleotide positions 219-221 and ending at the stop codon at nucleotide positions 852-854 (FIG. 25). The predicted polypeptide precursor is 211 amino acids long (FIG. 26; SEQ ID NO:26). The full-length PRO944 protein shown in FIG. 26 has an estimated molecular weight of about 22,744 daltons and a pI of about 8.51. Analysis of the full-length PRO944 sequence shown in FIG. 26 (SEQ ID NO:26) evidences the presence of the following: a signal peptide from about amino acid 1 to about amino acid 21, transmembrane domains from about amino acid 82 to about amino acid 102, from about amino acid 118 to about amino acid 142 and from about amino acid 161 to about amino acid 187, a potential N-glycosylation site from about amino acid 72 to about amino acid 75, a sequence block having homology to PMP-22/EMP/MP20 family of proteins from about amino acid 70 to about amino acid 111 and a sequence block having homology to ABC-2 type transport system integral membrane protein from about amino acid 119 to about amino acid 133. Clone UNQ481 (DNA52185-1370) has been deposited with ATCC on May 14, 1998 and is assigned ATCC deposit no. 209861.

Analysis of the amino acid sequence of the full-length PRO944 polypeptide suggests that it possesses significant sequence similarity to the CPE-R protein, thereby indicating that PRO944 may be a novel CPE-R homolog. More specifically, an analysis of the Dayhoff database (version 35.45 SwissProt 35) evidenced significant homology between the PRO944 amino acid sequence and the following Dayhoff sequences, AB000713_1, AB000714_1, AF035814_1, AF000959_1, HSU89916_1, EMP2_HUMAN, JC5732, CELF53B3_6, PM22_MOUSE and CGU49797_1.

Example 15

Isolation of cDNA Clones Encoding Human PRO994 Polypeptides [UNQ518]

Use of the signal sequence algorithm described in Example 3 above allowed identification of an EST cluster sequence from the Incyte database, designated 157555. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA55728.

In light of an observed sequence homology between the DNA55728 consensus sequence and an EST sequence encompassed within the Incyte EST clone no. 2860366, the Incyte EST clone 2860366 was purchased and the cDNA insert was obtained and sequenced. It was found that this insert encoded a full-length protein. The sequence of this cDNA insert is shown in FIG. 27 and is herein designated as DNA58855-1422.

Clone DNA58855-1422 contains a single open reading frame with an apparent translational initiation site at nucleotide positions 31-33 and ending at the stop codon at nucleotide positions 718-720 (FIG. 27; SEQ ID NO:27). The predicted polypeptide precursor is 229 amino acids long (FIG. 28; SEQ ID NO:28). The full-length PRO994 protein shown in FIG. 28 has an estimated molecular weight of about 25,109 daltons and a pI of about 6.83. Analysis of the full-length PRO994 sequence shown in FIG. 28 (SEQ ID NO:28) evidences the presence of the following: transmembrane domains from about amino acid 10 to about amino acid 31, from about amino acid 50 to about amino acid 72, from about amino acid 87 to about amino acid 110 and from about amino acid 191 to about amino acid 213, potential N-glycosylation sites from about amino acid 80 to about amino acid 83, from about amino acid 132 to about amino acid 135, from about amino acid 148 to about amino acid 151 and from about amino acid 163 to about amino acid 166 and an amino acid block having homology to TNFR/NGFR cysteine-rich region proteins from about amino acid 4 to about amino acid 11. Clone DNA58855-1422 has been deposited with ATCC on Jun. 23, 1998 and is assigned ATCC deposit no. 203018.

An analysis of the Dayhoff database (version 35.45 SwissProt 35), using a WU-BLAST2 sequence alignment analysis of the full-length sequence shown in FIG. 28 (SEQ ID NO:28), evidenced significant homology between the PRO994 amino acid sequence and the following Dayhoff sequences: AF027204_1, TAL6_HUMAN, ILT4_HUMAN, JC6205, MMU57570_1, S40363, ETU56093_1, S42858, P_R66849 an P_R74751.

Example 16

Isolation of cDNA Clones Encoding Human PRO1079 Polypeptides [UNQ536]

A consensus DNA sequence was assembled relative to other EST sequences using phrap as described in Example 1 above, and is herein designated DNA52714. Based on information provided by the assembly, the clone for Merck EST no. HO6898 was obtained and sequenced, thereby giving the nucleotide sequence designated herein as DNA56050-1455. The entire nucleotide sequence of DNA56050-1455 is shown in FIG. 29 (SEQ ID NO:29). Clone DNA56050-1455 contains a single open reading frame with an apparent translational initiation site at nucleotide positions 183-185 and ending at the stop codon at nucleotide positions 861-863 (FIG. 29). The predicted polypeptide precursor is 226 amino acids long (FIG. 30; SEQ ID NO:30). The full-length PRO1079 protein shown in FIG. 30 has an estimated molecular weight of about 24,611 Daltons and a pI of about 4.85. Analysis of the full-length PRO1079 sequence shown in FIG. 30 (SEQ ID NO:30) evidences the presence of the following features: a signal peptide at about amino acid 1-29; potential N-myristoylation sites at about amino acids 10-15, and 51-56; homology to photosystem I psaG and psaK proteins at about amino acids 2 to 20; and homology to prolyl endopeptidase family serine proteins at about amino acids 150 to 163.

Analysis of the amino acid sequence of the full-length PRO1079 polypeptide using the Dayhoff database (version 35.45 SwissProt 35) evidenced some sequence identity between the PRO1079 amino acid sequence and the following Dayhoff sequences: CEK10C3_4, MMU50734_1, D69503, AF051149_1, and VSMP_CVMS.

Clone UNQ536 (DNA56050-1455) was deposited with the ATCC on Jun. 23, 1998, and is assigned ATCC deposit no. 203011.

Example 17

Isolation of cDNA Clones Encoding Human PRO1110 Polypeptides [UNQ553]

A cDNA clone (DNA58727-1474) encoding a native human PRO1110 polypeptide was identified by a yeast screen, in a human fetal kidney cDNA library that preferentially represents the 5' ends of the primary cDNA clones. The yeast screen employed identified a single EST clone designated herein as DNA45566. The DNA45566 sequence was then compared to various EST databases including public EST databases (e.g., GenBank), and a proprietary EST database (LIFESEQ®, Incyte Pharmaceuticals, Palo Alto, Calif.) to identify homologous EST sequences. The comparison was performed using the computer program BLAST or BLAST2 [Altschul et al., Methods in Enzymology, 266:460-480 (1996)]. Those comparisons resulting in a BLAST score of 70 (or in some cases, 90) or greater that did not encode known proteins were clustered and assembled into a consensus DNA sequence with the program "phrap" (Phil Green, University of Washington, Seattle, Wash.). This consensus sequence is herein designated DNA46965. Oligonucleotide primers based upon the DNA46965 sequence were then synthesized and employed to screen a human SK-Lu-1 adenocarcinoma cDNA library (LIB247) which resulted in the identification of the DNA58727-1474 clone shown in FIG. 31.

The full-length DNA58727-1474 clone shown in FIG. 31 contains a single open reading frame with an apparent translational initiation site at nucleotide positions 131-133 and ending at the stop codon at nucleotide positions 1097-1099 (FIG. 31; SEQ ID NO:31). The predicted polypeptide precursor is 322 amino acids long (FIG. 32; SEQ ID NO:32). The full-length PRO1110 protein shown in FIG. 32 has an estimated molecular weight of about 35,274 daltons and a pI of about 8.57. Analysis of the full-length PRO1110 sequence shown in FIG. 32 (SEQ ID NO:32) evidences the presence of the following: transmembrane domains from about amino acid 41 to about amino acid 60, from about amino acid 66 to about amino acid 85, from about amino acid 101 to about amino acid 120, from about amino acid 137 to about amino acid 153, from about amino acid 171 to about amino acid 192, from about amino acid 205 to about amino acid 226, from about amino acid 235 to about amino acid 255 and from about amino acid 294 to about amino acid 312, a potential N-glycosylation site from about amino acid 6 to about amino acid 69, and a glycosaminoglycan attachment site from about amino acid 18 to about amino acid 21. Clone DNA58727-1474 has been deposited with ATCC on Sep. 1, 1998 and is assigned ATCC deposit no. 203171.

An analysis of the Dayhoff database (version 35.45 SwissProt 35), using a WU-BLAST2 sequence alignment analysis of the full-length sequence shown in FIG. 32 (SEQ ID NO:32), evidenced significant homology between the PRO1110 amino acid sequence and the following Dayhoff sequences: MMMYELUPR__1, P_R99799, MAL_HUMAN, P_P80929, RNMALGENE__1, S68406, PLLP_RAT, MMMALPROT__1, I38891 and S55622.

Example 18

Isolation of cDNA Clones Encoding Human PRO1122 Polypeptides [UNQ561]

An expressed sequence tag (EST) DNA database (LIFESEQ®, Incyte Pharmaceuticals, Palo Alto, Calif.) was searched and an EST was identified. The EST was Incyte 1347523 also called DNA49665. Based on DNA49665, oligonucleotides were synthesized: 1) to identify by PCR a cDNA library that contained the sequence of interest, and 2) for use as probes to isolated a clone of the full-length coding sequence for the PRO1122. [e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995)].

Forward and reverse PCR primers generally range from 20 to 30 nucleotides and are often designed to give a PCR product of about 100-1000 bp in length. The probes sequences are typically 40-55 bp in length. In some cases, additional oligonucleotides are synthesized when the consensus sequence is greater than about 1-1.5 kpb. In order to screen several libraries for a full-length clone, DNA from the libraries was screened by PCR amplification, as per Ausuble et al., Current Protocols in Molecular Biology, with the PCR primer pair. A positive library was then used to isolate clones encoding the gene of interest using the probe oligonucleotide and one of the primer pairs.

PCR primers (forward, reverse and hybridization) were synthesized:

```
forward PCR primer:
                                        (SEQ ID NO: 184)
5'-ATCCACAGAAGCTGGCCTTCGCCG-3'

reverse PCR primer:
                                        (SEQ ID NO: 185)
5'-GGGACGTGGATGAACTCGGTGTGG-3'

hybridization probe:
                                        (SEQ ID NO: 186)
5'-TATCCACAGAAGCTGGCCTTCGCCGAGTGCCTGTGCAGAG-3'.
```

In order to screen several libraries for a source of a full-length clone, DNA from the libraries was screened by PCR amplification with the PCR primer pair identified above. A positive library was then used to isolate clones encoding the PRO1122 gene using the probe oligonucleotide and one of the PCR primers.

RNA for construction of the cDNA libraries was isolated from human fetal kidney tissue. The cDNA libraries used to isolate the cDNA clones were constructed using standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 235: 1278-1280 (1991)) in the unique XhoI and NotI sites.

DNA sequencing of the clones isolated as described above gave the full-length DNA sequence for PRO1122 [herein designated as DNA62377-1381-1](SEQ ID NO:33) and the derived protein PRO1122 sequence (UNQ561)(SEQ ID NO:34).

The entire nucleotide sequence of DNA62377-1381-1 (SEQ ID NO:33) is shown in FIG. 33 (SEQ ID NO:33). Clone DNA62377-1381-1 (SEQ ID NO:33) contains a single open reading frame with an apparent translational initiation site at nucleotide positions 50-52 and ending at the stop codon at nucleotide positions 641-643 of SEQ ID NO:33 (FIG. 33). The predicted polypeptide precursor is 197 amino acids long (FIG. 34; SEQ ID NO:34). The full-length PRO1122 protein shown in FIG. 34 (UNQ561)(SEQ ID NO:34) has an estimated molecular weight of about 21765 daltons and a pI of about 8.53. Clone DNA62377-1381-1 has been deposited with the ATCC on Dec. 22, 1998 and has been assigned deposit number 203552. It is understood that in the event or a sequencing irregularity or error in the sequences provided herein, the correct sequence is the sequence deposited. Furthermore, all sequences provided herein are the result of known sequencing techniques.

Analysis of the amino acid sequence of the isolated full-length PRO1122 (UNQ561) suggests that it possesses similarity with IL-17, thereby indicating that PRO1122 (UNQ561) may be a novel cytokine and is herein designated IL-17C. FIG. 34 (SEQ ID NO:34) also shows the approximate locations of the signal peptide, leucine zipper pattern, and a region having sequence identity with IL-17.

Example 19

Isolation of cDNA Clones Encoding Human PRO1138 Polypeptides [UNQ576]

Use of the signal sequence algorithm described in Example 3 above allowed identification of a single Incyte EST sequence, Incyte cluster sequence no. 165212. This cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated as DNA54224. The assembly included a proprietary Genentech EST designated herein as DNA49140.

In light of an observed sequence homology between the DNA54224 consensus sequence and an EST sequence encompassed within the Incyte EST clone no. 3836613, the Incyte EST clone 3836613 was purchased and the cDNA insert was obtained and sequenced. It was found that this insert encoded a full-length protein. The sequence of this cDNA insert is shown in FIG. 35 and is the full-length DNA sequence for PRO1138. Clone DNA58850-1495 was deposited with the ATCC on Jun. 9, 1998, and is assigned ATCC deposit no. 209956.

The entire nucleotide sequence of DNA58850-1495 is shown in FIG. 35 (SEQ ID NO:35). Clone DNA58850-1495 contains a single open reading frame with an apparent translational initiation site at nucleotide positions 38-40 and ending at the stop codon at nucleotide positions 1043-1045 (FIG. 35). The predicted polypeptide precursor is 335 amino acids long (FIG. 36; SEQ ID NO:36). The full-length PRO1138 protein shown in FIG. 36 has an estimated molecular weight of about 37,421 Daltons and a pI of about 6.36. Analysis of the full-length PRO1138 sequence shown in FIG. 36 (SEQ ID NO:36) evidences the presence of the following features: a signal peptide at about amino acid 1 to about amino acid 22; a transmembrane domain at about amino acids 224 to about 250; a leucine zipper pattern at about amino acids 229 to about 250; and potential N-glycosylation sites at about amino acids 98-101, 142-145, 148-151, 172-175, 176-179, 204-207, and 291-295.

Analysis of the amino acid sequence of the full-length PRO1138 polypeptide suggests that it possesses significant sequence similarity to the CD84, thereby indicating that PRO1138 may be a novel member of the Ig superfamily of polypeptides. More particularly, analysis of the amino acid sequence of the full-length PRO1138 polypeptide using the Dayhoff database (version 35.45 SwissProt 35) evidenced homology between the PRO1138 amino acid sequence and the following Dayhoff sequences: HSU82988_1, HUMLY9_1, P_R97631, P_R97628, P_R97629, P_R97630, CD48_RAT, CD2_HUMAN, P_P93996, and HUMBGP_1.

Clone DNA58850-1495 was deposited with ATCC on Jun. 9, 1998, and is assigned ATCC deposit no. 209956.

Example 20

Isolation of cDNA Clones Encoding Human PRO1190 Polypeptides [UNQ604]

The method described in Example 1 above allowed the identification of a single Merck/Washington University EST sequence, EST no. AA339802, which is designated herein as "DNA53943". Based on the DNA53943 sequence, oligonucleotides were synthesized: 1) to identify by PCR a cDNA library that contained the sequence of interest, and 2) for use as probes to isolate a clone of the full-length coding sequence for PRO1190.

PCR primers (forward and reverse) were synthesized:

```
forward PCR primer:
                                        (SEQ ID NO: 187)
(53943.f1) GGGAAACACAGCAGTCATTGCCTGC

reverse PCR primer:
                                        (SEQ ID NO: 188)
(53943.r1) GCACACGTAGCCTGTCGCTGGAGC
```

Additionally, a synthetic oligonucleotide hybridization probe was constructed from the DNA53943 sequence which had the following nucleotide sequence:

```
hybridization probe:
(53943.p1) CACCCCAAAGCCCAGGTCCGGT  (SEQ ID NO: 189)
ACAGCGTCAAACAAGAGTGG
```

In order to screen several libraries for a source of a full-length clone, DNA from the libraries was screened by PCR amplification with the PCR primer pair identified above. A positive library was then used to isolate clones encoding the PRO1190 gene using the probe oligonucleotide and one of the PCR primers. RNA for construction of the cDNA libraries was isolated from human bone marrow.

DNA sequencing of the clones isolated as described above gave the full-length DNA sequence for PRO1190 (designated herein as DNA59586-1520 [FIG. 37, SEQ ID NO:37]; and the derived protein sequence for PRO1190.

The entire coding sequence of PRO1190 is shown in FIG. 37 (SEQ ID NO:37). Clone DNA59586-1520 contains a single open reading frame with an apparent translational initiation site at nucleotide positions 340-342 and an apparent stop codon at nucleotide positions 3685-3687. The predicted polypeptide precursor is 1115 amino acids long. The full-length PRO1190 protein shown in FIG. 38 (SEQ ID NO:38) has an estimated molecular weight of about 121,188 daltons and a pI of about 7.07. Other features of the PRO1190 protein include: two transmembrane domains at amino acids 16-30 and 854-879; a cytochrome P450 cysteine heme-iron ligand signature at amino acids 1051-1060; an N-6 adenine-specific DNA methylases signature at amino acids 1045-1051; and potential N-glycosylation sites at amino acids 65-68, 76-79, 98-101, 189-192, 275-278, 518-521, 726-729, and 760-763. Clone DNA59586-1520 was deposited with the ATCC on Sep. 29, 1998, and is assigned ATCC deposit no. 203288.

An analysis of the Dayhoff database (version 35.45 SwissProt 35), using a WU-BLAST2 sequence alignment analysis of the full-length sequence shown in FIG. 38 (SEQ ID NO:38), revealed homology between the PRO1190 amino acid sequence and the following Dayhoff sequences: AF004840_1, AF004841_1, AF026465_1, HSU72391_1, P_R13144, AXO1_HUMAN, GEN13349, I58164, D87212_1, A53449, and D86983_1, and KIAA0230.

Example 21

Isolation of cDNA Clones Encoding Human PRO1272 Polypeptides [UNQ642]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58753.

In light of an observed sequence homology between the DNA58753 sequence and an EST sequence contained within the EST clone 3049165, the Incyte clone (from a lung library) including EST 3049165 was purchased and the cDNA insert was obtained and sequenced. The sequence of this cDNA insert is shown in FIG. 39 and is herein designated as DNA64896-1539.

The full length clone shown in FIG. 39 contained a single open reading frame with an apparent translational initiation site at nucleotide positions 58-60 and ending at the stop codon found at nucleotide positions 556-558 (FIG. 39; SEQ ID NO:39). The predicted polypeptide precursor (FIG. 40, SEQ ID NO:40) is 166 amino acids long. The signal peptide is at about amino acids 1-23 of SEQ ID NO:40. PRO1272 has a calculated molecular weight of approximately 19,171 daltons and an estimated pI of approximately 8.26. Clone DNA64896-1539 was deposited with the ATCC on Sep. 9, 1998 and is assigned ATCC deposit no. 203238.

An analysis of the Dayhoff database (version 35.45 SwissProt 35), using a WU-BLAST2 sequence alignment analysis of the full-length sequence shown in FIG. 40 (SEQ ID NO:40), revealed sequence identity between the PRO1272 amino acid sequence and the following Dayhoff sequences (information from database incorporated herein): AF025474_1, D69100, AE000757_10, H69466, CELC50E3_12, XLRANBP1_1, YD67_SCHPO, B69459, H36856, and FRU40755_1.

Example 22

Isolation of cDNA Clones Encoding Human PRO1286 Polypeptides [UNQ655]

Use of the signal sequence algorithm described in Example 3 above allowed identification of an EST cluster sequence from the LIFESEQ® database, designated EST Cluster No. 86809. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program “phrap” (Phil Green, University of Washington, Seattle, Wash.). ESTs in the assembly included those identified from tumors, cell lines, or diseased tissue. One or more of the ESTs was obtained from a cDNA library constructed from RNA isolated from diseased colon tissue. The consensus sequence obtained therefrom is herein designated DNA58822.

In light of the sequence homology between the DNA58822 sequence and an EST sequence contained within EST no. 1695434, EST clone no. 1695434 was purchased and the cDNA insert was obtained and sequenced. The sequence of this cDNA insert is shown in FIG. 41 and is herein designated DNA64903-1553 (SEQ ID NO:41).

The full length clone shown in FIG. 41 contained a single open reading frame with an apparent translational initiation site at nucleotide positions 93-95 and ending at the stop codon found at nucleotide positions 372-374 (FIG. 41; SEQ ID NO:41). The predicted polypeptide precursor (FIG. 42, SEQ ID NO:42) is 93 amino acids long, with a signal sequence at about amino acids 1-18. PRO1286 has a calculated molecular weight of approximately 10,111 daltons and an estimated pI of approximately 9.70.

An analysis of the Dayhoff database (version 35.45 SwissProt 35), using a WU-BLAST2 sequence alignment analysis of the full-length sequence shown in FIG. 42 (SEQ ID NO:42), revealed some homology between the PRO1286 amino acid sequence and the following Dayhoff sequences: SR5C_ARATH, CELC17H12_11, MCPD_ENTAE, JQ2283, INVO_LEMCA, P_R07309, ADEVBCAGN_4, AF020947_1, CELT23H2_1, and MDH_STRAR.

Clone DNA64903-1553 was deposited with the ATCC on Sep. 15, 1998 and is assigned ATCC deposit no. 203223.

Example 23

Isolation of cDNA Clones Encoding Human PRO1295 Polypeptides [UNQ664]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. One or more of the ESTs was derived from a thymus tissue library. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program “phrap” (Phil Green, University of Washington, Seattle, Wash.). The consensus sequence obtained therefrom is herein designated DNA56262.

In light of the sequence homology between the DNA56262 sequence and an EST contained within the Incyte EST 3743334, the clone including this EST was purchased and the cDNA insert was obtained and sequenced. The sequence of this cDNA insert is shown in FIG. 43 and is herein designated as DNA59218-1559.

The full length clone shown in FIG. 43 contained a single open reading frame with an apparent translational initiation site at nucleotide positions 207-209 and ending at the stop codon found at nucleotide positions 1047-1049 (FIG. 43; SEQ ID NO:43). The predicted polypeptide precursor (FIG. 44, SEQ ID NO:44) is 280 amino acids long. The signal peptide is at about amino acids 1-18 of SEQ ID NO:44. A targeting signal and N-glycosylation site are also indicated in FIG. 44. PRO1295 has a calculated molecular weight of approximately 30,163 daltons and an estimated pI of approximately 6.87. Clone DNA59218-1559 was deposited with the ATCC on Sep. 29, 1998 and is assigned ATCC deposit no. 203287.

An analysis of the Dayhoff database (version 35.45 SwissProt 35), using a WU-BLAST2 sequence alignment analysis of the full-length sequence shown in FIG. 44 (SEQ ID NO:44), revealed sequence identity between the PRO1295 amino acid sequence and the following Dayhoff sequences (data incorporated herein): AB011099_1, ILVE_MYCTU, ATTECR_2, AF010496_27, P_R15346, S37191, PER_DROMS, L2MU_ADECC and P_W34238.

Example 24

Isolation of cDNA Clones Encoding Human PRO1309 Polypeptides [UNQ675]

An expressed sequence tag (EST) DNA database (LIFESEQ®, Incyte Pharmaceuticals, Palo Alto, Calif.) was searched and an EST was identified which showed homology to SLIT.

RNA for construction of cDNA libraries was isolated from human fetal brain tissue. The cDNA libraries used to isolate the cDNA clones encoding human PRO1309 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278-1280 (1991)) in the unique XhoI and NotI.

The cDNA libraries (prepared as described above), were screened by hybridization with a synthetic oligonucleotide probe derived from the above described Incyte EST sequence:

```
5'-TCCGTGCAGGGGGACGCCTTTCAGAAACTGC (SEQ ID NO: 190)
GCCGAGTTAAGGAAC-3'
```

A cDNA clone was isolated and sequenced in entirety. The entire nucleotide sequence of DNA59588-1571 is shown in FIG. 45 (SEQ ID NO:45). Clone DNA59588-1571 contains a single open reading frame with an apparent translational initiation site at nucleotide positions 720-722 and a stop codon at nucleotide positions 2286-2288 (FIG. 45; SEQ ID NO:45). The predicted polypeptide precursor is 522 amino acids long (FIG. 46; SEQ ID NO:46). The signal peptide is approximately at 1-34 and the transmembrane domain is at approximately 428-450 of SEQ ID NO:278. Clone DNA59588-1571 has been deposited with ATCC on Aug. 11, 1998 and is assigned ATCC deposit no. 203106. The full-length PRO1309 protein shown in FIG. 46 has an estimated molecular weight of about 58,614 daltons and a pI of about 7.42.

An analysis of the Dayhoff database (version 35.45 SwissProt 35), using a WU-BLAST2 sequence alignment analysis of the full-length sequence shown in FIG. 46 (SEQ ID NO:46), revealed sequence identity between the PRO1309 amino acid sequence and the following Dayhoff sequences: AB007876_1, GPV_MOUSE, ALS_RAT, P_R85889, LUM_CHICK, AB014462_1, PGS1_CANFA, CEM88_7, A58532 and GEN11209.

Example 25

Isolation of cDNA Clones Encoding Human PRO1316 Polypeptides [UNQ682]

The extracellular domain (ECD) which includes the signal sequence, if any, of publicly available databases known to contain secreted sequences were used to search various publicly available EST (Expressed Sequenced Tag) databases (GenBank, Merck/Wash. U). The search was performed using the computer program BLAST or BLAST2 [Altschul et al., Methods in Enzymology 266: 460-480 (1996)] as a comparison of the ECD protein sequences to a 6 frame translation of the EST sequences. Those comparisons resulting in a BLAST score of 70 (or in some cases 90) or greater that did not did not encode known proteins were clustered and assembled into consensus DNA sequences with the program "phrap" (Phil Green, University of Washington, Seattle, Wash.).

The above search resulted in the identification of the EST, designated W55979 which showed homology with the secreted protein Dkk-1. The clone corresponding to EST W55979 (clone NbHH19W) was purchased from Merck/Washington University and the cDNA insert was obtained and sequenced in its entirety.

The nucleic acid sequence corresponding to the full length PRO1316 (designated DNA60608-1577) encoded by the purchased clone, is shown in FIG. 47 (SEQ ID NO:47). DNA60608-1577 contains a single open reading frame with an apparent translational initiation site at nucleotide positions 211-213, and a stop codon at nucleotide positions 988-990 (FIG. 47; SEQ ID NO:47). The predicted polypeptide precursor is 259 amino acids long (FIG. 48; SEQ ID NO:48). Additional regions of significant interest include the nucleotide residues encoding the signal peptide (211-283), an N-glycosylation site (364-366), and the Zn(2)-Cys(6) binuclear cluster domain (505-655). Clone DNA60608-1577 has been deposited with ATCC on Aug. 18, 1998 and is assigned ATCC deposit no. 203126. The full-length PRO1316 protein shown in FIG. 48 has an estimated molecular weight of about 28,447 daltons and a pI of about 9.48.

Based on a BLAST and FastA sequence alignment analysis (using the ALIGN computer program) of the full-length sequence, PRO1316 shows significant amino acid sequence identity to the dickkopf family of proteins. Additionally, DNA60608 has shown homology to AF030433_1, LFE4_CHICK, COL_RABIT, YQI6_CAEEL, ITB6_HUMAN, CONO_LYMST, S41033, D63483_1, D86864_1 and AB001978_1.

Example 26

Isolation of cDNA Clones Encoding Human PRO1383 Polypeptides [UNQ719]

A consensus DNA sequence was assembled relative to other EST sequences using phrap as described in Example 1 above. This consensus sequence is herein designated DNA53961. Based on the DNA53961 consensus sequence, oligonucleotides were synthesized: 1) to identify by PCR a cDNA library that contained the sequence of interest, and 2) for use as probes to isolate a clone of the full-length coding sequence for PRO1383.

PCR primers (forward and reverse) were synthesized:

```
forward PCR primer
5'-CATTTCCTTACCCTGGACCCAGCTCC-3' (SEQ ID NO: 191)

reverse PCR primer
5'-GAAAGGCCCACAGCACATCTGGCAG-3'  (SEQ ID NO: 192)
```

Additionally, a synthetic oligonucleotide hybridization probe was constructed from the consensus DNA53961 sequence which had the following nucleotide sequence

```
hybridization probe
5'-CCACGACCCGAGCAACTTCCTCAAGACCGAC (SEQ ID NO: 193)
TTGTTTCTCTACAGC-3'
```

In order to screen several libraries for a source of a full-length clone, DNA from the libraries was screened by PCR amplification with the PCR primer pair identified above. A positive library was then used to isolate clones encoding the PRO1383 gene using the probe oligonucleotide and one of the PCR primers. RNA for construction of the cDNA libraries was isolated from human fetal brain tissue.

DNA sequencing of the clones isolated as described above gave the full-length DNA sequence for PRO1383 (designated herein as DNA58743-1609 [FIG. 49, SEQ ID NO:49]) and the derived protein sequence for PRO1383.

The entire nucleotide sequence of DNA58743-1609 is shown in FIG. 49 (SEQ ID NO:49). Clone DNA58743-1609 contains a single open reading frame with an apparent translational initiation site at nucleotide positions 122-124 and ending at the stop codon at nucleotide positions 1391-1393 (FIG. 49). The predicted polypeptide precursor is 423 amino acids long (FIG. 50; SEQ ID NO:50). The full-length PRO1383 protein shown in FIG. 50 has an estimated molecular weight of about 46,989 daltons and a pI of about 6.77. Analysis of the full-length PRO1383 sequence shown in FIG. 50 (SEQ ID NO:50) evidences the presence of the following: a signal peptide from about amino acid 1 to about amino acid 24, a transmembrane domain from about amino acid 339 to about amino acid 362, and potential N-glycosylation sites from about amino acid 34 to about amino acid 37, from about amino acid 58 to about amino acid 61, from about amino acid 142 to about amino acid 145, from about amino acid 197 to about amino acid 200, from about amino acid 300 to about amino acid 303 and from about amino acid 364 to about amino acid 367. Clone DNA58743-1609 has been deposited with ATCC on Aug. 25, 1998 and is assigned ATCC deposit no. 203154.

An analysis of the Dayhoff database (version 35.45 Swiss Prot 35), using a WU-BLAST2 sequence alignment analysis of the full-length sequence shown in FIG. 50 (SEQ ID NO:50), evidenced significant homology between the PRO1383 amino acid sequence and the following Dayhoff sequences: NMB_HUMAN, QNR_COTJA, P_W38335, P115_CHICK, P_W38164, A45993_1, MMU70209_1, D83704_1 and P_W39176.

Example 27

Isolation of cDNA Clones Encoding Human PRO1384 Polypeptides [UNQ721]

A consensus DNA sequence was assembled relative to other EST sequences using phrap as described in Example 1 above. This consensus sequence is herein designated DNA54192. Based on the DNA54192 sequence, oligonucleotides were synthesized: 1) to identify by PCR a cDNA library that contained the sequence of interest, and 2) for use as probes to isolate a clone of the full-length coding sequence for PRO1384.

PCR primers (forward and reverse) were synthesized:

```
forward PCR primer
5'-TGCAGCCCCTGTGACACAAACTGG-3'    (SEQ ID NO: 194)

reverse PCR primer
5'-CTGAGATAACCGAGCCATCCTCCCAC-3'  (SEQ ID NO: 195)
```

Additionally, a synthetic oligonucleotide hybridization probe was constructed from the DNA54192 sequence which had the following nucleotide sequence:

```
hybridization probe
5'-GGAGATAGCTGCTATGGGTTCTTCAGGCACA (SEQ ID NO: 196)
ACTTAACATGGGAAG-3'
```

In order to screen several libraries for a source of a full-length clone, DNA from the libraries was screened by PCR amplification with the PCR primer pair identified above. A positive library was then used to isolate clones encoding the PRO1384 gene using the probe oligonucleotide and one of the PCR primers. RNA for construction of the cDNA libraries was isolated from human fetal liver.

DNA sequencing of the clones isolated as described above gave the full-length DNA sequence for PRO1384 (designated herein as DNA71159-1617 [FIG. 51, SEQ ID NO:51]; and the derived protein sequence for PRO1384.

The entire coding sequence of PRO1384 is shown in FIG. 51 (SEQ ID NO:51). Clone DNA71159-1617 contains a single open reading frame with an apparent translational initiation site at nucleotide positions 182-184 and an apparent stop codon at nucleotide positions 869-871. The predicted polypeptide precursor is 229 amino acids long (FIG. 52; SEQ ID NO:52). The full-length PRO1384 protein shown in FIG. 52 has an estimated molecular weight of about 26,650 daltons and a pI of about 8.76. Additional features include a type II transmembrane domain at about amino acids 32-57, and potential N-glycosylation sites at about amino acids 68-71, 120-123, and 134-137.

An analysis of the Dayhoff database (version 35.45 Swiss Prot 35), using a WU-BLAST2 sequence alignment analysis of the full-length sequence shown in FIG. 52 (SEQ ID NO:52), revealed homology between the PRO1384 amino acid sequence and the following Dayhoff sequences: AF054819_1, HSAJ1687_1, AF009511_1, AB010710_1, GEN13595, HSAJ673_1, GEN13961, AB005900_1, LECH_CHICK, AF021349_1, and NK13_RAT.

Clone DNA71159-1617 has been deposited with ATCC on Aug. 18, 1998 and is assigned ATCC deposit no. 203135.

Example 28

Isolation of cDNA Clones Encoding Human PRO1431 Polypeptides [UNQ737]

An expressed sequence tag (EST) DNA database (LIFESEQ®, Incyte Pharmaceuticals, Palo Alto, Calif.) was searched and an EST (isolated from adult brain stem tissue) was identified (1370141, DNA66505) which showed homology to SH3. RNA for construction of cDNA libraries was isolated from human bone marrow. A full length cDNA corresponding to the isolated EST was isolated using an in vitro cloning technique (DNA73401-1633) in pRK5.

The cDNA libraries used to isolate the cDNA clones encoding human PRO1431 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI.

A cDNA clone was sequenced in entirety. The entire nucleotide sequence of DNA73401-1633 (SEQ ID NO:53) is shown in FIG. 53. Clone DNA73401-1633 contains a single open reading frame with an apparent translational initiation site at about nucleotide positions 630-632 and a stop codon at about nucleotide positions 1740-1742. The predicted polypeptide precursor encoded by DNA73401-1633 is 370 amino acids long (FIG. 54; SEQ ID NO:54). Clone DNA73401 (designated as DNA73402-1633) has been deposited with ATCC on Sep. 22, 1998 and is assigned ATCC deposit no. 203273.

Based sequence alignment analysis (using the ALIGN computer program) of the full-length sequence, PRO1431 shows significant amino acid sequence identity to SH17_HUMAN, an SH3 containing protein known as SH3P17. Additional significant identity score were found with D89164_1, AF032118_1, EXLP_TOBAC, YHR4_YEAST, S46992, RATP130CAS_2, AF043259_1, RATP130CAS_1 and MYSC_ACACA.

Example 29

Isolation of cDNA Clones Encoding Human PRO1434 Polypeptides [UNQ739]

A consensus DNA sequence was assembled relative to other EST sequences using phrap as described in Example 1 above. This consensus sequence is herein designated DNA54187. Based on the DNA54187 consensus sequence, oligonucleotides were synthesized: 1) to identify by PCR a cDNA library that contained the sequence of interest, and 2) for use as probes to isolate a clone of the full-length coding sequence for PRO1434.

PCR primers (forward and reverse) were synthesized:

```
forward PCR primer
5'-GAGGTGTCGCTGTGAAGCCAACGG-3'    (SEQ ID NO: 197)

reverse PCR primer
5'-CGCTCGATTCTCCATGTGCCTTCC-3'    (SEQ ID NO: 198)
```

Additionally, a synthetic oligonucleotide hybridization probe was constructed from the consensus DNA54187 sequence which had the following nucleotide sequence

```
hybridization probe
5'-GACGGAGTGTGTGGACCCTGTGTA    (SEQ ID NO: 199)
CGAGCCTGATCAGTGCTGTCC-3'
```

RNA for construction of the cDNA libraries was isolated from human retina tissue (LIB94).

DNA sequencing of the clones isolated as described above gave the full-length DNA sequence for PRO1434 (designated herein as DNA68818-2536 [FIG. 55, SEQ ID NO:55]; and the derived protein sequence for PRO1434.

The entire nucleotide sequence of DNA68818-2536 is shown in FIG. 55 (SEQ ID NO:55). Clone DNA68818-2536 contains a single open reading frame with an apparent translational initiation site at nucleotide positions 581-583 and ending at the stop codon at nucleotide positions 1556-1558 (FIG. 55). The predicted polypeptide precursor is 325 amino acids long (FIG. 56; SEQ ID NO:56). The full-length PRO1434 protein shown in FIG. 56 has an estimated molecular weight of about 35,296 daltons and a pI of about 5.37. Analysis of the full-length PRO1434 sequence shown in FIG. 56 (SEQ ID NO:56) evidences the presence of a variety of important protein domains as shown in FIG. 56. Clone DNA68818-2536 has been deposited with ATCC on Feb. 9, 1999 and is assigned ATCC deposit no. 203657.

An analysis of the Dayhoff database (version 35.45 Swiss Prot 35), using a WU-BLAST2 sequence alignment analysis of the full-length sequence shown in FIG. 56 (SEQ ID NO:56), evidenced significant homology between the PRO1434 amino acid sequence and the following Dayhoff sequences: NEL_MOUSE, APMU_PIG, P_W37501, NEL_RAT, TSP1_CHICK, P_W37500, NEL2_HUMAN, MMU010792_1, D86983_1 and 10 MUCS_BOVIN.

Example 30

Isolation of cDNA Clones Encoding Human PRO1475 Polypeptides [UNQ746]

A consensus DNA sequence was assembled relative to other EST sequences using phrap as described in Example 1 above. This consensus sequence is herein designated DNA45639. Based on the DNA45639 consensus sequence, oligonucleotides were synthesized: 1) to identify by PCR a cDNA library that contained the sequence of interest, and 2) for use as probes to isolate a clone of the full-length coding sequence for PRO1475.

PCR primers (forward and reverse) were synthesized:

```
forward PCR primer (45639.f1)
5'-GATGGCAAAACGTGTGTTTGACACG-3'   (SEQ ID NO: 200)

forward PCR primer (45639.f2)
5'-CCTCAACCAGGCCACGGGCCAC-3'      (SEQ ID NO: 201)

reverse PCR primer (45639.r1)
5'-CCCAGGCAGAGATGCAGTACAGGC-3'    (SEQ ID NO: 202)

reverse PCR primer (45639.r2)
5'-CCTCCAGTAGGTGGATGGATTGGCTC-3'  (SEQ ID NO: 203)
```

Additionally, a synthetic oligonucleotide hybridization probe was constructed from the consensus DNA45639 sequence which had the following nucleotide sequence

```
hybridization probe (45639.p1)
5'-CTCACCTCATGAGGATGAGGCCAT       (SEQ ID NO: 204)
GGTGCTATTCCTCAACATGGTAG-3'
```

In order to screen several libraries for a source of a full-length clone, DNA from the libraries was screened by PCR amplification with the PCR primer pair identified above. A positive library was then used to isolate clones encoding the PRO1475 gene using the probe oligonucleotide and one of the PCR primers. RNA for construction of the cDNA libraries was isolated from human fetal brain tissue.

DNA sequencing of the clones isolated as described above gave the full-length DNA sequence for PRO1475 (designated herein as DNA61185-1646 [FIG. 57, SEQ ID NO:57]; and the derived protein sequence for PRO1475.

The entire nucleotide sequence of DNA61185-1646 is shown in FIG. 57 (SEQ ID NO:57). Clone DNA61185-1646 contains a single open reading frame with an apparent translational initiation site at nucleotide positions 130-132 and ending at the stop codon at nucleotide positions 2110-2112 (FIG. 57). The predicted polypeptide precursor is 660 amino acids long (FIG. 58; SEQ ID NO:58). The full-length PRO1475 protein shown in FIG. 58 has an estimated molecular weight of about 75,220 daltons and a pI of about 6.76. Analysis of the full-length PRO1475 sequence shown in FIG. 58 (SEQ ID NO:58) evidences the presence of the following: a transmembrane domain from about amino acid 38 to about amino acid 55 and a homologous region to mouse GNT1 from about amino acid 229 to about amino acid 660. Clone DNA61185-1646 has been deposited with ATCC on Nov. 17, 1998 and is assigned ATCC deposit no. 203464.

An analysis of the Dayhoff database (version 35.45 SwissProt 35), using a WU-BLAST2 sequence alignment analysis of the full-length sequence shown in FIG. 58 (SEQ ID NO:58), evidenced significant homology between the PRO1475 amino acid sequence and the following Dayhoff sequences: GNT1_MOUSE, CGU65792__1, CGU65791__1, P_R24781, CELF48E3__1, G786_HUMAN, P_W06547, GNT1_CAEEL, 219_HUMAN and EF07_MOUSE.

Example 31

Isolation of cDNA Clones Encoding Human PRO1481 Polypeptides [UNQ750]

An initial DNA sequence, referred to herein as DNA53254, was identified using a yeast screen, in a human fetal kidney cDNA library that preferentially represents the 5' ends of the primary cDNA clones. Based on the DNA53254 sequence, oligonucleotides were synthesized for use as probes (or primers) to isolate a clone of the full-length coding sequence for PRO1481 from a human fetal kidney cDNA library.

The full length DNA58732-1650 clone shown in FIG. 59 contained a single open reading frame with an apparent translational initiation site at nucleotide positions 320-322 and ending at the stop codon found at nucleotide positions 1322-1324 (FIG. 59; SEQ ID NO:59). The predicted polypeptide precursor (FIG. 60, SEQ ID NO:60) is 334 amino acids long. The signal peptide is at about amino acids 1-23, and a transmembrane domain is at about amino acids 235-262 of SEQ ID NO:60. The N-glycosylation sites are indicated in FIG. 60. PRO1481 has a calculated molecular weight of approximately 36,294 daltons and an estimated pI of approximately 4.98. Clone DNA58732-1650 has been deposited with the ATCC on Sep. 29, 1998 and is assigned ATCC deposit no. 203290.

An analysis of the Dayhoff database (version 35.45 SwissProt 35), using a WU-BLAST2 sequence alignment analysis of the full-length sequence shown in FIG. 60 (SEQ ID NO:60), revealed sequence identity between the PRO1481 amino acid sequence and the following Dayhoff sequences (data incorporated herein): YN23_YEAST, S67770, H36857, YLU2_PICAN, GEN12881, CVY15035__28, YM96_YEAST, ESC1_SCHPO, CELZK783__1 and S59310.

Example 32

Isolation of cDNA Clones Encoding Human PRO1568 Polypeptides [UNQ774]

A consensus DNA sequence was assembled relative to other EST sequences using phrap to form an assembly as described in Example 1 above. The consensus sequence is designated herein “DNA54208”. Based on the DNA54208 consensus sequence, the assembly and other information and discoveries provided herein, a clone including an EST in the assembly was ordered and sequenced. The EST is Incyte 3089490. Sequencing in full gave the sequence shown in FIG. 61.

The entire coding sequence of PRO1568 is included in FIG. 61 (SEQ ID NO:61). Clone DNA68880-1676 contains a single open reading frame with an apparent translational initiation site at nucleotide positions 208-210 and an apparent stop codon at nucleotide positions 1123-1125 of SEQ ID NO:61. The predicted polypeptide precursor is 305 amino acids long (FIG. 62; SEQ ID NO:62). The signal peptide, transmembrane regions, N-myristoylation and amidation sites are also indicated in FIG. 62. Clone DNA68880-1676 has been deposited with the ATCC on Oct. 6, 1998 and is assigned ATCC deposit no. 203319. The full-length PRO1568 protein shown in FIG. 62 has an estimated molecular weight of about 35,383 daltons and a pI of about 5.99.

An analysis of the Dayhoff database (version 35.45 Swiss Prot 35), using a WU-BLAST2 sequence alignment analysis of the full-length sequence shown in FIG. 62 (SEQ ID NO:62), revealed sequence identity between the PRO1568 amino acid sequence and the following Dayhoff sequences (incorporated herein): AF089749__1, AF054841__1, NAG2_HUMAN, CD63_HUMAN, CD82_HUMAN, P_W05732, P_R86834, A15_HUMAN, P_W27333 and CD37_HUMAN.

Example 33

Isolation of cDNA Clones Encoding Human PRO1573 Polypeptides [UNQ779]

EST 3628990 was identified in an Incyte Database, (LIFESEQ®, Incyte Pharmaceuticals, Palo Alto, Calif.) and extended in a comparison to other sequences in databases to form an assembly. The alignment search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program “phrap” (Phil Green, University of Washington, Seattle, Wash.). The consensus sequence is designated herein “DNA69561”.

Based on the DNA69561 consensus sequence and other information provided herein, a clone including another EST (Incyte DNA3752657) from the assembly was purchased and sequenced. This clone came from a breast tumor tissue library.

The entire coding sequence of PRO1573 is included in FIG. 63 (SEQ ID NO:63). Clone DNA73735-1681 contains a single open reading frame with an apparent translational initiation site at nucleotide positions 97-99 and an apparent stop codon at nucleotide positions 772-774. The predicted polypeptide precursor is 225 amino acids long (FIG. 64; SEQ ID NO:64). The signal peptide is at about amino acids 1-17 and the transmembrane domains are at about amino acids 82-101, 118-145, and 164-188 of SEQ ID NO:64. One or more of the transmembrane domains can be deleted or inactivated. A phosphorylation site, amidation site, and N-myristoylation sites are shown in FIG. 64. Clone DNA73735-1681 has been deposited with ATCC on Oct. 20, 1998 and is assigned ATCC deposit no. 203356. The full-length PRO1573 protein shown in FIG. 64 has an estimated molecular weight of about 24,845 daltons and a pI of about 9.07.

An analysis of the Dayhoff database (version 35.45 SwissProt 35), using a WU-BLAST2 sequence alignment analysis of the full-length sequence shown in FIG. 64 (SEQ ID NO:64), revealed sequence identity between the PRO1573 amino acid sequence and the following Dayhoff sequences (incorporated herein): AF007189__1, AB000714__1, AB000713_1, AB000712_1, A39484, AF000959_1, AF072127_, AF072128_1, AF068863_1 and AF077739_1.

Example 34

Isolation of cDNA Clones Encoding Human PRO1599 Polypeptides [UNQ782]

Incyte EST no. 1491360 was identified as a sequence of interest using the techniques described in Example 1 above having a BLAST score of 70 or greater that does not encode a known protein. The nucleotide sequence of EST no. 1491360 and its complementary sequence is designated herein "DNA37192". Based on the DNA37192 sequence, oligonucleotides were synthesized: 1) to identify by PCR a cDNA library that contained the sequence of interest, and 2) for use as probes to isolate a clone of the full-length coding sequence for PRO1599.

PCR primers (forward and reverse) were synthesized:

```
forward PCR primer:
GACGTCTGCAACAGCTCCTGGAAG (37192.f1; SEQ ID NO: 205)

reverse PCR primer:
CGAGAAGGAAACGAGGCCGTGAG  (37192.r1; SEQ ID NO: 206)
```

Additionally, a synthetic oligonucleotide hybridization probe was constructed from the consensus DNA37192 sequence which had the following nucleotide sequence:

```
hybridization probe:
TGACACTTACCATGCTCTGCACCCGCA   (SEQ ID NO: 207)
GTGGGGACAGCCACAGA.
```

In order to screen several libraries for a source of a full-length clone, DNA from the libraries was screened by PCR amplification with the PCR primer pair identified above. A positive library was then used to isolate clones encoding the PRO1599 gene using the probe oligonucleotide and one of the PCR primers. RNA for construction of the cDNA libraries was isolated from human fetal liver tissue.

DNA sequencing of the clones isolated as described above gave the full-length DNA sequence for PRO1599 (designated herein as DNA62845-1684 [FIG. 65, SEQ ID NO:65]; and the derived protein sequence for PRO1599.

The entire coding sequence of PRO1599 is shown in FIG. 65 (SEQ ID NO:65). Clone DNA62845-1684 contains a single open reading frame with an apparent translational initiation site at nucleotide positions 69-71 and an apparent stop codon at nucleotide positions 918-920. The predicted polypeptide precursor is 283 amino acids long (FIG. 66; SEQ ID NO:66). The full-length PRO1599 protein shown in FIG. 66 has an estimated molecular weight of about 30,350 daltons and a pI of about 9.66. Additional features of PRO1599 include: a signal peptide at about amino acids 1-30; potential N-glycosylation sites at about amino acids 129-132 and 189-192; a potential cAMP and cGMP-dependent protein kinase phosphorylation site at about amino acids 263-266; potential N-myristoylation sites at about amino acids 28-33, 55-60, 174-179, and 236-241; a potential amidation site at about amino acids 144-147; and a serine protease, trypsin family, histidine active site at about amino acids 70-75.

An analysis of the Dayhoff database (version 35.45 Swiss Prot 35), using a WU-BLAST2 sequence alignment analysis of the full-length sequence shown in FIG. 66 (SEQ ID NO:66), revealed significant homology between the PRO1599 amino acid sequence and the following Dayhoff sequence: CFAD_PIG. Homology was also found between the PRO1599 amino acids sequence and the following additional Dayhoff sequences. CFAD_HUMAN; P_R05421; P_R55757; P_R05772; GRAM_HUMAN; MUSLMET_1; P_P80335; P_R55758; A42048_1; and P_W05383.

Clone DNA62845-1684 was deposited with the ATCC on Oct. 20, 1998 and is assigned ATCC deposit no. 203361.

Example 35

Isolation of cDNA Clones Encoding Human PRO1604 Polypeptides [UNQ785]

An expressed sequence tag (EST) DNA database (LIFESEQ®, Incyte Pharmaceuticals, Palo Alto, Calif.) was searched. Incyte EST No. 3550440 was identified as having homology to HDGF. EST No. 3550440 was then compared to various EST databases including public EST databases (e.g. GenBank), and the LIFESEQ® database, to identify homologous EST sequences. The search was performed using the computer program BLAST or BLAST2 [Altschul et al., Methods in Enzymology, 266:460-480 (1996)]. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.). This consensus sequence is designated herein "DNA67237".

In light of the sequence homology between the DNA67237 sequence and EST no. 3367060 from the LIFESEQ® database, the clone containing Incyte EST No. 3367060 was purchased and the cDNA insert was obtained and sequenced to obtain the entire coding sequence of PRO1604 which is shown in FIG. 67 (SEQ ID NO:67).

Clone DNA71286-1687 contains a single open reading frame with an apparent translational initiation site at nucleotide positions 65-67 and an apparent stop codon at nucleotide positions 2078-2080. The predicted polypeptide precursor is 671 amino acids long (FIG. 68; SEQ ID NO:68). The full-length PRO1604 protein shown in FIG. 68 has an estimated molecular weight of about 74,317 daltons and a pI of about 7.62. Additional features include a signal peptide at about amino acids 1-13; potential cAMP- and cGMP-dependent protein kinase phosphorylation sites at about amino acids 156-159, 171-174, and 451-454; potential N-myristoylation sites at about amino acids 46-51, 365-370, and 367-372; and a cell attachment sequence at about amino acids 661-663.

An analysis of the Dayhoff database (version 35.45 SwissProt 35), using a WU-BLAST2 sequence alignment analysis of the full-length sequence shown in FIG. 68 (SEQ ID NO:68), revealed significant homology between the PRO1604 amino acid sequence and Dayhoff sequence no. P_W37483. Homology was also shown between the PRO1604 amino acid sequence and the following additional Dayhoff sequences: AF063020_1, P_R66727, P_W37482, JC5661, CEC25A1_11, CEU33058_1, I38073, MST2_DROHY, and HSATRX36_1.

Clone DNA71286-1687 was deposited with the ATCC on Oct. 20, 1998, and is assigned ATCC deposit no. 203357.

Example 36

Isolation of cDNA Clones Encoding Human PRO1605 Polypeptides [UNQ786]

A cDNA clone (DNA77648-1688) encoding a native human PRO1605 polypeptide was identified by a yeast screen, in a human fetal kidney cDNA library that preferentially represents the 5' ends of the primary cDNA clones.

The full-length DNA77648-1688 clone shown in FIG. 69 (SEQ ID NO:69) contains a single open reading frame with an apparent translational initiation site at nucleotide positions 425-427 and ending at the stop codon at nucleotide positions 845-847 (FIG. 69). The predicted polypeptide precursor is 140 amino acids long (FIG. 70; SEQ ID NO:70). The full-length PRO1605 protein shown in FIG. 70 has an estimated molecular weight of about 15,668 daltons and a pI of about 10.14. Analysis of the full-length PRO1605 sequence shown in FIG. 70 (SEQ ID NO:70) evidences the presence of the following: a signal peptide from about amino acid 1 to about amino acid 26. Clone DNA77648-1688 has been deposited with ATCC on Oct. 27, 1998 and is assigned ATCC deposit no. 203408.

An analysis of the Dayhoff database (version 35.45 SwissProt 35), using a WU-BLAST2 sequence alignment analysis of the full-length sequence shown in FIG. 70 (SEQ ID NO:70), evidenced significant homology between the PRO1605 amino acid sequence and the following Dayhoff sequences: GNT5_HUMAN, P_R48975, P_W22519, MM26SPROT__1, HSU86782__1, CH60_LEPIN, HMCT_HELPY, F65126, HIU08875__1 and P_R41724.

Example 37

Isolation of cDNA Clones Encoding Human PRO1693 Polypeptides [UNQ803]

A consensus DNA sequence was assembled relative to other EST sequences using phrap as described in Example 1 above. This consensus sequence is herein designated DNA38251. Based on the DNA38251 consensus sequence, oligonucleotides were synthesized: 1) to identify by PCR a cDNA library that contained the sequence of interest, and 2) for use as probes to isolate a clone of the full-length coding sequence for PRO1693.

PCR primers (forward and reverse) were synthesized:

```
forward PCR primer (3825.f1)
5'-CTGGGATCTGAACAGTTTCGGGGC-3'    (SEQ ID NO: 208)

reverse PCR primer (38251.r1)
5'-GGTCCCCAGGACATGGTCTGTCCC-3'    (SEQ ID NO: 209)
```

Additionally, a synthetic oligonucleotide hybridization probe was constructed from the consensus DNA38251 sequence which had the following nucleotide sequence

```
hybridization probe (38251.p1)
5'-GCTGAGTTTACATTTACGGTCTAACTC    (SEQ ID NO: 210)
CCTGAGAACCATCCCTGTGCG-3'
```

In order to screen several libraries for a source of a full-length clone, DNA from the libraries was screened by PCR amplification with the PCR primer pair identified above. A positive library was then used to isolate clones encoding the PRO1693 gene using the probe oligonucleotide and one of the PCR primers. RNA for construction of the cDNA libraries was isolated from human fetal kidney tissue.

DNA sequencing of the clones isolated as described above gave the full-length DNA sequence for PRO1693 (designated herein as DNA77301-1708 [FIG. 71, SEQ ID NO:71]; and the derived protein sequence for PRO1693.

The entire nucleotide sequence of DNA77301-1708 is shown in FIG. 71 (SEQ ID NO:71). Clone DNA77301-1708 contains a single open reading frame with an apparent translational initiation site at nucleotide positions 508-510 and ending at the stop codon at nucleotide positions 2047-2049 (FIG. 71). The predicted polypeptide precursor is 513 amino acids long (FIG. 72; SEQ ID NO:72). The full-length PRO1693 protein shown in FIG. 72 has an estimated molecular weight of about 58,266 daltons and a pI of about 9.84. Analysis of the full-length PRO1693 sequence shown in FIG. 72 (SEQ ID NO:72) evidences the presence of the following: a signal peptide from about amino acid 1 to about amino acid 33, a transmembrane domain from about amino acid 420 to about amino acid 442, potential N-glycosylation sites from about amino acid 126 to about amino acid 129, from about amino acid 357 to about amino acid 360, from about amino acid 496 to about amino acid 499 and from about amino acid 504 to about amino acid 507, a cAMP- and cGMP-dependent protein kinase phosphorylation site from about amino acid 465 to about amino acid 468, a tyrosine kinase phosphorylation site from about amino acid 136 to about amino acid 142 and potential N-myristolation sites from about amino acid 11 to about amino acid 16, from about amino acid 33 to about amino acid 38, from about amino acid 245 to about amino acid 250, from about amino acid 332 to about amino acid 337, from about amino acid 497 to about amino acid 502 and from about amino acid 507 to about amino acid 512. Clone DNA77301-1708 has been deposited with ATCC on Oct. 27, 1998 and is assigned ATCC deposit no. 203407.

An analysis of the Dayhoff database (version 35.45 SwissProt 35), using a WU-BLAST2 sequence alignment analysis of the full-length sequence shown in FIG. 72 (SEQ ID NO:72), evidenced significant homology between the PRO1693 amino acid sequence and the following Dayhoff sequences: AB007876__1, ALS_MOUSE, HSCHON03__1, P_R85889, AF062006__1, AB014462__1, A58532, MUSLRRPA__1, AB007865__1 and AF030435__1.

Example 38

Isolation of cDNA Clones Encoding Human PRO1753 Polypeptides [UNQ826]

DNA68883 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, designated Incyte Cluster No. 54463. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence is herein designated "DNA54233". In light of the sequence homology between the DNA54233 sequence and EST no. 2597444, the EST clone 2597444 was purchased and the cDNA insert was obtained and sequenced in its entirety. EST clone 2597444 was derived from RNA isolated from ovarian tumor tissue. The sequence of this cDNA insert is shown in FIG. 73 and is herein designated as "DNA68883-1691".

The full length clone shown in FIG. 73 contained a single open reading frame with an apparent translational initiation site at nucleotide positions 197 to 199 and ending at the stop codon found at nucleotide positions 1832 to 1834 (FIG. 73; SEQ ID NO:73). The predicted polypeptide precursor (FIG. 74, SEQ ID NO:74) is 545 amino acids long. PRO1753 has a calculated molecular weight of approximately 60022 daltons and an estimated pI of approximately 5.50. Additional features of PRO1753 include: a signal peptide at about amino acids 1-16; potential N-glycosylation sites at about amino acids 89-92, 116-119, 259-262, 291-294, and 299-302; potential tyrosine kinase phosphorylation sites at about amino acids 411-417 and 443-450; potential N-myristoylation sites at about amino acids 226-231, 233-238, 240-245, 252-257, 296-301, 300-305, 522-527, and 531-536; and an aspartic acid and asparagine hydroxylation site at about amino acids 197-208.

An analysis of the Dayhoff database (version 35.45 SwissProt 35), using a WU-BLAST2 sequence alignment analysis of the full-length sequence shown in FIG. 74 (SEQ ID NO:74), revealed significant homology between the PRO1753 amino acid sequence and Dayhoff sequence MMU72678_1. Homology was also revealed between the PRO1753 amino acid sequence and the following additional the following Dayhoff sequences: GP2_HUMAN; UROM_HUMAN; MMU69262_1; P_W52840; EGF_HUMAN; P_P50296; P_W31705; CET05A1_8; and HSAJ474_1.

Clone DNA68883 (UNQ826), designated as DNA68883-1691 was deposited with the ATCC on Dec. 15, 1998 and is assigned ATCC deposit no. 203535.

Example 39

Isolation of cDNA Clones Encoding Human PRO1755 Polypeptides [UNQ828]

Use of the signal sequence algorithm described in Example 3 above allowed identification of an EST cluster sequence from the LIFESEQ® database, designated EST Cluster No. 141872. This EST cluster sequence was then compared to a variety of ESTs from the databases listed above to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated "DNA55731".

In light of the sequence homology between the DNA55731 sequence and a sequence contained within Incyte EST no. 257323, the EST clone was purchased and the cDNA insert was obtained and sequenced. Incyte clone 257323 was derived from a library constructed using RNA isolated from the hNT2 cell line (Stratagene library no. STR9372310), which was derived from a human teratocarcinoma that exhibited properties characteristic of a committed neuronal precursor at an early stage of development. The sequence of this cDNA insert is shown in FIG. 75 and is herein designated "DNA76396-1698". Alternatively, the DNA76396-1698 sequence can be obtained by preparing oligonucleotide probes and primers and isolating the sequence from an appropriate library (e.g. STR9372310).

The full length clone shown in FIG. 75 contained a single open reading frame with an apparent translational initiation site at nucleotide positions 58 to 60 and ending at the stop codon found at nucleotide positions 886 to 888 (FIG. 75; SEQ ID NO:75). The predicted polypeptide precursor (FIG. 76, SEQ ID NO:76) is 276 amino acids long. PRO1755 has a calculated molecular weight of approximately 29,426 daltons and an estimated pI of approximately 9.40. Additional features include: a signal peptide sequence at about amino acids 1-31; a transmembrane domain at about amino acids 178-198; a cAMP and cGMP-dependent protein kinase phosphorylation site at about amino acids 210-213; potential N-myristoylation sites at about amino acids 117-122, 154-149, and 214-219; and a cell attachment sequence at about amino acids 149-151.

An analysis of the Dayhoff database (version 35.45 SwissProt 35), using a WU-BLAST2 sequence alignment analysis of the full-length sequence shown in FIG. 76 (SEQ ID NO:76), revealed some homology between the PRO1755 amino acid sequence and the following Dayhoff sequences: APG-BRANA, P_R37743, NAU88587_1, YHL1_EBV, P_W31855, CET10B10_4, AF039404_1, PRP1_HUMAN, AF038575_1, and AF053091_1.

Clone DNA76396-1698 was deposited with the ATCC on Nov. 17, 1998, and is assigned ATCC deposit no. 203471.

Example 40

Isolation of cDNA Clones Encoding Human PRO1777 Polypeptides [UNQ839]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated DNA47435.

Based on the DNA47435 consensus sequence oligonucleotides were synthesized: 1) to identify by PCR a cDNA library that contained the sequence of interest, and 2) for use as probes to isolate a clone of the full-length coding sequence for PRO1777. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer (47434.f1)
5'-CTGTTACACTGACGTGGCCCTCCC-3'    (SEQ ID NO: 211)

reverse PCR primer (47434.r1)
5'-CATTCTGACCCACGGGCCATTGTC-3'    (SEQ ID NO: 212)
```

Additionally, a synthetic oligonucleotide hybridization probe was constructed from the consensus DNA47435 sequence which had the following nucleotide sequence

```
hybridization probe (47434.p1)
5'-GTGGAGCAGCCGGTGAACTTGAG        (SEQ ID NO: 213)
CAGCCTTGCCCAGAAGTATGC-3'
```

RNA for construction of the cDNA libraries was isolated from human hippocampus tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO1777 (designated herein as DNA71235-1706 [FIG. 77, SEQ ID NO:77]; (UNQ839) and the derived protein sequence for PRO1777.

The entire nucleotide sequence of UNQ839 (DNA71235-1706) is shown in FIG. 77 (SEQ ID NO:77). Clone UNQ839 (DNA71235-1706) contains a single open reading frame with an apparent translational initiation site at nucleotide positions 797-799 and ending at the stop codon at nucleotide positions 2372-2374 (FIG. 77). The predicted polypeptide precursor is 525 amino acids long (FIG. 78; SEQ ID NO:78). The full-length PRO1777 protein shown in FIG. 78 has an estimated molecular weight of about 57,133 daltons and a pI of about 6.55. Analysis of the full-length PRO1777 sequence shown in FIG. 78 (SEQ ID NO:78) evidences the presence of the following: a signal peptide from about amino acid 1 to about amino acid 16, a transmembrane domain from about amino acid 353 to about amino acid 373, potential N-glycosylation sites from about amino acid 117 to about amino acid 120, from about amino acid 215 to about amino acid 218, from about amino acid 356 to about amino acid 359 and from about amino acid 497 to about amino acid 500, potential N-myristolation sites from about amino acid 12 to about amino acid 17, from about amino acid 33 to about amino acid 38, from about amino acid 52 to about amino acid 57, from about amino acid 97 to about amino acid 102, from about amino acid 101 to about amino acid 106, from about amino acid 113 to about amino acid 118, from about amino acid 158 to about amino acid 163, from about amino acid 328 to about amino acid 333, from about amino acid 388 to about amino acid 393, from about amino acid 418 to about amino acid 423, from about amino acid 435 to about amino acid 440 and from about amino acid 436 to about amino acid 441, an amidation site from about amino acid 382 to about amino acid 385 and a sulfatase signature 2 sequence from about amino acid 129 to about amino acid 138. Clone UNQ839 (DNA71235-1706) has been deposited with ATCC on Jan. 12, 1999 and is assigned ATCC deposit no. 203584.

An analysis of the Dayhoff database (version 35.45 SwissProt 35), using a WU-BLAST2 sequence alignment analysis of the full-length sequence shown in FIG. 78 (SEQ ID NO:78), evidenced significant homology between the PRO1777 amino acid sequence and the following Dayhoff sequences: G02857, GA6S_HUMAN, HGS_A139, GEN12647, STS_HUMAN, GEN12648, SPHM_HUMAN, P_W47298, GEN13892 and AF050145_1.

Example 41

Isolation of cDNA Clones Encoding Human PRO1788 Polypeptides [UNQ850]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Incyte Clone No. 2968304 was identified as a sequence of interest having a BLAST score of 70 or greater that did not encode known proteins. The nucleotide sequence of Incyte Clone No. 2968304 is designated herein as "DNA6612".

In addition, the DNA6612 sequence was extended using repeated cycles of BLAST and phrap (Phil Green, University of Washington, Seattle, Wash.) to extend the sequence as far as possible using the sources of EST sequences discussed above. The extended consensus sequence is designated herein as "DNA49648". Based on the DNA49648 consensus sequence, oligonucleotides were synthesized: 1) to identify by PCR a cDNA library that contained the sequence of interest, and 2) for use as probes to isolate a clone of the full-length coding sequence for PRO1788.

PCR primers (forward and reverse) were synthesized:

```
forward PCR primer:
CCCTGCCAGCCGAGAGCTTCACC   (49648.f1; SEQ ID NO: 214)

reverse PCR primer:
GGTTGGTGCCCGAAAGGTCCAGC   (49648.r1; SEQ ID NO: 215)
```

Additionally, a synthetic oligonucleotide hybridization probe was constructed from the consensus DNA49648 sequence which had the following nucleotide sequence:

```
hybridization probe:
CAACCCCAAGCTTAACTGGGCA    (49648 p1; SEQ ID NO: 216)
GGAGCTGAGGTGTTTTCAGGCC
```

In order to screen several libraries for a source of a full-length clone, DNA from the libraries was screened by PCR amplification with the PCR primer pair identified above. A positive library was then used to isolate clones encoding the PRO1788 gene using the probe oligonucleotide and one of the PCR primers. RNA for construction of the cDNA libraries was isolated from human fetal kidney tissue.

DNA sequencing of the clones isolated as described above gave the full-length DNA sequence for PRO1788 (designated herein as DNA77652-2505 [FIG. 79, SEQ ID NO:79]; and the derived protein sequence for PRO1788.

The entire coding sequence of DNA77652-2505 is shown in FIG. 79 (SEQ ID NO:79). Clone DNA77652-2505 contains a single open reading frame with an apparent translational initiation site at nucleotide positions 64-66 and an apparent stop codon at nucleotide positions 1123-1125. The predicted polypeptide precursor is 353 amino acids long (FIG. 80; SEQ ID NO:80). The full-length PRO1788 protein shown in FIG. 80 has an estimated molecular weight of about 37,847 daltons and a pI of about 6.80. Additional features of PRO1788 include: a signal peptide at about amino acids 1-16; transmembrane domains at about amino acids 215-232 and 287-304; potential N-glycosylation sites at about amino acids 74-77 and 137-140; a glycosaminoglycan attachment site at about amino acids 45-48; a tyrosine kinase phosphorylation site at about amino acids 318-325; N-myristoylation sites at about amino acids 13-18, 32-37, 88-93, 214-219, and 223-228; and a leucine zipper pattern at about amino acids 284-305.

An analysis of the Dayhoff database (version 35.45 SwissProt 35), using a WU-BLAST2 sequence alignment analysis of the full-length sequence shown in FIG. 80 (SEQ ID NO:80), revealed significant homology between the PRO1788 amino acid sequence and the following Dayhoff sequences: AF030435_1; AF062006_1; DMTARTAN_1; GARP_HUMAN; S42799; P_R71294; HSU88879_1; DROWHEELER_1; A58532; and AF068920_1.

Clone DNA77652-2505 was deposited with the ATCC on Nov. 17, 1998, and is assigned ATCC deposit no. 203480.

Example 42

Isolation of cDNA Clones Encoding Human PRO1864 Polypeptides [UNQ855]

The extracellular domain (ECD) sequences (including the secretion signal sequence, if any) from about 950 known secreted proteins from the Swiss-Prot public database were used to search EST databases. The EST databases included public EST databases (e.g., GenBank), a proprietary EST database (LIFESEQ®, Incyte Pharmaceuticals, Palo Alto, Calif.), and proprietary ESTs from Genentech. The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated Concen1424. In addition, the Consen1424 consensus DNA sequence was extended using repeated cycles of BLAST and phrap to extend the consensus sequence as far as possible using the sources of EST sequences discussed above. The extended consensus sequence is herein designated DNA40649.

Based on the DNA40649 consensus sequence, oligonucleotides were synthesized: 1) to identify by PCR a cDNA library that contained the sequence of interest, and 2) for use as probes to isolate a clone of the full-length coding sequence for PRO1864. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer (40649.f1)
5'-CTCCTCCAGGATGAACCACCTGCC-3'    (SEQ ID NO: 217)

forward PCR primer (40649.f2)
5'-CAGGATGCTTCAGAGAGG-3'          (SEQ ID NO: 218)

reverse PCR primer (40649.r1)
5'-CCTGCCTTCGGATTCCAGGAGGGG-3'    (SEQ ID NO: 219)
```

Additionally, a synthetic oligonucleotide hybridization probe was constructed from the consensus DNA40649 sequence which had the following nucleotide sequence

```
hybridization probe (40649.p1)
5'-CCATCAACCCCACACAACTCATG        (SEQ ID NO: 220)
GCCAGGATTGAGTCCTATG-3'
```

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO1864 (designated herein as DNA45409-2511 [FIG. 81, SEQ ID NO: 81]; (UNQ855) and the derived protein sequence for PRO1864.

The entire nucleotide sequence of UNQ855 (DNA45409-2511) is shown in FIG. 81 (SEQ ID NO:81). Clone UNQ855 (DNA45409-2511) contains a single open reading frame with an apparent translational initiation site at nucleotide positions 100-102 and ending at the stop codon at nucleotide positions 802-804 (FIG. 81). The predicted polypeptide precursor is 234 amino acids long (FIG. 82; SEQ ID NO:82). The full-length PRO1864 protein shown in FIG. 82 has an estimated molecular weight of about 26,655 daltons and a p1 of about 4.79. Analysis of the full-length PRO1864 sequence shown in FIG. 82 (SEQ ID NO:82) evidences the presence of the following: a signal peptide from about amino acid 1 to about amino acid 20 and transmembrane domains from about amino acid 54 to about amino acid 72, from about amino acid 100 to about amino acid 118, from about amino acid 130 to about amino acid 144 and from about amino acid 146 to about amino acid 166. Clone UNQ855 (DNA45409-2511) has been deposited with ATCC on Jan. 12, 1999 and is assigned ATCC deposit no. 203579.

An analysis of the Dayhoff database (version 35.45 SwissProt 35), using a WU-BLAST2 sequence alignment analysis of the full-length sequence shown in FIG. 82 (SEQ ID NO:82), evidenced significant homology between the PRO1864 amino acid sequence and the following Dayhoff sequences: P_W25768, I38027, D38255_1, MMES64_1, OCU92812_1, DRPATCH_1, DPOD_PLAFK, RTM1_YEAST, P_R77844 and P_R90765.

Example 43

Isolation of cDNA Clones Encoding Human PRO1925 Polypeptides [UNQ904]

DNA82302 was identified by applying a proprietary signal sequence finding algorithm developed by Genentech, Inc. (South San Francisco, Calif.) upon expressed sequence tags (ESTs) as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, designated cluster sequence no. 31113_2. This EST cluster sequence was then compared to the EST databases listed above to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated "DNA73884". In light of the sequence homology between the DNA73884 sequence and EST no. 3271608HI from the LIFESEQ® database, EST clone no. 3271608HI was purchased and the cDNA insert was obtained and sequenced. The clone originated from a library constructed using diseased human brain tissue. The sequence of this cDNA insert is shown in FIG. 83 and is herein designated as DNA82302.

The full length clone shown in FIG. 83 contained a single open reading frame with an apparent translational initiation site at nucleotide positions 89 to 91 and ending at the stop codon found at nucleotide positions 1409 to 1411 (FIG. 83; SEQ ID NO:83). The predicted polypeptide precursor (FIG. 84, SEQ ID NO:84) is 440 amino acids long. PRO1925 has a calculated molecular weight of approximately 49,403 daltons and an estimated pI of approximately 7.16. Additional features include a type II transmembrane domain at about amino acids 39-56; tyrosine kinase phosphorylation sites at about amino acids 149-155 and 274-281; N-myristoylation sites at about amino acids 10-15, 20-25, 63-68, and 208-213; an amidation site at about acids 10-13; and a glycoprotein hormones beta chain signature 1 at about amino acids 230-236.

An analysis of the Dayhoff database (version 35.45 SwissProt 35), using a WU-BLAST2 sequence alignment analysis of the full-length sequence shown in FIG. 84 (SEQ ID NO:84), revealed some homology between the PRO1925 amino acid sequence and the following Dayhoff sequences: P_R95913, AF010144_1, HSAF000996_1, HUMTRRP_1, P_W00838, I54374, PVPVA1_1, REL_HUMAN, HSU94362_1, and P_W19943.

Clone DNA82302 (UNQ904), designated as DNA82302-2529 was deposited with the ATCC on Dec. 15, 1998 and is assigned ATCC deposit no. 203534.

Example 44

Isolation of cDNA Clones Encoding Human PRO1926 Polypeptides [UNQ905]

DNA82340 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

An EST sequence which was identified was then compared to a variety of ESTs from the databases mentioned above to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA73887. In light of the sequence homology between the DNA73887 sequence and EST no. 3577105 from the LIFESEQ®, the EST clone, which was obtained from a cDNA library constructed from human bronchial tissue, was purchased and the cDNA insert was obtained and sequenced. The sequence of this cDNA insert is shown in FIG. 85 and is herein designated "DNA82340-2530".

The full length clone shown in FIG. 85 contained a single open reading frame with an apparent translational initiation site at nucleotide positions 74 to 76 and ending at the stop codon found at nucleotide positions 800 to 802 (FIG. 85; SEQ ID NO:85). The predicted polypeptide precursor (FIG. 86, SEQ ID NO:86) is 242 amino acids long. PRO1926 has a calculated molecular weight of approximately 26,471 daltons and an estimated pI of approximately 9.50. Additional features include: a signal peptide at about amino acids 1-23; a transmembrane domain at about amino acids 136-180; a potential N-glycosylation site at about amino acids 184-187; glycosaminoglycan attachment sites at about amino acids 37-40 and 236-239; a cAMP- and cGMP-dependent protein kinase phosphorylation site at about amino acids 151-154; potential N-myristoylation sites at about amino acids 33-38, 36-41, 38-43, and 229-234; an amidation site at about amino acids 238-241; and an ATP/GTP binding site motif A (P-loop) at about amino acids 229-236.

An analysis of the Dayhoff database (version 35.45 SwissProt 35), using a WU-BLAST2 sequence alignment analysis of the full-length sequence shown in FIG. 86 (SEQ ID NO:86), revealed 100 percent sequence identity between the last 81 carboxy terminus amino acids of the PRO1926 sequence and Dayhoff sequences P_W57893. Some homology was also found between the PRO1926 amino acid sequence and the following Dayhoff sequences: S72578, AR20_CAEEL, HGS_A198, HGS A273, AF007570_1, GEN12401, DMSTKIN_1, FAT_DROME, MNB_DROME.

Clone DNA82340 (UNQ905), designated as DNA82340-2530 was deposited with the ATCC on Dec. 22, 1998, and is assigned ATCC deposit no. 203547.

Example 45

Isolation of cDNA Clones Encoding Human PRO3566 Polypeptides [UNQ1840]

DNA59844-2542 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56016. In light of the sequence homology between the DNA56016 sequence and the Incyte EST clone no. 2603392, the Incyte EST clone no. 2603392 was purchased and the cDNA insert was obtained and sequenced. The sequence of this cDNA insert is shown in FIG. 87 and is herein designated as DNA59844-2542.

Clone UNQ1840 (DNA59844-2542) contains a single open reading frame with an apparent translational initiation site at nucleotide positions 5-7 and ending at the stop codon at nucleotide positions 980-982 (FIG. 87; SEQ ID NO:87). The predicted polypeptide precursor is 325 amino acids long (FIG. 88; SEQ ID NO:88). The full-length PRO3566 protein shown in FIG. 88 has an estimated molecular weight of about 34,256 daltons and a pI of about 7.14. Analysis of the full-length PRO3566 sequence shown in FIG. 88 (SEQ ID NO: 88) evidences the presence of the following: a signal peptide from about amino acid 1 to about amino acid 26, and various other regions shown in FIG. 88. Clone UNQ1840 (DNA59844-2542) has been deposited with ATCC on Feb. 9, 1999 and is assigned ATCC deposit no. 203650.

An analysis of the Dayhoff database (version 35.45 SwissProt 35), using a WU-BLAST2 sequence alignment analysis of the full-length sequence shown in FIG. 88 (SEQ ID NO:88), evidenced significant homology between the PRO3566 amino acid sequence and the following Dayhoff sequences: HELWAMIDE_1, CA21_MOUSE, SP62_HUMAN, AF095464_1, HMU92813_1, PRIO_BOVIN, SN24_HUMAN, TPM4_DROME, SYN1_RAT and CELT28F2_7.

Example 46

Isolation of cDNA Clones Encoding Human PRO4330 Polypeptides [UNQ1886]

An expressed sequence tag (EST) DNA database (LIFESEQ®, Incyte Pharmaceuticals, Palo Alto, Calif.) was searched and an EST, 4287529H1, (SEQ ID NO:3, also referred to herein as DNA85538 or from DNA) was identified which showed homology to thrombospondin.

RNA for construction of cDNA libraries was isolated from human aortic endothelial cells. The cDNA libraries used to isolate the cDNA clones encoding human PRO4330 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278-1280 (1991)) in the unique XhoI and NotI.

The human cDNA libraries (prepared as described above), were screened by hybridization with a synthetic oligonucleotide probe:

(forward, SEQ ID NO: 221)
5'GGAGACATGTTTCGAATGGACAACTGTC3';

(reverse, SEQ ID NO: 222)
5'CTGGATCTTCACACACTGGGCAGC3';
and (plasmid, SEQ ID NO: 223)
5'CCCAGTGTGGTGAGATAAACTGCGAGAGGTACTACGTGCCCGAAGG
3'.

A cDNA clone was sequenced in entirety. The entire nucleotide sequence including that coding PRO4330 is shown in FIG. 89 (SEQ ID NO:89). Clone DNA90842-2574 contains a single open reading frame with an apparent translational initiation site at nucleotide positions 368-370, and a stop codon at nucleotide positions 3476-3478 (FIG. 89; SEQ ID NO:89). The predicted polypeptide precursor is 1036 amino acids long (FIG. 90; SEQ ID NO:90).

The full-length PRO4330 protein shown in FIG. 90 has an estimated molecular weight of about 113738 daltons and a pI of about 5.14.

An analysis of the Dayhoff database (version 35.45 SwissProt 35), using a WU-BLAST2 sequence alignment analysis of the full-length sequence shown in FIG. 90 (SEQ ID NO:90), revealed homology between the PRO4330 amino acid sequence and the following Dayhoff sequences (incorporated herein): D83017_1, P_W37500, NEL_RAT, P_W37501, NEL2_HUMAN, AF034606_1, P_W40288, CHRD_XENLA, TSP1_CHICK, and SOG_DROME.

Example 47

Isolation of cDNA Clones Encoding Human PRO4423 Polypeptides [UNQ1940]

DNA96893-2621 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the Incyte database, a proprietary EST DNA database (LIFESEQ®, Incyte Pharmaceuticals, Palo Alto, Calif.). Based on DNA80594, DNA96893-2621 was identified and sequenced.

The full length clone shown in FIG. 91 contained a single open reading frame with an apparent translational initiation site at nucleotide positions 110-112 and ending at the stop codon found at nucleotide positions 639-641 (FIG. 91; SEQ ID NO:91). The predicted polypeptide precursor (FIG. 92, SEQ ID NO:92) is 173 amino acids long. PRO4423 has a calculated molecular weight of approximately 19733 daltons and an estimated pI of approximately 8.78.

An analysis of the Dayhoff database (version 35.45 SwissProt 35), using a WU-BLAST2 sequence alignment analysis of the full-length sequence shown in FIG. 92 (SEQ ID NO:92), revealed homology between the PRO4423 amino acid sequence and the following Dayhoff sequences: S09646 and YHY4_YEAST.

Clone DNA96893-2621 (UNQ1940), designated as DNA96893-2621 was deposited with the ATCC on May 4, 1999 and is assigned ATCC deposit no. PTA-12.

Example 48

Isolation of cDNA Clones Encoding Human PRO4977 Polypeptides [UNQ2420]

A consensus DNA sequence was assembled relative to other EST sequences using phrap as described in Example 1 above. Based on this consensus sequence, oligonucleotides were synthesized to identify by PCR a cDNA library that contained the sequence of interest and for use as probes to isolate a clone of the full-length coding sequence for PRO4977.

A pair of PCR primers (forward and reverse) were synthesized:

```
forward PCR primer
5'-ATGCCAATAACTTTGCCTCGGAGC-3'    (SEQ ID NO: 224)

reverse PCR primer
5'-CCAGAAGGCCAGGGCTTTCTCTG-3'     (SEQ ID NO: 225)
```

A hybridization probe was also synthesized:

```
                                       (SEQ ID NO: 226)
5'-GAGTGCATGAGCAGCTGCCAGGGATCTCTCCATGGGCCCC-3'
```

In order to screen several libraries for a source of a full-length clone, DNA from the libraries was screened by PCR amplification with the PCR primer pair identified above. A positive library was then used to isolate clones encoding the PRO4977 gene using the probe oligonucleotide and one of the PCR primers.

RNA for construction of the cDNA libraries was isolated from a human fetal kidney library. DNA sequencing of the clones isolated as described above gave the full-length DNA sequence and the derived protein sequence for PR4977.

The entire nucleotide sequence of DNA62849-2647 is shown in FIG. 95 (SEQ ID NO:95). Clone DNA62849-2647 contains a single open reading frame with an apparent translational initiation site at nucleotide positions 330-332, and an apparent stop codon at nucleotide positions 1761-1763. The predicted polypeptide precursor is 477 amino acids long (FIG. 96; SEQ ID NO:96). Clone DNA62849-2647 has been deposited with ATCC on Jun. 8, 1999 (designated as DNA62849-2647) and is assigned ATCC deposit no. PTA-205. The full-length PRO4977 protein has An estimated molecular weight of about 51112 daltons and a pI of about 6.66.

An analysis of the Dayhoff database (version 35.45 SwissProt 35), using a WU-BLAST2 sequence alignment analysis of the full-length sequence shown in FIG. 96 (SEQ ID NO:96), revealed homology between PTO4977 amino acid sequence and the following Dayhoff sequences: DJ534K4_3, AF41053_1, CELZK3777_2. AF060570_1, AF026465_1; I50600, HSU61262_1, DMU88578_1, P_W08747, and DMNRG2_2.

Example 49

Isolation of cDNA Clones Encoding Human PRO4980 Polypeptides [UNQ2422]

An initial DNA sequence, referred to herein as DNA81573 was identified by a yeast screen, in a human cDNA library that preferentially represents the 5' ends of the primary cDNA clones. This cDNA was then compared to ESTs from public databases (e.g., GenBank), and a proprietary EST database (LIFESEQ®, Incyte Pharmaceuticals, Palo Alto, Calif.), using the computer program BLAST or BLAST2 [Altschul et al., Methods in Enzymology, 266:460-480 (1996)]. The ESTs were clustered and assembled into a consensus DNA sequence with the program "phrap" (Phil Green, University of Washington, Seattle, Wash.). This consensus sequence is herein designated DNA90613.

PCR primers (forward and reverse) were synthesized based upon the DNA90613 sequence for use as probes to isolate a clone of the full-length coding sequence for PRO4980 from a human aortic endothelial cell cDNA library:

```
forward PCR primer:
                                        (SEQ ID NO: 227)
5'-CAACCGTATGGGACCGATACTCG-3'

reverse PCR primer:
                                        (SEQ ID NO: 228)
5'-CACGCTCAACGAGTCTTCATG-3'

hybridization probe:
                                        (SEQ ID NO: 229)
5'-GTGGCCCTCGCAGTGCAGGCCTTCTACGTCCAATACAAGTG-3'
```

RNA for construction of the cDNA libraries was isolated from human aortic endothelial cell tissue. The cDNA libraries used to isolate the cDNA clones were constructed by standard methods using commercially available reagents such as those from Invitrogen, San Diego, Calif. The cDNA was primed with oligo dT containing a Not site, linked with blunt to Sal hemikinased adaptors, cleaved with Not, sized appropriately by gel electrophoresis, and cloned in a defined orientation into a suitable cloning vector (such as pRKB or pRKD; pRK5B is a precursor of pRK5D that does not contain the Sfi site; see, Holmes et al., Science, 253:1278-1280 (1991)) in the unique Xho and Not sites.

The full-length DNA97003-2649 clone obtained from this screen is shown in FIG. 99 [SEQ ID NO:99] and contains a single open reading frame with an apparent translational initiation site at nucleotide positions 286-288, and an apparent stop codon at nucleotide positions 1900-1902. The predicted polypeptide precursor is 538 amino acids long (FIG. 100; SEQ ID NO:100). The full-length PRO4980 protein shown in FIG. 100 has an estimated molecular weight of about 59,268 daltons and a pI of about 8.94. Analysis of the full-length PRO4980 sequence shown in FIG. 100 (SEQ ID NO: 100) evidences the presence of a variety of important polypeptide domains, wherein the locations given for those important polypeptide domains are approximate as described above. Analysis of the full-length PRO4980 polypeptide shown in FIG. 100 evidences the presence of the following: a signal peptide from about amino acid 1 to about amino acid 36; transmembrane domains from about amino acid 77 to about amino acid 95, from about amino acid 111 to about amino acid 133, from about amino acid 161 to about amino acid 184, from about amino acid 225 to about amino acid 248, from about amino acid 255 to about amino acid 273, from about amino acid 299 to about amino acid 314, from about amino acid 348 to about amino acid 373, from about amino acid 406 to about amino acid 421, from about amino acid 435 to about amino acid 456, and from about amino acid 480 to about amino acid 497; an N-glycosylation site from about amino acid 500 to about amino acid 504; a cAMP- and cGMP-dependent protein kinase phosphorylation site from about amino acid 321 to about amino acid 325; N-myristoylation sites from about amino acid 13 to about amino acid 19, from about amino acid 18 to about amino acid 24, from about amino acid 80 to about amino acid 86, from about amino acid 111 to about amino acid 117, from about amino acid 118 to about amino acid 124, from about amino acid 145 to about amino acid 151, from about amino acid 238 to about amino acid 244, from about amino acid 251 to about amino acid 257, from about amino acid 430 to about amino acid 436, from about amino acid 433 to about amino acid 439, from about amino acid 448 to about amino acid 454, from about amino acid 458 to about amino acid 464, from about amino acid 468 to about amino acid 474, from about amino acid 475 to about amino acid 481, from about amino acid 496 to about amino acid 502, and from about amino acid 508 to about amino acid 514; and a prokaryotic membrane lipoprotein lipid attachment site from about amino acid 302 to about amino acid 313. Clone DNA97003-2649 has been deposited with the ATCC on May 11, 1999 and is assigned ATCC deposit no. PTA-43.

An analysis of the Dayhoff database (version 35.45 SwissProt 35), using a WU-BLAST2 sequence alignment analysis of the full-length sequence shown in FIG. 100 (SEQ ID NO: 100), evidenced significant homology between the PRO4980 amino acid sequence and the following Dayhoff sequences: SC59_YEAST, S76857, CELF31F4_12, AC002464_1, NU5M_CHOCR, S59109, SAY10108_2, AF055482_2, F69049, and G70433.

Example 50

Isolation of cDNA Clones Encoding Human PRO4981 Polypeptides [UNQ2423]

A cDNA clone (DNA94849-2960) encoding a native human PRO4981 polypeptide was identified using a yeast screen, in a human Human testis cDNA library that preferentially represents the 5' ends of the primary cDNA clones.

Clone DNA94849-2960 contains a single open reading frame with an apparent translational initiation site at nucleotide positions 145-147 and ending at the stop codon at nucleotide positions 1690-1692 (FIG. 101; SEQ ID NO: 101). The predicted polypeptide precursor is 515 amino acids long (FIG. 102; SEQ ID NO: 102). The full-length PRO4981 protein shown in FIG. 102 has an estimated molecular weight of about 59357 daltons and a pI of about 9.40. Analysis of the full-length PRO4981 sequence shown in FIG. 102 (SEQ ID NO:102) evidences the presence of a variety of important polypeptide domains as shown in FIG. 102, wherein the locations given for those important polypeptide domains are approximate as described above. Clone DNA94849-2960 has been deposited with ATCC on Jul. 25, 2000 and is assigned ATCC deposit no. PTA-2306.

An analysis of the Dayhoff database (version 35.45 SwissProt 35), using the ALIGN-2 sequence alignment analysis of the full-length sequence shown in FIG. 102 (SEQ ID NO: 102), evidenced sequence identity between the PRO4981 amino acid sequence and the following Dayhoff sequences: TMA272073_1, AK001324_1, AE003806_12, AE003745_18, MS2_ARATH, AF149917_1, ATMS2LIPR_1, HETM_ANASP, T18552, LYS2_YEAST.

Example 51

Isolation of cDNA Clones Encoding Human PRO5801 Polypeptides [UNQ2501]

The extracellular domain (ECD) sequences (including the secretion signal sequence, if any) from about 950 known secreted proteins from the Swiss-Prot public database were used to search EST databases. The EST databases included (1) public EST databases (e.g., GenBank) and (2) a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA105850. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA105850 consensus sequence, oligonucleotides were synthesized: 1) to identify by PCR a cDNA library that contained the sequence of interest, and 2) for use as probes to isolate a clone of the full-length coding sequence for PRO5801. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer 1
5'-ACTCCATATTTTCCTACTTGTGGCA-3'    (SEQ ID NO: 230)

forward PCR primer 2
5'-CCCAAAGTGACCTAAGAAC-3'          (SEQ ID NO: 231)

reverse PCR primer
5'-TCACTGAATTTCTTCAAAACCATTGCA-3'  (SEQ ID NO: 232)
```

Additionally, a synthetic oligonucleotide hybridization probe was constructed from the consensus DNA105850 sequence which had the following nucleotide sequence

```
hybridization probe
5'-TGTGGCAGCGACTGCATCCGACATAAAGGAA (SEQ ID NO: 233)
CAGTTGTGCTCTGCCCACA-3'
```

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO5801 polypeptide (designated herein as DNA115291-2681 [FIG. 103, SEQ ID NO: 103]) and the derived protein sequence for that PRO5801 polypeptide.

The full length clone identified above contained a single open reading frame with an apparent translational initiation site at nucleotide positions 7-9 and a stop signal at nucleotide positions 1513-1515 (FIG. 103, SEQ ID NO:103). The predicted polypeptide precursor is 502 amino acids long, has a calculated molecular weight of approximately 55,884 daltons and an estimated pI of approximately 8.52. Analysis of the full-length PRO5801 sequence shown in FIG. 104 (SEQ ID NO:104) evidences the presence of a variety of important polypeptide domains as shown in FIG. 104, wherein the locations given for those important polypeptide domains are approximate as described above. Clone DNA115291-2681 has been deposited with ATCC on Jun. 8, 1999 and is assigned ATCC deposit no. PTA-202.

An analysis of the Dayhoff database shows that PRO5801 has sequence similarity to an IL-17 receptor protein and PRO5801 is also designated herein as IL-17RH1. Specifically, an analysis of the Dayhoff database (version 35.45 SwissProt 35), using the ALIGN-2 sequence alignment analysis of the full-length sequence shown in FIG. 104 (SEQ ID NO: 104), evidenced sequence identity between the PRO5801 amino acid sequence and the following Dayhoff sequences: HSU58917_1, P_W92409, P_W61272, P_W04185, P_W61271, P_W04184, P_W92408, GEN13979, MMU31993_1 and YSO2_CAEEL.

Example 52

Isolation of cDNA Clones Encoding Human PRO5995 Polypeptides [UNQ2507]

The extracellular domain (ECD) sequences (including the secretion signal sequence, if any) from about 950 known secreted proteins from the Swiss-Prot public database were used to search EST databases. The EST databases included (1) public EST databases (e.g., Merck/Washington University) and (2) a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA92934. In some cases, the DNA92934 consensus sequence derives from an intermediate consensus DNA sequence which was extended using repeated cycles of BLAST and phrap to extend that intermediate consensus sequence as far as possible using the sources of EST sequences discussed above.

Based on the DNA92934 consensus sequence, oligonucleotides were synthesized: 1) to identify by PCR a cDNA library that contained the sequence of interest, and 2) for use as probes to isolate a clone of the full-length coding sequence for PRO5995. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'GGATCTCTTGTTCAAGCATCCTACCAAC 3'   (SEQ ID NO: 234)

reverse PCR primer
5'TGTCATCACTGCAAGTTAAGGCTTCCC 3'    (SEQ ID NO: 235)
```

Additionally, a synthetic oligonucleotide hybridization probe was constructed from the consensus DNA92934 sequence which had the following nucleotide sequence

```
hybridization probe
5'CGTAGAGAAGTTATAATGCTGGCCTGCAGTT   (SEQ ID NO: 236)
TTGGCAACAAGCACTG 3'
```

RNA for construction of the cDNA libraries was isolated from human fetal kidney tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO5995 polypeptide (designated herein as DNA96988-2685 [FIG. 105, SEQ ID NO: 105]) and the derived protein sequence for that PRO5995 polypeptide.

The full length clone identified above contained a single open reading frame with an apparent translational initiation site at nucleotide positions 24-26 and a stop signal at nucleotide positions 3096-3098 (FIG. 105, SEQ ID NO: 105). The predicted polypeptide precursor is 1024 amino acids long, has a calculated molecular weight of approximately 117049 daltons and an estimated pI of approximately 6.90. Analysis of the full-length PRO5995 sequence shown in FIG. 106 (SEQ ID NO: 106) evidences the presence of a variety of important polypeptide domains as shown in FIG. 106, wherein the locations given for those important polypeptide domains are approximate as described above. Clone DNA96988-2685 has been deposited with ATCC on Jul. 20, 1999 and is assigned ATCC Deposit No. PTA-384.

An analysis of the Dayhoff database (version 35.45 SwissProt 35), using the ALIGN-2 sequence alignment analysis of the full-length sequence shown in FIG. 106 (SEQ ID NO: 106), evidenced sequence identity between the PRO5995 amino acid sequence and the following Dayhoff sequences: I59331; AMPN_RAT; AMPN_HUMAN; AMPE_HUMAN; P_R94512; HUMPLAA_1; A65888_1; AAP1_YEAST; P_W33661; AF049234_1.

Example 53

Isolation of cDNA Clones Encoding Human PRO6095 Polypeptides [UNQ2543]

A cDNA clone (DNA105680-2710) encoding a native human PRO6095 polypeptide was identified using a yeast screen, in a human bone marrow cDNA library that preferentially represents the 5' ends of the primary cDNA clones.

Clone DNA105680-2710 contains a single open reading frame with an apparent translational initiation site at nucleotide positions 372-374 and ending at the stop codon at nucleotide positions 458-460 (FIG. 109; SEQ ID NO: 109). The predicted polypeptide precursor is 457 amino acids long (FIG. 110; SEQ ID NO: 110). The full-length PRO6095 protein shown in FIG. 110 has an estimated molecular weight of about 52,015 daltons and a pI of about 9.22. Analysis of the full-length PRO6095 sequence shown in FIG. 110 (SEQ ID NO: 110) evidences the presence of a variety of important polypeptide domains as shown in FIG. 110, wherein the locations given for those important polypeptide domains are approximate as described above. Clone DNA105680-2710 has been deposited with ATCC on Aug. 3, 1999 and is assigned ATCC Deposit No. PTA-483.

An analysis of the Dayhoff database (version 35.45 SwissProt 35), using the ALIGN-2 sequence alignment analysis of the full-length sequence shown in FIG. 110 (SEQ ID NO: 110), evidenced sequence identity between the PRO6095 amino acid sequence and the following Dayhoff sequences: CELZC328_5, F15K9_2, S59792, S78570, S53021, F1003_10, A57514, GAR2_SCHPO, A70387, and CELW09C3_4.

Example 54

Isolation of cDNA Clones Encoding Human PRO6182 Polypeptides [UNQ2553]

A cDNA clone (DNA110700-2716) encoding a native human PRO6182 polypeptide was identified using a yeast screen, in a human breast carcinoma cDNA library that preferentially represents the 5' ends of the primary cDNA clones.

Clone DNA110700-2716 contains a single open reading frame with an apparent translational initiation site at nucleotide positions 18-20 and ending at the stop codon at nucleotide positions 1236-1238 (FIG. 111; SEQ ID NO:111). The predicted polypeptide precursor is 406 amino acids long (FIG. 112). The full-length PRO6182 protein shown in FIG. 112 has an estimated molecular weight of about 43,878 daltons and a pI of about 6.50. Analysis of the full-length PRO6182 sequence shown in FIG. 112 (SEQ ID NO: 112) evidences the presence of a variety of important polypeptide domains as shown in FIG. 112, wherein the locations given for those important polypeptide domains are approximate as described above. Clone DNA110700-2716 has been deposited with ATCC on Aug. 10, 1999 and is assigned ATCC Deposit No. PTA-512.

An analysis of the Dayhoff database (version 35.45 SwissProt 35), using the ALIGN-2 sequence alignment analysis of the full-length sequence shown in FIG. 112 (SEQ ID NO: 112), evidenced sequence identity between the PRO6182 amino acid sequence and the following Dayhoff sequences: AB011161_1; AC005542_2; EMU41602_1;

HUMIGCH06_1; PTN8_MOUSE; HUMIGCH08_1; AF012848_1; S17597; P_P40254; DTC_HUMAN.

Example 55

Isolation of cDNA Clones Encoding Human PRO7170 Polypeptides [UNQ2782]

DNA108722-2743 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, Incyte Pharmaceuticals, Palo Alto, designated herein as CLU57836. This EST cluster sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58756.

In light of an observed sequence homology between the DNA58756 sequence and an EST sequence encompassed within clone no. 2251462 from the LIFESEQ® database, Incyte Pharmaceuticals, Palo Alto, Calif., clone no. 2251462 was purchased and the cDNA insert was obtained and sequenced. It was found herein that that cDNA insert encoded a full-length protein. The sequence of this cDNA insert is shown in FIG. 113 and is herein designated as DNA108722-2743.

Clone DNA108722-2743 contains a single open reading frame with an apparent translational initiation site at nucleotide positions 60-62 and ending at the stop codon at nucleotide positions 1506-1508 (FIG. 113; SEQ ID NO:113). The predicted polypeptide precursor is 482 amino acids long (FIG. 114; SEQ ID NO:114). The full-length PRO7170 protein shown in FIG. 114 has an estimated molecular weight of about 49,060 daltons and a pI of about 4.74. Analysis of the full-length PRO7170 sequence shown in FIG. 114 (SEQ ID NO: 114) evidences the presence of a variety of important polypeptide domains as shown in FIG. 114, wherein the locations given for those important polypeptide domains are approximate as described above. Clone DNA108722-2743 has been deposited with ATCC on Aug. 17, 1999 and is assigned ATCC Deposit No. PTA-552.

An analysis of the Dayhoff database (version 35.45 SwissProt 35), using the ALIGN-2 sequence alignment analysis of the full-length sequence shown in FIG. 114 (SEQ ID NO: 114), evidenced sequence identity between the PRO7170 amino acid sequence and the following Dayhoff sequences: P_Y12291, I47141, D88733_1, DMC56G7_1, P_Y11606, HWP1_CANAL, HSMUC5BEX_1, HSU78550_1, HSU70136_1, and SGS3_DROME Example 56

Isolation of cDNA Clones Encoding Human PRO7171 Polypeptides [UNQ2783]

DNA108670-2744 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the LIFESEQ® database, Incyte Pharmaceuticals, Palo Alto, Calif., designated herein as 212369. This EST sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA79089.

In light of an observed sequence homology between the DNA79089 sequence and an EST sequence encompassed within clone no. 212369 from the LIFESEQ® database, Incyte Pharmaceuticals, Palo Alto, Calif., clone no. 212369 was purchased and the cDNA insert was obtained and sequenced. It was found herein that that cDNA insert encoded a full-length protein. The sequence of this cDNA insert is shown in FIG. 115 and is herein designated as DNA108670-2744.

Clone DNA108670-2744 contains a single open reading frame with an apparent translational initiation site at nucleotide positions 93-95 and ending at the stop codon at nucleotide positions 495-497 (FIG. 115; SEQ ID NO:115). The predicted polypeptide precursor is 134 amino acids long (FIG. 116; SEQ ID NO:116). The full-length PRO7171 protein shown in FIG. 116 has an estimated molecular weight of about 14,120 daltons and a pI of about 4.77. Analysis of the full-length PRO7171 sequence shown in FIG. 116 (SEQ ID NO: 116) evidences the presence of a variety of important polypeptide domains as shown in FIG. 116, wherein the locations given for those important polypeptide domains are approximate as described above. Clone DNA108670-2744 has been deposited with ATCC on Aug. 17,1999 and is assigned ATCC Deposit No. PTA-546.

An analysis of the Dayhoff database (version 35.45 SwissProt 35), using the ALIGN-2 sequence alignment analysis of the full-length sequence shown in FIG. 116 (SEQ ID NO: 116), evidenced sequence identity between the PRO7171 amino acid sequence and the following Dayhoff sequences: AC007504_28, AF103900_1, OPUD_BACSU, G69670, T02361, and TS11_GIALA.

Example 57

Isolation of cDNA Clones Encoding Human PRO7436 Polypeptides [UNQ2973]

DNA119535-2756 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the LIFESEQ® database, Incyte Pharmaceuticals, Palo Alto, Calif., designated herein as 5325636. This EST sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program “phrap” (Phil Green, University of Washington, Seattle, Wash.). The consensus sequence obtained therefrom is herein designated DNA105428.

In light of an observed sequence homology between the DNA105428 sequence and an EST sequence encompassed within clone no. 5325636 from the LIFESEQ® database, Incyte Pharmaceuticals, Palo Alto, Calif., clone no. 5325636 was purchased and the cDNA insert was obtained and sequenced. It was found herein that that cDNA insert encoded a full-length protein. The sequence of this cDNA insert is shown in FIG. 117 and is herein designated as DNA119535-2756.

Clone DNA119535-2756 contains a single open reading frame with an apparent translational initiation site at nucleotide positions 211-213 and ending at the stop codon at nucleotide positions 1111-1113 (FIG. 117; SEQ ID NO:117). The predicted polypeptide precursor is 300 amino acids long (FIG. 118; SEQ ID NO:118). The full-length PRO7436 protein shown in FIG. 118 has an estimated molecular weight of about 32,638 daltons and a pI of about 6.02. Analysis of the full-length PRO7436 sequence shown in FIG. 118 (SEQ ID NO: 118) evidences the presence of a variety of important polypeptide domains as shown in FIG. 118, wherein the locations given for those important polypeptide domains are approximate as described above. Clone DNA119535-2756 has been deposited with ATCC on Aug. 31, 1999 and is assigned ATCC Deposit No. PTA-613.

An analysis of the Dayhoff database (version 35.45 SwissProt 35), using the ALIGN-2 sequence alignment analysis of the full-length sequence shown in FIG. 118 (SEQ ID NO: 118), evidenced sequence identity between the PRO7436 amino acid sequence and the following Dayhoff sequences: AC005955_1, CGM1_HUMAN, P_R22041, CCEM_HUMAN, P_R06434, P_P93996, CE10_MOUSE, HOM6PSG2_1, PSG6_HUMAN, and ECTO_RAT.

Example 58

Isolation of cDNA clones Encoding Human PRO9912 Polypeptides [UNQ3077]

An expressed sequence tag (EST) DNA database LIFESEQ (Incyte Pharmaceuticals, Palo Alto, Calif.) was searched and an EST was identified which showed homology to autotaxin.

EST clone no. 2921845 was then purchased from LIFESEQ (Incyte Pharmaceuticals, Palo Alto, Calif.) and the cDNA insert of that clone was obtained and sequenced in entirety. The entire nucleotide sequence of the clone, designated herein as DNA108700-2802, is shown in FIG. 119 (SEQ ID NO: 119). The DNA 108700-2802 clone contains a single open reading frame with an apparent translational initiation site at nucleotide positions 4-6 and a stop signal at nucleotide positions 1378-1380 (FIG. 119, SEQ ID NO:119). The predicted polypeptide precursor is 458 amino acids long, has a calculated molecular weight of approximately 51506 daltons and an estimated pI of approximately 6.79. Analysis of the full-length PRO9912 sequence shown in FIG. 120 (SEQ ID NO:120) evidences the presence of a variety of important polypeptide domains as shown in FIG. 120, wherein the locations given for those important polypeptide domains are approximate as described above. Clone DNA108700-2802 has been deposited with ATCC on Dec. 22, 1999 and is assigned ATCC deposit no. PTA-1093.

An analysis of the Dayhoff database (version 35.45 SwissProt 35), using the ALIGN-2 sequence alignment analysis of the full-length sequence shown in FIG. 120 (SEQ ID NO: 120), evidenced sequence identity between the PRO9912 amino acid sequence and the following Dayhoff sequences: HS8B1_1, P_W75859, AB020686_1, P_Y17529, P_Y34324, T09933, PDNP3_1, PC1_HUMAN, HUMATXT_1 and P_R86595.

Example 59

Isolation of cDNA Clones Encoding Human PRO9917 Polypeptides [UNQ3079]

An expressed sequence tag (EST) DNA database LIFESEQ (Incyte Pharmaceuticals, Palo Alto, Calif.) was searched and an EST was identified which showed homology to a human prostate stem cell antigen.

EST clone no. 2498349 was then purchased from Incyte Pharmaceuticals, Palo Alto, Calif., and the cDNA insert of that clone was obtained and sequenced in entirety.

The entire nucleotide sequence of the clone, designated herein as DNA119474-2803, is shown in FIG. 121 (SEQ ID NO: 121). The DNA119474-2803 clone contains a single open reading frame with an apparent translational initiation site at nucleotide positions 121-123 and a stop signal at nucleotide positions 544-546 (FIG. 121, SEQ ID NO:121). The predicted polypeptide precursor is 141 amino acids long, has a calculated molecular weight of approximately 15240 daltons and an estimated pI of approximately 8.47. Analysis of the full-length PRO9917 sequence shown in FIG. 122 (SEQ ID NO:122) evidences the presence of a variety of important polypeptide domains as shown in FIG. 122, wherein the locations given for those important polypeptide domains are approximate as described above. Chromosome mapping evidences that the PRO9917-encoding nucleic acid maps to 2q21-q22 in humans. Clone DNA119474-2803 has been deposited ATCC on Dec. 22, 1999 and is assigned ATCC deposit no. PTA-1097.

An analysis of the Dayhoff database (version 35.45 SwissProt 35), using the ALIGN-2 sequence alignment analysis of the full-length sequence shown in FIG. 122 (SEQ ID NO:122), evidenced sequence identity between the PRO9917 amino acid sequence and the following Dayhoff sequences: PSCA_1, P_W80956, AF043498_1, P_W70522, P_W86024, P_W62066, P_Y13938, P_Y13347, D45835 and HSU08839_1. Interestingly, the PRO9917 polypeptide lacks the GPI tail that almost all members of the Prostate Stem Cell Antigen (PSCA) family have.

Example 60

Isolation of cDNA Clones Encoding Human PRO19646 Polypeptides [UNQ5827]

The extracellular domain (ECD) sequences (including the secretion signal sequence, if any) from about 950 known secreted proteins from the Swiss-Prot public database were used to search EST databases. The EST databases included (1) public EST databases (e.g., GenBank), (2) a proprietary EST database (LIFESEQ®, Incyte Pharmaceuticals, Palo Alto, Calif.), (3) a proprietary EST database from Genentech. The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA144267. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA144267 consensus sequence, oligonucleotides were synthesized: 1) to identify by PCR a cDNA library that contained the sequence of interest, and 2) for use as probes to isolate a clone of the full-length coding sequence for PRO19646. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer 5'--3'
                                    (SEQ ID NO: 237)
GTCGCCCCATTTCCTGCAACAG

reverse PCR primer 5'--3'
                                    (SEQ ID NO: 238)
GGGCCTGCTCTCCCTCTGAAGC
```

Additionally, a synthetic oligonucleotide hybridization probe was constructed from the consensus DNA144267 sequence which had the following nucleotide sequence

```
hybridization probe 5'--3'
                                    (SEQ ID NO: 239)
GTGCTGGGCTCTGGAGCCACACTGCGTCTTCCGTC
```

RNA for construction of the cDNA libraries was isolated from human [identify tissue type] tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO19646 polypeptide (designated herein as DNA145841-2868 [FIG. 127, SEQ ID NO: 127]) and the derived protein sequence for that PRO19646 polypeptide.

The full length clone identified above contained a single open reading frame with an apparent translational initiation site at nucleotide positions 199-201 and a stop signal at nucleotide positions 2322-2324 (FIG. 127, SEQ ID NO:127). The predicted polypeptide precursor is 708 amino acids long, has a calculated molecular weight of approximately 75093 daltons and an estimated pI of approximately 6.65. Analysis of the full-length PRO19646 sequence shown in FIG. 128 (SEQ ID NO:128) evidences the presence of a variety of important polypeptide domains as shown in FIG. 128, wherein the locations given for those important polypeptide domains are approximate as described above. Clone DNA 145841-2868 has been deposited with ATCC on Apr. 11, 2000 and is assigned ATCC deposit no. PTA-1678.

An analysis of the Dayhoff database (version 35.45 SwissProt 35), using the ALIGN-2 sequence alignment analysis of the full-length sequence shown in FIG. 128 (SEQ ID NO: 128), evidenced sequence identity between the PRO19646 amino acid sequence and the following Dayhoff sequences: DMC163A10_1, ICCR_DROME, NM_004646_1, AF210316_1, PGBM_HUMAN, NM_002821_1, P_W83927, HSU33G35_1, MAG_HUMAN, NM_001771_1.

Example 61

Isolation of cDNA Clones Encoding Human PRO19820 Polypeptides [UNQ5926]

DNA149911-2885 was identified by applying a proprietary signal sequence finding algorithm developed by Genentech, Inc. (South San Francisco, Calif.) upon genomic DNA from public (e.g., GenBank) and/or private databases. In this instance, a genomic sequence from GenBank (Accession No:) was analyzed using the gene prediction program GENSCAN, licensed from Stanford University. GENSCAN analysis predicts gene coding regions by identifying the potential exons and removing introns, creating DNA sequences which are then subjected to the signal algorithm. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. In order to determine whether the sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of a sequence from the GenBank database, designated herein as DNA144336.

Based on the DNA144336 sequence, oligonucleotides were synthesized: 1) to identify by PCR a cDNA library that contained the sequence of interest, and 2) for use as probes to isolate a clone of the full-length coding sequence for PRO19820. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-AGCCCCAGGGAGCACAGGCT-3'     (SEQ ID NO: 240)

reverse PCR primer
5'-GCTCGTCACGGCCATCTTCACC-3'  (SEQ ID NO: 241)
```

Additionally, a synthetic oligonucleotide hybridization probe was constructed from the consensus DNA144389 sequence which had the following nucleotide sequence

```
hybridization probe
5'-TGCGACAGCGGCATCAGGCGGTTCTTC-3'  (SEQ ID NO: 242)
```

RNA for construction of the cDNA libraries was isolated from human mixed tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO19820 polypeptide (designated herein as DNA149911-2885 [FIG. 131, SEQ ID NO: 131]) the derived protein sequence for that PRO19820 polypeptide.

Clone DNA149911-2885 contains a single open reading frame with an apparent translational initiation site at nucleotide positions 9-11 and ending at the stop codon at nucleotide positions 342-344 (FIG. 131). The predicted polypeptide precursor is 111 amino acids long (FIG. 132; SEQ ID NO: 132). The full-length PRO19820 protein shown in FIG. 132 has an estimated molecular weight of about 12447 daltons and a pI of about 8.31. Analysis of the full-length PRO19820 sequence shown in FIG. 132 (SEQ ID NO: 132) evidences the presence of a variety of important polypeptide domains as shown in FIG. 132, wherein the locations given for those important polypeptide domains are approximate as described above. Clone DNA149911-2885 has been deposited with ATCC on Apr. 25, 2000 and is assigned ATCC deposit no. PTA-1776.

An analysis of the Dayhoff database (version 35.45 SwissProt 35), using the ALIGN-2 sequence alignment analysis of the full-length sequence shown in FIG. 132 (SEQ ID NO: 132), evidenced sequence identity between the PRO19820 amino acid sequence and the following Dayhoff sequences: P_Y41705, NM_000727_1, G70864, CCG1_HUMAN, MNT_HUMAN, P_Y06527, T13049, P_W47524, AF030100_1, and RNAJ696_1.

Example 62

Isolation of cDNA Clones Encoding Human PRO21201 Polypeptides [UNQ6098]

DNA168028-2956 was identified by applying a proprietary signal sequence finding algorithm developed by Genentech, Inc. (South San Francisco, Calif.) upon genomic DNA from public (e.g., GenBank) and/or private databases. In this instance, a genomic sequence from GenBank (Accession No: Z98200) was analyzed using the gene prediction program GENSCAN, licensed from Stanford University. GENSCAN analysis predicts gene coding regions by identifying the potential exons and removing introns, creating DNA sequences which are then subjected to the signal algorithm. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. In order to determine whether the sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of a sequence from the GenBank database, designated herein as DNA144330.

Based on the DNA144330 sequence, oligonucleotides were synthesized: 1) to identify by PCR a cDNA library that contained the sequence of interest, and 2) for use as probes to isolate a clone of the full-length coding sequence for PRO21201. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-TCCACGACCTCCTGTCGGAGC-3'    (SEQ ID NO: 243)

reverse PCR primer
5'-AGACCCTGTGCGGACTGCTGC-3'    (SEQ ID NO: 244)
```

Additionally, a synthetic oligonucleotide hybridization probe was constructed from the consensus DNA144330 sequence which had the following nucleotide sequence

```
hybridization probe
5'-AGCCCCGACCACAGCAGCAGCCCC-3'    (SEQ ID NO: 245)
```

RNA for construction of the cDNA libraries was isolated from a mixture of human tissues. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO21201 polypeptide (designated herein as DNA 168028-2956 [FIG. 133, SEQ ID NO: 133]) and the derived protein sequence for that PRO21201 polypeptide.

Clone DNA168028-2956 contains a single open reading frame with an apparent translational initiation site at nucleotide positions 78-80 and ending at the stop codon at nucleotide positions 1080-1082 (FIG. 133). The predicted polypeptide precursor is 334 amino acids long (FIG. 134; SEQ ID NO:134). The full-length PRO21201 protein shown in FIG. 134 has an estimated molecular weight of about 37257 daltons and a pI of about 5.95. Analysis of the full-length PRO21201 sequence shown in FIG. 134 (SEQ ID NO:134) evidences the presence of a variety of important polypeptide domains as shown in FIG. 134, wherein the locations given for those important polypeptide domains are approximate as described above. Clone DNA168028-2956 has been deposited with ATCC on Jul. 25, 2000 and is assigned ATCC deposit no. PTA-2304.

An analysis of the Dayhoff database (version 35.45 SwissProt 35), using the ALIGN-2 sequence alignment analysis of the full-length sequence shown in FIG. 134 (SEQ ID NO: 134), evidenced sequence identity between the PRO21201 amino acid sequence and the following Dayhoff sequences: NM_014028_1, AF077205_1, YR53_CAEEL and T22084.

Example 63

Isolation of cDNA Clones Encoding Human PRO20026 Polypeptides [UNQ6115]

The extracellular domain (ECD) sequences (including the secretion signal sequence, if any) from about 950 known secreted proteins from the Swiss-Prot public database were used to search EST databases. The EST databases included a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA149870. In some cases, the DNA149870 consensus sequence derives from an intermediate consensus DNA sequence which was extended using repeated cycles of BLAST and phrap to extend that intermediate consensus sequence as far as possible using the sources of EST sequences discussed above.

Based on the DNA149870 consensus sequence, flip cloning was performed. Oligonucleotides were synthesized: 1) to identify by PCR a cDNA library that contained the sequence of interest, and 2) for use as probes to isolate a clone of the full-length coding sequence for PRO20026. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by Flip PCR amplification, as per Schanke et al., BioTechniques, 16:414-416 (1994), with the PCR primer pair. A positive library was then used isolate clones encoding the gene of interest using the probe oligonucleotide and one of the primer pairs.

PCR primers (forward and reverse) were synthesized:

```
forward PCR primer:
5'-CGTTGTTTGTCAGTGGAGAGCAGGG-3'    (SEQ ID NO: 246)

reverse PCR primer
5'-CAGGAACACCTGAGGCAGAAGCG-3'    (SEQ ID NO: 247)
```

Additionally, a synthetic oligonucleotide hybridization probe was constructed from the consensus DNA149870 sequence which had the following nucleotide sequence

```
hybridization probe
                                        (SEQ ID NO: 248)
5'-CTATCTCCCTGCCAGGAGGCCGGAGTGGGGGAGGTCAGAC-3'
```

RNA for construction of the cDNA libraries was isolated from human tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO20026 polypeptide (designated herein as DNA 154095-2998 [FIG. 135, SEQ ID NO: 135]) and the derived protein sequence for that PRO20026 polypeptide.

The full length clone identified above contained a single open reading frame with an apparent translational initiation site at nucleotide positions 70-72 and a stop signal at nucleotide positions 2254-2256 (FIG. 135, SEQ ID NO: 135). The predicted polypeptide precursor is 728 amino acids long, has a calculated molecular weight of approximately 81,310 daltons and an estimated pI of approximately 6.84. Analysis of the full-length PRO20026 sequence shown in FIG. 136 (SEQ ID NO: 136) evidences the presence of a variety of important polypeptide domains as shown in FIG. 136, wherein the locations given for those important polypeptide domains are approximate as described above. Clone DNA154095-2998 has been deposited with ATCC on Oct. 10, 2000 and is assigned ATCC Deposit No. PTA-2591.

An analysis of the Dayhoff database shows that PRO20026 has sequence similarity to an IL-17 receptor protein and PRO2006 is also designated herein as IL-17RH4. Specifically, an analysis of the Dayhoff database (version 35.45 SwissProt 35), using the ALIGN-2 sequence alignment analysis of the full-length sequence shown in FIG. 136 (SEQ ID NO: 136), evidenced sequence identity between the PRO20026 amino acid sequence and the following Dayhoff sequences: T42695, P_W04185, P_W92409, P_W61272, NM_014339_1, HSU58917_1, MMU31993_1, GEN13979, P_W04184, P_W61271.

Example 64

Isolation of cDNA Clones Encoding Human PRO23202 Polypeptides [UNQ6507]

An expressed sequence tag (EST) DNA database (LIFESEQ®, Incyte Pharmaceuticals, Palo Alto, Calif.) was searched and an EST was identified by GEPIS. Gene expression profiling in silico (GEPIS) is a bioinformatics tool that characterizes genes of interest for new therapeutic targets. GEPIS takes advantage of the vast amount of EST sequence and library information to determine gene expression profiles. GEPIS is based on the assumption that the expression level of a gene is proportionally correlated with the number of its occurrences in EST databases, and it works by integrating the Incyte EST relational database and Genentech proprietary information in a stringent and statistically meaningful way. In this example, it is used to identify and cross-validate new tumor antigens, although GEPIS can be configured to either perform very specific analyses or broad screening tasks. For the initial screen, GEPIS is used to go from libraries to sequence. The entire Incyte database was used to cluster sequence based on its library information. Breast, colon, lung and prostate were the target organs specified. The sequences found in this initial cluster were then subjected to a screen for secreted and transmembrane containing domains. The remaining sequences were then screened for novelty and those individual sequences identified. In a final step, each individual sequence was then put through a GEPIS screen, this time going from sequence to library, confirming its expression profile in the original target tissue. Using this type of screening bioinformatics, DNA182753 was identified, and PCR primers designed using this sequence were used to screen libraries for the full length clone.

RNA for construction of cDNA libraries was then isolated from human prostate tissue. The cDNA libraries used to isolate the cDNA clones encoding human PRO23203 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278-1280 (1991)) in the unique XhoI and NotI.

Oligonucleotides probes based upon the above described EST sequence were then synthesized: 1) to identify by PCR a cDNA library that contained the sequence of interest, and 2) for use as probes to isolate a clone of the full-length coding sequence for PRO23203. Forward and reverse PCR primers generally range from 20 to 30 nucleotides and are often designed to give a PCR product of about 100-1000 bp in length. The probe sequences are typically 40-55 bp in length. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

The oligonucleotide probes employed were as follows:

```
forward PCR primer
                                        (SEQ ID NO: 249)
5'-GATATTTGTTTCTCAACATGGCTTATCAGCAGG-3'

reverse PCR primer
                                        (SEQ ID NO: 250)
5'-TCTCTGACCTTCTCATCGGTAAGCAGAGG-3'

hybridization probe
                                        (SEQ ID NO: 251)
5'-TCTTTTGCAGCTTTGCAGATACCCAGACTGAGCTGGAACTGGA-3'
```

A full length clone [herein designated DNA185171-2994] was identified that contained a single open reading frame with an apparent translational initiation site at nucleotide positions 188-190 and a stop signal at nucleotide positions 1550-1552 (FIG. 139, SEQ ID NO: 139). The predicted polypeptide precursor is 454 amino acids long, has a calculated molecular weight of approximately 52008 daltons and an estimated pI of approximately 8.83. Analysis of the full-length PRO23203 sequence shown in FIG. 140 (SEQ ID NO: 140) evidences the presence of a variety of important polypeptide domains as shown in FIG. 140, wherein the locations given for those important polypeptide domains are approximate as described above. Clone DNA185171-2994 has been deposited with ATCC on Sep. 26, 2000 and is assigned ATCC deposit no. PTA-2513.

An analysis of the protein database (version 35.45 SwissProt 35), using the ALIGN-2 sequence alignment analysis of the full-length sequence shown in FIG. 140 (SEQ ID NO: 140), evidenced sequence identity between the PRO23203 amino acid sequence and the following sequences: AK001691_1.

Example 65

Isolation of cDNA Clones Encoding Human PRO35250 Polypeptides [UNQ9574]

DNA171732-3100 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the LIFESEQ® (Incyte Pharmaceuticals, Palo Alto, Calif.) database, designated herein as 248197.2. The source of the EST sequence was a library prepared from right temporal lobe tissue removed from a 45-year-old black male during a brain lobectomy. CDNA synthesis was initiated using a NotI-anchored oligo (dT) primer. Double-stranded cDNA was blunted, ligated to EcoRI adaptors, digested with NotI, size-selected, and cloned into the NotI and EcoRI sites of the pINCY vector (Incyte). This EST sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA130657.

In light of an observed sequence homology between the DNA130657 sequence and an EST sequence encompassed within clone no. 4028188 from the LIFESEQ® (Incyte Pharmaceuticals, Palo Alto, Calif.) database, clone no. 4028188 was purchased and the cDNA insert was obtained and sequenced. It was found herein that the cDNA insert encoded a full-length protein. The sequence of this cDNA insert is shown in FIG. 141 and is herein designated as DNA171732-3100.

Clone DNA171732-3100 contains a single open reading frame with an apparent translational initiation site at nucleotide positions 52-54 and ending at the stop codon at nucleotide positions 604-606 (FIG. 141; SEQ ID NO: 141). The predicted polypeptide precursor is 184 amino acids long (FIG. 142; SEQ ID NO: 142). The full-length PRO35250 protein shown in FIG. 142 has an estimated molecular weight of about 19,806 daltons and a pI of about 4.74. Analysis of the full-length PRO35250 sequence shown in FIG. 142 (SEQ ID NO: 142) evidences the presence of a variety of important polypeptide domains as shown in FIG. 142, wherein the locations given for those important polypeptide domains are approximate as described above. Clone DNA171732-3100 has been deposited with ATCC on Apr. 24, 2001 and is assigned ATCC deposit no. PTA-3329.

An analysis of the Dayhoff database (version 35.45 SwissProt 35), using the ALIGN-2 sequence alignment analysis of the full-length sequence shown in FIG. 142 (SEQ ID NO: 142), evidenced sequence identity between the PRO35250 amino acid sequence and the following Dayhoff sequence: AK003305_1.

Example 66

Generation and Analysis of Mice Comprising PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Gene Disruptions To investigate the role of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides, disruptions in PRO69122, PRO204, PRO214, PRO222, PRO234, PRO265, PRO309, PRO332, PRO342, PRO356, PRO540, PRO618, PRO944, PRO944, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 genes were produced by homologous recombination or retroviral insertion techniques. Specifically, transgenic mice comprising disruptions in PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wild type, heterozygote and homozygote cohorts which were used for phenotypic analysis. Rarely, if not enough F 1 heterozygotes were produced, the F1 hets were bred to wildtype C57 mice to produce sufficient heterozygotes to breed for cohorts to be analyzed for a phenotype. All phenotypic analysis was performed from 12-16 weeks after birth.

Overall Summary of Phenotypic Results 66.1. Generation and Analysis of Mice Comprising DNA284870 (UNQ128) Gene Disruptions In these knockout experiments, the gene encoding PRO69122 polypeptides (designated as DNA284870) (UNQ128) was disrupted. The gene specific information for these studies is as follows: the mutated mouse gene corresponds to nucleotide reference: AK005023 *Mus musculus* adult male liver cDNA, RIKEN full-length enriched library, clone: 1300016D21 product: SelI (suppressor of lin-12) 1 homolog (*C. elegans*); protein reference: Q9Z2G6 ACCESSION:Q9Z2G6 NID: *Mus musculus* (Mouse). Sel-1 homolog precursor (Suppressor of lin-12-like protein) (Sel-1L); the human gene sequence reference: NM_005065 ACCESSION:NM_005065 NID: 19923668 *Homo sapiens Homo sapiens* sel-1 suppressor of lin-12-like (*C. elegans*) (SEL1L); the human protein sequence corresponds to reference: Q9UBV2 ACCESSION:Q9UBV2 NID: *Homo sapiens* (Human). SEL-1 HOMOLOG PRECURSOR (SUPPRESSOR OF LIN-12-LIKE PROTEIN) (SEL-1L).

The mouse gene of interest is Sel1h (Sel1 [suppressor of lin-12] 1 homolog [*C. elegans*]), ortholog of human SEL1 L (sel-1 suppressor of lin-12-like [*C. elegans*]). Aliases include IBD2; SEL1-LIKE; sel-1 (suppressor of lin-12, *C. elegans*)-like; and Suppressor of lin 12 (sel-1), *C. elegans*, homolog of.

SEL1L is an intracellular vesicle-associated protein, consisting of a signal peptide, a fibronectin type II domain, a transmembrane segment, and a proline-rich C terminus. Although the function of this protein is unknown, SEL1L has been proposed to play a role in processes such as Notch signaling, intracellular protein trafficking, secretion, cell growth inhibition, and tumor aggressiveness; the gene is expressed during pancreas development and in neural tube and dorsal root ganglia (Donoviel et al, *Mech Dev* 78(1-2): 203-7 (1998); Cattaneo et al, *Gene* 326:149-56 (2004); Chiaramonte et al, *Anticancer Res* 22(6C):4211-4 (2002); Orlandi et al, *Cancer Res* 62(2):567-74 (2002); Biunno et al, *Genomics* 46(2):284-6 (1997); Grant and Greenwald, *Development* 124(3):637-44 (1997)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 36 | 0 | 52 |
| Expected | 13.0 | 26.0 | 13.0 | 52 |

Chi-Sq.=33.49 Significance=5.3424262E-8 (hom/n)=0.0 Avg. Litter Size=8

Mutation Information

Mutation Type: Homologous Recombination (standard)

Description: Coding exon 1 was targeted (NCBI accession NM_011344.1).

Wild-type Expression Panel: Expression of the target gene was detected in embryonic stem (ES) cells and in all 13 adult tissue samples tested by RT-PCR.

QC Expression: Disruption of the target gene was confirmed by Southern hybridization analysis.

66.1.1. Phenotypic Analysis (for Disrupted Gene: DNA284870 (UNQ128)

(a) Overall Phenotypic Summary:

Mutation of the gene encoding the ortholog of human sel-1 suppressor of lin-12-like (*C. elegans*) (SEL1L) resulted in lethality of (−/−) mutants. Gene disruption was confirmed by Southern blot.

(b) Microarray Analysis

Tissue microarray analysis shows UNQ128 to be strongly expressed in the pancreas and down regulated in pancreatic carcinomas. In addition, UNQ 128 is also overexpressed in breast tumors compared to normal breast tissue.

(c) Pathology

Microscopic: Not tested due to embryonic lethality. At 12.5 days, there were 40 embryos observed: 21(+/−) embryos, 2 (+/+) embryos, 4 resorption moles, 10 to-be-determined, and 3 inconclusive.

Gene Expression: LacZ activity was not detected in the panel of tissues by immunohistochemistry. Transverse sections of LacZ whole mounts in heterozygous embryos at 12.5 dpc shows expression in the inner layer of the retina; fore limb muscle; endothelium of the cranial vasculature and floor plate expression in the neural tube which is indicative of a role in neural patterning.

Discussion Related to Embryonic Developmental Abnormality of Lethality:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

66.2. Generation and Analysis of Mice Comprising DNA30871-1157 (UNQ178) Gene Disruptions In these knockout experiments, the gene encoding PRO204 polypeptides (designated as DNA30871-1157) (UNQ178) was disrupted. The gene specific information for these studies is as follows: the mutated mouse gene corresponds to nucleotide reference: NM_019790 *Mus musculus* transmembrane protein with EGF-like and two follistatin-like domains 2 (Tmeff2); protein reference: Q9QYM9 ACCESSION: Q9QYM9 NID: *Mus musculus* (Mouse). TMEFF2 PROTEIN PRECURSOR; the human gene sequence reference: NM_016192 ACCESSION:NM_016192 NID: 12383050 *Homo sapiens Homo sapiens* transmembrane protein with EGF-like and two follistatin-like domains 2 (TMEFF2); the human protein sequence corresponds to reference:Q9UIK5 ACCESSION:Q9UIK5 NID: *Homo sapiens* (Human). TMEFF2 PROTEIN PRECURSOR (TRANSMEMBRANE PROTEIN TENB2) (TPEF) (TRANSMEMBRANE PROTEIN WITH EGF-LIKE AND TWO FOLLISTATIN-LIKE DOMAINS 2).

The mouse gene of interest is Tmeff2 (transmembrane protein with EGF-like and two follistatin-like domains 2), ortholog of human TMEFF2. Aliases include 4832418D20Rik, TR, HPP1, TPEF, TENB2, tomoregulin, transmembrane protein TENB2, and putative transmembrane protein with EGF-like and two follistatin-like domains 2.

TMEFF2 is a type I plasma membrane protein that may function as a protease inhibitor or signal transducing receptor. The protein contains a signal peptide, two Kazal-type serine protease inhibitor domains (Pfam accession PF00050), an EGF-like domain, a transmembrane segment, and a cytoplasmic C-terminal G protein-activating motif. TMEFF2 undergoes ectodomain shedding to produce a secreted form, consisting of the protease domains and the EGF-like domain. The extracellular segment of TMEFF2 is capable of stimulating tyrosine phosphorylation of receptor tyrosine kinase ERBB4, suggesting that TMEFF2 functions as a signal-transducing ligand. Moreover, the TMEFF2 extracellular segment can increase survival of cultured neurons, suggesting that TMEFF2 functions as a survival factor. TMEFF2 gene is hypermethylated in several types of cancer, and ectopic TMEFF2 gene expression in prostate cancer cell lines inhibits growth, suggesting that TMEFF2 functions as a tumor suppressor. TMEFF2 is primarily expressed in distinct subsets of neurons in brain but is also expressed in colon, bladder, prostate, and several other tissues. A monoclonal antibody reactive with TMEFF2 and conjugated with the cytotoxic agent auristatin-E has been validated in mice as a treatment for prostate cancer (Uchida et al, *Biochem Biophys Res Commun* 266(2):593-602 (1999); Horie et al, *Genomics* 67(2):146-52 (2000); Liang et al, *Cancer Res* 60(17):4907-12 (2000); Lin et al, *Life Sci* 73(13):1617-27 (2003); Gery et al, *Oncogene* 21(31):4739-46 (2002); Gery and Koeffler, *J Mol Biol* 328 (5):977-83 (2003); Afar et al, *Mol Cancer Ther* 3(8):921-32 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 39 | 20 | 82 |
| Expected | 20.5 | 41.0 | 20.5 | 82 |

Chi-Sq.=1.02 Significance=0.6004956 (hom/n)=0.29 Avg. Litter Size=8

Mutation Information

Mutation Type: Homologous Recombination (standard)

Description: Coding exons 1 and 2 were targeted (NCBI accession NM_019790.2).

1. Wild-type Expression Panel: Expression of the target gene was detected in embryonic stem (ES) cells and in all 13 adult tissue samples tested by RT-PCR, except bone.

2. QC Expression: Disruption of the target gene was confirmed by Southern hybridization analysis.

66.2.1. Phenotypic Analysis (for Disrupted Gene: DNA30871-1157 (UNQ178)

(a) Overall Phenotypic Summary;

Mutation of the gene encoding the ortholog of human transmembrane protein with EGF-like and two follistatin-like domains 2 (TMEFF2) resulted in small (−/−) mice that failed to thrive. The homozygous mutant mice were small and sickly, with several dying by 3 weeks of age. The remaining homozygous mutants were transferred to necropsy, where microscopic analysis revealed leukopenia and bone marrow hypoplasia. In addition, there was widespread apoptosis and loss of T lymphocytes in the thymic cortex and depletion of T cell areas in the spleen. Leukopenia and bone marrow hypoplasia were noted in the (−/−) mice. Gene disruption was confirmed by Southern blot.

(b) Pathology Assay-Specific Summary

Gross: The homozygous mutant mice were small and failed to thrive, exhibiting body weights less than half that of normal age-matched wild-type mice. Most organs were small in proportion to reduced overall weight in the (−/−) mice. The spleen and thymus were especially reduced in size compared with the wildtype littermate controls.

Microscopic: The (−/−) mice exhibited leukopenia, due to both lymphopenia and granulocytopenia, and granulocytic hypoplasia of bone marrow. The bone marrow was diffusely hypoplastic in (−/−) mice, with normal amounts of erythropoiesis but markedly decreased numbers of myeloid granulocytic cell precursors, suggesting that decreased granulocytopoiesis caused the leukopenia. There was widespread apoptosis and loss of T lymphocytes in the thymic cortex and depletion of T cell areas in the spleen. Thymic involution is a common finding in stressed or severely ill mice and often results in lymphopenia.

Gene Expression: LacZ activity was not detected in the panel of tissues by immunohistochemical analysis.

(c) Bone Metabolism & Body Diagnostics (1) Tissue Mass & Lean Body Mass Measurements—Dexa Dexa Analysis—Test Description:

Procedure: A cohort of 4 wild type and 4 heterozygotes and 8 homozygotes were tested in this assay.

Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Results: Obvious: The (−/−) mice were small and sickly, with several dying by 3 weeks of age. Of the surviving (−/−) mutants, 6 were transferred to necropsy at 3 weeks of age and the rest were euthanized for pathology at 3.5 weeks of age.

66.3. Generation and Analysis of Mice Comprising DNA32286-1191 (UNQ188) Gene Disruptions In these knockout experiments, the gene encoding PRO214 polypeptides (designated as DNA32286-1191) (UNQ188) was disrupted. The gene specific information for these studies is as follows: the mutated mouse gene corresponds to nucleotide reference: NM-133930 ACCESSION:NM_133930 NID: gi 19527147 ref NM_133930.1 *Mus musculus* cysteine-rich with EGF-like domains 1 (Creld1); protein reference: Q91XD7 ACCESSION:Q91XD7 NID: *Mus musculus* (Mouse). UNKNOWN; the human gene sequence reference: NM_015513 ACCESSION:NM_015513 NID: gi 22095396 ref NM_015513.2 *Homo sapiens* cysteine-rich with EGF-like domains 1 (CRELD1); the human protein sequence corresponds to reference: Q9Y409 ACCESSION:Q9Y409 NID: *Homo sapiens* (Human). HYPOTHETICAL 44.9 KDA PROTEIN.

The mouse gene of interest is Creld1 (cysteine-rich with EGF-like domains 1), ortholog of human CRELD1. Aliases include AVSD2, CIRRIN, DKFZP566D213, and atrioventricular septal defect 2. CRELD1 is a type III plasma membrane protein that may function as a cell adhesion molecule. The protein contains a signal peptide, a tryptophan- and glutamate-rich (WE) domain, a tandem array of EGF-like repeats, and two C-terminal transmembrane segments separated by a short cytoplasmic domain. Mutations in the CRELD1 gene may increase the risk of developing atrioventricular septal defect (Robinson et al, *Am J Hum Genet* 72(4): 1047-52 (2003); Rupp et al, *Gene* 293(1-2):47-57 (2002)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 30 | 0 | 46 |
| Expected | 11.5 | 23.0 | 11.5 | 46 |

Chi-Sq.=34.36 Significance=3.4579656E-8 (hom/n)=0.0 Avg. Litter Size=8

Mutation Information

Mutation Type: Homologous Recombination (standard)

Description: Coding exons 1 and 2 were targeted (NCBI accession NM_133930.1).

1. Wild-type Expression Panel: Expression of the target gene was detected in all 13 adult tissue samples tested by RT-PCR, except adipose and stomach, small intestine, and colon.

2. QC Expression: Disruption of the target gene was confirmed by Southern hybridization analysis.

66.3.1. Phenotypic (for Disrupted Gene: DNA32286-1191 (UNQ188)

(a) Overall Phenotypic Summary:

Mutation of the gene encoding the ortholog of human cysteine-rich with EGF-like domains 1 (CRELD1) resulted in lethality of (−/−) mutants. Gene disruption was confirmed by Southern blot.

(b) Pathology

Microscopic: Not tested due to embryonic lethality. At 12.5 days, there were 50 embryos observed: 19 (+/−) embryos, 13 (+/+) embryos, 16 resorption moles, and 2 inconclusive.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

UNQ188 deficient mice have heart defects and die about mid-gestation from cardiac insufficiency. Ex vivo analysis shows that UNQ188 is required for endothelial cell migration during heart development, defining the developmental pathway for UNQ188 function in the embryonic heart.

66.4. Generation and Analysis of Mice Comprising DNA33107-1135 (UNQ196) Gene Disruptions In these knockout experiments, the gene encoding PRO222 polypeptides (designated as DNA33107-1135) (UNQ196) was disrupted. The gene specific information for these studies is as follows: the mutated mouse gene corresponds to nucleotide reference: NM_144796 *Mus musculus* RIKEN cDNA E430021N18 gene (E430021N18Rik); protein reference: Q8BH32 ACCESSION:Q8BH32 NID: *Mus musculus* (Mouse). *Mus musculus* 16 days neonate cerebellum cDNA, RIKEN full-length enriched library, clone: 9630004A14 product: hypothetical Sushi domain/SCR repeat/CCP module containing protein, full insert sequence (*Mus musculus* 2 days neonate thymus thymic cells cDNA, RIKEN full-length enriched library, clone: E430021N18 product: hypothetical Sushi domain/SCR repeat/CCP module containing protein, full insert sequence); the human gene sequence reference: AY358495 *Homo sapiens* clone DNA33107 YHGM196 (UNQ196); the human protein sequence corresponds to reference: Q6UX62 ACCESSION:Q6UX62 NID: *Homo sapiens* (Human). YHGM196.

The mouse gene of interest is RIKEN cDNA E430021N18 gene, ortholog of human "clone DNA33107 YHGM196" (YHGM196). Aliases include MGC30368 and UNQ196.

YHGM196 is a putative type I plasma membrane protein, consisting of a signal peptide, four sushi domains, a transmembrane segment, and a cytoplasmic C terminus. The function of this protein is not known; however, sushi domains are frequently found in cell adhesion molecules and complement (Pfam accession PF00084).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 14 | 43 | 19 | 76 |
| Expected | 19.0 | 38.0 | 19.0 | 76 |

Chi-Sq.=0.04 Significance=0.9801987 (hom/n)=0.25 Avg. Litter Size=9

Mutation Type: Homologous Recombination (standard)

Description: Coding exon 1 (NCBI accession NM_144796.2) and the preceding noncoding exon (NCBI accession BM944003) were targeted.

1. Wild-type Expression Panel: Expression of the target gene was detected in embryonic stem (ES) cells and in all 13 adult tissue samples tested by RT-PCR, except skeletal muscle; bone; and stomach, small intestine, and colon.

2. QC Expression: Disruption of the target gene was confirmed by Southern hybridization analysis.

66.4.1. Phenotypic Analysis (for Disrupted Gene: DNA33107-1135 (UNQ196)

(a) Overall Phenotypic Summary:

Mutation of the gene encoding the ortholog of human "clone DNA33107 YHGM196" (YHGM196) resulted in decreased systolic blood pressure in the (−/−) mice. In addition, the mutant (−/−) mice showed increased mean serum IgG3 levels compared with the control (+/+) littermates. Gene disruption was confirmed by Southern blot.

(b) Microarray Analysis

Microarray analysis reveals that UNQ196 is overexpressed or upregulated in breast cancer compared to normal breast tissue. In addition, UNQ196 is expressed in the embryonic mammary gland.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains.

Any value <6 is not significant.

Results:

The (−/−) mice exhibited increased mean serum IgG3 levels compared to their gender-matched (+/+) littermate controls, the (+/+) mice for the project run and the historical median.

The serum immunoglobulin isotyping assay revealed that homozygous adults exhibited increased serum IgG3 levels. Thus, homozygotes showed elevated serum immunoglobulins compared with the (+/+) littermates. IgG3 immunoglobulins have neutralization effects and to a lesser extent are important for activation of the complement system. These immunological abnormalities suggest that antagonists or inhibitors of PRO222 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO222 polypeptides or agonists thereof acting as a negative regulator would inhibit the immune response and would be useful candidates for suppressing harmful immune responses, e.g. in the case of graft rejection or graft-versus-host diseases.

(d) Cardiology—Blood Pressure

Test Description: Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results

The (−/−) mice exhibited decreased mean systolic blood pressure (1 SD below the historic means) when compared with that of their gender-matched (+/+) littermates and the historical mean.

66.5. Generation and Analysis of Mice Comprising DNA35557-1137 (UNQ208) Gene Disruptions In these knockout experiments, the gene encoding PRO234 polypeptides (designated as DNA3557-1137) (UNQ208) was disrupted. The gene specific information for these studies is as follows: the mutated mouse gene corresponds to nucleotide reference: XM_146887 PREDICTED: *Mus musculus* RIKEN cDNA E030012M19 gene (E030012M19Rik); protein reference: XP_146887 similar to layilin [*Mus musculus*]; the human gene sequence reference: NM_178834 *Homo sapiens* layilin (LOC 143903); the human protein sequence corresponds to reference: Q96NF3 ACCESSION: Q96NF3 NID: *Homo sapiens* (Human). CDNA FLJ30977 FIS, CLONE HHDPC2000095, HIGHLY SIMILAR TO CRICETULUS GRISEUS LAYILIN.

The mouse gene of interest is RIKEN cDNA E030012M19 gene, ortholog of human layilin. Aliases include Gm511.

Layilin is a type I integral plasma membrane protein that likely functions as a cell adhesion molecule or receptor. The protein binds with the extracellular matrix protein hyaluronan and associates with cytoskeletal adaptor protein talin. Layilin likely plays a role in processes such as cell adhesion, motility, and wound healing (Borowsky and Hynes, *J Cell Biol* 143 (2):429-42 (1998); Bono et al, *Mol Biol Cell* 12(4):891-900 (2001)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 39 | 10 | 72 |
| Expected | 18 | 36 | 18 | 72 |

Mutation Type: Homologous Recombination (standard)

Description: Coding exons 1 through 3 were targeted (NCBI accession XM_146887.3).

Chi-Sq.=3.56 Significance=0.16863815 (hom/n)=0.23 Avg. Liter Size=9

1. Wild-type Expression Panel: Expression of the target gene was detected in embryonic stem (ES) cells and in all 13 adult tissue samples tested by RT-PCR, except skeletal muscle and bone.

2. QC Expression: Disruption of the target gene was confirmed by Southern hybridization analysis.

66.5.1. Phenotypic Analysis (for Disrupted Gene: DNA35557-1137 (UNQ208)

(a) Overall Phenotypic Summary:

Mutation of the gene encoding the ortholog of human layilin resulted in about half the expected numbers of homozygotes genotyped. The male (−/−) mice also exhibited decreased mean lean body mass. In addition, the male knockout mice showed decreased bone mineral content (BMC) and decreased bone mineral density (BMD) in total body, femurs, and vertebrae. Gene disruption was confirmed by Southern blot.

(b) Bone Metabolism & Body Diagnostics/Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

Mutant (−/−) mice deficient in the gene encoding PRO234 polypeptides show a phenotype consistent with tissue wasting diseases marked by decreased lean body mass. In addition, the male knockout mice showed decreased bone mineral content (BMC) and decreased bone mineral density (BMD) in total body, femurs and vertebrae. Thus, the (−/−) mice showed signs of tissue wasting disease and bone metabolism abnormalities which are commonly associated with osteoporosis. PRO234 polypeptides or agonists thereof would be useful for bone healing or for treating bone related disorders such as osteoporosis, whereas antagonists or inhibitors of PRO234 polypeptides would mimic the negative bone phenotype.

66.6. Generation and Analysis of Mice Comprising DNA36350-1158 (UNQ232) Gene Disruptions In these knockout experiments, the gene encoding PRO265 polypeptides (designated as DNA36350-1158) (UNQ232) was disrupted. The gene specific information for these studies is as follows: the mutated mouse gene corresponds to nucleotide reference: NM_201518 *Mus musculus* fibronectin leucine rich transmembrane protein 2 (Flrt2); protein reference: Q8BLU0 ACCESSION:Q8BLU0 NID: *Mus musculus* (Mouse). *Mus musculus* adult male aorta and vein cDNA, RIKEN full-length enriched library, clone: A530098L04 product: KIAA0405 (LEUCINE-RICH REPEAT TRANSMEMBRANE PROTEIN FLRT2) homolog (Fibronectin leucine rich transmembrane protein 2); the human gene sequence reference: NM_013231 *Homo sapiens* fibronectin leucine rich transmembrane protein 2 (FLRT2); the human protein sequence corresponds to reference: O43155 ACCESSION:O43155 NID: *Homo sapiens* (Human). Leucine-rich repeat transmembrane protein FLRT2 precursor (Fibronectin-like domain-containing leucine-rich transmembrane protein 2) (UNQ232/PRO265).

The mouse gene of interest is Flrt2 (fibronectin leucine rich transmembrane protein 2), ortholog of human FLRT2. Aliases include KIAA0405.

FLRT2 is a putative type I plasma membrane protein expressed in pancreas, skeletal muscle, brain, and heart. The protein contains a signal peptide, several leucine-rich repeats, a fibronectin domain, a transmembrane segment, and a short cytoplasmic C terminus. FLRT2 is likely to function in receptor signaling (Lacy et al, *Genomics* 62(3):417-26 (1999); FLRT3 promotes neurite outgrowth and is upregulated upon nerve damage [Botcher et al, *Nat Cell Biol* 6(1):38-44 (2004)].

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 25 | 46 | 2 | 73 |
| Expected | 18.25 | 36.5 | 18.25 | 73 |

Chi-Sq.=39.54 Significance=2.5941669E-9 (hom/n)=0.03 Avg. Liter Size=8

Mutation Information

Mutation Type: Homologous Recombination (standard)

Description: Coding exon 1 was targeted (NCBI accession NM_201518.1).

1. Wild-type Expression Panel: Expression of the target gene was detected in all 13 adult tissue samples tested by RT-PCR, except skeletal muscle and bone.

2. QC Expression: Disruption of the target gene was confirmed by Southern hybridization analysis.

66.6.1. Phenotypic Analysis (for Disrupted Gene: DNA36350-1158 (UNQ232)

(a) Overall Phenotypic Summary:

Mutation of the gene encoding the ortholog of human fibronectin leucine rich transmembrane protein 2 (FLRT2) resulted in greatly reduced viability of (−/−) mutants. Genetic data indicate that this mutation resulted in greatly reduced viability of the homozygous mutants. Three of the identified (−/−) mice were embryonic submissions. The 2 surviving mutant mice were smaller than their wild-type littermates and exhibited numerous abnormalities, including a hearing impairment. Microscopic analysis revealed cardiomyopathy in the homozygous mutants, leading to heart failure. In addition, the female homozygous and heterozygous mice exhibited increased skin fibroblast proliferation rates. In addition, the surviving knockout mice exhibited several immunological abnormalities marked by increased mean serum IgG2a and IgG1 levels. However, a single (−/−) mouse also exhibited decreased serum TNF-alpha, MCP-1 and IL-6 responses to LPS challenge. The surviving (−/−) mice also exhibited decreased total tissue mass, decreased percentage of body fat and decreased fat mass. The female knockout mice showed decreased volumetric bone mineral density (vBMD) and total body mineral bone density (BMD). The male (−/−) mice exhibited increased micro-CT bone measurements. The single female (−/−) mouse also showed a dilated optic disc. Gene disruption was confirmed by Southern blot.

(b) Pathology

Microscopic: At 12.5 days, there were 51 embryos observed: 3 (−/−) embryos, 22 (+/−) embryos, 11 (+/+) embryos, 8 resorption moles, and 7 inconclusive. The 3 (−/−) embryos available for analysis exhibited cardiomyopathy, characterized by tightly packed myocytes with highly condensed eosinophilic sarcoplasm. These small dense myocytes were arranged in thin bands that formed the thin walls and trabeculae of the ventricles and atria. The myocytes were surrounded by increased numbers of large primitive endocardial cells that partially filled the ventricular lumen. There was diffuse vascular congestion in the abdominal organs with dilatation of vessels in the embryo, suggesting that congestive heart failure resulted from defective myocardial development. The living (−/−) embryos were generally smaller than their (+/+) littermates, but there was also evidence of embryonic death and resorption at necropsy. The defective structure and arrangement of the cardiac myocytes apparently led to a progressive decrease in prenatal cardiac function, development of heart failure, and embryonic death.

Gene Expression: LacZ activity was detected in the parathyroid among the panel of tissues analyzed by immunohistochemistry.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 2 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB–pp4, 78 dB+120 dB–pp8, 82 dB+120 dB–pp12, and 90 dB+120 dB–pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

Sensor/motor Gating/Attention: Both of the mutant (–/–) mice failed to exhibit a startle response, suggesting hearing impairment in the mutants.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains.

Any value <6 is not significant.

Results:

Serum Immunoglobulin isotyping resulted in the observation that (–/–) mice exhibited an increase in mean serum IgG2a and IgG1 levels compared to the (+/+) littermates, the (+/+) mice within the project run, and the historical means.

Mutant (–/–) mice exhibited elevation of IgG2a and IgG1 serum immunoglobulins compared to their gender-matched (+/+) littermates. These immunoglobulins have neutralization effects and to a lesser extent are important for activation of the complement system. The observed phenotype suggests that the PRO265 polypeptide is a negative regulator of inflammatory responses. These immunological abnormalities suggest that inhibitors (antagonists) of PRO265 polypeptides would be important agents which could stimulate the immune system and would find utility in the cases wherein this effect would be beneficial to the individual such as in the case of leukemia, and other types of cancer, and in immunocompromised patients, such as AIDS sufferers. Accordingly, PRO265 polypeptides or agonists thereof would be useful in inhibiting the immune response and would be useful candidates for suppressing harmful immune responses, e.g. in the case of graft rejection or graft-versus-host diseases.

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACSCalibur instrument.

Results:

The (−/−) mice exhibited decreased mean serum TNF-alpha, MCP-1 and IL-6 responses to LPS challenge when compared with their (+/+) littermates and the historical means.

In summary, the LPS endotoxin challenge demonstrated that knockout mice deficient in the gene encoding PRO265 polypeptides exhibit immunological abnormalities when compared with their wild-type littermates. In particular, the mutant mice exhibited a decreased ability to elicit an immunological response (TNF-alpha, MCP-1 and IL-6 production) when challenged with the LPS endotoxin indicating a decreased inflammatory response. TNF-alpha, MCP-1 and IL-6 contributes to the later stages of B cell activation. In addition, IL-6 plays a critical role in inducing the acute phase response and systemic inflammation.

(e) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes.

Results:

The single male and female (−/−) mice available for analysis exhibited increased uric acid and potassium levels when compared with their gender-matched (+/+) littermate controls and historical means. Thus, mutant (−/−) mice exhibit a negative phenotype associated with notably elevated uric acid in the blood which is indicative of renal calculi (and associated kidney diseases) which is common in a type of gout (abnormal purine metabolism). The heterozygous (+/−) mice also trended higher than the wild-type (+/+) littermate controls. PRO265 polypeptides and agonists thereof would be useful in the treatment of such diseases associated with formation of renal calculi and/or abnormal purine metabolism. In addition, the mutant mice showed decreased mean serum glucose levels which could be associated with the reduced viability of these mice.

(f) Adult Skin Cell Proliferation:

Procedure: Skin cells were isolated from 16 week old animals (wild type, heterozygous and 1 homozygous). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

One third (⅓) of the heterozygous (+/−) mice exhibited an increased mean skin fibroblast proliferation rate when compared with their gender-matched (+/+) littermates. In addition, the single (−/−) mouse also showed elevated proliferation.

Thus, both homozygous and heterozygous mutant mice demonstrated a hyper-proliferative phenotype. As suggested by these observations, PRO265 polypeptides or agonists thereof could function as tumor suppressors and would be useful in decreasing abnormal cell proliferation.

(g) Bone Metabolism & Body Diagnostics (1) Tissue Mass & Lean Body Mass Measurements—Dexa Dexa Analysis—Test Description:

Procedure: A cohort of 4 wild type, 4 heterozygotes and homozygote were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The single male (−/−) mouse exhibited decreased mean body weight and mean body length (2-3 SD below the mean) when compared with their gender-matched (+/+) littermates and the historical mean.

Fertility:

The single male (−/−) mouse available for analysis produced no pups after mating twice with female (+/+) mice thus demonstrating impaired fertility.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 2 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 2 homozygous mice. Measurements were taken of lumbar 5 veterbra traebecular bone volume, traebecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The single male and single female (−/−) mice available for analysis exhibited decreased total tissue mass, total fat mass, and percent total body fat when compared with their gender-matched (+/+) littermates and the historical means. In addition, the female knockouts also showed decreased volumetric bone mineral density (VBMD) and total body bone mineral density (BMD).

Micro CT: The single male (−/−) mouse available for analysis (M-225) exhibited increased vertebral trabecular bone volume, number, and connectivity density when compared with its gender-matched (+/+) littermates and the historical means. This is interesting because the mouse is smaller in size.

The (−/−) mice analyzed by DEXA and bone micro CT analysis exhibited decreased bone measurements and decreased body mass measurements when compared with their (+/+) littermates, suggestive of abnormal bone disorders. In addition, the knockout mice exhibited decreased total tissue mass and body fat suggestive of growth related disorders and/or tissue wasting diseases such as cachexia. These results are consistent with the reduced viability of the (−/−) mice. The (−/−) mice also exhibited a negative bone phenotype with abnormal decreased bone measurements reflective of bone metabolic disorders. The negative bone and metabolic phenotype indicates that PRO265 polypeptides or agonists thereof would be useful for maintaining bone homeostasis or useful for treatment of other metabolic disorders. In addition, PRO265 polypeptides would be useful in bone healing or for the treatment of arthritis or osteoporosis, whereas antagonists (or inhibitors) of PRO265 polypeptides or its encoding gene would lead to abnormal or pathological bone disorders including inflammatory diseases associated with abnormal bone metabolism including arthritis, osteoporosis and osteopenia.

(h) Heart Rate:

Test Description: Heart rate is measured via a noninvasive tail-cuff method for four days on the Visitech BP-2000 Blood Pressure Analysis System. Heart rate is measured ten times each day for four days. The four days are then averaged to obtain a mouse's conscious heart rate.

Results:

The single surviving female (−/−) mouse available for analysis exhibited a notably decreased heart rate (~3 SD below the mean) when compared with its gender-matched (+/+) littermates and the historical mean. These results are consistent with the pathology report indicating a progressive decrease in cardiac function.

66.7. Generation and Analysis of Mice Comprising DNA61601-1223 (UNQ272) Gene Disruptions In these knockout experiments, the gene encoding PRO309 polypeptides (designated as DNA61601-1223) (UNQ272) was disrupted. The gene specific information for these studies is as follows: the mutated mouse gene corresponds to nucleotide reference: NM_013781 *Mus musculus* SH2 domain containing 3C (Sh2d3c); protein reference: Q9QZS8 ACCESSION:Q9QZS8 NID: *Mus musculus* (Mouse). SH2 domain-containing EPH receptor-binding protein SHEP1 (CHAT-H); the human gene sequence reference: BC032365 ACCESSION:BC032365 NID:21619056 *Homo sapiens Homo sapiens*, SH2 domain-containing 3C, clone MGC:40418 IMAGE:4521962; the human protein sequence corresponds to reference: Q8N5H7 ACCESSION:Q8N5H7 NID: *Homo sapiens* (Human). SH2 domain-containing 3C.

The mouse gene of interest is Sh2d3c (SH2 domain containing 3C), ortholog of human SH2D3C. Aliases include Chat, Nsp3, Shep1, novel SH2-containing protein 3, Cas/HEF1-associated signal transducer, SH2 domain-containing 3C, and SH2-containing Eph receptor-binding protein 1.

SH2D3C is a cytoplasmic protein that functions as a signal-transducing adaptor molecule, linking small Ras superfamily GTPases to activated receptor-tyrosine kinases. The protein consists of an SH2 domain and a Ras guanine nucleotide exchange factor domain, suggesting that SH2D3C may also function as a guanine nucleotide exchange factor. SH2D3C binds with GTPases R-Ras and Rap1A, with scaffolding protein Crk-associated substrate (Cas), and with receptor tyrosine kinase EphB2. Moreover, SH2D3C may also function as an adaptor for epidermal growth factor receptor, nerve growth factor receptor, T-cell receptors, and integrins. SH2D3C likely regulates processes such as membrane ruffling, cell migration, T-cell activation, and cytokine production (Dail et al, *J Biol Chem* 279(40):41892-902 (2004); Sakakibara et al, *J Biol Chem* 278(8):6012-7 (2003); Sakakibara et al, *J Cell Sci* 115 (Pt 24):4915-24 (2002); Sakakibara and Hattori, *J Biol Chem* 275(9):6404-10 (2000); Dodelet et al, *J Biol Chem* 274(45):31941-6 (1999)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 44 | 13 | 78 |
| Expected | 19.5 | 39.0 | 19.5 | 78 |

Chi-Sq.=1.66 Significance=0.43604928 (hom/n)=0.22 Avg. Litter Size=8

Mutation Information

Mutation Type: Homologous Recombination (standard)

Description: Coding exons 4 through 6 were targeted (NCBI accession NM_013781.2).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.7.1. Phenotypic Analysis (for Disrupted Gene: DNA61601-1223 (UNQ272)

(a) Overall Phenotypic Summary:

Mutation of the gene encoding the ortholog of human SH2 domain containing 3C (SH2D3C) resulted in a decreased percentage of CD21hi CD23med B cells in spleen in (−/−) mice. In addition, the (−/−) mice showed decreased mean body weight, decreased mean total tissue mass and lean body mass. Male knockout (−/−) mice exhibited a notably decreased vertebrae bone mineral density (BMD). Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body weight was performed at approximately 16 weeks of age.

Results:

The male (−/−) mice exhibited decreased mean body weight when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited decreased mean total tissue mass and lean body mass when compared with that of their gender-matched (+/+) littermates and the historical means. In addition, male knockout (−/−) mice showed a notably decreased vertebrae bone mineral density (BMD).

The (−/−) mice analyzed by DEXA exhibited notably decreased total tissue mass and lean body mass as well as decreased bone measurements when compared with their (+/+) littermates, suggestive of growth retardation in these mutants. This in conjunction with the observations of decreased body weight suggests a tissue wasting condition such as cachexia or other growth related disorders. Thus, PRO309 polypeptides or agonists thereof would be useful in the treatment or prevention of growth disorders including cachexia or other tissue wasting diseases.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Fluorescence-Activated Cell-Sorting (FACS) Analysis—Tissue Specific FACS

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

Test Description: The mononuclear cell profile is derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples are analyzed using a Becton Dickinson FACSCalibur flow cytometer with CellQuest software Results:

Tissue Specific FACS-Mouse: Analyes of lymphocyte and antigen presenting cell subsets in blood, spleen, bone marrow and peritoneal lavage resulted in the following major findings: Total spleen cell numbers are lower than wildtype or heterozygous littermates. Also observed were statistically significant decreased in knockout cell numbers in the following subsets: spleen—marginal zone B cells, follicular B cells, T1/B cells, T2/marginal zone B cells, activated CD4 T cells, naive CD8 T cells, myeloid dendritic cells and plasmacytoid dendritic cells; bone marrow—total cell numbers, immature B cells, pre-B cells, pro B cells, IgM+ and IgM− plasma cells. The (−/−) mice exhibited a notably decreased percentage of CD21hi CD23med B cells in spleen when compared with that of the (+/+) mice. These results indicate that the knockout mice exhibited a decrease in a subset of B cells (marginal zone B cells) that contain a pool of memory cells and participate in the fast immune response. Thus, the mutant homozygous mice exhibited immunological abnormalities associated with decreased levels of B cell progenitor cells in the spleen.

These results show that knockout (−/−) mice exhibit immunological abnormalities compared to their wild-type (+/+) littermates. Antagonists (inhibitors) of PRO309 polypeptides would be expected to mimic this phenotype. PRO309 polypeptides or agonists thereof would be useful in the development or maturation of B cells which could then participate in fast immune responses.

66.8. Generation and Analysis of Mice Comprising DNA40982-1235 (UNQ293) Gene Disruptions In these knockout experiments, the gene encoding PRO332 polypeptides (designated as DNA40982-1235) (UNQ293) was disrupted. The gene specific information for these studies is as follows: the mutated mouse gene corresponds to nucleotide reference: NM-172874 *Mus musculus* podocan (Podn); protein reference: Q7TQ62 ACCESSION:Q7TQ62 NID: *Mus musculus* (Mouse). Podocan protein; the human gene sequence reference: NM_153703 *Homo sapiens* podocan (PODN); the human protein sequence corresponds to reference: Q5VVZ3 ACCESSION:Q5VVZ3 NID: *Homo sapiens* (Human). Podocan.

The mouse gene of interest is Podn (podocan), ortholog of human PODN. Aliases include Pcan, SLRR5A, 9430070G18, and MGC24995.

PODN is a putative secreted protein that can bind with type-1 collagen and likely functions as an extracellular matrix protein. The 611-amino acid protein is a member of the small leucine-rich repeat (SLR) family of non-collagenous extracellular matrix proteins, consisting of a cysteine-rich N terminus, 20 leucine-rich repeats, and an acidic C-terminal domain. Within the renal glomerulus, PODN is expressed in podocytes and vascular endothelial cells and is found in basement membrane. PODN is also expressed in other tissues, including heart and vascular smooth muscle cells. PODN likely modulates fibrillogenesis in glomerular basement membrane and may play a role in glomerular filtration, sclerotic glomerular lesion formation associated with HIV infection, and growth regulation of cardiovascular tissues (Ross et al, *J Biol Chem* 278(35) :33248-55 (2003); Shimizu-Hirota et al, *FEBS Len* 563(1-3):69-74 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 24 | 46 | 19 | 89 |
| Expected | 22.25 | 44.5 | 22.25 | 89 |

Chi-Sq.=2.61 Significance=0.27117255 (hom/n)=0.24 Avg. Liner Size=9

Mutation Information

Mutation Type: Homologous Recombination (standard)

Description: Coding exons 1 through 5 were targeted (NCBI accession NM_172874.2).

1. Wild-type Expression Panel: Expression of the target gene was detected in embryonic stem (ES) cells and in all 13 adult tissue samples tested by RT-PCR, except skeletal muscle.

2. QC Expression: Disruption of the target gene was confirmed by Southern hybridization analysis.

66.8.1. Phenotypic Analysis (for Disrupted Gene: DNA40982-1235 (UNQ293)

(a) Overall Phenotypic Summary:

Mutation of the gene encoding the ortholog of human podocan (PODN) resulted in an increased serum IgG3 level. In addition, the mutant (−/−) mice exhibited increased bone mineral density measurements and increased mean femoral mid-shaft cross-sectional area. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value $<6$ is not significant.

Results:

The (−/−) mice exhibited increased mean serum IgG3 levels compared to their gender-matched (+/+) littermate controls.

The serum immunoglobulin isotyping assay revealed that homozygous adults exhibited increased serum IgG3 levels. Thus, homozygotes showed elevated serum immunoglobulins compared with the (+/+) littermates. IgG3 immunoglobulins have neutralization effects and to a lesser extent are important for activation of the complement system. These immunological abnormalities suggest that antagonists or inhibitors of PRO332 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO332 polypeptides or agonists thereof would inhibit the immune response and would be useful candidates for suppressing harmful immune responses, e.g. in the case of graft rejection or graft-versus-host diseases.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited increased mean volumetric bone mineral density and total body bone mineral density when compared with the values for their gender-matched (+/+) littermates and the historical means.

Micro CT: The male (−/−) mice exhibited increased mean femoral mid-shaft cross-sectional area when compared with that of their gender-matched (+/+) littermates and the historical mean.

The male (−/−) mice exhibited increased bone mineral content, and total body and femoral bone mineral density when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO332 polypeptides or agonists thereof may be beneficial for the treatment of osteopetrosis. A phenotype associated with an increased bone mineral content, and total body and femoral bone mineral density suggests that agents which mimic these effects (e.g. antagonists of PRO332 polypeptides) would be useful in bone healing.

66.9. Generation and Analysis of Mice Comprising DNA38649 (UNQ301) Gene Disruptions In these knockout experiments, the gene encoding PRO342 polypeptides (designated as DNA38649) (UNQ301) was disrupted. The gene specific information for these studies is as follows: the mutated mouse gene corresponds to nucleotide reference: NM_023059 ACCESSION:NM_023059 NID: 12746439 *Mus musculus Mus musculus* single Ig IL-1 receptor related protein (Sigirr-pending); protein reference: Q9JLZ8 ACCESSION:Q9JLZ8 NID: *Mus musculus* (Mouse). TOLL/INTERLEUKIN-1 RECEPTOR 8; the human gene sequence reference: NM_021805 ACCESSION:NM_021805 NID:11141876 *Homo sapiens Homo sapiens* single Ig IL-1R-related molecule (SIGIRR); the human protein sequence corresponds to reference: Q9H733 ACCESSION:Q9H733 NID: *Homo sapiens* (Human). CDNA: FLJ21446 FIS, CLONE COL04458.

The mouse gene of interest is AI256711 (expressed sequence AI256711), ortholog of human SIGIRR (single Ig IL-1R-related molecule). Aliases include TIR8, single Ig IL-1R-related protein, and single Ig IL-1 receptor related protein.

SIGIRR is a type I plasma membrane protein that functions as a "non-signaling" or "decoy" receptor. The protein consists of an extracellular immunoglobulin domain, a transmembrane segment, and an intracellular toll/interleukin-1 receptor (TIR) domain. Upon stimulation, proinflammatory interleukin-1 receptor (IL-1R) and toll-like receptors (TLRs) recruit SIGIRR, which then sequesters downstream signaling molecules interleukin-1 receptor-associated kinase (IRAK) and TNF receptor-associated factor 6 (TRAF6), inhibiting signal transduction. SIGIRR is involved in negatively modulating innate immune responses. The protein is expressed in many tissues and cells, including dendritic cells and epithelial cells in kidney, colon, and other mucosal tissues, and is down-regulated in response to lipopolysaccharides (LPS). Thus, SIGIRR blocks innate immune reactions in non-stimulated cells, presumably preventing detrimental effects, such as chronic inflammation and sepsis (Thomassen et al, *Cytokine* 11 (6):389-99 (1999); Polentarutti et al, *Eur Cytokine Netw* 14(4):211-8 (2003); Wald et al, *Nat Immunol* 4(9):920-7 (2003); Mantovani et al, *J Leukoc Biol* 75(5):738-42 (2004); O'Neill, *Nat Immunol* 4(9):823-4 (2003); Garlanda et al, *Proc Natl Acad Sci USA* 101(10):3522-6 (2004)).

Wald and colleagues [*Nat Immunol* 4(9):920-7(2003)], as well as Garlanda and colleagues [*Proc Natl Acad Sci USA* 101(10):3522-6 (2004)], investigated the physiological role of SIGIRR using knockout m showed that inflammation in response to IL-1 or LPS and intestinal inflammation susceptibility was greater in SIGIRR-deficient mice than in wild-type mice. These authors concluded that SIGIRR is essential for modulating innate immune responses and may be important for regulating inflammation in the gastrointestinal tract.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 18 | 20 | 54 |
| Expected | 13.5 | 27 | 13.5 | 54 |

Chi-Sq.=0.73 Significance=0.69419664 (hom/n)=0.26 Avg. Litter Size=8

Mutation Information

Mutation Type: Homologous Recombination (standard)

Description: Coding exons 1 through 9 were targeted (NCBI accession NM_023059.1).

1. Wild-type Expression Panel: Expression of the target gene was detected in embryonic stem (ES) cells and in all 13 adult tissue samples tested by RT-PCR, except bone and adipose.

2. QC Expression: Disruption of the target gene was confirmed by Southern hybridization analysis.

66.9.1. Phenotypic Analysis (for Disrupted Gene: DNA38649 (UNQ301)

(a) Overall Phenotypic Summary:

Mutation of the gene encoding the ortholog of human single Ig IL-1R-related molecule (SIGIRR) resulted in a decreased mean percentage of CD4 cells in the peripheral blood as well as a decreased mean serum IgA level. The homozygous mice also showed a decreased pain response (decreased sensitivity to heat-induced pain). In addition, the mutant male (−/−) and (+/−) mice showed increased mean serum cholesterol and triglyceride levels. Radiology results indicated that the female (−/−) mice showed decreased bone mineral content and bone mineral density index measurements. Gene disruption was confirmed by Southern blot.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) and (+/−) mice exhibited increased mean serum cholesterol and triglyceride levels [cholesterol>2 SD in (−/−) males; >2 SD in (+/−) males; triglycerides>1-2 SD in (−/−) males] when compared with their gender-matched (+/+) littermates and the historical means.

As summarized above, the (−/−) mice exhibited notably increased mean serum cholesterol and triglyceride levels when compared with their gender-matched (+/+) littermates and the historical means. Thus, mutant mice deficient in the PRO342 gene can serve as a model for cardiovascular disease. PRO342 polypeptides or its encoding gene would be useful in regulating blood lipids such as cholesterol and triglycerides. Thus, PRO342 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

(1) Fluorescence-Activated Cell-Sorting (FA CS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio, The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The (−/−) mice exhibited an altered distribution of leukocyte subsets in the peripheral blood, characterized by a decreased mean percentage of CD4 cells when compared with their (+/+) littermates, the (+/+) mice for the project run and the historical mean.

The (−/−) mice exhibited an altered distribution of leukocyte subsets in the peripheral blood, characterized by decreased mean percentages of CD4 cells in the cell population when compared with their (+/+) littermates and the historical means.

Thus, knocking out the gene which encodes PRO342 polypeptides causes a decrease in the T cell population. From these observations, PRO342 polypeptides or the gene encoding PRO342 appears to act as a regulator of T cell proliferation. Thus, PRO342 polypeptides would be beneficial in enhancing T cell proliferation.

(2) Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

The (–/–) mice exhibited a decreased mean serum IgA level when compared with that of their (+/+) littermates, the (+/+) mice for the project run, and the historical median.

These results suggest that the phenotype associated with these knockout mice is immunoglobulin deficiency in IgA. The most common inherited form of immunoglobulin deficiency is selective IgA deficiency, which is seen in about one person in 800. IgA mainly functions as an epithelial cell protector which can neutralize bacterial toxins and viruses. Although no obvious disease susceptibility is associated with selective IgA defects, they are commoner in people with chronic lung disease than in the general population. This suggests that lack of IgA may result in a predisposition to lung infections with various pathogens and is consistent with the role of IgA in defense at the body surfaces. Thus PRO342 polypeptides or agonists thereof, play an important role in protecting against as a natural immunity protection against skin infections and more importantly would prevent susceptibility to lung infections.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Hot Plate Testing

Test Description: The hot plate test for nociception is carried out by placing each mouse on a small enclosed 55° C. hot plate. Latency to a hind limb response (lick, shake, or jump) is recorded, with a maximum time on the hot plate of 30 sec. Each animal is tested once.

Results:

Hot Plate: The (–/–) mice exhibited an increased latency to respond during hot plate testing when compared with their (+/+) littermates and the historical mean, suggesting decreased sensitivity to acute pain in the mutants.

(e) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The female (–/–) mice exhibited decreased mean bone mineral content, bone mineral density index, and bone mineral density in total body, femurs, and vertebrae when compared with their gender-matched (+/+) littermates and the historical means.

The (–/–) mice analyzed by DEXA and bone micro CT analysis exhibited decreased bone measurements when compared with their (+/+) littermates, suggestive of abnormal bone disorders. The (–/–) mice exhibited a negative bone phenotype with abnormal decreased bone measurements reflective of bone metabolic disorders. The negative bone phenotype indicates that PRO342 polypeptides or agonists thereof would be useful for maintaining bone homeostasis. In addition, PRO342 polypeptides would be useful in bone healing or for the treatment of arthritis or osteoporosis, whereas antagonists (or inhibitors) of PRO342 polypeptides or its encoding gene would lead to abnormal or pathological bone disorders including inflammatory diseases associated with abnormal bone metabolism including arthritis, osteoporosis and osteopenia.

66.10. Generation and Analysis of Mice Comprising DNA47470-1130P1 (UNQ313) Gene Disruptions In these knockout experiments, the gene encoding PRO356 polypeptides (designated as DNA47470-1130P1) (UNQ313) was disrupted. The gene specific information for these studies is as follows: the mutated mouse gene corresponds to nucleotide reference: BC023373 ACCESSION:BC023373 NID: 19483941 *Mus musculus Mus musculus*, Similar to angiopoietin-like factor, clone MGC:32448 IMAGE:5043159; protein reference: Q8R1Q3 ACCESSION:Q8R1Q3 NID: *Mus musculus* (Mouse). Similar to angiopoietin-like factor (*Mus musculus* 13 days embryo male testis cDNA, RIKEN full-length enriched library, clone: 6030482D04 product: CDT6 (ANGIOPOIETIN-LIKE FACTOR) (CDT6 PROTEIN) homolog); the human gene sequence reference: NM_021146 ACCESSION:NM_021146NID:20127595 *Homo sapiens Homo sapiens* angiopoietin-like factor (CDT6); the human protein sequence corresponds to reference: O43827 ACCESSION:O43827 NID: *Homo sapiens* (Human). CDT6 (ANGIOPOIETIN-LIKE FACTOR) (CDT6 PROTEIN).

The mouse gene of interest is defined as \"similar to angiopoietin-like factor,\" which is the ortholog of human CDT6 (cornea-derived transcript 6). Aliases include angiopoietin-like factor, AngX, and dJ647M16.1.

CDT6 is a secreted protein expressed in corneal stroma that likely functions as a ligand. CDT6 is structurally similar to proteins of the angiopoietin family, which bind to receptors that generally regulate angiogenesis. In a mouse xenograft model, CDT6 inhibited tumor growth and aberrant blood vessel formation and stimulated extracellular matrix deposition. Thus, CDT6 likely prevents vascularization in the cornea and functions as a morphogen that induces a corneal phenotype. The potential of CDT6 as an anti-tumor agent, however, is questionable (Peek et al, *Invest Ophthalmol Vis Sci* 39(10) 1782-8 (1998); Peek et al, *J Biol Chem* 277(1): 686-93 (2002); Bouis et al, *In Vivo* 17(2):157-61 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 19 | 45 | 14 | 78 |
| Expected | 19.5 | 39 | 19.5 | 78 |

Mutation Information

Mutation Type: Homologous Recombination (standard)

Description: Coding exon 1 was targeted (NCBI accession BC023373).

Chi-Sq.=0.21 Significance=0.9003245 (hom/n)=0.26 Avg. Litter Size=9

1. Wild-type Expression Panel: Expression of the target gene was detected in embryonic stem (ES) cells and in all 13 adult tissue samples tested by RT-PCR, except heart.

2. QC Expression: Disruption of the target gene was confirmed by Southern hybridization analysis.

66.10.1. Phenotypic Analysis (for Disrupted Gene: DNA47470-1130P1 (UNQ313)

(a) Overall Phenotypic Summary:

Mutation of the gene encoding the ortholog of human cornea-derived transcript 6 (CDT6) resulted in increased bone mineral density measurements in the (−/−) mice. Gene disruption was confirmed by Southern blot.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited increased mean volumetric bone mineral density in total body and femur when compared with their gender-matched (+/+) littermates and the historical means.

Micro CT: The male (−/−) mice exhibited increased mean femoral mid-shaft cross-sectional area when compared with their gender-matched (+/+) littermates and the historical mean.

The male (−/−) mice exhibited increased bone mineral content, and total body and femoral mid-shaft cross-sectional area when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO356 polypeptides or agonists thereof would be beneficial for the treatment of osteopetrosis. A phenotype associated with an increased bone mineral content, and total body and femoral bone mineral density suggests that agents which mimic these effects (e.g. antagonists of PRO356 polypeptides) would be useful in bone healing.

66.11. Generation and Analysis of Mice Comprising DNA44189-1322 (UNQ341) Gene Disruptions In these knockout experiments, the gene encoding PRO540 polypeptides (designated as DNA44189-1322) (UNQ341) was disrupted. The gene specific information for these studies is as follows: the mutated mouse gene corresponds to nucleotide reference: NM_133792 *Mus musculus* lysophospholipase 3 (Lypla3); protein reference: Q8VEB4 ACCESSION: Q8VEB4 NID: *Mus musculus* (Mouse). Similar to LCAT-like lysophospholipase (Lysosomal phospholipase A2); the human gene sequence reference: NM_012320 ACCESSION:NM_012320NID: gi 20302150 ref NM_012320.2 *Homo sapiens* lysophospholipase 3 (lysosomal phospholipase A2) (LYPLA3); the human protein sequence corresponds to reference: Q8NCC3 ACCESSION:Q8NCC3 NID: *Homo sapiens* (Human). Hypothetical protein FLJ90347.

The mouse gene of interest is Lypla3 (lysophospholipase 3), ortholog of human LYPLA3 (lysophospholipase 3 [lysosomal phospholipase A2]). Aliases include ACS, LLPL, LPLA2, lysosomal phospholipase A2, DKFZp564A0122, 1-O-acylceramide synthase, and LCAT-like lysophospholipase.

LYPLA3 is a likely lysosomal enzyme that functions as an acyltransferase, catalyzing the transfer of acyl groups at the sn-2 position in phospholipids to the C-1 hydroxyl group of ceramide, forming 1-O-acylceramide.

In the absence of ceramide, the enzyme can also function as a phospholipase, forming lysophospholipid and free fatty acid from phospholipids. The enzyme may also have weak lysophospholipase activity and has been detected in plasma. LYPLA3 is calcium-independent, is optimally active at acidic pH, and is expressed in a wide variety of tissues (Taniyama et al, *Biochem Biophys Res Commun* 257(1):50-6 (1999); Hiraoka et al, *J Biol Chem* 277(12): 10090-9 (2002)). LYPLA3 may play a role in lung surfactant catabolism by alveolar macrophages (Abe et al, *J Biol Chem* 279(41):42605-11 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 33 | 19 | 75 |
| Expected | 18.75 | 37.5 | 18.75 | 75 |

Chi-Sq.=1.53 Significance=0.46533394 (hom/n)=0.26 Avg. Litter Size=9

Mutation Information

Mutation Type: Homologous Recombination (standard)

Description: Coding exon 1 was targeted (NCBI accession NM_133792.2).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.11.1. Phenotypic Analysis (for Disrupted Gene: DNA44189-1322 (UNQ341)

(a) Overall Phenotypic Summary:

Mutation of the gene encoding the ortholog of human lysophospholipase 3 (lysosomal phospholipase A2) (LYPLA3) resulted in decreased bone mineral density measurements in the male (−/−) mice. The knockout mice also exhibited an impaired glucose tolerance. Gene disruption was confirmed by Southern blot.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean bone mineral content and bone mineral density in total body femur and vertebrae when compared with the values for their gender-matched (+/+) littermates and the historical means. However, difference in vertebrae bone mineral density is ~1 SD below the median.

Micro CT: The male (−/−) mice exhibited decreased mean femoral mid-shaft cross-sectional area when compared with that of their gender-matched (+/+) littermates and the historical mean.

The (−/−) mice analyzed by DEXA and bone micro CT analysis exhibited decreased bone measurements when compared with their (+/+) littermates, suggestive of abnormal bone disorders. The (−/−) mice exhibited a negative bone phenotype with abnormal decreased bone measurements reflective of bone metabolic disorders. The negative bone phenotype indicates that PRO540 polypeptides or agonists thereof would be useful for maintaining bone homeostasis. In addition, PRO540 polypeptides would be useful in bone healing or for the treatment of arthritis or osteoporosis, whereas antagonists (or inhibitors) of PRO540 polypeptides or its encoding gene would lead to abnormal or pathological bone disorders including inflammatory diseases associated with abnormal bone metabolism including arthritis, osteoporosis and osteopenia.

(c) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygote mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

The male (−/−) mice exhibited impaired glucose tolerance when placed on a high fat diet compared with their gender-matched (+/+) littermates and the historical means.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefore PRO540 polypeptides (or agonists thereof) or its encoding gene would be useful in the treatment of conditions associated with an impaired glucose homeostasis and/or various cardiovascular diseases, including diabetes.

66.12. Generation and Analysis of Mice Comprising DNA49152-1324 (UNQ354) Gene Disruptions In these knockout experiments, the gene encoding PRO618 polypeptides (designated as DNA49152-1324) (UNQ354) was disrupted. The gene specific information for these studies is as follows: the mutated mouse gene corresponds to nucleotide reference: BC029645 ACCESSION:BC029645 NID: 20987285 *Mus musculus Mus musculus* transmembrane serine protease 6, mRNA (cDNA clone MGC:25857 IMAGE:4195486); protein reference: Q9DBI0 ACCESSION:Q9DBI0 NID: *Mus musculus* (Mouse). 1300008A22RIK PROTEIN; the human gene sequence reference: NM_153609 *Homo sapiens* transmembrane protease, serine 6 (TMPRSS6); the human protein sequence corresponds to reference: Q8IU80 ACCESSION:Q8IU80 NID: *Homo sapiens* (Human). Type II transmembrane serine protease 6.

The mouse gene of interest is Tmprss6 (transmembrane serine protease 6), ortholog of human TMPRSS6. Aliases include 1300008A22Rik, matriptase-2, type II transmembrane serine protease 6, FLJ30744, and membrane-bound mosaic serine proteinase.

TMPRSS6 is a type II plasma membrane protein expressed primarily in liver that functions as a trypsin-like serine protease, catalyzing the hydrolysis of extracellular matrix proteins. TMPRSS6 likely plays a role in extracellular matrix remodeling in liver. TMPRSS6 is elevated in invasive ductal cell carcinoma, suggesting that TMPRSS6 may also play a role in metastasis (Hooper et al, *Biochem J* 373(Pt 3):689-702 (2003); Overall et al, *Biol Chem* 385(6):493-504 (2004); Velasco et al, *J Biol Chem* 277(40):37637-46 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 26 | 41 | 14 | 81 |
| Expected | 20.25 | 40.5 | 20.25 | 81 |

Chi-Sq.=2.05 Significance=0.35879648 (hom/n)=0.21 Avg. Litter Size=8

Mutation Information

Mutation Type: Homologous Recombination (standard)

Description: Coding exons 1 through 3 were targeted (NCBI accession NM_027902.1).

1. Wild-type Expression Panel: Expression of the target gene was detected in all 13 adult tissue samples tested by RT-PCR, except thymus, spleen, lung, skeletal muscle, bone, and adipose.

2. QC Expression: Disruption of the target gene was confirmed by Southern hybridization analysis.

66.12.1. Phenotypic Analysis (for Disrupted Gene: DNA49152-1324 (UNQ354)

(a) Overall Phenotypic Summary:

Mutation of the gene encoding the ortholog of human transmembrane serine protease 6 (TMPRSS6) resulted in the homozygous mutant mice exhibiting signs of growth retardation, including decreased body weight and length, total tissue mass, and lean body mass and decreased bone mineral content and density measurements. The mutant (−/−) mice also showed signs of anemia and an increased mean platelet count. Circadian testing revealed no circadian rhythm (or hypoactivity). In addition, the mutants exhibited alopecia, hypochromasia and anisocytosis characterized by abnormal erythrocytes suggestive of a defect in RBCs or hemoglobin. Gene disruption was confirmed by Southern blot.

(b) Pathology

Gross Observations: The (−/−) mice exhibited alopecia and epidermal hyperkeratosis.

Microscopic: The (−/−) mice exhibited hypochromasia and anisocytosis, characterized by abnormal erythrocytes that contained less than normal amount of hemoglobin and by less than expected levels of erythropoiesis in the bone marrow and spleen, suggestive of a defect in red blood cell or hemoglobin production. In addition, the (−/−) mutants exhibited diffuse alopecia and epidermal hyperkeratosis.

Gene Expression: LacZ activity was not detected in the panel of tissues by immunohistochemical analysis.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited decreased mean hemoglobin and hematocrit levels and an increased mean red blood cell count when compared with the levels in their (+/+) littermates and the historical means. In addition, the mean corpuscular volume and mean corpuscular hemoglobin were decreased in the (−/−) mice whereas the red cell distribution width was increased, indicating that the size of the red blood cells was variable in the mutants. The (−/−) mice also exhibited an increased mean platelet count.

These results are related to a phenotype associated with anemia. Thus, PRO618 polypeptides, agonists thereof or the encoding gene for PRO618 polypeptides must be essential for normal red blood cell production and as such would be useful in the treatment of blood disorders associated with anemia or a low hematocrit.

In addition, the (−/−) mice exhibited an increased mean platelet count when compared with their (+/+) littermates and the historical mean. Thus, mutant mice deficient in the DNA49152-1324 gene resulted in a phenotype related to coagulation disorders.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

(1) Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The female (–/–) mice exhibited hypoactivity with no circadian rhythm and hypoactivity during the 1-hour and 12-hour habituation periods and all light and dark periods suggesting an abnormal sleep/wake cycle during the last 24 hours of testing when compared with the levels measured in their gender-matched (+/+) littermates and the historical means. These results demonstrate an abnormal circadian rhythm. Home-cage activity testing is also suggestive of decreased activity or hypoactivity which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO618 polypeptides and agonists thereof would be useful for the treatment or amelioration of the symptoms associated with depressive disorders.

(2) Functional Observational Battery (FOB) Test

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

All 8 of the (–/–) mice exhibited thinning fur and/or bald patches.

(e) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The male (–/–) mice exhibited decreased mean body weight and mean body length when compared with their gender-matched (+/+) littermates and the historical mean.

Obvious General Appearance: The (–/–) mice exhibited alopecia in the dorsal and ventral regions of the thorax and abdomen. The tails of all of the (–/–) mice and some of the (+/–) mice appeared shorter with lateral curvature or slight kinks.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: Both the male and female (–/–) mice exhibited decreased lean body mass, and bone mineral content and density measurements when compared with those of their gender-matched (+/+) littermates and the historical means. Male knockouts also showed decreased mean total tissue mass (TTM).

Mutant (–/–) mice deficient in the gene encoding PRO618 polypeptides show a phenotype consistent with growth retardation and tissue wasting diseases marked by decreased mean total mass, lean body mass. These results are consistent with the observation of decreased mean body weight and mean body length reported above. In addition, the mutant (–/–) mice exhibited decreased bone mineral content and density measurements suggestive of osteoporosis. Thus, antagonists or inhibitors of PRO618 polypeptides or its encoding gene would mimic these abnormal metabolic related effects. On the other hand, PRO618 polypeptides or agonists thereof would be useful in the prevention and/or treatment of such metabolic disorders related to growth or diseases such as cachexia or other tissue wasting diseases as well as useful in the treatment of bone disorders associated with bone loss.

66.13. Generation and Analysis of Mice Comprising DNA52185-1370 (UNQ481) Gene Disruptions In these knockout experiments, the gene encoding PRO944 polypeptides (designated as DNA52185-1370) (UNQ481) was disrupted. The gene specific information for these studies is as follows: the mutated mouse gene corresponds to nucleotide reference: NM_016674 *Mus musculus* claudin 1 (Cldn1); protein reference: O88551 ACCESSION:088551 NID: *Mus musculus* (Mouse). Claudin-1; the human gene sequence reference: NM_021101 ACCESSION:NM_021101 NID: gi21536297 ref NM_021101.3 *Homo sapiens* claudin 1 (CLDN1); the human protein sequence corresponds to reference: O95832 ACCESSION:O95832 NID: *Homo sapiens* (Human). Claudin-1 (Senescence-associated epithelial membrane protein).

The mouse gene of interest is Cldn1 (claudin 1), ortholog of human CLDN1. Aliases include CLD1, SEMP1, and senescence-associated epithelial membrane protein 1.

CLDN1 is an integral plasma membrane protein that functions as a component of tight junctions, cell adhesion molecules that form a barrier between cells to limit paracellular transport of solutes and water. The extracellular segments of CLDN1 interact adhesively with claudins on adjacent cells and co-polymerize laterally, forming tight junction strands. CLDN1 is expressed in liver, airway epithelium, pancreas, placenta, adrenals, prostate and ovary. CLDN1 likely plays an important role in maintenance and regulation of cell polarity and permeability (Furuse et al, *J Cell Biol* 141(7):1539-50 (1998); Swisshelm et al, *Gene* 226(2):285-95 (1999); Heiskala et al, *Traffic* 2(2):93-8 (2001); Furuse et al, *J Cell Biol* 156(6):1099-111 (2002); Coyne et al, *Am J Physiol Lung Cell Mol Physiol* 285(5):L1166-78 (2003); Sasaki et al, *Proc Natl Acad Sci USA* 100(7):3971-6 (2003)).

Furuse and colleagues (2002) investigated the physiological role of CLDN1 using knockout mice. CLDN1 homozygous null mice died within 1 day after birth. Although tight junctions were clearly evident in the epidermis of CLDN1 homozygous null mice, 600-dalton tracer dye diffused through epidermal tight junctions of the CLDN1 homozygous null mice but not through those of the wild-type mice. Furuse and colleagues concluded that CLDN1 is required for barrier function in mammalian skin.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 40 | 2 | 60 |
| Expected | 15.0 | 30 | 15.0 | 60 |

Chi-Sq.=12.72 Significance=0.0017293665 (hom/n)=0.12 Avg. Litter Size=9

Mutation Type: Homologous Recombination (standard)

Coding exon 1 was targeted (NCBI accession NM_016674.2).

1. Wild-type Expression Panel: Expression of the target gene was detected in embryonic stem (ES) cells and in all 13 adult tissue samples tested by RT-PCR, except bone, heart, and adipose.

2. QC Expression: Disruption of the target gene was confirmed by Southern hybridization analysis.

66.13.1. Phenotypic Analysis (for Disrupted Gene: DNA52185-1370 (UNQ481)

(a) Overall Phenotypic Summary:

Mutation of the gene encoding the ortholog of human claudin 1 (CLDN1) resulted in lethality of (−/−) mutants. The (−/−) pups were dead at the time of genotyping. Gene disruption was confirmed by Southern blot.

(b) Pathology

Microscopic: At 12.5 days, there were 41 embryos observed: 9 (−/−) embryos, 20 (+/−) embryos, 8 (+/+) embryos, 2 resorption moles, 1 to-be-determined, and 1 inconclusive. No developmental abnormalities were detected in the 12.5 day mutant embryos by histologic examination.

Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethal mice are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

66.14. Generation and Analysis of Mice Comprising DNA58855-1422 (UNQ518) Gene Disruptions In these knockout experiments, the gene encoding PRO994 polypeptides (designated as DNA58855-1422) (UNQ518) was disrupted. The gene specific information for these studies is as follows: the mutated mouse gene corresponds to nucleotide reference: NM_025453 ACCESSION:NM_025453 NID: gi 13384857 ref NM_025453.1 *Mus musculus* RIKEN cDNA 1810018L02 gene (1810018L02Rik); protein reference: Q9CQY8 ACCESSION:Q9CQY8 NID: *Mus musculus* (Mouse). 1810018L02Rik protein; the human gene sequence reference: NM_024795 ACCESSION:NM_024795 NID: gi 13376165 ref NM_024795.1 *Homo sapiens* hypothetical protein FLJ22800 (FLJ22800); the human protein sequence corresponds to reference: Q9H5X9 ACCESSION:Q9H5X9 NID: *Homo sapiens* (Human). Hypothetical protein FLJ22800.

The mouse gene of interest is RIKEN cDNA 1810018L02 gene, ortholog of human hypothetical protein FLJ22800.

Hypothetical protein FLJ22800 is a putative integral plasma membrane protein, consisting of a signal peptide and four transmembrane domains contained within an L6 membrane protein domain (Pfam accession PF05805). The function of this hypothetical protein is unknown; however, other L6 membrane family members have been implicated in cancer (Wright et al, *Protein Sci* 9(8):1594-600 (2000)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 41 | 23 | 80 |
| Expected | 20 | 40 | 20 | 80 |

Chi-Sq.=1.62 Significance=0.44485807 (hom/n)=0.25 Avg. Litter Size=9

Mutation Information

Mutation Type: Homologous Recombination (standard)

Description: Coding exon 1 was targeted (NCBI accession NM_025453.1).

1. Wild-type Expression Panel: Panel: Expression of the target gene was detected in all 13 adult tissue samples tested by RT-PCR, except skeletal muscle and bone.

2. QC Expression: Disruption of the target gene was confirmed by Southern hybridization analysis.

66.14.1. Phenotypic Analysis (for Disrupted Gene: DNA58855-1422 (UNQ518)

(a) Overall Phenotypic Summary:

Mutation of the gene encoding the ortholog of a human hypothetical protein (FLJ22800) resulted in a decreased anxiety-related response in (−/−) mice. UNQ518 is expressed at higher levels in the pancreas and small intestine compared with other tissues. The (−/−) mice also exhibited enhanced motor coordination. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. Feb. 15, 1996; 379(6566):606-12), and the GABA receptor (Homanics et al., Proc Natl Acad Sci USA. Apr. 15, 2997; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The (−/−) mice exhibited an increased median sumtime-in-center during open field testing when compared with their gender-matched (+/+) littermates and the historical mean, suggesting a decreased anxiety-like response in the mutants.

A notable difference was observed during open field activity testing. The male (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO994 polypeptides and agonists thereof would be useful for the treatment or amelioration of the symptoms associated with depressive disorders.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The female (−/−) mice exhibited decreased ambulatory activity during the 12-hour habituation period and all light and dark periods suggesting an abnormal sleep/wake cycle during the last 24 hours of testing when compared with the levels measured in their gender-matched (+/+) littermates and the historical means. These results demonstrate an abnormal circadian rhythm. Home-cage activity testing is also suggestive of decreased activity or hypoactivity which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO994 polypeptides and agonists thereof would be useful for the treatment or amelioration of the symptoms associated with depressive disorders.

Inverted Screen Testing:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

Results:

| Genotype | Ratio Fell Down % | | Ratio Climbed up % | |
|---|---|---|---|---|
| +/+ (n = 8) | 0/8 | 0 | 4/8 | 50 |
| −/− (n = 8) | 0/8 | 0 | 8/8 | 100 |
| wt population | Fell Down 3.62% | | Climbed up 60.04% | |

A motor strength deficit is apparent when there is a 50% point difference between (−/−) or (+/−) mice and (+/+) mice for the fell down response. 0/8 or 1/8 (−/−) or (+/−) mice not climbing indicates impaired motor coordination. 7/8 or 8/8 (−/−) or (+/−) mice climbing up indicates enhanced motor coordination.

The Inverted Screen Test is designed to measure basic sensory & motor observations:

Among the 8 (−/−) mice analyzed, all 8 (−/−) mice climbed up the screen whereas 4/8 (+/+) mice climbed up, suggesting an enhanced motor coordination in the mutants.

66.15. Generation and Analysis of Mice Comprising DNA56050-1455 (UNQ536) Gene Disruptions In these knockout experiments, the gene encoding PRO1079 polypeptides (designated as DNA56050-1455) (UNQ536) was disrupted. The gene specific information for these studies is as follows: the mutated mouse gene corresponds to nucleotide reference: NM_029537 ACCESSION: NM_029537 NID: gi 22095006 ref NM_029537.1 *Mus musculus* RIKEN cDNA 6530411B15 gene (6530411B15Rik); protein reference: Q91X86 ACCESSION:Q91X86 NID: *Mus musculus* (Mouse). Unknown (Protein for MGC:19304); the human gene sequence reference: NM_015544 ACCESSION:NM_015544 NID: gi 7661615 ref NM_015544.1 *Homo sapiens* DKFZP564K1964 protein (DKFZP564K1964); the human protein sequence corresponds to reference: Q9Y2Y6 ACCESSION:Q9Y2Y6 NID: *Homo sapiens* (Human). TADA1 protein (DKFZP564K1964 protein).

The mouse gene of interest is RIKEN cDNA 6530411B15 gene, ortholog of human DKFZP564K1964 protein. Aliases include TADA1 protein, ETVV536, and UNQ536.

DKFZP564K1964 protein is a putative secreted protein, consisting of a weakly predicted signal peptide and no other conserved domain.

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 11 | 31 | 2 | 44 |
| Expected | 11 | 22 | 11 | 44 |

Chi-Sq.=13.06 Significance=0.0014590055 (hom/n)=0.09 Avg. Litter Size=7

Mutation Information

Mutation Type: Homologous Recombination (standard)

Description: Coding exons 1 and 2 were targeted (NCBI accession NM_029537.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

Reduced viability of (−/−) mice was observed. Seven of the (−/−) mice identified were submitted as embryonic samples.

66.15.1. Phenotypic Analysis (for Disrupted Gene: DNA56050-1455 (UNQ536)

(a) Overall Phenotypic Summary:

Mutation of the gene encoding the ortholog of a human putative secreted protein resulted in greatly reduced viability of (−/−) mutants. Seven of the (−/−) mice identified were submitted as embryonic samples. Of the 2 surviving mutants, the male died shortly after blood pressure analysis, while the female underwent the majority of Level 1 testing. The homozygous mutants exhibited numerous immunological abnormalities including anemia. Open field testing results indicated hyperactivity in the mutant (−/−) mice. The single male (−/−) mouse exhibited decreased total tissue mass and lean body mass but the female (−/−) knockout showed increased total tissue mass, fat mass (g) and % total body fat. One mouse exhibited retinal hemorrhage. Disruption of the target gene was confirmed by Southern hybridization analysis.

(b) Pathology

Microscopic: At day 12.5, there were 39 embryos observed: 7 (−/−) embryos, 9 (+/+) embryos, 9 (+/+) 4 resorption moles, and 10 inconclusive. The (−/−) embryos were generally smaller than their (+/+) littermates but no other developmental abnormalities were detected in the day 12.5 embryos.

Gene Expression: LacZ activity was not detected in the panel of tissues by immunohistochemical analysis.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 2 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. Feb. 15, 1996; 379(6566):606-12), and the GABA receptor (Homanics et al., Proc Natl Acad Sci USA. Apr. 15, 1997; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

Anxiety: The (−/−) mice exhibited increased sum total distance traveled during open field testing when compared with their gender-matched (+/+) littermates and the historical mean, suggesting hyperactivity or an increased anxiety-like response in the mutants.

In summary, the open field testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO1079 polypeptides or agonists thereof would be useful in the treatment of such neurological disorders.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

(1) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The female (−/−) mouse available for analysis was anemic, exhibiting a decreased red blood cell count, hemoglobin concentration, and hematocrit with an increase in mean corpuscular volume and red blood cell distribution width when compared with their (+/+) littermates and the historical means.

These results are related to a phenotype associated with anemia. Thus, PRO1079 polypeptides, agonists thereof or the encoding gene for PRO1079 polypeptides must be essential for normal red blood cell production and as such would be useful in the treatment of blood disorders associated with anemia or a low hematocrit.

(2) Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 1 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRbAPC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The single female (−/−) mouse analyzed exhibited an altered distribution of leukocyte subsets in the peripheral blood, characterized by an increased percentage of natural killer cells when compared with its (+/+) littermates and the historical mean.

FACS results indicate that the homozygous mutant mice have an increased mean percentage of natural killer cells. Thus, PRO1079 polypeptides or agonists thereof function as negative regulators of NK cell production. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. Thus, antagonists (inhibitors) of PRO1079 polypeptides would be useful in the production of NK cells which are important for antibody dependent cell-mediated cytotoxicity.

(3) Ovalbumin Challenge

Procedure: This assay was carried out on 7 wild types and 2 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Feund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

The (−/−) mice exhibited decreased (low/no) mean serum IgG1 and IgG2a responses when compared with their (+/+) littermates and the historical mean.

In summary, the ovalbumin challenge studies indicate that knockout mice deficient in the gene encoding PRO1079 polypeptides exhibit immunological abnormalities when compared with their wild-type littermates. In particular, the mutant mice exhibited a decreased ability to elicit an immunological response when challenged with the T-cell dependent OVA antigen. Thus, PRO1079 polypeptides or agonists thereof, would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO1079 polypeptides would be useful for inhibiting the immune response and thus would be useful candidates for suppressing harmful immune responses, e.g. in the case of graft rejection or graft-versus-host diseases.

(e) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 1 homozygote were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

Fundus: One (−/−) (M-99) mouse exhibited retinal hemorrhage, preventing analysis of the artery-to-vein ratio.

Angiogram: One (−/−) mouse (M-99) exhibited retinal vascular leakage.

Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to ophthalmological disorders such as retinal degeneration. Thus, antagonists of PRO1079 encoding genes would lead to similar pathological retinal changes, whereas agonists may be useful as therapeutic agents in the treatment of hypertension, atherosclerosis or other opthamological disorders including retinal degeneration and diseases associated with this condition (as indicated above).

(f) Bone Metabolism & Body Diagnostics/Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 1 homozygote were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The single male (−/−) mouse available for analysis exhibited decreased total tissue mass and lean body mass when compared with its gender-matched (+/+) littermates and the historical means, whereas the female (−/−) mouse analyzed exhibited increased total tissue mass (TTM), total fat mass and percent total body fat (single (−/−) female mouse had 34% body fat).

The male (−/−) mice analyzed by DEXA exhibited notably decreased total tissue mass and lean body mass as well as decreased bone measurements when compared with their (+/+) littermates, suggestive of growth retardation in these mutants. These observations are consistent with the reduced viability shown in the knockout mice. This in conjunction with the observations of decreased body weight and length is indicative of growth retardation, a tissue wasting condition such as cachexia or other growth related disorders. Thus, PRO1079 polypeptides or agonists thereof would be useful in the treatment or prevention of growth disorders and/or decreased viability. It is interesting that the female (−/−) mouse showed signs of obesity with notable increased body fat.

66.16. Generation and Analysis of Mice Comprising DNA58727-1474 (UNQ553) Gene Disruptions In these knockout experiments, the gene encoding PRO1110 polypeptides (designated as DNA58727-1474) (UNQ553) was disrupted. The gene specific information for these studies is as follows: the mutated mouse gene corresponds to nucleotide reference: NM_016969 ACCESSION: NM_016969 NID: gi 8393799 ref NM_016969.1 *Mus musculus* myeloid-associated differentiation marker (Myadm); protein reference: O35682 ACCESSION:O35682 NID: *Mus musculus* (Mouse). Myeloid-associated differentiation marker (Myeloid upregulated protein); the human gene sequence reference: NM_138373 *Homo sapiens* myeloid-associated differentiation marker (MYADM); the human protein sequence corresponds to reference: Q96S97 ACCESSION:Q96S97 NID: *Homo sapiens* (Human). Myeloid-associated differentiation marker (SB135).

The mouse gene of interest is Myadm (myeloid-associated differentiation marker), ortholog of human MYADM. Aliases include D7Wsu62e.

MYADM is a likely integral plasma membrane protein, consisting of eight transmembrane segments contained within two MARVEL domains. MARVEL domains are often found in lipid-associating proteins that participate in transport vesicle biogenesis (Pfam accession PF01284). MYADM is expressed in myeloid cells and is likely involved in myeloid differentiation (Pettersson et al, *J Leukoc Biol* 67(3):423-31 (2000); Cui et al, *Mol Biol Rep* 28(3):123-38 (2001)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 11 | 33 | 16 | 60 |
| Expected | 15 | 30 | 15 | 60 |

Chi-Sq.=4.24 Significance=0.12003164 (hom/n)=0.24 Avg. Litter Size=8

Mutation Information

Mutation Type: Homologous Recombination (standard)

Description: Coding exon 1 was targeted (NCBI accession NM_016969.1).

1. Wild-type Expression Panel: Expression of the target gene was detected in all 13 adult tissue samples tested by RT-PCR, except bone and adipose.

2. QC Expression: Disruption of the target gene was confirmed by Southern hybridization analysis.

66.16.1. Phenotypic Analysis (for Disrupted Gene: DNA58727-1474 (UNQ553)

(a) Overall Phenotypic Summary:

Mutation of the gene encoding the ortholog of human myeloid-associated differentiation marker (MYADM) resulted in increased TNF-alpha, MCP-1, and IL-6 responses to LPS challenge in (−/−) mice. In addition, mutant (−/−) mice on a high fat diet exhibited a slightly enhanced glucose tolerance. The mutant (−/−) mice exhibited a decreased or absent startle response indicating deafness. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (−/−) mice exhibited increased mean serum TNF-alpha, MCP-1 and IL-6 responses to LPS challenge when compared with their (+/+) littermates and the historical means.

In summary, the LPS endotoxin challenge demonstrated that knockout mice deficient in the gene encoding PRO1110 polypeptides exhibit immunological abnormalities when compared with their wild-type littermates. In particular, the mutant mice exhibited an increased ability to elicit an immunological response (TNF-alpha, MCP-1 and IL-6 production) when challenged with the LPS endotoxin indicating a pro-inflammatory response. TNF-alpha, MCP-1 and IL-6 contribute to the later stages of B cell activation. TNF-alpha is an important inflammatory mediator. In addition, TNF-alpha, MCP-1 and IL-6 play a critical role in inducing the acute phase response and systemic inflammation. TNF-alpha can substitute for the membrane-bound signal in macrophage activation (thus serving as an effector molecule). This suggests that inhibitors or antagonists to PRO1110 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1110 polypeptides or agonists thereof would be useful in inhibiting the immune response and would be useful candidates for suppressing harmful immune responses, e.g. in the case of graft rejection or graft-versus-host diseases.

(c) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Glucose Tolerance Test: The male mutant (−/−) mice on a high fat diet exhibited a slightly enhanced glucose tolerance when compared with their gender-matched (+/+) littermates.

In these studies the mutant (−/−) mice showed an increased or enhanced glucose tolerance in the presence of normal fasting glucose at all 3 intervals tested when compared with their gender-matched (+/+) littermates and the historical means. Thus, knockout mice exhibited a slightly increased insulin sensitivity or the opposite phenotypic pattern of an impaired glucose homeostasis, and as such antagonists (inhibitors) to PRO1110 polypeptides or its encoding gene would be useful in the treatment of an impaired glucose homeostasis.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

The knockout mutant (−/−) mice exhibited a decreased or absent startle response which is indicative of deafness.

66.17. Generation and Analysis of Mice Comprising DNA62377-1381-1 (UNQ561) Gene Disruptions In these knockout experiments, the gene encoding PRO1122 polypeptides (designated as DNA62377-1381-1) (UNQ561) was disrupted. The gene specific information for these studies is as follows: the mutated mouse gene corresponds to nucleotide reference: NM_145834 ACCESSION: NM_145834 NID: gi 22003879 ref NM_145834.1 *Mus musculus* interleukin 17C (Il17c); protein reference:Q8K4C5 ACCESSION:Q8K4C5 NID: *Mus musculus* (Mouse). IL-17C; the human gene sequence reference: NM_013278 ACCESSION:NM_013278 NID: gi 27477078 ref NM_013278.3 *Homo sapiens* interleukin 17C (IL17C); the human protein sequence corresponds to reference: Q9P0M4 ACCESSION:Q9P0M4 NID: *Homo sapiens* (Human). Interleukin-17C precursor (IL-17C) (Cytokine CX2).

The mouse gene of interest is Il17c (interleukin 17C), ortholog of human IL17C. Aliases include IL-17C, CX2, IL-21, and cytokine CX2.

IL17C is a secreted protein that likely functions as a ligand for an interleukin-17 family receptor. Cells that express this cytokine have not been identified; however, IL17C stimulates release of tumor necrosis factor-alpha and IL-1beta from monocytic cell line THP-1. Moreover, IL17C induces neutrophilia and expression of interferon-gamma and interleukin-6 in lung airway, supporting a role for IL17C in immune function (Li et al, *Proc Natl Acad Sci USA* 97(2):773-8 (2000); Hurst et al, *J Immunol* 169(1):443-53 (2002); Moseley et al, *Cytokine Growth Factor Rev* 14(2):155-74 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 34 | 13 | 65 |
| Expected | 16.25 | 32.5 | 16.25 | 65 |

Chi-Sq.=2.59 Significance=0.2738979 (hom/n)=0.21 Avg. Litter Size=9

Mutation Information

Mutation Type: Homologous Recombination (standard)

Description: Coding exons 1 and 2 were targeted (NCBI accession NM_145834.1).

1. Wild-type Expression Panel: Expression of the target gene was detected in embryonic stem (ES) cells and in all 13 adult tissue samples tested by RT-PCR, except liver; skeletal muscle; bone; stomach, small intestine, and colon; and adipose.

2. QC Expression: Disruption of the target gene was confirmed by Southern hybridization analysis.

66.17.1. Phenotypic Analysis (for Disrupted Gene: DNA62377-1381-1 (UNQ561)

(a) Overall Phenotypic Summary:

Mutation of the gene encoding the ortholog of human interleukin 17C (IL17C) resulted in elevated mean serum levels of IgM serum immunoglobulins in the (−/−) mice. The mutant (−/−) mice also showed an increased in IL-6 response to LPS. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

The (−/−) mice exhibited an increased mean serum IgM level when compared with that of their (+/+) littermates and the historical medians.

Mutant (−/−) mice exhibited elevation of IgM serum immunoglobulins compared to their gender-matched (+/+) littermates. IgM immunoglobulins are the first to be produced in a humoral immune response for neutralization of bacterial toxins and are particularly important in activating the complement system. The observed phenotype suggests that the PRO1122 polypeptide is a negative regulator of inflammatory responses. These immunological abnormalities suggest that inhibitors (antagonists) of PRO1122 polypeptides would be important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO1122 polypeptides or agonists thereof would be useful in inhibiting the immune response and would be useful candidates for suppressing harmful immune responses, e.g. in the case of graft rejection or graft-versus-host diseases.

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sub-lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (−/−) mice exhibited an increased mean serum IL-6 response to LPS challenge when compared with their (+/+) littermates and the historical means.

In summary, the LPS endotoxin challenge demonstrated that knockout mice deficient in the gene encoding PRO1122 polypeptides exhibit immunological abnormalities when compared with their wild-type littermates. In particular, the mutant mice exhibited an increased ability to elicit an immunological response (IL-6 production) when challenged with the LPS endotoxin indicating a pro-inflammatory response. IL-6 contributes to the later stages of B cell activation playing a critical role in inducing the acute phase response and systemic inflammation. This suggests that inhibitors or antagonists to PRO1122 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1122 polypeptides or agonists thereof would be useful in inhibiting the immune response and would be useful candidates for suppressing harmful immune responses, e.g. in the case of graft rejection or graft-versus-host diseases.

66.18. Generation and Analysis of Mice Comprising DNA58850-1495 (UNQ576) Gene Disruptions In these knockout experiments, the gene encoding PRO1138 polypeptides (designated as DNA58850-1495) (UNQ576) was disrupted. The gene specific information for these studies is as follows: the mutated mouse gene corresponds to nucleotide reference: NM_144539 *Mus musculus* SLAM family member 7 (Slamf7); protein reference: Q8BHK6 ACCESSION:Q8BHK6NID: *Mus musculus* (Mouse). *Mus musculus* adult male testis cDNA, RIKEN full-length enriched library, clone:4932702H22 product: SIMILAR TO 19A24 PROTEIN homolog (*Mus musculus* adult male testis cDNA, RIKEN full-length enriched library, clone:4932704K11 product:SIMILAR TO 19A24 PROTEIN homolog) (*Mus musculus* adult male aorta and vein cDNA, RIKEN full-length enriched library, clone:A530014C02 product:SIMILAR TO 19A24 PROTEIN homolog); the human gene sequence reference: NM_021181 *Homo sapiens* SLAM family member 7 (SLAMF7); the human protein sequence corresponds to reference: Q9NY08 ACCESSION: Q9NY08 NID: *Homo sapiens* (Human). 19A protein.

The mouse gene of interest is Slamf7 (SLAM family member 7), ortholog of human SLAMF7. Aliases include 19A, CS1, 19A24, CRACC, 4930560D03Rik, CD2-like receptor activating cytotoxic cells, novel Ly9, and novel LY9 (lymphocyte antigen 9) like protein.

SLAMF7 is a type I plasma membrane protein that functions as a homophilic receptor or cell adhesion molecule and is expressed primarily on natural killer cells, T-cells, and activated B-cells. The protein consists of two extracellular immunoglobulin-like domains, a transmembrane segment, and an 88-amino acid cytoplasmic domain. SLAMF7 likely plays a role in regulating NK cell cytolytic activity and lymphocyte adhesion (Kumaresan et al, *Mol Immunol* 39(1-2): 1-8 (2002); Murphy et al, *Biochem J* 361(Pt 3):431-6 (2002); Bouchon et al, *J Immunol* 167(10):5517-21 (2001); Tovar et al, *Immunogenetics* 54(6):394-402 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 22 | 37 | 16 | 75 |
| Expected | 18.75 | 37.5 | 18.75 | 75 |

Chi-Sq.=1.63 Significance=0.44263932 (hom/n)=0.22 Avg. Liter Size=10

Mutation Information

Mutation Type: Homologous Recombination (standard)

Description: Coding exons 2 through 6 were targeted (NCBI accession NM_144539.2).

1. Wild-type Expression Panel: Expression of the target gene was detected in all 13 adult tissue samples tested by RT-PCR, except skeletal muscle and bone.

2. QC Expression: Disruption of the target gene was confirmed by Southern hybridization analysis.

66.18.1. Phenotypic Analysis (for Disrupted Gene: DNA58850-1495 (UNQ576)

(a) Overall Phenotypic Summary:

Mutation of the gene encoding the ortholog of human SLAM family member 7 (SLAMF7) resulted in an increase in the IL-6 response to LPS. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sub-lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (−/−) mice exhibited an increased mean serum IL-6 response to LPS challenge when compared with their (+/+) littermates and the historical means.

In summary, the LPS endotoxin challenge demonstrated that knockout mice deficient in the gene encoding PRO1138 polypeptides exhibit immunological abnormalities when compared with their wild-type littermates. In particular, the mutant mice exhibited an increased ability to elicit an immunological response (IL-6 production) when challenged with the LPS endotoxin indicating a pro-inflammatory response. IL-6 contributes to the later stages of B cell activation playing a critical role in inducing the acute phase response and systemic inflammation. This suggests that inhibitors or antagonists to PRO1138 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1138 polypeptides or agonists thereof would be useful in inhibiting the immune response and would be useful candidates for suppressing harmful immune responses, e.g. in the case of graft rejection or graft-versus-host diseases.

66.19. Generation and Analysis of Mice Comprising DNA59586-1520 (UNQ604) Gene Disruptions In these knockout experiments, the gene encoding PRO1190 polypeptides (designated as DNA59586-1520) (UNQ604) was disrupted. The gene specific information for these studies is as follows: the mutated mouse gene corresponds to nucleotide reference: NM_172506 *Mus musculus* biregional cell adhesion molecule-related/down-regulated by oncogenes (Cdon) binding protein (Boc); protein reference: Q8CE91 ACCESSION:Q8CE91 NID: *Mus musculus* (Mouse). *Mus musculus* 10 days neonate skin cDNA, RIKEN full-length enriched library, clone:4732455C11 product:biregional cell adhesion molecule-related/down-regulated by oncogenes (Cdon) binding protein, full insert sequence; the human gene sequence reference: NM_033254 ACCESSION:NM_033254 NID: gi 15147239 ref NM_033254.1 *Homo sapiens* brother of CDO (BOC); the human protein sequence corresponds to reference: Q9BWV1 ACCESSION: Q9BWV1 NID: *Homo sapiens* (Human). BROTHER OF CDO.

The mouse gene of interest is Boc (biregional cell adhesion molecule-related/down-regulated by oncogenes (Cdon) binding protein), ortholog of human BOC (brother of CDO). Aliases include 4732455C11 and Biregional Cdon binding protein.

BOC is a type I plasma membrane protein that likely functions as a receptor subunit for cell-cell communication. The protein interacts with homolog CDON (cell adhesion molecule-related/down-regulated by oncogenes), N-cadherins, and M-cadherins in a cis fashion, forming a receptor complex at sites of cell-cell contact in myoblasts. During embryonic development, BOC is expressed in musculoskeletal and central nervous systems and in areas of proliferation and differentiation. BOC likely plays a role in muscle cell differentiation and transformation (Wegorzewska et al, *Mol Carcinog* 37(1):1-4 (2003); Mulieri et al, *Dev Dyn* 223(3):379-88 (2002); Kang et al, *EMBO J* 21(1-2):114-24 (2002); Kang et al, *Proc Natl Acad Sci USA* 100 (7):3989-94 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 30 | 20 | 68 |
| Expected | 17 | 34 | 17 | 68 |

Chi-Sq.=1.3 Significance=0.5220458 (hom/n)=0.25 Avg. Litter Size=9

Mutation Information

Mutation Type: Homologous Recombination (standard)

Description: Coding exons 1 and 2 were targeted (NCBI accession NM_172506.1).

1. Wild-type Expression Panel: Expression of the target gene was detected in embryonic stem (ES) cells and in all 13 adult tissue samples tested by RT-PCR, except skeletal muscle and bone.

2. QC Expression: Disruption of the target gene was confirmed by Southern hybridization analysis.

66.19.1. Phenotypic Analysis (for Disrupted Gene: DNA59586-1520 (UNQ604)

(a) Overall Phenotypic Summary:

Mutation of the gene encoding the ortholog of human brother of CDO (BOC) resulted in two knockout mice exhibiting a systemic histiocytic storage disease affecting only the macrophages in several organs. Gene disruption was confirmed by Southern blot.

(b) Pathology

Gross: Two of the (−/−) mice examined (M-138 and F-139) exhibited an enlarged liver, spleen, and mesenteric lymph nodes.

Microscopic: Among the (−/−) mice analyzed, 2 (F-139 and M-138) exhibited a systemic histiocytic storage disease affecting only the macrophages in several organs. The liver, spleen, and mesenteric lymph nodes were the most affected histologically. The cytoplasm of the macrophages was markedly enlarged and contained predominantly clear vacuoles and less prominent fibrillar material. The clear vacuoles were the artifactual remnants of structures containing material dissolved during the process required to prepare histological slides. The removed material presumably contained lipid predominantly. These lesions were characteristic of a group of genetic diseases known as lipid storage diseases.

66.20. Generation and Analysis of Mice Comprising DNA64896-1539 (UNQ642) Gene Disruptions In these knockout experiments, the gene encoding PRO1272 polypeptides (designated as DNA64896-1539) (UNQ642) was disrupted. The gene specific information for these studies is as follows: the mutated mouse gene corresponds to nucleotide reference: NM_207531 *Mus musculus* RIKEN cDNA E030025L21 gene (E030025L21Rik); protein reference: Q8R3W7 ACCESSION:Q8R3W7 NID: *Mus musculus* (Mouse). RIKEN cDNA E030025L21 gene; the human gene sequence reference: NM_176813 *Homo sapiens* breast cancer membrane protein 11 (BCMP11); the human protein sequence corresponds to reference: Q8TD06 ACCESSION: Q8TD06 NID: *Homo sapiens* (Human). Anterior gradient protein 3 (MLHS642) (Breast cancer membrane protein 11).

The mouse gene of interest is RIKEN cDNA E030025L21 gene, ortholog of human BCMP11 (breast cancer membrane protein 11). Aliases include Gm888, HAG-3, hAG-3, and anterior gradient protein 3.

BCMP11 is a putative secreted protein expressed primarily in estrogen receptor-positive breast ductal carcinoma epithelial cells. The 166-amino acid protein contains a signal peptide but no other discernable conserved domain. BCMP11 is concentrated in cytoplasmic vesicles but is capable of interacting with glycosylphosphatidylinositol-anchored metastasis-associated protein C4.4A and extracellular alpha-dystrogly can (DAG-1). Moreover, BCMP11 is homologous with secreted *Xenopus laevis* proteins XAG-1 and XAG-2, further supporting the function of BCMP11 as a secreted extracellular protein. BCMP11 may play a role in breast tumor cell growth or metastasis (Adam et al, *J Biol Chem* 278(8):6482-9 (2003); Fletcher et al, *Br J Cancer* 88(4):579-85 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 22 | 23 | 17 | 62 |
| Expected | 15.5 | 31 | 15.5 | 62 |

Chi-Sq.=0.79 Significance=0.67368 (hom/n)=0.26 Avg. Litter Size=8

Mutation Information

Mutation Type: Homologous Recombination (standard)

Description: Coding exons 3 through 7 were targeted (NCBI accession NM_207531.1).

1. Wild-type Expression Panel: Expression of the target gene was detected in brain; spinal cord; eye; lung; and stomach, small intestine, and colon among the 13 adult tissue samples tested by RT-PCR.

2. QC Expression: Disruption of the target gene was confirmed by Southern hybridization analysis.

66.20.1. Phenotypic Analysis (for Disrupted Gene: DNA64896-1539 (UNQ642)

(a) Overall Phenotypic Summary:

Mutation of the gene encoding the ortholog of human breast cancer membrane protein 11 (BCMP11) resulted in the homozygous mutant mice exhibiting an increased mean serum glucose levels with an impaired glucose tolerance when compared with those of their gender-matched wild-type littermates and the historical means. In addition, impaired glucose tolerance was observed in the male mutants. Glucosuria and ketonuria were also evident in the (−/−) mice. The homozygous mutant mice also exhibited decreased bone mineral content and density measurements and decreased heart rates. Neurological analysis revealed numerous abnormalities, including impaired motor coordination and shaky behavior. The (−/−) mice exhibited diffuse abiotrophy of the cerebellum granule cell layer. The male (−/−) mice also showed testicular degeneration and the female (−/−) mice exhibited ovarian and uterine hypoplasia. Disruption of the target gene was confirmed by Southern hybridization analysis.

(b) Pathology

Microscopic: The (−/−) mice exhibited diffuse abiotrophy of the cerebellum granule cell layer, characterized by a diffuse loss of granule cells and gliosis, resulting in thinning of both the granule cell layer and molecular cell layer of the cerebellum. Notably, there was sparing of Purkinje and Golgi cells and the granule cell layer of the cerebellar paraflocculus was less severely affected by gliosis and neuron loss. The male (−/−) mice exhibited small testes, testicular degeneration, and hypospermia. Evidence of degeneration in the seminiferous tubules was minimal and restricted to late stage spermatids and spermatozoa. However, almost no normal sperm were present in the epididymides or vas deferens, and degeneration and clumping of spermatozoa was a frequent finding. The female (−/−) mice exhibited ovarian and uterine hypoplasia, with the ovaries and uterus appearing juvenile. The mammary gland was represented by just a few ducts. Heart weights were increased in the (−/−) mice, but no histopathologic lesions were noted. The pancreatic islets of Langerhans in the mutants tended to be smaller than in the (+/+) controls and the distribution of alpha (glucagon) and beta (insulin) cells was altered. Normally, glucagon-producing islet cells are arranged around the periphery of the islets, but the glucagon cells in the mutants were evenly distributed throughout the islets.

Gene Expression: LacZ activity was not detected in the panel of tissues by immunohistochemical analysis.

(c) Cardiology—Heart Rate

Test Description: Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results

Heart Rate: The (−/−) mice exhibited decreased mean heart rates (male (−/−)>2 SD below the mean; female (−/−)>3 SD below the mean) when compared with that of their gender-matched (+/+) littermates and the historical mean, the difference being more notable in the females.

(d) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

Both the male and female mutant (−/−) mice exhibited notably increased mean serum glucose levels when compared with that of their gender-matched (+/+) littermates and the historical means. In addition, the (−/−) mice exhibited impaired glucose tolerance at each of the intervals tested when compared with their gender-matched (+/+) littermates and the historical means. Glucosuria and ketonuria was evident in the (−/−) mutant mice.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO1272 polypeptides (or agonists thereof) or its encoding gene would be useful in the treatment of conditions associated with an impaired glucose homeostasis and/or various cardiovascular diseases, including diabetes.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

(1) Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The (−/−) mice exhibited decreased ambulatory activity during both light phases and a decreased light-to-total activity ratio during home-cage activity testing. These results demonstrate an abnormal circadian rhythm and is suggestive of decreased activity or hypoactivity which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO1272 polypeptides and agonists thereof would be useful for the treatment or amelioration of the symptoms associated with depressive disorders.

(2) Functional Observational Battery (FOB) Test

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Among the 8 (−/−) mice analyzed, 4 exhibited shaky behavior during the 1-minute observation period. In addition, rearing was absent in the (−/−) mice.

(3) Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

Results:

| Genotype | Ratio Fell Down | % | Ratio Climbed up | % |
|---|---|---|---|---|
| +/+ (n = 8) | 0/8 | 0 | 6/8 | 75 |
| −/− (n = 8) | 1/8 | 13 | 1/8 | 13 |
| WT Population | Fell Down | | Climbed Up | |
| | 3.62 | | 60.04 | |

A motor strength deficit is apparent when there is a 50% point difference between (−/−) or (+/−) mice and (+/+) mice for the fell down response. 0/8 or 1/8 (−/−) or (+/−) mice not climbing indicates impaired motor coordination. 7/8 or 8/8(−/−) or (+/−) mice climbing up indicates enhanced motor coordination.

The Inverted Screen Test is designed to measure basic sensory & motor observations:

Among the 8 (−/−) mice analyzed, only one (−/−) mouse climbed up the screen whereas 6/8 (+/+) mice climbed up. These results indicate an impaired motor strength in the mutants. These results are consistent with the observations in bone-related measurements as shown below.

Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight when compared with their gender-matched (+/+) littermates and the historical mean.

Fertility: The male (−/−) mouse produced no pups after 60 days of breeding and 4 matings.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited decreased mean total tissue mass and lean body mass. Both the male and female (−/−) mice exhibited decreased mean bone mineral content, bone mineral content index, and bone mineral density in total body, femur, and vertebrae when compared with that of their gender-matched (+/+) littermates and the historical means.

Mutant (−/−) mice deficient in the gene encoding PRO1272 polypeptides show a phenotype consistent with growth retardation and/or tissue wasting diseases marked by decreased mean total mass, lean body mass. These results are consistent to the observation of decreased mean body weight reported above. In addition, the mutant (−/−) mice exhibited decreased bone mineral content and density measurements suggestive of osteoporosis. Thus, antagonists or inhibitors of PRO1272 polypeptides or its encoding gene would mimic these abnormal metabolic related effects. On the other hand, PRO1272 polypeptides or agonists thereof would be useful in the prevention and/or treatment of such metabolic disorders as growth retardation, cachexia or other tissue wasting diseases as well as useful in the treatment of bone disorders associated with bone loss.

(g) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

The female (−/−) mice exhibited a increased mean skin fibroblast proliferation rate when compared with their gender-matched (+/+) littermates.

Thus, homozygous mutant mice demonstrated a hyperproliferative phenotype. As suggested by these observations, PRO1272 polypeptides or agonists thereof would be useful in decreasing abnormal cell proliferation.

66.21. Generation and Analysis of Mice Comprising DNA64903-1553 (UNQ655) Gene Disruptions In these knockout experiments, the gene encoding PRO1286 polypeptides (designated as DNA64903-1553) (UNQ655) was disrupted. The gene specific information for these studies is as follows: the mutated mouse gene corresponds to nucleotide reference: BC029863 ACCESSION: BC029863 NID:20987635 *Mus musculus Mus musculus*, clone MGC:36861 IMAGE:4460168; protein reference: Q8K2T4 ACCESSION:Q8K2T4 NID: *Mus musculus* (Mouse). Hypothetical protein; the human gene sequence reference: AY358935 *Homo sapiens* clone DNA64903 DSLR655 (UNQ655); the human protein sequence corresponds to reference: Q6UW78 Protein UNQ655/PRO1286 precursor.

The mouse gene of interest encodes "protein UNQ655/PRO1286 precursor" (UNQ655), ortholog of human UNQ655.

UNQ655 is a putative secreted protein, consisting of 93 amino acids. The protein contains a signal peptide but no other discernible conserved domain.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 34 | 0 | 55 |
| Expected | 13.75 | 27.5 | 13.75 | 55 |

Chi-Sq.=38.76 Significance=3.8315395E-9 (hom/n)=0.0 Avg. Litter Size=7

Mutation Information

Mutation Type: Homologous Recombination (standard)

Description: Coding exons 1 and 2 were targeted (NCBI accession BC029863.1).

1. Wild-type Expression Panel: Panel: Expression of the target gene was detected in embryonic stem (ES) cells and in all 13 adult tissue samples tested by RT-PCR, except bone.

2. QC Expression: Disruption of the target gene was confirmed by Southern hybridization analysis.

66.21.1. Phenotypic Analysis (for Disrupted Gene: DNA64903-1553 (UNQ655)

(a) Overall Phenotypic Summary:

Mutation of the gene encoding the ortholog of human UNQ655 resulted in lethality of (−/−) mutants. The heterozygous mice exhibited decreased mean serum IgG2a levels. Gene disruption was confirmed by Southern blot.

(b) Pathology

Microscopic: Not tested due to embryonic lethality. At 12.5 days, there were 49 embryos observed: 18 (+/−) embryos, 8 (+/+) embryos, 22 resorption moles, and 1 inconclusive.

Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (+/−) mice exhibited a decreased mean serum IgG2a level when compared with that of their (+/+) littermates, the (+/+) mice within the project run, and the historical median.

The serum immunoglobulin isotyping assay showed decreased or reduced levels of IgG2a in the heterozygous (+/−) mice compared to their gender-matched littermate (+/+) controls.

The serum immunoglobulin isotyping assay revealed that heterozygous adults exhibited decreased serum IgG2a levels. Thus, heterozygotes showed an abnormally low serum immunoglobulins compared with the (+/+) littermates. Thus, the gene encoding PRO1286 polypeptides is essential for making immunoglobulins (or gamma globulins). Likewise, IgG2a immunoglobulins have neutralization effects and to a lesser extent are important for activation of the complement system. These immunological abnormalities suggest that PRO1286 polypeptides or agonists thereof would be useful in stimulating the immune system and would find utility in the cases wherein this effect would be beneficial to the individual such as in the case of leukemia, and other types of cancer, and in immunocompromised patients, such as AIDS sufferers. Accordingly, inhibitors (antagonists) of PRO1286 polypeptides would inhibit the immune response and would be useful candidates for suppressing harmful immune responses, e.g. in the case of graft rejection or graft-versus-host diseases.

66.22. Generation and Analysis of Mice Comprising DNA59218-1559 (UNQ664) Gene Disruptions In these knockout experiments, the gene encoding PRO1295 polypeptides (designated as DNA59218-1559) (UNQ664) was disrupted. The gene specific information for these studies is as follows: the mutated mouse gene corresponds to nucleotide reference: XM_485054 PREDICTED: *Mus musculus* congenital dyserythropoietic anemia, type I (human) (Cdan1); protein reference: XP_485054 congenital dyserythropoietic anemia, type I [*Mus musculus*]; the human gene sequence reference: NM_138477 *Homo sapiens* congenital dyserythropoietic anemia, type I (CDAN1); the human protein sequence corresponds to reference: Q8IWY9 ACCESSION:Q8IWY9 NID: *Homo sapiens* (Human). Codanin 1 (UNQ664/PRO1295).

The mouse gene of interest is Cdan1 (congenital dyserythropoietic anemia, type I [human]), ortholog of human CDAN1. Aliases include CDA1, CDAI, CDA-I, 1500015A01Rik, codanin, and codanin 1.

CDAN1 is a ubiquitously expressed protein located in the cytoplasm that likely functions as a structural protein, connecting the nuclear membrane with microtubules. CDAN1 may be involved in preserving nuclear membrane integrity. Mutations in CDAN1 can cause congenital dyserythropoietic anemias, a rare group of inherited red blood cell disorders associated with dysplastic changes in late erythroid precursors (Dgany et al, *Am J Hum Genet* 71(6):1467-74 (2002); Pielage et al, *Dev Cell* 5(6):841-51 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 32 | 0 | 53 |
| Expected | 13.25 | 26.5 | 13.25 | 53 |

Chi-Sq.=47.76 Significance=4.256456E-11 (hom/n)=0.0 Avg. Litter Size=8

Mutation Information

Mutation Type: Homologous Recombination (standard)

Description: Coding exons 3 through 8 were targeted (NCBI accession XM_485054.1).

1. Wild-type Expression Panel: Expression of the target gene was detected in embryonic stem (ES) cells and in all 13 adult tissue samples tested by RT-PCR, except bone and adipose.

2. QC Expression: Disruption of the target gene was confirmed by Southern hybridization analysis.

66.22.1. Phenotypic Analysis (for Disrupted Gene: DNA59218-1559 (UNQ664)

(a) Overall Phenotypic Summary:

Mutation of the gene encoding the ortholog of human congenital dyserythropoietic anemia, type I (human) (CDAN1) resulted in lethality of (−/−) mutants. Lethality is likely due to a defect in erythropoiesis. UNQ675 is highly expressed in the CNS compared to other tissues. Gene disruption was confirmed by Southern blot.

(b) Pathology

Microscopic: Not tested due to embryonic lethality. At 12.5 days, 51 embryos were observed: 23 (+/−) embryos, 15 (+/+) embryos, 9 resorptions, and 4 to-be-determined.

Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

66.23. Generation and Analysis of Mice Comprising DNA59588-1571 (UNQ675) Gene Disruptions In these knockout experiments, the gene encoding PRO1309 polypeptides (designated as DNA59588-1571) (UNQ675) was disrupted. The gene specific information for these studies is as follows: the mutated mouse gene corresponds to nucleotide reference: NM_028880 *Mus musculus* leucine rich repeat transmembrane neuronal 1 (Lrrtm1); protein reference: Q8K377 ACCESSION:Q8K377 NID: *Mus musculus* (Mouse). Lrrtm1 protein (*Mus musculus* 0 day neonate eyeball cDNA, RIKEN full-length enriched library, clone:E130010O21 product:hypothetical RNI-like structure containing protein, full insert sequence) (*Mus musculus* 0 day neonate eyeball cDNA, RIKEN full-length enriched library, clone:E130012A05 product:hypothetical RNI-like structure containing protein, full insert sequence) (Leucine-rich repeat transmembrane neuronal 1 protein); the human gene sequence reference: NM_178839 *Homo sapiens* leucine rich repeat transmembrane neuronal 1 (LRRTM1); the human protein sequence corresponds to reference: Q86UE6 ACCESSION:Q86UE6 NID: *Homo sapiens* (Human). LRRTM1 protein (DFLL675).

The mouse gene of interest is Lrrtm1 (leucine rich repeat transmembrane neuronal 1), ortholog of human LRRTM1. Aliases include 4632401D06Rik, leucine-rich repeat transmembrane neuronal 1, DFLL675, and FLJ32082.

LRRTM1 is a putative integral plasma membrane protein expressed primarily in the nervous system that likely functions as a cell adhesion molecule or receptor. The protein consists of a signal peptide, several leucine-rich repeats, and a transmembrane segment. LRRTM1 may play a role in development and maintenance of the nervous system (Lauren et al, *Genomics* 81(4):411-21 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 46 | 15 | 82 |
| Expected | 20.5 | 41 | 20.5 | 82 |

Chi-Sq.=0.71 Significance=0.7011734 (hom/n)=0.23 Avg. Liter Size=8

Mutation Information

Mutation Type: Homologous Recombination (standard)

Description: Coding exon 2 was targeted (NCBI accession NM_028880.2).

1. Wild-type Expression Panel: Expression of the target gene was detected only in brain, spinal cord, eye, and adipose among the 13 adult tissue samples tested by RT-PCR.

2. QC Expression: Disruption of the target gene was confirmed by Southern hybridization analysis.

66.23.1. Phenotypic Analysis (for Disrupted Gene: DNA59588-1571 (UNQ675)

(a) Overall Phenotypic Summary:

Mutation of the gene encoding the ortholog of human leucine rich repeat transmembrane neuronal 1 (LRRTM1) resulted in increased body fat in (−/−) and (+/−) mice. In addition, the mutant (−/−) mice exhibited decreased median ambulatory counts during circadian rhythm testing. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal’s movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The (−/−) mice exhibited decreased median ambulatory counts during both dark periods during home-cage activity testing compared with their gender-matched (+/+) littermates and the historical mean.

These results demonstrate an abnormal circadian rhythm and is suggestive of decreased activity or hypoactivity which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO1309 polypeptides and agonists thereof would be useful for the treatment or amelioration of the symptoms associated with depressive disorders.

(c) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: Both the male and female (+/−) and (−/−) mice exhibited increased mean percent total body fat and total fat mass when compared with their gender-matched (+/+) littermates and the historical means, the difference being more notable in the females. The female (−/−) mice also exhibited notably increased mean total tissue mass.

These studies suggest that mutant (−/−) non-human transgenic animals exhibit a negative phenotype that would be associated with obesity. Thus, PRO1309 polypeptides or agonists thereof are essential for normal growth and metabolic processes and especially would be important in the prevention and/or treatment of obesity.

66.24. Generation and Analysis of Mice Comprising DNA60608-1577 (UNQ682) Gene Disruptions In these knockout experiments, the gene encoding PRO1316 polypeptides (designated as DNA60608-1577) (UNQ682) was disrupted. The gene specific information for these studies is as follows: the mutated mouse gene corresponds to nucleotide reference: NM_020265 *Mus musculus* dickkopf homolog 2 (*Xenopus laevis*) (Dkk2); protein reference: Q9QYZ8 Dickkopf related protein-2 precursor (Dkk-2) (Dickkopf-2) (mDkk-2) gi|6272205|emb|CAB60110.1| dickkopf-2 *[Mus musculus*]; the human gene sequence reference: NM_014421 *Homo sapiens* dickkopf homolog 2 (*Xenopus laevis*) (DKK2); the human protein sequence corresponds to reference: Q9UBU2 ACCESSION:Q9UBU2 NID: *Homo sapiens* (Human). Dickkopf related protein-2 precursor (Dkk-2) (Dickkopf-2) (hDkk-2).

The mouse gene of interest is Dkk2 (dickkopf homolog 2 *[Xenopus laevis*]), ortholog of human DKK2. Aliases include DKK-2, dickkopf 2, mRNA for dickkopf-2 (dkk-2 gene), dickkopf homolog 1 (*Xenopus laevis*), Dickkopf gene 2, and dickkopf (*Xenopus laevis*) homolog 2.

DKK2 is a secreted protein that functions as a ligand for coreceptors of the canonical Wnt/beta-catenin signaling pathway. In the absence of coreceptor KREMEN2 (kringle containing transmembrane protein 2), DKK2 activates Wnt signaling by binding with coreceptor LRP6 (low density lipoprotein receptor-related protein 6). However, in the presence of KREMEN2, DKK2 inhibits Wnt signaling by binding with KREMEN2 (Mao and Niehrs, *Gene* 302(1-2):179-83 (2003); Brott and Sokol, *Mol Cell Biol* 22(17):6100-10 (2002); Li et al, *J Biol Chem* 277(8):5977-81 (2002); Krupnik et al, *Gene* 238(2):301-13 (1999)). DKK2 is involved in development (Monaghan et al, *Mech Dev* 87(1-2):45-56 (1999); Ang et al, *Gene Expr Patterns* 4(3):289-95 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 43 | 19 | 80 |
| Expected | 20 | 40 | 20 | 80 |

Chi-Sq.=3.62 Significance=0.16365415 (hom/n)=0.26 Avg. Litter Size=8

Mutation Information

Mutation Type: Homologous Recombination (standard)

Description: Coding exon 1 was targeted (NCBI accession NM_020265.2).

1. Wild-type Expression Panel: Expression of the target gene was detected in embryonic stem (ES) cells and in all 13 adult tissue samples tested by RT-PCR, except spinal cord, thymus, and bone.

2. QC Expression: Disruption of the target gene was confirmed by Southern hybridization analysis.

66.24.1. Phenotypic Analysis (for Disrupted Gene: DNA60608-1577 (UNQ682)

(a) Overall Phenotypic Summary:

Mutation of the gene encoding the ortholog of human dickkopf homolog 2 (*Xenopus laevis*) (DKK2) resulted in the homozygous mutant mice exhibiting corneal epithelialization with underdeveloped eyelids and agenesis of the Harderian gland, resulting in impaired vision in the mutants. All eight of the (−/−) mice exhibited abnormalities of the eye, including 6 (−/−) mice exhibiting palpebral closure. Gene disruption was confirmed by Southern blot.

(b) Pathology

Gross: All eight (−/−) mice exhibited severe corneal epidermidalization, characterized by thickening of the corneal stroma and scarring that blocked the vision of the mutants. The eyelids of the (−/−) mice were also underdeveloped, resulting in incomplete closure of the eyelids. Some appeared to have smaller than normal eyes. Both eyelids were notably hypoplastic and the Harderian glands were not visible upon gross examination of the (−/−) mice.

Microscopic: The (−/−) mice exhibited corneal epithelialization with underdeveloped eyelids and agenesis of the Harderian gland, resulting in impaired vision in the mutants. The (−/−) mice exhibited diffuse metaplasia of the cornea and sclera, characterized by diffuse fibrosis of the collageneous stroma and keratinizing hyperkeratosis of the surface epithelium with multifocal chronic-active keratitis and ulceration. Multifocally, there were sebaceous glands and hair follicles in the cornea and sclera. These changes were more severe in the male mutants than in the females. The (−/−) mice also exhibited agenesis of the Harderian gland. Although intraorbital lacrimal glands were present in some sections, the Harderian gland was uniformly absent and the eyelids were severely hypoplastic in all mutant mice.

Gene Expression: LacZ activity was not detected in the panel of tissues by immunohistochemical analysis.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

Fundus: All 8 (−/−) mice exhibited severe corneal epidermidalization, characterized by thickening of the corneal stroma and scarring that blocked the vision of the mutants. The eyelids of the (−/−) mice were also underdeveloped, resulting in incomplete closure of the eyelids. Therefore, the artery-to-vein ratio could not be measured in the mutants.

Angiogram: Only 1 of the (−/−) mice was successfully analyzed. No notable posterior chamber anomaly was observed.

66.25. Generation and Analysis of Mice Comprising DNA58743-1609 (UNQ719) Gene Disruptions In these knockout experiments, the gene encoding PRO1383 polypeptides (designated as DNA58743-1609) (UNQ719) was disrupted. The gene specific information for these studies is as follows: the mutated mouse gene corresponds to nucleotide reference: NM_177735 *Mus musculus* hypothetical protein C130036G08 (C130036G08); protein reference: Q6NXM3 ACCESSION:Q6NXM3 NID: *Mus musculus* (Mouse). Hypothetical protein C130036G08; the human gene sequence reference: NM_152913 ACCESSION:NM_152913 NID: gi 23097273 refNM_152913.1 *Homo sapiens* hypothetical protein DKFZp761L1417 (DKFZp761L11417); the human protein sequence corresponds to reference: Q8N0W9 ACCESSION:Q8NOW9 NID: *Homo sapiens* (Human). Similar to QNR-71 protein (Hypothetical protein).

The mouse gene of interest is "hypothetical protein C130036G08," ortholog of human "hypothetical protein DKFZp761L1417." Aliases include C130036G08 and DKFZp761L1417.

Hypothetical protein DKFZp761L1417 is a putative type I integral plasma membrane protein, containing a signal peptide, a PKD (repeats in polycystic kidney disease 1 [PKD1] and other proteins) domain (SMART accession SM00089), and a transmembrane segment. PKD domains are likely involved in protein-protein or protein-carbohydrate interactions, suggesting that hypothetical protein DKFZp761L1417 functions as a cell adhesion molecule or signal-transducing receptor.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 15 | 44 | 19 | 78 |
| Expected | 19.5 | 39 | 19.5 | 78 |

Chi-Sq.=1.42 Significance=0.4916442 (hom/n)=0.27 Avg. Litter Size=10

Mutation Information

Mutation Type: Homologous Recombination (standard)

Description: Coding exons 3 through 5 were targeted (NCBI accession NM_177735.3).

1. Wild-type Expression Panel: Expression of the target gene was detected in embryonic stem (ES) cells and in all 13 adult tissue samples tested by RT-PCR, except liver, skeletal muscle, and bone.

2. QC Expression: Disruption of the target gene was confirmed by Southern hybridization analysis.

66.25.1. Phenotypic Analysis (for Disrupted Gene: DNA58743-1609 (UNQ719)

(a) Overall Phenotypic Summary:

Mutation of the gene encoding the ortholog of human “hypothetical protein DKFZp761L1417” resulted in the homozygous mutant mice exhibiting decreased locomotor activity or mild hypoactivity during open field testing when compared with the level for their wild-type littermates and the historical mean. UNQ719 shows high expression in the CNS compared to other tissues. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. Feb. 15, 1996; 379(6566):606-12), and the GABA receptor (Homanics et al., Proc Natl Acad Sci USA. Apr. 15, 1997; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects’ first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

A notable difference was observed during open field activity testing. The (−/−) mice exhibited a decreased median sum total distance traveled Thus, knockout mice demonstrated a phenotype consistent with depression, cognitive disorders, hyperalgesia and sensory disorders and/or bipolar disorders. Thus, PRO1383 polypeptides and agonists thereof would be useful for the treatment or amelioration of the symptoms associated with depressive disorders.

66.26. Generation and Analysis of Mice Comprising DNA71159-1617 (UNQ721) Gene Disruptions In these knockout experiments, the gene encoding PRO1384 polypeptides (designated as DNA71159-1617) (UNQ721) was disrupted. The gene specific information for these studies is as follows: the mutated mouse gene corresponds to nucleotide reference: NM_019985 *Mus musculus* C-type lectin-like receptor 2 (Clec2); protein reference: Q9JL99 ACCESSION:Q9JL99 NID: *Mus musculus* (Mouse). C-TYPE LECTIN-LIKE RECEPTOR 2; the human gene sequence reference: NM_016509 ACCESSION:NM_016509 NID:7706060 *Homo sapiens Homo sapiens* C-type lectin-like receptor-2 (LOC51266); the human protein sequence corresponds to reference: Q9P126 ACCESSION:Q9P126 NID: *Homo sapiens* (Human). C-TYPE LECTIN-LIKE RECEPTOR-2. The mouse gene of interest is Clec2 (C-type lectin-like receptor 2), ortholog of human CLEC2. Aliases include Clec-2, mCLEC-2, 1810061I13Rik, PRO1384, and QDED721.

CLEC2 is a type II integral plasma membrane protein that likely functions as a receptor. CLEC2 consists of a signal anchor and a C-type lectin domain, which binds with carbohydrate residues. CLEC2 is expressed in liver and in myeloid and natural killer cells. CLEC2 may play a role in signal transduction and immunity (Colonna et al, *Eur J Immunol* 30(2):697-704 (2000); Sobanov et al, *Eur J Immunol* 31(12): 3493-503 (2001)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 43 | 3 | 62 |
| Expected | 15.5 | 31 | 15.5 | 62 |

Chi-Sq.=10.34 Significance=0.0056845685 (hom/n)=0.12 Avg. Litter Size=8

Mutation Information

Mutation Type: Homologous Recombination (standard)

Description: Coding exons 1 and 2 were targeted (NCBI accession NM_019985.2).

1. Wild-type Expression Panel: Expression of the target gene was detected in all 13 adult tissue samples tested by RT-PCR, except skeletal muscle; bone; stomach, small intestine, and colon; heart; and adipose.

2. QC Expression: Disruption of the target gene was confirmed by Southern hybridization analysis.

66.26.1. Phenotypic Analysis (for Disrupted Gene: DNA71159-1617 (UNQ721)

(a) Overall Phenotypic Summary:

Mutation of the gene encoding the ortholog of human C-type lectin-like receptor 2 (CLEC2) resulted in greatly reduced viability of (–/–) mutants. Genetic data indicate that this mutation resulted in greatly reduced viability of the homozygous mutants. Microscopic analysis revealed numerous brain defects including mild-to-moderate congestion and hemorrhage in the diencephalon and vestibulocochlear ganglion of the homozygous embryos. The 2 surviving female homozygous mutant mice exhibited signs of anemia and decreased serum cholesterol, heart rate, and blood pressure. The mutants also exhibited an increased mean percentage of CD4 cells in the peripheral blood. Disruption of the target gene was confirmed by Southern hybridization analysis.

(b) Pathology

General Observations: Reduced viability of the (–/–) mice was observed. All but 2 of the (–/–) mice were dead at the time of genotyping. Thus, high embryonic and prenatal lethality was observed.

Microscopic: At 12.5 days there were 45 embryos observed: 11 (–/–) embryos, 18 (+/–) embryos, 11 (+/+) embryos, 3 resorption moles, and 2 inconclusive. The (–/–) embryos available for analysis exhibited mild-to-moderate brain (diencephalon) and vestibulocochlear ganglion congestion and hemorrhage. There were multiple foci of congestion and hemorrhage detected in the diencephalon of all 4 (–/–) embryos examined and unilaterally in the vestibulocochlear ganglion of 2/4 12.5 day (–/–) embryos. In addition, an increased number of dilated capillaries were observed in the affected areas of the developing brains. In addition, circulating blood cells were found throughout the embryos especially the fetal liver. Gene Expression: LacZ activity was not detected in the panel of tissues by immunohistochemical analysis.

(c) Cardiology—Blood Pressure/Heart Rate

Test Description: Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results

Blood Pressure: The 2 surviving (–/–) mice exhibited decreased mean systolic blood pressure when compared with that of their gender-matched (+/+) littermates and the historical mean.

Heart Rate: The 2 surviving (–/–) mice exhibited a decreased mean heart rate (~1-2 SD below the historic mean) when compared with that of their gender-matched (+/+) littermates and the historical mean.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 2 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The 2 surviving female (–/–) mice (F-104 and F-133) exhibited a decreased mean serum cholesterol level when compared with that of their gender-matched (+/+) littermates and the historical mean.

As summarized above, the (−/−) mice exhibited notably decreased mean serum cholesterol levels when compared with their gender-matched (+/+) littermates and the historical means. Thus, mutant mice deficient in the PRO1384 gene resulted in hypocholestremia which could lead to defective membrane formation and/or function.

(e) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized proteins directly or via the use of antibody agonists) to inhibit the immune response and thus ameliorate immune related disease.

The following tests were performed:

(1) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The 2 surviving (−/−) mice (F-104 and F-133) exhibited a decreased mean red blood cell count, hemoglobin concentration, and hematocrit level when compared with the levels for their (+/+) littermates and the historical means.

These results are related to a phenotype associated with anemia. Thus, PRO1384 polypeptides, agonists thereof or the encoding gene for PRO1384 polypeptides must be essential for normal red blood cell production and as such would be useful in the treatment of blood disorders associated with anemia or a low hematocrit.

(2) Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 2 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The (−/−) mice exhibited an altered distribution of leukocyte subsets in the peripheral blood, characterized by an increased mean percentage of CD4 cells when compared with that of their (+/+) littermates and the historical mean.

Thus, knocking out the gene which encodes PRO1384 polypeptides causes an increase in the T cell population. From these observations, PRO1384 polypeptides or the gene encoding PRO1384 appears to act as a negative regulator of T cell proliferation. Thus, antagonists (inhibitors) of PRO1384 polypeptides would mimic this phenotype and would be beneficial in enhancing T cell proliferation.

66.27. Generation and Analysis of Mice Comprising DNA73401-1633 (UNQ737) Gene Disruptions In these knockout experiments, the gene encoding PRO1431 polypeptides (designated as DNA73401-1633) (UNQ737) was disrupted. The gene specific information for these studies is as follows: the mutated mouse gene corresponds to nucleotide reference: NM_175684 *Mus musculus* FCH and double SH3 domains 1 (Fchsd1); protein reference:

Q6PFY1 ACCESSION:Q6PFY1 NID: *Mus musculus* (Mouse). FCH and double SH3 domains 1; the human gene sequence reference: NM_033449 *Homo sapiens* FCH and double SH3 domains 1 (FCHSD1); the human protein sequence corresponds to reference: Q86WN1 ACCESSION: Q86WN1 NID: *Homo sapiens* (Human). FLJ00007-like protein.

The mouse gene of interest is Fchsd1 (FCH and double SH3 domains 1), ortholog of human FCHSD1. Aliases include A030002D08Rik and FLJ00007.

FCHSD1 is a putative cytoplasmic protein, consisting of a Fes/CIP4 (Fes tyrosine kinase/Cdc42-interacting protein) homology domain, two SH3 (src homology-3) domains, and a proline-rich C terminus (Katoh and Katoh, *Int J Mol* Med 13(5):749-54 (2004)). FES-CIP4 homology domain binds with tubulin (Takahashi et al, *J Biol Chem* 278(49):49129-33 (2003); Laurent et al, *Mol Cell Biol* 24(21):9351-8(2004)). SH3 domains likely mediate processes such as increasing the local concentration proteins, determining the subcellular location of proteins, and mediating assembly of large multiprotein complexes (InterPro accession IPRO01452). Thus, FCHSD1 may function as a docking protein for processes involving cytoskeletal rearrangement.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 38 | 19 | 78 |
| Expected | 19.5 | 39 | 19.5 | 78 |

Chi-Sq.=0.9 Significance=0.63762814 (hom/n)=0.22 Avg. Litter Size=9

Mutation Information

Mutation Type: Homologous Recombination (standard)

Description: Coding exons 1 through 7 were targeted (NCBI accession NM_175684.3).

1. Wild-type Expression Panel: Expression of the target gene was detected in embryonic stem (ES) cells and in all 13 adult tissue samples tested by RT-PCR, except bone.

2. QC Expression: Disruption of the target gene was confirmed by Southern hybridization analysis.

66.27.1. Phenotypic Analysis (for Disrupted Gene: DNA73401-1633 (UNQ737)

(a) Overall Phenotypic Summary:

Mutation of the gene encoding the ortholog of human FCH and double SH3 domains 1 (FCHSD1) resulted in the mutant (−/−) mice exhibiting elevated mean serum glucose levels. Male knockout (−/−) mice also exhibited increased fat percentages and increased fat mass (g) as well as female (−/−) mice showed a decreased femur bone mineral density and total body bone mineral density. In addition, the male (−/−) mice showed a decreased mean systolic blood pressure. Gene disruption was confirmed by Southern blot.

(b) Phenotypic Analysis: Metabolism-Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Blood Chemistry: The (−/−) mice exhibited a notably increased mean serum glucose levels when compared with their gender-matched (+/+) littermates and the historical means. However, glucose tolerance testing was normal.

As summarized above, the (−/−) mice exhibited increased mean serum glucose levels suggesting abnormal glucose metabolism or a pre-diabetic condition.

(c) Cardiology—Blood Pressure/Heart Rate

Test Description: Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results

Blood Pressure: The male (−/−) mice exhibited decreased mean systolic blood pressure when compared with that of their gender-matched (+/+) littermates and the historical mean.

(d) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited increased mean percent total body fat and total fat mass when compared with their gender-matched (+/+) littermates and the historical means. The female (−/−) mice exhibited decreased femur bone mineral density and total bone mineral density.

These studies suggest that mutant male (−/−) non-human transgenic animals exhibit a negative phenotype that would be associated with obesity. Thus, PRO1431 polypeptides or agonists thereof are essential for normal growth and metabolic processes and especially would be important in the prevention and/or treatment of obesity. The female knockout mice exhibited a negative bone phenotype associated with decreased bone mineral density measurements which could be due to osteoporosis. Thus, PRO1431 polypeptides or agonists thereof would be useful in the treatment of such bone disorders that are characterized by decreased bone mineral density.

66.28. Generation and Analysis of Mice Comprising DNA68818-2536 (UNQ739) Gene Disruptions In these knockout experiments, the gene encoding PRO1434 polypeptides (designated as DNA68818-2536) (UNQ739) was disrupted. The gene specific information for these studies is as follows: the mutated mouse gene corresponds to nucleotide reference: NM_177033 *Mus musculus* RIKEN cDNA A930041G11 gene (A930041G11Rik); protein reference: Q8C8N3 ACCESSION:Q8C8N3 NID: *Mus musculus* (Mouse). Hypothetical von Willebrand factor; the human gene sequence reference: NM_198570 *Homo sapiens* PSST739 (UNQ739); the human protein sequence corresponds to reference: Q6UXE2 ACCESSION:Q6UXE2 NID: *Homo sapiens* (Human). PSST739.

The mouse gene of interest is RIKEN cDNA A930041G11 gene, ortholog of human UNQ739. Aliases include PSST739.

UNQ739 is a putative secreted protein, containing a signal peptide, and two tandem von Willebrand factor type C (VWC) domains. VWC domains are found in numerous plasma proteins as well as intracellular proteins. VWC domains likely participate in oligomerization or complex formation (Pfam accession 00093).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 34 | 27 | 86 |
| Expected | 21.5 | 43 | 21.5 | 86 |

Chi-Sq.=1.21 Significance=0.5460744 (hom/n)=0.27 Avg. Litter Size=10

Mutation Information

Mutation Type: Homologous Recombination (standard)

Description: The exon preceding coding exon 1 and coding exon 1 were targeted (NCBI accession AK033944.1).

1. Wild-type Expression Panel: Expression of the target gene was detected in brain, spinal cord, eye, thymus, spleen, lung, and heart among the 13 adult tissue samples tested by RT-PCR.

2. QC Expression: Disruption of the target gene was confirmed by Southern hybridization analysis.

66.28.1. Phenotypic Analysis (for Disrupted Gene: DNA68818-2536 (UNQ739)

(a) Overall Phenotypic Summary:

Mutation of the gene encoding the ortholog of a human putative secreted protein (UNQ739) resulted in enhanced sensorimotor gating/attention in (−/−) mice. The homozygous mutant mice exhibited enhanced sensorimotor gating/attention at 3 of 4 prepulse intensities when compared with the level for their wild-type littermates and the historical means. In addition, the (−/−) mice exhibited a trend in decreased alkaline phosphatase levels. Hematology revealed decreased mean total white blood cell count and absolute lymphocyte counts in the (−/−) mice. Disruption of the target gene was confirmed by Southern hybridization analysis.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PP1 paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: The (−/−) mice exhibited notably increased median prepulse inhibition during pp4, pp8, and pp12 when compared with the levels for their (+/+) littermates and the historical means, suggesting enhanced sensorimotor gating/attention in the mutants.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

(1) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited decreased mean total white blood cell and absolute lymphocyte counts when compared with those of their (+/+) littermates and the historical means.

These results indicate that mutant (−/−) mice have immunological abnormalities compared with their wild-type littermates. The (−/−) mice showed a decreased absolute lymphocyte count indicative of abnormal adaptive immunity. Thus, PRO1434 polypeptides must be essential for maintaining a normal immunological profile especially for adaptive immunity.

66.29. Generation and Analysis of Mice Comprising DNA61185-1646 (UNQ746) Gene Disruptions In these knockout experiments, the gene encoding PRO1475 polypeptides (designated as DNA61185-1646) (UNQ746) was disrupted. The gene specific information for these studies is as follows: the mutated mouse gene corresponds to nucleotide reference: NM_026651 ACCESSION: NM_026651 NID:22267451 *Mus musculus Mus musculus* RIKEN cDNA 4930467B06 gene (4930467B06Rik); protein reference: Q91X88 ACCESSION:Q91X88 NID: *Mus musculus* (Mouse). O-mannosyl N-acetylglucosaminyltransferase; the human gene sequence reference: NM_017739 ACCESSION:NM_017739 NID:8923252 *Homo sapiens Homo sapiens* O-linked mannose beta1,2-N-acetylglucosaminyltransferase (FLJ20277); the human protein sequence corresponds to reference: Q9NXF9 ACCESSION: Q9NXF9 NID: *Homo sapiens* (Human). CDNA FLJ20277 FIS, CLONE HEP02567.

The mouse gene of interest is RIKEN cDNA 4930467B06 gene, ortholog of human FLJ20277 (O-linked mannose beta1,2-N-acetylglucosaminyltransferase). Aliases include 0610016107Rik, O-mannosyl N-acetylglucosaminyltransferase, MEB, GnTI.2, MGAT1.2, POMGNT1, and UDP-GlcNAc.

FLJ20277 is a Golgi membrane glycosyltransferase that catalyzes the addition of N-acetylglucosamine (GlcNAc) to the alpha-linked terminal mannose (Man) of O-mannosylated proteins (Zhang e al, *Biochem J* 361 (Pt 1):153-62 (2002); Schacter, *Biochim Biophys Acta* 1573(3):292-300 (2002)). This enzyme participates in O-mannosyl glycan synthesis, which occurs primarily brain, nerve and skeletal muscle (Yoshida et al, *Dev Cell* 1(5):717-24 (2001)). Mutations in FLJ20277 cause muscle-eye-brain diseases, an autosomal recessive disorder characterized by congenital muscular dystrophy, brain malformation, and ocular abnormalities (Vervoort et al, *Ann Neurol* 56(1):143-8 (2004); Manya et al, *Biochem Biophys Res Commun* 306(1):93-7 (2003); Taniguchi et al, *Hum Mol Genet* 12(5):527-34 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 39 | 13 | 73 |
| Expected | 18.25 | 36.5 | 18.25 | 73 |

Chi-Sq.=10.29 Significance=0.0058284746 (hom/n)=0.18 Avg. Litter Size=9

Mutation Information

Mutation Type: Homologous Recombination (standard)

Description: The exon preceding coding exon 1 and coding exons 1 through 5 were targeted (NCBI accession NM_026651.1).

1. Wild-type Expression Panel: Expression of the target gene was detected in brain and spinal cord among 13 adult tissues samples tested by RT-PCR.

2. QC Expression: Disruption of the target gene was confirmed by Southern hybridization analysis.

66.29.1. Phenotypic Analysis (for Disrupted Gene: DNA61185-1646 (UNQ746)

(a) Overall Phenotypic Summary:

Mutation of the gene encoding the ortholog of human O-linked mannose beta1,2-N-acetylglucosaminyltransferase (FLJ20277) resulted in developmental malformation of the brain in (−/−) mice. Retinal vessel disorganization, peripheral retinal degeneration, and microaneurysms were observed in the homozygous mutant mice upon fundus examination. Microscopic analysis confirmed the retinal abnormalities and revealed developmental malformation of the brain in the mutants. In addition, both the male and female (−/−) mice exhibited an impaired glucose tolerance when compared with their gender-matched wild-type littermates and the historical means. The (−/−) mice were smaller than their (+/+) littermates and showed decreased mean body weight and length. Radiological observations showed abnormal bone-related measurements related to osteoporosis. Several neurological abnormalities were also observed in the knockout (−/−) mice. Disruption of the target gene was confirmed by Southern hybridization analysis.

(b) Pathology

Microscopic: The (−/−) mice exhibited mild-to-moderate multifocal developmental malformation of the brain. There was widespread evidence of defective neuronal migration in the brain as shown by the retention of nests of external granular cell neurons in the cerebellum and associated fusion of cerebellar folia, the scalloped appearance of the ventral arm of the dentate gyrus of the hippocampus, the diffuse disorganization of neurons and loss of neuronal cell layers in the cerebral cortex, and the fusion of both hemispheres in the area of the dorsal median sulcus. Frequently, mild dilatation of the lateral ventricles was also observed. The (−/−) mice also exhibited diffuse retinal atrophy, characterized by a general reduction in ganglion cell numbers, more severely at the periphery, with associated thinning of the inner and outer nuclear layers of the retina. The retinal vessels frequently lay on the surface of the retina, in direct contact with the vitreous, instead of being embedded in the ganglion cell layer as normal. In some eyes, retinoschisis is evident within the peripheral inner nuclear layer.

Gene Expression: LacZ activity was not detected in the panel of tissues by immunohistochemical analysis.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wild-type (+/+) littermates would be indicative of such pathological conditions.

Results:

Fundus: The (−/−) mice exhibited optic nerve fiber layer striation and aggregation, retinal vessel disorganization, and peripheral retinal degeneration. One (−/−) mouse (F-174) also exhibited bulging eyes, suggesting increased intraocular pressure.

Angiogram: The (−/−) mice exhibited severe retinal vessel disorganization, microaneurysms, and retinal capillary leakage.

In summary, in this study, (–/–) mice showed opthamological abnormalities which would lead to abnormal retinal vessels and retinal degeneration when compared with their (+/+) littermates. In summary, by knocking out the gene identified as DNA61185-1646 encoding PRO1475 polypeptides, homozygous mutant progeny exhibit phenotypes which are associated with optic nerve and retinal artery abnormalities. Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to ophthalmological disorders such as retinal degeneration and even blindness. Thus, antagonists of PRO1475 encoding genes would lead to similar pathological retinal changes, whereas agonists would be useful as therapeutic agents in the treatment of hypertension, atherosclerosis or other opthamological disorders including retinal degeneration and diseases associated with this condition (as indicated above).

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The female (–/–) mice exhibited decreased median ambulatory counts especially during the light phase when compared with the number for their gender-matched (+/+) littermates and the historical mean. These results demonstrate an abnormal circadian rhythm. Home-cage activity testing is also suggestive of decreased activity or hypoactivity which is indicative of a decreased anxiety-like response in the mutants. Thus, knockout mice demonstrated a phenotype consistent with depression, cognitive disorders, hyperalgesia and sensory disorders and/or bipolar disorders. Thus, PRO1475 polypeptides and agonists thereof would be useful for the treatment or amelioration of the symptoms associated with depressive disorders.

Inverted Screen Testing:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

Results:

| Genotype | Ratio Fell Down % | | Ratio Climbed up % | |
|---|---|---|---|---|
| +/+ (n = 8) | 1/8 | 12.5% | 0/8 | 0 |
| –/– (n = 8) | 4/8 | 50% | 0/8 | 0 |

A motor strength deficit is apparent when there is a 50% point difference between (–/–) or (+/–) mice and (+/+) mice for the fell down response. 0/8 or 1/8 (–/–) or (+/–) mice not climbing indicates impaired motor coordination. 7/8 or 8/8(–/–) or (+/–) mice climbing up indicates enhanced motor coordination.

The Inverted Screen Test is designed to measure basic sensory & motor observations:

Among the 8 (–/–) mice analyzed, all 4 (–/–) mice fell off in the screen whereas 1/8 (+/+) mice fell off suggesting an impaired motor coordination in the mutants.

(e) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

Oral Glucose Tolerance: The (–/–) mice exhibited an impaired glucose tolerance when compared with that of their gender-matched (+/+) littermates and the historical mean.

These studies indicated that (–/–) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO1475 polypeptides (or agonists thereof) or its encoding gene would be useful in the treatment of conditions associated with an impaired glucose homeostasis and/or various cardiovascular diseases, including diabetes.

(f) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Obvious Observations: Obvious: The (–/–) mice were smaller than their (+/+) littermates and displayed clutched hind limbs when suspended by their tails.

Weight/Length:

The (–/–) mice exhibited decreased mean body weight and mean body length when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: micro CT: The male (–/–) mice exhibited decreased mean vertebral trabecular bone volume, number, thickness, and connectivity density when compared with their gender-matched (+/+) littermates and the historical means.

Mutant (–/–) mice deficient in the gene encoding PRO1475 polypeptides show a phenotype consistent with growth retardation and/or tissue wasting diseases as well as abnormal bone metabolism. These results are consistent with the observation of smaller appearance than their (+/+) littermates as well as decreased mean body weight and mean body length reported above. In addition, the mutant (–/–) mice exhibited decreased vertebral trabecular bone mineral content and density measurements suggestive of osteoporosis. Thus, antagonists or inhibitors of PRO1475 polypeptides or its encoding gene would mimic these abnormal metabolic related effects. On the other hand, PRO1475 polypeptides or agonists thereof would be useful in the prevention and/or treatment of such metabolic disorders as growth retardation, cachexia or other tissue wasting diseases as well as useful in the treatment of bone disorders associated with bone loss.

66.30. Generation and Analysis of Mice Comprising DNA58732-1650 (UNQ750) Gene Disruptions In these knockout experiments, the gene encoding PRO1481 polypeptides (designated as DNA58732-1650) (UNQ750) was disrupted. The gene specific information for these studies is as follows: the mutated mouse gene corresponds to nucleotide reference: NM_172979 *Mus musculus* RIKEN cDNA D730046L02 gene (D730046L02Rik); protein reference: Q8C6Z1 ACCESSION:Q8C6Z1 NID: *Mus musculus* (Mouse). Mucin 15 precursor; the human gene sequence reference: NM_145650 *Homo sapiens* mucin 15 (MUC15); the human protein sequence corresponds to reference: Q8N387 ACCESSION:Q8N387NID: *Homo sapiens* (Human). MUC15 protein precursor.

The mouse gene of interest is RIKEN cDNA D730046L02 gene, ortholog of human MUC 15 (mucin 15). Aliases include 4732460F09, PASIII, PAS3, GLYCOPROTEIN C, GLYCOPROTEIN 4, and COMPONENT II. MUC 15 is a type I plasma membrane protein, consisting of a signal peptide, an extracellular, heavily glycosylated segment, a transmembrane segment, and short cytoplasmic C-terminus. A second isoform lacking the transmembrane segment may be secreted. The protein is expressed in a wide variety of tissues, including spleen, thymus, prostate, testis, ovary, small intestine, colon, peripheral blood leukocyte, bone marrow, lymph node and lung. MUC15 likely plays a role in cell adhesion to extracellular matrix (Pallesen et al, *Eur J Biochem* 269(11):2755-63 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 19 | 39 | 23 | 81 |
| Expected | 20.25 | 40.5 | 20.25 | 81 |

Chi-Sq.=2.06 Significance=0.35700697 (hom/n)=0.29 Avg. Litter Size=9

Mutation Information

Mutation Type: Homologous Recombination (standard)

Description: Coding exon 1 was targeted (NCBI accession NM_172979.1).

1. Wild-type Expression Panel: Expression of the target gene was detected in embryonic stem (ES) cells and in all 13 adult tissue samples tested by RT-PCR, except liver, skeletal muscle, and bone.

2. QC Expression: Disruption of the target gene was confirmed by Southern hybridization analysis.

66.30.1. Phenotypic Analysis (for Disrupted Gene: DNA58732-1650 (UNQ750)

(a) Overall Phenotypic Summary:

Mutation of the gene encoding the ortholog of human mucin 15 (MUC 15) resulted in the homozygous mutant mice exhibiting an enhanced sensorimotor gating/attention during prepulse inhibition testing when compared with their wild-type littermates and the historical means. In addition, the mutant (−/−) mice exhibited immunological abnormalities. Gene disruption was confirmed by Southern blot.

(b) Microarray Analysis

Microarray analysis reveals overexpression of UNQ750 in breast tumors compared to normal breast tissue.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when aloud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: The (−/−) mice exhibited increased median prepulse inhibition during pp4, pp8, and pp12 when compared with the levels for their (+/+) littermates and the historical means, which is an indication of an enhanced sensorimotor gating/attention in the mutants.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

(1) Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

Tissue Specific FACS-Project: The (−/−) mice exhibited an increased percentage of TCRB+ and a decreased percentage of B220+ cells in Peyer's patches when compared with those of the (+/+) mice. These results are indicative of an increase in activated T cells (TCRB+CD38+).

These results indicate that the knockout mice exhibited a decrease in a subset of B cells (pre-B cells, immature and mature B cells). Thus, the mutant homozygous mice exhibited immunological abnormalities associated with decreased levels of B cell progenitor cells. In addition, the knockout mice exhibit an increase in T cells.

These results show that knockout (−/−) mice exhibit immunological abnormalities compared to their wild-type (+/+) littermates. Antagonists (inhibitors) of PRO1481 polypeptides would be expected to mimic this phenotype. PRO1481 polypeptides or agonists thereof appear to act as a negative regulator of T cell production and a positive regulator of B cell development and would be useful in the development or maturation of B cells which could then participate in fast immune responses. Antagonists (inhibitors) of PRO1481 polypeptides would be useful in stimulating the production of T cells.

66.31. Generation and Analysis of Mice Comprising DNA68880-1676 (UNQ774) Gene Disruptions In these knockout experiments, the gene encoding PRO1568 polypeptides (designated as DNA68880-1676) (UNQ774) was disrupted. The gene specific information for these studies is as follows: the mutated mouse gene corresponds to nucleotide reference: NM_173007 *Mus musculus* transmembrane 4 superfamily member 12 (Tm4sf12); protein reference: Q8BKT6 ACCESSION:Q8BKT6 NID: *Mus musculus* (Mouse). *Mus musculus* 9 days embryo whole body cDNA, RIKEN full-length enriched library, clone: D030012P12 product:TETRASPAN NET-2 homolog (Tm4sf12 protein); the human gene sequence reference: NM_012338 ACCESSION:NM_012338 NID:21264567 *Homo sapiens Homo sapiens* transmembrane 4 superfamily member tetraspan NET-2 (NET-2); the human protein sequence corresponds to reference: O95859 ACCESSION: O95859 NID: *Homo sapiens* (Human). TETRASPAN NET-2.

The mouse gene of interest is Tm4sf12 (transmembrane 4 superfamily member 12), ortholog of human TM4SF12. Aliases include 9030619E17, EST AI426782, NET-2, and tetraspan NET-2.

TM4SF12 is a putative integral plasma membrane protein and subunit of larger cell surface complexes that likely function in cell adhesion and signal transduction. TM4SF12 is a member of the tetraspanin superfamily, containing four transmembrane segments within a tetraspanin family domain. Although the physiological role of TM4SF12 is not known, tetraspanins are involved in adhesion-dependent signaling mediated by integrins, generally playing a role in processes such as cell adhesion, migration, fertilization, immunity, development, and metastasis (Serru et al, *Biochim Biophys Acta* 1478(1):159-63 (2000); Berditchevski, *J Cell Sci* 114(Pt 23):4143-51 (2001); Tarrant et al, *Trends Immunol* 24(11): 610-7 (2003); Le Naour et al, *Cancer Immunol Immunother* 53(3): 148-52 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 20 | 36 | 25 | 81 |
| Expected | 20.25 | 40.5 | 20.25 | 81 |

Chi-Sq.=0.99 Significance=0.6095709 (hom/n)=0.26 Avg. Litter Size=8

Mutation Information

Mutation Type: Homologous Recombination (standard)

Coding exon 1 was targeted (NCBI accession NM_173007.1).

1. Wild-type Expression Panel: Expression of the target gene was detected in all 13 adult tissue samples tested by RT-PCR, except bone.

2. QC Expression: Disruption of the target gene was confirmed by Southern hybridization analysis.

66.31.1. Phenotypic Analysis (for Disrupted Gene: DNA68880-1676 (UNQ774)

(a) Overall Phenotypic Summary:

Mutation of the gene encoding the ortholog of human transmembrane 4 superfamily member 12 (TM4SF12) resulted in the homozygous mutant mice exhibited numerous ophthalmological abnormalities, including retinal microaneurysms and non-homogeneous retinal backgrounds. In addition, CAT-Scan analysis revealed moderate hydronephrosis in 2 of 3 homozygous mutants and 1 of 2 heterozygous mice analyzed. Disruption of the target gene was confirmed by Southern hybridization analysis.

(b) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

Fundus: The (−/−) mice exhibited unhealthy retinal beds with non-homogeneous backgrounds. Two (−/−) mice (M-79 and M-98) also exhibited white deposits above the retinal vessels that were approximately 2-3 times larger than the optic disc.

Angiogram: All 8 (−/−) mice exhibited multiple microaneurysms and leakage of the retinal capillaries bilaterally.

Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to ophthalmological disorders such as retinal degeneration. Thus, antagonists of PRO1568 encoding genes would lead to similar pathological retinal changes, whereas agonists may be useful as therapeutic agents in the treatment of hypertension, atherosclerosis or other opthamological disorders including retinal degeneration and diseases associated with this condition (as indicated above).

Subsequent studies showed a sprouting angiogenesis defect in the UNQ774 knockout retina specifically in the nerve fiber layer (NFL); inner plexiform layer (IPL); and in the outer plexiform layer (OPL) (thus a three layered organization of the retinal vasculature showed a defective angiogenesis (sprouts) when compared with the wildtype (+/+) and heterozygous (+/−) sections [wholemount isolectin staining of the retina, 10× confocal images].

(c) Pathology/CAT Scan

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

Among the 6 mice analyzed, 1 (+/−) mouse and 2 (−/−) mice exhibited moderate hydronephosis.

66.32. Generation and Analysis of Mice Comprising DNA73735-1681 (UNQ779) Gene Disruptions In these knockout experiments, the gene encoding PRO1573 polypeptides (designated as DNA73735-1681) (UNQ779) was disrupted. The gene specific information for these studies is as follows: the mutated mouse gene corresponds to nucleotide reference: NM_018778 *Mus musculus* claudin 8 (Cldn8); protein reference: Q9Z260 ACCESSION:

Q9Z260 NID: *Mus musculus* (Mouse). Claudin-8; the human gene sequence reference: NM_199328 *Homo sapiens* claudin 8 (CLDN8); the human protein sequence corresponds to reference: P56748 ACCESSION:P56748 NID: *Homo sapiens* (Human). Claudin-8.

The mouse gene of interest is Cldn8 (claudin 8), ortholog of human CLDN8.

CLDN8 is an integral plasma membrane protein that functions as an adhesion molecule and component of tight junctions. The protein consists of a single claudin family domain (Pfam accession PF00822), which contains 4 transmembrane segments. CLDN8 is expressed primarily in lung and kidney and is particularly concentrated at the tight junctions along the aldosterone-sensitive nephron. CLDN8 is likely to play a role in paracellular cationtransport and permeability (Yu et al, *J Biol Chem* 278(19):17350-9 (2003); Morita et al, *Proc Natl Acad Sci USA* 96(2):511-6 (1999); Heiskala et al, *Traffic* 2(2):93-8 (2001); Li et al, Am J Physiol Renal Physiol 286 (6):F1063-71 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 17 | 47 | 19 | 83 |
| Expected | 20.75 | 41.5 | 20.75 | 83 |

Chi-Sq.=2.58 Significance=0.2752708 (hom/n)=0.21 Avg. Litter Size=9

Mutation Information

Mutation Type: Homologous Recombination (standard)

Description: Coding exon 1 was targeted (NCBI accession NM_018778.2).

1. Wild-type Expression Panel: Expression of the target gene was detected in all 13 adult tissue samples tested by RT-PCR, except spleen, bone, heart, and adipose.

2. QC Expression: Disruption of the target gene was confirmed by Southern hybridization analysis.

66.32.1. Phenotypic Analysis (for Disrupted Gene: DNA73735-1681 (UNQ779)

(a) Overall Phenotypic Summary:

Mutation of the gene encoding the ortholog of human claudin 8 (CLDN8) resulted in a decreased startle reflex in the mutant (−/−) mice. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: The (−/−) mice exhibited a decreased startle response, suggesting a hearing impairment in the mutants.

66.33. Generation and Analysis of Mice Comprising DNA62845-1684 (UNQ782) Gene Disruptions In these knockout experiments, the gene encoding PRO1599 polypeptides (designated as DNA62845-1684) (UNQ782) was disrupted. The gene specific information for these studies is as follows: the mutated mouse gene corresponds to nucleotide reference: XM_196763 PREDICTED: *Mus musculus* RIKEN cDNA 2900092M14 gene (2900092M14Rik); protein reference: XP_196763 RIKEN cDNA 2900092M 14 *[Mus musculus]*; the human gene sequence reference: NM_214710 *Homo sapiens* protease, serine-like 1 (PRSSL1); the human protein sequence corresponds to reference: Q6UWY2 ACCESSION:Q6UWY2 NID: *Homo sapiens* (Human). GLGL782.

The mouse gene of interest is Prssl1 (protease, serine-like 1), ortholog of human PRSSL1. Aliases include UNQ782, GLGL782, and 2900092M14Rik.

PRSSL1 is a putative secreted protease, consisting of a signal peptide and a trypsin-like serine protease domain (SMART accession SM00020).

Unfortunately, another mammalian locus (KLK10, kallikrein 10, GeneID: 5655) has also been referred to as PRSSL1 in the scientific literature and sequence databases. The disrupted locus described herein is not KLK10, and represents another gene altogether. No published information concerning PRSSL1 (the gene of interest for this project) could be found at the time of this writing—thus all refers to KLK10. Therefore, care is required in interpreting the scientific literature as database sequences.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 33 | 24 | 80 |
| Expected | 20 | 40 | 20 | 80 |

Chi-Sq.=1.1 Significance=0.5769498 (hom/n)=0.28 Avg. Litter Size=10

Mutation Information

Mutation Type: Homologous Recombination (standard)

Description: Coding exons 2 and 3 were targeted (NCBI accession XM_196763.2).

1. Wild-type Expression Panel: Expression of the target gene was detected only in spinal cord, thymus, and spleen among the 13 adult tissue samples tested by RT-PCR.

2. QC Expression: Disruption of the target gene was confirmed by Southern hybridization analysis.

66.33.1. Phenotypic Analysis (for Disrupted Gene: DNA62845-1684 (UNQ782)

(a) Overall Phenotypic Summary:

Mutation of the gene encoding the ortholog of human protease, serine-like 1 (PRSSL1) resulted in immunological abnormalities in (−/−) mice. The homozygous mutant mice exhibited decreased mean percentages of CD8 and NK cells and an increased mean percentage of B cells in the peripheral blood. In addition, the mutants exhibited increased mean serum TNF-alpha and MCP-1 responses to LPS challenge and an increased mean serum IgG2a response to ovalbumin challenge when compared with those of their wild-type littermates and the historical means. The knockout mice also showed inflammation of several tissues. In addition, the mutant (−/−) mice showed signs of obesity with increased mean total mass, percent total body fat, and total fat mass. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

(1) Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19

FITC. The two FITC and PE labeled antibodies stain mutually exclusive cell types. The samples were analyzed using a Becton Dickinson FACSCalibur flow cytometer with CellQuest software.

Results:

FACS3: The (−/−) mice exhibited an altered distribution of leukocyte subsets in the peripheral blood, characterized by decreased mean percentages of CD8 and NK cells and an increased mean percentage of B cells when compared with their (+/+) littermates and the historical means.

In summary, FACS analysis of immune cell composition indicates that knockout (−/−) mice exhibit immunological differences with respect to both B cells and cytotoxic T cells (CD8—thymocyte subset which functions as a co-receptor for MHC class I molecules). Inhibitors or antagonists of PRO1599 would be useful in B cell production, whereas PRO1599 polypeptides would be expected to lead to the opposite effects. On the other hand, PRO1599 polypeptides appear to function as a positive regulator of CD8 and NK cells (the FACS results indicate that the homozygous mutant mice have a decreased mean percentage of both CD8 and natural killer cells). Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. Thus, PRO1599 polypeptides or agonists thereof would be useful in the production of cytotoxic T cells and NK cells important for antibody dependent cell-mediated cytotoxicity.

(2) Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sub-lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

Acute Phase Response: The (−/−) mice exhibited increased mean serum TNF-alpha and MCP-1 responses to LPS challenge when compared with their gender-matched (+/+) littermates and the historical means.

In summary, the LPS endotoxin challenge demonstrated that knockout mice deficient in the gene encoding PRO1599 polypeptides exhibit immunological abnormalities when compared with their wild-type littermates. In particular, the mutant mice exhibited an increased ability to elicit an immunological response (TNF-alpha and MCP-1 production) when challenged with the LPS endotoxin indicating a pro-inflammatory response. TNF-alpha and MCP-1 contribute to the later stages of B cell activation. This suggests that inhibitors or antagonists to PRO1599 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1599 polypeptides or agonists thereof would be useful in inhibiting the immune response and would be useful candidates for suppressing harmful immune responses, e.g. in the case of graft rejection or graft-versus-host diseases.

(3) Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Feund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

Ovalbumin: The (−/−) mice exhibited an increased mean serum IgG2a response to ovalbumin challenge when compared with that of their (+/+) littermates and the historical mean.

In summary, the ovalbumin challenge studies indicate that knockout mice deficient in the gene encoding PRO1599 polypeptides exhibit immunological abnormalities when compared with their wild-type littermates. In particular, the mutant mice exhibited an increased ability to elicit an immunological response when challenged with the T-cell dependent OVA antigen. Thus, antagonists (inhibitors) of PRO1599 polypeptides would be useful for stimulating the immune system and would find utility in the cases wherein this effect would be beneficial to the individual such as in the case of leukemia, and other types of cancer, and in immunocompromised patients, such as AIDS sufferers. Accordingly, PRO1599 polypeptides or agonists thereof, would be useful for inhibiting the immune response and thus would be useful candidates for suppressing harmful immune responses, e.g. in the case of graft rejection or graft-versus-host diseases or autoimmune disease.

(c) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited increased mean total tissue mass, percent total body fat, and total fat mass when compared with their gender-matched (+/+) littermates and the historical means.

These studies suggest that mutant (−/−) non-human transgenic animals exhibit a negative phenotype that would be associated with obesity. Thus, PRO1599 polypeptides or agonists thereof are essential for normal growth and metabolic processes and especially would be important in the prevention and/or treatment of lipid storage diseases and/or obesity.

66.34. Generation and Analysis of Mice Comprising DNA71286-1687 (UNQ785) Gene Disruptions In these knockout experiments, the gene encoding PRO1604 polypeptides (designated as DNA71286-1687) (UNQ785) was disrupted. The gene specific information for these studies is as follows: the mutated mouse gene corresponds to nucleotide reference: NM_008233 ACCESSION: NM_008233 NID:6680200 *Mus musculus Mus musculus* hepatoma-derived growth factor, related protein 2 (Hdgfrp2); protein reference: O35540 O35540 O35540 HEPATOMA-DERIVED GROWTH FACTOR; the human gene sequence reference: NM_032631 *Homo sapiens* hepatoma-derived growth factor-related protein 2 (HDGF2), transcript variant 2; the human protein sequence corresponds to reference: Q9BW08 ACCESSION:Q9BW08 NID: *Homo sapiens* (Human). Similar to hepatoma-derived growth factor, related protein 2.

The mouse gene of interest is Hdgfrp2 (hepatoma-derived growth factor, related protein 2), ortholog of human HDGF2. Aliases include MGC2641, hepatoma-derived growth factor 2, and HRP-2.

HDGF2 is a putative nuclear protein expressed primarily in testis and skeletal muscle. The protein contains a PWWP domain and a bipartite nuclear localization signal. PWWP domains are typically found in nuclear proteins and are likely involved in protein-protein interactions. HDGF2 is structurally similar to hepatoma-derived growth factor (HDGF), a nuclear protein that stimulates DNA synthesis and cell proliferation when over-expressed in cell lines or when applied exogenously to cells. The apparent mitogenic activity of HDGF is dependent on its ability to enter the nucleus (Izumoto et al, *Biochem Biophys Res Commun* 238(1):26-32 (1997); Kishima et al, *J Biol Chem* 277(12):10315-22 (2002)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 20 | 36 | 17 | 73 |
| Expected | 18.25 | 36.5 | 18.25 | 73 |

Chi-Sq.=7.54 Significance=0.023052063 (hom/n)=0.18 Avg. Litter Size=9

Mutation Information

Mutation Type: Homologous Recombination (standard)

Description: Coding exons 1 through 3 were targeted (NCBI accession NM_008233.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.34.1. Phenotypic Analysis (for Disrupted Gene: DNA71286-1687 (UNQ785)

(a) Overall Phenotypic Summary:

Mutation of the gene encoding the ortholog of human hepatoma-derived growth factor, related protein 2 (HDGF2) resulted in the homozygous mutant mice exhibiting increased mean serum alkaline phosphatase levels when compared with that of their wild-type littermates and the historical means. During circadian testing, the mutant (−/−) mice exhibited hyperactivity during all light and dark periods. In addition, the female mutants exhibited a decreased mean skin fibroblast proliferation rate. Male (−/−) mice exhibited decreased bone mineral content and density measurements. Disruption of the target gene was confirmed by Southern hybridization analysis.

(b) Phenotypic Analysis: Metabolism-Blood Chemistry

In the area of metabolism, targets may be identified for the treatment of metabolic disorders. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride.

Results:

Both the male and female (−/−) mice exhibited increased mean serum alkaline phosphatase levels when compared with that of their gender-matched (+/+) littermates and the historical means. This result is most likely due to changes in the liver.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

The female (−/−) mice exhibited increased ambulatory counts (hyperactivity) during the 12-hour habituation and all light and dark periods of home-cage activity testing when compared with their gender-matched (+/+) littermates and the historical mean. These results demonstrate an enhanced circadian rhythm. Home-cage activity testing is also suggestive of increased activity or hyperactivity which is consistent with generalized anxiety disorders, attention deficit hyperactivity disorder, obsessive compulsive disorder, schizophrenia, cognitive disorders, and sensory disorders.

(d) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

The female (−/−) mice exhibited a decreased mean skin fibroblast proliferation rate when compared with their gender-matched (+/+) littermates.

Thus, homozygous mutant mice demonstrated a hypo-proliferative phenotype. As suggested by these observations, antagonists or inhibitors of PRO1604 polypeptides would mimic this hypo-proliferative phenotype and could function as tumor suppressors and would be useful in decreasing abnormal cell proliferation.

(e) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone Microct Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice seemed to show a trend for decreased bone mineral content and vertebrae bone mineral density as well as total body and femur bone mineral density when compared with the values for their gender-matched (+/+) littermates and the historical means.

MicroCT: The male knockouts seemed to show a trend for decreased trabecular thickness and connectivity density as well as midshaft femur total area when compared with that of their gender-matched (+/+) littermates and the historical mean. Both the DEXA and MicroCT results are barely 1 SD below the median.

66.35. Generation and Analysis of Mice Comprising DNA77648-1688 (UNQ786) Gene Disruptions In these knockout experiments, the gene encoding PRO1605 polypeptides (designated as DNA77648-1688) (UNQ786) was disrupted. The gene specific information for these studies is as follows: the mutated mouse gene corresponds to nucleotide reference: NM_175098 *Mus musculus* RIKEN cDNA 6330407D12 gene (6330407D12Rik); protein reference: Q8BIS8 ACCESSION:Q8BIS8 NID: *Mus musculus* (Mouse). *Mus musculus* adult male medulla oblongata cDNA, RIKEN full-length enriched library, clone: 6330407D12 product:weakly similar to N-ACETYLGLU- COSAMINYLTRANSFERASE; the human gene sequence reference: NM_138771 ACCESSION:NM_138771 NID: gi 20270308 ref NM_138771.1 *Homo sapiens* alpha-1,3(6)-mannosylglycoprotein beta-1,6-N-acetyl-glucosaminyl-transferase-like (LOC90693); the human protein sequence corresponds to reference: Q96EE4 ACCESSION:Q96EE4 NID: *Homo sapiens* (Human). Hypothetical protein.

The mouse gene of interest is RIKEN cDNA 6330407D12 gene, ortholog of human alpha-1,3(6)-mannosylglycoprotein beta-1,6-N-acetyl-glucosaminyltransferase-like. Aliases include EST AA675040.

The hypothetical protein of 140 amino acids, which consists of a signal peptide and no other conserved domain, is predicted to be located in the Golgi apparatus or in the extracellular space (secreted). The protein is structurally related to N-terminal segments of MGAT5 (mannosyl [alpha-1,6-]-glycoprotein beta-1,6-N-acetyl-glucosaminyltransferase) and MGAT5B (mannosyl [alpha-1,6-]-glycoprotein beta-1,6-N-acetyl-glucosaminyltransferase, isoenzyme B), glycosyltransferases of approximately 750 amino acids that catalyze glycoproteinoligosaccharide biosynthesis. MGAT5 is located in the membrane of the Golgi apparatus and is also secreted. Secreted MGAT5 is likely to release fibroblast growth factor from heparan sulfate proteoglycans by a mechanism independent of glycosylation, enabling FGF-2 to activate its receptor on target cells (Saito et al, *J Biol Chem* 277(19):17002-8 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 14 | 50 | 26 | 90 |
| Expected | 22.5 | 45 | 22.5 | 90 |

Chi-Sq.=1.3 Significance=0.5220458 (hom/n)=0.27 Avg. Litter Size=9

Mutation Information

Mutation Type: Homologous Recombination (standard)

Description: The first coding exon was targeted (NM_175098.2).

1. Wild-type Expression Panel: Expression of the target gene was detected in embryonic stem (ES) cells and in all 13 adult tissue samples tested by RT-PCR, except skeletal muscle and bone.

2. QC Expression: Disruption of the target gene was confirmed by Southern hybridization analysis.

66.35.1. Phenotypic Analysis (for Disrupted Gene: DNA77648-1688 (UNQ786)

(a) Overall Phenotypic Summary:

Mutation of the gene encoding the ortholog of human alpha-1,3(6)-mannosylglycoprotein beta-1,6-N-acetyl-glucosaminyl transferase-like resulted in the mutant (−/−) mice exhibiting increased triglyceride levels. Four of the (−/−) mice exhibited an increased intra-cytoplasmic vacuolization of glycogen in hepatocytes. Gene disruption was confirmed by Southern blot.

(b) Pathology

Microscopic: Among the 6 (−/−) mice analyzed, 4 exhibited moderately increased intra-cytoplasmic vacuolization of glycogen in hepatocytes.

Gene Expression: LacZ activity was not detected in the panel of tissues by immunohistochemical analysis.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) mice exhibited increased mean serum triglyceride levels when compared with their gender-matched (+/+) littermates and the historical means.

As summarized above, the (−/−) mice exhibited increased mean serum triglyceride levels when compared with their gender-matched (+/+) littermates and the historical means. Thus, mutant mice deficient in the PRO1605 gene can serve as a model for cardiovascular disease. PRO1605 polypeptides or its encoding gene would be useful in regulating blood lipids such as triglycerides. Thus, PRO1605 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

66.36. Generation and Analysis of Mice Comprising DNA77301-1708 (UNQ803) Gene Disruptions In these knockout experiments, the gene encoding PRO1693 polypeptides (designated as DNA77301-1708) (UNQ803) was disrupted. The gene specific information for these studies is as follows: the mutated mouse gene corresponds to nucleotide reference: NM_178678 *Mus musculus* leucine rich repeat transmembrane neuronal 3 (Lrrtm3); protein reference: Q8BGJ7 ACCESSION:Q8BGJ7 NID: *Mus musculus* (Mouse). *Mus musculus* 16 days neonate cerebellum cDNA, RIKEN full-length enriched library, clone: 9630003D05 product:hypothetical Leucine-rich repeat, typical subtype containing protein, full insert sequence; the human gene sequence reference: NM_178011 *Homo sapiens* leucine rich repeat transmembrane neuronal 3 (LRRTM3); the human protein sequence corresponds to reference: Q86VH5 ACCESSION:Q86VH5 NID: *Homo sapiens* (Human). Leucine-rich repeat transmembrane neuronal 3 protein (GFNV803).

The mouse gene of interest is Lrrtm3 (leucine rich repeat transmembrane neuronal 3), ortholog of human LRRTM3.

Aliases include 9630044H04Rik and leucine-rich repeat transmembrane neuronal 3 protein.

LRRTM3 is a putative integral plasma membrane protein, consisting of a signal peptide, several leucine-rich repeats, a transmembrane segment, and a potential cytoplasmic C-terminal domain. The protein is expressed primarily in the nervous system of vertebrates. LRRTM3 may function as a cell adhesion molecule or signal-transducing receptor, possibly playing a role in development and maintenance of the nervous system (Lauren et al, *Genomics* 81(4):411-21 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 24 | 25 | 15 | 64 |
| Expected | 16 | 32 | 16 | 64 |

Chi-Sq.=0.15 Significance=0.9277435 (hom/n)=0.25 Avg. Litter Size=9

Mutation Information

Mutation Type: Homologous Recombination (standard)

Description: Coding exon 2 was targeted (NCBI accession NM_178678.2).

1. Wild-type Expression Panel: Expression of the target gene was detected only in brain, spinal cord, and eye among the 13 adult tissue samples tested by RT-PCR.

2. QC Expression: Disruption of the target gene was confirmed by Southern hybridization analysis.

66.36.1. Phenotypic Analysis (for Disrupted Gene: DNA77301-1708 (UNQ803)

(a) Overall Phenotypic Summary:

Mutation of the gene encoding the ortholog of human leucine rich repeat transmembrane neuronal 3 (LRRTM3) resulted in the homozygous mutant mice exhibiting an increased mean absolute neutrophil count when compared with the levels for their wild-type littermates and the historical means. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited an increased mean absolute neutrophil count when compared with that of their (+/+) littermates and the historical mean.

These results indicate that mutant (−/−) mice exhibit immunological abnormalities compared with their wildtype littermates. In summary, the hematology results indicate that the homozygous mutant mice exhibited increased neutrophils indicating elevated levels of precursors of macrophages with increased phagocytic activity or ability to engulf or kill extracellular pathogens.

66.37. Generation and Analysis of Mice Comprising DNA68883-1691 (UNQ826) Gene Disruptions In these knockout experiments, the gene encoding PRO1753 polypeptides (designated as DNA68883-1691)

(UNQ826) was disrupted. The gene specific information for these studies is as follows: the mutated mouse gene corresponds to nucleotide reference: NM_010959 *Mus musculus* oncoprotein induced transcript 3 (Oit3); protein reference: Q8C9U1 ACCESSION:Q8C9U1 NID: *Mus musculus* (Mouse). *Mus musculus* 0 day neonate thymus cDNA, RIKEN full-length enriched library, clone: A430107A04 product: ALC homolog; the human gene sequence reference: NM_152635 *Homo sapiens* oncoprotein induced transcript 3 (OIT3); the human protein sequence corresponds to reference: Q8WWZ8 ACCESSION:Q8WWZ8 NID: *Homo sapiens* (Human). LZP (Hypothetical protein FLJ39116) (PPFL826).

The mouse gene of interest is Oit3 (oncoprotein induced transcript 3), ortholog of human OIT3. Aliases include LZP, EF-9, FLJ39116, and liver-specific ZP domain-containing protein.

OIT3 is a putative secreted protein expressed primarily in liver. The protein contains a signal peptide, three tandem epidermal growth factor-like domains, and a novel zona pellucida domain. Although a truncated form of the protein can be detected in blood, OIT3 is located mainly on the nuclear envelope of hepatocytes. OIT3 gene is activated by oncoprotein E2a-Pbx1 in NIH 3T3 fibroblasts but is rarely expressed in hepatocellular carcinoma, suggesting that OIT3 may be a useful negative marker for hepatocellular carcinoma. The biological role of OIT3 is not known (Fu and Kamp, *Mol Cell Biol* 17(3):1503-12 (1997); Xu et al, *Hepatology* 38(3):735-44 (2003); Xu et al, *DNA Seq* 15(2):81-7 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 19 | 41 | 15 | 75 |
| Expected | 18.75 | 37.5 | 18.75 | 75 |

Chi-Sq.=5.82 Significance=0.054475725 (hom/n)=0.2 Avg. Litter Size=10

Mutation Information

Mutation Type: Homologous Recombination (standard)

Description: Coding exons 1 and 2 were targeted (NCBI accession NM_010959.1).

1. Wild-type Expression Panel: Expression of the target gene was detected in all 13 adult tissue samples tested by RT-PCR, except adipose.

2. QC Expression: Disruption of the target gene was confirmed by Southern hybridization analysis.

66.37.1. Phenotypic Analysis (for Disrupted Gene: DNA68883-1691 (UNQ826)

(a) Overall Phenotypic Summary:

Mutation of the gene encoding the ortholog of human oncoprotein induced transcript 3 (OIT3) resulted in the male homozygous mutant mice exhibiting an increased anxiety-like response during open field testing when compared with their gender-matched wild-type littermates and the historical mean. In addition, tissue specific FACS revealed an immunological alteration in the mutant (−/−) mice marked by decreased percentage of B220hiCD43−, IgM+, and IgD+. Female (−/−) mice exhibited decreased bone mineral content and bone mineral density measurements. UNQ826 shows high expression in both normal and diseased liver tissue. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Flourescence-Activated Cell-Sorting (FACS) Analysis/Tissue Specific FACS

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

Tissue Specific FACS-Project: The (−/−) mice exhibited a decreased percentage of B220hiCD43−, IgM+, and IgD+ cells in bone marrow when compared with that of their (+/+) littermates. These results are indicative of a decrease in the bone marrow of a subset of pre-B, immature and mature B cells. Thus, PRO1753 polypeptides are important in the development of B cell population in the bone marrow and would be useful in stimulating B cell production.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

Openfield2: The male (−/−) mice exhibited decreased median sum time-in-center when compared with their gender-matched (+/+) littermates and the historical mean, suggesting an increased anxiety-like response in the mutants. In addition, whiskers were absent in 2 of 8 (+/+) wild-type mice and 6 of 8 (−/−) knockout mice. Knockout mice with absent whiskers at increased frequency is probably related to the anxiety phenotype.

In summary, the open field testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO1753 polypeptides or agonists thereof would be useful in the treatment of such neurological disorders.

(d) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA:

The female (−/−) mice exhibited decreased mean bone mineral content and bone mineral density in total body and vertebrae when compared with their gender-matched (+/+) littermates and the historical means.

Thus, mutant (−/−) mice deficient in the gene encoding PRO1753 polypeptides show a phenotype consistent with osteoporosis marked by decreased bone mineral content and density measurements. Thus, antagonists or inhibitors of PRO1753 polypeptides or its encoding gene would mimic these abnormal metabolic related effects. On the other hand, PRO1753 polypeptides or agonists thereof would be useful in the prevention and/or treatment of bone disorders associated with bone loss.

66.38. Generation and Analysis of Mice Comprising DNA76396-1698 (UNQ828) Gene Disruptions In these knockout experiments, the gene encoding PRO1755 polypeptides (designated as DNA76396-1698) (UNQ828) was disrupted. The gene specific information for these studies is as follows: the mutated mouse gene corresponds to nucleotide reference: NM_175696 *Mus musculus* RIKEN cDNA C530028021 gene (C530028O21Rik); protein reference: Q6P1B3 ACCESSION:Q6P1B3 NID: *Mus musculus* (Mouse). C530028O21Rik protein; the human gene sequence reference: NM_153685 *Homo sapiens* hypothetical protein DKFZp547D2210 (DKFZp547D2210); the human protein sequence corresponds to reference: Q8IYJ0 ACCESSION:Q8IYJ0 NID: *Homo sapiens* (Human). Hypothetical protein DKFZp547D2210.

The mouse gene of interest is RIKEN cDNA C530028021 gene, ortholog of human hypothetical protein DKFZp547D2210. Aliases include EST A1255183 and DKFZp547D2210.

Hypothetical protein DKFZp547D2210 is a likely type I integral membrane protein, consisting of a signal peptide and a transmembrane domain. The function of this protein is not known, and its predicted cell location is ambiguous.

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 33 | 16 | 65 |
| Expected | 16.25 | 32.5 | 16.25 | 65 |

Chi-Sq.=0.09 Significance=0.95599747 (hom/n)=0.26 Avg. Litter Size=8

Mutation Information

Mutation Type: Homologous Recombination (standard)

Description: Coding exons 1 through 4 were targeted (NCBI accession NM_175696.2).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.38.1. Phenotypic Analysis (for Disrupted Gene: DNA76396-1698 (UNQ828)

(a) Overall Phenotypic Summary:

Mutation of the gene encoding the ortholog of a human hypothetical membrane protein resulted in an the female homozygous mutant mice exhibiting an increased mean skin fibroblast proliferation rate when compared with that of their gender-matched wild-type littermates and the historical mean. In addition, the male (−/−) mice showed an impaired glucose tolerance. The (−/−) mice also exhibited decreased mean serum IgG1 levels. UNQ828 is highly expressed in the CNS compared to other normal tissues. The endothelium also shows moderately high expression. Disruption of the target gene was confirmed by Southern hybridization analysis.

(b) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

Oral Glucose Tolerance: The male (−/−) mice exhibited a modestly impaired glucose tolerance when compared with that of their gender-matched (+/+) littermates and the historical mean.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO1755 polypeptides (or agonists thereof) or its encoding gene would be useful in the treatment of conditions associated with an impaired glucose homeostasis and/or various cardiovascular diseases, including diabetes.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited a decreased mean serum IgG1 level when compared with that of their (+/+) littermates, the (+/+) mice for the project run, and the historical median.

Thus, mutant (−/−) mice showed decreased IgG1 serum immunoglobulins compared to their gender-matched (+/+) littermates. These immunoglobulins have neutralization effects and to a lesser extent are important for activation of the complement system. The observed phenotype suggests that the PRO1755 polypeptide is a regulator of inflammatory responses. Thus, the gene encoding PRO1755 polypeptides is essential for making IgG1 immunoglobulins (or gamma globulins). These immunological abnormalities suggest that PRO1755 polypeptides may be important agents which could stimulate the immune system and would find utility in the cases wherein this effect would be beneficial to the individual such as in the case of leukemia, and other types of cancer, and in immunocompromised patients, such as AIDS sufferers. Accordingly, antagonists (inhibitors) of PRO1755 polypeptides can play a role in inhibiting the immune response and would be useful candidates for suppressing harmful immune responses, e.g. in the case of graft rejection or graft-versus-host diseases.

(d) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

Skin Proliferation: The female (−/−) mice exhibited an increased mean skin fibroblast proliferation rate when compared with that of their gender-matched (+/+) littermates and the historical mean. Two out of the four (−/−) mice showed significantly increased proliferation.

Thus, homozygous mutant mice demonstrated a hyper-proliferative phenotype. As suggested by these observations, PRO1755 polypeptides or agonists thereof could function as tumor suppressors and would be useful in decreasing abnormal cell proliferation.

66.39. Generation and Analysis of Mice Comprising DNA71235-1706 (UNQ839) Gene Disruptions In these knockout experiments, the gene encoding PRO1777 polypeptides (designated as DNA71235-1706) (UNQ839) was disrupted. The gene specific information for these studies is as follows: the mutated mouse gene corresponds to nucleotide reference: NM_028710 *Mus musculus* RIKEN cDNA 6330406P08 gene (6330406P08Rik); protein reference: Q9D3B4 ACCESSION:Q9D3B4 NID: *Mus musculus* (Mouse) 6330406P08RIK PROTEIN; the human gene sequence reference: NM_014960 *Homo sapiens* Arylsulfatase G (KIAA1001); the human protein sequence corresponds to reference: Q96EG1 ACCESSION:Q96EG1 NID: *Homo sapiens* (Human). Arylsulfatase G.

The mouse gene of interest is RIKEN cDNA 6330406P08 gene, ortholog of human ARSG (Arylsulfatase G). Aliases include KIAA1001.

ARSG is an enzyme that likely catalyzes the hydrolysis of arylsulfoester bonds. The location of this enzyme is not clearly known. Bioinformatic analyses of ARSG suggest that the enzyme may be located in lysosomes or may be secreted. ARSG expressed in COS7 cells is located in the endoplasmic reticulum (Ferrante et al, *Eur J Hum Genet* 10(12):813-8 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 12 | 33 | 12 | 57 |
| Expected | 14.25 | 28.5 | 14.25 | 57 |

Chi-Sq.=0.01 Significance=0.99501246 (hom/n)=0.25 Avg. Litter Size=8

Mutation Information

Mutation Type: Homologous Recombination (standard)

Description: Coding exon 1 was targeted (NCBI accession NM_028710.2).

1. Wild-type Expression Panel: Expression of the target gene was detected in embryonic stem (ES) cells and in all 13 adult tissue samples tested by RT-PCR, except skeletal muscle, bone, and adipose.

2. QC Expression: Disruption of the target gene was confirmed by Southern hybridization analysis.

66.39.1. Phenotypic Analysis (for Disrupted Gene: DNA71235-1706 (UNQ839)

(a) Overall Phenotypic Summary:

Mutation of the gene encoding the ortholog of human Arylsulfatase G (ARSG) resulted in immunological abnormalities in (−/−) mice. The homozygous mutant mice exhibited a decreased mean percentage of natural killer cells in the peripheral blood and an increased mean serum IgG3 level when compared with the levels for their wild-type littermates and the historical means. The female mutants also exhibited a decreased mean skin fibroblast proliferation rate. The male (−/−) mice also exhibited an increased mean percent total body fat mass and decreased mean bone mineral density-related measurements. Micro-CT results showed a decreased mean femoral mid-shaft cross-sectional area. The female (−/−) mice exhibited an increased median ambulatory counts during home cage testing indicating an enhanced circadian rhythm. Disruption of the target gene was confirmed by Southern hybridization analysis.

(b) Microarray Analysis

Microarray analysis shows UNQ839 being highly overexpressed in breast tumors compared to normal breast tissue.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

(1) Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS: The (−/−) mice exhibited an altered distribution of different leukocyte subsets, characterized by a decreased mean percentage of natural killer cells in the peripheral blood when compared with their wild-type littermates and the historical mean.

In summary, the FACS results indicate that the homozygous mutant mice have an impaired immune system, especially in view of the decreased mean percentage of natural killer cells which is an indicator of a negative phenotype associated with knocking out the DNA71235-1706 gene which encodes PRO1777 polypeptides. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses. Thus, PRO1777 polypeptides and agonists thereof would be important for a healthy immune system and would be useful in stimulating the immune system particularly during viral infections.

(2) Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value $<6$ is not significant.

Results:

Serum Imm. 2: The (−/−) mice exhibited an increased mean serum IgG3 level when compared with that of their (+/+) littermates, the (+/+) mice for the project run, and the historical median.

The serum immunoglobulin isotyping assay revealed that homozygous adults exhibited increased serum IgG3 levels. Thus, homozygotes showed elevated serum immunoglobulins compared with the (+/+) littermates. IgG3 immunoglobulins have neutralization effects and to a lesser extent are important for activation of the complement system. These immunological abnormalities suggest that antagonists or inhibitors of PRO1777 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1777 polypeptides or agonists thereof would inhibit the immune response and would be useful candidates for suppressing harmful immune responses, e.g. in the case of graft rejection or graft-versus-host diseases.

(d) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

Skin Proliferation: The female (−/−) mice exhibited a decreased mean skin fibroblast proliferation rate when compared with that of their gender-matched (+/+) littermates and the historical mean.

Thus, homozygous mutant mice demonstrated a hypo-proliferative phenotype. As suggested by these observations, antagonists or inhibitors of PRO1777 polypeptides would mimic this hypo-proliferative phenotype and could function as tumor suppressors and would be useful in decreasing abnormal cell proliferation. These results are consistent with the microarray data showing overexpression of this gene in breast tumors.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The female (−/−) mice exhibited a notably increased median ambulatory counts during both dark periods when compared with the number for their gender-matched (+/+) littermates and the historical means.

These results demonstrate an enhanced circadian rhythm. Home-cage activity testing is also suggestive of increased activity or hyperactivity which is consistent with generalized anxiety disorders, attention deficit hyperactivity disorder, obsessive compulsive disorder, schizophrenia, cognitive disorders, and sensory disorders.

(f) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured. The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [ i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean bone mineral density-related measurements with decreased bone mineral content and mean bone mineral density when compared with those of their gender-matched (+/+) littermates and the historical means.

Micro CT: The male (−/−) mice also exhibited decreased mean femoral mid-shaft cross-sectional area when compared with that of their gender-matched (+/+) littermates and the historical mean.

These results demonstrate that knockout mutant mice exhibit abnormal bone metabolism with decreased bone measurements similar to osteoporosis characterized by decrease in bone mass with decreased density and possibly fragility leading to bone fractures. Thus, it appears that PRO1777 polypeptides or agonists thereof would be useful in maintaining bone homeostasis. In addition, PRO1777 polypeptides or its encoding gene would be useful in bone healing or for the treatment of arthritis or osteoporosis; whereas antagonists to PRO1777 polypeptides or its encoding gene would lead to abnormal or pathological bone disorders including arthritis, osteoporosis, and osteopenia.

The male (−/−) mice also exhibited increased mean percent total body fat and total fat mass when compared with their gender-matched (+/+) littermates and the historical means.

These studies suggest that mutant (−/−) non-human transgenic animals exhibit a negative phenotype that would be associated with obesity. Pathological observations are consistent with the radiological findings. Thus, PRO1777 polypeptides or agonists thereof are essential for normal growth and metabolic processes and especially would be important in the prevention and/or treatment of lipid storage diseases and/or obesity.

66.40. Generation and Analysis of Mice Comprising DNA77652-2505 (UNQ850) Gene Disruptions In these knockout experiments, the gene encoding PRO1788 polypeptides (designated as DNA77652-2505) (UNQ850) was disrupted. The gene specific information for these studies is as follows: the mutated mouse gene corresponds to nucleotide reference: XM_485965 PREDICTED: *Mus musculus RIKEN cDNA* 9530051K01 gene (9530051K01Rik); protein reference: XP_485965 similar to hypothetical protein, estradiol-induced [*Mus musculus*]; the human gene sequence reference: NM_015516 *Homo sapiens* hypothetical protein, estradiol-induced (E21G4); the human protein sequence corresponds to reference: Q9UJX9 ACCESSION:Q9UJX9 NID: *Homo sapiens* (Human). E21G4.

The mouse gene of interest is RIKEN cDNA 9530051K01 gene, ortholog of human TSK (likely ortholog of chicken tsukushi). Aliases include E21G4.

TSK is a secreted protein, consisting of a signal peptide, a leucine-rich repeat N-terminal domain, and several leucine-rich repeats. TSK binds with bone morphogenic protein or chordin to form a ternary complex and inhibits BMP-induced Hensen's node formation during gastrulation. TSK likely plays a role in dorsalization during embryonic development (Ohta et al, *Dev Cell* 7(3):347-58 (2004)). TSK is also expressed in estrogen-responsive breast cancer cells and is proposed to play a role in breast tissue remodeling or epithelium-stroma interactions (Charpaentier et al, *Cancer Res* 60(21):5977-83 (2000)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 42 | 26 | 89 |
| Expected | 22.25 | 44.5 | 22.25 | 89 |

Chi-Sq.=0.78 Significance=0.6770569 (hom/n)=0.27 Avg. Litter Size=10

Mutation Information

Mutation Type: Homologous Recombination (standard)

Coding exon 2 was targeted (NCBI accession AK035461.1).

1. Wild-type Expression Panel: Expression of the target gene was detected in embryonic stem (ES) cells and in spleen; liver; skeletal muscle; stomach, small intestine, and colon; heart; and adipose among the 13 adult tissue samples tested by RT-PCR.

2. QC Expression: Disruption of the target gene was confirmed by Southern hybridization analysis.

66.40.1. Phenotypic Analysis (for Disrupted Gene: DNA77652-2505 (UNQ850)

(a) Overall Phenotypic Summary:

Mutation of the gene encoding the ortholog of human likely ortholog of chicken tsukushi (TSK) resulted in the mutant (−/−) mice exhibiting increased mean serum IgM levels. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited an increased mean serum IgM level when compared with that of their (+/+) littermates, the (+/+) mice for the project run, and the historical median.

Mutant (−/−) mice exhibited elevation of IgM serum immunoglobulins compared to their gender-matched (+/+)

littermates. IgM immunoglobulins are the first to be produced in a humoral immune response for neutralization of bacterial toxins and are particularly important in activating the complement system. The observed phenotype suggests that the PRO1788 polypeptide is a negative regulator of inflammatory responses. These immunological abnormalities suggest that inhibitors (antagonists) of PRO1788 polypeptides would be important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO1788 polypeptides or agonists thereof would be useful in inhibiting the immune response and would be useful candidates for suppressing harmful immune responses, e.g. in the case of graft rejection or graft-versus-host diseases.

66.41. Generation and Analysis of Mice Comprising DNA45409-2511 (UNQ855) Gene Disruptions In these knockout experiments, the gene encoding PRO1864 polypeptides (designated as DNA45409-2511) (UNQ855) was disrupted. The gene specific information for these studies is as follows: the mutated mouse gene corresponds to nucleotide reference: NM_024270 *Mus musculus STARD*3 N-terminal like (Stard3nl); protein reference: Q9DCI3 ACCESSION:Q9DCI3 NID: *Mus musculus* (Mouse). MLN64 N-terminal domain homolog (STARD3 N-terminal like protein); the human gene sequence reference: NM_032016 *Homo sapiens* STARD3 N-terminal like (STARD3NL); the human protein sequence corresponds to reference: O95772 ACCESSION:095772 NID: *Homo sapiens* (Human). H_NH1021A08.1 PROTEIN (UNKNOWN) (PROTEIN FOR MGC: 14607) (SIMILAR TO STEROIDOGENIC ACUTE REGULATORY PROTEIN RELATED). The mouse gene of interest is Stard3nl (STARD3 N-terminal like), ortholog of human STARD3NL. Aliases include MENTHO, 0610035N01Rik, 6530409L22Rik, MGC3251, and MLN64 N-terminal domain homolog. STARD3NL is a ubiquitously expressed integral membrane protein located primarily on late endosomes. Bioinformatic analyses suggest that STARD3NL may also be an extracellular protein. STARD3NL consists of four transmembrane segments within a MENTAL (MLN64 N-terminal) domain, which is involved in targeting and anchoring proteins to late endosomes. STARD3NL is likely to play a role in endosomal transport (Alpy et al, *J Biol Chem* 277(52): 50780-7 (2002); Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 15 | 35 | 24 | 74 |
| Expected | 18.5 | 37 | 18.5 | 74 |

Chi-Sq.=2.82 Significance=0.24414329 (hom/n)=0.3 Avg. Litter Size=9

Mutation Information

Mutation Type: Homologous Recombination (standard)

Description: Coding exon 1 was targeted (NCBI accession NM_024270.1).

1. Wild-type Expression Panel: Expression of the target gene was detected in embryonic stem (ES) cells and in all 13 adult tissue samples tested by RT-PCR, except bone.

2. QC Expression: Disruption of the target gene was confirmed by Southern hybridization analysis.

66.41.1. Phenotypic Analysis (for Disrupted Gene: DNA45409-2511 (UNQ855)

(a) Overall Phenotypic Summary:

Mutation of the gene encoding the ortholog of human STARD3 N-terminal like (STARD3NL) resulted in the mutant (−/−) mice exhibiting hydronephrosis. Whiskers were absent in 4 of 8 (+/+) mice and 5 of 8 (−/−) mice; defecation was absent in 4 of 8 (+/+) mice and 5 of 8 (−/−) mice. Blood chemistry results showed abnormal levels of urobilinogen, nitrites, protein and ketone bodies in (+/+), (+/−) and (−/−) mice. Gene disruption was confirmed by Southern blot.

(b) CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

Of the three (−/−) mice examined, two (−/−) [M-226 and F-180] exhibited hydronephosis. Hydronephosis is a condition wherein there is cystic distension of the kidney caused by an accumulation of urine in the kidney pelvis as a result of obstruction to outflow and is accompanied by atrophy of the kidney structure and cyst formation. Therefore, deletion of the gene encoding PRO1864 polypeptides causes atrophy of the kidneys and cyst formation.

(c) Phenotypic Analysis: Metabolism-Blood Chemistry

In the area of metabolism, targets may be identified for the treatment of diabetes or other metabolic disorders. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes.

Results:

Blood chemistry analysis showed abnormalities in wild-type mice, heterozygous mice and homozygous mice. Urobilinogen was found in 4 of 8 mutant (−/−) mice; nitrites in 2 of 4 (+/+) wild-type mice, 1 of 4 (+/−) heterozygous mice and 4 of 8 (−/−) mice; protein in 2 of 4 (+/+) wild-type mice, 1 of 4 (+/−) mice and 3 of 8 (−/−) mice; and ketone bodies in 2 of 4 (+/+) wild-type mice, 2 of 4 (+/−) heterozygous mice and 5 of 8 mutant (−/−) mice. Increased incidence of protein, nitrites and ketone bodies in the heterozygous (+/−) and homozygous (−/−) mice is related to the abnormal kidney results discovered in the CAT-scan. These results are consistent with CAT-Scan results showing hydronephrosis.

66.42. Generation and Analysis of Mice Comprising DNA82302-2529 (UNQ904) Gene Disruptions In these knockout experiments, the gene encoding PRO1925 polypeptides (designated as DNA82302-2529) (UNQ904) was disrupted. The gene specific information for these studies is as follows: the mutated mouse gene corresponds to nucleotide reference: XM_155973 PREDICTED: *Mus musculus* similar to SARG904 (LOC239691); protein reference: XP_155973 similar to SARG904 *[Mus musculus]* gi|51769442|ref|XP_358755.2| similar to SARG904 *[Mus musculus]*; the human gene sequence reference: NM_152459 *Homo sapiens* hypothetical protein MGC45438 (MGC45438); the human protein sequence corresponds to reference: Q8N213 ACCESSION:Q8N213 NID: *Homo sapiens* (Human). Hypothetical protein FLJ90761.

The mouse gene of interest is "similar to SARG904," ortholog of human hypothetical protein MGC45438. Hypothetical protein MGC45438 is a putative secreted protein, consisting of a signal peptide and several weakly predicted, partial conserved domains, such as serpin (serine proteinase inhibitor) domain (SMART accession SM00093), B-cell lymphoma (BCL; anti-apoptotic) domain (SMART accession SM00337), and topoisomerase II domain (SMART accession SM00433). The function of this protein is not known.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 30 | 15 | 66 |
| Expected | 16.5 | 33 | 16.5 | 66 |

Chi-Sq.=4.38 Significance=0.11191674 (hom/n)=0.19 Avg. Litter Size=9

Mutation Information

Mutation Type: Homologous Recombination (standard)

Description: Coding exons 1 and 2 were targeted (NCBI accession BM453823.1).

1. Wild-type Expression Panel: Expression of the target gene was detected in all 13 adult tissue samples tested by RT-PCR, except bone and stomach, small intestine, and colon.

2. QC Expression: Disruption of the target gene was confirmed by Southern hybridization analysis.

66.42.1. Phenotypic Analysis (for Disrupted Gene: DNA82302-2529 (UNQ904)

(a) Overall Phenotypic Summary:

Mutation of the gene encoding the ortholog of a human hypothetical protein (MGC45438) resulted in the (−/−) mice exhibiting increased total fat mass and percent total body fat as well as increased total tissue mass. Leukocytes were in 1 of 4 (+/+) wild-type mice and 4 of 8 mutant (−/−) mice. Gene disruption was confirmed by Southern blot.

(b) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: Both the male and female (−/−) mice exhibited increased mean total tissue mass, percent total body fat, and total fat mass when compared with their gender-matched (+/+) littermates and the historical means.

These studies suggest that mutant (−/−) non-human transgenic animals exhibit a negative phenotype that would be associated with obesity. Thus, PRO1925 polypeptides or agonists thereof are essential for normal fat and lipid metabolic processes and especially would be important in the prevention and/or treatment of lipid storage diseases and/or obesity.

66.43. Generation and Analysis of Mice Comprising DNA82340-2530 (UNQ905) Gene Disruptions In these knockout experiments, the gene encoding PRO1926 polypeptides (designated as DNA82340-2530) (UNQ905) was disrupted. The gene specific information for these studies is as follows: the mutated mouse gene corresponds to nucleotide reference: NM_133749 ACCESSION: NM_133749 NID: gi 19526955 ref NM_133749.1 *Mus musculus* RIKEN cDNA 2900064A13 gene (2900064A13Rik); protein reference: Q9EP72 ACCESSION:Q9EP72 NID: *Mus musculus* (Mouse). Hypothetical protein (Putative ATG/GTP binding protein precursor); the human gene sequence reference: NM_020154 ACCESSION:NM_020154 NID: gi 9910345 ref NM_020154.1 *Homo sapiens* chromosome 11 hypothetical protein ORF3 (LOC56851); the human protein sequence corresponds to reference: Q9NPA0 ACCESSION:Q9NPA0 NID: *Homo sapiens* (Human). Putative ATG/GTP binding protein precursor (HT022).

The mouse gene of interest is RIKEN cDNA 2900064A13 gene, ortholog of human C15orf24 (chromosome 15 open reading frame 24). Aliases include c11orf3, HT022, ORF1-FL1, and chromosome 15 hypothetical ATP/GTP binding protein.

C15orf24 is a putative integral plasma membrane protein, containing a signal peptide, a transmembrane segment, and a potential ATP/GTP binding site (O'Brien et al, *Biochem Biophys Res Commun* 273(1):90-4 (2000)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 50 | 0 | 73 |
| Expected | 18.25 | 36.5 | 18.25 | 73 |

Chi-Sq.=47.17 Significance=5.7169585E-11 (hom/n)=0.0
Avg. Litter Size=8

Mutation Information

Mutation Type: Homologous Recombination (standard)

Description: Coding exons 1 and 2 were targeted (NCBI accession NM_133749.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.43.1. Phenotypic Analysis (for Disrupted Gene: DNA82340-2530 (UNQ905)

(a) Overall Phenotypic Summary:

Mutation of the gene encoding the ortholog of human chromosome 15 open reading frame 24 (C15orf24) resulted in genetic data indicating that this mutation resulted in lethality of homozygous mutants. The male heterozygous mice exhibited an increased anxiety-like response during stress-induced hyperthermia testing. Disruption of the target gene was confirmed by Southern hybridization analysis.

(b) Pathology

Microscopic: No notable difference was observed in the (+/−) mouse analyzed. However, no (−/−) mice were available for analysis. At 12.5 days, 51 embryos were observed: 27 (+/−) embryos, 10 (+/+) embryos, 12 resorption moles, and 2 inconclusive.

Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type and 4 heterozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Stress-Induced Hyperthermia:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Stress-Induced Hyperthermia: The male (+/−) mice exhibited increased sensitivity to stress-induced hyperthermia when compared with the level for their gender-matched (+/+) littermates and the historical mean, suggesting an increased anxiety-like response in the mutants.

In summary, the functional observation testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO1926 polypeptides or agonists thereof would be useful in the treatment of such neurological disorders.

66.44. Generation and Analysis of Mice Comprising DNA59844-2542 (UNQ1840) Gene Disruptions In these knockout experiments, the gene encoding PRO3566 polypeptides (designated as DNA59844-2542) (UNQ1840) was disrupted. The gene specific information for these studies is as follows: the mutated mouse gene corresponds to nucleotide reference: NM_175148 *Mus musculus* RIKEN cDNA 2300002M23 gene (2300002M23Rik); protein reference: Q8BM15 ACCESSION:Q8BM15 NID: *Mus*

*musculus* (Mouse). Weakly similar to TASTE bud-specific protein precursor; the human gene sequence reference: NM_014070 *Homo sapiens* chromosome 6 open reading frame 15 (C6orf15); the human protein sequence corresponds to reference: Q9UIG3 ACCESSION:Q9UIG3 NID: *Homo sapiens* (Human). STG protein.

The mouse gene of interest is RIKEN cDNA 2300002M23 gene, ortholog of human C6orf15 (chromosome 6 open reading frame 15). Aliases include STG and STG protein.

C6orf15 is a putative secreted protein, containing a signal peptide and several internal repeats within a major prion protein (PRP) domain. The function of C6orf15 is not known; however, it is expressed in a small subset of taste cells, suggesting that C6orf15 may play a role in taste cell physiology (Neira et al, *Mamm Genome* 12(1):60-6 (2001); Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 13 | 39 | 21 | 73 |
| Expected | 18.25 | 36.5 | 18.25 | 73 |

Chi-Sq.=3.68 Significance=0.15881743 (hom/n)=0.29 Avg. Litter Size=8

Mutation Information

Mutation Type: Homologous Recombination (standard)

Description: Coding exons 1 and 2 were targeted (NCBI accession NM_175148.2).

1. Wild-type Expression Panel: Expression of the target gene was detected in embryonic stem (ES) cells and in brain; thymus; spleen; lung; kidney; liver; and stomach, small intestine, and colon among the 13 adult tissue samples tested by RT-PCR.

2. QC Expression: Disruption of the target gene was confirmed by Southern hybridization analysis.

66.44.1. Phenotypic Analysis (for Disrupted Gene: DNA59844-2542 (UNQ1840)

(a) Overall Phenotypic Summary:

Mutation of the gene encoding the ortholog of human chromosome 6 open reading frame 15 (C6orf15) resulted in the female homozygous mutant mice exhibiting decreased total tissue mass and total body fat when compared with that of their gender-matched wild-type littermates and the historical means. Disruption of the target gene was confirmed by Southern hybridization analysis.

(b) Bone Metabolism & Body Diagnostics/Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited decreased mean total tissue mass, percent total body fat, and total fat mass when compared with the levels for their gender-matched (+/+) littermates and the historical means.

These studies suggest that mutant (−/−) non-human transgenic animals exhibit a negative phenotype that would be associated with growth retardation and/or tissue wasting disorders. Thus, PRO3566 polypeptides or agonists thereof are essential for normal fat and lipid metabolic processes and especially would be important in the prevention and/or treatment of tissue wasting disorders such as cachexia.

66.45. Generation and Analysis of Mice Comprising DNA90842-2574 (UNQ1886) Gene Disruptions In these knockout experiments, the gene encoding PRO4330 polypeptides (designated as DNA90842-2574) (UNQ1886) was disrupted. The gene specific information for these studies is as follows: the mutated mouse gene corresponds to nucleotide reference: AF168680 ACCESSION: AF168680 NID: 6979312 *Mus musculus Mus musculus* cysteine-rich repeat-containing protein CRIM1 (Crim1); protein reference: Q9JLL0 ACCESSION:Q9JLL0 NID: *Mus musculus* (Mouse). CYSTEINE-RICH REPEAT-CONTAINING PROTEIN CRIM1 PRECURSOR (FRAGMENT); the human gene sequence reference: NM_016441 ACCESSION:NM_016441 NID:10092638 *Homo sapiens Homo sapiens* cysteine-rich motor neuron 1 (CRIM1); the human protein sequence corresponds to reference: Q9NZV1 ACCESSION:Q9NZV1 NID: *Homo sapiens* (Human). CYSTEINE-RICH REPEAT-CONTAINING PROTEIN S52 PRECURSOR (CRIM1 PROTEIN).

The mouse gene of interest is Crim1 (cysteine-rich motor neuron 1), ortholog of human CRIM1. Aliases include S52 and cysteine-rich repeat-containing protein S52 precursor.

CRIM1 is a type I plasma membrane protein that likely functions as a cell adhesion molecule or receptor. CRIM1 is also a secreted protein, probably because the extracellular domain is proteolytically cleaved from the plasma membrane. CRIM1 binds with bone morphogenic protein (BMP)-4 and BMP-7 and inhibits BMP signaling (Wilkinson et al, *J Biol Chem* 278(36):34181-8 (2003)). Crim1 is expressed in the developing spinal chord, eye, lens, and testis, potentially playing a role in CNS development and organogenesis (Kolle et al, *Mech Dev* 90(2):181-93 (2000); Lovicu et al, *Mech Dev* 94(1-2):261-5 (2000); Georgas et al, *Dev Dyn* 219(4):582-7 (2000)). CRIM1 is also expressed in endothelial cells, where it likely plays a role in capillary formation during angiogenesis (Glienke et al, *Mech Dev* 119(2):165-75 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is Performed on mice from this generation

| | wt | het | hom | Total |
|---|---|---|---|---|
| Observed | 14 | 22 | 0 | 36 |
| Expected | 9 | 18 | 9 | 36 |

Chi-Sq.=14.85 Significance=5.9616077E-4 (hom/n)=0.09 Avg. Litter Size=8

Mutation Information

Mutation Type: Homologous Recombination (standard)

Description: Coding exon 5 was targeted (NCBI accession XM_128751.5).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.45.1. Phenotypic Analysis (for Disrupted Gene: DNA90842-2574 (UNQ1886)

(a) Overall Phenotypic Summary:

Mutation of the gene encoding the ortholog of human cysteine-rich motor neuron 1 (CRIM1) resulted in genetic data indicating that this mutation resulted in lethality of the homozygous mutants. UNQ1886 is highly expressed in blood vessels and is also involved in regulating bone morphogenic proteins. The heterozygous mice exhibited an increased mean percentage of B cells in the peripheral blood when compared with their wild-type littermates and the historical mean. Disruption of the target gene was confirmed by Southern hybridization analysis.

(b) Pathology

Microscopic: At 12.5 days there were 53 embryos observed: 10 (−/−) embryos, 21 (+/−) embryos, 13 (+/+) embryos, and 9 resorption moles. No developmental abnormalities were detected in the 12.5 day embryos by histologic examination.

Gene Expression: LacZ activity was detected only in brain among the panel of tissues analyzed by immunohistochemistry.

UNQ1886 Knockout Embryo Studies:

Tissue Embryo studies of the UNQ1886 knockout embryos showed a skin blister and hemorrhagic phenotypes suggesting that UNQ1886 is involved in maintaining tight interaction between two tissue layers. The E12.5 knockout embryo shows skin blisters on both sides of the head (at eye level) as shown by a 6 um FFPE section through the embryo forehead. Skin blisters were also noted in the E13.5 knockout embryo at the back of the skull, mid spine and eye level. Hemorrhage was also noted in the forehead skull. The E14 knockout embryo (14 um frozen section through lacZ stained forehead—level of the ear) shows expression of UNQ186 in the developing skin. Gene 3 beta-gal activity staining of the uterus section of the wholemount uterus showed expression of UNQ1886. Multi-focal hemorrhage in the knockout embryos [E13.5 and E15.5] occurred in the frontal head section [eye and nasal cavity] as well as hemorrhage in the forelimbs and abdomen.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 heterozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The (+/−) mice exhibited an altered distribution of leukocyte subsets in the peripheral blood, characterized by an increased mean percentage of B cells in the (−/−) mice when compared with that of their (+/+) littermates and the historical mean.

In summary, FACS analysis of immune cell composition indicates that heterozygous (+/−) mice exhibit immunological differences with respect to B cells.

66.46. Generation and Analysis of Mice Comprising DNA96893-2621 (UNQ1940) Gene Disruptions In these knockout experiments, the gene encoding PRO4423 polypeptides (designated as DNA96893-2621) (UNQ1940) was disrupted. The gene specific information for these studies is as follows: the mutated mouse gene corresponds to nucleotide reference: NM_173375 ACCESSION: NM_173375 NID: gi 27734065 ref NM_173375.1 *Mus musculus* hypothetical protein B230314019 (B230314O19); protein reference: Q8BR21 ACCESSION:Q8BR21 NID: *Mus musculus* (Mouse). Hypothetical protein; the human gene sequence reference: NM_205855 *Homo sapiens* HWKM1940 (UNQ1940); the human protein sequence corresponds to reference: Q6UWF9 ACCESSION:Q6UWF9 NID: *Homo sapiens* (Human). HWKM1940.

The mouse gene of interest is cDNA sequence BC064033, ortholog of human UNQ1940. Aliases include B230314O19 and HWKM1940.

UNQ1940 is a putative 173-amino acid secreted protein, containing a signal peptide and no other defined conserved domain.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 13 | 30 | 19 | 62 |
| Expected | 15.5 | 31 | 15.5 | 62 |

Chi-Sq.=0.68 Significance=0.7117703 (hom/n)=0.24 Avg. Litter Size=8

Mutation Information

Mutation Type: Homologous Recombination (standard)

Description: Coding exons 2 and 3 were targeted (NCBI accession NM_173375.1).

1. Wild-type Expression Panel: Expression of the target gene was detected in embryonic stem (ES) cells and in all 13 adult tissue samples tested by RT-PCR, except skeletal muscle and bone.

2. QC Expression: Disruption of the target gene was confirmed by Southern hybridization analysis.

66.46.1. Phenotypic Analysis (for Disrupted Gene: DNA96893-2621 (UNQ1940)

(a) Overall Phenotypic Summary:

Mutation of the gene encoding the ortholog of a human putative secreted protein (UNQ1940) resulted in a decreased percentage of CD4 cells and an increased percentage of B cells in the peripheral blood of (−/−) mice. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

The homozygous (−/−) mice exhibited decreased mean percentages of CD4 cells in the peripheral blood when compared with their (+/+) littermates and the historical means. In addition, the (−/−) mice showed increased percentages of B cells.

In summary, the FACS results indicate that the homozygous mutant mice demonstrate immunological abnormalities marked by decreased T cell populations and increased B cell populations. From these observations, PRO4423 polypeptides or the gene encoding PRO4423 appears to act as a positive regulator of T cell proliferation. But a negative regulator of B cell production. PRO4423 polypeptides and agonists thereof would be important for a healthy immune system and would be useful in stimulating the immune system particularly for increasing T cell proliferation.

66.47. Generation and Analysis of Mice Comprising DNA336539 (UNQ2257) Gene Disruptions In these knockout experiments, the gene encoding PRO36935 polypeptides (designated as DNA336539) (UNQ2257) was disrupted. The gene specific information for these studies is as follows: the mutated mouse gene corresponds to nucleotide reference: NM_011627 *Mus musculus* trophoblast glycoprotein (Tpbg); protein reference: Q9Z0L0 ACCESSION:Q9Z0L0 NID: *Mus musculus* (Mouse). 5T4 oncofetal trophoblast glycoprotein precursor; the human gene sequence reference: NM_006670 *Homo sapiens* trophoblast glycoprotein (TPBG); the human protein sequence corresponds to reference: Q13641 ACCESSION:Q13641 NID: *Homo sapiens* (Human). 5T4 oncofoetal antigen precursor (5T4 oncofetal trophoblast glycoprotein precursor).

The mouse gene of interest is Tpbg (trophoblast glycoprotein), ortholog of human TPBG. Aliases include 5T4, M6P1, 5T4-AG, 5T4-antigen, and 5T4 oncofetal trophoblast glycoprotein.

TPBG is an integral plasma membrane protein, consisting of a signal peptide, several leucine-rich repeats, a transmembrane segment, and a short cytoplasmic C-terminus. TPBG is expressed in trophoblastic cells, amniotic epithelium, brain, ovary, and a variety of carcinomas. TPBG may play a role in processes such as placentation and metastasis by modulating cell adhesion, shape, and motility (Ward et al, *J Cell Sci* 116(Pt 22):4533-42 (2003); Shaw et al, *Biochem J* 363(Pt 1): 137-45 (2002); King et al, *Biochim Biophys Acta* 1445(3) 257-70 (1999); Myers et al, *J Biol Chem* 269(12):9319-24 (1994)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 29 | 16 | 68 |
| Expected | 17 | 34 | 17 | 68 |

Chi-Sq.=4.25 Significance=0.11943297 (hom/n)=0.23 Avg. Litter Size=9

Mutation Information

Mutation Type: Homologous Recombination (standard)

Description: Coding exon 1 was targeted (NCBI accession NM_011627.2).

1. Wild-type Expression Panel: Expression of the target gene was detected in embryonic stem (ES) cells and in brain, spinal cord, eye, and spleen among the 13 adult tissue samples tested by RT-PCR.

2. QC Expression: Disruption of the target gene was confirmed by Southern hybridization analysis.

66.47.1. Phenotypic Analysis (for Disrupted Gene: DNA336539 (UNQ2257)

(a) Overall Phenotypic Summary:

Mutation of the gene encoding the ortholog of human trophoblast glycoprotein (TPBG) resulted in an increased depressive-like response in tail suspension testing in (−/−) mice. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

The (−/−) mice exhibited an increased immobility time in the tail suspension testing compared with that of the (+/+) littermates and the historical mean, which is indicative of an increased depressive-like response. Thus, knockout mice demonstrated a phenotype consistent with depression, generalized anxiety disorders, cognitive disorders, hyperalgesia and sensory disorders and/or bipolar disorders. Thus, PRO36935 polypeptides and agonists thereof would be useful for the treatment or amelioration of the symptoms associated with depressive disorders.

66.48. Generation and Analysis of Mice Comprising DNA62849-2647 (UNQ2420) Gene Disruptions In these knockout experiments, the gene encoding PRO4977 polypeptides (designated as DNA62849-2647) (UNQ2420) was disrupted. The gene specific information for these studies is as follows: the mutated mouse gene corresponds to nucleotide reference: NM_130887 ACCESSION: NM_130887 NID: 18700029 *Mus musculus Mus musculus* papilin (LOC170721); protein reference: Q9EPX2 ACCESSION:Q9EPX2 NID: *Mus musculus* (Mouse). PAPILIN; the human gene sequence reference: NM_173462 *Homo sapiens* papilin, proteoglycan-like sulfated glycoprotein (PAPLN); the human protein sequence corresponds to reference: NP_775733 ACCESSION:NP_775733 NID: gi 50083295 ref NP_775733.2 papilin [*Homo sapiens]*.

The mouse gene of interest is Papln (papilin, proteoglycan-like sulfated glycoprotein), ortholog of human PAPLN. Aliases include E030033C16Rik and MGC50452.

PAPLN is a secreted protein that associates with extracellular matrix and likely functions as a protease inhibitor (Kramerova et al, 2000). PAPLN consists of a signal peptide, several thrombospondin repeats (extracellular matrix association and cell adhesion; Pfam accession PF00090), a Kunitz/bovine pancreatic trypsin inhibitor domain (indicative of serine protease inhibitors; Pfam accession PF00014), and three C-terminal immunoglobulin domains protein-protein or protein-ligand interactions; Pfam accession PF00047). PAPLN may play a role in development and organogenesis (Kramerova et al, *Development* 127(24):5475-85 (2000); Fessler et al, *Int J Biochem Cell Biol* 36(6):1079-84 (2004); Tucker, *Int J Biochem Cell Biol* 36(6):969-74 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 27 | 34 | 16 | 77 |
| Expected | 19.25 | 38.5 | 19.25 | 77 |

Chi-Sq.=5.11 Significance=0.077692226 (hom/n)=0.2 Avg. Litter Size=8

Mutation Information

Mutation Type: Homologous Recombination (standard)

Description: Coding exon 1 and the preceding noncoding exon was targeted (NCBI accession NM_130887.1).

1. Wild-type Expression Panel: Expression of the target gene was detected in all 13 adult tissue samples tested by RT-PCR.

2. QC Expression: Disruption of the target gene was confirmed by Southern hybridization analysis.

66.48.1. Phenotypic Analysis (for Disrupted Gene: DNA62849-2647 (UNQ2420)

(a) Overall Phenotypic Summary:

Mutation of the gene encoding the ortholog of human papilin, proteoglycan-like sulfated glycoprotein (PAPLN) resulted in an increased percentage of CD4 cells in the peripheral blood of (−/−) mice. The mutant (−/−) mice also exhibited a trend towards increased prepulse inhibition. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS: The (−/−) mice exhibited an altered distribution of leukocyte subsets in the peripheral blood, characterized by an increased mean percentage of CD4 cells when compared with their (+/+) littermates and the historical mean. Thus, knocking out the gene which encodes PRO4977 polypeptides causes an increase in the T cell population. From these observations, PRO4977 polypeptides or the gene encoding PRO4977 appears to act as a negative regulator of T cell proliferation. Thus, PRO4977 polypeptides or agonists thereof would be beneficial as a negative regulator of T cell proliferation in those instances wherein a pronounced T-cell proliferation is present such as occurs in autoimmune diseases (for example rheumatoid arthritis patients). In addition, PRO4977 polypeptides would be especially useful in preventing skin graft rejections.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when aloud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

The mutant (−/−) mice exhibited a trend towards increased prepulse inhibition of the acoustic startle reflex which is indicative of an enhanced sensorimotor gating/attention.

66.49. Generation and Analysis of Mice Comprising DNA222844 (UNQ2421) Gene Disruptions In these knockout experiments, the gene encoding PRO4979 polypeptides (also known as PRO38844 polypeptides) (designated as DNA222844) (UNQ2421) was disrupted. The gene specific information for these studies is as follows: the mutated mouse gene corresponds to nucleotide reference: NM_173182 *Mus musculus* RIKEN cDNA 1600019O04 gene (1600019O04Rik); protein reference: Q6NWW9 ACCESSION:Q6NWW9 NID: *Mus musculus* (Mouse). FAD104; the human gene sequence reference: NM_022763 *Homo sapiens* FAD104 (FAD104); the human protein sequence corresponds to reference: Q8IXB2 ACCESSION:Q8IXB2 NID: *Homo sapiens* (Human). FAD104.

The mouse gene of interest is RIKEN cDNA 1600019O04 gene, ortholog of human FAD104 (factor for adipocyte differentiation 104). Aliases include FLJ23399 and DKFZp762K137.

FAD104 is a putative integral plasma membrane protein that likely functions as a receptor or cell adhesion molecule. The protein contains nine fibronectin type III domains and a C-terminal transmembrane segment. FAD104 may play a role in adipogenesis (Tominaga et al, *FEBS Lett* 577(1-2):49-54 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 17 | 36 | 1 | 54 |
| Expected | 13.5 | 27 | 13.5 | 54 |

Chi-Sq.=20.47 Significance=3.5891873E-5 (hom/n)=0.08 Avg. Litter Size=8

Mutation Information

Mutation Type: Homologous Recombination (standard)

Description: Coding exon 1 was targeted (NCBI accession NM_173182.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.49.1. Phenotypic Analysis (for Disrupted Gene: DNA222844 (UNQ2421)

(a) Overall Phenotypic Summary:

Mutation of the gene encoding the ortholog of human factor for adipocyte differentiation 104 (FAD104) resulted in genetic data indicating that this mutation resulted in lethality of the homozygous mutants. The heterozygous mice exhibited an increased mean serum IgG2a level when compared with that of their wild-type littermates. Disruption of the target gene was confirmed by Southern hybridization analysis.

(b) Pathology

Genetics: Homozygous lethal. The (−/−) pups were dead at the time of genotyping.

Microscopic: No developmental abnormalities were detected in the 12.5 d embryos by histologic examination.

Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value $<6$ is not significant.

Results:

Serum Imm. 2: The (+/−) mice exhibited an increased mean serum IgG2a level when compared with that of their (+/+) littermates, the (+/+) mice for the project run, and the historical median.

Heterozygous (+/−) mice exhibited elevation of IgG2a serum immunoglobulins compared to their gender-matched (+/+) littermates. IgG2a efficiently opsonizes pathogens for engulfment by phagocytes and activates the complement system. The observed phenotype suggests that the PRO4979 polypeptide is a negative regulator of inflammatory responses.

66.50. Generation and Analysis of Mice Comprising DNA97003-2649 (UNQ2422) Gene Disruptions In these knockout experiments, the gene encoding PRO4980 polypeptides (designated as DNA97003-2649) (UNQ2422) was disrupted. The gene specific information for these studies is as follows: the mutated mouse gene corresponds to nucleotide reference: NM_177648 *Mus musculus* transmembrane protein 15 (Tmem15); protein reference: Q8R2Y3 ACCESSION:Q8R2Y3 NID: *Mus musculus* (Mouse). Similar to KIAA1094 protein; the human gene sequence reference: NM_014908 *Homo sapiens* transmembrane protein 15 (TMEM15); the human protein sequence corresponds to reference: Q9UPQ8 ACCESSION:Q9UPQ8 NID: *Homo sapiens* (Human). Hypothetical protein KIAA1094.

The mouse gene of interest is Tmem15 (transmembrane protein 15), ortholog of human TMEM15. Aliases include MGC36683, mKIAA1094, cDNA sequence BC026973, and KIAA1094.

TMEM15 is a likely integral plasma membrane protein, consisting of a signal peptide and 11 to 14 transmembrane segments within a weakly predicted actin-like ATPase domain (SCOP).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 33 | 0 | 51 |
| Expected | 12.75 | 25.5 | 12.75 | 51 |

Chi-Sq.=41.74 Significance=8.6352275E-10 (hom/n)=0.0 Avg. Litter Size=7

Mutation Information

Mutation Type: Homologous Recombination (standard)

Description: Coding exon 1 was targeted (NCBI accession NM_177648.2).

1. Wild-type Expression Panel: Expression of the target gene was detected in all 13 adult tissue samples tested by RT-PCR, except bone.

2. QC Expression: Disruption of the target gene was confirmed by Southern hybridization analysis.

66.50.1. Phenotypic Analysis (for Disrupted Gene: DNA97003-2649 (UNQ2422)

(a) Overall Phenotypic Summary:

Mutation of the gene encoding the ortholog of human transmembrane protein 15 (TMEM15) resulted in genetic data indicating that this mutation resulted in lethality of the homozygous mutants. The heterozygous mice exhibited a decreased depressive-like response. Disruption of the target gene was confirmed by Southern hybridization analysis.

(b) Pathology

Microscopic: Not tested due to embryonic lethality. At 12.5 days, there were 39 embryos observed: 23 (+/−) embryos, 11 (+/+) embryos, 3 to-be-determined, and 2 inconclusive. Wholemount data at 7.5 dpc and 12.5 dpc shows broad and ubiquitous staining in the wildtype embryos. There is strong LacZ staining in the extraembryonic ectoderm at 6.5 dpc and 7.5 dpc in the heterozygous (+/−) embryos.

Gene Expression: LacZ activity was not detected in the panel of tissues by immunohistochemical analysis.

Discussion related to embryonic developmental abnormality of lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type and 4 heterozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Tail Suspension2: The (+/−) mice exhibited decreased immobility time during tail suspension testing when compared with their (+/+) littermates and the historical mean, suggesting a decreased depressive-like response in the mutants.

Thus, heterozygous mice demonstrated a phenotype consistent with depression, generalized anxiety disorders, cognitive disorders, hyperalgesia and sensory disorders and/or bipolar disorders. Thus, PRO4980 polypeptides and agonists thereof would be useful for the treatment or amelioration of the symptoms associated with depressive disorders.

66.51. Generation and Analysis of Mice Comprising DNA94849-2960 (UNQ2423) Gene Disruptions In these knockout experiments, the gene encoding PRO4981 polypeptides (designated as DNA94849-2960) (UNQ2423) was disrupted. The gene specific information for these studies is as follows: the mutated mouse gene corresponds to nucleotide reference: NM_027379 *Mus musculus* male sterility domain containing 2 (Mlstd2); protein reference: Q922J9 ACCESSION:Q922J9 NID: *Mus musculus* (Mouse). RIKEN cDNA 3732409C05 gene; the human gene sequence reference: NM_032228 *Homo sapiens* male sterility domain containing 2 (MLSTD2); the human protein sequence corresponds to reference: Q8WVX9 ACCESSION: Q8WVX9 NID: *Homo sapiens* (Human). Similar to RIKEN cDNA 3732409C05 gene.

The mouse gene of interest is Mlstd2 (male sterility domain containing 2), ortholog of human MLSTD2. Aliases include FAR1, 2600011M19Rik, 3732409CO5Rik, FAR1, FLJ22728, and fatty acyl CoA reductase 1.

MLSTD2 is a peroxisomal enzyme that catalyzes the formation of fatty alcohols by reducing fatty acyl-CoA with co-substrate NADPH, preferring unsaturated fatty acids of 16 or 18 carbons. The enzyme is expressed primarily in preputial gland, a type of sebaceous gland, and in brain, a lipid ether-rich tissue. MLSTD2 likely plays a role in the biosynthesis of wax monoesters and lipid ethers (Cheng and Russell, *J Biol Chem* 279(36):37789-97 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 30 | 16 | 64 |
| Expected | 16 | 32 | 16 | 64 |

Chi-Sq.=3.51 Significance=0.17290725 (hom/n)=0.31 Avg. Litter Size=8

Mutation Information

Mutation Type: Homologous Recombination (standard)

Description: Coding exons 1 and 2 were targeted (NCBI accession NM_027379.1).

1. Wild-type Expression Panel: Expression of the target gene was detected in embryonic stem (ES) cells and in brain, spinal cord, eye, thymus, spleen, lung, and kidney among the 13 adult tissue samples tested by RT-PCR.

2. QC Expression: Disruption of the target gene was confirmed by Southern hybridization analysis.

66.51.1. Phenotypic Analysis (for Disrupted Gene: DNA94849-2960 (UNQ2423)

(a) Overall Phenotypic Summary:

Mutation of the gene encoding the ortholog of human male sterility domain containing 2 (MLSTD2) resulted in the homozygous mutant mice exhibiting a hearing impairment. The knockout (−/−) mice also showed an increased stress-induced hyperthermia and a trend towards an enhanced circadian rhythm. Microscopic analysis revealed testicular degeneration in the male mutants, consistent with the infertility noted diagnostically. In addition, decreased bone mineral content and density measurements were observed in the homozygous mutant mice, along with notably increased body fat in the female mutants. Disruption of the target gene was confirmed by Southern hybridization analysis.

(b) Pathology

Gross: The 2 male (−/−) mice available for analysis exhibited significantly decreased tesis weight in male knockouts.

Microscopic: The 2 male (−/−) mice analyzed (M-214 and M-226) exhibited marked testicular degeneration characterized by large multinuclear giant cells in the seminiferous tubules and no sperm in the epididymides. The hepatocytes had cytoplasmic vacuoles characteristic of glycogen accumulation of marked and moderate intensity in the females but slight in the males.

Gene Expression: LacZ activity was detected in testes among the panel of tissues analyzed by immunohistochemistry.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. Prepulse inhibition of the acoustic startle reflex Prepulse inhibition of the acoustic startle reflex occurs when aloud 120 decibel (dB) startle-inducing tone is preceded by a softer (prepulse) tone. The PPI paradigm consists of six different trial types (70 dB background noise, 120 dB alone, 74dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: Only 3/8 (−/−) mice lacked a startle response, suggesting a hearing impairment in the mutants.

Functional Observational Battery (FOB) Test—Stress-induced Hyperthermia:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Stress-Induced Hyperthermia: The (−/−) mice exhibited an increased stress-induced hyperthermia when compared with the value for their gender-matched (+/+) littermates and the historical mean, suggesting a increased anxiety-like response in the mutants. These results are consistent with the circadian rhythm neurological testing. Thus, PRO4981 polypeptides or agonists thereof would be useful in the treatment of anxiety related disorders.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The (−/−) mice exhibited increased ambulatory counts during the 12-hour habituation period of home-cage activity testing when compared with their gender-matched (+/+) littermates and the historical mean. These results demonstrate an enhanced circadian rhythm. Home-cage activity testing is also suggestive of increased activity or hyperactivity which could be related to an anxiety-like response.

(d) Cardiology/Blood Pressure and Heart Rate

Description:

Systolic blood pressure is measured via a noninvasive tail-cuff method for four days on the Visitech BP-2000 Blood Pressure Analysis System. The blood pressure is measured ten times each day for four days.

Blood Pressure Results:

The (−/−) mouse exhibited decreased systolic blood pressure when compared to its gender-matched (+/+) littermates and the historical mean.

(e) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes.

Results:

Blood Chemistry: Both male and female the (−/−) mice exhibited a decreased mean serum calcium level. The decreased calcium levels is consistent with the observation of decreased bone mineral content and density measurements.

(f) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

The (−/−) mice exhibited a significantly impaired glucose tolerance when placed on a high fat diet compared with their gender-matched (+/+) littermates and the historical means.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefore PRO4981 polypeptides (or agonists thereof) or its encoding gene would be useful in the treatment of conditions associated with an impaired glucose homeostasis and/or various cardiovascular diseases, including diabetes.

(g) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Body Weight and Length: The male (−/−) mice exhibited decreased mean body weight and mean body length when compared with their gender-matched (+/+) littermates and the historical mean.

Fertility: The male (−/−) mouse available for analysis produced no pups after 40 days of breeding and 4 matings with female (+/+) mice.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebrae trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male and female (−/−) mice exhibited decreased mean lean body mass, bone mineral content, and bone mineral density in total body and vertebrae when compared with that of their gender-matched (+/+) littermates and the historical means. The female (−/−) mice also exhibited an increased mean total tissue mass and slight increase in total fat mass, and percent total body fat.

Micro CT: The male (−/−) mice exhibited decreased mean femoral mid-shaft cross-sectional area when compared with that of their gender-matched (+/+) littermates and the historical mean.

The (−/−) mice analyzed by DEXA and bone micro CT analysis exhibited decreased bone measurements when compared with their (+/+) littermates, suggestive of abnormal bone disorders. However, the mutant (−/−) mice also exhibited decreased body weight and length and lean body mass as well as infertility in male (−/−) mice. On the other hand, female (−/−) mice exhibited a slight increase in mean percentage of body fat. These observations suggest that for the most part male mutant mice deficient in the gene which encodes PRO4981 polypeptides leads to metabolic disorders associated with growth retardation in (−/−) mice but also abnormal bone measurements reflective of osteoporosis. Thus, PRO4981 polypeptides or agonists thereof would be useful in the treatment of bone related disorders such as osteoporosis or would be useful in maintaining bone homeostasis. Antagonists (or inhibitors) of PRO4981 polypeptides or its encoding gene would lead to abnormal or pathological bone disorders including inflammatory diseases associated with abnormal bone metabolism including arthritis, osteoporosis and osteopenia.

66.52. Generation and Analysis of Mice Comprising DNA115291-2681 (UNQ2501) Gene Disruptions In these knockout experiments, the gene encoding PRO5801 polypeptides (designated as DNA115291-2681) (UNQ2501) was disrupted. The gene specific information for these studies is as follows: the mutated mouse gene corresponds to nucleotide reference: BC026546 *Mus musculus* interleukin 17 receptor B, mRNA (cDNA clone MGC:35924 IMAGE:5042466); protein reference: Q9JIP3 ACCESSION: Q9JIP3 NID: *Mus musculus* (Mouse). INTERLEUKIN-17B RECEPTOR PRECURSOR (IL-17B RECEPTOR) (IL-17 RECEPTOR HOMOLOG 1) (IL-17RH1) (IL17RH1) (IL-17ER); the human gene sequence reference: NM_018725 *Homo sapiens* interleukin 17 receptor B (IL17RB), transcript variant 1; the human protein sequence corresponds to reference: Q9NRM6 ACCESSION:Q9NRM6 NID: *Homo sapiens* (Human). INTERLEUKIN-17B RECEPTOR PRECURSOR (IL-17B RECEPTOR) (IL-17 RECEPTOR HOMOLOG1) (IL-17RH1) (IL17RH1) (CYTOKINE RECEPTOR CRL4).

The mouse gene of interest is Il17rb (interleukin 17 receptor B), ortholog of human IL17RB. Aliases include Evi27, Il17br, IL-17ER, IL17RH1, IL-17Rh1, CRL4, MGC5245, IL-17B receptor, cytokine receptor CRL4, interleukin 17B receptor, interleukin 17 receptor homolog, interleukin 17 receptor homolog 1, and ecotropic viral integration site 27.

IL17RB is a type I plasma membrane protein that functions as a receptor for cytokines IL17E and IL17B. The receptor is capable of activating nuclear factor kappaB and stimulating production of proinflammatory chemokine IL-8. IL17RB is expressed in liver, kidney, pancreas, testis, colon, brain, and small intestine. IL17RB likely plays a role in inflammation and may participate in various disease processes, such as rheumatoid arthritis, psoriasis, multiple sclerosis, tumor growth promotion, and transplant rejection (Lee et al, *J Biol Chem* 276(2): 1660-4 (2001); Tian et al, *Oncogene* 19(17): 2098-109 (2000); Shi et al, *J Biol Chem* 275(25):19167-76 (2000); Moseley et al, *Cytokine Growth Factor Rev* 14(2): 155-74 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 19 | 34 | 24 | 77 |
| Expected | 19.25 | 38.5 | 19.25 | 77 |

Chi-Sq.=2.18 Significance=0.33621648 (hom/n)=0.29 Avg. Litter Size=9

Mutation Information

Mutation Type: Homologous Recombination (standard)

Description: Coding exons 1 through 4 were targeted (NCBI accession NM_019583.1).

1. Wild-type Expression Panel: Expression of the target gene was detected in all 13 adult tissue samples tested by RT-PCR, except skeletal muscle, bone, and heart.

2. QC Expression: Disruption of the target gene was confirmed by Southern hybridization analysis.

66.52.1. Phenotypic Analysis (for Disrupted Gene: DNA115291-2681 (UNQ2501)

(a) Overall Phenotypic Summary:

Mutation of the gene encoding the ortholog of human interleukin 17 receptor B (IL17RB) resulted in the (−/−) mice exhibited an enhanced glucose tolerance. Gene disruption was confirmed by Southern blot.

(b) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Glucose Tolerance Test: The male mutant (−/−) mice on a high fat diet exhibited an enhanced glucose tolerance when compared with their gender-matched (+/+) littermates.

In these studies the mutant (−/−) mice showed an increased or enhanced glucose tolerance in the presence of normal fasting glucose at all 3 intervals tested when compared with their gender-matched (+/+) littermates and the historical means. Thus, knockout mice exhibited an increased insulin sensitivity or the opposite phenotypic pattern of an impaired glucose homeostasis, and as such antagonists (inhibitors) to PRO5801 polypeptides or its encoding gene would be useful in the treatment of an impaired glucose homeostasis.

66.53. Generation and Analysis of Mice Comprising DNA96988-2685 (UNQ2507) Gene Disruptions In these knockout experiments, the gene encoding PRO5995 polypeptides (designated as DNA96988-2685) (UNQ2507) was disrupted. The gene specific information for these studies is as follows: the mutated mouse gene corresponds to nucleotide reference: NM_146241 ACCESSION: NM_146241 NID: gi 22122816 ref NM_146241.1 *Mus musculus* thyrotropin-releasing hormone degrading ectoenzyme (Trhde-pending); protein reference: Q8K093 ACCESSION:Q8K093 NID: *Mus musculus* (Mouse). Hypothetical protein; the human gene sequence reference: NM_013381 ACCESSION:NM_013381 NID: gi 7019560 refNM_013381.1 *Homo sapiens* thyrotropin-releasing hormone degrading ectoenzyme (TRHDE); the human protein sequence corresponds to reference: Q6UWJ4 ACCESSION: Q6UWJ4 NID: *Homo sapiens* (Human). TRHDE.

The mouse gene of interest is Trhde (thyrotropin-releasing hormone degrading ectoenzyme), ortholog of human TRHDE. Aliases include MGC40831, 9330155P21Rik, PAP-II, pyroglutamyl-peptidase II, TRH-degrading ectoenzyme, TRH-DE, TRH-specific aminopeptidase, and thyroliberinase.

TRHDE is an extracellular type II plasma membrane protein and zinc metalloprotease that catalyzes the removal of the N-terminal pyroglutamyl group from thyrotropin-releasing hormone (TRH). TRHDE likely plays a role in TRH signaling by inactivating the neuropeptide after its release. TRHDE is expressed primarily in brain but is also expressed in heart, lung, liver, skeletal muscle, and serum (Baeza et al, *Life Sci* 68(17):2051-60 (2001); Schomburg et al, *Eur J Biochem* 265(1):415-22 (1999); Kelly et al, *J Biol Chem* 275(22): 16746-51 (2000); Schmitmeier et al, *Eur J Biochem* 269(4): 1278-86 (2002)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 27 | 35 | 27 | 89 |
| Expected | 22.25 | 44.5 | 22.25 | 89 |

Chi-Sq.=0.98 Significance=0.6126264 (hom/n)=0.27 Avg. Litter Size=10

Mutation Information

Mutation Type: Homologous Recombination (standard)

Description: Coding exon 1 was targeted (NCBI accession NM_146241.1).

1. Wild-type Expression Panel: Expression of the target gene was detected in embryonic stem (ES) cells and in all 13 adult tissue samples tested by RT-PCR, except lung, skeletal muscle, bone, and adipose.

2. QC Expression: Disruption of the target gene was confirmed by Southern hybridization analysis.

66.53.1. Phenotypic Analysis (for Disrupted Gene: DNA96988-2685 (UNQ2507)

(a) Overall Phenotypic Summary:

Mutation of the gene encoding the ortholog of human thyrotropin-releasing hormone degrading ectoenzyme (TRHDE) resulted in the mutant (−/−) mice exhibiting decreased mean body weight and length as well as decreased total tissue mass and lean body mass. Tail suspension testing showed increased immobility in the (+/+) mice. Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Body Weight and Length: The male (−/−) mice exhibited decreased mean body weight and mean body length when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean total tissue mass and lean body mass when compared with that of their gender-matched (+/+) littermates and the historical means.

Thus mutant (−/−) mice show a negative phenotype marked by decreased body weights and body length and total tissue mass and lean body mass which can be due to growth retardation or a tissue-wasting condition such as cachexia. Thus, antagonists or inhibitors of PRO5995 polypeptides or its encoding gene would mimic these abnormal metabolic related effects. On the other hand, PRO5995 polypeptides or agonists thereof would be useful in the prevention and/or treatment of such metabolic disorders as cachexia or other tissue wasting diseases as well as being important for normal growth development (c) Phenotypic Analysis: CNS/Neurology In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Tail Suspension2: The (−/−) mice exhibited increased immobility time when compared with the value for their (+/+) littermates and the historical mean, which is indicative of a depressive-like response in the mutants. Thus, knockout mice demonstrated a phenotype consistent with depression, generalized anxiety disorders, cognitive disorders, hyperalgesia and sensory disorders and/or bipolar disorders. Thus, PRO5995 polypeptides and agonists thereof would be useful for the treatment or amelioration of the symptoms associated with depressive disorders.

66.54. Generation and Analysis of Mice Comprising DNA98380 (UNQ2512) Gene Disruptions In these knockout experiments, the gene encoding PRO6001 polypeptides (designated as DNA98380) (UNQ2512) was disrupted. The gene specific information for these studies is as follows: the mutated mouse gene corresponds to nucleotide reference: NM_133187 ACCESSION: NM_133187 NID: gi 18875327 ref NM_133187.1 *Mus musculus* RIKEN cDNA 1110032E23 gene (1110032E23Rik); protein reference: Q9ET25 ACCESSION:Q9ET25 NID: *Mus musculus* (Mouse). Hypothetical basic protein 1-19; the human gene sequence reference: NM_016613 *Homo sapiens* hypothetical protein DKFZp434L142 (DKFZp434L142); the human protein sequence corresponds to reference: Q6UWII4 ACCESSION: Q6UWII4 NID: *Homo sapiens* (Human). TCPD2512.

The mouse gene of interest is RIKEN cDNA 1110032E23 gene, ortholog of human hypothetical protein DKFZp434L142. Aliases include AD021 and AD036.

Hypothetical protein DKFZp434L142 is a putative 517-amino acid protein, containing no conserved domains except for a transmembrane segment near the N terminus.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 43 | 21 | 82 |
| Expected | 20.5 | 41 | 20.5 | 82 |

Chi-Sq.=8.57 Significance=0.013773624 (hom/n)=0.24 Avg. Litter Size=9

Mutation Information

Mutation Type: Homologous Recombination (standard)

Description: Coding exon 1 was targeted (NCBI accession NM_133187.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.54.1. Phenotypic Analysis (for Disrupted Gene: DNA98380 (UNQ2512)

(a) Overall Phenotypic Summary:

Mutation of the gene encoding the ortholog of a human hypothetical protein (DKFZp434L142) resulted in impaired glucose tolerance in (−/−) mice. Male (−/−) mice also exhibited a decreased basal body temperature. Gene disruption was confirmed by Southern blot.

(b) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

The (−/−) mice exhibited impaired glucose tolerance when placed on a high fat diet compared with their gender-matched (+/+) littermates and the historical means.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefore PRO6001 polypeptides (or agonists thereof) or its encoding gene would be useful in the treatment of conditions associated with an impaired glucose homeostasis and/or various cardiovascular diseases, including diabetes.

66.55. Generation and Analysis of Mice Comprising DNA105680-2710 (UNQ2543) Gene Disruptions In these knockout experiments, the gene encoding PRO6095 polypeptides (designated as DNA105680-2710) (UNQ2543) was disrupted. The gene specific information for these studies is as follows: the mutated mouse gene corresponds to nucleotide reference: NM_153528 *Mus musculus* RIKEN cDNA 4921521N14 gene (4921521N14Rik); protein reference: Q8CI52 ACCESSION:Q8CI52 NID: *Mus musculus* (Mouse). RIKEN cDNA 4921521N14; the human gene sequence reference: BC035040 *Homo sapiens* hypothetical protein DKFZp434C0328; the human protein sequence corresponds to reference: Q8IYS0 ACCESSION:Q8IYS0 NID: *Homo sapiens* (Human). DKFZp434C0328 protein.

The mouse gene of interest is RIKEN cDNA 4921521N14 gene, ortholog of human hypothetical protein DKFZp434C0328. Aliases include MGC47315.

Hypothetical protein DKFZp434C0328 is a putative membrane protein, consisting of a GRAM domain, a transmembrane segment, and a potential glycosylphospholipid (GPI) anchor site. GRAM domains are found in proteins such as glucosyltransferases, myotubularins, and other membrane-associated proteins and are likely to function in membrane targeting (Doerks et al, *Trends Biochem Sci* 25(10):483-5 (2000)). The cell location of hypothetical protein DKFZp434C0328 is ambiguous. The transmembrane segment suggests that the hypothetical protein may be an integral membrane protein, whereas the GPI anchor site suggests that the protein may be associated with the extracellular surface of the plasma membrane. Because GRAM domains may be involved in association of proteins with target membranes (Oku et al, *EMBO J* 22(13)3231-41 (2003)), hypothetical protein DKFZp434C0328 may be located on intracellular membranes.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 20 | 30 | 18 | 68 |
| Expected | 17 | 34 | 17 | 68 |

Chi-Sq.=1.86 Significance=0.39455372 (hom/n)=0.29 Avg. Litter Size=9

Mutation Information

Mutation Type: Homologous Recombination (standard)

Description: Coding exons 1 and 2 were targeted (NCBI accession NM_153528.1).

1. Wild-type Expression Panel: Panel: Expression of the target gene was detected in embryonic stem (ES) cells and in all 13 adult tissue samples tested by RT-PCR, except bone.

QC Images: Disruption of the target gene was confirmed by Southern hybridization analysis.

66.55.1. Phenotypic Analysis (for Disrupted Gene: DNA105680-2710 (UNQ2543)

(a) Overall Phenotypic Summary:

Mutation of the gene encoding the ortholog of a human hypothetical protein (DKFZp434C0328) resulted in immunological abnormalities in (−/−) mice. The homozygous mutant mice exhibited increased IgM+, IgD+ B cells, and B220hi CD43− cells in bone marrow when compared with the levels for their wild-type littermates. In addition, the mutant (−/−) mice showed increased total tissue mass and fat content (accompanied by elevated cholesterol levels) with increased body weight and length as well as increased bone-mineral density measurements.

Disruption of the target gene was confirmed by Southern hybridization analysis.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) mice exhibited an increased mean serum cholesterol level when compared with that of their gender-matched (+/+) littermates and the historical mean.

As summarized above, the (−/−) mice exhibited increased mean serum cholesterol levels when compared with their gender-matched (+/+) littermates and the historical means. Thus, mutant mice deficient in the PRO6095 gene can serve as a model for cardiovascular disease. PRO6095 polypeptides or its encoding gene would be useful in regulating blood lipids such as cholesterol. Thus, PRO6095 polypeptides or agonists thereof would be useful in the treatment of such cardiovascular diseases as hypertension, atherosclerosis, heart failure, stroke, various coronary diseases, hypercholesterolemia, diabetes and/or obesity.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

Tissue Specific FACS-Project: The (−/−) mice exhibited increased IgM+, IgD+ B cells, and B220hi CD43− cells in bone marrow when compared with those of their (+/+) littermates. Mature naive B cells co-express IgM and IgD and leave the bone marrow to circulate through the lymphoid organs. By knocking out the gene encoding PRO6095 polypeptides, the mutant (−/−) mice exhibited increased percentages of B cell progenitors as well as the immunoglobulins that are expressed by these cells. Thus, PRO6095 polypeptides appear to act as a negative regulator for B cell differentiation and/or proliferation. Antagonists (inhibitors) of PRO6095 polypeptides would be useful in the stimulation of B cell production.

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains.

Any value <6 is not significant.

Results:

The (−/−) mice exhibited increased mean serum IgG3 levels compared to their gender-matched (+/+) littermate controls, the (+/+) mice for the project run and the historical median.

The serum immunoglobulin isotyping assay revealed that homozygous adults exhibited increased serum IgG3 levels. Thus, homozygotes showed elevated serum immunoglobulins compared with the (+/+) littermates. IgG3 immunoglobulins have neutralization effects and to a lesser extent are important for activation of the complement system. These immunological abnormalities suggest that antagonists or inhibitors of PRO6095 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO6095 polypeptides or agonists thereof would inhibit the immune response and would be useful candidates for suppressing harmful immune responses, e.g. in the case of graft rejection or graft-versus-host diseases.

(d) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Body Weight and Length: The male (−/−) mice exhibited increased mean body weight and mean body length when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited increased mean total tissue mass, total fat mass, and percent total body fat when compared with those of their gender-matched (+/+) littermates and the historical means.

Micro CT: The male (−/−) mice exhibited increased mean vertebral trabecular bone connectivity density when compared with the levels for their gender-matched (+/+) littermates and the historical means.

These results demonstrate that knockout mutant mice exhibit abnormal bone metabolism with increased mean vertebral trabecular bone measurements similar to osteopetrosis characterized by increase in bone mass density. Thus, it appears that PRO6095 polypeptides or agonists thereof would be useful in maintaining bone homeostasis and for bone remodeling by balancing osteoclast and osteoblast activity. In addition, antagonists or inhibitors PRO6095 polypeptides or its encoding gene would be useful in bone healing or for the treatment of other bone related abnormalities associated with increased bone mineralization.

The (−/−) mice also exhibited increased mean total tissue mass and increased mean percent total body fat and total fat mass when compared with their gender-matched (+/+) littermates and the historical means. These findings are consistent with the increased mean body weight and length exhibited by the (−/−) mutant mice.

These studies show that mutant (−/−) non-human transgenic animals exhibit a negative phenotype that is associated with obesity. Thus, PRO6095 polypeptides or agonists thereof are essential for normal growth and metabolic processes and especially would be useful in the prevention and/or treatment of lipid storage diseases and/or obesity.

66.56. Generation and Analysis of Mice Comprising DNA110700-2716 (UNQ2553) Gene Disruptions In these knockout experiments, the gene encoding PRO6182 polypeptides (designated as DNA110700-2716) (UNQ2553) was disrupted. The gene specific information for these studies is as follows: the mutated mouse gene corresponds to nucleotide reference: NM_020003 ACCESSION: NM_020003 NID: gi 9910457 ref NM_020003.1 *Mus musculus* RIKEN cDNA 0610031J06 gene (0610031J06Rik); protein reference: Q9JHJ3 ACCESSION:Q9JHJ3 NID: *Mus musculus* (Mouse). Kidney predominant protein (RIKEN cDNA 0610031J06 gene); the human gene sequence reference: NM_144580 ACCESSION:NM_144580 NID: gi 24307870 ref NM_144580.1 *Homo sapiens* hypothetical protein MGC31963 (MGC31963); the human protein sequence corresponds to reference: Q8WWB7 ACCESSION:Q8WWB7NID: *Homo sapiens* (Human). Hypothetical protein NT2RP1000567.

The mouse gene of interest is RIKEN cDNA 0610031J06 gene, ortholog of human MGC31963 (kidney predominant protein NCU-G1). Aliases include NCU-G1.

MGC31963 is a putative type I integral plasma membrane protein, containing a signal peptide and a transmembrane segment near the C-terminus. The protein is expressed at high levels in the kidney cortex and at lower levels in several other tissues (Kawamura et al, *Biochem Genet* 39(1-2):33-42 (2001); Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 24 | 40 | 13 | 77 |
| Expected | 19.25 | 38.5 | 19.25 | 77 |

Chi-Sq.=0.53 Significance=0.76720595 (hom/n)=0.26 Avg. Litter Size=9

Mutation Information

Mutation Type: Homologous Recombination (standard)

Description: Coding exons 1 through 6 were targeted (NCBI accession NM_020003.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.56.1. Phenotypic Analysis (for Disrupted Gene: DNA110700-2716 (UNQ2553)

(a) Overall Phenotypic Summary:

Mutation of the gene encoding the ortholog of human kidney predominant protein NCU-G1 (MGC31963) resulted in hepatitis in (−/−) mice. The homozygous mutant mice exhibited signs of anemia and immunological abnormalities when compared with the levels for their wild-type littermates and the historical means. In addition, both the male and female homozygous mutant mice exhibited increased mean serum alkaline phosphatase levels and decreased mean serum glucose levels. The (−/−) mice also exhibited decreased vBMD and BMD in total body as well as decreased mean vertebral trabecular number and connectivity density. The (−/−) mice showed a trend towards increased prepulse inhibition. The livers of the mutants were smaller than normal upon gross examination; microscopic analysis revealed mild-to-moderate necrotizing hepatitis. Disruption of the target gene was confirmed by Southern hybridization analysis.

(b) Pathology

Gross: The livers of the (−/−) mice were smaller than normal, and the hepatic capsular surface was irregular and pitted due to the underlying loss/collapse of parenchyma.

Microscopic: The (−/−) mice analyzed exhibited mild-to-moderate multifocal necrotizing hepatitis, characterized by minimal ongoing hepatocellular necrosis and degeneration. Minimal-to-mild subacute and active inflammatory infiltrates were also present in areas of parenchymal loss. Multifocally, there were clusters of hematopoietic cells (granulocytic) in the liver and diffuse hyperplasia of granulocytic precursors, with concurrent decreases in erythroid cell precursors, in the spleen and bone marrow. The minimal hepatic fibrosis present in these mutants reflect the known decreased hepatic fibrogenic response of C57B1/6 mice to hepatic injury.

Gene Expression: LacZ activity was not detected in the panel of tissues by immunohistochemical analysis.

(c) Pathology/CAT Scan

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

CATScan: All 3 (−/−) mice analyzed (M-218, M-249, and F-254) exhibited reduced liver size.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized proteins directly or via the use of antibody agonists) to inhibit the immune response and thus ameliorate immune related disease.

The following tests were performed:

(1) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

(1) Hematology (Platelet Count):

The (−/−) mice exhibited a notably decreased mean platelet count and increased mean platelet volume when compared with their (+/+) littermates and the historical mean.

Thus, mutant mice deficient in the DNA110700-2716 gene resulted in a phenotype related to coagulation disorders. In this regard, PRO6182 polypeptides or agonists thereof would be useful in treating disorders related to abnormal blood coagulation such as hemophilia.

(2) Hematology (Red Blood Cell & Hemoglobin):

The (−/−) mice also exhibited decreased mean total white blood cell and absolute lymphocyte counts and an increased mean absolute monocyte count when compared with the levels for their (+/+) littermates and the historical means. The (−/−) mice also exhibited signs of anemia, including a decreased mean red blood cell count, hemoglobin concentration, and hematocrit and an increased red cell distribution width when compared with their (+/+) littermates and the historical means.

These results are related to a phenotype associated with anemia as well as a depressed immune system. Thus, PRO6182 polypeptides, agonists thereof or the encoding gene for PRO6182 polypeptides must be essential for normal red blood cell production and as such would be useful in the treatment of blood disorders associated with anemia or a low hematocrit. In addition, the (−/−) mice exhibit an impaired lymphocyte count important for the adaptive immune response.

(2) Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited decreased mean serum IgG1, IgG2a, IgG2b, and IgG3 levels when compared with those of their (+/+) littermates, the (+/+) mice in the project run, and the historical medians.

The serum immunoglobulin isotyping assay revealed that hemizygous mutant adults exhibited decreased serum IgG immunoglobulin levels. Thus, homozygous (−/−) mice showed an abnormally low serum immunoglobulins compared with the (+/+) littermates. Thus, the gene encoding PRO6182 is essential for making immunoglobulins (or gamma globulins). Gamma globulins have neutralization effects and to a lesser extent are important for activation of the complement system. These immunological abnormalities suggest that PRO6182 polypeptides or agonists thereof would be useful in stimulating the immune system and would find utility in the cases wherein this effect would be beneficial to the individual such as in the case of leukemia, and other types of cancer, and in immunocompromised patients, such as AIDS sufferers. Accordingly, inhibitors (antagonists) of PRO6182 polypeptides would inhibit the immune response and would be useful candidates for suppressing harmful immune responses, e.g. in the case of graft rejection or graft-versus-host diseases.

(3) Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRbAPC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The (−/−) mice exhibited an altered distribution of leukocyte subsets in the peripheral blood, characterized by a decreased mean percentage of CD8 cells and an increased mean percentage of monocytes when compared with the levels for their (+/+) littermates.

Tissue Specific FACS-Mouse: The (−/−) mice exhibited increased CD11b+CD11c− cells in spleen when compared with that of their (+/+) littermates.

In summary, the (−/−) mice exhibited increased IgM+, IgD+, and B220hi CD43− cells in bone marrow when compared with those of their (+/+) littermates. Mature naive B cells co-express IgM and IgD and leave the bone marrow to circulate through the lymphoid organs. By knocking out the gene encoding PRO6095 polypeptides, the mutant (−/−) mice exhibited increased percentages of B cell progenitors as well as the immunoglobulins that are expressed by these cells. Thus, PRO6095 polypeptides appear to act as a negative regulator for B cell differentiation and/or proliferation. In addition, the (−/−) mice exhibited a decreased mean percentage of CD8 cells. CD8 proteins are the co-receptor molecules which bind/recognize the MHC Class I molecules for cooperation with the T cell receptor in antigen recognition.

(4) Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sub-lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (+/−) mice exhibited increased mean serum TNF-alpha, MCP-1 and especially IL-6 responses to LPS challenge when compared with their (+/+) littermates and the historical means.

In summary, the LPS endotoxin challenge demonstrated that knockout mice deficient in the gene encoding PRO6182 polypeptides exhibit immunological abnormalities when compared with their wild-type littermates. In particular, the mutant mice exhibited an increased ability to elicit an immunological response (TNF-alpha, MCP-1 and IL-6 production) when challenged with the LPS endotoxin indicating a pro-inflammatory response. TNF-alpha, MCP-1 and IL-6 contribute to the later stages of B cell activation. TNF-alpha is an important inflammatory mediator. In addition, both TNF-alpha, MCP-1 and IL-6 play a critical role in inducing the acute phase response and systemic inflammation. TNF-alpha can substitute for the membrane-bound signal in macrophage activation (thus serving as an effector molecule).

(e) Phenotypic Analysis: Metabolism—Blood Chemistry

In the area of metabolism, targets may be identified for the treatment of diabetes or other metabolic disorders. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes.

Results:

Blood Chemistry: Both the male and female (−/−) mice exhibited increased mean serum alkaline phosphatase levels and decreased mean serum glucose levels when compared with the levels for their gender-matched (+/+) littermates and the historical means. The increased mean serum alkaline phosphatase levels are consistent with the observation of decreased mean bone-mineral density measurements as well as the observed liver abnormalities and chronic hepatitis.

(f) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

Sensorimotor Gating/Attention: The mutant (−/−) mice exhibited a trend towards increased prepulse inhibition of the acoustic startle reflex which is indicative of an enhanced sensorimotor gating/attention.

(g) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The female (−/−) mice exhibited decreased mean body weight when compared with that of their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The female (−/−) mice exhibited decreased mean bone mineral content, volumetric bone mineral density, and bone mineral density in total body, femurs, and vertebrae when compared with the levels for their gender-matched (+/+) littermates and the historical means.

Micro CT: The male (−/−) mice exhibited decreased mean vertebral trabecular bone volume, number, and connectivity density when compared with the levels for their gender-matched (+/+) littermates and the historical means.

The (−/−) mice analyzed by DEXA and bone micro CT analysis exhibited decreased bone measurements and decreased body mass measurements when compared with their (+/+) littermates, suggestive of abnormal bone disorders. The (−/−) mice exhibited a negative bone phenotype with abnormal decreased bone measurements reflective of bone metabolic disorders. The negative bone phenotype indicates that PRO6182 polypeptides or agonists thereof would be useful for maintaining bone homeostasis. In addition, PRO6182 polypeptides would be useful in bone healing or for the treatment of arthritis or osteoporosis, whereas antagonists (or inhibitors) of PRO6182 polypeptides or its encoding gene would lead to abnormal or pathological bone disorders including inflammatory diseases associated with abnormal bone metabolism including arthritis, osteoporosis and osteopenia. The (−/−) mice also showed signs of growth retardation.

66.57. Generation and Analysis of Mice Comprising DNA108722-2743 (UNQ2782) Gene Disruptions In these knockout experiments, the gene encoding PRO7170 polypeptides (designated as DNA108722-2743) (UNQ2782) was disrupted. The gene specific information for these studies is as follows: the mutated mouse gene corresponds to nucleotide reference: AB098732 *Mus musculus* mRNA for transmembrane mucin MUC20; protein reference: Q76184 ACCESSION:Q76184 NID: *Mus musculus* (Mouse). Transmembrane mucin MUC20; the human gene sequence reference: BC029267 *Homo sapiens* mucin 20, mRNA (cDNA clone MGC:34717 IMAGE:3851952); the human protein sequence corresponds to reference: Q8N307 ACCESSION:Q8N307 NID: *Homo sapiens* (Human). MUC20 protein.

The mouse gene of interest is Muc20 (mucin 20), ortholog of human MUC20. Aliases include MGC31081, FLJ14408, KIAA1359, and cDNA sequence BC026367.

MUC20 is an integral plasma membrane protein expressed primarily in renal proximal tubule epithelial cells. MUC20 is also expressed at moderate levels in placenta, colon, lung, prostate, and liver. MUC20 can interact with the Grb2 docking site on hepatocyte growth factor receptor MET, inhibiting MET signal transduction via the Grb2-Ras pathway. Moreover, MUC20 inhibits hepatocyte growth factor-induced matrix metalloproteinase expression and cell proliferation. These functions suggest that MUC20 plays a regulatory role in HGF signal transduction. MUC20 is upregulated in patients with moderate immunoglobulin A nephropathy and in experimental mouse models of glomerulonephritis, suggesting that MUC20 may play a role in the progression of glomerulonephritis and other renal injuries (Higuchi, Orita, Katsuya et al, *Mol Cell Biol* 24(17):7456-68 (2004); Higuchi, Orita, Nakanishi et al, *J Biol Chem* 279(3):1968-79 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 35 | 21 | 74 |
| Expected | 18.5 | 37 | 18.5 | 74 |

Chi-Sq.=1.69 Significance=0.42955735 (hom/n)=0.25 Avg. Litter Size=9

Mutation Information

Mutation Type: Homologous Recombination (standard)

Description: Coding exons 1 and 2 were targeted (NCBI accession NM_146071.1).

1. Wild-type Expression Panel: Expression of the target gene was detected in eye; lung; kidney; and stomach, small intestine, and colon among 13 adult tissue samples tested by RT-PCR.

2. QC Expression: Disruption of the target gene was confirmed by Southern hybridization analysis.

66.57.1. Phenotypic Analysis (for Disrupted Gene: DNA108722-2743 (UNQ2782)

(a) Overall Phenotypic Summary:

Mutation of the gene encoding the ortholog of human mucin 20 (MUC20) resulted in immunological abnormalities in (−/−) mice. Although T cell percentages are normal in blood and spleen, there is a reduction in naive T cells in lymph nodes. IgM B cells are increased in bone marrow, but significantly decreased in lymph nodes. In addition, the male mutants exhibited a decreased mean serum insulin level. Male knockout (−/−) mice showed increased total tissue mass and lean body mass. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

Tissue Specific FACS-Project: The (−/−) mice exhibited increased IgM+ and CD117+ B cells in bone marrow when compared with those of their (+/+) littermates. Although T cell percentages are normal in blood and spleen, there is a reduction in naive T cells in lymph nodes (especially CD4+). In addition, the (−/−) mice exhibited a higher proportion of dead cells, decreased B cells, and increased CD4 and CD8 T cells in lymph node (although there is a slight decrease of CD8 cells). The (−/−) mice also exhibited an increased CD11b+CD11c− cells (monocytes) in the spleen consistent with the observation of increased monocyte count in the hematological results.

Thus, knocking out the gene which encodes PRO7170 polypeptides causes numerous immunological abnormalities presenting a complex pattern. Essentially there is a pronounced decrease in the B cell population (including pre-B or pro-B cells, immature and mature B cells), as well as a decrease in the T cell population (especially in naive T cells) in the lymph nodes. From these observations, PRO7170 polypeptides or the gene encoding PRO7170 appears to be important for the development of the population of both B and T cells in the lymph nodes. Thus, PRO7170 polypeptides would be beneficial in enhancing or development of both B cell and T cell proliferation.

(c) Blood Chemistry

Blood chemistry analysis was performed using the COBAS Integra 400 (mfr: Roche) in its clinical settings for running blood chemistry tests on mice.

Insulin Data:

Test Description: Lexicon Genetics uses the Cobra II Series Auto-Gamma Counting System in its clinical settings for running quantitative Insulin assays on mice.

Results:

Insulin: The male (−/−) mice exhibited a decreased mean serum insulin level when compared with that of their gender-matched (+/+) littermates and the historical mean.

Mutant (−/−) mice deficient in the gene encoding PRO7170 polypeptides show a phenotype marked by low insulin levels which can be indicative of diabetes. Thus, antagonists or inhibitors of PRO7170 polypeptides or its encoding gene would mimic these metabolic related effects. On the other hand, PRO7170 polypeptides or agonists thereof would be useful in the prevention and/or treatment of such metabolic disorders as diabetes.

(d) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: Male (−/−) mice exhibited increased mean total tissue mass and lean body mass.

These studies suggest that mutant (−/−) non-human transgenic animals exhibit a negative phenotype that would be associated with obesity. Thus, PRO7170 polypeptides or agonists thereof are essential for normal growth and metabolic processes and especially would be important in the prevention and/or treatment of obesity or other growth related disorders.

66.58. Generation and Analysis of Mice Comprising DNA108670-2744 (UNQ2783) Gene Disruptions In these knockout experiments, the gene encoding PRO7171 polypeptides (designated as DNA108670-2744) (UNQ2783) was disrupted. The gene specific information for these studies is as follows: the mutated mouse gene corresponds to nucleotide reference: AA030296 ACCESSION: AA030296 NID:1497436 *Mus musculus* mi02d10.r1 Soares mouse placenta 4NbMP13.5 14.5 *Mus musculus* cDNA clone IMAGE:4592835\'; the human gene sequence reference: AY358621 *Homo sapiens* clone DNA108670 WWLS2783 (UNQ2783); the human protein sequence corresponds to reference: Q6UWV7 ACCESSION:Q6UWV7 NID: *Homo sapiens* (Human). WWLS2783.

The mouse gene of interest is represented by a partial cDNA (NCBI accession AA030296), which is orthologous with *Homo sapiens* clone DNA108670 WWLS2783 (UNQ2783). Aliases include hypothetical protein MGC52498 and PRO7171.

UNQ2783 is a putative secreted protein, consisting of 134 amino acids and containing a signal peptide (Clark et al, *Genome Res* 13(10):2265-70 (2003)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 23 | 32 | 12 | 67 |
| Expected | 16.75 | 33.5 | 16.75 | 67 |

Chi-Sq.=3.5 Significance=0.17377394 (hom/n)=0.2 Avg. Litter Size=8

Mutation Information

Mutation Type: Homologous Recombination (standard)

Description: Coding exon 1 was targeted.

1. Wild-type Expression Panel: Expression of the target gene was detected in embryonic stem (ES) cells and in all 13 adult tissue samples tested by RT-PCR, except spleen, kidney, liver, bone, and adipose.

2. QC Expression: Disruption of the target gene was confirmed by Southern hybridization analysis.

66.58.1. Phenotypic Analysis (for Disrupted Gene: DNA108670-2744 (UNQ2783)

(a) Overall Phenotypic Summary:

Mutation of the gene encoding the ortholog of a human putative secreted protein (UNQ2783) resulted in the female homozygous mutant mice exhibiting increased total tissue mass and body fat when compared with that of their gender-matched wild-type littermates and the historical mean. The mutant (−/−) mice also exhibited increased triglyceride levels. Microarray analysis shows overexpression of UNQ2783 in lymphoid tumors. Gene disruption was confirmed by Southern blot.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited increased mean total tissue mass, percent total body fat, and total fat mass when compared with the levels for their gender-matched (+/+) littermates and the historical means.

These results demonstrate that knockout mutant mice exhibit abnormal body mass and fat measurements marked by increased mean total tissue mass, lean body mass and increased mean percent total body fat and total fat mass when compared with their gender-matched (+/+) littermates and the historical means.

These studies show that mutant (−/−) non-human transgenic animals exhibit a negative phenotype that is associated with obesity. Thus, PRO7171 polypeptides or agonists thereof are essential for normal growth and metabolic processes and especially would be useful in the prevention and/or treatment of lipid storage diseases and/or obesity.

(c) Diagnostics—Heart Rate/Blood Pressure

Description

Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure. The single (−/−) male mouse also exhibited a decreased heart rate (>two standard deviations below historic means.

Heart rate is measured via a noninvasive tail-cuff method for four days on the Visitech BP-2000 Blood Pressure Analysis System. Heart rate is measured ten times each day for four days. The four days are then averaged to obtain a mouse's conscious heart rate.

Results:

Blood Pressure: The (−/−) mice exhibited decreased mean systolic blood pressure when compared with that of their gender-matched (+/+) littermates and the historical mean.

Heart Rate: The (−/−) mice exhibited an increased mean heart rate when compared with that of their gender-matched (+/+) littermates and the historical mean.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum triglycerides.

Blood Lipids

Procedure: A cohort of4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The (−/−) mice exhibited increased mean serum triglyceride levels when compared with their gender-matched (+/+) littermates and the historical means.

As summarized above, the (−/−) mice exhibited notably increased mean serum triglyceride levels when compared with their gender-matched (+/+) littermates and the historical means. Thus, mutant mice deficient in the PRO7171 gene can serve as a model for cardiovascular disease. PRO7171 polypeptides or its encoding gene would be useful in regulating blood lipids such as triglycerides. Thus, PRO7171 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

66.59. Generation and Analysis of Mice Comprising DNA 119535-2756 (UNQ2973) Gene Disruptions In these knockout experiments, the gene encoding PRO7436 polypeptides (designated as DNA119535-2756) (UNQ2973) was disrupted. The gene specific information for these studies is as follows: the mutated mouse gene corresponds to nucleotide reference: NM_177036 *Mus musculus* RIKEN cDNA C130022P09 gene (C130022P09Rik); protein reference: NP_796010 RIKEN cDNA C130022P09 gene [*Mus musculus*] gi|26347895|dbj|BAC37596.1| unnamed protein product [*Mus musculus*]; the human gene sequence reference: NM_020219 *Homo sapiens* carcinoembryonic antigen-like 1 (CEAL1); the human protein sequence corresponds to reference: Q7Z692 ACCESSION:Q7Z692 NID: *Homo sapiens* (Human). Carcinoembryonic antigen-like 1 precursor (UNQ2973/PRO7436).

The mouse gene of interest is RIKEN cDNA C130022P09 gene, ortholog of human CEAL1 (carcinoembryonic antigen-like 1). Aliases include DKFZp547N157.

CEAL1 is a putative type I integral membrane protein, containing a signal peptide, an immunoglobulin-like domain, and a transmembrane segment. A second CEAL1 variant lacks the immunoglobulin-like domain. By similarity to other carcinoembryonic antigen (CEA) family members, CEAL1 is likely to be located in the plasma membrane. CEAL1 is broadly expressed and may be overexpressed in subsets of clinically aggressive ovarian cancers. [Scorilas et al., *Gene* 310:79-89(2003)]

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 46 | 21 | 85 |
| Expected | 21.25 | 42.5 | 21.25 | 85 |

Chi-Sq.=2.38 Significance=0.30422124 (hom/n)=0.23 Avg. Litter Size=9

Mutation Information

Mutation Type: Homologous Recombination (standard)

Description: Coding exons 1 and 2 were targeted (NCBI accession NM_177036.2).

1. Wild-type Expression Panel: Expression of the target gene was detected in embryonic stem (ES) cells and in spinal cord; eye; thymus; spleen; lung; kidney; and stomach, small intestine, and colon among the 13 adult tissue samples tested by RT-PCR.

2. QC Expression: Disruption of the target gene was confirmed by Southern hybridization analysis.

66.59.1. Phenotypic Analysis (for Disrupted Gene: DNA119535-2756 (UNQ2973)

(a) Overall Phenotypic Summary:

Mutation of the gene encoding the ortholog of human carcinoembryonic antigen-like 1 (CEAL1) resulted in the homozygous mutant mice exhibiting a significant increase in mean skin fibroblast proliferation rate. The female (−/−) mice also showed decreased body weight and decreased total tissue mass with decreased levels of total body fat and cholesterol. Disruption of the target gene was confirmed by Southern hybridization analysis.

(b) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

Skin Proliferation: The female (−/−) mice exhibited a notably increased mean skin fibroblast proliferation rate when compared with that of their gender-matched (+/+) littermates and the historical mean.

Thus, homozygous mutant mice demonstrated a hyper-proliferative phenotype. As suggested by these observations, PRO7436 polypeptides or agonists thereof could function as tumor suppressors and would be useful in decreasing abnormal cell proliferation.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The female (−/−) mice exhibited decreased mean body weight when compared with that of their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The single female (−/−) mice available for analysis exhibited decreased total tissue mass, total fat mass, and percent total body fat when compared with their gender-matched (+/+) littermates and the historical means.

The (−/−) mice analyzed by DEXA exhibited notably decreased total tissue mass and lean body mass as well as decreased fat measurements when compared with their (+/+) littermates, suggestive of growth retardation in these mutants. This in conjunction with the observations of decreased body weight and length suggest a tissue wasting condition such as cachexia or other growth related disorders. Thus, PRO7436 polypeptides or agonists thereof would be useful in the treatment or prevention of growth disorders including cachexia or other tissue wasting diseases.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The female (−/−) mice exhibited a decreased mean serum cholesterol level when compared with that of their gender-matched (+/+) littermates and the historical mean.

As summarized above, the (−/−) mice exhibited notably increased mean serum cholesterol levels when compared with their gender-matched (+/+) littermates and the historical means. Thus, mutant mice deficient in the PRO7436 gene can serve as a model for cardiovascular disease. PRO7436 polypeptides or its encoding gene would be useful in regulating blood lipids such as cholesterol.

66.60. Generation and Analysis of Mice Comprising DNA 108700-2802 (UNQ3077) Gene Disruptions In these knockout experiments, the gene encoding PRO9912 polypeptides (designated as DNA108700-2802) (UNQ3077) was disrupted. The gene specific information for these studies is as follows: the mutated mouse gene corresponds to nucleotide reference: XM_137914 PREDICTED: *Mus musculus* similar to ectonucleotide pyrophosphatase/phosphodiesterase 7; alkaline sphingomyelinase (LOC238011); protein reference: XP_137914 ACCESSION:XP_137914 NID: gi 51766567 ref XP_137914.4 similar to ectonucleotide pyrophosphatase/phosphodiesterase 7; alkaline sphingomyelinase [*Mus musculus*]; the human gene sequence reference: BC041453 ACCESSION: BC041453 NID:27371235 *Homo sapiens Homo sapiens*, Similar to ectonucleotide pyrophosphatase/phosphodiesterase 5, clone IMAGE:5186743; the human protein sequence corresponds to reference: Q8IUS8 ACCESSION: Q8IUS8 NID: *Homo sapiens* (Human). Similar to ectonucleotide pyrophosphatase/phosphodiesterase 5 (Fragment).

The mouse gene of interest is "similar to ectonucleotide pyrophosphatase/phosphodiesterase 7; alkaline sphingomyelinase," ortholog of human ENPP7 (ectonucleotide pyrophosphatase/phosphodiesterase 7). Aliases include MGC50179, ALK-SMase, and alkaline sphingomyelinase.

ENPP7 is a an ectoenzyme expressed primarily in intestine and liver that catalyzes the hydrolysis of sphingomyelin. The protein consists of a signal peptide, a type I phosphodiesterase/nucleotide pyrophosphatase domain (Pfam accession PF01663), and a hydrophobic region near the C terminus that may loosely anchor the protein to the extracellular surface of the plasma membrane (Duan et al, 2003). Unlike other sphingomyelinases, ENPP7 displays optimal catalytic activity at alkaline pH, trypsin resistance, and specific bile salt dependence. The enzyme is particularly concentrated on the extracellular surface of the microvillar membrane of intestinal epithelial cells and in bile. ENPP7 likely plays a role in dietary sphingomyelin digestion, cholesterol absorption, and colonic tumorigenesis (Duan et al, *J Biol Chem* 278(40): 38528 (2003); Wu et al, *Carcinogenesis* 25(8):1327-33 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 22 | 37 | 11 | 70 |
| Expected | 17.5 | 35 | 17.5 | 70 |

Chi-Sq.=5.18 Significance=0.075020045 (hom/n)=0.19 Avg. Litter Size=8

Mutation Information

Mutation Type: Homologous Recombination (standard)

Description: Coding exons 1 through 3 were targeted (XM_137914.4).

1. Wild-type Expression Panel: Expression of the target gene was detected in brain; thymus; spleen; and stomach, small intestine, and colon among the 13 adult tissue samples tested by RT-PCR.

2. QC Expression: Disruption of the target gene was confirmed by Southern hybridization analysis.

66.60.1. Phenotypic Analysis (for Disrupted Gene: DNA108700-2802 (UNQ3077)

(a) Overall Phenotypic Summary:

Mutation of the gene encoding the ortholog of human ectonucleotide pyrophosphatase/phosphodiesterase 7 (ENPP7) resulted in both the male and female heterozygous and homozygous mutant mice exhibiting increased total tissue mass and total body fat when compared with the measurements for their gender-matched wild-type littermates and the historical means. In addition, the knockout (−/−) mice exhibited a decreased anxiety-like response. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. Feb. 15, 1996; 379(6566):606-12), and the GABA receptor (Homanics et al., Proc Natl Acad Sci USA. Apr. 15, 1997; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

Openfield2: The male (−/−) mice exhibited increased sum time-in-center when compared with the value for their gender-matched (+/+) littermates and the historical mean, suggesting a decreased anxiety-like response in the male mutants.

A notable difference was observed during open field activity testing. The male (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO9912 polypeptides and agonists thereof would be useful for the treatment or amelioration of the symptoms associated with depressive disorders.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male and female (+/−) and (−/−) mice exhibited increased total tissue mass and mean percent total body fat and total fat mass when compared with that of their gender-matched (+/+) littermates and the historical mean.

These studies show that both homozygous mutant (−/−) mice and heterozygous (+/−) mice exhibit a negative phenotype that is associated with obesity. Thus, PRO9912 polypeptides or agonists thereof are essential for normal growth and metabolic processes and especially would be useful in the prevention and/or treatment of lipid storage diseases, dyslipidemia and/or obesity.

66.61. Generation and Analysis of Mice Comprising DNA119474-2803 (UNQ3079) Gene Disruptions In these knockout experiments, the gene encoding PRO9917 polypeptides (designated as DNA119474-2803) (UNQ3079) was disrupted. The gene specific information for these studies is as follows: the mutated mouse gene corresponds to nucleotide reference: NM_145100 *Mus musculus* RIKEN cDNA 2700050C12 gene (2700050C12Rik); protein reference: Q9JJ96 ACCESSION:Q9JJ96 NID: *Mus musculus* (Mouse). *Mus musculus* brain cDNA, clone MNCb-0671; the human gene sequence reference: NM_144586 *Homo sapiens* hypothetical protein MGC29643 (MGC29643); the human protein sequence corresponds to reference: Q8N2G4 ACCESSION:Q8N2G4 NID: *Homo sapiens* (Human). Hypothetical protein PSEC0181.

The mouse gene of interest is RIKEN cDNA 2700050C12 gene, ortholog of human hypothetical protein MGC29643. Aliases include C530008016Rik.

MGC29643 is a putative secreted protein, consisting of a signal peptide and an Ly-6 antigen/uPA receptor-like domain. This domain occurs in urokinase-type plasminogen activator receptor and several glycosylphosphatidylinositol (GPI)-linked cell surface glycoproteins, such as leukocyte antigens. Proteins with this domain can function as cell adhesion or signaling molecules (SMART accession SM00134).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 18 | 29 | 16 | 63 |
| Expected | 15.75 | 31.5 | 15.75 | 63 |

Chi-Sq.=5.42 Significance=0.06653681 (hom/n)=0.23 Avg. Litter Size=8

Mutation Information

Mutation Type: Homologous Recombination (standard)

Description: Coding exons 1 and 2 were targeted (NCBI accession NM_145100.2).

1. Wild-type Expression Panel: Expression of the target gene was detected in brain; spinal cord; eye; thymus; lung; stomach, small intestine, and colon; and heart among the 13 adult tissue samples tested by RT-PCR.

2. QC Expression: Disruption of the target gene was confirmed by Southern hybridization analysis.

66.61.1. Phenotypic Analysis (for Disrupted Gene: DNA119474-2803 (UNQ3079)

(a) Overall Phenotypic Summary:

Mutation of the gene encoding the ortholog of human hypothetical protein MGC29643 resulted in the homozygous mutant mice exhibiting a decreased depressive-like response during tail suspension testing and a decreased anxiety-like response during stress-induced hyperthermia testing. In addition, both the male and female mutant mice exhibited increased heart rates when compared with those of their gender-matched wild-type littermates and the historical means. The mutant (−/−) mice also exhibited increased mean serum cholesterol levels and an impaired glucose tolerance. Both male and female (−/−) mice showed increased total tissue mass and total body fat. Disruption of the target gene was confirmed by Southern hybridization analysis.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) mice exhibited an increased mean serum cholesterol level when compared with that of their gender-matched (+/+) littermates and the historical mean.

As summarized above, the (−/−) mice exhibited notably increased mean serum cholesterol levels when compared with their gender-matched (+/+) littermates and the historical means. Thus, mutant mice deficient in the PRO9917 gene can serve as a model for cardiovascular disease. PRO9917 polypeptides or its encoding gene would be useful in regulating blood lipids such as cholesterol. Thus, PRO9917 polypeptides or agonists thereof would be useful in the treatment of such cardiovascular diseases as hypertension, atherosclerosis, heart failure, stroke, various coronary diseases, hypercholesterolemia, diabetes and/or obesity.

(c) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

The male (−/−) mice exhibited impaired glucose tolerance when placed on a high fat diet compared with their gender-matched (+/+) littermates and the historical means.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefore PRO9917 polypeptides (or agonists thereof) or its encoding gene would be useful in the treatment of conditions associated with an impaired glucose homeostasis and/or various cardiovascular diseases, including diabetes.

(d) Diagnostics—Heart Rate

Description

Heart rate is measured via a noninvasive tail-cuff method for four days on the Visitech BP-2000 Blood Pressure Analysis System. Heart rate is measured ten times each day for four days. The four days are then averaged to obtain a mouse's conscious heart rate.

Results:

Heart Rate: The (−/−) mice exhibited increased mean heart rates (~2 SD above the mean) when compared with those of their gender-matched (+/+) littermates and the historical means.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Tail Suspension2: The (−/−) mice exhibited decreased immobility time when compared with the value for their (+/+) littermates and the historical mean, which is indicative of a decreased depressive-like response in the mutants. Thus, antagonists (inhibitors) of PRO9917 would be expected to mimic this phenotype.

Functional Observational Battery (FOB) Test—Stress-induced Hyperthermia:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Stress-Induced Hyperthermia: The (−/−) mice exhibited resistance to stress-induced hyperthermia when compared with the value for their gender-matched (+/+) littermates and the historical mean, suggesting a decreased anxiety-like response in the mutants. Thus antagonists or inhibitors of PRO9917 polypeptides would be expected to mimic this phenotype and would be useful in the treatment of anxiety related disorders.

(f) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (−/−) mice exhibited increased total tissue mass and mean percent total body fat and total fat mass when compared with that of their gender-matched (+/+) littermates and the historical mean.

These studies show that mutant (−/−) mice exhibit a negative phenotype that is associated with obesity. Thus, PRO9917 polypeptides or agonists thereof are essential for normal growth and metabolic processes and especially would be useful in the prevention and/or treatment of lipid storage diseases, dyslipidemia and/or obesity.

66.62. Generation and Analysis of Mice Comprising DNA226874 (UNQ5291) Gene Disruptions In these knockout experiments, the gene encoding PRO37337 polypeptides (designated as DNA226874) (UNQ5291) was disrupted. The gene specific information for these studies is as follows: the mutated mouse gene corresponds to nucleotide reference: NM_010128 *Mus musculus* epithelial membrane protein 1 (Emp1); protein reference: P47801 ACCESSION:P47801 NID: *Mus musculus* (Mouse). Epithelial membrane protein-1 (EMP-1) (Tumor-associated membrane protein); the human gene sequence reference: NM_001423 *Homo sapiens* epithelial membrane protein 1 (EMP1); the human protein sequence corresponds to reference: P54849 ACCESSION:P54849 NID: *Homo sapiens* (Human). Epithelial membrane protein-1 (EMP-1) (Tumor-associated membrane protein) (CL-20) (B4B protein).

The mouse gene of interest is Emp1 (epithelial membrane protein 1), ortholog of human EMP1. Aliases include tumor-associated membrane protein, TMP, B4B protein, and CL-20.

EMP1 is a putative integral plasma membrane glycoprotein, consisting of four transmembrane segments within a single PMP22 family domain (Lobsiger et al, *Genomics* 36(3):379-87 (1996); Marvin et al, *J Biol Chem* 270(48): 28910-6 (1995); Ruegg et al, *J Immunol* 157(1):72-80 (1996)). EMP1 is structurally similar to claudins, which function as components of tight junctions, and voltage-dependent calcium channel gamma subunits, which function as regulatory subunits (InterPro accession IPRO04031). EMP1 is expressed primarily in neurons during development (Wulf and Suter, *Brain Res Dev Brain Res* 116(2):169-80 (1999)) but is also expressed in several other tissues, including tumors (Ben-Porath and Benvenisty, *Gene* 183(1-2):69-75 (1996)), squamous-different bronchial epithelial cells (Chen et al, *Genomics* 41(1):40-8 (1997)), and a subpopulation of immature B (Ruegg et al, *J Immunol* 157(1):72-80 (1996)). EMP1 may play a role in processes such as cell proliferation, development, differentiation, and cell death (Ruegg et al, *J Immunol* 157(1):72-80 (1996); Wang et al, *World J Gastroenterol* 9(3):392-8 (2003); Wulf and Suter, *Brain Res Dev Brain Res* 116(2):169-80 (1999)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 10 | 41 | 13 | 64 |
| Expected | 16 | 32 | 16 | 64 |

Chi-Sq.=1.35 Significance=0.5091564 (hom/n)=0.23 Avg. Litter Size=8

Mutation Information

Mutation Type: Homologous Recombination (standard)

Description: Coding exon 1 was targeted (NCBI accession NM_010128.3).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.62.1. Phenotypic Analysis (for Disrupted Gene: DNA226874 (UNQ5291)

(a) Overall Phenotypic Summary:

Mutation of the gene encoding the ortholog of human epithelial membrane protein 1 (EMP1) resulted in the mutant (−/−) mice exhibiting increased bone-mineral density measurements. Both the male and female (−/−) mice exhibited increased total tissue mass and total body fat. The female (−/−) mice also exhibited decreased mean systolic blood pressure when compared with their gender-matched (+/+) littermates and the historical mean. Embryonic expression showed a strong signal in the vasculature. Gene disruption was confirmed by Southern blot.

(b) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased total tissue mass and total body fat. In addition, the male (−/−) mice exhibited increased mean volumetric bone mineral density and bone mineral density in total body and femur when compared with their gender-matched (+/+) littermates and the historical means.

Micro CT: The male (−/−) mice exhibited increased mean femoral mid-shaft cross-sectional area when compared with their gender-matched (+/+) littermates and the historical mean.

These results demonstrate that knockout mutant mice exhibit abnormal bone metabolism with increased bone measurements similar to osteopetrosis characterized by increase in bone mass. The knockout (−/−) mice also exhibited signs of an obesity phenotype. Thus, it appears that PRO37337 polypeptides or agonists thereof would be useful in maintaining bone homeostasis and for bone remodeling by balancing osteoclast and osteoblast activity. In addition, antagonists or inhibitors of PRO37337 polypeptides or its encoding gene would be useful in bone healing or for the treatment of other bone related abnormalities associated with increased bone mineralization. PRO37337 polypeptides or agonists thereof would also be useful for maintaining normal lipid metabolism.

66.63. Generation and Analysis of Mice Comprising DNA227033 (UNQ5407) Gene Disruptions In these knockout experiments, the gene encoding PRO37496 polypeptides (designated as DNA227033) (UNQ5407) was disrupted. The gene specific information for these studies is as follows: the mutated mouse gene corresponds to nucleotide reference: NM_010762 *Mus musculus* myelin and lymphocyte protein, T-cell differentiation protein (Mal); protein reference: O09198 ACCESSION:O09198 NID: *Mus musculus* (Mouse). Myelin and lymphocyte protein (T-lymphocyte maturation-associated protein); the human gene sequence reference: NM_002371 ACCESSION:NM_002371 NID: gi 12408666 ref NM_002371.2 *Homo sapiens* mal, T-cell differentiation protein (MAL), transcript variant a; the human protein sequence corresponds to reference: P21145 ACCESSION:P21145 NID: *Homo sapiens* (Human). Myelin and lymphocyte protein (T-lymphocyte maturation-associated protein).

The mouse gene of interest is Mal (myelin and lymphocyte protein, T-cell differentiation protein), ortholog of human MAL (mal, T-cell differentiation protein). Aliases include MPV17, VIP17, myelin and lymphocyte protein, and T-cell differentiation protein MAL.

MAL is a lipophilic integral membrane protein, consisting of four transmembrane segments contained within a MARVEL (membrane-associated) domain (Pfam accession PF01284). MAL is found in glycolipid-enriched microdomains of epithelial cells, mature T-cells, and myelin-forming cells. Moreover, MAL has been detected in several subcellular locations, including endoplasmic reticulum, Golgi apparatus, large vesicles, and plasma membrane. The function of MAL is not clearly known; however, it may play a role in polarized glycolipid and protein transport, vesicle formation, and myelination (Marazuela and Alonso, *Histol Histopathol* 19(3):925-33 (2004); Puertollano et al, *J Biol Chem* 272(29):18311-5 (1997); Magyar et al, *Gene* 189(2):269-75 (1997); Erne et al, *J Neurochem* 82(3):550-62 (2002); Schaeren-Wieme 166(5):731-42 (2004); Saravanan et al, *Neurobiol Dis* 16(2):396-406 (2004); Frank et al, *J Neurochem* 73(2):587-97 (1999); Frank, *Prog Neurobiol* 60(6):531-44 (2000)).

Schaeren-Wiemers and colleagues (2004) investigated the physiological role of MAL using knockout mice. They showed that myelin formation and paranode-axon interface structure were abnormal in MAL-deficient mice but not in wild-type mice. The authors concluded that MAL is critical for paranode formation in the central nervous system. They proposed that MAL likely controls trafficking or sorting of various membrane components in oligodendrocytes.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 21 | 37 | 18 | 76 |
| Expected | 19 | 38 | 19 | 76 |

Chi-Sq.=2.09 Significance=0.35169184 (hom/n)=0.24 Avg. Litter Size=9

Mutation Information

Mutation Type: Homologous Recombination (standard)

Description: Coding exon 1 was targeted (NCBI accession NM_010762.2).

1. Wild-type Expression Panel: Expression of the target gene was detected in embryonic stem (ES) cells and in all 13 adult tissue samples tested by RT-PCR, except thymus, lung, liver, skeletal muscle, and bone.

2. QC Expression: Disruption of the target gene was confirmed by Southern hybridization analysis.

66.63.1. Phenotypic Analysis (for Disrupted Gene: DNA227033 (UNQ5407)

(a) Overall Phenotypic Summary:

Mutation of the gene encoding the ortholog of human mal, T-cell differentiation protein (MAL) resulted in the homozygous mutant mice exhibiting a decreased mean percentage of CD8 cells in the peripheral blood and decreased naive CD4 and CD8 T cells in the lymph nodes when compared with that of their wild-type littermates and the historical mean. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis/Tissue Specific FACS

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS3: The (−/−) mice exhibited an altered distribution of leukocyte subsets in the peripheral blood, characterized by a decreased mean percentage of CD8 cells and reduced percentages of naive CD4 and CD8 T cells in lymph nodes when compared with that of their (+/+) littermates.

By knocking out the gene encoding PRO37496 polypeptides, the mutant (−/−) mice exhibited a decreased mean percentage of CD8 cells and CD4 naive T cells. CD8 proteins are the co-receptor molecules which bind/recognize the MHC Class I molecules for cooperation with the T cell receptor in antigen recognition. Thus, PRO379496 polypeptides or agonists thereof would stimulate the immune system and would find utility in the cases wherein this effect would be beneficial to the individual such as in the case of leukemia, and other types of cancer, and in immunocompromised patients, such as AIDS sufferers. Accordingly, antagonists or inhibitors of PRO37496 polypeptides would be useful in inhibiting the immune response and would be useful candidates for suppressing harmful immune responses, e.g. in the case of graft rejection or graft-versus-host diseases.

In addition, the (−/−) mice exhibited decreased mean percentages of naive CD4 cells in the cell population when compared with their (+/+) littermates and the historical means. Thus, knocking out the gene which encodes PRO37496 polypeptides causes a decrease in the T cell population. From these observations, PRO37496 polypeptides or the gene encoding PRO37496 appears to act as a regulator of T cell proliferation. Thus, PRO37496 polypeptides would be beneficial in enhancing T cell proliferation.

66.64. Generation and Analysis of Mice Comprising DNA145841-2868 (UNQ5827) Gene Disruptions In these knockout experiments, the gene encoding PRO19646 polypeptides (designated as DNA145841-2868) (UNQ5827) was disrupted. The gene specific information for these studies is as follows: the mutated mouse gene corresponds to nucleotide reference: NM_172898 *Mus musculus* kin of IRRE like 2 (*Drosophila*) (Kirrel2); protein reference: Q7TSU7 ACCESSION:Q7TSU7 NID: *Mus musculus* (Mouse). Kin of IRRE-like 2; the human gene sequence reference: NM_199180 *Homo sapiens* kin of IRRE like 2 (*Drosophila*) (KIRREL2), transcript variant 3; the human protein sequence corresponds to reference: Q6UWL6 ACCESSION:Q6UWL6 NID: *Homo sapiens* (Human). Kin of IRRE-like protein 2 precursor (Kin of irregular chiasm-like protein 2) (Nephrin-like protein 3) (UNQ5827/PRO19646).

The mouse gene of interest is Kirrel2 (kin of IRRE like 2 [*Drosophila*]), ortholog of human KIRREL2. Aliases include NLG1, NEPH3, FILTRIN, MGC15718, DKFZP564A1164, C330019F22Rik, kin of irregular chiasm-like 2, X kin of IRRE like 2 (*Drosophila*), nephrin-like 3, and nephrin-like gene 1.

KIRREL2 is a type I integral plasma membrane protein that likely functions as a cell adhesion molecule. The protein contains a signal peptide, 5 Ig-like domains, a transmembrane segment, and a cytoplasmic C-terminus containing nine amino acids conserved in family members KIRREL and KIRREL3. The C-terminal domain of KIRREL2, like those of KIRREL and KIRREL3, is capable of interacting with podocin, a component of a structure (slit diaphragm) that functions as a glomerular filtration barrier. KIRREL2 is expressed in many different tissues but appears to be primarily expressed in pancreatic islet beta cells and in lymph nodes. Moreover, expression of KIRREL2 negatively correlates with T-cell invasion of pancreatic islets and development of diabetes in nonobese diabetic (NOD) mice. KIRREL2 may be involved in physiological processes such as glomerular filtration, pancreatic beta cell function, and immunity (Ihalmo et al, *Biochem Biophys Res Commun* 300(2):364-70 (2003); Sellin et al, *FASEB J* 17(1):115-7 (2003); Sun et al, *Genomics* 82(2): 130-42 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 14 | 31 | 13 | 58 |
| Expected | 14.5 | 29 | 14.5 | 58 |

Chi-Sq.=0.74 Significance=0.6907343 (hom/n)=0.22 Avg. Litter Size=8

Mutation Information

Mutation Type: Homologous Recombination (standard)

Description: Coding exons 1 through 3 were targeted (NCBI accession NM_172898.1).

1. Wild-type Expression Panel: Expression of the target gene was detected in embryonic stem (ES) cells and in brain; spinal cord; eye; and stomach, small intestine, and colon among the 13 adult tissue samples tested by RT-PCR.

2. QC Expression: Disruption of the target gene was confirmed by Southern hybridization analysis.

66.64.1. Phenotypic Analysis (for Disrupted Gene: DNA145841-2868 (UNQ5827)

(a) Overall Phenotypic Summary:

Mutation of the gene encoding the ortholog of human kin of IRRE like 2 (*Drosophila*) (KIRREL2) resulted in the mutant (−/−) mice exhibiting decreased mean body weight and length. In addition, the male (−/−) mice showed degeneration of the seminiferous tubules. Gene disruption was confirmed by Southern blot.

(b) Pathology

Microscopic: Both of the male (−/−) mice analyzed exhibited vacuolar degeneration of the seminiferous tubules. One (−/−) mouse (M-173) also exhibited a microvesicular fatty change in the centrilobular portion of the liver.

Gene Expression: Expression of the target gene was not detected in the panel of tissues by immunohistochemical analysis.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Body Weight and Length: The male (−/−) mice exhibited decreased mean body weight and mean body length when compared with their gender-matched (+/+) littermates and the historical mean. Thus, the mutant (−/−) mice exhibited a phenotype that could be associated with growth retardation. PRO19646 polypeptides or agonists thereof would be useful in promoting normal growth whereas inhibitors or antagonists of PRO19646 polypeptides would mimic this negative phenotype.

66.65. Generation and Analysis of Mice Comprising DNA188342 (UNQ5893) Gene Disruptions In these knockout experiments, the gene encoding PRO21718 polypeptides (designated as DNA188342) (UNQ5893) was disrupted. The gene specific information for these studies is as follows: the mutated mouse gene corresponds to nucleotide reference: BC024587 ACCESSION: BC024587 NID:19354042 *Mus musculus Mus musculus*, Similar to RIKEN cDNA 5830408F06 gene, clone MGC: 37716 IMAGE:5066283; protein reference: Q9D3G2 ACCESSION:Q9D3G2NID: *Mus musculus* (Mouse). 5830408F06Rik protein; the human gene reference: NM_020125 ACCESSION:NM_020125 NID: gi 9910341 ref NM_020125.1 *Homo sapiens* B lymphocyte activator macrophage expressed (BLAME); the human protein sequence corresponds to reference: Q9P0V8 ACCESSION: Q9P0V8 NID: *Homo sapiens* (Human). BCM-like membrane protein (Hypothetical protein FLJ90188).

The mouse gene of interest is Slamf8 (SLAM family member 8), ortholog of human SLAMF8. Aliases include Blame, SBBI42, 5830408F06Rik, B lymphocyte activator macrophage expressed, and BCM-like membrane protein precursor.

SLAMF8 is a type I plasma membrane protein that likely functions as a receptor or B-cell co-receptor. SLAMF8 is expressed in several lymphoid tissues, including lymph node, spleen, thymus, and bone marrow, and in interferon-gamma-activated peripheral blood mononuclear cells, adherence-activated monocytes and dendritic cell subsets. SLAMF8 likely plays a role in B-cell lineage commitment or B-cell receptor signaling (Kingsbury et al, *J Immunol* 166(9):5675-80 (2001)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 28 | 41 | 20 | 89 |
| Expected | 22.25 | 44.5 | 22.25 | 89 |

Chi-Sq.=2.35 Significance=0.308819 (hom/n)=0.26 Avg. Litter Size=10

Mutation Information

Mutation Type: Homologous Recombination (standard)

Description: Coding exons 1 and 2 were targeted (NCBI accession BC024587.1).

1. Wild-type Expression Panel: Expression of the target gene was detected in all 13 adult tissue samples tested by RT-PCR, except skeletal muscle, bone, and adipose.

2. QC Expression: Disruption of the target gene was confirmed by Southern hybridization analysis.

66.65.1. Phenotypic Analysis (for Disrupted Gene: DNA188342 (UNQ5893)

(a) Overall Phenotypic Summary:

Mutation of the gene encoding the ortholog of human SLAM family member 8 (SLAMF8) resulted in the mutant (−/−) mice exhibiting an impaired glucose tolerance. Gene disruption was confirmed by Southern blot.

(b) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Glucose Levels/Glucose Tolerance Test:

The (−/−) mice exhibited impaired glucose tolerance when placed on a high fat diet and when compared with their gender-matched (+/+) littermates and the historical means.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO21718 polypeptides (or agonists thereof) or its encoding gene would be useful in the treatment of conditions associated with an impaired glucose homeostasis and/or various cardiovascular diseases, including diabetes.

66.66. Generation and Analysis of Mice Comprising DNA 149911-2885 (UNQ5926) Gene Disruptions In these knockout experiments, the gene encoding PRO19820 polypeptides (designated as DNA149911-2885) (UNQ5926) was disrupted. The gene specific information for these studies is as follows: the mutated mouse gene corresponds to nucleotide reference: NM_026516 ACCESSION: NM_026516 NID: gi 21312655 ref NM_026516.1 *Mus musculus* RIKEN cDNA 2810417M05 gene (2810417M05Rik); protein reference: Q9CZ16 ACCESSION:Q9CZ16 NID: *Mus musculus* (Mouse). 2810417M05Rik protein; the human gene sequence reference: NM_152390 ACCESSION:NM_152390 NID: gi 22748834 ref NM_152390.1 *Homo sapiens* hypothetical protein MGC33926 (MGC33926); the human protein sequence corresponds to reference: Q8NBL3 ACCESSION: Q8NBL3 NID: *Homo sapiens* (Human). Hypothetical protein PLACE 1004322.

The mouse gene of interest is RIKEN cDNA 2810417M05 gene, ortholog of human hypothetical protein MGC33926.

Hypothetical protein MGC33926 is a 297-amino acid polypeptide, containing a signal peptide, three potential transmembrane segments, and a potential glycosylphosphatidylinositol (GPI) anchor site near the C-terminus. The predicted function and cell location of this hypothetical protein is ambiguous. Bioinformatic analyses suggest that the transmembrane domains are similar to those of claudins, integral plasma membrane proteins that typically function as components of tight junctions (TrEMBL accession Q8NBL3; InterPro accession IPRO06187). Other bioinformatic analyses suggest that the human protein is tethered to the extracellular surface of the plasma membrane by a GPI anchor.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 14 | 40 | 19 | 73 |
| Expected | 18.25 | 36.5 | 18.25 | 73 |

Chi-Sq.=2.42 Significance=0.29819727 (hom/n)=0.29 Avg. Litter Size=8

Mutation Information

Mutation Type: Homologous Recombination (standard)

Description: Coding exon 1 was targeted (NCBI accession NM_026516.1).

1. Wild-type Expression Panel: Expression of the target gene was detected in the 13 adult tissue samples tested by RT-PCR, except skeletal muscle; bone; stomach, small intestine, and colon; and adipose.

2. QC Expression: Disruption of the target gene was confirmed by Southern hybridization analysis.

66.66.1. Phenotypic Analysis (for Disrupted Gene: DNA149911-2885 (UNQ5926)

(a) Overall Phenotypic Summary:

Mutation of the gene encoding the ortholog of a human hypothetical protein (MGC33926) resulted in the male homozygous mutant mice exhibiting an increased anxiety-like response during stress-induced hyperthermia testing when compared with the level for their gender-matched wild-type littermates and the historical mean. Defecation was absent in 3 of 8 (−/−) mutant mice. Disruption of the target gene was confirmed by Southern hybridization analysis.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Results:

Stress-Induced Hyperthermia: The male (−/−) mice exhibited increased sensitivity to stress-induced hyperthermia when compared with the level for their gender-matched (+/+) littermates and the historical mean, suggesting an increased anxiety-like response in the mutants.

In summary, the functional observational testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO19820 polypeptides or agonists thereof would be useful in the treatment of such neurological disorders.

66.67. Generation and Analysis of Mice Comprising DNA168028-2956 (UNQ6098) Gene Disruptions In these knockout experiments, the gene encoding PRO21201 polypeptides (designated as DNA168028-2956) (UNQ6098) was disrupted. The gene specific information for these studies is as follows: the mutated mouse gene corresponds to nucleotide reference: NM_172416 ACCESSION: NM_172416 NID: gi 29293830 ref NM_172416.2 *Mus musculus* grey lethal osteopetrosis (Gl-pending); protein reference: Q8BGT0 ACCESSION:Q8BGT0 NID: *Mus musculus* (Mouse). Osteopetrosis associated transmembrane protein 1 precursor (Gray-lethal protein); the human gene sequence reference: NM_014028 ACCESSION:NM_014028 NID: gi 30025025 ref NM_014028.2 *Homo sapiens* grey-lethal osteopetrosis (GL); the human protein sequence corresponds to reference: Q86WC4 ACCESSION:Q86WC4 NID: *Homo sapiens* (Human). Osteopetrosis associated transmembrane protein 1 precursor (HSPC019) (UNQ6098/PRO21201).

The mouse gene of interest is Ostm1 (osteopetrosis associated transmembrane protein 1), ortholog of human OSTM1. Aliases include GL, GIPN, HSPC019, 1200002H13Rik, grey-lethal, grey-lethal osteopetrosis, grey lethal osteopetrosis, and GAIP-interacting protein N terminus.

OSTM1 is a putative E3 ubiquitin ligase expressed in osteoblasts, melanocytes, kidney, brain, thymus, spleen, and several other tissues. The protein is located in the cytosol and in cytoplasmic membrane compartments, particularly the basolateral membrane of the renal distal tubule. OSTM1 catalyzes the ubiquitination of the G protein alpha subunit i3 (GNAI3); thus, the protein likely regulates G protein-mediated signal transduction by degradation via the proteasome pathway. OSTM1 is also required for osteoclast and melanocyte maturation and function. Loss-of-function mutations in the OSTM1 gene cause osteopetrosis in humans and mice and coat color defect in mice (Chalhoub et al, *Nat Med* 9(4):395-406 (2003); Fischer et al, *Proc Natl Acad Sci USA* 100(14):8270-5 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 26 | 39 | 26 | 91 |
| Expected | 22.75 | 45.5 | 22.75 | 91 |

Chi-Sq.=3.18 Significance=0.20392561 (hom/n)=0.31 Avg. Litter Size=9

Mutation Information

Mutation Type: Homologous Recombination (standard)

Description: Coding exon 1 was targeted (NCBI accession NM_172416.2).

1. Wild-type Expression Panel: Expression of the target gene was detected in embryonic stem (ES) cells and in all 13 adult tissue samples tested by RT-PCR, except bone.

2. QC Expression: Disruption of the target gene was confirmed by Southern hybridization analysis.

66.67.1. Phenotypic Analysis (for Disrupted Gene: DNA168028-2956 (UNQ6098)

(a) Overall Phenotypic Summary:

Mutation of the gene encoding the ortholog of human osteopetrosis associated transmembrane protein 1 (OSTM1) resulted in the homozygous mutant mice being notably smaller than their wild-type littermates. The knockout (−/−) mice exhibited a failure to thrive, showed very reduced mean body weight, had a grey coat color, and possessed no teeth. Microscopic analysis revealed retinal degeneration, neuronal necrosis, and osteopetrosis in the homozygous mutants. The heterozygous mice exhibited an increased mean serum IL-6 response to LPS challenge when compared with their wild-type littermates and the historical mean. Disruption of the target gene was confirmed by Southern hybridization analysis.

(b) Pathology

Microscopic: The (−/−) mice exhibited diffuse marked osteopetrosis, diffuse moderate retinal degeneration, and multifocal mild neuronal necrosis. The medullary cavities of all long bones, vertebrae, and sternebra were filled with woven trabecular bone. Osteoclasts were increased in number and frequently had large vesicular nuclei (activated). In some areas, there were degenerating and necrotic osteoclasts. Osteoblasts were also numerous, although they tended to be elongated and fibroblastic. Bones in the skull, nasal trabeculae, and epiphyses of long bones contained abundant loosely woven bone and trabeculae. Molar teeth failed to erupt through the bony matrix and there were disorganized dysplastic odontogenic tissues at the base of the impacted incisor teeth. The retinal degeneration affected the receptor and external nuclear layers. Numerous macrophages were present in the photoreceptor layer. In the cerebral cortex, there was laminar degeneration and necrosis/apoptosis of layer IV/V neurons. Similarly affected neurons were also present in the hippocampus and dentate gyrus. All of the mutant (−/−) mice organs were small, but most were proportional to the weight of the mice (½ to ⅓ the weight of the (+/+) littermates). However, the thymus tended to be smaller (about 1/10th the weight for (+/+) littermates).

Gene Expression: LacZ activity was not detected in the panel of tissues by immunohistochemical analysis.

(c) Bone Metabolism & Body Diagnostics (1) Tissue Mass & Lean Body Mass Measurements—Dexa Dexa Analysis—Test Description:

Procedure: A cohort of wild type, heterozygotes and homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Obvious General Observations: The (−/−) mice were small with a grey coat color and no teeth. The mutants either died or were sacrificed due to their failure to thrive.

Weight: The (−/−) mice exhibited notably decreased mean body weight when compared with their gender-matched (+/+) littermates and the historical means at the 2- and 4-week measurements. Length data was not collected for the (−/−) mice but in the gross photo the (−/−) mice appeared to be shorter than the (+/+) sibling.

Thus, the mutant (−/−) mice exhibited a phenotype that could be associated with reduced viability and growth retardation. The absence of teeth is consistent with the pathological observations that the molar teeth failed to erupt though the bony matrix. Thus, PRO21201 polypeptides or agonists thereof appear to be essential for normal growth and development, whereas inhibitors or antagonists of PRO21201 polypeptides would mimic this negative phenotype.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sub-lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (+/−) mice exhibited increased mean serum IL-6 responses to LPS challenge when compared with their (+/+) littermates and the historical means.

In summary, the LPS endotoxin challenge demonstrated that knockout mice deficient in the gene encoding PRO21201 polypeptides exhibit immunological abnormalities when compared with their wild-type littermates. In particular, the mutant mice exhibited an increased ability to elicit an immunological response (IL-6 production) when challenged with the LPS endotoxin indicating a pro-inflammatory response. IL-6 contribute to the later stages of B cell activation. In addition, IL-6 plays a critical role in inducing the acute phase response and systemic inflammation.

66.68. Generation and Analysis of Mice Comprising DNA154095-2998 (UNQ6115) Gene Disruptions In these knockout experiments, the gene encoding PRO20026 polypeptides (designated as DNA154095-2998) (UNQ6115) was disrupted. The gene specific information for these studies is as follows: the mutated mouse gene corresponds to nucleotide reference: NM_134437 ACCESSION: NM_134437 NID: gi 24025661 ref NM_134437.1 *Mus musculus* similar expression to Fgf genes (Sef-pending); protein reference: Q8JZL1 ACCESSION:Q8JZL1 NID: *Mus musculus* (Mouse). Transmembrane protein (Interleukin 17 receptor-like protein long form); the human gene sequence reference: AF494208 *Homo sapiens* interleukin 17 receptor-like protein long form (IL17RLM); the human protein sequence corresponds to reference: Q8NFM7 ACCESSION: Q8NFM7 NID: *Homo sapiens* (Human). Interleukin 17 receptor-like protein long form.

The mouse gene of interest is I117rd (interleukin 17 receptor D), ortholog of human IL17RD. Aliases include Sef, Sef-S, similar expression to Fgf genes, IL17RLM, FLJ35755, DKFZp434N1928, and similar expression to FGF protein.

IL17RD is a type I plasma membrane protein that likely functions as a receptor or signaling molecule involved in feedback inhibition of fibroblast growth factor (FGF) signaling and in activation of pathways regulating apoptosis. A shorter cytosolic isoform of IL17RD generated by alternative splicing also inhibits FGF signaling. IL17RD inhibits FGF signaling by blocking FGF receptor tyrosine phosphorylation and RAS/ERK MAP kinase pathway. IL17RD stimulates apoptosis by activating TAK1/c-JunN-terminal kinase pathway. IL17RD is expressed in vascular endothelial cells, in highly vascularized tissues, such as kidney, colon, skeletal muscle, heart, and small intestine, and in ductal epithelial cells of kidney, salivary glands, and seminal vesicles. Expression of the cytosolic form of IL17RD is apparently more limited. IL17RD likely plays a role in processes such as cell proliferation, cell migration, differentiation, apoptosis, and angiogenesis (Yang et al, *J Biol Chem* 279(37) :38099-102 (2004); Torii et al, *Dev Cell* 7(1):33-44 (2004); Preger et al, *Proc Natl Acad Sci USA* 101(5): 1229-34 (2004); Xiong et al, *J Biol Chem* 278(50):50273-82 (2003); Yang et al, *J Biol Chem* 278(35):33232-8 (2003); Kovalenko et al, *J Biol Chem* 278(16):14087-91 (2003); Furthauer et al, *Nat Cell Biol* 4(2): 170-4 (2002); Tsang et al, *Nat Cell Biol* 4(2):165-9 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 16 | 25 | 14 | 55 |
| Expected | 13.75 | 27.5 | 13.75 | 55 |

Chi-Sq.=0.2 Significance=0.9048374 (hom/n)=0.25 Avg. Litter Size=8

Mutation Information

Mutation Type: Homologous Recombination (standard)

Coding exon 4 was targeted (NCBI accession NM_134437.1).

1. Wild-type Expression Panel: Expression of the target gene was detected in all 13 adult tissue samples tested by RT-PCR, except thymus; liver; stomach, small intestine, and colon; and adipose.

2. QC Expression: Disruption of the target gene was confirmed by Southern hybridization analysis.

66.68.1. Phenotypic Analysis (for Disrupted Gene: DNA154095-2998 (UNQ6115)

(a) Overall Phenotypic Summary:

Mutation of the gene encoding the ortholog of human interleukin 17 receptor D (IL17RD) resulted in the male homozygous mutant mice being larger than their gender-matched wild-type littermates, exhibiting increased body weight and length, increased total tissue mass, and increased lean body mass. The male (−/−) mice showed increased total fat mass with a similar trend in serum triglyceride levels. The male (−/−) mice also showed decreased blood pressure and an atrophic testes. The male mutants exhibited enhanced glucose tolerance. Disruption of the target gene was confirmed by Southern hybridization analysis.

(b) Cardiology—Blood Pressure

Test Description: Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results

Blood Pressure: The male (−/−) mice exhibited decreased blood pressure when compared with that of the (+/+) littermates and the historical mean.

(c) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Oral Glucose Tolerance: The male (−/−) mice exhibited enhanced glucose tolerance when compared with that of their gender-matched (+/+) littermates and the historical means.

In these studies the mutant (−/−) mice showed an increased or enhanced glucose tolerance in the presence of normal fasting glucose at all 3 intervals tested when compared with their gender-matched (+/+) littermates and the historical means. Thus, knockout mice exhibited an increased insulin sensitivity or the opposite phenotypic pattern of an impaired glucose homeostasis, and as such antagonists (inhibitors) to PRO20026 polypeptides or its encoding gene would be useful in the treatment of an impaired glucose homeostasis.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The (−/−) mice exhibited increased mean serum triglyceride levels when compared with their gender-matched (+/+) littermates and the historical means.

As summarized above, the (−/−) mice exhibited notably increased mean serum triglyceride levels when compared with their gender-matched (+/+) littermates and the historical means. Thus, mutant mice deficient in the PRO20026 gene can serve as a model for cardiovascular disease. PRO20026 polypeptides or its encoding gene would be useful in regulating blood lipids such as triglycerides. Thus, PRO20026 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

(e) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

DEXA: The male (−/−) mice exhibited increased mean total tissue mass, lean body mass, and total fat mass when compared with that of their gender-matched (+/+) littermates and the historical means.

These studies suggest that mutant (−/−) non-human transgenic animals exhibit a negative phenotype that would be associated with obesity. Thus, PRO20026 polypeptides or agonists thereof are essential for normal growth and metabolic processes and especially would be important in the prevention and/or treatment of obesity.

CAT Scan: The two male (−/−) mice analyzed (M-75 and M-100) exhibited atrophic left testes.

66.69. Generation and Analysis of Mice Comprising DNA166819-P1381R1C1P1 (UNQ6129) Gene Disruptions In these knockout experiments, the gene encoding PRO20110 polypeptides (designated as DNA166819-1381R1C1P1) (UNQ6129) was disrupted. The gene specific information for these studies is as follows: the mutated mouse gene corresponds to nucleotide reference: NM_145856 ACCESSION:NM_145856 NID: gi 22003915 ref NM_145856.1 *Mus musculus* interleukin 17F (IL-17F); protein reference: Q8K4C3 ACCESSION:Q8K4C3 NID: *Mus musculus* (Mouse). IL-17F; the human gene sequence reference: NM_052872 *Homo sapiens* interleukin 17F (IL17F), transcript variant 1; the human protein sequence corresponds to reference: Q6NSI0 ACCESSION:Q6NSI0 NID: *Homo sapiens* (Human). Interleukin 17F, isoform 1.

The mouse gene of interest is I117f (interleukin 17F), ortholog of human IL17F. Aliases include ML1, IL24, ML-1, IL-24, IL-26, IL-17F, cytokine ML-1, and interleukin-24.

IL17F is a cytokine that functions as a signal-transducing ligand, stimulating the production of inflammatory cytokines and chemokines typical of a T-cell helper type 1 (Th1) response. IL17F stimulates production of IL-6, IL-8, granulocyte-macrophage colony stimulating factor (GM-CSF), IL-2, transforming growth factor-beta, and monocyte chemoattractant protein-1 in bronchial epithelial cells or vascular endothelial cells (Kawaguchi et al, *J Biol Chem* 277 (18):15229-32 (2002); Starnes et al, *J Immunol* 167(8):4137-40 (2001); Numasake et al, *Immunol Lett* 95(2):175-84 (2004); Kawaguchi et al, *J Allergy Clin Immunol* 114 (2):444-50 (2004)). The signaling pathway for IL17F-induced cytokine or chemokine production likely involves activation of extracellular signal-regulated kinase (ERK) ½ (Kawaguchi et al, *J Biol Chem* 277(18):15229-32 (2002); Kawaguchi et al, *J Allergy Clin Immunol* 114(2):444-50 (2004)). IL17F plays a role in inhibiting angiogenesis (Starnes et al, *J Immunol* 167 (8):4137-40 (2001), inducing neutrophilia, and amplifying antigen-induced allergic responses (Oda et al, *Am J Respir Crit Care Med* 171(1):12-18 (2004)).

Targeted or gene trap mutations are generated in strain $129SvEv^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 20 | 40 | 18 | 78 |
| Expected | 19.5 | 39 | 19.5 | 78 |

Chi-Sq.=9.65 Significance=0.008026555 (hom/n)=0.18 Avg. Litter Size=8

Mutation Information

Mutation Type: Homologous Recombination (standard)

Description: Coding exons 1 and 2 were targeted (NCBI accession NM_145856.1).

1. Wild-type Expression Panel: Expression of the target gene was detected in embryonic stem (ES) cells and, in brain, spinal cord, thymus, spleen, and kidney among the 13 adult tissue samples tested by RT-PCR.

2. QC Expression: Disruption of the target gene was confirmed by Southern hybridization analysis.

66.69.1. Phenotypic Analysis (for Disrupted Gene: DNA166819-P1381R1C1P1 (UNQ6129)

(a) Overall Phenotypic Summary:

Mutation of the gene encoding the ortholog of human interleukin 17F (IL17F) resulted in an increased anxiety-related response in (−/−) mice. In addition, the mutant (−/−) mice exhibited increased mean serum IgG1, IgG2a and IgG3 levels; increased mean body weight and length as well as increased total tissue mass, lean body mass and total body fat percent and mass with increased bone mineral density measurements. The (−/−) mice exhibited increased mean trabecular bone volume, number and connectivity density. The male (−/−) mice also showed an increasing trend for elevated cholesterol and triglyceride levels. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited increased mean serum IgG1, IgG2a and IgG3 levels when compared with those of their (+/+) littermates, the (+/+) mice within the project run, and the historical medians.

Mutant (−/−) mice exhibited elevation of IgG1, IgG2a and IgG3 serum immunoglobulins. These immunoglobulins have neutralization effects and to a lesser extent are important for activation of the complement system. The observed phenotype suggests that the PRO20110 polypeptide is a negative regulator of inflammatory responses. These immunological abnormalities suggest that inhibitors (antagonists) of PRO20110 polypeptides would be useful in stimulating the immune system and would find utility in the cases wherein this effect would be beneficial to the individual such as in the case of leukemia, and other types of cancer, and in immunocompromised patients, such as AIDS sufferers. Accordingly, PRO20110 polypeptides or agonists thereof would be useful in inhibiting the immune response and would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Results:

Stress-Induced Hyperthermia: The male (−/−) mice exhibited increased sensitivity to stress-induced hyperthermia when compared with the level for their gender-matched (+/+) littermates and the historical mean, suggesting an increased anxiety-like response in the mutants.

In summary, the functional observational testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO20110 polypeptides or agonists thereof would be useful in the treatment of such neurological disorders.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: Both the male and female (−/−) mice exhibited increased mean serum cholesterol and triglyceride levels when compared with those of their gender-matched (+/+) littermates and the historical means.

As summarized above, the (−/−) mice exhibited notably increased mean serum cholesterol and triglyceride levels when compared with their gender-matched (+/+) littermates and the historical means. Thus, mutant mice deficient in the PRO20110 gene can serve as a model for cardiovascular disease. PRO20110 polypeptides or its encoding gene would be useful in regulating blood lipids such as cholesterol and triglycerides. Thus, PRO20110 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

(e) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Body Weight and Length: The male (−/−) mice exhibited increased mean body weight and mean body length when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited increased mean total tissue mass when compared with that of their gender-matched (+/+) littermates. The male mutants also exhibited increased mean lean body mass, percent total body fat, and total fat mass; the female mutants exhibited increased mean percent total body fat and total fat mass.

Micro CT: The male (−/−) mice exhibited increased mean vertebral trabecular bone volume, number and connectivity density when compared with their gender-matched (+/+) littermates and the historical means.

The (−/−) mice analyzed by DEXA and bone micro CT analysis exhibited increased bone measurements when compared with their (+/+) littermates, suggestive of abnormal bone disorders such as osteopetrosis. However, the mutant (−/−) mice also exhibited increased body weight and length and total tissue mass and lean body mass. The female (−/−) mice exhibited an increased mean percentage of body fat and fat mass suggestive of an obesity. These observations suggest that mutant mice deficient in the gene which encodes PRO20110 polypeptides leads to metabolic disorders associated with accumulation of fat but also abnormal bone measurements reflective of osteopetrosis. Thus, PRO20110 polypeptides or agonists thereof would be useful in the treatment of bone related disorders such as osteopetrosis or would be useful in maintaining bone homeostasis. In addition, PRO20110 polypeptides would be useful in maintaining normal lipid metabolism. As well as useful in the treatment of obesity and hypercholesterolemia and hypertriglyceridemia. Antagonists (or inhibitors) of PRO20110 polypeptides or its encoding gene would lead to abnormal or pathological bone disorders including inflammatory diseases associated with abnormal bone metabolism.

66.70. Generation and Analysis of Mice Comprising DNA185171-2994 (UNQ6507) Gene Disruptions In these knockout experiments, the gene encoding PRO23203 polypeptides (designated as DNA185171-2994) (UNQ6507) was disrupted. The gene specific information for these studies is as follows: the mutated mouse gene corresponds to nucleotide reference: AK052981 *Mus musculus* 15 days embryo head cDNA, RIKEN full-length enriched library, clone:D930007L06 product:weakly similar to TUMOR SUPPRESSOR PHYDE [*Rattus norvegicus*], full insert sequence; protein reference: Q8BWB6 ACCESSION: Q8BWB6 NID: *Mus musculus* (Mouse). *Mus musculus* 15 days embryo head cDNA, RIKEN full-length enriched library, clone:D930007L06 product:weakly similar to TUMOR SUPPRESSOR PHYDE; the human gene sequence reference: NM_152999 ACCESSION:NM_152999 NID: gi 25092600 ref NM_152999.2 *Homo sapiens* six transmembrane epithelial antigen of prostate 2 (STEAP2); the human protein sequence corresponds to reference: Q8NFT2 ACCESSION:Q8NFT2 NID: *Homo sapiens* (Human). Six-transmembrane epithelial antigen of prostate 2.

The mouse gene of interest is Steap2 (six transmembrane epithelial antigen of prostate 2), ortholog of human STEAP2. Aliases include STMP, IPCA1, IPCA-1, STAMP1, PCANAP1, 4921538B17Rik, prostate cancer associated gene 1, six transmembrane prostate protein, prostate cancer associated protein 1, and SixTransMembrane Protein of Prostate 1.

STEAP2 is an integral membrane protein located primarily in the plasma membrane and trans-Golgi network but also in cytosolic vesicular tubule structures and in endosomes. The protein contains a six transmembrane (6TM) domain that is structurally similar to the 6TM heme-binding domains of NADPH oxidase family members and TedZ bacterial oxidoreductase family members. Expression of STEAP2 is high in prostate gland epithelium but is detectable in other tissues, such as heart, brain, kidney, pancreas, and ovary. STEAP2 may play a role in vesicle transport from the Golgi apparatus to the plasma membrane or in regulated secretion. Because STEAP2 expression is generally higher in prostate cancer cells than in normal prostate epithelial cells, STEAP2 may also play a role in development or progression of prostate cancer (Korkmaz et al, *J Biol Chem* 277(39):36689-96 (2002); Porkka et al, *Lab Invest* 82(11):1573-82 (2002); Sanchez-Pulido et al, *BMC Cancer* 4(1):98 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 20 | 42 | 20 | 82 |
| Expected | 20.5 | 41 | 20.5 | 82 |

Chi-Sq.=0.43 Significance=0.80654144 (hom/n)=0.27 Avg. Litter Size=8

Mutation Information

Mutation Type: Homologous Recombination (standard)

Description: The exon preceding coding exon 1 and coding exon 1 were targeted (NCBI accession AK052981.1).

1. Wild-type Expression Panel: Expression of the target gene was detected in embryonic stem (ES) cells and in all 13 adult tissue samples tested by RT-PCR.

2. QC Expression: Disruption of the target gene was confirmed by Southern hybridization analysis.

66.70.1. Phenotypic Analysis (for Disrupted Gene: DNA185171-2994 (UNQ6507)

(a) Overall Phenotypic Summary:

Mutation of the gene encoding the ortholog of human six transmembrane epithelial antigen of prostate 2 (STEAP2) resulted in the homozygous mutant mice exhibiting increased mean serum IgG1 and IgG2a responses to ovalbumin challenge when compared with those of their wild-type littermates and the historical means. In addition, the female (−/−) mice exhibited increased anxiety during circadian rhythm testing. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Feund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

Ovalbumin: The (−/−) mice exhibited increased mean serum IgG1 and IgG2a responses to ovalbumin challenge when compared with those of their (+/+) littermates and the historical means.

In summary, the ovalbumin challenge studies indicate that knockout mice deficient in the gene encoding PRO23203 polypeptides exhibit immunological abnormalities when compared with their wild-type littermates.

In particular, the mutant mice exhibited an increased ability to elicit an immunological response when challenged with the T-cell dependent OVA antigen. Thus, antagonists (inhibitors) of PRO23203 polypeptides would be useful for stimulating the immune system and would find utility in the cases wherein this effect would be beneficial to the individual such as in the case of leukemia, and other types of cancer, and in immunocompromised patients, such as AIDS sufferers. Accordingly, PRO23203 polypeptides or agonists thereof, would be useful for inhibiting the immune response and thus would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

Circadian: The female (−/−) mice exhibited increased median ambulatory counts during the 12-hour habituation and both dark periods when compared with the number for their gender-matched (+/+) littermates and the historical means.

These observations during home-cage activity testing is indicative of hyperactivity and increased anxiety which is consistent with neurological disorders such as generalized anxiety disorders, attention deficit hyperactivity disorder, obsessive compulsive disorder, schizophrenia, cognitive disorders generalized anxiety disorder.

66.71. Generation and Analysis of Mice Comprising DNA171732-3100 (UNQ9574) Gene Disruptions In these knockout experiments, the gene encoding PRO35250 polypeptides (designated as DNA171732-3100) (UNQ9574) was disrupted. The gene specific information for these studies is as follows: the mutated mouse gene corresponds to nucleotide reference: XM_128001 PREDICTED: *Mus musculus* GPI-anchored HDL-binding protein 1 (Gpihbp1); protein reference: Q9D1N2 ACCESSION: Q9D1N2 NID: *Mus musculus* (Mouse). 1110002J19RIK PROTEIN; the human gene sequence reference: NM_178172 *Homo sapiens* high density lipoprotein-binding protein (LOC338328); the human protein sequence corresponds to reference: Q6P3T2 ACCESSION: Q6P3T2 NID: *Homo sapiens* (Human). High density lipoprotein-binding protein.

The mouse gene of interest is Gpihbp1 (GPI-anchored HDL-binding protein 1), ortholog of human "high density lipoprotein-binding protein." Aliases include GPI-HBP1 and 1110002J19Rik.

Gpihbp1 is a glycosylphosphatidylinositol (GPI)-anchored extracellular membrane protein that functions as a high-density lipoprotein-binding protein. The protein contains a signal peptide, an acidic region, an Ly-6 domain highly conserved among the lymphocyte antigen family, and a hydrophobic C-terminal region. Gpihbp1 is capable of mediating selective lipid uptake but not cholesterol efflux. Gpihbp1 is expressed in liver Kupfer cells, liver sinusoidal epithelium, cardiac muscle cells, bronchial epithelial cells, and alveolar macrophages and is likely to play a role in initial uptake of HDL cholesterol (Ioka et al, *J Biol Chem* 278(9): 7344-9 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

| | wt | het | hom | Total |
|---|---|---|---|---|
| Observed | 14 | 58 | 14 | 86 |
| Expected | 21.5 | 43 | 21.5 | 86 |

Chi-Sq.=13.97 Significance=9.2566316E-4 (hom/n)=0.18 Avg. Litter Size=9

Mutation Information

Mutation Type: Homologous Recombination (standard)

Description: Coding exons 1 through 4 were targeted (NCBI accession BC061225).

1. Wild-type Expression Panel: Expression of the target gene was detected in all 13 adult tissue samples tested by RT-PCR, except brain, eye, skeletal muscle, and bone.

2. QC Expression: Disruption of the target gene was confirmed by Southern hybridization analysis.

66.71.1. Phenotypic Analysis (for Disrupted gene: DNA171732-3100 (UNQ9574)

(a) Overall Phenoptypic Summary:

Mutation of the gene encoding the ortholog of human "high density lipoprotein-binding protein" resulted in lipemia in (−/−) mice. Blood chemistry measurements and microscopic analysis revealed that the homozygous mutant mice were notably lipemic. The greatly increased concentration of serum lipids in the mutants affected several other Level 1 parameters, including the total bilirubin measurement and the fundus and angiogram analyses. In addition, the homozygous mutant mice exhibited signs of anemia and immunological abnormalities when compared with the measurements for their wild-type littermates and the historical means. Disruption of the target gene was confirmed by Southern hybridization analysis.

(b) Pathology

Microscopic: Among the 6 (−/−) mice examined, 4 exhibited markedly hyperlipidemic blood at necropsy. Histopathology revealed increased amounts of pale-staining acellular material in scattered blood vessels. In the 4 (−/−) mice with lipemia, the only notable histopathologic alteration was in the cytoplasm of all cells in the zona fasciculata of the adrenal gland which is consistent with the altered lipid/cholesterol uptake or metabolism in these cells. Instead of the normal microvacuolated cytoplasm typical of these cells in normal tissue, the cytoplasm of these cells lacked microvacuoles in the hyperlipidemic mice. Instead, the cytoplasm of the zona fasciculata cells in the mutants was uniformly finely granular and eosinophilic, which would be consistent with altered lipid/cholesterol uptake or metabolism in these cells.

Gene Expression: LacZ activity was not detected in the panel of tissues by immunohistochemical analysis.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

Fundus: The (−/−) mice all exhibited semi-transparent retinal vessels that appeared pink in color. The bloodstream could be observed under the fundus microscope, suggesting anomalies of the retinal vasculature in the mutants.

Angiogram: The main retinal vasculature of the (−/−) mice could be clearly visualized with blue light illumination before administration of the fluorescein dye, suggesting increased fluorescent material was already present in the blood of the mutant mice. After administration of the fluorescein dye, no notable difference was observed between the (−/−) mice and their (+/+) littermates.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc. Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized proteins directly or via the use of antibody agonists) to inhibit the immune response and thus ameliorate immune related disease.

The following tests were performed:

(1) Hematology

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited a notably increased mean absolute neutrophil count and a decreased mean absolute lymphocyte count when compared with those of their (+/+) littermates and the historical means. The (−/−) mice also exhibited a decreased mean red blood cell count and a decreased mean hematocrit level. In addition, the (−/−) mice exhibited increased mean corpuscular volume, mean corpuscular hemoglobin, mean corpuscular hemoglobin concentration, and red blood cell distribution width, suggesting that the red blood cells in the mutant mice are a little larger than normal with increased variation in size.

These results are related to a phenotype associated with anemia. Thus, PRO35250 polypeptides, agonists thereof or the encoding gene for PRO35350 polypeptides must be essential for normal red blood cell production and as such would be useful in the treatment of blood disorders associated with anemia or a low hematocrit.

(2) Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

Acute Phase Response: The (−/−) mice exhibited a notably increased mean serum IL-6 response to LPS challenge when compared with that of their (+/+) littermates and the historical mean.

In summary, the LPS endotoxin challenge demonstrated that knockout mice deficient in the gene encoding PRO35250 polypeptides exhibit immunological abnormalities when compared with their wild-type littermates.

In particular, the mutant mice exhibited an increased ability to elicit an immunological response (IL-6 production) when challenged with the LPS endotoxin indicating a pro-inflammatory response. I1-6 contributes to the later stages of B cell activation. In addition, I1-6 plays a critical role in inducing the acute phase response and systemic inflammation. Thus, PRO35250 polypeptides function as a negative regulator of the immune response.

(3) Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited an increased mean serum IgM level and an increased mean serum IgG3 level when compared with that of their (+/+) littermates, the (+/+) mice within the project run, and the historical medians.

Mutant (−/−) mice exhibited elevation of IgM serum immunoglobulins compared to their gender-matched (+/+) littermates. IgM immunoglobulins are the first to be produced in a humoral immune response for neutralization of bacterial toxins and are particularly important in activating the complement system. The mutant (−/−) mice also exhibited elevation of IgG3 serum immunoglobulins compared to their gender-matched (+/+) littermates. These immunoglobulins have neutralization effects and to a lesser extent are important for activation of the complement system. The observed phenotype suggests that the PRO35250 polypeptide is a negative regulator of inflammatory responses. These immunological abnormalities suggest that inhibitors (antagonists) of PRO35250 polypeptides would be important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO35250 polypeptides or agonists thereof would be useful in inhibiting the immune response and would be useful candidates for suppressing harmful immune responses, e.g. in the case of graft rejection or graft-versus-host diseases.

(e) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides. In addition to measuring blood lipid levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride.

Blood Lipids & Blood Chemistry Results

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: Both the male and female (−/−) mice exhibited enormously elevated mean serum cholesterol (>11 SD above the mean) and triglyceride (~214 SD above the mean) levels. Alkaline phosphatase levels were also elevated as well as total bilirubin (~29 times the normal) and decreased calcium levels (8 SD below the mean) when compared with those of their gender-matched (+/+) littermates and the historical means.

As summarized above, the (−/−) mice exhibited notably increased mean serum cholesterol and triglyceride levels when compared with their gender-matched (+/+) littermates and the historical means. Thus, mutant mice deficient in the PRO35250 gene can serve as a model for cardiovascular disease. PRO35250 polypeptides or its encoding gene would be useful in regulating blood lipids such as cholesterol and triglycerides. Thus, PRO35250 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

The (−/−) mice exhibited notably decreased mean serum calcium, sodium, and chloride levels. The (−/−) mice also exhibited an increased mean serum bilirubin level; however, the notable lipemia in the mutant samples could have skewed this reading, since the presence of even slight lipemia is known to affect the reliability of bilirubin measurements. The depressed levels of sodium and chloride are an indication of an electrolyte imbalance. The decreased mean serum calcium levels could be indicative of the increased alkaline phosphatase activity noted above.

(f) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured. The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: The male (−/−) mice exhibited increased mean vertebral trabecular number and connectivity density when compared with that of their gender-matched (+/+) littermates and the historical means.

The (−/−) mice analyzed by bone micro CT analysis exhibited increased bone measurements when compared with their (+/+) littermates, suggestive of abnormal bone disorders such as osteopetrosis. These observations suggest that mutant mice deficient in the gene which encodes PRO35250 polypeptides leads to metabolic disorders abnormal bone measurements reflective of osteopetrosis. Thus, PRO35250 polypeptides or agonists thereof would be useful in the treatment of bone related disorders such as osteopetrosis or would be useful in maintaining bone homeostasis. Antagonists (or inhibitors) of PRO35250 polypeptides or its encoding gene would lead to abnormal or pathological bone disorders including inflammatory diseases associated with abnormal bone metabolism.

Example 67

Use of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 as a hybridization probe The following method describes use of a nucleotide sequence encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide as a hybridization probe.

DNA comprising the coding sequence of full-length or mature PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides as disclosed herein is employed as a probe to screen for homologous DNAs (such as those encoding naturally-occurring variants of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 polypeptides) in human tissue cDNA libraries or human tissue genomic libraries.

Hybridization and washing of filters containing either library DNAs is performed under the following high stringency conditions. Hybridization of radio labeled PRO69122-, PRO204-, PRO214-, PRO222-, PRO234-, PRO265-, PRO309-, PRO332-, PRO342-, PRO356-, PRO540-, PRO618-, PRO944-, PRO994-, PRO1079-, PRO1110-, PRO1122-, PRO1138-, PRO1190-, PRO1272-, PRO1286-, PRO1295-, PRO1309-, PRO1316-, PRO1383-, PRO1384-, PRO1431-, PRO1434-, PRO1475-, PRO1481-, PRO1568-, PRO1573-, PRO1599-, PRO1604-, PRO1605-, PRO1693-, PRO1753-, PRO1755-, PRO1777-, PRO1788-, PRO1864-, PRO1925-, PRO1926-, PRO3566-, PRO4330-, PRO4423-, PRO36935-, PRO4977-, PRO4979-, PRO4980-, PRO4981-, PRO5801-, PRO5995-, PRO6001-, PRO6095-, PRO6182-, PRO7170-, PRO7171-, PRO7436-, PRO9912-, PRO9917-, PRO37337-, PRO37496-, PRO19646-, PRO21718-, PRO19820-, PRO21201-, PRO20026-, PRO20110-, PRO23203- or PRO35250-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides can then be identified using standard techniques known in the art.

Example 68

Expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in *E. Coli*

This example illustrates preparation of an unglycosylated form of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides by recombinant expression in *E. Coli.*

The DNA sequence encoding a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. Coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4077, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 coding region, lambda transcriptional terminator, and an argU gene.

The ligation mixture is then used to transform a selected *E. Coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 protein can then be purified using a metal chelating column under conditions that allow tight binding of the protein.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may be expressed in *E. Coli* in a poly-His tagged form, using the following procedure. The DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. Coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate•2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. Coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 69

Expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in mammalian cells This example illustrates preparation of a potentially glycosylated form of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by recombinant expression in mammalian cells.

The vector, pRK5 (see EP 307,247, published Mar. 15, 1989), is employed as the expression vector. Optionally, the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 DNA is ligated into pRK5 with selected restriction enzymes to allow insertion of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 DNA using ligation methods such as described in Sambrook et al., supra. The resulting vector is called pRK5-PRO69122, pRK5-PRO204, pRK5-PRO214, pRK5-PRO222, pRK5-PRO234, pRK5-PRO265, pRK5-PRO309, pRK5-PRO332, pRK5-PRO342, pRK5-PRO356, pRK5-PRO618, pRK5-PRO944, pRK5-PRO994, pRK5-PRO1079, pRK5-PRO1110, pRK5-PRO1122, pRK5-PRO1138, pRK5-PRO190, pRK5-PRO1272, pRK5-PRO1286, pRK5-PRO1295, pRK5-PRO1309, pRK5-PRO1316, pRK5-pRK5-PRO1383, pRK5-PRO1384, pRK5-PRO1431, pRK5-PRO1434, pRK5-PRO1475, pRK5-PRO1481, pRK5-PRO1568, pRK5-PRO1573, pRK5-PRO1599, pRK5-PRO1604, pRK5-PRO1605, pRK5-PRO1693, pRK5-PRO1753, pRK5-PRO1755, pRK5-PRO1777, pRK5-PRO1788, pRK5-PRO1864, pRK5-PRO1925, pRK5-PRO1926, pRK5-PRO3566, pRK5-PRO4330, pRK5-PRO4423, pRK5-PRO36935, pRK5-PRO4977, pRK5-PRO4979, pRK5-PRO4980, pRK5-PRO4981, pRK5-PRO5801, pRK5-PRO5995, pRK5-PRO6001, pRK5-PRO6095, pRK5-PRO6182, pRK5-PRO7170, pRK5-PRO7171, pRK5-PRO7436, pRK5-PRO9912, pRK5-PRO9917, pRK5-PRO37337, pRK5-PRO37496, pRK5-PRO19646, pRK5-PRO21718, pRK5-PRO19820, pRK5-PRO21201, pRK5-PRO20026, pRK5-PRO20110, pRK5-PRO23203 or pRK5-PRO35250.

The selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO69122, pRK5-PRO204, pRK5-PRO214, pRK5-PRO222, pRK5-PRO234, pRK5-PRO265, pRK5-PRO309, pRK5-PRO332, pRK5-PRO342, pRK5-PRO356, pRK5-PRO540, pRK5-PRO618, pRK5-PRO944, pRK5-PRO994, pRK5-PRO1079, pRK5-PRO1110, pRK5-pRK5-PRO1138, pRK5-PRO1190, pRK5-PRO1272, pRK5-PRO1286, pRK5-PRO1295, pRK5-PRO1309, pRK5-PRO1316, pRK5-pRK5-PRO1383, pRK5-PRO1384, pRK5-PRO1431, pRK5-PRO1434, pRK5-PRO1475, pRK5-PRO1481, pRK5-PRO1568, pRK5-PRO1573, pRK5-PRO1599, pRK5-PRO1604, pRK5-PRO1605, pRK5-PRO1693, pRK5-PRO1753, pRK5-PRO1755, pRK5-PRO1777, pRK5-PRO1788, pRK5-PRO1864, pRK5-PRO1925, pRK5-PRO1926, pRK5-PRO3566, pRK5-PRO4330, pRK5-PRO4423, pRK5-PRO36935, pRK5-PRO4977, pRK5-PRO4979, pRK5-PRO4980, pRK5-PRO4981, pRK5-PRO5801, pRK5-PRO5995, pRK5-PRO6001, pRK5-PRO6095, pRK5-PRO6182, pRK5-PRO7170, pRK5-PRO7171, pRK5-PRO7436, pRK5-PRO9912, pRK5-PRO9917, pRK5-PRO37337, pRK5-PRO37496, pRK5-PRO19646, pRK5-PRO21718, pRK5-PRO19820, pRK5-PRO21201, pRK5-PRO20026, pRK5-PRO20110, pRK5-PRO23203 or pRK5-PRO35250 DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides. The cultures containing transfected cells may undergo further incubation (in serum free medium) and the medium is tested in selected bioassays.

In an alternative technique, PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-PRO69122, pRK5-PRO204, pRK5-PRO214, pRK5-PRO222, pRK5-PRO234, pRK5-PRO265, pRK5-PRO309, pRK5-PRO332, pRK5-PRO342, pRK5-PRO356, pRK5-PRO540, pRK5-PRO618, pRK5-PRO944, pRK5-PRO994, pRK5-PRO1079, pRK5-PRO1110, pRK5-PRO1122, pRK5-PRO1138, pRK5-PRO1190, pRK5-PRO1272, pRK5-PRO1286, pRK5-PRO1295, pRK5-PRO1309, pRK5-PRO1316, pRK5-pRK5-PRO1383, pRK5-PRO1384, pRK5-PRO1431, pRK5-PRO1434, pRK5-PRO1475, pRK5-PRO1481, pRK5-PRO1568, pRK5-PRO1573, pRK5-PRO1599, pRK5-PRO1604, pRK5-PRO1605, pRK5-PRO1693, pRK5-PRO1753, pRK5-PRO1755, pRK5-PRO1777, pRK5-PRO1788, pRK5-PRO1864, pRK5-PRO1925, pRK5-PRO1926, pRK5-PRO3566, pRK5-PRO4330, pRK5-PRO4423, pRK5-PRO36935, pRK5-PRO4977, pRK5-PRO4979, pRK5-PRO4980, pRK5-PRO4981, pRK5-PRO5801, pRK5-PRO5995, pRK5-PRO6001, pRK5-PRO6095, pRK5-PRO6182, pRK5-PRO7170, pRK5-PRO7171, pRK5-PRO7436, pRK5-PRO9912, pRK5-PRO9917, pRK5-PRO37337, pRK5-PRO37496, pRK5-PRO19646, pRK5-PRO21718, pRK5-PRO19820, pRK5-PRO21201, pRK5-PRO20026, pRK5-

PRO20110, pRK5-PRO23203 or pRK5-PRO35250 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can then be concentrated and purified by any selected method, such as dialysis and/or column chromatography.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can be expressed in CHO cells. The pRK5-PRO69122, pRK5-PRO204, pRK5-PRO214, pRK5-PRO222, pRK5-PRO234, pRK5-PRO265, pRK5-PRO309, pRK5-PRO332, pRK5-PRO342, pRK5-PRO356, pRK5-PRO540, pRK5-PRO618, pRK5-PRO944, pRK5-PRO994, pRK5-PRO1079, pRK5-PRO1110, pRK5-PRO1122, pRK5-PRO1138, pRK5-PRO1190, pRK5-PRO1272, pRK5-PRO1286, pRK5-PRO1295, pRK5-PRO1309, pRK5-PRO1316, pRK5-pRK5-PRO1383, pRK5-PRO1384, pRK5-PRO1431, pRK5-PRO1434, pRK5-PRO1475, pRK5-PRO1481, pRK5-PRO1568, pRK5-PRO1573, pRK5-PRO1599, pRK5-PRO1604, pRK5-PRO1605, pRK5-PRO1693, pRK5-PRO1753, pRK5-PRO1755, pRK5-PRO1777, pRK5-PRO1788, pRK5-PRO1864, pRK5-PRO1925, pRK5-PRO1926, pRK5-PRO3566, pRK5-PRO4330, pRK5-PRO4423, pRK5-PRO36935, pRK5-PRO4977, pRK5-PRO4979, pRK5-PRO4980, pRK5-PRO4981, pRK5-PRO5801, pRK5-PRO5995, pRK5-PRO6001, pRK5-PRO6095, pRK5-PRO6182, pRK5-PRO7170, pRK5-PRO7171, pRK5-PRO7436, pRK5-PRO9912, pRK5-PRO9917, pRK5-PRO37337, pRK5-PRO37496, pRK5-PRO19646, pRK5-PRO21718, pRK5-PRO19820, pRK5-PRO21201, pRK5-PRO20026, pRK5-PRO20110, pRK5-PRO23203, or pRK5-PRO35250 can be transfected into CHO cells using known reagents such as $CaPO_{4o}$r DEAE-dextran. As described above, the cell cultures can be incubated, and the medium replaced with culture medium (alone) or medium containing a radio label such as $^{35}$S-methionine. After determining the presence of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the culture medium may be replaced with serum free medium. Preferably, the cultures are incubated for about 6 days, and then the conditioned medium is harvested. The medium containing the expressed PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can then be concentrated and purified by any selected method.

Epitope-tagged PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may also be expressed in host CHO cells. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may be subcloned out of the pRK5 vector. The subclone insert can undergo PCR to fuse in frame with a selected epitope tag such as a poly-his tag into a Baculovirus expression vector. The poly-his tagged PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can then be concentrated and purified by any selected method, such as by $Ni^{2+}$-chelate affinity chromatography.

PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL an mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxance emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions PRO1434, pro-PRO1475, pro-PRO1481, pro-PRO1568, pro-PRO1573, pro-PRO1599, pro-PRO1604, pro-PRO1605, pro-PRO1693, pro-PRO1753, pro-PRO1755, pro-PRO1777, pro-PRO1788, pro-PRO1864, pro-PRO1925, pro-PRO1926, pro-PRO3566, pro-PRO4330, pro- PRO4423, pro-PRO36935, pro-PRO4977, pro-PRO4979, pro-PRO4980, pro-PRO4981, pro-PRO5801, pro-PRO5995, pro-PRO6001, pro-PRO6095, pro-PRO6182, pro-PRO7170, pro-PRO7171, pro-PRO7436, pro-PRO9912, pro-PRO9917, pro-PRO37337, pro-PRO37496, pro-PRO19646, pro-PRO21718, pro-PRO19820, pro-PRO21201, pro-PRO20026, pro-PRO20110, pro-PRO23203 or pro-PRO35250 polypeptide, mature PRO69122, mature PRO204, mature PRO214, mature PRO222, mature PRO234, mature PRO265, mature PRO309, mature PRO332, mature PRO342, mature PRO356, mature PRO540, mature PRO618, mature PRO944, mature PRO994, mature PRO1079, mature PRO1110, mature PRO1122, mature PRO1138, mature PRO1190, mature PRO1272, mature PRO1286, mature PRO1295, mature PRO1309, mature PRO1316, mature PRO1383, mature PRO1384, mature PRO1431, mature PRO1434, mature PRO1475, mature PRO1481, mature PRO1568, mature PRO1573, mature PRO1599, mature PRO1604, mature PRO1605, mature PRO1693, mature PRO1753, mature PRO1755, mature PRO1777, mature PRO1788, mature PRO1864, mature PRO1925, mature PRO1926, mature PRO3566, mature PRO4330, mature PRO4423, mature PRO36935, mature PRO4977, mature PRO4979, mature PRO4980, mature PRO4981, mature PRO5801, mature PRO5995, mature PRO6001, mature PRO6095, mature PRO6182, mature PRO7170, mature PRO7171, mature PRO7436, mature PRO9912, mature PRO9917, mature PRO37337, mature PRO37496, mature PRO19646, mature PRO21718, mature PRO19820, mature PRO21201, mature PRO20026, mature PRO20110, mature PRO23203 or mature PRO35250 polypeptide, or pre-PRO69122, pre-PRO204, pre-PRO214, pre-PRO222, pre-PRO234, pre-PRO265, pre-PRO309, pre-PRO332, pre-PRO342, pre-PRO356, pre-PRO540, pre-PRO618, pre-PRO944, pre-PRO994, pre-PRO1079, pre-PRO1110, pre-PRO1122, pre-PRO1138, pre-PRO1190, pre-PRO1272, pre-PRO1286, pre-PRO1295, pre-PRO1309, pre-PRO1316, per-PRO1383, pre-PRO1384, pre-PRO1431, pre-PRO1434, pre-PRO1475, pre-PRO1481, pre-PRO1568, pre-PRO1573, pre-PRO1599, pre-PRO1604, pre-PRO1605, pre-PRO1693, pre-PRO1753, pre-PRO1755, pre-PRO1777, pre-PRO1788, pre-PRO1864, pre-PRO1925, pre-PRO1926, pre-PRO3566, pre-PRO4330, pre-PRO4423, pre-PRO36935, pre-PRO4977, pre-PRO4979, pre-PRO4980, pre-PRO4981, pre-PRO5801, pre-PRO5995, pre-PRO6001, pre-PRO6095, pre-PRO6182, pre-PRO7170, pre-PRO7171, pre-PRO7436, pre-PRO9912, pre-PRO9917, pre-PRO37337, pre-PRO37496, pre-PRO19646, pre-PRO21718, pre-PRO19820, pre-PRO21201, pre-PRO20026, pre-PRO20110, pre-PRO23203 or pre-PRO35250 polypeptide is purified by immunoaffinity chromatography using antibodies specific for the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7435, PRO9912, PRO9917, PRO37337, PRO37496, PRO19646, PRO21718, PRO19820, PRO21201, PRO20026, PRO20110, PRO23203 or PRO35250 polypeptide of interest. In general, an immunoaffinity column is constructed by covalently coupling the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 70

Expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in Yeast The following method describes recombinant expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in yeast.

First, yeast expression vectors are constructed for intracellular production or secretion of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37227, PRO37496, PRO19646, PRO21718, PRO19820, PRO21201, PRO20026, PRO20110, PRO23203 or PRO35250, from the ADH2/GAPDH promoter. DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 and the promoter is inserted into suitable restriction enzyme sites in the selected plasmid to direct intracellular expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250. For secretion, DNA encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can be cloned into the selected plasmid, together with DNA encoding the ADH2/GAPDH promoter, a native PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 signal peptide or other mammalian signal peptide, or, for example, a yeast alpha-factor or invertase secretory signal/leader sequence, and linker sequences (if needed) for expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can subsequently be isolated and purified by removing the yeast cells from the fermentation medium by centrifugation and then concentrating the medium using selected cartridge filters. The concentrate containing PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 may further be purified using selected column chromatography resins.

Example 71

Expression of PRO69122, PRO204, PRO214, PRO222, PRO234, PRO265, PRO309, PRO332, PRO342 PRO356 PRO540 PRO618, PRO944 PRO994, PRO1079 PRO1110, PRO1122 PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in Baculovirus-Infected Insect Cells The following method describes recombinant expression of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 in Baculovirus-infected insect cells.

The sequence coding for PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 or the desired portion of the coding sequence of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 are pooled and dialyzed against loading buffer.

Alternatively, purification of the IgG tagged (or Fc tagged) PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 can be performed using known chromatography techniques, including for instance, Protein A or protein G column chromatography.

Example 72

Preparation of Antibodies that Bind PRO69122 PRO204 PRO214 PRO222 PRO234 PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250, This example illustrates preparation of monoclonal antibodies which can specifically bind PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250.

Techniques for producing the monoclonal antibodies are known in the art and are described, for instance, in Goding, supra. Immunogens that may be employed include purified PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides, fusion proteins containing PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides, and cells expressing recombinant PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides on the cell surface. Selection of the immunogen can be made by the skilled artisan without undue experimentation.

Mice, such as Balb/c, are immunized with the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 immunogen emulsified in complete Freund's adjuvant and injected subcutaneously or intraperitoneally in an amount from 1-100 micrograms.

Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti- PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 antibodies.

After a suitable antibody titer has been detected, the animals "positive" for antibodies can be injected with a final intravenous injection of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250. Determination of "positive" hybridoma cells secreting the desired monoclonal antibodies against PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 is within the skill in the art.

The positive hybridoma cells can be injected intraperitoneally into syngeneic Balb/c mice to produce ascites containing the anti-PRO69122, anti-PRO204, anti-PRO214, anti-PRO222, anti-PRO234, anti-PRO265, anti-PRO309, anti-PRO332, anti-PRO342, anti-PRO356, anti-PRO540, anti-PRO618, anti-PRO944, anti-994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 73

Purification of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 Polypeptides Using Specific Antibodies Native or recombinant PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides may be purified by a variety of standard techniques in the art of protein purification. For example, pro-PRO69122, pro-PRO204, pro-PRO214, pro-PRO222, pro-PRO234, pro-PRO265, pro-PRO309, pro-PRO332, pro-PRO342, pro-PRO356, pro-PRO540, pro-PRO618, pro-PRO944, pro-PRO994, pro-PRO1079, pro- PRO1110, pro-PRO1122, pro-PRO1138, pro-PRO1190, pro-PRO1272, pro-PRO1286, pro-PRO1295, pro-PRO1309, pro-PRO1316, pro-PRO1383, pro-PRO1384, pro-PRO1431, pro-anti-PRO994, anti-PRO1079, anti-PRO1110, anti-PRO1122, anti-PRO1138, anti-PRO1190, anti-PRO1272, anti-PRO1286, anti-PRO1295, anti-PRO1309, anti-PRO1316, anti-PRO1383, anti-PRO1384, anti-PRO1431, anti-PRO1434, anti-PRO1475, anti-PRO1481, anti-PRO1568, anti-PRO1573, anti-PRO1599, anti-PRO1604, anti-PRO1605, anti-PRO1693, anti-PRO1753, anti-PRO1755, anti-PRO1777, anti-PRO1788, anti-PRO1864, anti-PRO1925, anti-PRO1926, anti-PRO3566, anti-PRO4330, anti-PRO4423, anti-PRO36935, anti-PRO4977, anti-PRO4979, anti-PRO4980, anti-PRO4981, anti-PRO5801, anti-PRO5995, anti-PRO6001, anti-PRO6095, anti-PRO6182, anti-PRO7170, anti-PRO7171, anti-PRO7436, anti-PRO9912, anti-PRO9917, anti-PRO37337, anti-PRO37496, anti-PRO19646, anti-PRO21718, anti-PRO19820, anti-PRO21201, anti-PRO20026, anti-PRO20110, anti-PRO23203 or anti-PRO35250 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide by preparing a fraction from cells containing PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide in a soluble form. This preparation is derived by solubilization of the whole cell or of a subcellular fraction obtained via differential centrifugation by the addition of detergent or by other methods well known in the art. Alternatively, soluble polypeptide containing a signal sequence may be secreted in useful quantity into the medium in which the cells are grown.

A soluble PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide-containing preparation is passed over the immunoaffinity column, and the column is washed under conditions that allow the preferential absorbance of PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide (e.g., high ionic strength buffers in the presence of detergent). Then, the column is eluted under conditions that disrupt antibody/PRO69122, antibody/PRO204, antibody/PRO214, antibody/PRO222, antibody/PRO234, antibody/PRO265, antibody/PRO309, antibody/PRO332, antibody/PRO342, antibody/PRO356, antibody/PRO540, antibody/PRO618, antibody/PRO944, antibody/PRO994, antibody/PRO1079, antibody/PRO1110, antibody/PRO1122, antibody/PRO1138, antibody/PRO1190, antibody/PRO1272, antibody/PRO1286, antibody/PRO1295, antibody/PRO1309, antibody/PRO1316, antibody/PRO1383, antibody/PRO1384, antibody/PRO1431, antibody/PRO1434, antibody/PRO1475, antibody/PRO1481, antibody/PRO1568, antibody/PRO1573, antibody/PRO1599, antibody/PRO1604, antibody/PRO1605, antibody/PRO1693, antibody/PRO1753, antibody/PRO1755, antibody/PRO1777, antibody/PRO1788, antibody/PRO1864, antibody/PRO1925, antibody/PRO1926, antibody/PRO3566, antibody/PRO4330, antibody/PRO4423, antibody/PRO36935, antibody/PRO4977, antibody/PRO4979, antibody/PRO4980, antibody/PRO4981, antibody/PRO5801, antibody/PRO5995, antibody/PRO6001, antibody/PRO6095, antibody/PRO6182, antibody/PRO7170, antibody/PRO7171, antibody/PRO7436, antibody/PRO9912, antibody/PRO9917, antibody/PRO37337, antibody/PRO37496, antibody/PRO19646, antibody/PRO21718, antibody/PRO19820, antibody/PRO21201, antibody/PRO20026, antibody/PRO20110, antibody/PRO23203 or antibody/PRO35250 polypeptide binding (e.g., a low pH buffer such as approximately pH 2-3, or a high concentration of a chaotrope such as urea or thiocyanate ion), and PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is collected.

Example 74

Drug Screening

This invention is particularly useful for screening compounds by using PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptides or binding fragment thereof in any of a variety of drug screening techniques. The PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment. Drugs are screened against such transformed cells in competitive binding assays. Such cells, either in viable or fixed form, can be used for standard binding assays. One may measure, for example, the formation of complexes between PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 polypeptide or a fragment and the agent being tested. Alternatively, one can examine the diminution in complex formation between the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and its target cell or target receptors caused by the agent being tested.

Thus, the present invention provides methods of screening for drugs or any other agents which can affect a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 polypeptide-associated disease or disorder. These methods comprise contacting such an agent with an PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment thereof and assaying (I) for the presence of a complex between the agent and the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment, or (ii) for the presence of a complex between the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250, polypeptide or fragment and the cell, by methods well known in the art. In such competitive binding assays, the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment is typically labeled. After suitable incubation, free PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragment is separated from that present in bound form, and the amount of free or uncomplexed label is a measure of the ability of the particular agent to bind to PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or to interfere with the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250, polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, the peptide test compounds are reacted with PRO69122, PRO204, PRO214, PRO222, PRO234, PRO265, PRO309, PRO332, PRO3420, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide and washed. Bound PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide is detected by methods well known in the art. Purified PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide specifically compete with a test compound for binding to PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or fragments thereof. In this manner, the antibodies can be used to detect the presence of any peptide which shares one or more antigenic determinants with PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide.

Example 75

Rational Drug Design

The goal of rational drug design is to produce structural analogs of biologically active polypeptide of interest (i.e., a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190 PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide) or of small molecules with which they interact, e.g., agonists, antagonists, or inhibitors. Any of these examples can be used to fashion drugs which are more active or stable forms of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide or which enhance or interfere with the function of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide in vivo (c.f., Hodgson, *Bio/Technology,* 9: 19-21(1991)).

In one approach, the three-dimensional structure of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide, or of a PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203, or PRO35250 polypeptide-inhibitor complex, is determined by x-ray crystallography, by computer modeling or, most typically, by a combination of the two approaches. Both the shape and charges of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide must be ascertained to elucidate the structure and to determine active site(s) of the molecule. Less often, useful information regarding the structure of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be gained by modeling based on the structure of homologous proteins. In both cases, relevant structural information is used to design analogous PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250, polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al, *J. Biochem.,* 113:742-746(1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide may be made available to perform such analytical studies as X-ray crystallography. In addition, knowledge of the PRO69122, PRO204, PRO214, PRO222, PRO234, PRO265, PRO309, PRO332, PRO342, PRO356, PRO540, PRO618, PRO944, PRO994, PRO1079, PRO1110, PRO1122, PRO1138, PRO1190, PRO1272, PRO1286, PRO1295, PRO1309, PRO1316, PRO1383, PRO1384, PRO1431, PRO1434, PRO1475, PRO1481, PRO1568, PRO1573, PRO1599, PRO1604, PRO1605, PRO1693, PRO1753, PRO1755, PRO1777, PRO1788, PRO1864, PRO1925, PRO1926, PRO3566, PRO4330, PRO4423, PRO36935, PRO4977, PRO4979, PRO4980, PRO4981, PRO5801, PRO5995, PRO6001, PRO6095, PRO6182, PRO7170, PRO7171, PRO7436, PRO9912, PRO9917, PRO37337, PRO37496, PRO19646, PRO21718, PRO19820, PRO21201, PRO20026, PRO20110, PRO23203 or PRO35250 polypeptide amino acid sequence provided herein will provide guidance to those employing computer modeling techniques in place of or in addition to x-ray crystallography.

What is claimed is:

1. A method of identifying a lipid metabolic disorder phenotype associated with a disruption of a gene which encodes for a PRO20110 polypeptide, the method comprising:

(a) providing a non-human transgenic animal whose genome comprises a disruption of a gene which is an ortholog of a human gene that encodes for a PRO20110 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype of a lipid metabolic disorder resulting from the gene disruption in the non-human transgenic animal.

2. The method of claim 1, wherein the non-human transgenic animal is heterozygous for the disruption of a gene which encodes for a PRO20110 polypeptide.

3. The method of claim 1, wherein the non-human transgenic animal exhibits at least one of the following physiological characteristics compared with gender matched wild-type littermates: increased mean serum cholesterol levels; decreased mean serum cholesterol levels; increased mean serum triglyceride levels.

* * * * *

SEQUENCE LISTING

<160> NUMBER OF SEQ ID NOS: 251

<210> SEQ ID NO 1
<211> LENGTH: 3473
<212> TYPE: DNA
<213> ORGANISM: Homo sapiens

<400> SEQUENCE: 1

```
aagagcagcg gcgaggcggc ggtggtggct gagtccgtgg tggcagaggc      50
gaaggcgaca gctctagggg ttggcaccgg ccccgagagg aggatgcggg     100
tccggatagg gctgacgctg ctgctgtgtg cggtgctgct gagcttggcc     150
tcggcgtcct cggatgaaga aggcagccag gatgaatcct tagattccaa     200
gactactttg acatcagatg agtcagtaaa ggaccacact actgcaggca     250
gagtagttgc tggtcaaata tttcttgatt cagaagaatc tgaattagaa     300
tcctctattc aagaagagga agacagcctc aagagccaag agggggagag     350
tgtcacagaa gatatcagct ttctagagtc tccaaatcca gaaaacaagg     400
actatgaaga gccaaagaaa gtacggaaac cagctttgac cgccattgaa     450
ggcacagcac atggggagcc ctgccacttc ccttttcttt tcctagataa     500
ggagtatgat gaatgtacat cagatgggag ggaagatggc agactgtggt     550
gtgctacaac ctatgactac aaagcagatg aaaagtgggg cttttgtgaa     600
actgaagaag aggctgctaa gagacggcag atgcaggaag cagaaatggt     650
gtatcaaact ggaatgaaaa tccttaatgg aagcaataag aaaagccaaa     700
aaagagaagc atatcggtat ctccaaaagg cagcaagcat gaaccatacc     750
aaagccctgg agagagtgtc atatgctctt ttatttggtg attacttgcc     800
acagaatatc caggcagcga gagagatgtt tgagaagctg actgaggaag     850
gctctcccaa gggacagact gctcttggct ttctgtatgc ctctggactt     900
ggtgttaatt caagtcaggc aaaggctctt gtatattata catttggagc     950
tcttgggggc aatctaatag cccacatggt tttgggttac agatactggg    1000
ctggcatcgg cgtcctccag agttgtgaat ctgccctgac tcactatcgt    1050
cttgttgcca atcatgttgc tagtgatatc tcgctaacag gaggctcagt    1100
agtacagaga atacggctgc ctgatgaagt ggaaaatcca ggaatgaaca    1150
gtggaatgct agaagaagat ttgattcaat attaccagtt cctagctgaa    1200
aaaggtgatg tacaagcaca ggttggtctt ggacaactgc acctgcacgg    1250
agggcgtgga gtagaacaga atcatcagag agcatttgac tacttcaatt    1300
tagcagcaaa tgctggcaat tcacatgcca tggccttttt gggaaagatg    1350
tattcggaag gaagtgacat tgtacctcag agtaatgaga cagctctcca    1400
ctactttaag aaagctgctg acatgggcaa cccagttgga cagagtgggc    1450
ttggaatggc ctacctctat gggagaggag ttcaagttaa ttatgatcta    1500
gcccttaagt atttccagaa agctgctgaa caaggctggg tggatgggca    1550
gctacagctt ggttccatgt actataatgg cattggagtc aagagagatt    1600
ataaacaggc cttgaagtat tttaatttag cttctcaggg aggccatatc    1650
ttggctttct ataacctagc tcagatgcat gccagtggca ccggcgtgat    1700
```

-continued

```
gcgatcatgt cacactgcag tggagttgtt taagaatgta tgtgaacgag      1750
gccgttggtc tgaaaggctt atgactgcct ataacagcta taaagatggc      1800
gattacaatg ctgcagtgat ccagtacctc ctcctggctg aacagggcta      1850
tgaagtggca caaagcaatg cagcctttat tcttgatcag agagaagcaa      1900
gcattgtagg tgagaatgaa acttatccca gagctttgct acattggaac      1950
agggccgcct ctcaaggcta tactgtggct agaattaagc tcggagacta      2000
ccatttctat gggtttggca ccgatgtaga ttatgaaact gcatttattc      2050
attaccgtct ggcttctgag cagcaacaca gtgcacaagc tatgtttaat      2100
ctgggatata tgcatgagaa aggactgggc attaaacagg atattcacct      2150
tgcgaaacgt ttttatgaca tggcagctga agccagccca gatgcacaag      2200
ttccagtctt cctagccctc tgcaaattgg gcgtcgtcta tttcttgcag      2250
tacatacggg aaacaaacat tcgagatatg ttcacccaac ttgatatgga      2300
ccagcttttg ggacctgagt gggaccttta cctcatgacc atcattgcgc      2350
tgctgttggg aacagtcata gcttacaggc aaaggcagca ccaagacatg      2400
cctgcaccca ggcctccagg gccacggcca gctccacccc agcaggaggg      2450
gccaccagag cagcagccac cacagtaata ggcactgggt ccagccttga      2500
tcagtgacag cgaaggaagt tatctgctgg gaacacttgc atttgattta      2550
ggaccttgga tcagtggtca cctcccagaa gaggcacggc acaaggaagc      2600
attgaattcc taaagctgct tagaatctga tgcctttatt ttcagggata      2650
agtaactctt acctaaactg agctgaatgt ttgtttcagt gccatatgga      2700
ataacaactt tcagtggctt ttttttttct tttctggaaa catatgtgag      2750
acactcagag taatgtctac tgtatccagc tatctttctt ggatcctttt      2800
ggtcattatt tcagtgtgca taagttctta atgtcaacca tctttaaggt      2850
attgtgcatc gacactaaaa actgatcagt gtaaaaagga aaacccagtt      2900
gcaagtttaa acgtgttcga aagtctgaaa atagaacttg ccttttaagt      2950
taaaaaaaaa aaaagctatc ttgaaaatgt tttggaactg cgataactga      3000
gaaactctta ccagtccaca tgcaattaga catattcagc atatttgtta      3050
ttttaaaagg gagggttggg aggtttctta ttggtgattg tcacacggta      3100
taccatactc ctctccttca aagaatgaaa ggccttgtta aggagttttt      3150
tgtgagcttt acttctttgg aatggaatat acttatgcaa aaccttgtga      3200
actgactcct tgcactaacg cgagtttgcc ccacctactc tgtaatttgc      3250
ttgtttgttt tgaatataca gagccttgat ccagaagcca gaggatggac      3300
taagtgggag aaattagaaa acaaaacgaa ctctggttgg ggtactacga      3350
tcacagacac agacatactt ttcctaaagt tgaagcattt gttcccagga      3400
tttattttac tttgcatttc cttttgcaca aagaacacat caccatttcc      3450
ttttgcacaa agaacacatc  acc                                  3473
```

<210> SEQ ID NO 2
<211> LENGTH: 794
<212> TYPE: PRT
<213> ORGANISM: Homo sapiens -continued

<400> SEQUENCE: 2

```
Met Arg Val Arg Ile Gly Leu Thr Leu Leu Leu Cys Ala Val Leu
1               5                   10                  15

Leu Ser Leu Ala Ser Ala Ser Ser Asp Glu Glu Gly Ser Gln Asp
                20                  25                  30

Glu Ser Leu Asp Ser Lys Thr Thr Leu Thr Ser Asp Glu Ser Val
                35                  40                  45

Lys Asp His Thr Thr Ala Gly Arg Val Val Ala Gly Gln Ile Phe
                50                  55                  60

Leu Asp Ser Glu Glu Ser Glu Leu Glu Ser Ser Ile Gln Glu Glu
                65                  70                  75

Glu Asp Ser Leu Lys Ser Gln Glu Gly Glu Ser Val Thr Glu Asp
                80                  85                  90

Ile Ser Phe Leu Glu Ser Pro Asn Pro Glu Asn Lys Asp Tyr Glu
                95                  100                 105

Glu Pro Lys Lys Val Arg Lys Pro Ala Leu Thr Ala Ile Glu Gly
                110                 115                 120

Thr Ala His Gly Glu Pro Cys His Phe Pro Phe Leu Phe Leu Asp
                125                 130                 135

Lys Glu Tyr Asp Glu Cys Thr Ser Asp Gly Arg Glu Asp Gly Arg
                140                 145                 150

Leu Trp Cys Ala Thr Thr Tyr Asp Tyr Lys Ala Asp Glu Lys Trp
                155                 160                 165

Gly Phe Cys Glu Thr Glu Glu Glu Ala Ala Lys Arg Arg Gln Met
                170                 175                 180

Gln Glu Ala Glu Met Val Tyr Gln Thr Gly Met Lys Ile Leu Asn
                185                 190                 195

Gly Ser Asn Lys Lys Ser Gln Lys Arg Glu Ala Tyr Arg Tyr Leu
                200                 205                 210

Gln Lys Ala Ala Ser Met Asn His Thr Lys Ala Leu Glu Arg Val
                215                 220                 225

Ser Tyr Ala Leu Leu Phe Gly Asp Tyr Leu Pro Gln Asn Ile Gln
                230                 235                 240

Ala Ala Arg Glu Met Phe Glu Lys Leu Thr Glu Glu Gly Ser Pro
                245                 250                 255

Lys Gly Gln Thr Ala Leu Gly Phe Leu Tyr Ala Ser Gly Leu Gly
                260                 265                 270

Val Asn Ser Ser Gln Ala Lys Ala Leu Val Tyr Tyr Thr Phe Gly
                275                 280                 285

Ala Leu Gly Gly Asn Leu Ile Ala His Met Val Leu Gly Tyr Arg
                290                 295                 300

Tyr Trp Ala Gly Ile Gly Val Leu Gln Ser Cys Glu Ser Ala Leu
                305                 310                 315

Thr His Tyr Arg Leu Val Ala Asn His Val Ala Ser Asp Ile Ser
                320                 325                 330

Leu Thr Gly Gly Ser Val Val Gln Arg Ile Arg Leu Pro Asp Glu
                335                 340                 345

Val Glu Asn Pro Gly Met Asn Ser Gly Met Leu Glu Glu Asp Leu
                350                 355                 360

Ile Gln Tyr Tyr Gln Phe Leu Ala Glu Lys Gly Asp Val Gln Ala
                365                 370                 375

Gln Val Gly Leu Gly Gln Leu His Leu His Gly Gly Arg Gly Val
                380                 385                 390
```

-continued

```
Glu Gln Asn His Gln Arg Ala Phe Asp Tyr Phe Asn Leu Ala Ala
                395                 400                 405

Asn Ala Gly Asn Ser His Ala Met Ala Phe Leu Gly Lys Met Tyr
                410                 415                 420

Ser Glu Gly Ser Asp Ile Val Pro Gln Ser Asn Glu Thr Ala Leu
                425                 430                 435

His Tyr Phe Lys Lys Ala Ala Asp Met Gly Asn Pro Val Gly Gln
                440                 445                 450

Ser Gly Leu Gly Met Ala Tyr Leu Tyr Gly Arg Gly Val Gln Val
                455                 460                 465

Asn Tyr Asp Leu Ala Leu Lys Tyr Phe Gln Lys Ala Ala Glu Gln
                470                 475                 480

Gly Trp Val Asp Gly Gln Leu Gln Leu Gly Ser Met Tyr Tyr Asn
                485                 490                 495

Gly Ile Gly Val Lys Arg Asp Tyr Lys Gln Ala Leu Lys Tyr Phe
                500                 505                 510

Asn Leu Ala Ser Gln Gly Gly His Ile Leu Ala Phe Tyr Asn Leu
                515                 520                 525

Ala Gln Met His Ala Ser Gly Thr Gly Val Met Arg Ser Cys His
                530                 535                 540

Thr Ala Val Glu Leu Phe Lys Asn Val Cys Glu Arg Gly Arg Trp
                545                 550                 555

Ser Glu Arg Leu Met Thr Ala Tyr Asn Ser Tyr Lys Asp Gly Asp
                560                 565                 570

Tyr Asn Ala Ala Val Ile Gln Tyr Leu Leu Leu Ala Glu Gln Gly
                575                 580                 585

Tyr Glu Val Ala Gln Ser Asn Ala Ala Phe Ile Leu Asp Gln Arg
                590                 595                 600

Glu Ala Ser Ile Val Gly Glu Asn Glu Thr Tyr Pro Arg Ala Leu
                605                 610                 615

Leu His Trp Asn Arg Ala Ala Ser Gln Gly Tyr Thr Val Ala Arg
                620                 625                 630

Ile Lys Leu Gly Asp Tyr His Phe Tyr Gly Phe Gly Thr Asp Val
                635                 640                 645

Asp Tyr Glu Thr Ala Phe Ile His Tyr Arg Leu Ala Ser Glu Gln
                650                 655                 660

Gln His Ser Ala Gln Ala Met Phe Asn Leu Gly Tyr Met His Glu
                665                 670                 675

Lys Gly Leu Gly Ile Lys Gln Asp Ile His Leu Ala Lys Arg Phe
                680                 685                 690

Tyr Asp Met Ala Ala Glu Ala Ser Pro Asp Ala Gln Val Pro Val
                695                 700                 705

Phe Leu Ala Leu Cys Lys Leu Gly Val Val Tyr Phe Leu Gln Tyr
                710                 715                 720

Ile Arg Glu Thr Asn Ile Arg Asp Met Phe Thr Gln Leu Asp Met
                725                 730                 735

Asp Gln Leu Leu Gly Pro Glu Trp Asp Leu Tyr Leu Met Thr Ile
                740                 745                 750

Ile Ala Leu Leu Leu Gly Thr Val Ile Ala Tyr Arg Gln Arg Gln
                755                 760                 765

His Gln Asp Met Pro Ala Pro Arg Pro Pro Gly Pro Arg Pro Ala
                770                 775                 780
```

-continued

```
Pro Pro Gln Gln Glu Gly Pro Pro Glu Gln Gln Pro Pro Gln
                785                 790
```

<210> SEQ ID NO 3
<211> LENGTH: 1788
<212> TYPE: DNA
<213> ORGANISM: Homo sapiens

<400> SEQUENCE: 3

```
tgccgggctg cggggcgcct tgactctccc tccaccctgc ctcctcgggc        50
tccactcgtc tgcccctgga ctcccgtctc ctcctgtcct ccggcttccc       100
agagctccct ccttatggca gcagcttccc gcgtctccgg cgcagcttct       150
cagcggacga ccctctcgct ccggggctga gcccagtccc tggatgttgc       200
tgaaactctc gagatcatgc gcgggtttgg ctgctgcttc cccgccgggt       250
gccactgcca ccgccgccgc ctctgctgcc gccgtccgcg ggatgctcag       300
tagcccgctg cccggccccc gcgatcctgt gttcctcgga agccgtttgc       350
tgctgcagag ttgcacgaac tagtcatggt gctgtgggag tccccgcggc       400
agtgcagcag ctggacactt tgcgagggct tttgctggct gctgctgctg       450
cccgtcatgc tactcatcgt agcccgcccg gtgaagctcg ctgctttccc       500
tacctcctta agtgactgcc aaacgcccac cggctggaat tgctctggtt       550
atgatgacag agaaaatgat ctcttcctct gtgacaccaa cacctgtaaa       600
tttgatgggg aatgtttaag aattggagac actgtgactt gcgtctgtca       650
gttcaagtgc aacaatgact atgtgcctgt gtgtggctcc aatggggaga       700
gctaccagaa tgagtgttac ctgcgacagg ctgcatgcaa acagcagagt       750
gagatacttg tggtgtcaga aggatcatgt gccacagatg caggatcagg       800
atctggagat ggagtccatg aaggctctgg agaaactagt caaaaggaga       850
catccacctg tgatatttgc cagtttggtg cagaatgtga cgaagatgcc       900
gaggatgtct ggtgtgtgtg taatattgac tgttctcaaa ccaacttcaa       950
tcccctctgc gcttctgatg ggaaatctta tgataatgca tgccaaatca      1000
aagaagcatc gtgtcagaaa caggagaaaa ttgaagtcat gtctttgggt      1050
cgatgtcaag ataacacaac tacaactact aagtctgaag atgggcatta      1100
tgcaagaaca gattatgcag agaatgctaa caaattagaa gaaagtgcca      1150
gagaacacca cataccttgt ccggaacatt acaatggctt ctgcatgcat      1200
gggaagtgtg agcattctat caatatgcag gagccatctt gcaggtgtga      1250
tgctggttat actggacaac actgtgaaaa aaaggactac agtgttctat      1300
acgttgttcc cggtcctgta cgatttcagt atgtcttaat cgcagctgtg      1350
attggaacaa ttcagattgc tgtcatctgt gtggtggtcc tctgcatcac      1400
aaggaaatgc cccagaagca acagaattca cagacagaag caaaatacag      1450
ggcactacag ttcagacaat acaacaagag cgtccacgag gttaatctaa      1500
agggagcatg tttcacagtg gctggactac cgagagcttg gactacacaa      1550
tacagtatta tagacaaaag aataagacaa gagatctaca catgttgcct      1600
tgcatttgtg gtaatctaca ccaatgaaaa catgtactac agctatattt      1650
gattatgtat ggatatattt gaaatagtat acattgtctt gatgtttttt      1700
```

-continued

```
ctgtaatgta aataaactat ttatatcaca caatatagtt ttttctttcc            1750

catgtatttg ttatatataa taaatactca  gtgatgag                         1788


<210> SEQ ID NO 4
<211> LENGTH: 374
<212> TYPE: PRT
<213> ORGANISM: Homo sapiens

<400> SEQUENCE: 4

Met Val Leu Trp Glu Ser Pro Arg Gln Cys Ser Ser Trp Thr Leu
  1               5                  10                  15

Cys Glu Gly Phe Cys Trp Leu Leu Leu Leu Pro Val Met Leu Leu
                 20                  25                  30

Ile Val Ala Arg Pro Val Lys Leu Ala Ala Phe Pro Thr Ser Leu
                 35                  40                  45

Ser Asp Cys Gln Thr Pro Thr Gly Trp Asn Cys Ser Gly Tyr Asp
                 50                  55                  60

Asp Arg Glu Asn Asp Leu Phe Leu Cys Asp Thr Asn Thr Cys Lys
                 65                  70                  75

Phe Asp Gly Glu Cys Leu Arg Ile Gly Asp Thr Val Thr Cys Val
                 80                  85                  90

Cys Gln Phe Lys Cys Asn Asn Asp Tyr Val Pro Val Cys Gly Ser
                 95                 100                 105

Asn Gly Glu Ser Tyr Gln Asn Glu Cys Tyr Leu Arg Gln Ala Ala
                110                 115                 120

Cys Lys Gln Gln Ser Glu Ile Leu Val Val Ser Glu Gly Ser Cys
                125                 130                 135

Ala Thr Asp Ala Gly Ser Gly Ser Gly Asp Gly Val His Glu Gly
                140                 145                 150

Ser Gly Glu Thr Ser Gln Lys Glu Thr Ser Thr Cys Asp Ile Cys
                155                 160                 165

Gln Phe Gly Ala Glu Cys Asp Glu Asp Ala Glu Asp Val Trp Cys
                170                 175                 180

Val Cys Asn Ile Asp Cys Ser Gln Thr Asn Phe Asn Pro Leu Cys
                185                 190                 195

Ala Ser Asp Gly Lys Ser Tyr Asp Asn Ala Cys Gln Ile Lys Glu
                200                 205                 210

Ala Ser Cys Gln Lys Gln Glu Lys Ile Glu Val Met Ser Leu Gly
                215                 220                 225

Arg Cys Gln Asp Asn Thr Thr Thr Thr Thr Lys Ser Glu Asp Gly
                230                 235                 240

His Tyr Ala Arg Thr Asp Tyr Ala Glu Asn Ala Asn Lys Leu Glu
                245                 250                 255

Glu Ser Ala Arg Glu His His Ile Pro Cys Pro Glu His Tyr Asn
                260                 265                 270

Gly Phe Cys Met His Gly Lys Cys Glu His Ser Ile Asn Met Gln
                275                 280                 285

Glu Pro Ser Cys Arg Cys Asp Ala Gly Tyr Thr Gly Gln His Cys
                290                 295                 300

Glu Lys Lys Asp Tyr Ser Val Leu Tyr Val Val Pro Gly Pro Val
                305                 310                 315

Arg Phe Gln Tyr Val Leu Ile Ala Ala Val Ile Gly Thr Ile Gln
                320                 325                 330

Ile Ala Val Ile Cys Val Val Val Leu Cys Ile Thr Arg Lys Cys
```

-continued

```
                335                 340                 345

Pro Arg Ser Asn Arg Ile His Arg Gln Lys Gln Asn Thr Gly His
                350                 355                 360

Tyr Ser Ser Asp Asn Thr Thr Arg Ala Ser Thr Arg Leu Ile
                365                 370
```

<210> SEQ ID NO 5
<211> LENGTH: 1838
<212> TYPE: DNA
<213> ORGANISM: Homo sapiens

<400> SEQUENCE: 5

```
cggacgcgtg ggcggacgcg tgggcggccc acggcgcccg cgggctgggg            50

cggtcgcttc ttccttctcc gtggcctacg agggtcccca gcctgggtaa           100

agatggcccc atggcccccg aagggcctag tcccagctgt gctctggggc           150

ctcagcctct tcctcaacct cccaggacct atctggctcc agccctctcc           200

acctccccag tcttctcccc cgcctcagcc ccatccgtgt catacctgcc           250

ggggactggt tgacagcttt aacaagggcc tggagagaac catccgggac           300

aactttggag gtggaaacac tgcctgggag gaagagaatt tgtccaaata           350

caaagacagt gagacccgcc tggtagaggt gctggagggt gtgtgcagca           400

agtcagactt cgagtgccac cgcctgctgg agctgagtga ggagctggtg           450

gagagctggt ggtttcacaa gcagcaggag gccccggacc tcttccagtg           500

gctgtgctca gattccctga agctctgctg ccccgcaggc accttcgggc           550

cctcctgcct tccctgtcct gggggaacag agaggccctg cggtggctac           600

gggcagtgtg aaggagaagg gacacgaggg ggcagcgggc actgtgactg           650

ccaagccggc tacgggggtg aggcctgtgg ccagtgtggc cttggctact           700

ttgaggcaga acgcaacgcc agccatctgg tatgttcggc ttgttttggc           750

ccctgtgccc gatgctcagg acctgaggaa tcaaactgtt tgcaatgcaa           800

gaagggctgg gccctgcatc acctcaagtg tgtagacatt gatgagtgtg           850

gcacagaggg agccaactgt ggagctgacc aattctgcgt gaacactgag           900

ggctcctatg agtgccgaga ctgtgccaag gcctgcctag gctgcatggg           950

ggcagggcca ggtcgctgta agaagtgtag ccctggctat cagcaggtgg          1000

gctccaagtg tctcgatgtg gatgagtgtg agacagaggt gtgtccggga          1050

gagaacaagc agtgtgaaaa caccgagggc ggttatcgct gcatctgtgc          1100

cgagggctac aagcagatgg aaggcatctg tgtgaaggag cagatcccag          1150

agtcagcagg cttcttctca gagatgacag aagacgagtt ggtggtgctg          1200

cagcagatgt tctttggcat catcatctgt gcactggcca cgctggctgc          1250

taagggcgac ttggtgttca ccgccatctt cattggggct gtggcggcca          1300

tgactggcta ctggttgtca gagcgcagtg accgtgtgct ggagggcttc          1350

atcaagggca gataatcgcg gccaccacct gtaggacctc ctcccaccca          1400

cgctgccccc agagcttggg ctgccctcct gctggacact caggacagct          1450

tggtttattt ttgagagtgg ggtaagcacc cctacctgcc ttacagagca          1500

gcccaggtac ccaggcccgg gcagacaagg cccctggggt aaaaagtagc          1550

cctgaaggtg gataccatga gctcttcacc tggcggggac tggcaggctt          1600
```

-continued

```
cacaatgtgt gaatttcaaa agtttttcct taatggtggc tgctagagct           1650

ttggcccctg cttaggatta ggtggtcctc acaggggtgg ggccatcaca           1700

gctccctcct gccagctgca tgctgccagt tcctgttctg tgttcaccac           1750

atccccacac cccattgcca cttatttatt catctcagga aataaagaaa           1800

ggtcttggaa agttaaaaaa aaaaaaaaaa  aaaaaaaa                       1838


<210> SEQ ID NO 6
<211> LENGTH: 420
<212> TYPE: PRT
<213> ORGANISM: Homo sapiens

<400> SEQUENCE: 6

Met Ala Pro Trp Pro Pro Lys Gly Leu Val Pro Ala Val Leu Trp
  1               5                  10                  15

Gly Leu Ser Leu Phe Leu Asn Leu Pro Gly Pro Ile Trp Leu Gln
                 20                  25                  30

Pro Ser Pro Pro Pro Gln Ser Ser Pro Pro Pro Gln Pro His Pro
                 35                  40                  45

Cys His Thr Cys Arg Gly Leu Val Asp Ser Phe Asn Lys Gly Leu
                 50                  55                  60

Glu Arg Thr Ile Arg Asp Asn Phe Gly Gly Gly Asn Thr Ala Trp
                 65                  70                  75

Glu Glu Glu Asn Leu Ser Lys Tyr Lys Asp Ser Glu Thr Arg Leu
                 80                  85                  90

Val Glu Val Leu Glu Gly Val Cys Ser Lys Ser Asp Phe Glu Cys
                 95                 100                 105

His Arg Leu Leu Glu Leu Ser Glu Glu Leu Val Glu Ser Trp Trp
                110                 115                 120

Phe His Lys Gln Gln Glu Ala Pro Asp Leu Phe Gln Trp Leu Cys
                125                 130                 135

Ser Asp Ser Leu Lys Leu Cys Cys Pro Ala Gly Thr Phe Gly Pro
                140                 145                 150

Ser Cys Leu Pro Cys Pro Gly Gly Thr Glu Arg Pro Cys Gly Gly
                155                 160                 165

Tyr Gly Gln Cys Glu Gly Glu Gly Thr Arg Gly Gly Ser Gly His
                170                 175                 180

Cys Asp Cys Gln Ala Gly Tyr Gly Gly Glu Ala Cys Gly Gln Cys
                185                 190                 195

Gly Leu Gly Tyr Phe Glu Ala Glu Arg Asn Ala Ser His Leu Val
                200                 205                 210

Cys Ser Ala Cys Phe Gly Pro Cys Ala Arg Cys Ser Gly Pro Glu
                215                 220                 225

Glu Ser Asn Cys Leu Gln Cys Lys Lys Gly Trp Ala Leu His His
                230                 235                 240

Leu Lys Cys Val Asp Ile Asp Glu Cys Gly Thr Glu Gly Ala Asn
                245                 250                 255

Cys Gly Ala Asp Gln Phe Cys Val Asn Thr Glu Gly Ser Tyr Glu
                260                 265                 270

Cys Arg Asp Cys Ala Lys Ala Cys Leu Gly Cys Met Gly Ala Gly
                275                 280                 285

Pro Gly Arg Cys Lys Lys Cys Ser Pro Gly Tyr Gln Gln Val Gly
                290                 295                 300
```

-continued

Ser Lys Cys Leu Asp Val Asp Glu Cys Glu Thr Glu Val Cys Pro
305 310 315

Gly Glu Asn Lys Gln Cys Glu Asn Thr Glu Gly Gly Tyr Arg Cys
320 325 330

Ile Cys Ala Glu Gly Tyr Lys Gln Met Glu Gly Ile Cys Val Lys
335 340 345

Glu Gln Ile Pro Glu Ser Ala Gly Phe Phe Ser Glu Met Thr Glu
350 355 360

Asp Glu Leu Val Val Leu Gln Gln Met Phe Phe Gly Ile Ile Ile
365 370 375

Cys Ala Leu Ala Thr Leu Ala Ala Lys Gly Asp Leu Val Phe Thr
380 385 390

Ala Ile Phe Ile Gly Ala Val Ala Ala Met Thr Gly Tyr Trp Leu
395 400 405

Ser Glu Arg Ser Asp Arg Val Leu Glu Gly Phe Ile Lys Gly Arg
410 415 420

<210> SEQ ID NO 7
<211> LENGTH: 1843
<212> TYPE: DNA
<213> ORGANISM: Homo sapiens
<220> FEATURE:
<221> NAME/KEY: Unsure
<222> LOCATION: 1837
<223> OTHER INFORMATION: Unknown base

<400> SEQUENCE: 7
cccacgcgtc cggtctcgct cgctcgcgca gcggcggcag cagaggtcgc 50
gcacagatgc gggttagact ggcgggggga ggaggcggag gagggaagga 100
agctgcatgc atgagaccca cagactcttg caagctggat gccctctgtg 150
gatgaaagat gtatcatgga atgaacccga gcaatggaga tggatttcta 200
gagcagcagc agcagcagca gcaacctcag tccccccaga gactcttggc 250
cgtgatcctg tggtttcagc tggcgctgtg cttcggccct gcacagctca 300
cgggcgggtt cgatgacctt caagtgtgtg ctgaccccgg cattcccgag 350
aatggcttca ggacccccag cggaggggtt ttctttgaag gctctgtagc 400
ccgatttcac tgccaagacg gattcaagct gaagggcgct acaaagagac 450
tgtgtttgaa gcattttaat ggaaccctag gctggatccc aagtgataat 500
tccatctgtg tgcaagaaga ttgccgtatc cctcaaatcg aagatgctga 550
gattcataac aagacatata gacatggaga gaagctaatc atcacttgtc 600
atgaaggatt caagatccgg taccccgacc tacacaatat ggtttcatta 650
tgtcgcgatg atggaacgtg gaataatctg cccatctgtc aaggctgcct 700
gagacctcta gcctcttcta atggctatgt aaacatctct gagctccaga 750
cctccttccc ggtggggact gtgatctcct atcgctgctt tcccggattt 800
aaacttgatg ggtctgcgta tcttgagtgc ttacaaaacc ttatctggtc 850
gtccagccca ccccggtgcc ttgctctgga agcccaagtc tgtccactac 900
ctccaatggt gagtcacgga gatttcgtct gccacccgcg gccttgtgag 950
cgctacaacc acggaactgt ggtggagttt tactgcgatc ctggctacag 1000
cctcaccagc gactacaagt acatcacctg ccagtatgga gagtggtttc 1050
cttcttatca agtctactgc atcaaatcag agcaaacgtg gcccagcacc 1100

-continued

```
catgagaccc tcctgaccac gtggaagatt gtggcgttca cggcaaccag          1150

tgtgctgctg gtgctgctgc tcgtcatcct ggccaggatg ttccagacca          1200

agttcaaggc ccactttccc cccagggggc ctccccggag ttccagcagt          1250

gaccctgact ttgtggtggt agacggcgtg cccgtcatgc tcccgtccta          1300

tgacgaagct gtgagtggcg gcttgagtgc cttaggcccc gggtacatgg          1350

cctctgtggg ccagggctgc cccttacccg tggacgacca gagcccccca          1400

gcataccccg gctcagggga cacggacaca ggcccagggg agtcagaaac          1450

ctgtgacagc gtctcaggct cttctgagct gctccaaagt ctgtattcac          1500

ctcccaggtg ccaagagagc acccaccctg cttcggacaa ccctgacata          1550

attgccagca cggcagagga ggtggcatcc accagcccag gcatccatca          1600

tgcccactgg gtgttgttcc taagaaactg attgattaaa aaatttccca          1650

aagtgtcctg aagtgtctct tcaaatacat gttgatctgt ggagttgatt          1700

cctttccttc tcttggtttt agacaaatgt aaacaaagct ctgatcctta          1750

aaattgctat gctgatagag tggtgagggc tggaagcttg atcaagtcct          1800

gtttcttctt gacacagact gattaaaaat taaaagnaaa  aaa                1843
```

<210> SEQ ID NO 8
<211> LENGTH: 490
<212> TYPE: PRT
<213> ORGANISM: Homo sapiens

<400> SEQUENCE: 8

```
Met Tyr His Gly Met Asn Pro Ser Asn Gly Asp Gly Phe Leu Glu
  1               5                  10                  15

Gln Gln Gln Gln Gln Gln Gln Pro Gln Ser Pro Gln Arg Leu Leu
                 20                  25                  30

Ala Val Ile Leu Trp Phe Gln Leu Ala Leu Cys Phe Gly Pro Ala
                 35                  40                  45

Gln Leu Thr Gly Gly Phe Asp Asp Leu Gln Val Cys Ala Asp Pro
                 50                  55                  60

Gly Ile Pro Glu Asn Gly Phe Arg Thr Pro Ser Gly Gly Val Phe
                 65                  70                  75

Phe Glu Gly Ser Val Ala Arg Phe His Cys Gln Asp Gly Phe Lys
                 80                  85                  90

Leu Lys Gly Ala Thr Lys Arg Leu Cys Leu Lys His Phe Asn Gly
                 95                 100                 105

Thr Leu Gly Trp Ile Pro Ser Asp Asn Ser Ile Cys Val Gln Glu
                110                 115                 120

Asp Cys Arg Ile Pro Gln Ile Glu Asp Ala Glu Ile His Asn Lys
                125                 130                 135

Thr Tyr Arg His Gly Glu Lys Leu Ile Ile Thr Cys His Glu Gly
                140                 145                 150

Phe Lys Ile Arg Tyr Pro Asp Leu His Asn Met Val Ser Leu Cys
                155                 160                 165

Arg Asp Asp Gly Thr Trp Asn Asn Leu Pro Ile Cys Gln Gly Cys
                170                 175                 180

Leu Arg Pro Leu Ala Ser Ser Asn Gly Tyr Val Asn Ile Ser Glu
                185                 190                 195

Leu Gln Thr Ser Phe Pro Val Gly Thr Val Ile Ser Tyr Arg Cys
```

-continued

```
                200                 205                 210

Phe Pro Gly Phe Lys Leu Asp Gly Ser Ala Tyr Leu Glu Cys Leu
                215                 220                 225

Gln Asn Leu Ile Trp Ser Ser Ser Pro Pro Arg Cys Leu Ala Leu
                230                 235                 240

Glu Ala Gln Val Cys Pro Leu Pro Pro Met Val Ser His Gly Asp
                245                 250                 255

Phe Val Cys His Pro Arg Pro Cys Glu Arg Tyr Asn His Gly Thr
                260                 265                 270

Val Val Glu Phe Tyr Cys Asp Pro Gly Tyr Ser Leu Thr Ser Asp
                275                 280                 285

Tyr Lys Tyr Ile Thr Cys Gln Tyr Gly Glu Trp Phe Pro Ser Tyr
                290                 295                 300

Gln Val Tyr Cys Ile Lys Ser Glu Gln Thr Trp Pro Ser Thr His
                305                 310                 315

Glu Thr Leu Leu Thr Thr Trp Lys Ile Val Ala Phe Thr Ala Thr
                320                 325                 330

Ser Val Leu Leu Val Leu Leu Leu Val Ile Leu Ala Arg Met Phe
                335                 340                 345

Gln Thr Lys Phe Lys Ala His Phe Pro Pro Arg Gly Pro Pro Arg
                350                 355                 360

Ser Ser Ser Ser Asp Pro Asp Phe Val Val Val Asp Gly Val Pro
                365                 370                 375

Val Met Leu Pro Ser Tyr Asp Glu Ala Val Ser Gly Gly Leu Ser
                380                 385                 390

Ala Leu Gly Pro Gly Tyr Met Ala Ser Val Gly Gln Gly Cys Pro
                395                 400                 405

Leu Pro Val Asp Asp Gln Ser Pro Pro Ala Tyr Pro Gly Ser Gly
                410                 415                 420

Asp Thr Asp Thr Gly Pro Gly Glu Ser Glu Thr Cys Asp Ser Val
                425                 430                 435

Ser Gly Ser Ser Glu Leu Leu Gln Ser Leu Tyr Ser Pro Pro Arg
                440                 445                 450

Cys Gln Glu Ser Thr His Pro Ala Ser Asp Asn Pro Asp Ile Ile
                455                 460                 465

Ala Ser Thr Ala Glu Glu Val Ala Ser Thr Ser Pro Gly Ile His
                470                 475                 480

His Ala His Trp Val Leu Phe Leu Arg Asn
                485                 490


<210> SEQ ID NO 9
<211> LENGTH: 1815
<212> TYPE: DNA
<213> ORGANISM: Homo sapiens

<400> SEQUENCE: 9

cccacgcgtc cgctccgcgc cctccccccc gcctcccgtg cggtccgtcg        50

gtggcctaga gatgctgctg ccgcggttgc agttgtcgcg cacgcctctg       100

cccgccagcc cgctccaccg ccgtagcgcc cgagtgtcgg ggggcgcacc       150

cgagtcgggc catgaggccg ggaaccgcgc tacaggccgt gctgctggcc       200

gtgctgctgg tggggctgcg ggccgcgacg ggtcgcctgc tgagtgcctc       250

ggatttggac ctcagaggag ggcagccagt ctgccgggga gggacacaga       300
```

-continued

```
ggccttgtta taaagtcatt tacttccatg atacttctcg aagactgaac           350

tttgaggaag ccaaagaagc ctgcaggagg gatggaggcc agctagtcag           400

catcgagtct gaagatgaac agaaactgat agaaaagttc attgaaaacc           450

tcttgccatc tgatggtgac ttctggattg ggctcaggag gcgtgaggag           500

aaacaaagca atagcacagc ctgccaggac ctttatgctt ggactgatgg           550

cagcatatca caatttagga actggtatgt ggatgagccg tcctgcggca           600

gcgaggtctg cgtggtcatg taccatcagc catcggcacc cgctggcatc           650

ggaggcccct acatgttcca gtggaatgat gaccggtgca acatgaagaa           700

caatttcatt tgcaaatatt ctgatgagaa accagcagtt ccttctagag           750

aagctgaagg tgaggaaaca gagctgacaa cacctgtact tccagaagaa           800

acacaggaag aagatgccaa aaaaacattt aaagaaagta gagaagctgc           850

cttgaatctg gcctacatcc taatccccag cattcccctt ctcctcctcc           900

ttgtggtcac cacagttgta tgttgggttt ggatctgtag aaaaagaaaa           950

cgggagcagc cagaccctag cacaaagaag caacacacca tctggccctc          1000

tcctcaccag ggaaacagcc cggacctaga ggtctacaat gtcataagaa          1050

aacaaagcga agctgactta gctgagaccc ggccagacct gaagaatatt          1100

tcattccgag tgtgttcggg agaagccact cccgatgaca tgtcttgtga          1150

ctatgacaac atggctgtga acccatcaga aagtgggttt gtgactctgg          1200

tgagcgtgga gagtggattt gtgaccaatg acatttatga gttctcccca          1250

gaccaaatgg ggaggagtaa ggagtctgga tgggtggaaa atgaaatata          1300

tggttattag gacatataaa aaactgaaac tgacaacaat ggaaaagaaa          1350

tgataagcaa aatcctctta ttttctataa ggaaaataca cagaaggtct          1400

atgaacaagc ttagatcagg tcctgtggat gagcatgtgg tccccacgac          1450

ctcctgttgg acccccacgt tttggctgta tcctttatcc cagccagtca          1500

tccagctcga ccttatgaga aggtaccttg cccaggtctg gcacatagta          1550

gagtctcaat aaatgtcact tggttggttg tatctaactt ttaagggaca          1600

gagctttacc tggcagtgat aaagatgggc tgtggagctt ggaaaaccac          1650

ctctgttttc cttgctctat acagcagcac atattatcat acagacagaa          1700

aatccagaat cttttcaaag cccacatatg gtagcacagg ttggcctgtg          1750

catcggcaat tctcatatct gtttttttca aagaataaaa tcaaataaag          1800

agcaggaaaa  aaaaa                                                1815
```

<210> SEQ ID NO 10
<211> LENGTH: 382
<212> TYPE: PRT
<213> ORGANISM: Homo sapiens

<400> SEQUENCE: 10

```
Met Arg Pro Gly Thr Ala Leu Gln Ala Val Leu Leu Ala Val Leu
  1               5                  10                  15

Leu Val Gly Leu Arg Ala Ala Thr Gly Arg Leu Leu Ser Ala Ser
                 20                  25                  30

Asp Leu Asp Leu Arg Gly Gly Gln Pro Val Cys Arg Gly Gly Thr
                 35                  40                  45
```

```
Gln Arg Pro Cys Tyr Lys Val Ile Tyr Phe His Asp Thr Ser Arg
                50                  55                  60

Arg Leu Asn Phe Glu Glu Ala Lys Glu Ala Cys Arg Arg Asp Gly
                65                  70                  75

Gly Gln Leu Val Ser Ile Glu Ser Glu Asp Glu Gln Lys Leu Ile
                80                  85                  90

Glu Lys Phe Ile Glu Asn Leu Leu Pro Ser Asp Gly Asp Phe Trp
                95                  100                 105

Ile Gly Leu Arg Arg Arg Glu Glu Lys Gln Ser Asn Ser Thr Ala
                110                 115                 120

Cys Gln Asp Leu Tyr Ala Trp Thr Asp Gly Ser Ile Ser Gln Phe
                125                 130                 135

Arg Asn Trp Tyr Val Asp Glu Pro Ser Cys Gly Ser Glu Val Cys
                140                 145                 150

Val Val Met Tyr His Gln Pro Ser Ala Pro Ala Gly Ile Gly Gly
                155                 160                 165

Pro Tyr Met Phe Gln Trp Asn Asp Asp Arg Cys Asn Met Lys Asn
                170                 175                 180

Asn Phe Ile Cys Lys Tyr Ser Asp Glu Lys Pro Ala Val Pro Ser
                185                 190                 195

Arg Glu Ala Glu Gly Glu Glu Thr Glu Leu Thr Thr Pro Val Leu
                200                 205                 210

Pro Glu Glu Thr Gln Glu Glu Asp Ala Lys Lys Thr Phe Lys Glu
                215                 220                 225

Ser Arg Glu Ala Ala Leu Asn Leu Ala Tyr Ile Leu Ile Pro Ser
                230                 235                 240

Ile Pro Leu Leu Leu Leu Leu Val Val Thr Thr Val Val Cys Trp
                245                 250                 255

Val Trp Ile Cys Arg Lys Arg Lys Arg Glu Gln Pro Asp Pro Ser
                260                 265                 270

Thr Lys Lys Gln His Thr Ile Trp Pro Ser Pro His Gln Gly Asn
                275                 280                 285

Ser Pro Asp Leu Glu Val Tyr Asn Val Ile Arg Lys Gln Ser Glu
                290                 295                 300

Ala Asp Leu Ala Glu Thr Arg Pro Asp Leu Lys Asn Ile Ser Phe
                305                 310                 315

Arg Val Cys Ser Gly Glu Ala Thr Pro Asp Asp Met Ser Cys Asp
                320                 325                 330

Tyr Asp Asn Met Ala Val Asn Pro Ser Glu Ser Gly Phe Val Thr
                335                 340                 345

Leu Val Ser Val Glu Ser Gly Phe Val Thr Asn Asp Ile Tyr Glu
                350                 355                 360

Phe Ser Pro Asp Gln Met Gly Arg Ser Lys Glu Ser Gly Trp Val
                365                 370                 375

Glu Asn Glu Ile Tyr Gly Tyr
                380
```

```
<210> SEQ ID NO 11
<211> LENGTH: 2479
<212> TYPE: DNA
<213> ORGANISM: Homo sapiens

<400> SEQUENCE: 11

acttgccatc acctgttgcc agtgtggaaa aattctccct gttgaatttt              50
```

-continued

```
ttgcacatgg aggacagcag caaagagggc aacacaggct gataagacca      100
gagacagcag ggagattatt ttaccatacg ccctcaggac gttccctcta      150
gctggagttc tggacttcaa cagaacccca tccagtcatt ttgattttgc      200
tgtttatttt ttttttcttt ttctttttcc caccacattg tattttattt      250
ccgtacttca gaaatgggcc tacagaccac aaagtggccc agccatgggg      300
ctttttttcct gaagtcttgg cttatcattt ccctggggct ctactcacag     350
gtgtccaaac tcctggcctg ccctagtgtg tgccgctgcg acaggaactt      400
tgtctactgt aatgagcgaa gcttgacctc agtgcctctt gggatcccgg      450
agggcgtaac cgtactctac ctccacaaca accaaattaa taatgctgga      500
tttcctgcag aactgcacaa tgtacagtcg gtgcacacgg tctacctgta      550
tggcaaccaa ctggacgaat tccccatgaa ccttcccaag aatgtcagag      600
ttctccattt gcaggaaaac aatattcaga ccatttcacg ggctgctctt      650
gcccagctct tgaagcttga agagctgcac ctggatgaca actccatatc      700
cacagtgggg gtggaagacg gggccttccg ggaggctatt agcctcaaat      750
tgttgttttt gtctaagaat cacctgagca gtgtgcctgt tgggcttcct      800
gtggacttgc aagagctgag agtggatgaa aatcgaattg ctgtcatatc      850
cgacatggcc ttccagaatc tcacgagctt ggagcgtctt attgtggacg      900
ggaacctcct gaccaacaag ggtatcgccg agggcacctt cagccatctc      950
accaagctca aggaattttc aattgtacgt aattcgctgt cccaccctcc     1000
tcccgatctc ccaggtacgc atctgatcag gctctatttg caggacaacc     1050
agataaacca cattcctttg acagccttct caaatctgcg taagctggaa     1100
cggctggata tatccaacaa ccaactgcgg atgctgactc aaggggtttt     1150
tgataatctc tccaacctga agcagctcac tgctcggaat aacccttggt     1200
tttgtgactg cagtattaaa tgggtcacag aatggctcaa atatatccct     1250
tcatctctca acgtgcgggg tttcatgtgc caaggtcctg aacaagtccg     1300
ggggatggcc gtcagggaat taaatatgaa tcttttgtcc tgtcccacca     1350
cgacccccgg cctgcctctc ttcaccccag ccccaagtac agcttctccg      1400
accactcagc ctcccaccct ctctattcca aaccctagca gaagctacac      1450
gcctccaact cctaccacat cgaaacttcc cacgattcct gactgggatg      1500
gcagagaaag agtgacccca cctatttctg aacggatcca gctctctatc      1550
cattttgtga atgatacttc cattcaagtc agctggctct ctctcttcac      1600
cgtgatggca tacaaactca catgggtgaa aatgggccac agtttagtag      1650
ggggcatcgt tcaggagcgc atagtcagcg gtgagaagca acacctgagc      1700
ctggttaact tagagccccg atccacctat cggatttgtt tagtgccact      1750
ggatgctttt aactaccgcg cggtagaaga caccatttgt tcagaggcca      1800
ccacccatgc ctcctatctg aacaacggca gcaacacagc gtccagccat      1850
gagcagacga cgtcccacag catgggctcc ccctttctgc tggcgggctt      1900
gatcgggggc gcggtgatat ttgtgctggt ggtcttgctc agcgtctttt      1950
gctggcatat gcacaaaaag gggcgctaca cctcccagaa gtggaaatac      2000
aaccggggcc ggcggaaaga tgattattgc gaggcaggca ccaagaagga      2050
```

-continued

```
caactccatc ctggagatga cagaaaccag ttttcagatc gtctccttaa            2100

ataacgatca actccttaaa ggagatttca gactgcagcc catttacacc            2150

ccaaatgggg gcattaatta cacagactgc catatcccca acaacatgcg            2200

atactgcaac agcagcgtgc cagacctgga gcactgccat acgtgacagc            2250

cagaggccca gcgttatcaa ggcggacaat tagactcttg agaacacact            2300

cgtgtgtgca cataaagaca cgcagattac atttgataaa tgttacacag            2350

atgcatttgt gcatttgaat actctgtaat ttatacggtg tactatataa            2400

tgggatttaa aaaaagtgct atcttttcta tttcaagtta attacaaaca            2450

gttttgtaac tctttgcttt  ttaaatctt                                  2479
```

```
<210> SEQ ID NO 12
<211> LENGTH: 660
<212> TYPE: PRT
<213> ORGANISM: Homo sapiens

<400> SEQUENCE: 12

Met Gly Leu Gln Thr Thr Lys Trp Pro Ser His Gly Ala Phe Phe
1               5                   10                  15

Leu Lys Ser Trp Leu Ile Ile Ser Leu Gly Leu Tyr Ser Gln Val
                20                  25                  30

Ser Lys Leu Leu Ala Cys Pro Ser Val Cys Arg Cys Asp Arg Asn
                35                  40                  45

Phe Val Tyr Cys Asn Glu Arg Ser Leu Thr Ser Val Pro Leu Gly
                50                  55                  60

Ile Pro Glu Gly Val Thr Val Leu Tyr Leu His Asn Asn Gln Ile
                65                  70                  75

Asn Asn Ala Gly Phe Pro Ala Glu Leu His Asn Val Gln Ser Val
                80                  85                  90

His Thr Val Tyr Leu Tyr Gly Asn Gln Leu Asp Glu Phe Pro Met
                95                  100                 105

Asn Leu Pro Lys Asn Val Arg Val Leu His Leu Gln Glu Asn Asn
                110                 115                 120

Ile Gln Thr Ile Ser Arg Ala Ala Leu Ala Gln Leu Leu Lys Leu
                125                 130                 135

Glu Glu Leu His Leu Asp Asp Asn Ser Ile Ser Thr Val Gly Val
                140                 145                 150

Glu Asp Gly Ala Phe Arg Glu Ala Ile Ser Leu Lys Leu Leu Phe
                155                 160                 165

Leu Ser Lys Asn His Leu Ser Ser Val Pro Val Gly Leu Pro Val
                170                 175                 180

Asp Leu Gln Glu Leu Arg Val Asp Glu Asn Arg Ile Ala Val Ile
                185                 190                 195

Ser Asp Met Ala Phe Gln Asn Leu Thr Ser Leu Glu Arg Leu Ile
                200                 205                 210

Val Asp Gly Asn Leu Leu Thr Asn Lys Gly Ile Ala Glu Gly Thr
                215                 220                 225

Phe Ser His Leu Thr Lys Leu Lys Glu Phe Ser Ile Val Arg Asn
                230                 235                 240

Ser Leu Ser His Pro Pro Pro Asp Leu Pro Gly Thr His Leu Ile
                245                 250                 255

Arg Leu Tyr Leu Gln Asp Asn Gln Ile Asn His Ile Pro Leu Thr
```

-continued

```
                260                 265                 270

Ala Phe Ser Asn Leu Arg Lys Leu Glu Arg Leu Asp Ile Ser Asn
                275                 280                 285

Asn Gln Leu Arg Met Leu Thr Gln Gly Val Phe Asp Asn Leu Ser
                290                 295                 300

Asn Leu Lys Gln Leu Thr Ala Arg Asn Asn Pro Trp Phe Cys Asp
                305                 310                 315

Cys Ser Ile Lys Trp Val Thr Glu Trp Leu Lys Tyr Ile Pro Ser
                320                 325                 330

Ser Leu Asn Val Arg Gly Phe Met Cys Gln Gly Pro Glu Gln Val
                335                 340                 345

Arg Gly Met Ala Val Arg Glu Leu Asn Met Asn Leu Leu Ser Cys
                350                 355                 360

Pro Thr Thr Thr Pro Gly Leu Pro Leu Phe Thr Pro Ala Pro Ser
                365                 370                 375

Thr Ala Ser Pro Thr Thr Gln Pro Pro Thr Leu Ser Ile Pro Asn
                380                 385                 390

Pro Ser Arg Ser Tyr Thr Pro Pro Thr Pro Thr Thr Ser Lys Leu
                395                 400                 405

Pro Thr Ile Pro Asp Trp Asp Gly Arg Glu Arg Val Thr Pro Pro
                410                 415                 420

Ile Ser Glu Arg Ile Gln Leu Ser Ile His Phe Val Asn Asp Thr
                425                 430                 435

Ser Ile Gln Val Ser Trp Leu Ser Leu Phe Thr Val Met Ala Tyr
                440                 445                 450

Lys Leu Thr Trp Val Lys Met Gly His Ser Leu Val Gly Gly Ile
                455                 460                 465

Val Gln Glu Arg Ile Val Ser Gly Glu Lys Gln His Leu Ser Leu
                470                 475                 480

Val Asn Leu Glu Pro Arg Ser Thr Tyr Arg Ile Cys Leu Val Pro
                485                 490                 495

Leu Asp Ala Phe Asn Tyr Arg Ala Val Glu Asp Thr Ile Cys Ser
                500                 505                 510

Glu Ala Thr Thr His Ala Ser Tyr Leu Asn Asn Gly Ser Asn Thr
                515                 520                 525

Ala Ser Ser His Glu Gln Thr Thr Ser His Ser Met Gly Ser Pro
                530                 535                 540

Phe Leu Leu Ala Gly Leu Ile Gly Gly Ala Val Ile Phe Val Leu
                545                 550                 555

Val Val Leu Leu Ser Val Phe Cys Trp His Met His Lys Lys Gly
                560                 565                 570

Arg Tyr Thr Ser Gln Lys Trp Lys Tyr Asn Arg Gly Arg Arg Lys
                575                 580                 585

Asp Asp Tyr Cys Glu Ala Gly Thr Lys Lys Asp Asn Ser Ile Leu
                590                 595                 600

Glu Met Thr Glu Thr Ser Phe Gln Ile Val Ser Leu Asn Asn Asp
                605                 610                 615

Gln Leu Leu Lys Gly Asp Phe Arg Leu Gln Pro Ile Tyr Thr Pro
                620                 625                 630

Asn Gly Gly Ile Asn Tyr Thr Asp Cys His Ile Pro Asn Asn Met
                635                 640                 645

Arg Tyr Cys Asn Ser Ser Val Pro Asp Leu Glu His Cys His Thr
                650                 655                 660
```

-continued

<210> SEQ ID NO 13
<211> LENGTH: 2153
<212> TYPE: DNA
<213> ORGANISM: Homo sapiens

<400> SEQUENCE: 13

```
taggaggtcc ccgggttgcc ggcggcgaca gcgggggaag catgactgct      50

gtgggccgaa ggtgccccgc gctggggtcc cgaggggctg ctggagagcc     100

agaggctggc agcgactatg tgaagttctc caaggagaag tacatcctgg     150

actcatcgcc agagaaactc cacaaggaat tggaggagga gctcaaactc     200

agcagcacgg atctccgcag ccatgcctgg taccatggcc gcatccccccg     250

agaggtctcg gagaccttgg tacaacgcaa cggcgacttc ctcatccggg     300

actcgctcac cagcctgggc gactatgtgc tcacgtgccg ctggcgcaac     350

caggccttgc acttcaagat caacaaggtg gtggtgaagg caggcgagag     400

ctacacacac atccagtacc tgtttgagca ggagagcttt gaccacgtgc     450

ccgccctcgt gcgctatcat gtgggcagcc gcaaggctgt gtcagagcag     500

agtggtgcca tcatctactg cccggtgaac cgcaccttcc cactgcgcta     550

cctcgaggcc agctatggcc tgggacaggg gagtagcaag cctgctagcc     600

ccgtcagccc ctcaggcccc aagggcagcc acatgaagcg gcgcagcgtc     650

accatgaccg atgggctcac tgctgacaag gtcacccgca gcgatggctg     700

ccccaccagt acgtcgctgc cccgccctcg ggactccatc cgcagctgtg     750

ccctcagcat ggaccagatc ccagacctgc actcacccat gtcgcccatc     800

tccgagagcc ctagctcccc tgcctacagc actgtaaccc gtgtccatgc     850

cgcccctgca gccccttctg ccacagcatt gcctgcctcc cctgtcgccc     900

gctgttccag tgagccccag ctgtgtcccg gaagtgcccc aaagacccat     950

ggggagtcag acaagggccc ccacaccagc ccctcccaca cccttggcaa    1000

ggcctccccg tcaccatcac tcagcagcta cagtgacccg gactctggcc    1050

actactgcca gctccagcct cccgtgcgtg gcagccgaga gtgggcagcg    1100

actgagacct ccagccagca ggccaggagc tatggggaga ggctaaagga    1150

actgtcagaa aatggggccc ctgaagggga ctggggcaag accttcacag    1200

tccccatcgt ggaagtcact tcttccttca acccggccac cttccagtca    1250

ctactgatcc ccagggataa ccggccactg gaggtgggcc ttctgcgcaa    1300

ggtcaaggag ctgctggcag aagtggatgc ccggacgctg gcccggcatg    1350

tcaccaaggt ggactgcctg gttgctagga tactgggcgt taccaaggag    1400

atgcagaccc taatgggagt ccgctggggc atggaactgc tcaccctccc    1450

ccatggccgg cagctacgcc tagacctgct ggaaaggttc cacaccatgt    1500

ccatcatgct ggccgtggac atcctgggct gcaccggctc tgcggaggag    1550

cgggcagcgc tgctgcacaa gaccattcag ctggcggccg agctacgggg    1600

gactatgggc aacatgttca gcttcgcggc ggtcatgggt gccctggaca    1650

tggctcagat ttctcggctg gagcagacat gggtgaccct gcggcagcga    1700

cacacagagg gtgccatcct gtacgagaag aagctcaagc cttttctcaa    1750
```

-continued

```
gagcctcaac gagggcaaag aaggcccgcc gctgagcaac accacgtttc           1800

ctcatgtgct gcccctcatc accctgctgg agtgtgactc ggccccacca           1850

gagggccctg agccctgggg cagcacggag cacggcgtgg aggtggtgct           1900

ggctcacctg gaggccgccc gcacagtggc acaccacgga ggcctgtacc           1950

acaccaatgc tgaagtcaag ctgcaggggt tccaggcccg gccggagctc           2000

ctggaggtgt tcagcacgga gttccagatg cgccttctct ggggcagtca           2050

gggtgccagc agcagccagg cccggcgcta tgagaagttc gacaaggtcc           2100

tcactgccct gtcccacaag ctggaacctg ctgtccgctc cagcgagctg           2150

tga 2153


<210> SEQ ID NO 14
<211> LENGTH: 703
<212> TYPE: PRT
<213> ORGANISM: Homo sapiens

<400> SEQUENCE: 14

Met Thr Ala Val Gly Arg Arg Cys Pro Ala Leu Gly Ser Arg Gly
  1               5                  10                  15

Ala Ala Gly Glu Pro Glu Ala Gly Ser Asp Tyr Val Lys Phe Ser
                 20                  25                  30

Lys Glu Lys Tyr Ile Leu Asp Ser Ser Pro Glu Lys Leu His Lys
                 35                  40                  45

Glu Leu Glu Glu Glu Leu Lys Leu Ser Ser Thr Asp Leu Arg Ser
                 50                  55                  60

His Ala Trp Tyr His Gly Arg Ile Pro Arg Glu Val Ser Glu Thr
                 65                  70                  75

Leu Val Gln Arg Asn Gly Asp Phe Leu Ile Arg Asp Ser Leu Thr
                 80                  85                  90

Ser Leu Gly Asp Tyr Val Leu Thr Cys Arg Trp Arg Asn Gln Ala
                 95                 100                 105

Leu His Phe Lys Ile Asn Lys Val Val Val Lys Ala Gly Glu Ser
                110                 115                 120

Tyr Thr His Ile Gln Tyr Leu Phe Glu Gln Glu Ser Phe Asp His
                125                 130                 135

Val Pro Ala Leu Val Arg Tyr His Val Gly Ser Arg Lys Ala Val
                140                 145                 150

Ser Glu Gln Ser Gly Ala Ile Ile Tyr Cys Pro Val Asn Arg Thr
                155                 160                 165

Phe Pro Leu Arg Tyr Leu Glu Ala Ser Tyr Gly Leu Gly Gln Gly
                170                 175                 180

Ser Ser Lys Pro Ala Ser Pro Val Ser Pro Ser Gly Pro Lys Gly
                185                 190                 195

Ser His Met Lys Arg Arg Ser Val Thr Met Thr Asp Gly Leu Thr
                200                 205                 210

Ala Asp Lys Val Thr Arg Ser Asp Gly Cys Pro Thr Ser Thr Ser
                215                 220                 225

Leu Pro Arg Pro Arg Asp Ser Ile Arg Ser Cys Ala Leu Ser Met
                230                 235                 240

Asp Gln Ile Pro Asp Leu His Ser Pro Met Ser Pro Ile Ser Glu
                245                 250                 255

Ser Pro Ser Ser Pro Ala Tyr Ser Thr Val Thr Arg Val His Ala
                260                 265                 270
```

-continued

```
Ala Pro Ala Ala Pro Ser Ala Thr Ala Leu Pro Ala Ser Pro Val
                275                 280                 285

Ala Arg Cys Ser Ser Glu Pro Gln Leu Cys Pro Gly Ser Ala Pro
                290                 295                 300

Lys Thr His Gly Glu Ser Asp Lys Gly Pro His Thr Ser Pro Ser
                305                 310                 315

His Thr Leu Gly Lys Ala Ser Pro Ser Pro Ser Leu Ser Ser Tyr
                320                 325                 330

Ser Asp Pro Asp Ser Gly His Tyr Cys Gln Leu Gln Pro Pro Val
                335                 340                 345

Arg Gly Ser Arg Glu Trp Ala Ala Thr Glu Thr Ser Ser Gln Gln
                350                 355                 360

Ala Arg Ser Tyr Gly Glu Arg Leu Lys Glu Leu Ser Glu Asn Gly
                365                 370                 375

Ala Pro Glu Gly Asp Trp Gly Lys Thr Phe Thr Val Pro Ile Val
                380                 385                 390

Glu Val Thr Ser Ser Phe Asn Pro Ala Thr Phe Gln Ser Leu Leu
                395                 400                 405

Ile Pro Arg Asp Asn Arg Pro Leu Glu Val Gly Leu Leu Arg Lys
                410                 415                 420

Val Lys Glu Leu Leu Ala Glu Val Asp Ala Arg Thr Leu Ala Arg
                425                 430                 435

His Val Thr Lys Val Asp Cys Leu Val Ala Arg Ile Leu Gly Val
                440                 445                 450

Thr Lys Glu Met Gln Thr Leu Met Gly Val Arg Trp Gly Met Glu
                455                 460                 465

Leu Leu Thr Leu Pro His Gly Arg Gln Leu Arg Leu Asp Leu Leu
                470                 475                 480

Glu Arg Phe His Thr Met Ser Ile Met Leu Ala Val Asp Ile Leu
                485                 490                 495

Gly Cys Thr Gly Ser Ala Glu Glu Arg Ala Ala Leu Leu His Lys
                500                 505                 510

Thr Ile Gln Leu Ala Ala Glu Leu Arg Gly Thr Met Gly Asn Met
                515                 520                 525

Phe Ser Phe Ala Ala Val Met Gly Ala Leu Asp Met Ala Gln Ile
                530                 535                 540

Ser Arg Leu Glu Gln Thr Trp Val Thr Leu Arg Gln Arg His Thr
                545                 550                 555

Glu Gly Ala Ile Leu Tyr Glu Lys Lys Leu Lys Pro Phe Leu Lys
                560                 565                 570

Ser Leu Asn Glu Gly Lys Glu Gly Pro Pro Leu Ser Asn Thr Thr
                575                 580                 585

Phe Pro His Val Leu Pro Leu Ile Thr Leu Leu Glu Cys Asp Ser
                590                 595                 600

Ala Pro Pro Glu Gly Pro Glu Pro Trp Gly Ser Thr Glu His Gly
                605                 610                 615

Val Glu Val Val Leu Ala His Leu Glu Ala Ala Arg Thr Val Ala
                620                 625                 630

His His Gly Gly Leu Tyr His Thr Asn Ala Glu Val Lys Leu Gln
                635                 640                 645

Gly Phe Gln Ala Arg Pro Glu Leu Leu Glu Val Phe Ser Thr Glu
                650                 655                 660
```

-continued

```
Phe Gln Met Arg Leu Leu Trp Gly Ser Gln Gly Ala Ser Ser Ser
                665                 670                 675

Gln Ala Arg Arg Tyr Glu Lys Phe Asp Lys Val Leu Thr Ala Leu
                680                 685                 690

Ser His Lys Leu Glu Pro Ala Val Arg Ser Ser Glu Leu
                695                 700


<210> SEQ ID NO 15
<211> LENGTH: 3296
<212> TYPE: DNA
<213> ORGANISM: Homo sapiens

<400> SEQUENCE: 15

caaaacttgc gtcgcggaga gcgcccagct tgacttgaat ggaaggagcc          50

cgagcccgcg gagcgcagct gagactgggg gagcgcgttc ggcctgtggg         100

gcgccgctcg gcgccggggc gcagcaggga aggggaagct gtggtctgcc         150

ctgctccacg aggcgccact ggtgtgaacc gggagagccc ctgggtggtc         200

ccgtccccta tccctccttt atatagaaac cttccacact gggaaggcag         250

cggcgaggca ggagggctca tggtgagcaa ggaggccggc tgatctgcag         300

gcgcacagca ttccgagttt acagattttt acagatacca aatggaaggc         350

gaggaggcag aacagcctgc ctggttccat cagccctggc gcccaggcgc         400

atctgactcg gcaccccctg caggcaccat ggcccagagc cgggtgctgc         450

tgctcctgct gctgctgccg ccacagctgc acctgggacc tgtgcttgcc         500

gtgagggccc caggatttgg ccgaagtggc ggccacagcc tgagccccga         550

agagaacgaa tttgcggagg aggagccggt gctggtactg agccctgagg         600

agcccgggcc tggcccagcc gcggtcagct gcccccgaga ctgtgcctgt         650

tcccaggagg gcgtcgtgga ctgtggcggt attgacctgc gtgagttccc         700

gggggacctg cctgagcaca ccaaccacct atctctgcag aacaaccagc         750

tggaaaagat ctaccctgag gagctctccc ggctgcaccg gctggagaca         800

ctgaacctgc aaaacaaccg cctgacttcc cgagggctcc cagagaaggc         850

gtttgagcat ctgaccaacc tcaattacct gtacttggcc aataacaagc         900

tgaccttggc accccgcttc ctgccaaacg ccctgatcag tgtggacttt         950

gctgccaact atctcaccaa gatctatggg ctcacctttg gccagaagcc        1000

aaacttgagg tctgtgtacc tgcacaacaa caagctggca gacgccgggc        1050

tgccggacaa catgttcaac ggctccagca acgtcgaggt cctcatcctg        1100

tccagcaact tcctgcgcca cgtgcccaag cacctgccgc ctgccctgta        1150

caagctgcac ctcaagaaca acaagctgga gaagatcccc ccgggggcct        1200

tcagcgagct gagcagcctg cgcgagctat acctgcagaa caactacctg        1250

actgacgagg gcctggacaa cgagaccttc tggaagctct ccagcctgga        1300

gtacctggat ctgtccagca acaacctgtc tcgggtccca gctgggctgc        1350

cgcgcagcct ggtgctgctg cacttggaga agaacgccat ccggagcgtg        1400

gacgcgaatg tgctgacccc catccgcagc ctggagtacc tgctgctgca        1450

cagcaaccag ctgcgggagc agggcatcca cccactggcc ttccagggcc        1500

tcaagcggtt gcacacggtg cacctgtaca acaacgcgct ggagcgcgtg        1550
```

-continued

```
cccagtggcc tgcctcgccg cgtgcgcacc ctcatgatcc tgcacaacca      1600
gatcacaggc attggccgcg aagactttgc caccacctac ttcctggagg      1650
agctcaacct cagctacaac cgcatcacca gcccacaggt gcaccgcgac      1700
gccttccgca agctgcgcct gctgcgctcg ctggacctgt cgggcaaccg      1750
gctgcacacg ctgccacctg ggctgcctcg aaatgtccat gtgctgaagg      1800
tcaagcgcaa tgagctggct gccttggcac gaggggcgct ggcgggcatg      1850
gctcagctgc gtgagctgta cctcaccagc aaccgactgc gcagccgagc      1900
cctgggcccc cgtgcctggg tggacctcgc ccatctgcag ctgctggaca      1950
tcgccgggaa tcagctcaca gagatccccg aggggctccc cgagtcactt      2000
gagtacctgt acctgcagaa caacaagatt agtgcggtgc ccgccaatgc      2050
cttcgactcc acgcccaacc tcaaggggat ctttctcagg tttaacaagc      2100
tggctgtggg ctccgtggtg gacagtgcct tccggaggct gaagcacctg      2150
caggtcttgg acattgaagg caacttagag tttggtgaca tttccaagga      2200
ccgtggccgc ttggggaagg aaaaggagga ggaggaagag gaggaggagg      2250
aggaagagga aacaagatag tgacaaggtg atgcagatgt gacctaggat      2300
gatggaccgc cggactcttt tctgcagcac acgcctgtgt gctgtgagcc      2350
ccccactctg ccgtgctcac acagacacac ccagctgcac acatgaggca      2400
tcccacatga cacgggctga cacagtctca tatccccacc ccttcccacg      2450
gcgtgtccca cggccagaca catgcacaca catcacaccc tcaaacaccc      2500
agctcagcca cacacaacta ccctccaaac caccacagtc tctgtcacac      2550
ccccactacc gctgccacgc cctctgaatc atgcagggaa gggtctgccc      2600
ctgccctggc acacacaggc acccattccc tccccctgct gacatgtgta      2650
tgcgtatgca tacacaccac acacacacac atgcacaagt catgtgcgaa      2700
cagccctcca aagcctatgc cacagacagc tcttgcccca gccagaatca      2750
gccatagcag ctcgccgtct gccctgtcca tctgtccgtc cgttccctgg      2800
agaagacaca agggtatcca tgctctgtgg ccaggtgcct gccaccctct      2850
ggaactcaca aaagctggct tttattcctt tcccatccta tggggacagg      2900
agccttcagg actgctggcc tggcctggcc caccctgctc ctccaggtgc      2950
tgggcagtca ctctgctaag agtccctccc tgccacgccc tggcaggaca      3000
caggcacttt tccaatgggc aagcccagtg gaggcaggat gggagagccc      3050
cctgggtgct gctggggcct tggggcagga gtgaagcaga ggtgatgggg      3100
ctgggctgag ccagggagga aggacccagc tgcacctagg agacaccttt      3150
gttcttcagg cctgtggggg aagttccggg tgcctttatt ttttattctt      3200
ttctaaggaa aaaaatgata aaaatctcaa agctgatttt tcttgttata      3250
gaaaaactaa tataaaagca ttatccctat ccctgcaaaa  aaaaaa         3296
```

<210> SEQ ID NO 16
<211> LENGTH: 642
<212> TYPE: PRT
<213> ORGANISM: Homo sapiens

<400> SEQUENCE: 16

Met Glu Gly Glu Glu Ala Glu Gln Pro Ala Trp Phe His Gln Pro

-continued

```
1               5                   10                  15

Trp Arg Pro Gly Ala Ser Asp Ser Ala Pro Pro Ala Gly Thr Met
                20                  25                  30

Ala Gln Ser Arg Val Leu Leu Leu Leu Leu Leu Leu Pro Pro Gln
                35                  40                  45

Leu His Leu Gly Pro Val Leu Ala Val Arg Ala Pro Gly Phe Gly
                50                  55                  60

Arg Ser Gly Gly His Ser Leu Ser Pro Glu Glu Asn Glu Phe Ala
                65                  70                  75

Glu Glu Glu Pro Val Leu Val Leu Ser Pro Glu Glu Pro Gly Pro
                80                  85                  90

Gly Pro Ala Ala Val Ser Cys Pro Arg Asp Cys Ala Cys Ser Gln
                95                  100                 105

Glu Gly Val Val Asp Cys Gly Gly Ile Asp Leu Arg Glu Phe Pro
                110                 115                 120

Gly Asp Leu Pro Glu His Thr Asn His Leu Ser Leu Gln Asn Asn
                125                 130                 135

Gln Leu Glu Lys Ile Tyr Pro Glu Glu Leu Ser Arg Leu His Arg
                140                 145                 150

Leu Glu Thr Leu Asn Leu Gln Asn Asn Arg Leu Thr Ser Arg Gly
                155                 160                 165

Leu Pro Glu Lys Ala Phe Glu His Leu Thr Asn Leu Asn Tyr Leu
                170                 175                 180

Tyr Leu Ala Asn Asn Lys Leu Thr Leu Ala Pro Arg Phe Leu Pro
                185                 190                 195

Asn Ala Leu Ile Ser Val Asp Phe Ala Ala Asn Tyr Leu Thr Lys
                200                 205                 210

Ile Tyr Gly Leu Thr Phe Gly Gln Lys Pro Asn Leu Arg Ser Val
                215                 220                 225

Tyr Leu His Asn Asn Lys Leu Ala Asp Ala Gly Leu Pro Asp Asn
                230                 235                 240

Met Phe Asn Gly Ser Ser Asn Val Glu Val Leu Ile Leu Ser Ser
                245                 250                 255

Asn Phe Leu Arg His Val Pro Lys His Leu Pro Pro Ala Leu Tyr
                260                 265                 270

Lys Leu His Leu Lys Asn Asn Lys Leu Glu Lys Ile Pro Pro Gly
                275                 280                 285

Ala Phe Ser Glu Leu Ser Ser Leu Arg Glu Leu Tyr Leu Gln Asn
                290                 295                 300

Asn Tyr Leu Thr Asp Glu Gly Leu Asp Asn Glu Thr Phe Trp Lys
                305                 310                 315

Leu Ser Ser Leu Glu Tyr Leu Asp Leu Ser Ser Asn Asn Leu Ser
                320                 325                 330

Arg Val Pro Ala Gly Leu Pro Arg Ser Leu Val Leu Leu His Leu
                335                 340                 345

Glu Lys Asn Ala Ile Arg Ser Val Asp Ala Asn Val Leu Thr Pro
                350                 355                 360

Ile Arg Ser Leu Glu Tyr Leu Leu Leu His Ser Asn Gln Leu Arg
                365                 370                 375

Glu Gln Gly Ile His Pro Leu Ala Phe Gln Gly Leu Lys Arg Leu
                380                 385                 390

His Thr Val His Leu Tyr Asn Asn Ala Leu Glu Arg Val Pro Ser
                395                 400                 405
```

-continued

```
Gly Leu Pro Arg Arg Val Arg Thr Leu Met Ile Leu His Asn Gln
                410                 415                 420

Ile Thr Gly Ile Gly Arg Glu Asp Phe Ala Thr Thr Tyr Phe Leu
                425                 430                 435

Glu Glu Leu Asn Leu Ser Tyr Asn Arg Ile Thr Ser Pro Gln Val
                440                 445                 450

His Arg Asp Ala Phe Arg Lys Leu Arg Leu Leu Arg Ser Leu Asp
                455                 460                 465

Leu Ser Gly Asn Arg Leu His Thr Leu Pro Pro Gly Leu Pro Arg
                470                 475                 480

Asn Val His Val Leu Lys Val Lys Arg Asn Glu Leu Ala Ala Leu
                485                 490                 495

Ala Arg Gly Ala Leu Ala Gly Met Ala Gln Leu Arg Glu Leu Tyr
                500                 505                 510

Leu Thr Ser Asn Arg Leu Arg Ser Arg Ala Leu Gly Pro Arg Ala
                515                 520                 525

Trp Val Asp Leu Ala His Leu Gln Leu Leu Asp Ile Ala Gly Asn
                530                 535                 540

Gln Leu Thr Glu Ile Pro Glu Gly Leu Pro Glu Ser Leu Glu Tyr
                545                 550                 555

Leu Tyr Leu Gln Asn Asn Lys Ile Ser Ala Val Pro Ala Asn Ala
                560                 565                 570

Phe Asp Ser Thr Pro Asn Leu Lys Gly Ile Phe Leu Arg Phe Asn
                575                 580                 585

Lys Leu Ala Val Gly Ser Val Val Asp Ser Ala Phe Arg Arg Leu
                590                 595                 600

Lys His Leu Gln Val Leu Asp Ile Glu Gly Asn Leu Glu Phe Gly
                605                 610                 615

Asp Ile Ser Lys Asp Arg Gly Arg Leu Gly Lys Glu Lys Glu Glu
                620                 625                 630

Glu Glu Glu Glu Glu Glu Glu Glu Glu Glu Thr Arg
                635                 640
```

```
<210> SEQ ID NO 17
<211> LENGTH: 1649
<212> TYPE: DNA
<213> ORGANISM: Homo sapiens

<400> SEQUENCE: 17

agtcctgccc agctcttgga tcagtctgct ggccgaggag cccggtggag            50

ccaggggtga ccctggagcc cagcctgccc cgaggaggcc ccggctcaga           100

gccatgccag gtgtctgtga tagggcccct gacttcctct ccccgtctga           150

agaccaggtg ctgaggcctg ccttgggcag ctcagtggct ctgaactgca           200

cggcttgggt agtctctggg ccccactgct ccctgccttc agtccagtgg           250

ctgaaagacg ggcttccatt gggaattggg ggccactaca gcctccacga           300

gtactcctgg gtcaaggcca acctgtcaga ggtgcttgtg tccagtgtcc           350

tgggggtcaa cgtgaccagc actgaagtct atggggcctt cacctgctcc           400

atccagaaca tcagcttctc ctccttcact cttcagagag ctggccctac           450

aagccacgtg gctgcggtgc tggcctccct cctggtcctg ctggccctgc           500

tgctggccgc cctgctctat gtcaagtgcc gtctcaacgt gctgctctgg           550
```

-continued

```
taccaggacg cgtatgggga ggtggagata aacgacggga agctctacga          600

cgcctacgtc tcctacagcg actgccccga ggaccgcaag ttcgtgaact          650

tcatcctaaa gccgcagctg gagcggcgtc ggggctacaa gctcttcctg          700

gacgaccgcg acctcctgcc gcgcgctgag ccctccgccg acctcttggt          750

gaacctgagc cgctgccgac gcctcatcgt ggtgctttcg gacgccttcc          800

tgagccgggc ctggtgcagc cacagcttcc gggagggcct gtgccggctg          850

ctggagctca cccgcagacc catcttcatc accttcgagg gccagaggcg          900

cgaccccgcg cacccggcgc tccgcctgct gcgccagcac cgccacctgg          950

tgaccttgct gctctggagg cccggctccg tgactccttc ctccgatttt         1000

tggaaagaag tgcagctggc gctgccgcgg aaggtgcggt acaggccggt         1050

ggaaggagac ccccagacgc agctgcagga cgacaaggac cccatgctga         1100

ttcttcgagg ccgagtccct gagggccggg ccctggactc agaggtggac         1150

ccggaccctg agggcgacct gggtatgccc gcccagcccc actccccaac         1200

tggagaagct cagcacaggg cggagtgggg gcaggcacag ggcacagggc         1250

ctggaggggc tctaggtgtt gaggactctt cccggcaccg ggagcccctg         1300

cacggcctct gccctggagg tgctcggccc tcggtctgcc tgggaacttc         1350

ctgggcctca caggccatca cagcaggggg tgagcagggg cagcccctgg         1400

cagtgggtct gggccaaggc tgtgggtggc cacctcaggc gtctcggtct         1450

ccccacccca ggtgtccggg ggcctgtttt tggagagcca tcagctccac         1500

cgcacaccag tggggtctcg ctgggagaga gccggagcag cgaagtggac         1550

gtctcggatc tcggctcgcg aaactacagt gcccgcacag acttctactg         1600

cctggtgtcc aaggatgata tgtagctccc accccagagt  gcaggatca         1649
```

```
<210> SEQ ID NO 18
<211> LENGTH: 504
<212> TYPE: PRT
<213> ORGANISM: Homo sapiens

<400> SEQUENCE: 18

Met Pro Gly Val Cys Asp Arg Ala Pro Asp Phe Leu Ser Pro Ser
  1               5                  10                  15

Glu Asp Gln Val Leu Arg Pro Ala Leu Gly Ser Ser Val Ala Leu
                 20                  25                  30

Asn Cys Thr Ala Trp Val Val Ser Gly Pro His Cys Ser Leu Pro
                 35                  40                  45

Ser Val Gln Trp Leu Lys Asp Gly Leu Pro Leu Gly Ile Gly Gly
                 50                  55                  60

His Tyr Ser Leu His Glu Tyr Ser Trp Val Lys Ala Asn Leu Ser
                 65                  70                  75

Glu Val Leu Val Ser Ser Val Leu Gly Val Asn Val Thr Ser Thr
                 80                  85                  90

Glu Val Tyr Gly Ala Phe Thr Cys Ser Ile Gln Asn Ile Ser Phe
                 95                 100                 105

Ser Ser Phe Thr Leu Gln Arg Ala Gly Pro Thr Ser His Val Ala
                110                 115                 120

Ala Val Leu Ala Ser Leu Leu Val Leu Leu Ala Leu Leu Leu Ala
                125                 130                 135
```

-continued

Ala Leu Leu Tyr Val Lys Cys Arg Leu Asn Val Leu Leu Trp Tyr
140 145 150

Gln Asp Ala Tyr Gly Glu Val Glu Ile Asn Asp Gly Lys Leu Tyr
155 160 165

Asp Ala Tyr Val Ser Tyr Ser Asp Cys Pro Glu Asp Arg Lys Phe
170 175 180

Val Asn Phe Ile Leu Lys Pro Gln Leu Glu Arg Arg Arg Gly Tyr
185 190 195

Lys Leu Phe Leu Asp Asp Arg Asp Leu Leu Pro Arg Ala Glu Pro
200 205 210

Ser Ala Asp Leu Leu Val Asn Leu Ser Arg Cys Arg Arg Leu Ile
215 220 225

Val Val Leu Ser Asp Ala Phe Leu Ser Arg Ala Trp Cys Ser His
230 235 240

Ser Phe Arg Glu Gly Leu Cys Arg Leu Leu Glu Leu Thr Arg Arg
245 250 255

Pro Ile Phe Ile Thr Phe Glu Gly Gln Arg Arg Asp Pro Ala His
260 265 270

Pro Ala Leu Arg Leu Leu Arg Gln His Arg His Leu Val Thr Leu
275 280 285

Leu Leu Trp Arg Pro Gly Ser Val Thr Pro Ser Ser Asp Phe Trp
290 295 300

Lys Glu Val Gln Leu Ala Leu Pro Arg Lys Val Arg Tyr Arg Pro
305 310 315

Val Glu Gly Asp Pro Gln Thr Gln Leu Gln Asp Asp Lys Asp Pro
320 325 330

Met Leu Ile Leu Arg Gly Arg Val Pro Glu Gly Arg Ala Leu Asp
335 340 345

Ser Glu Val Asp Pro Asp Pro Glu Gly Asp Leu Gly Met Pro Ala
350 355 360

Gln Pro His Ser Pro Thr Gly Glu Ala Gln His Arg Ala Glu Trp
365 370 375

Gly Gln Ala Gln Gly Thr Gly Pro Gly Gly Ala Leu Gly Val Glu
380 385 390

Asp Ser Ser Arg His Arg Glu Pro Leu His Gly Leu Cys Pro Gly
395 400 405

Gly Ala Arg Pro Ser Val Cys Leu Gly Thr Ser Trp Ala Ser Gln
410 415 420

Ala Ile Thr Ala Gly Gly Glu Gln Gly Gln Pro Leu Ala Val Gly
425 430 435

Leu Gly Gln Gly Cys Gly Trp Pro Pro Gln Ala Ser Arg Ser Pro
440 445 450

His Pro Arg Cys Pro Gly Ala Cys Phe Trp Arg Ala Ile Ser Ser
455 460 465

Thr Ala His Gln Trp Gly Leu Ala Gly Arg Glu Pro Glu Gln Arg
470 475 480

Ser Gly Arg Leu Gly Ser Arg Leu Ala Lys Leu Gln Cys Pro His
485 490 495

Arg Leu Leu Leu Pro Gly Val Gln Gly
500

<210> SEQ ID NO 19
<211> LENGTH: 2211
<212> TYPE: DNA

-continued

<213> ORGANISM: Homo sapiens

<400> SEQUENCE: 19

```
gaaagctata ggctacccat tcagctcccc tgtcagagac tcaagctttg     50
agaaaggcta gcaaagagca aggaaagaga gaaaacaaca aagtggcgag    100
gccctcagag tgaaagcgta aggttcagtc agcctgctgc agctttgcag    150
acctcagctg ggcatctcca gactcccctg aaggaagagc cttcctcacc    200
caaacccaca aaagatgctg aaaaagcctc tctcagctgt gacctggctc    250
tgcattttca tcgtggcctt tgtcagccac ccagcgtggc tgcagaagct    300
ctctaagcac aagacaccag cacagccaca gctcaaagcg gccaactgct    350
gtgaggaggt gaaggagctc aaggcccaag ttgccaacct tagcagcctg    400
ctgagtgaac tgaacaagaa gcaggagagg gactgggtca gcgtggtcat    450
gcaggtgatg gagctggaga gcaacagcaa gcgcatggag tcgcggctca    500
cagatgctga gagcaagtac tccgagatga acaaccaaat tgacatcatg    550
cagctgcagg cagcacagac ggtcactcag acctccgcag atgccatcta    600
cgactgctct tccctctacc agaagaacta ccgcatctct ggagtgtata    650
agcttcctcc tgatgacttc ctgggcagcc ctgaactgga ggtgttctgt    700
gacatggaga cttcaggcgg aggctggacc atcatccaga gacgaaaaag    750
tggccttgtc tccttctacc gggactggaa gcagtacaag cagggctttg    800
gcagcatccg tggggacttc tggctgggga acgaacacat ccaccggctc    850
tccagacagc caacccggct gcgtgtagag atggaggact gggagggcaa    900
cctgcgctac gctgagtata gccactttgt tttgggcaat gaactcaaca    950
gctatcgcct cttcctgggg aactacactg gcaatgtggg gaacacgccc   1000
tccagtatca taacaacaca gccttcagca ccaaggacaa ggacaatgac   1050
aactgcttgg acaagtgtgc acagctccgc aaaggtggct actggtacaa   1100
ctgctgcaca gactccaacc tcaatggagt gtactaccgc ctgggtgagc   1150
acaataagca cctggatggc atcacctggt atggctggca tggatctacc   1200
tactccctca aacgggtgga gatgaaaatc cgcccagaag acttcaagcc   1250
ttaaaaggag gctgccgtgg agcacggata cagaaactga gacacgtgga   1300
gactggatga gggcagatga ggacaggaag agagtgttag aaagggtagg   1350
actgagaaac agcctataat ctccaaagaa agaataagtc tccaaggagc   1400
acaaaaaaat catatgtacc aaggatgtta cagtaaacag gatgaactat   1450
ttaaacccac tgggtcctgc cacatccttc tcaaggtggt agactgagtg   1500
gggtctctct gcccaagatc cctgacatag cagtagcttg tcttttccac   1550
atgatttgtc tgtgaaagaa aataattttg agatcgtttt atctattttc   1600
tctacggctt aggctatgtg agggcaaaac acaaatccct ttgctaaaaa   1650
gaaccatatt attttgattc tcaaaggata ggcctttgag tgttagagaa   1700
aggagtgaag gaggcaggtg ggaaatggta tttctatttt taaatccagt   1750
gaaattatct tgagtctaca cattattttt aaaacacaaa aattgttcgg   1800
ctggaactga cccaggctgg acttgcgggg aggaaactcc agggcactgc   1850
atctggcgat cagactctga gcactgcccc tgctcgcctt ggtcatgtac   1900
```

-continued

```
agcactgaaa ggaatgaagc accagcagga ggtggacaga gtctctcatg          1950

gatgccggca caaaactgcc ttaaaatatt catagttaat acaggtatat          2000

ctatttttat ttactttgta agaaacaagc tcaaggagct tccttttaaa          2050

ttttgtctgt aggaaatggt tgaaaactga aggtagatgg tgttatagtt          2100

aataataaat gctgtaaata agcatctcac tttgtaaaaa taaaatattg          2150

tggttttgtt ttaaacattc aacgtttctt ttccttctac aataaacact          2200

ttcaaaatgt  g                                                   2211


<210> SEQ ID NO 20
<211> LENGTH: 346
<212> TYPE: PRT
<213> ORGANISM: Homo sapiens

<400> SEQUENCE: 20

Met Leu Lys Lys Pro Leu Ser Ala Val Thr Trp Leu Cys Ile Phe
  1               5                  10                  15

Ile Val Ala Phe Val Ser His Pro Ala Trp Leu Gln Lys Leu Ser
                 20                  25                  30

Lys His Lys Thr Pro Ala Gln Pro Gln Leu Lys Ala Ala Asn Cys
                 35                  40                  45

Cys Glu Glu Val Lys Glu Leu Lys Ala Gln Val Ala Asn Leu Ser
                 50                  55                  60

Ser Leu Leu Ser Glu Leu Asn Lys Lys Gln Glu Arg Asp Trp Val
                 65                  70                  75

Ser Val Val Met Gln Val Met Glu Leu Glu Ser Asn Ser Lys Arg
                 80                  85                  90

Met Glu Ser Arg Leu Thr Asp Ala Glu Ser Lys Tyr Ser Glu Met
                 95                 100                 105

Asn Asn Gln Ile Asp Ile Met Gln Leu Gln Ala Ala Gln Thr Val
                110                 115                 120

Thr Gln Thr Ser Ala Asp Ala Ile Tyr Asp Cys Ser Ser Leu Tyr
                125                 130                 135

Gln Lys Asn Tyr Arg Ile Ser Gly Val Tyr Lys Leu Pro Pro Asp
                140                 145                 150

Asp Phe Leu Gly Ser Pro Glu Leu Glu Val Phe Cys Asp Met Glu
                155                 160                 165

Thr Ser Gly Gly Gly Trp Thr Ile Ile Gln Arg Arg Lys Ser Gly
                170                 175                 180

Leu Val Ser Phe Tyr Arg Asp Trp Lys Gln Tyr Lys Gln Gly Phe
                185                 190                 195

Gly Ser Ile Arg Gly Asp Phe Trp Leu Gly Asn Glu His Ile His
                200                 205                 210

Arg Leu Ser Arg Gln Pro Thr Arg Leu Arg Val Glu Met Glu Asp
                215                 220                 225

Trp Glu Gly Asn Leu Arg Tyr Ala Glu Tyr Ser His Phe Val Leu
                230                 235                 240

Gly Asn Glu Leu Asn Ser Tyr Arg Leu Phe Leu Gly Asn Tyr Thr
                245                 250                 255

Gly Asn Val Gly Asn Asp Ala Leu Gln Tyr His Asn Asn Thr Ala
                260                 265                 270

Phe Ser Thr Lys Asp Lys Asp Asn Asp Asn Cys Leu Asp Lys Cys
                275                 280                 285
```

-continued

```
Ala Gln Leu Arg Lys Gly Gly Tyr Trp Tyr Asn Cys Cys Thr Asp
                290                 295                 300

Ser Asn Leu Asn Gly Val Tyr Tyr Arg Leu Gly Glu His Asn Lys
                305                 310                 315

His Leu Asp Gly Ile Thr Trp Tyr Gly Trp His Gly Ser Thr Tyr
                320                 325                 330

Ser Leu Lys Arg Val Glu Met Lys Ile Arg Pro Glu Asp Phe Lys
                335                 340                 345

Pro


<210> SEQ ID NO 21
<211> LENGTH: 2680
<212> TYPE: DNA
<213> ORGANISM: Homo sapiens

<400> SEQUENCE: 21

tgcggcgacc gtcgtacacc atgggcctcc acctccgccc ctaccgtgtg        50

gggctgctcc cggatggcct cctgttcctc ttgctgctgc taatgctgct       100

cgcggaccca gcgctcccgg ccggacgtca ccccccagtg gtgctggtcc       150

ctggtgattt gggtaaccaa ctggaagcca agctggacaa gccgacagtg       200

gtgcactacc tctgctccaa gaagaccgaa agctacttca caatctggct       250

gaacctggaa ctgctgctgc ctgtcatcat tgactgctgg attgacaata       300

tcaggctggt ttacaacaaa acatccaggg ccacccagtt tcctgatggt       350

gtggatgtac gtgtccctgg ctttgggaag accttctcac tggagttcct       400

ggaccccagc aaaagcagcg tgggttccta tttccacacc atggtggaga       450

gccttgtggg ctggggctac acacggggtg aggatgtccg aggggctccc       500

tatgactggc gccgagcccc aaatgaaaac gggccctact tcctggccct       550

ccgcgagatg atcgaggaga tgtaccagct gtatgggggc cccgtggtgc       600

tggttgccca cagtatgggc aacatgtaca cgctctactt tctgcagcgg       650

cagccgcagg cctggaagga caagtatatc cgggccttcg tgtcactggg       700

tgcgccctgg gggggcgtgg ccaagaccct gcgcgtcctg gcttcaggag       750

acaacaaccg gatcccagtc atcgggcccc tgaagatccg ggagcagcag       800

cggtcagctg tctccaccag ctggctgctg ccctacaact acacatggtc       850

acctgagaag gtgttcgtgc agacacccac aatcaactac acactgcggg       900

actaccgcaa gttcttccag gacatcggct ttgaagatgg ctggctcatg       950

cggcaggaca cagaagggct ggtggaagcc acgatgccac ctggcgtgca      1000

gctgcactgc ctctatggta ctggcgtccc cacaccagac tccttctact      1050

atgagagctt ccctgaccgt gaccctaaaa tctgctttgg tgacggcgat      1100

ggtactgtga acttgaagag tgccctgcag tgccaggcct ggcagagccg      1150

ccaggagcac caagtgttgc tgcaggagct gccaggcagc gagcacatcg      1200

agatgctggc caacgccacc accctggcct atctgaaacg tgtgctcctt      1250

gggccctgac tcctgtgcca caggactcct gtggctcggc cgtggacctg      1300

ctgttggcct ctggggctgt catggcccac gcgttttgca aagtttgtga      1350

ctcaccattc aaggccccga gtcttggact gtgaagcatc tgccatgggg      1400
```

-continued

```
aagtgctgtt tgttatcctt tctctgtggc agtgaagaag gaagaaatga        1450

gagtctagac tcaagggaca ctggatggca agaatgctgc tgatggtgga        1500

actgctgtga ccttaggact ggctccacag ggtggactgg ctgggccctg        1550

gtcccagtcc ctgcctgggg ccatgtgtcc ccctattcct gtgggctttt        1600

catacttgcc tactgggccc tggccccgca gccttcctat gagggatgtt        1650

actgggctgt ggtcctgtac ccagaggtcc cagggatcgg ctcctggccc        1700

ctcgggtgac ccttcccaca caccagccac agataggcct gccactggtc        1750

atgggtagct agagctgctg gcttccctgt ggcttagctg gtggccagcc        1800

tgactggctt cctgggcgag cctagtagct cctgcaggca ggggcagttt        1850

gttgcgttct tcgtggttcc caggccctgg gacatctcac tccactccta        1900

cctcccttac caccaggagc attcaagctc tggattgggc agcagatgtg        1950

cccccagtcc cgcaggctgt gttccagggg ccctgatttc ctcggatgtg        2000

ctattggccc caggactgaa gctgcctccc ttcaccctgg gactgtggtt        2050

ccaaggatga gagcaggggt tggagccatg gccttctggg aacctatgga        2100

gaaagggaat ccaaggaagc agccaaggct gctcgcagct tccctgagct        2150

gcacctcttg ctaaccccac catcacactg ccaccctgcc ctagggtctc        2200

actagtacca agtgggtcag cacagggctg aggatggggc tcctatccac        2250

cctggccagc acccagctta gtgctgggac tagcccagaa acttgaatgg        2300

gaccctgaga gagccagggg tcccctgagg ccccccctagg ggctttctgt        2350

ctgccccagg gtgctccatg gatctccctg tggcagcagg catggagagt        2400

cagggctgcc ttcatggcag taggctctaa gtgggtgact ggccacaggc        2450

cgagaaaagg gtacagcctc taggtggggt tcccaaagac gccttcaggc        2500

tggactgagc tgctctccca cagggtttct gtgcagctgg attttctctg        2550

ttgcatacat gcctggcatc tgtctcccct tgttcctgag tggccccaca        2600

tggggctctg agcaggctgt atctggattc tggcaataaa agtactctgg        2650

atgctgtaaa aaaaaaaaaa aaaaaaaaaa                              2680


<210> SEQ ID NO 22
<211> LENGTH: 412
<212> TYPE: PRT
<213> ORGANISM: Homo sapiens

<400> SEQUENCE: 22

Met Gly Leu His Leu Arg Pro Tyr Arg Val Gly Leu Leu Pro Asp
 1               5                  10                  15

Gly Leu Leu Phe Leu Leu Leu Leu Leu Met Leu Leu Ala Asp Pro
                20                  25                  30

Ala Leu Pro Ala Gly Arg His Pro Pro Val Val Leu Val Pro Gly
                35                  40                  45

Asp Leu Gly Asn Gln Leu Glu Ala Lys Leu Asp Lys Pro Thr Val
                50                  55                  60

Val His Tyr Leu Cys Ser Lys Lys Thr Glu Ser Tyr Phe Thr Ile
                65                  70                  75

Trp Leu Asn Leu Glu Leu Leu Leu Pro Val Ile Ile Asp Cys Trp
                80                  85                  90

Ile Asp Asn Ile Arg Leu Val Tyr Asn Lys Thr Ser Arg Ala Thr
```

-continued

```
                95                  100                 105

Gln Phe Pro Asp Gly Val Asp Val Arg Val Pro Gly Phe Gly Lys
                110                 115                 120

Thr Phe Ser Leu Glu Phe Leu Asp Pro Ser Lys Ser Ser Val Gly
                125                 130                 135

Ser Tyr Phe His Thr Met Val Glu Ser Leu Val Gly Trp Gly Tyr
                140                 145                 150

Thr Arg Gly Glu Asp Val Arg Gly Ala Pro Tyr Asp Trp Arg Arg
                155                 160                 165

Ala Pro Asn Glu Asn Gly Pro Tyr Phe Leu Ala Leu Arg Glu Met
                170                 175                 180

Ile Glu Glu Met Tyr Gln Leu Tyr Gly Gly Pro Val Val Leu Val
                185                 190                 195

Ala His Ser Met Gly Asn Met Tyr Thr Leu Tyr Phe Leu Gln Arg
                200                 205                 210

Gln Pro Gln Ala Trp Lys Asp Lys Tyr Ile Arg Ala Phe Val Ser
                215                 220                 225

Leu Gly Ala Pro Trp Gly Gly Val Ala Lys Thr Leu Arg Val Leu
                230                 235                 240

Ala Ser Gly Asp Asn Asn Arg Ile Pro Val Ile Gly Pro Leu Lys
                245                 250                 255

Ile Arg Glu Gln Gln Arg Ser Ala Val Ser Thr Ser Trp Leu Leu
                260                 265                 270

Pro Tyr Asn Tyr Thr Trp Ser Pro Glu Lys Val Phe Val Gln Thr
                275                 280                 285

Pro Thr Ile Asn Tyr Thr Leu Arg Asp Tyr Arg Lys Phe Phe Gln
                290                 295                 300

Asp Ile Gly Phe Glu Asp Gly Trp Leu Met Arg Gln Asp Thr Glu
                305                 310                 315

Gly Leu Val Glu Ala Thr Met Pro Pro Gly Val Gln Leu His Cys
                320                 325                 330

Leu Tyr Gly Thr Gly Val Pro Thr Pro Asp Ser Phe Tyr Tyr Glu
                335                 340                 345

Ser Phe Pro Asp Arg Asp Pro Lys Ile Cys Phe Gly Asp Gly Asp
                350                 355                 360

Gly Thr Val Asn Leu Lys Ser Ala Leu Gln Cys Gln Ala Trp Gln
                365                 370                 375

Ser Arg Gln Glu His Gln Val Leu Leu Gln Glu Leu Pro Gly Ser
                380                 385                 390

Glu His Ile Glu Met Leu Ala Asn Ala Thr Thr Leu Ala Tyr Leu
                395                 400                 405

Lys Arg Val Leu Leu Gly Pro
                410
```

<210> SEQ ID NO 23
<211> LENGTH: 3143
<212> TYPE: DNA
<213> ORGANISM: Homo sapiens

<400> SEQUENCE: 23

```
gagccaccta ccctgctccg aggccaggcc tgcagggcct catcggccag                50

agggtgatca gtgagcagaa ggatgcccgt ggccgaggcc ccccaggtgg               100

ctggcgggca gggggacgga ggtgatggcg aggaagcgga gccagagggg               150
```

-continued

```
atgttcaagg cctgtgagga ctccaagaga aaagcccggg gctacctccg      200
cctggtgccc ctgtttgtgc tgctggccct gctcgtgctg gcttcggcgg      250
gggtgctact ctggtatttc ctagggtaca aggcggaggt gatggtcagc      300
caggtgtact caggcagtct gcgtgtactc aatcgccact tctcccagga      350
tcttacccgc cgggaatcta gtgccttccg cagtgaaacc gccaaagccc      400
agaagatgct caaggagctc atcaccagca cccgcctggg aacttactac      450
aactccagct ccgtctattc ctttggggag ggacccctca cctgcttctt      500
ctggttcatt ctccaaatcc ccgagcaccg ccggctgatg ctgagccccg      550
aggtggtgca ggcactgctg gtggaggagc tgctgtccac agtcaacagc      600
tcggctgccg tcccctacag ggccgagtac gaagtggacc ccgagggcct      650
agtgatcctg gaagccagtg tgaaagacat agctgcattg aattccacgc      700
tgggttgtta ccgctacagc tacgtgggcc agggccaggt cctccggctg      750
aaggggcctg accacctggc ctccagctgc ctgtggcacc tgcagggccc      800
caaggacctc atgctcaaac tccggctgga gtggacgctg gcagagtgcc      850
gggaccgact ggccatgtat gacgtggccg ggcccctgga gaagaggctc      900
atcacctcgg tgtacggctg cagccgccag gagcccgtgg tggaggttct      950
ggcgtcgggg gccatcatgg cggtcgtctg gaagaagggc ctgcacagct     1000
actacgaccc cttcgtgctc tccgtgcagc cggtggtctt ccaggcctgt     1050
gaagtgaacc tgacgctgga caacaggctc gactcccagg gcgtcctcag     1100
caccccgtac ttccccagct actactcgcc ccaaacccac tgctcctggc     1150
acctcacggt gccctctctg gactacggct tggccctctg gtttgatgcc     1200
tatgcactga ggaggcagaa gtatgatttg ccgtgcaccc agggccagtg     1250
gacgatccag aacaggaggc tgtgtggctt gcgcatcctg cagccctacg     1300
ccgagaggat ccccgtggtg gccacggccg ggatcaccat caacttcacc     1350
tcccagatct ccctcaccgg gcccggtgtg cgggtgcact atggcttgta     1400
caaccagtcg gacccctgcc ctggagagtt cctctgttct gtgaatggac     1450
tctgtgtccc tgcctgtgat ggggtcaagg actgccccaa cggcctggat     1500
gagagaaact gcgtttgcag agccacattc cagtgcaaag aggacagcac     1550
atgcatctca ctgcccaagg tctgtgatgg gcagcctgat tgtctcaacg     1600
gcagcgatga agagcagtgc caggaagggg tgccatgtgg gacattcacc     1650
ttccagtgtg aggaccggag ctgcgtgaag aagcccaacc cgcagtgtga     1700
tgggcggccc gactgcaggg acggctcgga tgaggagcac tgtgactgtg     1750
gcctccaggg cccctccagc cgcattgttg gtggagctgt gtcctccgag     1800
ggtgagtggc catggcaggc cagcctccag gttcggggtc gacacatctg     1850
tggggggggcc ctcatcgctg accgctgggt gataacagct gcccactgct     1900
tccaggagga cagcatggcc tccacggtgc tgtggaccgt gttcctgggc     1950
aaggtgtggc agaactcgcg ctggcctgga gaggtgtcct tcaaggtgag     2000
ccgcctgctc ctgcacccgt accacgaaga ggacagccat gactacgacg     2050
tggcgctgct gcagctcgac cacccggtgg tgcgctcggc cgccgtgcgc     2100
cccgtctgcc tgcccgcgcg ctcccacttc ttcgagcccg gcctgcactg     2150
```

-continued

```
ctggattacg ggctggggcg ccttgcgcga gggcggcccc atcagcaacg              2200

ctctgcagaa agtggatgtg cagttgatcc cacaggacct gtgcagcgag              2250

gcctatcgct accaggtgac gccacgcatg ctgtgtgccg gctaccgcaa              2300

gggcaagaag gatgcctgtc agggtgactc aggtggtccg ctggtgtgca              2350

aggcactcag tggccgctgg ttcctggcgg ggctggtcag ctggggcctg              2400

ggctgtggcc ggcctaacta cttcggcgtc tacacccgca tcacaggtgt              2450

gatcagctgg atccagcaag tggtgacctg aggaactgcc cccctgcaaa              2500

gcagggccca cctcctggac tcagagagcc cagggcaact gccaagcagg              2550

gggacaagta ttctggcggg gggtggggga gagagcaggc cctgtggtgg              2600

caggaggtgg catcttgtct cgtccctgat gtctgctcca gtgatggcag              2650

gaggatggag aagtgccagc agctgggggt caagacgtcc cctgaggacc              2700

caggcccaca cccagccctt ctgcctccca attctctctc ctccgtcccc              2750

ttcctccact gctgcctaat gcaaggcagt ggctcagcag caagaatgct              2800

ggttctacat cccgaggagt gtctgaggtg cgccccactc tgtacagagg              2850

ctgtttgggc agccttgcct ccagagagca gattccagct tcggaagccc              2900

ctggtctaac ttgggatctg ggaatggaag gtgctcccat cggaggggac              2950

cctcagagcc ctggagactg ccaggtgggc ctgctgccac tgtaagccaa              3000

aaggtgggga agtcctgact ccagggtcct tgccccaccc ctgcctgcca              3050

cctgggccct cacagcccag accctcactg ggaggtgagc tcagctgccc              3100

tttggaataa agctgcctga tcaaaaaaaa aaaaaaaaaa  aaa                   3143
```

<210> SEQ ID NO 24
<211> LENGTH: 802
<212> TYPE: PRT
<213> ORGANISM: Homo sapiens

<400> SEQUENCE: 24

```
Met Pro Val Ala Glu Ala Pro Gln Val Ala Gly Gly Gln Gly Asp
  1               5                  10                  15

Gly Gly Asp Gly Glu Glu Ala Glu Pro Glu Gly Met Phe Lys Ala
                 20                  25                  30

Cys Glu Asp Ser Lys Arg Lys Ala Arg Gly Tyr Leu Arg Leu Val
                 35                  40                  45

Pro Leu Phe Val Leu Leu Ala Leu Leu Val Leu Ala Ser Ala Gly
                 50                  55                  60

Val Leu Leu Trp Tyr Phe Leu Gly Tyr Lys Ala Glu Val Met Val
                 65                  70                  75

Ser Gln Val Tyr Ser Gly Ser Leu Arg Val Leu Asn Arg His Phe
                 80                  85                  90

Ser Gln Asp Leu Thr Arg Arg Glu Ser Ser Ala Phe Arg Ser Glu
                 95                 100                 105

Thr Ala Lys Ala Gln Lys Met Leu Lys Glu Leu Ile Thr Ser Thr
                110                 115                 120

Arg Leu Gly Thr Tyr Tyr Asn Ser Ser Ser Val Tyr Ser Phe Gly
                125                 130                 135

Glu Gly Pro Leu Thr Cys Phe Phe Trp Phe Ile Leu Gln Ile Pro
                140                 145                 150
```

-continued

```
Glu His Arg Arg Leu Met Leu Ser Pro Glu Val Val Gln Ala Leu
                155                 160                 165

Leu Val Glu Glu Leu Leu Ser Thr Val Asn Ser Ser Ala Ala Val
                170                 175                 180

Pro Tyr Arg Ala Glu Tyr Glu Val Asp Pro Glu Gly Leu Val Ile
                185                 190                 195

Leu Glu Ala Ser Val Lys Asp Ile Ala Ala Leu Asn Ser Thr Leu
                200                 205                 210

Gly Cys Tyr Arg Tyr Ser Tyr Val Gly Gln Gly Gln Val Leu Arg
                215                 220                 225

Leu Lys Gly Pro Asp His Leu Ala Ser Ser Cys Leu Trp His Leu
                230                 235                 240

Gln Gly Pro Lys Asp Leu Met Leu Lys Leu Arg Leu Glu Trp Thr
                245                 250                 255

Leu Ala Glu Cys Arg Asp Arg Leu Ala Met Tyr Asp Val Ala Gly
                260                 265                 270

Pro Leu Glu Lys Arg Leu Ile Thr Ser Val Tyr Gly Cys Ser Arg
                275                 280                 285

Gln Glu Pro Val Val Glu Val Leu Ala Ser Gly Ala Ile Met Ala
                290                 295                 300

Val Val Trp Lys Lys Gly Leu His Ser Tyr Tyr Asp Pro Phe Val
                305                 310                 315

Leu Ser Val Gln Pro Val Val Phe Gln Ala Cys Glu Val Asn Leu
                320                 325                 330

Thr Leu Asp Asn Arg Leu Asp Ser Gln Gly Val Leu Ser Thr Pro
                335                 340                 345

Tyr Phe Pro Ser Tyr Tyr Ser Pro Gln Thr His Cys Ser Trp His
                350                 355                 360

Leu Thr Val Pro Ser Leu Asp Tyr Gly Leu Ala Leu Trp Phe Asp
                365                 370                 375

Ala Tyr Ala Leu Arg Arg Gln Lys Tyr Asp Leu Pro Cys Thr Gln
                380                 385                 390

Gly Gln Trp Thr Ile Gln Asn Arg Arg Leu Cys Gly Leu Arg Ile
                395                 400                 405

Leu Gln Pro Tyr Ala Glu Arg Ile Pro Val Val Ala Thr Ala Gly
                410                 415                 420

Ile Thr Ile Asn Phe Thr Ser Gln Ile Ser Leu Thr Gly Pro Gly
                425                 430                 435

Val Arg Val His Tyr Gly Leu Tyr Asn Gln Ser Asp Pro Cys Pro
                440                 445                 450

Gly Glu Phe Leu Cys Ser Val Asn Gly Leu Cys Val Pro Ala Cys
                455                 460                 465

Asp Gly Val Lys Asp Cys Pro Asn Gly Leu Asp Glu Arg Asn Cys
                470                 475                 480

Val Cys Arg Ala Thr Phe Gln Cys Lys Glu Asp Ser Thr Cys Ile
                485                 490                 495

Ser Leu Pro Lys Val Cys Asp Gly Gln Pro Asp Cys Leu Asn Gly
                500                 505                 510

Ser Asp Glu Glu Gln Cys Gln Glu Gly Val Pro Cys Gly Thr Phe
                515                 520                 525

Thr Phe Gln Cys Glu Asp Arg Ser Cys Val Lys Lys Pro Asn Pro
                530                 535                 540

Gln Cys Asp Gly Arg Pro Asp Cys Arg Asp Gly Ser Asp Glu Glu
```

-continued

```
                545                 550                 555

His Cys Asp Cys Gly Leu Gln Gly Pro Ser Ser Arg Ile Val Gly
                560                 565                 570

Gly Ala Val Ser Ser Glu Gly Glu Trp Pro Trp Gln Ala Ser Leu
                575                 580                 585

Gln Val Arg Gly Arg His Ile Cys Gly Gly Ala Leu Ile Ala Asp
                590                 595                 600

Arg Trp Val Ile Thr Ala Ala His Cys Phe Gln Glu Asp Ser Met
                605                 610                 615

Ala Ser Thr Val Leu Trp Thr Val Phe Leu Gly Lys Val Trp Gln
                620                 625                 630

Asn Ser Arg Trp Pro Gly Glu Val Ser Phe Lys Val Ser Arg Leu
                635                 640                 645

Leu Leu His Pro Tyr His Glu Glu Asp Ser His Asp Tyr Asp Val
                650                 655                 660

Ala Leu Leu Gln Leu Asp His Pro Val Val Arg Ser Ala Ala Val
                665                 670                 675

Arg Pro Val Cys Leu Pro Ala Arg Ser His Phe Phe Glu Pro Gly
                680                 685                 690

Leu His Cys Trp Ile Thr Gly Trp Gly Ala Leu Arg Glu Gly Gly
                695                 700                 705

Pro Ile Ser Asn Ala Leu Gln Lys Val Asp Val Gln Leu Ile Pro
                710                 715                 720

Gln Asp Leu Cys Ser Glu Ala Tyr Arg Tyr Gln Val Thr Pro Arg
                725                 730                 735

Met Leu Cys Ala Gly Tyr Arg Lys Gly Lys Lys Asp Ala Cys Gln
                740                 745                 750

Gly Asp Ser Gly Gly Pro Leu Val Cys Lys Ala Leu Ser Gly Arg
                755                 760                 765

Trp Phe Leu Ala Gly Leu Val Ser Trp Gly Leu Gly Cys Gly Arg
                770                 775                 780

Pro Asn Tyr Phe Gly Val Tyr Thr Arg Ile Thr Gly Val Ile Ser
                785                 790                 795

Trp Ile Gln Gln Val Val Thr
                800
```

<210> SEQ ID NO 25
<211> LENGTH: 2747
<212> TYPE: DNA
<213> ORGANISM: Homo sapiens

<400> SEQUENCE: 25

```
gcaacctcag cttctagtat ccagactcca gcgccgcccc gggcgcggac      50

cccaaccccg acccagagct tctccagcgg cggcgcagcg agcagggctc     100

cccgccttaa cttcctccgc ggggcccagc caccttcggg agtccgggtt     150

gcccacctgc aaactctccg ccttctgcac ctgccacccc tgagccagcg     200

cgggcccccg agcgagtcat ggccaacgcg gggctgcagc tgttgggctt     250

cattctcgcc ttcctgggat ggatcggcgc catcgtcagc actgccctgc     300

cccagtggag gatttactcc tatgccggcg acaacatcgt gaccgcccag     350

gccatgtacg aggggctgtg gatgtcctgc gtgtcgcaga gcaccgggca     400

gatccagtgc aaagtctttg actccttgct gaatctgagc agcacattgc     450
```

-continued

```
aagcaacccg tgccttgatg gtggttggca tcctcctggg agtgatagca       500
atctttgtgg ccaccgttgg catgaagtgt atgaagtgct tggaagacga       550
tgaggtgcag aagatgagga tggctgtcat tgggggtgcg atatttcttc       600
ttgcaggtct ggctatttta gttgccacag catggtatgg caatagaatc       650
gttcaagaat tctatgaccc tatgacccca gtcaatgcca ggtacgaatt       700
tggtcaggct ctcttcactg gctgggctgc tgcttctctc tgccttctgg       750
gaggtgccct actttgctgt tcctgtcccc gaaaaacaac ctcttaccca       800
acaccaaggc cctatccaaa acctgcacct tccagcggga aagactacgt       850
gtgacacaga ggcaaaagga gaaaatcatg ttgaaacaaa ccgaaaatgg       900
acattgagat actatcatta acattaggac cttagaattt tgggtattgt       950
aatctgaagt atggtattac aaaacaaaca aacaaacaaa aaacccatgt      1000
gttaaaatac tcagtgctaa acatggctta atcttatttt atcttctttc      1050
ctcaatatag gagggaagat tttccattt gtattactgc ttcccattga       1100
gtaatcatac tcaaatgggg gaaggggtgc tccttaaata tatatagata      1150
tgtatatata catgtttttc tattaaaaat agacagtaaa atactattct      1200
cattatgttg atactagcat acttaaaata tctctaaaat aggtaaatgt      1250
atttaattcc atattgatga agatgtttat tggtatattt tctttttcgt      1300
ccttatatac atatgtaaca gtcaaatatc atttactctt cttcattagc      1350
tttgggtgcc tttgccacaa gacctagcct aatttaccaa ggatgaattc      1400
tttcaattct tcatgcgtgc ccttttcata tacttatttt atttttacc       1450
ataatcttat agcacttgca tcgttattaa gcccttattt gttttgtgtt      1500
tcattggtct ctatctcctg aatctaacac atttcatagc ctacatttta      1550
gtttctaaag ccaagaagaa tttattacaa atcagaactt tggaggcaaa      1600
tctttctgca tgaccaaagt gataaattcc tgttgacctt cccacacaat      1650
ccctgtactc tgacccatag cactcttgtt tgctttgaaa atatttgtcc      1700
aattgagtag ctgcatgctg ttcccccagg tgttgtaaca caactttatt      1750
gattgaattt ttaagctact tattcatagt tttatatccc cctaaactac      1800
ctttttgttc cccattcctt aattgtattg ttttcccaag tgtaattatc      1850
atgcgtttta tatcttccta ataaggtgtg gtctgtttgt ctgaacaaag      1900
tgctagactt tctggagtga taatctggtg acaaatattc tctctgtagc      1950
tgtaagcaag tcacttaatc tttctacctc ttttttctat ctgccaaatt      2000
gagataatga tacttaacca gttagaagag gtagtgtgaa tattaattag      2050
tttatattac tcttattctt tgaacatgaa ctatgcctat gtagtgtctt      2100
tatttgctca gctggctgag acactgaaga agtcactgaa caaaacctac      2150
acacgtacct tcatgtgatt cactgccttc ctctctctac cagtctattt      2200
ccactgaaca aaacctacac acataccttc atgtggttca gtgccttcct      2250
ctctctacca gtctatttcc actgaacaaa acctacgcac ataccttcat      2300
gtggctcagt gccttcctct ctctaccagt ctatttccat tctttcagct      2350
gtgtctgaca tgtttgtgct ctgttccatt ttaacaactg ctcttacttt      2400
tccagtctgt acagaatgct atttcacttg agcaagatga tgtaatggaa      2450
```

```
agggtgttgg cactggtgtc tggagacctg gatttgagtc ttggtgctat              2500

caatcaccgt ctgtgtttga gcaaggcatt tggctgctgt aagcttattg              2550

cttcatctgt aagcggtggt ttgtaattcc tgatcttccc acctcacagt              2600

gatgttgtgg ggatccagtg agatagaata catgtaagtg tggttttgta              2650

atttaaaaag tgctatacta agggaaagaa ttgaggaatt aactgcatac              2700

gttttggtgt tgcttttcaa atgtttgaaa ataaaaaaaa  tgttaag                2747


<210> SEQ ID NO 26
<211> LENGTH: 211
<212> TYPE: PRT
<213> ORGANISM: Homo sapiens

<400> SEQUENCE: 26

Met Ala Asn Ala Gly Leu Gln Leu Leu Gly Phe Ile Leu Ala Phe
  1               5                  10                  15

Leu Gly Trp Ile Gly Ala Ile Val Ser Thr Ala Leu Pro Gln Trp
                 20                  25                  30

Arg Ile Tyr Ser Tyr Ala Gly Asp Asn Ile Val Thr Ala Gln Ala
                 35                  40                  45

Met Tyr Glu Gly Leu Trp Met Ser Cys Val Ser Gln Ser Thr Gly
                 50                  55                  60

Gln Ile Gln Cys Lys Val Phe Asp Ser Leu Leu Asn Leu Ser Ser
                 65                  70                  75

Thr Leu Gln Ala Thr Arg Ala Leu Met Val Val Gly Ile Leu Leu
                 80                  85                  90

Gly Val Ile Ala Ile Phe Val Ala Thr Val Gly Met Lys Cys Met
                 95                 100                 105

Lys Cys Leu Glu Asp Asp Glu Val Gln Lys Met Arg Met Ala Val
                110                 115                 120

Ile Gly Gly Ala Ile Phe Leu Leu Ala Gly Leu Ala Ile Leu Val
                125                 130                 135

Ala Thr Ala Trp Tyr Gly Asn Arg Ile Val Gln Glu Phe Tyr Asp
                140                 145                 150

Pro Met Thr Pro Val Asn Ala Arg Tyr Glu Phe Gly Gln Ala Leu
                155                 160                 165

Phe Thr Gly Trp Ala Ala Ala Ser Leu Cys Leu Leu Gly Gly Ala
                170                 175                 180

Leu Leu Cys Cys Ser Cys Pro Arg Lys Thr Thr Ser Tyr Pro Thr
                185                 190                 195

Pro Arg Pro Tyr Pro Lys Pro Ala Pro Ser Ser Gly Lys Asp Tyr
                200                 205                 210

Val


<210> SEQ ID NO 27
<211> LENGTH: 766
<212> TYPE: DNA
<213> ORGANISM: Homo sapiens

<400> SEQUENCE: 27

ggctcgagcg tttctgagcc aggggtgacc atgacctgct gcgaaggatg                50

gacatcctgc aatggattca gcctgctggt tctactgctg ttaggagtag               100

ttctcaatgc gatacctcta attgtcagct tagttgagga agaccaattt               150
```

-continued

```
tctcaaaacc ccatctcttg ctttgagtgg tggttcccag gaattatagg              200

agcaggtctg atggccattc cagcaacaac aatgtccttg acagcaagaa              250

aaagagcgtg ctgcaacaac agaactggaa tgtttctttc atcatttttc              300

agtgtgatca cagtcattgg tgctctgtat tgcatgctga tatccatcca              350

ggctctctta aaaggtcctc tcatgtgtaa ttctccaagc aacagtaatg              400

ccaattgtga attttcattg aaaaacatca gtgacattca tccagaatcc              450

ttcaacttgc agtggttttt caatgactct tgtgcacctc ctactggttt              500

caataaaccc accagtaacg acaccatggc gagtggctgg agagcatcta              550

gtttccactt cgattctgaa gaaaacaaac ataggcttat ccacttctca              600

gtatttttag gtctattgct tgttggaatt ctggaggtcc tgtttgggct              650

cagtcagata gtcatcggtt tccttggctg tctgtgtgga gtctctaagc              700

gaagaagtca aattgtgtag tttaatggga ataaaatgta agtatcagta              750

gtttgaaaaa  aaaaaa                                                  766


<210> SEQ ID NO 28
<211> LENGTH: 229
<212> TYPE: PRT
<213> ORGANISM: Homo sapiens

<400> SEQUENCE: 28

Met Thr Cys Cys Glu Gly Trp Thr Ser Cys Asn Gly Phe Ser Leu
  1               5                  10                  15

Leu Val Leu Leu Leu Leu Gly Val Val Leu Asn Ala Ile Pro Leu
                 20                  25                  30

Ile Val Ser Leu Val Glu Glu Asp Gln Phe Ser Gln Asn Pro Ile
                 35                  40                  45

Ser Cys Phe Glu Trp Trp Phe Pro Gly Ile Ile Gly Ala Gly Leu
                 50                  55                  60

Met Ala Ile Pro Ala Thr Thr Met Ser Leu Thr Ala Arg Lys Arg
                 65                  70                  75

Ala Cys Cys Asn Asn Arg Thr Gly Met Phe Leu Ser Ser Phe Phe
                 80                  85                  90

Ser Val Ile Thr Val Ile Gly Ala Leu Tyr Cys Met Leu Ile Ser
                 95                 100                 105

Ile Gln Ala Leu Leu Lys Gly Pro Leu Met Cys Asn Ser Pro Ser
                110                 115                 120

Asn Ser Asn Ala Asn Cys Glu Phe Ser Leu Lys Asn Ile Ser Asp
                125                 130                 135

Ile His Pro Glu Ser Phe Asn Leu Gln Trp Phe Phe Asn Asp Ser
                140                 145                 150

Cys Ala Pro Pro Thr Gly Phe Asn Lys Pro Thr Ser Asn Asp Thr
                155                 160                 165

Met Ala Ser Gly Trp Arg Ala Ser Ser Phe His Phe Asp Ser Glu
                170                 175                 180

Glu Asn Lys His Arg Leu Ile His Phe Ser Val Phe Leu Gly Leu
                185                 190                 195

Leu Leu Val Gly Ile Leu Glu Val Leu Phe Gly Leu Ser Gln Ile
                200                 205                 210

Val Ile Gly Phe Leu Gly Cys Leu Cys Gly Val Ser Lys Arg Arg
                215                 220                 225
```

-continued

Ser Gln Ile Val

<210> SEQ ID NO 29
<211> LENGTH: 1532
<212> TYPE: DNA
<213> ORGANISM: Homo sapiens

<400> SEQUENCE: 29
ggcacgaggc ggcggggcag tcgcgggatg cgcccgggag ccacagcctg 50
aggccctcag gtctctgcag gtgtcgtgga ggaacctagc acctgccatc 100
ctcttcccca atttgccact tccagcagct ttagcccatg aggaggatgt 150
gaccgggact gagtcaggag ccctctggaa gcatggagac tgtggtgatt 200
gttgccatag gtgtgctggc caccatcttt ctggcttcgt ttgcagcctt 250
ggtgctggtt tgcaggcagc gctactgccg gccgcgagac ctgctgcagc 300
gctatgattc taagcccatt gtggacctca ttggtgccat ggagacccag 350
tctgagccct ctgagttaga actggacgat gtcgttatca ccaacccccca 400 cattgaggcc attctggaga atgaagactg gatcgaagat gcctcgggtc 450
tcatgtccca ctgcattgcc atcttgaaga tttgtcacac tctgacagag 500
aagcttgttg ccatgacaat gggctctggg gccaagatga agacttcagc 550
cagtgtcagc gacatcattg tggtggccaa gcggatcagc cccagggtgg 600
atgatgttgt gaagtcgatg taccctccgt tggaccccaa actcctggac 650
gcacggacga ctgccctgct cctgtctgtc agtcacctgg tgctggtgac 700
aaggaatgcc tgccatctga cgggaggcct ggactggatt gaccagtctc 750
tgtcggctgc tgaggagcat ttggaagtcc ttcgagaagc agccctagct 800
tctgagccag ataaaggcct cccaggccct gaaggcttcc tgcaggagca 850
gtctgcaatt tagtgcctac aggccagcag ctagccatga aggcccctgc 900
cgccatccct ggatggctca gcttagcctt ctacttttc ctatagagtt 950 agttgttctc cacggctgga gagttcagct gtgtgtgcat agtaaagcag 1000
gagatccccg tcagtttatg cctcttttgc agttgcaaac tgtggctggt 1050
gagtggcagt ctaatactac agttagggga gatgccattc actctctgca 1100
agaggagtat tgaaaactgg tggactgtca gctttattta gctcacctag 1150
tgttttcaag aaaattgagc caccgtctaa gaaatcaaga ggtttcacat 1200
taaaattaga atttctggcc tctctcgatc ggtcagaatg tgtggcaatt 1250
ctgatctgca ttttcagaag aggacaatca attgaaacta agtaggggtt 1300
tcttcttttg gcaagacttg tactctctca cctggcctgt ttcatttatt 1350
tgtattatct gcctggtccc tgaggcgtct gggtctctcc tctcccttgc 1400
aggtttgggt ttgaagctga ggaactacaa agttgatgat ttctttttta 1450
tctttatgcc tgcaatttta cctagctacc actaggtgga tagtaaattt 1500
atacttatgt ttccctcaaa aaaaaaaaaa aa 1532

<210> SEQ ID NO 30
<211> LENGTH: 226
<212> TYPE: PRT
<213> ORGANISM: Homo sapiens

<400> SEQUENCE: 30

-continued

```
Met Glu Thr Val Val Ile Val Ala Ile Gly Val Leu Ala Thr Ile
1               5                   10                  15

Phe Leu Ala Ser Phe Ala Ala Leu Val Leu Val Cys Arg Gln Arg
                20                  25                  30

Tyr Cys Arg Pro Arg Asp Leu Leu Gln Arg Tyr Asp Ser Lys Pro
                35                  40                  45

Ile Val Asp Leu Ile Gly Ala Met Glu Thr Gln Ser Glu Pro Ser
                50                  55                  60

Glu Leu Glu Leu Asp Asp Val Val Ile Thr Asn Pro His Ile Glu
                65                  70                  75

Ala Ile Leu Glu Asn Glu Asp Trp Ile Glu Asp Ala Ser Gly Leu
                80                  85                  90

Met Ser His Cys Ile Ala Ile Leu Lys Ile Cys His Thr Leu Thr
                95                  100                 105

Glu Lys Leu Val Ala Met Thr Met Gly Ser Gly Ala Lys Met Lys
                110                 115                 120

Thr Ser Ala Ser Val Ser Asp Ile Ile Val Val Ala Lys Arg Ile
                125                 130                 135

Ser Pro Arg Val Asp Asp Val Val Lys Ser Met Tyr Pro Pro Leu
                140                 145                 150

Asp Pro Lys Leu Leu Asp Ala Arg Thr Thr Ala Leu Leu Leu Ser
                155                 160                 165

Val Ser His Leu Val Leu Val Thr Arg Asn Ala Cys His Leu Thr
                170                 175                 180

Gly Gly Leu Asp Trp Ile Asp Gln Ser Leu Ser Ala Ala Glu Glu
                185                 190                 195

His Leu Glu Val Leu Arg Glu Ala Ala Leu Ala Ser Glu Pro Asp
                200                 205                 210

Lys Gly Leu Pro Gly Pro Glu Gly Phe Leu Gln Glu Gln Ser Ala
                215                 220                 225

Ile
```

<210> SEQ ID NO 31
<211> LENGTH: 2128
<212> TYPE: DNA
<213> ORGANISM: Homo sapiens

<400> SEQUENCE: 31

```
ctgtcgtctt tgcttcagcc gcagtcgcca ctggctgcct gaggtgctct      50

tacagcctgt tccaagtgtg gcttaatccg tctccaccac cagatctttc     100

tccgtggatt cctctgctaa gaccgctgcc atgccagtga cggtaacccg     150

caccaccatc acaaccacca cgacgtcatc ttcgggcctg gggtccccca     200

tgatcgtggg gtcccctcgg gccctgacac agcccctggg tctccttcgc     250

ctgctgcagc tggtgtctac ctgcgtggcc ttctcgctgg tggctagcgt     300

gggcgcctgg acggggtcca tgggcaactg gtccatgttc acctggtgct     350

tctgcttctc cgtgaccctg atcatcctca tcgtggagct gtgcgggctc     400

caggcccgct tcccccctgtc ttggcgcaac ttccccatca ccttcgcctg     450

ctatgcggcc ctcttctgcc tctcggcctc catcatctac cccaccacct     500

atgtccagtt cctgtcccac ggccgttcgc gggaccacgc catcgccgcc     550

accttcttct cctgcatcgc gtgtgtggct tacgccaccg aagtggcctg     600
```

-continued gacccgggcc cggcccggcg agatcactgg ctatatggcc accgtacccg 650
ggctgctgaa ggtgctggag accttcgttg cctgcatcat cttcgcgttc 700
atcagcgacc ccaacctgta ccagcaccag ccggccctgg agtggtgcgt 750
ggcggtgtac gccatctgct tcatcctagc ggccatcgcc atcctgctga 800
acctggggga gtgcaccaac gtgctaccca tcccccttccc cagcttcctg 850 tcggggctgg ccttgctgtc tgtcctcctc tatgccaccg cccttgttct 900
ctggcccctc taccagttcg atgagaagta tggcggccag cctcggcgct 950
cgagagatgt aagctgcagc cgcagccatg cctactacgt gtgtgcctgg 1000
gaccgccgac tggctgtggc catcctgacg gccatcaacc tactggcgta 1050
tgtggctgac ctggtgcact ctgcccacct ggtttttgtc aaggtctaag 1100
actctcccaa gaggctcccg ttccctctcc aacctctttg ttcttcttgc 1150
ccgagttttc tttatggagt acttctttcc tccgcctttc ctctgttttc 1200
ctcttcctgt ctcccctccc tcccaccttt ttctttcctt cccaattcct 1250
tgcactctaa ccagttcttg gatgcatctt cttccttccc tttcctcttg 1300
ctgtttcctt cctgtgttgt tttgttgccc acatcctgtt ttcacccctg 1350
agctgtttct ctttttcttt tctttctttt tttttttttt ttttaagacg 1400
gattctcact ctgtggccca ggctggagtg cagtggtgcg atctcagctc 1450
actgcaaccc ccgcctcctg ggttcaagcg attctcctcc cccagcctcc 1500
caagtagctg ggaggacagg tgtgagctgc cgcacccagc ctgtttctct 1550
ttttccactc ttctttttttc tcatctcttt tctgggttgc ctgtcggctt 1600
tcttatctgc ctgttttgca agcaccttct cctgtgtcct tgggagccct 1650
gagacttctt tctctccttg cctccaccca cctccaaagg tgctgagctc 1700
acatccacac cccttgcagc cgtccatgcc acagccccccc aaggggcccc 1750 attgccaaag catgcctgcc caccctcgct gtgccttagt cagtgtgtac 1800
gtgtgtgtgt gtgtgtgttt ggggggtggg gggtgggtag ctggggattg 1850
ggccctcttt ctcccagtgg aggaaggtgt gcagtgtact tccccctttaa 1900 attaaaaaac atatatatat atatatttgg aggtcagtaa tttccaatgg 1950
gcgggaggca ttaagcaccg accctgggtc cctaggcccc gcctggcact 2000
cagccttgcc agagattggc tccagaattt ttgccaggct tacagaacac 2050
ccactgccta gaggccatct taaaggaagc aggggctgga tgcctttcat 2100
cccaactatt ctctgtggta tgaaaaag 2128

<210> SEQ ID NO 32
<211> LENGTH: 322
<212> TYPE: PRT
<213> ORGANISM: Homo sapiens

<400> SEQUENCE: 32

Met Pro Val Thr Val Thr Arg Thr Thr Ile Thr Thr Thr Thr Thr
1 5 10 15

Ser Ser Ser Gly Leu Gly Ser Pro Met Ile Val Gly Ser Pro Arg
20 25 30

Ala Leu Thr Gln Pro Leu Gly Leu Leu Arg Leu Leu Gln Leu Val
35 40 45

-continued

```
Ser Thr Cys Val Ala Phe Ser Leu Val Ala Ser Val Gly Ala Trp
                50                  55                  60

Thr Gly Ser Met Gly Asn Trp Ser Met Phe Thr Trp Cys Phe Cys
                65                  70                  75

Phe Ser Val Thr Leu Ile Ile Leu Ile Val Glu Leu Cys Gly Leu
                80                  85                  90

Gln Ala Arg Phe Pro Leu Ser Trp Arg Asn Phe Pro Ile Thr Phe
                95                 100                 105

Ala Cys Tyr Ala Ala Leu Phe Cys Leu Ser Ala Ser Ile Ile Tyr
               110                 115                 120

Pro Thr Thr Tyr Val Gln Phe Leu Ser His Gly Arg Ser Arg Asp
               125                 130                 135

His Ala Ile Ala Ala Thr Phe Phe Ser Cys Ile Ala Cys Val Ala
               140                 145                 150

Tyr Ala Thr Glu Val Ala Trp Thr Arg Ala Arg Pro Gly Glu Ile
               155                 160                 165

Thr Gly Tyr Met Ala Thr Val Pro Gly Leu Leu Lys Val Leu Glu
               170                 175                 180

Thr Phe Val Ala Cys Ile Ile Phe Ala Phe Ile Ser Asp Pro Asn
               185                 190                 195

Leu Tyr Gln His Gln Pro Ala Leu Glu Trp Cys Val Ala Val Tyr
               200                 205                 210

Ala Ile Cys Phe Ile Leu Ala Ala Ile Ala Ile Leu Leu Asn Leu
               215                 220                 225

Gly Glu Cys Thr Asn Val Leu Pro Ile Pro Phe Pro Ser Phe Leu
               230                 235                 240

Ser Gly Leu Ala Leu Leu Ser Val Leu Leu Tyr Ala Thr Ala Leu
               245                 250                 255

Val Leu Trp Pro Leu Tyr Gln Phe Asp Glu Lys Tyr Gly Gly Gln
               260                 265                 270

Pro Arg Arg Ser Arg Asp Val Ser Cys Ser Arg Ser His Ala Tyr
               275                 280                 285

Tyr Val Cys Ala Trp Asp Arg Arg Leu Ala Val Ala Ile Leu Thr
               290                 295                 300

Ala Ile Asn Leu Leu Ala Tyr Val Ala Asp Leu Val His Ser Ala
               305                 310                 315

His Leu Val Phe Val Lys Val
               320
```

<210> SEQ ID NO 33
<211> LENGTH: 1047
<212> TYPE: DNA
<213> ORGANISM: Homo sapiens

<400> SEQUENCE: 33

```
gccaggtgtg caggccgctc caagcccagc ctgccccgct gccgccacca        50

tgacgctcct ccccggcctc ctgtttctga cctggctgca cacatgcctg       100

gcccaccatg acccctccct caggggggcac ccccacagtc acggtacccc       150

acactgctac tcggctgagg aactgcccct cggccaggcc cccccacacc       200

tgctggctcg aggtgccaag tgggggcagg ctttgcctgt agccctggtg       250

tccagcctgg aggcagcaag ccacaggggg aggcacgaga ggccctcagc       300

tacgacccag tgcccggtgc tgcggccgga ggaggtgttg gaggcagaca       350
```

-continued

```
cccaccagcg ctccatctca ccctggagat accgtgtgga cacggatgag        400

gaccgctatc cacagaagct ggccttcgcc gagtgcctgt gcagaggctg        450

tatcgatgca cggacgggcc gcgagacagc tgcgctcaac tccgtgcggc        500

tgctccagag cctgctggtg ctgcgccgcc ggccctgctc ccgcgacggc        550

tcggggctcc ccacacctgg ggcctttgcc ttccacaccg agttcatcca        600

cgtccccgtc ggctgcacct gcgtgctgcc ccgttcagtg tgaccgccga        650

ggccgtgggg cccctagact ggacacgtgt gctccccaga gggcaccccc        700

tatttatgtg tatttattgt tatttatatg cctcccccaa cactaccctt        750

ggggtctggg cattccccgt gtctggagga cagcccccca ctgttctcct        800

catctccagc ctcagtagtt gggggtagaa ggagctcagc acctcttcca        850

gcccttaaag ctgcagaaaa ggtgtcacac ggctgcctgt accttggctc        900

cctgtcctgc tcccggcttc ccttacccta tcactggcct caggccccgc        950

aggctgcctc ttcccaacct ccttggaagt acccctgttt cttaaacaat       1000

tatttaagtg tacgtgtatt attaaactga tgaacacatc  cccaaaa         1047
```

```
<210> SEQ ID NO 34
<211> LENGTH: 197
<212> TYPE: PRT
<213> ORGANISM: Homo sapiens

<400> SEQUENCE: 34

Met Thr Leu Leu Pro Gly Leu Leu Phe Leu Thr Trp Leu His Thr
  1               5                  10                  15

Cys Leu Ala His His Asp Pro Ser Leu Arg Gly His Pro His Ser
                 20                  25                  30

His Gly Thr Pro His Cys Tyr Ser Ala Glu Glu Leu Pro Leu Gly
                 35                  40                  45

Gln Ala Pro Pro His Leu Leu Ala Arg Gly Ala Lys Trp Gly Gln
                 50                  55                  60

Ala Leu Pro Val Ala Leu Val Ser Ser Leu Glu Ala Ala Ser His
                 65                  70                  75

Arg Gly Arg His Glu Arg Pro Ser Ala Thr Thr Gln Cys Pro Val
                 80                  85                  90

Leu Arg Pro Glu Glu Val Leu Glu Ala Asp Thr His Gln Arg Ser
                 95                 100                 105

Ile Ser Pro Trp Arg Tyr Arg Val Asp Thr Asp Glu Asp Arg Tyr
                110                 115                 120

Pro Gln Lys Leu Ala Phe Ala Glu Cys Leu Cys Arg Gly Cys Ile
                125                 130                 135

Asp Ala Arg Thr Gly Arg Glu Thr Ala Ala Leu Asn Ser Val Arg
                140                 145                 150

Leu Leu Gln Ser Leu Leu Val Leu Arg Arg Arg Pro Cys Ser Arg
                155                 160                 165

Asp Gly Ser Gly Leu Pro Thr Pro Gly Ala Phe Ala Phe His Thr
                170                 175                 180

Glu Phe Ile His Val Pro Val Gly Cys Thr Cys Val Leu Pro Arg
                185                 190                 195

Ser Val
```

-continued

<210> SEQ ID NO 35
<211> LENGTH: 1076
<212> TYPE: DNA
<213> ORGANISM: Homo sapiens

<400> SEQUENCE: 35

```
gtggcttcat ttcagtggct gacttccaga gagcaatatg gctggttccc          50
caacatgcct caccctcatc tatatccttt ggcagctcac agggtcagca         100
gcctctggac ccgtgaaaga gctggtcggt tccgttggtg gggccgtgac         150
tttcccccctg aagtccaaag taaagcaagt tgactctatt gtctggacct        200
tcaacacaac ccctcttgtc accatacagc cagaaggggg cactatcata         250
gtgacccaaa atcgtaatag ggagagagta gacttcccag atggaggcta         300
ctccctgaag ctcagcaaac tgaagaagaa tgactcaggg atctactatg         350
tggggatata cagctcatca ctccagcagc cctccaccca ggagtacgtg         400
ctgcatgtct acgagcacct gtcaaagcct aaagtcacca tgggtctgca         450
gagcaataag aatggcacct gtgtgaccaa tctgacatgc tgcatggaac         500
atggggaaga ggatgtgatt tatacctgga aggccctggg gcaagcagcc         550
aatgagtccc ataatgggtc catcctcccc atctcctgga gatggggaga         600
aagtgatatg accttcatct gcgttgccag gaaccctgtc agcagaaact         650
tctcaagccc catccttgcc aggaagctct gtgaaggtgc tgctgatgac         700
ccagattcct ccatggtcct cctgtgtctc ctgttggtgc ccctcctgct         750
cagtctcttt gtactggggc tatttctttg gtttctgaag agagagagac         800
aagaagagta cattgaagag aagaagagag tggacatttg tcgggaaact         850
cctaacatat gcccccattc tggagagaac acagagtacg acacaatccc         900
tcacactaat agaacaatcc taaaggaaga tccagcaaat acggtttact         950
ccactgtgga aataccgaaa aagatggaaa atccccactc actgctcacg        1000
atgccagaca caccaaggct atttgcctat gagaatgtta tctagacagc        1050
agtgcactcc cctaagtctc  tgctca                                 1076
```

<210> SEQ ID NO 36
<211> LENGTH: 335
<212> TYPE: PRT
<213> ORGANISM: Homo sapiens

<400> SEQUENCE: 36

```
Met Ala Gly Ser Pro Thr Cys Leu Thr Leu Ile Tyr Ile Leu Trp
  1               5                  10                  15

Gln Leu Thr Gly Ser Ala Ala Ser Gly Pro Val Lys Glu Leu Val
                 20                  25                  30

Gly Ser Val Gly Gly Ala Val Thr Phe Pro Leu Lys Ser Lys Val
                 35                  40                  45

Lys Gln Val Asp Ser Ile Val Trp Thr Phe Asn Thr Thr Pro Leu
                 50                  55                  60

Val Thr Ile Gln Pro Glu Gly Gly Thr Ile Ile Val Thr Gln Asn
                 65                  70                  75

Arg Asn Arg Glu Arg Val Asp Phe Pro Asp Gly Gly Tyr Ser Leu
                 80                  85                  90

Lys Leu Ser Lys Leu Lys Lys Asn Asp Ser Gly Ile Tyr Tyr Val
                 95                 100                 105
```

```
Gly Ile Tyr Ser Ser Ser Leu Gln Gln Pro Ser Thr Gln Glu Tyr
                110                 115                 120

Val Leu His Val Tyr Glu His Leu Ser Lys Pro Lys Val Thr Met
                125                 130                 135

Gly Leu Gln Ser Asn Lys Asn Gly Thr Cys Val Thr Asn Leu Thr
                140                 145                 150

Cys Cys Met Glu His Gly Glu Glu Asp Val Ile Tyr Thr Trp Lys
                155                 160                 165

Ala Leu Gly Gln Ala Ala Asn Glu Ser His Asn Gly Ser Ile Leu
                170                 175                 180

Pro Ile Ser Trp Arg Trp Gly Glu Ser Asp Met Thr Phe Ile Cys
                185                 190                 195

Val Ala Arg Asn Pro Val Ser Arg Asn Phe Ser Ser Pro Ile Leu
                200                 205                 210

Ala Arg Lys Leu Cys Glu Gly Ala Ala Asp Asp Pro Asp Ser Ser
                215                 220                 225

Met Val Leu Leu Cys Leu Leu Leu Val Pro Leu Leu Leu Ser Leu
                230                 235                 240

Phe Val Leu Gly Leu Phe Leu Trp Phe Leu Lys Arg Glu Arg Gln
                245                 250                 255

Glu Glu Tyr Ile Glu Glu Lys Lys Arg Val Asp Ile Cys Arg Glu
                260                 265                 270

Thr Pro Asn Ile Cys Pro His Ser Gly Glu Asn Thr Glu Tyr Asp
                275                 280                 285

Thr Ile Pro His Thr Asn Arg Thr Ile Leu Lys Glu Asp Pro Ala
                290                 295                 300

Asn Thr Val Tyr Ser Thr Val Glu Ile Pro Lys Lys Met Glu Asn
                305                 310                 315

Pro His Ser Leu Leu Thr Met Pro Asp Thr Pro Arg Leu Phe Ala
                320                 325                 330

Tyr Glu Asn Val Ile
                335


<210> SEQ ID NO 37
<211> LENGTH: 4277
<212> TYPE: DNA
<213> ORGANISM: Homo sapiens

<400> SEQUENCE: 37

gtttctcata gttggcgtct tctaaaggaa aaacactaaa atgaggaact              50

cagcggaccg ggagcgacgc agcttgaggg aagcatccct agctgttggc             100

gcagaggggc gaggctgaag ccgagtggcc cgaggtgtct gaggggctgg             150

ggcaaaggtg aaagagtttc agaacaagct tcctggaacc catgacccat             200

gaagtcttgt cgacatttat accgtctgag ggtagcagct cgaaactaga             250

agaagtggag tgttgccagg gacggcagta tctctttgtg tgaccctggc             300

ggcctatggg acgttggctt cagacctttg tgatacacca tgctgcgtgg             350

gacgatgacg gcgtggagag gaatgaggcc tgaggtcaca ctggcttgcc             400

tcctcctagc cacagcaggc tgctttgctg acttgaacga ggtccctcag             450

gtcaccgtcc agcctgcgtc caccgtccag aagcccggag gcactgtgat             500

cttgggctgc gtggtggaac ctccaaggat gaatgtaacc tggcgcctga             550
```

-continued

```
atggaaagga gctgaatggc tcggatgatg ctctgggtgt cctcatcacc        600
cacgggaccc tcgtcatcac tgcccttaac aaccacactg tgggacggta        650
ccagtgtgtg gcccggatgc ctgcgggggc tgtggccagc gtgccagcca        700
ctgtgacact agccaatctc caggacttca agttagatgt gcagcacgtg        750
attgaagtgg atgagggaaa cacagcagtc attgcctgcc acctgcctga        800
gagccacccc aaagcccagg tccggtacag cgtcaaacaa gagtggctgg        850
aggcctccag aggtaactac ctgatcatgc cctcagggaa cctccagatt        900
gtgaatgcca gccaggagga cgagggcatg tacaagtgtg cagcctacaa        950
cccagtgacc caggaagtga aaacctccgg ctccagcgac aggctacgtg       1000
tgcgccgctc caccgctgag gctgcccgca tcatctaccc cccagaggcc       1050
caaaccatca tcgtcaccaa aggccagagt ctcattctgg agtgtgtggc       1100
cagtggaatc ccacccccac gggtcacctg ggccaaggat gggtccagtg       1150
tcaccggcta caacaagacg cgcttcctgc tgagcaacct cctcatcgac       1200
accaccagcg aggaggactc aggcacctac cgctgcatgg ccgacaatgg       1250
ggttgggcag cccggggcag cggtcatcct ctacaatgtc caggtgtttg       1300
aaccccctga ggtcaccatg gagctatccc agctggtcat cccctggggc       1350
cagagtgcca agcttacctg tgaggtgcgt gggaaccccc cgccctccgt       1400
gctgtggctg aggaatgctg tgcccctcat ctccagccag cgcctccggc       1450
tctcccgcag ggccctgcgc gtgctcagca tggggcctga ggacgaaggc       1500
gtctaccagt gcatggccga gaacgaggtt gggagcgccc atgccgtagt       1550
ccagctgcgg acctccaggc caagcataac cccaaggcta tggcaggatg       1600
ctgagctggc tactggcaca cctcctgtat caccctccaa actcggcaac       1650
cctgagcaga tgctgagggg gcaaccggcg ctccccagac ccccaacgtc       1700
agtggggcct gcttccccga agtgtccagg agagaagggg caggggggctc       1750
ccgccgaggc tcccatcatc ctcagctcgc cccgcacctc caagacagac       1800
tcatatgaac tggtgtggcg gcctcggcat gagggcagtg gccgggcgcc       1850
aatcctctac tatgtggtga aacaccgcaa gcaggtcaca aattcctctg       1900
acgattggac catctctggc attccagcca accagcaccg cctgaccctc       1950
accagacttg accccgggag cttgtatgaa gtggagatgg cagcttacaa       2000
ctgtgcggga gagggccaga cagccatggt caccttccga actggacggc       2050
ggcccaaacc cgagatcatg gccagcaaag agcagcagat ccagagagac       2100
gaccctggag ccagtcccca gagcagcagc cagccagacc acggccgcct       2150
ctccccccca gaagctcccg acaggcccac catctccacg gcctccgaga       2200
cctcagtgta cgtgacctgg attccccgtg ggaatggtgg gttcccaatc       2250
cagtccttcc gtgtggagta caagaagcta aagaaagtgg gagactggat       2300
tctggccacc agcgccatcc ccccatcgcg gctgtccgtg gagatcacgg       2350
gcctagagaa aggcacctcc tacaagtttc gagtccgggc tctgaacatg       2400
ctgggggaga gcgagcccag cgccccctct cggccctacg tggtgtcggg       2450
ctacagcggt cgcgtgtacg agaggcccgt ggcaggtcct tatatcacct       2500
tcacggatgc ggtcaatgag accaccatca tgctcaagtg gatgtacatc       2550
```

-continued ccagcaagta acaacaacac cccaatccat ggcttttata tctattatcg 2600
acccacagac agtgacaatg atagtgacta caagaaggat atggtggaag 2650
gggacaagta ctggcactcc atcagccacc tgcagccaga gacctcctac 2700
gacattaaga tgcagtgctt caatgaagga ggggagagcg agttcagcaa 2750
cgtgatgatc tgtgagacca aagctcggaa gtcttctggc cagcctggtc 2800
gactgccacc cccaactctg gccccaccac agccgcccct tcctgaaacc 2850
atagagcggc cggtgggcac tggggccatg gtggctcgct ccagcgacct 2900
gccctatctg attgtcgggg tcgtcctggg ctccatcgtt ctcatcatcg 2950
tcaccttcat ccccttctgc ttgtggaggg cctggtctaa gcaaaaacat 3000
acaacagacc tgggttttcc tcgaagtgcc cttccaccct cctgcccgta 3050
tactatggtg ccattgggag gactcccagg ccaccaggcc agtggacagc 3100
cctacctcag tggcatcagt ggacgggcct gtgctaatgg gatccacatg 3150 aatagggggct gcccctcggc tgcagtgggc tacccgggca tgaagcccca 3200
gcagcactgc ccaggcgagc ttcagcagca gagtgacacc agcagcctgc 3250
tgaggcagac ccatcttggc aatggatatg acccccaaag tcaccagatc 3300
acgaggggtc ccaagtctag cccggacgag ggctctttct tatacacact 3350
gcccgacgac tccactcacc agctgctgca gccccatcac gactgctgcc 3400
aacgccagga gcagcctgct gctgtgggcc agtcaggggt gaggagagcc 3450
cccgacagtc ctgtcctgga agcagtgtgg gaccctccat ttcactcagg 3500
gcccccatgc tgcttgggcc ttgtgccagt tgaagaggtg gacagtcctg 3550
actcctgcca agtgagtgga ggagactggt gtccccagca ccccgtaggg 3600
gcctacgtag gacaggaacc tggaatgcag ctctccccgg ggccactggt 3650
gcgtgtgtct tttgaaacac cacctctcac aatttaggca gaagctgata 3700
tcccagaaag actatatatt gttttttttt taaaaaaaaa agaagaaaaa 3750
agagacagag aaaattggta tttatttttc tattatagcc atatttatat 3800
atttatgcac ttgtaaataa atgtatatgt tttataattc tggagagaca 3850
taaggagtcc tacccgttga ggttggagag ggaaaataaa gaagctgcca 3900
cctaacagga gtcacccagg aaagcaccgc acaggctggc gcgggacaga 3950
ctcctaacct ggggcctctg cagtggcagg cgaggctgca ggaggcccac 4000
agataagctg gcaagaggaa ggatcccagg cacatggttc atcacgagca 4050
tgagggaaca gcaaggggca cggtatcaca gcctggagac acccacacag 4100
atggctggat ccggtgctac gggaaacatt ttcctaagat gcccatgaga 4150
acagaccaag atgtgtacag cactatgagc attaaaaaac cttccagaat 4200
caataatccg tggcaacata tctctgtaaa aacaaacact gtaacttcta 4250
aataaatgtt tagtcttccc tgtaaaa 4277

<210> SEQ ID NO 38
<211> LENGTH: 1115
<212> TYPE: PRT
<213> ORGANISM: Homo sapiens

<400> SEQUENCE: 38

-continued

```
Met Leu Arg Gly Thr Met Thr Ala Trp Arg Gly Met Arg Pro Glu
  1               5                  10                  15

Val Thr Leu Ala Cys Leu Leu Leu Ala Thr Ala Gly Cys Phe Ala
                 20                  25                  30

Asp Leu Asn Glu Val Pro Gln Val Thr Val Gln Pro Ala Ser Thr
                 35                  40                  45

Val Gln Lys Pro Gly Gly Thr Val Ile Leu Gly Cys Val Val Glu
                 50                  55                  60

Pro Pro Arg Met Asn Val Thr Trp Arg Leu Asn Gly Lys Glu Leu
                 65                  70                  75

Asn Gly Ser Asp Asp Ala Leu Gly Val Leu Ile Thr His Gly Thr
                 80                  85                  90

Leu Val Ile Thr Ala Leu Asn Asn His Thr Val Gly Arg Tyr Gln
                 95                 100                 105

Cys Val Ala Arg Met Pro Ala Gly Ala Val Ala Ser Val Pro Ala
                110                 115                 120

Thr Val Thr Leu Ala Asn Leu Gln Asp Phe Lys Leu Asp Val Gln
                125                 130                 135

His Val Ile Glu Val Asp Glu Gly Asn Thr Ala Val Ile Ala Cys
                140                 145                 150

His Leu Pro Glu Ser His Pro Lys Ala Gln Val Arg Tyr Ser Val
                155                 160                 165

Lys Gln Glu Trp Leu Glu Ala Ser Arg Gly Asn Tyr Leu Ile Met
                170                 175                 180

Pro Ser Gly Asn Leu Gln Ile Val Asn Ala Ser Gln Glu Asp Glu
                185                 190                 195

Gly Met Tyr Lys Cys Ala Ala Tyr Asn Pro Val Thr Gln Glu Val
                200                 205                 210

Lys Thr Ser Gly Ser Ser Asp Arg Leu Arg Val Arg Arg Ser Thr
                215                 220                 225

Ala Glu Ala Ala Arg Ile Ile Tyr Pro Pro Glu Ala Gln Thr Ile
                230                 235                 240

Ile Val Thr Lys Gly Gln Ser Leu Ile Leu Glu Cys Val Ala Ser
                245                 250                 255

Gly Ile Pro Pro Pro Arg Val Thr Trp Ala Lys Asp Gly Ser Ser
                260                 265                 270

Val Thr Gly Tyr Asn Lys Thr Arg Phe Leu Leu Ser Asn Leu Leu
                275                 280                 285

Ile Asp Thr Thr Ser Glu Glu Asp Ser Gly Thr Tyr Arg Cys Met
                290                 295                 300

Ala Asp Asn Gly Val Gly Gln Pro Gly Ala Ala Val Ile Leu Tyr
                305                 310                 315

Asn Val Gln Val Phe Glu Pro Pro Glu Val Thr Met Glu Leu Ser
                320                 325                 330

Gln Leu Val Ile Pro Trp Gly Gln Ser Ala Lys Leu Thr Cys Glu
                335                 340                 345

Val Arg Gly Asn Pro Pro Pro Ser Val Leu Trp Leu Arg Asn Ala
                350                 355                 360

Val Pro Leu Ile Ser Ser Gln Arg Leu Arg Leu Ser Arg Arg Ala
                365                 370                 375

Leu Arg Val Leu Ser Met Gly Pro Glu Asp Glu Gly Val Tyr Gln
                380                 385                 390

Cys Met Ala Glu Asn Glu Val Gly Ser Ala His Ala Val Val Gln
```

-continued

```
                395                 400                 405

Leu Arg Thr Ser Arg Pro Ser Ile Thr Pro Arg Leu Trp Gln Asp
                410                 415                 420

Ala Glu Leu Ala Thr Gly Thr Pro Pro Val Ser Pro Ser Lys Leu
                425                 430                 435

Gly Asn Pro Glu Gln Met Leu Arg Gly Gln Pro Ala Leu Pro Arg
                440                 445                 450

Pro Pro Thr Ser Val Gly Pro Ala Ser Pro Lys Cys Pro Gly Glu
                455                 460                 465

Lys Gly Gln Gly Ala Pro Ala Glu Ala Pro Ile Ile Leu Ser Ser
                470                 475                 480

Pro Arg Thr Ser Lys Thr Asp Ser Tyr Glu Leu Val Trp Arg Pro
                485                 490                 495

Arg His Glu Gly Ser Gly Arg Ala Pro Ile Leu Tyr Tyr Val Val
                500                 505                 510

Lys His Arg Lys Gln Val Thr Asn Ser Ser Asp Asp Trp Thr Ile
                515                 520                 525

Ser Gly Ile Pro Ala Asn Gln His Arg Leu Thr Leu Thr Arg Leu
                530                 535                 540

Asp Pro Gly Ser Leu Tyr Glu Val Glu Met Ala Ala Tyr Asn Cys
                545                 550                 555

Ala Gly Glu Gly Gln Thr Ala Met Val Thr Phe Arg Thr Gly Arg
                560                 565                 570

Arg Pro Lys Pro Glu Ile Met Ala Ser Lys Glu Gln Gln Ile Gln
                575                 580                 585

Arg Asp Asp Pro Gly Ala Ser Pro Gln Ser Ser Ser Gln Pro Asp
                590                 595                 600

His Gly Arg Leu Ser Pro Pro Glu Ala Pro Asp Arg Pro Thr Ile
                605                 610                 615

Ser Thr Ala Ser Glu Thr Ser Val Tyr Val Thr Trp Ile Pro Arg
                620                 625                 630

Gly Asn Gly Gly Phe Pro Ile Gln Ser Phe Arg Val Glu Tyr Lys
                635                 640                 645

Lys Leu Lys Lys Val Gly Asp Trp Ile Leu Ala Thr Ser Ala Ile
                650                 655                 660

Pro Pro Ser Arg Leu Ser Val Glu Ile Thr Gly Leu Glu Lys Gly
                665                 670                 675

Thr Ser Tyr Lys Phe Arg Val Arg Ala Leu Asn Met Leu Gly Glu
                680                 685                 690

Ser Glu Pro Ser Ala Pro Ser Arg Pro Tyr Val Val Ser Gly Tyr
                695                 700                 705

Ser Gly Arg Val Tyr Glu Arg Pro Val Ala Gly Pro Tyr Ile Thr
                710                 715                 720

Phe Thr Asp Ala Val Asn Glu Thr Thr Ile Met Leu Lys Trp Met
                725                 730                 735

Tyr Ile Pro Ala Ser Asn Asn Asn Thr Pro Ile His Gly Phe Tyr
                740                 745                 750

Ile Tyr Tyr Arg Pro Thr Asp Ser Asp Asn Asp Ser Asp Tyr Lys
                755                 760                 765

Lys Asp Met Val Glu Gly Asp Lys Tyr Trp His Ser Ile Ser His
                770                 775                 780

Leu Gln Pro Glu Thr Ser Tyr Asp Ile Lys Met Gln Cys Phe Asn
                785                 790                 795
```

```
Glu Gly Gly Glu Ser Glu Phe Ser Asn Val Met Ile Cys Glu Thr
                800                 805                 810

Lys Ala Arg Lys Ser Ser Gly Gln Pro Gly Arg Leu Pro Pro Pro
                815                 820                 825

Thr Leu Ala Pro Pro Gln Pro Pro Leu Pro Glu Thr Ile Glu Arg
                830                 835                 840

Pro Val Gly Thr Gly Ala Met Val Ala Arg Ser Ser Asp Leu Pro
                845                 850                 855

Tyr Leu Ile Val Gly Val Val Leu Gly Ser Ile Val Leu Ile Ile
                860                 865                 870

Val Thr Phe Ile Pro Phe Cys Leu Trp Arg Ala Trp Ser Lys Gln
                875                 880                 885

Lys His Thr Thr Asp Leu Gly Phe Pro Arg Ser Ala Leu Pro Pro
                890                 895                 900

Ser Cys Pro Tyr Thr Met Val Pro Leu Gly Gly Leu Pro Gly His
                905                 910                 915

Gln Ala Ser Gly Gln Pro Tyr Leu Ser Gly Ile Ser Gly Arg Ala
                920                 925                 930

Cys Ala Asn Gly Ile His Met Asn Arg Gly Cys Pro Ser Ala Ala
                935                 940                 945

Val Gly Tyr Pro Gly Met Lys Pro Gln Gln His Cys Pro Gly Glu
                950                 955                 960

Leu Gln Gln Gln Ser Asp Thr Ser Ser Leu Leu Arg Gln Thr His
                965                 970                 975

Leu Gly Asn Gly Tyr Asp Pro Gln Ser His Gln Ile Thr Arg Gly
                980                 985                 990

Pro Lys Ser Ser Pro Asp Glu Gly Ser Phe Leu Tyr Thr Leu Pro
                995                 1000                1005

Asp Asp Ser Thr His Gln Leu Leu Gln Pro His His Asp Cys Cys
                1010                1015                1020

Gln Arg Gln Glu Gln Pro Ala Ala Val Gly Gln Ser Gly Val Arg
                1025                1030                1035

Arg Ala Pro Asp Ser Pro Val Leu Glu Ala Val Trp Asp Pro Pro
                1040                1045                1050

Phe His Ser Gly Pro Pro Cys Cys Leu Gly Leu Val Pro Val Glu
                1055                1060                1065

Glu Val Asp Ser Pro Asp Ser Cys Gln Val Ser Gly Gly Asp Trp
                1070                1075                1080

Cys Pro Gln His Pro Val Gly Ala Tyr Val Gly Gln Glu Pro Gly
                1085                1090                1095

Met Gln Leu Ser Pro Gly Pro Leu Val Arg Val Ser Phe Glu Thr
                1100                1105                1110

Pro Pro Leu Thr Ile
                1115
```

<210> SEQ ID NO 39
<211> LENGTH: 728
<212> TYPE: DNA
<213> ORGANISM: Homo sapiens

<400> SEQUENCE: 39

```
catttccaac aagagcactg gccaagtcag cttcttctga gagagtctct                50

agaagacatg atgctacact cagctttggg tctctgcctc ttactcgtca               100
```

-continued

```
cagtttcttc caaccttgcc attgcaataa aaaaggaaaa gaggcctcct      150

cagacactct caagaggatg gggagatgac atcacttggg tacaaactta      200

tgaagaaggt ctcttttatg ctcaaaaaag taagaagcca ttaatggtta      250

ttcatcacct ggaggattgt caatactctc aagcactaaa gaaagtattt      300

gcccaaaatg aagaaataca agaaatggct cagaataagt tcatcatgct      350

aaaccttatg catgaaacca ctgataagaa tttatcacct gatgggcaat      400

atgtgcctag aatcatgttt gtagaccctt ctttaacagt tagagctgac      450

atagctggaa gatactctaa cagattgtac acatatgagc ctcgggattt      500

acccctattg atagaaaaca tgaagaaagc attaagactt attcagtcag      550

agctataaga gatgatggaa aaaagccttc acttcaaaga agtcaaattt      600

catgaagaaa acctctggca cattgacaaa tactaaatgt gcaagtatat      650

agattttgta atattactat ttagtttttt taatgtgttt gcaatagtct      700

tattaaaata aatgtttttt  aaatctga                             728
```

<210> SEQ ID NO 40
<211> LENGTH: 166
<212> TYPE: PRT
<213> ORGANISM: Homo sapiens

<400> SEQUENCE: 40

```
Met Met Leu His Ser Ala Leu Gly Leu Cys Leu Leu Leu Val Thr
  1               5                  10                  15

Val Ser Ser Asn Leu Ala Ile Ala Ile Lys Lys Glu Lys Arg Pro
                 20                  25                  30

Pro Gln Thr Leu Ser Arg Gly Trp Gly Asp Asp Ile Thr Trp Val
                 35                  40                  45

Gln Thr Tyr Glu Glu Gly Leu Phe Tyr Ala Gln Lys Ser Lys Lys
                 50                  55                  60

Pro Leu Met Val Ile His His Leu Glu Asp Cys Gln Tyr Ser Gln
                 65                  70                  75

Ala Leu Lys Lys Val Phe Ala Gln Asn Glu Glu Ile Gln Glu Met
                 80                  85                  90

Ala Gln Asn Lys Phe Ile Met Leu Asn Leu Met His Glu Thr Thr
                 95                 100                 105

Asp Lys Asn Leu Ser Pro Asp Gly Gln Tyr Val Pro Arg Ile Met
                110                 115                 120

Phe Val Asp Pro Ser Leu Thr Val Arg Ala Asp Ile Ala Gly Arg
                125                 130                 135

Tyr Ser Asn Arg Leu Tyr Thr Tyr Glu Pro Arg Asp Leu Pro Leu
                140                 145                 150

Leu Ile Glu Asn Met Lys Lys Ala Leu Arg Leu Ile Gln Ser Glu
                155                 160                 165

Leu
```

<210> SEQ ID NO 41
<211> LENGTH: 693
<212> TYPE: DNA
<213> ORGANISM: Homo sapiens

<400> SEQUENCE: 41

```
ctagcctgcg ccaaggggta gtgagaccgc gcggcaacag cttgcggctg       50
```

-continued

```
cggggagctc ccgtgggcgc tccgctggct gtgcaggcgg ccatggattc      100

cttgcggaaa atgctgatct cagtcgcaat gctgggcgca ggggctggcg      150

tgggctacgc gctcctcgtt atcgtgaccc cgggagagcg gcggaagcag      200

gaaatgctaa aggagatgcc actgcaggac ccaaggagca gggaggaggc      250

ggccaggacc cagcagctat tgctggccac tctgcaggag gcagcgacca      300

cgcaggagaa cgtggcctgg aggaagaact ggatggttgg cggcgaaggc      350

ggcgccagcg ggaggtcacc gtgagaccgg acttgcctcc gtgggcgccg      400

gaccttggct tgggcgcagg aatccgaggc agcctttctc cttcgtgggc      450

ccagcggaga gtccggaccg agataccatg ccaggactct ccggggtcct      500

gtgagctgcc gtcgggtgag cacgtttccc ccaaaccctg gactgactgc      550

tttaaggtcc gcaaggcggg ccagggccga gacgcgagtc ggatgtggtg      600

aactgaaaga accaataaaa tcatgttcct ccaaaaaaaa aaaaaaaaaa      650

aaaaaaaaaa aaaaaaaaaa aaaaaaaaaa aaaaaaaaaa  aaa            693
```

```
<210> SEQ ID NO 42
<211> LENGTH: 93
<212> TYPE: PRT
<213> ORGANISM: Homo sapiens

<400> SEQUENCE: 42

Met Asp Ser Leu Arg Lys Met Leu Ile Ser Val Ala Met Leu Gly
  1               5                  10                  15

Ala Gly Ala Gly Val Gly Tyr Ala Leu Leu Val Ile Val Thr Pro
                 20                  25                  30

Gly Glu Arg Arg Lys Gln Glu Met Leu Lys Glu Met Pro Leu Gln
                 35                  40                  45

Asp Pro Arg Ser Arg Glu Glu Ala Ala Arg Thr Gln Gln Leu Leu
                 50                  55                  60

Leu Ala Thr Leu Gln Glu Ala Ala Thr Thr Gln Glu Asn Val Ala
                 65                  70                  75

Trp Arg Lys Asn Trp Met Val Gly Gly Glu Gly Gly Ala Ser Gly
                 80                  85                  90

Arg Ser Pro


<210> SEQ ID NO 43
<211> LENGTH: 3580
<212> TYPE: DNA
<213> ORGANISM: Homo sapiens

<400> SEQUENCE: 43

gaccggtccc tccggtcctg gatgtgcgga ctctgctgca gcgagggctg       50

caggcccgcc gggcggtgct caccgtgccc tggctggtgg agtttctctc      100

ctttgctgac catgttgttc ccttgctgga atattaccgg gacatcttca      150

ctctcctgct gcgcctgcac cggagcttgg tgttgtcgca ggagagtgag      200

gggaagatgt gtttcctgaa caagctgctg ctacttgctg tcctgggctg      250

gcttttccag attcccacag tccctgagga cttgttcttt ctggaagagg      300

gtccctcata tgcctttgag gtggacacag tagccccaga gcatggcttg      350

gacaatgcgc ctgtggtgga ccagcagctg ctctacacct gctgccccta      400

catcggagag ctccggaaac tgctcgcttc gtgggtgtca ggcagtagtg      450
```

-continued

```
gacggagtgg gggcttcatg aggaaaatca cccccaccac taccaccagc        500
ctgggagccc agccttccca gaccagccag gggctgcagg cacagctcgc        550
ccaggccttt ttccacaacc agccgccctc cttgcgccgg accgtagagt        600
tcgtggcaga aagaattgga tcaaactgtg tcaaacatat caaggctaca        650
ctggtggcag atctggtgcg ccaggcagag tcacttctcc aagagcagct        700
ggtgacacag ggagaggaag gggagaccc agcccagctg ttggagatct         750
tgtgttccca gctgtgccct cacggggccc aggcattggc cctggggcgg        800
gagttctgtc aaaggaagag ccctggggct gtgcgggcgc tgcttccaga        850
ggagaccccg gcagccgttc tgagcagtgc agagaacatt gctgtggggc        900
ttgcaacaga gaaagcctgt gcttggctgt cagccaacat cacagcactg        950
atcaggaggg aggtgaaagc agcagtgagt cgcacacttc gagcccaggg       1000
tcctgaacct gctgcccggg gggagcggag gggctgctcc cgcgcctgac       1050
gtgctctcct tggccgtggg gccacgggac cctgacgagg gagtctcccc       1100
agagcatctg gaacagctcc taggccagct gggccagacg ctgcggtgcc       1150
gccagttcct gtgcccacct gctgagcagc atctggcaaa gtgctctgtg       1200
gagttagctt ccctcctcgt tgcagatcaa attcctatcc tagggccccc       1250
ggcacagtac aggctggaga gagggcaggc tcgaaggctt ctgcacatgc       1300
tgctttcctt gtggaaggaa gactttcagg ggccggttcc gctgcagctg       1350
ctgctgagcc caagaaatgt ggggcttctg gcagacacaa ggccaaggga       1400
gtgggacttg ctgctattct tgctacggga gctggtggag aagggtctga       1450
tgggacggat ggagatagag gcctgcctgg gcagcctcca ccaggcccag       1500
tggccagggg actttgctga agaattagca acactgtcta atctgtttct       1550
agccgagccc cacctgccag aaccccagct aagagcctgt gagttggtgc       1600
agccaaaccg gggcactgtg ctggcccaga gctagggctg agaagtggcc       1650
ctgccttggg cattgcacca gaaccctgga cccccgcctc acgaggaggc       1700
ccaagtgccc aatgcagacc ctcactggtt ggggtgtagc tgggtctaca       1750
gtcagacttc ctgctctaag ggtgtcactg cctggcatcc caccacgcga       1800
atcctagagg aaggagagtt ggcctgattt gggattatgg cagaaaagtc       1850
cagagatgcc agtcctggag tagaagaggt ggtgtttgtt tatctcttgg       1900
atactaaatg aaatgaggtg tgtgggcttg tcaacacaga attcaagcct       1950
catttgctat cccagcatct cttaaaactt tgtagtcttg gaattcatga       2000
cagaggcaaa tgactcctgc ttaacttatg aagaaagtta aaacatgaat       2050
cttgggagtc tacattttct tatcaccagg agctggactg ccatctcctt       2100
ataaatgcct aacacaggcc gggtctggtg gctcatgcct gtaatcccag       2150
cactttgaga ggcctgaggt cggcggactg cctgaggtca ggaattcaag       2200
accagcctgg ccaacatggc aaaaccccat ctctactaaa aataaaaaaa       2250
ttattagctg ggcatggtgg tgtgtgcctg taatcccagc tactcaggag       2300
gatgaggcag gagacctgct tgaacctgga ggtggaggtt gcagtgagcc       2350
gaggtcgcac cactgcactc cagtctgggt aacagagcga gactttctag       2400
```

-continued

```
aaaaagccta acaaacagat aaggtaggac tcaaccaact gaaacctgac          2450

tttccccctg taccttcagc ccctgtgcag gtagtaacct cttgagacct          2500

ctccctgacc agggaccaag cacagggcat ttagagcttt ttagaataaa          2550

ctggttttct ttaaaaaaaa aaaaaaaaaa agggcggccg ccctttttttt          2600

tttttttttt tttttttttt tttttttttt tttttttttt taaaaagggc          2650

ttttattaaa attctcccca cacgatggct cctgcaatct gccacagctc          2700

tggggcgtgt cctgtaggga aaggccctgt tttccctgag gcggggctgg          2750

gcttgtccat gggtccgcgg agctggccgt gcttggcgcc ctggcgtgtg          2800

tctagctgct tcttgccggg cacagagctg cggggtctgg gggcaccggg          2850

agctaagagc aggctctggt gcaggggtgg aggcctgtct cttaaccgac          2900

accctgaggt gctcctgaga tgctgggtcc accctgagtg gcacggggag          2950

cagctgtggc cggtgctcct tcytaggcca gtcctgggga aactaagctc          3000

gggcccttct ttgcaaagac cgaggatggg gtgggtgtgg gggactcatg          3050

gggaatggcc tgaggagcta cgtgtgaaga gggcgccggt ttgttggctg          3100

cagcggcctg gagcgcctct ctcctgagcc tcagtttccc tttccgtcta          3150

atgaagaaca tgccgtctcg gtgtctcagg gctattagga cttgccctca          3200

ggaagtggcc ttggacgagc gtcatgttat tttcacaact gtcctgcgac          3250

gttggcctgg gcacgtcatg gaatggccca tgtccctctg ctgcgtggac          3300

gtcgcggtcg ggagtgcgca gccagaggcg gggccagacg tgcgcctggg          3350

ggtgagggga ggcgccccgg gagggcctca caggaagttg ggctcccgca          3400

ccaccaggca gggcgggctc ccgccgccgc cgccgccacc accgtccagg          3450

ggccggtaga caaagtggaa gtcgcgcttg ggctcgctgc gcagcaggta          3500

gcccttgatg cagtgcggca gcgcgtcgtc cgccagctgg aagcagcgcc          3550

cgtccaccag cacgaacagc cggtgcgcct                                3580


<210> SEQ ID NO 44
<211> LENGTH: 280
<212> TYPE: PRT
<213> ORGANISM: Homo sapiens

<400> SEQUENCE: 44

Met Cys Phe Leu Asn Lys Leu Leu Leu Leu Ala Val Leu Gly Trp
  1               5                  10                  15

Leu Phe Gln Ile Pro Thr Val Pro Glu Asp Leu Phe Phe Leu Glu
                 20                  25                  30

Glu Gly Pro Ser Tyr Ala Phe Glu Val Asp Thr Val Ala Pro Glu
                 35                  40                  45

His Gly Leu Asp Asn Ala Pro Val Val Asp Gln Gln Leu Leu Tyr
                 50                  55                  60

Thr Cys Cys Pro Tyr Ile Gly Glu Leu Arg Lys Leu Leu Ala Ser
                 65                  70                  75

Trp Val Ser Gly Ser Ser Gly Arg Ser Gly Gly Phe Met Arg Lys
                 80                  85                  90

Ile Thr Pro Thr Thr Thr Thr Ser Leu Gly Ala Gln Pro Ser Gln
                 95                 100                 105

Thr Ser Gln Gly Leu Gln Ala Gln Leu Ala Gln Ala Phe Phe His
                110                 115                 120
```

-continued

```
Asn Gln Pro Pro Ser Leu Arg Arg Thr Val Glu Phe Val Ala Glu
                125                 130                 135

Arg Ile Gly Ser Asn Cys Val Lys His Ile Lys Ala Thr Leu Val
                140                 145                 150

Ala Asp Leu Val Arg Gln Ala Glu Ser Leu Leu Gln Glu Gln Leu
                155                 160                 165

Val Thr Gln Gly Glu Glu Gly Gly Asp Pro Ala Gln Leu Leu Glu
                170                 175                 180

Ile Leu Cys Ser Gln Leu Cys Pro His Gly Ala Gln Ala Leu Ala
                185                 190                 195

Leu Gly Arg Glu Phe Cys Gln Arg Lys Ser Pro Gly Ala Val Arg
                200                 205                 210

Ala Leu Leu Pro Glu Glu Thr Pro Ala Ala Val Leu Ser Ser Ala
                215                 220                 225

Glu Asn Ile Ala Val Gly Leu Ala Thr Glu Lys Ala Cys Ala Trp
                230                 235                 240

Leu Ser Ala Asn Ile Thr Ala Leu Ile Arg Arg Glu Val Lys Ala
                245                 250                 255

Ala Val Ser Arg Thr Leu Arg Ala Gln Gly Pro Glu Pro Ala Ala
                260                 265                 270

Arg Gly Glu Arg Arg Gly Cys Ser Arg Ala
                275                 280
```

<210> SEQ ID NO 45
<211> LENGTH: 4104
<212> TYPE: DNA
<213> ORGANISM: Homo sapiens

<400> SEQUENCE: 45

```
cccacgcgtc cgcccacgcg tccgcccacg cgtccgccca cgcgtccgcc          50

cacgcgtccg cccacgcgtc cgcccacgcg tccggtgcaa gctcgcgccg         100

cacactgcct ggtggaggga aggagcccgg gcgcctctcg ccgctccccg         150

cgccgccgtc cgcacctccc caccgcccgc cgcccgccgc ccgccgcccg         200

caaagcatga gtgagcccgc tctctgcagc tgcccggggc gcgaatggca         250

ggctgtttcc gcggagtaaa aggtggcgcc ggtcagtggt cgtttccaat         300

gacggacatt aaccagactg tcagatcctg gggagtcgcg agccccgagt         350

ttggagtttt ttccccccac aacgtcacag tccgaactgc agagggaaag         400

gaaggcggca ggaaggcgaa gctcgggctc cggcacgtag ttgggaaact         450

tgcgggtcct agaagtcgcc tccccgcctt gccggccgcc cttgcagccc         500

cgagccgagc agcaaagtga gacattgtgc gcctgccaga tccgccggcc         550

gcggaccggg gctgcctcgg aaacacagag ggtcttctc tcgccctgca          600

tataattagc ctgcacacaa agggagcagc tgaatggagg ttgtcactct         650

ctggaaaagg atttctgacc gagcgcttcc aatggacatt ctccagtctc         700

tctggaaaga ttctcgctaa tggatttcct gctgctcggt ctctgtctat         750

actggctgct gaggaggccc tcgggggtgg tcttgtgtct gctgggggcc         800

tgctttcaga tgctgcccgc cgcccccagc gggtgcccgc agctgtgccg         850

gtgcgagggg cggctgctgt actgcgaggc gctcaacctc accgaggcgc         900

cccacaacct gtccggcctg ctgggcttgt ccctgcgcta caacagcctc         950
```

-continued

```
tcggagctgc gcgccggcca gttcacgggg ttaatgcagc tcacgtggct      1000
ctatctggat cacaatcaca tctgctccgt gcagggggac gcctttcaga      1050
aactgcgccg agttaaggaa ctcacgctga gttccaacca gatcacccaa      1100
ctgcccaaca ccaccttccg gcccatgccc aacctgcgca gcgtggacct      1150
ctcgtacaac aagctgcagg cgctcgcgcc cgacctcttc cacgggctgc      1200
ggaagctcac cacgctgcat atgcgggcca acgccatcca gtttgtgccc      1250
gtgcgcatct tccaggactg ccgcagcctc aagtttctcg acatcggata      1300
caatcagctc aagagtctgg cgcgcaactc tttcgccggc ttgtttaagc      1350
tcaccgagct gcacctcgag cacaacgact tggtcaaggt gaacttcgcc      1400
cacttcccgc gcctcatctc cctgcactcg ctctgcctgc ggaggaacaa      1450
ggtggccatt gtggtcagct cgctggactg ggtttggaac ctggagaaaa      1500
tggacttgtc gggcaacgag atcgagtaca tggagcccca tgtgttcgag      1550
accgtgccgc acctgcagtc cctgcagctg gactccaacc gcctcaccta      1600
catcgagccc cggatcctca actcttggaa gtccctgaca agcatcaccc      1650
tggccgggaa cctgtgggat tgcgggcgca acgtgtgtgc cctagcctcg      1700
tggctcagca acttccaggg gcgctacgat ggcaacttgc agtgcgccag      1750
cccggagtac gcacagggcg aggacgtcct ggacgccgtg tacgccttcc      1800
acctgtgcga ggatggggcc gagcccacca gcggccacct gctctcggcc      1850
gtcaccaacc gcagtgatct ggggcccccct gccagctcgg ccaccacgct      1900
cgcggacggc ggggaggggc agcacgacgg cacattcgag cctgccaccg      1950
tggctcttcc aggcggcgag cacgccgaga acgccgtgca gatccacaag      2000
gtggtcacgg gcaccatggc cctcatcttc tccttcctca tcgtggtcct      2050
ggtgctctac gtgtcctgga agtgtttccc agccagcctc aggcagctca      2100
gacagtgctt tgtcacgcag cgcaggaagc aaaagcagaa acagaccatg      2150
catcagatgg ctgccatgtc tgcccaggaa tactacgttg attacaaacc      2200
gaaccacatt gagggagccc tggtgatcat caacgagtat ggctcgtgta      2250
cctgccacca gcagcccgcg agggaatgcg aggtgtgatt gtcccagtgg      2300
ctctcaaccc atgcgctacc aaatacgcct gggcagccgg gacgggccgg      2350
cgggcaccag gctggggtct ccttgtctgt gctctgatat gctccttgac      2400
tgaaacttta aggggatctc tcccagagac ttgacatttt agctttattg      2450
tgtcttaaaa acaaaagcga attaaaacac aacaaaaaac cccaccccac      2500
aaccttcagg acagtctatc ttaaatttca tatgagaact ccttcctccc      2550
tttgaagatc tgtccatatt caggaatctg agagtgtaaa aaaggtggcc      2600
ataagacaga gagagaataa tcgtgctttg ttttatgcta ctcctcccac      2650
cctgcccatg attaaacatc atgtatgtag aagatcttaa gtccatacgc      2700
atttcatgaa gaaccattgg aaagaggaat ctgcaatctg ggagcttaag      2750
agcaaatgat gaccatagaa agctatgttc ttactttgtg tgtgtgtctg      2800
tatgtttctg cgttgtgtgt ctttgtaggc aagcaaacgt tgtctacaca      2850
aacgggaatt tagctcacat catttcatgc ccctgtgcct ctagctctgg      2900
```

-continued

```
agattggtgg ggggaggtgg ggggaaacgg caggaataag ggaaagtggt        2950

agttttaact aaggttttgt aacacttgaa atctttttctt tctcaaatta       3000

attatcttta agcttcaaga aacttgctct gacccctcta agcaaactac        3050

taagcattta aaagagaatc taatttttaa aggtgtagca cctttttttt        3100

tattcttccc acagagggtg ctaatctcat tatgctgtgc tatctgaaaa        3150

gaacttaagg ccacaattca cgtctcgtcc tgggcattgt gatggattga        3200

ccctccattt gcagtacctt cccagctgat taaagttcag cagtggtatt        3250

gaggtttttc gaatatttat atagaaaaaa agtcttttca catgacaaat        3300

gacactctca caccagtctt agccctagta gtttttttagg ttggaccaga       3350

ggaagcaggt taaatgagac ctgtcctctg ctgcactcag aaaaaatagg        3400

cagtccctga tgctcagatc ttagccttga tattaatagt tgagaccacc        3450

tacccacaat gcagcctata ctcccaagac tacaaagtta ccatcgcaaa        3500

ggaaaggtta ttccagtaaa aggaaatagt tttctcaacc atttaaaaat        3550

attcttctga actcatcaaa gtagaagagc ccccaacctt ttctctctgc        3600

cttcaagaag gcagacattt ggtatgattt agcatcaaca acacatttat        3650

gagtatatgt aagtaatcag aggggcaaat gccacttgtt attcctccca        3700

agttttccaa gcaagtacac acagatctct ggtaggatta ggggccactt        3750

gtgtttccgg cttattttag tcgacttgtc agcaagtttg atgcctagtc        3800

tatctgacat ggcccagtag aacagggcat tgatggatca catgagatgg        3850

tagaaggaac atcatcacat acccctctca cagagaaaat tatcaaagaa        3900

ccagaaatta tatctgtttt ggagcaagag tgtcataatg tttcagggta        3950

gtcaaaataa acataaatta tctcctctag atgagtggcg atgttggctg        4000

atttgggtct gccattgaca gaatgtcaaa taaaaaggaa ttagctagaa        4050

tatgaccatt aaatgtgctt ctgaaatata ttttgagata ggtttagaat        4100

gtca                                                           4104
```

<210> SEQ ID NO 46
<211> LENGTH: 522
<212> TYPE: PRT
<213> ORGANISM: Homo sapiens

<400> SEQUENCE: 46

```
Met Asp Phe Leu Leu Leu Gly Leu Cys Leu Tyr Trp Leu Leu Arg
  1               5                  10                  15

Arg Pro Ser Gly Val Val Leu Cys Leu Leu Gly Ala Cys Phe Gln
                 20                  25                  30

Met Leu Pro Ala Ala Pro Ser Gly Cys Pro Gln Leu Cys Arg Cys
                 35                  40                  45

Glu Gly Arg Leu Leu Tyr Cys Glu Ala Leu Asn Leu Thr Glu Ala
                 50                  55                  60

Pro His Asn Leu Ser Gly Leu Leu Gly Leu Ser Leu Arg Tyr Asn
                 65                  70                  75

Ser Leu Ser Glu Leu Arg Ala Gly Gln Phe Thr Gly Leu Met Gln
                 80                  85                  90

Leu Thr Trp Leu Tyr Leu Asp His Asn His Ile Cys Ser Val Gln
                 95                 100                 105
```

-continued

```
Gly Asp Ala Phe Gln Lys Leu Arg Arg Val Lys Glu Leu Thr Leu
                110                 115                 120

Ser Ser Asn Gln Ile Thr Gln Leu Pro Asn Thr Thr Phe Arg Pro
                125                 130                 135

Met Pro Asn Leu Arg Ser Val Asp Leu Ser Tyr Asn Lys Leu Gln
                140                 145                 150

Ala Leu Ala Pro Asp Leu Phe His Gly Leu Arg Lys Leu Thr Thr
                155                 160                 165

Leu His Met Arg Ala Asn Ala Ile Gln Phe Val Pro Val Arg Ile
                170                 175                 180

Phe Gln Asp Cys Arg Ser Leu Lys Phe Leu Asp Ile Gly Tyr Asn
                185                 190                 195

Gln Leu Lys Ser Leu Ala Arg Asn Ser Phe Ala Gly Leu Phe Lys
                200                 205                 210

Leu Thr Glu Leu His Leu Glu His Asn Asp Leu Val Lys Val Asn
                215                 220                 225

Phe Ala His Phe Pro Arg Leu Ile Ser Leu His Ser Leu Cys Leu
                230                 235                 240

Arg Arg Asn Lys Val Ala Ile Val Val Ser Ser Leu Asp Trp Val
                245                 250                 255

Trp Asn Leu Glu Lys Met Asp Leu Ser Gly Asn Glu Ile Glu Tyr
                260                 265                 270

Met Glu Pro His Val Phe Glu Thr Val Pro His Leu Gln Ser Leu
                275                 280                 285

Gln Leu Asp Ser Asn Arg Leu Thr Tyr Ile Glu Pro Arg Ile Leu
                290                 295                 300

Asn Ser Trp Lys Ser Leu Thr Ser Ile Thr Leu Ala Gly Asn Leu
                305                 310                 315

Trp Asp Cys Gly Arg Asn Val Cys Ala Leu Ala Ser Trp Leu Ser
                320                 325                 330

Asn Phe Gln Gly Arg Tyr Asp Gly Asn Leu Gln Cys Ala Ser Pro
                335                 340                 345

Glu Tyr Ala Gln Gly Glu Asp Val Leu Asp Ala Val Tyr Ala Phe
                350                 355                 360

His Leu Cys Glu Asp Gly Ala Glu Pro Thr Ser Gly His Leu Leu
                365                 370                 375

Ser Ala Val Thr Asn Arg Ser Asp Leu Gly Pro Pro Ala Ser Ser
                380                 385                 390

Ala Thr Thr Leu Ala Asp Gly Gly Glu Gly Gln His Asp Gly Thr
                395                 400                 405

Phe Glu Pro Ala Thr Val Ala Leu Pro Gly Gly Glu His Ala Glu
                410                 415                 420

Asn Ala Val Gln Ile His Lys Val Val Thr Gly Thr Met Ala Leu
                425                 430                 435

Ile Phe Ser Phe Leu Ile Val Val Leu Val Leu Tyr Val Ser Trp
                440                 445                 450

Lys Cys Phe Pro Ala Ser Leu Arg Gln Leu Arg Gln Cys Phe Val
                455                 460                 465

Thr Gln Arg Arg Lys Gln Lys Gln Lys Gln Thr Met His Gln Met
                470                 475                 480

Ala Ala Met Ser Ala Gln Glu Tyr Tyr Val Asp Tyr Lys Pro Asn
                485                 490                 495

His Ile Glu Gly Ala Leu Val Ile Ile Asn Glu Tyr Gly Ser Cys
```

-continued

```
                500                 505                 510

Thr Cys His Gln Gln Pro Ala Arg Glu Cys Glu Val
                515                 520


<210> SEQ ID NO 47
<211> LENGTH: 3170
<212> TYPE: DNA
<213> ORGANISM: Homo sapiens

<400> SEQUENCE: 47

agcgggtctc gcttgggttc cgctaatttc tgtcctgagg cgtgagactg                 50

agttcatagg gtcctgggtc cccgaaccag gaagggttga gggaacacaa                100

tctgcaagcc cccgcgaccc aagtgagggg ccccgtgttg gggtcctccc                150

tcccttttgca ttcccacccc tccgggcttt gcgtcttcct ggggaccccc                200

tcgccgggag atggccgcgt tgatgcggag caaggattcg tcctgctgcc                250

tgctcctact ggccgcggtg ctgatggtgg agagctcaca gatcggcagt                300

tcgcgggcca aactcaactc catcaagtcc tctctgggcg gggagacgcc                350

tggtcaggcc gccaatcgat ctgcgggcat gtaccaagga ctggcattcg                400

gcggcagtaa gaagggcaaa aacctggggc aggcctaccc ttgtagcagt                450

gataaggagt gtgaagttgg gaggtattgc cacagtcccc accaaggatc                500

atcggcctgc atggtgtgtc ggagaaaaaa gaagcgctgc caccgagatg                550

gcatgtgctg ccccagtacc cgctgcaata atggcatctg tatcccagtt                600

actgaaagca tcttaacccc tcacatcccg gctctggatg gtactcggca                650

cagagatcga aaccacggtc attactcaaa ccatgacttg ggatggcaga                700

atctaggaag accacacact aagatgtcac atataaaagg gcatgaagga                750

gacccctgcc tacgatcatc agactgcatt gaagggtttt gctgtgctcg                800

tcatttctgg accaaaatct gcaaaccagt gctccatcag gggggaagtct                850

gtaccaaaca acgcaagaag ggttctcatg ggctggaaat tttccagcgt                900

tgcgactgtg cgaagggcct gtcttgcaaa gtatggaaag atgccaccta                950

ctcctccaaa gccagactcc atgtgtgtca gaaaatttga tcaccattga               1000

ggaacatcat caattgcaga ctgtgaagtt gtgtatttaa tgcattatag               1050

catggtggaa aataaggttc agatgcagaa gaatggctaa aataagaaac               1100

gtgataagaa tatagatgat cacaaaaagg gagaaagaaa acatgaactg               1150

aatagattag aatgggtgac aaatgcagtg cagccagtgt ttccattatg               1200

caacttgtct atgtaaataa tgtacacatt tgtggaaaat gctattatta               1250

agagaacaag cacacagtgg aaattactga tgagtagcat gtgactttcc               1300

aagagtttag gttgtgctgg aggagaggtt tccttcagat tgctgattgc               1350

ttatacaaat aacctacatg ccagatttct attcaacgtt agagtttaac               1400

aaaatactcc tagaataact tgttatacaa taggttctaa aaataaaatt               1450

gctaaacaag aaatgaaaac atggagcatt gttaatttac aacagaaaat               1500

taccttttga tttgtaacac tacttctgct gttcaatcaa gagtcttggt               1550

agataagaaa aaaatcagtc aatatttcca aataattgca aaataatggc               1600

cagttgttta ggaaggcctt taggaagaca aataaataac aaacaaacag               1650
```

-continued

```
ccacaaatac ttttttttca aaattttagt tttacctgta attaataaga        1700

actgatacaa gacaaaaaca gttccttcag attctacgga atgacagtat        1750

atctctcttt atcctatgtg attcctgctc tgaatgcatt atattttcca        1800

aactataccc ataaattgtg actagtaaaa tacttacaca gagcagaatt        1850

ttcacagatg gcaaaaaaat ttaaagatgt ccaatatatg tgggaaaaga        1900

gctaacagag agatcattat ttcttaaaga ttggccataa cctatatttt        1950

gatagaatta gattggtaaa tacatgtatt catacatact ctgtggtaat        2000

agagacttaa gctggatctg tactgcactg gagtaagcaa gaaaattggg        2050

aaaacttttt cgtttgttca ggttttggca acacatagat catatgtctg        2100

aggcacaagt tggctgttca tctttgaaac caggggatgc acagtctaaa        2150

tgaatatctg catgggattt gctatcataa tatttactat gcagatgaat        2200

tcagtgtgag gtcctgtgtc cgtactatcc tcaaattatt tattttatag        2250

tgctgagatc ctcaaataat ctcaatttca ggaggtttca caaaatgtac        2300

tcctgaagta gacagagtag tgaggtttca ttgccctcta taagcttctg        2350

actagccaat ggcatcatcc aattttcttc ccaaacctct gcagcatctg        2400

ctttattgcc aaagggctag tttcggtttt ctgcagccat tgcggttaaa        2450

aaatataagt aggataactt gtaaaacctg catattgcta atctatagac        2500

accacagttt ctaaattctt tgaaaccact ttactacttt ttttaaactt        2550

aactcagttc taaatacttt gtctggagca caaaacaata aaaggttatc        2600

ttatagtcgt gactttaaac ttttgtagac cacaattcac tttttagttt        2650

tcttttactt aaatcccatc tgcagtctca aatttaagtt ctcccagtag        2700

agattgagtt tgagcctgta tatctattaa aaatttcaac ttcccacata        2750

tatttactaa gatgattaag acttacattt tctgcacagg tctgcaaaaa        2800

caaaaattat aaactagtcc atccaagaac caaagtttgt ataaacaggt        2850

tgctataagc ttgtgaaatg aaaatggaac atttcaatca aacatttcct        2900

atataacaat tattatattt acaatttggt ttctgcaata tttttcttat        2950

gtccaccctt ttaaaaatta ttatttgaag taatttattt acaggaaatg        3000

ttaatgagat gtattttctt atagagatat ttcttacaga aagctttgta        3050

gcagaatata tttgcagcta ttgactttgt aatttaggaa aaatgtataa        3100

taagataaaa tctattaaat ttttctcctc taaaaactga aaaaaaaaaa        3150

aaaaaaaaaa aaaaaaaaaa                                          3170
```

<210> SEQ ID NO 48
<211> LENGTH: 259
<212> TYPE: PRT
<213> ORGANISM: Homo sapiens

<400> SEQUENCE: 48

```
Met Ala Ala Leu Met Arg Ser Lys Asp Ser Ser Cys Cys Leu Leu
  1               5                  10                  15

Leu Leu Ala Ala Val Leu Met Val Glu Ser Ser Gln Ile Gly Ser
                 20                  25                  30

Ser Arg Ala Lys Leu Asn Ser Ile Lys Ser Ser Leu Gly Gly Glu
                 35                  40                  45
```

-continued

```
Thr Pro Gly Gln Ala Ala Asn Arg Ser Ala Gly Met Tyr Gln Gly
                50                  55                  60

Leu Ala Phe Gly Gly Ser Lys Lys Gly Lys Asn Leu Gly Gln Ala
                65                  70                  75

Tyr Pro Cys Ser Ser Asp Lys Glu Cys Glu Val Gly Arg Tyr Cys
                80                  85                  90

His Ser Pro His Gln Gly Ser Ser Ala Cys Met Val Cys Arg Arg
                95                 100                 105

Lys Lys Lys Arg Cys His Arg Asp Gly Met Cys Cys Pro Ser Thr
               110                 115                 120

Arg Cys Asn Asn Gly Ile Cys Ile Pro Val Thr Glu Ser Ile Leu
               125                 130                 135

Thr Pro His Ile Pro Ala Leu Asp Gly Thr Arg His Arg Asp Arg
               140                 145                 150

Asn His Gly His Tyr Ser Asn His Asp Leu Gly Trp Gln Asn Leu
               155                 160                 165

Gly Arg Pro His Thr Lys Met Ser His Ile Lys Gly His Glu Gly
               170                 175                 180

Asp Pro Cys Leu Arg Ser Ser Asp Cys Ile Glu Gly Phe Cys Cys
               185                 190                 195

Ala Arg His Phe Trp Thr Lys Ile Cys Lys Pro Val Leu His Gln
               200                 205                 210

Gly Glu Val Cys Thr Lys Gln Arg Lys Lys Gly Ser His Gly Leu
               215                 220                 225

Glu Ile Phe Gln Arg Cys Asp Cys Ala Lys Gly Leu Ser Cys Lys
               230                 235                 240

Val Trp Lys Asp Ala Thr Tyr Ser Ser Lys Ala Arg Leu His Val
               245                 250                 255

Cys Gln Lys Ile


<210> SEQ ID NO 49
<211> LENGTH: 2567
<212> TYPE: DNA
<213> ORGANISM: Homo sapiens

<400> SEQUENCE: 49

cgtgggccgg ggtcgcgcag cgggctgtgg gcgcgcccgg aggagcgacc          50

gccgcagttc tcgagctcca gctgcattcc ctccgcgtcc gccccacgct         100

tctcccgctc cgggccccgc aatggcccag gcagtgtggt cgcgcctcgg         150

ccgcatcctc tggcttgcct gcctcctgcc ctgggccccg gcaggggtgg         200

ccgcaggcct gtatgaactc aatctcacca ccgatagccc tgccaccacg         250

ggagcggtgg tgaccatctc ggccagcctg gtggccaagg acaacggcag         300

cctggccctg cccgctgacg cccacctcta ccgcttccac tggatccaca         350

ccccgctggt gcttactggc aagatggaga agggtctcag ctccaccatc         400

cgtgtggtcg gccacgtgcc cggggaattc ccggtctctg tctgggtcac         450

tgccgctgac tgctggatgt gccagcctgt ggccaggggc tttgtggtcc         500

tccccatcac agagttcctc gtgggggacc ttgttgtcac ccagaacact         550

tccctaccct ggcccagctc ctatctcact aagaccgtcc tgaaagtctc         600

cttcctcctc cacgacccga gcaacttcct caagaccgcc ttgtttctct         650

acagctggga cttcggggac gggacccaga tggtgactga agactccgtg         700
```

-continued

```
gtctattata actattccat catcgggacc ttcaccgtga agctcaaagt          750
ggtggcggag tgggaagagg tggagccgga tgccacgagg gctgtgaagc          800
agaagaccgg ggacttctcc gcctcgctga agctgcagga aacccttcga          850
ggcatccaag tgttggggcc caccctaatt cagaccttcc aaaagatgac          900
cgtgaccttg aacttcctgg ggagccctcc tctgactgtg tgctggcgtc          950
tcaagcctga gtgcctcccg ctggaggaag gggagtgcca ccctgtgtcc         1000
gtggccagca cagcgtacaa cctgacccac accttcaggg accctgggga         1050
ctactgcttc agcatccggg ccgagaatat catcagcaag acacatcagt         1100
accacaagat ccaggtgtgg ccctccagaa tccagccggc tgtctttgct         1150
ttcccatgtg ctacacttat cactgtgatg ttggccttca tcatgtacat         1200
gaccctgcgg aatgccactc agcaaaagga catggtggag aacccggagc         1250
caccctctgg ggtcaggtgc tgctgccaga tgtgctgtgg gcctttcttg         1300
ctggagactc catctgagta cctggaaatt gttcgtgaga accacgggct         1350
gctcccgccc ctctataagt ctgtcaaaac ttacaccgtg tgagcactcc         1400
ccctccccac cccatctcag tgttaactga ctgctgactt ggagtttcca         1450
gcagggtggt gtgcaccact gaccaggagg ggttcatttg cgtggggctg         1500
ttggcctgga tcatccatcc atctgtacag ttcagccact gccacaagcc         1550
cctccctctc tgtcacccct gaccccagcc attcacccat ctgtacagtc         1600
cagccactga cataagcccc actcggttac cacccccttg acccccctacc        1650
tttgaagagg cttcgtgcag gactttgatg cttggggtgt tccgtgttga         1700
ctcctaggtg ggcctggctg cccactgccc attcctctca tattggcaca         1750
tctgctgtcc attgggggtt ctcagtttcc tcccccagac agccctacct         1800
gtgccagaga gctagaaaga aggtcataaa gggttaaaaa tccataacta         1850
aaggttgtac acatagatgg gcacactcac agagagaagt gtgcatgtac         1900
acacaccaca cacacacaca cacacacaca cacagaaata taaacacatg         1950
cgtcacatgg gcatttcaga tgatcagctc tgtatctggt taagtcggtt         2000
gctgggatgc accctgcact agagctgaaa ggaaatttga cctccaagca         2050
gccctgacag gttctgggcc cgggccctcc ctttgtgctt tgtctctgca         2100
gttcttgcgc cctttataag gccatcctag tccctgctgg ctggcagggg         2150
cctggatggg gggcaggact aatactgagt gattgcagag tgctttataa         2200
atatcacctt attttatcga aacccatctg tgaaactttc actgaggaaa         2250
aggccttgca gcggtagaag aggttgagtc aaggccgggc gcggtggctc         2300
acgcctgtaa tcccagcact ttgggaggcc gaggcgggtg gatcacgaga         2350
tcaggagatc gagaccaccc tggctaacac ggtgaaaccc cgtctctact         2400
aaaaaaatac aaaaagttag ccgggcgtgg tggtgggtgc ctgtagtccc         2450
agctactcgg gaggctgagg caggagaatg gtgcgaaccc gggaggcgga         2500
gcttgcagtg agcccagatg gcgccactgc actccagcct gagtgacaga         2550
gcgagactct  gtctcca                                            2567
```

<210> SEQ ID NO 50

-continued

<211> LENGTH: 423
<212> TYPE: PRT
<213> ORGANISM: Homo sapiens

<400> SEQUENCE: 50

Met Ala Gln Ala Val Trp Ser Arg Leu Gly Arg Ile Leu Trp Leu
1               5                   10                  15

Ala Cys Leu Leu Pro Trp Ala Pro Ala Gly Val Ala Ala Gly Leu
                20                  25                  30

Tyr Glu Leu Asn Leu Thr Thr Asp Ser Pro Ala Thr Thr Gly Ala
                35                  40                  45

Val Val Thr Ile Ser Ala Ser Leu Val Ala Lys Asp Asn Gly Ser
                50                  55                  60

Leu Ala Leu Pro Ala Asp Ala His Leu Tyr Arg Phe His Trp Ile
                65                  70                  75

His Thr Pro Leu Val Leu Thr Gly Lys Met Glu Lys Gly Leu Ser
                80                  85                  90

Ser Thr Ile Arg Val Val Gly His Val Pro Gly Glu Phe Pro Val
                95                  100                 105

Ser Val Trp Val Thr Ala Ala Asp Cys Trp Met Cys Gln Pro Val
                110                 115                 120

Ala Arg Gly Phe Val Val Leu Pro Ile Thr Glu Phe Leu Val Gly
                125                 130                 135

Asp Leu Val Val Thr Gln Asn Thr Ser Leu Pro Trp Pro Ser Ser
                140                 145                 150

Tyr Leu Thr Lys Thr Val Leu Lys Val Ser Phe Leu Leu His Asp
                155                 160                 165

Pro Ser Asn Phe Leu Lys Thr Ala Leu Phe Leu Tyr Ser Trp Asp
                170                 175                 180

Phe Gly Asp Gly Thr Gln Met Val Thr Glu Asp Ser Val Val Tyr
                185                 190                 195

Tyr Asn Tyr Ser Ile Ile Gly Thr Phe Thr Val Lys Leu Lys Val
                200                 205                 210

Val Ala Glu Trp Glu Glu Val Glu Pro Asp Ala Thr Arg Ala Val
                215                 220                 225

Lys Gln Lys Thr Gly Asp Phe Ser Ala Ser Leu Lys Leu Gln Glu
                230                 235                 240

Thr Leu Arg Gly Ile Gln Val Leu Gly Pro Thr Leu Ile Gln Thr
                245                 250                 255

Phe Gln Lys Met Thr Val Thr Leu Asn Phe Leu Gly Ser Pro Pro
                260                 265                 270

Leu Thr Val Cys Trp Arg Leu Lys Pro Glu Cys Leu Pro Leu Glu
                275                 280                 285

Glu Gly Glu Cys His Pro Val Ser Val Ala Ser Thr Ala Tyr Asn
                290                 295                 300

Leu Thr His Thr Phe Arg Asp Pro Gly Asp Tyr Cys Phe Ser Ile
                305                 310                 315

Arg Ala Glu Asn Ile Ile Ser Lys Thr His Gln Tyr His Lys Ile
                320                 325                 330

Gln Val Trp Pro Ser Arg Ile Gln Pro Ala Val Phe Ala Phe Pro
                335                 340                 345

Cys Ala Thr Leu Ile Thr Val Met Leu Ala Phe Ile Met Tyr Met
                350                 355                 360

Thr Leu Arg Asn Ala Thr Gln Gln Lys Asp Met Val Glu Asn Pro

-continued

```
                365                 370                 375

Glu Pro Pro Ser Gly Val Arg Cys Cys Cys Gln Met Cys Cys Gly
                380                 385                 390

Pro Phe Leu Leu Glu Thr Pro Ser Glu Tyr Leu Glu Ile Val Arg
                395                 400                 405

Glu Asn His Gly Leu Leu Pro Pro Leu Tyr Lys Ser Val Lys Thr
                410                 415                 420

Tyr Thr Val


<210> SEQ ID NO 51
<211> LENGTH: 963
<212> TYPE: DNA
<213> ORGANISM: Homo sapiens

<400> SEQUENCE: 51

ctatgaagaa gcttcctgga aaacaataag caaaggaaaa caaatgtgtc        50

ccatctcaca tggttctacc ctactaaaga caggaagatc ataaactgac       100

agatactgaa attgtaagag ttggaaacta cattttgcaa agtcattgaa       150

ctctgagctc agttgcagta ctcgggaagc catgcaggat gaagatggat       200

acatcacctt aaatattaaa actcggaaac cagctctcgt ctccgttggc       250

cctgcatcct cctcctggtg gcgtgtgatg gctttgattc tgctgatcct       300

gtgcgtgggg atggttgtcg ggctggtggc tctggggatt tggtctgtca       350

tgcagcgcaa ttacctacaa gatgagaatg aaaatcgcac aggaactctg       400

caacaattag caaagcgctt ctgtcaatat gtggtaaaac aatcagaact       450

aaagggcact ttcaaaggtc ataaatgcag cccctgtgac acaaactgga       500

gatattatgg agatagctgc tatgggttct tcaggcacaa cttaacatgg       550

gaagagagta agcagtactg cactgacatg aatgctactc tcctgaagat       600

tgacaaccgg aacattgtgg agtacatcaa agccaggact catttaattc       650

gttgggtcgg attatctcgc cagaagtcga atgaggtctg gaagtgggag       700

gatggctcgg ttatctcaga aaatatgttt gagtttttgg aagatggaaa       750

aggaaatatg aattgtgctt attttcataa tgggaaaatg caccctacct       800

tctgtgagaa caaacattat ttaatgtgtg agaggaaggc tggcatgacc       850

aaggtggacc aactacctta atgcaaagag gtggacagga taacacagat       900

aagggcttta ttgtacaata aaagatatgt atgaatgcat cagtagctga       950

aaaaaaaaaa  aaa                                              963


<210> SEQ ID NO 52
<211> LENGTH: 229
<212> TYPE: PRT
<213> ORGANISM: Homo sapiens

<400> SEQUENCE: 52

Met Gln Asp Glu Asp Gly Tyr Ile Thr Leu Asn Ile Lys Thr Arg
  1               5                  10                  15

Lys Pro Ala Leu Val Ser Val Gly Pro Ala Ser Ser Ser Trp Trp
                 20                  25                  30

Arg Val Met Ala Leu Ile Leu Leu Ile Leu Cys Val Gly Met Val
                 35                  40                  45

Val Gly Leu Val Ala Leu Gly Ile Trp Ser Val Met Gln Arg Asn
```

-continued

```
                50                  55                  60

Tyr Leu Gln Asp Glu Asn Glu Asn Arg Thr Gly Thr Leu Gln Gln
                65                  70                  75

Leu Ala Lys Arg Phe Cys Gln Tyr Val Val Lys Gln Ser Glu Leu
                80                  85                  90

Lys Gly Thr Phe Lys Gly His Lys Cys Ser Pro Cys Asp Thr Asn
                95                  100                 105

Trp Arg Tyr Tyr Gly Asp Ser Cys Tyr Gly Phe Phe Arg His Asn
                110                 115                 120

Leu Thr Trp Glu Glu Ser Lys Gln Tyr Cys Thr Asp Met Asn Ala
                125                 130                 135

Thr Leu Leu Lys Ile Asp Asn Arg Asn Ile Val Glu Tyr Ile Lys
                140                 145                 150

Ala Arg Thr His Leu Ile Arg Trp Val Gly Leu Ser Arg Gln Lys
                155                 160                 165

Ser Asn Glu Val Trp Lys Trp Glu Asp Gly Ser Val Ile Ser Glu
                170                 175                 180

Asn Met Phe Glu Phe Leu Glu Asp Gly Lys Gly Asn Met Asn Cys
                185                 190                 195

Ala Tyr Phe His Asn Gly Lys Met His Pro Thr Phe Cys Glu Asn
                200                 205                 210

Lys His Tyr Leu Met Cys Glu Arg Lys Ala Gly Met Thr Lys Val
                215                 220                 225

Asp Gln Leu Pro


<210> SEQ ID NO 53
<211> LENGTH: 3934
<212> TYPE: DNA
<213> ORGANISM: Homo sapiens

<400> SEQUENCE: 53

ccctgacctc cctgagccac actgagctgg aagccgcaga ggtcatcctg                50

gagcatgccc accgcgggga gcagacaacc tcccaggtaa gctgggagca               100

agacctgaag ctgtttcttc aggagcctgg tgtattttcc cccaccccac               150

ctcagcagtt tcagccagca gggactgatc aggtgtgtgt cctggagtgg               200

ggagcagaag gcgtggctgg caagagtggc ctggagaaag aggttcagcg               250

cttgaccagc cgagctgccc gtgactacaa gatccagaac catgggcatc               300

gggtgaggtg ggggggcaca ggtgtcatgt gcaccttctt gtctcagcaa               350

gaagagctga gagaggggat cttggagcca ttgagggtgt catggagcta               400

cagaggggag ggaaaggtat tttaaggtaa cagtgtggca caatagttaa               450

gagcacagtt tttggagcta gaccgacata ggttcaaatt ctcttctgtt               500

gcttcctagt tctgtagccc caggtaaggg agtgacttaa cctctctgga               550

cttcaatttc ctcatcacta aagtagggcc aataatagca cccacctcat               600

agggaagatt aaatgacata atgtatgtga tgcaactagc aaagtaccag               650

tcccatagta agtcatgccc cacagtattt ccacccaccc ctgttctctg               700

ccttcccaac caggtactgc aacgactgga gcagaggcgg cagcaggctt               750

cagagcggga ggctccaagc atagaacaga ggttacagga agtgcgagag               800

agcatccgcc gggcacaggt gagccaggtg aagggggctg cccggctggc               850
```

-continued

```
cctgctgcag ggggctggct tagatgtgga gcgctggctg aagccagcca      900
tgacccaggc ccaggatgag gtggagcagg agcggcggct cagtgaggct      950
cggctgtccc agagggacct ctctccaacc gctgaggatg ctgagctttc     1000
tgactttgag gaatgtgagg agacgggaga gctctttgag gagcctgccc     1050
cccaagccct ggccacgagg gccctcccct gccctgcaca cgtggtattt     1100
cgctatcagg cagggcgtga ggatgagctg acaatcacgg agggtgagtg     1150
gctggaggtc atagaggagg gagatgctga cgaatgggtc aaggctcgga     1200
accagcacgg cgaggtaggc tttgtccctg agcgatatct caacttcccg     1250
gacctctccc tcccagagag cagccaagac agtgacaatc cctgcggggc     1300
agagcccaca gcattcctgg cacaggccct gtacagctac accggacaga     1350
gtgcagagga gctgagcttc cctgaggggg cactcatccg tctgctgccc     1400
cgggcccaag atggagtaga tgacggcttc tggaggggag aatttggggg     1450
ccgtgttggg gtcttcccct ccctgctggt ggaagagctg cttggccccc     1500
cagggccacc tgaactctct gaccctgaac agatgctgcc gtccccttct     1550
cctcccagct tctccccacc tgcacctacc tctgtgttgg atgggccccc     1600
tgcacctgtc ctgcctgggg acaaagccct ggacttccct gggttcctgg     1650
acatgatggc acctcgactc aggccgatgc gtccaccacc tcccccgccg     1700
gctaaagccc cggatcctgg ccacccagat cccctcacct gaaggccagg     1750
gaagccttga cccccagtga tgctgctgtc cctatcttca agctgtcaga     1800
ccacaccatc aatgatccag agcaacacag ccaaaagctg gaatcgccct     1850
tatttccacc ctcacctcca agggtggaaa cttgcccctt cccatttcta     1900
gagctggaac ccactccttt ttttcccatt gttctatcat ctctaggacc     1950
ggaactacta ccttctcttc tgtcatgacc ctatctaggg tggtgaaatg     2000
cctgaaatct ctggggctgg aaaccatcca tcaaggtctc tagtagttct     2050
ggcccacctc tttccccacc ctggctccat gacccacccc actctggatg     2100
ccagggtcac tggggttggg ctggggagag gaacaggcct tgggaatcag     2150
gagctggagc caggatgcga agcagctgta atggtctgag cggatttatt     2200
gacaatgaat aaagggcacg aaggccaggc cagggcctgg gcctcttgtg     2250
ctaagagggc agggggccta cggtgctatt gctttagggg cccaccacgg     2300
gcaggggcct gctcccagct gccacgctct atcatatgga gcgaggtgtt     2350
ggggaaggcg gggcaggcag cctgttgcag gcaggggaag gagaagagac     2400
tgaggggctg tgacctctcc tgaggccccc agcctgagac tgtgcaactc     2450
caggtggaag tagagctggt ccctcagctg gggggcagtg ctgtccagtg     2500
gaggggaggg ctttcacgcc cacccacccc ctggccctgc cagctggtag     2550
tccatcagca caatgaagga gacttggaga agaggaagaa taacactgtt     2600
gcttcctgtt caagctgtgt ccagcttttc ccctggggct ccaggacctt     2650
ccctacctcc accaccaaac caagggattt atagcaaagg ctaagcctgc     2700
agtttactct gggggttcag ggagccgaaa ggcttaaata gtttaagtag     2750
gtgatgggaa gatgagatta cctcatttag ggctcaggca gactcacctc     2800
acatactccc tgctccctgt ggtagagaca cctgagagaa aggggagggg     2850
```

-continued

```
tcaacaatga gagaccagga gtaggtccta tcagtgcccc ccagagtaga           2900

gagcaataag agcccagccc agtgcagtcc cggctgtgtt ttcctacctg           2950

gtgatcagaa gtgtctggtt tgcttggctg cccatttgcc tcttgagtgg           3000

gcagccctgg gcttgggccc ctccctccgg ccctcagtgt tggctctgca           3050

gaagctctgg ggttcccttc aagtgcacga ggggttaggc tgctgtccct           3100

gagtcctcca ttctgtactg gggggctggc taggacctgg ggctgtggcc           3150

tctcaggggg cagcctctcc atggcaggca tccctgcctt gggctgccct           3200

cccccagacc cctgaccacc ccctgggtcc tgtcccccac cagagcccca           3250

gctcctgtct gtgggggagc catcacggtg ttcgtgcagt ccatagcgct           3300

tctcaatgtg tgtcacccgg aacctgggag gggagggaac actggggttt           3350

aggaccacaa ctcagaggct gcttggccct cccctctgac cagggacatc           3400

ctgagtttgg tggctacttc cctctggcct aaggtagggg aggccttctc           3450

agattgtggg gcacattgtg tagcctgact tctgctggag ctcccagtcc           3500

aggaggaaag agccaaggcc cacttttggg atcaggtgcc tgatcactgg           3550

gccccctacc tcagcccccc tttccctgga gcacctgccc cacctgccca           3600

cagagaacac agtggtctcc cctgtccggg ggcggctttt tccttccttg           3650

gagcgtccct gacggacaag tggaggcctc ttgctgcggc tgcaatggat           3700

gcaaggggct gcagagccca ggtgcactgt gtgatgatgg gagggggctc           3750

cgtcctgcag gctggaggtg gcatccacac tggacagcag gaggagggga           3800

gtgagggtaa catttccatt tcccttcatg ttttgtttct tacgttcttt           3850

cagcatgctc cttaaaaccc cagaagcccc aatttcccca agccccattt           3900

tttcttgtct ttatctaata aactcaatat  taag                           3934


<210> SEQ ID NO 54
<211> LENGTH: 370
<212> TYPE: PRT
<213> ORGANISM: Homo sapiens

<400> SEQUENCE: 54

Met Gln Leu Ala Lys Tyr Gln Ser His Ser Lys Ser Cys Pro Thr
  1               5                  10                  15

Val Phe Pro Pro Thr Pro Val Leu Cys Leu Pro Asn Gln Val Leu
                 20                  25                  30

Gln Arg Leu Glu Gln Arg Arg Gln Gln Ala Ser Glu Arg Glu Ala
                 35                  40                  45

Pro Ser Ile Glu Gln Arg Leu Gln Glu Val Arg Glu Ser Ile Arg
                 50                  55                  60

Arg Ala Gln Val Ser Gln Val Lys Gly Ala Ala Arg Leu Ala Leu
                 65                  70                  75

Leu Gln Gly Ala Gly Leu Asp Val Glu Arg Trp Leu Lys Pro Ala
                 80                  85                  90

Met Thr Gln Ala Gln Asp Glu Val Glu Gln Glu Arg Arg Leu Ser
                 95                 100                 105

Glu Ala Arg Leu Ser Gln Arg Asp Leu Ser Pro Thr Ala Glu Asp
                110                 115                 120

Ala Glu Leu Ser Asp Phe Glu Glu Cys Glu Glu Thr Gly Glu Leu
                125                 130                 135
```

-continued

```
Phe Glu Glu Pro Ala Pro Gln Ala Leu Ala Thr Arg Ala Leu Pro
                140                 145                 150

Cys Pro Ala His Val Val Phe Arg Tyr Gln Ala Gly Arg Glu Asp
                155                 160                 165

Glu Leu Thr Ile Thr Glu Gly Glu Trp Leu Glu Val Ile Glu Glu
                170                 175                 180

Gly Asp Ala Asp Glu Trp Val Lys Ala Arg Asn Gln His Gly Glu
                185                 190                 195

Val Gly Phe Val Pro Glu Arg Tyr Leu Asn Phe Pro Asp Leu Ser
                200                 205                 210

Leu Pro Glu Ser Ser Gln Asp Ser Asp Asn Pro Cys Gly Ala Glu
                215                 220                 225

Pro Thr Ala Phe Leu Ala Gln Ala Leu Tyr Ser Tyr Thr Gly Gln
                230                 235                 240

Ser Ala Glu Glu Leu Ser Phe Pro Glu Gly Ala Leu Ile Arg Leu
                245                 250                 255

Leu Pro Arg Ala Gln Asp Gly Val Asp Asp Gly Phe Trp Arg Gly
                260                 265                 270

Glu Phe Gly Gly Arg Val Gly Val Phe Pro Ser Leu Leu Val Glu
                275                 280                 285

Glu Leu Leu Gly Pro Pro Gly Pro Pro Glu Leu Ser Asp Pro Glu
                290                 295                 300

Gln Met Leu Pro Ser Pro Ser Pro Pro Ser Phe Ser Pro Pro Ala
                305                 310                 315

Pro Thr Ser Val Leu Asp Gly Pro Pro Ala Pro Val Leu Pro Gly
                320                 325                 330

Asp Lys Ala Leu Asp Phe Pro Gly Phe Leu Asp Met Met Ala Pro
                335                 340                 345

Arg Leu Arg Pro Met Arg Pro Pro Pro Pro Pro Pro Ala Lys Ala
                350                 355                 360

Pro Asp Pro Gly His Pro Asp Pro Leu Thr
                365                 370
```

<210> SEQ ID NO 55
<211> LENGTH: 1942
<212> TYPE: DNA
<213> ORGANISM: Homo sapiens

<400> SEQUENCE: 55

```
cccacgcgtc cgcccacgcg tccgggtgcc actcgcgcgc cggccgcgct        50

ccgggcttct cttttccctc cgacgcgcca cggctgccca gacattccgg       100

ctgccgggtc tggagagctc cccgaacccc tccgcggaga ggagcgaggc       150

ggcgccaggg tggcccccgg ggcgcgcttg gtctcggaga agcggggacg       200

aggccggagg atgagcgact gagggcgacg cgggcactga cgcgagttgg       250

ggccgcgact accggcagct gacagcgcga tgagcgactc cccagagacg       300

ccctagcccg gtgtgcgcgc caggcggagc gcgcaggtgg ggctgggctg       350

ttagtggtcc gccccacgcg ggtcgccggc cggcccagga tgggcgctgg       400

caacccgggc ccgcgcccgc cgctgctacc cctgcgcccg ctgcgagccc       450

ggcgtccggc ccgcgccctg cgctcatgga cggcggctcc cggctggcgg       500

cggcgcgccc ccgggctgtg aatgcgactc gcccctcggc cgcgctcccc       550
```

-continued

```
gcccgcccgc ccgccgggac gtggtagggg atgcccagct ccactgcgat          600

ggcagttggc gcgctctcca gttccctcct ggtcacctgc tgcctgatgg          650

tggctctgtg cagtccgagc atcccgctgg agaagctggc ccaggcacca          700

gagcagccgg gccaggagaa gcgtgagcac gccactcggg acggcccggg          750

gcgggtgaac gagctcgggc gcccggcgag ggacgagggc ggcagcggcc          800

gggactggaa gagcaagagc ggccgtgggc tcgccggccg tgagccgtgg          850

agcaagctga agcaggcctg ggtctcccag ggcgggggcg ccaaggccgg          900

ggatctgcag gtccggcccc gcggggacac cccgcaggcg gaagccctgg          950

ccgcagccgc ccaggacgcg attggcccgg aactcgcgcc cacgcccgag         1000

ccacccgagg agtacgtgta cccggactac cgtggcaagg gctgcgtgga         1050

cgagagcggc ttcgtgtacg cgatcgggga gaagttcgcg ccgggcccct         1100

cggcctgccc gtgcctgtgc accgaggagg ggccgctgtg cgcgcagccc         1150

gagtgcccga ggctgcaccc gcgctgcatc cacgtcgaca cgagccagtg         1200

ctgcccgcag tgcaaggaga ggaagaacta ctgcgagttc cggggcaaga         1250

cctatcagac tttggaggag ttcgtggtgt ctccatgcga gaggtgtcgc         1300

tgtgaagcca acggtgaggt gctatgcaca gtgtcagcgt gtccccagac         1350

ggagtgtgtg gaccctgtgt acgagcctga tcagtgctgt cccatctgca         1400

aaaatggtcc aaactgcttt gcagaaaccg cggtgatccc tgctggcaga         1450

gaagtgaaga ctgacgagtg caccatatgc cactgtactt atgaggaagg         1500

cacatggaga atcgagcggc aggccatgtg cacgagacat gaatgcaggc         1550

aaatgtagac gcttcccaga acacaaactc tgactttttc tagaacattt         1600

tactgatgtg aacattctag atgactctgg gaactatcag tcaaagaaga         1650

cttttgatga ggaataatgg aaaattgttg gtacttttcc ttttcttgat         1700

aacagttact acaacagaag gaaatggata tatttcaaaa catcaacaag         1750

aactttgggc ataaaatcct tctctaaata aatgtgctat tttcacagta         1800

agtacacaaa agtacactat tatatatcaa atgtatttct ataatccctc         1850

cattagagag cttatataag tgttttctat agatgcagat taaaaatgct         1900

gtgttgtcaa ccgtcaaaaa aaaaaaaaaa aaaaaaaaaa  aa                1942


<210> SEQ ID NO 56
<211> LENGTH: 325
<212> TYPE: PRT
<213> ORGANISM: Homo sapiens

<400> SEQUENCE: 56

Met Pro Ser Ser Thr Ala Met Ala Val Gly Ala Leu Ser Ser Ser
1               5                   10                  15

Leu Leu Val Thr Cys Cys Leu Met Val Ala Leu Cys Ser Pro Ser
                20                  25                  30

Ile Pro Leu Glu Lys Leu Ala Gln Ala Pro Glu Gln Pro Gly Gln
                35                  40                  45

Glu Lys Arg Glu His Ala Thr Arg Asp Gly Pro Gly Arg Val Asn
                50                  55                  60

Glu Leu Gly Arg Pro Ala Arg Asp Glu Gly Gly Ser Gly Arg Asp
                65                  70                  75
```

-continued

```
Trp Lys Ser Lys Ser Gly Arg Gly Leu Ala Gly Arg Glu Pro Trp
                80                  85                  90

Ser Lys Leu Lys Gln Ala Trp Val Ser Gln Gly Gly Gly Ala Lys
                95                  100                 105

Ala Gly Asp Leu Gln Val Arg Pro Arg Gly Asp Thr Pro Gln Ala
                110                 115                 120

Glu Ala Leu Ala Ala Ala Ala Gln Asp Ala Ile Gly Pro Glu Leu
                125                 130                 135

Ala Pro Thr Pro Glu Pro Pro Glu Glu Tyr Val Tyr Pro Asp Tyr
                140                 145                 150

Arg Gly Lys Gly Cys Val Asp Glu Ser Gly Phe Val Tyr Ala Ile
                155                 160                 165

Gly Glu Lys Phe Ala Pro Gly Pro Ser Ala Cys Pro Cys Leu Cys
                170                 175                 180

Thr Glu Glu Gly Pro Leu Cys Ala Gln Pro Glu Cys Pro Arg Leu
                185                 190                 195

His Pro Arg Cys Ile His Val Asp Thr Ser Gln Cys Cys Pro Gln
                200                 205                 210

Cys Lys Glu Arg Lys Asn Tyr Cys Glu Phe Arg Gly Lys Thr Tyr
                215                 220                 225

Gln Thr Leu Glu Glu Phe Val Val Ser Pro Cys Glu Arg Cys Arg
                230                 235                 240

Cys Glu Ala Asn Gly Glu Val Leu Cys Thr Val Ser Ala Cys Pro
                245                 250                 255

Gln Thr Glu Cys Val Asp Pro Val Tyr Glu Pro Asp Gln Cys Cys
                260                 265                 270

Pro Ile Cys Lys Asn Gly Pro Asn Cys Phe Ala Glu Thr Ala Val
                275                 280                 285

Ile Pro Ala Gly Arg Glu Val Lys Thr Asp Glu Cys Thr Ile Cys
                290                 295                 300

His Cys Thr Tyr Glu Glu Gly Thr Trp Arg Ile Glu Arg Gln Ala
                305                 310                 315

Met Cys Thr Arg His Glu Cys Arg Gln Met
                320                 325
```

<210> SEQ ID NO 57
<211> LENGTH: 2725
<212> TYPE: DNA
<213> ORGANISM: Homo sapiens

<400> SEQUENCE: 57

```
ggaggcggag gccgcggcga gccgggccga gcagtgaggg ccctagcggg          50

gcccgagcgg ggcccggggc ccctaagcca ttcctgaagt catgggctgg         100

ccaggacatt ggtgacccgc caatccggta tggacgactg gaagcccagc         150

cccctcatca agccctttgg ggctcggaag aagcggagct ggtaccttac         200

ctggaagtat aaactgacaa accagcgggc cctgcggaga ttctgtcaga         250

caggggccgt gcttttcctg ctggtgactg tcattgtcaa tatcaagttg         300

atcctggaca ctcggcgagc catcagtgaa gccaatgaag acccagagcc         350

agagcaagac tatgatgagg ccctaggccg cctggagccc ccacggcgca         400

gaggcagtgg tccccggcgg gtcctggacg tagaggtgta ttcaagtcgc         450

agcaaagtat atgtggcagt ggatggcacc acggtgctgg aggatgaggc         500
```

-continued

```
ccgggagcag ggccggggca tccatgtcat tgtcctcaac caggccacgg      550
gccacgtgat ggcaaaacgt gtgtttgaca cgtactcacc tcatgaggat      600
gaggccatgg tgctattcct caacatggta gcgcccggcc gagtgctcat      650
ctgcactgtc aaggatgagg gctccttcca cctcaaggac acagccaagg      700
ctctgctgag gagcctgggc agccaggctg gccctgccct gggctggagg      750
gacacatggg ccttcgtggg acgaaaagga ggtcctgtct tcggggagaa      800
acattctaag tcacctgccc tctcttcctg gggggaccca gtcctgctga      850
agacagatgt gccattgagc tcagcagaag aggcagagtg ccactgggca      900
gacacagagc tgaaccgtcg ccgccggcgc ttctgcagca aagttgaggg      950
ctatggaagt gtatgcagct gcaaggaccc cacacccatc gagttcagcc     1000
ctgacccact cccagacaac aaggtcctca atgtgcctgt ggctgtcatt     1050
gcagggaacc gacccaatta cctgtacagg atgctgcgct ctctgctttc     1100
agcccagggg gtgtctcctc agatgataac agttttcatt gacggctact     1150
atgaggaacc catggatgtg gtggcactgt ttggtctgag gggcatccag     1200
catactccca tcagcatcaa gaatgcccgc gtgtctcagc actacaaggc     1250
cagcctcact gccactttca acctgtttcc ggaggccaag tttgctgtgg     1300
ttctggaaga ggacctggac attgctgtgg attttttcag tttcctgagc     1350
caatccatcc acctactgga ggaggatgac agcctgtact gcatctctgc     1400
ctggaatgac caggggtatg aacacacggc tgaggaccca gcactactgt     1450
accgtgtgga gaccatgcct gggctgggct gggtgctcag gaggtccttg     1500
tacaaggagg agcttgagcc caagtggcct acaccggaaa agctctggga     1550
ttgggacatg tggatgcgga tgcctgaaca acgccggggc cgagagtgca     1600
tcatccctga cgtttcccga tcctaccact ttggcatcgt cggcctcaac     1650
atgaatggct actttcacga ggcctacttc aagaagcaca agttcaacac     1700
ggttccaggt gtccagctca ggaatgtgga cagtctgaag aaagaagctt     1750
atgaagtgga agttcacagg ctgctcagtg aggctgaggt tctggaccac     1800
agcaagaacc cttgtgaaga ctctttcctg ccagacacag agggccacac     1850
ctacgtggcc tttattcgaa tggagaaaga tgatgacttc accacctgga     1900
cccagcttgc caagtgcctc catatctggg acctggatgt gcgtggcaac     1950
catcggggcc tgtggagatt gtttcggaag aagaaccact tcctggtggt     2000
gggggtcccg gcttccccct actcagtgaa gaagccaccc tcagtcaccc     2050
caattttcct ggagccaccc ccaaaggagg agggagcccc aggagcccca     2100
gaacagacat gagacctcct ccaggaccct gcggggctgg gtactgtgta     2150
cccccaggct ggctagccct tccctccatc ctgtaggatt ttgtagatgc     2200
tggtaggggc tggggctacc ttgtttttaa catgagactt aattactaac     2250
tccaagggga gggttcccct gctccaacac cccgttcctg agttaaaagt     2300
ctatttattt acttccttgt tggagaaggg caggagagta cctgggaatc     2350
attacgatcc ctagcagctc atcctgccct ttgaataccc tcactttcca     2400
ggcctggctc agaatctaac ctatttattg actgtcctga gggccttgaa     2450
aacaggccga acctggaggg cctggatttc tttttgggct ggaatgctgc     2500
```

-continued

```
cctgagggtg gggctggctc ttactcagga aactgctgtg cccaacccat              2550

ggacaggccc agctggggcc cacatgctga cacagactca ctcagagacc              2600

cttagacact ggaccaggcc tcctctcagc cttctctttg tccagatttc              2650

caaagctgga taagttggtc attgattaaa aaaggagaag ccctctggga              2700

aaaaaaaaaa aaaaaaaaaa  aaaaa                                        2725


<210> SEQ ID NO 58
<211> LENGTH: 660
<212> TYPE: PRT
<213> ORGANISM: Homo sapiens

<400> SEQUENCE: 58

Met Asp Asp Trp Lys Pro Ser Pro Leu Ile Lys Pro Phe Gly Ala
  1               5                  10                  15

Arg Lys Lys Arg Ser Trp Tyr Leu Thr Trp Lys Tyr Lys Leu Thr
                 20                  25                  30

Asn Gln Arg Ala Leu Arg Arg Phe Cys Gln Thr Gly Ala Val Leu
                 35                  40                  45

Phe Leu Leu Val Thr Val Ile Val Asn Ile Lys Leu Ile Leu Asp
                 50                  55                  60

Thr Arg Arg Ala Ile Ser Glu Ala Asn Glu Asp Pro Glu Pro Glu
                 65                  70                  75

Gln Asp Tyr Asp Glu Ala Leu Gly Arg Leu Glu Pro Pro Arg Arg
                 80                  85                  90

Arg Gly Ser Gly Pro Arg Arg Val Leu Asp Val Glu Val Tyr Ser
                 95                 100                 105

Ser Arg Ser Lys Val Tyr Val Ala Val Asp Gly Thr Thr Val Leu
                110                 115                 120

Glu Asp Glu Ala Arg Glu Gln Gly Arg Gly Ile His Val Ile Val
                125                 130                 135

Leu Asn Gln Ala Thr Gly His Val Met Ala Lys Arg Val Phe Asp
                140                 145                 150

Thr Tyr Ser Pro His Glu Asp Glu Ala Met Val Leu Phe Leu Asn
                155                 160                 165

Met Val Ala Pro Gly Arg Val Leu Ile Cys Thr Val Lys Asp Glu
                170                 175                 180

Gly Ser Phe His Leu Lys Asp Thr Ala Lys Ala Leu Leu Arg Ser
                185                 190                 195

Leu Gly Ser Gln Ala Gly Pro Ala Leu Gly Trp Arg Asp Thr Trp
                200                 205                 210

Ala Phe Val Gly Arg Lys Gly Gly Pro Val Phe Gly Glu Lys His
                215                 220                 225

Ser Lys Ser Pro Ala Leu Ser Ser Trp Gly Asp Pro Val Leu Leu
                230                 235                 240

Lys Thr Asp Val Pro Leu Ser Ser Ala Glu Glu Ala Glu Cys His
                245                 250                 255

Trp Ala Asp Thr Glu Leu Asn Arg Arg Arg Arg Arg Phe Cys Ser
                260                 265                 270

Lys Val Glu Gly Tyr Gly Ser Val Cys Ser Cys Lys Asp Pro Thr
                275                 280                 285

Pro Ile Glu Phe Ser Pro Asp Pro Leu Pro Asp Asn Lys Val Leu
                290                 295                 300
```

-continued

```
Asn Val Pro Val Ala Val Ile Ala Gly Asn Arg Pro Asn Tyr Leu
                305                 310                 315

Tyr Arg Met Leu Arg Ser Leu Leu Ser Ala Gln Gly Val Ser Pro
                320                 325                 330

Gln Met Ile Thr Val Phe Ile Asp Gly Tyr Tyr Glu Glu Pro Met
                335                 340                 345

Asp Val Val Ala Leu Phe Gly Leu Arg Gly Ile Gln His Thr Pro
                350                 355                 360

Ile Ser Ile Lys Asn Ala Arg Val Ser Gln His Tyr Lys Ala Ser
                365                 370                 375

Leu Thr Ala Thr Phe Asn Leu Phe Pro Glu Ala Lys Phe Ala Val
                380                 385                 390

Val Leu Glu Glu Asp Leu Asp Ile Ala Val Asp Phe Phe Ser Phe
                395                 400                 405

Leu Ser Gln Ser Ile His Leu Leu Glu Glu Asp Asp Ser Leu Tyr
                410                 415                 420

Cys Ile Ser Ala Trp Asn Asp Gln Gly Tyr Glu His Thr Ala Glu
                425                 430                 435

Asp Pro Ala Leu Leu Tyr Arg Val Glu Thr Met Pro Gly Leu Gly
                440                 445                 450

Trp Val Leu Arg Arg Ser Leu Tyr Lys Glu Glu Leu Glu Pro Lys
                455                 460                 465

Trp Pro Thr Pro Glu Lys Leu Trp Asp Trp Asp Met Trp Met Arg
                470                 475                 480

Met Pro Glu Gln Arg Arg Gly Arg Glu Cys Ile Ile Pro Asp Val
                485                 490                 495

Ser Arg Ser Tyr His Phe Gly Ile Val Gly Leu Asn Met Asn Gly
                500                 505                 510

Tyr Phe His Glu Ala Tyr Phe Lys Lys His Lys Phe Asn Thr Val
                515                 520                 525

Pro Gly Val Gln Leu Arg Asn Val Asp Ser Leu Lys Lys Glu Ala
                530                 535                 540

Tyr Glu Val Glu Val His Arg Leu Leu Ser Glu Ala Glu Val Leu
                545                 550                 555

Asp His Ser Lys Asn Pro Cys Glu Asp Ser Phe Leu Pro Asp Thr
                560                 565                 570

Glu Gly His Thr Tyr Val Ala Phe Ile Arg Met Glu Lys Asp Asp
                575                 580                 585

Asp Phe Thr Thr Trp Thr Gln Leu Ala Lys Cys Leu His Ile Trp
                590                 595                 600

Asp Leu Asp Val Arg Gly Asn His Arg Gly Leu Trp Arg Leu Phe
                605                 610                 615

Arg Lys Lys Asn His Phe Leu Val Val Gly Val Pro Ala Ser Pro
                620                 625                 630

Tyr Ser Val Lys Lys Pro Pro Ser Val Thr Pro Ile Phe Leu Glu
                635                 640                 645

Pro Pro Pro Lys Glu Glu Gly Ala Pro Gly Ala Pro Glu Gln Thr
                650                 655                 660
```

```
<210> SEQ ID NO 59
<211> LENGTH: 2084
<212> TYPE: DNA
<213> ORGANISM: Homo sapiens

<400> SEQUENCE: 59
```

-continued

```
ggttcctggg cgctctgtta cacaagcaag atacagccag ccccacctaa        50
ttttgtttcc ctggcaccct cctgctcagt gcgacattgt cacacttaac       100
ccatctgttt tctctaatgc acgacagatt cctttcagac aggacaactg       150
tgatatttca gttcctgatt gtaaatacct cctaagcctg aagcttctgt       200
tactagccat tgtgagcttc agtttcttca tctgcaaaat gggcataata       250
caatctattc ttgccacatc aagggattgt tattccttta aaaaaaaacc       300
aataccaaag aagcctacaa tgttggcctt agccaaaatt ctgttgattt       350
caacgttgtt ttattcactt ctatcgggga gccatggaaa agaaaatcaa       400
gacataaaca caacacagaa cattgcagaa gtttttaaaa caatggaaaa       450
taaacctatt tctttggaaa gtgaagcaaa cttaaactca gataaagaaa       500
atataaccac ctcaaatctc aaggcgagtc attcccctcc tttgaatcta       550
cccaacaaca gccacggaat aacagatttc tccagtaact catcagcaga       600
gcattctttg ggcagtctaa aacccacatc taccatttcc acaagccctc       650
ccttgatcca tagctttgtt tctaaagtgc cttggaatgc acctatagca       700
gatgaagatc ttttgcccat ctcagcacat cccaatgcta cacctgctct       750
gtcttcagaa aacttcactt ggtctttggt caatgacacc gtgaaaactc       800
ctgataacag ttccattaca gttagcatcc tctcttcaga accaacttct       850
ccatctgtga ccccccttgat agtggaacca agtggatggc ttaccacaaa       900
cagtgatagc ttcactgggt ttacccctta tcaagaaaaa acaactctac       950
agcctacctt aaaattcacc aataattcaa aactctttcc aaatacgtca      1000
gatccccaaa aagaaaatag aaatacagga atagtattcg gggccatttt      1050
aggtgctatt ctgggtgtct cattgcttac tcttgtgggc tacttgttgt      1100
gtggaaaaag gaaaacggat tcattttccc atcggcgact ttatgacgac      1150
agaaatgaac cagttctgcg attagacaat gcaccggaac cttatgatgt      1200
gagttttggg aattctagct actacaatcc aactttgaat gattcagcca      1250
tgccagaaag tgaagaaaat gcacgtgatg gcattcctat ggatgacata      1300
cctccacttc gtacttctgt atagaactaa cagcaaaaag gcgttaaaca      1350
gcaagtgtca tctacatcct agccttttga caaattcatc tttcaaaagg      1400
ttacacaaaa ttactgtcac gtggattttg tcaaggagaa tcataaaagc      1450
aggagaccag tagcagaaat gtagacagga tgtatcatcc aaaggttttc      1500
tttcttacaa tttttggcca tcctgaggca tttactaagt agccttaatt      1550
tgtattttag tagtattttc ttagtagaaa atatttgtgg aatcagataa      1600
aactaaaaga tttcaccatt acagccctgc ctcataacta aataataaaa      1650
attattccac caaaaaattc taaaacaatg aagatgactc tttactgctc      1700
tgcctgaagc cctagtacca taattcaaga ttgcattttc ttaaatgaaa      1750
attgaaaggg tgctttttaa agaaaatttg acttaaagct aaaaagagga      1800
catagcccag agtttctgtt attgggaaat tgaggcaata gaaatgacag      1850
acctgtattc tagtacgtta taattttcta gatcagcaca cacatgatca      1900
gcccactgag ttatgaagct gacaatgact gcattcaacg gggccatggc      1950
```

-continued

```
aggaaagctg accctaccca ggaaagtaat agcttcttta aaagtcttca            2000

aaggttttgg gaattttaac ttgtcttaat atatcttagg cttcaattat            2050

ttgggtgcct taaaaactca atgagaatca  tggt                            2084


<210> SEQ ID NO 60
<211> LENGTH: 334
<212> TYPE: PRT
<213> ORGANISM: Homo sapiens

<400> SEQUENCE: 60

Met Leu Ala Leu Ala Lys Ile Leu Leu Ile Ser Thr Leu Phe Tyr
  1               5                  10                  15

Ser Leu Leu Ser Gly Ser His Gly Lys Glu Asn Gln Asp Ile Asn
                 20                  25                  30

Thr Thr Gln Asn Ile Ala Glu Val Phe Lys Thr Met Glu Asn Lys
                 35                  40                  45

Pro Ile Ser Leu Glu Ser Glu Ala Asn Leu Asn Ser Asp Lys Glu
                 50                  55                  60

Asn Ile Thr Thr Ser Asn Leu Lys Ala Ser His Ser Pro Pro Leu
                 65                  70                  75

Asn Leu Pro Asn Asn Ser His Gly Ile Thr Asp Phe Ser Ser Asn
                 80                  85                  90

Ser Ser Ala Glu His Ser Leu Gly Ser Leu Lys Pro Thr Ser Thr
                 95                 100                 105

Ile Ser Thr Ser Pro Pro Leu Ile His Ser Phe Val Ser Lys Val
                110                 115                 120

Pro Trp Asn Ala Pro Ile Ala Asp Glu Asp Leu Leu Pro Ile Ser
                125                 130                 135

Ala His Pro Asn Ala Thr Pro Ala Leu Ser Ser Glu Asn Phe Thr
                140                 145                 150

Trp Ser Leu Val Asn Asp Thr Val Lys Thr Pro Asp Asn Ser Ser
                155                 160                 165

Ile Thr Val Ser Ile Leu Ser Ser Glu Pro Thr Ser Pro Ser Val
                170                 175                 180

Thr Pro Leu Ile Val Glu Pro Ser Gly Trp Leu Thr Thr Asn Ser
                185                 190                 195

Asp Ser Phe Thr Gly Phe Thr Pro Tyr Gln Glu Lys Thr Thr Leu
                200                 205                 210

Gln Pro Thr Leu Lys Phe Thr Asn Asn Ser Lys Leu Phe Pro Asn
                215                 220                 225

Thr Ser Asp Pro Gln Lys Glu Asn Arg Asn Thr Gly Ile Val Phe
                230                 235                 240

Gly Ala Ile Leu Gly Ala Ile Leu Gly Val Ser Leu Leu Thr Leu
                245                 250                 255

Val Gly Tyr Leu Leu Cys Gly Lys Arg Lys Thr Asp Ser Phe Ser
                260                 265                 270

His Arg Arg Leu Tyr Asp Asp Arg Asn Glu Pro Val Leu Arg Leu
                275                 280                 285

Asp Asn Ala Pro Glu Pro Tyr Asp Val Ser Phe Gly Asn Ser Ser
                290                 295                 300

Tyr Tyr Asn Pro Thr Leu Asn Asp Ser Ala Met Pro Glu Ser Glu
                305                 310                 315

Glu Asn Ala Arg Asp Gly Ile Pro Met Asp Asp Ile Pro Pro Leu
                320                 325                 330
```

-continued

Arg Thr Ser Val

<210> SEQ ID NO 61
<211> LENGTH: 2397
<212> TYPE: DNA
<213> ORGANISM: Homo sapiens

<400> SEQUENCE: 61
agagaaagaa gcgtctccag ctgaagccaa tgcagccctc cggctctccg 50
cgaagaagtt ccctgccccg atgagccccc gccgtgcgtc cccgactatc 100
cccaggcggg cgtggggcac cgggcccagc gccgacgatc gctgccgttt 150
tgcccttggg agtaggatgt ggtgaaagga tggggcttct cccttacggg 200
gctcacaatg gccagagaag attccgtgaa gtgtctgcgc tgcctgctct 250
acgccctcaa tctgctcttt tggttaatgt ccatcagtgt gttggcagtt 300
tctgcttgga tgagggacta cctaaataat gttctcactt taactgcaga 350
aacgagggta gaggaagcag tcattttgac ttactttcct gtggttcatc 400
cggtcatgat tgctgtttgc tgtttcctta tcattgtggg gatgttagga 450
tattgtggaa cggtgaaaag aaatctgttg cttcttgcat ggtactttgg 500
aagtttgctt gtcattttct gtgtagaact ggcttgtggc gtttggacat 550
atgaacagga acttatggtt ccagtacaat ggtcagatat ggtcactttg 600
aaagccagga tgacaaatta tggattacct agatatcggt ggcttactca 650
tgcttggaat ttttttcaga gagagtttaa gtgctgtgga gtagtatatt 700
tcactgactg gttggaaatg acagagatgg actggccccc agattcctgc 750
tgtgttagag aattcccagg atgttccaaa caggcccacc aggaagatct 800
cagtgacctt tatcaagagg gttgtgggaa gaaaatgtat tcctttttga 850
gaggaaccaa acaactgcag gtgctgaggt ttctgggaat ctccattggg 900
gtgacacaaa tcctggccat gattctcacc attactctgc tctgggctct 950
gtattatgat agaagggagc ctgggacaga ccaaatgatg tccttgaaga 1000
atgacaactc tcagcacctg tcatgtccct cagtagaact gttgaaacca 1050
agcctgtcaa gaatctttga acacacatcc atggcaaaca gctttaatac 1100
acactttgag atggaggagt tataaaaaga aatgtcacag aagaaaacca 1150
caaacttgtt ttattggact tgtgaatttt tgagtacata ctatgtgttt 1200
cagaaatatg tagaaataaa aatgttgcca taaaataaca cctaagcata 1250
tactattcta tgctttaaaa tgaggatgga aaagtttcat gtcataagtc 1300
accacctgga caataattga tgcccttaaa atgctgaaga cagatgtcat 1350
acccactgtg tagcctgtgt atgactttta ctgaacacag ttatgttttg 1400
aggcagcatg gtttgattag catttccgca tccatgcaaa cgagtcacat 1450
atggtgggac tggagccata gtaaaggttg atttacttct accaactagt 1500
atataaagta ctaattaaat gctaacatag gaagttagaa aatactaata 1550
acttttatta ctcagcgatc tattcttctg atgctaaata aattatatat 1600
cagaaaactt tcaatattgg tgactaccta aatgtgattt ttgctggtta 1650
ctaaaatatt cttaccactt aaaagagcaa gctaacacat tgtcttaagc 1700

-continued

```
tgatcaggga ttttttgtat ataagtctgt gttaaatctg tataattcag          1750

tcgatttcag ttctgataat gttaagaata accattatga aaaggaaaat          1800

ttgtcctgta tagcatcatt atttttagcc tttcctgtta ataaagcttt          1850

actattctgt cctgggctta tattacacat ataactgtta tttaaatact          1900

taaccactaa ttttgaaaat taccagtgtg atacatagga atcattattc          1950

agaatgtagt ctggtcttta ggaagtatta ataagaaaat ttgcacataa          2000

cttagttgat tcagaaagga cttgtatgct gtttttctcc caaatgaaga          2050

ctctttttga cactaaacac tttttaaaaa gcttatcttt gccttctcca          2100

aacaagaagc aatagtctcc aagtcaatat aaattctaca gaaaatagtg          2150

ttctttttct ccagaaaaat gcttgtgaga atcattaaaa catgtgacaa          2200

tttagagatt ctttgtttta tttcactgat taatatactg tggcaaatta          2250

cacagattat taaatttttt tacaagagta tagtatattt atttgaaatg          2300

ggaaaagtgc attttactgt attttgtgta ttttgtttat ttctcagaat          2350

atggaaagaa aattaaaatg tgtcaataaa tattttctag  agagtaa            2397


<210> SEQ ID NO 62
<211> LENGTH: 305
<212> TYPE: PRT
<213> ORGANISM: Homo sapiens

<400> SEQUENCE: 62

Met Ala Arg Glu Asp Ser Val Lys Cys Leu Arg Cys Leu Leu Tyr
  1               5                  10                  15

Ala Leu Asn Leu Leu Phe Trp Leu Met Ser Ile Ser Val Leu Ala
                 20                  25                  30

Val Ser Ala Trp Met Arg Asp Tyr Leu Asn Asn Val Leu Thr Leu
                 35                  40                  45

Thr Ala Glu Thr Arg Val Glu Glu Ala Val Ile Leu Thr Tyr Phe
                 50                  55                  60

Pro Val Val His Pro Val Met Ile Ala Val Cys Cys Phe Leu Ile
                 65                  70                  75

Ile Val Gly Met Leu Gly Tyr Cys Gly Thr Val Lys Arg Asn Leu
                 80                  85                  90

Leu Leu Leu Ala Trp Tyr Phe Gly Ser Leu Leu Val Ile Phe Cys
                 95                 100                 105

Val Glu Leu Ala Cys Gly Val Trp Thr Tyr Glu Gln Glu Leu Met
                110                 115                 120

Val Pro Val Gln Trp Ser Asp Met Val Thr Leu Lys Ala Arg Met
                125                 130                 135

Thr Asn Tyr Gly Leu Pro Arg Tyr Arg Trp Leu Thr His Ala Trp
                140                 145                 150

Asn Phe Phe Gln Arg Glu Phe Lys Cys Cys Gly Val Val Tyr Phe
                155                 160                 165

Thr Asp Trp Leu Glu Met Thr Glu Met Asp Trp Pro Pro Asp Ser
                170                 175                 180

Cys Cys Val Arg Glu Phe Pro Gly Cys Ser Lys Gln Ala His Gln
                185                 190                 195

Glu Asp Leu Ser Asp Leu Tyr Gln Glu Gly Cys Gly Lys Lys Met
                200                 205                 210

Tyr Ser Phe Leu Arg Gly Thr Lys Gln Leu Gln Val Leu Arg Phe
```

-continued

```
                215                 220                 225

Leu Gly Ile Ser Ile Gly Val Thr Gln Ile Leu Ala Met Ile Leu
                230                 235                 240

Thr Ile Thr Leu Leu Trp Ala Leu Tyr Tyr Asp Arg Arg Glu Pro
                245                 250                 255

Gly Thr Asp Gln Met Met Ser Leu Lys Asn Asp Asn Ser Gln His
                260                 265                 270

Leu Ser Cys Pro Ser Val Glu Leu Leu Lys Pro Ser Leu Ser Arg
                275                 280                 285

Ile Phe Glu His Thr Ser Met Ala Asn Ser Phe Asn Thr His Phe
                290                 295                 300

Glu Met Glu Glu Leu
                305


<210> SEQ ID NO 63
<211> LENGTH: 2010
<212> TYPE: DNA
<213> ORGANISM: Homo sapiens

<400> SEQUENCE: 63

ggaaaaactg ttctcttctg tggcacagag aaccctgctt caaagcagaa          50

gtagcagttc cggagtccag ctggctaaaa ctcatcccag aggataatgg         100

caacccatgc cttagaaatc gctgggctgt ttcttggtgg tgttggaatg         150

gtgggcacag tggctgtcac tgtcatgcct cagtggagag tgtcggcctt         200

cattgaaaac aacatcgtgg tttttgaaaa cttctgggaa ggactgtgga         250

tgaattgcgt gaggcaggct aacatcagga tgcagtgcaa aatctatgat         300

tccctgctgg ctctttctcc ggacctacag gcagccagag gactgatgtg         350

tgctgcttcc gtgatgtcct tcttggcttt catgatggcc atccttggca         400

tgaaatgcac caggtgcacg gggacaatg agaaggtgaa ggctcacatt          450

ctgctgacgg ctggaatcat cttcatcatc acgggcatgg tggtgctcat         500

ccctgtgagc tgggttgcca atgccatcat cagagatttc tataactcaa         550

tagtgaatgt tgcccaaaaa cgtgagcttg gagaagctct ctacttagga         600

tggaccacgg cactggtgct gattgttgga ggagctctgt tctgctgcgt         650

tttttgttgc aacgaaaaga gcagtagcta cagatactcg ataccttccc         700

atcgcacaac ccaaaaaagt tatcacaccg gaaagaagtc accgagcgtc         750

tactccagaa gtcagtatgt gtagttgtgt atgttttttt aactttacta         800

taaagccatg caaatgacaa aaatctatat tactttctca aaatggaccc         850

caaagaaact ttgatttact gttcttaact gcctaatctt aattacagga         900

actgtgcatc agctatttat gattctataa gctatttcag cagaatgaga         950

tattaaaccc aatgctttga ttgttctaga aagtatagta atttgttttc        1000

taaggtggtt caagcatcta ctctttttat catttacttc aaaatgacat        1050

tgctaaagac tgcattattt tactactgta atttctccac gacatagcat        1100

tatgtacata gatgagtgta acatttatat ctcacataga gacatgctta        1150

tatggtttta tttaaaatga aatgccagtc cattacactg aataaataga        1200

actcaactat tgcttttcag ggaaatcatg gatagggttg aagaaggtta        1250

ctattaattg tttaaaaaca gcttagggat taatgtcctc catttataat        1300
```

-continued

```
gaagattaaa atgaaggctt taatcagcat tgtaaaggaa attgaatggc    1350

tttctgatat gctgtttttt agcctaggag ttagaaatcc taacttcttt    1400

atcctcttct cccagaggct tttttttct tgtgtattaa attaacattt     1450

ttaaaacgca gatattttgt caaggggctt tgcattcaaa ctgcttttcc    1500

agggctatac tcagaagaaa gataaaagtg tgatctaaga aaaagtgatg    1550

gttttaggaa agtgaaaata tttttgtttt tgtatttgaa gaagaatgat    1600

gcattttgac aagaaatcat atatgtatgg atatatttta ataagtattt    1650

gagtacagac tttgaggttt catcaatata aataaaagag cagaaaaata    1700

tgtcttggtt ttcatttgct taccaaaaaa acaacaacaa aaaaagttgt    1750

cctttgagaa cttcacctgc tcctatgtgg gtacctgagt caaaattgtc    1800

atttttgttc tgtgaaaaat aaatttcctt cttgtaccat ttctgtttag    1850

ttttactaaa atctgtaaat actgtatttt tctgtttatt ccaaatttga    1900

tgaaactgac aatccaattt gaaagtttgt gtcgacgtct gtctagctta    1950

aatgaatgtg ttctatttgc tttatacatt tatattaata aattgtacat    2000

ttttctaatt                                                2010
```

```
<210> SEQ ID NO 64
<211> LENGTH: 225
<212> TYPE: PRT
<213> ORGANISM: Homo sapiens

<400> SEQUENCE: 64

Met Ala Thr His Ala Leu Glu Ile Ala Gly Leu Phe Leu Gly Gly
  1               5                  10                  15

Val Gly Met Val Gly Thr Val Ala Val Thr Val Met Pro Gln Trp
                 20                  25                  30

Arg Val Ser Ala Phe Ile Glu Asn Asn Ile Val Val Phe Glu Asn
                 35                  40                  45

Phe Trp Glu Gly Leu Trp Met Asn Cys Val Arg Gln Ala Asn Ile
                 50                  55                  60

Arg Met Gln Cys Lys Ile Tyr Asp Ser Leu Leu Ala Leu Ser Pro
                 65                  70                  75

Asp Leu Gln Ala Ala Arg Gly Leu Met Cys Ala Ala Ser Val Met
                 80                  85                  90

Ser Phe Leu Ala Phe Met Met Ala Ile Leu Gly Met Lys Cys Thr
                 95                 100                 105

Arg Cys Thr Gly Asp Asn Glu Lys Val Lys Ala His Ile Leu Leu
                110                 115                 120

Thr Ala Gly Ile Ile Phe Ile Ile Thr Gly Met Val Val Leu Ile
                125                 130                 135

Pro Val Ser Trp Val Ala Asn Ala Ile Ile Arg Asp Phe Tyr Asn
                140                 145                 150

Ser Ile Val Asn Val Ala Gln Lys Arg Glu Leu Gly Glu Ala Leu
                155                 160                 165

Tyr Leu Gly Trp Thr Thr Ala Leu Val Leu Ile Val Gly Gly Ala
                170                 175                 180

Leu Phe Cys Cys Val Phe Cys Cys Asn Glu Lys Ser Ser Ser Tyr
                185                 190                 195

Arg Tyr Ser Ile Pro Ser His Arg Thr Thr Gln Lys Ser Tyr His
```

-continued

```
                200                 205                 210

Thr Gly Lys Lys Ser Pro Ser Val Tyr Ser Arg Ser Gln Tyr Val
                215                 220                 225


<210> SEQ ID NO 65
<211> LENGTH: 1114
<212> TYPE: DNA
<213> ORGANISM: Homo sapiens

<400> SEQUENCE: 65

cggacgcgtg ggcggacgcg tgggcggacg cgtgggtctc tgcggggaga              50

cgccagcctg cgtctgccat ggggctcggg ttgaggggct ggggacgtcc             100

tctgctgact gtggccaccg ccctgatgct gcccgtgaag ccccccgcag             150

gctcctgggg ggcccagatc atcgggggcc acgaggtgac cccccactcc             200

aggccctaca tggcatccgt gcgcttcggg ggccaacatc actgcggagg             250

cttcctgctg cgagcccgct gggtggtctc ggccgcccac tgcttcagcc             300

acagagacct ccgcactggc ctggtggtgc tgggcgccca cgtcctgagt             350

actgcggagc ccacccagca ggtgtttggc atcgatgctc tcaccacgca             400

ccccgactac caccccatga cccacgccaa cgacatctgc ctgctgcggc             450

tgaacggctc tgctgtcctg ggccctgcag tggggctgct gaggctgcca             500

gggagaaggg ccaggccccc cacagcgggg acacggtgcc gggtggctgg             550

ctggggcttc gtgtctgact ttgaggagct gccgcctgga ctgatggagg             600

ccaaggtccg agtgctggac ccggacgtct gcaacagctc ctggaagggc             650

cacctgacac ttaccatgct ctgcacccgc agtggggaca gccacagacg             700

gggcttctgc tcggccgact ccggagggcc cctggtgtgc aggaaccggg             750

ctcacggcct cgtttccttc tcgggcctct ggtgcggcga ccccaagacc             800

cccgacgtgt acacgcaggt gtccgccttt gtggcctgga tctgggacgt             850

ggttcggcgg agcagtcccc agcccggccc cctgcctggg accaccaggc             900

ccccaggaga agccgcctga gccacaacct tgcggcatgc aaatgagatg             950

gccgctccag gcctggaatg ttccgtggct gggccccacg ggaagcctga            1000

tgttcagggt tggggtggga cgggcagcgg tggggcacac ccattccaca            1050

tgcaaagggc agaagcaaac ccagtaaaat gttaactgac aaaaaaaaaa            1100

aaaaaaaaaa  gaaa                                                  1114


<210> SEQ ID NO 66
<211> LENGTH: 283
<212> TYPE: PRT
<213> ORGANISM: Homo sapiens

<400> SEQUENCE: 66

Met Gly Leu Gly Leu Arg Gly Trp Gly Arg Pro Leu Leu Thr Val
  1               5                  10                  15

Ala Thr Ala Leu Met Leu Pro Val Lys Pro Pro Ala Gly Ser Trp
                 20                  25                  30

Gly Ala Gln Ile Ile Gly Gly His Glu Val Thr Pro His Ser Arg
                 35                  40                  45

Pro Tyr Met Ala Ser Val Arg Phe Gly Gly Gln His His Cys Gly
                 50                  55                  60
```

-continued

```
Gly Phe Leu Leu Arg Ala Arg Trp Val Val Ser Ala Ala His Cys
                65                  70                  75

Phe Ser His Arg Asp Leu Arg Thr Gly Leu Val Val Leu Gly Ala
                80                  85                  90

His Val Leu Ser Thr Ala Glu Pro Thr Gln Gln Val Phe Gly Ile
                95                  100                 105

Asp Ala Leu Thr Thr His Pro Asp Tyr His Pro Met Thr His Ala
                110                 115                 120

Asn Asp Ile Cys Leu Leu Arg Leu Asn Gly Ser Ala Val Leu Gly
                125                 130                 135

Pro Ala Val Gly Leu Leu Arg Leu Pro Gly Arg Arg Ala Arg Pro
                140                 145                 150

Pro Thr Ala Gly Thr Arg Cys Arg Val Ala Gly Trp Gly Phe Val
                155                 160                 165

Ser Asp Phe Glu Glu Leu Pro Pro Gly Leu Met Glu Ala Lys Val
                170                 175                 180

Arg Val Leu Asp Pro Asp Val Cys Asn Ser Ser Trp Lys Gly His
                185                 190                 195

Leu Thr Leu Thr Met Leu Cys Thr Arg Ser Gly Asp Ser His Arg
                200                 205                 210

Arg Gly Phe Cys Ser Ala Asp Ser Gly Gly Pro Leu Val Cys Arg
                215                 220                 225

Asn Arg Ala His Gly Leu Val Ser Phe Ser Gly Leu Trp Cys Gly
                230                 235                 240

Asp Pro Lys Thr Pro Asp Val Tyr Thr Gln Val Ser Ala Phe Val
                245                 250                 255

Ala Trp Ile Trp Asp Val Val Arg Arg Ser Ser Pro Gln Pro Gly
                260                 265                 270

Pro Leu Pro Gly Thr Thr Arg Pro Pro Gly Glu Ala Ala
                275                 280
```

<210> SEQ ID NO 67
<211> LENGTH: 2272
<212> TYPE: DNA
<213> ORGANISM: Homo sapiens

<400> SEQUENCE: 67

```
ccgccgccgc agccgctacc gccgctgcag ccgctttccg cggcctgggc      50

ctctcgccgt cagcatgcca cacgccttca agcccgggga cttggtgttc     100

gctaagatga agggctaccc tcactggcct gccaggatcg acgacatcgc     150

ggatggcgcc gtgaagcccc cacccaacaa gtaccccatc tttttctttg     200

gcacacacga aacagccttc ctgggaccca aggacctgtt cccctacgac     250

aaatgtaaag acaagtacgg gaagcccaac aagaggaaag gcttcaatga     300

agggctgtgg gagatccaga acaacccccca cgccagctac agcgcccctc     350

cgccagtgag ctcctccgac agcgaggccc ccgaggccaa ccccgccgac     400

ggcagtgacg ctgacgagga cgatgaggac cggggggtca tggccgtcac     450

agcggtaacc gccacagctg ccagcgacag gatggagagc gactcagact     500

cagacaagag tagcgacaac agtggcctga agaggaagac gcctgcgcta     550

aagatgtcgg tctcgaaacg agcccgaaag gcctccagcg acctggatca     600

ggccagcgtg tccccatccg aagaggagaa ctcggaaagc tcatctgagt     650
```

-continued

```
cggagaagac cagcgaccag gacttcacac ctgagaagaa agcagcggtc        700

cgggcgccac ggaggggccc tctgggggga cggaaaaaaa agaaggcgcc        750

gtcagcctcc gactccgact ccaaggccga ttcggacggg gccaagcctg        800

agccggtggc catggcgcgg tcggcgtcct cctcctcctc ttcctcctcc        850

tcctccgact ccgatgtgtc tgtgaagaag cctccgaggg gcaggaagcc        900

agcggagaag cctctcccga agccgcgagg gcggaaaccg aagcctgaac        950

ggcctccgtc cagctccagc agtgacagtg acagcgacga ggtggaccgc       1000

atcagtgagt ggaagcggcg ggacgaggcg cggaggcgcg agctggaggc       1050

ccggcggcgg cgagagcagg aggaggagct gcggcgcctg cgggagcagg       1100

agaaggagga gaaggagcgg aggcgcgagc gggccgaccg cggggaggct       1150

gagcggggca gcggcggcag cagcggggac gagctcaggg aggacgatga       1200

gcccgtcaag aagcggggac gcaagggccg gggccggggt cccccgtcct       1250

cctctgactc cgagcccgag gccgagctgg agagagaggc caagaaatca       1300

gcgaagaagc cgcagtcctc aagcacagag cccgccagga aacctggcca       1350

gaaggagaag agagtgcggc ccgaggagaa gcaacaagcc aagcccgtga       1400

aggtggagcg gacccggaag cggtccgagg gcttctcgat ggacaggaag       1450

gtagagaaga agaaagagcc ctccgtggag gagaagctgc agaagctgca       1500

cagtgagatc aagtttgccc taaaggtcga cagcccggac gtgaagaggt       1550

gcctgaatgc cctagaggag ctgggaaccc tgcaggtgac ctctcagatc       1600

ctccagaaga acacagacgt ggtggccacc ttgaagaaga ttcgccgtta       1650

caaagcgaac aaggacgtaa tggagaaggc agcagaagtc tatacccggc       1700

tcaagtcgcg ggtcctcggc ccaaagatcg aggcggtgca gaaagtgaac       1750

aaggctggga tggagaagga gaaggccgag gagaagctgg ccggggagga       1800

gctggccggg gaggaggccc cccaggagaa ggcggaggac aagcccagca       1850

ccgatctctc agccccagtg aatggcgagg ccacatcaca gaagggggag       1900

agcgcagagg acaaggagca cgaggagggt cgggactcgg aggaggggcc       1950

aaggtgtggc tcctctgaag acctgcacga cagcgtacgg gagggtcccg       2000

acctggacag gcctgggagc gaccggcagg agcgcgagag ggcacggggg       2050

gactcggagg ccctggacga ggagagctga gccgcgggca gccaggccca       2100

gcccccgccc gagctcaggc tgcccctctc cttccccggc tcgcaggaga       2150

gcagagcaga gaactgtggg gaacgctgtg ctgtttgtat ttgttccctt       2200

gggttttttt ttcctgccta atttctgtga tttccaacca acatgaaatg       2250

actataaacg gtttttaat ga                                      2272
```

<210> SEQ ID NO 68
<211> LENGTH: 671
<212> TYPE: PRT
<213> ORGANISM: Homo sapiens

<400> SEQUENCE: 68

```
Met Pro His Ala Phe Lys Pro Gly Asp Leu Val Phe Ala Lys Met
  1               5                  10                  15

Lys Gly Tyr Pro His Trp Pro Ala Arg Ile Asp Asp Ile Ala Asp
                 20                  25                  30
```

-continued

```
Gly Ala Val Lys Pro Pro Pro Asn Lys Tyr Pro Ile Phe Phe Phe
                35                  40                  45

Gly Thr His Glu Thr Ala Phe Leu Gly Pro Lys Asp Leu Phe Pro
                50                  55                  60

Tyr Asp Lys Cys Lys Asp Lys Tyr Gly Lys Pro Asn Lys Arg Lys
                65                  70                  75

Gly Phe Asn Glu Gly Leu Trp Glu Ile Gln Asn Asn Pro His Ala
                80                  85                  90

Ser Tyr Ser Ala Pro Pro Pro Val Ser Ser Ser Asp Ser Glu Ala
                95                 100                 105

Pro Glu Ala Asn Pro Ala Asp Gly Ser Asp Ala Asp Glu Asp Asp
               110                 115                 120

Glu Asp Arg Gly Val Met Ala Val Thr Ala Val Thr Ala Thr Ala
               125                 130                 135

Ala Ser Asp Arg Met Glu Ser Asp Ser Asp Ser Asp Lys Ser Ser
               140                 145                 150

Asp Asn Ser Gly Leu Lys Arg Lys Thr Pro Ala Leu Lys Met Ser
               155                 160                 165

Val Ser Lys Arg Ala Arg Lys Ala Ser Ser Asp Leu Asp Gln Ala
               170                 175                 180

Ser Val Ser Pro Ser Glu Glu Glu Asn Ser Glu Ser Ser Ser Glu
               185                 190                 195

Ser Glu Lys Thr Ser Asp Gln Asp Phe Thr Pro Glu Lys Lys Ala
               200                 205                 210

Ala Val Arg Ala Pro Arg Arg Gly Pro Leu Gly Gly Arg Lys Lys
               215                 220                 225

Lys Lys Ala Pro Ser Ala Ser Asp Ser Asp Ser Lys Ala Asp Ser
               230                 235                 240

Asp Gly Ala Lys Pro Glu Pro Val Ala Met Ala Arg Ser Ala Ser
               245                 250                 255

Ser Ser Ser Ser Ser Ser Ser Ser Ser Asp Ser Asp Val Ser Val
               260                 265                 270

Lys Lys Pro Pro Arg Gly Arg Lys Pro Ala Glu Lys Pro Leu Pro
               275                 280                 285

Lys Pro Arg Gly Arg Lys Pro Lys Pro Glu Arg Pro Pro Ser Ser
               290                 295                 300

Ser Ser Ser Asp Ser Asp Ser Asp Glu Val Asp Arg Ile Ser Glu
               305                 310                 315

Trp Lys Arg Arg Asp Glu Ala Arg Arg Arg Glu Leu Glu Ala Arg
               320                 325                 330

Arg Arg Arg Glu Gln Glu Glu Glu Leu Arg Arg Leu Arg Glu Gln
               335                 340                 345

Glu Lys Glu Glu Lys Glu Arg Arg Arg Glu Arg Ala Asp Arg Gly
               350                 355                 360

Glu Ala Glu Arg Gly Ser Gly Gly Ser Ser Gly Asp Glu Leu Arg
               365                 370                 375

Glu Asp Asp Glu Pro Val Lys Lys Arg Gly Arg Lys Gly Arg Gly
               380                 385                 390

Arg Gly Pro Pro Ser Ser Ser Asp Ser Glu Pro Glu Ala Glu Leu
               395                 400                 405

Glu Arg Glu Ala Lys Lys Ser Ala Lys Lys Pro Gln Ser Ser Ser
               410                 415                 420
```

-continued

Thr Glu Pro Ala Arg Lys Pro Gly Gln Lys Glu Lys Arg Val Arg
425 430 435

Pro Glu Glu Lys Gln Gln Ala Lys Pro Val Lys Val Glu Arg Thr
440 445 450

Arg Lys Arg Ser Glu Gly Phe Ser Met Asp Arg Lys Val Glu Lys
455 460 465

Lys Lys Glu Pro Ser Val Glu Glu Lys Leu Gln Lys Leu His Ser
470 475 480

Glu Ile Lys Phe Ala Leu Lys Val Asp Ser Pro Asp Val Lys Arg
485 490 495

Cys Leu Asn Ala Leu Glu Glu Leu Gly Thr Leu Gln Val Thr Ser
500 505 510

Gln Ile Leu Gln Lys Asn Thr Asp Val Val Ala Thr Leu Lys Lys
515 520 525

Ile Arg Arg Tyr Lys Ala Asn Lys Asp Val Met Glu Lys Ala Ala
530 535 540

Glu Val Tyr Thr Arg Leu Lys Ser Arg Val Leu Gly Pro Lys Ile
545 550 555

Glu Ala Val Gln Lys Val Asn Lys Ala Gly Met Glu Lys Glu Lys
560 565 570

Ala Glu Glu Lys Leu Ala Gly Glu Glu Leu Ala Gly Glu Glu Ala
575 580 585

Pro Gln Glu Lys Ala Glu Asp Lys Pro Ser Thr Asp Leu Ser Ala
590 595 600

Pro Val Asn Gly Glu Ala Thr Ser Gln Lys Gly Glu Ser Ala Glu
605 610 615

Asp Lys Glu His Glu Glu Gly Arg Asp Ser Glu Glu Gly Pro Arg
620 625 630

Cys Gly Ser Ser Glu Asp Leu His Asp Ser Val Arg Glu Gly Pro
635 640 645

Asp Leu Asp Arg Pro Gly Ser Asp Arg Gln Glu Arg Glu Arg Ala
650 655 660

Arg Gly Asp Ser Glu Ala Leu Asp Glu Glu Ser
665 670

<210> SEQ ID NO 69
<211> LENGTH: 2340
<212> TYPE: DNA
<213> ORGANISM: Homo sapiens

<400> SEQUENCE: 69
gagcggagta aaatctccac aagctgggaa caaacctcgt cccaactccc 50
acccaccggc gtttctccag ctcgatctgg aggctgcttc gccagtgtgg 100
gacgcagctg acgcccgctt attagctctc gctgcgtcgc cccggctcag 150
aagctccgtg gcggcggcga ccgtgacgag aagcccacgg ccagctcagt 200
tctcttctac tttgggagag agagaaagtc agatgcccct tttaaactcc 250
ctcttcaaaa ctcatctcct gggtgactga gttaatagag tggatacaac 300
cttgctgaag atgaagaata tacaatattg aggatatttt tttctttttt 350
ttttcaagtc ttgatttgtg gcttacctca agttaccatt tttcagtcaa 400
gtctgtttgt ttgcttcttc agaaatgttt ttttacaatct caagaaaaaa 450 tatgtcccag aaattgagtt tactgttgct tgtatttgga ctcatttggg 500

-continued

```
gattgatgtt actgcactat acttttcaac aaccaagaca tcaaagcagt      550

gtcaagttac gtgagcaaat actagactta agcaaaagat atgttaaagc      600

tctagcagag gaaaataaga acacagtgga tgtcgagaac ggtgcttcta      650

tggcaggata tgcggatctg aaaagaacaa ttgctgtcct tctggatgac      700

attttgcaac gattggtgaa gctggagaac aaagttgact atattgttgt      750

gaatggctca gcagccaaca ccaccaatgg tactagtggg aatttggtgc      800

cagtaaccac aaataaaaga acgaatgtct cgggcagtat cagatagcag      850

ttgaaaatca ccttgtgctg ctccatccac tgtggattat atcctatggc      900

agaaaagctt tataattgct ggcttaggac agagcaatac tttacaataa      950

aagctctaca cattttcaag gagtatgctg gattcatgga actctaattc     1000

tgtacataaa aattttaaag ttatttgttt gctttcaggc aagtctgttc     1050

aatgctgtac tatgtcctta aagagaattt ggtaacttgg ttgatgtggt     1100

aagcagatag gtgagttttg tataaatctt ttgtgtttga gatcaagctg     1150

aaatgaaaac actgaaaaac atggattcat ttctataaca catttattta     1200

agtatataac acgtttttg gacaagtgaa gaatgtttaa tcattctgtc      1250

atttgttctc aatagatgta actgttagac tacggctatt tgaaaaaatg     1300

tgcttattgt actatatttt gttattccaa ttatgagcag agaaaggaaa     1350

tataatgttg aaaataatgt tttgaaatca tgacccaaag aatgtattga     1400

tttgcactat ccttcagaat aactgaaggt taattattgt atatttttaa     1450

aaattacact tataagagta taatcttgaa atgggtagca gccactgtcc     1500

attacctatc gtaaacattg gggcaattta ataacagcat taaaatagtt     1550

gtaaactcta atcttatact tattgaagaa taaaagatat ttttatgatg     1600

agagtaacaa taaagtattc atgatttttc acatacatga atgttcattt     1650

aaaagtttaa tcctttgagt gtctatgcta tcaggaaagc acattatttc     1700

catatttggg ttaattttgc ttttattata ttggtctagg aggaagggac     1750

tttggagaat ggaactcttg aggactttag ccaggtgtat ataataaagg     1800

tacttttgtg ctgcattaaa ttgcttggaa agtgttaaca ttatattata     1850

taagagtatc ctttatgaaa ttttgaattt gtataacaga tgcattagat     1900

attcatttta tataatggcc acttaaaata agaacattta aaatataaac     1950

tatgaagatt gactatcttt tcaggaaaaa agctgtatat agcacaggga     2000

accctaatct tgggtaattc tagtataaaa caaattatac ttttatttaa     2050

atttcccttg tagcaaatct aattgccaca tggtgcccta tatttcatag     2100

tatttattct ctatagtaac tgcttaagtg cagctagctt ctagatttag     2150

actatataga atttagatat tgtattgttc gtcattataa tatgctacca     2200

catgtagcaa taattacaat attttattaa aataaatatg tgaaatattg     2250

tttcatgaaa gacagatttc caaatctctc ttctcttctc tgtactgtct     2300

acctttatgt gaagaaatta attatatgcc attgccaggt                2340
```

<210> SEQ ID NO 70
<211> LENGTH: 140
<212> TYPE: PRT
<213> ORGANISM: Homo sapiens -continued

<400> SEQUENCE: 70

```
Met Phe Phe Thr Ile Ser Arg Lys Asn Met Ser Gln Lys Leu Ser
  1               5                  10                  15

Leu Leu Leu Leu Val Phe Gly Leu Ile Trp Gly Leu Met Leu Leu
                 20                  25                  30

His Tyr Thr Phe Gln Gln Pro Arg His Gln Ser Ser Val Lys Leu
                 35                  40                  45

Arg Glu Gln Ile Leu Asp Leu Ser Lys Arg Tyr Val Lys Ala Leu
                 50                  55                  60

Ala Glu Glu Asn Lys Asn Thr Val Asp Val Glu Asn Gly Ala Ser
                 65                  70                  75

Met Ala Gly Tyr Ala Asp Leu Lys Arg Thr Ile Ala Val Leu Leu
                 80                  85                  90

Asp Asp Ile Leu Gln Arg Leu Val Lys Leu Glu Asn Lys Val Asp
                 95                 100                 105

Tyr Ile Val Val Asn Gly Ser Ala Ala Asn Thr Thr Asn Gly Thr
                110                 115                 120

Ser Gly Asn Leu Val Pro Val Thr Thr Asn Lys Arg Thr Asn Val
                125                 130                 135

Ser Gly Ser Ile Arg
                140
```

<210> SEQ ID NO 71
<211> LENGTH: 2379
<212> TYPE: DNA
<213> ORGANISM: Homo sapiens

<400> SEQUENCE: 71

```
gctgagcgtg tgcgcggtac ggggctctcc tgccttctgg gctccaacgc              50
agctctgtgg ctgaactggg tgctcatcac gggaactgct gggctatgga             100
atacagatgt ggcagctcag gtagccccaa attgcctgga agaatacatc             150
atgtttttcg ataagaagaa attgtaggat ccagtttttt ttttaaccgc             200
cccctcccca ccccccaaaa aaactgtaaa gatgcaaaaa cgtaatatcc             250
atgaagatcc tattacctag gaagattttg atgttttgct gcgaatgcgg             300
tgttgggatt tatttgttct tggagtgttc tgcgtggctg gcaaagaata             350
atgttccaaa atcggtccat ctcccaaggg gtccaatttt tcttcctggg             400
tgtcagcgag ccctgactca ctacagtgca gctgacaggg gctgtcatgc             450
aactggcccc taagccaaag caaaagacct aaggacgacc tttgaacaat             500
acaaaggatg ggtttcaatg taattaggct actgagcgga tcagctgtag             550
cactggttat agcccccact gtcttactga caatgctttc ttctgccgaa             600
cgaggatgcc ctaagggctg taggtgtgaa ggcaaaatgg tatattgtga             650
atctcagaaa ttacaggaga taccctcaag tatatctgct ggttgcttag             700
gtttgtccct tcgctataac agccttcaaa aacttaagta taatcaattt             750
aaagggctca accagctcac ctggctatac cttgaccata accatatcag             800
caatattgac gaaaatgctt ttaatggaat acgcagactc aaagagctga             850
ttcttagttc caatagaatc tcctattttc ttaacaatac cttcagacct             900
gtgacaaatt tacggaactt ggatctgtcc tataatcagc tgcattctct             950
```

-continued

```
gggatctgaa cagtttcggg gcttgcggaa gctgctgagt ttacatttac            1000

ggtctaactc cctgagaacc atccctgtgc gaatattcca agactgccgc            1050

aacctggaac ttttggacct gggatataac cggatccgaa gtttagccag            1100

gaatgtcttt gctggcatga tcagactcaa agaacttcac ctggagcaca            1150

atcaattttc caagctcaac ctggcccttt ttccaaggtt ggtcagcctt            1200

cagaaccttt acttgcagtg gaataaaatc agtgtcatag gacagaccat            1250

gtcctggacc tggagctcct tacaaaggct tgatttatca ggcaatgaga            1300

tcgaagcttt cagtggaccc agtgttttcc agtgtgtccc gaatctgcag            1350

cgcctcaacc tggattccaa caagctcaca tttattggtc aagagatttt            1400

ggattcttgg atatccctca atgacatcag tcttgctggg aatatatggg            1450

aatgcagcag aaatatttgc tcccttgtaa actggctgaa aagttttaaa            1500

ggtctaaggg agaatacaat tatctgtgcc agtcccaaag agctgcaagg            1550

agtaaatgtg atcgatgcag tgaagaacta cagcatctgt ggcaaaagta            1600

ctacagagag gtttgatctg gccagggctc tcccaaagcc gacgtttaag            1650

cccaagctcc ccaggccgaa gcatgagagc aaaccccctt tgcccccgac            1700

ggtgggagcc acagagcccg gcccagagac cgatgctgac gccgagcaca            1750

tctctttcca taaaatcatc gcgggcagcg tggcgctttt cctgtccgtg            1800

ctcgtcatcc tgctggttat ctacgtgtca tggaagcggt accctgcgag            1850

catgaagcag ctgcagcagc gctccctcat gcgaaggcac aggaaaaaga            1900

aaagacagtc cctaaagcaa atgactccca gcacccagga attttatgta            1950

gattataaac ccaccaacac ggagaccagc gagatgctgc tgaatgggac            2000

gggaccctgc acctataaca aatcgggctc cagggagtgt gaggtatgaa            2050

ccattgtgat aaaaagagct cttaaaagct gggaaataag tggtgcttta            2100

ttgaactctg gtgactatca agggaacgcg atgccccccc tccccttccc            2150

tctccctctc actttggtgg caagatcctt ccttgtccgt tttagtgcat            2200

tcataatact ggtcattttc ctctcataca taatcaaccc attgaaattt            2250

aaataccaca atcaatgtga agcttgaact ccggtttaat ataataccta            2300

ttgtataaga ccctttactg attccattaa tgtcgcattt gttttaagat            2350

aaaacttctt tcataggtaa  aaaaaaaaa                                   2379
```

```
<210> SEQ ID NO 72
<211> LENGTH: 513
<212> TYPE: PRT
<213> ORGANISM: Homo sapiens

<400> SEQUENCE: 72

Met Gly Phe Asn Val Ile Arg Leu Leu Ser Gly Ser Ala Val Ala
  1               5                  10                  15

Leu Val Ile Ala Pro Thr Val Leu Leu Thr Met Leu Ser Ser Ala
                 20                  25                  30

Glu Arg Gly Cys Pro Lys Gly Cys Arg Cys Glu Gly Lys Met Val
                 35                  40                  45

Tyr Cys Glu Ser Gln Lys Leu Gln Glu Ile Pro Ser Ser Ile Ser
                 50                  55                  60

Ala Gly Cys Leu Gly Leu Ser Leu Arg Tyr Asn Ser Leu Gln Lys
```

-continued

```
                65                  70                  75

Leu Lys Tyr Asn Gln Phe Lys Gly Leu Asn Gln Leu Thr Trp Leu
                80                  85                  90

Tyr Leu Asp His Asn His Ile Ser Asn Ile Asp Glu Asn Ala Phe
                95                  100                 105

Asn Gly Ile Arg Arg Leu Lys Glu Leu Ile Leu Ser Ser Asn Arg
                110                 115                 120

Ile Ser Tyr Phe Leu Asn Asn Thr Phe Arg Pro Val Thr Asn Leu
                125                 130                 135

Arg Asn Leu Asp Leu Ser Tyr Asn Gln Leu His Ser Leu Gly Ser
                140                 145                 150

Glu Gln Phe Arg Gly Leu Arg Lys Leu Leu Ser Leu His Leu Arg
                155                 160                 165

Ser Asn Ser Leu Arg Thr Ile Pro Val Arg Ile Phe Gln Asp Cys
                170                 175                 180

Arg Asn Leu Glu Leu Leu Asp Leu Gly Tyr Asn Arg Ile Arg Ser
                185                 190                 195

Leu Ala Arg Asn Val Phe Ala Gly Met Ile Arg Leu Lys Glu Leu
                200                 205                 210

His Leu Glu His Asn Gln Phe Ser Lys Leu Asn Leu Ala Leu Phe
                215                 220                 225

Pro Arg Leu Val Ser Leu Gln Asn Leu Tyr Leu Gln Trp Asn Lys
                230                 235                 240

Ile Ser Val Ile Gly Gln Thr Met Ser Trp Thr Trp Ser Ser Leu
                245                 250                 255

Gln Arg Leu Asp Leu Ser Gly Asn Glu Ile Glu Ala Phe Ser Gly
                260                 265                 270

Pro Ser Val Phe Gln Cys Val Pro Asn Leu Gln Arg Leu Asn Leu
                275                 280                 285

Asp Ser Asn Lys Leu Thr Phe Ile Gly Gln Glu Ile Leu Asp Ser
                290                 295                 300

Trp Ile Ser Leu Asn Asp Ile Ser Leu Ala Gly Asn Ile Trp Glu
                305                 310                 315

Cys Ser Arg Asn Ile Cys Ser Leu Val Asn Trp Leu Lys Ser Phe
                320                 325                 330

Lys Gly Leu Arg Glu Asn Thr Ile Ile Cys Ala Ser Pro Lys Glu
                335                 340                 345

Leu Gln Gly Val Asn Val Ile Asp Ala Val Lys Asn Tyr Ser Ile
                350                 355                 360

Cys Gly Lys Ser Thr Thr Glu Arg Phe Asp Leu Ala Arg Ala Leu
                365                 370                 375

Pro Lys Pro Thr Phe Lys Pro Lys Leu Pro Arg Pro Lys His Glu
                380                 385                 390

Ser Lys Pro Pro Leu Pro Pro Thr Val Gly Ala Thr Glu Pro Gly
                395                 400                 405

Pro Glu Thr Asp Ala Asp Ala Glu His Ile Ser Phe His Lys Ile
                410                 415                 420

Ile Ala Gly Ser Val Ala Leu Phe Leu Ser Val Leu Val Ile Leu
                425                 430                 435

Leu Val Ile Tyr Val Ser Trp Lys Arg Tyr Pro Ala Ser Met Lys
                440                 445                 450

Gln Leu Gln Gln Arg Ser Leu Met Arg Arg His Arg Lys Lys Lys
                455                 460                 465
```

-continued

```
Arg Gln Ser Leu Lys Gln Met Thr Pro Ser Thr Gln Glu Phe Tyr
                470                 475                 480

Val Asp Tyr Lys Pro Thr Asn Thr Glu Thr Ser Glu Met Leu Leu
                485                 490                 495

Asn Gly Thr Gly Pro Cys Thr Tyr Asn Lys Ser Gly Ser Arg Glu
                500                 505                 510

Cys Glu Val


<210> SEQ ID NO 73
<211> LENGTH: 2339
<212> TYPE: DNA
<213> ORGANISM: Homo sapiens

<400> SEQUENCE: 73

ccaaggccag agctgtggac accttatccc actcatcctc atcctcttcc       50

tctgataaag cccctaccag tgctgataaa gtctttctcg tgagagccta      100

gaggccttaa aaaaaaaagt gcttgaaaga gaaggggaca aaggaacacc      150

agtattaaga ggattttcca gtgtttctgg cagttggtcc agaaggatgc      200

ctccattcct gcttctcacc tgcctcttca tcacaggcac ctccgtgtca      250

cccgtggccc tagatccttg ttctgcttac atcagcctga atgagccctg      300

gaggaacact gaccaccagt tggatgagtc tcaaggtcct cctctatgtg      350

acaaccatgt gaatggggag tggtaccact tcacgggcat ggcgggagat      400

gccatgccta ccttctgcat accagaaaac cactgtggaa cccacgcacc      450

tgtctggctc aatggcagcc acccccctaga aggcgacggc attgtgcaac     500

gccaggcttg tgccagcttc aatgggaact gctgtctctg gaacaccacg      550

gtggaagtca aggcttgccc tggaggctac tatgtgtatc gtctgaccaa      600

gcccagcgtc tgcttccacg tctactgtgg tcatttttat gacatctgcg      650

acgaggactg ccatggcagc tgctcagata ccagcgagtg cacatgcgct      700

ccaggaactg tgctaggccc tgacaggcag acatgctttg atgaaaatga      750

atgtgagcaa aacaacggtg gctgcagtga gatctgtgtg aacctcaaaa      800

actcctaccg ctgtgagtgt ggggttggcc gtgtgctaag aagtgatggc      850

aagacttgtg aagacgttga aggatgccac aataacaatg gtggctgcag      900

ccactcttgc cttggatctg agaaaggcta ccagtgtgaa tgtccccggg      950

gcctggtgct gtctgaggat aaccacactt gccaagtccc tgtgttgtgc     1000

aaatcaaatg ccattgaagt gaacatcccc agggagctgg ttggtggcct     1050

ggagctcttc ctgaccaaca cctcctgccg aggagtgtcc aacggcaccc     1100

atgtcaacat cctcttctct ctcaagacat gtggtacagt ggtcgatgtg     1150

gtgaatgaca agattgtggc cagcaacctc gtgacaggtc tacccaagca     1200

gaccccgggg agcagcgggg acttcatcat ccgaaccagc aagctgctga     1250

tcccggtgac ctgcgagttt ccacgcctgt acaccatttc tgaaggatac     1300

gttcccaacc ttcgaaactc cccactggaa atcatgagcc gaaatcatgg     1350

gatcttccca ttcactctgg agatcttcaa ggacaatgag tttgaagagc     1400

cttaccggga agctctgccc accctcaagc ttcgtgactc cctctacttt     1450

ggcattgagc ccgtggtgca cgtgagcggc ttggaaagct tggtggagag     1500
```

-continued

```
ctgctttgcc acccccacct ccaagatcga cgaggtcctg aaatactacc          1550

tcatccggga tggctgtgtt tcagatgact cggtaaagca gtacacatcc          1600

cgggatcacc tagcaaagca cttccaggtc cctgtcttca agtttgtggg          1650

caaagaccac aaggaagtgt ttctgcactg ccgggttctt gtctgtggag          1700

tgttggacga gcgttcccgc tgtgcccagg gttgccaccg gcgaatgcgt          1750

cgtggggcag gaggagagga ctcagccggt ctacagggcc agacgctaac          1800

aggcggcccg atccgcatcg actgggagga ctagttcgta gccatacctc          1850

gagtccctgc attggacggc tctgctcttt ggagcttctc cccccaccgc          1900

cctctaagaa catctgccaa cagctgggtt cagacttcac actgtgagtt          1950

cagactccca gcaccaactc actctgattc tggtccattc agtgggcaca          2000

ggtcacagca ctgctgaaca atgtggcctg ggtggggttt catctttcta          2050

gggttgaaaa ctaaactgtc cacccagaaa gacactcacc ccatttccct          2100

catttctttc ctacacttaa atacctcgtg tatggtgcaa tcagaccaca          2150

aaatcagaag ctgggtataa tatttcaagt tacaaaccct agaaaaatta          2200

aacagttact gaaattatga cttaaatacc caatgactcc ttaaatatgt          2250

aaattatagt tataccttga aatttcaatt caaatgcaga ctaattatag          2300

ggaatttgga agtgtatcaa taaaacagta  tataatttt                     2339


<210> SEQ ID NO 74
<211> LENGTH: 545
<212> TYPE: PRT
<213> ORGANISM: Homo sapiens

<400> SEQUENCE: 74

Met Pro Pro Phe Leu Leu Leu Thr Cys Leu Phe Ile Thr Gly Thr
  1               5                  10                  15

Ser Val Ser Pro Val Ala Leu Asp Pro Cys Ser Ala Tyr Ile Ser
                 20                  25                  30

Leu Asn Glu Pro Trp Arg Asn Thr Asp His Gln Leu Asp Glu Ser
                 35                  40                  45

Gln Gly Pro Pro Leu Cys Asp Asn His Val Asn Gly Glu Trp Tyr
                 50                  55                  60

His Phe Thr Gly Met Ala Gly Asp Ala Met Pro Thr Phe Cys Ile
                 65                  70                  75

Pro Glu Asn His Cys Gly Thr His Ala Pro Val Trp Leu Asn Gly
                 80                  85                  90

Ser His Pro Leu Glu Gly Asp Gly Ile Val Gln Arg Gln Ala Cys
                 95                 100                 105

Ala Ser Phe Asn Gly Asn Cys Cys Leu Trp Asn Thr Thr Val Glu
                110                 115                 120

Val Lys Ala Cys Pro Gly Gly Tyr Tyr Val Tyr Arg Leu Thr Lys
                125                 130                 135

Pro Ser Val Cys Phe His Val Tyr Cys Gly His Phe Tyr Asp Ile
                140                 145                 150

Cys Asp Glu Asp Cys His Gly Ser Cys Ser Asp Thr Ser Glu Cys
                155                 160                 165

Thr Cys Ala Pro Gly Thr Val Leu Gly Pro Asp Arg Gln Thr Cys
                170                 175                 180
```

-continued

```
Phe Asp Glu Asn Glu Cys Glu Gln Asn Asn Gly Gly Cys Ser Glu
                185                 190                 195

Ile Cys Val Asn Leu Lys Asn Ser Tyr Arg Cys Glu Cys Gly Val
                200                 205                 210

Gly Arg Val Leu Arg Ser Asp Gly Lys Thr Cys Glu Asp Val Glu
                215                 220                 225

Gly Cys His Asn Asn Asn Gly Gly Cys Ser His Ser Cys Leu Gly
                230                 235                 240

Ser Glu Lys Gly Tyr Gln Cys Glu Cys Pro Arg Gly Leu Val Leu
                245                 250                 255

Ser Glu Asp Asn His Thr Cys Gln Val Pro Val Leu Cys Lys Ser
                260                 265                 270

Asn Ala Ile Glu Val Asn Ile Pro Arg Glu Leu Val Gly Gly Leu
                275                 280                 285

Glu Leu Phe Leu Thr Asn Thr Ser Cys Arg Gly Val Ser Asn Gly
                290                 295                 300

Thr His Val Asn Ile Leu Phe Ser Leu Lys Thr Cys Gly Thr Val
                305                 310                 315

Val Asp Val Val Asn Asp Lys Ile Val Ala Ser Asn Leu Val Thr
                320                 325                 330

Gly Leu Pro Lys Gln Thr Pro Gly Ser Ser Gly Asp Phe Ile Ile
                335                 340                 345

Arg Thr Ser Lys Leu Leu Ile Pro Val Thr Cys Glu Phe Pro Arg
                350                 355                 360

Leu Tyr Thr Ile Ser Glu Gly Tyr Val Pro Asn Leu Arg Asn Ser
                365                 370                 375

Pro Leu Glu Ile Met Ser Arg Asn His Gly Ile Phe Pro Phe Thr
                380                 385                 390

Leu Glu Ile Phe Lys Asp Asn Glu Phe Glu Glu Pro Tyr Arg Glu
                395                 400                 405

Ala Leu Pro Thr Leu Lys Leu Arg Asp Ser Leu Tyr Phe Gly Ile
                410                 415                 420

Glu Pro Val Val His Val Ser Gly Leu Glu Ser Leu Val Glu Ser
                425                 430                 435

Cys Phe Ala Thr Pro Thr Ser Lys Ile Asp Glu Val Leu Lys Tyr
                440                 445                 450

Tyr Leu Ile Arg Asp Gly Cys Val Ser Asp Asp Ser Val Lys Gln
                455                 460                 465

Tyr Thr Ser Arg Asp His Leu Ala Lys His Phe Gln Val Pro Val
                470                 475                 480

Phe Lys Phe Val Gly Lys Asp His Lys Glu Val Phe Leu His Cys
                485                 490                 495

Arg Val Leu Val Cys Gly Val Leu Asp Glu Arg Ser Arg Cys Ala
                500                 505                 510

Gln Gly Cys His Arg Arg Met Arg Arg Gly Ala Gly Gly Glu Asp
                515                 520                 525

Ser Ala Gly Leu Gln Gly Gln Thr Leu Thr Gly Gly Pro Ile Arg
                530                 535                 540

Ile Asp Trp Glu Asp
                545
```

<210> SEQ ID NO 75
<211> LENGTH: 2524
<212> TYPE: DNA

-continued

<213> ORGANISM: Homo sapiens

<400> SEQUENCE: 75
cgccaagcat gcagtaaagg ctgaaaatct gggtcacagc tgaggaagac 50
ctcagacatg gagtccagga tgtggcctgc gctgctgctg tcccacctcc 100
tccctctctg gccactgctg ttgctgcccc tcccaccgcc tgctcagggc 150
tcttcatcct cccctcgaac cccaccagcc ccagcccgcc ccccgtgtgc 200
caggggaggc ccctcggccc cacgtcatgt gtgcgtgtgg gagcgagcac 250
ctccaccaag ccgatctcct cgggtcccaa gatcacgtcg gcaagtcctg 300
cctggcactg cacccccagc caccccatca ggctttgagg aggggccgcc 350
ctcatcccaa tacccctggg ctatcgtgtg gggtcccacc gtgtctcgag 400
aggatggagg ggaccccaac tctgccaatc ccggatttct ggactatggt 450
tttgcagccc ctcatgggct cgcaacccca caccccaact cagactccat 500
gcgaggtgat ggagatgggc ttatccttgg agaggcacct gccaccctgc 550
ggccattcct gttcgggggc cgtggggaag gtgtggaccc ccagctctat 600
gtcacaatta ccatctccat catcattgtt ctcgtggcca ctggcatcat 650
cttcaagttc tgctgggacc gcagccagaa gcgacgcaga ccctcagggc 700
agcaaggtgc cctgaggcag gaggagagcc agcagccact gacagacctg 750
tccccggctg gagtcactgt gctgggggcc ttcggggact cacctacccc 800
cacccctgac catgaggagc cccgaggggg accccggcct gggatgcccc 850
accccaaggg ggctccagcc ttccagttga accggtgagg gcaggggcaa 900
tgggatggga gggcaaagag ggaaggcaac ttaggtcttc agagctgggg 950
tgggggtgcc ctctggatgg gtagtgagga ggcaggcgtg gcctcccaca 1000
gcccctggcc ctcccaaggg ggctggacca gctcctctct gggaggcacc 1050
cttccttctc ccagtctctc aggatctgtg tcctattctc tgctgcccat 1100
aactccaact ctgccctctt tggtttttc tcatgccacc ttgtctaaga 1150
caactctgcc ctcttaacct tgattccccc tctttgtctt gaacttcccc 1200
ttctattctg gcctacccct tggttcctga ctgtgccctt tccctcttcc 1250
tctcaggatt cccctggtga atctgtgatg cccccaatgt tggggtgcag 1300
ccaagcagga ggccaagggg ccggcacagc ccccatccca ctgagggtgg 1350
ggcagctgtg gggagctggg gccacagggg ctcctggctc ctgccccttg 1400
cacaccaccc ggaacactcc ccagccccac gggcaatcct atctgctcgc 1450
cctcctgcag gtgggggcct cacatatctg tgacttcggg tccctgtccc 1500
caccccttgtg cactcacatg aaagccttgc acactcacct ccaccttcac 1550
aggccatttg cacacgctcc tgcaccctct ccccgtccat accgctccgc 1600
tcagctgact ctcatgttct ctcgtctcac atttgcactc tctccttccc 1650
acattctgtg ctcagctcac tcagtggtca gcgtttcctg cacactttac 1700
ctctcatgtg cgtttcccgg cctgatgttg tggtggtgtg cggcgtgctc 1750
actctctccc tcatgaacac ccacccacct cgtttccgca gcccctgcgt 1800
gctgctccag aggtgggtgg gaggtgagct gggggctcct tgggccctca 1850
tcggtcatgg tctcgtccca ttccacacca tttgtttctc tgtctcccca 1900

-continued

```
tcctactcca aggatgccgg catcaccctg agggctcccc cttgggaatg          1950

gggtagtgag gccccagact tcacccccag cccactgcta aaatctgttt          2000

tctgacagat gggttttggg gagtcgcctg ctgcactaca tgagaaaggg          2050

actcccattt gcccttccct ttctcctaca gtcccttttg tcttgtctgt          2100

cctggctgtc tgtgtgtgtg ccattctctg gacttcagag ccccctgagc          2150

cagtcctccc ttcccagcct ccctttgggc ctccctaact ccacctaggc          2200

tgccagggac cggagtcagc tggttcaagg ccatcgggag ctctgcctcc          2250

aagtctaccc ttcccttccc ggactccctc ctgtcccctc ctttcctccc          2300

tccttccttc cactctcctt ccttttgctt ccctgccctt tccccctcct          2350

caggttcttc cctccttctc actggttttt ccaccttcct ccttcccttc          2400

ttccctggct cctaggctgt gatatatatt tttgtattat ctctttcttc          2450

ttcttgtggt gatcatcttg aattactgtg ggatgtaagt ttcaaaattt          2500

tcaaataaag cctttgcaag  ataa                                     2524
```

<210> SEQ ID NO 76
<211> LENGTH: 276
<212> TYPE: PRT
<213> ORGANISM: Homo sapiens

<400> SEQUENCE: 76

```
Met Glu Ser Arg Met Trp Pro Ala Leu Leu Leu Ser His Leu Leu
  1               5                  10                  15

Pro Leu Trp Pro Leu Leu Leu Leu Pro Leu Pro Pro Pro Ala Gln
                 20                  25                  30

Gly Ser Ser Ser Ser Pro Arg Thr Pro Pro Ala Pro Ala Arg Pro
                 35                  40                  45

Pro Cys Ala Arg Gly Gly Pro Ser Ala Pro Arg His Val Cys Val
                 50                  55                  60

Trp Glu Arg Ala Pro Pro Pro Ser Arg Ser Pro Arg Val Pro Arg
                 65                  70                  75

Ser Arg Arg Gln Val Leu Pro Gly Thr Ala Pro Pro Ala Thr Pro
                 80                  85                  90

Ser Gly Phe Glu Glu Gly Pro Pro Ser Ser Gln Tyr Pro Trp Ala
                 95                 100                 105

Ile Val Trp Gly Pro Thr Val Ser Arg Glu Asp Gly Gly Asp Pro
                110                 115                 120

Asn Ser Ala Asn Pro Gly Phe Leu Asp Tyr Gly Phe Ala Ala Pro
                125                 130                 135

His Gly Leu Ala Thr Pro His Pro Asn Ser Asp Ser Met Arg Gly
                140                 145                 150

Asp Gly Asp Gly Leu Ile Leu Gly Glu Ala Pro Ala Thr Leu Arg
                155                 160                 165

Pro Phe Leu Phe Gly Gly Arg Gly Glu Gly Val Asp Pro Gln Leu
                170                 175                 180

Tyr Val Thr Ile Thr Ile Ser Ile Ile Ile Val Leu Val Ala Thr
                185                 190                 195

Gly Ile Ile Phe Lys Phe Cys Trp Asp Arg Ser Gln Lys Arg Arg
                200                 205                 210

Arg Pro Ser Gly Gln Gln Gly Ala Leu Arg Gln Glu Glu Ser Gln
                215                 220                 225
```

-continued

```
Gln Pro Leu Thr Asp Leu Ser Pro Ala Gly Val Thr Val Leu Gly
                230                 235                 240

Ala Phe Gly Asp Ser Pro Thr Pro Thr Pro Asp His Glu Glu Pro
                245                 250                 255

Arg Gly Gly Pro Arg Pro Gly Met Pro His Pro Lys Gly Ala Pro
                260                 265                 270

Ala Phe Gln Leu Asn Arg
                275
```

<210> SEQ ID NO 77
<211> LENGTH: 2737
<212> TYPE: DNA
<213> ORGANISM: Homo sapiens

<400> SEQUENCE: 77

```
ggctgcgccc aggccggcgg gcccagcagc tgcgaaccgc cggcgcacca           50
cctgtttccg cgcccgggga cttccccggc ggggctcaga agtgtggggt          100
cggtcgcttg gcttcccctg gcgtcagcga cccagggtaa cctcctccac          150
tgctgcgtgc cgtgcaggcc tgcctgtgtg agagccacgt gtgccgcgct          200
ctgggcacag ccttggaaag tcaggaccgc gacggcagca gagcagaaac          250
cttacagaaa catgaagccc tcaaccatct gctactcagt tattcggggc          300
tgacggcggc ttctagaaca tccaggtgtt ctgcagatgc gagaactcat          350
cctgtagtca ccagatggag tcccaaacag ccaagcagat gtaaggcctg          400
tgctgtggct ctgaggccct gaatacagaa gggtcacttt cttagtggcc          450
aaagagcagt tgttgacatt gatgtctaat tattgaacac gaccagtcat          500
tttactgagc tgcagtgagg aaacactgac catagaagat caagccaaat          550
gagggattgc aaatttcctg attcttttga attaggattc cagatggggg          600
cctcatttct acagccccca acattcctat agccgttatc actgccatca          650
ccactgccac cagcatcttc ttgcagattc cacccctgct ccccagagac          700
ttcctgcttt gaaagtgagc agaaaggaag ctctcagaaa aatctctagt          750
ggtggctgcc gtcgctccag acaatcggaa tcctgccttc accaccatgg          800
gctggctttt tctaaaggtt ttgttggcgg gagtgagttt ctcaggattt          850
ctttatcctc ttgtggattt ttgcatcagt gggaaaacaa gaggacagaa          900
gccaaacttt gtgattattt tggccgatga catggggtgg ggtgacctgg          950
gagcaaactg ggcagaaaca aaggacactg ccaaccttga taagatggct         1000
tcggagggaa tgaggtttgt ggatttccat gcagctgcct ccacctgctc         1050
accctcccgg gcttccttgc tcaccggccg gcttggcctt cgcaatggag         1100
tcacacgcaa ctttgcagtc acttctgtgg gaggccttcc gctcaacgag         1150
accaccttgg cagaggtgct gcagcaggcg ggttacgtca ctgggataat         1200
aggcaaatgg catcttggac accacggctc ttatcacccc aacttccgtg         1250
gttttgatta ctactttgga atcccatata gccatgatat gggctgtact         1300
gatactccag gctacaacca ccctccttgt ccagcgtgtc cacagggtga         1350
tggaccatca aggaaccttc aaagagactg ttacactgac gtggccctcc         1400
ctctttatga aaacctcaac attgtggagc agccggtgaa cttgagcagc         1450
```

-continued

```
cttgcccaga agtatgctga gaaagcaacc cagttcatcc agcgtgcaag      1500

caccagcggg aggcccttcc tgctctatgt ggctctggcc cacatgcacg      1550

tgcccttacc tgtgactcag ctaccagcag cgccacgggg cagaagcctg      1600

tatggtgcag ggctctggga gatggacagt ctggtgggcc agatcaagga      1650

caaagttgac cacacagtga aggaaaacac attcctctgg tttacaggag      1700

acaatggccc gtgggctcag aagtgtgagc tagcgggcag tgtgggtccc      1750

ttcactggat tttggcaaac tcgtcaaggg ggaagtccag ccaagcagac      1800

gacctgggaa ggagggcacc gggtcccagc actggcttac tggcctggca      1850

gagttccagt taatgtcacc agcactgcct tgttaagcgt gctggacatt      1900

tttccaactg tggtagccct ggcccaggcc agcttacctc aaggacggcg      1950

ctttgatggt gtggacgtct ccgaggtgct ctttggccgg tcacagcctg      2000

ggcacagggt gctgttccac cccaacagcg gggcagctgg agagtttgga      2050

gccctgcaga ctgtccgcct ggagcgttac aaggccttct acattaccgg      2100

tggagccagg gcgtgtgatg gagcatggt gcctgagctg cagcataagt       2150

ttcctctgat tttcaacctg gaagacgata ccgcagaagc tgtgccccta      2200

gaaagaggtg gtgcggagta ccaggctgtg ctgcccgagg tcagaaaggt      2250

tcttgcagac gtcctccaag acattgccaa cgacaacatc tccagcgcag      2300

attacactca ggacccttca gtaactccct gctgtaatcc ctaccaaatt      2350

gcctgccgct gtcaagccgc ataacagacc aatttttatt ccacgaggag      2400

gagtacctgg aaattaggca agtttgcttc caaatttcat ttttaccctc      2450

tttacaaaca cacgctttag tttagtcttg gagtttagtt ttggagttag      2500

ccttgcatat cccttctgta tcctgtcccc cctccacgcc gacccgagag      2550

cagctgagct gcgctggctc tgggcaggga gtgtgcctta atgggaagca      2600

cacgggcttt ggagtcaggc acaggtgcca gctccagctt ttgaacttgg      2650

gcaattgttt aacctaacct gcaagttgat tttgagggtt aaataaaggc      2700

atacatgaaa atgcctggca actttaaaaa  aaaaaaa                   2737


<210> SEQ ID NO 78
<211> LENGTH: 525
<212> TYPE: PRT
<213> ORGANISM: Homo sapiens

<400> SEQUENCE: 78

Met Gly Trp Leu Phe Leu Lys Val Leu Leu Ala Gly Val Ser Phe
  1               5                  10                  15

Ser Gly Phe Leu Tyr Pro Leu Val Asp Phe Cys Ile Ser Gly Lys
                 20                  25                  30

Thr Arg Gly Gln Lys Pro Asn Phe Val Ile Ile Leu Ala Asp Asp
                 35                  40                  45

Met Gly Trp Gly Asp Leu Gly Ala Asn Trp Ala Glu Thr Lys Asp
                 50                  55                  60

Thr Ala Asn Leu Asp Lys Met Ala Ser Glu Gly Met Arg Phe Val
                 65                  70                  75

Asp Phe His Ala Ala Ala Ser Thr Cys Ser Pro Ser Arg Ala Ser
                 80                  85                  90

Leu Leu Thr Gly Arg Leu Gly Leu Arg Asn Gly Val Thr Arg Asn
```

-continued

```
                95                  100                 105

Phe Ala Val Thr Ser Val Gly Gly Leu Pro Leu Asn Glu Thr Thr
                110                 115                 120

Leu Ala Glu Val Leu Gln Gln Ala Gly Tyr Val Thr Gly Ile Ile
                125                 130                 135

Gly Lys Trp His Leu Gly His His Gly Ser Tyr His Pro Asn Phe
                140                 145                 150

Arg Gly Phe Asp Tyr Tyr Phe Gly Ile Pro Tyr Ser His Asp Met
                155                 160                 165

Gly Cys Thr Asp Thr Pro Gly Tyr Asn His Pro Pro Cys Pro Ala
                170                 175                 180

Cys Pro Gln Gly Asp Gly Pro Ser Arg Asn Leu Gln Arg Asp Cys
                185                 190                 195

Tyr Thr Asp Val Ala Leu Pro Leu Tyr Glu Asn Leu Asn Ile Val
                200                 205                 210

Glu Gln Pro Val Asn Leu Ser Ser Leu Ala Gln Lys Tyr Ala Glu
                215                 220                 225

Lys Ala Thr Gln Phe Ile Gln Arg Ala Ser Thr Ser Gly Arg Pro
                230                 235                 240

Phe Leu Leu Tyr Val Ala Leu Ala His Met His Val Pro Leu Pro
                245                 250                 255

Val Thr Gln Leu Pro Ala Ala Pro Arg Gly Arg Ser Leu Tyr Gly
                260                 265                 270

Ala Gly Leu Trp Glu Met Asp Ser Leu Val Gly Gln Ile Lys Asp
                275                 280                 285

Lys Val Asp His Thr Val Lys Glu Asn Thr Phe Leu Trp Phe Thr
                290                 295                 300

Gly Asp Asn Gly Pro Trp Ala Gln Lys Cys Glu Leu Ala Gly Ser
                305                 310                 315

Val Gly Pro Phe Thr Gly Phe Trp Gln Thr Arg Gln Gly Gly Ser
                320                 325                 330

Pro Ala Lys Gln Thr Thr Trp Glu Gly Gly His Arg Val Pro Ala
                335                 340                 345

Leu Ala Tyr Trp Pro Gly Arg Val Pro Val Asn Val Thr Ser Thr
                350                 355                 360

Ala Leu Leu Ser Val Leu Asp Ile Phe Pro Thr Val Val Ala Leu
                365                 370                 375

Ala Gln Ala Ser Leu Pro Gln Gly Arg Arg Phe Asp Gly Val Asp
                380                 385                 390

Val Ser Glu Val Leu Phe Gly Arg Ser Gln Pro Gly His Arg Val
                395                 400                 405

Leu Phe His Pro Asn Ser Gly Ala Ala Gly Glu Phe Gly Ala Leu
                410                 415                 420

Gln Thr Val Arg Leu Glu Arg Tyr Lys Ala Phe Tyr Ile Thr Gly
                425                 430                 435

Gly Ala Arg Ala Cys Asp Gly Ser Met Val Pro Glu Leu Gln His
                440                 445                 450

Lys Phe Pro Leu Ile Phe Asn Leu Glu Asp Asp Thr Ala Glu Ala
                455                 460                 465

Val Pro Leu Glu Arg Gly Gly Ala Glu Tyr Gln Ala Val Leu Pro
                470                 475                 480

Glu Val Arg Lys Val Leu Ala Asp Val Leu Gln Asp Ile Ala Asn
                485                 490                 495
```

-continued

Asp Asn Ile Ser Ser Ala Asp Tyr Thr Gln Asp Pro Ser Val Thr
500 505 510

Pro Cys Cys Asn Pro Tyr Gln Ile Ala Cys Arg Cys Gln Ala Ala
515 520 525

<210> SEQ ID NO 79
<211> LENGTH: 2639
<212> TYPE: DNA
<213> ORGANISM: Homo sapiens

<400> SEQUENCE: 79
cgcggccggg ccgccggggt gagcgtgccg aggcggctgt ggcgcaggct 50
tccagccccc accatgccgt ggcccctgct gctgctgctg gccgtgagtg 100
gggcccagac aacccggcca tgcttccccg ggtgccaatg cgaggtggag 150
accttcggcc ttttcgacag cttcagcctg actcgggtgg attgtagcgg 200
cctgggcccc cacatcatgc cggtgcccat ccctctggac acagcccact 250
tggacctgtc ctccaaccgg ctggagatgg tgaatgagtc ggtgttggcg 300
gggccgggct acacgacgtt ggctggcctg gatctcagcc acaacctgct 350
caccagcatc tcacccactg ccttctcccg ccttcgctac ctggagtcgc 400
ttgacctcag ccacaatggc ctgacagccc tgccagccga gagcttcacc 450
agctcacccc tgagcgacgt gaaccttagc cacaaccagc tccgggaggt 500
ctcagtgtct gccttcacga cgcacagtca gggccgggca ctacacgtgg 550
acctctccca caacctcatt caccgcctcg tgccccaccc cacgagggcc 600
ggcctgcctg cgcccaccat tcagagcctg aacctggcct ggaaccggct 650
ccatgccgtg cccaacctcc gagacttgcc cctgcgctac ctgagcctgg 700
atgggaaccc tctagctgtc attggtccgg gtgccttcgc ggggctggga 750
ggccttacac acctgtctct ggccagcctg cagaggctcc ctgagctggc 800
gcccagtggc ttccgtgagc taccgggcct gcaggtcctg gacctgtcgg 850
gcaaccccaa gcttaactgg gcaggagctg aggtgttttc aggcctgagc 900
tccctgcagg agctggacct ttcgggcacc aacctggtgc cctgcctga 950 ggcgctgctc ctccacctcc cggcactgca gagcgtcagc gtgggccagg 1000
atgtgcggtg ccggcgcctg gtgcgggagg gcacctaccc ccggaggcct 1050
ggctccagcc ccaaggtgcc cctgcactgc gtagacaccc gggaatctgc 1100
tgccaggggc cccaccatct tgtgacaaat ggtgtggccc agggccacat 1150
aacagactgc tgtcctgggc tgcctcaggt cccgagtaac ttatgttcaa 1200
tgtgccaaca ccagtgggga gcccgcaggc ctatgtggca gcgtcaccac 1250
aggagttgtg ggcctaggag aggctttgga cctgggagcc acacctagga 1300
gcaaagtctc acccctttgt ctacgttgct tccccaaacc atgagcagag 1350
ggacttcgat gccaaaccag actcgggtcc cctcctgctt cccttcccca 1400
cttatccccc aagtgccttc cctcatgcct gggccggcct gacccgcaat 1450
gggcagaggg tgggtgggac cccctgctgc agggcagagt tcaggtccac 1500
tgggctgagt gtccccttgg gcccatggcc cagtcactca ggggcgagtt 1550
tcttttctaa catagccctt tctttgccat gaggccatga ggcccgcttc 1600

-continued

```
atccttttct atttccctag aaccttaatg gtagaaggaa ttgcaaagaa             1650

tcaagtccac ccttctcatg tgacagatgg ggaaactgag gccttgagaa             1700

ggaaaaaggc taatctaagt tcctgcgggc agtggcatga ctggagcaca             1750

gcctcctgcc tcccagcccg gacccaatgc actttcttgt ctcctctaat             1800

aagccccacc ctccccgcct gggctcccct tgctgccctt gcctgttccc             1850

cattagcaca ggagtagcag cagcaggaca ggcaagagcc tcacaagtgg             1900

gactctgggc ctctgaccag ctgtgcggca tgggctaagt cactctgccc             1950

ttcggagcct ctggaagctt agggcacatt ggttccagcc tagccagttt             2000

ctcaccctgg gttggggtcc cccagcatcc agactggaaa cctacccatt             2050

ttcccctgag catcctctag atgctgcccc aaggagttgc tgcagttctg             2100

gagcctcatc tggctgggat ctccaagggg cctcctggat tcagtcccca             2150

ctggccctga gcacgacagc ccttcttacc ctcccaggaa tgccgtgaaa             2200

ggagacaagg tctgcccgac ccatgtctat gctctacccc cagggcagca             2250

tctcagcttc cgaaccctgg gctgtttcct tagtcttcat tttataaaag             2300

ttgttgcctt tttaacggag tgtcactttc aaccggcctc ccctacccct             2350

gctggccggg gatggagaca tgtcatttgt aaaagcagaa aaaggttgca             2400

tttgttcact tttgtaatat tgtcctgggc ctgtgttggg gtgttggggg             2450

aagctgggca tcagtggcca catgggcatc aggggctggc cccacagaga             2500

ccccacaggg cagtgagctc tgtcttcccc cacctgccta gcccatcatc             2550

tatctaaccg gtccttgatt taataaacac tataaaaggt ttaaaaaaaa             2600

aaaaaaaaaa aaaaaaaaaa aaaaaaaaaa  aaaaaaaaa                        2639
```

<210> SEQ ID NO 80
<211> LENGTH: 353
<212> TYPE: PRT
<213> ORGANISM: Homo sapiens

<400> SEQUENCE: 80

```
Met Pro Trp Pro Leu Leu Leu Leu Leu Ala Val Ser Gly Ala Gln
  1               5                  10                  15

Thr Thr Arg Pro Cys Phe Pro Gly Cys Gln Cys Glu Val Glu Thr
                 20                  25                  30

Phe Gly Leu Phe Asp Ser Phe Ser Leu Thr Arg Val Asp Cys Ser
                 35                  40                  45

Gly Leu Gly Pro His Ile Met Pro Val Pro Ile Pro Leu Asp Thr
                 50                  55                  60

Ala His Leu Asp Leu Ser Ser Asn Arg Leu Glu Met Val Asn Glu
                 65                  70                  75

Ser Val Leu Ala Gly Pro Gly Tyr Thr Thr Leu Ala Gly Leu Asp
                 80                  85                  90

Leu Ser His Asn Leu Leu Thr Ser Ile Ser Pro Thr Ala Phe Ser
                 95                 100                 105

Arg Leu Arg Tyr Leu Glu Ser Leu Asp Leu Ser His Asn Gly Leu
                110                 115                 120

Thr Ala Leu Pro Ala Glu Ser Phe Thr Ser Ser Pro Leu Ser Asp
                125                 130                 135

Val Asn Leu Ser His Asn Gln Leu Arg Glu Val Ser Val Ser Ala
                140                 145                 150
```

-continued

```
Phe Thr Thr His Ser Gln Gly Arg Ala Leu His Val Asp Leu Ser
                155                 160                 165

His Asn Leu Ile His Arg Leu Val Pro His Pro Thr Arg Ala Gly
                170                 175                 180

Leu Pro Ala Pro Thr Ile Gln Ser Leu Asn Leu Ala Trp Asn Arg
                185                 190                 195

Leu His Ala Val Pro Asn Leu Arg Asp Leu Pro Leu Arg Tyr Leu
                200                 205                 210

Ser Leu Asp Gly Asn Pro Leu Ala Val Ile Gly Pro Gly Ala Phe
                215                 220                 225

Ala Gly Leu Gly Gly Leu Thr His Leu Ser Leu Ala Ser Leu Gln
                230                 235                 240

Arg Leu Pro Glu Leu Ala Pro Ser Gly Phe Arg Glu Leu Pro Gly
                245                 250                 255

Leu Gln Val Leu Asp Leu Ser Gly Asn Pro Lys Leu Asn Trp Ala
                260                 265                 270

Gly Ala Glu Val Phe Ser Gly Leu Ser Ser Leu Gln Glu Leu Asp
                275                 280                 285

Leu Ser Gly Thr Asn Leu Val Pro Leu Pro Glu Ala Leu Leu Leu
                290                 295                 300

His Leu Pro Ala Leu Gln Ser Val Ser Val Gly Gln Asp Val Arg
                305                 310                 315

Cys Arg Arg Leu Val Arg Glu Gly Thr Tyr Pro Arg Arg Pro Gly
                320                 325                 330

Ser Ser Pro Lys Val Pro Leu His Cys Val Asp Thr Arg Glu Ser
                335                 340                 345

Ala Ala Arg Gly Pro Thr Ile Leu
                350
```

```
<210> SEQ ID NO 81
<211> LENGTH: 1572
<212> TYPE: DNA
<213> ORGANISM: Homo sapiens

<400> SEQUENCE: 81

cgggccagcc tggggcggcc ggccaggaac cacccgttaa ggtgtcttct              50

ctttagggat ggtgaggttg gaaaaagact cctgtaaccc tcctccagga             100

tgaaccacct gccagaagac atggagaacg ctctcaccgg gagccagagc             150

tcccatgctt ctctgcgcaa tatccattcc atcaacccca cacaactcat             200

ggccaggatt gagtcctatg aaggaaggga aaagaaaggc atatctgatg             250

tcaggaggac tttctgtttg tttgtcacct ttgacctctt attcgtaaca             300

ttactgtgga taatagagtt aaatgtgaat ggaggcattg agaacacatt             350

agagaaggag gtgatgcagt atgactacta ttcttcatat tttgatatat             400

ttcttctggc agtttttcga tttaaagtgt taatacttgc atatgctgtg             450

tgcagactgc gccattggtg ggcaatagcg ttgacaacgg cagtgaccag             500

tgccttttta ctagcaaaag tgatcctttc gaagcttttc tctcaagggg             550

cttttggcta tgtgctgccc atcatttcat tcatccttgc ctggattgag             600

acgtggttcc tggatttcaa agtgttacct caagaagcag aagaagaaaa             650

cagactcctg atagttcagg atgcttcaga gagggcagca cttatacctg             700
```

-continued

```
gtggtctttc tgatggtcag ttttattccc ctcctgaatc cgaagcagga        750

tctgaagaag ctgaagaaaa acaggacagt gagaaaccac ttttagaact        800

atgagtacta cttttgttaa atgtgaaaaa ccctcacaga aagtcatcga        850

ggcaaaaaga ggcaggcagt ggagtctccc tgtcgacagt aaagttgaaa        900

tggtgacgtc cactgctggc tttattgaac agctaataaa gatttattta        950

ttgtaatacc tcacaaacgt tgtaccatat ccatgcacat ttagttgcct       1000

gcctgtggct ggtaaggtaa tgtcatgatt catcctctct tcagtgagac       1050

tgagcctgat gtgttaacaa ataggtgaag aaagtcttgt gctgtattcc       1100

taatcaaaag acttaatata ttgaagtaac acttttttag taagcaagat       1150

acctttttat ttcaattcac agaatggaat ttttttgttt catgtctcag       1200

atttattttg tatttctttt ttaacactct acatttccct tgttttttaa       1250

ctcatgcaca tgtgctcttt gtacagtttt aaaaagtgta ataaaatctg       1300

acatgtcaat gtggctagtt ttattttttct tgttttgcat tatgtgtatg       1350

gcctgaagtg ttggacttgc aaaaggggaa gaaaggaatt gcgaatacat       1400

gtaaaatgtc accagacatt tgtattattt ttatcatgaa atcatgtttt       1450

tctctgattg ttctgaaatg ttctaaatac tcttattttg aatgcacaaa       1500

atgacttaaa ccattcatat catgtttcct ttgcgttcag ccaatttcaa       1550

ttaaaatgaa ctaaattaaa  aa                                    1572
```

<210> SEQ ID NO 82
<211> LENGTH: 234
<212> TYPE: PRT
<213> ORGANISM: Homo sapiens

<400> SEQUENCE: 82

```
Met Asn His Leu Pro Glu Asp Met Glu Asn Ala Leu Thr Gly Ser
  1               5                  10                  15

Gln Ser Ser His Ala Ser Leu Arg Asn Ile His Ser Ile Asn Pro
                 20                  25                  30

Thr Gln Leu Met Ala Arg Ile Glu Ser Tyr Glu Gly Arg Glu Lys
                 35                  40                  45

Lys Gly Ile Ser Asp Val Arg Arg Thr Phe Cys Leu Phe Val Thr
                 50                  55                  60

Phe Asp Leu Leu Phe Val Thr Leu Leu Trp Ile Ile Glu Leu Asn
                 65                  70                  75

Val Asn Gly Gly Ile Glu Asn Thr Leu Glu Lys Glu Val Met Gln
                 80                  85                  90

Tyr Asp Tyr Tyr Ser Ser Tyr Phe Asp Ile Phe Leu Leu Ala Val
                 95                 100                 105

Phe Arg Phe Lys Val Leu Ile Leu Ala Tyr Ala Val Cys Arg Leu
                110                 115                 120

Arg His Trp Trp Ala Ile Ala Leu Thr Thr Ala Val Thr Ser Ala
                125                 130                 135

Phe Leu Leu Ala Lys Val Ile Leu Ser Lys Leu Phe Ser Gln Gly
                140                 145                 150

Ala Phe Gly Tyr Val Leu Pro Ile Ile Ser Phe Ile Leu Ala Trp
                155                 160                 165

Ile Glu Thr Trp Phe Leu Asp Phe Lys Val Leu Pro Gln Glu Ala
                170                 175                 180
```

-continued

```
Glu Glu Glu Asn Arg Leu Leu Ile Val Gln Asp Ala Ser Glu Arg
                185                 190                 195

Ala Ala Leu Ile Pro Gly Gly Leu Ser Asp Gly Gln Phe Tyr Ser
                200                 205                 210

Pro Pro Glu Ser Glu Ala Gly Ser Glu Glu Ala Glu Glu Lys Gln
                215                 220                 225

Asp Ser Glu Lys Pro Leu Leu Glu Leu
                230


<210> SEQ ID NO 83
<211> LENGTH: 1882
<212> TYPE: DNA
<213> ORGANISM: Homo sapiens

<400> SEQUENCE: 83

ccgtcatccc cctgcagcca cccttcccag agtcctttgc ccaggccacc          50

ccaggcttct tggcagccct gccgggccac ttgtcttcat gtctgccagg         100

gggaggtggg aaggaggtgg gaggagggcg tgcagaggca gtctgggctt         150

ggccagagct cagggtgctg agcgtgtgac cagcagtgag cagaggccgg         200

ccatggccag cctggggctg ctgctcctgc tcttactgac agcactgcca         250

ccgctgtggt cctcctcact gcctgggctg gacactgctg aaagtaaagc         300

caccattgca gacctgatcc tgtctgcgct ggagagagcc accgtcttcc         350

tagaacagag gctgcctgaa atcaacctgg atggcatggt gggggtccga         400

gtgctggaag agcagctaaa aagtgtccgg gagaagtggg cccaggagcc         450

cctgctgcag ccgctgagcc tgcgcgtggg gatgctgggg gagaagctgg         500

aggctgccat ccagagatcc ctccactacc tcaagctgag tgatcccaag         550

tacctaagag agttccagct gaccctccag cccgggtttt ggaagctccc         600

acatgcctgg atccacactg atgcctcctt ggtgtacccc acgttcgggc         650

cccaggactc attctcagag gagagaagtg acgtgtgcct ggtgcagctg         700

ctgggaaccg ggacggacag cagcgagccc tgcggcctct cagacctctg         750

caggagcctc atgaccaagc ccggctgctc aggctactgc ctgtcccacc         800

aactgctctt cttcctctgg gccagaatga ggggatgcac acagggacca         850

ctccaacaga gccaggacta tatcaacctc ttctgcgcca acatgatgga         900

cttgaaccgc agagctgagg ccatcggata cgcctaccct acccgggaca         950

tcttcatgga aaacatcatg ttctgtggaa tgggcggctt ctccgacttc        1000

tacaagctcc ggtggctgga ggccattctc agctggcaga aacagcagga        1050

aggatgcttc ggggagcctg atgctgaaga tgaagaatta tctaaagcta        1100

ttcaatatca gcagcatttt tcgaggagag tgaagaggcg agaaaaacaa        1150

tttccagatt ctcgctctgt tgctcaggct ggagtacagt ggcgcaatct        1200

cggctcactg caacctttgc ctcctgggtt caagcaattc tcttgcctca        1250

tcctcccgag tagctgggac tacaggagcg tgccaccata cctggctaat        1300

ttttatattt ttttagtaga gacagggttt catcatgttg ctcatgctgg        1350

tctcgaactc ctgatctcaa gagatccgcc cacctcaggc tcccaaagtg        1400

tgggattata ggtgtgagcc accgtgtctg gctgaaaagc actttcaaag        1450
```

-continued

```
agactgtgtt gaataaaggg ccaaggttct tgccacccag cactcatggg           1500

ggctctctcc cctagatggc tgctcctccc acaacacagc cacagcagtg           1550

gcagccctgg gtggcttcct atacatcctg gcagaatacc ccccagcaaa           1600

cagagagcca cacccatcca caccgccacc accaagcagc cgctgagacg           1650

gacggttcca tgccagctgc ctggaggagg aacagacccc tttagtcctc           1700

atcccttaga tcctggaggg cacggatcac atcctgggaa gaaggcatct           1750

ggaggataag caaagccacc ccgacaccca atcttggaag ccctgagtag           1800

gcagggccag ggtaggtggg ggccgggagg gacccaggtg tgaacggatg           1850

aataaagttc aactgcaact gaaaaaaaaa  aa                             1882


<210> SEQ ID NO 84
<211> LENGTH: 440
<212> TYPE: PRT
<213> ORGANISM: Homo sapiens

<400> SEQUENCE: 84

Met Ser Ala Arg Gly Arg Trp Glu Gly Gly Gly Arg Arg Ala Cys
  1               5                  10                  15

Arg Gly Ser Leu Gly Leu Ala Arg Ala Gln Gly Ala Glu Arg Val
                 20                  25                  30

Thr Ser Ser Glu Gln Arg Pro Ala Met Ala Ser Leu Gly Leu Leu
                 35                  40                  45

Leu Leu Leu Leu Leu Thr Ala Leu Pro Pro Leu Trp Ser Ser Ser
                 50                  55                  60

Leu Pro Gly Leu Asp Thr Ala Glu Ser Lys Ala Thr Ile Ala Asp
                 65                  70                  75

Leu Ile Leu Ser Ala Leu Glu Arg Ala Thr Val Phe Leu Glu Gln
                 80                  85                  90

Arg Leu Pro Glu Ile Asn Leu Asp Gly Met Val Gly Val Arg Val
                 95                 100                 105

Leu Glu Glu Gln Leu Lys Ser Val Arg Glu Lys Trp Ala Gln Glu
                110                 115                 120

Pro Leu Leu Gln Pro Leu Ser Leu Arg Val Gly Met Leu Gly Glu
                125                 130                 135

Lys Leu Glu Ala Ala Ile Gln Arg Ser Leu His Tyr Leu Lys Leu
                140                 145                 150

Ser Asp Pro Lys Tyr Leu Arg Glu Phe Gln Leu Thr Leu Gln Pro
                155                 160                 165

Gly Phe Trp Lys Leu Pro His Ala Trp Ile His Thr Asp Ala Ser
                170                 175                 180

Leu Val Tyr Pro Thr Phe Gly Pro Gln Asp Ser Phe Ser Glu Glu
                185                 190                 195

Arg Ser Asp Val Cys Leu Val Gln Leu Leu Gly Thr Gly Thr Asp
                200                 205                 210

Ser Ser Glu Pro Cys Gly Leu Ser Asp Leu Cys Arg Ser Leu Met
                215                 220                 225

Thr Lys Pro Gly Cys Ser Gly Tyr Cys Leu Ser His Gln Leu Leu
                230                 235                 240

Phe Phe Leu Trp Ala Arg Met Arg Gly Cys Thr Gln Gly Pro Leu
                245                 250                 255

Gln Gln Ser Gln Asp Tyr Ile Asn Leu Phe Cys Ala Asn Met Met
                260                 265                 270
```

-continued

```
Asp Leu Asn Arg Arg Ala Glu Ala Ile Gly Tyr Ala Tyr Pro Thr
                275                 280                 285

Arg Asp Ile Phe Met Glu Asn Ile Met Phe Cys Gly Met Gly Gly
                290                 295                 300

Phe Ser Asp Phe Tyr Lys Leu Arg Trp Leu Glu Ala Ile Leu Ser
                305                 310                 315

Trp Gln Lys Gln Gln Glu Gly Cys Phe Gly Glu Pro Asp Ala Glu
                320                 325                 330

Asp Glu Glu Leu Ser Lys Ala Ile Gln Tyr Gln Gln His Phe Ser
                335                 340                 345

Arg Arg Val Lys Arg Arg Glu Lys Gln Phe Pro Asp Ser Arg Ser
                350                 355                 360

Val Ala Gln Ala Gly Val Gln Trp Arg Asn Leu Gly Ser Leu Gln
                365                 370                 375

Pro Leu Pro Pro Gly Phe Lys Gln Phe Ser Cys Leu Ile Leu Pro
                380                 385                 390

Ser Ser Trp Asp Tyr Arg Ser Val Pro Pro Tyr Leu Ala Asn Phe
                395                 400                 405

Tyr Ile Phe Leu Val Glu Thr Gly Phe His His Val Ala His Ala
                410                 415                 420

Gly Leu Glu Leu Leu Ile Ser Arg Asp Pro Pro Thr Ser Gly Ser
                425                 430                 435

Gln Ser Val Gly Leu
                440


<210> SEQ ID NO 85
<211> LENGTH: 1094
<212> TYPE: DNA
<213> ORGANISM: Homo sapiens

<400> SEQUENCE: 85

ggtctgagtg cagagctgct gtcatggcgg ccgctctgtg gggcttcttt          50

cccgtcctgc tgctgctgct gctatcgggg gatgtccaga gctcggaggt         100

gcccggggct gctgctgagg gatcgggagg gagtggggtc ggcataggag         150

atcgcttcaa gattgagggg cgtgcagttg ttccaggggt gaagcctcag         200

gactggatct cggcggcccg agtgctggta gacggagaag agcacgtcgg         250

tttccttaag acagatggga gttttgtggt tcatgatata ccttctggat         300

cttatgtagt ggaagttgta tctccagctt acagatttga tcccgttcga         350

gtggatatca cttcgaaagg aaaaatgaga gcaagatatg tgaattacat         400

caaaacatca gaggttgtca gactgcccta tcctctccaa atgaaatctt         450

caggtccacc ttcttacttt attaaaaggg aatcgtgggg ctggacagac         500

tttctaatga acccaatggt tatgatgatg gttcttcctt tattgatatt         550

tgtgcttctg cctaaagtgg tcaacacaag tgatcctgac atgagacggg         600

aaatggagca gtcaatgaat atgctgaatt ccaaccatga gttgcctgat         650

gtttctgagt tcatgacaag actcttctct tcaaaatcat ctggcaaatc         700

tagcagcggc agcagtaaaa caggcaaaag tggggctggc aaaaggaggt         750

agtcaggccg tccagagctg gcatttgcac aaacacggca acactgggtg         800

gcatccaagt cttggaaaac cgtgtgaagc aactactata aacttgagtc         850
```

-continued

```
atcccgacgt tgatctctta caactgtgta tgttaacttt ttagcacatg              900

ttttgtactt ggtacacgag aaaacccagc tttcatcttt tgtctgtatg              950

aggtcaatat tgatgtcact gaattaatta cagtgtccta tagaaaatgc             1000

cattaataaa ttatatgaac tactatacat tatgtatatt aattaaaaca             1050

tcttaatcca gaaatcaaaa aaaaaaaaaa aaaaaaaaaa  aaaa                  1094
```

```
<210> SEQ ID NO 86
<211> LENGTH: 242
<212> TYPE: PRT
<213> ORGANISM: Homo sapiens

<400> SEQUENCE: 86

Met Ala Ala Ala Leu Trp Gly Phe Phe Pro Val Leu Leu Leu Leu
  1               5                  10                  15

Leu Leu Ser Gly Asp Val Gln Ser Ser Glu Val Pro Gly Ala Ala
                 20                  25                  30

Ala Glu Gly Ser Gly Gly Ser Gly Val Gly Ile Gly Asp Arg Phe
                 35                  40                  45

Lys Ile Glu Gly Arg Ala Val Val Pro Gly Val Lys Pro Gln Asp
                 50                  55                  60

Trp Ile Ser Ala Ala Arg Val Leu Val Asp Gly Glu Glu His Val
                 65                  70                  75

Gly Phe Leu Lys Thr Asp Gly Ser Phe Val Val His Asp Ile Pro
                 80                  85                  90

Ser Gly Ser Tyr Val Val Glu Val Val Ser Pro Ala Tyr Arg Phe
                 95                 100                 105

Asp Pro Val Arg Val Asp Ile Thr Ser Lys Gly Lys Met Arg Ala
                110                 115                 120

Arg Tyr Val Asn Tyr Ile Lys Thr Ser Glu Val Val Arg Leu Pro
                125                 130                 135

Tyr Pro Leu Gln Met Lys Ser Ser Gly Pro Pro Ser Tyr Phe Ile
                140                 145                 150

Lys Arg Glu Ser Trp Gly Trp Thr Asp Phe Leu Met Asn Pro Met
                155                 160                 165

Val Met Met Met Val Leu Pro Leu Leu Ile Phe Val Leu Leu Pro
                170                 175                 180

Lys Val Val Asn Thr Ser Asp Pro Asp Met Arg Arg Glu Met Glu
                185                 190                 195

Gln Ser Met Asn Met Leu Asn Ser Asn His Glu Leu Pro Asp Val
                200                 205                 210

Ser Glu Phe Met Thr Arg Leu Phe Ser Ser Lys Ser Ser Gly Lys
                215                 220                 225

Ser Ser Ser Gly Ser Ser Lys Thr Gly Lys Ser Gly Ala Gly Lys
                230                 235                 240

Arg Arg
```

```
<210> SEQ ID NO 87
<211> LENGTH: 1234
<212> TYPE: DNA
<213> ORGANISM: Homo sapiens

<400> SEQUENCE: 87

caggatgcag ggccgcgtgg cagggagctg cgctcctctg ggcctgctcc               50

tggtctgtct tcatctccca ggcctctttg cccggagcat cggtgttgtg              100
```

-continued

```
gaggagaaag tttcccaaaa cttcgggacc aacttgcctc agctcggaca         150

accttcctcc actggcccct ctaactctga acatccgcag cccgctctgg         200

accctaggtc taatgacttg gcaagggttc ctctgaagct cagcgtgcct         250

ccatcagatg gcttcccacc tgcaggaggt tctgcagtgc agaggtggcc         300

tccatcgtgg gggctgcctg ccatggattc ctggcccccct gaggatcctt        350

ggcagatgat ggctgctgcg gctgaggacc gcctgggga agcgctgcct          400

gaagaactct cttacctctc cagtgctgcg gccctcgctc cgggcagtgg         450

ccctttgcct ggggagtctt ctcccgatgc cacaggcctc tcacctgagg         500

cttcactcct ccaccaggac tcggagtcca gacgactgcc ccgttctaat         550

tcactgggag ccgggggaaa aatcctttcc caacgccctc cctggtctct         600

catccacagg gttctgcctg atcacccctg gggtaccctg aatcccagtg         650

tgtcctgggg aggtggaggc cctgggactg gttggggaac gaggcccatg         700

ccacaccctg agggaatctg gggtatcaat aatcaacccc caggtaccag         750

ctggggaaat attaatcggt atccaggagg cagctgggga aatattaatc         800

ggtatccagg aggcagctgg gggaatatta atcggtatcc aggaggcagc         850

tgggggaata ttcatctata cccaggtatc aataacccat ttcctcctgg         900

agttctccgc cctcctggct cttcttggaa catcccagct ggcttcccta         950

atcctccaag ccctaggttg cagtggggct agagcacgat agagggaaac        1000

ccaacattgg gagttagagt cctgctcccg ccccttgctg tgtgggctca        1050

atccaggccc tgttaacatg tttccagcac tatccccact tttcagtgcc        1100

tcccctgctc atctccaata aaataaaagc acttatgaaa aaaaaaaaaa        1150

aaaaaaaaaa aaaaaaaaaa aaaaaaaaaa aaaaaaaaaa aaaaaaaaaa        1200

aaaaaaaaaa aaaaaaaaaa aaaaaaaaaa  aaaa                        1234
```

<210> SEQ ID NO 88
<211> LENGTH: 325
<212> TYPE: PRT
<213> ORGANISM: Homo sapiens

<400> SEQUENCE: 88

```
Met Gln Gly Arg Val Ala Gly Ser Cys Ala Pro Leu Gly Leu Leu
  1               5                  10                  15

Leu Val Cys Leu His Leu Pro Gly Leu Phe Ala Arg Ser Ile Gly
                 20                  25                  30

Val Val Glu Glu Lys Val Ser Gln Asn Phe Gly Thr Asn Leu Pro
                 35                  40                  45

Gln Leu Gly Gln Pro Ser Ser Thr Gly Pro Ser Asn Ser Glu His
                 50                  55                  60

Pro Gln Pro Ala Leu Asp Pro Arg Ser Asn Asp Leu Ala Arg Val
                 65                  70                  75

Pro Leu Lys Leu Ser Val Pro Pro Ser Asp Gly Phe Pro Pro Ala
                 80                  85                  90

Gly Gly Ser Ala Val Gln Arg Trp Pro Pro Ser Trp Gly Leu Pro
                 95                 100                 105

Ala Met Asp Ser Trp Pro Pro Glu Asp Pro Trp Gln Met Met Ala
                110                 115                 120
```

-continued

```
Ala Ala Ala Glu Asp Arg Leu Gly Glu Ala Leu Pro Glu Glu Leu
                125                 130                 135

Ser Tyr Leu Ser Ser Ala Ala Ala Leu Ala Pro Gly Ser Gly Pro
                140                 145                 150

Leu Pro Gly Glu Ser Ser Pro Asp Ala Thr Gly Leu Ser Pro Glu
                155                 160                 165

Ala Ser Leu Leu His Gln Asp Ser Glu Ser Arg Arg Leu Pro Arg
                170                 175                 180

Ser Asn Ser Leu Gly Ala Gly Gly Lys Ile Leu Ser Gln Arg Pro
                185                 190                 195

Pro Trp Ser Leu Ile His Arg Val Leu Pro Asp His Pro Trp Gly
                200                 205                 210

Thr Leu Asn Pro Ser Val Ser Trp Gly Gly Gly Gly Pro Gly Thr
                215                 220                 225

Gly Trp Gly Thr Arg Pro Met Pro His Pro Glu Gly Ile Trp Gly
                230                 235                 240

Ile Asn Asn Gln Pro Pro Gly Thr Ser Trp Gly Asn Ile Asn Arg
                245                 250                 255

Tyr Pro Gly Gly Ser Trp Gly Asn Ile Asn Arg Tyr Pro Gly Gly
                260                 265                 270

Ser Trp Gly Asn Ile Asn Arg Tyr Pro Gly Gly Ser Trp Gly Asn
                275                 280                 285

Ile His Leu Tyr Pro Gly Ile Asn Asn Pro Phe Pro Pro Gly Val
                290                 295                 300

Leu Arg Pro Pro Gly Ser Ser Trp Asn Ile Pro Ala Gly Phe Pro
                305                 310                 315

Asn Pro Pro Ser Pro Arg Leu Gln Trp Gly
                320                 325
```

<210> SEQ ID NO 89
<211> LENGTH: 3671
<212> TYPE: DNA
<213> ORGANISM: Homo sapiens

<400> SEQUENCE: 89

```
gccgccggcc cgggctggag ccgagcgcag cagccaccgc cgccgccgcg        50

ccagaagttt gggttgaacc ggagctgccg ggaggaaact tttttctttt       100

ttccccctcc ctcccgggag gaggaggagg aggaggaggg gaagctgccg       150

ccggcgccaa ggctcgtggg ctcggggtcg gcgcggcccg cagaaggggc       200

gggggcctcg ccccgcgagg ggaggcgcgc cccgggggcc ccgagagggg       250

cggtgaggac cgcgggctgc tggtgcggcg gcggcggcgc gtgtgccccg       300

cgcaggggag ggcgcccgcc ccgctcccgg cccggctgcg aggaggaggc       350

ggcggcggcg caggaggatg tacttggtgg cgggggacag ggggttggcc       400

ggctgcgggc acctcctggt ctcgctgctg gggctgctgc tgctgctggc       450

gcgctccggc acccgggcgc tggtctgcct gccctgtgac gagtccaagt       500

gcgaggagcc caggaactgc ccggggagca tcgtgcaggg cgtctgcggc       550

tgctgctaca cgtgcgccag ccagaggaac gagagctgcg gcggcacctt       600

cgggatttac ggaacctgcg accgggggct gcgttgtgtc atccgccccc       650

cgctcaatgg cgactccctc accgagtacg aagcgggcgt ttgcgaagat       700

gagaactgga ctgatgacca actgcttggt tttaaaccat gcaatgaaaa       750
```

-continued

```
ccttattgct ggctgcaata taatcaatgg gaaatgtgaa tgtaacacca      800
ttcgaacctg cagcaatccc tttgagtttc caagtcagga tatgtgcctt      850
tcagctttaa agagaattga agaagagaag ccagattgct ccaaggcccg      900
ctgtgaagtc cagttctctc cacgttgtcc tgaagattct gttctgatcg      950
agggttatgc tcctcctggg gagtgctgtc ccttacccag ccgctgcgtg     1000
tgcaaccccg caggctgtct gcgcaaagtc tgccagccgg gaaacctgaa     1050
catactagtg tcaaaagcct cagggaagcc gggagagtgc tgtgacctct     1100
atgagtgcaa accagttttc ggcgtggact gcaggactgt ggaatgccct     1150
cctgttcagc agaccgcgtg tcccccggac agctatgaaa ctcaagtcag     1200
actaactgca gatggttgct gtactttgcc aacaagatgc gagtgtctct     1250
ctggcttatg tggtttcccc gtgtgtgagg tgggatccac tccccgcata     1300
gtctctcgtg gcgatgggac acctggaaag tgctgtgatg tctttgaatg     1350
tgttaatgat acaaagccag cctgcgtatt taacaatgtg gaatattatg     1400
atggagacat gtttcgaatg gacaactgtc ggttctgtcg atgccaaggg     1450
ggcgttgcca tctgcttcac tgcccagtgt ggtgagataa actgcgagag     1500
gtactacgtg cccgaaggag agtgctgccc agtgtgtgaa gatccagtgt     1550
atccttttaa taatcccgct ggctgctatg ccaatggcct gatccttgcc     1600
cacggagacc ggtggcggga agacgactgc acattctgcc agtgcgtcaa     1650
cggtgaacgc cactgcgttg cgaccgtctg cggacagacc tgcacaaacc     1700
ctgtgaaagt gcctggggag tgttgccctg tgtgcgaaga accaaccatc     1750
atcacagttg atccacctgc atgtggggag ttatcaaact gcactctgac     1800
agggaaggac tgcattaatg gtttcaaacg cgatcacaat ggttgtcgga     1850
cctgtcagtg cataaacacc gaggaactat gttcagaacg taaacaaggc     1900
tgcaccttga actgtccctt cggtttcctt actgatgccc aaaactgtga     1950
gatctgtgag tgccgcccaa ggcccaagaa gtgcagaccc ataatctgtg     2000
acaagtattg tccacttgga ttgctgaaga ataagcacgg ctgtgacatc     2050
tgtcgctgta agaaatgtcc agagctctca tgcagtaaga tctgcccctt     2100
gggtttccag caggacagtc acggctgtct tatctgcaag tgcagagagg     2150
cctctgcttc agctgggcca cccatcctgt cgggcacttg tctcaccgtg     2200
gatggtcatc atcataaaaa tgaggagagc tggcacgatg ggtgccggga     2250
atgctactgt ctcaatggac gggaaatgtg tgccctgatc acctgcccgg     2300
tgcctgcctg tggcaacccc accattcacc ctggacagtg ctgcccatca     2350
tgtgcagatg actttgtggt gcagaagcca gagctcagta ctccctccat     2400
ttgccacgcc cctggaggag aatactttgt ggaaggagaa acgtggaaca     2450
ttgactcctg tactcagtgc acctgccaca gcggacgggt gctgtgtgag     2500
acagaggtgt gcccaccgct gctctgccag aacccctcac gcacccagga     2550
ttcctgctgc ccacagtgta cagatcaacc ttttcggcct tccttgtccc     2600
gcaataacag cgtacctaat tactgcaaaa atgatgaagg ggatatattc     2650
ctggcagctg agtcctggaa gcctgacgtt tgtaccagct gcatctgcat     2700
```

-continued

```
tgatagcgta attagctgtt tctctgagtc ctgcccttct gtatcctgtg        2750

aaagacctgt cttgagaaaa ggccagtgtt gtccctactg catagaagac        2800

acaattccaa agaaggtggt gtgccacttc agtgggaagg cctatgccga        2850

cgaggagcgg tgggaccttg acagctgcac ccactgctac tgcctgcagg        2900

gccagaccct ctgctcgacc gtcagctgcc cccctctgcc ctgtgttgag        2950

cccatcaacg tggaaggaag ttgctgccca atgtgtccag aaatgtatgt        3000

cccagaacca accaatatac ccattgagaa gacaaaccat cgaggagagg        3050

ttgacctgga ggttcccctg tggcccacgc ctagtgaaaa tgatatcgtc        3100

catctcccta gagatatggg tcacctccag gtagattaca gagataacag        3150

gctgcaccca agtgaagatt cttcactgga ctccattgcc tcagttgtgg        3200

ttcccataat tatatgcctc tctattataa tagcattcct attcatcaat        3250

cagaagaaac agtggatacc actgctttgc tggtatcgaa caccaactaa        3300

gccttcttcc ttaaataatc agctagtatc tgtggactgc aagaaaggaa        3350

ccagagtcca ggtggacagt tcccagagaa tgctaagaat tgcagaacca        3400

gatgcaagat tcagtggctt ctacagcatg caaaaacaga accatctaca        3450

ggcagacaat ttctaccaaa cagtgtgaag aaaggcaact aggatgaggt        3500

ttcaaaagac ggaagacgac taaatctgct ctaaaaagta aactagaatt        3550

tgtgcacttg cttagtggat tgtattggat tgtgacttga tgtacagcgc        3600

taagacctta ctgggatggg ctctgtctac agcaatgtgc agaacaagca        3650

ttcccacttt tcctcaaaaa a                                       3671


<210> SEQ ID NO 90
<211> LENGTH: 1036
<212> TYPE: PRT
<213> ORGANISM: Homo sapiens

<400> SEQUENCE: 90

Met Tyr Leu Val Ala Gly Asp Arg Gly Leu Ala Gly Cys Gly His
1               5                   10                  15

Leu Leu Val Ser Leu Leu Gly Leu Leu Leu Leu Leu Ala Arg Ser
                20                  25                  30

Gly Thr Arg Ala Leu Val Cys Leu Pro Cys Asp Glu Ser Lys Cys
                35                  40                  45

Glu Glu Pro Arg Asn Cys Pro Gly Ser Ile Val Gln Gly Val Cys
                50                  55                  60

Gly Cys Cys Tyr Thr Cys Ala Ser Gln Arg Asn Glu Ser Cys Gly
                65                  70                  75

Gly Thr Phe Gly Ile Tyr Gly Thr Cys Asp Arg Gly Leu Arg Cys
                80                  85                  90

Val Ile Arg Pro Pro Leu Asn Gly Asp Ser Leu Thr Glu Tyr Glu
                95                  100                 105

Ala Gly Val Cys Glu Asp Glu Asn Trp Thr Asp Asp Gln Leu Leu
                110                 115                 120

Gly Phe Lys Pro Cys Asn Glu Asn Leu Ile Ala Gly Cys Asn Ile
                125                 130                 135

Ile Asn Gly Lys Cys Glu Cys Asn Thr Ile Arg Thr Cys Ser Asn
                140                 145                 150

Pro Phe Glu Phe Pro Ser Gln Asp Met Cys Leu Ser Ala Leu Lys
```

-continued

```
                155                 160                 165

Arg Ile Glu Glu Glu Lys Pro Asp Cys Ser Lys Ala Arg Cys Glu
                170                 175                 180

Val Gln Phe Ser Pro Arg Cys Pro Glu Asp Ser Val Leu Ile Glu
                185                 190                 195

Gly Tyr Ala Pro Pro Gly Glu Cys Cys Pro Leu Pro Ser Arg Cys
                200                 205                 210

Val Cys Asn Pro Ala Gly Cys Leu Arg Lys Val Cys Gln Pro Gly
                215                 220                 225

Asn Leu Asn Ile Leu Val Ser Lys Ala Ser Gly Lys Pro Gly Glu
                230                 235                 240

Cys Cys Asp Leu Tyr Glu Cys Lys Pro Val Phe Gly Val Asp Cys
                245                 250                 255

Arg Thr Val Glu Cys Pro Pro Val Gln Gln Thr Ala Cys Pro Pro
                260                 265                 270

Asp Ser Tyr Glu Thr Gln Val Arg Leu Thr Ala Asp Gly Cys Cys
                275                 280                 285

Thr Leu Pro Thr Arg Cys Glu Cys Leu Ser Gly Leu Cys Gly Phe
                290                 295                 300

Pro Val Cys Glu Val Gly Ser Thr Pro Arg Ile Val Ser Arg Gly
                305                 310                 315

Asp Gly Thr Pro Gly Lys Cys Cys Asp Val Phe Glu Cys Val Asn
                320                 325                 330

Asp Thr Lys Pro Ala Cys Val Phe Asn Asn Val Glu Tyr Tyr Asp
                335                 340                 345

Gly Asp Met Phe Arg Met Asp Asn Cys Arg Phe Cys Arg Cys Gln
                350                 355                 360

Gly Gly Val Ala Ile Cys Phe Thr Ala Gln Cys Gly Glu Ile Asn
                365                 370                 375

Cys Glu Arg Tyr Tyr Val Pro Glu Gly Glu Cys Cys Pro Val Cys
                380                 385                 390

Glu Asp Pro Val Tyr Pro Phe Asn Asn Pro Ala Gly Cys Tyr Ala
                395                 400                 405

Asn Gly Leu Ile Leu Ala His Gly Asp Arg Trp Arg Glu Asp Asp
                410                 415                 420

Cys Thr Phe Cys Gln Cys Val Asn Gly Glu Arg His Cys Val Ala
                425                 430                 435

Thr Val Cys Gly Gln Thr Cys Thr Asn Pro Val Lys Val Pro Gly
                440                 445                 450

Glu Cys Cys Pro Val Cys Glu Glu Pro Thr Ile Ile Thr Val Asp
                455                 460                 465

Pro Pro Ala Cys Gly Glu Leu Ser Asn Cys Thr Leu Thr Gly Lys
                470                 475                 480

Asp Cys Ile Asn Gly Phe Lys Arg Asp His Asn Gly Cys Arg Thr
                485                 490                 495

Cys Gln Cys Ile Asn Thr Glu Glu Leu Cys Ser Glu Arg Lys Gln
                500                 505                 510

Gly Cys Thr Leu Asn Cys Pro Phe Gly Phe Leu Thr Asp Ala Gln
                515                 520                 525

Asn Cys Glu Ile Cys Glu Cys Arg Pro Arg Pro Lys Lys Cys Arg
                530                 535                 540

Pro Ile Ile Cys Asp Lys Tyr Cys Pro Leu Gly Leu Leu Lys Asn
                545                 550                 555
```

-continued

```
Lys His Gly Cys Asp Ile Cys Arg Cys Lys Lys Cys Pro Glu Leu
                560                 565                 570

Ser Cys Ser Lys Ile Cys Pro Leu Gly Phe Gln Gln Asp Ser His
                575                 580                 585

Gly Cys Leu Ile Cys Lys Cys Arg Glu Ala Ser Ala Ser Ala Gly
                590                 595                 600

Pro Pro Ile Leu Ser Gly Thr Cys Leu Thr Val Asp Gly His His
                605                 610                 615

His Lys Asn Glu Glu Ser Trp His Asp Gly Cys Arg Glu Cys Tyr
                620                 625                 630

Cys Leu Asn Gly Arg Glu Met Cys Ala Leu Ile Thr Cys Pro Val
                635                 640                 645

Pro Ala Cys Gly Asn Pro Thr Ile His Pro Gly Gln Cys Cys Pro
                650                 655                 660

Ser Cys Ala Asp Asp Phe Val Val Gln Lys Pro Glu Leu Ser Thr
                665                 670                 675

Pro Ser Ile Cys His Ala Pro Gly Gly Glu Tyr Phe Val Glu Gly
                680                 685                 690

Glu Thr Trp Asn Ile Asp Ser Cys Thr Gln Cys Thr Cys His Ser
                695                 700                 705

Gly Arg Val Leu Cys Glu Thr Glu Val Cys Pro Pro Leu Leu Cys
                710                 715                 720

Gln Asn Pro Ser Arg Thr Gln Asp Ser Cys Cys Pro Gln Cys Thr
                725                 730                 735

Asp Gln Pro Phe Arg Pro Ser Leu Ser Arg Asn Asn Ser Val Pro
                740                 745                 750

Asn Tyr Cys Lys Asn Asp Glu Gly Asp Ile Phe Leu Ala Ala Glu
                755                 760                 765

Ser Trp Lys Pro Asp Val Cys Thr Ser Cys Ile Cys Ile Asp Ser
                770                 775                 780

Val Ile Ser Cys Phe Ser Glu Ser Cys Pro Ser Val Ser Cys Glu
                785                 790                 795

Arg Pro Val Leu Arg Lys Gly Gln Cys Cys Pro Tyr Cys Ile Glu
                800                 805                 810

Asp Thr Ile Pro Lys Lys Val Val Cys His Phe Ser Gly Lys Ala
                815                 820                 825

Tyr Ala Asp Glu Glu Arg Trp Asp Leu Asp Ser Cys Thr His Cys
                830                 835                 840

Tyr Cys Leu Gln Gly Gln Thr Leu Cys Ser Thr Val Ser Cys Pro
                845                 850                 855

Pro Leu Pro Cys Val Glu Pro Ile Asn Val Glu Gly Ser Cys Cys
                860                 865                 870

Pro Met Cys Pro Glu Met Tyr Val Pro Glu Pro Thr Asn Ile Pro
                875                 880                 885

Ile Glu Lys Thr Asn His Arg Gly Glu Val Asp Leu Glu Val Pro
                890                 895                 900

Leu Trp Pro Thr Pro Ser Glu Asn Asp Ile Val His Leu Pro Arg
                905                 910                 915

Asp Met Gly His Leu Gln Val Asp Tyr Arg Asp Asn Arg Leu His
                920                 925                 930

Pro Ser Glu Asp Ser Ser Leu Asp Ser Ile Ala Ser Val Val Val
                935                 940                 945
```

-continued

```
Pro Ile Ile Ile Cys Leu Ser Ile Ile Ile Ala Phe Leu Phe Ile
                950                 955                 960

Asn Gln Lys Lys Gln Trp Ile Pro Leu Leu Cys Trp Tyr Arg Thr
                965                 970                 975

Pro Thr Lys Pro Ser Ser Leu Asn Asn Gln Leu Val Ser Val Asp
                980                 985                 990

Cys Lys Lys Gly Thr Arg Val Gln Val Asp Ser Ser Gln Arg Met
                995                 1000                1005

Leu Arg Ile Ala Glu Pro Asp Ala Arg Phe Ser Gly Phe Tyr Ser
               1010                1015                1020

Met Gln Lys Gln Asn His Leu Gln Ala Asp Asn Phe Tyr Gln Thr
               1025                1030                1035

Val


<210> SEQ ID NO 91
<211> LENGTH: 1671
<212> TYPE: DNA
<213> ORGANISM: Homo sapiens

<400> SEQUENCE: 91

gcaaaaggaa gggagggaag cactccatca tctcactggg aagaacggca              50

cgggcatacc tgcagctact ggggttccac tgggcttgag ggtcgatttt             100

tcaccttttg aaggacaaga tgcattggaa gatgttgctg cttctgctgt             150

tgtattacaa tgctgaggct tctatgtgcc acaggtggag cagggctgtg             200

ctcttccctg ccgcccaccg gccaaagagg tcctcatcac tgccattgaa             250

cccagtcctg cagacctccc tggaggaggt ggagctgctc tacgagttcc             300

tgctggccga acttgagatc agccctgacc tgcagatctc catcaaggac             350

gaggagctgg cctccttgcg gaaggcctca gacttccgca ccgtctgcaa             400

caacgtcatc cccaagagca tcccagacat ccgccggctc agcgccagcc             450

tctccagcca ccctggcatc ctcaagaaag aagactttga aaggacagtg             500

ctgaccctgg cctacacagc ctaccgcaca gccctgtccc acggccatca             550

gaaggacatc tgggcgcagt ccctcgttag cctcttccag gccctgaggc             600

acgacttgat gcgctcctca cagccgggag tacctccctg agagactggc             650

ccacaccagg acctcagagc agggaccagc acagtaatcc agaaagtctt             700

cattctctac tccatttaca gagaccagca acaaaacact taccgctgac             750

acagagcagc agagatcaaa cagtaacccc gatgctcttt tctccttgta             800

gtttcctgga agacacatct gattcatgcc atcatgtgac ctgggctgga             850

agaaagggct ggaatggtca ttcaagacgc ctccatgggc agaatggttt             900

gcctatggca ggcagaattc tgatatgctt caacccagag cagtggccac             950

acactcaaga gtgagaacag gcgtgagcca ccgtgcctgg cccaggatct            1000

aaaaactttc taagtttcct ccatcgttgg catcctcaca gctatctcca            1050

atgtcactca agagacatca acagacattt aactgctgca gacttcattg            1100

ctctgtcacc tcaccttgaa tctaacaaat caaagtattt ctgcaggtcc            1150

aatggtctaa aatcaaatgc ttgttaaatg actttttaca acacccctta            1200

ctttcctaat ccatttcaat cttatttttt ttattgtggt aaaaaacaca            1250

tcacgtaaaa tgtaccatct taaccatttt taagcatatg gtacagcagt            1300
```

-continued gttaactcca tgcatgttgt gaaacagacc cccggaactt tctcatcttg 1350
taattctgaa gttctatacc caccgaacaa ctcctctttt ccccttcccc 1400
ctgcctgccc cagctcttgg caccattatt ctgctttctg tttttgagag 1450
tctgactact taagatacct catacaagcg ggatctggct tacatttctt 1500
gagcattgta ttctggaaaa gtgtttcctt cctctgaaaa atgggtagag 1550
ttctgaagga gaactactgg tcttattgta cacttgctgt acctattttt 1600
atttaacaaa tattcatcta tggtataata aagatgtcat ggttggaaaa 1650
aaaaaaaaaa aaaaaaaaaa a 1671

<210> SEQ ID NO 92
<211> LENGTH: 173
<212> TYPE: PRT
<213> ORGANISM: Homo sapiens

<400> SEQUENCE: 92

Met His Trp Lys Met Leu Leu Leu Leu Leu Leu Tyr Tyr Asn Ala
1 5 10 15

Glu Ala Ser Met Cys His Arg Trp Ser Arg Ala Val Leu Phe Pro
20 25 30

Ala Ala His Arg Pro Lys Arg Ser Ser Ser Leu Pro Leu Asn Pro
35 40 45

Val Leu Gln Thr Ser Leu Glu Glu Val Glu Leu Leu Tyr Glu Phe
50 55 60

Leu Leu Ala Glu Leu Glu Ile Ser Pro Asp Leu Gln Ile Ser Ile
65 70 75

Lys Asp Glu Glu Leu Ala Ser Leu Arg Lys Ala Ser Asp Phe Arg
80 85 90

Thr Val Cys Asn Asn Val Ile Pro Lys Ser Ile Pro Asp Ile Arg
95 100 105

Arg Leu Ser Ala Ser Leu Ser Ser His Pro Gly Ile Leu Lys Lys
110 115 120

Glu Asp Phe Glu Arg Thr Val Leu Thr Leu Ala Tyr Thr Ala Tyr
125 130 135

Arg Thr Ala Leu Ser His Gly His Gln Lys Asp Ile Trp Ala Gln
140 145 150

Ser Leu Val Ser Leu Phe Gln Ala Leu Arg His Asp Leu Met Arg
155 160 165

Ser Ser Gln Pro Gly Val Pro Pro
170

<210> SEQ ID NO 93
<211> LENGTH: 1312
<212> TYPE: DNA
<213> ORGANISM: Homo sapiens

<400> SEQUENCE: 93
caccatgcct ggggggtgct cccggggccc cgccgccggg gacgggcgtc 50
tgcggctggc gcgactagcg ctggtactcc tgggctgggt ctcctcgtct 100
tctcccacct cctcggcatc ctccttctcc tcctcggcgc cgttcctggc 150
ttccgccgtg tccgcccagc ccccgctgcc ggaccagtgc cccgcgctgt 200
gcgagtgctc cgaggcagcg cgcacagtca agtgcgttaa ccgcaatctg 250

-continued

```
accgaggtgc ccacggacct gcccgcctac gtgcgcaacc tcttccttac              300

cggcaaccag ctggccgtgc tccctgccgg cgccttcgcc cgccggccgc              350

cgctggcgga gctggccgcg ctcaacctca gcggcagccg cctggacgag              400

gtgcgcgcgg gcgccttcga gcatctgccc agcctgcgcc agctcgacct              450

cagccacaac ccactggccg acctcagtcc cttcgctttc tcgggcagca              500

atgccagcgt ctcggccccc agtccccttg tggaactgat cctgaaccac              550

atcgtgcccc ctgaagatga gcggcagaac cggagcttcg agggcatggt              600

ggtggcggcc ctgctggcgg gccgtgcact gcaggggctc cgccgcttgg              650

agctggccag caaccacttc ctttacctgc cgcgggatgt gctggcccaa              700

ctgcccagcc tcaggcacct ggacttaagt aataattcgc tggtgagcct              750

gacctacgtg tccttccgca acctgacaca tctagaaagc ctccacctgg              800

aggacaatgc cctcaaggtc cttcacaatg gcaccctggc tgagttgcaa              850

ggtctacccc acattagggt tttcctggac aacaatccct gggtctgcga              900

ctgccacatg gcagacatgg tgacctggct caaggaaaca gaggtagtgc              950

agggcaaaga ccggctcacc tgtgcatatc cggaaaaaat gaggaatcgg             1000

gtcctcttgg aactcaacag tgctgacctg gactgtgacc cgattcttcc             1050

cccatccctg caaacctctt atgtcttcct gggtattgtt ttagccctga             1100

taggcgctat tttcctcctg gttttgtatt tgaaccgcaa ggggataaaa             1150

aagtggatgc ataacatcag agatgcctgc agggatcaca tggaagggta             1200

tcattacaga tatgaaatca atgcggaccc cagattaaca aacctcagtt             1250

ctaactcgga tgtctgagaa atattagagg acagaccaag gacaactctg             1300

catgagatgt  ag                                                     1312


<210> SEQ ID NO 94
<211> LENGTH: 420
<212> TYPE: PRT
<213> ORGANISM: Homo sapiens

<400> SEQUENCE: 94

Met Pro Gly Gly Cys Ser Arg Gly Pro Ala Ala Gly Asp Gly Arg
  1               5                  10                  15

Leu Arg Leu Ala Arg Leu Ala Leu Val Leu Leu Gly Trp Val Ser
                 20                  25                  30

Ser Ser Ser Pro Thr Ser Ser Ala Ser Ser Phe Ser Ser Ser Ala
                 35                  40                  45

Pro Phe Leu Ala Ser Ala Val Ser Ala Gln Pro Pro Leu Pro Asp
                 50                  55                  60

Gln Cys Pro Ala Leu Cys Glu Cys Ser Glu Ala Ala Arg Thr Val
                 65                  70                  75

Lys Cys Val Asn Arg Asn Leu Thr Glu Val Pro Thr Asp Leu Pro
                 80                  85                  90

Ala Tyr Val Arg Asn Leu Phe Leu Thr Gly Asn Gln Leu Ala Val
                 95                 100                 105

Leu Pro Ala Gly Ala Phe Ala Arg Arg Pro Pro Leu Ala Glu Leu
                110                 115                 120

Ala Ala Leu Asn Leu Ser Gly Ser Arg Leu Asp Glu Val Arg Ala
                125                 130                 135
```

-continued

```
Gly Ala Phe Glu His Leu Pro Ser Leu Arg Gln Leu Asp Leu Ser
                140                 145                 150

His Asn Pro Leu Ala Asp Leu Ser Pro Phe Ala Phe Ser Gly Ser
                155                 160                 165

Asn Ala Ser Val Ser Ala Pro Ser Pro Leu Val Glu Leu Ile Leu
                170                 175                 180

Asn His Ile Val Pro Pro Glu Asp Glu Arg Gln Asn Arg Ser Phe
                185                 190                 195

Glu Gly Met Val Val Ala Ala Leu Leu Ala Gly Arg Ala Leu Gln
                200                 205                 210

Gly Leu Arg Arg Leu Glu Leu Ala Ser Asn His Phe Leu Tyr Leu
                215                 220                 225

Pro Arg Asp Val Leu Ala Gln Leu Pro Ser Leu Arg His Leu Asp
                230                 235                 240

Leu Ser Asn Asn Ser Leu Val Ser Leu Thr Tyr Val Ser Phe Arg
                245                 250                 255

Asn Leu Thr His Leu Glu Ser Leu His Leu Glu Asp Asn Ala Leu
                260                 265                 270

Lys Val Leu His Asn Gly Thr Leu Ala Glu Leu Gln Gly Leu Pro
                275                 280                 285

His Ile Arg Val Phe Leu Asp Asn Asn Pro Trp Val Cys Asp Cys
                290                 295                 300

His Met Ala Asp Met Val Thr Trp Leu Lys Glu Thr Glu Val Val
                305                 310                 315

Gln Gly Lys Asp Arg Leu Thr Cys Ala Tyr Pro Glu Lys Met Arg
                320                 325                 330

Asn Arg Val Leu Leu Glu Leu Asn Ser Ala Asp Leu Asp Cys Asp
                335                 340                 345

Pro Ile Leu Pro Pro Ser Leu Gln Thr Ser Tyr Val Phe Leu Gly
                350                 355                 360

Ile Val Leu Ala Leu Ile Gly Ala Ile Phe Leu Leu Val Leu Tyr
                365                 370                 375

Leu Asn Arg Lys Gly Ile Lys Lys Trp Met His Asn Ile Arg Asp
                380                 385                 390

Ala Cys Arg Asp His Met Glu Gly Tyr His Tyr Arg Tyr Glu Ile
                395                 400                 405

Asn Ala Asp Pro Arg Leu Thr Asn Leu Ser Ser Asn Ser Asp Val
                410                 415                 420


<210> SEQ ID NO 95
<211> LENGTH: 3719
<212> TYPE: DNA
<213> ORGANISM: Homo sapiens

<400> SEQUENCE: 95

ggcttctaca gtccacaaca cccaccagcc ccaggcccag cagaatgagc                50

ccagtgagtg ccggggctcc cagtttggct gttgctatga caacgtggcc               100

actgcagccg gtcctcttgg ggaaggctgt gtgggccagc ccagccatgc               150

ctaccccgtg cggtgcctgc tgcccagtgc ccatggctct tgtgcagact               200

gggctgcccg ctggtacttc gttgcctctg tgggccaatg taaccgcttc               250

tggtatggcg gctgccatgg caatgccaat aactttgcct cggagcaaga               300

gtgcatgagc agctgccagg gatctctcca tgggccccgt cgtccccagc               350
```

-continued

```
ctggggcttc tggaaggagc acccacacgg atggtggcgg cagcagtcct       400
gcaggcgagc aggaacccag ccagcacagg acaggggccg cggtgcagag       450
aaagccctgg ccttctggtg gtctctggcg gcaagaccaa cagcctgggc       500
caggggaggc cccccacacc caggcctttg gagaatggcc atgggggcag       550
gagcttgggt ccagggcccc tggactgggt ggagatgccg gatcaccagc       600
gccacccttc cacagctcct cctacagatc tcacttccca cctctccagg       650
attagcttgg caggtgtgga gccctcgttg gtgcaggcag ccctggggca       700
gttggtgcgg ctctcctgct cagacgacac tgccccggaa tcccaggctg       750
cctggcagaa agatggccag cccatctcct ctgacaggca caggctgcag       800
ttcgacggat ccctgatcat ccacccccctg caggcagagg acgcgggcac       850
ctacagctgt ggcagcaccc ggccaggccg cgactcccag aagatccaac       900
tccgcattat agggggtgac atggccgtgc tgtctgaggc tgagctgagc       950
cgcttccctc agcccaggga cccagctcag gactttggcc aagcgggggc      1000
tgctgggccc ctgggggcca tcccctcttc acacccacag cctgcaaaca      1050
ggctgcgttt ggaccagaac cagccccggg tggtggatgc cagtccaggc      1100
cagcggatcc ggatgacctg ccgtgccgaa ggcttcccgc cccagccat       1150
cgagtggcag agagatgggc agcctgtctc ttctcccaga caccagctgc      1200
agcctgatgg ctccctggtc attagccgag tggctgtaga agatggcggc      1250
ttctacacct gtgtcgcttt caatgggcag gaccgagacc agcgatgggt      1300
ccagctcaga gttctggggg agctgacaat ctcaggactg ccccctactg      1350
tgacagtgcc agagggtgat acggccaggc tattgtgtgt ggtagcagga      1400
gaaagtgtga acatcaggtg gtccaggaac gggctacctg tgcaggctga      1450
tggccaccgt gtccaccagt ccccagatgg cacgctgctc atttacaact      1500
tgcgggccag ggatgagggc tcctacatgt gcagtgccta ccaggggagc      1550
caggcagtca gccgcagcac cgaggtgaag gtggtctcac cagcacccac      1600
cgcccagccc agggaccctg gcagggactg cgtcgaccag ccagagctgg      1650
ccaactgtga tttgatcctg caggcccagc tttgtggcaa tgagtattac      1700
tccagcttct gctgtgccag ctgttcacgt ttccagcctc acgctcagcc      1750
catctggcag tagggatgaa ggctagttcc agccccagtc caaaatagtt      1800
catagggcta gggagaaagg aagatggact cttggcttcc tctctctggc      1850
tggcaaaggg agttatcttc tggaatacat tagctctttc aaaaacccac      1900
ccagtgttta gcctcaacgg cagccagtta ccagcttctc tctgtagcct      1950
tcagcagtgt ttgcatctct gacataacca caggctgctg ttttcaagaa      2000
gagcaatctg tttggataag aaaaaccttt actttacagc ttccctttat      2050
aatttgttac acaggaatag ttaaatgcat ttgtttgttt gttttttgag      2100
acggagtttc actcttgttg cccaggctgg agggcaatgg cgcgatctca      2150
gctcactgca acctccgtct cctgggttct tgattctcct gtgtcagcct      2200
tctgagtagc tgggattaca gatgcctatc accatgcctg ggtaattttt      2250
gtatttttag ttgagatggg gtttcgccat gttggccagg ctggtctcga      2300
acttctgacc tcagatgatc tgcccgcctc agcctcccaa agtgctggga      2350
```

-continued

```
ttacaggcat gagccaccac gcccagccat caatgcattt tttttatttt          2400

tttttgaga cagagtttcg cacttcttgc ccaggctgga gtacaatggt           2450

gcgatcttgg ctcactgcaa cctccacctc ctgggttcaa gcgcttctcc          2500

agcctcagcc tcctgagtag ctgggattac aggtatgtgc caccatgcct          2550

ggctaatttt gtatttttgg tggagacggg gtttctccat gttggtcaga          2600

ctggtcttga actcccgacc tcaggtaatc cgcccgcctc cgcctcccaa          2650

aatgctggga ttagaggtgt gagccactgt gcccagccca tcaatgtgtt          2700

ttaaagctag ctgtcagggt tccacttaat ttaaagctgg gcagggagat          2750

gtgtaatgat ttcaaagtta acacctgttt gttttctaaa gggcatgcca          2800

agtcctgctg tatcagggaa gtattctgtg ctaaaatcag cgatggttca          2850

ttgctctagt ctctctcacc cttctaggca gtgcatcagt cagctctaaa          2900

tctggtgcag agggttaaca gcataaccct tgttggcaaa atggaataga          2950

tgttaagacc tcaaataggg atttgggatg aaacagctgc agttagcact          3000

gttatctgag catgaaagaa ctggaaacgc tccttacgtc gagatgttgg          3050

accttgaagc cctcctgagg ccaacatgca aatctggctg tgacggttca          3100

tctgacacct gtgtaaagct gaccagcctg ctctgtacag tgacaatgag          3150

gagcccctct cttccttaag taggaatctg tgaagcaaaa tgtttgctgc          3200

caaagacaaa tcagactgtc agtcattaaa aacagcatta gcaggatgag          3250

gatagcaatg gggaagggtt gtgggcaatg cagtaacagg gaaatggctt          3300

cagaaatggt ttgagttgga agacaacatt cttcatctct caggacttct          3350

aattccttga tgctaaaaga agaggcatgg attctatgag cttccaagtc          3400

cctttccact ttaaccttct acaaatcttt cagaggactg cctagtagca          3450

aaggttattc ctggacacag gaaagacggg cattacaggg accaaagctc          3500

tgaaaggtga cttttattac caacacactg gctggaaaag ggacaaacca          3550

catcacgggt gagtgatact tctcagtctt ctctactcat tcaacaaagg          3600

aaatgtgggc tggggcagag gtcttttttc atttaatact ggaaaaatat          3650

tgaagagcat ccatgttcac ttatggctgg ttttgctata gaaattggaa          3700

aataaaggcc  actttttg                                            3719
```

<210> SEQ ID NO 96
<211> LENGTH: 477
<212> TYPE: PRT
<213> ORGANISM: Homo sapiens

<400> SEQUENCE: 96

```
Met Gly Pro Val Val Pro Ser Leu Gly Leu Leu Glu Gly Ala Pro
  1               5                  10                  15

Thr Arg Met Val Ala Ala Ala Val Leu Gln Ala Ser Arg Asn Pro
                 20                  25                  30

Ala Ser Thr Gly Gln Gly Pro Arg Cys Arg Glu Ser Pro Gly Leu
                 35                  40                  45

Leu Val Val Ser Gly Gly Lys Thr Asn Ser Leu Gly Gln Gly Arg
                 50                  55                  60

Pro Pro Thr Pro Arg Pro Leu Glu Asn Gly His Gly Gly Arg Ser
                 65                  70                  75
```

-continued

```
Leu Gly Pro Gly Pro Leu Asp Trp Val Glu Met Pro Asp His Gln
                80                  85                  90

Arg His Pro Ser Thr Ala Pro Pro Thr Asp Leu Thr Ser His Leu
                95                  100                 105

Ser Arg Ile Ser Leu Ala Gly Val Glu Pro Ser Leu Val Gln Ala
                110                 115                 120

Ala Leu Gly Gln Leu Val Arg Leu Ser Cys Ser Asp Asp Thr Ala
                125                 130                 135

Pro Glu Ser Gln Ala Ala Trp Gln Lys Asp Gly Gln Pro Ile Ser
                140                 145                 150

Ser Asp Arg His Arg Leu Gln Phe Asp Gly Ser Leu Ile Ile His
                155                 160                 165

Pro Leu Gln Ala Glu Asp Ala Gly Thr Tyr Ser Cys Gly Ser Thr
                170                 175                 180

Arg Pro Gly Arg Asp Ser Gln Lys Ile Gln Leu Arg Ile Ile Gly
                185                 190                 195

Gly Asp Met Ala Val Leu Ser Glu Ala Glu Leu Ser Arg Phe Pro
                200                 205                 210

Gln Pro Arg Asp Pro Ala Gln Asp Phe Gly Gln Ala Gly Ala Ala
                215                 220                 225

Gly Pro Leu Gly Ala Ile Pro Ser Ser His Pro Gln Pro Ala Asn
                230                 235                 240

Arg Leu Arg Leu Asp Gln Asn Gln Pro Arg Val Val Asp Ala Ser
                245                 250                 255

Pro Gly Gln Arg Ile Arg Met Thr Cys Arg Ala Glu Gly Phe Pro
                260                 265                 270

Pro Pro Ala Ile Glu Trp Gln Arg Asp Gly Gln Pro Val Ser Ser
                275                 280                 285

Pro Arg His Gln Leu Gln Pro Asp Gly Ser Leu Val Ile Ser Arg
                290                 295                 300

Val Ala Val Glu Asp Gly Gly Phe Tyr Thr Cys Val Ala Phe Asn
                305                 310                 315

Gly Gln Asp Arg Asp Gln Arg Trp Val Gln Leu Arg Val Leu Gly
                320                 325                 330

Glu Leu Thr Ile Ser Gly Leu Pro Pro Thr Val Thr Val Pro Glu
                335                 340                 345

Gly Asp Thr Ala Arg Leu Leu Cys Val Val Ala Gly Glu Ser Val
                350                 355                 360

Asn Ile Arg Trp Ser Arg Asn Gly Leu Pro Val Gln Ala Asp Gly
                365                 370                 375

His Arg Val His Gln Ser Pro Asp Gly Thr Leu Leu Ile Tyr Asn
                380                 385                 390

Leu Arg Ala Arg Asp Glu Gly Ser Tyr Met Cys Ser Ala Tyr Gln
                395                 400                 405

Gly Ser Gln Ala Val Ser Arg Ser Thr Glu Val Lys Val Val Ser
                410                 415                 420

Pro Ala Pro Thr Ala Gln Pro Arg Asp Pro Gly Arg Asp Cys Val
                425                 430                 435

Asp Gln Pro Glu Leu Ala Asn Cys Asp Leu Ile Leu Gln Ala Gln
                440                 445                 450

Leu Cys Gly Asn Glu Tyr Tyr Ser Ser Phe Cys Cys Ala Ser Cys
                455                 460                 465
```

-continued

Ser Arg Phe Gln Pro His Ala Gln Pro Ile Trp Gln
470 475

<210> SEQ ID NO 97
<211> LENGTH: 3979
<212> TYPE: DNA
<213> ORGANISM: Homo sapiens

<400> SEQUENCE: 97
ggcggcggga gcagcgaagg gggcggcagg gatcctccag gctgccggct 50
gggaaggcgt gggcgacccg gtgtgtggcg cgcccagagc cccgcgtttc 100
agccctaggg aaggaagcca gttgagggaa gttctccatg aatgtacgtc 150
acaatgatga tgaccgacca aatccctctg gaactgccac cattgctgaa 200
cggagaggta gccatgatgc cccacttggt gaatggagat gcagctcagc 250
atgttattct cgttcaagtt aatccaggtg agactttcac aataagagca 300
gaggatggaa cacttcagtg cattcaagga cctgctgaag ttcccatgat 350
gtcacccaat ggatccattc ctcccattca tgtgcctcca ggttatatct 400
cacaggtgat tgaagatagt actggagtcc gccgggtggt ggtcacaccc 450
cagtctcctg agtgttatcc cccaagctac ccctcagcca tgtctccaac 500
ccatcatctc cctccctatc tgactcacca tccacatttt attcataact 550
cacacacggc ttactaccca cctgttaccg gacctggaga tatgccgcct 600 cagtttttc cccagcatca tcttccccac acaatatatg gtgagcaaga 650
aattatacca ttttatggaa tgtcaagcta catcacccga gaagaccagt 700
acagcaagcc tccgcacaaa aaactgaaag accgccagat cgatcgccag 750
aaccgcctca acagccctcc ttcttctatc tacaaaagca gctgcacaac 800
agtatacaat ggctatggga agggccatag tggtggaagt ggcggaggcg 850
gcagcggtag tggtcccgga attaagaaaa cagagcgacg agcaagaagc 900
agcccaaagt cgaatgattc agacttgcaa gaatatgagt tggaagtaaa 950
gagggtgcaa gacattcttt cgggaataga gaaaccacag gtttctaata 1000
ttcaggcaag agcagttgtg ttgtcctggg ctccccctgt tggactttcc 1050
tgtggacccc acagtggtct ttccttcccc tacagttacg aggtggcctt 1100
atcagacaaa ggacgagatg gaaaatacaa gataatttac agtggagaag 1150
aattagaatg taacctgaaa gatcttagac cagcaacaga ttatcatgtg 1200
agggtgtatg ccatgtacaa ttccgtaaag ggatcctgct ccgagcctgt 1250
tagcttcacc acccacagct gtgcacccga gtgtcctttc ccccctaagc 1300
tggcacatag gagcaaaagt tcactaaccc tgcagtggaa ggcaccaatt 1350
gacaacggtt caaaaatcac caactacctt ttagagtggg atgagggaaa 1400
aagaaatagt ggtttcagac agtgcttctt cgggagccag aagcactgca 1450
agttgacaaa gctttgtccg gcaatggggt acacattcag gctggccgct 1500
cgaaacgaca ttggcaccag tggttatagc caagaggtgg tgtgctacac 1550
attaggaaat atccctcaga tgccttctgc actaaggctg gttcgagctg 1600
gcatcacatg ggtcacgttg cagtggagta agccagaagg ctgttcaccc 1650
gaggaagtga tcacctacac cttggaaatt caggaggatg aaaatgataa 1700

-continued

```
ccttttccac ccaaaataca ctggagagga tttaacctgt actgtgaaaa     1750
atctcaaaag aagcacacag tataaattca ggctgactgc ttctaatacg     1800
gaaggaaaaa gctgtccaag cgaagttctt gtttgtacga cgagtcctga     1850
caggcctgga cctcctacca gaccgcttgt caaaggccca gttacatctc     1900
atggctttag tgtcaaatgg gatcccccta aggacaatgg tggttcagaa     1950
atcctcaagt acttgctaga gattactgat ggaaattctg aagcgaatca     2000
gtgggaagtg gcctacagtg ggtcggctac cgaatacacc ttcacccact     2050
tgaaaccagg cactttgtac aaactccgag catgctgcat cagtaccggc     2100
ggacacagcc agtgttctga aagtctccct gttcgcacac taagcattgc     2150
accaggtcaa tgtcgaccac cgagggtttt gggtagacca aagcacaaag     2200
aagtccactt agagtgggat gttcctgcat cggaaagtgg ctgtgaggtc     2250
tcagagtaca gcgtggagat gacggagccc gaagacgtag cctcggaagt     2300
gtaccatggc ccagagctgg agtgcaccgt cggcaacctg cttcctggaa     2350
ccgtgtatcg cttccgggtg agggctctga atgatggagg gtatggtccc     2400
tattctgatg tctcagaaat taccactgct gcagggcctc ctggacaatg     2450
caaagcacct tgtatttctt gtacacctga tggatgtgtc ttagtgggtt     2500
gggagagtcc tgatagttct ggtgctgaca tctcagagta caggttggaa     2550
tggggagaag atgaagaatc cttagaactc atttatcatg ggacagacac     2600
ccgttttgaa ataagagacc tgttgcctgc tgcacagtat tgctgtagac     2650
tacaggcctt caatcaagca ggggcagggc cgtacagtga acttgtcctt     2700
tgccagacgc cagcgtctgc ccctgacccc gtctccactc tctgtgtcct     2750
ggaggaggag ccccttgatg cctaccctga ttcaccttct gcgtgccttg     2800
tactgaactg ggaagagccg tgcaataacg gatctgaaat ccttgcttac     2850
accattgatc taggagacac tagcattacc gtgggcaaca ccaccatgca     2900
tgttatgaaa gatctccttc cagaaaccac ctaccggatc agaattcagg     2950
ctataaatga aattggagct ggaccattta gtcagttcat taaagcaaaa     3000
actcggccat taccaccctt gcctcctagg ctagaatgtg ctgctgctgg     3050
tcctcagagc ctgaagctaa aatggggaga cagtaactcc aagacacatg     3100
ctgctgagga cattgtgtac acactacagc tggaggacag aaacaagagg     3150
tttatttcaa tctacagagg acccagccac acctacaagg tccagagact     3200
gacggaattc acatgctact ccttcagaat ccaggcagca agcgaggctg     3250
gagaagggcc cttctcagaa acctatacct tcagcacaac caaaagtgtc     3300
ccccccacca tcaaagcacc tcgagtaaca cagttagaag taaattcatg     3350
tgaaatttta tgggagacgg taccatcaat gaaaggtgac cctgttaact     3400
acattctgca ggtattggtt ggaagagaat ctgagtacaa acaggtgtac     3450
aagggagaag aagccacatt ccaaatctca ggcctccaga ccaacacaga     3500
ctacaggttc cgcgtatgtg cgtgtcgtcg ctgtttagac acctctcagg     3550
agctaagcgg agccttcagc ccctctgcgg cttttgtatt acaacgaagt     3600
gaggtcatgc ttacagggga catggggagc ttagatgatc ccaaaatgaa     3650
gagcatgatg cctactgatg aacagtttgc agccatcatt gtgcttggct     3700
```

-continued

```
ttgcaacttt gtccatttta tttgccttta tattacagta cttcttaatg          3750

aagtaaaccc aacaaaacta gaggtatgaa ttaatgctac acattttaat          3800

acacacattt attcagatac tcccctttt aaagcccttt tgttttttga          3850

tttatatact ctgttttaca gatttagcta gaaaaaaaat gtcagtgttt          3900

tggtgcacct ttttgaaatg caaaactagg aaaaggttaa actggatttt          3950

tttttaaaaa aaaaaaaaaa  aaaaaaaaa                                3979
```

<210> SEQ ID NO 98
<211> LENGTH: 1204
<212> TYPE: PRT
<213> ORGANISM: Homo sapiens

<400> SEQUENCE: 98

```
Met Tyr Val Thr Met Met Met Thr Asp Gln Ile Pro Leu Glu Leu
  1               5                  10                  15

Pro Pro Leu Leu Asn Gly Glu Val Ala Met Met Pro His Leu Val
                 20                  25                  30

Asn Gly Asp Ala Ala Gln His Val Ile Leu Val Gln Val Asn Pro
                 35                  40                  45

Gly Glu Thr Phe Thr Ile Arg Ala Glu Asp Gly Thr Leu Gln Cys
                 50                  55                  60

Ile Gln Gly Pro Ala Glu Val Pro Met Met Ser Pro Asn Gly Ser
                 65                  70                  75

Ile Pro Pro Ile His Val Pro Pro Gly Tyr Ile Ser Gln Val Ile
                 80                  85                  90

Glu Asp Ser Thr Gly Val Arg Arg Val Val Val Thr Pro Gln Ser
                 95                 100                 105

Pro Glu Cys Tyr Pro Pro Ser Tyr Pro Ser Ala Met Ser Pro Thr
                110                 115                 120

His His Leu Pro Pro Tyr Leu Thr His His Pro His Phe Ile His
                125                 130                 135

Asn Ser His Thr Ala Tyr Tyr Pro Pro Val Thr Gly Pro Gly Asp
                140                 145                 150

Met Pro Pro Gln Phe Phe Pro Gln His His Leu Pro His Thr Ile
                155                 160                 165

Tyr Gly Glu Gln Glu Ile Ile Pro Phe Tyr Gly Met Ser Ser Tyr
                170                 175                 180

Ile Thr Arg Glu Asp Gln Tyr Ser Lys Pro Pro His Lys Lys Leu
                185                 190                 195

Lys Asp Arg Gln Ile Asp Arg Gln Asn Arg Leu Asn Ser Pro Pro
                200                 205                 210

Ser Ser Ile Tyr Lys Ser Ser Cys Thr Thr Val Tyr Asn Gly Tyr
                215                 220                 225

Gly Lys Gly His Ser Gly Gly Ser Gly Gly Gly Gly Ser Gly Ser
                230                 235                 240

Gly Pro Gly Ile Lys Lys Thr Glu Arg Arg Ala Arg Ser Ser Pro
                245                 250                 255

Lys Ser Asn Asp Ser Asp Leu Gln Glu Tyr Glu Leu Glu Val Lys
                260                 265                 270

Arg Val Gln Asp Ile Leu Ser Gly Ile Glu Lys Pro Gln Val Ser
                275                 280                 285

Asn Ile Gln Ala Arg Ala Val Val Leu Ser Trp Ala Pro Pro Val
```

-continued

```
                290                 295                 300
Gly Leu Ser Cys Gly Pro His Ser Gly Leu Ser Phe Pro Tyr Ser
                305                 310                 315
Tyr Glu Val Ala Leu Ser Asp Lys Gly Arg Asp Gly Lys Tyr Lys
                320                 325                 330
Ile Ile Tyr Ser Gly Glu Glu Leu Glu Cys Asn Leu Lys Asp Leu
                335                 340                 345
Arg Pro Ala Thr Asp Tyr His Val Arg Val Tyr Ala Met Tyr Asn
                350                 355                 360
Ser Val Lys Gly Ser Cys Ser Glu Pro Val Ser Phe Thr Thr His
                365                 370                 375
Ser Cys Ala Pro Glu Cys Pro Phe Pro Pro Lys Leu Ala His Arg
                380                 385                 390
Ser Lys Ser Ser Leu Thr Leu Gln Trp Lys Ala Pro Ile Asp Asn
                395                 400                 405
Gly Ser Lys Ile Thr Asn Tyr Leu Leu Glu Trp Asp Glu Gly Lys
                410                 415                 420
Arg Asn Ser Gly Phe Arg Gln Cys Phe Phe Gly Ser Gln Lys His
                425                 430                 435
Cys Lys Leu Thr Lys Leu Cys Pro Ala Met Gly Tyr Thr Phe Arg
                440                 445                 450
Leu Ala Ala Arg Asn Asp Ile Gly Thr Ser Gly Tyr Ser Gln Glu
                455                 460                 465
Val Val Cys Tyr Thr Leu Gly Asn Ile Pro Gln Met Pro Ser Ala
                470                 475                 480
Leu Arg Leu Val Arg Ala Gly Ile Thr Trp Val Thr Leu Gln Trp
                485                 490                 495
Ser Lys Pro Glu Gly Cys Ser Pro Glu Glu Val Ile Thr Tyr Thr
                500                 505                 510
Leu Glu Ile Gln Glu Asp Glu Asn Asp Asn Leu Phe His Pro Lys
                515                 520                 525
Tyr Thr Gly Glu Asp Leu Thr Cys Thr Val Lys Asn Leu Lys Arg
                530                 535                 540
Ser Thr Gln Tyr Lys Phe Arg Leu Thr Ala Ser Asn Thr Glu Gly
                545                 550                 555
Lys Ser Cys Pro Ser Glu Val Leu Val Cys Thr Thr Ser Pro Asp
                560                 565                 570
Arg Pro Gly Pro Pro Thr Arg Pro Leu Val Lys Gly Pro Val Thr
                575                 580                 585
Ser His Gly Phe Ser Val Lys Trp Asp Pro Pro Lys Asp Asn Gly
                590                 595                 600
Gly Ser Glu Ile Leu Lys Tyr Leu Leu Glu Ile Thr Asp Gly Asn
                605                 610                 615
Ser Glu Ala Asn Gln Trp Glu Val Ala Tyr Ser Gly Ser Ala Thr
                620                 625                 630
Glu Tyr Thr Phe Thr His Leu Lys Pro Gly Thr Leu Tyr Lys Leu
                635                 640                 645
Arg Ala Cys Cys Ile Ser Thr Gly Gly His Ser Gln Cys Ser Glu
                650                 655                 660
Ser Leu Pro Val Arg Thr Leu Ser Ile Ala Pro Gly Gln Cys Arg
                665                 670                 675
Pro Pro Arg Val Leu Gly Arg Pro Lys His Lys Glu Val His Leu
                680                 685                 690
```

-continued

```
Glu Trp Asp Val Pro Ala Ser Glu Ser Gly Cys Glu Val Ser Glu
                695                 700                 705

Tyr Ser Val Glu Met Thr Glu Pro Glu Asp Val Ala Ser Glu Val
                710                 715                 720

Tyr His Gly Pro Glu Leu Glu Cys Thr Val Gly Asn Leu Leu Pro
                725                 730                 735

Gly Thr Val Tyr Arg Phe Arg Val Arg Ala Leu Asn Asp Gly Gly
                740                 745                 750

Tyr Gly Pro Tyr Ser Asp Val Ser Glu Ile Thr Thr Ala Ala Gly
                755                 760                 765

Pro Pro Gly Gln Cys Lys Ala Pro Cys Ile Ser Cys Thr Pro Asp
                770                 775                 780

Gly Cys Val Leu Val Gly Trp Glu Ser Pro Asp Ser Ser Gly Ala
                785                 790                 795

Asp Ile Ser Glu Tyr Arg Leu Glu Trp Gly Glu Asp Glu Glu Ser
                800                 805                 810

Leu Glu Leu Ile Tyr His Gly Thr Asp Thr Arg Phe Glu Ile Arg
                815                 820                 825

Asp Leu Leu Pro Ala Ala Gln Tyr Cys Cys Arg Leu Gln Ala Phe
                830                 835                 840

Asn Gln Ala Gly Ala Gly Pro Tyr Ser Glu Leu Val Leu Cys Gln
                845                 850                 855

Thr Pro Ala Ser Ala Pro Asp Pro Val Ser Thr Leu Cys Val Leu
                860                 865                 870

Glu Glu Glu Pro Leu Asp Ala Tyr Pro Asp Ser Pro Ser Ala Cys
                875                 880                 885

Leu Val Leu Asn Trp Glu Glu Pro Cys Asn Asn Gly Ser Glu Ile
                890                 895                 900

Leu Ala Tyr Thr Ile Asp Leu Gly Asp Thr Ser Ile Thr Val Gly
                905                 910                 915

Asn Thr Thr Met His Val Met Lys Asp Leu Leu Pro Glu Thr Thr
                920                 925                 930

Tyr Arg Ile Arg Ile Gln Ala Ile Asn Glu Ile Gly Ala Gly Pro
                935                 940                 945

Phe Ser Gln Phe Ile Lys Ala Lys Thr Arg Pro Leu Pro Pro Leu
                950                 955                 960

Pro Pro Arg Leu Glu Cys Ala Ala Ala Gly Pro Gln Ser Leu Lys
                965                 970                 975

Leu Lys Trp Gly Asp Ser Asn Ser Lys Thr His Ala Ala Glu Asp
                980                 985                 990

Ile Val Tyr Thr Leu Gln Leu Glu Asp Arg Asn Lys Arg Phe Ile
                995                 1000                1005

Ser Ile Tyr Arg Gly Pro Ser His Thr Tyr Lys Val Gln Arg Leu
                1010                1015                1020

Thr Glu Phe Thr Cys Tyr Ser Phe Arg Ile Gln Ala Ala Ser Glu
                1025                1030                1035

Ala Gly Glu Gly Pro Phe Ser Glu Thr Tyr Thr Phe Ser Thr Thr
                1040                1045                1050

Lys Ser Val Pro Pro Thr Ile Lys Ala Pro Arg Val Thr Gln Leu
                1055                1060                1065

Glu Val Asn Ser Cys Glu Ile Leu Trp Glu Thr Val Pro Ser Met
                1070                1075                1080
```

-continued

Lys Gly Asp Pro Val Asn Tyr Ile Leu Gln Val Leu Val Gly Arg
1085 1090 1095

Glu Ser Glu Tyr Lys Gln Val Tyr Lys Gly Glu Glu Ala Thr Phe
1100 1105 1110

Gln Ile Ser Gly Leu Gln Thr Asn Thr Asp Tyr Arg Phe Arg Val
1115 1120 1125

Cys Ala Cys Arg Arg Cys Leu Asp Thr Ser Gln Glu Leu Ser Gly
1130 1135 1140

Ala Phe Ser Pro Ser Ala Ala Phe Val Leu Gln Arg Ser Glu Val
1145 1150 1155

Met Leu Thr Gly Asp Met Gly Ser Leu Asp Asp Pro Lys Met Lys
1160 1165 1170

Ser Met Met Pro Thr Asp Glu Gln Phe Ala Ala Ile Ile Val Leu
1175 1180 1185

Gly Phe Ala Thr Leu Ser Ile Leu Phe Ala Phe Ile Leu Gln Tyr
1190 1195 1200

Phe Leu Met Lys

<210> SEQ ID NO 99
<211> LENGTH: 2065
<212> TYPE: DNA
<213> ORGANISM: Homo sapiens

<400> SEQUENCE: 99
cccaaagagg tgaggagccg gcagcggggg cggctgtaac tgtgaggaag 50
gctgcagagt ggcgacgtct acgccgtagg ttggaggctg tggggggtgg 100
ccgggcgcca gctcccaggc cgcagaagtg acctgcggtg gagttccctc 150
ctcgctgctg gagaacggag ggagaaggtt gctggccggg tgaaagtgcc 200
tccctctgct tgacggggct gaggggcccg aagtctaggg cgtccgtagt 250
cgccccggcc tccgtgaagc cccaggtcta gagatatgac ccgagagtgc 300
ccatctccgg ccccggggcc tggggctccg ctgagtggat cggtgctggc 350
agaggcggca gtagtgtttg cagtggtgct gagcatccac gcaaccgtat 400
gggaccgata ctcgtggtgc gccgtggccc tcgcagtgca ggccttctac 450
gtccaataca agtgggaccg gctgctacag cagggaagcg ccgtcttcca 500
gttccgaatg tccgcaaaca gtggcctatt gcccgcctcc atggtcatgc 550
ctttgcttgg actagtcatg aaggagcggt gccagactgc tgggaacccg 600
ttctttgagc gttttggcat tgtggtggca gccactggca tggcagtggc 650
cctcttctca tcagtgttgg cgctcggcat cactcgccca gtgccaacca 700
acacttgtgt catcttgggc ttggctggag gtgttatcat ttatatcatg 750
aagcactcgt tgagcgtggg ggaggtgatc gaagtcctgg aagtccttct 800
gatcttcgtt tatctcaaca tgatcctgct gtacctgctg ccccgctgct 850
tcacccctgg tgaggcactg ctggtattgg gtggcattag ctttgtcctc 900
aaccagctca tcaagcgctc tctgacactg gtggaaagtc agggggaccc 950
agtggacttc ttcctgctgg tggtggtagt agggatggta ctcatgggca 1000
ttttcttcag cactctgttt gtcttcatgg actcaggcac ctgggcctcc 1050
tccatcttct tccacctcat gacctgtgtg ctgagccttg gtgtggtcct 1100
accctggctg caccggctca tccgcaggaa tcccctgctc tggcttcttc 1150

-continued

```
agtttctctt ccagacagac acccgcatct acctcctagc ctattggtct         1200

ctgctggcca ccttggcctg cctggtggtg ctgtaccaga atgccaagcg         1250

gtcatcttcc gagtccaaga agcaccaggc ccccaccatc gcccgaaagt         1300

atttccacct cattgtggta gccacctaca tcccaggtat catctttgac         1350

cggccactgc tctatgtagc cgccactgta tgcctggcgg tcttcatctt         1400

cctggagtat gtgcgctact tccgcatcaa gcctttgggt cacactctac         1450

ggagcttcct gtcccttttt ctggatgaac gagacagtgg accactcatt         1500

ctgacacaca tctacctgct cctgggcatg tctcttccca tctggctgat         1550

ccccagaccc tgcacacaga agggtagcct gggaggagcc agggccctcg         1600

tcccctatgc cggtgtcctg gctgtgggtg tgggtgatac tgtggcctcc         1650

atcttcggta gcaccatggg ggagatccgc tggcctggaa ccaaaaagac         1700

ttttgagggg accatgacat ctatatttgc gcagatcatt tctgtagctc         1750

tgatcttaat ctttgacagt ggagtggacc taaactacag ttatgcttgg         1800

attttggggt ccatcagcac tgtgtccctc ctggaagcat acactacaca         1850

gatagacaat ctccttctgc ctctctacct cctgatattg ctgatggcct         1900

agctgttaca gtgcagcagc agtgacggag gaaacagaca tggggagggt         1950

gaacagtccc cacagcagac agctacttgg gcatgaagag ccaaggtgtg         2000

aaaagcagat ttgatttttc agttgattca gatttaaaat aaaaagcaaa         2050

gctctcctag  ttcta                                              2065
```

```
<210> SEQ ID NO 100
<211> LENGTH: 538
<212> TYPE: PRT
<213> ORGANISM: Homo sapiens

<400> SEQUENCE: 100

Met Thr Arg Glu Cys Pro Ser Pro Ala Pro Gly Pro Gly Ala Pro
  1               5                  10                  15

Leu Ser Gly Ser Val Leu Ala Glu Ala Ala Val Val Phe Ala Val
                 20                  25                  30

Val Leu Ser Ile His Ala Thr Val Trp Asp Arg Tyr Ser Trp Cys
                 35                  40                  45

Ala Val Ala Leu Ala Val Gln Ala Phe Tyr Val Gln Tyr Lys Trp
                 50                  55                  60

Asp Arg Leu Leu Gln Gln Gly Ser Ala Val Phe Gln Phe Arg Met
                 65                  70                  75

Ser Ala Asn Ser Gly Leu Leu Pro Ala Ser Met Val Met Pro Leu
                 80                  85                  90

Leu Gly Leu Val Met Lys Glu Arg Cys Gln Thr Ala Gly Asn Pro
                 95                 100                 105

Phe Phe Glu Arg Phe Gly Ile Val Val Ala Ala Thr Gly Met Ala
                110                 115                 120

Val Ala Leu Phe Ser Ser Val Leu Ala Leu Gly Ile Thr Arg Pro
                125                 130                 135

Val Pro Thr Asn Thr Cys Val Ile Leu Gly Leu Ala Gly Gly Val
                140                 145                 150

Ile Ile Tyr Ile Met Lys His Ser Leu Ser Val Gly Glu Val Ile
                155                 160                 165
```

-continued

```
Glu Val Leu Glu Val Leu Leu Ile Phe Val Tyr Leu Asn Met Ile
                170                 175                 180

Leu Leu Tyr Leu Leu Pro Arg Cys Phe Thr Pro Gly Glu Ala Leu
                185                 190                 195

Leu Val Leu Gly Gly Ile Ser Phe Val Leu Asn Gln Leu Ile Lys
                200                 205                 210

Arg Ser Leu Thr Leu Val Glu Ser Gln Gly Asp Pro Val Asp Phe
                215                 220                 225

Phe Leu Leu Val Val Val Val Gly Met Val Leu Met Gly Ile Phe
                230                 235                 240

Phe Ser Thr Leu Phe Val Phe Met Asp Ser Gly Thr Trp Ala Ser
                245                 250                 255

Ser Ile Phe Phe His Leu Met Thr Cys Val Leu Ser Leu Gly Val
                260                 265                 270

Val Leu Pro Trp Leu His Arg Leu Ile Arg Arg Asn Pro Leu Leu
                275                 280                 285

Trp Leu Leu Gln Phe Leu Phe Gln Thr Asp Thr Arg Ile Tyr Leu
                290                 295                 300

Leu Ala Tyr Trp Ser Leu Leu Ala Thr Leu Ala Cys Leu Val Val
                305                 310                 315

Leu Tyr Gln Asn Ala Lys Arg Ser Ser Ser Glu Ser Lys Lys His
                320                 325                 330

Gln Ala Pro Thr Ile Ala Arg Lys Tyr Phe His Leu Ile Val Val
                335                 340                 345

Ala Thr Tyr Ile Pro Gly Ile Ile Phe Asp Arg Pro Leu Leu Tyr
                350                 355                 360

Val Ala Ala Thr Val Cys Leu Ala Val Phe Ile Phe Leu Glu Tyr
                365                 370                 375

Val Arg Tyr Phe Arg Ile Lys Pro Leu Gly His Thr Leu Arg Ser
                380                 385                 390

Phe Leu Ser Leu Phe Leu Asp Glu Arg Asp Ser Gly Pro Leu Ile
                395                 400                 405

Leu Thr His Ile Tyr Leu Leu Leu Gly Met Ser Leu Pro Ile Trp
                410                 415                 420

Leu Ile Pro Arg Pro Cys Thr Gln Lys Gly Ser Leu Gly Gly Ala
                425                 430                 435

Arg Ala Leu Val Pro Tyr Ala Gly Val Leu Ala Val Gly Val Gly
                440                 445                 450

Asp Thr Val Ala Ser Ile Phe Gly Ser Thr Met Gly Glu Ile Arg
                455                 460                 465

Trp Pro Gly Thr Lys Lys Thr Phe Glu Gly Thr Met Thr Ser Ile
                470                 475                 480

Phe Ala Gln Ile Ile Ser Val Ala Leu Ile Leu Ile Phe Asp Ser
                485                 490                 495

Gly Val Asp Leu Asn Tyr Ser Tyr Ala Trp Ile Leu Gly Ser Ile
                500                 505                 510

Ser Thr Val Ser Leu Leu Glu Ala Tyr Thr Thr Gln Ile Asp Asn
                515                 520                 525

Leu Leu Leu Pro Leu Tyr Leu Leu Ile Leu Leu Met Ala
                530                 535
```

<210> SEQ ID NO 101
<211> LENGTH: 2506

-continued

<212> TYPE: DNA
<213> ORGANISM: Homo sapiens

<400> SEQUENCE: 101

```
cactgcccgt ccgctcttca gcagccggtc gcgggcggtg gaaaagcgag      50
tgaagagagc gcgacggcgg cggcggcggc ggcgcagcta ttgctggacg     100
gccagtggga gagcgaggcc tgagcctctg cgtctaggat caaaatggtt     150
tcaatcccag aatactatga aggcaagaac gtcctcctca caggagctac     200
cggttttcta gggaaggtgc ttctggaaaa gttgctgagg tcttgtccta     250
aggtgaattc agtatatgtt ttggtgaggc agaaagctgg acagacacca     300
caagagcgag tggaagaagt ccttagtggc aagctttttg acagattgag     350
agatgaaaat ccagatttta gagagaaaat tatagcaatc aacagcgaac     400
tcacccaacc taaactggct ctcagtgaag aagataaaga ggtgatcata     450
gattctacca atattatatt ccactgtgca gctacagtaa ggtttaatga     500
aaatttaaga gatgctgttc agttaaatgt gattgcaacg cgacagctta     550
ttctccttgc acaacaaatg aagaatctgg aagtgttcat gcatgtatca     600
acagcatatg cctactgtaa tcgcaagcat attgatgaag tagtctatcc     650
accacctgtg gatcccaaga agctgattga ttctttagag tggatggatg     700
atggcctagt aaatgatatc acgccaaaat tgataggaga cagacctaat     750
acatacatat acacaaaagc attggcagaa tatgttgtac aacaagaagg     800
agcaaaacta aatgtggcaa ttgtaaggcc atcgattgtt ggtgccagtt     850
ggaaagaacc ttttccagga tggattgata actttaatgg accaagtggt     900
ctctttattg cggcagggaa aggaattctt cgaacaatac gtgcctccaa     950
caatgccctt gcagatcttg ttcctgtaga tgtagttgtc aacatgagtc    1000
ttgcggcagc ctggtattcc ggagttaata gaccaagaaa catcatggtg    1050
tataattgta caacaggcag cactaatcct ttccactggg gtgaagttga    1100
gtaccatgta atttccactt tcaagaggaa tcctctcgaa caggccttca    1150
gacggcccaa tgtaaatcta acctccaatc atcttttata tcattactgg    1200
attgctgtaa gccataaggc cccagcattc ctgtatgata tctacctcag    1250
gatgactgga agaagcccaa ggatgatgaa aacaataact cgtcttcaca    1300
aagctatggt gtttcttgaa tatttcacaa gtaattcttg ggtttggaat    1350
actgagaatg tcaatatgtt aatgaatcaa ctaaaccctg aagataaaaa    1400
gaccttcaat attgatgtac ggcagttaca ttgggcagaa tatatagaga    1450
actactgctt gggaactaag aagtacgtat tgaatgaaga aatgtctggc    1500
ctccctgcag ccagaaaaca tctgaacaag ttgcggaata tacgttatgg    1550
ttttaatact atccttgtga tcctcatctg gcgcattttt attgcaagat    1600
cacaaatggc aagaaatatc tggtactttg tggttagtct gtgttacaag    1650
tttttgtcat acttccgagc atccagcact atgagatact gaagaccaag    1700
gattcagcat tagaacatct atacatatgg tgatctaaat gtacaaaatg    1750
taaaatgtat aagtcatctc actttttgtc aagacattaa accatcttag    1800
atcggagtgt gaagtaaatt atggtatatt ttatgtaaca ttttaatgtt    1850
```

-continued

```
tatgctcata aaacttagtg aacacactgt gttatgccag ctcaaatcta      1900

cagtagccac caaaaccatg acttaatatt ttgagcccta gaagaaaggg      1950

gtgtgctgag gacaagagtg gggaaatagg aacactgacc agtataactg      2000

tgcaattctg gaacatatta attaaaataa tatgccttaa catatagtga      2050

atttctaatt ctaatgttca gtgcaatgga agacatttat ttggacagta      2100

tactagcaaa gttggtagat atttgattct tcattttttg tttttttcat      2150

tagttgaagt gggttttagt tttgtttaaa attataacca gcgtattttc      2200

acatcattct gtaagttaaa tgatatcaaa catgaaagag atgttctcat      2250

ttttcttttt ctgattaaac gtctgatgca tatcattttt ctataagtaa      2300

tcagttgctt ttaaaatcag aaggctatat tattctaatg accctattcg      2350

atctaaatgg gtttgagaat ccatatcagc aacatacgtg ttttttgaca      2400

gaaagtgaaa acaaattccg taaaactgtt agtatcaaaa agaataggaa      2450

tacagttttc ttttccacat tatgatcaaa taaaaatctt gtgagattgt      2500

taaaaa                                                      2506
```

<210> SEQ ID NO 102
<211> LENGTH: 515
<212> TYPE: PRT
<213> ORGANISM: Homo sapiens

<400> SEQUENCE: 102

```
Met Val Ser Ile Pro Glu Tyr Tyr Glu Gly Lys Asn Val Leu Leu
  1               5                  10                  15

Thr Gly Ala Thr Gly Phe Leu Gly Lys Val Leu Leu Glu Lys Leu
                 20                  25                  30

Leu Arg Ser Cys Pro Lys Val Asn Ser Val Tyr Val Leu Val Arg
                 35                  40                  45

Gln Lys Ala Gly Gln Thr Pro Gln Glu Arg Val Glu Glu Val Leu
                 50                  55                  60

Ser Gly Lys Leu Phe Asp Arg Leu Arg Asp Glu Asn Pro Asp Phe
                 65                  70                  75

Arg Glu Lys Ile Ile Ala Ile Asn Ser Glu Leu Thr Gln Pro Lys
                 80                  85                  90

Leu Ala Leu Ser Glu Glu Asp Lys Glu Val Ile Ile Asp Ser Thr
                 95                 100                 105

Asn Ile Ile Phe His Cys Ala Ala Thr Val Arg Phe Asn Glu Asn
                110                 115                 120

Leu Arg Asp Ala Val Gln Leu Asn Val Ile Ala Thr Arg Gln Leu
                125                 130                 135

Ile Leu Leu Ala Gln Gln Met Lys Asn Leu Glu Val Phe Met His
                140                 145                 150

Val Ser Thr Ala Tyr Ala Tyr Cys Asn Arg Lys His Ile Asp Glu
                155                 160                 165

Val Val Tyr Pro Pro Pro Val Asp Pro Lys Lys Leu Ile Asp Ser
                170                 175                 180

Leu Glu Trp Met Asp Asp Gly Leu Val Asn Asp Ile Thr Pro Lys
                185                 190                 195

Leu Ile Gly Asp Arg Pro Asn Thr Tyr Ile Tyr Thr Lys Ala Leu
                200                 205                 210

Ala Glu Tyr Val Val Gln Gln Glu Gly Ala Lys Leu Asn Val Ala
```

-continued

```
                215                 220                 225

Ile Val Arg Pro Ser Ile Val Gly Ala Ser Trp Lys Glu Pro Phe
                230                 235                 240

Pro Gly Trp Ile Asp Asn Phe Asn Gly Pro Ser Gly Leu Phe Ile
                245                 250                 255

Ala Ala Gly Lys Gly Ile Leu Arg Thr Ile Arg Ala Ser Asn Asn
                260                 265                 270

Ala Leu Ala Asp Leu Val Pro Val Asp Val Val Val Asn Met Ser
                275                 280                 285

Leu Ala Ala Ala Trp Tyr Ser Gly Val Asn Arg Pro Arg Asn Ile
                290                 295                 300

Met Val Tyr Asn Cys Thr Thr Gly Ser Thr Asn Pro Phe His Trp
                305                 310                 315

Gly Glu Val Glu Tyr His Val Ile Ser Thr Phe Lys Arg Asn Pro
                320                 325                 330

Leu Glu Gln Ala Phe Arg Arg Pro Asn Val Asn Leu Thr Ser Asn
                335                 340                 345

His Leu Leu Tyr His Tyr Trp Ile Ala Val Ser His Lys Ala Pro
                350                 355                 360

Ala Phe Leu Tyr Asp Ile Tyr Leu Arg Met Thr Gly Arg Ser Pro
                365                 370                 375

Arg Met Met Lys Thr Ile Thr Arg Leu His Lys Ala Met Val Phe
                380                 385                 390

Leu Glu Tyr Phe Thr Ser Asn Ser Trp Val Trp Asn Thr Glu Asn
                395                 400                 405

Val Asn Met Leu Met Asn Gln Leu Asn Pro Glu Asp Lys Lys Thr
                410                 415                 420

Phe Asn Ile Asp Val Arg Gln Leu His Trp Ala Glu Tyr Ile Glu
                425                 430                 435

Asn Tyr Cys Leu Gly Thr Lys Lys Tyr Val Leu Asn Glu Glu Met
                440                 445                 450

Ser Gly Leu Pro Ala Ala Arg Lys His Leu Asn Lys Leu Arg Asn
                455                 460                 465

Ile Arg Tyr Gly Phe Asn Thr Ile Leu Val Ile Leu Ile Trp Arg
                470                 475                 480

Ile Phe Ile Ala Arg Ser Gln Met Ala Arg Asn Ile Trp Tyr Phe
                485                 490                 495

Val Val Ser Leu Cys Tyr Lys Phe Leu Ser Tyr Phe Arg Ala Ser
                500                 505                 510

Ser Thr Met Arg Tyr
                515
```

<210> SEQ ID NO 103
<211> LENGTH: 1515
<212> TYPE: DNA
<213> ORGANISM: Homo sapiens

<400> SEQUENCE: 103

```
ccggcgatgt cgctcgtgct gctaagcctg gccgcgctgt gcaggagcgc          50

cgtaccccga gagccgaccg ttcaatgtgg ctctgaaact gggccatctc         100

cagagtggat gctacaacat gatctaatcc ccggagactt gagggacctc         150

cgagtagaac ctgttacaac tagtgttgca acaggggact attcaatttt         200

gatgaatgta agctgggtac tccgggcaga tgccagcatc cgcttgttga         250
```

-continued

```
aggccaccaa gatttgtgtg acgggcaaaa gcaacttcca gtcctacagc       300
tgtgtgaggt gcaattacac agaggccttc cagactcaga ccagaccctc       350
tggtggtaaa tggacatttt cctacatcgg cttccctgta gagctgaaca       400
cagtctattt cattggggcc cataatattc ctaatgcaaa tatgaatgaa       450
gatggccctt ccatgtctgt gaatttcacc tcaccaggct gcctagacca       500
cataatgaaa tataaaaaaa agtgtgtcaa ggccggaagc ctgtgggatc       550
cgaacatcac tgcttgtaag aagaatgagg agacagtaga agtgaacttc       600
acaaccactc ccctgggaaa cagatacatg gctcttatcc aacacagcac       650
tatcatcggg ttttctcagg tgtttgagcc acaccagaag aaacaaacgc       700
gagcttcagt ggtgattcca gtgactgggg atagtgaagg tgctacggtg       750
cagctgactc catattttcc tacttgtggc agcgactgca tccgacataa       800
aggaacagtt gtgctctgcc cacaaacagg cgtccctttc cctctggata       850
acaacaaaag caagccggga ggctggctgc ctctcctcct gctgtctctg       900
ctggtggcca catgggtgct ggtggcaggg atctatctaa tgtggaggca       950
cgaaaggatc aagaagactt ccttttctac caccacacta ctgcccccca      1000
ttaaggttct tgtggtttac ccatctgaaa tatgtttcca tcacacaatt      1050
tgttacttca ctgaatttct tcaaaaccat tgcagaagtg aggtcatcct      1100
tgaaaagtgg cagaaaaaga aaatagcaga gatgggtcca gtgcagtggc      1150
ttgccactca aaagaaggca gcagacaaag tcgtcttcct tctttccaat      1200
gacgtcaaca gtgtgtgcga tggtacctgt ggcaagagcg agggcagtcc      1250
cagtgagaac tctcaagacc tcttccccct tgcctttaac cttttctgca      1300
gtgatctaag aagccagatt catctgcaca aatacgtggt ggtctacttt      1350
agagagattg atacaaaaga cgattacaat gctctcagtg tctgccccaa      1400
gtaccacctc atgaaggatg ccactgcttt ctgtgcagaa cttctccatg      1450
tcaagcagca ggtgtcagca ggaaaaagat cacaagcctg ccacgatggc      1500
tgctgctcct  tgtag                                           1515
```

```
<210> SEQ ID NO 104
<211> LENGTH: 502
<212> TYPE: PRT
<213> ORGANISM: Homo sapiens

<400> SEQUENCE: 104

Met Ser Leu Val Leu Leu Ser Leu Ala Ala Leu Cys Arg Ser Ala
  1               5                  10                  15

Val Pro Arg Glu Pro Thr Val Gln Cys Gly Ser Glu Thr Gly Pro
                 20                  25                  30

Ser Pro Glu Trp Met Leu Gln His Asp Leu Ile Pro Gly Asp Leu
                 35                  40                  45

Arg Asp Leu Arg Val Glu Pro Val Thr Thr Ser Val Ala Thr Gly
                 50                  55                  60

Asp Tyr Ser Ile Leu Met Asn Val Ser Trp Val Leu Arg Ala Asp
                 65                  70                  75

Ala Ser Ile Arg Leu Leu Lys Ala Thr Lys Ile Cys Val Thr Gly
                 80                  85                  90
```

-continued

```
Lys Ser Asn Phe Gln Ser Tyr Ser Cys Val Arg Cys Asn Tyr Thr
                95                  100                 105

Glu Ala Phe Gln Thr Gln Thr Arg Pro Ser Gly Gly Lys Trp Thr
                110                 115                 120

Phe Ser Tyr Ile Gly Phe Pro Val Glu Leu Asn Thr Val Tyr Phe
                125                 130                 135

Ile Gly Ala His Asn Ile Pro Asn Ala Asn Met Asn Glu Asp Gly
                140                 145                 150

Pro Ser Met Ser Val Asn Phe Thr Ser Pro Gly Cys Leu Asp His
                155                 160                 165

Ile Met Lys Tyr Lys Lys Lys Cys Val Lys Ala Gly Ser Leu Trp
                170                 175                 180

Asp Pro Asn Ile Thr Ala Cys Lys Lys Asn Glu Glu Thr Val Glu
                185                 190                 195

Val Asn Phe Thr Thr Thr Pro Leu Gly Asn Arg Tyr Met Ala Leu
                200                 205                 210

Ile Gln His Ser Thr Ile Ile Gly Phe Ser Gln Val Phe Glu Pro
                215                 220                 225

His Gln Lys Lys Gln Thr Arg Ala Ser Val Val Ile Pro Val Thr
                230                 235                 240

Gly Asp Ser Glu Gly Ala Thr Val Gln Leu Thr Pro Tyr Phe Pro
                245                 250                 255

Thr Cys Gly Ser Asp Cys Ile Arg His Lys Gly Thr Val Val Leu
                260                 265                 270

Cys Pro Gln Thr Gly Val Pro Phe Pro Leu Asp Asn Asn Lys Ser
                275                 280                 285

Lys Pro Gly Gly Trp Leu Pro Leu Leu Leu Leu Ser Leu Leu Val
                290                 295                 300

Ala Thr Trp Val Leu Val Ala Gly Ile Tyr Leu Met Trp Arg His
                305                 310                 315

Glu Arg Ile Lys Lys Thr Ser Phe Ser Thr Thr Thr Leu Leu Pro
                320                 325                 330

Pro Ile Lys Val Leu Val Val Tyr Pro Ser Glu Ile Cys Phe His
                335                 340                 345

His Thr Ile Cys Tyr Phe Thr Glu Phe Leu Gln Asn His Cys Arg
                350                 355                 360

Ser Glu Val Ile Leu Glu Lys Trp Gln Lys Lys Lys Ile Ala Glu
                365                 370                 375

Met Gly Pro Val Gln Trp Leu Ala Thr Gln Lys Lys Ala Ala Asp
                380                 385                 390

Lys Val Val Phe Leu Leu Ser Asn Asp Val Asn Ser Val Cys Asp
                395                 400                 405

Gly Thr Cys Gly Lys Ser Glu Gly Ser Pro Ser Glu Asn Ser Gln
                410                 415                 420

Asp Leu Phe Pro Leu Ala Phe Asn Leu Phe Cys Ser Asp Leu Arg
                425                 430                 435

Ser Gln Ile His Leu His Lys Tyr Val Val Val Tyr Phe Arg Glu
                440                 445                 450

Ile Asp Thr Lys Asp Asp Tyr Asn Ala Leu Ser Val Cys Pro Lys
                455                 460                 465

Tyr His Leu Met Lys Asp Ala Thr Ala Phe Cys Ala Glu Leu Leu
                470                 475                 480

His Val Lys Gln Gln Val Ser Ala Gly Lys Arg Ser Gln Ala Cys
```

-continued 485 490 495

His Asp Gly Cys Cys Ser Leu
500

<210> SEQ ID NO 105
<211> LENGTH: 4060
<212> TYPE: DNA
<213> ORGANISM: Homo sapiens

<400> SEQUENCE: 105
gcagctcacc cttcgcagcc gcgatggggg aagacgacgc cgcgcttcgg 50
gctggcagca gggggctctc cgacccgtgg gcagactcag tgggagtgcg 100
accccgcacc acggagcgcc acatcgccgt acacaagcgg cttgtgctgg 150
ccttcgctgt gtccctcgtg gcattgctcg cggtcacaat gctcgctgtg 200
ctgctcagcc tgcgcttcga cgagtgcggg gcgagtgcca cgccaggcgc 250
cgacggtggc ccctcaggct ttccggagcg cggcggcaac gggagcctcc 300
ctggatcggc ccggcgcaac caccacgcag gcggggactc ctggcagccc 350
gaggcgggtg gggtggccag tccggggacc acgtcggccc agccgccgtc 400
ggaggaggag cgggagccgt gggagccgtg gacgcagctg cgcctgtcgg 450
gccacctgaa gccgctgcac tacaatctga tgctcaccgc cttcatggag 500
aacttcacct tctccgggga ggtcaacgtg gagatcgcgt gccggaacgc 550
cacccgctac gtagtgctgc acgcttcccg agtggcggtg gagaaagtgc 600
agctggccga ggaccgggcg ttcggggctg tccctgtagc cggttttttc 650
ctctacccgc aaacccaggt cttagtggtg gtgctgaata ggacactgga 700
cgcgcagagg aattacaatc tgaagattat ctacaacgcg ctcatcgaga 750
atgagctcct gggcttcttc cgcagctcct atgtgctcca cggggagaga 800
agattccttg gtgttactca gttttcgcct acacatgcca gaaaggcatt 850
tccttgtttt gatgagccaa tctacaaggc tactttcaaa atcagcatca 900
agcatcaagc aacctattta tctttatcta atatgccagt ggaaacttcc 950
gtgtttgagg aagatggatg ggttacggat cacttttcac agacccctct 1000
catgtccaca tattatttag cctgggcaat ttgcaacttc acatacagag 1050
aaactaccac caagagtggg gttgtagtac gattatatgc aagacctgat 1100
gctatcagaa gaggatccgg ggactatgct ctccatataa caaagagatt 1150
aatagaattt tatgaagact actttaaagt gccctattcc ttgccaaaac 1200
tagatctttt agctgtgcct aagcatccgt atgctgctat ggagaactgg 1250
ggactaagta tttttgtgga acaaagaata ctgctggatc ccagtgtttc 1300
atctatttct tatttgctgg atgtcaccat ggtcattgtt catgagatat 1350
gtcaccagtg gtttggtgac cttgtgacgc ctgtgtggtg ggaagacgtg 1400
tggctgaagg aagggtttgc tcactacttt gaatttgttg gtacagacta 1450
cctctatcct ggctggaaca tggaaaagca gaggtttctg accgatgttc 1500
tgcatgaagt gatgctgctg gacggtttgg ccagttccca tccagtatca 1550
caggaagtgc tgcaggcaac agatattgac agggtgtttg actggatcgc 1600
atataaaaag ggtgctgctt taataagaat gctggctaat tttatgggcc 1650

-continued attcagtttt ccagaggggt ttgcaagatt atttaaccat tcataagtat 1700
ggtaatgcag ccagaaatga tctctggaat acattatcgg aggctttaaa 1750
aagaaatggg aaatatgtaa atatacaaga agtaatggat cagtggacac 1800
tccagatggg ttatcctgtt atcaccatct tgggaaacac aacagcagaa 1850
aatagaataa taattaccca acagcatttt atctatgata tcagtgctaa 1900
aactaaagca cttaaacttc agaataacag ttacctgtgg cagattccat 1950
taactattgt ggtaggaaat agaagccatg tgtcttcaga agcaattatt 2000
tgggtgtcta acaaatcaga gcaccacaga ataacttatt tggacaaagg 2050
aagctggctg ctggggaaca tcaatcaaac tggctatttt agagtcaact 2100
atgacctaag gaactggaga ttattaattg atcaattaat ccggaatcat 2150
gaggttcttt ctgtcagtaa ccgagcgggc ttgatcgatg atgccttcag 2200
cctagccagg gctggctatt tgcctcagaa tattcctctg gagattatca 2250
gatacctgtc tgaggagaag gattttcttc cttggcatgc tgccagccga 2300
gctctttatc ctctagataa attactggac cgcatggaaa actacaacat 2350
tttcaatgaa tatattttaa agcaagttgc aacaacatat atcaagcttg 2400
ggtggccgaa aaataatttt aatggatctc ttgttcaagc atcctaccaa 2450
catgaagaac tacgtagaga agttataatg ctggcctgca gttttggcaa 2500
caagcactgt caccaacagg catcaacact tatttcagat tggatttcca 2550
gcaacaggaa cagaatacca ctaaatgtta gagacatcgt atactgtaca 2600
ggagtgtcac tactggatga ggatgtctgg gaattcatat ggatgaaatt 2650
ccattccacc acagcagttt ctgagaagaa aatattattg gaagccttaa 2700
cttgcagtga tgacaggaat ttattaaaca ggcttctaaa tctgtcactg 2750
aattctgagg tggtgctgga tcaagatgca attgatgtca taatccatgt 2800
agctcgaaat ccacatggtc gagaccttgc ctggaagttt ttcagggata 2850
aatggaagat attaaatacc aggtatggag aagcattgtt tatgtattcc 2900
aaactcatca gtggtgtcac agaatttctt aatactgaag gtgaactcaa 2950
agagctcaag aacttcatga aaaactatga tggggtagct gctgcttctt 3000
tctcacgagc tgtggaaact gtcgaagcca atgtgcgctg gaaaatgctt 3050
taccaagacg agcttttcca atggttagga aaagctctaa gacactaata 3100
tatgtatctt ataaacaaac aattcaactc agaagtttat gagaagacac 3150
gctttttgtg gaatgaggaa aatgtactac ctagaaaatg gccagatttt 3200
cagtgttaac gtgtgggagg aatttttttt tttagttttt attttttggt 3250
tttgggggat atttttattt tgtttcattc attctgttct gtttctctac 3300
tgggtgttcc tctctaaaga aactcttgca agtgaaacta gccatgattg 3350
cttcagctgt acattccttg ctgtacagga ccaaatatga tagtgatgca 3400
tgttgatgtt acagtcaatt tggaaaaaca tattcagaat atctgtgcat 3450
ggatatattg tcctgcctgt gttccagcat gcttatttca aacgtccagt 3500
gttgtgtgtg aatatgtgtt acacctagga tgggcattat gcaaaagcac 3550
aaagattata tatgacaatc agtattgcaa tgaaagaaaa actaaaaaca 3600
gaaatgatat tctcaatttt gggcaatgtg agaggtaaaa tagcccttga 3650

-continued

```
catgatgaac atcacttatt tcagcacttg gattgtctgg caatgattac            3700

tgtgttgcta actcattttc tttgagttaa agctgtgtat acattttaaa            3750

aggcatatag atagtgtatg catatgtata tgtacatagg gaagccccat            3800

atgtatatag tatgttgtac actgcacatg tacaaagaat gtcttcagat            3850

caaagaaaat ttatctcttt ttataaactt aaggacagtt gcaaaaggct            3900

tcaaggaatt tatctcaaca ttattctttc tatgtcctaa ctaaatttct            3950

caactgttat gaatttttca tctacttctt gaacagtggt ctattctgct            4000

acatgaagat gaatacaaac aaaatttttg tataaactcc caaaaaaaaa            4050

aaaaaaaaaa                                                        4060


<210> SEQ ID NO 106
<211> LENGTH: 1024
<212> TYPE: PRT
<213> ORGANISM: Homo sapiens

<400> SEQUENCE: 106

Met Gly Glu Asp Asp Ala Ala Leu Arg Ala Gly Ser Arg Gly Leu
  1               5                  10                  15

Ser Asp Pro Trp Ala Asp Ser Val Gly Val Arg Pro Arg Thr Thr
                 20                  25                  30

Glu Arg His Ile Ala Val His Lys Arg Leu Val Leu Ala Phe Ala
                 35                  40                  45

Val Ser Leu Val Ala Leu Leu Ala Val Thr Met Leu Ala Val Leu
                 50                  55                  60

Leu Ser Leu Arg Phe Asp Glu Cys Gly Ala Ser Ala Thr Pro Gly
                 65                  70                  75

Ala Asp Gly Gly Pro Ser Gly Phe Pro Glu Arg Gly Gly Asn Gly
                 80                  85                  90

Ser Leu Pro Gly Ser Ala Arg Arg Asn His His Ala Gly Gly Asp
                 95                 100                 105

Ser Trp Gln Pro Glu Ala Gly Gly Val Ala Ser Pro Gly Thr Thr
                110                 115                 120

Ser Ala Gln Pro Pro Ser Glu Glu Glu Arg Glu Pro Trp Glu Pro
                125                 130                 135

Trp Thr Gln Leu Arg Leu Ser Gly His Leu Lys Pro Leu His Tyr
                140                 145                 150

Asn Leu Met Leu Thr Ala Phe Met Glu Asn Phe Thr Phe Ser Gly
                155                 160                 165

Glu Val Asn Val Glu Ile Ala Cys Arg Asn Ala Thr Arg Tyr Val
                170                 175                 180

Val Leu His Ala Ser Arg Val Ala Val Glu Lys Val Gln Leu Ala
                185                 190                 195

Glu Asp Arg Ala Phe Gly Ala Val Pro Val Ala Gly Phe Phe Leu
                200                 205                 210

Tyr Pro Gln Thr Gln Val Leu Val Val Val Leu Asn Arg Thr Leu
                215                 220                 225

Asp Ala Gln Arg Asn Tyr Asn Leu Lys Ile Ile Tyr Asn Ala Leu
                230                 235                 240

Ile Glu Asn Glu Leu Leu Gly Phe Phe Arg Ser Ser Tyr Val Leu
                245                 250                 255

His Gly Glu Arg Arg Phe Leu Gly Val Thr Gln Phe Ser Pro Thr
```

-continued

```
                260                 265                 270

His Ala Arg Lys Ala Phe Pro Cys Phe Asp Glu Pro Ile Tyr Lys
                275                 280                 285

Ala Thr Phe Lys Ile Ser Ile Lys His Gln Ala Thr Tyr Leu Ser
                290                 295                 300

Leu Ser Asn Met Pro Val Glu Thr Ser Val Phe Glu Glu Asp Gly
                305                 310                 315

Trp Val Thr Asp His Phe Ser Gln Thr Pro Leu Met Ser Thr Tyr
                320                 325                 330

Tyr Leu Ala Trp Ala Ile Cys Asn Phe Thr Tyr Arg Glu Thr Thr
                335                 340                 345

Thr Lys Ser Gly Val Val Val Arg Leu Tyr Ala Arg Pro Asp Ala
                350                 355                 360

Ile Arg Arg Gly Ser Gly Asp Tyr Ala Leu His Ile Thr Lys Arg
                365                 370                 375

Leu Ile Glu Phe Tyr Glu Asp Tyr Phe Lys Val Pro Tyr Ser Leu
                380                 385                 390

Pro Lys Leu Asp Leu Leu Ala Val Pro Lys His Pro Tyr Ala Ala
                395                 400                 405

Met Glu Asn Trp Gly Leu Ser Ile Phe Val Glu Gln Arg Ile Leu
                410                 415                 420

Leu Asp Pro Ser Val Ser Ser Ile Ser Tyr Leu Leu Asp Val Thr
                425                 430                 435

Met Val Ile Val His Glu Ile Cys His Gln Trp Phe Gly Asp Leu
                440                 445                 450

Val Thr Pro Val Trp Trp Glu Asp Val Trp Leu Lys Glu Gly Phe
                455                 460                 465

Ala His Tyr Phe Glu Phe Val Gly Thr Asp Tyr Leu Tyr Pro Gly
                470                 475                 480

Trp Asn Met Glu Lys Gln Arg Phe Leu Thr Asp Val Leu His Glu
                485                 490                 495

Val Met Leu Leu Asp Gly Leu Ala Ser Ser His Pro Val Ser Gln
                500                 505                 510

Glu Val Leu Gln Ala Thr Asp Ile Asp Arg Val Phe Asp Trp Ile
                515                 520                 525

Ala Tyr Lys Lys Gly Ala Ala Leu Ile Arg Met Leu Ala Asn Phe
                530                 535                 540

Met Gly His Ser Val Phe Gln Arg Gly Leu Gln Asp Tyr Leu Thr
                545                 550                 555

Ile His Lys Tyr Gly Asn Ala Ala Arg Asn Asp Leu Trp Asn Thr
                560                 565                 570

Leu Ser Glu Ala Leu Lys Arg Asn Gly Lys Tyr Val Asn Ile Gln
                575                 580                 585

Glu Val Met Asp Gln Trp Thr Leu Gln Met Gly Tyr Pro Val Ile
                590                 595                 600

Thr Ile Leu Gly Asn Thr Thr Ala Glu Asn Arg Ile Ile Ile Thr
                605                 610                 615

Gln Gln His Phe Ile Tyr Asp Ile Ser Ala Lys Thr Lys Ala Leu
                620                 625                 630

Lys Leu Gln Asn Asn Ser Tyr Leu Trp Gln Ile Pro Leu Thr Ile
                635                 640                 645

Val Val Gly Asn Arg Ser His Val Ser Ser Glu Ala Ile Ile Trp
                650                 655                 660
```

-continued

```
Val Ser Asn Lys Ser Glu His His Arg Ile Thr Tyr Leu Asp Lys
                665                 670                 675

Gly Ser Trp Leu Leu Gly Asn Ile Asn Gln Thr Gly Tyr Phe Arg
                680                 685                 690

Val Asn Tyr Asp Leu Arg Asn Trp Arg Leu Leu Ile Asp Gln Leu
                695                 700                 705

Ile Arg Asn His Glu Val Leu Ser Val Ser Asn Arg Ala Gly Leu
                710                 715                 720

Ile Asp Asp Ala Phe Ser Leu Ala Arg Ala Gly Tyr Leu Pro Gln
                725                 730                 735

Asn Ile Pro Leu Glu Ile Ile Arg Tyr Leu Ser Glu Glu Lys Asp
                740                 745                 750

Phe Leu Pro Trp His Ala Ala Ser Arg Ala Leu Tyr Pro Leu Asp
                755                 760                 765

Lys Leu Leu Asp Arg Met Glu Asn Tyr Asn Ile Phe Asn Glu Tyr
                770                 775                 780

Ile Leu Lys Gln Val Ala Thr Thr Tyr Ile Lys Leu Gly Trp Pro
                785                 790                 795

Lys Asn Asn Phe Asn Gly Ser Leu Val Gln Ala Ser Tyr Gln His
                800                 805                 810

Glu Glu Leu Arg Arg Glu Val Ile Met Leu Ala Cys Ser Phe Gly
                815                 820                 825

Asn Lys His Cys His Gln Gln Ala Ser Thr Leu Ile Ser Asp Trp
                830                 835                 840

Ile Ser Ser Asn Arg Asn Arg Ile Pro Leu Asn Val Arg Asp Ile
                845                 850                 855

Val Tyr Cys Thr Gly Val Ser Leu Leu Asp Glu Asp Val Trp Glu
                860                 865                 870

Phe Ile Trp Met Lys Phe His Ser Thr Thr Ala Val Ser Glu Lys
                875                 880                 885

Lys Ile Leu Leu Glu Ala Leu Thr Cys Ser Asp Asp Arg Asn Leu
                890                 895                 900

Leu Asn Arg Leu Leu Asn Leu Ser Leu Asn Ser Glu Val Val Leu
                905                 910                 915

Asp Gln Asp Ala Ile Asp Val Ile Ile His Val Ala Arg Asn Pro
                920                 925                 930

His Gly Arg Asp Leu Ala Trp Lys Phe Phe Arg Asp Lys Trp Lys
                935                 940                 945

Ile Leu Asn Thr Arg Tyr Gly Glu Ala Leu Phe Met Tyr Ser Lys
                950                 955                 960

Leu Ile Ser Gly Val Thr Glu Phe Leu Asn Thr Glu Gly Glu Leu
                965                 970                 975

Lys Glu Leu Lys Asn Phe Met Lys Asn Tyr Asp Gly Val Ala Ala
                980                 985                 990

Ala Ser Phe Ser Arg Ala Val Glu Thr Val Glu Ala Asn Val Arg
                995                 1000                1005

Trp Lys Met Leu Tyr Gln Asp Glu Leu Phe Gln Trp Leu Gly Lys
               1010                1015                1020

Ala Leu Arg His
```

<210> SEQ ID NO 107
<211> LENGTH: 2915
<212> TYPE: DNA

-continued

<213> ORGANISM: Homo sapiens

<400> SEQUENCE: 107
ctttccttat ctgtgtgtac tcttatctca ctgttctatt ttttctcctc 50
atttatatta actctttctt accttttttt ctgaacttct aggccttctc 100
tttccagaac tggtggaaga caaatgaaac ggccaagatg gtaagaaaca 150
agccgcattt ctccttgggg agactgataa tttaaaaggt ttgttgtgtc 200
agaaacattc ccagcttcat caccaaccct ttccttccac ctctgcccac 250
tggagaccac ttacatcccg aagcggacgc ggcagctgaa gtcaggaaac 300
catgcatcac attagcagga gccaactgca gactttaaac tccgttcaac 350
atgtggatgc ggcagagaaa tgacctgtcc agacaagccg gggcagctca 400
taaactggtt catctgctcc ctgtgcgtcc cgcgggtgcg taagctctgg 450
agcagccggc gtccaaggac ccggagaaac cttctgctgg gcactgcgtg 500
tgccatctac ttgggcttcc tggtgagcca ggtggggagg gcctctctcc 550
agcatggaca ggcggctgag aaggggccac atcgcagccg cgacaccgcc 600
gagccatcct tccctgagat accccctggat ggtaccctgg cccctccaga 650
gtcccagggc aatgggtcca ctctgcagcc caatgtggtg tacattaccc 700
tacgctccaa gcgcagcaag ccggccaata tccgtggcac cgtgaagccc 750
aagcgcagga aaaagcatgc agtggcatcg gctgccccag ggcaggaggc 800
tttggtcgga ccatcccttc agccgcagga agcggcaagg gaagctgatg 850
ctgtagcacc tgggtacgct cagggagcaa acctggttaa gattggagag 900
cgaccctgga ggttggtgcg ggtccggga gtgcgagccg ggggcccaga 950
cttcctgcag cccagctcca gggagagcaa cattaggatc tacagcgaga 1000
gcgccccctc ctggctgagc aaagatgaca tccgaagaat gcgactcttg 1050
gcggacagcg cagtggcagg gctccggcct gtgtcctcta ggagcggagc 1100
ccgtttgctg gtgctggagg ggggcgcacc tggcgctgtg ctccgctgtg 1150
gccctagccc ctgtgggctt ctcaagcagc ccttggacat gagtgaggtg 1200
tttgccttcc acctagacag gatcctgggg ctcaacagga ccctgccgtc 1250
tgtgagcagg aaagcagagt tcatccaaga tggccgccca tgccccatca 1300
ttctttggga tgcatcttta tcttcagcaa gtaatgacac ccattcttct 1350
gttaagctca cctggggaac ttatcagcag ttgctgaaac agaaatgctg 1400
gcagaatggc cgagtaccca agcctgaatc aggttgtact gaaatacatc 1450
atcatgagtg gtccaagatg gcactctttg attttttgtt acagatttat 1500
aatcgcttag atacaaattg ctgtggattc agacctcgca aggaagatgc 1550
ctgtgtacag aatggattga ggccaaaatg tgatgaccaa ggttctgcgg 1600
ctctagcaca cattatccag cgaaagcatg acccaaggca tttggttttt 1650
atagacaaca agggtttctt tgacaggagt gaagataact taaacttcaa 1700
attgttagaa ggcatcaaag agtttccagc ttctgcagtt tctgttttga 1750
agagccagca cttacggcag aaacttcttc agtctctgtt tcttgataaa 1800
gtgtattggg aaagtcaagg aggtagacaa ggaattgaaa agcttatcga 1850
tgtaatagaa cacagagcca aaattcttat cacctatatc aatgcacacg 1900

-continued

```
gggtcaaagt attacctatg aatgaatgac aaaagaatct tctggctagg    1950

gtgttagata tatttatgca tttttggttt tgtttttaaa tcaagcacat    2000

caacctcaag cccgtttagc aatgaggcag tgtagatgaa tacgtaaaat    2050

aaatgacttt aaccaagtag ctataaaggg acttagcact gtatgcatac    2100

ttaaaaaggt tttgaaaaac aaactacttg agaaatattt gtttatattt    2150

ttctctaaca tcatgctatg tgtcagtctg aacatctgac aacagaaatt    2200

tcagttatta ttctagctaa gttttgaaaa catttgtcat gctgtttaat    2250

agaaaactgc aaaccagaga tactgactcc attaataaac catattttgt    2300

gccgttttga ctgttctgac caaatactaa tgggaacaat tcttgacgtt    2350

tttctgttgc tgattgttaa catagagcag tctctacact accctgaggc    2400

aactctacat tggaacactg aggcttacag cctgcaagag catcagagct    2450

gaccatacat ttaaacagaa atgctggttt atttgcaaaa tcaccagtat    2500

attttctatt gtgtctataa aaaatcagtc atttaagtac aagaatcata    2550

ttttccattc ctttttagaa atttattttg ttgtccctat ggaaatcatt    2600

cacatctgac aatttatatg ttaaagagtt ttactctctc tattttggtc    2650

caatttgtat ctagtggctg agaaattaaa taattctaaa gtatgaagtt    2700

acctatctga aaatgtactt acagagtatc attttaaaat ggatgtctct    2750

ttaaaaattt tgttactttt accaacaatg taatataatt tatgtatatt    2800

ttattaataa tagtgaattc cttaaaattt gttctatgta cttatattta    2850

atttgattta atggttactg cccagatatt gagaaatggt tcaaatattg    2900

agtgtgtttc  aataa                                         2915
```

<210> SEQ ID NO 108
<211> LENGTH: 519
<212> TYPE: PRT
<213> ORGANISM: Homo sapiens

<400> SEQUENCE: 108

```
Met Thr Cys Pro Asp Lys Pro Gly Gln Leu Ile Asn Trp Phe Ile
  1               5                  10                  15

Cys Ser Leu Cys Val Pro Arg Val Arg Lys Leu Trp Ser Ser Arg
                 20                  25                  30

Arg Pro Arg Thr Arg Arg Asn Leu Leu Leu Gly Thr Ala Cys Ala
                 35                  40                  45

Ile Tyr Leu Gly Phe Leu Val Ser Gln Val Gly Arg Ala Ser Leu
                 50                  55                  60

Gln His Gly Gln Ala Ala Glu Lys Gly Pro His Arg Ser Arg Asp
                 65                  70                  75

Thr Ala Glu Pro Ser Phe Pro Glu Ile Pro Leu Asp Gly Thr Leu
                 80                  85                  90

Ala Pro Pro Glu Ser Gln Gly Asn Gly Ser Thr Leu Gln Pro Asn
                 95                 100                 105

Val Val Tyr Ile Thr Leu Arg Ser Lys Arg Ser Lys Pro Ala Asn
                110                 115                 120

Ile Arg Gly Thr Val Lys Pro Lys Arg Arg Lys Lys His Ala Val
                125                 130                 135

Ala Ser Ala Ala Pro Gly Gln Glu Ala Leu Val Gly Pro Ser Leu
```

-continued

```
                140                 145                 150

Gln Pro Gln Glu Ala Ala Arg Glu Ala Asp Ala Val Ala Pro Gly
                155                 160                 165

Tyr Ala Gln Gly Ala Asn Leu Val Lys Ile Gly Glu Arg Pro Trp
                170                 175                 180

Arg Leu Val Arg Gly Pro Gly Val Arg Ala Gly Gly Pro Asp Phe
                185                 190                 195

Leu Gln Pro Ser Ser Arg Glu Ser Asn Ile Arg Ile Tyr Ser Glu
                200                 205                 210

Ser Ala Pro Ser Trp Leu Ser Lys Asp Asp Ile Arg Arg Met Arg
                215                 220                 225

Leu Leu Ala Asp Ser Ala Val Ala Gly Leu Arg Pro Val Ser Ser
                230                 235                 240

Arg Ser Gly Ala Arg Leu Leu Val Leu Glu Gly Gly Ala Pro Gly
                245                 250                 255

Ala Val Leu Arg Cys Gly Pro Ser Pro Cys Gly Leu Leu Lys Gln
                260                 265                 270

Pro Leu Asp Met Ser Glu Val Phe Ala Phe His Leu Asp Arg Ile
                275                 280                 285

Leu Gly Leu Asn Arg Thr Leu Pro Ser Val Ser Arg Lys Ala Glu
                290                 295                 300

Phe Ile Gln Asp Gly Arg Pro Cys Pro Ile Ile Leu Trp Asp Ala
                305                 310                 315

Ser Leu Ser Ser Ala Ser Asn Asp Thr His Ser Ser Val Lys Leu
                320                 325                 330

Thr Trp Gly Thr Tyr Gln Gln Leu Leu Lys Gln Lys Cys Trp Gln
                335                 340                 345

Asn Gly Arg Val Pro Lys Pro Glu Ser Gly Cys Thr Glu Ile His
                350                 355                 360

His His Glu Trp Ser Lys Met Ala Leu Phe Asp Phe Leu Leu Gln
                365                 370                 375

Ile Tyr Asn Arg Leu Asp Thr Asn Cys Cys Gly Phe Arg Pro Arg
                380                 385                 390

Lys Glu Asp Ala Cys Val Gln Asn Gly Leu Arg Pro Lys Cys Asp
                395                 400                 405

Asp Gln Gly Ser Ala Ala Leu Ala His Ile Ile Gln Arg Lys His
                410                 415                 420

Asp Pro Arg His Leu Val Phe Ile Asp Asn Lys Gly Phe Phe Asp
                425                 430                 435

Arg Ser Glu Asp Asn Leu Asn Phe Lys Leu Leu Glu Gly Ile Lys
                440                 445                 450

Glu Phe Pro Ala Ser Ala Val Ser Val Leu Lys Ser Gln His Leu
                455                 460                 465

Arg Gln Lys Leu Leu Gln Ser Leu Phe Leu Asp Lys Val Tyr Trp
                470                 475                 480

Glu Ser Gln Gly Gly Arg Gln Gly Ile Glu Lys Leu Ile Asp Val
                485                 490                 495

Ile Glu His Arg Ala Lys Ile Leu Ile Thr Tyr Ile Asn Ala His
                500                 505                 510

Gly Val Lys Val Leu Pro Met Asn Glu
                515
```

<210> SEQ ID NO 109

-continued

<211> LENGTH: 3442
<212> TYPE: DNA
<213> ORGANISM: Homo sapiens

<400> SEQUENCE: 109
ggaaagagtg ctggtactac aaccaggaag tgacagataa tgtgctttaa 50
actacattag aaaagcttct catagcaaaa ctgagagatt gaagcagtga 100
ttatttttac atagttgtca ttaaatattt ggagctctgc tgtgcataga 150
gatggcaaca tacttagaat acacagcttt ctgggccaga aattgatctt 200
ctgacttttg agccttatct gattactgct tggttcatct ttattttgtt 250
aaactactct gtaggctgaa agggagagac tctccttggt ttgcagagcc 300
tgactagaca ggaattctgg caactgctcc agcagaacta tggcactgag 350
ctaggtttaa atgctgagga gatggaaaac ttgtcactgt cgattgagga 400
tgtgcagcca agaagtccag gaagaagcag cttggatgac tctggggaga 450
gagatgaaaa attatccaag tcaatcagtt ttaccagtga atcaattagt 500
cgggtttcag aaacagagtc attcgatgga aattcatcaa aaggaggatt 550
aggcaaagag gagtcccaaa atgagaaaca gaccaaaaag agtctcttac 600
caactttgga aaagaagtta actagagtgc catcaaagtc actggacttg 650
aataaaaatg aatatctttc tctggacaaa agcagcactt cagattctgt 700
tgatgaagaa aatgttcctg agaaagatct tcatggaaga ctttttatca 750
accgtatttt tcatatcagt gctgacagaa tgtttgaatt gctctttacc 800
agttcacgct ttatgcagaa atttgccagt tctagaaata taatagatgt 850
agtatctacc ccttggactg cagaacttgg aggtgatcag ctgagaacga 900
tgacctacac tatagtcctt aatagtccac ttactggaaa atgcactgct 950
gccactgaaa agcagacact gtataaagaa agtcgggaag cacgatttta 1000
tttggtagat tcagaagtac tgacacatga tgtcccctac catgattact 1050
tctataccgt gaacagatac tgtatcatcc gatcttcaaa acagaaatgc 1100
aggctaagag tttccacaga tttgaaatac agaaaacagc catggggcct 1150
tgtcaaatct ttaattgaaa agaattcctg gagttctttg gaggactatt 1200
tcaaacagct tgaatcagat ttgttaattg aagaatctgt attaaatcag 1250
gccattgaag accctggaaa acttactggc ctacgaagga gaaggcgaac 1300
cttcaaccga acagcagaaa cagttcctaa actttcctct cagcattcct 1350
ctggagatgt gggcttaggt gccaaagggg atattacagg aaagaaaaag 1400
gaaatggaaa actataacgt cactcttatt gtggtaatga gtatttttgt 1450
gttgttatta gttttgttga atgtgacact gtttctgaag ctgtcaaaga 1500
tagaacatgc tgctcagtcc ttttaccgtc tccgcctcca agaagagaaa 1550
tctttaaatt tagcctctga tatggtgtca agagcagaaa ctattcagaa 1600
gaataaagat caggcccatc gtttaaaggg agtgctccga gactccatag 1650
tgatgcttga acagctgaag agctcactca ttatgcttca gaaaacgttt 1700
gatctactaa ataagaataa gactggcatg gctgttgaaa gctagtgatc 1750
tgaaggacta aaaccgcaga gatacttgga acttaaagaa aatacctgga 1800
agaaaaccag acgaatgaag gattttggca tagaacattt ctatgttttt 1850

-continued

```
tcattattga gatttctaat atgaacattt ctttcagtaa catttatttg          1900

ataattagtt tctgctggcc ttaataatcc atcctttcac ttcttataga          1950

tatttttaag ctgtgaattt cttcagtgaa ccatgaaata tattatagaa          2000

ctgaatttct ctgatacaaa aagaaaatga cacaccctga attgagtggt          2050

atggtctcat ttctacagtg aagtctgatg ctttgttagc acagaatccg          2100

tacatgtcca ataggtcgct tttgtaactg agataagacc aagaggataa          2150

acaggacaat ataagaagaa acctctatgt cattactgat tttaaaggtt          2200

ctgttttcag gcatataaca tttccaggtt tgtgtactgt aaagattata          2250

atgtcttcat ttatttagca tgcaaattta atagtcaaac tttttgaatc          2300

tgcatgttga tgatgattat cagaaagggt cttctgccat gctgtatctt          2350

tatgaaagaa atagttgttt tttcttaagg taactatcag aggtgggatt          2400

atcttgcctc ctcacttaga ataccaacag tcaaaaggaa gaaccatcct          2450

ctgagtttta aaaaccagaa ggttatgtta aaatctgggc atttagtgac          2500

agatcaaatg catacttgaa ctaagattgg cttcagctta gcagtctttc          2550

atggtggaag tgacacatct ggttgaaaat aatttgtgta ttttcagtaa          2600

ccatgtatgg cttccttctt tatgtatgtg tgtgacttgt tttaattggt          2650

aagttataag ccagacatag attttagctc tttaataaaa acttcagggg          2700

cacgtatgtc ccagtacaag tgtactgact atcaagtttt aactcagatg          2750

caagctttgg ctctttcata aaaagttttt atgcatatgt gtctccatac          2800

aagtggctca ttaaaataag aactttgtaa actgacttaa aatcagatat          2850

tttttcaaga gttagggaaa gttgaagtgt tttactgttt tgtctcttga          2900

gccctttctc tggggaaaaa atacatatcc atctatctat ctatatataa          2950

actgtgtata cattcttact gtttgaacaa ctattgcctt taattaaatg          3000

tttcattttt ctccagagtc cccaaagcca catggcatta ttatagtcat          3050

ttttgagatg cctgtagaga atgaaagtat tgactccgtt agagggaaaa          3100

tgggtttctc tgggtgaatt ccaacgaagc atacctaggg gtaacagtga          3150

acctacctgg gtttgttttg ttttggtaag gatttatgta gtgtctggct          3200

gtaagcaaga atgagtggat tataaacttg aagatttctc tgttaaagtc          3250

acaaaaatga tcgacaaaca atatttttgt gatgtttatt taaacgttgt          3300

attttataac atacttcaag gaagagtatc gaagtaagtt gctttataaa          3350

ttaagactaa attcgtatgg atgcagaatt caattaataa aatttgagcc          3400

tgttacgtaa attgaatatt aataaaattg aaaatttcaa  aa                  3442


<210> SEQ ID NO 110
<211> LENGTH: 457
<212> TYPE: PRT
<213> ORGANISM: Homo sapiens

<400> SEQUENCE: 110

Met Glu Asn Leu Ser Leu Ser Ile Glu Asp Val Gln Pro Arg Ser
  1               5                  10                  15

Pro Gly Arg Ser Ser Leu Asp Asp Ser Gly Glu Arg Asp Glu Lys
                 20                  25                  30
```

-continued

```
Leu Ser Lys Ser Ile Ser Phe Thr Ser Glu Ser Ile Ser Arg Val
                35                  40                  45

Ser Glu Thr Glu Ser Phe Asp Gly Asn Ser Ser Lys Gly Gly Leu
                50                  55                  60

Gly Lys Glu Glu Ser Gln Asn Glu Lys Gln Thr Lys Lys Ser Leu
                65                  70                  75

Leu Pro Thr Leu Glu Lys Lys Leu Thr Arg Val Pro Ser Lys Ser
                80                  85                  90

Leu Asp Leu Asn Lys Asn Glu Tyr Leu Ser Leu Asp Lys Ser Ser
                95                  100                 105

Thr Ser Asp Ser Val Asp Glu Glu Asn Val Pro Glu Lys Asp Leu
                110                 115                 120

His Gly Arg Leu Phe Ile Asn Arg Ile Phe His Ile Ser Ala Asp
                125                 130                 135

Arg Met Phe Glu Leu Leu Phe Thr Ser Ser Arg Phe Met Gln Lys
                140                 145                 150

Phe Ala Ser Ser Arg Asn Ile Ile Asp Val Val Ser Thr Pro Trp
                155                 160                 165

Thr Ala Glu Leu Gly Gly Asp Gln Leu Arg Thr Met Thr Tyr Thr
                170                 175                 180

Ile Val Leu Asn Ser Pro Leu Thr Gly Lys Cys Thr Ala Ala Thr
                185                 190                 195

Glu Lys Gln Thr Leu Tyr Lys Glu Ser Arg Glu Ala Arg Phe Tyr
                200                 205                 210

Leu Val Asp Ser Glu Val Leu Thr His Asp Val Pro Tyr His Asp
                215                 220                 225

Tyr Phe Tyr Thr Val Asn Arg Tyr Cys Ile Ile Arg Ser Ser Lys
                230                 235                 240

Gln Lys Cys Arg Leu Arg Val Ser Thr Asp Leu Lys Tyr Arg Lys
                245                 250                 255

Gln Pro Trp Gly Leu Val Lys Ser Leu Ile Glu Lys Asn Ser Trp
                260                 265                 270

Ser Ser Leu Glu Asp Tyr Phe Lys Gln Leu Glu Ser Asp Leu Leu
                275                 280                 285

Ile Glu Glu Ser Val Leu Asn Gln Ala Ile Glu Asp Pro Gly Lys
                290                 295                 300

Leu Thr Gly Leu Arg Arg Arg Arg Arg Thr Phe Asn Arg Thr Ala
                305                 310                 315

Glu Thr Val Pro Lys Leu Ser Ser Gln His Ser Ser Gly Asp Val
                320                 325                 330

Gly Leu Gly Ala Lys Gly Asp Ile Thr Gly Lys Lys Lys Glu Met
                335                 340                 345

Glu Asn Tyr Asn Val Thr Leu Ile Val Val Met Ser Ile Phe Val
                350                 355                 360

Leu Leu Leu Val Leu Leu Asn Val Thr Leu Phe Leu Lys Leu Ser
                365                 370                 375

Lys Ile Glu His Ala Ala Gln Ser Phe Tyr Arg Leu Arg Leu Gln
                380                 385                 390

Glu Glu Lys Ser Leu Asn Leu Ala Ser Asp Met Val Ser Arg Ala
                395                 400                 405

Glu Thr Ile Gln Lys Asn Lys Asp Gln Ala His Arg Leu Lys Gly
                410                 415                 420

Val Leu Arg Asp Ser Ile Val Met Leu Glu Gln Leu Lys Ser Ser
```

-continued

```
                425                 430                 435

Leu Ile Met Leu Gln Lys Thr Phe Asp Leu Leu Asn Lys Asn Lys
                440                 445                 450

Thr Gly Met Ala Val Glu Ser
                455
```

<210> SEQ ID NO 111
<211> LENGTH: 1606
<212> TYPE: DNA
<213> ORGANISM: Homo sapiens

<400> SEQUENCE: 111

```
cggacgcgtg gggccgtatg cgcggctctg tggagtgcac ctggggttgg        50

gggcactgtg cccccagccc cctgctcctt tggactctac ttctgtttgc       100

agccccattt ggcctgctgg gggagaagac ccgccaggtg tctctggagg       150

tcatccctaa ctggctgggc cccctgcaga acctgcttca tatacgggca       200

gtgggcacca attccacact gcactatgtg tggagcagcc tggggcctct       250

ggcagtggta atggtggcca ccaacacccc ccacagcacc ctgagcatca       300

actggagcct cctgctatcc cctgagcccg atgggggcct gatggtgctc       350

cctaaggaca gcattcagtt ttcttctgcc cttgttttta ccaggctgct       400

tgagtttgac agcaccaacg tgtccgatac ggcagcaaag cctttgggaa       450

gaccatatcc tccatactcc ttggccgatt tctcttggaa caacatcact       500

gattcattgg atcctgccac cctgagtgcc acatttcaag gccaccccat       550

gaacgaccct accaggactt ttgccaatgg cagcctggcc ttcagggtcc       600

aggccttttc caggtccagc cgaccagccc aacccccctcg cctcctgcac      650

acagcagaca cctgtcagct agaggtggcc ctgattggag cctctccccg       700

gggaaaccgt tccctgtttg ggctggaggt agccacattg ggccagggcc       750

ctgactgccc ctcaatgcag gagcagcact ccatcgacga tgaatatgca       800

ccggccgtct tccagttgga ccagctactg tggggctccc tcccatcagg       850

ctttgcacag tggcgaccag tggcttactc ccagaagccg gggggccgag       900

aatcagccct gccctgccaa gcttcccctc ttcatcctgc cttagcatac       950

tctcttcccc agtcacccat tgtccgagcc ttctttgggt cccagaataa      1000

cttctgtgcc ttcaatctga cgttcggggc ttccacaggc cctggctatt      1050

gggaccaaca ctacctcagc tggtcgatgc tcctgggtgt gggcttccct      1100

ccagtggacg gcttgtcccc actagtcctg ggcatcatgg cagtggccct      1150

gggtgcccca gggctcatgc tgctaggggg cggcttggtt ctgctgctgc      1200

accacaagaa gtactcagag taccagtcca taaattaagg cccgctctct      1250

ggagggaagg acattactga acctgtcttg ctgtgcctcg aaactctgga      1300

ggttggagca tcaagttcca gccggcccct tcactccccc atcttgcttt      1350

tctgtggaac ctcagaggcc agcctcgact tcctggagac ccccaggtgg      1400

ggcttccttc atactttgtt gggggacttt ggaggcgggc aggggacagg      1450

gctattgata aggtcccctt ggtgttgcct tcttgcatct ccacacattt      1500

cccttggatg ggacttgcag gcctaaatga gaggcattct gactggttgg      1550

ctgccctgga aggcaagaaa atagatttat tttttttcac agggaaaaaa      1600
```

-continued aaaaaa 1606

<210> SEQ ID NO 112
<211> LENGTH: 406
<212> TYPE: PRT
<213> ORGANISM: Homo sapiens

<400> SEQUENCE: 112

Met Arg Gly Ser Val Glu Cys Thr Trp Gly Trp Gly His Cys Ala
1 5 10 15

Pro Ser Pro Leu Leu Leu Trp Thr Leu Leu Leu Phe Ala Ala Pro
20 25 30

Phe Gly Leu Leu Gly Glu Lys Thr Arg Gln Val Ser Leu Glu Val
35 40 45

Ile Pro Asn Trp Leu Gly Pro Leu Gln Asn Leu Leu His Ile Arg
50 55 60

Ala Val Gly Thr Asn Ser Thr Leu His Tyr Val Trp Ser Ser Leu
65 70 75

Gly Pro Leu Ala Val Val Met Val Ala Thr Asn Thr Pro His Ser
80 85 90

Thr Leu Ser Ile Asn Trp Ser Leu Leu Leu Ser Pro Glu Pro Asp
95 100 105

Gly Gly Leu Met Val Leu Pro Lys Asp Ser Ile Gln Phe Ser Ser
110 115 120

Ala Leu Val Phe Thr Arg Leu Leu Glu Phe Asp Ser Thr Asn Val
125 130 135

Ser Asp Thr Ala Ala Lys Pro Leu Gly Arg Pro Tyr Pro Pro Tyr
140 145 150

Ser Leu Ala Asp Phe Ser Trp Asn Asn Ile Thr Asp Ser Leu Asp
155 160 165

Pro Ala Thr Leu Ser Ala Thr Phe Gln Gly His Pro Met Asn Asp
170 175 180

Pro Thr Arg Thr Phe Ala Asn Gly Ser Leu Ala Phe Arg Val Gln
185 190 195

Ala Phe Ser Arg Ser Ser Arg Pro Ala Gln Pro Pro Arg Leu Leu
200 205 210

His Thr Ala Asp Thr Cys Gln Leu Glu Val Ala Leu Ile Gly Ala
215 220 225

Ser Pro Arg Gly Asn Arg Ser Leu Phe Gly Leu Glu Val Ala Thr
230 235 240

Leu Gly Gln Gly Pro Asp Cys Pro Ser Met Gln Glu Gln His Ser
245 250 255

Ile Asp Asp Glu Tyr Ala Pro Ala Val Phe Gln Leu Asp Gln Leu
260 265 270

Leu Trp Gly Ser Leu Pro Ser Gly Phe Ala Gln Trp Arg Pro Val
275 280 285

Ala Tyr Ser Gln Lys Pro Gly Gly Arg Glu Ser Ala Leu Pro Cys
290 295 300

Gln Ala Ser Pro Leu His Pro Ala Leu Ala Tyr Ser Leu Pro Gln
305 310 315

Ser Pro Ile Val Arg Ala Phe Phe Gly Ser Gln Asn Asn Phe Cys
320 325 330

Ala Phe Asn Leu Thr Phe Gly Ala Ser Thr Gly Pro Gly Tyr Trp
335 340 345

-continued

```
Asp Gln His Tyr Leu Ser Trp Ser Met Leu Leu Gly Val Gly Phe
                350                 355                 360

Pro Pro Val Asp Gly Leu Ser Pro Leu Val Leu Gly Ile Met Ala
                365                 370                 375

Val Ala Leu Gly Ala Pro Gly Leu Met Leu Leu Gly Gly Gly Leu
                380                 385                 390

Val Leu Leu Leu His His Lys Lys Tyr Ser Glu Tyr Gln Ser Ile
                395                 400                 405

Asn


<210> SEQ ID NO 113
<211> LENGTH: 2015
<212> TYPE: DNA
<213> ORGANISM: Homo sapiens

<400> SEQUENCE: 113

ggaaaaggta cccgcgagag acagccagca gttctgtgga gcagcggtgg              50

ccggctagga tgggctgtct ctggggtctg gctctgcccc ttttcttctt             100

ctgctgggag gttggggtct ctgggagctc tgcaggcccc agcacccgca             150

gagcagacac tgcgatgaca acggacgaca cagaagtgcc cgctatgact             200

ctagcaccgg gccacgccgc tctggaaact caaacgctga gcgctgagac             250

ctcttctagg gcctcaaccc cagccggccc cattccagaa gcagagacca             300

ggggagccaa gagaatttcc cctgcaagag agaccaggag tttcacaaaa             350

acatctccca acttcatggt gctgatcgcc acctccgtgg agacatcagc             400

cgccagtggc agccccgagg gagctggaat gaccacagtt cagaccatca             450

caggcagtga tcccgaggaa gccatctttg acaccctttg caccgatgac             500

agctctgaag aggcaaagac actcacaatg gacatattga cattggctca             550

cacctccaca gaagctaagg gcctgtcctc agagagcagt gcctcttccg             600

acggccccca tccagtcatc accccgtcac gggcctcaga gagcagcgcc             650

tcttccgacg gcccccatcc agtcatcacc ccgtcacggg cctcagagag             700

cagcgcctct tccgacggcc cccatccagt catcaccccg tcatggtccc             750

cgggatctga tgtcactctc ctcgctgaag ccctggtgac tgtcacaaac             800

atcgaggtta ttaattgcag catcacagaa atagaaacaa caacttccag             850

catccctggg gcctcagaca tagatctcat ccccacggaa ggggtgaagg             900

cctcgtccac ctccgatcca ccagctctgc ctgactccac tgaagcaaaa             950

ccacacatca ctgaggtcac agcctctgcc gagaccctgt ccacagccgg            1000

caccacagag tcagctgcac ctcatgccac ggttgggacc ccactcccca            1050

ctaacagcgc cacagaaaga gaagtgacag cacccggggc cacgaccctc            1100

agtggagctc tggtcacagt tagcaggaat cccctggaag aaacctcagc            1150

cctctctgtt gagacaccaa gttacgtcaa agtctcagga gcagctccgg            1200

tctccataga ggctgggtca gcagtgggca aaacaacttc ctttgctggg            1250

agctctgctt cctcctacag cccctcggaa gccgccctca agaacttcac            1300

cccttcagag acaccgacca tggacatcgc aaccaagggg cccttcccca            1350

ccagcaggga ccctcttcct tctgtccctc cgactacaac caacagcagc            1400
```

-continued

```
cgagggacga acagcacctt agccaagatc acaacctcag cgaagaccac          1450

gatgaagccc caacagccac gcccacgact gcccggacga ggccgaccac          1500

agacgtgagt gcaggtgaaa atggaggttt cctcctcctg cggctgagtg          1550

tggcttcccc ggaagacctc actgacccca gagtggcaga aaggctgatg          1600

cagcagctcc accgggaact ccacgcccac gcgcctcact tccaggtctc          1650

cttactgcgt gtcaggagag gctaacggac atcagctgca gccaggcatg          1700

tcccgtatgc caaaagaggg tgctgcccct agcctgggcc cccaccgaca          1750

gactgcagct gcgttactgt gctgagaggt acccagaagg ttcccatgaa          1800

gggcagcatg tccaagcccc taaccccaga tgtggcaaca ggaccctcgc          1850

tcacatccac cggagtgtat gtatggggag gggcttcacc tgttcccaga          1900

ggtgtccttg gactcacctt ggcacatgtt ctgtgtttca gtaaagagag          1950

acctgatcac ccatctgtgt gcttccatcc tgcattaaaa ttcactcagt          2000

gtggcccaaa  aaaaa                                               2015


<210> SEQ ID NO 114
<211> LENGTH: 482
<212> TYPE: PRT
<213> ORGANISM: Homo sapiens

<400> SEQUENCE: 114

Met Gly Cys Leu Trp Gly Leu Ala Leu Pro Leu Phe Phe Phe Cys
  1               5                  10                  15

Trp Glu Val Gly Val Ser Gly Ser Ser Ala Gly Pro Ser Thr Arg
                 20                  25                  30

Arg Ala Asp Thr Ala Met Thr Thr Asp Asp Thr Glu Val Pro Ala
                 35                  40                  45

Met Thr Leu Ala Pro Gly His Ala Ala Leu Glu Thr Gln Thr Leu
                 50                  55                  60

Ser Ala Glu Thr Ser Ser Arg Ala Ser Thr Pro Ala Gly Pro Ile
                 65                  70                  75

Pro Glu Ala Glu Thr Arg Gly Ala Lys Arg Ile Ser Pro Ala Arg
                 80                  85                  90

Glu Thr Arg Ser Phe Thr Lys Thr Ser Pro Asn Phe Met Val Leu
                 95                 100                 105

Ile Ala Thr Ser Val Glu Thr Ser Ala Ala Ser Gly Ser Pro Glu
                110                 115                 120

Gly Ala Gly Met Thr Thr Val Gln Thr Ile Thr Gly Ser Asp Pro
                125                 130                 135

Glu Glu Ala Ile Phe Asp Thr Leu Cys Thr Asp Asp Ser Ser Glu
                140                 145                 150

Glu Ala Lys Thr Leu Thr Met Asp Ile Leu Thr Leu Ala His Thr
                155                 160                 165

Ser Thr Glu Ala Lys Gly Leu Ser Ser Glu Ser Ser Ala Ser Ser
                170                 175                 180

Asp Gly Pro His Pro Val Ile Thr Pro Ser Arg Ala Ser Glu Ser
                185                 190                 195

Ser Ala Ser Ser Asp Gly Pro His Pro Val Ile Thr Pro Ser Arg
                200                 205                 210

Ala Ser Glu Ser Ser Ala Ser Ser Asp Gly Pro His Pro Val Ile
                215                 220                 225
```

-continued

```
Thr Pro Ser Trp Ser Pro Gly Ser Asp Val Thr Leu Leu Ala Glu
                230                 235                 240

Ala Leu Val Thr Val Thr Asn Ile Glu Val Ile Asn Cys Ser Ile
                245                 250                 255

Thr Glu Ile Glu Thr Thr Thr Ser Ser Ile Pro Gly Ala Ser Asp
                260                 265                 270

Ile Asp Leu Ile Pro Thr Glu Gly Val Lys Ala Ser Ser Thr Ser
                275                 280                 285

Asp Pro Pro Ala Leu Pro Asp Ser Thr Glu Ala Lys Pro His Ile
                290                 295                 300

Thr Glu Val Thr Ala Ser Ala Glu Thr Leu Ser Thr Ala Gly Thr
                305                 310                 315

Thr Glu Ser Ala Ala Pro His Ala Thr Val Gly Thr Pro Leu Pro
                320                 325                 330

Thr Asn Ser Ala Thr Glu Arg Glu Val Thr Ala Pro Gly Ala Thr
                335                 340                 345

Thr Leu Ser Gly Ala Leu Val Thr Val Ser Arg Asn Pro Leu Glu
                350                 355                 360

Glu Thr Ser Ala Leu Ser Val Glu Thr Pro Ser Tyr Val Lys Val
                365                 370                 375

Ser Gly Ala Ala Pro Val Ser Ile Glu Ala Gly Ser Ala Val Gly
                380                 385                 390

Lys Thr Thr Ser Phe Ala Gly Ser Ser Ala Ser Ser Tyr Ser Pro
                395                 400                 405

Ser Glu Ala Ala Leu Lys Asn Phe Thr Pro Ser Glu Thr Pro Thr
                410                 415                 420

Met Asp Ile Ala Thr Lys Gly Pro Phe Pro Thr Ser Arg Asp Pro
                425                 430                 435

Leu Pro Ser Val Pro Pro Thr Thr Thr Asn Ser Ser Arg Gly Thr
                440                 445                 450

Asn Ser Thr Leu Ala Lys Ile Thr Thr Ser Ala Lys Thr Thr Met
                455                 460                 465

Lys Pro Gln Gln Pro Arg Pro Arg Leu Pro Gly Arg Gly Arg Pro
                470                 475                 480

Gln Thr


<210> SEQ ID NO 115
<211> LENGTH: 526
<212> TYPE: DNA
<213> ORGANISM: Homo sapiens

<400> SEQUENCE: 115

gcgaggcggc cgctgtcttc tgctgcggct tccgcgacca caagtactgc                50

tgcgacgacc cgcacagctt cttcccctac gagcacagct acatgtggtg               100

gctcagcatt ggcgctctca taggcctgtc cgtagcagca gtggttcttc               150

tcgccttcat tgttaccgcc tgtgtgctct gctacctgtt catcagctct               200

aagccccaca caaagttgga cctgggcttg agcttacaga cagcaggccc               250

tgaggaggtt tctcctgact gccaaggtgt gaacacaggc atggcggcag               300

aagtgccaaa agtgagccct ctccagcaga gttactcctg cttgaacccg               350

cagctggaga gcaatgaggg gcaggctgtg aactccaaac gcctcctcca               400

tcattgcttc atggccacag tgaccaccag tgacattcca ggcagccctg               450
```

-continued

```
aggaagcctc tgtacccaac cctgacctat gtggaccagt cccataaaca           500

ttcaataaat gtctccatac  catcaa                                    526
```

<210> SEQ ID NO 116
<211> LENGTH: 134
<212> TYPE: PRT
<213> ORGANISM: Homo sapiens

<400> SEQUENCE: 116

```
Met Trp Trp Leu Ser Ile Gly Ala Leu Ile Gly Leu Ser Val Ala
  1               5                  10                  15

Ala Val Val Leu Leu Ala Phe Ile Val Thr Ala Cys Val Leu Cys
                 20                  25                  30

Tyr Leu Phe Ile Ser Ser Lys Pro His Thr Lys Leu Asp Leu Gly
                 35                  40                  45

Leu Ser Leu Gln Thr Ala Gly Pro Glu Glu Val Ser Pro Asp Cys
                 50                  55                  60

Gln Gly Val Asn Thr Gly Met Ala Ala Glu Val Pro Lys Val Ser
                 65                  70                  75

Pro Leu Gln Gln Ser Tyr Ser Cys Leu Asn Pro Gln Leu Glu Ser
                 80                  85                  90

Asn Glu Gly Gln Ala Val Asn Ser Lys Arg Leu Leu His His Cys
                 95                 100                 105

Phe Met Ala Thr Val Thr Thr Ser Asp Ile Pro Gly Ser Pro Glu
                110                 115                 120

Glu Ala Ser Val Pro Asn Pro Asp Leu Cys Gly Pro Val Pro
                125                 130
```

<210> SEQ ID NO 117
<211> LENGTH: 1863
<212> TYPE: DNA
<213> ORGANISM: Homo sapiens

<400> SEQUENCE: 117

```
cctctgtctg tgctcccatc ccagggagta taggtggagc ctccagagcc            50

catggacagg gcatgctggg gctgggccag ccccagcggt gtctctaagg           100

cacccctggg atccccactg agctggccta cttcagacag ccagggccca           150

cccctctggc ccccttagtg tccagctcgt ggccccttgg catttccaca           200

agacgccaag atggagattc ccatggggac ccagggctgc ttctcaaaga           250

gcctcctgct ctcagcctca atcctggtcc tctggatgct ccaaggctcc           300

caggcagctc tctacatcca gaagattcca gagcagcctc aaaagaacca           350

ggaccttctc ctgtcagtcc agggtgtccc agacaccttc caggacttca           400

actggtacct gggggaggag acgtacggag gcacgaggct atttacctac           450

atccctggga tacaacggcc tcagagggat ggcagtgcca tgggacagcg           500

agacatcgtg ggcttcccca atggttccat gctgctgcgc cgcgcccagc           550

ctacagacag tggcacctac caagtagcca ttaccatcaa ctctgaatgg           600

actatgaagg ccaagactga ggtccaggta gctgaaaaga ataaggagct           650

gcccagtaca cacctgccca ccaacgctgg gatcctggcg gccaccatca           700

ttggatctct tgctgccggg gcccttctca tcagctgcat tgcctatctc           750

ctggtgacaa ggaactggag gggccagagc cacagactgc ctgctccgag           800
```

-continued

```
gggccaggga tctctgtcca tcttgtgctc ggctgtatcc ccagtgcctt         850

cagtgacgcc cagcacatgg atggcgacca cagagaagcc agaattgggc         900

cctgctcatg atgctggtga caacaacatc tatgaagtga tgccctctcc         950

agtcctcctg gtgtccccca tcagtgacac aaggtccata aacccagccc        1000

ggcccctgcc cacaccccca cacctgcagg cggagccaga gaaccaccag        1050

taccagcagg acctgctaaa ccccgaccct gccccctact gccagctggt        1100

gccaacttcc tgatgggtcc tgggccaggc cagccaggga gaagacaagg        1150

ccccagccct cctctgggag cctcacacct gagaccagca ggacaaggcc        1200

attgggggct gtggggccga tgaggtggac tcagccaaag actcagcagc        1250

acatggggca ggtgtcctgg caggggggaca ggagactgta acaggcccag        1300

gtccttgtgc agcccctgaa tgcacgcccg ccttcggtct gttccttcaa        1350

gcaagctggc ctgggccatg tgcctgtgaa aggcaggctc tggccccttt        1400

ccatgccaaa gtcccccaag atctggatat ctggggacaa gatggtggcc        1450

tcaggcctgc ctcccaggca gttggctggg ctcccaactg tctgtcctca        1500

atgccctacc ccaactccac tagtgaccct cagagtcttc tccccttagg        1550

acaaggcaga caccccacca tgcgggcctc aggtggcaga gaggcccagc        1600

ctcacaggcc tgtggcccca cacaccagtc ccagcaaggt gaccacggct        1650

gctggacccc ttccctgttc aggcaggccc agcccctctc agaacctgct        1700

gccagctgct ggtcttggcc cccaccctga atcttactga gtccctctgg        1750

gcagcagctc ccttctccac cccaccccag cacccgtccc aaatgtggcc        1800

tcagcttgtc ctccccttcc ccaaactatg cattcattca gcaataaatg        1850

agcctttgct  gca                                               1863
```

<210> SEQ ID NO 118
<211> LENGTH: 300
<212> TYPE: PRT
<213> ORGANISM: Homo sapiens

<400> SEQUENCE: 118

```
Met Glu Ile Pro Met Gly Thr Gln Gly Cys Phe Ser Lys Ser Leu
  1               5                  10                  15

Leu Leu Ser Ala Ser Ile Leu Val Leu Trp Met Leu Gln Gly Ser
                 20                  25                  30

Gln Ala Ala Leu Tyr Ile Gln Lys Ile Pro Glu Gln Pro Gln Lys
                 35                  40                  45

Asn Gln Asp Leu Leu Leu Ser Val Gln Gly Val Pro Asp Thr Phe
                 50                  55                  60

Gln Asp Phe Asn Trp Tyr Leu Gly Glu Glu Thr Tyr Gly Gly Thr
                 65                  70                  75

Arg Leu Phe Thr Tyr Ile Pro Gly Ile Gln Arg Pro Gln Arg Asp
                 80                  85                  90

Gly Ser Ala Met Gly Gln Arg Asp Ile Val Gly Phe Pro Asn Gly
                 95                 100                 105

Ser Met Leu Leu Arg Arg Ala Gln Pro Thr Asp Ser Gly Thr Tyr
                110                 115                 120

Gln Val Ala Ile Thr Ile Asn Ser Glu Trp Thr Met Lys Ala Lys
                125                 130                 135
```

-continued

```
Thr Glu Val Gln Val Ala Glu Lys Asn Lys Glu Leu Pro Ser Thr
                140                 145                 150

His Leu Pro Thr Asn Ala Gly Ile Leu Ala Ala Thr Ile Ile Gly
                155                 160                 165

Ser Leu Ala Ala Gly Ala Leu Leu Ile Ser Cys Ile Ala Tyr Leu
                170                 175                 180

Leu Val Thr Arg Asn Trp Arg Gly Gln Ser His Arg Leu Pro Ala
                185                 190                 195

Pro Arg Gly Gln Gly Ser Leu Ser Ile Leu Cys Ser Ala Val Ser
                200                 205                 210

Pro Val Pro Ser Val Thr Pro Ser Thr Trp Met Ala Thr Thr Glu
                215                 220                 225

Lys Pro Glu Leu Gly Pro Ala His Asp Ala Gly Asp Asn Asn Ile
                230                 235                 240

Tyr Glu Val Met Pro Ser Pro Val Leu Leu Val Ser Pro Ile Ser
                245                 250                 255

Asp Thr Arg Ser Ile Asn Pro Ala Arg Pro Leu Pro Thr Pro Pro
                260                 265                 270

His Leu Gln Ala Glu Pro Glu Asn His Gln Tyr Gln Gln Asp Leu
                275                 280                 285

Leu Asn Pro Asp Pro Ala Pro Tyr Cys Gln Leu Val Pro Thr Ser
                290                 295                 300
```

<210> SEQ ID NO 119
<211> LENGTH: 1830
<212> TYPE: DNA
<213> ORGANISM: Homo sapiens

<400> SEQUENCE: 119

```
agcatgagag gcctggccgt cctcctcact gtggctctgg ccacgctcct          50

ggctcccggg gccggagcac cggtacaaag tcagggctcc cagaacaagc         100

tgctcctggt gtccttcgac ggcttccgct ggaactacga ccaggatgtg         150

gacaccccca acctggacgc catggcccga gacggggtga aggcacgcta         200

catgaccccc gcctttgtca ccatgaccag cccctgccac ttcaccctgg         250

tcaccggcaa atatatcgag aaccacgggg tggttcacaa catgtactac         300

aacatcacca gcaaggtgaa gctgccctac cacgccacgc tgggcatcca         350

gaggtggtgg gacaacggca gcgtgcccat ctggatcaca gcccagaggc         400

agggcctgag ggctggctcc ttcttctacc cgggcgggaa cgtcacctac         450

caaggggtgg ctgtgacgcg gagccggaaa gaaggcatcg cacacaacta         500

caaaaatgag acggagtgga gagcgaacat cgacacagtg atggcgtggt         550

tcacagagga ggacctggat ctggtcacac tctacttcgg ggagccggac         600

tccacgggcc acaggtacgg ccccgagtcc ccggagagga gggagatggt         650

gcggcaggtg gaccggaccg tgggctacct ccgggagagc atcgcgcgca         700

accacctcac agaccgcctc aacctgatca tcacatccga ccacggcatg         750

acgaccgtgg acaaacgggc tggcgacctg gttgaattcc acaagttccc         800

caacttcacc ttccgggaca tcgagtttga gctcctggac tacggaccaa         850

acgggatgct gctccctaaa gaagggaggc tggagaaggt gtacgatgcc         900

ctcaaggacg cccaccccaa gctccacgtc tacaagaagg aggcgttccc         950
```

-continued

```
cgaggccttc cactacgcca acaaccccag ggtcacaccc ctgctgatgt    1000

acagcgacct tggctacgtc atccatggga gaattaacgt ccagttcaac    1050

aatggggagc acggctttga caacaaggac atggacatga agaccatctt    1100

ccgcgctgtg ggccctagct tcagggcggg cctggaggtg gagccctttg    1150

agagcgtcca cgtgtacgag ctcatgtgcc ggctgctggg catcgtgccc    1200

gaggccaacg atgggcacct agctactctg ctgcccatgc tgcacacaga    1250

atctgctctt ccgcctgatg gaaggcctac tctcctgccc aagggaagat    1300

ctgctctccc gcccagcagc aggcccctcc tcgtgatggg actgctgggg    1350

accgtgattc ttctgtctga ggtcgcataa cgccccatgg ctcaaggaag    1400

ccgccgggag ctgcccgcag gccctgggcc ggctgtctcg ctgcgatgct    1450

ctgctggtcg cggacggacc ctgcctcccc agcttatccc aggccagagg    1500

ctgcatgcca ctgtccccgg cagcgccaac ccctgcttgg ctgttatggt    1550

gctggtaata agcctcgcag cccaggtcca gagcccccgg cgagccggtc    1600

ccataaccgg ccccctgccc ctgcccctgc tcctgctcct cccccttcggg    1650

cccctcctc ctgcaaaacc cgctcccgaa gcggcgctgc cgtctgcagc    1700

cacgcggggg cgcgcgggag ctctgcgggc gctggaacct gcagacccgg    1750

cctcggtcag ctgggagggg cccgccccgg cacaaagcac ccatgggaat    1800

aaaggccaag ccgcgacagt caaaaaaaaa                          1830
```

<210> SEQ ID NO 120
<211> LENGTH: 458
<212> TYPE: PRT
<213> ORGANISM: Homo sapiens

<400> SEQUENCE: 120

```
Met Arg Gly Leu Ala Val Leu Leu Thr Val Ala Leu Ala Thr Leu
  1               5                  10                  15

Leu Ala Pro Gly Ala Gly Ala Pro Val Gln Ser Gln Gly Ser Gln
                 20                  25                  30

Asn Lys Leu Leu Leu Val Ser Phe Asp Gly Phe Arg Trp Asn Tyr
                 35                  40                  45

Asp Gln Asp Val Asp Thr Pro Asn Leu Asp Ala Met Ala Arg Asp
                 50                  55                  60

Gly Val Lys Ala Arg Tyr Met Thr Pro Ala Phe Val Thr Met Thr
                 65                  70                  75

Ser Pro Cys His Phe Thr Leu Val Thr Gly Lys Tyr Ile Glu Asn
                 80                  85                  90

His Gly Val Val His Asn Met Tyr Tyr Asn Ile Thr Ser Lys Val
                 95                 100                 105

Lys Leu Pro Tyr His Ala Thr Leu Gly Ile Gln Arg Trp Trp Asp
                110                 115                 120

Asn Gly Ser Val Pro Ile Trp Ile Thr Ala Gln Arg Gln Gly Leu
                125                 130                 135

Arg Ala Gly Ser Phe Phe Tyr Pro Gly Gly Asn Val Thr Tyr Gln
                140                 145                 150

Gly Val Ala Val Thr Arg Ser Arg Lys Glu Gly Ile Ala His Asn
                155                 160                 165

Tyr Lys Asn Glu Thr Glu Trp Arg Ala Asn Ile Asp Thr Val Met
                170                 175                 180
```

-continued

Ala Trp Phe Thr Glu Glu Asp Leu Asp Leu Val Thr Leu Tyr Phe
185 190 195

Gly Glu Pro Asp Ser Thr Gly His Arg Tyr Gly Pro Glu Ser Pro
200 205 210

Glu Arg Arg Glu Met Val Arg Gln Val Asp Arg Thr Val Gly Tyr
215 220 225

Leu Arg Glu Ser Ile Ala Arg Asn His Leu Thr Asp Arg Leu Asn
230 235 240

Leu Ile Ile Thr Ser Asp His Gly Met Thr Thr Val Asp Lys Arg
245 250 255

Ala Gly Asp Leu Val Glu Phe His Lys Phe Pro Asn Phe Thr Phe
260 265 270

Arg Asp Ile Glu Phe Glu Leu Leu Asp Tyr Gly Pro Asn Gly Met
275 280 285

Leu Leu Pro Lys Glu Gly Arg Leu Glu Lys Val Tyr Asp Ala Leu
290 295 300

Lys Asp Ala His Pro Lys Leu His Val Tyr Lys Lys Glu Ala Phe
305 310 315

Pro Glu Ala Phe His Tyr Ala Asn Asn Pro Arg Val Thr Pro Leu
320 325 330

Leu Met Tyr Ser Asp Leu Gly Tyr Val Ile His Gly Arg Ile Asn
335 340 345

Val Gln Phe Asn Asn Gly Glu His Gly Phe Asp Asn Lys Asp Met
350 355 360

Asp Met Lys Thr Ile Phe Arg Ala Val Gly Pro Ser Phe Arg Ala
365 370 375

Gly Leu Glu Val Glu Pro Phe Glu Ser Val His Val Tyr Glu Leu
380 385 390

Met Cys Arg Leu Leu Gly Ile Val Pro Glu Ala Asn Asp Gly His
395 400 405

Leu Ala Thr Leu Leu Pro Met Leu His Thr Glu Ser Ala Leu Pro
410 415 420

Pro Asp Gly Arg Pro Thr Leu Leu Pro Lys Gly Arg Ser Ala Leu
425 430 435

Pro Pro Ser Ser Arg Pro Leu Leu Val Met Gly Leu Leu Gly Thr
440 445 450

Val Ile Leu Leu Ser Glu Val Ala
455

<210> SEQ ID NO 121
<211> LENGTH: 1524
<212> TYPE: DNA
<213> ORGANISM: Homo sapiens

<400> SEQUENCE: 121
gcggcagcag cgcgggcccc agcagcctcg gcagccacag ccgctgcagc 50
cggggcagcc tccgctgctg tcgcctcctc tgatgcgctt gccctctccc 100
ggccccggga ctccgggaga atgtgggtcc taggcatcgc ggcaactttt 150
tgcggattgt tcttgcttcc aggctttgcg ctgcaaatcc agtgctacca 200
gtgtgaagaa ttccagctga acaacgactg ctcctccccc gagttcattg 250
tgaattgcac ggtgaacgtt caagacatgt gtcagaaaga agtgatggag 300
caaagtgccg ggatcatgta ccgcaagtcc tgtgcatcat cagcggcctg 350

-continued

```
tctcatcgcc tctgccgggt accagtcctt ctgctcccca gggaaactga          400
actcagtttg catcagctgc tgcaacaccc ctctttgtaa cgggccaagg          450
cccaagaaaa ggggaagttc tgcctcggcc ctcaggccag ggctccgcac          500
caccatcctg ttcctcaaat tagccctctt ctcggcacac tgctgaagct          550
gaaggagatg ccacccccctc ctgcattgtt cttccagccc tcgcccccaa         600
ccccccacct ccctgagtga gtttcttctg ggtgtccttt tattctgggt          650
agggagcggg agtccgtgtt ctcttttgtt cctgtgcaaa taatgaaaga          700
gctcggtaaa gcattctgaa taaattcagc ctgactgaat tttcagtatg          750
tacttgaagg aaggaggtgg agtgaaagtt cacccccatg tctgtgtaac          800
cggagtcaag gccaggctgg cagagtcagt ccttagaagt cactgaggtg          850
ggcatctgcc ttttgtaaag cctccagtgt ccattccatc cctgatgggg          900
gcatagtttg agactgcaga gtgagagtga cgttttctta gggctggagg          950
gccagttccc actcaaggct ccctcgcttg acattcaaac ttcatgctcc         1000
tgaaaaccat tctctgcagc agaattggct ggtttcgcgc ctgagttggg         1050
ctctagtgac tcgagactca atgactggga cttagactgg ggctcggcct         1100
cgctctgaaa agtgcttaag aaaatcttct cagttctcct tgcagaggac         1150
tggcgccggg acgcgaagag caacgggcgc tgcacaaagc gggcgctgtc         1200
ggtggtggag tgcgcatgta cgcgcaggcg cttctcgtgg ttggcgtgct         1250
gcagcgacag gcggcagcac agcacctgca cgaacacccg ccgaaactgc         1300
tgcgaggaca ccgtgtacag gagcgggttg atgaccgagc tgaggtagaa         1350
aaacgtctcc gagaagggga ggaggatcat gtacgcccgg aagtaggacc         1400
tcgtccagtc gtgcttgggt ttggccgcag ccatgatcct ccgaatctgg         1450
ttgggcatcc agcatacggc caatgtcaca acaatcagcc ctgggcagac         1500
acgagcagga gggagagaca  gaga                                    1524
```

```
<210> SEQ ID NO 122
<211> LENGTH: 141
<212> TYPE: PRT
<213> ORGANISM: Homo sapiens

<400> SEQUENCE: 122

Met Trp Val Leu Gly Ile Ala Ala Thr Phe Cys Gly Leu Phe Leu
  1               5                  10                  15

Leu Pro Gly Phe Ala Leu Gln Ile Gln Cys Tyr Gln Cys Glu Glu
                 20                  25                  30

Phe Gln Leu Asn Asn Asp Cys Ser Ser Pro Glu Phe Ile Val Asn
                 35                  40                  45

Cys Thr Val Asn Val Gln Asp Met Cys Gln Lys Glu Val Met Glu
                 50                  55                  60

Gln Ser Ala Gly Ile Met Tyr Arg Lys Ser Cys Ala Ser Ser Ala
                 65                  70                  75

Ala Cys Leu Ile Ala Ser Ala Gly Tyr Gln Ser Phe Cys Ser Pro
                 80                  85                  90

Gly Lys Leu Asn Ser Val Cys Ile Ser Cys Cys Asn Thr Pro Leu
                 95                 100                 105

Cys Asn Gly Pro Arg Pro Lys Lys Arg Gly Ser Ser Ala Ser Ala
```

-continued

```
                110                 115                 120

Leu Arg Pro Gly Leu Arg Thr Thr Ile Leu Phe Leu Lys Leu Ala
                125                 130                 135

Leu Phe Ser Ala His Cys
                140


<210> SEQ ID NO 123
<211> LENGTH: 2786
<212> TYPE: DNA
<213> ORGANISM: Homo sapiens

<400> SEQUENCE: 123

agcactctcc agcctctcac cgcaaaatta cacaccccag tacaccagca        50

gaggaaactt ataacctcgg gaggcgggtc cttcccctca gtgcggtcac       100

atacttccag aagagcggac cagggctgct gccagcacct gccactcaga       150

gcgcctctgt cgctgggacc cttcagaact ctctttgctc acaagttacc       200

aaaaaaaaaa gagccaacat gttggtattg ctggctggta tctttgtggt       250

ccacatcgct actgttatta tgctatttgt tagcaccatt gccaatgtct       300

ggttggtttc caatacggta gatgcatcag taggtctttg gaaaaactgt       350

accaacatta gctgcagtga cagcctgtca tatgccagtg aagatgccct       400

caagacagtg caggccttca tgattctctc tatcatcttc tgtgtcattg       450

ccctcctggt cttcgtgttc cagctcttca ccatggagaa gggaaaccgg       500

ttcttcctct caggggccac cacactggtg tgctggctgt gcattcttgt       550

gggggtgtcc atctacacta gtcattatgc gaatcgtgat ggaacgcagt       600

atcaccacgg ctattcctac atcctgggct ggatctgctt ctgcttcagc       650

ttcatcatcg gcgttctcta tctggtcctg agaaagaaat aaggccggac       700

gagttcatgg ggatctgggg ggtggggagg aggaagccgt tgaatctggg       750

agggaagtgg aggttgctgt acaggaaaaa ccgagatagg ggaggggggga       800

gggggaagca aagggggggag gtcaaatccc aaaccattac tgaggggatt       850

ctctactgcc aagcccctgc cctggggaga aagtagttgg ctagtacttt       900

gatgctccct tgatggggtc cagagagcct ccctgcagcc accagacttg       950

gcctccagct gttcttagtg acacacactg tctggggccc catcagctgc      1000

cacaacacca gccccacttc tgggtcatgc actgaggtcc acagacctac      1050

tgcactgagt taaaatagcg gtacaagttc tggcaagagc agatactgtc      1100

tttgtgctga atacgctaag cctggaagcc atcctgccct tctgacccaa      1150

agcaaaacat cacattccag tctgaagtgc ctactggggg gctttggcct      1200

gtgagccatt gtccctcttt ggaacagata tttagctctg tggaattcag      1250

tgacaaaatg ggaggaggaa agagagtttg taaggtcatg ctggtgggtt      1300

agctaaacca agaaggagac cttttcacaa tggaaaacct gggggatggt      1350

cagagcccag tcgagacctc acacacggct gtccctcatg gagacctcat      1400

gccatggtct ttgctaggcc tcttgctgaa agccaaggca gctcttctgg      1450

agtttctcta aagtcactag tgaacaattc ggtggtaaaa gtaccacaca      1500

aactatggga tccaaggggc agtcttgcaa cagtgccatg ttagggttat      1550

gtttttagga ttcccctcaa tgcagtcagt gtttctttta agtatacaac      1600
```

-continued

```
aggagagaga tggacatggc tcattgtagc acaatcctat tactcttcct        1650

ctaacatttt tgaggaagtt ttgtctaatt atcaatattg aggatcaggg        1700

ctcctaggct cagtggtagc tctggcttag acaccacctg gagtgatcac        1750

ctcttgggga ccctgcctat cccacttcac aggtgaggca tggcaattct        1800

ggaagctgat taaaacacac ataaaccaaa accaaacaac aggcccttgg        1850

gtgaaaggtg ctatataatt gtgaagtatt aagcctaccg tatttcagcc        1900

atgataagaa cagagtgcct gcattcccag gaaaatacga aaatcccatg        1950

agataaataa aaatataggt gatgggcaga tcttttcttt aaaataaaaa        2000

agcaaaaact cttgtggtac ctagtcagat ggtagacgag ctgtctgctg        2050

ccgcaggagc acctctatac aggacttaga agtagtatgt tattcctggt        2100

taagcaggca ttgctttgcc ctggagcagc tattttaagc catctcagat        2150

tctgtctaaa ggggtttttt gggaagacgt tttctttatc gccctgagaa        2200

gatctacccc agggagaatc tgagacatct tgcctacttt tctttattag        2250

ctttctcctc atccatttct tttatacctt tcctttttgg ggagttgtta        2300

tgccatgatt tttggtattt atgtaaaagg attattacta attctatttc        2350

tctatgttta ttctagttaa ggaaatgttg agggcaagcc accaaattac        2400

ctaggctgag gttagagaga ttggccagca aaaactgtgg gaagatgaac        2450

tttgtcatta tgatttcatt atcacatgat tatagaaggc tgtcttagtg        2500

caaaaaacat acttacattt cagacatatc caaagggaat actcacattt        2550

tgttaagaag ttgaactatg actggagtaa accatgtatt cccttatctt        2600

ttactttttt tctgtgacat ttatgtctca tgtaatttgc attactctgg        2650

tggattgttc tagtactgta ttgggcttct tcgttaatag attatttcat        2700

atactataat tgtaaatatt ttgatacaaa tgtttataac tctagggata        2750

taaaaacaga ttctgattcc cttcaaaaaa  aaaaaa                      2786
```

```
<210> SEQ ID NO 124
<211> LENGTH: 157
<212> TYPE: PRT
<213> ORGANISM: Homo sapiens

<400> SEQUENCE: 124

Met Leu Val Leu Leu Ala Gly Ile Phe Val Val His Ile Ala Thr
  1               5                  10                  15

Val Ile Met Leu Phe Val Ser Thr Ile Ala Asn Val Trp Leu Val
                 20                  25                  30

Ser Asn Thr Val Asp Ala Ser Val Gly Leu Trp Lys Asn Cys Thr
                 35                  40                  45

Asn Ile Ser Cys Ser Asp Ser Leu Ser Tyr Ala Ser Glu Asp Ala
                 50                  55                  60

Leu Lys Thr Val Gln Ala Phe Met Ile Leu Ser Ile Ile Phe Cys
                 65                  70                  75

Val Ile Ala Leu Leu Val Phe Val Phe Gln Leu Phe Thr Met Glu
                 80                  85                  90

Lys Gly Asn Arg Phe Phe Leu Ser Gly Ala Thr Thr Leu Val Cys
                 95                 100                 105

Trp Leu Cys Ile Leu Val Gly Val Ser Ile Tyr Thr Ser His Tyr
```

-continued

```
                110                 115                 120

Ala Asn Arg Asp Gly Thr Gln Tyr His His Gly Tyr Ser Tyr Ile
                125                 130                 135

Leu Gly Trp Ile Cys Phe Cys Phe Ser Phe Ile Ile Gly Val Leu
                140                 145                 150

Tyr Leu Val Leu Arg Lys Lys
                155


<210> SEQ ID NO 125
<211> LENGTH: 1056
<212> TYPE: DNA
<213> ORGANISM: Homo sapiens

<400> SEQUENCE: 125

gtctgcgcgg agtctgagcg gcgctcgtcc cgtcccaagg ccgacgccag                50

cacgccgtca tggcccccgc agcggcgacg gggggcagca ccctgcccag               100

tggcttctcg gtcttcacca ccttgcccga cttgctcttc atctttgagt               150

ttatcttcgg gggcctggtg tggatcctgg tggcctcctc cctggtgccc               200

tggcccctgg tccagggctg ggtgatgttc gtgtctgtgt tctgcttcgt               250

ggccaccacc accttgatca tcctgtacat aattggagcc cacggtggag               300

agacttcctg ggtcaccttg gacgcagcct accactgcac cgctgccctc               350

ttttacctca gcgcctcagt cctggaggcc ctggccacca tcacgatgca               400

agacggcttc acctacaggc actaccatga aaacattgct gccgtggtgt               450

tctcctacat agccactctg ctctacgtgg tccatgcggt gttctcttta               500

atcagatgga agtcttcata aagccgcagt agaacttgag ctgaaaaccc               550

agatggtgtt aactggccgc ccccactttcc ggcataactt tttagaaaac              600

agaaatgccc ttgatggtgg aaaaaagaaa acaaccaccc ccccactgcc               650

caaaaaaaaa agccctgccc tgttgctcgt gggtgctgtg tttactctcc               700

cgtgtgcctt cgcgtccggg ttgggagctt gctgtgtcta acctccaact               750

gctgtgctgt ctgctagggt cacctcctgt ttgtgaaagg ggaccttctt               800

gttcgggggt gggaagtggc gaccgtgacc tgagaaggaa agaaagatcc               850

tctgctgacc cctggagcag ctctcgagaa ctacctgttg gtattgtcca               900

caagctctcc cgagcgcccc atcttgtgcc atgttttaag tcttcatgga               950

tgttctgcat gtcatgggga ctaaaactca cccaacagat ctttccagag              1000

gtccatggtg gaagacgata accctgtgaa atactttata aaatgtctta              1050

atgttc                                                              1056


<210> SEQ ID NO 126
<211> LENGTH: 153
<212> TYPE: PRT
<213> ORGANISM: Homo sapiens

<400> SEQUENCE: 126

Met Ala Pro Ala Ala Ala Thr Gly Gly Ser Thr Leu Pro Ser Gly
  1               5                  10                  15

Phe Ser Val Phe Thr Thr Leu Pro Asp Leu Leu Phe Ile Phe Glu
                 20                  25                  30

Phe Ile Phe Gly Gly Leu Val Trp Ile Leu Val Ala Ser Ser Leu
                 35                  40                  45
```

-continued

Val Pro Trp Pro Leu Val Gln Gly Trp Val Met Phe Val Ser Val
50 55 60

Phe Cys Phe Val Ala Thr Thr Thr Leu Ile Ile Leu Tyr Ile Ile
65 70 75

Gly Ala His Gly Gly Glu Thr Ser Trp Val Thr Leu Asp Ala Ala
80 85 90

Tyr His Cys Thr Ala Ala Leu Phe Tyr Leu Ser Ala Ser Val Leu
95 100 105

Glu Ala Leu Ala Thr Ile Thr Met Gln Asp Gly Phe Thr Tyr Arg
110 115 120

His Tyr His Glu Asn Ile Ala Ala Val Val Phe Ser Tyr Ile Ala
125 130 135

Thr Leu Leu Tyr Val Val His Ala Val Phe Ser Leu Ile Arg Trp
140 145 150

Lys Ser Ser

<210> SEQ ID NO 127
<211> LENGTH: 2973
<212> TYPE: DNA
<213> ORGANISM: Homo sapiens

<400> SEQUENCE: 127
ccgcggaact ggcaggcgtt tcagagcgtc agaggctgcg gatgagcaga 50
cttggaggac tccaggccag agactaggct gggcgaagag tcgagcgtga 100
agggggctcc gggccagggt gacaggaggc gtgcttgaga ggaagaagtt 150
gacgggaagg ccagtgcgac ggcaaatctc gtgaaccttg gggacgaat 200 gctcaggatg cgggtccccg ccctcctcgt cctcctcttc tgcttcagag 250
ggagagcagg cccgtcgccc catttcctgc aacagccaga ggacctggtg 300
gtgctgctgg gggaggaagc ccggctgccg tgtgctctgg gcgcctactg 350
ggggctagtt cagtggacta agagtgggct ggccctaggg ggccaaaggg 400
acctaccagg gtggtcccgg tactggatat cagggaatgc agccaatggc 450
cagcatgacc tccacattag gcccgtggag ctagaggatg aagcatcata 500
tgaatgtcag gctacacaag caggcctccg ctccagacca gcccaactgc 550
acgtgctggt ccccccagaa gccccccagg tgctgggcgg cccctctgtg 600
tctctggttg ctggagttcc tgcgaacctg acatgtcgga gccgtgggga 650
tgcccgccct accccctgaat tgctgtggtt ccgagatggg gtcctgttgg 700
atggagccac ctttcatcag accctgctga aggaagggac ccctgggtca 750
gtggagagca ccttaaccct gaccccctttc agccatgatg atggagccac 800
ctttgtctgc cgggcccgga gccaggccct gcccacagga agagacacag 850
ctatcacact gagcctgcag taccccccag aggtgactct gtctgcttcg 900
ccacacactg tgcaggaggg agagaaggtc attttcctgt gccaggccac 950
agcccagcct cctgtcacag gctacaggtg ggcaaaaggg ggctctccgg 1000
tgctcggggc ccgcgggcca aggttagagg tcgtggcaga cgcctcgttc 1050
ctgactgagc ccgtgtcctg cgaggtcagc aacgccgtgg gtagcgccaa 1100
ccgcagtact gcgctggatg tgctgtttgg gccgattctg caggcaaagc 1150
cggagcccgt gtccgtggac gtgggggaag acgcttcctt cagctgcgcc 1200

-continued

```
tggcgcggga acccgcttcc acgggtaacc tggacccgcc gcggtggcgc      1250
gcaggtgctg ggctctggag ccacactgcg tcttccgtcg gtggggcccg      1300
aggacgcagg cgactatgtg tgcagagctg aggctgggct atcgggcctg      1350
cggggcggcg ccgcggaggc tcggctgact gtgaacgctc ccccagtagt      1400
gaccgccctg cactctgcgc ctgccttcct gaggggccct gctcgcctcc      1450
agtgtctggt tttcgcctct cccgccccag atgccgtggt ctggtcttgg      1500
gatgagggct tcctggaggc ggggtcgcag ggccggttcc tggtggagac      1550
attccctgcc ccagagagcc gcgggggact gggtccgggc ctgatctctg      1600
tgctacacat ttcggggacc caggagtctg actttagcag gagctttaac      1650
tgcagtgccc ggaaccggct gggcgaggga ggtgcccagg ccagcctggg      1700
ccgtagagac ttgctgccca ctgtgcggat agtggccgga gtggccgctg      1750
ccaccacaac tctccttatg gtcatcactg ggggtggccct ctgctgctgg     1800
cgccacagca aggcctcagc ctctttctcc gagcaaaaga acctgatgcg      1850
aatccctggc agcagcgacg gctccagttc acgaggtcct gaagaagagg      1900
agacaggcag ccgcgaggac cggggcccca ttgtgcacac tgaccacagt      1950
gatctggttc tggaggagga agggactctg gagaccaagg acccaaccaa      2000
cggttactac aaggtccgag gagtcagtgt gagcctgagc cttggcgaag      2050
cccctggagg aggtctcttc ctgccaccac cctccccccct tgggccccca     2100
gggaccccta ccttctatga cttcaaccca cacctgggca tggtcccccc      2150
ctgcagactt tacagagcca gggcaggcta tctcaccaca ccccaccctc      2200
gagctttcac cagctacatc aaacccacat cctttgggcc cccagatctg      2250
gcccccggga ctccccccctt cccatatgct gccttcccca cacctagcca     2300
cccgcgtctc cagactcacg tgtgacatct ttccaatgga agagtcctgg      2350
gatctccaac ttgccataat ggattgttct gatttctgag gagccaggac      2400
aagttggcga ccttactcct ccaaaactga acacaagggg agggaaagat      2450
cattacattt gtcaggagca tttgtataca gtcagctcag ccaaaggaga      2500
tgccccaagt gggagcaaca tggccaccca atatgcccac ctattccccg      2550
gtgtaaaaga gattcaagat ggcaggtagg ccctttgagg agagatgggg      2600
acagggcagt gggtgttggg agtttggggc cgggatggaa gttgtttcta      2650
gccactgaaa gaagatattt caagatgacc atctgcattg agaggaaagg      2700
tagcatagga tagatgaaga tgaagagcat accaggcccc accctggctc      2750
tccctgaggg gaactttgct cggccaatgg aaatgcagcc aagatggcca      2800
tatactccct aggaacccaa aatggccacc atcttgattt tactttcctt      2850
aaagactcag aaagacttgg acccaaggag tggggataca gtgagaatta      2900
ccactgttgg ggcaaaatat tgggataaaa atatttatgt ttaataataa      2950
aaaaaagtca aagagaaaaa  aaa                                  2973
```

<210> SEQ ID NO 128
<211> LENGTH: 708
<212> TYPE: PRT
<213> ORGANISM: Homo sapiens -continued

<400> SEQUENCE: 128

```
Met Leu Arg Met Arg Val Pro Ala Leu Leu Val Leu Leu Phe Cys
  1               5                  10                  15

Phe Arg Gly Arg Ala Gly Pro Ser Pro His Phe Leu Gln Gln Pro
                 20                  25                  30

Glu Asp Leu Val Val Leu Leu Gly Glu Glu Ala Arg Leu Pro Cys
                 35                  40                  45

Ala Leu Gly Ala Tyr Trp Gly Leu Val Gln Trp Thr Lys Ser Gly
                 50                  55                  60

Leu Ala Leu Gly Gly Gln Arg Asp Leu Pro Gly Trp Ser Arg Tyr
                 65                  70                  75

Trp Ile Ser Gly Asn Ala Ala Asn Gly Gln His Asp Leu His Ile
                 80                  85                  90

Arg Pro Val Glu Leu Glu Asp Glu Ala Ser Tyr Glu Cys Gln Ala
                 95                 100                 105

Thr Gln Ala Gly Leu Arg Ser Arg Pro Ala Gln Leu His Val Leu
                110                 115                 120

Val Pro Pro Glu Ala Pro Gln Val Leu Gly Gly Pro Ser Val Ser
                125                 130                 135

Leu Val Ala Gly Val Pro Ala Asn Leu Thr Cys Arg Ser Arg Gly
                140                 145                 150

Asp Ala Arg Pro Thr Pro Glu Leu Leu Trp Phe Arg Asp Gly Val
                155                 160                 165

Leu Leu Asp Gly Ala Thr Phe His Gln Thr Leu Leu Lys Glu Gly
                170                 175                 180

Thr Pro Gly Ser Val Glu Ser Thr Leu Thr Leu Thr Pro Phe Ser
                185                 190                 195

His Asp Asp Gly Ala Thr Phe Val Cys Arg Ala Arg Ser Gln Ala
                200                 205                 210

Leu Pro Thr Gly Arg Asp Thr Ala Ile Thr Leu Ser Leu Gln Tyr
                215                 220                 225

Pro Pro Glu Val Thr Leu Ser Ala Ser Pro His Thr Val Gln Glu
                230                 235                 240

Gly Glu Lys Val Ile Phe Leu Cys Gln Ala Thr Ala Gln Pro Pro
                245                 250                 255

Val Thr Gly Tyr Arg Trp Ala Lys Gly Gly Ser Pro Val Leu Gly
                260                 265                 270

Ala Arg Gly Pro Arg Leu Glu Val Val Ala Asp Ala Ser Phe Leu
                275                 280                 285

Thr Glu Pro Val Ser Cys Glu Val Ser Asn Ala Val Gly Ser Ala
                290                 295                 300

Asn Arg Ser Thr Ala Leu Asp Val Leu Phe Gly Pro Ile Leu Gln
                305                 310                 315

Ala Lys Pro Glu Pro Val Ser Val Asp Val Gly Glu Asp Ala Ser
                320                 325                 330

Phe Ser Cys Ala Trp Arg Gly Asn Pro Leu Pro Arg Val Thr Trp
                335                 340                 345

Thr Arg Arg Gly Gly Ala Gln Val Leu Gly Ser Gly Ala Thr Leu
                350                 355                 360

Arg Leu Pro Ser Val Gly Pro Glu Asp Ala Gly Asp Tyr Val Cys
                365                 370                 375

Arg Ala Glu Ala Gly Leu Ser Gly Leu Arg Gly Gly Ala Ala Glu
                380                 385                 390
```

-continued

```
Ala Arg Leu Thr Val Asn Ala Pro Pro Val Val Thr Ala Leu His
                395                 400                 405

Ser Ala Pro Ala Phe Leu Arg Gly Pro Ala Arg Leu Gln Cys Leu
                410                 415                 420

Val Phe Ala Ser Pro Ala Pro Asp Ala Val Val Trp Ser Trp Asp
                425                 430                 435

Glu Gly Phe Leu Glu Ala Gly Ser Gln Gly Arg Phe Leu Val Glu
                440                 445                 450

Thr Phe Pro Ala Pro Glu Ser Arg Gly Gly Leu Gly Pro Gly Leu
                455                 460                 465

Ile Ser Val Leu His Ile Ser Gly Thr Gln Glu Ser Asp Phe Ser
                470                 475                 480

Arg Ser Phe Asn Cys Ser Ala Arg Asn Arg Leu Gly Glu Gly Gly
                485                 490                 495

Ala Gln Ala Ser Leu Gly Arg Arg Asp Leu Leu Pro Thr Val Arg
                500                 505                 510

Ile Val Ala Gly Val Ala Ala Ala Thr Thr Thr Leu Leu Met Val
                515                 520                 525

Ile Thr Gly Val Ala Leu Cys Cys Trp Arg His Ser Lys Ala Ser
                530                 535                 540

Ala Ser Phe Ser Glu Gln Lys Asn Leu Met Arg Ile Pro Gly Ser
                545                 550                 555

Ser Asp Gly Ser Ser Ser Arg Gly Pro Glu Glu Glu Glu Thr Gly
                560                 565                 570

Ser Arg Glu Asp Arg Gly Pro Ile Val His Thr Asp His Ser Asp
                575                 580                 585

Leu Val Leu Glu Glu Glu Gly Thr Leu Glu Thr Lys Asp Pro Thr
                590                 595                 600

Asn Gly Tyr Tyr Lys Val Arg Gly Val Ser Val Ser Leu Ser Leu
                605                 610                 615

Gly Glu Ala Pro Gly Gly Gly Leu Phe Leu Pro Pro Pro Ser Pro
                620                 625                 630

Leu Gly Pro Pro Gly Thr Pro Thr Phe Tyr Asp Phe Asn Pro His
                635                 640                 645

Leu Gly Met Val Pro Pro Cys Arg Leu Tyr Arg Ala Arg Ala Gly
                650                 655                 660

Tyr Leu Thr Thr Pro His Pro Arg Ala Phe Thr Ser Tyr Ile Lys
                665                 670                 675

Pro Thr Ser Phe Gly Pro Pro Asp Leu Ala Pro Gly Thr Pro Pro
                680                 685                 690

Phe Pro Tyr Ala Ala Phe Pro Thr Pro Ser His Pro Arg Leu Gln
                695                 700                 705

Thr His Val
```

<210> SEQ ID NO 129
<211> LENGTH: 3197
<212> TYPE: DNA
<213> ORGANISM: Homo sapiens

<400> SEQUENCE: 129

```
ggaccacagc tcctcccgtg catccactcg gcctgggagg ttctggattt       50

tggctgtcga gggagtttgc ctgcctctcc agagaaagat ggtcatgagg      100

cccctgtgga gtctgcttct ctgggaagcc ctacttccca ttacagttac      150
```

-continued

```
tggtgcccaa gtgctgagca aagtcggggg ctcggtgctg ctggtggcag      200
cgcgtccccc tggcttccaa gtccgtgagg ctatctggcg atctctctgg      250
ccttcagaag agctcctggc cacgtttttc cgaggctccc tggagactct      300
gtaccattcc cgcttcctgg gccgagccca gctacacagc aacctcagcc      350
tggagctcgg gccgctggag tctggagaca gcggcaactt ctccgtgttg      400
atggtggaca caaggggcca gccctggacc cagaccctcc agctcaaggt      450
gtacgatgca gtgcccaggc ccgtggtaca agtgttcatt gctgtagaaa      500
gggatgctca gccctccaag acctgccagg ttttcttgtc ctgttgggcc      550
cccaacatca gcgaaataac ctatagctgg cgacgggaga caaccatgga      600
ctttggtatg gaaccacaca gcctcttcac agacggacag gtgctgagca      650
tttccctggg accaggagac agagatgtgg cctattcctg cattgtctcc      700
aaccctgtca gctgggactt ggccacagtc acgccctggg atagctgtca      750
tcatgaggca gcaccaggga aggcctccta caaagatgtg ctgctggtgg      800
tggtgcctgt ctcgctgctc ctgatgctgg ttactctctt ctctgcctgg      850
cactggtgcc cctgctcagg gaaaaagaaa aaggatgtcc atgctgacag      900
agtgggtcca gagacagaga acccccttgt gcaggatctg ccataaagga      950
caatatgaac tgatgcctgg actatcagta accccactgc acaggcacac     1000
gatgctctgg gacataactg gtgcctggaa atcaccatgg tcctcatatc     1050
tcccatggga atcctgtcct gcctcgaagg agcagcctgg gcagccatca     1100
caccacgagg acaggaagca ccagcacgtt tcacacctcc cccttccctc     1150
tcccatcttc tcatatcctg gctcttctct gggcaagatg agccaagcag     1200
aacattccat ccaggacact ggaagttctc caggatccag atccatgggg     1250
acattaatag tccaaggcat tccctccccc accactattc ataaagtatt     1300
aaccaactgg caccaaggaa ttgcctccag cctgagtcct aggctctaaa     1350
agatattaca tatttgaact aatagaggaa ctctgagtca cccatgccag     1400
catcagcttc agccccagac cctgcagttt gagatctgat gcttcctgag     1450
ggccaaggca ttgctgtaag aaaaggtcta gaaataggtg aaagtgagag     1500
gtgggggaca ggggtttctc tttctggcct aaggactttc aggtaatcag     1550
agttcatggg ccctcaaagg taaattgcag ttgtagacac cgaggatggt     1600
tgacaaccca tggttgagat gggcaccgtt ttgcaggaaa caccatatta     1650
atagacatcc tcaccatctc catccgctct cacgcctcct gcaggatctg     1700
ggagtgaggg tggagagtct ttcctcacgc tccagcacag tggccaggaa     1750
aagaaatact gaatttgccc cagccaacag gacgttcttg cacaacttca     1800
agaaaagcag ctcagctcag gatgagtctt cctgcctgaa actgagagag     1850
tgaagaacca taaaacgcta tgcagaagga acattatgga gagaaagggt     1900
actgaggcac tctagaatct gccacattca ttttcaaatg caaatgcaga     1950
agacttacct tagttcaagg ggaggggaca aagaccccac agcccaacag     2000
caggactgta gaggtcactc tgactccatc aaacttttta ttgtggccat     2050
cttaggaaaa tacattctgc ccctgaatga ttctgtctag aaaagctctg     2100
```

-continued

```
gagtattgat cactactgga aaaacactta aggagctaaa cttaccttcg         2150

gggattatta gctgataagg ttcacagttt ctctcaccca ggtgtaactg         2200

gatttttct ggggcctcaa tccagtcttg ataacagcga ggaaagaggt          2250

attgaagaaa caggggtggg tttgaagtac tattttcccc agggtggctt         2300

caatctcccc acctaggatg tcagccctgt ccaaggacct tccctcttct         2350

cccccagttc cctgggcaat cacttcacct tggacaaagg atcagcacag         2400

ctggcctcca gatccacatc accactcttc cactcgattg ttcccagatc         2450

ctccctgcct ggcctgctca gaggttccct gttggtaacc tggctttatc         2500

aaattctcat ccctttccca cacccacttc tctcctatca ccttccccca         2550

agattacctg aacagggtcc atggccactc aacctgtcag cttgcaccat         2600

ccccacctgc cacctacagt caggccacat gcctggtcac tgaatcatgc         2650

aaaactggcc tcagtcccta aaaatgatgt ggaaaggaaa gcccaggatc         2700

tgacaatgag ccctggtgga tttgtgggga aaaaatacac agcactcccc         2750

acctttcttt cgttcatctc cagggcccca cctcagatca aagcagctct         2800

ggatgagatg ggacctgcag ctctccctcc acaaggtgac tcttagcaac         2850

ctcatttcga cagtggtttg tagcgtggtg caccagggcc ttgttgaaca         2900

gatccacact gctctaataa agttcccatc cttaatgact cacttgtcaa         2950

ctagtggact aattaaccct ccaccaaaaa aacacaaagt gcttctgtga         3000

gaccaatttt gtgctaatga gcattgagac tgatgctttg taagtcacac         3050

cacaacaaat attgattgag ggcgctgcat gtgctgggta catttcttgg         3100

cacttgggaa tcagtagtca agcgaaaccc ttgcctttga gagtttatgg         3150

tctggataat ataaataaac aagtaagcat aaaaaaaaaa  aaaaaaa           3197
```

```
<210> SEQ ID NO 130
<211> LENGTH: 285
<212> TYPE: PRT
<213> ORGANISM: Homo sapiens

<400> SEQUENCE: 130

Met Val Met Arg Pro Leu Trp Ser Leu Leu Leu Trp Glu Ala Leu
  1               5                  10                  15

Leu Pro Ile Thr Val Thr Gly Ala Gln Val Leu Ser Lys Val Gly
                 20                  25                  30

Gly Ser Val Leu Leu Val Ala Ala Arg Pro Pro Gly Phe Gln Val
                 35                  40                  45

Arg Glu Ala Ile Trp Arg Ser Leu Trp Pro Ser Glu Glu Leu Leu
                 50                  55                  60

Ala Thr Phe Phe Arg Gly Ser Leu Glu Thr Leu Tyr His Ser Arg
                 65                  70                  75

Phe Leu Gly Arg Ala Gln Leu His Ser Asn Leu Ser Leu Glu Leu
                 80                  85                  90

Gly Pro Leu Glu Ser Gly Asp Ser Gly Asn Phe Ser Val Leu Met
                 95                 100                 105

Val Asp Thr Arg Gly Gln Pro Trp Thr Gln Thr Leu Gln Leu Lys
                110                 115                 120

Val Tyr Asp Ala Val Pro Arg Pro Val Val Gln Val Phe Ile Ala
                125                 130                 135
```

-continued

```
Val Glu Arg Asp Ala Gln Pro Ser Lys Thr Cys Gln Val Phe Leu
                140                 145                 150

Ser Cys Trp Ala Pro Asn Ile Ser Glu Ile Thr Tyr Ser Trp Arg
                155                 160                 165

Arg Glu Thr Thr Met Asp Phe Gly Met Glu Pro His Ser Leu Phe
                170                 175                 180

Thr Asp Gly Gln Val Leu Ser Ile Ser Leu Gly Pro Gly Asp Arg
                185                 190                 195

Asp Val Ala Tyr Ser Cys Ile Val Ser Asn Pro Val Ser Trp Asp
                200                 205                 210

Leu Ala Thr Val Thr Pro Trp Asp Ser Cys His His Glu Ala Ala
                215                 220                 225

Pro Gly Lys Ala Ser Tyr Lys Asp Val Leu Leu Val Val Val Pro
                230                 235                 240

Val Ser Leu Leu Leu Met Leu Val Thr Leu Phe Ser Ala Trp His
                245                 250                 255

Trp Cys Pro Cys Ser Gly Lys Lys Lys Lys Asp Val His Ala Asp
                260                 265                 270

Arg Val Gly Pro Glu Thr Glu Asn Pro Leu Val Gln Asp Leu Pro
                275                 280                 285
```

<210> SEQ ID NO 131
<211> LENGTH: 1288
<212> TYPE: DNA
<213> ORGANISM: Homo sapiens

<400> SEQUENCE: 131

```
gggaagccat ggagccgcgg gcgctcgtca cggcgctcag cctcggcctc          50

agcctgtgct ccctggggct gctcgtcacg gccatcttca ccgaccactg         100

gtacgagacc gacccccggc gccacaagga gagctgcgag cgcagccgcg         150

cgggcgccga ccccccggac cagaagaacc gcctgatgcc gctgtcgcac         200

ctactcgggc ctctggagga agtgctactt cctgggcatc gaccgggaca         250

tcgacaccct catcctgaaa ggtattgcgc agcgatgcac ggccatcaag         300

taccactttt ctcagcccat ccgcttgcga aacattcctt ttaatttaac         350

caagaccata cagcaagatg agtggcacct gcttcggata ttttgcacca         400

tttccctctg tacttatgcc gccagtatct cgtatgattt gaaccggctc         450

ccaaagctaa tttatagcct gcctgctgat gtggaacatg gttacagctg         500

gtccatcttt tgcgcctggt gcagtttagg ctttattgtg gcagctggag         550

gtctctgcat cgcttatccg tttattagcc ggaccaagat tgcacagcta         600

aagtctggca gagactccac ggtatgactg tcctcactgg gcctgtccaa         650

gcacaaagcg gtcttttaca ttccaacctg ttgcctgcca gccctttctg         700

gattactgat agaaaatcat gcaaaacctc ccaacctttc taaggacaag         750

actactgtgg attcaagtgc tttaatgact atttatgcgt tgactgtgag         800

aatagggagc agtgccatgg gacatttcta ggtgtagaga aagaagaaac         850

tgcaatggaa aaatttgtat gatttccatt tatttcagaa agtttgtatg         900

taacaattac ccgagagtca tttctacttg caaaaggatt cgtaacaaag         950

cgagtataat tttcttgtca ttgtatcatg cttgttaaat tttaatgcag        1000

catcttcaga acttgtcctg atggtgtctt attgtgtcag caccaaatat        1050
```

-continued

| | |
|---|---|
| ttgtgcatta tttgtggacg ttccttgtca caggaagatt cttcttctgt | 1100 |
| tgccttattg tttttttttt tttttttaagt ctcttctctg tctttgtact | 1150 |
| ggaatcgaaa tcataagata aacagatcaa acgtgcttaa gagctaactc | 1200 |
| gtgacactat gcagtattgt ttgaagacct gttgttcaac ctctgtctct | 1250 |
| ttatgttaat ggatttctgc attaaatgac tgcccccc | 1288 |

<210> SEQ ID NO 132
<211> LENGTH: 111
<212> TYPE: PRT
<213> ORGANISM: Homo sapiens

<400> SEQUENCE: 132

Met Glu Pro Arg Ala Leu Val Thr Ala Leu Ser Leu Gly Leu Ser
1               5                  10                  15
Leu Cys Ser Leu Gly Leu Leu Val Thr Ala Ile Phe Thr Asp His
                20                  25                  30
Trp Tyr Glu Thr Asp Pro Arg Arg His Lys Glu Ser Cys Glu Arg
            35                  40                  45
Ser Arg Ala Gly Ala Asp Pro Pro Asp Gln Lys Asn Arg Leu Met
        50                  55                  60
Pro Leu Ser His Leu Leu Gly Pro Leu Glu Glu Val Leu Leu Pro
    65                  70                  75
Gly His Arg Pro Gly His Arg His Pro His Pro Glu Arg Tyr Cys
                80                  85                  90
Ala Ala Met His Gly His Gln Val Pro Leu Phe Ser Ala His Pro
                95                  100                 105
Leu Ala Lys His Ser Phe
                110

<210> SEQ ID NO 133
<211> LENGTH: 1285
<212> TYPE: DNA
<213> ORGANISM: Homo sapiens

<400> SEQUENCE: 133

| | |
|---|---|
| caaagcggcg gctgtccgcg gtgccggctg ggggcggaga ggcggcggtg | 50 |
| ggctccctgg ggtgtgtgag cccggtgatg gagccgggcc cgacagccgc | 100 |
| gcagcggagg tgttcgttgc cgccgtggct gccgctgggg ctgctgctgt | 150 |
| ggtcggggct ggccctgggc gcgctcccct tcggcagcag tccgcacagg | 200 |
| gtcttccacg acctcctgtc ggagcagcag ttgctggagg tggaggactt | 250 |
| gtccctgtcc ctcctgcagg gtggagggct ggggcctctg tcgctgcccc | 300 |
| cggacctgcc ggatctggat cctgagtgcc gggagctcct gctggacttc | 350 |
| gccaacagca gcgcagagct gacagggtgt ctggtgcgca gcgcccggcc | 400 |
| cgtgcgcctc tgtcagacct gctaccccct cttccaacag gtcgtcagca | 450 |
| agatggacaa catcagccga gccgcgggga atacttcaga gagtcagagt | 500 |
| tgtgccagaa gtctcttaat ggcagataga atgcaaatag ttgtgattct | 550 |
| ctcagaattt tttaatacca catggcagga ggcaaattgt gcaaattgtt | 600 |
| taacaaacaa cagtgaagaa ttatcaaaca gcacagtata tttccttaat | 650 |
| ctatttaatc acaccctgac ctgctttgaa cataaccttc aggggaatgc | 700 |

-continued

```
acatagtctt ttacagacaa aaaattattc agaagtatgc aaaaactgcc            750

gtgaagcata caaaactctg agtagtctgt acagtgaaat gcaaaaaatg            800

aatgaacttg agaataaggc tgaacctgga acacatttat gcattgatgt            850

ggaagatgca atgaacatca ctcgaaaact atggagtcga actttcaact            900

gttcagtccc ttgcagtgac acagtgcctg taattgctgt ttctgtgttc            950

attctctttc tacctgttgt cttctacctt agtagctttc ttcactcaga           1000

gcaaaagaaa cgcaaactca ttctgcccaa acgtctcaag tccagtacca           1050

gttttgcaaa tattcaggaa aattcaaact gagacctaca aaatggagaa           1100

ttgacatatc acgtgaatga atggtggaag acacaacttg gtttcagaaa           1150

gaagataaac tgtgatttga caagtcaagc tcttaagaaa tacaaggact           1200

tcagatccat ttttaaataa gaattttcga tttttctttc cttttccact           1250

tctttctaac agatttggat atttttaatt  tccag                          1285


<210> SEQ ID NO 134
<211> LENGTH: 334
<212> TYPE: PRT
<213> ORGANISM: Homo sapiens

<400> SEQUENCE: 134

Met Glu Pro Gly Pro Thr Ala Ala Gln Arg Arg Cys Ser Leu Pro
  1               5                  10                  15

Pro Trp Leu Pro Leu Gly Leu Leu Leu Trp Ser Gly Leu Ala Leu
                 20                  25                  30

Gly Ala Leu Pro Phe Gly Ser Ser Pro His Arg Val Phe His Asp
                 35                  40                  45

Leu Leu Ser Glu Gln Gln Leu Leu Glu Val Glu Asp Leu Ser Leu
                 50                  55                  60

Ser Leu Leu Gln Gly Gly Gly Leu Gly Pro Leu Ser Leu Pro Pro
                 65                  70                  75

Asp Leu Pro Asp Leu Asp Pro Glu Cys Arg Glu Leu Leu Leu Asp
                 80                  85                  90

Phe Ala Asn Ser Ser Ala Glu Leu Thr Gly Cys Leu Val Arg Ser
                 95                 100                 105

Ala Arg Pro Val Arg Leu Cys Gln Thr Cys Tyr Pro Leu Phe Gln
                110                 115                 120

Gln Val Val Ser Lys Met Asp Asn Ile Ser Arg Ala Ala Gly Asn
                125                 130                 135

Thr Ser Glu Ser Gln Ser Cys Ala Arg Ser Leu Leu Met Ala Asp
                140                 145                 150

Arg Met Gln Ile Val Val Ile Leu Ser Glu Phe Phe Asn Thr Thr
                155                 160                 165

Trp Gln Glu Ala Asn Cys Ala Asn Cys Leu Thr Asn Asn Ser Glu
                170                 175                 180

Glu Leu Ser Asn Ser Thr Val Tyr Phe Leu Asn Leu Phe Asn His
                185                 190                 195

Thr Leu Thr Cys Phe Glu His Asn Leu Gln Gly Asn Ala His Ser
                200                 205                 210

Leu Leu Gln Thr Lys Asn Tyr Ser Glu Val Cys Lys Asn Cys Arg
                215                 220                 225

Glu Ala Tyr Lys Thr Leu Ser Ser Leu Tyr Ser Glu Met Gln Lys
                230                 235                 240
```

-continued

Met Asn Glu Leu Glu Asn Lys Ala Glu Pro Gly Thr His Leu Cys
245 250 255

Ile Asp Val Glu Asp Ala Met Asn Ile Thr Arg Lys Leu Trp Ser
260 265 270

Arg Thr Phe Asn Cys Ser Val Pro Cys Ser Asp Thr Val Pro Val
275 280 285

Ile Ala Val Ser Val Phe Ile Leu Phe Leu Pro Val Val Phe Tyr
290 295 300

Leu Ser Ser Phe Leu His Ser Glu Gln Lys Lys Arg Lys Leu Ile
305 310 315

Leu Pro Lys Arg Leu Lys Ser Ser Thr Ser Phe Ala Asn Ile Gln
320 325 330

Glu Asn Ser Asn

<210> SEQ ID NO 135
<211> LENGTH: 2319
<212> TYPE: DNA
<213> ORGANISM: Homo sapiens

<400> SEQUENCE: 135
gccaggccct atctccctgc caggaggccg gagtggggga ggtcagacgg 50
ggcggttgga gggggaggga tgccacgcgc ttctgcctca ggtgttcctg 100
cgttgtttgt cagtggagag cagggagtgg ggccagccag cagaaacagt 150
gggctgtaca acatcacctt caaatatgac aattgtacca cctacttgaa 200
tccagtgggg aagcatgtga ttgctgacgc ccagaatatc accatcagcc 250
agtatgcttg ccatgaccaa gtggcagtca ccattctttg gtccccaggg 300
gccctcggca tcgaattcct gaaaggattt cgggtaatac tggaggagct 350
gaagtcggag ggaagacagt gccaacaact gattctaaag gatccgaagc 400
agctcaacag tagcttcaaa agaactggaa tggaatctca acctttcctg 450
aatatgaaat ttgaaacgga ttatttcgta aaggttgtcc cttttccttc 500
cattaaaaac gaaagcaatt accacccttt cttctttaga acccgagcct 550
gtgacctgtt gttacagccg gacaatctag cttgtaaacc cttctggaag 600
cctcggaacc tgaacatcag ccagcatggc tcggacatgc aggtgtcctt 650
cgaccacgca ccgcatggct cggacatgca ggtgtccttc gaccacgcac 700
cgcacaactt cggcttccgt ttcttctatc ttcactacaa gctcaagcac 750
gaaggacctt tcaagcgaaa gacctgtaag caggagcaaa ctacagagat 800
gaccagctgc ctccttcaaa atgtttctcc aggggattat ataattgagc 850
tggtggatga cactaacaca acaagaaaag tgatgcatta tgccttaaag 900
ccagtgcact ccccgtgggc cggcccatc agagccgtgg ccatcacagt 950
gccactggta gtcatatcgg cattcgcgac gctcttcact gtgatgtgcc 1000
gcaagaagca acaagaaaat atatattcac atttagatga agagagctct 1050
gagtcttcca catacactgc agcactccca agagagaggc tccggccgcg 1100
gccgaaggtc tttctctgct attccagtaa agatggccag aatcacatga 1150
atgtcgtcca gtgtttcgcc tacttcctcc aggacttctg tggctgtgag 1200
gtggctctgg acctgtggga agacttcagc ctctgtagag aagggcagag 1250

-continued

```
agaatgggtc atccagaaga tccacgagtc ccagttcatc attgtggttt    1300

gttccaaagg tatgaagtac tttgtggaca agaagaacta caaacacaaa    1350

ggaggtggcc gaggctcggg gaaaggagag ctcttcctgg tggcggtgtc    1400

agccattgcc gaaaagctcc gccaggccaa gcagagttcg tccgcggcgc    1450

tcagcaagtt tatcgccgtc tactttgatt attcctgcga gggagacgtc    1500

cccggtatcc tagacctgag taccaagtac agactcatgg acaatcttcc    1550

tcagctctgt tcccacctgc actcccgaga ccacggcctc caggagccgg    1600

ggcagcacac gcgacagggc agcagaagga actacttccg gagcaagtca    1650

ggccggtccc tatacgtcgc catttgcaac atgcaccagt ttattgacga    1700

ggagcccgac tggttcgaaa agcagttcgt tcccttccat cctcctccac    1750

tgcgctaccg ggagccagtc ttggagaaat ttgattcggg cttggtttta    1800

aatgatgtca tgtgcaaacc agggcctgag agtgacttct gcctaaaggt    1850

agaggcggct gttcttgggg caaccggacc agccgactcc cagcacgaga    1900

gtcagcatgg gggcctggac caagacgggg aggcccggcc tgcccttgac    1950

ggtagcgccg ccctgcaacc cctgctgcac acggtgaaag ccggcagccc    2000

ctcggacatg ccgcgggact caggcatcta tgactcgtct gtgccctcat    2050

ccgagctgtc tctgccactg atggaaggac tctcgacgga ccagacagaa    2100

acgtcttccc tgacggagag cgtgtcctcc tcttcaggcc tgggtgagga    2150

ggaacctcct gcccttcctt ccaagctcct ctcttctggg tcatgcaaag    2200

cagatcttgg ttgccgcagc tacactgatg aactccacgc ggtcgcccct    2250

ttgtaacaaa acgaaagagt ctaagcattg ccactttaaa aaaaaaaaaa    2300

aaaaaaaaaa  aaaaaaaaa                                     2319
```

```
<210> SEQ ID NO 136
<211> LENGTH: 728
<212> TYPE: PRT
<213> ORGANISM: Homo sapiens

<400> SEQUENCE: 136

Met Pro Arg Ala Ser Ala Ser Gly Val Pro Ala Leu Phe Val Ser
1               5                   10                  15

Gly Glu Gln Gly Val Gly Pro Ala Ser Arg Asn Ser Gly Leu Tyr
                20                  25                  30

Asn Ile Thr Phe Lys Tyr Asp Asn Cys Thr Thr Tyr Leu Asn Pro
                35                  40                  45

Val Gly Lys His Val Ile Ala Asp Ala Gln Asn Ile Thr Ile Ser
                50                  55                  60

Gln Tyr Ala Cys His Asp Gln Val Ala Val Thr Ile Leu Trp Ser
                65                  70                  75

Pro Gly Ala Leu Gly Ile Glu Phe Leu Lys Gly Phe Arg Val Ile
                80                  85                  90

Leu Glu Glu Leu Lys Ser Glu Gly Arg Gln Cys Gln Gln Leu Ile
                95                  100                 105

Leu Lys Asp Pro Lys Gln Leu Asn Ser Ser Phe Lys Arg Thr Gly
                110                 115                 120

Met Glu Ser Gln Pro Phe Leu Asn Met Lys Phe Glu Thr Asp Tyr
                125                 130                 135
```

-continued

```
Phe Val Lys Val Val Pro Phe Pro Ser Ile Lys Asn Glu Ser Asn
                140                 145                 150

Tyr His Pro Phe Phe Phe Arg Thr Arg Ala Cys Asp Leu Leu Leu
                155                 160                 165

Gln Pro Asp Asn Leu Ala Cys Lys Pro Phe Trp Lys Pro Arg Asn
                170                 175                 180

Leu Asn Ile Ser Gln His Gly Ser Asp Met Gln Val Ser Phe Asp
                185                 190                 195

His Ala Pro His Gly Ser Asp Met Gln Val Ser Phe Asp His Ala
                200                 205                 210

Pro His Asn Phe Gly Phe Arg Phe Phe Tyr Leu His Tyr Lys Leu
                215                 220                 225

Lys His Glu Gly Pro Phe Lys Arg Lys Thr Cys Lys Gln Glu Gln
                230                 235                 240

Thr Thr Glu Met Thr Ser Cys Leu Leu Gln Asn Val Ser Pro Gly
                245                 250                 255

Asp Tyr Ile Ile Glu Leu Val Asp Asp Thr Asn Thr Thr Arg Lys
                260                 265                 270

Val Met His Tyr Ala Leu Lys Pro Val His Ser Pro Trp Ala Gly
                275                 280                 285

Pro Ile Arg Ala Val Ala Ile Thr Val Pro Leu Val Val Ile Ser
                290                 295                 300

Ala Phe Ala Thr Leu Phe Thr Val Met Cys Arg Lys Lys Gln Gln
                305                 310                 315

Glu Asn Ile Tyr Ser His Leu Asp Glu Glu Ser Ser Glu Ser Ser
                320                 325                 330

Thr Tyr Thr Ala Ala Leu Pro Arg Glu Arg Leu Arg Pro Arg Pro
                335                 340                 345

Lys Val Phe Leu Cys Tyr Ser Ser Lys Asp Gly Gln Asn His Met
                350                 355                 360

Asn Val Val Gln Cys Phe Ala Tyr Phe Leu Gln Asp Phe Cys Gly
                365                 370                 375

Cys Glu Val Ala Leu Asp Leu Trp Glu Asp Phe Ser Leu Cys Arg
                380                 385                 390

Glu Gly Gln Arg Glu Trp Val Ile Gln Lys Ile His Glu Ser Gln
                395                 400                 405

Phe Ile Ile Val Val Cys Ser Lys Gly Met Lys Tyr Phe Val Asp
                410                 415                 420

Lys Lys Asn Tyr Lys His Lys Gly Gly Gly Arg Gly Ser Gly Lys
                425                 430                 435

Gly Glu Leu Phe Leu Val Ala Val Ser Ala Ile Ala Glu Lys Leu
                440                 445                 450

Arg Gln Ala Lys Gln Ser Ser Ser Ala Ala Leu Ser Lys Phe Ile
                455                 460                 465

Ala Val Tyr Phe Asp Tyr Ser Cys Glu Gly Asp Val Pro Gly Ile
                470                 475                 480

Leu Asp Leu Ser Thr Lys Tyr Arg Leu Met Asp Asn Leu Pro Gln
                485                 490                 495

Leu Cys Ser His Leu His Ser Arg Asp His Gly Leu Gln Glu Pro
                500                 505                 510

Gly Gln His Thr Arg Gln Gly Ser Arg Arg Asn Tyr Phe Arg Ser
                515                 520                 525

Lys Ser Gly Arg Ser Leu Tyr Val Ala Ile Cys Asn Met His Gln
```

-continued

```
                530                 535                 540

Phe Ile Asp Glu Glu Pro Asp Trp Phe Glu Lys Gln Phe Val Pro
                545                 550                 555

Phe His Pro Pro Pro Leu Arg Tyr Arg Glu Pro Val Leu Glu Lys
                560                 565                 570

Phe Asp Ser Gly Leu Val Leu Asn Asp Val Met Cys Lys Pro Gly
                575                 580                 585

Pro Glu Ser Asp Phe Cys Leu Lys Val Glu Ala Ala Val Leu Gly
                590                 595                 600

Ala Thr Gly Pro Ala Asp Ser Gln His Glu Ser Gln His Gly Gly
                605                 610                 615

Leu Asp Gln Asp Gly Glu Ala Arg Pro Ala Leu Asp Gly Ser Ala
                620                 625                 630

Ala Leu Gln Pro Leu Leu His Thr Val Lys Ala Gly Ser Pro Ser
                635                 640                 645

Asp Met Pro Arg Asp Ser Gly Ile Tyr Asp Ser Ser Val Pro Ser
                650                 655                 660

Ser Glu Leu Ser Leu Pro Leu Met Glu Gly Leu Ser Thr Asp Gln
                665                 670                 675

Thr Glu Thr Ser Ser Leu Thr Glu Ser Val Ser Ser Ser Ser Gly
                680                 685                 690

Leu Gly Glu Glu Glu Pro Pro Ala Leu Pro Ser Lys Leu Leu Ser
                695                 700                 705

Ser Gly Ser Cys Lys Ala Asp Leu Gly Cys Arg Ser Tyr Thr Asp
                710                 715                 720

Glu Leu His Ala Val Ala Pro Leu
                725
```

<210> SEQ ID NO 137
<211> LENGTH: 559
<212> TYPE: DNA
<213> ORGANISM: Homo sapiens

<400> SEQUENCE: 137

```
caactgcacc tcggttctat cgatagccac cagcgcaaca tgacagtgaa      50

gaccctgcat ggcccagcca tggtcaagta cttgctgctg tcgatattgg     100

ggcttgcctt tctgagtgag gcggcagctc ggaaaatccc caaagtagga     150

catacttttt tccaaaagcc tgagagttgc ccgcctgtgc caggaggtag     200

tatgaagctt gacattggca tcatcaatga aaaccagcgc gtttccatgt     250

cacgtaacat cgagagccgc tccacctccc cctggaatta cactgtcact     300

tgggacccca accggtaccc ctcggaagtt gtacaggccc agtgtaggaa     350

cttgggctgc atcaatgctc aaggaaagga agacatctcc atgaattccg     400

ttcccatcca gcaagagacc ctggtcgtcc ggaggaagca ccaaggctgc     450

tctgtttctt tccagttgga gaaggtgctg gtgactgttg gctgcacctg     500

cgtcacccct gtcatccacc atgtgcagta agaggtgcat atccactcag     550

ctgaagaag                                                  559
```

<210> SEQ ID NO 138
<211> LENGTH: 163
<212> TYPE: PRT
<213> ORGANISM: Homo sapiens -continued

<400> SEQUENCE: 138

```
Met Thr Val Lys Thr Leu His Gly Pro Ala Met Val Lys Tyr Leu
  1               5                  10                  15

Leu Leu Ser Ile Leu Gly Leu Ala Phe Leu Ser Glu Ala Ala Ala
                 20                  25                  30

Arg Lys Ile Pro Lys Val Gly His Thr Phe Phe Gln Lys Pro Glu
                 35                  40                  45

Ser Cys Pro Pro Val Pro Gly Gly Ser Met Lys Leu Asp Ile Gly
                 50                  55                  60

Ile Ile Asn Glu Asn Gln Arg Val Ser Met Ser Arg Asn Ile Glu
                 65                  70                  75

Ser Arg Ser Thr Ser Pro Trp Asn Tyr Thr Val Thr Trp Asp Pro
                 80                  85                  90

Asn Arg Tyr Pro Ser Glu Val Val Gln Ala Gln Cys Arg Asn Leu
                 95                 100                 105

Gly Cys Ile Asn Ala Gln Gly Lys Glu Asp Ile Ser Met Asn Ser
                110                 115                 120

Val Pro Ile Gln Gln Glu Thr Leu Val Val Arg Arg Lys His Gln
                125                 130                 135

Gly Cys Ser Val Ser Phe Gln Leu Glu Lys Val Leu Val Thr Val
                140                 145                 150

Gly Cys Thr Cys Val Thr Pro Val Ile His His Val Gln
                155                 160
```

<210> SEQ ID NO 139
<211> LENGTH: 2283
<212> TYPE: DNA
<213> ORGANISM: Homo sapiens

<400> SEQUENCE: 139

```
ttctgctata gagatggaac agtatatgga aagctcccaa gaaagtgaag       50

agaggaaatt ggaaaattgt gagtggacct tctgatactg ctcctccttg      100

cgtggaaaag gggaaagaac tgcatgcata ttattcagcg tcctatattc      150

aaaggatatt cttggtgatc ttggaagtgt ccgtatcatg gaatcaatct      200

ctatgatggg aagccctaag agccttagtg aaacttgttt acctaatggc      250

ataaatggta tcaaagatgc aaggaaggtc actgtaggtg tgattggaag      300

tggagatttt gccaaatcct tgaccattcg acttattaga tgcggctatc      350

atgtggtcat aggaagtaga aatcctaagt ttgcttctga atttttttcct      400

catgtggtag atgtcactca tcatgaagat gctctcacaa aaacaaatat      450

aatatttgtt gctatacaca gagaacatta tacctccctg tgggacctga      500

gacatctgct tgtgggtaaa atcctgattg atgtgagcaa taacatgagg      550

ataaaccagt acccagaatc caatgctgaa tatttggctt cattattccc      600

agattctttg attgtcaaag gatttaatgt tgtctcagct tgggcacttc      650

agttaggacc taaggatgcc agccggcagg tttatatatg cagcaacaat      700

attcaagcgc gacaacaggt tattgaactt gcccgccagt tgaatttcat      750

tcccattgac ttgggatcct tatcatcagc cagagagatt gaaaatttac      800

ccctacgact ctttactctc tggagagggc cagtggtggt agctataagc      850

ttggccacat tttttttcct ttattccttt gtcagagatg tgattcatcc      900
```

-continued

```
atatgctaga aaccaacaga gtgactttta caaaattcct atagagattg        950

tgaataaaac cttacctata gttgccatta ctttgctctc cctagtatac       1000

cttgcaggtc ttctggcagc tgcttatcaa ctttattacg gcaccaagta       1050

taggagattt ccaccttggt tggaaacctg gttacagtgt agaaaacagc       1100

ttggattact aagtttttc ttcgctatgg tccatgttgc ctacagcctc        1150

tgcttaccga tgagaaggtc agagagatat ttgtttctca acatggctta       1200

tcagcaggtt catgcaaata ttgaaaactc ttggaatgag gaagaagttt       1250

ggagaattga aatgtatatc tcctttggca taatgagcct tggcttactt       1300

tccctcctgg cagtcacttc tatcccttca gtgagcaatg ctttaaactg       1350

gagagaattc agttttattc agtctacact tggatatgtc gctctgctca       1400

taagtacttt ccatgtttta atttatggat ggaaacgagc ttttgaggaa       1450

gagtactaca gattttatac accaccaaac tttgttcttg ctcttgtttt       1500

gccctcaatt gtaattctgg atcttttgca gctttgcaga tacccagact       1550

gagctggaac tggaatttgt cttcctattg actctacttc tttaaaagcg       1600

gctgcccatt acattcctca gctgtccttg cagttaggtg tacatgtgac       1650

tgagtgttgg ccagtgagat gaagtctcct caaaggaagg cagcatgtgt       1700

ccttttcat cccttcatct tgctgctggg attgtggata taacaggagc         1750

cctggcagct gtctccagag gatcaaagcc acacccaaag agtaaggcag       1800

attagagacc agaaagacct tgactacttc cctacttcca ctgcttttc        1850

ctgcatttaa gccattgtaa atctgggtgt gttacatgaa gtgaaaatta       1900

attctttctg cccttcagtt ctttatcctg ataccattta acactgtctg       1950

aattaactag actgcaataa ttctttcttt tgaaagcttt taaaggataa       2000

tgtgcaattc acattaaaat tgattttcca ttgtcaatta gttatactca       2050

ttttcctgcc ttgatctttc attagatatt ttgtatctgc ttggaatata       2100

ttatcttctt tttaactgtg taattggtaa ttactaaaac tctgtaatct       2150

ccaaaatatt gctatcaaat tacacaccat gttttctatc attctcatag       2200

atctgcctta taaacattta aataaaaagt actatttaat gatttaactt       2250

ctgttttgaa aaaaaaaaaa aaaaaaaaaa  aaa                        2283
```

<210> SEQ ID NO 140
<211> LENGTH: 454
<212> TYPE: PRT
<213> ORGANISM: Homo sapiens

<400> SEQUENCE: 140

```
Met Glu Ser Ile Ser Met Met Gly Ser Pro Lys Ser Leu Ser Glu
  1               5                  10                  15

Thr Cys Leu Pro Asn Gly Ile Asn Gly Ile Lys Asp Ala Arg Lys
                 20                  25                  30

Val Thr Val Gly Val Ile Gly Ser Gly Asp Phe Ala Lys Ser Leu
                 35                  40                  45

Thr Ile Arg Leu Ile Arg Cys Gly Tyr His Val Val Ile Gly Ser
                 50                  55                  60

Arg Asn Pro Lys Phe Ala Ser Glu Phe Phe Pro His Val Val Asp
                 65                  70                  75
```

-continued

Val Thr His His Glu Asp Ala Leu Thr Lys Thr Asn Ile Ile Phe
80 85 90

Val Ala Ile His Arg Glu His Tyr Thr Ser Leu Trp Asp Leu Arg
95 100 105

His Leu Leu Val Gly Lys Ile Leu Ile Asp Val Ser Asn Asn Met
110 115 120

Arg Ile Asn Gln Tyr Pro Glu Ser Asn Ala Glu Tyr Leu Ala Ser
125 130 135

Leu Phe Pro Asp Ser Leu Ile Val Lys Gly Phe Asn Val Val Ser
140 145 150

Ala Trp Ala Leu Gln Leu Gly Pro Lys Asp Ala Ser Arg Gln Val
155 160 165

Tyr Ile Cys Ser Asn Asn Ile Gln Ala Arg Gln Gln Val Ile Glu
170 175 180

Leu Ala Arg Gln Leu Asn Phe Ile Pro Ile Asp Leu Gly Ser Leu
185 190 195

Ser Ser Ala Arg Glu Ile Glu Asn Leu Pro Leu Arg Leu Phe Thr
200 205 210

Leu Trp Arg Gly Pro Val Val Val Ala Ile Ser Leu Ala Thr Phe
215 220 225

Phe Phe Leu Tyr Ser Phe Val Arg Asp Val Ile His Pro Tyr Ala
230 235 240

Arg Asn Gln Gln Ser Asp Phe Tyr Lys Ile Pro Ile Glu Ile Val
245 250 255

Asn Lys Thr Leu Pro Ile Val Ala Ile Thr Leu Leu Ser Leu Val
260 265 270

Tyr Leu Ala Gly Leu Leu Ala Ala Ala Tyr Gln Leu Tyr Tyr Gly
275 280 285

Thr Lys Tyr Arg Arg Phe Pro Pro Trp Leu Glu Thr Trp Leu Gln
290 295 300

Cys Arg Lys Gln Leu Gly Leu Leu Ser Phe Phe Phe Ala Met Val
305 310 315

His Val Ala Tyr Ser Leu Cys Leu Pro Met Arg Arg Ser Glu Arg
320 325 330

Tyr Leu Phe Leu Asn Met Ala Tyr Gln Gln Val His Ala Asn Ile
335 340 345

Glu Asn Ser Trp Asn Glu Glu Glu Val Trp Arg Ile Glu Met Tyr
350 355 360

Ile Ser Phe Gly Ile Met Ser Leu Gly Leu Leu Ser Leu Leu Ala
365 370 375

Val Thr Ser Ile Pro Ser Val Ser Asn Ala Leu Asn Trp Arg Glu
380 385 390

Phe Ser Phe Ile Gln Ser Thr Leu Gly Tyr Val Ala Leu Leu Ile
395 400 405

Ser Thr Phe His Val Leu Ile Tyr Gly Trp Lys Arg Ala Phe Glu
410 415 420

Glu Glu Tyr Tyr Arg Phe Tyr Thr Pro Pro Asn Phe Val Leu Ala
425 430 435

Leu Val Leu Pro Ser Ile Val Ile Leu Asp Leu Leu Gln Leu Cys
440 445 450

Arg Tyr Pro Asp

<210> SEQ ID NO 141

-continued

<211> LENGTH: 2301
<212> TYPE: DNA
<213> ORGANISM: Homo sapiens

<400> SEQUENCE: 141
cagagccctg cgggaggact cagagtcagg gacacagcag cgtccggcga 50
gatgaaggcg cttggggctg tcctgcttgc cctcttgctg tgcgggcggc 100
cagggagagg gcagacacag caggaggaag aggaagagga cgaggaccac 150
gggccagatg actacgacga ggaagatgag gatgaggtgg aagaggagga 200
gaccaacagg ctccctggtg gcaggagcag agtgctgctg cggtgctaca 250
cctgcaagtc cctgcccagg gacgagcgct gcaacctgac gcagaactgc 300
tcacatggcc agacctgcac aaccctcatt gcccacggga acaccgagtc 350
aggcctcctg accacccact ccacgtggtg cacagacagc tgccagccca 400
tcaccaagac ggtggagggg acccaggtga ccatgacctg ctgccagtcc 450
agcctgtgca atgtcccacc ctggcaaagc tcccgagtcc aggacccaac 500
aggcaagggg gcaggcggcc cccggggcag ctccgaaact gtgggcgcag 550
ccctcctgct caacctcctt gccggccttg gagcaatggg ggccaggaga 600
ccctgaccca cggcccctcc ccacccccac ccggctcacc cccggccctg 650
ccagcactct gtctggtacc ttcccctcct gcccctgcac cagctttgga 700
gaatggattt ggagtgtctt gggcgatcca gccagcgcag gccccccggc 750
ccggttgctt cctcagttcc cggctgtgtc cttggtgtcc tttctccacc 800
acctgtgagc agcaagactg ccgcacgtgg gcgctgggtc cagacctcgg 850
ctgccacgtc ccaggacctg cagccctcac gggggctggg gatccccatc 900
agcacagcca ggcagagatg atacccacca cacacctggg ggcccccaca 950
cccagtcctc acccttaact tctgccatgg gaatttctcc atctgcagca 1000
gtcacacggg cccaccctgc ccttccccag gtcggcctct ccgctgtctg 1050
gagggaaggg gatttggagg gaggctgtcg tcgcccccag gaaagacggg 1100
cctgggggag gcgggacagt gggagaggcg cgctgaggat gagagggcac 1150
agggaggtgg gttggggtga ggccacatgc ggaggggcgg ggcggggcgg 1200
ggctgggggg acaggcacca agtatgaaga ggatggggcc agcggggcct 1250
gtctggctgt ggcgtgagca ccgctatggg agaccctgct tggaaagtga 1300
acttgcagcc ttggatgggg aagggccaga tgctgggtgg gtgcctgtca 1350
ccttgaggtg accatctagg gtcagtacct gctgggctta ggacagcgcc 1400
tgaggctggg aatacctgtc tctgctctag cagaggctaa agcaggctag 1450
agcagtggag gggtggagtt gatgaaagga gaggagtaga tgagatggaa 1500
tttttccagc ctcatcctgg cctgccctct agactccagt ccccaagccc 1550
tcagcctagt gggtgtcatg gatggatctg gggtgtcag acaggctacc 1600 ctgtgccagg gagggggcag aatgggcctg cagcttcctg cagaggaagc 1650
aggactgggt agcagagccg ggaaggtggg tggcccatta caggggggtc 1700
cccagggtgt cctctggcag ggctgtgact gctgcaagct ctgccttcac 1750
cagtagctgg tgccaggaca gagctctggg acagcaggca gaggccgagc 1800
ctgggccaca gctcagccac tgacttgggt atcagtttcc ccttctgaga 1850

-continued

```
agtacagagt gagacttaaa gaacccctag atccccacca gttcaacact              1900

ccattaactg ggaagcccag agtcctgtcc ggcctgccaa gttcatcctg              1950

gtggacagcg ggaggcctcc gctaactgtt ctcttctttt ccttattaat              2000

aaaacacaca atgcctagct ggggggtcgg aaggcaaatg ccctagatgg              2050

tggggtcacg tctttctcct tctccttcct ccttctgctg gctgaagtga              2100

tgactggagc tcagcaacca ctttgcacca tgaggcagca ctgagcacgg              2150

tagggcagcc tggtgagagg ggcctagctc gctgccgaca gaagtcactg              2200

cctacctcag ggtcccctta cctgggtggg aaataaattt ctgctgtgtt              2250

gaagctaaaa aaaaaaaaaa aaaaaaaaaa aaaaaaaaaa aaaaaaaaaa              2300

a                                                                   2301
```

<210> SEQ ID NO 142
<211> LENGTH: 184
<212> TYPE: PRT
<213> ORGANISM: Homo sapiens

<400> SEQUENCE: 142

```
Met Lys Ala Leu Gly Ala Val Leu Leu Ala Leu Leu Leu Cys Gly
  1               5                  10                  15

Arg Pro Gly Arg Gly Gln Thr Gln Gln Glu Glu Glu Glu Glu Asp
                 20                  25                  30

Glu Asp His Gly Pro Asp Asp Tyr Asp Glu Glu Asp Glu Asp Glu
                 35                  40                  45

Val Glu Glu Glu Glu Thr Asn Arg Leu Pro Gly Gly Arg Ser Arg
                 50                  55                  60

Val Leu Leu Arg Cys Tyr Thr Cys Lys Ser Leu Pro Arg Asp Glu
                 65                  70                  75

Arg Cys Asn Leu Thr Gln Asn Cys Ser His Gly Gln Thr Cys Thr
                 80                  85                  90

Thr Leu Ile Ala His Gly Asn Thr Glu Ser Gly Leu Leu Thr Thr
                 95                 100                 105

His Ser Thr Trp Cys Thr Asp Ser Cys Gln Pro Ile Thr Lys Thr
                110                 115                 120

Val Glu Gly Thr Gln Val Thr Met Thr Cys Cys Gln Ser Ser Leu
                125                 130                 135

Cys Asn Val Pro Pro Trp Gln Ser Ser Arg Val Gln Asp Pro Thr
                140                 145                 150

Gly Lys Gly Ala Gly Gly Pro Arg Gly Ser Ser Glu Thr Val Gly
                155                 160                 165

Ala Ala Leu Leu Leu Asn Leu Leu Ala Gly Leu Gly Ala Met Gly
                170                 175                 180

Ala Arg Arg Pro
```

<210> SEQ ID NO 143
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 143

```
tgtaaaacga cggccagtta aatagacctg caattattaa  tct                      43
```

-continued

<210> SEQ ID NO 144
<211> LENGTH: 41
<212> TYPE: DNA
<213> ORGANISM: Artificial sequence
<220> FEATURE:
<223> OTHER INFORMATION: Oligonucleotide Probe

<400> SEQUENCE: 144
caggaaacag ctatgaccac ctgcacacct gcaaatccat t 41

<210> SEQ ID NO 145
<211> LENGTH: 42
<212> TYPE: DNA
<213> ORGANISM: Artificial sequence
<220> FEATURE:
<223> OTHER INFORMATION: Oligonucleotide Probe

<400> SEQUENCE: 145
ggcatgcagc agctggacat ttgcgagggc ttttgctggc tg 42

<210> SEQ ID NO 146
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 146
ctgctgcaga gttgcacgaa c 21

<210> SEQ ID NO 147
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 147
cagttgttgt tgtcacagag aag 23

<210> SEQ ID NO 148
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 148
agttcgtgca actctgcagc ag 22

<210> SEQ ID NO 149
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 149
cctggctatc agcaggtggg ctccaagtgt ctcgatgtgg atgagtgtga 50

<210> SEQ ID NO 150
<211> LENGTH: 22
<212> TYPE: DNA
<213> ORGANISM: Artificial sequence
<220> FEATURE:
<223> OTHER INFORMATION: Oligonucleotide Probe -continued

<400> SEQUENCE: 150
attctgcgtg aacactgagg gc 22

<210> SEQ ID NO 151
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 151
atctgcttgt agccctcggc ac 22

<210> SEQ ID NO 152
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 152
atctcctatc gctgctttcc cgg 23

<210> SEQ ID NO 153
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 153
agccaggatc gcagtaaaac tcc 23

<210> SEQ ID NO 154
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 154
atttaaactt gatgggtctg cgtatcttga gtgcttacaa aaccttatct 50

<210> SEQ ID NO 155
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 155
gttcattgaa aacctcttgc catctgatgg tgacttctgg attgggctca 50

<210> SEQ ID NO 156
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 156
aagccaaaga agcctgcagg aggg 24

<210> SEQ ID NO 157

-continued

<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 157
cagtccaagc ataaaggtcc tggc 24

<210> SEQ ID NO 158
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 158
cggtctacct gtatggcaac c 21

<210> SEQ ID NO 159
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 159
gcaggacaac cagataaacc ac 22

<210> SEQ ID NO 160
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 160
acgcagattt gagaaggctg tc 22

<210> SEQ ID NO 161
<211> LENGTH: 46
<212> TYPE: DNA
<213> ORGANISM: Artificial sequence
<220> FEATURE:
<223> OTHER INFORMATION: Oligonucleotide Probe

<400> SEQUENCE: 161
ttcacgggct gctcttgccc agctcttgaa gcttgaagag ctgcac 46

<210> SEQ ID NO 162
<211> LENGTH: 30
<212> TYPE: DNA
<213> ORGANISM: Artificial sequence
<220> FEATURE:
<223> OTHER INFORMATION: Oligonucleotide Probe

<400> SEQUENCE: 162
actgaggcct gttgaaagtg cagagctcag 30

<210> SEQ ID NO 163
<211> LENGTH: 18
<212> TYPE: DNA
<213> ORGANISM: Artificial sequence
<220> FEATURE:
<223> OTHER INFORMATION: Oligonucleotide Probe

<400> SEQUENCE: 163

-continued gctgaagaag agcttcag 18

<210> SEQ ID NO 164
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 164
ggccagcatg atggacatgg tgtggaacct ttccagcagg tctaggcgta 50

<210> SEQ ID NO 165
<211> LENGTH: 18
<212> TYPE: DNA
<213> ORGANISM: Artificial sequence
<220> FEATURE:
<223> OTHER INFORMATION: Oligonucleotide Probe

<400> SEQUENCE: 165
ggtgcagccc aggatgtc 18

<210> SEQ ID NO 166
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 166
gcattggccg cgagactttg cc 22

<210> SEQ ID NO 167
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 167
gcggccacgg tccttggaaa tg 22

<210> SEQ ID NO 168
<211> LENGTH: 45
<212> TYPE: DNA
<213> ORGANISM: Artificial sequence
<220> FEATURE:
<223> OTHER INFORMATION: Oligonucleotide Probe

<400> SEQUENCE: 168
tggaggagct caacctcagc tacaaccgca tcaccagccc acagg 45

<210> SEQ ID NO 169
<211> LENGTH: 31
<212> TYPE: DNA
<213> ORGANISM: Artificial sequence
<220> FEATURE:
<223> OTHER INFORMATION: Oligonucleotide Probe

<400> SEQUENCE: 169
ttcagcacca aggacaagga caatgacaac t 31

<210> SEQ ID NO 170
<211> LENGTH: 32
<212> TYPE: DNA

-continued

<213> ORGANISM: Artificial sequence
<220> FEATURE:
<223> OTHER INFORMATION: Oligonucleotide Probe

<400> SEQUENCE: 170
tgtgcacact tgtccaagca gttgtcattg tc 32

<210> SEQ ID NO 171
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 171
gtagtacact ccattgaggt tgg 23

<210> SEQ ID NO 172
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 172
ctggggctac acacggggtg agg 23

<210> SEQ ID NO 173
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 173
ggtgccgctg cagaaagtag agcg 24

<210> SEQ ID NO 174
<211> LENGTH: 45
<212> TYPE: DNA
<213> ORGANISM: Artificial sequence
<220> FEATURE:
<223> OTHER INFORMATION: Oligonucleotide Probe

<400> SEQUENCE: 174
gccccaaatg aaaacgggcc ctacttcctg gccctccgcg agatg 45

<210> SEQ ID NO 175
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 175
taacagctgc ccactgcttc cagg 24

<210> SEQ ID NO 176
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 176
taatccagca gtgcaggccg gg 22

-continued

<210> SEQ ID NO 177
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 177
atggcctcca cggtgctgtg gaccgtgttc ctgggcaagg tgtggcagaa 50

<210> SEQ ID NO 178
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 178
tgcctatgca ctgaggaggc agaag 25

<210> SEQ ID NO 179
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 179
aggcagggac acagagtcca ttcac 25

<210> SEQ ID NO 180
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 180
agtatgattt gccgtgcacc cagggccagt ggacgatcca gaacaggagg 50

<210> SEQ ID NO 181
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 181
cgagcgagtc atggccaacg c 21

<210> SEQ ID NO 182
<211> LENGTH: 26
<212> TYPE: DNA
<213> ORGANISM: Artificial sequence
<220> FEATURE:
<223> OTHER INFORMATION: Oligonucleotide Probe

<400> SEQUENCE: 182
gtgtcacacg tagtctttcc cgctgg 26

<210> SEQ ID NO 183
<211> LENGTH: 43
<212> TYPE: DNA
<213> ORGANISM: Artificial sequence
<220> FEATURE:

-continued

<223> OTHER INFORMATION: Oligonucleotide Probe

<400> SEQUENCE: 183
ctgcagctgt tgggcttcat tctcgccttc ctgggatgga tcg 43

<210> SEQ ID NO 184
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 184
atccacagaa gctggccttc gccg 24

<210> SEQ ID NO 185
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 185
gggacgtgga tgaactcggt gtgg 24

<210> SEQ ID NO 186
<211> LENGTH: 40
<212> TYPE: DNA
<213> ORGANISM: Artificial sequence
<220> FEATURE:
<223> OTHER INFORMATION: Oligonucleotide Probe

<400> SEQUENCE: 186
tatccacaga agctggcctt cgccgagtgc ctgtgcagag 40

<210> SEQ ID NO 187
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 187
gggaaacaca gcagtcattg cctgc 25

<210> SEQ ID NO 188
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 188
gcacacgtag cctgtcgctg gagc 24

<210> SEQ ID NO 189
<211> LENGTH: 42
<212> TYPE: DNA
<213> ORGANISM: Artificial sequence
<220> FEATURE:
<223> OTHER INFORMATION: Oligonucleotide Probe

<400> SEQUENCE: 189
caccccaaag cccaggtccg gtacagcgtc aaacaagagt gg 42

-continued

<210> SEQ ID NO 190
<211> LENGTH: 46
<212> TYPE: DNA
<213> ORGANISM: Artificial sequence
<220> FEATURE:
<223> OTHER INFORMATION: Oligonucleotide Probe

<400> SEQUENCE: 190
tccgtgcagg gggacgcctt tcagaaactg cgccgagtta aggaac 46

<210> SEQ ID NO 191
<211> LENGTH: 26
<212> TYPE: DNA
<213> ORGANISM: Artificial sequence
<220> FEATURE:
<223> OTHER INFORMATION: Oligonucleotide Probe

<400> SEQUENCE: 191
catttcctta ccctggaccc agctcc 26

<210> SEQ ID NO 192
<211> LENGTH: 25
<212> TYPE: DNA
<213> ORGANISM: Artificial sequence
<220> FEATURE:
<223> OTHER INFORMATION: Oligonucleotide Prob

<400> SEQUENCE: 192
gaaaggccca cagcacatct ggcag 25

<210> SEQ ID NO 193
<211> LENGTH: 46
<212> TYPE: DNA
<213> ORGANISM: Artificial sequence
<220> FEATURE:
<223> OTHER INFORMATION: Oligonucleotide Probe

<400> SEQUENCE: 193
ccacgacccg agcaacttcc tcaagaccga cttgtttctc tacagc 46

<210> SEQ ID NO 194
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 194
tgcagcccct gtgacacaaa ctgg 24

<210> SEQ ID NO 195
<211> LENGTH: 26
<212> TYPE: DNA
<213> ORGANISM: Artificial sequence
<220> FEATURE:
<223> OTHER INFORMATION: Oligonucleotide Probe

<400> SEQUENCE: 195
ctgagataac cgagccatcc tcccac 26

<210> SEQ ID NO 196
<211> LENGTH: 46
<212> TYPE: DNA
<213> ORGANISM: Artificial sequence
<220> FEATURE:
<223> OTHER INFORMATION: Oligonucleotide Probe -continued

<400> SEQUENCE: 196
ggagatagct gctatgggtt cttcaggcac aacttaacat gggaag 46

<210> SEQ ID NO 197
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 197
gaggtgtcgc tgtgaagcca acgg 24

<210> SEQ ID NO 198
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 198
cgctcgattc tccatgtgcc ttcc 24

<210> SEQ ID NO 199
<211> LENGTH: 45
<212> TYPE: DNA
<213> ORGANISM: Artificial sequence
<220> FEATURE:
<223> OTHER INFORMATION: Oligonucleotide Probe

<400> SEQUENCE: 199
gacggagtgt gtggaccctg tgtacgagcc tgatcagtgc tgtcc 45

<210> SEQ ID NO 200
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 200
gatggcaaaa cgtgtgtttg acacg 25

<210> SEQ ID NO 201
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 201
cctcaaccag gccacgggcc ac 22

<210> SEQ ID NO 202
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 202
cccaggcaga gatgcagtac aggc 24

<210> SEQ ID NO 203
<211> LENGTH: 26

-continued

<212> TYPE: DNA
<213> ORGANISM: Artificial sequence
<220> FEATURE:
<223> OTHER INFORMATION: Oligonucleotide Probe

<400> SEQUENCE: 203
cctccagtag gtggatggat tggctc 26

<210> SEQ ID NO 204
<211> LENGTH: 47
<212> TYPE: DNA
<213> ORGANISM: Artificial sequence
<220> FEATURE:
<223> OTHER INFORMATION: Oligonucleotide Probe

<400> SEQUENCE: 204
ctcacctcat gaggatgagg ccatggtgct attcctcaac atggtag 47

<210> SEQ ID NO 205
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 205
gacgtctgca acagctcctg gaag 24

<210> SEQ ID NO 206
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 206
cgagaaggaa acgaggccgt gag 23

<210> SEQ ID NO 207
<211> LENGTH: 44
<212> TYPE: DNA
<213> ORGANISM: Artificial sequence
<220> FEATURE:
<223> OTHER INFORMATION: Oligonucleotide Probe

<400> SEQUENCE: 207
tgacacttac catgctctgc acccgcagtg gggacagcca caga 44

<210> SEQ ID NO 208
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 208
ctgggatctg aacagtttcg gggc 24

<210> SEQ ID NO 209
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 209

-continued ggtccccagg acatggtctg tccc 24

<210> SEQ ID NO 210
<211> LENGTH: 48
<212> TYPE: DNA
<213> ORGANISM: Artificial sequence
<220> FEATURE:
<223> OTHER INFORMATION: Oligonucleotide Probe

<400> SEQUENCE: 210
gctgagttta catttacggt ctaactccct gagaaccatc cctgtgcg 48

<210> SEQ ID NO 211
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 211
ctgttacact gacgtggccc tccc 24

<210> SEQ ID NO 212
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 212
cattctgacc cacgggccat tgtc 24

<210> SEQ ID NO 213
<211> LENGTH: 44
<212> TYPE: DNA
<213> ORGANISM: Artificial sequence
<220> FEATURE:
<223> OTHER INFORMATION: Oligonucleotide Probe

<400> SEQUENCE: 213
gtggagcagc cggtgaactt gagcagcctt gcccagaagt atgc 44

<210> SEQ ID NO 214
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 214
ccctgccagc cgagagcttc acc 23

<210> SEQ ID NO 215
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 215
ggttggtgcc cgaaaggtcc agc 23

<210> SEQ ID NO 216
<211> LENGTH: 44
<212> TYPE: DNA
<213> ORGANISM: Artificial sequence -continued
<220> FEATURE:
<223> OTHER INFORMATION: Oligonucleotide Probe

<400> SEQUENCE: 216
caaccccaag cttaactggg caggagctga ggtgttttca ggcc 44

<210> SEQ ID NO 217
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 217
ctcctccagg atgaaccacc tgcc 24

<210> SEQ ID NO 218
<211> LENGTH: 18
<212> TYPE: DNA
<213> ORGANISM: Artificial sequence
<220> FEATURE:
<223> OTHER INFORMATION: Oligonucleotide Probe

<400> SEQUENCE: 218
caggatgctt cagagagg 18

<210> SEQ ID NO 219
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 219
cctgccttcg gattccagga gggg 24

<210> SEQ ID NO 220
<211> LENGTH: 42
<212> TYPE: DNA
<213> ORGANISM: Artificial sequence
<220> FEATURE:
<223> OTHER INFORMATION: Oligonucleotide Probe

<400> SEQUENCE: 220
ccatcaaccc cacacaactc atggccagga ttgagtccta tg 42

<210> SEQ ID NO 221
<211> LENGTH: 28
<212> TYPE: DNA
<213> ORGANISM: Artificial sequence
<220> FEATURE:
<223> OTHER INFORMATION: Oligonucleotide Probe

<400> SEQUENCE: 221
ggagacatgt ttcgaatgga caactgtc 28

<210> SEQ ID NO 222
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 222
ctggatcttc acacactggg cagc 24

<210> SEQ ID NO 223
<211> LENGTH: 46
<212> TYPE: DNA
<213> ORGANISM: Artificial sequence
<220> FEATURE:
<223> OTHER INFORMATION: Oligonucleotide Probe

<400> SEQUENCE: 223
cccagtgtgg tgagataaac tgcgagaggt actacgtgcc cgaagg 46

<210> SEQ ID NO 224
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 224
atgccaataa ctttgcctcg gagc 24

<210> SEQ ID NO 225
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 225
ccagaaggcc agggctttct ctg 23

<210> SEQ ID NO 226
<211> LENGTH: 40
<212> TYPE: DNA
<213> ORGANISM: Artificial sequence
<220> FEATURE:
<223> OTHER INFORMATION: Oligonucleotide Probe

<400> SEQUENCE: 226
gagtgcatga gcagctgcca gggatctctc catgggcccc 40

<210> SEQ ID NO 227
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 227
caaccgtatg ggaccgatac tcg 23

<210> SEQ ID NO 228
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 228
cacgctcaac gagtcttcat g 21

<210> SEQ ID NO 229
<211> LENGTH: 41
<212> TYPE: DNA
<213> ORGANISM: Artificial sequence
<220> FEATURE:
<223> OTHER INFORMATION: Oligonucleotide Probe -continued

<400> SEQUENCE: 229
gtggccctcg cagtgcaggc cttctacgtc caatacaagt g 41

<210> SEQ ID NO 230
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 230
actccatatt ttcctacttg tggca 25

<210> SEQ ID NO 231
<211> LENGTH: 19
<212> TYPE: DNA
<213> ORGANISM: Artificial sequence
<220> FEATURE:
<223> OTHER INFORMATION: Oligonucleotide Probe

<400> SEQUENCE: 231
cccaaagtga cctaagaac 19

<210> SEQ ID NO 232
<211> LENGTH: 27
<212> TYPE: DNA
<213> ORGANISM: Artificial sequence
<220> FEATURE:
<223> OTHER INFORMATION: Oligonucleotide Probe

<400> SEQUENCE: 232
tcactgaatt tcttcaaaac cattgca 27

<210> SEQ ID NO 233
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 233
tgtggcagcg actgcatccg acataaagga acagttgtgc tctgcccaca 50

<210> SEQ ID NO 234
<211> LENGTH: 28
<212> TYPE: DNA
<213> ORGANISM: Artificial sequence
<220> FEATURE:
<223> OTHER INFORMATION: Oligonucleotide Probe

<400> SEQUENCE: 234
ggatctcttg ttcaagcatc ctaccaac 28

<210> SEQ ID NO 235
<211> LENGTH: 27
<212> TYPE: DNA
<213> ORGANISM: Artificial sequence
<220> FEATURE:
<223> OTHER INFORMATION: Oligonucleotide Probe

<400> SEQUENCE: 235
tgtcatcact gcaagttaag gcttccc 27

<210> SEQ ID NO 236

<211> LENGTH: 47
<212> TYPE: DNA
<213> ORGANISM: Artificial sequence
<220> FEATURE:
<223> OTHER INFORMATION: Oligonucleotide Probe

<400> SEQUENCE: 236
cgtagagaag ttataatgct ggcctgcagt tttggcaaca agcactg 47

<210> SEQ ID NO 237
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 237
gtcgccccat ttcctgcaac ag 22

<210> SEQ ID NO 238
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 238
gggcctgctc tccctctgaa gc 22

<210> SEQ ID NO 239
<211> LENGTH: 35
<212> TYPE: DNA
<213> ORGANISM: Artificial sequence
<220> FEATURE:
<223> OTHER INFORMATION: Oligonucleotide Probe

<400> SEQUENCE: 239
gtgctgggct ctggagccac actgcgtctt ccgtc 35

<210> SEQ ID NO 240
<211> LENGTH: 20
<212> TYPE: DNA
<213> ORGANISM: Artificial sequence
<220> FEATURE:
<223> OTHER INFORMATION: Oligonucleotide Probe

<400> SEQUENCE: 240
agccccaggg agcacaggct 20

<210> SEQ ID NO 241
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 241
gctcgtcacg gccatcttca cc 22

<210> SEQ ID NO 242
<211> LENGTH: 27
<212> TYPE: DNA
<213> ORGANISM: Artificial sequence
<220> FEATURE:
<223> OTHER INFORMATION: Oligonucleotide Probe

<400> SEQUENCE: 242

-continued

```
tgcgacagcg gcatcaggcg  gttcttc                                    27


<210> SEQ ID NO 243
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 243

tccacgacct cctgtcggag  c                                          21


<210> SEQ ID NO 244
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 244

agaccctgtg cggactgctg  c                                          21


<210> SEQ ID NO 245
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 245

agccccgacc acagcagcag  cccc                                       24


<210> SEQ ID NO 246
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 246

cgttgtttgt cagtggagag  caggg                                      25


<210> SEQ ID NO 247
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 247

caggaacacc tgaggcagaa  gcg                                        23


<210> SEQ ID NO 248
<211> LENGTH: 40
<212> TYPE: DNA
<213> ORGANISM: Artificial sequence
<220> FEATURE:
<223> OTHER INFORMATION: Oligonucleotide Probe

<400> SEQUENCE: 248

ctatctccct gccaggaggc cggagtgggg gaggtcagac                       40


<210> SEQ ID NO 249
<211> LENGTH: 33
<212> TYPE: DNA
```

-continued

<213> ORGANISM: Artificial sequence
<220> FEATURE:
<223> OTHER INFORMATION: Oligonucleotide Probe

<400> SEQUENCE: 249
gatatttgtt tctcaacatg gcttatcagc agg 33

<210> SEQ ID NO 250
<211> LENGTH: 29
<212> TYPE: DNA
<213> ORGANISM: Artificial sequence
<220> FEATURE:
<223> OTHER INFORMATION: Oligonucleotide Probe

<400> SEQUENCE: 250
tctctgacct tctcatcggt aagcagagg 29

<210> SEQ ID NO 251
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 251
tcttttgcag ctttgcagat acccagactg agctggaact gga 43